(12) United States Patent
Pauls et al.

(10) Patent No.: US 9,580,390 B2
(45) Date of Patent: Feb. 28, 2017

(54) INDAZOLE COMPOUNDS AS KINASE INHIBITORS AND METHOD OF TREATING CANCER WITH SAME

(71) Applicant: University Health Network, Toronto (CA)

(72) Inventors: Heinz W. Pauls, Oakville (CA); Radoslaw Laufer, Oakville (CA); Yong Liu, Oakville (CA); Sze-Wan Li, Toronto (CA); Bryan T. Forrest, Burlington (CA); Yunhui Lang, Markham (CA); Narendra Kumar B. Patel, Brampton (CA); Louise G. Edwards, Mississauga (CA); Grace Ng, Richmond Hill (CA); Peter Brent Sampson, Oakville (CA); Miklos Feher, New York, NY (US); Donald E. Awrey, Simcoe (CA)

(73) Assignee: University Health Network, Toronto (CA)

( * ) Notice: Subject to any disclaimer, the term of this patent is extended or adjusted under 35 U.S.C. 154(b) by 193 days.

(21) Appl. No.: 14/351,381

(22) PCT Filed: Oct. 12, 2012

(86) PCT No.: PCT/CA2012/000955
§ 371 (c)(1),
(2) Date: Sep. 2, 2014

(87) PCT Pub. No.: WO2013/053051
PCT Pub. Date: Apr. 18, 2013

(65) Prior Publication Data
US 2014/0371202 A1 Dec. 18, 2014

Related U.S. Application Data

(60) Provisional application No. 61/546,533, filed on Oct. 12, 2011.

(51) Int. Cl.
| | | |
|---|---|---|
| *C07D 231/56* | (2006.01) | |
| *C07D 401/14* | (2006.01) | |
| *C07D 413/14* | (2006.01) | |
| *C07D 409/12* | (2006.01) | |
| *C07D 409/14* | (2006.01) | |
| *C07D 405/14* | (2006.01) | |
| *C07D 451/06* | (2006.01) | |
| *C07D 491/107* | (2006.01) | |
| *C07D 401/10* | (2006.01) | |
| *C07D 401/12* | (2006.01) | |
| *C07D 403/10* | (2006.01) | |

(Continued)

(52) U.S. Cl.
CPC ........... *C07D 231/56* (2013.01); *C07D 401/10* (2013.01); *C07D 401/12* (2013.01); *C07D 401/14* (2013.01); *C07D 403/10* (2013.01);

*C07D 405/14* (2013.01); *C07D 409/12* (2013.01); *C07D 409/14* (2013.01); *C07D 413/04* (2013.01); *C07D 413/10* (2013.01); *C07D 413/14* (2013.01); *C07D 451/06* (2013.01); *C07D 491/107* (2013.01); *C07D 493/10* (2013.01)

(58) Field of Classification Search
None
See application file for complete search history.

(56) References Cited

U.S. PATENT DOCUMENTS 8,980,934 B2 * 3/2015 Pauls ................. C07D 491/107
514/406

FOREIGN PATENT DOCUMENTS

| CA | 2440842 A1 | 10/2002 |
| CA | 2473986 A1 | 8/2003 |

(Continued)

*Primary Examiner* — Kamal Saeed
(74) *Attorney, Agent, or Firm* — McCarter & English, LLP; Steven G. Davis; Wei Song

(57) ABSTRACT

The present teaching provide indazole compounds represented by Structural Formulae (I) or (I') or a pharmaceutically acceptable salt thereof. Also described are pharmaceutical compositions and methods of use thereof as protein kinase inhibitors, such as TTK protein kinase, polo-like kinase 4 (PLK4) and Aurora kinases having anticancer activity against breast cancer cells, colon cancer cells, and ovarian cancer cells.

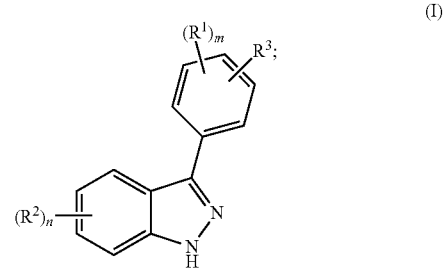

(I)

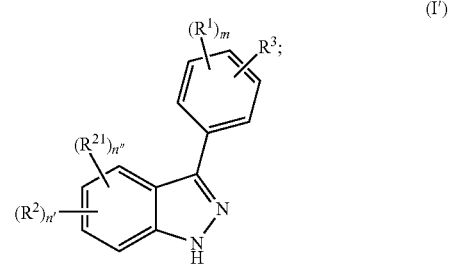

(I')

21 Claims, No Drawings

(51) Int. Cl.
*C07D 413/04* (2006.01)
*C07D 413/10* (2006.01)
*C07D 493/10* (2006.01)

(56) References Cited

FOREIGN PATENT DOCUMENTS

| | | |
|---|---|---|
| WO | 03/064397 A1 | 8/2003 |
| WO | 2011/016330 A1 | 2/2011 |
| WO | 2011/123937 A1 | 10/2011 |
| WO | 2012/087772 A1 | 6/2012 |

\* cited by examiner

INDAZOLE COMPOUNDS AS KINASE INHIBITORS AND METHOD OF TREATING CANCER WITH SAME

CROSS-REFERENCE TO RELATED APPLICATIONS

This application is a 35 U.S.C. §371 national stage filing of International Application No. PCT/CA2012/000955, filed Oct. 12, 2012, which, in turn, is related and claims priority to U.S. Provisional Application Ser. No. 61/546,533, filed Oct. 12, 2011, the entire contents of which are expressly incorporated herein by this reference.

BACKGROUND OF THE INVENTION

Protein kinases have been the subject of extensive study in the search for new therapeutic agents in various diseases, for example, cancer. Protein kinases are known to mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell.

Human TTK protein kinase (TTK), also known as tyrosine threonine kinase, dual specificity protein kinase TTK, Monopolar Spindle 1 (Mps1) and Phosphotyrosine-Picked Threonine Kinase (PYT), is a conserved multispecific kinase that is capable of phosphorylating serine, threonine and tyrosine residues when expressed in E. coli (Mills et al., J. Biol. Chem. 22(5): 16000-16006 (1992)). TTK mRNA is not expressed in the majority of physiologically normal tissues in human (Id). TTK mRNA is expressed in some rapidly proliferating tissues, such as testis and thymus, as well as in some tumors (for example, TTK mRNA was not expressed in renal cell carcinoma, was expressed in 50% of breast cancer samples, was expressed in testicular tumors and ovarian cancer samples) (Id). TTK is expressed in some cancer cell lines and tumors relative to normal counterparts (Id.; see also WO 02/068444 A1).

Therefore, agents which inhibit a protein kinase, in particular TTK, have the potential to treat cancer. There is a need for additional agents which can act as protein kinase inhibitors, in particular TTK inhibitors.

In addition, cancer recurrence, drug resistance or metastasis is one of the major challenges in cancer therapies. Cancer patients who responded favorably to the initial anti-cancer therapy often develop drug resistance and secondary tumors that lead to the relapse of the disease. Recent research evidences suggest that the capability of a tumor to grow and propagate is dependent on a small subset of cells within the tumor. These cells are termed tumor-initiating cells (TICs) or cancer stem cells. It is thought that the TICs are responsible for drug resistance, cancer relapse and metastasis. Compounds that can inhibit the growth and survival of these tumor-initiating cells can be used to treat cancer, metastasis or prevent recurrence of cancer. Therefore, a need exists for new compounds that can inhibit the growth and survival of tumor-initiating cells.

SUMMARY OF THE INVENTION

Applicants have now discovered that certain indazole compounds are potent kinase inhibitors, such as TTK protein kinase, polo-like kinase 4 (PLK4) and Aurora kinases (see Example B, E, and F). Applicants have also now discovered that these indazole compounds have potent anticancer activity against breast cancer cells, colon cancer cells, and ovarian cancer cells in cell culture study (see Examples C-D). Based on these discoveries, indazole compounds, pharmaceutical compositions thereof, and methods of treating cancer with the indazole compounds are disclosed herein.

The present teachings are directed, at least in part, to an indazole compound represented by the following structural formula:

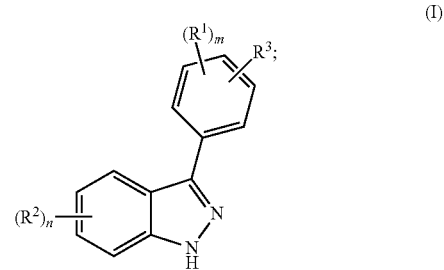

(I)

or a pharmaceutically acceptable salt thereof, wherein:
each $R^1$ is independently selected from —H, -halogen, —CN, —$NO_2$, —$OR^c$, —$NR^aR^b$, —$S(O)_iR^c$, —$NR^d S(O)_iR^c$, —$S(O)_iNR^eR^f$, —C(=O)$OR^c$, —OC(=O)$OR^c$, —C(=S)$OR^c$, —O(C=S)$R^c$, —C(=O)$NR^eR^f$, —$NR^d$C(=O)$R^c$, —C(=S)$NR^eR^f$, —$NR^d$C(=S)$R^c$, —$NR^d$(C=O)$OR^c$, —O(C=O)$NR^eR^f$, —$NR^d$(C=S)$OR^c$, —O(C=S)$NR^eR^f$, —$NR^d$(C=O)$NR^eR^f$, —$NR^d$(C=S)$NR^eR^f$, —C(=S)$R^c$, —C(=O)$R^c$, heterocycloalkyl or alkyl, wherein the heterocycloalkyl or the alkyl is optionally substituted with 1 to 3 substituents independently selected from -halogen, —CN, —$NO_2$, —$OR^c$, —$NR^aR^b$, —$S(O)_iR^c$, —$NR^d S(O)_iR^c$, —$S(O)_iNR^eR^f$, —C(=O)$OR^c$, —OC(=O)$OR^c$, —C(=S)$OR^c$, —O(C=S)$R^c$, —C(=O)$NR^eR^f$, —$NR^d$C(=O)$R^c$, —C(=S)$NR^eR^f$, —$NR^d$C(=S)$R^c$, —$NR^d$(C=O)$OR^c$, —O(C=O)$NR^eR^f$, —$NR^d$(C=S)$OR^c$, —O(C=S)$NR^eR^f$, —$NR^d$(C=O)$NR^eR^f$, —$NR^d$(C=S)$NR^eR^f$, —C(=S)$R^c$ and —C(=O)$R^c$;

each $R^2$ is independently selected from: —$(CH_2)_{0-2}$C(=O)$NR^4(CH_2)_{0-2}Z$—$R^5$, —$(CH_2)_{0-2}NR^4$C(=O)$(CH_2)_{0-2}Z$—$R^5$ and —$(CH_2)_{0-2}NR^4$C(=O)$NR^4(CH_2)_{0-2}Z$—$R^5$;

$R^3$ is

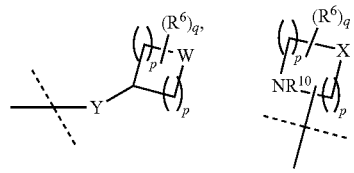

or —O—$(C_1-C_6)$alkyl-$NR^aR^b$; or $R^3$ taken together with an instance of $R^1$ and the phenyl ring to which they are attached form a fused ring heteroaryl or heterocycloalkyl, wherein the heteroaryl or heterocycloalkyl are optionally substituted with 1 to 3 $(C_1-C_3)$ alkyl, provided that $R^3$ is meta or para to the indazole ring;

W is —O—, —$NR^7$—, —$S(O)_i$— or —$CR_8R_9$—;
X is —O—, —$CR^8R^9$—, —$NR^{11}$— or —$S(O)_i$—;
Y is —O—$(CH_2)_r$—, —$NR^{12}$—$(CH_2)_r$—, —$CH_2$— or —$S(O)_i$—$(CH_2)_r$—;

R⁴ is —H or an alkyl group optionally substituted with 1 to 3 substituents independently selected from halogen, hydroxy and (C₁-C₃)alkoxy;

R⁵ is alkyl, cycloalkyl, heterocycloalkyl, aryl or heteroaryl, each of which is optionally substituted with 1 to 3 groups individually represented by R¹⁵ or R¹⁶;

Z is a bond or —CR¹³R¹⁴—;

R⁶ is halogen, hydroxyl, (C₁-C₃)alkyl, (C₁-C₃)alkoxy, (C₁-C₃)alkyl-OR^c or —NR_aR_b; or two instances of R⁶ on the same carbon are taken together form =O; or two instances of R⁶ on different carbons, together with the ring to which they are attached, form a bridged bicyclic group;

R⁷ is —H, (C₁-C₆)alkyl, cycloalkyl, cycloalkyl(C₁-C₆)alkyl, heterocycloalkyl, heterocycloalkyl(C₁-C₆)alkyl, —C(=O)R^c or —C(=O)OR^c, wherein each of the (C₁-C₆)alkyl, cycloalkyl, cycloalkyl(C₁-C₆)alkyl, heterocycloalkyl and heterocycloalkyl(C₁-C₆)alkyl groups is optionally substituted with 1 to 3 substituents independently selected from halogen, hydroxy, (C₁-C₃)alkoxy and —C(=O)NR^eR^f;

R⁸ and R⁹ are each independently selected from —H, —OR^c, and (C₁-C₆)alkyl, wherein the (C₁-C₆)alkyl group is optionally substituted with 1 to 3 substituents independently selected from halogen, hydroxy and (C₁-C₃)alkoxy;

R¹⁰ is —H or (C₁-C₃)alkyl, or is absent when the nitrogen to which it is attached is attached directly to the

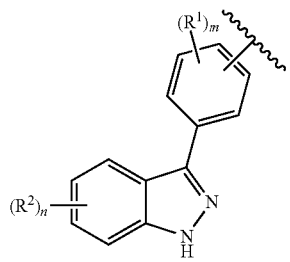

moiety;

R¹¹ is —H, (C₁-C₆)alkyl, cycloalkyl, cycloalkyl(C₁-C₆)alkyl, heterocycloalkyl, heterocycloalkyl(C₁-C₆)alkyl, —C(=O)R^c or —C(=O)OR^c, wherein each of the (C₁-C₆)alkyl, cycloalkyl, cycloalkyl(C₁-C₆)alkyl, heterocycloalkyl and heterocycloalkyl(C₁-C₆)alkyl groups is optionally substituted with 1 to 3 substituents independently selected from halogen, hydroxy, (C₁-C₃)alkoxy and —C(=O)NR^eR^f;

R¹² is —H or (C₁-C₃)alkyl;

R¹³ and R¹⁴ are each independently selected from —H, alkyl, —OR^c, —NR^aR^b, —(C₁-C₃)alkylene-NR^aR^b, —(C₁-C₃)alkylene-OR^c, —(C₁-C₃)alkylene-OH, cycloalkyl, —O-cycloalkyl and heterocycloalkyl, wherein each of the cycloalkyl or heterocycloalkyl groups is optionally substituted with 1 to 3 substituents independently selected from (C₁-C₃)alkyl and (C₁-C₃)alkoxy, provided that R¹³ and R¹⁴ are not both selected from —OR^c and —NR^aR^b;

each R¹⁵ and R¹⁶ are independently selected from halogen, —CN, —NO₂, =O, —OR^c, —NR^aR^b, —S(O)_iR^c, —NR^dS(O)_iR^c, —S(O)_iNR^eR^f, C(=O)OR^c, —OC(=O)OR^c, —C(=S)OR^c, —O(C=S)R^c, —C(=O)NR^eR^f, —NR^dC(=O)R^c, —C(=S)NR^eR^f, —NR^dC(=S)R^c, —NR^d(C=O)OR^c, —O(C=O)NR^eR^f, —NR^d(C=S)OR^c, —O(C=S)NR^eR^f, —NR^d(C=O)NR^eR^f, —NR^d(C=S)NR^eR^f, —C(=S)R^c, —C(=O)R^c, (C₁-C₆)alkyl, aryl, aryl(C₁-C₃)alkyl, heterocycloalkyl and heteroaryl; wherein each (C₁-C₆)alkyl, aryl, aryl(C₁-C₃)alkyl, heterocycloalkyl and heteroaryl represented by R¹⁵ is optionally substituted with 1 to 3 substituents independently selected from -halogen, —CN, —OR^c, (C₁-C₆)alkyl, halo(C₁-C₆)alkyl, (C₁-C₃)alkoxy, halo(C₁-C₃)alkoxy, (C₁-C₃)alkoxy(C₁-C₆)alkyl, 3 to 8 membered heterocycloalkyl and 3 to 8 membered heteroaryl;

R^a and R^b are each independently selected from —H and (C₁-C₆)alkyl, optionally substituted with 1 to 3 substituents independently selected from halogen, hydroxy, —NR^gR^h and (C₁-C₃)alkoxy;

R^c is —H or (C₁-C₆)alkyl, optionally substituted with 1 to 3 substituents independently selected from halogen, —NR^gR^h, hydroxy and (C₁-C₃)alkoxy;

R^d is —H or (C₁-C₆)alkyl, optionally substituted with 1 to 3 substituents independently selected from halogen, —NR^gR^h, hydroxy and (C₁-C₃)alkoxy;

R^e and R^f are each independently selected from —H and (C₁-C₆)alkyl optionally substituted with 1 to 3 substituents independently selected from halogen, —NR^gR^h, hydroxy and (C₁-C₃)alkoxy;

or R^e and R^f, together with the nitrogen to which they are attached, form a 3-8 membered ring optionally substituted with 1 to 3 substituents independently selected from halogen, —NR^gR^h, —CN, (C₁-C₆)alkyl, halo(C₁-C₆)alkyl, (C₁-C₃)alkoxy, halo(C₁-C₃)alkoxy, and (C₁-C₃)alkoxy(C₁-C₆)alkyl;

R^g and R^h are each independently selected from —H, (C₁-C₆)alkyl, halo(C₁-C₆)alkyl, hydroxy(C₁-C₆)alkyl and (C₁-C₃)alkoxy(C₁-C₆)alkyl;

i is 0, 1 or 2;

n is an integer from 1 to 4;

m is an integer from 1 to 4;

each p is 1, 2 or 3;

q is 0, 1 or 2; and r is 0, 1, 2 or 3.

In another embodiment, the present teachings are directed to an indazole compound represented by the following structural formula:

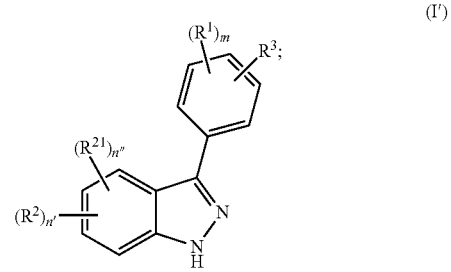

or a pharmaceutically acceptable salt thereof, wherein:
R³ is

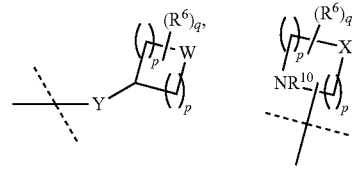

or —O—(C₁-C₆)alkyl-NR^aR^b; or R³ taken together with an instance of R¹ and the phenyl ring to which they are attached form a fused ring heteroaryl or heterocycloalkyl, wherein the heteroaryl or heterocycloalkyl are optionally substituted with 1 to 4 (C₁-C₃) alkyl, oxo, hydroxyl, spirocycloalkyl and spiroheterocycloalkyl, provided that $R^3$ is meta or para to the indazole ring;

$R^7$ is —H, $(C_1$-$C_6)$alkyl, cycloalkyl, cycloalkyl($C_1$-$C_6$) alkyl, heterocycloalkyl, heterocycloalkyl($C_1$-$C_6$)alkyl, —C(=O)$R^c$ or —C(=O)O$R^c$, wherein each of the $(C_1$-$C_6)$alkyl, cycloalkyl, cycloalkyl($C_1$-$C_6$)alkyl, heterocycloalkyl and heterocycloalkyl($C_1$-$C_6$)alkyl groups is optionally substituted with 1 to 4 substituents independently selected from halogen, hydroxy, $(C_1$-$C_3)$ alkoxy and —C(=O)N$R^eR^f$;

$R^8$ and $R^9$ are each independently selected from —H, —O$R^c$, $(C_1$-$C_6)$alkyl, and heterocycloalkyl, wherein the $(C_1$-$C_6)$alkyl group and heterocycloalkyl are optionally substituted with 1 to 3 substituents independently selected from halogen, hydroxy and $(C_1$-$C_3)$ alkoxy;

$R^{10}$ is —H, $(C_1$-$C_3)$alkyl, or heterocycloalkyl, or is absent when the nitrogen to which it is attached is attached directly to the

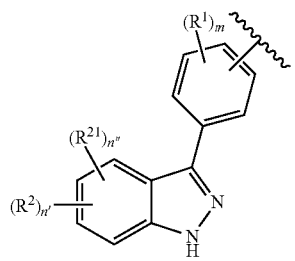

moiety; wherein the heterocycloalkyl is optionally substituted with 1 to 3 substituents independently selected from halogen, hydroxy and $(C_1$-$C_3)$alkoxy;

$R^{13}$ and $R^{14}$ are each independently selected from H, alkyl, —O$R^c$, —N$R^aR^b$, —($C_1$-$C_3$)alkylene-N$R^aR^b$, —($C_1$-$C_3$)alkylene-O$R^c$, —($C_1$-$C_3$)alkylene-OH, cycloalkyl, —O-cycloalkyl and heterocycloalkyl, wherein each of the cycloalkyl or heterocycloalkyl groups is optionally substituted with 1 to 3 substituents independently selected from ($C_1$-$C_3$)alkyl and ($C_1$-$C_3$) alkoxy, provided that $R^{13}$ and $R^{14}$ are not both selected from —O$R^c$ and —N$R^aR^b$; wherein each of the alkyl is optionally substituted with 1 to 3 substituents independently selected from halogen, ($C_1$-$C_3$)alkyl, and ($C_1$-$C_3$)alkoxy.

each $R^{21}$ is halogen;

$R^c$ is H, cycloalkyl, or $(C_1$-$C_6)$alkyl, wherein the $(C_1$-$C_6)$ alkyl is optionally substituted with 1 to 3 substituents independently selected from halogen, —N$R^gR^h$, hydroxy and $(C_1$-$C_3)$alkoxy;

n' is an integer from 1 to 4;

n" is an integer from 0 to 2, provided that n'+n"≤4; and values and alternative values for the remainder of the variables are as described for Structural Formula (I).

In another embodiment, the present teachings include a pharmaceutical composition comprising a pharmaceutically acceptable carrier or diluent and a compound represented by Structural Formula (I) or (I') described above or a pharmaceutically acceptable salt thereof.

Another embodiment of the present teachings provides a method of treating a subject having cancer comprising administering to the subject an effective amount of a compound of Structural Formula (I), (I') or a pharmaceutically acceptable salt thereof.

Another embodiment of the present teachings provides a method of inhibiting TTK activity in a subject in need of inhibition of TTK activity, comprising administering to the subject an effective amount of a compound represented by Structural Formula (I), (I') or a pharmaceutically acceptable salt thereof.

Another embodiment of the present teachings includes the use of a compound represented by Structural Formula (I), (I') or a pharmaceutically acceptable salt thereof in therapy. In some embodiments, the therapy is for treating a subject with cancer. Alternatively, the therapy is for inhibiting TTK activity in a subject in need of inhibition of TTK activity.

Another embodiment of the present teachings includes the use of a compound represented by Structural Formula (I), (I') or a pharmaceutically acceptable salt thereof for the manufacture of a medicament for treating a subject with cancer.

Another embodiment of the present teachings includes the use of a compound represented by Structural Formulas (I), (I') or a pharmaceutically acceptable salt thereof for the manufacture of a medicament for inhibiting TTK activity in a subject in need of inhibition of TTK activity.

DETAILED DESCRIPTION OF THE INVENTION

In one embodiment, the present teachings are directed to a compound represented by Structural Formula (I) or (I') or a pharmaceutically acceptable salt thereof; and values and alternative values for the variables in Structural Formula (I) and (I') are provided in the following paragraphs:

In a first embodiment, W is —O— or —N$R^7$—; X is —O—, —C$R^8R^9$— or —N$R^{11}$—; and Y is —O—(CH$_2$)$_r$—, —N$R^{12}$—(CH$_2$)$_r$— or —CH$_2$—; and values and alternative values for the remainder of the variables are as described for Structural Formula (I) or (I').

In a second embodiment, $R^5$ is cycloalkyl, heterocycloalkyl, aryl or heteroaryl, each of which is optionally substituted with 1 to 3 groups individually represented by $R^{15}$ or $R^{16}$; and values and alternative values for the remainder of the variables are as described for Structural Formula (I), (I') or in the first embodiment.

In a third embodiment, the compound is represented by structural formula:

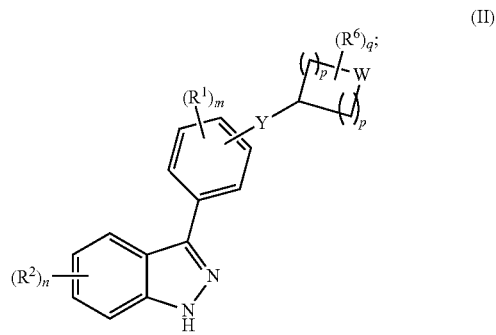

or a pharmaceutically acceptable salt thereof, wherein the group represented by

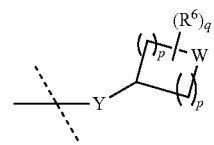

is meta or para to the indazole ring; and values and alternative values for the remainder of the variables are as described for Structural Formula (I), (I') or in the first or second embodiment.

In a fourth embodiment, the compound is represented by a structural formula selected from:

(II-A1)

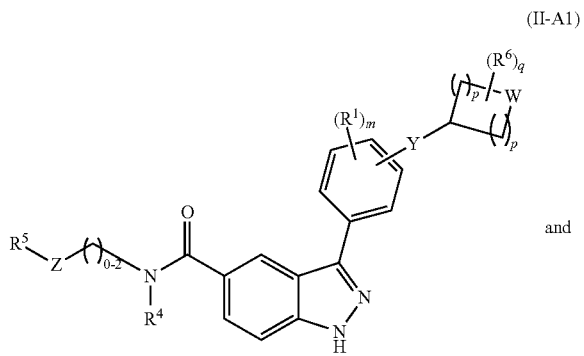

and (II-A2)

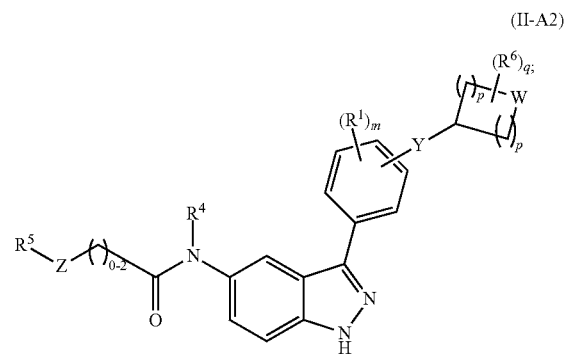

or a pharmaceutically acceptable salt thereof; and values and alternative values for the remainder of the variables are as described for Structural Formula (I), (I') or in the first or second embodiment.

In a fifth embodiment, the compound is represented by a structural formula selected from:

(II-B1)

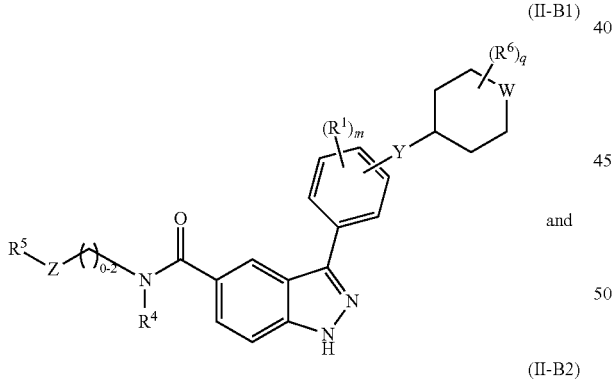

and (II-B2)

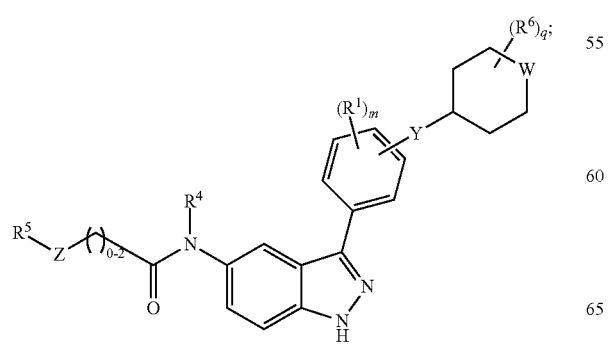

or a pharmaceutically acceptable salt thereof; and values and alternative values for the remainder of the variables are as described for Structural Formula (I), (I') or in the first or second embodiment.

In one embodiment, for compounds described in Structural Formula (I), (I') or in the first, second, third, fourth or fifth embodiment, Z is a bond. In another embodiment, for compounds described in Structural Formula (I), (I') or in the first, second, third, fourth or fifth embodiment, Z is —CR$^{13}$R$^{14}$—.

In a sixth embodiment, the compound is represented by a structural formula selected from:

(II-C1)

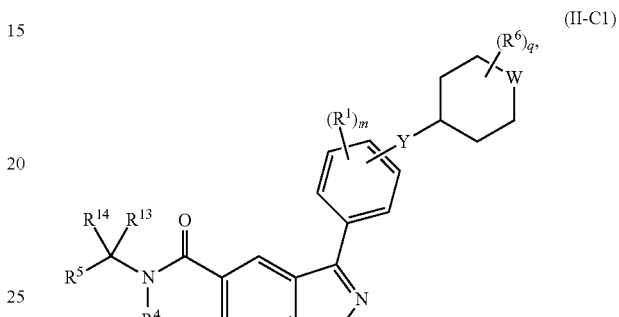

(II-C2)

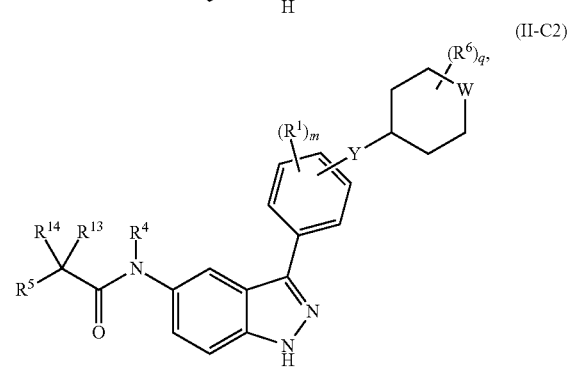

(II-C3) and

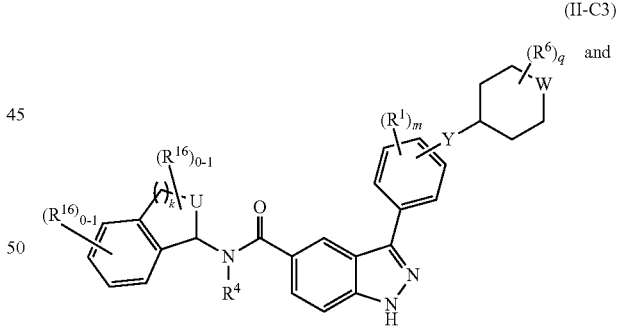

(II-C4)

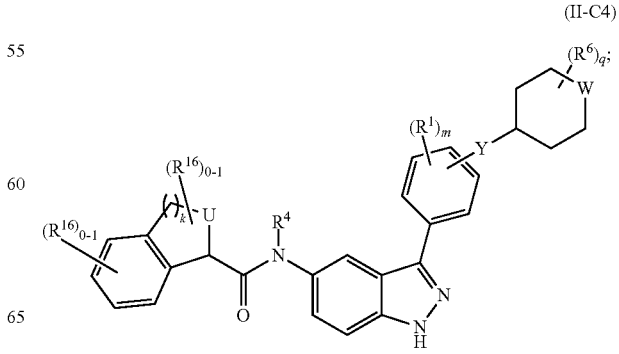

or a pharmaceutically acceptable salt thereof; wherein U is —CH₂—, —CHR¹⁵—, —NH—, —NR¹⁵— or —O—; k is 1 or 2; and values and alternative values for the remainder of the variables are as described for Structural Formula (I), (I') or in the first or second embodiment.

In a seventh embodiment, the compound is represented by a structural formula selected from:

or a pharmaceutically acceptable salt thereof; and values and alternative values for the remainder of the variables are as described for Structural Formula (I), (I') or in the first or second embodiment.

In an eighth embodiment, the compound is represented by a structural formula selected from:

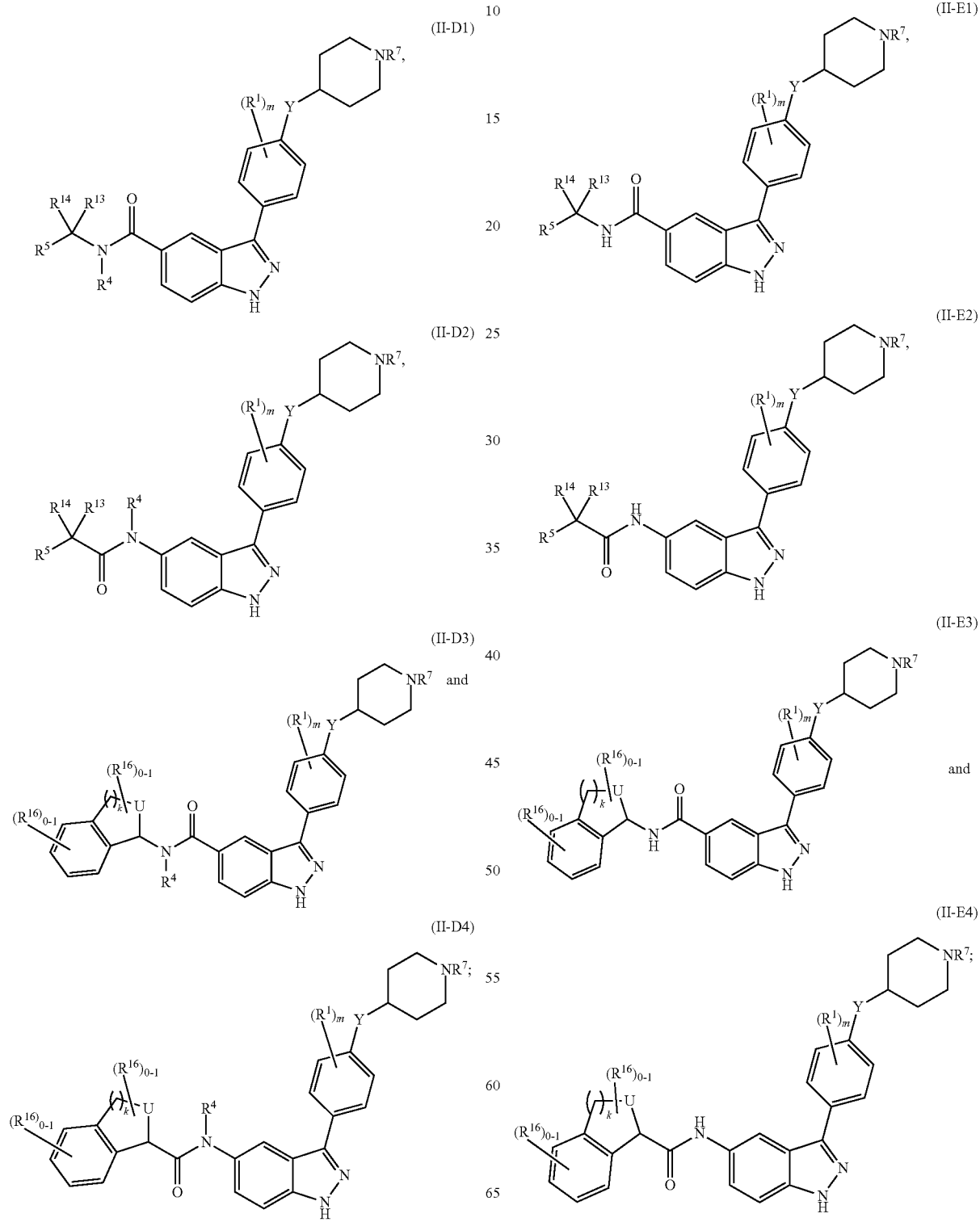

or a pharmaceutically acceptable salt thereof; and values and alternative values for the remainder of the variables are as described for Structural Formula (I), (I') or in the first or second embodiment.

In a ninth embodiment, the compound is represented by a structural formula selected from:

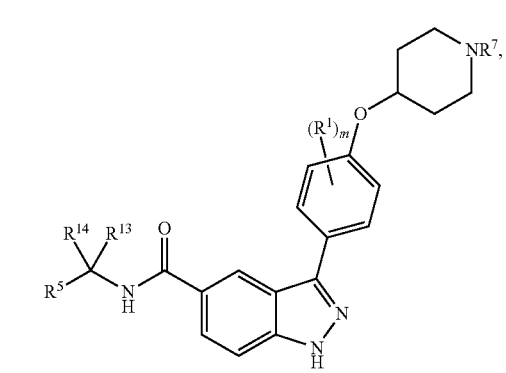
(II-F1)

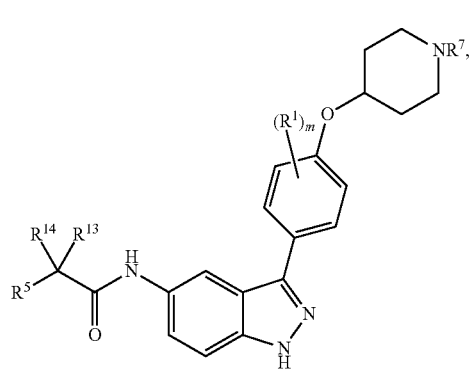
(II-F2)

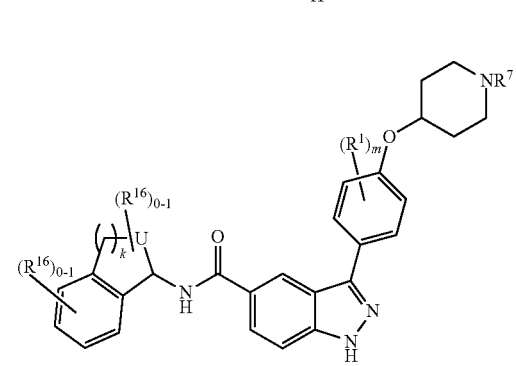
(II-F3)

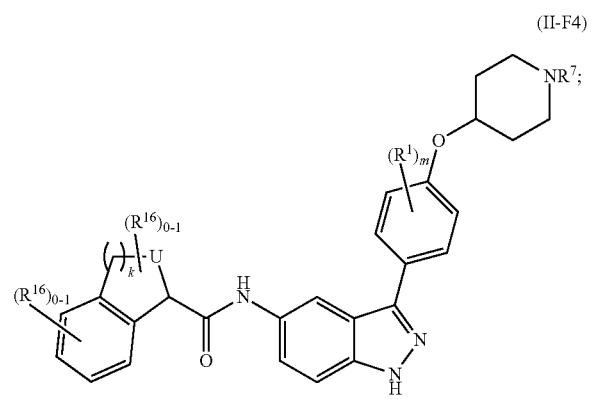
(II-F4)

or a pharmaceutically acceptable salt thereof; and values and alternative values for the remainder of the variables are as described for Structural Formula (I), (I') or in the first or second embodiment.

In a tenth embodiment, the compound is represented by a structural formula selected from:

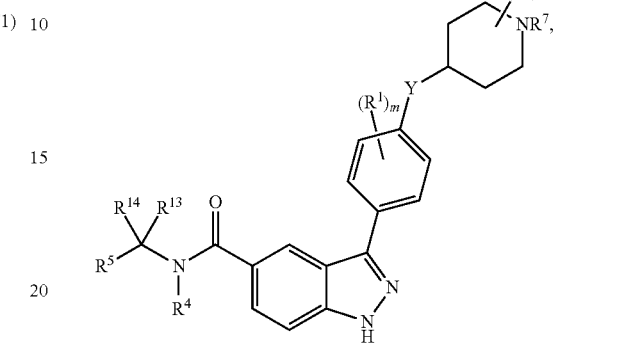
(II-G1)

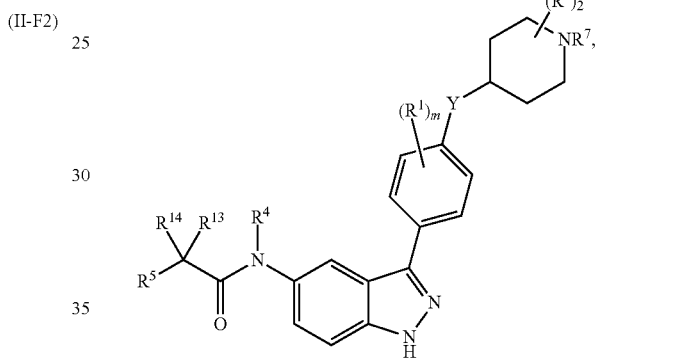
(II-G2)

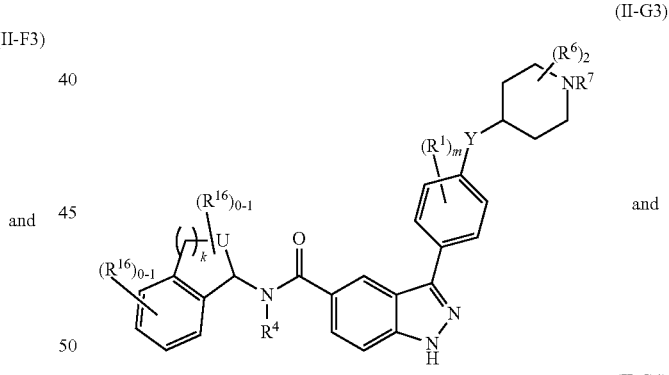
(II-G3)

and

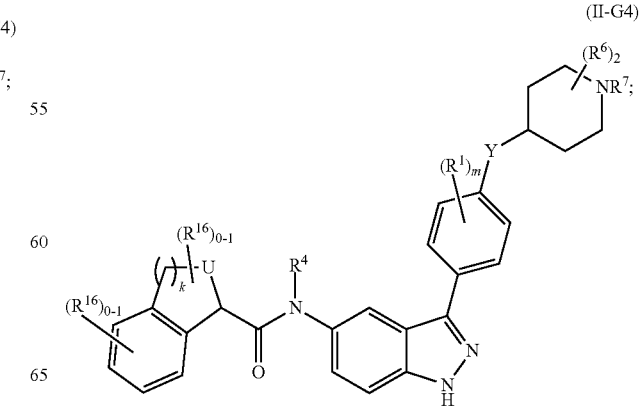
(II-G4)

or a pharmaceutically acceptable salt thereof; wherein the two $R^6$ groups, together with the

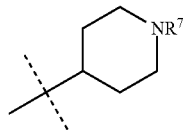

ring to which they are attached, form a 7 to 9 membered bridged bicyclic group containing 1 or 2 ring heteroatoms, wherein the bridged bicyclic group is optionally substituted with —OH, halogen, —NH$_2$ or (C$_1$-C$_3$)alkyl; and values and alternative values for the remainder of the variables are as described for Structural Formula (I), (I') or in the first or second embodiment.

In an eleventh embodiment, the compound is represented by a structural formula selected from:

(II-H1)

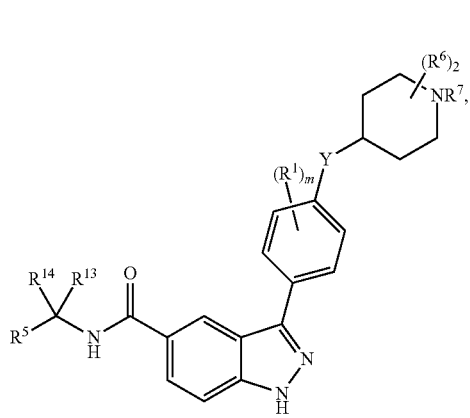

(II-H2)

(II-H3)

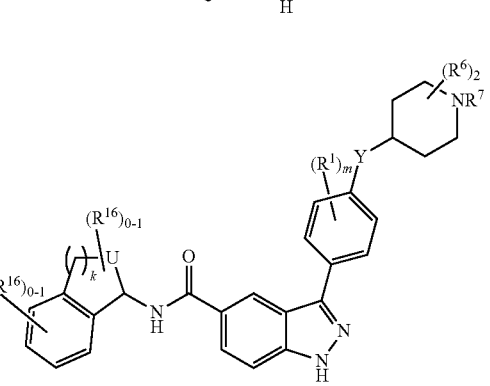

and (II-H4)

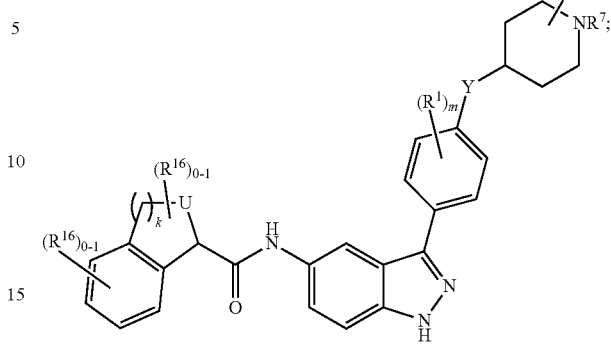

or a pharmaceutically acceptable salt thereof; wherein the two $R^6$ groups, together with the

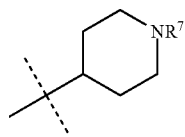

ring to which they are attached, form a 7 to 9 membered bridged bicyclic group containing 1 or 2 ring heteroatoms, wherein the bridged bicyclic group is optionally substituted with —OH, halogen, —NH$_2$ or (C$_1$-C$_3$)alkyl; and values and alternative values for the remainder of the variables are as described for Structural Formula (I), (I') or in the first or second embodiment.

In a twelfth embodiment, the compound is represented by a structural formula selected from:

(II-I1)

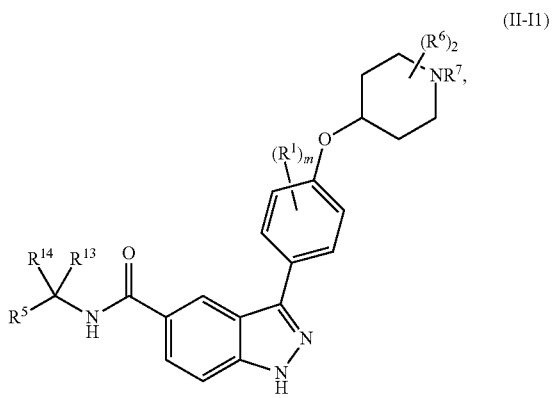

(II-I2)

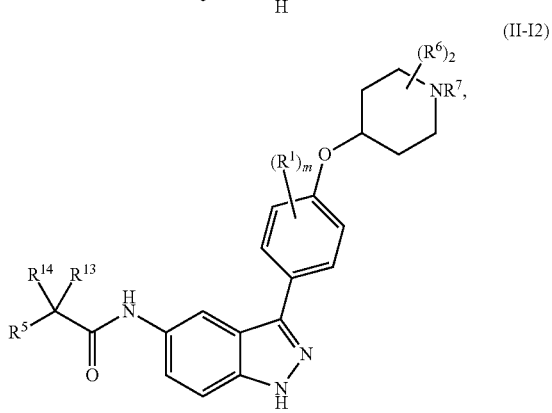

-continued

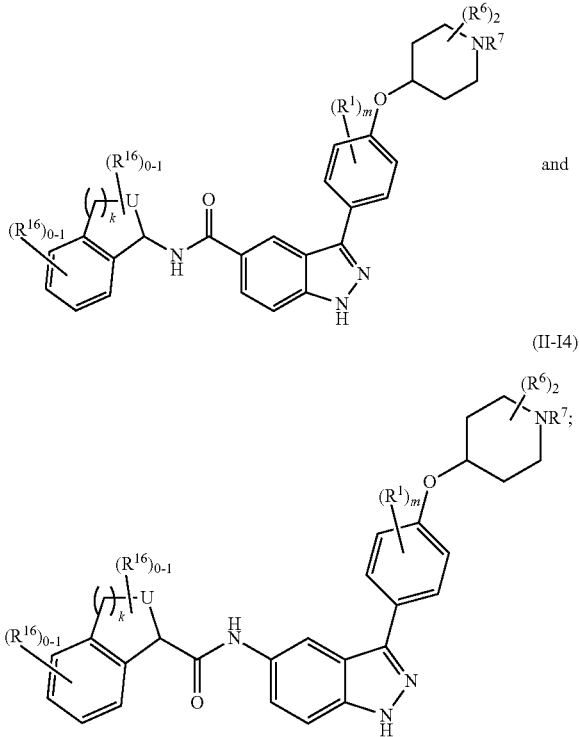

or a pharmaceutically acceptable salt thereof; wherein the two R⁶ groups, together with the

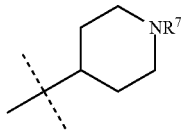

ring to which they are attached, form a 7 to 9 membered bridged bicyclic group containing 1 or 2 ring heteroatoms, wherein the bridged bicyclic group is optionally substituted with —OH, halogen, —NH$_2$ or (C$_1$-C$_3$)alkyl; and values and alternative values for the remainder of the variables are as described for Structural Formula (I), (I') or in the first or second embodiment.

In some embodiments, for compounds described in the tenth, eleventh or twelfth embodiment, the bridge formed by two R⁶ groups is exo to the —Y-indazole moiety or the —O-indazole moiety; and values and alternative values for the remainder of the variables are as described in Structural Formula (I), (I') or the first or second embodiment. In other embodiments, for compounds described in the tenth, eleventh or twelfth embodiment, the bridge formed by two R⁶ groups is endo to the —Y-indazole moiety or the —O-indazole moiety; and values and alternative values for the remainder of the variables are as described for Structural Formula (I), (I') or in the first or second embodiment.

In a thirteenth embodiment, for compounds represented by any one of structural formulas (I), (I'), (II) or (II-A1)-(II-I4), the group represented by Y is —O—(CH$_2$)$_r$—, or —NR$^{12}$—;

R⁴ is —H or an alkyl group optionally substituted with a substituent selected from halogen, hydroxy and (C$_1$-C$_3$) alkoxy;

R⁷ is —H, (C$_1$-C$_6$)alkyl, cycloalkyl, heterocycloalkyl, —C(=O)R$^c$ or —C(=O)OR$^c$, wherein each of the (C$_1$-C$_6$) alkyl, cycloalkyl, and heterocycloalkyl groups is optionally substituted with a substituent independently selected from halogen, hydroxy, (C$_1$-C$_3$)alkoxy and —C(=O)NR$^e$R$^f$;

R$^{13}$ and R$^{14}$ are each independently selected from —H, alkyl, —OR$^c$, —(C$_1$-C$_3$)alkylene-OR$^c$, —(C$_1$-C$_3$)alkylene-OH, (C$_3$-C$_8$)cycloalkyl, —O—(C$_3$-C$_8$)cycloalkyl and 3 to 8 membered heterocycloalkyl, provided that R$^{13}$ and R$^{14}$ are not both —OR$^c$, wherein each of the cycloalkyl or heterocycloalkyl groups is optionally substituted with a (C$_1$-C$_3$) alkyl;

n is an integer from 1 to 2;
m is an integer from 1 to 2;
each p is 1 or 2; and values and alternative values for the remainder of the variables are as described for Structural Formula (I), (I') or in the first or second embodiment.

In a fourteenth embodiment, for compounds represented by any one of structural formulas (I), (I'), (II) or (II-A1)-(II-I4), each R¹ is independently selected from —H, -halogen, —CN, —NO$_2$, —OR$^c$, —NR$^a$R$^b$, —S(O)$_t$R$^c$, —C(=O)OR$^c$, —OC(=O)OR$^c$, —C(=O)NR$^e$R$^f$, —NR$^d$C(=O)R$^c$, —C(=O)R$^c$ or (C$_1$-C$_6$)alkyl, wherein the alkyl is optionally substituted with a substituent selected from -halogen, —OR$^c$, —NR$^a$R$^b$, and —S(O)$_t$R$^c$;

R⁵ is (a) cyclopropyl, cyclobutyl, cyclopentyl, cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl or thienyl, each of which is optionally substituted with 1 to 3 groups represented by R$^{15}$ or (b) bicyclooctanyl, decahydronaphthyl, octahydroindenyl, dihydronaphthalenyl, tetrahydronaphthalenyl, dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydrobenzisoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, chromanyl, isochromanyl, chromenyl, isochromenyl, naphthyl, anthracenyl, fluorenyl, indanyl, indenyl, carbazolyl, benzimidazolyl, benzothienyl, benzofuranyl, isobenzofuranyl, indolyl, isoindolyl, benzotriazolyl, benzothiazolyl, benzoxazolyl, benzisoxazolyl, quinolinyl, isoquinolinyl, indazolyl or acridinyl, each of which is optionally substituted with 1 to 3 groups represented by R$^{16}$;

R⁶ is absent, halogen or (C$_1$-C$_4$)alkyl; or two instances of R⁶ on different carbons, together with the ring to which they are attached, form an azabicyclooctanyl, a diazabicyclooctanyl, an oxabicyclooctanyl, a dioxabicyclooctanyl, an oxa-azabicyclooctanyl, an azabicyclononanyl, a diazabicyclononanyl, an oxabicyclononanyl, a dioxabicyclononanyl, or an oxa-azabicyclononanyl;

R⁷ is —H, (C$_1$-C$_4$)alkyl, halo(C$_1$-C$_4$)alkyl, hydroxy(C$_1$-C$_4$)alkyl, methoxy(C$_1$-C$_4$)alkyl, —(C$_1$-C$_4$)alkyl-C(=O)NMe$_2$, —C(=O)—(C$_1$-C$_4$)alkyl-NMe$_2$, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, —C(=O)$R^c$ or —C(=O)O$R^c$, and wherein each $R^c$ is independently selected from —H, ($C_1$-$C_4$)alkyl, amino($C_1$-$C_4$)alkyl or dimethylamino($C_1$-$C_4$)alkyl;

$R^{13}$ is H and $R^{14}$ is —H, ($C_1$-$C_6$)alkyl, —O$R^c$, —($C_1$-$C_3$)alkylene-O$R^c$, —($C_1$-$C_3$)alkylene-OH, a cycloalkyl selected from cyclopropyl, cyclobutyl, cyclopentyl and cyclohexyl, a —O-cycloalkyl selected from —O-cyclopropyl, —O-cyclobutyl, and —O-cyclopentyl, —O-cyclohexyl, or a heterocycloalkyl selected from morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl and tetrahydrothiopyranyl, provided that $R^{13}$ and $R^{14}$ are not both —O$R^c$, wherein each of the —O-cycloalkyl, cycloalkyl or heterocycloalkyl groups is optionally substituted with a ($C_1$-$C_3$)alkyl; and $R^c$ is —H, or ($C_1$-$C_6$)alkyl;

each $R^{15}$ is independently selected from halogen, —CN, —$NO_2$, =O, —O$R^c$, —N$R^a R^b$, —C(=O)O$R^c$, —OC(=O)O$R^c$, —C(=O)N$R^e R^f$, —N$R^d$C(=O)$R^c$, —N$R^d$(C=O)O$R^c$, —O(C=O)N$R^e R^f$, —N$R^d$(C=O)N$R^e R^f$, —C(=O)$R^c$, ($C_1$-$C_6$)alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, benzyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; wherein the ($C_1$-$C_6$)alkyl represented by $R^{15}$ is optionally substituted with a substituent selected from -halogen, —O$R^c$, ($C_1$-$C_6$)alkyl, ($C_1$-$C_3$)alkoxy, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl;

each $R^{16}$ is independently selected from halogen, —O$R^c$, —N$R^a R^b$, —C(=O)O$R^c$, —C(=O)N$R^e R^f$, —N$R^d$C(=O)$R^c$, —C(=O)$R^c$, ($C_1$-$C_6$)alkyl, phenyl, phenyl($C_1$-$C_3$)alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; and values and alternative values for the remainder of the variables are as described for Structural Formula (I), (I') or in the first, second or thirteenth embodiment.

In a fifteenth embodiment, for compounds represented by any one of structural formulas (I), (I'), (II) or (II-A1)-(II-I4), $R^1$ is selected from —H, -halogen, —$OCH_3$, —N($CH_3$)$_2$, —S(O)$_2$$CH_3$, or methyl;

$R^5$ is (a) cyclopentyl, cyclohexyl, morpholinyl, pyrrolidinyl, piperidinyl, dihydropyridinyl, tetrahydropyridinyl, dihydropyrimidinyl, tetrahydropyrimidinyl, phenyl, furanyl, imidazolyl, pyrrolyl, pyridyl, pyrimidinyl or thienyl, each of which is optionally substituted with 1 to 3 groups represented by $R^{15}$ or (b) chromanyl, chromenyl, dihydroindolyl, dihydroisoindolyl, dihydrobenzothienyl, dihydrobenzofuranyl, dihydroisobenzofuranyl, dihydrobenzotriazolyl, dihydroquinolinyl, tetrahydroquinolinyl, dihydroisoquinolinyl, tetrahydroisoquinolinyl, dihydrobenzisoxazolyl, naphthyl, anthracenyl, fluorenyl, indanyl, indenyl, dihydronaphthalene, tetrahydronaphthalene, carbazolyl, benzimidazolyl, benzothienyl, benzofuranyl, isobenzofuranyl, indolyl, quinolinyl, isoquinolinyl or isoindolyl, each of which is optionally substituted with 1 to 3 groups represented by $R^{16}$;

$R^6$ is absent, halogen or ($C_1$-$C_4$)alkyl; or two instances of $R^6$ on different carbons, together with the ring to which they are attached, form an azabicyclooctanyl, a diazabicyclooctanyl, an oxa-azabicyclooctanyl, an azabicyclononanyl, a diazabicyclononanyl, or an oxa-azabicyclononanyl;

$R^7$ is —H, methyl, ethyl, propyl, isopropyl, methoxyethyl, hydroxyethyl, fluoroethyl, —C(=O)H, —C(=O)$CH_2$N($CH_3$)$_2$, —$CH_2$—C(=O)N($CH_3$)$_2$, oxetanyl, tetrahydrofuranyl, —$CH_2$C(=O)N($CH_3$)$_2$, —C(=O)O($C_1$-$C_4$)alkyl;

$R^{13}$ is —H and $R^{14}$ is —H, ($C_1$-$C_6$)alkyl, —O$R^c$, —($C_1$-$C_3$)alkylene-O$R^c$, —($C_1$-$C_3$)alkylene-OH, cyclopropyl, cyclobutyl, cyclopentyl, cyclohexyl, —O-cyclopropyl, —O-cyclobutyl, —O-cyclopentyl, —O-cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl or tetrahydrothiopyranyl; and $R^c$ is —H, or ($C_1$-$C_6$)alkyl;

each $R^{15}$ is independently selected from halogen, —O$R^c$, —N$R^a R^b$, ($C_1$-$C_6$)alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, isoxazolyl, oxadiazolyl, oxazolyl, pyrazolyl, pyrrolyl, pyridyl, pyrimidinyl, pyridazinyl, thiazolyl, isothiazolyl, triazolyl, tetrazolyl and thienyl; wherein the ($C_1$-$C_6$)alkyl represented by $R^{15}$ is optionally substituted with a substituent selected from -halogen, —O$R^c$, ($C_1$-$C_3$)alkoxy, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, isoxazolyl, oxadiazolyl, oxazolyl, pyrazolyl, pyrrolyl, pyridyl, pyrimidinyl, pyridazinyl, thiazolyl, isothiazolyl, triazolyl, tetrazolyl and thienyl;

each $R^{16}$ is independently selected from halogen, $-OR^c$, $-NR^aR^b$, and $(C_1-C_6)$alkyl;

m is 1; and values and alternative values for the remainder of the variables are as described for Structural Formula (I), (I') or in the first, second, thirteenth or fourteenth embodiment.

In a sixteenth embodiment, for compounds represented by any one of structural formulas (II-C1)-(II-I4), U is $-CH_2-$, $-NH-$, or $-O-$; each $(R^{16})_{0-1}$ is absent; and values and alternative values for the remainder of the variables are as described for Structural Formula (I), (I') or in the first, second, thirteenth, fourteenth or fifteenth embodiment.

In a seventeenth embodiment, for compounds represented by any one of structural formulas (I), (I') and (II-A1)-(II-I4), two instances of $R^6$ on different carbons, together with the ring to which they are attached, form an 8-azabicyclo[3.2.1]octanyl, a 9-azabicyclo[3.3.1]nonanyl, a 3-oxa-9-azabicyclo[3.3.1]nonanyl or a 3,9-diazabicyclo[3.3.1]nonanyl; and values and alternative values for the remainder of the variables are as described for Structural Formula (I), (I'), or in the first, second, thirteenth, fourteenth, fifteenth or sixteenth embodiment.

In an eighteenth embodiment, the compound is represented by structural formula (III)

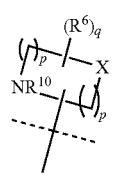

or a pharmaceutically acceptable salt thereof; wherein the group represented by is meta or para to the indazole ring; and values and alternative values for the remainder of the variables are as described for Structural Formula (I), (I') or in the first or second embodiment.

In a nineteenth embodiment, the compound is represented by a structural formula selected from:

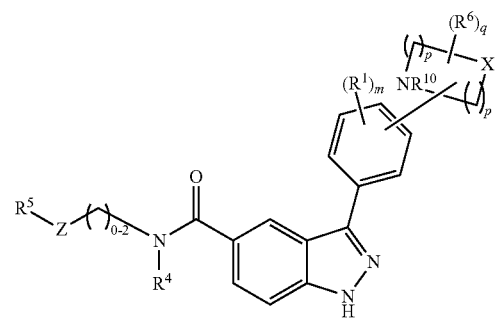

(III-A1)

and

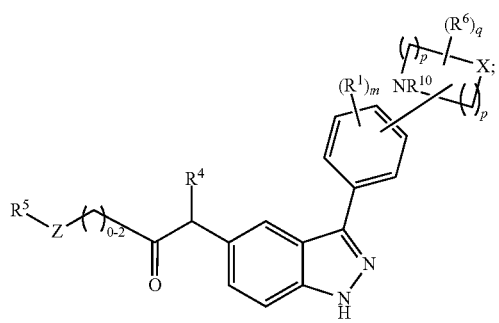

(III-A2)

or a pharmaceutically acceptable salt thereof; and values and alternative values for the remainder of the variables are as described for Structural Formula (I), (I') or in the first or second embodiment.

In a twentieth embodiment, the compound is represented by a structural formula selected from:

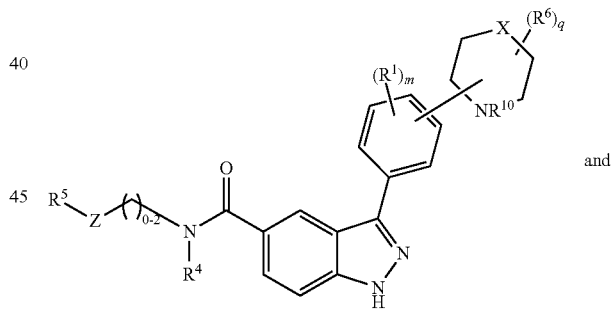

(III-B1)

and

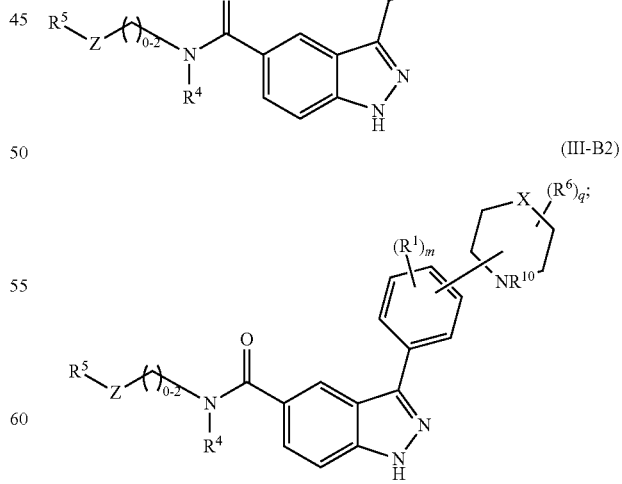

(III-B2)

or a pharmaceutically acceptable salt thereof; and values and alternative values for the remainder of the variables are as described for Structural Formula (I), (I') or in the first or second embodiment.

In one embodiment, for compounds described in Structural Formula (I), (I') or in the eighteenth, nineteenth or twentieth embodiment, Z is a bond. In another embodiment, for compounds described in Structural Formula (I), (I') or in the first, second, third, fourth or fifth embodiment, Z is —CR$^{13}$R$^{14}$—.

In a twenty-first embodiment, the compound is represented by a structural formula selected from:

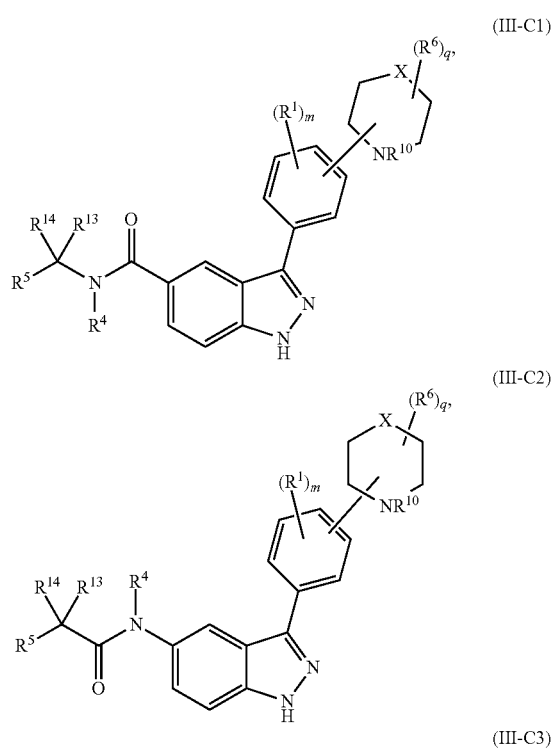

(III-C1)

(III-C2)

(III-C3)

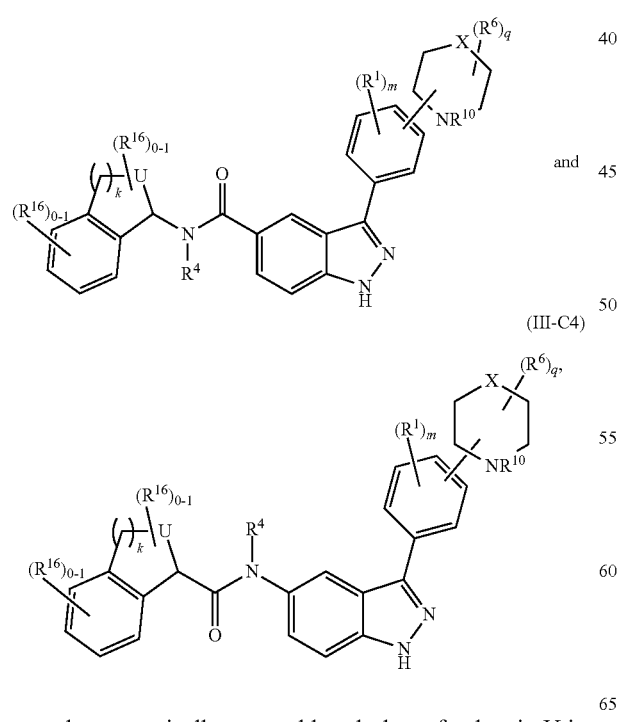

(III-C4)

or a pharmaceutically acceptable salt thereof; wherein U is —CH$_2$—, —CHR$^{15}$—, —NH—, —NR$^{15}$— or —O—; k is 1 or 2; and values and alternative values for the remainder of the variables are as described for Structural Formula (I), (I') or in the first or second embodiment.

In a twenty-second embodiment, the compound is represented by a structural formula selected from:

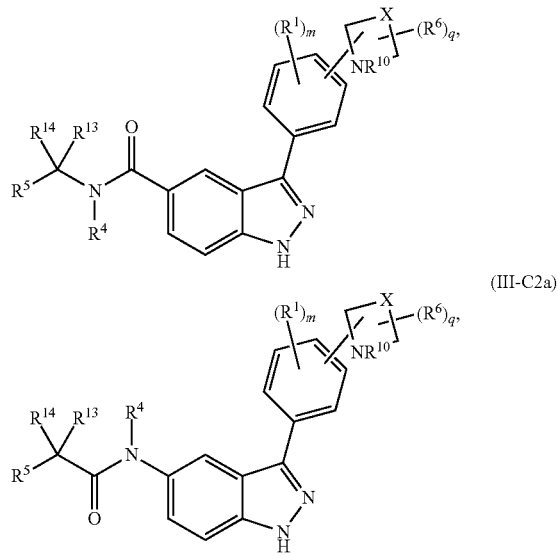

(III-C1a)

(III-C2a)

or a pharmaceutically acceptable salt thereof; wherein R$^6$ is halogen, hydroxyl, (C$_1$-C$_3$)alkyl, (C$_1$-C$_3$)alkoxy, (C$_1$-C$_3$)alkyl-OR$^c$ or —NR$_a$R$_b$, and values and alternative values for the remainder of the variables are as described for Structural Formula (I), (I') or in the first or second embodiment.

In a twenty-third embodiment, the compound is represented by a structural formula selected from:

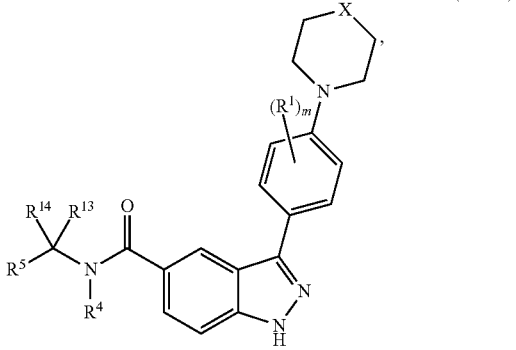

(III-D1)

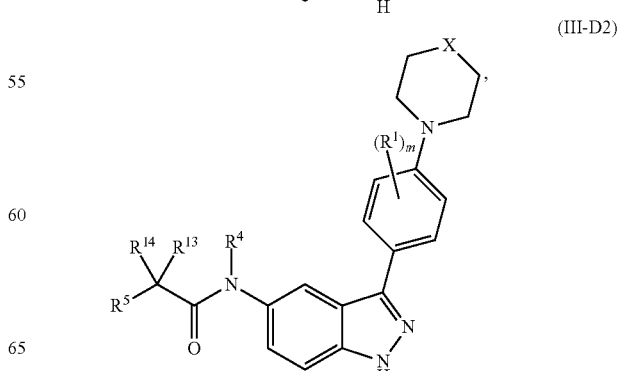

(III-D2)

-continued

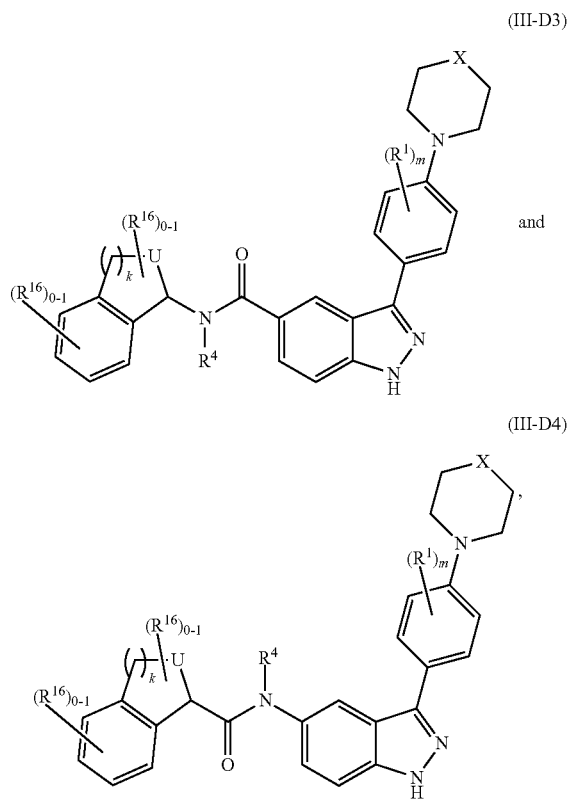

(III-D3)

(III-D4)

or a pharmaceutically acceptable salt thereof; and values and alternative values for the remainder of the variables are as described for Structural Formula (I), (I') or in the first or second embodiment.

In a twenty-fourth embodiment, the compound is represented by a structural formula selected from:

(III-D1a)

(III-D2-a)

or a pharmaceutically acceptable salt thereof; and values and alternative values for the remainder of the variables are as described for Structural Formula (I), (I') or in the first or second embodiment.

In a twenty-fifth embodiment, the compound is represented by a structural formula selected from:

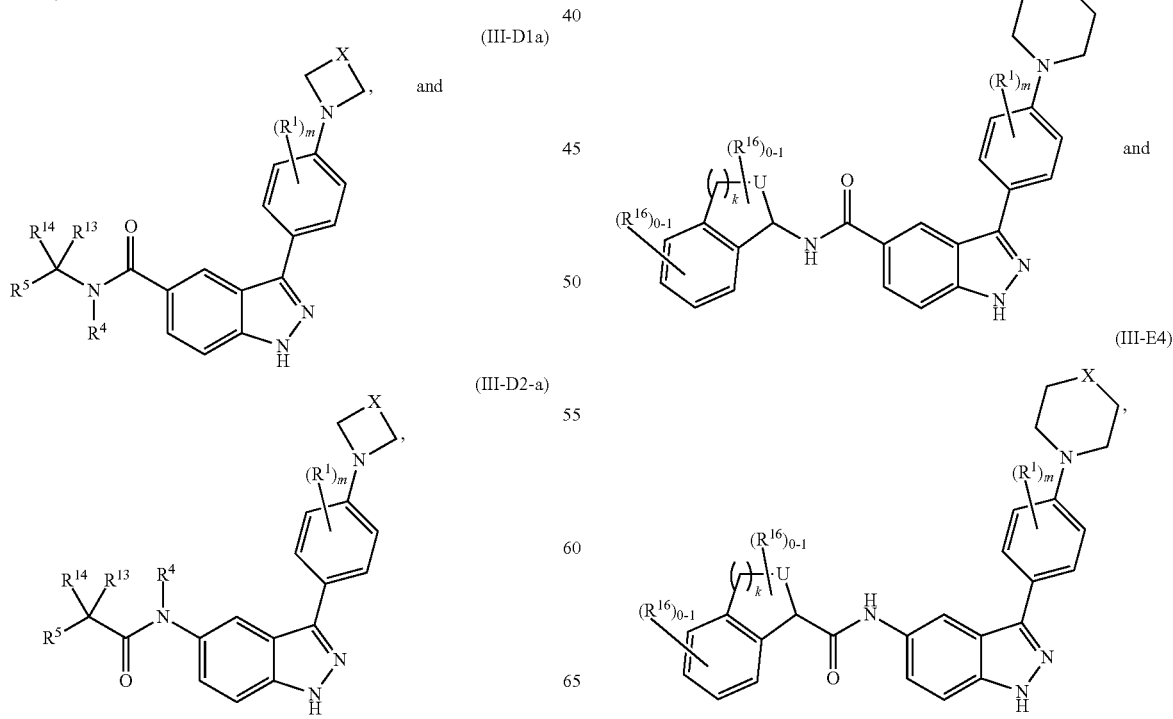

(III-E1)

(III-E2)

(III-E3)

(III-E4)

or a pharmaceutically acceptable salt thereof; and values and alternative values for the remainder of the variables are as described for Structural Formula (I), (I') or in the first or second embodiment.

In a twenty-sixth embodiment, the compound is represented by a structural formula selected from:

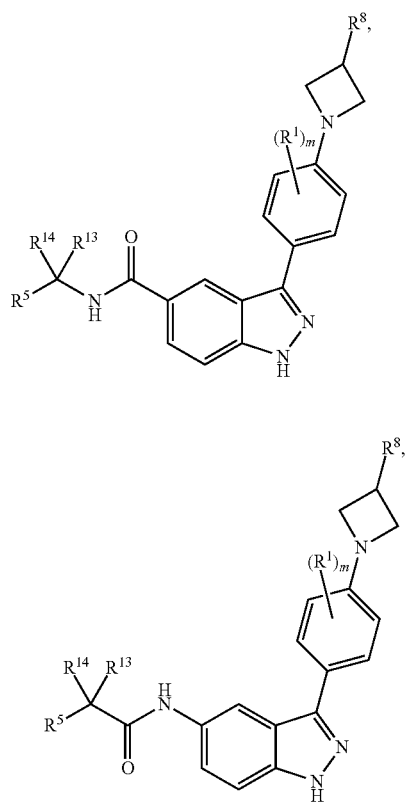

or a pharmaceutically acceptable salt thereof; and values and alternative values for the remainder of the variables are as described for Structural Formula (I), (I') or in the first or second embodiment.

In a twenty-seven embodiment, the compound is represented by a structural formula selected from:

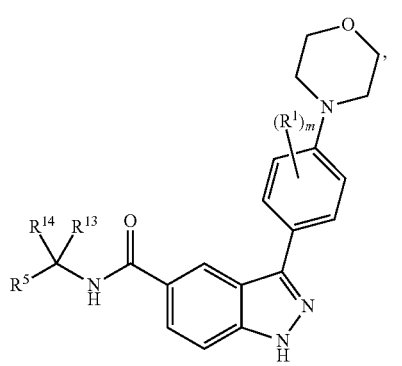

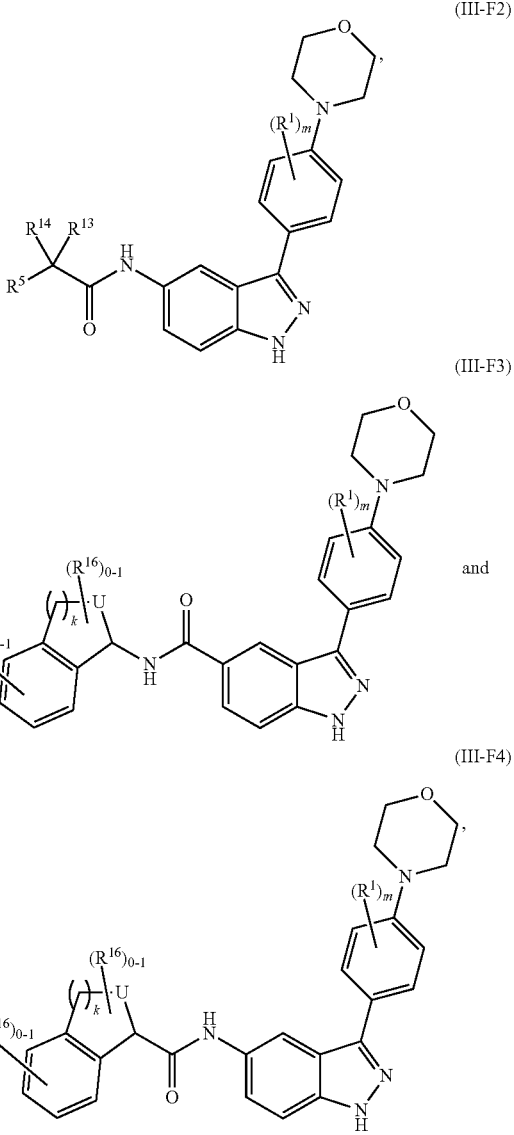

or a pharmaceutically acceptable salt thereof; and values and alternative values for the remainder of the variables are as described for Structural Formula (I), (I') or in the first or second embodiment.

In a twenty-eighth embodiment, the compound is represented by a structural formula selected from:

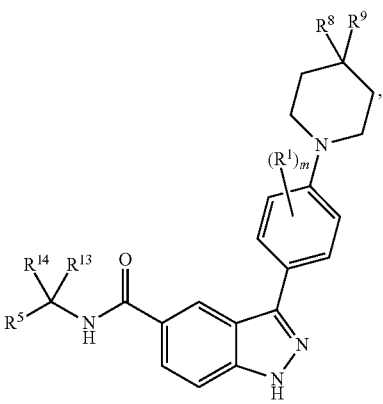

-continued

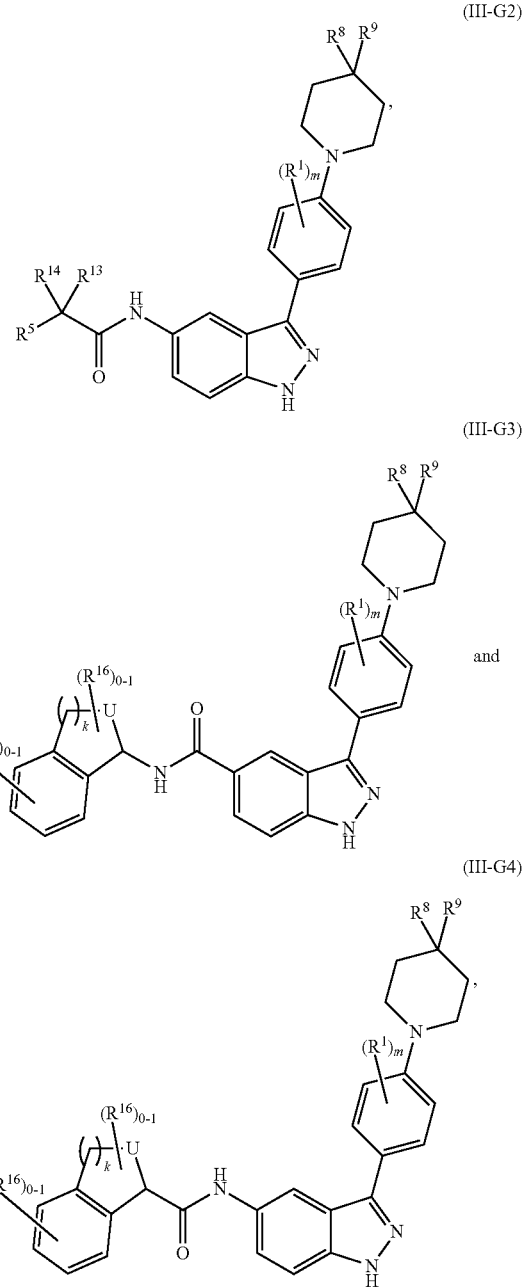

or a pharmaceutically acceptable salt thereof, wherein $R^8$ is —H or $(C_1-C_4)$alkyl; $R^9$ is —OR$^c$ or hydroxy$(C_1-C_4)$alkyl; $R^c$ is —H or $(C_1-C_4)$alkyl; and values and alternative values for the remainder of the variables are as described for Structural Formula (I), (I') or in the first or second embodiment.

In a twenty-ninth embodiment, for compounds represented by any one of structural formulas (I), (I'), (III), (III-A1)-(III-G4), or (III-C1a)-(III-E2a), the group represented by X is —O—, —CR$^8$R$^9$— or —NR$^{11}$—;

$R^4$ is —H or an alkyl group optionally substituted with a substituent selected from halogen, hydroxy and $(C_1-C_3)$alkoxy;

$R^8$ and $R^9$ are each independently selected from —H, —OR$^c$, and $(C_1-C_6)$alkyl, wherein the $(C_1-C_6)$alkyl group is optionally substituted with a substituent selected from halogen, hydroxy and $(C_1-C_3)$alkoxy;

$R^{11}$ is —H, $(C_1-C_6)$alkyl, wherein the $(C_1-C_6)$alkyl is optionally substituted with a substituent selected from halogen, hydroxy, $(C_1-C_3)$alkoxy and —C(═O)NR$^e$R$^f$;

$R^{13}$ and $R^{14}$ are each independently selected from —H, alkyl, —OR$^c$, —$(C_1-C_3)$alkylene-OR$^c$, —$(C_1-C_3)$alkylene-OH, $(C_3-C_8)$cycloalkyl, —O—$(C_3-C_8)$cycloalkyl and 3 to 8 membered heterocycloalkyl, provided that $R^{13}$ and $R^{14}$ are not both —OR$^c$, wherein each of the cycloalkyl or heterocycloalkyl groups is optionally substituted with a $(C_1-C_3)$alkyl;

n is an integer from 1 to 2;
m is an integer from 1 to 2;
each p is 1 or 2; and values and alternative values for the remainder of the variables are as described for Structural Formula (I), (I') or in the first or second embodiment.

In a thirtieth embodiment, for compounds represented by any one of structural formulas (I), (I'), (III), (III-A1)-(III-G4), or (III-C1a)-(III-E2a), each $R^1$ is independently selected from —H, -halogen, —CN, —NO$_2$, —OR$^c$, —NR$^a$R$^b$, —S(O)$_i$R$^c$, —C(═O)OR$^c$, —OC(═O)OR$^c$, —C(═O)NR$^e$R$^f$, —NR$^d$C(═O)R$^c$, —C(═O)R$^c$ or alkyl, wherein the alkyl is optionally substituted with a substituent selected from -halogen, —OR$^c$, —NR$^a$R$^b$, and —S(O)$_i$R$^c$;

$R^5$ is (a) cyclopropyl, cyclobutyl, cyclopentyl, cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydropyranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl or thienyl, each of which is optionally substituted with 1 to 3 groups represented by $R^{15}$ or (b) bicyclooctanyl, decahydronaphthyl, octahydroindenyl, dihydronaphthalenyl, tetrahydronaphthalenyl, dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydrobenzisoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, chromanyl, isochromanyl, chromenyl, isochromenyl, naphthyl, anthracenyl, fluorenyl, indanyl, indenyl, carbazolyl, benzimidazolyl, benzothienyl, benzofuranyl, isobenzofuranyl, indolyl, isoindolyl, benzotriazolyl, benzothiazolyl, benzoxazolyl, benzisoxazolyl, quinolinyl, isoquinolinyl, indazolyl or acridinyl, each of which is optionally substituted with 1 to 3 groups represented by $R^{16}$;

$R^{13}$ is H and $R^{14}$ is —H, $(C_1-C_6)$alkyl, —OR$^c$, —$(C_1-C_3)$alkylene-OR$^c$, —$(C_1-C_3)$alkylene-OH, a cycloalkyl selected from cyclopropyl, cyclobutyl, cyclopentyl and cyclohexyl, a —O-cycloalkyl selected from —O-cyclopropyl, —O-cyclobutyl, and —O-cyclopentyl, —O-cyclohexyl, or a heterocycloalkyl selected from morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl and tetrahydrothiopyranyl, provided that $R^{13}$ and $R^{14}$ are not both —OR$^c$, wherein each of the —O-cycloalkyl, cycloalkyl or heterocycloalkyl groups is optionally substituted with a $(C_1-C_3)$alkyl; and $R^c$ is —H, or $(C_1-C_6)$alkyl each $R^{15}$ is independently selected from halogen, —CN, —$NO_2$, =O, —$OR^c$, —$NR^aR^b$, —C(=O)$OR^c$, —OC(=O)$OR^c$, —C(=O)$NR^eR^f$, —$NR^dC(=O)R^c$, —$NR^d(C=O)OR^c$, —O(C=O)$NR^eR^f$, —$NR^d(C=O)NR^eR^f$, —C(=O)$R^c$, $(C_1-C_6)$alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, benzyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; wherein the $(C_1-C_6)$alkyl represented by $R^{15}$ is optionally substituted with a substituent selected from -halogen, —$OR^c$, $(C_1-C_6)$alkyl, $(C_1-C_3)$ alkoxy, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl;

each $R^{16}$ is independently selected from halogen, —$OR^c$, —$NR^aR^b$, —C(=O)$OR^c$, —C(=O)$NR^eR^f$, —$NR^dC(=O)R^c$, —C(=O)$R^c$, $(C_1-C_6)$alkyl, phenyl, phenyl$(C_1-C_3)$alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; and values and alternative values for the remainder of the variables are as described for Structural Formula (I), (I') or in the first, second or twenty-ninth embodiment.

In a thirty-first embodiment, for compounds represented by any one of structural formulas (I), (I'), (III), (III-A1)-(III-G4), or (III-C1a)-(III-E2a), $R^1$ is selected from —H, -halogen, —$OCH_3$, —$N(CH_3)_2$, —$S(O)_2CH_3$, or methyl;

$R^5$ is cyclopentyl, cyclohexyl, morpholinyl, pyrrolidinyl, piperidinyl, dihydropyridinyl, tetrahydropyridinyl, dihydropyrimidinyl, tetrahydropyrimidinyl, phenyl, furanyl, imidazolyl, pyrrolyl, pyridyl, pyrimidinyl or thienyl, each of which is optionally substituted with 1 to 3 groups represented by $R^{15}$ or (b) chromanyl, chromenyl, dihydroindolyl, dihydroisoindolyl, dihydrobenzothienyl, dihydrobenzofuranyl, dihydroisobenzofuranyl, dihydrobenzotriazolyl, dihydroquinolinyl, tetrahydroquinolinyl, dihydroisoquinolinyl, tetrahydroisoquinolinyl, dihydrobenzisoxazolyl, naphthyl, anthracenyl, fluorenyl, indanyl, indenyl, dihydronaphthalene, tetrahydronaphthalene, carbazolyl, benzimidazolyl, benzothienyl, benzofuranyl, isobenzofuranyl, indolyl, quinolinyl, isoquinolinyl or isoindolyl, each of which is optionally substituted with 1 to 3 groups represented by $R^{16}$;

$R^{13}$ is —H and $R^{14}$ is —H, $(C_1-C_6)$alkyl, cyclopropyl, cyclobutyl, cyclopentyl, cyclohexyl, —O-cyclopropyl, —O-cyclobutyl, —O-cyclopentyl, —O-cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl or tetrahydrothiopyranyl;

$R^{15}$ is independently selected from halogen, —$OR^c$, —$NR^aR^b$, and $(C_1-C_6)$alkyl;

each $R^{16}$ is independently selected from $(C_1-C_6)$alkyl;

m is 1; and values and alternative values for the remainder of the variables are as described for Structural Formula (I), (I'), or in the first, second, twenty-ninth or thirtieth embodiment.

In a thirty-second embodiment, for compounds represented by any one of structural formulas (III-C1)-(III-G4), U is —$CH_2$—, —NH—, or —O—; each $(R^{16})_{0-1}$ is absent.

In a thirty-third embodiment, for compounds represented by any one of structural formulas (I), (I'), (III), (III-A1)-(III-E4), or (III-C1a)-(III-D2a), X is —$NR^{11}$—; $R^{11}$ is $(C_1-C_4)$alkyl; and values and alternative values for the remainder of the variables are as described for Structural Formula (I), (I'), or in the first, second, twenty-ninth, thirtieth, thirty-first, or thirty-second embodiment.

In a thirty-fourth embodiment, for compounds represented by any one of structural formulas (I)-(III), (I'), (II-A1)-(II-I4), (III-A1)-(III-G4), or (III-C1a)-(III-E2a), $R^5$ is cyclohexyl, phenyl, pyridyl, or thienyl, each of which is optionally substituted with 1 to 3 groups selected from methyl, ethyl, propyl, halogen, hydroxymethyl, hydroxyethyl, methoxy, ethoxy, and —$(CH_2)_{0-2}$-morpholinyl; and values and alternative values for the remainder of the variables are as described for Structural Formula (I), (I'), or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, or thirty-third embodiment.

Alternatively, in a thirty-fifth embodiment, for compounds represented by any one of structural formulas (I)-(III), (I'), (II-A1)-(II-I4), (III-A1)-(III-G4), or (III-C1a)-(III-E2a), $R^5$ is cyclohexyl, phenyl, pyridyl, or thienyl, each of which is optionally substituted with 1 to 3 groups selected from methyl, ethyl, propyl and halogen; and values and alternative values for the remainder of the variables are as described for Structural Formula (I), (I'), or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth thirtieth, thirty-first, thirty-second, thirty-third, or thirty-fourth embodiment.

In a thirty-sixth embodiment, for compounds represented by any one of structural formulas (I)-(III), (I'), (II-A1)-(II-I4), (III-A1)-(III-G4), or (III-C1a)-(III-E2a), $R^{14}$ is —H, methyl, ethyl, propyl, hydroxymethyl, hydroxyethyl, hydroxypropyl, methoxy, ethoxy, propoxy, methoxymethyl, methoxyethyl, methoxypropyl, cyclopropyl, cyclobutyl, cyclopentyl, cyclohexyl, —O-cyclopropyl, —O-cyclobutyl, —O-cyclopentyl, —O-cyclohexyl, morpholinyl, oxetanyl, tetrahydrofuryl, tetrahydropyranyl, azetidinyl, pyrrolidinyl, piperidyl, wherein the morpholinyl, tetrahydrofuryl, tetrahydropyranyl, pyrrolidinyl or piperidyl are optionally substituted with methyl; and values and alternative values for the remainder of the variables are as described for Structural Formula (I), (I'), or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, or thirty-fifth embodiment.

In a thirty-seventh embodiment, for compounds represented by any one of structural formulas (I)-(III), (I'), (II-A1)-(II-M), or (III-A1)-(III-G4), $R^3$ is piperidyloxy, N-methylpiperidyloxy, morpholinyl or hydroxypiperidyl; and values and alternative values for the remainder of the variables are as described for Structural Formula (I), (I'), or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, or thirty-sixth embodiment.

The invention also includes the compounds depicted by structure and/or described by name in the Exemplification, as well as neutral forms and pharmaceutically acceptable salts thereof. Treatments with and/or uses of these compounds (including neutral forms and pharmaceutically acceptable salts thereof) as described herein are also included in the invention.

The term "alkyl" used alone or as part of a larger moiety, such as "alkoxy", "haloalkyl", "cycloalkylalkyl", "heterocycloalkylalkyl", "aralkyl", "heteroaralkyl" and the like, means saturated aliphatic straight-chain or branched monovalent hydrocarbon radical. Unless otherwise specified, an alkyl group typically has 1-6 carbon atoms, i.e. $(C_1-C_6)$ alkyl. As used herein, a "$(C_1-C_6)$alkyl" group is means a radical having from 1 to 6 carbon atoms in a linear or branched arrangement.

An "alkylene group" is a saturated aliphatic branched or straight-chain divalent hydrocarbon radical. Unless otherwise specified, an alkylene group typically has 1-6 carbon atoms, i.e. $(C_1-C_6)$alkylene.

An "alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e. $(C_2-C_6)$alkenyl. For example, "$(C_2-C_6)$alkenyl" means a radical having from 2-6 carbon atoms in a linear or branched arrangement.

"Alkynyl" means branched or straight-chain monovalent hydrocarbon radical containing at least one triple bond. Unless otherwise specified, an alkynyl group typically has 2-6 carbon atoms, i.e. $(C_2-C_6)$alkynyl. For example, "$(C_2-C_6)$alkynyl" means a radical having from 2-6 carbon atoms in a linear or branched arrangement.

"Alkoxy" means an alkyl radical attached through an oxygen linking atom, represented by O-alkyl. For example, "$(C_1-C_4)$alkoxy" includes methoxy, ethoxy, propoxy, and butoxy.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

The term "aryl group" used alone or as part of a larger moiety as in "aralkyl", "aralkoxy", or "aryloxyalkyl", means an aromatic hydrocarbon ring system. The term "aryl" may be used interchangeably with the terms "aryl ring" "aromatic ring", "aryl group" and "aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

"Cycloalkyl" means a saturated aliphatic cyclic hydrocarbon radical optionally containing one or more double bonds. It can be monocyclic, bicyclic, polycyclic (e.g., tricyclic), or fused. For example, monocyclic $(C_3-C_8)$cycloalkyl means a radical having from 3-8 carbon atoms arranged in a monocyclic ring. A $(C_3-C_8)$cycloalkyl includes, but is not limited to, cyclopropyl, cyclobutyl, cyclopentyl, cyclohexyl, cycloheptyl and cyclooctyl.

"Heterocycloalkyl" means a saturated or unsaturated non-aromatic 4-12 membered ring radical optionally containing one or more double bonds. It can be monocyclic, bicyclic, tricyclic, or fused. The heterocycloalkyl contains 1 to 4 heteroatoms, which may be the same or different, selected from N, O or S. The heterocycloalkyl ring optionally contains one or more double bonds and/or is optionally fused with one or more aromatic rings (e.g., phenyl ring). The term "heterocycloalkyl" is intended to include all the possible isomeric forms. Examples of heterocycloalkyl include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. Examples of polycyclic heterocycloalkyl groups include dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, dihydrobenzisoxazolyl, chroman, chromene, isochroman and isochromene.

The term "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

Unless otherwise indicated, suitable substituents for a substituted alkyl, cycloalkyl, heterocycloalkyl, aryl group and heteroaryl group include the groups represented by halogen, —OR$^c$, —NR$^a$R$^b$, —S(O)$_i$R$^c$, —NR$^d$S(O)$_i$R$^c$, —S(O)$_i$NR$^e$R$^f$, —C(=O)OR$^c$, —OC(=O)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, (C$_1$-C$_6$)alkyl, cycloalkyl, cycloalkyl(C$_1$-C$_3$)alkyl, heterocycloalkyl, heterocycloalkyl(C$_1$-C$_3$)alkyl, aryl, aryl(C$_1$-C$_3$)alkyl, heteroaryl and heteroaryl(C$_1$-C$_3$)alkyl, wherein R$^a$, R$^b$, R$^c$, R$^d$, R$^e$ and R$^f$ are described above for Structural Formula (I) or (I'). Each of the (C$_1$-C$_6$)alkyl, cycloalkyl, cycloalkyl(C$_1$-C$_3$)alkyl, heterocycloalkyl, heterocycloalkyl(C$_1$-C$_3$)alkyl, aryl, aryl(C$_1$-C$_3$)alkyl, heteroaryl and heteroaryl(C$_1$-C$_3$)alkyl substituents is optionally substituted with halogen, —NO$_2$, —CN, —NR$^d$C(=O)R$^c$, —NR$^g$R$^h$, (C$_1$-C$_3$)alkyl, halo(C$_1$-C$_3$)alkyl, (C$_1$-C$_3$)alkoxy (C$_1$-C$_3$)alkyl, (C$_1$-C$_3$)alkoxy and halo(C$_1$-C$_3$)alkoxy, wherein R$^g$ and R$^h$ are as described above for Structural Formula (I) or (I'). Suitable substituents for a substituted alkyl, cycloalkyl, heterocycloalkyl can also include =O. In certain embodiments, suitable substituents include alkyl, haloalkyl, alkoxy, haloalkoxy, cyano, nitro and halogen.

Regarding connectivity, an "arylalkyl" moiety, for example, refers to an alkyl group substituted with an aryl group (e.g., phenylmethyl (i.e., benzyl)). Similarly, a "heteroarylalkyl" moiety refers to an alkyl group substituted with a heteroaryl group.

As used herein, the term "bridged bicyclic group" refers to a ring system which includes two rings that share at least three adjacent ring atoms.

As used herein, the term "endo", when used in connection with saturated (or partially saturated) ring substitution, refers to two substituents being present on the same face of the ring. Similarly, the term "exo", when used in connection with saturated (or partially saturated) ring substitution, refers to two substituents being present on opposing faces of the ring. For example, endo and exo adducts of dimethylcyclohexane are as follows:

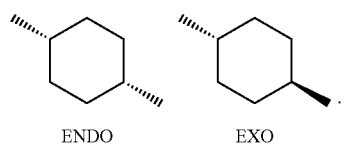

ENDO          EXO

Similarly, exemplary endo and exo adducts of a bridged bicyclic compound are as follows:

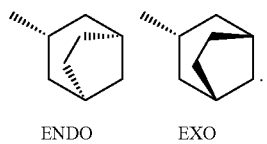

ENDO          EXO

The present teachings also include various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain of the compounds described herein may exist in various stereoisomeric or tautomeric forms. Stereoisomers are compounds which differ only in their spatial arrangement. The present teachings encompass all such forms, including compounds in the form of essentially pure enantiomers, racemic mixtures and tautomers, which includes forms not depicted structurally. When a disclosed compound is named or depicted by structure without indicating stereochemistry, it is understood that the name or structure encompasses all possible stereoisomers, tautomers, geometric isomers or a combination thereof.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Compounds described herein can inhibit various kinases, including the TTK, PLK (such as PLK4), Aurora A, Aurora B, CHK (such as CHK2), ALK, cKit(V560G), JNK3, MELK, and MUSK. Thus, generally, compounds described herein are useful in the treatment of diseases or conditions associated with such kinases. In some embodiments, compounds described herein can inhibit TTK, PLK (such as PLK4), and/or Aurora B kinases. In some embodiments, compounds described herein can inhibit ALK, Aurora B, cKit(V560G), JNK3, MELK, and/or MUSK kinases.

In one embodiment, the compounds described herein are TTK, PLK, Aurora A, Aurora B and/or CHK inhibitors, and are useful for treating diseases, such as cancer, associated with such kinase(s). Alternatively, the compounds described herein are TTK inhibitors and are useful for treating diseases associated with TTK, such as cancer. In another alternative embodiment, the compounds described herein are Aurora A and/or B inhibitors and are useful in inhibiting Aurora A and/or B activity for the treatment of various conditions such as cancers. In yet another specific embodiment, the compounds described herein are PLK inhibitors and are useful in inhibiting PLK activity for the treatment of various conditions such as cancers. Typically, the PLK is PLK4, PLK2 and/or PLK1. In one example, the PLK is PLK1 and/or PLK4. In another example, the PLK is PLK4. In another alternative embodiment, the compounds described herein are CHK inhibitors and are useful in inhibiting CHK activity for the treatment of various conditions such as cancers. In another alternative embodiment, the compounds described herein are ALK inhibitors and are useful in inhibiting ALK activity for the treatment of various conditions such as cancers. In another alternative embodiment, the compounds described herein are cKit(V560G)inhibitors and are useful in inhibiting cKit(V560G)activity for the treatment of various conditions such as cancers. In another alternative embodiment, the compounds described herein are JNK3 inhibitors and are useful in inhibiting JNK3 activity for the treatment of various conditions such as cancers. In another alternative embodiment, the compounds described herein are MELK inhibitors and are useful in inhibiting MELK activity for the treatment of various conditions such as cancers. In another alternative embodiment, the compounds described herein are MUSK inhibitors and are useful in inhibiting MUSK activity for the treatment of various conditions such as cancers.

Another aspect of the present teachings relates to a method of treating a subject with cancer comprising administering to the subject an effective amount of a compound described herein. In one embodiment, the compounds described herein inhibit the growth of a tumor. For example, the compounds described herein inhibit the growth of a tumor that overexpresses at least one of TTK, PLK, Aurora A, Aurora B, CHK, ALK, cKit(V560G), JNK3, MELK, and MUSK.

In one embodiment, the compounds described herein inhibit the growth of a tumor that overexpresses TTK.

Cancers that can be treated (including reduction in the likelihood of recurrence) by the methods of the present teachings include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma multiform or ovarian cancer. In another embodiment, the cancer is lung cancer, breast cancer, colon cancer, brain cancer, neuroblastoma, prostate cancer, melanoma, glioblastoma multiform or ovarian cancer. In yet another embodiment, the cancer is breast cancer, colon cancer and lung cancer. In yet another embodiment, the cancer is a breast cancer. In yet another embodiment, the cancer is a basal sub-type breast cancer or a luminal B sub-type breast cancer. In yet another embodiment, the cancer is a basal sub-type breast cancer that overexpresses TTK. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

In some embodiments, the present teachings provide methods of inhibiting the growth of tumor-initiating cells or reducing the likelihood of recurrence of a cancer in a subject who is undergoing an anti-cancer therapy. The method comprises the steps of:

a) assessing the subject to determine whether the cancer is in remission; and b) if the cancer is in remission; then administering to the subject an effective amount of a TTK inhibitor (e.g., a compound represented by Structural Formula (I) or (I')). If the cancer is not in remission, the method optionally further comprises the step of continuing the anti-cancer therapy until the cancer goes into remission and then the step b) of administering an effective amount of a TTK inhibitor (e.g., a compound represented by Structural Formula (I) or (I')).

As used herein, the term "tumor-initiating cells" or "TICs" refer to cells present within some tumors that possess the ability to self-renew and proliferate. These cells are sometimes called cancer stem cells (CSCs) and may be observed to share certain characteristics with normal stem cells, including a stem cell-like phenotype and function. In some embodiments, TICs are characterized by their ability to form tumors after xenotransplantation in immunodeficient mice.

In some embodiments, the present teachings provide methods of inhibiting the growth of tumor-initiating cells or reducing the likelihood of recurrence of a cancer in a subject whose cancer is in remission comprising administering to the subject an effective amount of a TTK inhibitor (e.g, a compound represented by Structural Formula (I) or (I')).

In some embodiments, e.g., where the subject is being treated to reduce the likelihood of recurrence of a cancer, the subject has already been treated with an anti-cancer therapy. Alternatively, the subject has already been treated with an anti-cancer therapy and the subject is in remission.

In some embodiments, the present teachings provide methods of treating a subject with a cancer comprising administering to the subject an effective amount of a compound represented by Structural Formula (I) or (I') in combination with an effective anti-cancer therapy. In one embodiment, the cancer is a metastatic cancer. A "metastatic cancer" is a cancer that has spread from its primary site to other parts of the body.

In another embodiment, the present teachings are directed to a method of treating a subject with a drug-resistant cancer. A "drug-resistant cancer" is a cancer that is not responsive to one, two, three, four, five or more drugs that are typically used for the treatment of the cancer. In one embodiment, the drug-resistant cancer is mediated by the growth of tumor-initiating cells.

Suitable methods known in the art can be used for assessing a subject to determine whether the cancer is in remission. For example, the size of the tumor and/or tumor markers, usually proteins associated with tumors, can be monitored to determine the state of the cancer. Size of the tumor can be monitored with imaging devices, such as X-ray, MRI, CAT scans, ultrasound, mammography, PET and the like or via biopsy.

For methods described herein, e.g., coadministration methods, the anti-cancer therapy is selected from the group consisting of surgery, radiation therapy, immunotherapy, endocrine therapy, gene therapy and administration of an anti-cancer agent. Alternatively, the anti-cancer therapy is radiation therapy. In another alternative, the anti-cancer therapy is immunotherapy. In another alternative, the anti-cancer therapy is administration of an anti-cancer agent. In yet another alternative, the anti-cancer therapy is surgery.

Radiation therapy is the use of radiation to kill, destroy or treat the cancers. Exemplary radiation therapy includes, but is not limited to, gamma-radiation, neutron beam radiotherapy, electron beam radiotherapy, proton therapy, brachytherapy, and radioisotope therapy (i.e., systemic radioactive isotopes therapy), An endocrine therapy is a treatment that adds, blocks or removes hormones. For example, chemotherapeutic agents that can block the production or activity of estrogen have been used for treating breast cancer. In addition, hormonal stimulation of the immune system has been used to treat specific cancers, such as renal cell carcinoma and melanoma. In one embodiment, the endocrine therapy comprises administration of natural hormones, synthetic hormones or other synthetic molecules that may block or increase the production of the body's natural hormones. In another embodiment, the endocrine therapy includes removal of a gland that makes a certain hormone.

As use herein, a gene therapy is the insertion of genes into a subject's cell and biological tissues to treat diseases, such as cancer. Exemplary gene therapy includes, but is not limited to, a germ line gene therapy and a somatic gene therapy.

Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-streptavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β$_2$ antibody (Cambridge Ab Tech).

Immunotherapies that can be used in the present teachings include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

Alternatively, the anti-cancer therapy described herein includes administration of an anti-cancer agent. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agent suitable for use in the methods described herein include any anti-cancer agents that have been approved for the treatment of cancer. In one embodiment, the anti-cancer agent includes, but is not limited to, a targeted antibody, an angiogenisis inhibitor, an alkylating agent, an antimetabolite, a vinca alkaloid, a taxane, a podophyllotoxin, a topoisomerase inhibitor, a hormonal antineoplastic agent and other antineoplastic agents.

Examples of alkylating agents useful in the methods of the present teachings include but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful in the methods of the present teachings include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of plant alkaloids and terpenoids or derivatives thereof include, but are not limited to, vinca alkaloids (e.g., vincristine, vinblastine, vinorelbine, vindesine), podophyllotoxin, and taxanes (e.g., paclitaxel, docetaxel). Examples of a topoisomerase inhibitor includes, but is not limited to, irinotecan, topotecan, amsacrine, etoposide, etoposide phosphate and teniposide. Examples of antineoplastic agents include, but are not limited to, actinomycin, anthracyclines (e.g., doxorubicin, daunorubicin, valrubicin, idarubicin, epirubicin), bleomycin, plicamycin and mitomycin.

In one embodiment, the anti-cancer agents that can be used in the present teachings include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anti-cancer agents/drugs that can be used in the present teachings include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin;

oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

In one embodiment, the anti-cancer agents that can be used in methods described herein are selected from the group consisting of paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan and a combination thereof.

In one embodiment, the anti-cancer agent and the compound represented by Structural Formula (I) or (I') are administered contemporaneously. When administered contemporaneously, the anti-cancer agent and the compound can be administered in the same formulation or in different formulations. Alternatively, the compound and the additional anti-cancer agent are administered separately.

In one embodiment, the subject in the methods described herein has not been previously treated with a TTK inhibitor (e.g., the compound represented by Structural Formula (I) or (I')).

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

The term "inhibiting the growth of tumor-initiating cells" refers to preventing or decreasing the rate of the proliferation and/or survival of the tumor-initiating cells.

As used herein, the term "reducing the likelihood of recurrence of a cancer" means partially or totally inhibiting, preventing or delaying the return of a cancer at or near a primary site and/or at a secondary site after a period of remission. It also means that the cancer is less likely to return with treatment described herein than in its absence.

As used herein, the term "remission" refers to a state of cancer, wherein the clinical symptoms or indicators associated with a cancer have disappeared or cannot be detected, typically after the subject has been successfully treated with an anti-cancer therapy.

As used herein, "treating a subject with a cancer" includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

In an embodiment, an effective amount of a compound taught herein ranges from about 0.1 to about 1000 mg/kg body weight, alternatively about 1 to about 500 mg/kg body weight, and in another alternative, from about 20 to about 300 mg/kg body weight. In another embodiment, an effective amount of a compound taught herein ranges from about 0.5 to about 5000 mg/m$^2$, alternatively about from 5 to about 2500 mg/m$^2$, and in another alternative from about 50 to about 1000 mg/m$^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

Moreover, for methods described herein (including treating a subject with a cancer or reducing the likelihood of recurrence of a cancer), a "treatment" or dosing regime of a subject with an effective amount of the compound of the present teachings may consist of a single administration, or alternatively comprise a series of applications. For example, the compound of the present teachings may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present teachings, or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds taught herein can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

The compounds of invention may be prepared by methods known to those skilled in the art, as illustrated by the general schemes and procedures below and by the preparative examples that follow. All starting materials are either commercially available or prepared by methods known to those skilled in the art and the procedures described below.

General synthetic approaches to the 1H-indazole core have been reviewed in literature (*Eur. J. Org. Chem.* 2008, 4073-4095).

In one general synthetic process, compounds described herein can be prepared according to the following reaction Scheme 1. Halogenation of an appropriately substituted indazole wherein the indazole is substituted as defined herein provides intermediate I that can be reacted with a suitable cross coupling partner, R$^2$Met (e.g. ArB(OH)$_2$), in the presence of a metal catalyst (e.g. PdCl$_2$(dppf) or Pd(PPh$_3$)$_4$).

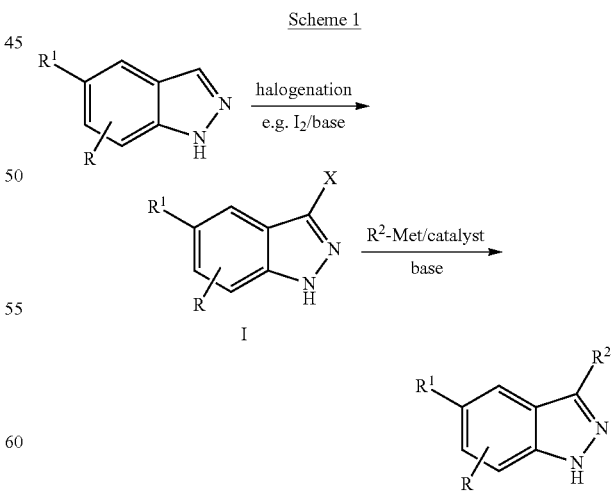

Alternatively, haloindazole II can be converted into a 3-(trialkylstannyl)-1H-indazole that can be subjected to Stille-type cross-coupling reaction as shown in Scheme 2 (e.g. 1. Me$_6$Sn$_2$/Pd(PPh$_3$)$_4$/PhMe 2. ArI/Pd(PPh$_3$)$_4$/CuI/THF ref. WO200102369).

Scheme 2

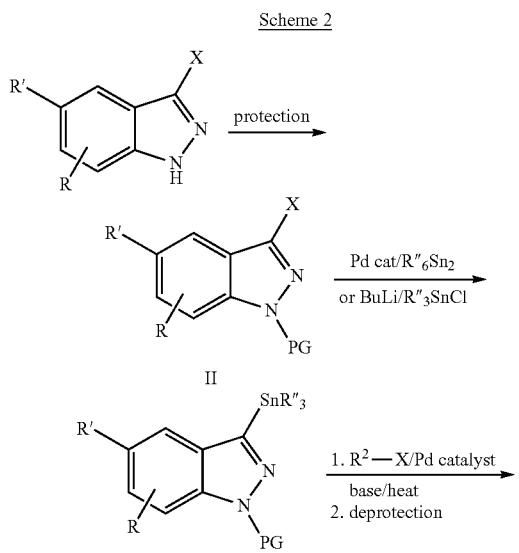

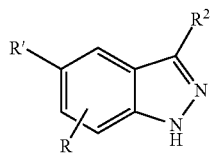

e.g. X = Cl, Br, I
e.g. PG = THP, SEM, Boc

Compounds described herein can also be prepared according to the general procedures shown in the Scheme 3. 5-Aminoindazole is protected by a suitable aniline protecting group such as a Boc group followed by halogenations (e.g. I$_2$/K$_2$CO$_3$). A sequence of Suzuki-Miyaura cross coupling and removal of the protecting group yields anilines III that can be reacted with a variety of electrophilic reagents (e.g. R—NCO, R'R"NH/phosgene or triphosgene, ROH/triphosgene, RNHSO$_2$NHC(=O)CH$_2$CH$_2$Cl, RSO$_2$Cl, RC(=O)R'/reducing agent, RCOCl or RCO$_2$H/coupling reagent: TBTU, EDC, DCC, HATU, pyBOP, COMU) leading to preparation of substituted ureas, carbamates, sulfamides, sulfonamides, anilines and amides.

Alternatively, 5-nitro-1H-indazole can be halogenated and reduced to provide 3-halo-5-amino indazoles IV that can be subjected to an amide formation followed by Pd-catalyzed cross-coupling.

Scheme 3

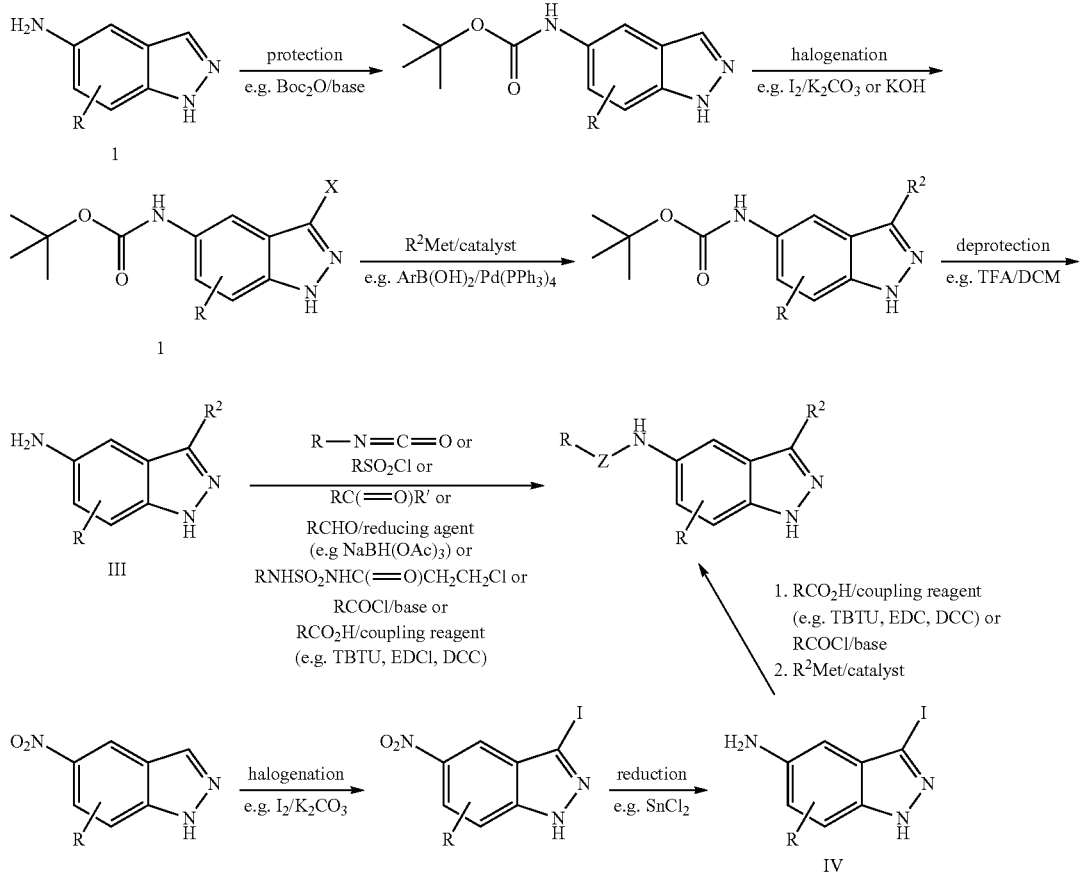

e.g Met = BR$_2$'''', SnR$_3$''''
catalyst = Pd(PPh$_3$)$_4$

Alternatively, compounds described herein, containing trisubstituted indazoles can be prepared as outlined in Scheme 4. 5-Nitro-1H-indazole is halogenated, protected with a suitable indazole protecting group such as tetrahydropyranyl, and subjected to Miyaura-Suzuki cross coupling conditions (e.g. ArBpin/dioxane/H$_2$O/PdCl$_2$(dppf)/Na$_2$CO$_3$). Hydrogenation of the intermediate V yields 1H-indazol-5-amine VI that can be modified in a reaction with electrophilic reagents (e.g. R—NCO, R'R"NH/triphosgene, ROH/triphosgene, RNHSO$_2$NHC(=O)CH$_2$CH$_2$Cl, RSO$_2$Cl, RC(=O)R'/reducing agent, RCOCl or RCO$_2$H/coupling reagent: TBTU, EDC, DCC, HATU, pyBOP, COMU) before a deprotection of the THP group.

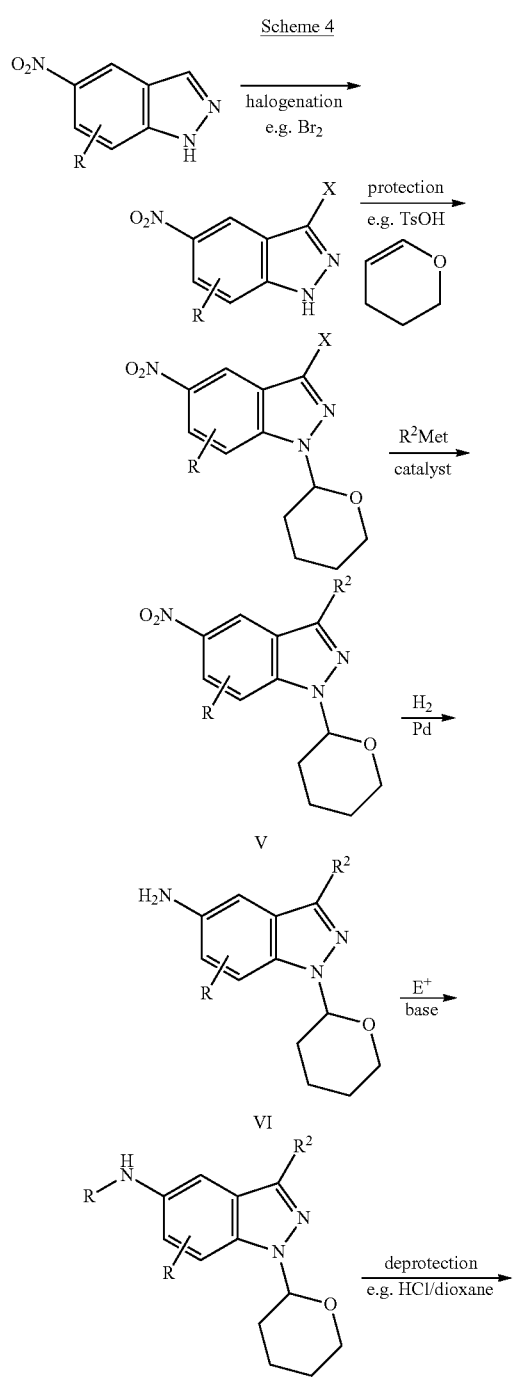

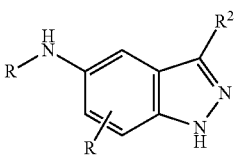

e.g. Met = BR$_2$'''' SnR$_3$'''', ZnX, MgX
catalyst = Pd, Ni

Compounds described herein having an carboxamide group can be synthesized from 3-halo-1H-indazole-5-carboxylic acid in a two-step sequence: amide formation followed by a metal-mediated cross-coupling reaction, as outlined below (Scheme 5).

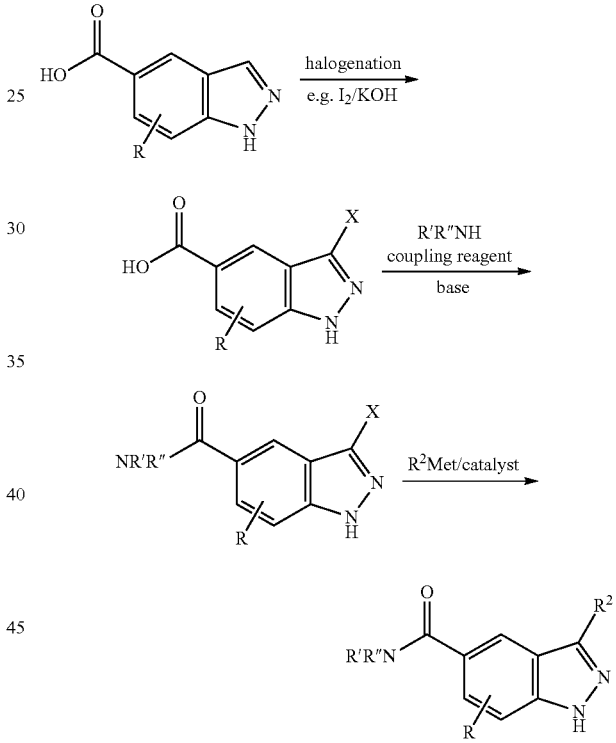

e.g. X = Cl, Br, I
coupling reagent e.g.
DCC, EDC, DIC, HBTU, HATU, HCTU, pyBOP, TBTU
BOP—Cl, SOCl$_2$ or (COCl)$_2$
e.g. Met = BR$_2$'''' SnR$_3$''''
catalyst = Pd/L The intermediate boronic esters VIII described herein can be prepared through a borylation (metal catalyzed borylation or alternatively a metal-halogen exchange reaction followed by a quench with B(OR)$_3$) of suitable arylhalides VII (Scheme 6). Aniline-based arylhalide VIIa can be prepared via Cu(I) catalyzed amination of an appropriately substituted dihalobenzene. Ether-based arylhalide VIIb can be prepared via reaction of an alcohol with an appropriately substituted halofluorobenzene in the presence of base (e.g. NaH).

Scheme 6

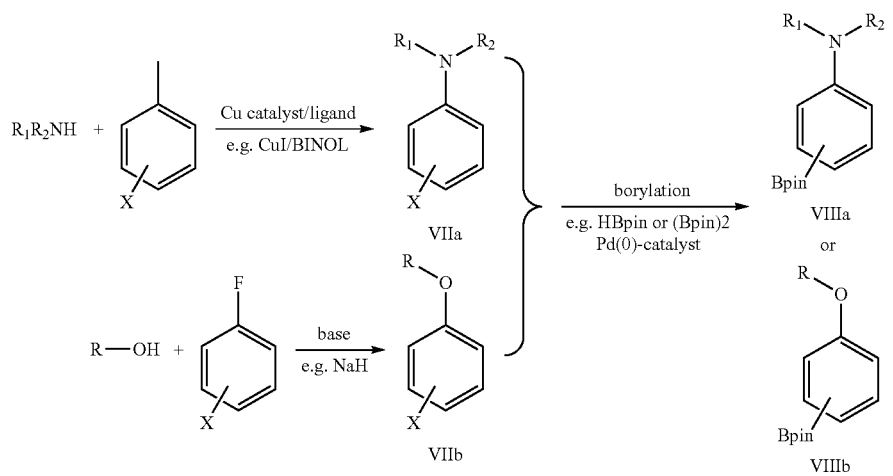

X = Cl, Br, I

Whereas tropine, pseudotropine, nortropine and norpseudotorpine are commercially available, nortropinone and its analogs can be made through an one-pot synthesis using para-haloaniline, 3-oxopentanedioic acid and suitable dialdehydes or their acetals as shown in Scheme 7. In consequence, reductions of thus obtained ketones IX afford the corresponding bicyclic alcohols X.

Scheme 7

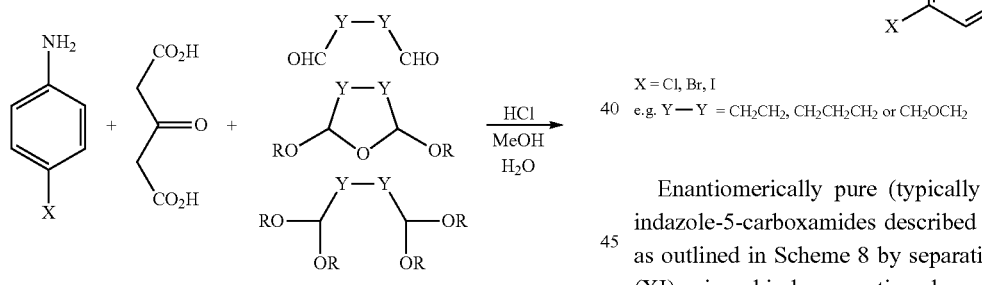

X = Cl, Br, I
e.g. Y—Y = $CH_2CH_2$, $CH_2CH_2CH_2$ or $CH_2OCH_2$

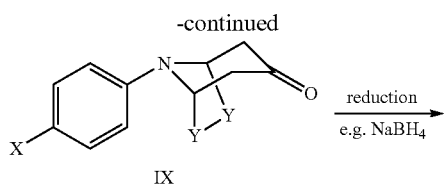

Enantiomerically pure (typically >98% ee) 3-iodo-1H-indazole-5-carboxamides described herein can be prepared as outlined in Scheme 8 by separating racemic compounds (XI) using chiral preparative chromatography.

Scheme 8

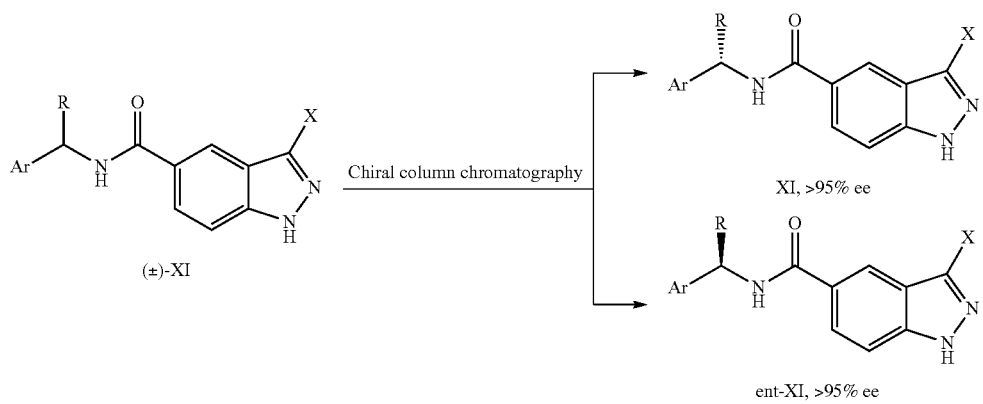

Racemic amines (XII) described herein can be synthesized in three steps as outlined in Scheme 9A. Nucleophilic addition of aldehyde using organometallic reagents such as Grignard, organolithium or organozinc reagents resulted in secondary alcohol XIII. Subsequent oxidation to the corresponding ketone followed by ra eductive amination step resulted in the desired racemic amine (XII). Alternatively, the desired racemic amines described herein can be obtained using a one-pot synthesis through a condensation of an organometalic reagent and an organonitirle as shown in Scheme 9B.

Scheme 9

A.

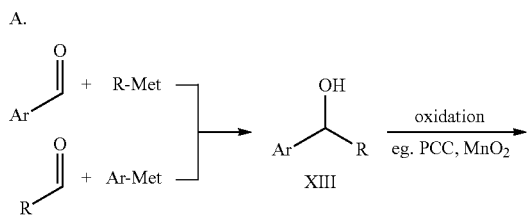

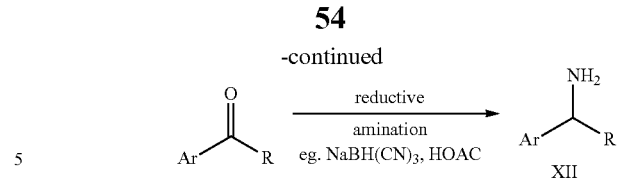

R = aliphatic group
Ar = aromatic group
Met = MgX, Li, ZnX

B.

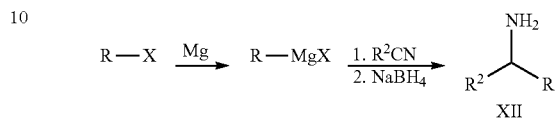

X = halogen

Alternatively, enantiomerically pure 3-iodo-1H-indazole-5-carboxamides can be prepared via an amide coupling using 3-halo-1H-indazole-5-carboxylic acid and enantiomerically pure amines XII. Such enantiomerically pure amine can be obtained by separating racemic amine using chiral preparative chromatography or recrystallization of salts of chiral acids such as, for example tartaric acid, mandelic acid and dibenzoyl-tartaric acid (Scheme 10).

Scheme 10

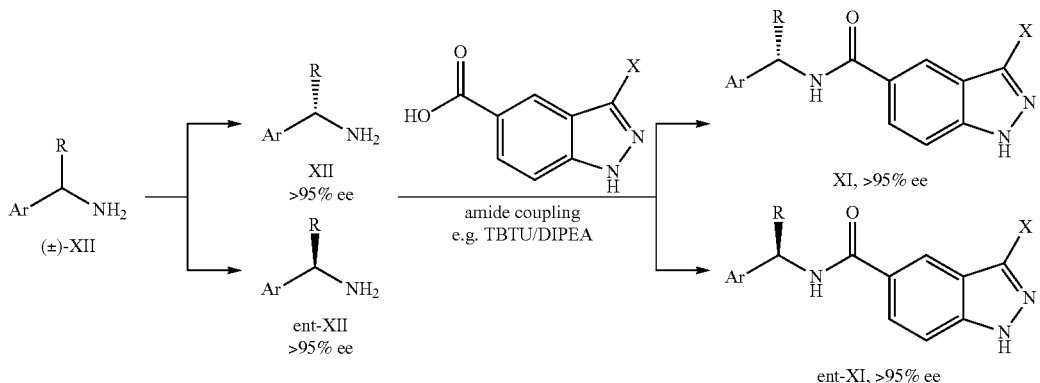

In addition, enantiomerically pure amines described herein can be synthesized using asymmetric nucleophilic addition of carboanions to chiral imines XIV (Scheme 11). In this approach, the desired chiral amine can be synthesized in two ways by switching the role of which fragment acts as a nucleophile and which acts as an electrophile in the addition step. The chiral auxiliary serves as a chiral directing group to provide addition product XV with high diastereoselectivity in general, or can be further enriched using standard purification methods. Removal of the chiral auxiliary affords the desired optically active amine XII. Enantiomeric excess of the amines described herein can be further improved by recrystallization.

Scheme 11

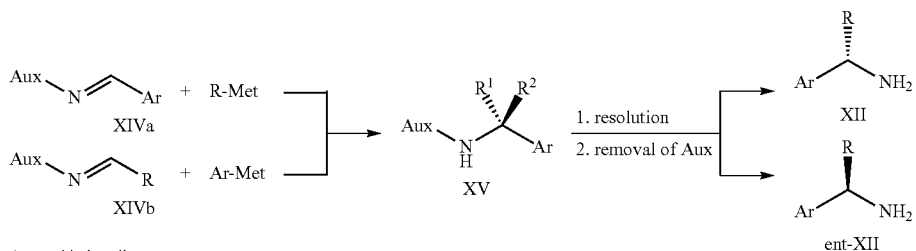

Aux = chiral auxilary
Met = metal, eg. MgX, Li, ZnX, CeX$_2$
X = halogens
R$^1$, R$^2$ = H, R or R, H A variety of chiral auxiliary can be employed in the synthesis of chiral imine XIV (Scheme 12A). A method developed by Ellman involved a condensation of tert-butylsulfinyl amide with aldehydes to provide intermediate XVI (Scheme 12B; ref: Chem. Rev. 2010, 110, 3600). Gringard reagents are added diastereoselectively and the auxiliary is removed under mild acidic conditions. Other examples of chiral auxiliaries that are commonly employed in this approach are 1-amino-2-methoxymethylpyrrolidine (ref: Tetrahedron: Asymmetry 1997, 8, 1895), and phenylglycinol (ref: J. Org. Chem. 1991, 56, 1340)

Scheme 12

A.

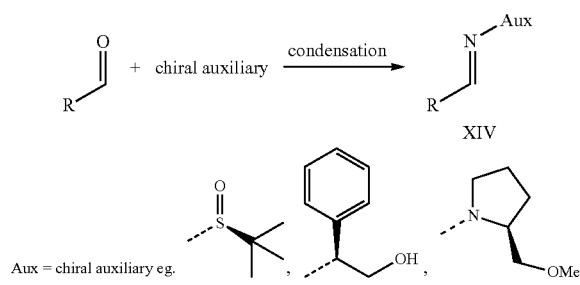

B.

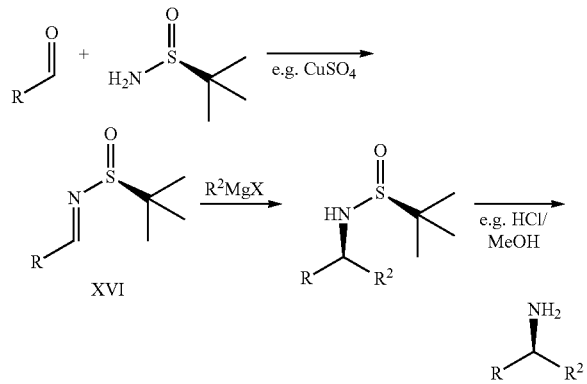

Compounds described herein can be prepared in a manner analogous to the general procedures described above or the detailed procedures described in the examples herein.

The invention is illustrated by the following examples which are not intended to be limiting in any way.

EXEMPLIFICATION

Example A

Synthesis

General Methods

Commercially available starting materials, reagents, and solvents were used as received. In general, anhydrous reactions were performed under an inert atmosphere such as nitrogen or Argon. PoraPak® Rxn CX refers to a commercial cation-exchange resin available from Waters.

Microwave reactions were performed with a Biotage Initiator microwave reactor. Reaction progress was generally monitored by TLC using Merck silica gel plates with visualization by UV at 254 nm, by analytical HPLC or by LCMS (Bruker Exquire 4000). Flash column chromatographic purification of intermediates or final products was performed using 230-400 mesh silica gel 60 from EMD chemicals or Silicycle, or purified using a Biotage Isolera with KP-SIL or HP-SIL silica cartridges, or KP-NH basic modified silica and corresponding samplets. Reverse-phase RPHPLC purification was performed on a Varian PrepStar model SD-1 HPLC system with a Varian Monochrom 10 u C-18 reverse-phase column using a of about 5-30% MeCN or MeOH/0.05% TFA-H$_2$O to 70-90% MeCN or MeOH/0.05% TFA-H$_2$O over a 20-40-min period at a flow rate of 30-50 mL/min. Reverse phase purification was also performed using a Biotage Isolera equipped with a KP-C18-H column using a between 10-95% MeOH/0.1% TFA in H$_2$O. Proton NMRs were recorded on a Bruker 400 MHz spectrometer, and mass spectra were obtained using a Bruker Esquire 4000 spectrometer. Optical rotations were measured at the sodium D-line (589.44 nM) using an AA-55 polarimeter from Optical Activity Ltd with a 2.5×100 mm unjacketed stainless steel tube at given sample concentrations (c, units of g/100 mL).

Compound names were generated using the software built into CambridgeSoft-PerkinElmer's ChemBioDraw Ultra version 11.0 or 12.0.

Abbreviations:
Ac Acetyl
aq aqueous
anh anhydrous
Ar argon
BINOL 1,1'-binaphthalene-2,2'-diol
Boc tert-butoxycarbonyl
BOP-Cl bis(2-oxo-3-oxazolidinyl)phosphinic chloride
br. broad
calcd calculated
COMU (1-cyano-2-ethoxy-2-oxoethylidenaminooxy)dimethylamino-morpholino-carbenium hexafluorophosphate
d doublet (only when used within 1H NMR spectra)
d day
DBTA dibenzoyl-L-tartaric acid monohydrate
DCE 1,2-dichloroethane
DCC N,N'-dicyclohexylcarbodiimide
DCM dichloromethane
DEA diethylamine
de diastereomeric excess
DIPEA diisopropylethylamine
DME 1,2-dimethoxyethane
DMF N,N-dimethylformamide
DMSO dimethylsulfoxide
dppf 1,1'-bis(diphenylphosphino) ferrocene
EDC 1-ethyl-3-(3-dimethylaminopropyl) carbodiimide
e.e. enantiomeric excess
h hour
hal halogen
HATU 2-(1H-7-azabenzotriazol-1-yl)-1,1,3,3-tetramethyluronium hexafluorophosphate
HPLC high performance liquid chromatography
IPA iso-propanol
LC-MS liquid chromatography coupled to mass spectrometry
min minute
m multiplet
MS ESI mass spectra, electrospray ionization
NMR nuclear magnetic resonance
NBS N-Bromosuccinimide
O/N overnight
PCC pyridinium chlorochromate
pin pinacol
prep preparative
PTSA p-toluenesulfonic acid PyBOP (benzotriazol-1-yl-oxytripyrrolidinophosphonium hexafluorophosphate
RBF round bottomed flask
rt room temperature
Rt retention time
s singlet
satd saturated
SMs starting materials
SPE solid phase extraction
S-Phos 2-dicyclohexylphosphino-2',6'-dimethoxybiphenyl
t triplet
TBTU O-(benzotriazol-1-yl)-N,N,N',N'-tetramethyluronium tetrafluoroborate
TEA triethylamine
temp. temperatureTFA trifluoroacetic acid
TLC thin layer chromatography
THF tetrahydrofuran
THP tetrahydropyranyl
TMS trimethylsilyl
Ts tosyl
xs excess
Preparation of Starting Materials
General Method A (Amide Coupling)
A DMF solution of 3-iodo-1H-indazol-5-amine 2,2,2-trifluoroacetate (1.0 equiv), DIPEA (3 equiv) and RCO$_2$H (1.05 equiv) at 0° C. was treated with TBTU (1.05 equiv) added in one portion. The reaction was stirred allowing slowly to warm to rt. After several h or overnight stirring the crude reaction was subsequently diluted with H$_2$O. In the majority of examples a filtration and washing (H$_2$O) of the precipitate provided the desired material with the required purity or alternatively the material was purified directly by prepHPLC or/and flash chromatography.
Alternatively, a DMF solution of 3-iodo-1H-indazole-5-carboxylic acid (1.0 equiv), DIPEA (3.0-5.0 equiv) and RR'NH (1.00-1.05 equiv) at 0° C. or rt was treated with TBTU or BOP-Cl (1.05 equiv) added in one portion. The reaction was stirred allowing slowly to warm to rt. After several h or overnight stirring the crude reaction was subsequently diluted with H$_2$O. In the majority of examples a filtration and washing (H$_2$O) of the precipitate provided the desired material with the required purity or alternatively the material was purified directly by prepHPLC or/and flash chromatography.
General Method B (Iodination)
To a cooled (0° C.) DMF solution indazole (1.0 equiv) and K$_2$CO$_3$ or KOH (~3 equiv) was added I$_2$ (2-4 equiv) in one portion. The reaction was stirred with cooling or rt for several h and then was treated with xs 10% aq NaHSO$_3$ and subsequently diluted with H$_2$O. In the majority of examples a filtration and washing (H$_2$O) of the precipitate provided the desired material with the required purity.
General Method C (Suzuki-Miyaura Cross Coupling)
A mixture of 3-iodo-1H-indazole (1.0 equiv), aryl boronic acid or boronate ester (1.2 equiv), base and palladium catalyst (0.05 equiv e.g. and PdCl$_2$dppf.DCM, Pd(PPh$_3$)$_4$) in solvents was degassed with Ar and heated sealed in a Biotage microwave reactor. The crude material was filtered through Celite using MeOH to rinse the pad. In the majority of examples, purification by RPHPLC provided the target material.
General Method C2 (Suzuki-Miyaura Cross Coupling with PdCl$_2$dppf.DCM-Na$_2$CO$_3$)
Aq Na$_2$CO$_3$ (2 M, 3-4 mmol) was added to a mixture of 5-substituted-3-iodo-1H-indazole (1.0 mmol), aryl boronic acid or boronate ester (1.0-1.4 mmol), and PdCl$_2$dppf.DCM (0.1 mmol) in PhMe:EtOH (1:1, 20 mL) was heated under Ar in a Biotage microwave reactor, an oil bath or a reaction block at temperatures from 100-130° C. The crude material was filtered through Celite using MeOH (alternatively, acetone/MeOH or EtOAc) to rinse the pad or partitioned between EtOAc and H$_2$O followed by drying (Na$_2$SO$_4$ or MgSO$_4$), and evaporated and purified by chromatography.
General Method C3(Suzuki-Miyaura Cross Coupling with Pd(PPh$_3$)$_4$-LiCl—Na$_2$CO$_3$)
Aq Na$_2$CO$_3$ (2 M, 5 mmol) was added to a mixture of 5-substituted-3-iodo-1H-indazole (1.0 mmol), aryl boronic acid or boronate ester (1.0-1.4 mmol), LiCl (3 mmol) and Pd(PPh$_3$)$_4$ (0.1 mmol) in dioxane (12 mL) was heated under Ar in a Biotage microwave reactor, an oil bath or a reaction block at temperatures from 120-130° C. The crude material was filtered through Celite using MeOH or acetone/MeOH to rinse the pad or partitioned between EtOAc and H$_2$O followed by drying (Na$_2$SO$_4$ or MgSO$_4$), evaporated and purified by chromatography.
General Method D (Petasis Reaction)

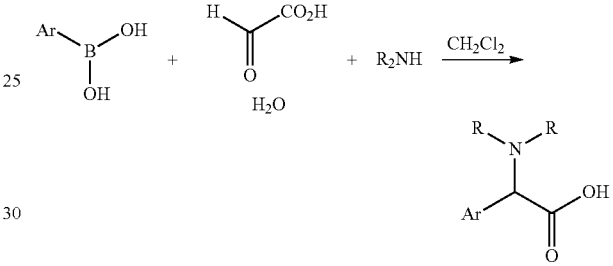

To a mixture of arylboronic acid (1 mmol) and glyoxylic acid monohydrate (1 mmol) in CH$_2$Cl$_2$ (5 mL) was added dialkylamine (1 mmol). The resulting mixture was stirred overnight at rt After evaporation of solvents, it was used crude or purified by column chromatography.
General Method E (Borylation of Aryl Halides): Using B$_2$pin$_2$/Pd
A mixture of aryliodide or arylbromide (1 equiv.), bis(pinacolato)diboron (1.2 to 1.5 equiv.), KOAc (3 equiv.) and DMF or DMSO was purged with Ar for 10 min. 1,1'-PdCl$_2$dppf*CH$_2$Cl$_2$ (3-5 mol %) was added, the vial sealed and heated at 85-100° C. for 2-3 h. The product was partitioned between EtOAc and satd aq NaHCO$_3$ solution, washed with brine, dried over Na$_2$SO$_4$ or MgSO$_4$, filtered, and concentrated to dryness. The crude product was purified by flash chromatography to give the title compound.
General Method F (Boronation of Aryl Halides): Using HBpin/Pd
To a solution of aryliodide or arylbromide (1.0 mmol) in NEt$_3$ (3.0 mmol) and dioxane (1.0 mL) was added under Ar and HBpin (1.5 mmol), S-Phos (0.040 mmol) and Cl$_2$Pd (CH$_3$CN)$_2$ (0.010 mmol) and the reaction heated to 110° C. for 3 h. The mixture was then transferred to a separatory funnel with EtOAc (10 mL) and washed with NaHCO$_3$ (satd) (2×10 mL), H$_2$O (10 mL), and brine (10 mL). The organic layer was dried over MgSO$_4$, filtered and the solvent removed to yield pinacol boronic esters which were used directly for subsequent steps.
General Method G (Reductive Amination)
NaBH$_3$CN (4 mmol) was added to a solution of aryl alkyl ketone (1 mmol) and NH$_4$OAc (12 mmol) in MeOH (4-5 mL) under Ar, and the reaction mixture was heated at 60° C. for 14-24 h. Aq. NaOH (2 M, 15 mL) was added and the product was extracted into Et$_2$O (3×40 mL). The combined Et$_2$O layer was washed with H$_2$O (10 mL) and brine (10 mL), dried (Na$_2$SO$_4$), filtered, concentrated to dryness and used crude or purified by chromatography.

General Method H (Nucleophilic Substitution on 1,4-hal-C$_6$H$_4$—F)

NaH (60% in mineral oil, 1.2 mmol) was added portionwise to a solution of the alcohol (1 mmol) and 1-fluoro-4-iodobenzene (1 mmol) in DMF (1.5 mL) at 0° C. After 15 min, the reaction mixture was allowed to warm to rt, then heated at 80-85° C. for 6-14 h in an oil bath. The mixture was quenched by adding H$_2$O (10 mL) and the product was extracted with EtOAc (30 mL). The organic layer was washed with brine (10 mL), dried (Na$_2$SO$_4$ or MgSO$_4$), concentrated to dryness and purified by chromatography.

General Method I (Copper Catalyzed Amination of Aryl-hal)

A microwave vial was charged with 1,4-diiodobenzene or 1-bromo-4-iodobenzene (1.0 equiv), CuI (20 mol %), BINOL (20 mol %), and K$_3$PO$_4$ (2 equiv.). The vial was capped and then evacuated and backfilled with Ar. Dialkylamine (1.2 equiv) and DMF were then added. The resulting mixture was stirred at rt for 2 to 4 d. The mixture was diluted with EtOAc, filtered through a cake of Celite and the filtrate was concentrated to give the crude product. Crude product was purified by flash chromatography to give the title compound.

General Method J (Urea Formation)

A solution of 3-(4-((1-methylpiperidin-4-yl)oxy)phenyl)-1H-indazol-5-amine bis(2,2,2-trifluoroacetate) (0.073 l mmol), DIPEA (5 mmol), and DMF (70 mL) was cooled to 0° C. and then 1,3-diethyl-2-isocyanatobenzene (2 mmol) was added dropwise. The reaction was stirred for 2 h while warming to rt. A mixture of mono- and di-urea products were obtained which was treated directly with NaOMe (80 uL of a 25% wt solution in MeOH) and the mixture stirred for 15 min and then transferred to a separatory funnel with EtOAc (15 mL). The mixture was then washed with satd aq NaHCO$_3$ (2×10 mL), H$_2$O (1×10 mL), and brine (1×10 mL). The organic layer was dried over MgSO4, filtered, and the solvent removed and the residue was purified by chromatography (prep-HPLC).

General Method K (Reaction of 2-Hydroxyacetophenone and a Ketone)

A mixture of 5-bromo-2-hydroxyacetophenone (1 equiv) and pyrrolidine (1.0 to 1.5 equiv) in MeOH was stirred at 25° C. for 20 min, in a sealed flask. The mixture was then treated with ketone (1.0 to 1.5 equiv) and heated it to 70-115° C. for 16 h. The reaction mixtures was then concentrated in vacuo and the residue purified by flash chromatography to give the desired compound.

General Method L (One-pot Synthesis of Cyclopropylmethanamine Using Arylnitrile)

To a microwave vial charged with Mg powder (2 equiv.) and THF was added bromocyclopropane (2 equiv.). The resulting mixture was stirred for 30 min at rt before a solution of arylnitrile (1 equiv.) in THF was added. It was microwaved 10 min at 100° C., cooled to rt and added dropwise to a cold solution of NaBH$_4$ (2 equiv.) in MeO at 0° C. The resulting mixture was stirred for 15 min at rt, quenched with H$_2$O, extracted with DCM and purified by Biotage SiO$_2$ column (gradient: MeOH/DCM 0-30%) to give the desired product.

General Method M (Synthesis of t-butylsulfinylimines)

Aryl or alkylaldehyde (1.2 eq.) was added to a stirred suspension of (S)-t-butylsulfinylamide (1.0 eq.) and flame-dried CuSO$_4$ (2.2 eq.) in dry CH$_2$Cl$_2$. The resulting mixture was stirred at rt for 69 h. The reaction mixture was filtered through a pad of Celite and the pad was extracted with CH$_2$Cl$_2$. The combined organic extracts were concentrated under reduced pressure yielding the crude product. Purification by repeated flash chromatography (SiO$_2$) using EtOAc-cyclohexane as eluent gave the desired product.

General Method N (Deprotection of Sulfinamides)

A solution of HCl (2.0 M in Et$_2$O, 2.0 eq.) was added carefully to a stirred 0° C. solution of sulfinamide (1.0 eq.) in MeOH. After the addition was complete the cooling bath was removed and the mixture was stirred at rt for 1 h. The reaction mixture was concentrated under reduced pressure and Et$_2$O was added and a white precipitation formed. The precipitation was filtered off and washed with Et$_2$O and dried under reduced pressure yielding the crude product.

Intermediates

Synthesis of 4-(4-iodophenoxy)-1-methylpiperidine

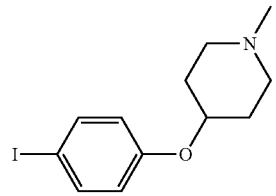

A solution of 1-methylpiperidin-4-ol (20.01 g, 174 mmol) in DMF (30 mL) was added via pipette to a cold (ice-bath) flask containing NaH (60% in mineral oil, 8.11 g, 203 mmol) suspended in DMF (100 mL) under Ar, and additional DMF (3×10 mL) was used to rinse the vial and pipette. After the mixture was stirred in ice bath for 30 min, 1-fluoro-4-iodobenzene (20.0 mL, 174 mmol) was added to the mixture and the reaction mixture was allowed to stir at rt for 30 min, then placed in an 85° C. oil bath. After a few min, due to excessive foaming, the flask was removed from the oil bath and allowed to stir at rt for 10 min. This was repeated 3 times until no longer foaming excessively on introduction to the oil bath, then the reaction flask was heated at 85° C. in oil bath for 24 h. After cooling to rt, H$_2$O (50 mL) was added dropwise at first, then rapidly when little gas evolution occurred. The reaction mass was then poured into H$_2$O (450 mL) and the resulting aq. suspension was cooled in ice bath, then the precipitate was collected by vacuum filtration, rinsing with H$_2$O (2×50 mL). The resulting solid was dissolved in MeOH and the solvent was removed in vacuo, then EtOH was added and the solution was evaporated in vacuo to yield the title compound as a tan solid (36.9 g, 67%). $^1$H NMR (400 MHz, CDCl$_3$) δ ppm 7.55 (d, J=8.9 Hz, 2 H), 6.69 (d, J=8.9 Hz, 2 H), 4.24-4.32 (m, 1 H), 2.68 (br. s., 2 H), 2.31 (s, 3 H), 2.23-2.29 (m, 2 H), 1.94-2.03 (m, 2 H), 1.78-1.88 (m, 2 H).

Synthesis of 1-methyl-4-(4-(4,4,5,5-tetramethyl-1,3,2-dioxaborolan-2-yl)phenoxy)piperidine

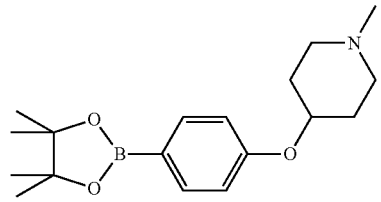

The title compound was prepared in a manner similar to General Method F using 4-(4-iodophenoxy)-1-methylpiperidine (9.5794 g, 30.2 mmol) with S-Phos (378.8 mg, 0.92 mmol) and Cl$_2$Pd(CH$_3$CN)$_2$ (59.8 mg, 0.23 mmol) at 110° C. for 6.5 h. MeOH (2 mL) was slowly added to quench excess borane, followed by DCM (200 mL) and NaHCO$_3$ (50 mL). After vacuum filtration through a pad of Celite and rinsing with DCM (150 mL) and NaHCO$_3$ (50 mL), the layers were separated and the aq. layer was extracted with DCM (100 mL). The combined DCM layers were washed with H$_2$O (50 mL), and brine (50 mL), and dried (Na$_2$SO$_4$), filtered and the solvent removed to yield the crude product. Purification by flash chromatography (SiO$_2$, 0-15% MeOH/DCM) gave 1-methyl-4-(4-(4,4,5,5-tetramethyl-1,3,2-dioxaborolan-2-yl)phenoxy)piperidine (white solid, 7.79 g, 90% pure, 73%). $^1$H NMR (400 MHz, CDCl$_3$) δ ppm 7.79 (d, J=8.3 Hz, 2 H), 6.90 (d, J=8.5 Hz, 2 H), 4.81 (br. s., 1 H), 3.42 (d, J=12.0 Hz, 1 H), 3.23 (t, J=12.0 Hz, 2 H), 2.79 (s, 3 H), 2.72 (t, J=14.3 Hz, 2 H), 2.25 (d, J=14.3 Hz, 2 H), 1.34 (s, 12 H). MS ESI 318.1 [M+H]$^+$, calcd for [C$_{18}$H$_{28}$BNO$_3$+H]$^+$ 318.22.

Synthesis of 4-(4-bromophenoxy)-1-(2-methoxyethyl)piperidine

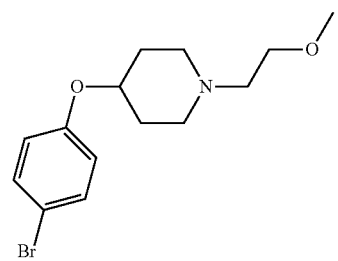 [SMILES: COCCN1CCC(Oc2ccc(Br)cc2)CC1]

A mixture or 4-(4-bromophenoxy)piperidine hydrochloride (1.5 g, 5.13 mmol), 1-bromo-2-methoxyethane (0.48 mL, 5.13 mmol), K$_2$CO$_3$ (2.13 g, 15.4 mmol) and DMF (15 mL) was heated to 40° C. and stirred for 18 h at which time the mixture was transferred to a separatory funnel with EtOAc (250 mL) and the organic layer washed with satd aq NaHCO$_3$ (1×100 mL) and brine (1×100 mL). The organic layer was dried over MgSO$_4$, filtered and the solvent removed to give the alkylated material which was used for the next step.

Synthesis of 1-(2-methoxyethyl)-4-(4-(4,4,5,5-tetramethyl-1,3,2-dioxaborolan-2-yl)phenoxy)piperidine

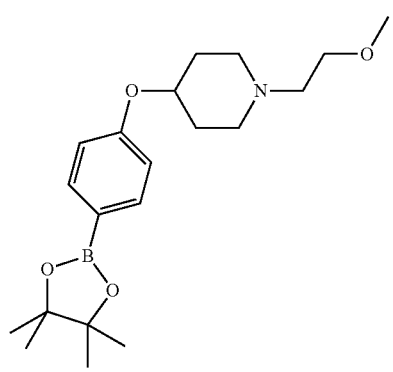

To a solution of 4-(4-bromophenoxy)-1-(2-methoxyethyl) piperidine (5.13 mmol from step A), NEt$_3$ (2.1 mL, 15.4 mmol), and dioxane (15 mL) under Ar was added HBpin (1.1 mL, 7.70 mmol), SPhos (86 mg, 0.210 mmol), and PdCl$_2$(CH$_3$CN)$_2$ (13 mg, 0.051 mmol) and the reaction heated to 110° C. for 2 h. The mixture was then transferred to a separatory funnel with EtOAc (100 mL) and washed successively with satd aq NaHCO$_3$ (2×50 mL), H$_2$O (2×50 mL), and brine (1×50 mL). The organic layer was dried over MgSO$_4$, filtered, and the solvent removed to give the product as a yellow oil. $^1$H NMR (400 MHz, CDCl$_3$) δ ppm 7.72 (d, J=8.4 Hz, 2H), 6.88 (d, J=8.4 Hz, 2H), 4.41-4.36 (m, 1H), 3.51 (t, J=5.6 Hz, 2H), 3.36 (s, 3H), 2.77-2.74 (m, 2H), 2.59 (t, J=5.6 Hz, 2H), 2.36-2.33 (m, 2H), 2.03-1.98 (m, 2H), 1.88-1.81 (m, 2H), 1.32 (s, 12H); MS ESI 362.1 [M+H]$^+$, calcd for [C$_{20}$H$_{32}$BNO$_4$+H]$^+$ 362.25.

Synthesis of tert-butyl 4-(4-(4,4,5,5-tetramethyl-1,3,2-dioxaborolan-2-yl)phenoxy)piperidine-1-carboxylate

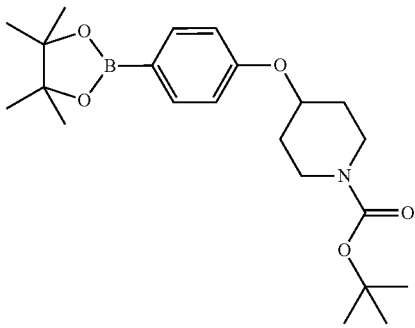 [SMILES: CC(C)(C)OC(=O)N1CCC(Oc2ccc(B3OC(C)(C)C(C)(C)O3)cc2)CC1]

Using General Method E with 3% catalyst in DMSO, tert-butyl 4-(4-iodophenoxy)piperidine-1-carboxylate (258.6 g, 96% pure, 0.61 mmol) gave the title compound (152.7 mg, 61%) after aq. work-up and purification by flash chromatography (SiO$_2$, 5-25% EtOAc in hexane). $^1$H NMR (400 MHz, CDCl$_3$) δ ppm 7.75 (d, J=8.8 Hz, 2 H), 6.91 (d, J=8.5 Hz, 2 H), 4.55 (tt, J=7.0, 3.4 Hz, 1 H), 3.69 (ddd, J=12.9, 8.2, 4.1 Hz, 2 H), 3.36 (ddd, J=13.0, 8.1, 4.3 Hz, 2 H), 1.92 (br. s., 2 H), 1.77 (br. s., 2 H), 1.34 (s, 12 H). In a separate experiment, using General Method E in DMF, tert-butyl 4-(4-iodophenoxy)piperidine-1-carboxylate gave the title compound as a white solid (112 mg, 28% yield). $^1$H NMR was identical to the previous sample; MS ESI [M−C$_4$H$_9$+H]$^+$ 348.1, calcd for [C$_{18}$H$_{26}$BNO$_5$+H]$^+$ 348.20.

Synthesis of 4-(4-bromophenoxy)-1-isopropylpiperidine

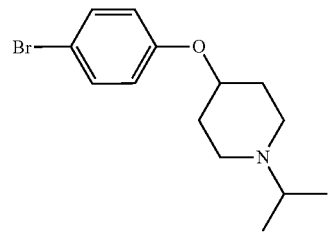 [SMILES: CC(C)N1CCC(Oc2ccc(Br)cc2)CC1]

AcOH (1 drop) was added to a mixture of acetone (0.12 mL, 1.65 mmol), NaBH(OAc)$_3$ (161.5 mg, 0.76 mmol) and 4-(4-bromophenoxy)piperidine (97 mg, 0.38 mmol) in THF (1 mL) and DCE (2 mL), and the mixture was stirred at rt under Ar for 20 h, when second portions of AcOH (1 drop), acetone (0.12 mL, 1.65 mmol) and NaBH(OAc)$_3$ (161.5 mg, 0.76 mmol) were added and the mixture was heated at 40° C. for 24 h. The mixture was partitioned between EtOAc (150 mL) and half satd aq NaHCO$_3$ (25 mL). The organic layer was washed with H$_2$O (25 mL) and brine (25 mL), dried, filtered and concentrated to dryness. Purification by flash chromatography (SiO$_2$, 2-5% 2 M NH$_3$-MeOH/DCM) gave the title compound (white solid, 80.4 mg, 71% yield). $^1$H NMR (400 MHz, CDCl$_3$) δ ppm 7.37 (d, J=9.0 Hz, 6 H), 6.80 (d, J=9.0 Hz, 6 H), 4.27 (br. s., 1 H), 2.74-2.84 (m, 3 H), 2.35-2.47 (m, 2 H), 2.01 (br. s., 2 H), 1.76-1.87 (m, 2 H), 1.08 (d, J=6.5 Hz, 6 H). MS ESI 298.0 [M+H]$^+$, calcd for [C$_{14}$H$_{20}$BrNO+H]$^+$ 298.08.

Synthesis of 1-isopropyl-4-(4-(4,4,5,5-tetramethyl-1,3,2-dioxaborolan-2-yl)phenoxy)piperidine

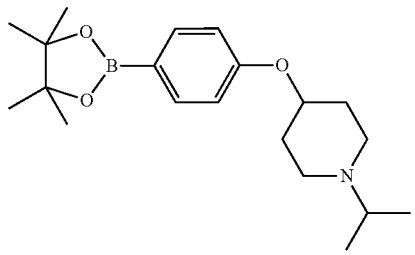 [SMILES: CC(C)N1CCC(Oc2ccc(B3OC(C)(C)C(C)(C)O3)cc2)CC1]

Using General Method E with 3.4% catalyst in DMSO, 4-(4-bromophenoxy)-1-isopropylpiperidine (80 mg, 0.27 mmol) gave the title compound (47.5 mg, 77% pure, 40% yield) after aq. work-up with EtOAc and purification by flash chromatography (SiO$_2$, 2-20% MeOH in DCM). $^1$H NMR (400 MHz, CDCl$_3$) δ ppm 7.74 (d, J=8.5 Hz, 2 H), 6.90 (d, J=8.5 Hz, 2 H), 4.40 (br. s., 1 H), 2.80 (d, J=4.0 Hz, 3 H), 2.45 (m, J=7.8 Hz, 2 H), 2.04 (br. s., 2 H), 1.85 (d, J=8.5 Hz, 2 H), 1.34 (s, 12 H), 1.09 (d, J=6.3 Hz, 6 H). MS ESI 346.2 [M+H]$^+$, calcd for [C$_{20}$H$_{32}$BNO$_3$+H]$^+$ 346.26.

Synthesis of tert-butyl 4-(2-chloro-4-(4,4,5,5-tetramethyl-1,3,2-dioxaborolan-2-yl)phenoxy)piperidine-1-carboxylate

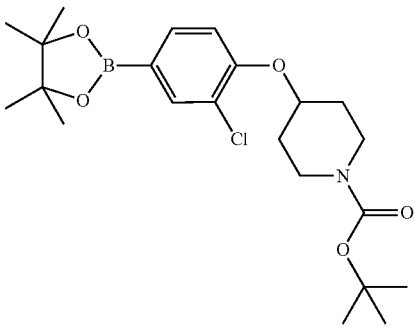 [SMILES: CC(C)(C)OC(=O)N1CCC(Oc2ccc(B3OC(C)(C)C(C)(C)O3)cc2Cl)CC1]

DIAD (0.24 mL, 1.22 mmol) was added drop-wise to a solution of PPh$_3$ (308.9 mg, 1.18 mmol), 2-chloro-4-(4,4,5,5-tetramethyl-1,3,2-dioxaborolan-2-yl)phenol (199.8 mg, 0.785 mmol) and tert-butyl 4-hydroxypiperidine-1-carboxylate (236.7 mg, 1.18 mmol) in DCM (5 mL) under Ar and the reaction was stirred at rt for 14 d. Purification on the Biotage without work-up or evaporation (SiO$_2$, 0-100% EtOAc in DCM) gave the title compound (244.8 mg, 90% pure, 64%). $^1$H NMR (400 MHz, CDCl$_3$) δ ppm 7.82 (d, J=1.5 Hz, 1 H), 7.63 (dd, J=8.2, 1.6 Hz, 1 H), 6.93 (d, J=8.3 Hz, 1 H), 4.59-4.65 (m, 1 H), 3.63 (ddd, J=13.2, 8.4, 4.3 Hz, 2 H), 3.42-3.54 (m, 2 H), 1.78-1.95 (m, 4 H), 1.47 (s, 9 H), 1.33 (s, 12 H).

Synthesis of 4-(2-chloro-4-(4,4,5,5-tetramethyl-1,3,2-dioxaborolan-2-yl)phenoxy)-1-methylpiperidine

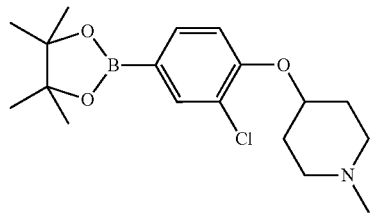

DIAD (0.48 mL, 2.4 mmol) was added drop-wise to a solution of PPh$_3$ (610 mg, 2.3 mmol), 2-chloro-4-(4,4,5,5-tetramethyl-1,3,2-dioxaborolan-2-yl)phenol (296 mg, 1.2 mmol) and 1-methylpiperidin-4-ol (270 mg, 2.3 mmol) in DCM (14 mL) under Ar and the reaction was stirred at rt for 4 d. Evaporation and purification on the Biotage (SiO$_2$, 5-30% MeOH in DCM) gave the title compound (403 mg, 80% pure, 79%). $^1$H NMR (400 MHz, CDCl$_3$) δ ppm 7.83 (d, J=1.5 Hz, 1 H), 7.64 (dd, J=8.3, 1.5 Hz, 1 H), 6.93 (d, J=8.3 Hz, 1 H), 4.53 (br. s., 1 H), 2.68-2.81 (m, 2 H), 2.39 (m+s, 5 H), 2.02-2.15 (m, 2 H), 1.94-2.02 (m, 2 H), 1.33 (s, 12 H)

Synthesis of 4-(4-bromo-2-methoxyphenoxy)piperidine

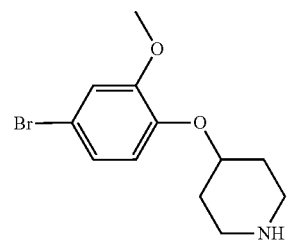 [SMILES: COc1cc(Br)ccc1OC1CCNCC1]

tert-Butyl 4-(4-bromo-2-methoxyphenoxy)piperidine-1-carboxylate (400 mg, 1.04 mmol) was dissolved in DCM (10 mL), and cooled to 0° C. TFA (3 mL) was added and the mixture was allowed to slowly warm to RT. After 1 h, solvent was removed under reduced pressure and dissolved in EtOAc (10 mL). The reaction was washed with NaHCO$_3$ (15 mL) and brine (15 mL), and dried with MgSO$_4$. Solvent was removed under reduced pressure to give the title compound (yellow oil, 287 mg, 96%). $^1$H NMR (400 MHz, CDCl$_3$) δ ppm 6.98-7.04 (m, 2 H), 6.80 (d, J=9.3 Hz, 1 H), 4.41-4.48 (br. m, 1 H), 3.84 (s, 3 H), 3.28-3.39 (m, 2 H), 2.97-3.07 (m, 2 H), 2.06-2.17 (m, 2 H), 1.97 (m, J=3.5 Hz, 2 H); MS ESI 285.9, 287.9 [M+H]$^+$, calcd for [C$_{12}$H$_{16}$BrNO$_2$+H]$^+$ 286.0, 288.0.

Synthesis of 4-(4-bromo-2-methoxyphenoxy)-1-methylpiperidine

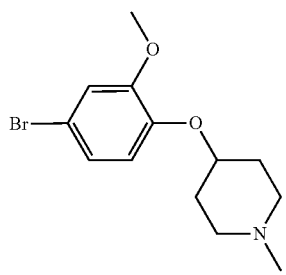 [SMILES: COc1cc(Br)ccc1OC1CCN(C)CC1]

In a microwave vial 4-(4-bromo-2-methoxyphenoxy)piperidine (430 mg, 1.5 mmol) was combined with formic acid (4.5 mL) and formalin (0.5 mL). The reaction was heated at 150° C. in the microwave reactor for 5 min. The mixture was concentrated under reduced pressure and partitioned between 0.5 M NaOH (20 mL) and EtOAc (10 mL). Reaction was washed with brine and dried with $MgSO_4$. Removal of solvent under reduced pressure gave the title compound (clear oil, 412 mg, 92%). $^1$H NMR (400 MHz, $CDCl_3$) δ ppm 6.98-7.03 (m, 2 H), 6.80 (d, J=9.0 Hz, 1 H), 4.27 (br. s, 1 H), 3.84 (s, 3 H), 2.77-2.89 (br. m, 2 H), 2.35-2.48 (br. m, 5 H), 2.00-2.10 (br. m, 2 H), 1.86-1.97 (br. m, 2 H); MS ESI 300.0, 302.0 [M+H]$^+$, calcd for $[C_{13}H_{18}BrNO_2+H]^+$ 300.1, 302.2.

Synthesis of 4-(2-methoxy-4-(4,4,5,5-tetramethyl-1,3,2-dioxaborolan-2-yl)phenoxy)-1-methylpiperidine

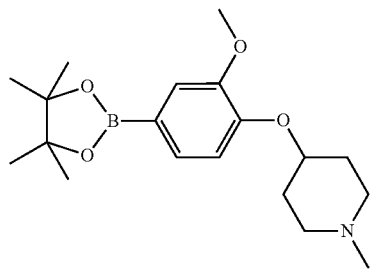

The title compound was synthesized according to the General Method E utilizing 4-(4-bromo-2-methoxyphenoxy)-1-methylpiperidine (400 mg, 1.33 mmol), bis(pinacolato)diboron (509 mg, 2 mmol), $PdCl_2$dppf (68 mg, 0.084 mmol), KOAc (655 mg, 6.68 mmol), and DMF (10 mL). The mixture was charged with Ar and heated at 100° C. in the microwave reactor for 2 h. Purification by RP column chromatography (Biotage $C_{18}$, 60 g, 90:10-10:90% 0.1% TFA-$H_2O$:MeOH) gave the title compound (off-white solid, 145 mg, 31%). $^1$H NMR (400 MHz, $CD_3OD$) δ ppm 7.27-7.34 (m, 2 H), 6.99 (d, J=8.3 Hz, 1 H), 4.46 (br. s, 1 H), 3.84 (s, 3 H), 2.86-2.95 (br. m, 2 H), 2.50-2.62 (br. m, 2 H), 2.43 (s, 3 H), 1.97-2.07 (br. m, 2 H), 1.82-1.93 (br. m, 2 H), 1.33 (s, 12 H); MS ESI 348.2 [M+H]$^+$, calcd for $[C_{19}H_{30}BNO_4+H]^+$ 348.2.

Synthesis of 4-(4-bromo-2-methoxyphenoxy)-1-(oxetan-3-yl)piperidine

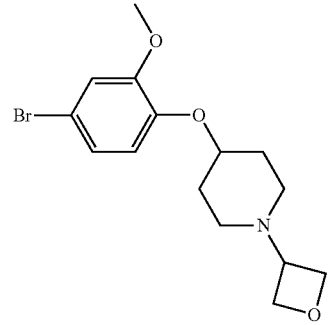 [SMILES: COc1cc(Br)ccc1OC1CCN(C2COC2)CC1]

The title compound was synthesized according to the General Method G, utilizing 4-(4-bromo-2-methoxyphenoxy)piperidine (287 mg, 1 mmol), oxetan-3-one (86 mg, 1.2 mmol), $NaBH(OAc)_3$ (318 mg, 1.5 mmol), DCE (10 mL), and 4 drops of acetic acid. Purification by flash chromatography ($SiO_2$, Biotage 25 g, 0-20% MeOH in $CH_2Cl_2$) gave the title compound (off-white solid, 230 mg, 67%). $^1$H NMR (400 MHz, $CDCl_3$) δ ppm 6.96-7.02 (m, 2 H), 6.79 (d, J=8.5 Hz, 1 H), 4.58-4.69 (m, 3 H), 4.20-4.30 (m, 1 H), 3.84 (s, 3 H), 3.45-3.54 (m, 2 H), 2.54-2.64 (m, 2 H), 2.07-2.20 (m, 2 H), 1.93-2.03 (m, 2 H), 1.80-1.93 (m, 2 H); MS ESI 342.2, 344.0 [M+H]$^+$% calcd for $[C_{15}H_{20}BrNO_3+H]^+$ 342.1, 344.1.

Synthesis of 4-(2-methoxy-4-(4,4,5,5-tetramethyl-1,3,2-dioxaborolan-2-yl)phenoxy)-1-(oxetan-3-yl)piperidine

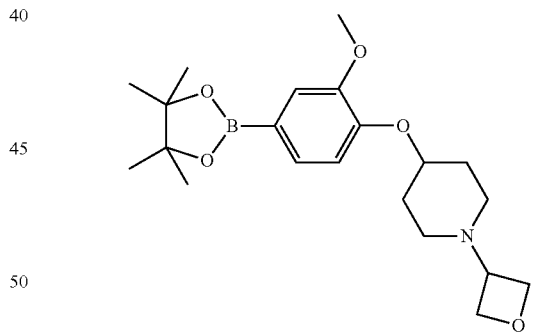

The title compound was synthesized according to the General Method E, utilizing 4-(4-bromo-2-methoxyphenoxy)-1-(oxetan-3-yl)piperidine (220 mg, 0.54 mmol), $B_2pin_2$ (195 mg, 0.77 mmol), KOAc (188 mg, 1.92 mmol), $PdCl_2$ddpf (26 mg, 0.032 mmol) and DMF. The mixture was heated in the microwave reactor for 2 h at 85° C. Purification by flash chromatography ($SiO_2$, Biotage 25 g, 0-25% MeOH in $CH_2Cl_2$) gave the title compound (brown oil, 95 mg, 38%). $^1$H NMR (400 MHz, $CD_3OD$) δ ppm 7.28-7.34 (m, 2 H), 6.97 (d, J=8.0 Hz, 1 H), 4.69 (t, J=6.8 Hz, 2 H), 4.60 (t, J=6.3 Hz, 2 H), 4.39-4.48 (m, 1 H), 3.83 (s, 3 H), 3.48-3.55 (m, 1 H), 2.56-2.67 (m, 2 H), 2.16-2.26 (m, 2 H), 1.94-2.04 (m, 2 H), 1.76-1.89 (m, 2 H), 1.33 (s, 12 H); MS ESI 390.1 [M+H]$^+$, calcd for $[C_{21}H_{32}BNO_5+H]^+$ 390.2.

Synthesis of 4-(4-bromo-2-methoxyphenoxy)piperidine-1-carbaldehyde

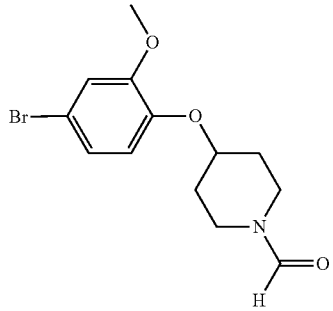 [SMILES: COc1cc(Br)ccc1OC1CCN(C=O)CC1]

The title compound was synthesized according to the General Method A utilizing 4-(4-bromo-2-methoxyphenoxy)piperidine (400 mg, 1.39 mmol), formic acid (64 mg, 1.39 mmol), TBTU (446 mg, 1.39 mmol), DIPEA (0.73 mL, 4.18 mmol), and DMF (4 mL) to gave the title compound (yellow solid, 372 mg, 85%). $^1$H NMR (400 MHz, CD$_3$OD) δ ppm 8.02 (s, 1 H), 7.12 (d, J=2.3 Hz, 1 H), 7.02 (dd, J=8.5, 2.3 Hz, 1 H), 6.94 (d, J=8.5 Hz, 1 H), 4.52-4.59 (m, 1 H), 3.83 (s, 3 H), 3.65-3.77 (m, 2 H), 3.45-3.53 (m, 1 H), 3.34-3.41 (m, 1 H), 1.68-1.99 (m, 4 H); MS ESI 314.2, 316.0 [M+H]$^+$, calcd for [C$_{13}$H$_{16}$BrNO$_3$+H]$^+$ 314.0, 316.0.

Synthesis of 4-(2-methoxy-4-(4,4,5,5-tetramethyl-1,3,2-dioxaborolan-2-yl)phenoxy)piperidine-1-carbaldehyde

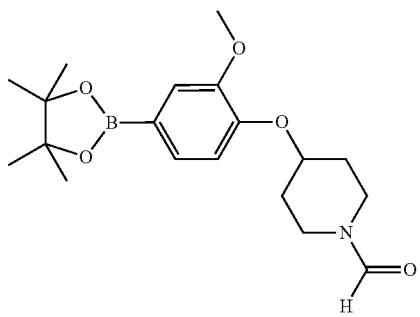 [SMILES: COc1cc(B2OC(C)(C)C(C)(C)O2)ccc1OC1CCN(C=O)CC1]

The title compound was synthesized according to the General Method E, utilizing 4-(4-bromo-2-methoxyphenoxy)piperidine-1-carbaldehyde (370 mg, 1.17 mmol), bis(pinacolato)diboron (356 mg, 1.40 mmol), KOAc (344 mg, 3.51 mmol), PdCl$_2$ddpf (48 mg, 0.06 mmol) and DMF (10 mL). The mixture was heated in the microwave reactor for 2 h at 85° C. Purification by flash chromatography (SiO$_2$, Biotage 25 g, 0-15% MeOH in CH$_2$Cl$_2$) gave the title compound (brown oil, 266 mg, 82%). $^1$H NMR (400 MHz, CD$_3$OD) δ ppm 8.02 (s, 1 H), 7.29-7.35 (m, 2 H), 7.03 (d, J=8.3 Hz, 1 H), 4.63-4.71 (m, 1 H), 3.84 (s, 3 H), 3.65-3.79 (m, 2 H), 3.45-3.54 (m, 1 H), 3.35-3.43 (m, 1 H), 1.86-2.02 (m, 2 H), 1.70-1.86 (m, 2 H), 1.34 (s, 12 H); MS ESI 362.3 [M+H]$^+$, calcd for [C$_{19}$H$_{28}$BNO$_5$+H]$^+$ 362.2.

Synthesis of 4-(4-bromophenoxy)piperidine-1-carbaldehyde

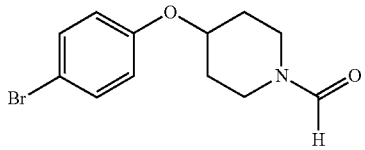 [SMILES: O=CN1CCC(Oc2ccc(Br)cc2)CC1]

The title compound was synthesized according to General Method A utilizing 4-(4-bromophenoxy)piperidine HCl salt and formic acid and obtained as a yellow solid (885 mg, 91% yield). $^1$H NMR (400 MHz, CDCl$_3$) δ ppm 8.07 (s, 1 H), 7.58 (d, J=8.78 Hz, 2 H), 6.71 (d, J=9.03 Hz, 2 H), 4.54-4.61 (m, 1 H), 3.56-3.68 (m, 3 H), 3.29-3.40 (m, 1 H), 1.76-1.98 (m, 4 H); MS ESI [M+H]$^+$ 284.0, calcd for [C$_{12}$H$_{14}$BrNO$_2$+H]$^+$ 284.03.

Synthesis of 4-(4-(4,4,5,5-tetramethyl-1,3,2-dioxaborolan-2-yl)phenoxy)piperidine-1-carbaldehyde

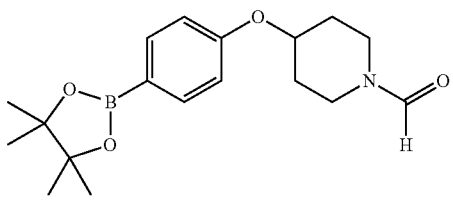 [SMILES: CC1(C)OB(c2ccc(OC3CCN(C=O)CC3)cc2)OC1(C)C]

A microwave oven vial was charged with 4-(4-bromophenoxy)piperidine-1-carbaldehyde (480 mg, 1.68 mmols), bis(pinacolato)diboron (513 mg, 2.02 mmols), KOAc (495 mg, 5.05 mmols) and DMF (8 mL). The mixture was purged with Ar for 2 min, then PdCl$_2$(dppf).DCM (69 mg, 0.05 mmol) was added and the vial was sealed. The resulting mixture was stirred at 85° C. for 2 h with microwave irradiation and then was filtered through Celite. The filtrate was concentrated under reduced pressure. The residue was purified by flash chromatography (EtOAc/hexanes 0% to 100%) to give the title compound as a light yellow solid (473 mg, 85%). $^1$H NMR (400 MHz, CDCl$_3$) δ ppm 8.06 (s, 1 H), 7.77 (d, J=8.5 Hz, 2 H), 6.88-6.94 (d, J=8.5 Hz, 2 H) 4.65-4.72 (m, 1 H), 3.55-3.69 (m, 3 H), 3.29-3.39 (m, 1 H), 1.90 (m, 4 H), 1.34 (s, 12 H); MS ESI [M-C$_4$H$_9$+H]$^+$ 332.3, calcd for [C$_{18}$H$_{26}$BNO$_4$+H]$^+$ 332.20.

Synthesis of 1-(2-fluoroethyl)-4-(4-iodophenoxy)piperidine

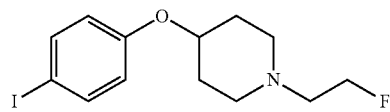 [SMILES: FCCN1CCC(Oc2ccc(I)cc2)CC1]

To the solution of 1-(2-fluoroethyl)piperidin-4-ol (500 mg, 3.4 mmols), 1-fluoro-4-iodobenzene (0.39 mL, 3.4 mmols) in anh DMF (6 mL) was added 60% NaH (272 mg, 6.8 mmols) in portions at rt. The resulting reaction mixture was stirred at 85° C. for 3 d under Ar. After cooled down to rt, the mixture was poured into ice/H₂O (5 mL/mmol) and stirred for 10 min before filtration to give the title compound as a light yellow solid (746 mg, 63% yield). $^1$H NMR (400 MHz, CDCl₃) δ ppm 7.50-7.59 (m, 2 H), 6.65-6.73 (m, 2 H), 4.65 (t, J=5.0 Hz, 1 H), 4.49-4.56 (m, 1 H), 4.26-4.35 (m, 1 H), 2.74-2.84 (m, 2 H), 2.70 (t, J=5.0 Hz, 1 H), 2.43 (t, J=8.3 Hz, 2 H), 1.95-2.05 (m, 2 H), 1.79-1.90 (m, 2 H), 0.88 (d, J=11.0 Hz, 1 H); MS ESI [M+H]⁺ 350.0, calcd for [C₁₉H₂₉BFNO₃+H]⁺ 350.04.

Synthesis of 1-(2-fluoroethyl)-4-(4-(4,4,5,5-tetramethyl-1,3,2-dioxaborolan-2-yl)phenoxy)piperidine

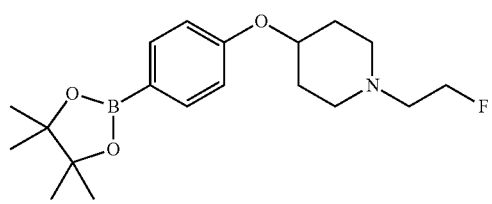 [SMILES: CC1(C)OB(c2ccc(OC3CCN(CCF)CC3)cc2)OC1(C)C]

The title compound was synthesized according to General Method E utilizing 1-(2-fluoroethyl)-4-(4-iodophenoxy)piperidine and obtained as a yellow solid (33 mg, 30% yield). $^1$H NMR (400 MHz, CDCl₃) δ ppm 7.75 (d, J=8.5 Hz, 2 H), 6.90 (d, J=8.5 Hz, 2 H), 4.73 (t, J=4.8 Hz, 1 H), 4.61 (t, J=4.8 Hz, 1 H), 4.43-4.52 (m, 1 H), 2.84-2.91 (m, 3 H), 2.77-2.83 (m, 1 H), 2.55-2.67 (m, 2 H), 2.07-2.18 (m, 2 H), 1.86-1.99 (m, 2 H), 1.34 (s, 12 H); MS ESI [M+H]⁺ 350.1, calcd for [C₁₉H₂₉BFNO₃+H]⁺ 350.23.

Synthesis of 2-(dimethylamino)-1-(4-(4-iodophenoxy)piperidin-1-yl)ethanone

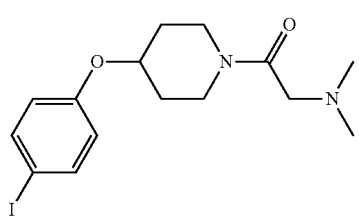 [SMILES: CN(C)CC(=O)N1CCC(Oc2ccc(I)cc2)CC1]

The title compound was synthesized according to the General Method A utilizing 4-(4-iodophenoxy)piperidine HCl salt and 2-(dimethylamino)acetic acid and obtained as a yellow solid (739 mg, 95% yield). $^1$H NMR (400 MHz, CDCl₃) δ ppm 7.52-7.60 (m, 2 H), 6.66-6.73 (m, 2 H), 4.50 (tt, J=6.6, 3.5 Hz, 1 H), 3.79 (dd, J=8.8, 4.0 Hz, 2 H), 3.57-3.66 (m, 1 H), 3.48-3.57 (m, 1 H), 3.13 (s, 2 H), 2.29 (s, 6 H), 1.73-2.00 (m, 4 H); MS ESI [M+H]⁺ 389.1, calcd for [C₁₅H₂₁IN₂O₂+H]⁺ 389.07.

Synthesis of 2-(dimethylamino)-1-(4-(4-(4,4,5,5-tetramethyl-1,3,2-dioxaborolan-2-yl)phenoxy)piperidin-1-yl)ethanone

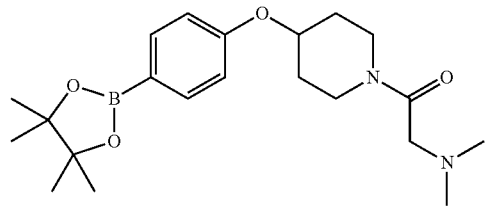

The title compound was synthesized according to General Method F utilizing 2-(dimethylamino)-1-(4-(4-iodophenoxy)piperidin-1-yl)ethanone and obtained as a pale solid (380 mg, 91% yield). $^1$H NMR (400 MHz, CDCl₃) δ ppm 7.76 (d, J=8.5 Hz, 2 H), 6.90 (d, J=8.5 Hz, 2 H), 4.62 (br. s., 1 H), 3.61-3.82 (m, 3 H), 3.47-3.57 (m, 1 H), 3.30 (m, 2 H), 2.31-2.47 (m, 6 H), 1.74-2.02 (m, 4 H), 1.34 (s, 9 H); MS ESI [M+H]⁺ 389.1, calcd for [C₂₁H₃₃BN₂O₄+H]⁺ 389.26.

Synthesis of 2-(4-(4-bromophenoxy)piperidin-1-yl)acetic acid

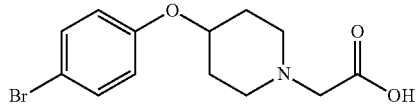 [SMILES: O=C(O)CN1CCC(Oc2ccc(Br)cc2)CC1]

The solution of ethyl 2-(4-(4-bromophenoxy)piperidin-1-yl)acetate (680 mg, 2 mmols), 2N NaOH (8 mL) in MeOH (8 mL) was stirred at rt for 30 min before solvent was removed under reduced pressure. The residue was suspended in H₂O and adjusted pH to 1 with 5% HCl. The resulting solution was concentrated under reduced pressure. The residue was purified with RP column to give a TFA salt of the title compound as a white solid (392 mg, 46% yield). $^1$H NMR (400 MHz, CD₃OD) δ ppm 7.41-7.46 (m, 2 H), 6.96 (d, J=8.8 Hz, 2 H), 4.67-4.73 (m, 1 H), 3.93 (s, 2 H), 3.35-3.57 (m, 4 H), 2.08-2.29 (m, 4 H); MS ESI [M+H]⁺ 314.2, calcd for [C₁₃H₁₆BrNO₃+H]⁺ 314.04.

Synthesis of 2-(4-(4-iodophenoxy)piperidin-1-yl)-N,N-dimethylacetamide

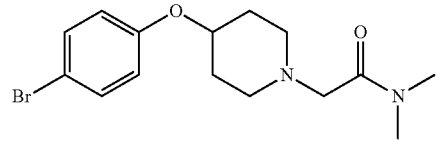 [SMILES: CN(C)C(=O)CN1CCC(Oc2ccc(Br)cc2)CC1]

The title compound was synthesized according to General Method A utilizing 2-(4-(4-bromophenoxy)piperidin-1-yl)

acetic acid TFA salt and dimethylamine and obtained as a yellow solid (171 mg, 100% yield). $^1$H NMR (400 MHz, CDCl$_3$) δ ppm 7.22-7.29 (m, 2 H), 6.66-6.73 (m, 2 H), 4.19 (dt, J=7.7, 3.8 Hz, 1 H), 3.11 (s, 2 H), 3.00 (s, 3 H), 2.86 (s, 3 H), 2.64-2.74 (m, 2 H), 2.28-2.38 (m, 2 H), 1.86-1.97 (m, 2 H), 1.67-1.78 (m, 2 H); MS ESI [M+H]$^+$ 341.2, calcd for [C$_{15}$H$_{21}$BrN$_2$O$_2$+H]$^+$ 341.09.

Synthesis of N,N-dimethyl-2-(4-(4-(4,4,5,5-tetramethyl-1,32-dioxaborolan-2-yl)phenoxy)piperidin-1-yl)acetamide

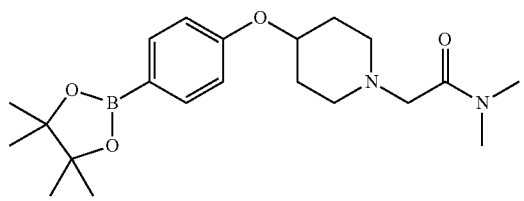

The title compound was synthesized according to General Method E utilizing 2-(4-(4-iodophenoxy)piperidin-1-yl)-N,N-dimethylacetamide and obtained as a white solid (74 mg, 41% yield). $^1$H NMR (400 MHz, CDCl$_3$) δ ppm 7.74 (d, J=8.5 Hz, 2 H), 6.89 (d, J=8.5 Hz, 2 H), 4.36-4.45 (m, 1 H), 3.22 (s, 2 H), 3.09 (s, 3 H), 2.96 (s, 3 H), 2.79 (br. s., 2 H), 2.48 (br. s., 2 H), 1.97-2.08 (m, 2 H), 1.85 (m, 2 H), 1.33 (s, 12 H); MS ESI [M+H]$^+$ 389.2, calcd for [C$_{21}$H$_{33}$BN$_2$O$_4$+H]$^+$ 38926.

Synthesis of 4-(4-iodophenoxy)-1-(oxetan-3-yl)piperidine

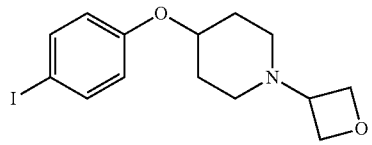 [SMILES: Ic1ccc(OC2CCN(C3COC3)CC2)cc1]

The suspension of 4-(4-iodophenoxy)piperidine HCl salt (528 mg, 1.55 mmols) in EtOAc was washed with satd aq NaHCO$_3$. The organic layer was dried over Na$_2$SO$_4$ and concentrated under reduced pressure. The residue was dissolved in DCE (4 mL) followed by adding of NaBH(OAc)$_3$ (493 mg, 2.33 mmols), oxetan-3-one (112 mg, 1.55 mmols), and HOAc (3 drops). The resulting suspension was stirred at rt for 2 h before the solvent was removed under reduced pressure. The residue was washed with satd aq NaHCO$_3$ and extracted with EtOAc. The combined organic layer was dried over Na$_2$SO$_4$ and concentrated under reduced pressure to give the title compound as a yellow solid (460 mg, 83% yield). $^1$H NMR (400 MHz, CDCl$_3$) δ ppm 7.51-7.59 (m, 2 H), 6.65-6.72 (m, 2 H), 4.60-4.70 (m, 4 H), 4.28-4.38 (m, 1 H), 3.51 (quin, J=6.5 Hz, 1 H), 2.54 (br. s., 2 H), 2.20 (br. s., 2 H), 1.93-2.04 (m, 2 H), 1.79-1.92 (m, 2 H); MS ESI [M+H]$^+$ 360.0, calcd for [C$_{14}$H$_{18}$INO$_2$+H]$^+$ 360.05.

Synthesis of 1-(oxetan-3-yl)-4-(4-(4,4,5,5-tetramethyl-1,3,2-dioxaborolan-2-yl)phenoxy)piperidine

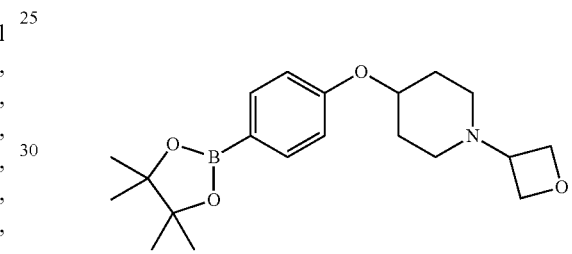

The title compound was synthesized according to General Method E utilizing 4-(4-iodophenoxy)-1-(oxetan-3-yl)piperidine and obtained as a pale solid (468 mg, 62% yield). $^1$H NMR (400 MHz, CDCl$_3$) δ ppm 7.70 (d, J=8.5 Hz, 2 H), 6.84 (d, J=8.5 Hz, 2 H), 4.55-4.65 (m, 4 H), 4.37-4.43 (m, 1 H), 3.47 (t, J=6.5 Hz, 1 H), 2.50 (d, J=7.8 Hz, 2 H), 2.19 (br. s., 2 H), 1.91-2.01 (m, 2 H), 1.84 (td, J=6.7, 3.4 Hz, 2 H), 1.28 (s, 12 H); MS ESI [M+H]$^+$ 360.1, calcd for [C$_{20}$H$_{30}$BNO$_4$+H]$^+$ 360.23.

The following compound was synthesized according to the method used for 4-(4-iodophenoxy)-1-(oxetan-3-yl)piperidine

| IUPAC name | Structure | MS calculated MS ESI [M + H]$^+$ | Yield; Appearance; Salt form |
|---|---|---|---|
| 1-(4-bromophenyl)-4-(oxetan-3-yl)piperazine | 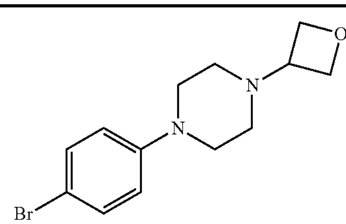 | [C$_{13}$H$_{17}$BrN$_2$O + H]$^+$ 296.1 296.1 | 11.30 g (96%), white solid; free base |

SMs: 1-(4-bromophenyl)piperazine (9.64 g, 40 mmol), oxetan-3-one (4.32 g, 60 mmol)
$^1$H NMR (400 MHz, CDCl$_3$) δ 7.36 (d, J = 9.2 Hz, 2H), 6.80 (d, J = 8.8 Hz, 2H), 4.71 (t, J = 6.4 Hz, 2H), 4.66 (t, J = 5.8 Hz, 2H), 3.56 (quintet, J = 6.4 Hz, 1H), 3.21 (t, J = 5.0 Hz, 4H), 2.50 (t, J = 5.0 Hz, 4H).

Synthesis of diisopropyl (4-((3R,4S)-3-fluoro-1-methylpiperidin-4-yl)oxy)phenyl)boronate compound with diisopropyl (4-(((3S,4R)-3-fluoro-1-methylpiperidin-4-yl)oxy)phenyl)boronate, a 1:1 Mixture

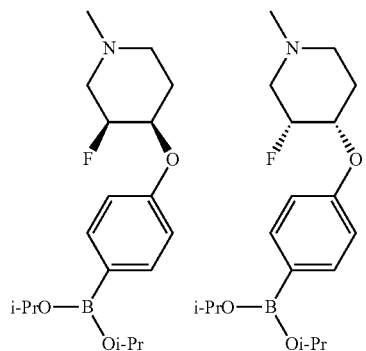

A. (3R,4S)-tert-butyl 3-fluoro-4-(4-iodophenoxy)piperidine-1-carboxylate compound with (3S,4R)-tert-butyl 3-fluoro-4-(4-iodophenoxy)piperidine-1-carboxylate (1:1 mixture) was synthesized according to General Method H utilizing 1-fluoro-4-iodobenzene (0.80 g, 3.6 mmol), (3R,4S)-tert-butyl 3-fluoro-4-hydroxypiperidine-1-carboxylate/(3S,4R)-tert-butyl 3-fluoro-4-hydroxypiperidine-1-carboxylate (1:1 mixture) (0.73 g, 3.3 mmol) and NaH (60% in mineral oil, 0.17, 4.3 mmol) in anh DMF (20 mL) under Ar. After 2 d of heating at 80° C., the reaction was quenched with $H_2O$/MeOH, concentrated under reduced pressure. The residue was taken into DCM (70 mL) and stirred with TFA (8 mL) at 0° C. for 3 h. The reaction was then concentrated under reduced pressure and purified by RP HPLC (Biotage C18 100 g, 5-90% MeOH/$H_2O$+0.1% TFA) to afford cis-3-fluoro-4-(4-iodophenoxy)piperidine 2,2,2-trifluoroacetate as a tan solid. MS ESI $[M+H]^+$ 321.9, calcd for $[C_{11}H_{13}FINO:+H]^+$ 322.0

B. The material (0.47 g, 1.1 mmol) in MeCN (70 mL) was treated with HCHO (30% in $H_2O$, 0.72 mL, 9.7 mmol) followed by $NaBH(OAc)_3$ (0.69 g, 3.2 mmol) at rt. After overnight stirring, the reaction was concentrated under reduced pressue and filtered through PoraPak CX columns (2×2 g, Waters) using MeOH to load and rinse and 2 M $NH_3$/MeOH to elute. The crude material was subsequently purified by flash chromatography ($SiO_2$, 0-40% 2 M $NH_3$/MeOH in DCM) to afford cis-3-fluoro-4-(4-iodophenoxy)-1-methylpiperidine as a clear gum (0.23 g, 64%). $^1$H NMR (400 MHz, $CD_3OD$) δ ppm 7.59 (d, J=8.8 Hz, 2 H), 6.82 (d, J=8.8 Hz, 2 H), 4.78-4.84 (m, 1 H), 4.44-4.60 (m, 1 H), 3.09 (br. s., 1 H), 2.82 (br. s., 1 H), 2.50-2.73 (m, 1 H), 2.45 (m, 1 H), 2.39 (s, 3 H), 2.03-2.17 (m, 1 H), 1.88-2.00 (m, 1 H); MS ESI 336.0 $[M+H]^+$, calcd for $[C_{12}H_{15}FINO:+H]^+$ 336.0.

C. To a stirred solution of cis-3-fluoro-4-(4-iodophenoxy)-1-methylpiperidine (0.12 g, 0.33 mmol) in anh THF (5 mL) under Ar was added n-BuLi (1.6 M in hexanes, 0.45 mL, 0.72 mmol) dropwise at −78° C. The reaction was stirred for 15 min at the temperature before $B(Oi-Pr)_3$ (1.2 mL, 5.2 mmol) was added rapidly. After additional 30 min at −78° C., the reaction was removed from the cooling bath and stirred for 1 h before it was concentrated under reduced pressure to afford a crude mixture of cis-(4-((3-fluoro-1-methylpiperidin-4-yl)oxy)phenyl)boronic acid and diisopropyl (4-((cis-3-fluoro-1-methylpiperidin-4-yl)oxy)phenyl) boronate as an off-white solid (0.34 g) that was used without further purification. MS ESI $[M+H]^+$ 254.1, calcd for $[C_{12}H_{17}BFNO_3:+H]^+$ 254.1.

Synthesis of (1R,3R,5S)-8-methyl-3-(4-(4,4,5,5-tetramethyl-1,3,2-dioxaborolan-2-yl)phenoxy)-8-azabicyclo[3.2.1]octane

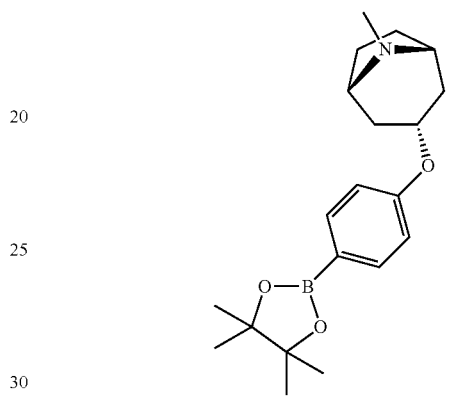

A. (1R,3R,5S)-3-(4-iodophenoxy)-8-methyl-8-azabicyclo[3.2.1]octane was synthesized according to General Method H utilizing 1-fluoro-4-iodobenzene (2.99 g, 13.5 mmol), (1R,3R,5S)-8-methyl-8-azabicyclo[3.2.1]octan-3-ol (1.9 g, 13.5 mmol) and NaH (60% in oil, 0.64 g, 16.1 mmol) in DMF (40 mL). After 1 d of heating at 85° C., the reaction was quenched with MeOH and concentrated under reduced pressure. The residue was partitioned between satd aq $NaHCO_3$ and EtOAc. The aq layer was extracted with EtOAc (2×). The organic fractions were combined, dried ($Na_2SO_4$) and concentrated under reduced pressure. The crude material was purified by RP HPLC (Biotage C18, 100 g, 5-90% MeOH/$H_2O$+0.1% TFA) to TFA salt of (1R,3R,5S)-3-(4-iodophenoxy)-8-methyl-8-azabicyclo[3.2.1]octane as an off-white solid (2.0 g, 33%). NMR (400 MHz, $CDCl_3$) δ ppm 7.60 (d, J=8.8 Hz, 2 H), 6.62 (d, J=8.8 Hz, 2 H), 4.65 (t, J=4.9 Hz, 1 H), 3.79 (br. s., 2 H), 2.71-2.83 (m, 5 H), 2.55-2.47 (m, 2 H), 2.15-2.32 (m, 4 H); MS ESI 344.0 $[M+H]^+$, calcd for $[C_{14}H_{18}INO:+H]^+$ 344.0.

B. (1R,3R,5S)-8-methyl-3-(4-(4,4,5,5-tetramethyl-1,3,2-dioxaborolan-2-yl)phenoxy)-8-azabicyclo[3.2.1]octane was synthesized according to General Method E utilizing (1R,3R,5S)-3-(4-iodophenoxy)-8-methyl-8-azabicyclo[3.2.1] octane 2,2,2-trifluoroacetate (0.50 g, 1.1 mmol). After aq workup (satd aq $NaHCO_3$/DCM) followed by a flash chromatography (25 g $SiO_2$, 0-30% MeOH-DCM), the desired compound was isolated as an off-white solid (44 mg, 13%). $^1$H NMR (400 MHz, $CDCl_3$) δ ppm 7.79 (d, J=8.5 Hz, 2 H), 6.84 (d, J=8.8 Hz, 2 H), 4.81 (br. s., 1 H), 3.82 (br. s., 2 H), 3.38-3.18 (m, 2 H), 2.77 (s, 3 H), 2.63-2.54 (m, 2 H), 2.21-2.36 (m, 4 H), 134 (s, 12 H); MS ESI 344.2 $[M+H]^+$, calcd for $[C_{20}H_{30}BNO_3:+H]^+$ 344.2.

Synthesis of 4,4,5,5-tetramethyl-2-(4-((tetrahydro-2H-pyran-4-yl)oxy)phenyl)-1,3,2-dioxaborolane

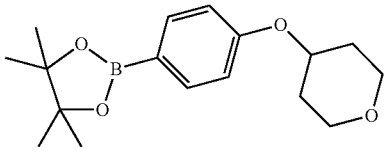 [SMILES: CC1(C)OB(c2ccc(OC3CCOCC3)cc2)OC1(C)C]

The title compound was synthesized according to General Method E by using a solution of 4-(4-bromophenoxy)tetrahydro-2H-pyran (800 mg, 3.11 mmol) in DMF (12 mL), bis(pinacolato)diboron (948 mg, 3.73 mmol), KOAc (916 mg, 9.33 mmol) and PdCl$_2$dppf (254 mg, 0.311 mmol) under Ar. The degassed suspension under Ar was sealed and heated in an oil bath at 125° C. for 5 h. The reaction mixture was diluted using EtOAc (60 mL) and H$_2$O (36 mL). The organic layer was separated and aq. layer extracted with EtOAc (36 mL). The combined EtOAc layer was washed with H$_2$O and brine, dried (Na$_2$SO$_4$) and concentrated under vacuum at 40° C./100 mbar to give crude brown thick oil. The crude oily product purified by Biotage (50 g SiO$_2$, 0-30% EtOAc in Hexane) to give title compound (cream color solid, 728 mg, 77%). $^1$H NMR (400 MHz, CDCl$_3$) δ 7.76-7.74 (d, J=2.8 Hz, 2H), 6.92 (d, J=2.8 Hz, 2H), 4.59-4.53 (m, 1H), 4.01-3.96 (m, 2H), 3.62-3.57 (m, 2H), 2.05-2.0 (m, 2H), 1.84-1.77 (m, 2H), 1.34 (s, 12H); MS ESI 305.1 [M+H]$^+$, calcd for [C$_{17}$H$_{25}$BO$_4$+H]$^+$ 305.1.

Synthesis of 1-(4-bromo-2-methoxyphenyl)-4-methylpiperazine

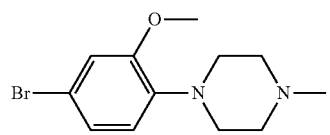 [SMILES: COc1cc(Br)ccc1N1CCN(C)CC1]

The title compound was synthesized according to the General Method I, utilizing 5-bromo-2-iodoanisole (683 mg, 2.18 mmol), 1-methylpiperazine (262 mg, 2.62 mmol), CuI (83 mg, 0.44 mmol), BINOL (125 mg, 0.44 mmol), K$_3$PO$_4$ (924 mg, 4.36 mmol), and DMF (4 mL) and purified in flash chromatography (SiO$_2$, Biotage 25 g, 5-25% MeOH in CH$_2$Cl$_2$) to give the title compound (light yellow solid, 213 mg, 34%). $^1$H NMR (400 MHz, CDCl$_3$) δ ppm 7.01 (d, J=8.3 Hz, 1 H), 6.94 (s, 1 H), 6.76 (d, J=8.3 Hz, 1 H), 3.83 (s, 3 H), 3.27 (br. s, 4 H), 2.99 (br. s, 4 H), 2.59 (s, 3 H).

Synthesis of 1-(2-methoxy-4-(4,4,5,5-tetramethyl-1,3,2-dioxaborolan-2-yl)phenyl)-4-methylpiperazine

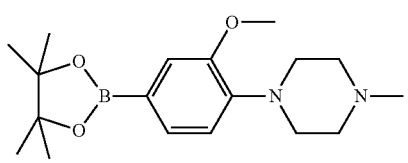

The title compound was synthesized according to the General Method E utilizing 1-(4-bromo-2-methoxyphenyl)-4-methylpiperazine (200 mg, 0.70 mmol), B$_2$pin$_2$ (213 mg, 0.84 mmol), PdCl$_2$dppf (17 mg, 0.021 mmol), KOAc (206 mg, 2.1 mmol), and DMSO (10 mL). The mixture was charged with Ar and heated at 85° C. in the microwave reactor for 2 h. Purification by flash chromatography (SiO$_2$, Biotage 25 g, 5-25% MeOH in CH$_2$Cl$_2$) gave the title compound (brown solid, 63 mg, 27%). MS ESI 333.3 [M+H]$^+$, calcd for [C$_{18}$H$_{29}$BN$_2$O$_3$+H]$^+$ 333.2.

Synthesis of 1-(4-(4,4,5,5-tetramethyl-1,3,2-dioxaborolan-2-yl)phenyl)piperidin-4-one

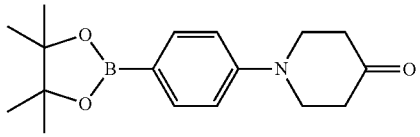 [SMILES: CC1(C)OB(c2ccc(N3CCC(=O)CC3)cc2)OC1(C)C]

The title compound was synthesized according to General Method E by using a mixture of 1-(4-bromophenyl)piperidin-4-one (1.5 g, 5.9 mmol), B$_2$pin$_2$ (2.62 g, 10.3 mmol), KOAc (1.73 g, 17.7 mmol) and DMF (15 mL) was purged with Ar for 10 min. PdCl$_2$dppf (0.32 g, 0.44 mmol) was added in round bottom flask and heated at 125° C. for 4 h in oil bath under Ar. The reaction mixture was diluted using 10% aq NaCl solution (100 mL) and the product extracted with EtOAc (2×100 mL) and the combined EtOAc layer was washed with brine (2×25 mL), dried (Na$_2$SO$_4$), and concentrated under vacuum at 40° C./100 mbar to give crude brown thick oil. The crude oily mass was purified by flash chromatography (50 g SiO$_2$, 0-40% EtOAc in Hexane) to give the title compound (pale yellow solid, 584 mg, 33%). $^1$H NMR (400 MHz, CDCl$_3$) δ ppm 7.77 (d, J=8.8 Hz, 2H), 6.97 (d, J=8.8 Hz, 2H), 3.71 (t, J=6.0 Hz, 4H), 2.56 (t, J=6.0 Hz, 4H), 1.34 (s, 12H); MS ESI 302 [M+H]$^+$, calcd for [C$_{17}$H$_{24}$BNO$_3$+H]$^+$ 302.1

Synthesis of 1-(4-(4,4,5,5-tetramethyl-1,3,2-dioxaborolan-2-yl)phenyl)piperidin-4-ol

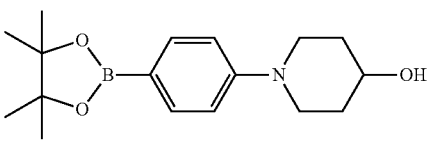 [SMILES: CC1(C)OB(c2ccc(N3CCC(O)CC3)cc2)OC1(C)C]

Using General Method F with excess HBpin (3 equiv) at 100° C. for 17 h, from 1-(4-bromophenyl)piperidin-4-one (1.4885 g, 5.86 mmol), after aq. work-up with EtOAc, purification by flash chromatography (SiO$_2$, 50-60% EtOAc in hexane) gave the title compound (1.59 g, 80% pure, 72%). $^1$H NMR (400 MHz, CDCl$_3$) δ ppm 7.70 (d, J=8.8 Hz, 2 H), 6.91 (d, J=8.8 Hz, 2 H), 3.88 (tt, J=8.6, 4.2 Hz, 1 H), 3.68 (dt, J=13.1, 4.1 Hz, 2 H), 3.00 (ddd, J=12.7, 10.1, 3.0 Hz, 2 H), 1.92-2.04 (m, 2 H), 1.60-1.73 (m, 2 H), 1.33 (s, 12 H).

Synthesis of (1-(4-iodophenyl)piperidin-4-yl)methanol

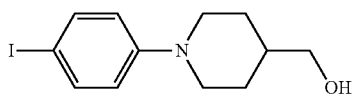

The title compound was synthesized according to the General Method I utilizing piperidin-4-ylmethanol and obtained as a white solid (989 mg, 31% yield). $^1$H NMR (400 MHz, CDCl$_3$) δ ppm 7.50 (d, J=9.0 Hz, 2 H), 6.71 (d, J=9.0 Hz, 2 H), 3.65-3.72 (m, 2 H), 3.53-3.58 (m, 2 H), 2.72 (td, J=12.6, 2.5 Hz, 2 H), 1.82-1.89 (m, 2 H), 1.62-1.73 (m, 1 H), 1.35-1.45 (m, 2 H), 1.32 (t, J=5.4 Hz, 1 H); MS ESI [M+H]+ 318.0, calcd for [C$_{12}$H$_{16}$INO+H]+ 318.04.

Synthesis of (1-(4-(4,4,5,5-tetramethyl-1,3,2-dioxaborolan-2-yl)phenyl)piperidin-4-yl)methanol

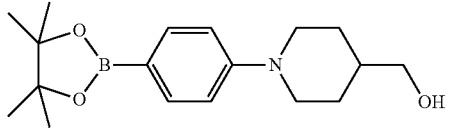 [SMILES: CC1(C)OB(c2ccc(N3CCC(CO)CC3)cc2)OC1(C)C]

The title compound was synthesized according to General Method E utilizing (1-(4-iodophenyl)piperidin-4-yl)methanol and obtained as a bright brown solid (272 mg, 70% yield). $^1$H NMR (400 MHz, CDCl$_3$) δ ppm 7.70 (d, J=8.8 Hz, 2 H), 6.91 (d, J=8.8 Hz, 2 H), 3.85 (d, J=12.6 Hz, 2 H), 3.55 (d, J=6.5 Hz, 2 H), 2.79 (td, J=12.4, 2.6 Hz, 2 H), 1.85 (d, J=13.0 Hz, 2 H), 1.64-1.77 (m, 1 H), 1.51-1.63 (m, 2 H), 1.39 (br. s., 1 H), 1.33 (s, 12 H); MS ESI [M+H]+ 318.1, calcd for [C$_{18}$H$_{28}$BNO$_3$+H]+ 318.22.

Synthesis of 1-(4-bromophenyl)-4-methylpiperidin-4-ol

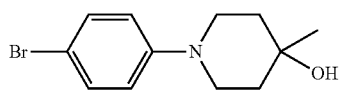

The mixture of 1-(4-bromophenyl)piperidin-4-one (254 mg, 1 mmol) in anhydrous THF (10 mL) was cooled down to −78° C. MeMgCl (3M in THF, 1.7 mL, 5 mmols) was added dropwise and stirred at −78° C. for 0.5 h then at 0° C. for 2 h. The reaction was quenched with satd aq NH$_4$Cl solution dropwise at 0° C. The mixture was poured into brine and extracted with EtOAc. The combined organic layer was dried over Na$_2$SO$_4$ and concentrated under reduced pressure to provide the title compound as a yellow solid (262 mg, 97% yield). $^1$H NMR (400 MHz, CDCl$_3$) δ ppm 7.33 (d, J=8.8 Hz, 2 H), 6.83 (d, J=8.8 Hz, 2 H), 3.33 (dt, J=12.5, 4.2 Hz, 2 H), 3.11-3.22 (m, 2 H), 1.65-1.83 (m, 4 H), 1.31 (s, 3 H); MS ESI [M+H]+ 270.2, calcd for [C$_{12}$H$_{16}$BrNO+H]+ 270.05.

Synthesis of 4-methyl-1-(4-(4,4,5,5-tetramethyl-1,3,2-dioxaborolan-2-yl)phenyl)piperidin-4-ol

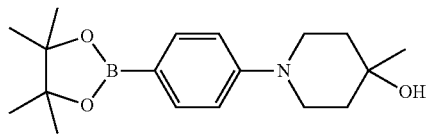

The title compound was synthesized according to General Method E utilizing 1-(4-bromophenyl)-4-methylpiperidin-4-ol and obtained as a white solid (42 mg, 27% yield). $^1$H NMR (400 MHz, CDCl$_3$) δ ppm 7.71 (d, J=8.8 Hz, 2 H), 6.92 (d, J=8.8 Hz, 2 H), 3.49 (dt, J=12.8, 4.4 Hz, 2 H), 3.27 (brs, 2 H), 1.63-1.81 (m, 4 H), 1.56 (s, 3 H), 1.33 (s, 12 H); MS ESI [M+H]+ 318.3, calcd for [C$_{18}$H$_{28}$BNO$_3$+H]+ 318.22.

Synthesis of methyl 1-(4-iodophenyl)piperidine-4-carboxylate

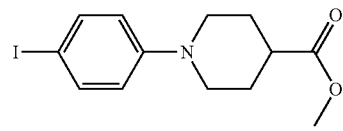

The title compound was synthesized according to the General Method I utilizing methyl piperidine-4-carboxylate and obtained as a yellow solid (471 mg, 14% yield). $^1$H NMR (400 MHz, CDCl$_3$) δ ppm 7.48-7.54 (m, 2 H), 6.70 (d, J=9.0 Hz, 2 H), 3.72 (s, 3 H), 3.61 (d, J=12.8 Hz, 2 H), 2.79 (td, J=12.0, 2.8 Hz, 2 H), 2.47 (s, 1 H), 2.03 (d, J=13.3 Hz, 2 H), 1.82-1.92 (m, 2 H); MS ESI [M+H]+ 346.0, calcd for [C$_{13}$H$_{16}$INO$_2$+H]+ 346.03.

Synthesis of 2-(1-(4-iodophenyl)piperidin-4-yl)propan-2-ol

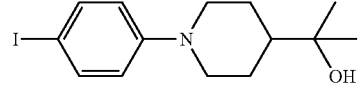

The title compound was synthesized according to the method of 1-(4-bromophenyl)-4-methylpiperidin-4-ol utilizing 1-(4-iodophenyl)piperidine-4-carboxylate and obtained as a white solid (81 mg, 81% yield). $^1$H NMR (400 MHz, CDCl$_3$) δ ppm 7.50 (d, J=9.0 Hz, 2 H), 6.71 (d, J=9.0 Hz, 2 H), 3.74 (d, J=12.3 Hz, 2 H), 2.65 (t, J=11.4 Hz, 2 H), 1.87 (m, J=9.8 Hz, 2 H), 1.40-1.54 (m, 3 H), 1.17-1.26 (m, 6 H); MS ESI [M+H]+ 346.1, calcd for [C$_{14}$H$_{20}$INO+H]+ 346.07.

Synthesis of 2-(1-(4-(4,4,5,5-tetramethyl-1,3,2-dioxaborolan-2-yl)phenyl)piperidin-4-yl)propan-2-ol

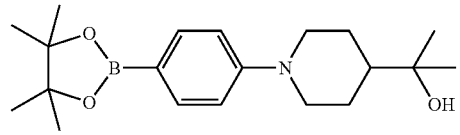 [SMILES: CC(C)(O)C1CCN(c2ccc(B3OC(C)(C)C(C)(C)O3)cc2)CC1]

The title compound was synthesized according to General Method F utilizing 2-(1-(4-iodophenyl)piperidin-4-yl)propan-2-ol and obtained as a white solid (74 mg, 91% yield). $^1$H NMR (400 MHz, CDCl$_3$) δ ppm 7.70 (d, J=8.8 Hz, 2 H), 6.92 (d, J=8.8 Hz, 2 H), 3.90 (d, J=12.3 Hz, 2 H), 2.72 (t, J=12.4 Hz, 2 H), 1.85 (br. s., 2 H), 1.47 (br. s., 3 H), 1.29-1.37 (m, 12 H), 1.18-1.25 (m, 6 H); MS ESI [M+H]+ 346.1, calcd for [C$_{20}$H$_{32}$BNO$_3$+H]+ 346.26.

Synthesis of (2S,6R)-2,6-dimethyl-4-(4-(4,4,5,5-tetramethyl-1,3,2-dioxaborolan-2-yl)phenyl)morpholine

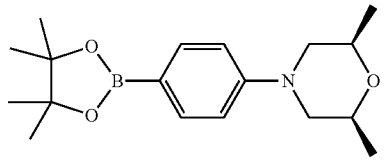

A. (2S,6R)-4-(4-iodophenyl)-2,6-dimethylmorpholine was synthesized according to the General Method I utilizing 1,4-diiodobenzene (2.4 g, 7.3 mmol) and (2R,6S)-2,6-dimethylmorpholine (1.0 g, 8.8 mmol). After heating for 2 d, the crude reaction mixture was cooled to rt, diluted with EtOAc (100 mL) and filtered through Celite. The filtrate was then washed (H$_2$O, brine), dried (Na$_2$SO$_4$) and concentrated under reduced pressure to provide as a light yellow solid (2.2 g) which was purified by flash chromatography (SiO$_2$, 0-20% MeOH-DCM) affording (2S,6R)-4-(4-iodophenyl)-2,6-dimethylmorpholine as a light yellow solid (0.68 g, 30%). MS ESI [M+H]$^+$ 318.0, calcd for [C$_{12}$H$_{16}$INO+H]$^+$ 318.0.

B. (2S,6R)-2,6-Dimethyl-4-(4-(4,4,5,5-tetramethyl-1,3,2-dioxaborolan-2-yl)phenyl)morpholine was synthesized according to the General Method F utilizing (2S,6R)-4-(4-iodophenyl)-2,6-dimethylmorpholine (0.20 g, 0.63 mmol). The crude reaction mixture was concentrated under reduced pressure, taken in DCM and filtered through a column made of two layers (Celite (10 g) and silica gel (10 g)) using hexanes-EtOAc as the eluent (1:1 then 1:3) to afford a pale yellow solid (0.25 g, 125%) which was used without further purification. MS ESI 318.2 [M+H]$^+$, calcd for [C$_{18}$H$_{28}$BNO$_3$+H]$^+$ 318.2.

The following intermediates were synthesized according to General Method H:

| IUPAC name | Structure | MS calculated MS ESI [M + H]$^+$ | Yield; Appearance; Salt form |
|---|---|---|---|
| cis-3-(4-iodophenoxy)cyclohexanol | 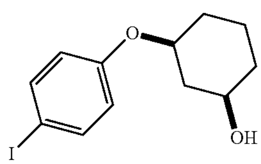 | [C$_{12}$H$_{15}$IO$_2$ + H]$^+$ 319.0 | 296 mg (19%), white solid |

SMs: cis-cyclohexane-1,3-diol (580 mg, 5 mmol), 1-fluoro-4-iodobenzene (1.11 g, 5 mmol)

$^1$H NMR (400 MHz, CDCl$_3$) δ ppm 7.52 (d, J = 8.8 Hz, 2H), 6.71 (d, J = 8.8 Hz, 2H), 4.24-4.16 (m, 1H), 3.68-3.59 (m, 1H), 2.40-2.34 (m, 1H), 2.07-2.00 (m, 1H), 1.97-1.90 (m, 1H), 1.84-1.77 (m, 1H), 1.40-1.15 (m, 4H).

| IUPAC name | Structure | MS calculated MS ESI [M + H]$^+$ | Yield; Appearance; Salt form |
|---|---|---|---|
| 1-(4-iodophenyl)-3-(oxetan-3-yl)azetidine | | [C$_{12}$H$_{14}$INO + H]$^+$ 316.01 316.0 | 1.27 g (57%); yellow solid; free base |

SMs: 1,4-diiodobenzene (2.3 g, 7.1 mmol), 3-(oxetan-3-yl)azetidine (0.80 g, 7.1 mmol)

$^1$H NMR (400 MHz, CDCl$_3$) δ ppm 7.37 (d, J = 8.8 Hz, 2 H), 6.06-6.18 (m, 2 H), 4.76 (dd, J = 7.8, 6.0 Hz, 2 H), 4.36 (t, J = 6.0 Hz, 2 H), 3.88 (t, J = 7.7 Hz, 2 H), 3.51 (dd, J = 7.4, 5.1 Hz, 2 H), 3.15-3.28 (m, 1 H), 2.91-3.03 (m, 1 H)

| IUPAC name | Structure | MS calculated MS ESI [M + H]$^+$ | Yield; Appearance; Salt form |
|---|---|---|---|
| 1-(4-iodophenyl)azetidin-3-ol | | [C$_9$H$_{10}$INO + H]$^+$ 275.98 276.2 | 5.8 g (35%); Pale yellow solid; free base |

SMs: 1,4-diiodobenzene (20 g, 61 mmol), azetidine-3-ol hydrochloride (8.0 g, 73 mmol)

$^1$H NMR (400 MHz, CDCl$_3$) δ ppm 7.47 (d, J = 8.8 Hz, 2 H), 6.26 (d, J = 9.0 Hz, 2 H), 4.71-4.83 (m, 1 H), 4.16 (dd, J = 8.8, 6.3 Hz, 2 H), 3.66 (dd, J = 8.5, 4.5 Hz, 2 H), 2.06 (d, J = 6.8 Hz, 1 H)

| IUPAC name | Structure | MS calculated MS ESI [M + H]$^+$ | Yield; Appearance; Salt form |
|---|---|---|---|
| (1R,3S,5S)-8-(4-iodophenyl)-8-azabicyclo[3.2.1]octan-3-ol | | [C$_{13}$H$_{16}$INO + H]$^+$ 330.2 330.0 | 2.36 g (36%), yellow solid; free base |

SMs: (1R,3S,5S)-8-azabicyclo[3.2.1]octan-3-ol hydrochloride (3.27 g 20 mmol), 1,4-diiodobenzene (6.60 g, 20 mmol)

$^1$H NMR (400 MHz, CDCl$_3$) δ ppm 7.52-7.47 (m, 2H), 6.60-6.56 (m, 2H), 4.25-4.11 (m, 3H), 2.11-2.04 (m, 2H), 1.88-1.82 (m, 2H), 1.69-1.61 (m, 2H), 1.18 (d, J = 6.4 Hz, 1H).

| IUPAC name | Structure | MS calculated MS ESI [M + H]+ | Yield; Appearance; Salt form |
|---|---|---|---|
| (1R,3S,5S)-3-(4-iodophenoxy)-8-methyl-8-azabicyclo[3.2.1]octane | 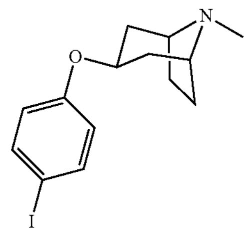 [SMILES: CN1C2CCC1CC(Oc1ccc(I)cc1)C2] | [C14H18INO + H]+ 344.0 344.0 | 9.36 g (55%), beige solid; free base |

SMs: (1R,3S,5S)-8-methyl-8-azabicyclo[3.2.1]octan-3-ol (7.05 g, 50 mmol), 1-fluoro-4-iodobenzene (11.1 g, 50 mmol)
¹H NMR (400 MHz, CDCl₃) δ ppm 7.53 (d, J = 9.2 Hz, 2H), 6.67 (d, J = 8.8 Hz, 2H), 4.50-4.40 (m, 1H), 3.28-3.24 (m, 2H), 2.37 (s, 3H), 2.12-2.05 (m, 2H), 1.98-1.89 (m, 2H), 1.87-1.77 (m, 2H), 1.66-1.58 (m, 2H).

| IUPAC name | Structure | MS calculated MS ESI [M + H]+ | Yield; Appearance; Salt form |
|---|---|---|---|
| 3-(4-iodophenoxy)-1-methylazetidine | | [C10H12INO + H]+ 290.0 289.9 | 3.673 g (64%), beige solid; free base |

SMs: 1-methylazetidin-3-ol hydrochloride (2.47 g, 20 mmol), 1-fluoro-4-iodobenzene (4.44 g, 20 mmol)
¹H NMR (400 MHz, DMSO-d₆) δ ppm 7.57 (d, J = 8.8 Hz, 2H), 6.67 (d, J = 8.4 Hz, 2H), 4.70 (quintet, J = 5.7 Hz, 1H), 3.72-3.66 (m, 2H), 2.96-2.89 (m, 2H), 2.26 (s, 3H).

| IUPAC name | Structure | MS calculated MS ESI [M + H]+ | Yield; Appearance; Salt form |
|---|---|---|---|
| 5-bromo-2-((1-(oxetan-3-yl)piperidin-4-yl)oxy)pyridine | | [C13H17BrN2O2 + H]+ 313.0 312.9 | 3.845 g (62%), light beige solid; free base |

SMs: 1-(oxetan-3-yl)piperidin-4-ol (3.30 g, 20 mmol), 5-bromo-2-fluoropyridine (3.24 g, 20 mmol)
¹H NMR (400 MHz, CDCl₃) δ ppm 8.16 (d, J = 2.4 Hz, 1H), 7.64 (dd, J = 8.8, 2.4 Hz, 1H), 6.64 (d, J = 8.8 Hz, 1H), 5.09-5.01 (m, 1H), 4.68 (t, J = 6.6 Hz, 2H), 4.64 (t, J = 6.2 Hz, 2H), 3.51 (quintet, J = 6.5 Hz, 1H), 2.62-2.55 (m, 2H), 2.19 (t, J = 8.8 Hz, 2H), 2.10-2.02 (m, 2H), 1.88-1.78 (m, 2H).

A. Synthesis of 1-(4-iodophenyl)-1,4-diazepane

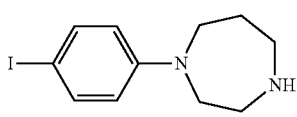 [SMILES: Ic1ccc(N2CCCNCC2)cc1]

The title compound was synthesized according to General Method I utilizing 1,4-diazepane (5 g, 49.9 mmol) and obtained as a white solid (2.2 g, 18%). ¹H NMR (400 MHz, CD₃OD) δ ppm 7.42-7.48 (m, 2 H), 6.60 (d, J=9.0 Hz, 2 H), 3.60-3.66 (m, 2 H), 3.57 (t, J=6.1 Hz, 2 H), 3.09-3.15 (m, 2 H), 2.93-2.99 (m, 2 H), 2.03 (d, J=5.8 Hz, 2 H); MS ESI [M+H]+ 303.2, calcd for [C11H15IN2+H]+ 303.0.

B. (1-(4-iodophenyl)-4-(oxetan-3-yl)-1,4-diazepane

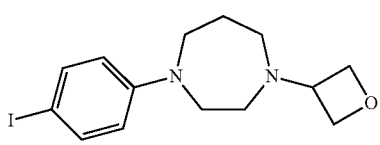 [SMILES: Ic1ccc(N2CCCN(C3COC3)CC2)cc1]

The title compound was synthesized using the same method of synthesis of (1R,3R,5S)-3-(4-iodophenoxy)-8-(oxetan-3-yl)-8-azabicyclo[3.2.1]octane utilizing 1-(4-iodophenyl)-1,4-diazepane (2.2 g, 7.28 mmol) and obtained as a yellow solid (1.52 g, 58%). ¹H NMR (400 MHz, CDCl₃) δ ppm 7.41-7.48 (m, 2 H), 6.44-6.50 (m, 2 H), 4.62-4.67 (m, 2 H), 4.55 (t, J=6.3 Hz, 2 H), 3.66 (t, J=6.3 Hz, 1 H), 3.47-3.57 (m, 4 H), 2.50-2.57 (m, 2 H), 2.33-2.42 (m, 2 H), 1.91-2.02 (m, 2 H); MS ESI [M+H]⁺ 359.2, calcd for [$C_{14}H_{19}IN_2O$+H]⁺ 359.1.

Synthesis of (R)-3-(4-iodophenoxy)-1-methylpyrrolidine

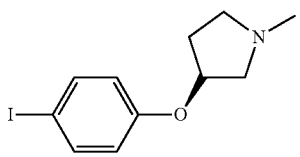

The title compound was synthesized as per 4-(4-bromophenoxy)-1-(oxetan-3-yl)piperidine by utilizing (R)-1-methylpyrrolidin-3-ol (500 mg, 4.94 mmol), 4-fluoro-1-iodobenzene (1.21 g, 5.44 mmol), NaH (55-60% in mineral oil, 247 mg, 6.17 mmol) and anh DMF (10 mL) at 85° C. for 18 h. After work up and purification the title compound was isolated as a white solid (115 mg, 7.6%). ¹H NMR (400 MHz, CDCl₃) δ 7.47-7.56 (m, 2 H), 6.59-6.66 (m, 2 H), 4.74-4.78 (m, 1 H), 2.74-2.87 (m, 3 H), 2.41-2.47 (m, 1 H), 2.39 (s, 3 H), 2.30 (d, J=7.8 Hz, 1 H), 1.92-2.01 (m, 1 H); MS ESI 303.9 [M+H]⁺, calcd for [$C_{11}H_{14}INO_4$+H]⁺ 304.

Synthesis of tert-butyl 4-(4-bromo-2-(methylsulfonyl)phenoxy)piperidine-1-carboxylate

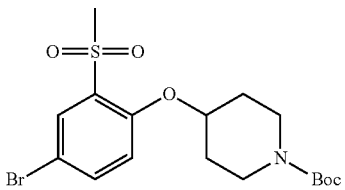 [SMILES: CC(C)(C)OC(=O)N1CCC(Oc2ccc(Br)cc2S(C)(=O)=O)CC1]

The title compound was synthesized as 4-(4-bromophenoxy)-1-(oxetan-3-yl)piperidine by utilizing 4-bromo-1-fluoro-2-(methylsulphonyl)benzene (250 mg, 0.98 mmol), tert-butyl 4-hydroxy-1-piperidinecarboxylate (250 mg, 1.24 mmol), NaH (55-60% in mineral oil, 65 mg, 1.48 mmol) and anh DMF (4 mL) at 85° C. for 18 h. After work up and purification by flash chromatography (Biotage Isolera, 50 g HP-SIL, 0-40% EtOAc in hexanes) white solid (230 mg, 53%). ¹H NMR (400 MHz, CDCl₃) δ ppm 8.08 (d, J=2.5 Hz, 1 H), 7.63 (dd, J=8.8, 2.4 Hz, 1 H), 6.94 (d, J=8.8 Hz, 1 H), 4.65-4.75 (m, 1 H), 3.58-3.72 (m, 2 H), 3.41-3.53 (m, 2 H), 3.20 (s, 3 H), 1.91-2.01 (m, 2 H), 1.81-1.91 (m, 2 H), 1.46 (s, 9 H); MS ESI 435.9 [M+H]⁺, calcd for [$C_{17}H_{24}BrNO_5S$+H]⁺ 435.

Synthesis of 4-(4-bromo-2-(methylsulfonyl)phenoxy)-1-methylpiperidine

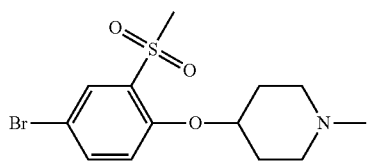

The title compound was synthesized as per 4-(4-bromophenoxy)-1-(oxetan-3-yl)piperidine by utilizing 4-bromo-1-fluoro-2-(methylsulphonyl)benzene (500 mg, 1.97 mmol), 1-methylpiperidin-4-ol (319 mg, 1.24 mmol), NaH (55-60% in mineral oil, 119 mg, 2.97 mmol) and anh DMF (10 mL) at 85° C. for 18 h. After work up and purification by flash chromatography (Biotage Isolera, 50 g HP-SIL, 0-40% MeOH in DCM) the title compound was isolated as a pale yellow thick oil (502 mg, 73%). ¹H NMR (400 MHz, CDCl₃) δ ppm 8.08 (s, 1 H), 7.63 (d, J=9.0 Hz, 1 H), 6.92 (d, J=8.8 Hz, 1 H), 4.55 (br. s, 1 H), 3.22 (s, 3 H), 2.68 (br. s, 2 H), 2.37 (br. s, 2 H), 2.31 (s, 3 H), 2.05 (d, J=3.8 Hz, 2 H), 1.96 (br. s, 2 H); MS ESI 349.9 [M+H]⁺, calcd for [$C_{13}H_{18}BrNO_3S$+H]⁺ 349.

Synthesis of (1R,3R,5S)-tert-butyl 3-(4-iodophenoxy)-8-azabicyclo[3.2.1]octane-8-carboxylate

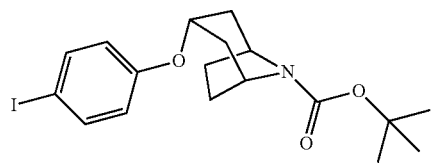 [SMILES: CC(C)(C)OC(=O)N1C2CCC1CC(Oc1ccc(I)cc1)C2]

The suspension of NaH (60%, 317 mg, 7.9 mmol) in DMF (10 mL) was degassed with Ar followed by addition of (1R,3R,5S)-tert-butyl 3-hydroxy-8-azabicyclo[3.2.1]octane-8-carboxylate (2 g, 7.2 mmol) at rt. The resulting mixture was degassed with Ar again and slowly warmed. the solution began bubbling at 45° C. and finished at 60° C. At 70° C., 1-fluoro-4-iodobenzene (0.83 mL, 7.2 mmol) was added dropwise and the reaction mixture was stirred at 85° C. overnight. After cooling to rt, H₂O and EtOAc was added. The organic phase was washed with H₂O and brine and dried (Na₂SO₄) and concentrated. The residue was purified by flash chromatography (Biotage Isolera, 100 g HP-SIL, 10-35% EtOAc in hexanes) to give the title compound as a white solid (1.g, 54%). ¹H NMR (400 MHz, CDCl₃) δ ppm 7.51-7.61 (m, 2 H), 6.62 (d, J=9.0 Hz, 2 H), 4.59 (br. s., 1 H), 4.09-4.32 (m, 2 H), 2.02-2.23 (m, 4 H), 1.89-2.00 (m, 4 H), 1.48 (s, 9 H); MS ESI [M-$C_4H_9$]⁺ 374.0, calcd for [$C_{18}H_{24}INO_3$–$C_4H_9$]⁺ 374.0.

Synthesis of (1R,3R,5S)-3-(4-iodophenoxy)-8-(oxetan-3-yl)-8-azabicyclo[3.2.1]octane

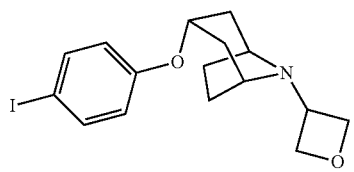 [SMILES: Ic1ccc(OC2CC3CCC(C2)N3C2COC2)cc1]

The suspension of (1R,3R,5S)-3-(4-iodophenoxy)-8-azabicyclo[3.2.1]octane (1055 mg, 3.2 mmol), 3-oxetanone (254 mg, 3.5 mmol), NaBH(OAc)₃ (1020 mg, 4.8 mmol), HOAc (8 drops) in DCE (15 mL) was stirred at rt for 1.5 h followed by removal of solvents under reduced pressure. The residue was washed with sat. aq NaHCO₃ and extracted with EtOAc. The organic phases were combined and dried over anhydrous Na₂SO₄ and concentrated. The residue was purified by flash chromatography (Biotage Isolera, 50 g HP-SIL, 10-100% EtOAc in hexanes then 0-10% MeOH in DCM) to give the title compound as a white solid (0.78 g, 63%). ¹H NMR (400 MHz, CDCl₃) δ ppm 7.55 (d, J=9.0 Hz, 2 H), 6.61 (d, J=8.8 Hz, 2 H), 4.70 (t, J=6.3 Hz, 2 H), 4.48-4.57 (m, 3 H), 3.67 (quin, J=6.0 Hz, 1 H), 3.04 (br. s., 2 H), 2.02-2.18 (m, 4 H), 1.93-2.01 (m, 2H,) 1.80-1.89 (m, 2 H); MS ESI [M+H]⁺ 386.0, calcd for [C₁₆H₂₀INO₂+H]⁺ 386.1.

Synthesis of (1R,3R,5S)-3-(4-iodophenoxy)-8-azabicyclo[3.2.1]octane-8-carbaldehyde

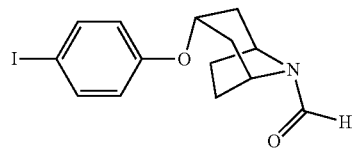 [SMILES: O=CN1C2CCC1CC(Oc1ccc(I)cc1)C2]

The suspension of (1R,3R,5S)-3-(4-iodophenoxy)-8-azabicyclo[3.2.1]octane (2.75 g, 8.36 mmol), DIEPA (4.2 mL, 25.08 mmol) in DMF (25 mL) was added HCOOH (0.35 mL, 9.19 mmol) and cooled to 0° C. followed by addition of TBTU (2.6 g, 8.36 mmol). After stirring at 0° C. for 1 h, the reaction mixture was quenched with H₂O and EtOAc. The organic phase was washed with H₂O and brine, dried (Na₂SO₄) and concentrated. The residue was triturated with EtOAc. The filter cake was collected to give the title compound as a white solid (1.g, 36%). ¹H NMR (400 MHz, CDCl₃) δ ppm 8.15 (s, 1 H), 7.58 (d, J=8.8 Hz, 2 H), 6.62 (d, J=8.8 Hz, 2 H), 4.63 (br. s., 2H,) 4.08 (br. s., 1 H), 1.90-2.28 (m, 8 H); MS ESI [M+H]⁺ 358.1, calcd for [C₁₄H₁₆INO₂+H]⁺ 358.0.

Synthesis of (1R,3R,5S)-8-(4-iodophenyl)-8-azabicyclo[3.2.1]octan-3-ol

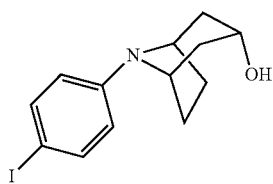 [SMILES: OC1CC2CCC(C1)N2c1ccc(I)cc1]

The title compound was synthesized according to General Method I by utilizing nortropine (2.0 g, 15.7 mmol), 1,4-diiodobenzene (7.78 g, 23.5 mmol), K₃PO₄(10 g, 47 mmol), BINOL (0.9 g, 3.14 mmol), CuI (0.6 g, 3.14 mmol) and anh DMF (48 mL) at 45° C. for 18 h. After reaction completion the solid sludge was filtered through Celite and washed with EtOAc and the filtrate was concentrated to give the crude product. Purification by flash chromatography (Biotage Isolera, 100 g HP-SIL, 0-45% EtOAc in hexanes) gave 2.90 gm of crude product. After trituration with MeOH, the title compound was isolated as light pink solid (1.14 g, crop-1). The filtrate was concentrated and repurified by flash chromatography (Biotage isolera 120 g C18-HS, 5-90% MeOH in H₂O) to give a further 1.12 gm (crop-2) (Combined yield: 2.26 g, 43.6%). ¹H NMR (400 MHz, CDCl₃) δ ppm 7.45-7.48 (m, 2 H), 6.52-6.55 (m, 2 H), 4.14 (br. s, 2 H), 4.01 (br. s, 1 H), 2.29-2.34 (m, 2 H), 2.17-2.23 (m, 2 H), 2.05-2.07 (m, 2 H), 1.56-1.60 (m, 2 H), 1.42 (d, J=2.4 Hz, 1 H); MS ESI 330 [M+H]⁺, calcd for [C₁₃H₁₆INO+H]⁺ 330.

Synthesis of (1R,5S)-3-(4-iodophenyl)-8-oxa-3-azabicyclo[3.2.1]octane

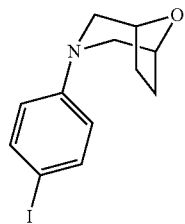 [SMILES: Ic1ccc(N2CC3CCC(C2)O3)cc1]

The title compound was synthesized according to General Method I by utilizing 8-oxa-3-azabicyclo[3.2.1]octane HCl salt (100 mg, 0.66 mmol), 1,4-diiodobenzene (330 mg, 1.0 mmol), K₃PO₄ (567 mg, 2.67 mmol), BINOL (38 mg, 0.13 mmol), CuI (26 mg, 0.13 mmol) and anh DMF (6 mL) at 24° C. for 48 h. After reaction work up and purification by flash chromatography (Biotage Isolera, 50 g HP-SIL, 0-75% EtOAc in hexanes) the title compound was isolated as a white solid (95 mg, 45%). ¹H NMR (400 MHz, CDCl₃) δ ppm 7.51 (d, J=8.3 Hz, 2 H), 6.58 (d, J=8.3 Hz, 2 H), 4.49 (br. s, 2 H), 3.28 (d, j=11.3 Hz, 2 H), 3.00 (d, J=11.3 Hz, 2 H), 1.84-2.05 (m, 4 H); MS ESI 316 [M+H]⁺, calcd for [C₁₂H₁₄INO+H]⁺ 316.

4-(1-(4-iodophenyl)azetidin-3-yl)morpholine

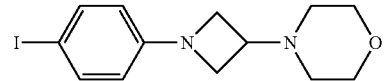 [SMILES: Ic1ccc(N2CC(N3CCOCC3)C2)cc1]

tert-Butyl 3-oxoazetidine-1-carboxylate (7.5 g, 0.043 mol) and morpholine (4.2 g, 0.048 mol) were dissolved into 1,2-DCE (90 mL) at 24° C. and stirred for 15 min. NaBH(OAc)₃ (11.14 g, 0.052 mol) was added portionwise at 24° C. and stirred for 24 h. After completion, 1M Na₂CO₃ (100 mL) was added and the layers were separated. The organic layer was washed with brine followed by H₂O, dried over anh Na₂SO₄ and concentrated in vacuo to give tert-butyl 3-morpholinoazetidine-1-carboxylate as a white solid (10 g, 94%) ¹H NMR (400 MHz, CDCl₃) δ ppm 3.90-3.94 (m, 2 H), 3.79-3.82 (m, 2 H), 3.74 (t, J=4.8 Hz, 4 H), 3.04-3.10 (m, 1 H), 2.36 (br. s, 4 H), 1.43 (s, 9 H); MS ESI 243.01 [M+H]⁺, calcd for [C₁₂H₂₂N₂O₃+H]⁺ 243.17.

tert-butyl 3-morpholinoazetidine-1-carboxylate (10 g, 0.041 mol) was dissolved in DCM (50 mL) and cooled to 5° C. The mixture was treated with 4M HCl-dioxane (50 mL) and stirred for 16 h at rt. The solid was filtered and washed with DCM to give 4-(azetidin-3-yl)morpholine as a white solid (2HCl salt, 8.92 g, 96%). ¹H (free base) (400 MHz, CDCl₃) δ ppm 3.70 (t, J=4 Hz, 4 H), 3.57-3.61 (m, 2 H), 3.51-3.55 (m, 2 H), 3.16-3.23 (m, 1 H), 2.56 (br. s, 1 H), 2.30 (br. s, 4 H); MS ESI 143 [M+H]⁺, calcd for [C₇H₁₄N₂O+H]⁺ 143.11.

The title compound was synthesized according to General Method I by utilizing 4-(azetidin-3-yl)morpholine 2HCl salt (8.1 g, 37 mmol), 1,4-diiodobenzene (15.5 g, 47 mmol), K₃PO₄ (31.4 g, 148 mmol), BINOL (2.1 g, 7.6 mmol), CuI (1.45 g, 7.6 mmol) and anh DMF (90 mL) at 24° C. for 48 h. Work up and purification by flash chromatography (Biotage Isolera, 100 g HP-SIL, 0-60% EtOAc in hexanes) gave a partially pure pale yellow solid. The partial pure product was triturated with MeOH to afford 4.3 gm cream solid (crop-1). The combined filtrates were concentrated and the residue purified by flash chromatography (Biotage Isolera 120 g C18, 5-90% MeOH in H$_2$O) to give 1.5 g cream solid (crop 2) (5.8 g total, 45%). $^1$H NMR (400 MHz, CDCl$_3$) δ ppm 7.46 (d, J=8.8 Hz, 2 H), 6.24 (d, J=8.8 Hz, 2 H), 3.94 (t, J=6.8 Hz, 2 H), 3.75 (t, J=4.4 Hz, 4 H), 3.67-3.70 (m, 2 H), 3.28-3.34 (m, 1 H), 2.43-2.44 (br. s, 4 H); MS ESI 345.0 [M+H]$^+$, calcd for [C$_{13}$H$_{17}$IN$_2$O+H]$^+$ 345.04.

Amide Coupling

The title compound was synthesized according to the General Method A

Synthesis of 6-bromo-1'-methylspiro[chroman-2,4'-piperidin]-4-one

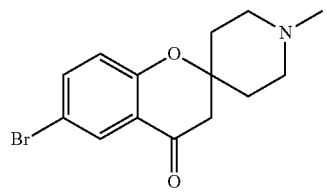

A mixture of 5-bromo-2-hydroxyacetophenone (2.0 g, 9.3 mmol), pyrrolidine (0.99 mL, 12.1 mmol), 1-methyl-4-

| IUPAC name | Structure | MS calculated MS ESI [M + H]$^+$ | Yield; Appearance; Salt form |
|---|---|---|---|
| (S)-1-(4-(4-bromophenoxy)piperidin-1-yl)-2-hydroxypropan-1-one | 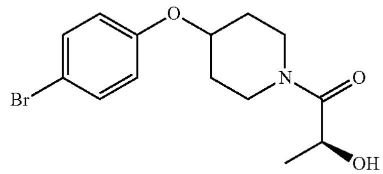 [SMILES: C[C@H](O)C(=O)N1CCC(Oc2ccc(Br)cc2)CC1] | [C$_{14}$H$_{18}$BrNO$_3$ + H]$^+$ 328.05, 330.04 330.0, 328.0 | 0.23 g (68%) pale yellow gum; free base |
| SMs: 4-(4-bromophenoxy)piperidine hydrochloride (0.30 g, 1.0 mmol), (S)-2-hydroxypropanoic acid (92 mg, 1.0 mmol) $^1$H NMR (400 MHz, CD$_3$OD) δ ppm 7.40 (d, J = 9.03 Hz, 2 H), 6.92 (d, J = 8.8 Hz, 2 H), 4.54-4.69 (m, 2 H), 3.70-3.99 (br.m, 2 H), 3.41-3.68 (br.m, 2 H), 1.89-2.09 (m, 2 H), 1.65-1.85 (m, 2 H), 1.33 (d, J = 6.5 Hz, 3 H) ||||
| (R)-1-(4-(4-bromophenoxy)piperidin-1-yl)-2-hydroxypropan-1-one | 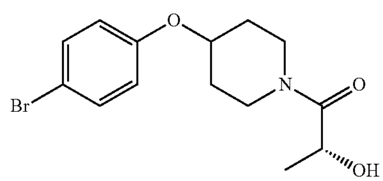 [SMILES: C[C@@H](O)C(=O)N1CCC(Oc2ccc(Br)cc2)CC1] | [C$_{14}$H$_{18}$BrNO$_3$ + H]$^+$ 328.05 328.3 | 0.22 g (61%); pale yellow oil; free base |
| SMs:: 4-(4-bromophenoxy)piperidine hydrochloride (0.32 g, 1.1 mmol), (R)-2-hydroxypropanoic acid (100 mg, 1.1 mmol) $^1$H NMR (400 MHz, CDCl$_3$) δ ppm 7.38 (d, J = 8.8 Hz, 2 H), 6.80 (d, J = 8.8 Hz, 2 H), 4.41-4.61 (m, 2 H), 4.20 (br. s., 1 H), 3.23-3.92 (m, 4 H), 1.77-1.98 (m, 4 H), 1.34 (d, J = 6.5 Hz, 3 H) ||||
| 1-(4-(4-bromophenoxy)piperidin-1-yl)-2-hydroxy-2-methylpropan-1-one | 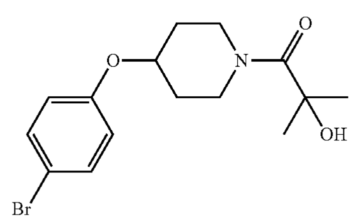 [SMILES: CC(C)(O)C(=O)N1CCC(Oc2ccc(Br)cc2)CC1] | [C$_{15}$H$_{20}$BrNO$_3$ + H]$^+$ 342.06, 344.06; 342.2, 344.0 | 184 mg (52%); pale yellow gum; free base |
| SMs: 4-(4-bromophenoxy)piperidine hydrochloride (0.30 g, 1.0 mmol), 2-hydroxy-2-methylpropanoic acid (107 mg, 1.0 mmol) $^1$H NMR (400 MHz, CDCl$_3$) δ ppm 7.39 (d, J = 9.0 Hz, 2 H), 6.80 (dd, J = 8.8, 1.8 Hz, 2 H), 4.47-4.62 (m, 1 H), 3.51-3.89 (m, 4 H), 1.73-2.02 (m, 4 H), 1.51 (s, 6 H) ||||
| 2-hydroxy-1-(4-(4-(4,4,5,5-tetramethyl-1,3,2-dioxaborolan-2-yl)phenoxy)piperidin-1-yl)ethanone | 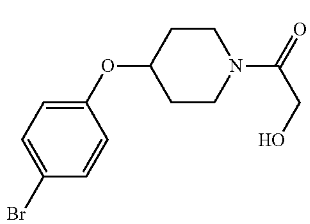 [SMILES: O=C(CO)N1CCC(Oc2ccc(Br)cc2)CC1] | [C$_{13}$H$_{16}$Br NO$_3$ + H]$^+$ 314.03, 316.03; 314.2, 315.9 | 0.22 g (64%); white powder; free base |
| SMs: 4-(4-bromophenoxy)piperidine hydrochloride (0.33 g, 1.1 mmol), 2-hydroxyacetic acid (85 mg, 1.2 mmol) $^1$H NMR (400 MHz, CD$_3$OD) δ ppm 7.39 (d, J = 8.8 Hz, 1 H), 6.91 (d, J = 8.8 Hz, 1 H), 4.56-4.67 (m, 1 H), 4.24 (s, 2 H), 3.78-3.89 (m, 1 H), 3.50-3.69 (m, 2 H), 3.27-3.42 (m, 1 H), 1.89-2.06 (m, 2 H), 1.66-1.82 (m, 2 H) |||| piperidone (1.41 mL, 12.1 mmol) and MeOH (40 mL) heated to 80° C. for 16 h. The reaction mixture was then concentrated in vacuo and the residue purified by flash chromatography (Biotage Isolera, 50 g HP-SIL, 0-25% EtOAc in hexanes) to give the title compound as a brown solid (2.52 g, 87%). $^1$H NMR (400 MHz, CD$_3$OD) δ ppm 7.97 (d, J=2.3 Hz, 1 H), 7.57 (dd, J=8.8, 2.5 Hz, 1 H), 6.91 (d, J=8.8 Hz, 1 H), 2.71 (s, 2 H), 2.60 (d, J=11.5 Hz, 2 H), 2.45-2.35 (m, 2 H), 2.33 (s, 3 H), 2.05 (d, J=12.0 Hz, 2 H), 1.69-1.83 (m, 2 H); MS ESI 298.1 [M+H]$^+$, calcd for [C$_{14}$H$_{16}$BrNO$_2$+H]$^+$ 311.0.

The following intermediates were synthesized according to the synthesis of General Method K (7.88 mL) was stirred at 25° C. The reaction mass was treated with 4M HCl-dioxane (7.8 mL) & stirred for 5 h at rt. The solvent was removed under reduced pressure to give a brown oil and was treated it with 2M aq Na$_2$CO$_3$ to alkaline pH. The product was extracted using EtOAc, dried (Na$_2$SO$_4$) and concentrated in vacuo to give a light brown oil (525 mg, 92%).

The oil was dissolved in DCM (10.5 mL) and formalin (0.206 mL, 2.37 mmol) was added at 25° C. NaBH(OAc)$_3$ (540 mg, 2.54 mmol) was added and the mixture was stirred for 2 h 25° C. The reaction mass washed with 1M aq

| IUPAC name | Structure | MS calculated MS ESI [M + H]$^+$ | Yield; Appearance; Salt form |
|---|---|---|---|
| 6-bromo-2',3',5',6'-tetrahydrospiro[chroman-2,4'-pyran]-4-one | 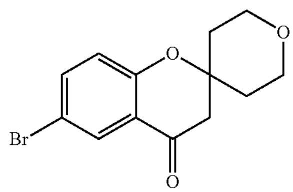 [SMILES: O=C1CC2(CCOCC2)Oc2ccc(Br)cc21] | [C$_{13}$H$_{13}$BrO$_3$ + H]$^+$ 298 299 | 1.35 g (49%); yellow oil |

SMs: 5-bromo-2-hydroxyacetophenone (2.0 g, 9.3 mmol), pyrrolidine (0.86 mL, 10.6 mmol), tetrahydropyran-4-one (0.86 mL, 9.3 mmol), MeOH (20 mL)
$^1$H NMR (400 MHz, CDCl$_3$) δ ppm 7.98 (d, J = 2.5 Hz, 1 H), 7.58 (dd, J = 8.8, 2.5 Hz, 1 H), 6.91-6.97 (m, 1 H), 3.74-3.87 (m, 4 H), 2.75 (s, 2 H), 1.93-2.01 (m, 2 H), 1.73-1.83 (m, 2 H)

| tert-butyl 6'-bromo-4'-oxospiro[azetidine-3,2'-chroman]-1-carboxylate | | [C$_{16}$H$_{18}$BrNO$_4$ + H]$^+$ 369.04 314.2 | 2.6 g (60%); yellow solid |

SMs: 5-bromo-2-hydroxyacetophenone (2.5 g, 11.7 mmol), pyrrolidine (0.97 mL, 11.7 mmol), tert-butyl 3-oxoazetidine-1-carboxylate (2.0 g, 11.7 mmol), MeOH (10 mL)
$^1$H NMR (400 MHz, CDCl$_3$) δ ppm 7.99 (d, J = 2.5 Hz, 1 H), 7.57-7.64 (m, 1 H), 6.98 (d, J = 8.8 Hz, 1 H), 4.08 (d, J = 9.3 Hz, 2 H), 3.96 (d, J = 9.5 Hz, 2 H), 3.04 (s, 2 H) 1.41-1.48 (m, 9 H)

| 6-bromo-2,2-dimethylchroman-4-one | | [C$_{11}$H$_{11}$BrO$_2$ + H]$^+$ 255.9 256.9 | 2.0 g (84%); pale yellow oil |

SMs: 5-bromo-2-hydroxyacetophenone (2.0 g, 18.6 mmol), pyrrolidine (0.90 mL, 22.3 mmol), Acetone (4.0 mL, 54.4 mmol), MeOH (12 mL)
$^1$H NMR (400 MHz, CDCl$_3$) δ ppm 7.97-7.98 (m, 1 H), 7.53-7.56 (m, 1 H), 6.83-6.85 (m, 1 H), 2.72 (s, 2 H), 1.46 (s, 6 H)

Synthesis of 6'-bromo-1-methylspiro[azetidine-3,2'-chroman]-4'-one

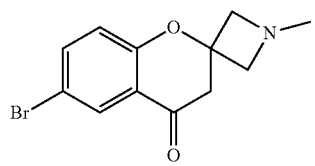 [SMILES: CN1CC2(CC(=O)c3cc(Br)ccc3O2)C1]

A solution of tert-butyl 6'-bromo-4'-oxospiro[azetidine-3,2'-chroman]-1-carboxylate (525 mg, 1.95 mmol) in DCM Na$_2$CO$_3$ solution, and the aqueous layer was extracted with DCM (25 mL) and the combined organic layer washed with H$_2$O, dried (Na$_2$SO$_4$) and concentrated in vacuo. Purification by flash chromatography (Biotage Isolera, 50 g HP-SIL, 0-10% MeOH in DCM) gave the title compound as a brown oil (465 mg, 84%). $^1$H NMR (400 MHz, CDCl$_3$) δ ppm 7.97 (d, J=2.8 Hz, 1 H), 7.58 (dd, J=9.0, 2.3 Hz, 1 H), 6.95 (d, J=8.8 Hz, 1 H), 3.45 (d, J=9.0 Hz, 2 H), 3.26 (d, J=8.8 Hz, 2 H), 3.06 (s, 2 H), 2.43 (s, 3 H); MS ESI 283.9 [M+H]$^+$, calcd for [C$_{12}$H$_{12}$BrNO$_2$+H]$^+$ 283.

Synthesis of 6-bromo-4-oxospiro[chroman-2,4'-piperidine]-1'-carbaldehyde

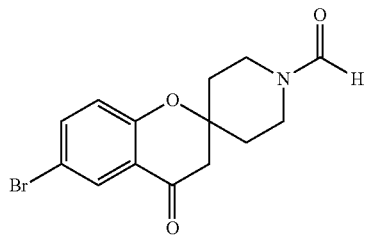 [SMILES: O=CN1CCC2(CC1)CC(=O)c1cc(Br)ccc1O2]

To a solution of 6-bromospiro[chroman-2,4'-piperidin]-4-one (1.2 g, 4 mmol) in PhMe (18 mL) was added HCOOH (0.28 g, 6 mmol). The reaction mixture was heated to 125° C. for 5 h and concentrated in vacuo to the title compound as a light brown oil (1.22 g, 93%). $^1$H NMR (400 MHz, CDCl$_3$) δ ppm 8.07 (s, 1H), 8.00 (s, 1 H), 7.61 (dd, J=8.8, 2.5 Hz, 1 H), 6.94 (d, J=8.8 Hz, 1 H), 4.17-4.34 (m, 1 H), 3.42-3.55 (m, 2 H), 3.10 (ddd, J=13.3, 12.4, 3.1 Hz, 1 H), 2.75 (d, J=1.5 Hz, 2 H), 2.06-2.21 (m, 2 H), 1.52-1.68 (m, 2 H); MS ESI 326 [M+H]$^+$, calcd for [C$_{14}$H$_{14}$BrNO$_3$+H]$^+$ 325.

Synthesis of 6-bromo-1',4-dimethylspiro[chromene-2,4'-piperidine]

A. 6-bromo-1',4-dimethylspiro[chroman-2,4'-piperidin]-4-ol

Trimethylaluminum (7 mL, 25% in hexanes, 24 mmol) was added drop wise to a degassed stirred solution of 6-bromo-1'-methylspiro[chroman-2,4'-piperidin]-4-one (1.5 g, 4.8 mmol) in PhMe (30 mL) at 0° C. The resulting solution was allowed to warm up to rt and left to stir for 16 h. The crude reaction mixture was poured into ice-cold sat. aq NaHCO$_3$ (50 mL), and the aqueous layer was extracted with EtOAc (2×150 mL), dried (Na$_2$SO$_4$,) filtered and solvents were removed in vacuo. Purification by flash chromatography (Biotage Isolera, 50 g HP-SIL, 0-25% 1MNH$_3$-MeOH in DCM) gave the title compound as a cream solid (1.27 g, 80%); $^1$H NMR (400 MHz, CD$_3$OD) δ ppm 7.62 (d, J=2.5 Hz, 1 H), 7.27 (dd, J=8.7, 2.4 Hz, 1 H), 6.77 (d, J=8.8 Hz, 1 H), 2.66 (br. s., 1 H), 2.50-2.62 (m, 2 H), 2.25-2.38 (m, 4 H), 2.04-2.20 (m, 2 H), 1.96 (s, 1 H) 1.67-1.88 (m, 3 H), 1.54 (s, 3 H); MS ESI 327.9 [M+H]$^+$, calcd for [C$_{15}$H$_{20}$BrNO$_2$+H]$^+$ 327.

B. 6-bromo-1',4-dimethylspiro[chromene-2,4'-piperidine]

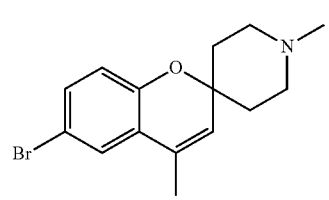 [SMILES: CC1=CC2(CCN(C)CC2)Oc2ccc(Br)cc21]

To a solution, of 6-bromo-1',4-dimethylspiro[chroman-2,4'-piperidin]-4-ol (1.5 g) in DCM (50 mL) was added PTSA.H$_2$O (1.27 g) at rt and left to stir for 16 h. The reaction mass washed with 0.5M aq Na$_2$CO$_3$ solution (50 mL) followed by H$_2$O, dried (Na$_2$SO$_4$,) and concentrated in vacuo to gave the title compound as a light brown oil (1.2 g, 80%). $^1$H NMR (400 MHz, CDCl$_3$) δ ppm 7.19-7.31 (m, 2 H), 6.75 (d, J=8.3 Hz, 1 H), 5.43 (s, 1 H), 2.58 (d, J=11.3 Hz, 2 H), 2.38-2.50 (m, 2 H), 2.34 (s, 3 H), 1.91-2.04 (m, 4 H), 1.58-1.88 (m, 3 H); MS ESI 310.1 [M+H]$^+$, calcd for [C$_{15}$H$_{18}$BrNO+H]$^+$ 309.

Synthesis of 6-bromo-2,2,4-trimethyl-2H-chromene

A. 6-bromo-2,2,4-trimethylchroman-4-ol

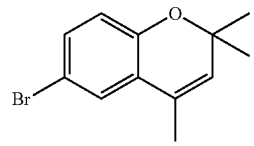

The title compound was synthesized as above by utilizing Me$_3$Al (1.98 mL, 25% in hexanes, 6.86 mmol), 6-bromo-2,2-dimethylchroman-4-one (0.5 g, 1.95 mmol) in PhMe (10 mL). After work up and purification by flash chromatography (Biotage Isolera, 50 g HP-SIL, 0-30% EtOAc in hexanes) gave the title compound as a white solid (0.46 g, 86.6%); $^1$H NMR (400 MHz, CDCl$_3$) δ 7.58 (d, J=2.4 Hz, 1 H), 7.25-7.28 (m, 1 H), 6.73 (d, J=8.8 Hz, 1 H), 2.00-2.11 (m, 2 H), 1.79 (s, 1 H), 1.52-1.61 (m, 3 H), 1.41 (d, J=5.8 Hz, 6 H)

B. 6-bromo-1',4-dimethylspiro[chromene-2,4'-piperidine]

To a solution, of 6-bromo-2,2,4-trimethylchroman-4-ol (0.45 g) in DCM (18 mL) was added PTSA.H$_2$O (0.45 g) at rt and left to stir for 16 h. The reaction was washed with sat. aq NaHCO$_3$ solution (2×20 mL) followed by H$_2$O, dried (Na$_2$SO$_4$,) and concentrated in vacuo to give the title compound as a colorless oil (0.4 g, 80%). $^1$H NMR (400 MHz, CDCl$_3$) δ ppm 7.16-7.30 (m, 2 H), 6.68 (d, J=8.5 Hz, 1 H), 5.46 (d, J=1.5 Hz, 1 H), 1.98 (d, J=1.3 Hz, 3 H), 1.36-1.44 (m, 6 H)

Synthesis of 6-bromo-1'-(oxetan-3-yl)spiro[chroman-2,4'-piperidin]-4-one

A. 6-bromospiro[chroman-2,4'-piperidin]-4-one hydrochloride

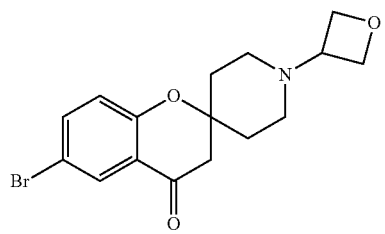 [SMILES: O=C1CC2(CCN(C3COC3)CC2)Oc2ccc(Br)cc21]

A mixture of 5-bromo-2-hydroxyacetophenone (6.0 g, 0.027 mol) and pyrrolidine (2.7 mL, 0.033 mol) in MeOH (48 mL) was stirred at 25° C. for 20 min in a sealed flask. The mixture was then treated with 1-Boc-4-piperidone (5.55 g, 0.027 mol) and heated to 80° C. for 16 h. The reaction mixture was then concentrated in vacuo and the residue dissolved in DCM (50 mL), cooled to 15° C., treated with 4M HCl-dioxane (30 mL) and stirred for 16 h at rt. The solid was filtered and washed with DCM to the title compound as a cream color HCl salt (8.92 g, 96%). $^1$H NMR (400 MHz, CD$_3$OD) δ 7.93 (d, J=2.5 Hz, 1 H), 7.71 (dd, J=8.9, 2.6 Hz, 1 H), 7.11 (d, J=9.0 Hz, 1 H), 3.32-3.41 (m, 4 H), 2.90 (s, 2 H), 2.23-2.36 (m, 2 H), 1.87-2.05 (m, 2 H), MS ESI 297 [M+H]$^+$, calcd for [C$_{13}$H$_{14}$BrNO$_2$+H]$^+$ 297.02.

B. 6-bromo-1'-(oxetan-3-yl)spiro[chroman-2,4'-piperidin]-4-one

A suspension of 6-bromospiro[chroman-2,4'-piperidin]-4-one hydrochloride (11.1 g, 0.033 mol) and H$_2$O (55 mL) was treated with 1N NaOH until pH: 10 at 25° C. for 30 min. The product was extracted with EtOAc (125 mL) and washed with H$_2$O and brine (50 mL each), dried (Na$_2$SO$_4$,) and concentrated under vacuum to give free base as brown thick oil (9.5 g, 96%). The oil was dissolved in 1,2-DCE (145 mL) and 3-oxetanone (2.88 g, 0.039 mol) was added at 5° C. NaBH(OAc)$_3$ (9.15 g, 0.043 mol) was added to an ice cooled reaction mass and the reaction mixture was stirred over night at rt. The reaction was washed with 1M Na$_2$CO$_3$ solution (100 mL) and the aqueous layer was extracted with DCM (50 mL) and the combined organic layer was washed with H$_2$O, dried (Na$_2$SO$_4$,) and concentrated in vacuo. Purification by flash chromatography (Biotage Isolera, 100 g HP-SIL, 10-15% MeOH in DCM) gave the title compound as a yellow solid (9.25 g, 78%). $^1$H NMR (400 MHz, CDCl$_3$) δ ppm 7.97 (d, J=2.5 Hz, 1 H), 7.57 (dd, J=8.9, 2.6 Hz, 1 H), 6.89 (d, J=8.8 Hz, 1 H), 4.64-4.71 (m, 2 H), 4.55-4.65 (m, 2 H), 3.55 (t, J=6.4 Hz, 1 H), 2.67-2.75 (m, 2 H), 2.45-2.55 (m, 2 H), 2.27 (td, J=11.5, 2.5 Hz, 2 H), 2.03-2.14 (m, 2 H), 1.71-1.83 (m, 2 H); MS ESI 352.1 [M+H]$^+$, calcd for [C$_{16}$H$_{18}$BrNO$_3$+H]$^+$ 352.2

Synthesis of (1R,5S)-8-(4-bromophenyl)-8-azabicyclo[3.2.1]octan-3-one

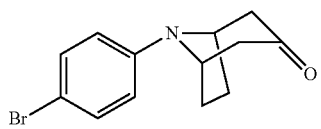 [SMILES: O=C1CC2CCC(C1)N2c1ccc(Br)cc1]

To a solution of 2,5-dimethoxytetrahydrofuran (43.5 g, 330 mmol) and 3-oxopentanedioic acid (16.8 g, 345 mmol) in H$_2$O (200 mL) was added concentrated HCl (24 mL). The resulting solution was stirred at rt for 30 min, then cooled to 0° C. A solution of 4-bromoaniline (51.6 g, 300 mmol) in MeOH (250 mL) was added over 20 min. After addition, the resulting mixture was stirred O/N at rt. Conc. HCl (6 mL) was added and reaction was heated at 55° C. for 2 h. After quenching with K$_2$CO$_3$/H$_2$O (27.6 g/200 mL) to pH about 7, it was stirred at rt for 45 min. The precipitated were collected by suction filtration, rinsed with H$_2$O, MeOH and dried to give the title compound as brown solid (73.98 g, 88%). $^1$H NMR (400 MHz, CDCl$_3$) δ ppm 7.40 (d, J=8.8 Hz, 2H), 6.77 (d, J=8.8 Hz, 2H), 4.48-4.44 (m, 2H), 2.65 (dd, J=15.6, 4.0 Hz, 2H), 2.33 (d, J=15.6 Hz, 2H), 2.14-2.07 (m, 2H), 1.85-1.78 (m, 2H). MS ESI 279.9 [M+H]$^+$, calcd for [C$_{13}$H$_{14}$BrNO+H]$^+$ 280.0.

The following intermediates were synthesized according to the synthesis of (1R,5S)-8-(4-bromophenyl)-8-azabicyclo [3.2.1]octan-3-one:

| IUPAC name | Structure | MS calculated<br>MS ESI [M + H]$^+$ | Yield;<br>Appearance;<br>Salt form |
|---|---|---|---|
| (1R,5S)-9-(4-bromophenyl)-3-oxa-9-azabicyclo[3.3.1]nonan-7-one | 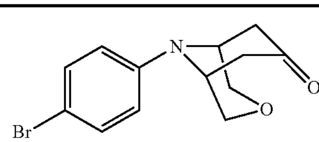 | [C$_{13}$H$_{14}$BrNO$_2$ + H]$^+$ 296.0<br>296.0 | 0.88 g (15%),<br>light brown<br>solid; free base |
| (1R,5S)-9-(4-bromophenyl)-9-azabicyclo[3.3.1]nonan-3-one | 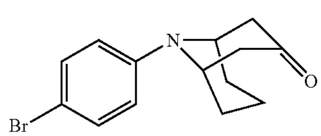 [SMILES: O=C1CC2CCCC(C1)N2c1ccc(Br)cc1] | [C$_{14}$H$_{16}$BrNO + H]$^+$ 294.0<br>294.0 | 2.97 g (10%),<br>brown solid<br>and 6.2 g<br>brown oil (used<br>without further<br>purification);<br>free base |

SMs: 2-(2,2-diethoxyethoxy)-1,1-diethoxyethane (5.00 g, 20 mmol), 3-oxopentanedioic acid (1.61 g, 22 mmol), 4-bromoaniline (3.44 g, 20 mmol)
$^1$H NMR (400 MHz, CDCl$_3$) δ ppm 7.42 (d, J = 9.2 Hz, 2H), 6.83 (d, J = 9.2 Hz, 2H), 4.19 (d, J = 5.6 Hz, 1H), 3.94 (d, J = 11.2 Hz, 2H), 3.88 (d, J = 11.2 Hz, 2H), 2.59 (dd, J = 15.6, 5.6 Hz, 2H), 2.48 (d, J = 15.2 Hz, 2H).

SMs: glutaraldehyde (50% wt in H$_2$O, 20 mL, 110 mmol), 3-oxopentanedioic acid (16.8 g, 115 mmol), 4-bromoaniline (17.2 g, 100 mmol)
$^1$H NMR (400 MHz, CDCl$_3$) δ ppm 7.37 (d, J = 8.8 Hz, 2H), 6.85 (d, J = 9.2 Hz, 2H), 4.45-4.38 (m, 2H), 2.65 (dd, J = 16.4, 6.4 Hz, 2H), 2.41 (d, J = 16.4 Hz, 2H), 2.02-1.90 (m, 2H), 1.80-1.73 (m, 2H), 1.70-1.61 (m, 2H).

Synthesis of 2-methyl-1-(4-(4-(4,4,5,5-tetramethyl-1,3,2-dioxaborolan-2-yl)phenoxy)piperidin-1-yl)propan-2-ol

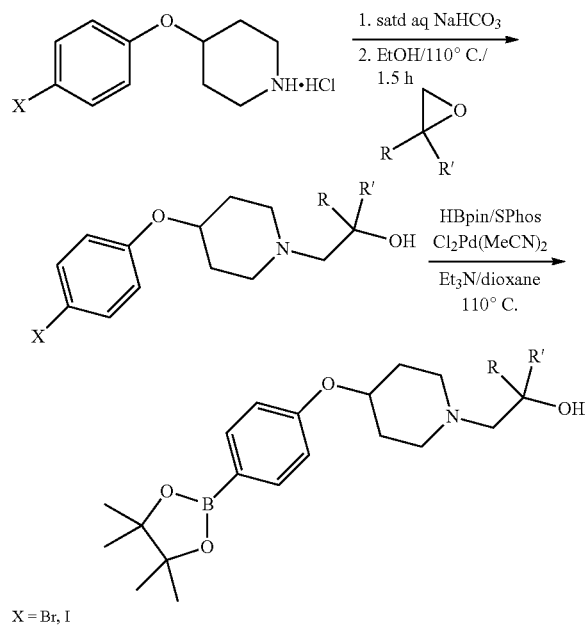

X = Br, I

A. 1-(4-(4-bromophenoxy)piperidin-1-yl)-2-methyl-propan-2-ol 4-(4-Bromophenoxy)piperidine hydrochloride (300 mg, 1.03 mmol) was free-based by washing with aqueous NaHCO$_3$ (sat.) (25 mL) and extracted into CH$_2$Cl$_2$ (3×50 mL). The organic layers were dried over MgSO$_4$ and the solvent removed by rotary evaporation to give a colourless oil that was transferred to microwave vial with 2 mL of EtOH. 2,2-Dimethyloxirane (91 uL, 1.03 mmol) was then added, the microwave vial capped and the reaction heated to 110° C. for 90 min. The solvent was evaporated and the material dried under high vacuum yielding 300 mg, 89% of the product as a pale-yellow oil. $^1$H NMR (400 MHz, CDCl$_3$) δ ppm 7.37-7.33 (m, 2H), 6.80-6.76 (m, 2H), 4.28 (m, 1H), 3.21-3.15 (bs, 1H), 2.89-2.84 (m, 2H), 2.55-2.49 (m, 2H), 2.32 (s, 2H), 1.97-1.93 (m, 2H), 1.83-1.75 (m, 2H), 1.16 (s, 6H); MS ESI 330.0 [M+H]$^+$, calcd for [C$_{15}$H$_{22}$BrNO$_2$+H]$^+$ 330.09.

B. 2-methyl-1-(4-(4-(4,4,5,5-tetramethyl-1,3,2-dioxaborolan-2-yl)phenoxy)piperidin-1-yl)propan-2-ol

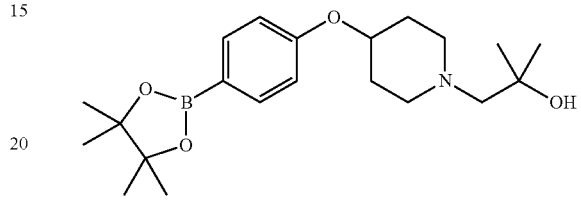

A mixture of 1-(4-(4-bromophenoxy)piperidin-1-yl)-2-methylpropan-2-ol (300 mg, 0.914 mmol), HBpin (0.26 mL, 1.83 mmol), S-Phos (15 mg, 0.036 mmol), Cl$_2$Pd(CH$_3$CN)$_2$ (2.3 mg, 0.0091 mmol), NEt$_3$ (0.38 mL, 2.74 mmol), and dioxane (1.8 mL) was heated to 110° C. for 3 h. The reaction was cooled to room temperature, diluted with EtOAc (50 mL) and then washed successively with aqueous NaHCO$_3$ (sat.) (25 mL), H$_2$O (25 mL), and brine (25 mL). The solvent was removed by rotary evaporation and the material was dried under high-vacuum which yielded 350 mg, ~quant. of a material of 85% purity that was used without further purification. $^1$H NMR (400 MHz, CD$_3$OD) δ ppm 7.73 (d, J=8.5 Hz, 2H), 6.88 (d, J=8.6 Hz, 2H), 4.38 (m, 1H), 2.87-2.85 (m, 2H), 2.57-2.51 (m, 2H), 2.34 (s, 2H), 1.94-1.85 (m, 2H), 1.84-1.74 (m, 2H), 1.33 (s, 12H), 1.16 (s, 6H); MS ESI 376.2 [M+H]$^+$, calcd for [C$_{21}$H$_{34}$BNO$_4$+H]$^+$ 376.27.

The following boronic esters were synthesized according to the method for methyl-1-(4-(4-(4,4,5,5-tetramethyl-1,3,2-dioxaborolan-2-yl)phenoxy)piperidin-1-yl)propan-2-ol

| IUPAC name | Structure | MS calculated MS ESI [M + H]$^+$ | Yield; Appearance; Salt form |
|---|---|---|---|
| (R)-1-(4-(4-(4,4,5,5-tetramethyl-1,3,2-dioxaborolan-2-yl)phenoxy)piperidin-1-yl)propan-2-ol | 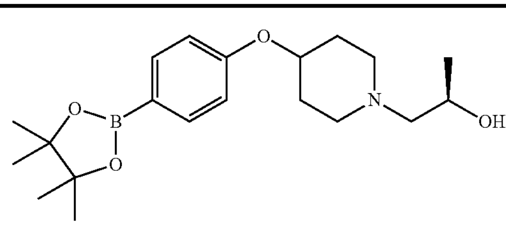 | [C$_{20}$H$_{32}$BNO$_4$ + H$^+$] 362.25 362.2 | 673 mg (90%); free base |

SMs: 4-(4-bromophenoxy)piperidine hydrochloride (600 mg, 2.1 mmol), 2(R)-2-methyloxirane (0.14 mL, 2.06 mmol), HBpin (0.76 mL, 5.2 mmol), S-Phos (68 mg, 0.16 mmol), Cl$_2$Pd(CH$_3$CN)$_2$ (11 mg, 0.041 mmol), NEt$_3$ (0.86 mL, 6.2 mmol)
$^1$H NMR (400 MHz, CDCl$_3$) δ ppm 7.73 (d, J = 8.5 Hz, 2H), 6.89 (d, J = 8.6 Hz, 2H), 4.40-4.37 (bs, 1H), 3.87-3.83 (bs, 1H), 2.92-2.84 (m, 1H), 2.71-2.60 (m, 2H), 1.99-1.60 (m, 8H), 1.32 (s, 12H), 1.13 (d, J = 6.0 Hz, 3H)

| IUPAC name | Structure | MS calculated MS ESI [M + H]+ | Yield; Appearance; Salt form |
|---|---|---|---|
| (R)-1,1,1-trifluoro-3-(4-(4-(4,4,5,5-tetramethyl-1,3,2-dioxaborolan-2-yl)phenoxy)piperidin-1-yl)propan-2-ol | 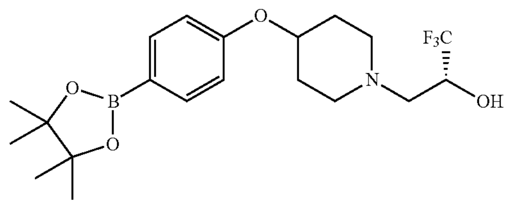 [SMILES: CC1(C)OB(c2ccc(OC3CCN(C[C@@H](O)C(F)(F)F)CC3)cc2)OC1(C)C] | [$C_{20}H_{29}BF_3NO_4$ + H]+ 416.22 416.3 | 730 mg (79%); free base |

SMs: 4-(4-bromophenoxy)piperidine hydrochloride (650 mg, 2.2 mmol), (R)-2-(trifluoromethyl)oxirane (250 mg, 2.2 mmol), HBpin (0.81 mL, 5.6 mmol), S-Phos (73 mg, 0.18 mmol), Cl$_2$Pd(CH$_3$CN)$_2$ (12 mg, 0.045 mmol), NEt$_3$ (0.93 mL, 6.7 mmol)

$^1$H NMR (400 MHz, CD$_3$OD) δ ppm 7.65 (d, J = 8.5 Hz, 2H), 6.89 (d, J = 8.6 Hz, 2H), 4.49-4.45 (m, 1H), 4.18-4.13 (m, 1H), 2.87-2.84 (m, 2H), 2.64-2.61 (m, 2H), 2.52-2.45 (m, 2H), 2.09-2.00 (m, 2H), 1.83-1.78 (m, 2H), 1.32 (m, 12H)

The following intermediates were synthesized according to General Method E (or F where indicated):

| IUPAC name | Structure | MS calculated MS ESI [M + H]+ | Yield; Appearance; Salt form |
|---|---|---|---|
| cis-3-(4-(4,4,5,5-tetramethyl-1,3,2-dioxaborolan-2-yl)phenoxy)cyclohexanol | 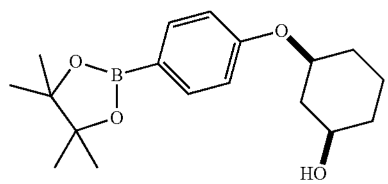 | [$C_{18}H_{27}BO_4$ + H]+ 319.2 | 350 mg (crude), colorless oil |

SMs: (method F) 3-(4-iodophenoxy)cyclohexanol (296 mg, 0.93 mmol), HBpin (0.54 mL, 3.72 mmol)

$^1$H NMR (400 MHz, CDCl$_3$) δ ppm 7.66 (d, J = 8.8 Hz, 2H), 6.90 (d, J = 8.4 Hz, 2H), 4.38-4.30 (m, 1H), 3.71-3.62, (m, 1H), 2.43-2.37 (m, 1H), 2.13-2.05 (m, 1H), 1.98-1.92 (m, 1H), 1.88-1.80 (m, 1H), 1.34 (s, 12H).

| IUPAC name | Structure | MS calculated MS ESI [M + H]+ | Yield; Appearance; Salt form |
|---|---|---|---|
| 1'-methyl-6-(4,4,5,5-tetramethyl-1,3,2-dioxaborolan-2-yl)Spiro[chroman-2,4'-piperidin]-4-one | 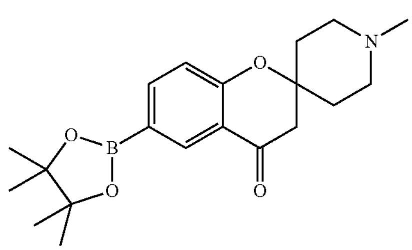 | [$C_{22}H_{30}BNO_5$ + H]+ 400.2 400.2 | 372 mg (43%); brown solid |

SMs: 6-bromo-1'-methylspiro [chroman-2,4'-piperidin]-4-one (750 mg, 2.41 mmol), B$_2$pin$_2$ (921 mg, 3.62 mmol), KOAc (712 mg, 0.063 mmol), PdCl$_2$dppf*CH$_2$Cl$_2$ (119 mg, 0.145 mmol), anh DMF (11.25 mL)

$^1$H NMR (400 MHz, CDCl$_3$) δ ppm 8.37 (s, 1 H), 7.85-7.96 (m, 1 H), 6.93-7.04 (m, 1 H), 2.78-2.85 (m, 2 H), 2.71-2.77 (m, 2 H), 2.54-2.67 (m, 2 H), 2.43 (s, 3 H), 2.08 (br. s., 2 H), 1.87-2.00 (m, 2 H), 1.33 (s, 12 H)

| IUPAC name | Structure | MS calculated MS ESI [M + H]⁺ | Yield; Appearance; Salt form |
|---|---|---|---|
| 6-(4,4,5,5-tetramethyl-1,3,2-dioxaborolan-2-yl)-2',3',5',6'-tetrahydrospiro[chroman-2,4'-pyran]-4-one | 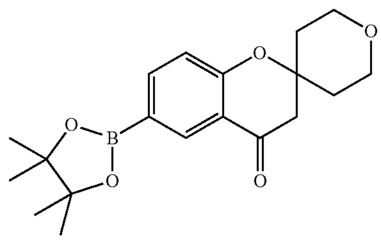 [SMILES: CC1(C)OB(c2ccc3c(c2)C(=O)CC2(CCOCC2)O3)OC1(C)C] | [$C_{19}H_{25}BO_5$ + H]⁺ 345.1 345.2 | 340 mg (58%); Light brown solid |

SMs: 6-bromo-2',3',5',6'-tetrahydrospiro[chroman-2,4'-pyran]-4-one (500 mg, 1.68 mmol), bis(pinacolato)diboron (640 mg, 2.52 mmol), KOAc (495 mg, 5.06 mmol), PdCl₂dppf*CH₂Cl₂ (68 mg, 0.084 mmol
¹H NMR (400 MHz, CDCl₃) δ ppm 8.33-8.39 (m, 1 H), 7.89-7.96 (m, 1 H), 6.98-7.04 (m, 1 H), 3.73-3.89 (m, 4 H), 2.75 (s, 2 H), 1.93-2.02 (m, 2 H,) 1.73-1.84 (m, 2 H), 1.34 (s, 12 H)

| IUPAC name | Structure | MS calculated | Yield |
|---|---|---|---|
| 1-methyl-6'-(4,4,5,5-tetramethyl-1,3,2-dioxaborolan-2-yl)spiro[azetidine-3,2'-chroman]-4'-one | | [$C_{18}H_{24}BNO_4$ + H]⁺ 330.1 330.2 | 251 mg (46%); brown semi solid |

SMs: 6'-bromo-1-methylspiro[azetidine-3,2'-chroman]-4'-one (465 mg, 1.64 mmol) B₂pin₂ (628 mg, 2.47 mmol), KOAc (485 mg, 4.94 mmol), PdCl₂dppf*CH₂Cl₂ (100 mg, 0.122 mmol
¹H NMR (400 MHz, CDCl₃) δ ppm 8.35 (s, 1 H), 7.82-7.98 (m, 1 H), 6.94-7.10 (m, 1 H), 3.61 (d, J = 9.3 Hz, 2 H), 3.36 (d, J = 8.8 Hz, 2 H), 3.07 (s, 2 H,) 2.48 (s, 3 H), 1.32 (s, 12 H)

| IUPAC name | Structure | MS calculated | Yield |
|---|---|---|---|
| 1'-(oxetan-3-yl)-6-(4,4,5,5-tetramethyl-1,3,2-dioxaborolan-2-yl)spiro[chroman-2,4'-piperidin]-4-one | | [$C_{22}H_{30}BNO_5$ + H]⁺ 400.2 400.3 | 8.1 g (96%); brown solid |

SMs: 6-bromo-1'-(oxetan-3-yl)spiro[chroman-2,4'-piperidin]-4-one (7.4 g, 0.021 mol), B₂pin₂ (8.0 g, 0.031 mol), KOAc (6.18 g, 0.063 mol), PdCl₂dppf*CH₂Cl₂ (0.74 g), anh DMF (74 mL)
¹H NMR (400 MHz, CDCl₃) δ ppm 8.37 (s, 1 H), 7.83-7.98 (m, 1 H), 6.90-7.02 (m, 1 H), 4.67 (d, J = 6.3 Hz, 2 H), 4.62 (d, J = 6.0 Hz, 2 H), 3.47-3.61 (m, 1 H), 2.73 (s, 2 H), 2.42-2.56 (m, 2 H), 2.29 (br. s, 2 H), 2.06 (br. s, 2 H), 1.68-1.85 (m, 2 H), 1.34 (s, 12 H)

| IUPAC name | Structure | MS calculated | Yield |
|---|---|---|---|
| 4-oxo-6-(4,4,5,5-tetramethyl-1,3,2-dioxaborolan-2-yl)spiro[chroman-2,4'-piperidine]-1'-carbaldehyde | | [$C_{20}H_{26}BNO_5$ + H]⁺ 372.1 372.3 | 360 mg (63%); cream solid |

SMs: 6-bromo-4-oxospiro [chroman-2,4'-piperidine]-1'-carbaldehyde (500 mg, 1.54 mmol), B₂pin₂ (587 mg, 2.31 mmol), KOAc (454 mg, 4.62 mmol), PdCl₂dppf*CH₂Cl₂ (63 mg, 0.077 mmol), anh DMF (10 mL)
¹H NMR (400 MHz, CDCl₃) δ ppm 8.35 (d, J = 1.0 Hz, 1 H), 8.03 (s, 1 H), 7.86-7.95 (m, 1 H), 6.99 (d, J = 8.3 Hz, 1 H), 4.16-4.27 (m, 1 H), 3.42-3.54 (m, 2 H), 3.04-3.15 (m, 1 H), 2.73 (d, J = 1.8 Hz, 2 H), 2.04-2.19 (m, 2 H), 1.51-1.65 (m, 2 H), 1.31 (s, 12 H)

| IUPAC name | Structure | MS calculated MS ESI [M + H]+ | Yield; Appearance; Salt form |
|---|---|---|---|
| 1',4-dimethyl-6-(4,4,5,5-tetramethyl-1,3,2-dioxaborolan-2-yl)spiro[chromene-2,4'-piperidine] | 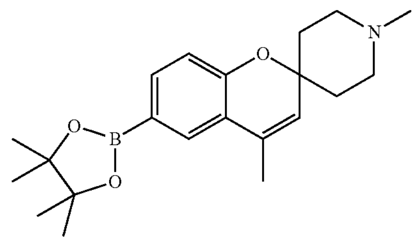 | [C$_{21}$H$_{30}$BNO$_3$ + H]$^+$ 356.2 356.3 | 1.2 g (87%); brown semi solid |

SMs: 6-bromo-1',4-dimethylspiro[chromene-2,4'-piperidine] (1.20 g, 3.8 mmol), bis(pinacolato)diboron (1.55 g, 6.1 mmol), KOAc (1.2 g, 12 mmol), PdCl$_2$dppf*CH$_2$Cl$_2$ (0.175 g, 0.21 mmol)

$^1$H NMR (400 MHz, CDCl$_3$) δ ppm 7.59-7.64 (m, 2 H), 6.84-6.88 (m, 1 H), 5.37 (s, 1 H), 2.64-2.77 (m, 2 H), 2.48-2.63 (m, 2 H), 2.38 (s, 3 H), 2.06 (d, J = 1.0 Hz, 2 H), 1.94-2.04 (m, 3 H), 1.73-1.88 (m, 2 H) 1.33 (s, 12 H)

| 2,2-dimethyl-6-(4,4,5,5-tetramethyl-1,3,2-dioxaborolan-2-yl)chroman-4-one | | [C$_{17}$H$_{23}$BO$_4$ + H]$^+$ 303.1 303.1 | 402 mg (85%); white solid |

SMs: 6-bromo-2,2-dimethylchroman-4-one (400 mg, 1.56 mmol), B$_2$pin$_2$ (598 mg, 2.35 mmol), KOAc (462 mg, 4.7 mmol), PdCl$_2$dppf*CH$_2$Cl$_2$ (64 mg, 0.078 mmol)

$^1$H NMR (400 MHz, CDCl$_3$) δ ppm 8.36 (d, J = 1.6 Hz, 1 H), 7.87-7.90 (m, 1 H), 6.92 (d, J = 8.0 Hz, 1 H), 2.37 (s, 2 H), 1.46 (s, 6 H) 1.33 (s, 12 H)

| 4,4,5,5-tetramethyl-2-(2,2,4-trimethyl-2H-chromen-6-yl)-1,3,2-dioxaborolane | | [C$_{18}$H$_{25}$BO$_3$ + H]$^+$ 301.1 301.1 | 370 mg (78%); cream solid |

SMs: 6-bromo-2,2,4-trimethyl-2H-chromene (400 mg, 1.58 mmol), B$_2$pin$_2$ (602 mg 2.37 mmol), KOAc (465 mg, 4.74 mmol), PdCl$_2$dppf*CH$_2$Cl$_2$ (64 mg, 0.078 mmol), DMF (8 mL)

$^1$H NMR (400 MHz, CDCl$_3$) δ ppm 7.59-7.62 (m, 2 H), 6.80 (d, J = 8.0 Hz, 1 H), 5.41 (s, 1 H), 2.06 (s, 3 H), 1.40 (s, 6 H) 1.34 (s, 12 H)

| 1,4-dimethyl-6-(4,4,5,5-tetramethyl-1,3,2-dioxaborolan-2-yl)quinolin-2(1H)-one | | [C$_{17}$H$_{22}$BNO$_3$ + H]$^+$ 300.1 300.1 | 165 mg (85%); white solid |

SMs: 6-bromo-1,4-dimethylquinolin-2(1H)-one (210 mg, 0.83 mmol), B$_2$pin$_2$ (317 mg, 1.24 mmol), KOAc (245 mg, 2.49 mmol), PdCl$_2$dppf*CH$_2$Cl$_2$ (34 mg, 0.041 mmol)

$^1$H NMR (400 MHz, CDCl$_3$) δ ppm 8.15 (s, 1 H), 7.99 (d, J = 8.4 Hz, 1 H), 7.37 (d, J = 8.4 Hz, 1 H), 6.59 (s, 1 H), 3.72 (s, 3 H), 2.53 (s, 3 H) 1.38 (s, 12 H)

| IUPAC name | Structure | MS calculated MS ESI [M + H]+ | Yield; Appearance; Salt form |
|---|---|---|---|
| 1-methyl-6-(4,4,5,5-tetramethyl-1,3,2-dioxaborolan-2-yl)quinolin-4(1H)-one | 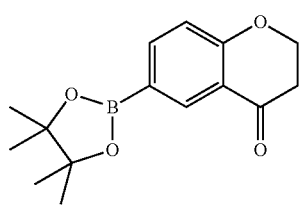 [SMILES: CC1(C)OB(c2ccc3c(c2)C(=O)CCO3)OC1(C)C] | [C$_{16}$H$_{20}$BNO$_3$ + H]$^+$ 286.1 286.3 | 201 mg (93%); brown thick oil |

SMs: 6-bromo-1-methylquinolin-4(1H)-one (180 mg, 0.75 mmol), B$_2$pin$_2$ (240 mg, 0.94 mmol), KOAc (222 mg, 2.26 mmol), PdCl$_2$dppf*CH$_2$Cl$_2$ (31 mg, 0.037 mmol)

$^1$H NMR (400 MHz, CDCl$_3$) δ ppm 8.96 (d, J = 1.6 Hz, 1 H), 8.05-8.07 (m, 1 H), 7.50 (d, J = 8.0 Hz, 1 H), 7.38 (d, J = 8.4 Hz, 1 H), 6.31 (d, J = 8.4 Hz, 1 H), 3.80 (s, 3 H), 1.36 (s, 12 H)

| 6-(4,4,5,5-tetramethyl-1,3,2-dioxaborolan-2-yl)chroman-4-one | 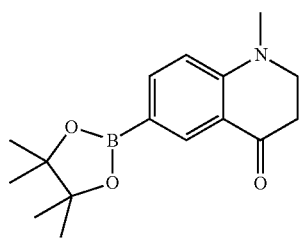 [SMILES: CN1CCC(=O)c2cc(B3OC(C)(C)C(C)(C)O3)ccc21] | [C$_{15}$H$_{19}$BO$_4$ + H]$^+$ 274.1 275.1 | 230 mg (63%); pale yellow thick oil |

SMs: 6-bromochroman-4-one (300 mg, 1.32 mmol), B$_2$pin$_2$ (503 mg, 1.98 mmol), KOAc (389 mg, 3.96 mmol), PdCl$_2$dppf*CH$_2$Cl$_2$ (54 mg, 0.066 mmol)

$^1$H NMR (400 MHz, CDCl$_3$) δ ppm 8.40 (d, J = 1.6 Hz, 1 H), 7.87-7.90 (m, 1 H), 6.97 (d, J = 8.4 Hz, 1 H), 4.56 (t, J = 6.0 Hz, 2 H), 2.82 (t, J = 6.8 Hz, 2 H), 1.33 (s, 12 H)

| 1-methyl-6-(4,4,5,5-tetramethyl-1,3,2-dioxaborolan-2-yl)-2,3-dihydroquinolin-4(1H)-one | | [C$_{16}$H$_{22}$BNO$_3$ + H]$^+$ 288.1 288.2 | 160 mg (63%); pale yellow thick oil |

SMs: 6-bromo-1-methyl-2,3-dihydroquinolin-4(1H)-one (245 mg, 1.02 mmol), B$_2$pin$_2$ (389 mg, 1.53 mmol), KOAc (309 mg, 3.14 mmol), PdCl$_2$dppf*CH$_2$Cl$_2$ (43 mg, 0.052 mmol)

$^1$H NMR (400 MHz, CDCl$_3$) δ ppm 8.39 (d, J = 2.0 Hz, 1 H), 7.79-7.81 (m, 1 H), 6.70 (d, J = 1.2 Hz, 1 H), 3.50-3.53 (m, 2 H), 3.03 (s, 3 H), 2.72-2.76 (m, 2 H), 1.32 (s, 12 H)

| 1-(oxetan-3-yl)-4-(4-(4,4,5,5-tetramethyl-1,3,2-dioxaborolan-2-yl)phenoxy)piperidine | 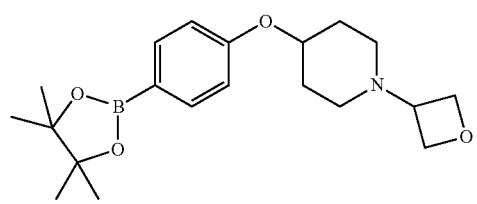 [SMILES: CC1(C)OB(c2ccc(OC3CCN(C4COC4)CC3)cc2)OC1(C)C] | [C$_{20}$H$_{30}$BNO$_4$ + H]$^+$ 360.2 360.1 | 4.8 g (55.6%); light brown solid |

SMs: 4-(4-bromophenoxy)-1-(oxetan-3-yl)piperidine (7.5 g, 24 mmol), B$_2$pin$_2$ (9.0 g, 35 mmol), KOAc (7.12 g, 72 mmol), PdCl$_2$dppf*CH$_2$Cl$_2$ (0.71 g, 0.8 mmol)

$^1$H NMR (400 MHz, CDCl$_3$) δ ppm 7.75 (d, J = 8.5 Hz, 2 H), 6.90 (d, J = 8.8 Hz, 2 H), 4.59-4.72 (m, 4 H), 4.40-4.50 (m, 1 H), 3.46-3.57 (m, 1 H), 2.48-2.62 (m, 2 H), 2.15-2.29 (m, 2 H), 1.97-2.08 (m, 2 H), 1.79-1.95 (m, 2 H), 1.34 (s, 12 H)

| IUPAC name | Structure | MS calculated MS ESI [M + H]⁺ | Yield; Appearance; Salt form |
|---|---|---|---|
| (R)-1-methyl-3-(4-(4,4,5,5-tetramethyl-1,3,2-dioxaborolan-2-yl)phenoxy)pyrrolidine | 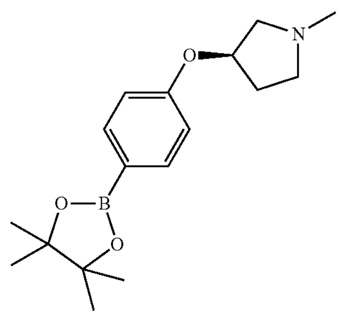 | [C₁₇H₂₆BNO₃ + H]⁺ 304.2 304.1 | 70 mg (61%); pale yellow oil |

SMs: (General Method F) (R)-3-(4-iodophenoxy)-1-methylpyrrolidine (115 mg, 39 mmol), HBpin (137 mmL, 94 mmol), Et₃N (128 mmL, 1.13 mmol), PdCl₂(CH₃CN)₂ (2 mg), S-Phos (12 mg, 0.03 mmol), 1,4-dioxane (3.5 mL)

¹H NMR (400 MHz, CDCl₃) δ ppm 7.74 (d, J = 8.5 Hz, 2 H), 6.85 (d, J = 8.5 Hz, 2 H), 4.81-4.90 (m, 1 H), 2.82 (d, J = 4.3 Hz, 4 H), 2.42-2.50 (m, 1 H), 2.37-2.42 (m, 3 H), 2.28-2.37 (m, 1 H), 1.34 (s, 12 H)

| IUPAC name | Structure | MS calculated MS ESI [M + H]⁺ | Yield; Appearance; Salt form |
|---|---|---|---|
| (1R,5S)-3-(4-(4,4,5,5-tetramethyl-1,3,2-dioxaborolan-2-yl)phenyl)-8-oxa-3-azabicyclo[3.2.1]octane | 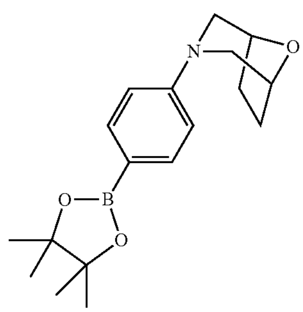 [SMILES: CC1(C)OB(c2ccc(N3CC4CCC(C3)O4)cc2)OC1(C)C] | [C₁₈H₂₆BNO₃ + H]⁺ 316.2 316.2 | 58 mg (61%); white solid |

SMs: (1R,5S)-3-(4-iodophenyl)-8-oxa-3-azabicyclo[3.2.1]octane (95 mg, 0.30 mmol), B₂pin₂ (115 mg, 0.45 mmol), KOAc (89 mg, 0.90 mmol), PdCl₂dppf*CH₂Cl₂ (24 mg, 0.029 mmol)

¹H NMR (400 MHz, CDCl₃) δ ppm 7.71 (d, J = 8.5 Hz, 2 H), 6.79 (d, J = 8.5 Hz, 2 H), 4.49 (br. s, 2 H), 3.41 (d, J = 11.3 Hz, 2 H), 3.07 (s, 2 H), 1.93 (br. s, 4 H), 1.31-1.36 (m, 12 H)

| IUPAC name | Structure | MS calculated MS ESI [M + H]⁺ | Yield; Appearance; Salt form |
|---|---|---|---|
| 1-methyl-4-(2-(methylsulfonyl)-4-(4,4,5,5-tetramethyl-1,3,2-dioxaborolan-2-yl)phenoxy)piperidine | 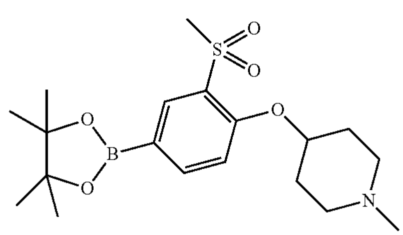 | [C₁₉H₃₀BNO₅S + H]⁺ 396.2 396.2 | 550 mg (68%); brown semi solid |

SMs: 4-(4-bromo-2-(methylsulfonyl)phenoxy)-1-methylpiperidine (500 mg, 1.43 mmol), B₂pin₂ (550 mg, 2.16 mmol), KOAc (425 mg, 4.33 mmol), PdCl₂dppf*CH₂Cl₂ (76 mg, 0.093 mmol)

¹H NMR (400 MHz, CDCl₃) δ ppm 8.40-8.47 (m, 1 H), 7.92-7.99 (m, 1 H), 6.96-7.03 (m, 1 H), 4.63-4.70 (m, 1 H), 3.22 (s, 3 H), 2.65-2.76 (m, 2 H), 2.39-2.49 (m, 2 H), 2.31-2.36 (m, 3 H), 1.93-2.16 (m, 4 H), 1.33 (s, 12 H)

| IUPAC name | Structure | MS calculated MS ESI [M + H]+ | Yield; Appearance; Salt form |
|---|---|---|---|
| tert-butyl 4-(2-(methylsulfonyl)-4-(4,4,5,5-tetramethyl-1,3,2-dioxaborolan-2-yl)phenoxy)piperidine-1-carboxylate | 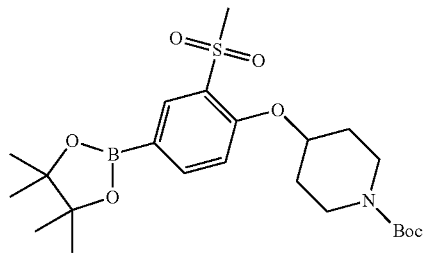 [SMILES: CC(C)(C)OC(=O)N1CCC(Oc2ccc(B3OC(C)(C)C(C)(C)O3)cc2S(C)(=O)=O)CC1] | [C$_{23}$H$_{36}$BNO$_7$S + H]$^+$ 482.2 482.2 | 135 mg (53%); white solid |

SMs: tert-butyl 4-(4-bromo-2-(methylsulfonyl)phenoxy)piperidine-1-carboxylate (230 mg, 0.52 mmol), B$_2$pin$_2$ (202 mg, 0.79 mmol), KOAc (156 mg, 1.58 mmol), PdCl$_2$dppf*CH$_2$Cl$_2$ (43 mg, 0.052 mmol)

$^1$H NMR (400 MHz, CDCl$_3$) δ ppm 8.42 (d, J = 1.5 Hz, 1 H), 7.91-8.01 (m, 1 H), 6.99 (d, J = 8.4 Hz, 1 H), 4.76-4.84 (m, 1 H), 3.59-3.70 (m, 2 H), 3.44-3.57 (m, 2 H), 3.18 (s, 3 H), 1.81-2.01 (m, 4 H), 1.45 (s, 9 H), 1.32 (s, 12 H)

| IUPAC name | Structure | MS calculated MS ESI [M + H]+ | Yield; Appearance; Salt form |
|---|---|---|---|
| 1-methyl-3-(4-(4,4,5,5-tetramethyl-1,3,2-dioxaborolan-2-yl)phenoxy)azetidine | 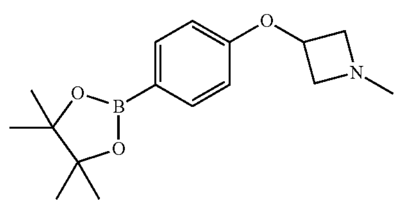 | [C$_{16}$H$_{24}$BNO$_3$ + H]$^+$ 290.2 290.3 | 179 mg (16%), brown oil; free base |

SMs: 3-(4-iodophenoxy)-1-methylazetidine (1.156 g, 4 mmol), B$_2$pin$_2$ (1.118 g, 4.4 mmol)

$^1$H NMR (400 MHz, CDCl$_3$) δ ppm 7.73 (d, J = 8.4 Hz, 2H), 6.75 (d, J = 8.4 Hz, 2H), 4.81 (t, J = 5.4 Hz, 1H), 3.92 (t, J = 6.4 Hz, 2H), 3.17 (t, J = 6.0 Hz, 2H), 2.44 (s, 3H), 1.32 (s, 12H).

| IUPAC name | Structure | MS calculated MS ESI [M + H]+ | Yield; Appearance; Salt form |
|---|---|---|---|
| 2-((1-(oxetan-3-yl)piperidin-4-yl)oxy)-5-(4,4,5,5-tetramethyl-1,3,2-dioxaborolan-2-yl)pyridine | 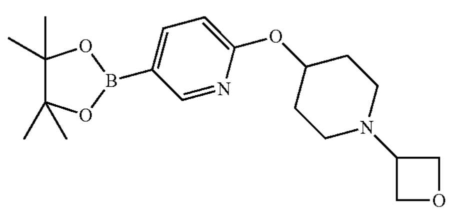 [SMILES: CC1(C)OB(c2ccc(OC3CCN(C4COC4)CC3)nc2)OC1(C)C] | [C$_{19}$H$_{29}$BN$_2$O$_4$ + H]$^+$ 361.2 361.4 | 295 mg (20%), brown solid; free base |

SMs: 5-iodo-2-((1-(oxetan-3-yl)piperidin-4-yl)oxy)pyridine (1.252 g, 4 mmol), B$_2$pin$_2$ (1.118 g, 4.4 mmol)

$^1$H NMR (400 MHz, CDCl$_3$) δ ppm 8.50 (s, 1H), 7.90 (d, J = 8.0 Hz, 1H), 6.98 (d, J = 8.0 Hz, 1H), 5.22-5.12 (m, 1H), 4.65 (t, J = 6.0 Hz, 4H), 3.51 (t, J = 5.8 Hz, 1H), 2.63-2.53 (m, 2H), 2.27-2.17 (m, 2H), 2.15-2.00 (m, 2H), 1.90-1.78 (m, 2H), 1.33 (s, 12H).

| IUPAC name | Structure | MS calculated MS ESI [M + H]+ | Yield; Appearance; Salt form |
|---|---|---|---|
| 1R,3S,5S)-8-methyl-3-(4-(4,4,5,5-tetramethyl-1,3,2-dioxaborolan-2-yl)phenoxy)-8-azabicyclo[3.2.1]octane | 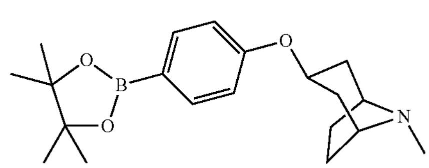 | [C$_{20}$H$_{30}$BNO$_3$ + H]$^+$ 344.2 344.2 | 5.14 g (75%), light yellow solid; free base |

SMs: (General Method F) (1R,3S,5S)-3-(4-iodophenoxy)-8-methyl-8-azabicyclo[3 2.1] octane (6.86 g, 20 mmol), HBpin (3.77 ml, 26 mmol)

$^1$H NMR (400 MHz, CDCl$_3$) δ ppm 7.20 (d, J = 8.0 Hz, 2H), 6.88 (d, J = 8.4 Hz, 2H), 4.62-4.52 (m, 1H), 3.33-3.27 (m, 2H), 3.40 (s, 3H), 2.15-1.85 (m, 6H), 1.72-1.65 (m, 2H), 1.34 (s, 12H).

| IUPAC name | Structure | MS calculated MS ESI [M + H]+ | Yield; Appearance; Salt form |
|---|---|---|---|
| (1R,3S,5S)-8-(4-(4,4,5,5-tetramethyl-1,3,2-dioxaborolan-2-yl)phenyl)-8-azabicyclo[3.2.1]octan-3-ol | 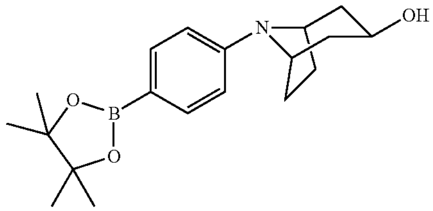 [SMILES: CC1(C)OB(c2ccc(N3C4CCC3CC(O)C4)cc2)OC1(C)C] | [C$_{19}$H$_{28}$BNO$_3$ + H]$^+$ 330.2 330.1 | 2.05 g (87%), off white solid; free base |

SMs: (General Method F) (1R,3s,5S)-8-(4-iodophenyl)-8-azabicyclo[3.2.1]octan-3-ol (2.35 g, 7 mmol), HBpin (3.05 ml, 21 mmol)
$^1$H NMR (400 MHz, CDCl$_3$) δ ppm 7.70 (d, J = 8.4 Hz, 2H), 6.77 (d, J = 8.4 Hz, 2H), 4.36-4.31 (m, 2H), 4.22-4.11 (m, 1H), 2.11-2.04 (m, 2H), 1.91-1.83 (m, 2H), 1.80-1.74 (m, 2H), 1.70-1.61 (m, 2H), 1.34 (s, 12H), 1.13 (d, J = 6.4 Hz, 1H, OH).

| IUPAC name | Structure | MS calculated MS ESI [M + H]+ | Yield; Appearance; Salt form |
|---|---|---|---|
| (1R,3R,5S)-8-(4-(4,4,5,5-tetramethyl-1,3,2-dioxaborolan-2-yl)phenyl)-8-azabicyclo[3.2.1]octan-3-ol | | [C$_{19}$H$_{28}$BNO$_3$ + H]$^+$ 330.2 330.1 | 6.70 g (100%), light purplish white solid; free base |

SMs: (method F) (1R,3R,5S)-8-(4-iodophenyl)-8-azabicyclo[3.2.1]octan-3-ol (6.58 g, 20 mmol), HBpin (8.7 ml, 60 mmol)
$^1$H NMR (400 MHz, CDCl$_3$) δ ppm 7.69 (d, J = 8.4 Hz, 2H), 6.74 (d, J = 8.8 Hz, 2H), 4.28-4.23 (m, 2H), 4.03-3.97 (m, 1H), 2.36-2.28 (m, 2H), 2.27-2.19 (m, 2H), 2.11-2.05 (m, 2H), 1.60 (d, J = 14.8 Hz, 2H), 1.33 (s, 12H).

| IUPAC name | Structure | MS calculated MS ESI [M + H]+ | Yield; Appearance; Salt form |
|---|---|---|---|
| 1-(oxetan-3-yl)-4-(4-(4,4,5,5-tetramethyl-1,3,2-dioxaborolan-2-yl)phenyl)piperazine | | [C$_{19}$H$_{29}$BN$_2$O$_3$ + H]$^+$ 345.2 345.1 | 5.32 g (77%), white solid; free base |

SMs: (method F) 1-(4-bromophenyl)-4-(oxetan-3-yl)piperazine (5.96 g, 20 mmol), HBpin (4.4 mL, 30 mmol)
$^1$H NMR (400 MHz, CDCl$_3$) δ ppm 7.32 (d, J = 8.4 Hz, 2H), 6.91 (d, J = 8.4 Hz, 2H), 4.71 (t, J = 6.6 Hz, 2H), 4.67 (t, J = 6.2 Hz, 2H), 3.56 (quintet, J = 6.0 Hz, 1H), 3.32 (t, J = 5.0 Hz, 4H), 2.49 (t, J = 5.0 Hz, 4H), 1.34 (s, 12H).

| IUPAC name | Structure | MS calculated MS ESI [M + H]+ | Yield; Appearance; Salt form |
|---|---|---|---|
| 3-(oxetan-3-yl)-1-(4-(4,4,5,5-tetramethyl-1,3,2-dioxaborolan-2-yl)phenyl)azetidine | | [C$_{18}$H$_{26}$BNO$_3$ + H]$^+$ 316.20 316.1 | 714 mg (73%); white solid; free base |

SMs: (method E) 1-(4-iodophenyl)-3-(oxetan-3-yl)azetidine (1.27 g, 2.9 mmol)
$^1$H NMR (400 MHz, CDCl$_3$) δ ppm 7.68 (d, J = 8.5 Hz, 1 H), 6.42 (d, J = 8.8 Hz, 1 H), 4.88 (dd, J = 7.8, 6.5 Hz, 1 H), 4.47 (t, J = 6.1 Hz, 1 H), 4.05 (d, J = 7.8 Hz, 1 H), 3.67 (dd, J = 7.4, 5.1 Hz, 1 H), 3.33 (s, 1 H), 3.09 (s, 1 H), 1.33 (s, 1 H)

| IUPAC name | Structure | MS calculated MS ESI [M + H]+ | Yield; Appearance; Salt form |
|---|---|---|---|
| 4-(1-(4-(4,4,5,5-tetramethyl-1,3,2-dioxaborolan-2-yl)phenyl)azetidin-3-yl)morpholine | | [C$_{19}$H$_{29}$BN$_2$O$_3$ + H]$^+$ 345.2 345.4 | 2.9 g (61%); yellow solid; free base |

SMs: (method E) 4-(1-(4-iodophenyl)azetidin-3-yl)morpholine (4.1 g, 12 mmol)
$^1$H NMR (400 MHz, CDCl$_3$) δ ppm 7.67 (d, J = 8.5 Hz, 2 H), 6.43 (d, J = 8.5 Hz, 2 H), 3.97-4.03 (m, 2 H), 3.72-3.79 (m, 6 H), 3.27-3.39 (m, 1 H), 2.38-2.50 (m, 4 H), 1.33 (s, 12 H)

| IUPAC name | Structure | MS calculated MS ESI [M + H]⁺ | Yield; Appearance; Salt form |
|---|---|---|---|
| (1R,3R,5S)-8-(oxetan-3-yl)-3-(4-(4,4,5,5-tetramethyl-1,3,2-dioxaborolan-2-yl)phenoxy)-8-azabicyclo[3.2.1]octane | 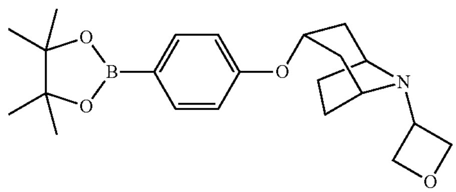 [SMILES: CC1(C)OB(c2ccc(OC3CC4CCC(C3)N4C3COC3)cc2)OC1(C)C] | $[C_{22}H_{32}BNO_4 + H]^+$ 386.3 386.2 | 85 mg (40%); off-white solid; free base |

SMs: (General Method E) (1R,3R,5S)-3-(4-iodophenoxy)-8-(oxetan-3-yl)-8-azabicyclo[3.2.1]octane (210 mg, 0.54 mmol)

| (1R,3R,5S)-3-(4-(4,4,5,5-tetramethyl-1,3,2-dioxaborolan-2-yl)phenoxy)-8-azabicyclo[3.2.1]octane-8-carbaldehyde | | $[C_{20}H_{28}INO_4 + H]^+$ 358.2 358.3 | 68 mg (62%); off-white solid |

SMs: (General Method E) (1R,3R,5S)-3-(4-iodophenoxy)-8-azabicyclo[3.2.1]octane-8-carbaldehyde (110 mg, 0.31 mmol)

| (1R,3R,5S)-tert-butyl 3-(4-(4,4,5,5-tetramethyl-1,3,2-dioxaborolan-2-yl)phenoxy)-8-azabicyclo[3.2.1]octane-8-carboxylate | | $[C_{24}H_{36}BNO_5 - C_4H_9]^+$ 374.2 374.1 | 337 mg (51%); white solid |

SMs: (General Method E) (1R,3r,5S)-tert-butyl 3-(4-iodophenoxy)-8-azabicyclo[3.2.1] octane-8-carboxylate (658 mg, 1.37 mmol)

| 1-(oxetan-3-yl)-4-(4-(4,4,5,5-tetramethyl-1,3,2-dioxaborolan-2-yl)phenyl)-1,4-diazepane | | $[C_{20}H_{31}BN_2O_3 + H]^+$ 359.2 359.4 | 700 mg (37%); brown solid; free base |

SMs: (General Method E) 1-(4-iodophenyl)-4-(oxetan-3-yl)-1,4-diazepane (1.62 g, 4.5 mmol)
¹H NMR (400 MHz, CD₃OD) δ ppm 7.57 (d, J = 8.8 Hz, 2 H), 6.71 (d, J = 8.8 Hz, 2 H), 4.66 (t, J = 6.7 Hz, 2 H), 4.51-4.58 (m, 2 H), 3.51-3.74 (m, 5 H), 3.32 (m, 3 H) 2.54-2.61 (m, 2 H) 2.35-2.42 (m, 2 H) 1.94-2.06 (m, 2 H) 1.32 (s, 9 H)

| (S)-2-hydroxy-1-(4-(4-(4,4,5,5-tetramethyl-1,3,2-dioxaborolan-2-yl)phenoxy)piperidin-1-yl)propan-1-one | | $[C_{20}H_{30}BNO_5 + H]^+$ 376.22 376.1 | 0.24 g (89%); colorless oil; free base |

SMs: (S)-1-(4-(4-bromophenoxy)piperidin-1-yl)-2-hydroxypropan-1-one (0.24 g, 0.73 mmol), B₂pin₂ (0.22 g, 0.88 mmol)
¹H NMR (400 MHz, CDCl₃) δ ppm 7.76 (d, J = 8.3 Hz, 2 H), 6.90 (d, J = 8.5 Hz, 2 H), 4.59-4.73 (m, 1 H), 4.37-4.53 (m, 1 H), 3.80-4.03 (m, 1 H), 3.71-3.80 (m, 1 H), 3.52-3.71 (m, 2 H), 3.29-3.44 (m, 1 H), 1.81-2.01 (m, 4 H), 1.33 (br.s, 15 H)

| IUPAC name | Structure | MS calculated MS ESI [M + H]⁺ | Yield; Appearance; Salt form |
|---|---|---|---|
| (R)-2-hydroxy-1-(4-(4-(4,4,5,5-tetramethyl-1,3,2-dioxaborolan-2-yl)phenoxy)piperidin-1-yl)propan-1-one | 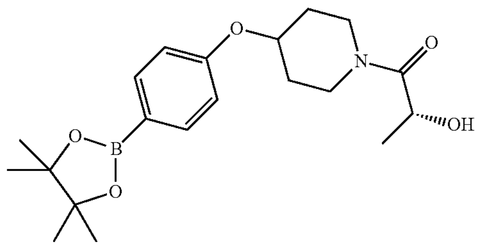 [SMILES: C[C@@H](O)C(=O)N1CCC(Oc2ccc(B3OC(C)(C)C(C)(C)O3)cc2)CC1] | [$C_{20}H_{30}BNO_5$ + H]⁺ 376.22 376.1 | 0.20 g (79%); colorless gum; free base |

SMs: (R)-1-(4-(4-bromophenoxy)piperidin-1-yl)-2-hydroxypropan-1-one (0.22 g, 0.68 mmol), $B_2pin_2$ (0.20 g, 0.81 mmol)

¹H NMR (400 MHz, CDCl₃) δ ppm 7.76 (d, J = 7.0 Hz, 1 H), 6.90 (d, J = 7.0 Hz, 1 H), 4.66 (br. s., 1 H), 4.43-4.58 (m, 1 H), 3.23-4.00 (m, 4 H), 1.90 (br. s., 4 H), 1.33 (br. s., 15 H)

| 2-hydroxy-2-methyl-1-(4-(4-(4,4,5,5-tetramethyl-1,3,2-dioxaborolan-2-yl)phenoxy)piperidin-1-yl)propan-1-one | | [$C_{21}H_{32}BNO_5$ + H]⁺ 390.24 390.2 | 86 mg (41%); colorless oil; free base |

SMs: 1-(4-(4-bromophenoxy)piperidin-1-yl)-2-hydroxy-2-methylpropan-1-one (0.19 g, 0.54 mmol), $B_2pin_2$ (0.16 g, 0.65 mmol)

| 2-hydroxy-1-(4-(4-(4,4,5,5-tetramethyl-1,3,2-dioxaborolan-2-yl)phenoxy)piperidin-1-yl)ethanone | | [$C_{19}H_{28}BNO_5$ + H]⁺ 362.21 362.2 | 0.10 g (43%) pale tan solid; free base |

SMs: 2-hydroxy-1-(4-(4-(4,4,5,5-tetramethyl-1,3,2-dioxaborolan-2-yl)phenoxy)piperidin-1-yl)ethanone (0.21 g, 0.67 mmol), $B_2pin_2$ (0.20 g, 0.80 mmol)

¹H NMR (400 MHz, CD₃OD) δ ppm 7.68 (d, J = 8.5 Hz, 1 H), 6.96 (d, J = 8.8 Hz, 1 H), 4.65-4.76 (m, 1 H), 4.25 (s, 2 H), 3.80-3.91 (m, 1 H), 3.52-3.70 (m, 2 H), 3.34-3.44 (m, 1 H), 1.90-2.07 (m, 2 H), 1.68-1.83 (m, 2 H), 1.34 (s, 12 H)

Synthesis of 2-(4-(((2R,4R,6S)-2,6-dimethyltetra-hydro-2H-pyran-4-yl)oxy)phenyl)-4,4,5,5-tetramethyl-1,3,2-dioxaborolane A. (2R,4S,6S)-2,6-dimethyltetrahydro-2H-pyran-4-ol

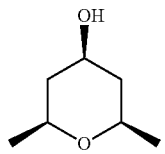

To a solution of 2,6-dimethyl-γ-pyrone (1.5 g, 12.1 mmol) in MeOH (15 mL) was added 10% Pd/C (150.8 mg) at rt and treated with H$_2$ (1 atm) for 24 h. After reaction completion the mixture was filtered through a Celite pad and washed with MeOH and the filtrate was concentrated under reduced pressure to give a pale yellow oil. Purification by flash chromatography using ELSD detector (Biotage Isolera, 50 g HP-SIL, 0-100% Et$_2$O in hexane) gave the title compound as a pale yellow oil (151 mg, 10%). $^1$H NMR (400 MHz, CDCl$_3$) δ ppm 3.74-3.81 (m, 1 H), 3.45-3.49 (m, 2 H), 1.90-1.94 (m, 2 H), 1.70 (br. s, 1 H), 1.50 (br. s, 1 H), 1.22 (d, J=6.4 Hz, 6 H)

B. (2R,4R,6S)-4-(4-iodophenoxy)-2,6-dimethyltetrahydro-2H-pyran

NaH (55-60% in mineral oil, 71.7 mg, 1.80 mmol) under Ar was added in anh. DMF (4 mL) at 24° C. To this suspension (2R,4R,6S)-2,6-dimethyltetrahydro-2H-pyran-4-ol (111.3 mg, 0.85 mmol) was added portionwise followed by 1-fluoro-4-iodobenzene (0.10 mL, 0.87 mmol). The mixture was stirred at 85° C. for 20 h. The mixture was then cooled to rt and diluted with EtOAc (50 mL), washed (H$_2$O, brine), dried (Na$_2$SO$_4$) and concentrated under vacuum. Purification by flash chromatography gave the title compound as brown oil (137 mg, 41%). and it with H$_2$O followed by brine to give the title compound as a cream solid (137 mg, 48%). $^1$H NMR (400 MHz, CDCl$_3$) δ ppm 7.49-7.60 (m, 2 H), 6.63-6.74 (m, 2 H), 4.35 (s, 1 H), 3.55 (ddd, J=11.2, 6.2, 1.6 Hz, 2 H), 2.00-2.12 (m, 2 H), 1.28-1.39 (m, 2 H), 1.26 (d, J=6.0 Hz, 6 H); MS ESI 333 [M+H]$^+$, calcd for [C$_{13}$H$_{17}$IO$_2$+H]$^+$ 333.02.

2-(4-(((2R,4R,6S)-2,6-dimethyltetrahydro-2H-pyran-4-yl)oxy)phenyl)-4,4,5,5-tetramethyl-1,3,2-dioxaborolane

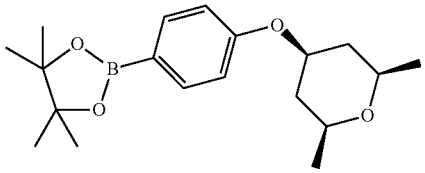

The title compound was prepared in a manner similar to General Method F using (2R,4R,6S)-4-(4-iodophenoxy)-2,6-dimethyltetrahydro-2H-pyran (136 mg, 0.40 mmol), (136 mg, 0.40 mmol), HBpin (77 mg, 0.60 mmol), S-Phos (6.5 mg, 0.015 mmol) and Cl$_2$Pd(CH$_3$CN)$_2$ (1 mg) at 110° C. for 1 h. MeOH (2 mL) was slowly added to quench excess borane, followed by DCM (10 mL) and NaHCO$_3$ (10 mL). After vacuum filtration through a cotton pad and rinsing with DCM (10 mL), the layers were separated. The combined DCM layers were washed with H$_2$O, dried over Na$_2$SO$_4$ and the solvent removed to yield the crude product. Purification by flash chromatography (Biotage Isolera, 25 g HP-SIL, 0-100% DCM in hexane) gave an off white solid (102 mg, 75%). $^1$H NMR (400 MHz, CDCl$_3$) δ ppm 7.75 (d, J=8.8 Hz, 2 H), 6.90 (d, J=8.5 Hz, 2 H), 4.42-4.52 (m, 1 H), 3.52-3.63 (m, 2 H), 2.06-2.15 (m, 2 H), 1.34 (s, 12 H); MS ESI 333.1 [M+H]$^+$, calcd for [C$_{19}$H$_{22}$BO$_4$+H]$^+$ 333.2

Synthesis of (1R,3R,5S)-9-(4-(4,4,5,5-tetramethyl-1,3,2-dioxaborolan-2-yl)phenyl)-9-azabicyclo[3.3.1]nonan-3-ol

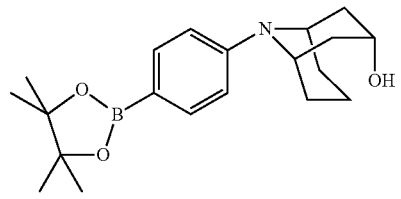 [SMILES: CC1(C)OB(c2ccc(N3C4CCCC3CC(O)C4)cc2)OC1(C)C]

To a solution of (1R,5S)-9-(4-bromophenyl)-9-azabicyclo[3.3.1]nonan-3-one (6.2 g, crude) in DCM (100 mL) and MeOH (60 mL) at 0° C. was added NaBH$_4$ (5.7 g, 15 mmol). The resulting mixture was stirred at 0° C. for 10 min, then rt for 30 min. After aqueous workup, the residue was purified by flash chromatography (EtOAc/DCM 0 to 10%) to give (1R,3R,5S)-9-(4-bromophenyl)-9-azabicyclo[3.3.1]nonan-3-ol as brown solid (1.30 g). MS ESI 295.9 [M+H]$^+$, calcd for [C$_{14}$H$_{18}$BrNO+H]$^+$ 296.1.

The title compound (727 mg, beige solid) was prepared using (1R,5S)-9-(4-bromophenyl)-9-azabicyclo[3.3.1]nonan-3-ol as brown solid (1.30 g, 4.4 mmol) and HBpin (1.9 mL) according to General Method F. $^1$H NMR (400 MHz, CDCl$_3$) δ ppm 7.67 (d, J=8.8 Hz, 2H), 6.82 (d, J=8.8 Hz, 2H), 4.36-4.27 (m, 2H), 3.85-3.75 (m, 1H), 2.48-2.38 (m, 2H), 1.83-1.73 (m, 2H), 1.63-1.43 (m, 6H), 1.33 (s, 12H). MS ESI 344.1 [M+H]$^+$, calcd for [C$_{20}$H$_{30}$13NO$_3$+H]$^+$ 344.2.

Synthesis of (1R,5S,7S)-9-(4-(4,4,5,5-tetramethyl-1,3,2-dioxaborolan-2-yl)phenyl)-3-oxa-9-azobicyclo[3.3.1]nonan-7-ol

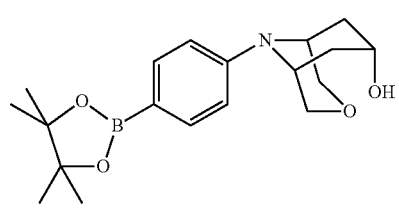 [SMILES: CC1(C)OB(c2ccc(N3C4COCC3CC(O)C4)cc2)OC1(C)C]

To a solution of (1R,5S)-9-(4-bromophenyl)-3-oxa-9-azabicyclo[3.3.1]nonan-7-one (0.98 g, 3.34 mmol) in THF (20 mL) and MeOH (0.5 mL) at 0° C. was added NaBH$_4$ (380 mL, 10 mmol). The resulting mixture was heated at 50° C. for 30 min. After cooling to rt, it was diluted with H$_2$O and extracted with DCM to give (1R,5S,7S)-9-(4-bromophenyl)-3-oxa-9-azabicyclo[3.3.1]nonan-7-ol as greenish yellow solid. MS ESI 298.0 [M+H]$^+$, calcd for [C$_{13}$H$_{16}$BrNO$_2$+H]$^+$ 298.0.

The title compound (336 mg, off white solid) was prepared using the above solid (1R,5S,)-9-(4-bromophenyl)-3-oxa-9-azabicyclo[3.3.1]nonan-7-ol and HBpin (1.45 mL, 10 mmol) according to General Method F. $^1$H NMR (400 MHz, CDCl$_3$) δ ppm 7.72 (d, J=8.4 Hz, 2H), 6.79 (d, J=8.8 Hz, 2H), 6.65 (d, J=12.4 Hz, 1H), 4.02-3.92 (m, 6H), 2.32-2.24 (m, 2H), 1.78 (d, J=14.8 Hz, 2H), 1.34 (s, 12H). MS ESI 346.1 [M+H]$^+$, calcd for [C$_{19}$H$_{28}$BNO$_4$+H]$^+$ 346.2.

Synthesis of (S)-2-((S)-2-methylpyrrolidin-1-yl)-2-(thiophen-3-yl)acetamide

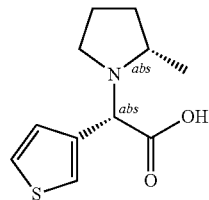

To a mixture of (S)-2-methylpyrrolidine (1.07 g, 12.6 mmol), glyoxylic acid hydrate (1.16 g, 12.6 mmol) in DCM (50 mL) was added thiophen-3-ylboronic acid (1.59 g, 12.6 mmol). The resulting mixture was stirred for 3 h at rt. Oil formed on the sides of flask and MeOH (5 mL) was added to make a clear solution. Reaction was stirred overnight at rt. After removing all the solvents, the residue was purified by Biotage column system (gradient: MeOH/DCM 0 to 30%) to give (S)-2-((S)-2-methylpyrrolidin-1-yl)-2-(thiophen-3-yl)acetic acid as a beige solid (1.294 g, 46%). $^1$H NMR (400 MHz, CD$_3$OD) δ 7.68 (dd, J=2.8, 1.2 Hz, 1H), 7.52 (dd, J=5.0, 3.0 Hz, 1H), 7.29 (dd, J=5.0, 0.8 Hz, 1H), 4.71 (s, 1H), 3.71-3.60 (m, 1H), 3.25-3.16 (m, 1H), 3.06-2.88 (s, br, 1H), 2.37-2.25 (m, 1H), 2.07-1.89 (m, 2H), 1.84-1.74 (m, 1H), 1.50 (s, 3H).

Synthesis of (S)-N-(1-(2-fluorophenyl)-3-methylbutyl)-3-iodo-1H-indazole-5-carboxamide A. (R,E)-N-(2-fluorobenzylidene)-2-methylpropane-2-sulfinamide

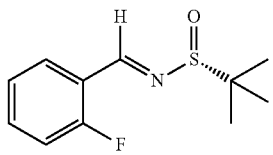

The title compound was synthesized by utilizing 2-fluorobenzaldehyde (10.0 g, 80.5 mmol), (S)-t-butylsulfinylamide (12.2 g, 100 mmol), flame-dried CuSO$_4$ (16 g, 100 mmol) and MgSO$_4$ (29 g, 240 mmol) in DCM (150 mL). The resulting mixture was stirred at rt for 72 h. The reaction mixture was filtered through a pad of Celite and the pad was rinsed with CH$_2$Cl$_2$ (5×100 mL). The combined organic extracts were concentrated under reduced pressure yielding pale yellow oil (24 g). Purification by flash chromatography (Biotage Isolera, 100 g HP-SIL, 0-15% EtOAc in hexanes) gave the product (11.3 g, 61% as a clear pale yellow oil. $^1$H NMR (300 MHz, CDCl$_3$) δ ppm 8.91 (s, 1 H), 8.01 (dt, J=7.6, 1.6 Hz, 1 H), 7.48-7.54 (m, 1 H), 7.23-7.27 (m, 1 H), 7.14-7.19 (m, 1 H), 1.28 (s, 9 H).

B. (S)-N-((S)-1-(2-fluorophenyl)-3-methylbutyl)-2-methylpropane-2-sulfinamide

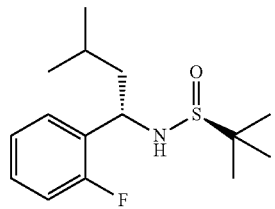 [SMILES: CC(C)C[C@H](N[S@@](=O)C(C)(C)C)c1ccccc1F]

Isobutyl magnesium bromide (2.0 M in Et$_2$O, 8.25 mL, 16.5 mmol) was added carefully to stirred dimethylzinc (1.2 M in toluene, 15.6 mL, 18.7 mmol) at rt. Dry THF (30 mL) was added and the mixture was stirred at rt for 30 min before being added slowly, drop wise over 30 min to a stirred −78° C. solution of (R,E)-N-(2-fluorobenzylidene)-2-methylpropane-2-sulfinamide (2.5 g, 11 mmol) in dry THF (30 mL). Once the addition was complete the mixture was stirred at this temperature for 3 h. The reaction was quenched by addition of saturated aq. NH$_4$Cl (50 mL). H$_2$O (200 mL) was added and the mixture was extracted with Et$_2$O (2×75 mL). The combined organic extracts were washed with brine (50 mL), dried (Na$_2$SO$_4$) and concentrated under reduced pressure yielding the crude product (3.05 g, 97%, 4:1 mixture of product and Me-added side product) as a clear yellow oil. $^1$H NMR (400 MHz, CDCl$_3$) δ 7.36-7.40 (m, 0.25 H), 7.29-7.33 (m, 1 H), 7.22-7.29 (m, 1.25 H), 7.11-7.17 (m, 1.25 H), 7.02-7.06 (m, 1.25 H), 4.79-4.82 (m, 0.25 H), 4.56-4.61 (m, 1 H), 3.53 (m, 1.25 H), 1.63-1.68 (m, 0.91 H), 1.55-1.60 (m, 1.50 H), 1.44-1.54 (m, 1.30 H), 1.21 (s, 9 H), 0.90-0.95 (m, 6 H), [C$_{15}$H$_{24}$FNOS+H]$^+$ C. (S)-1-(2-fluorophenyl)-3-methylbutan-1-amine

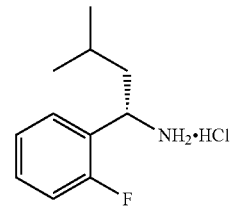

The deprotection of chiral auxiliary carried out by utilizing HCl (2.0 M in Et$_2$O, 25 mL) and a solution of (S)-N-((S)-1-(2-fluorophenyl)-3-methylbutyl)-2-methylpropane-2-sulfinamide (3.05 g, 10.6 mmol) in MeOH (30 mL). After the addition was complete, the cooling bath was removed and the mixture was stirred at rt for 1 h. The reaction mixture was concentrated under reduced pressure and the residue to give crude pale yellow solid (3.0 g). Purification by flash chromatography (Biotage isolera 120 g C18, 5-80% MeOH in H$_2$O) gave the title compound as a white solid HCl salt (1.52 g, 64%, 97% ee (S)). $^1$H NMR (400 MHz, CD$_3$OD) δ ppm 7.46-7.52 (m, 2H), 7.32 (t, J=7.6 Hz, 1H), 7.22-7.26 (m, 1H), 4.62-4.66 (m, 1H), 1.93-1.98 (m, 1H), 1.79-1.86 (m, 1H), 1.37-1.47 (m, 1H), 0.93-0.98 (m, 6H). The ee of the compound was determined by chiral HPLC, Daicel Chiralpak OD-H, 3:97 v/v 0.5% DEA-IPA:Hexane, 1.0 mL/min, λ=254 nm, $R_t$=6.08 min (R), $R_t$=6.89 min (S).

(S)-3-Methyl-1-(pyridin-2-yl)butan-1-amine

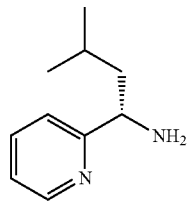

To a hot solution of (L)-DBTA (7.2 g, 20 mmol) in MeOH (75 mL) with stirring was added a solution of racemic 3-methyl-1-(pyridin-2-yl)butan-1-amine (3.3 g, 20 mmol) in MeOH (30 mL) dropwise. After addition, the resulting suspension was stirred for 5 min under reflux and cooled in air for about 5 min. The resulting precipitate was collected by vacuum filtration, washed with cold MeOH, air-dried and recrystallized from MeOH (200 mL) to give (L)-DBTA salt of (S)-3-methyl-1-(pyridin-2-yl)butan-1-amine as white solid (1.95 g, 95.6% ee). The ee of the compound was determined by acetylating small samples with acetyl chloride and analyzing the products by chiral HPLC: Daicel Chiralpak AD-H, 90:10 v/v hexanes-IPA (+0.5% Et$_3$N), 1.0 ml min$^{-1}$, λ=254 nm, $R_t$=5.8 mins (R), $R_t$=7.5 min (S). To a suspension of the above salt (1.9 g) in MeOH (5 mL) was added 4 M NaOH (3 mL). A clear solution was formed. After diluting with H$_2$O (50 mL), the aq layer was extracted with DCM (30 mL×2), and the combined organic layers were dried (Na$_2$SO$_4$) and solvent was removed to give the desired amine as a colorless oil (705 mg, 21%).

Synthesis of (S)-1-(2-chlorophenyl)-3-methylbutan-1-amine

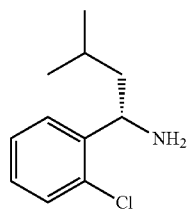

To a RBF under Ar charged with Me$_2$Zn (1.2 M in PhMe, 12.5 mmol, 1.5 eq) was carefully added i-BuMgBr (2.0 M in Et$^2$O, 7.5 mL 1.5 eq). The resulting mixture was stirred at rt for 30 min after diluting with THF (10 mL). The mixture was added over 10 min to a stirred solution of (S,E)-N-(2-chlorobenzylidene)-2-methylpropane-2-sulfinamide (2.44 g, 10 mmol, 1 eq) in THF (50 mL) at −78° C. After addition, it was stirred at −78° C. for 3 h, before quenching with sat. NH$_4$Cl and warming to rt. Extraction with Et$_2$O provided crude 1-((S)-1-((R)-tert-butylsulfinyl)-4-methylpentan-2-yl)-2-chlorobenzene as colorless viscous oil (3.06 g). $^1$H NMR indicated about 21% of methylated byproduct. The mixture was redissolved in MeOH (30 mL), cooled to 0° C. and treated with 1 M aq HCl in Et$_2$O (20 mL, 20 mmol). After stirring for 30 min, it was concentrated to dryness and purified by Biotage reverse phase (MeOH/H$_2$O 5 to 90%) to give the title compound as white solid (1.41 g, 60%, HCl salt). $^1$H NMR (400 MHz, CDCl$_3$) δ ppm 7.61 (dd, J=7.6, 1.6 Hz, 1H), 7.55 (dd, J=7.8, 1.4 Hz, 1H), 7.49 (dt, J=7.5, 1.5 Hz, 1H), 7.44 (dt, J=7.6, 2.0 Hz, 1H), 4.93-4.35 (m, 1H, partially buried in H$_2$O), 2.00-1.91 (m, 1H), 1.90-1.82 (m, 1H), 1.55-1.43 (m, 1H), 1.00 (d, J=6.4 Hz, 3H), 0.97 (d, J=6.8 Hz, 3H). MS ESI 181.0 [M+H]$^+$, calcd for [C$_{11}$H$_{16}$ClN+H−NH$_3$]$^+$ 181.1.

Synthesis of 3-iodo-N-(1-phenylpropyl)-1H-indazole-5-carboxamide

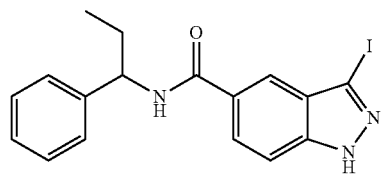 [SMILES: CCC(NC(=O)c1ccc2[nH]nc(I)c2c1)c1ccccc1]

The title compound was synthesized according to General Method A utilizing 1-phenylpropan-1-amine and obtained as a yellow solid (583 mg, 72% yield). $^1$H NMR (400 MHz, CDCl$_3$) δ 8.08 (d, J=0.8 Hz, 1 H), 7.97-7.91 (m, 1 H), 7.57 (d, J=8.8 Hz, 1 H), 7.45-7.39 (m, 2 H), 7.35 (s, 2 H), 7.26 (d, J=7.3 Hz, 1 H), 5.05-4.98 (m, 1 H), 2.05-1.89 (m, 2 H), 1.02 (t, J=7.3 Hz, 3 H); MS ESI [M+H]$^+$ 406.1, calcd for [C$_{17}$H$_{16}$IN$_3$O+H]$^+$ 406.04.

1-(2-chlorophenyl)-2-methylpropan-1-ol

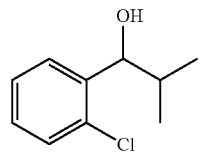

A solution of 2-chlorobenzaldehyde (2.75 g) in Et$_2$O (30 mL) was slowly added to a solution of i-PrMgBr (obtained from 0.98 g of Mg and 4.85 g 2-bromopropane in 70 mL anhydrous Et$_2$O and the mixture was stirred for 30 min at rt) at 0° C. The reaction mixture was stirred for 1 h at 0° C., and then quenched with aq. 25% NH$_4$Cl (100 mL). The organic layer was separated and the aq. layer was extracted with EtOAc (50 mL). The combined organic layer was washed with H$_2$O and brine, dried (Na$_2$SO$_4$) and concentrated under vacuum. Purification by flash chromatography (SiO$_2$, 0-25% EtOAc in hexanes) gave the title compound as a clear colorless oil (1.5 g, 41%). $^1$H NMR (400 MHz, DMSO-d$_6$) δ ppm 7.52 (d, J=7.2 Hz, 1H). 7.37-7.31 (m, 2H), 7.25-7.21

(m, 1H), 5.27 (d, J=4.4 Hz, 1H), 4.68 (dd, J=5.2 Hz, 1H). 1.88-1.80 (m, 1H), 0.86 (d, J=6.8 Hz, 6H).

1-(2-chlorophenyl)-2-methyl-propan-1-one

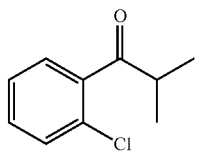

A solution of 1-(2-chlorophenyl)-2-methylpropan-1-ol (1.5 g in 15 mL DCM) was added to a suspension of PCC (2.62 g in 30 mL DCM) at 25° C., monitoring the reaction by TLC. After 2 h, Et$_2$O (120 mL) was added and the reaction mixture was stirred for 15 min. The supernatant was decanted, dried (Na$_2$SO$_4$) and concentrated under vacuum. Purification by flash chromatography (SiO$_2$, 0-10% EtOAc in hexanes) gave the title compound as a clear colorless oil (1.24 g, 82%). $^1$H NMR (400 MHz, CDCl$_3$) δ ppm 7.41-7.27 (m, 4H), 3.37-3.30 (m, 1H), 1.19 (d, J=6.8 Hz, 6H).

cyclopropyl(o-tolyl)methanamine

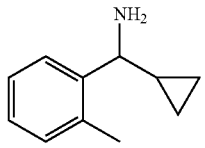

The title compound was synthesized according to method L, utilizing Mg powder (240 mg, 10 mmol), bromocyclopropane (1.21 g, 10 mmol), 2-methylbenzonitrile (468 mg, 4 mmol), and NaBH$_4$ (380 mg, 10 mmol). The reaction mixture was concentrated and purified by Biotage SiO$_2$ column (gradient: MeOH/DCM 0-20%) to give cyclopropyl (o-tolyl)methanamine as a yellow oil (0.70 g, 87%) which solidified upon standing. NMR (400 MHz, CD$_3$OD) δ ppm 8.49 (d, J=7.6 Hz, 1H), 7.27-7.22 (m, 1H), 7.20-7.17 (m, 2H), 3.75 (d, J=8.4 Hz, 1H), 2.35 (s, 3H), 1.37-1.27 (m, 1H), 0.71-0.63 (m, 1H), 0.53-0.46 (m, 1H), 0.38-0.31 (m, 1H), 0.29-0.33 (m, 1H); MS ESI 145.0 [M+H]$^+$, calcd for [C$_{11}$H$_{15}$N NH$_3$+H]$^+$ 145.1.

Cyclopropyl(pyridin-2-yl)methanamine

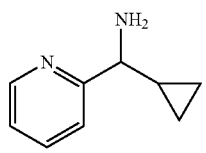 [SMILES: NC(c1ccccn1)C1CC1]

The title compound was synthesized according to method L, utilizing Mg powder (240 mg, 10 mmol), bromocyclopropane (1.21 g, 10 mmol), picolinonitrile (520 mg, 5 mmol) and NaBH$_4$ (380 mg, 10 mmol). The reaction mixture was quenched with H$_2$O, extracted with DCM and purified by Biotage SiO$_2$ column (gradient: MeOH/DCM 0-30%) to give cyclopropyl(pyridin-2-yl)methanamine as a light brown oil (590 mg). $^1$H NMR (400 MHz, CDCl$_3$) δ ppm 8.52 (d, J=4.0 Hz, 1H), 7.82 (dt, J=7.6 Hz, 1.6 Hz, 1H), 7.50 (d, J=8.0 Hz, 1H), 7.34-7.39 (m, 1H), 3.25 (d, J=8.8 Hz, 1H), 1.18-1.10 (m, 1H), 0.70-0.62 (m, 1H), 0.54-0.42 (m, 2H), 0.40-0.34 (m, 1H); MS ESI 132.0 [M+H]$^+$, calcd for [C$_9$H$_{12}$N$_2$–NH$_3$+H]$^+$ 132.1.

The following intermediates were synthesized via reductive amination using General Method G:

| IUPAC name | Structure | MS calculated<br>MS ESI [M + H]$^+$ | Yield;<br>Appearance;<br>Salt form |
|---|---|---|---|
| cyclopentyl(pyridin-2-yl)methanamine | 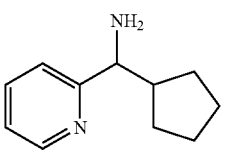 [SMILES: NC(c1ccccn1)C1CCCC1] | [C$_{11}$H$_{16}$N$_2$ + H]$^+$<br>177.1<br>177.1 | 931 mg<br>(93%); clear<br>oil;<br>free base |

Starting material: cyclopentyl-2-pyridyl ketone (1 g, 5.7 mmol)
$^1$H NMR (400 MHz, CD$_3$OD) δ ppm 8.50 (d, J = 4.0 Hz, 1 H), 7.80 (t, J = 7.9 Hz, 1 H), 7.41 (d, J = 8.0 Hz, 1 H), 7.31 (t, J = 5.0 Hz, 1 H), 3.76 (d, J = 8.8 Hz, 1 H), 2.14-2.27 (m, 1 H), 1.88-1.99 (m, 1 H), 1.36-1.75 (m, 5 H), 1.25-1.35 (m, 1 H), 1.2-1.24 (m, 1 H)

| 1-(2-chlorophenyl)-2-methylpropan-1-amine | 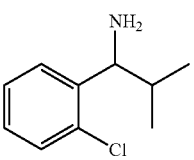 | [C$_{10}$H$_{14}$ClN + H]$^+$<br>184.1<br>184.1 | 348 mg<br>(23%);<br>colourless oil;<br>free base |

Starting material: 1-(2-chlorophenyl)-2-methyl-propan-1-one (1.5 g, 8.2 mmol)
$^1$H NMR (400 MHz, DMSO-d$_6$) δ ppm 7.38-7.21 (m, 4H), 4.87 (br. s, 2H), 4.16 (d, J = 8.0 Hz, 1H), 2.12-2.04 (m, 1H). 1.02 (d, J = 6.4 Hz, 3H), 0.82 (d, J = 6.8 Hz, 3H)

| IUPAC name | Structure | MS calculated MS ESI [M + H]+ | Yield; Appearance; Salt form |
|---|---|---|---|
| cyclopentyl(thiophen-3-yl)methanamine | NH2 on thiophene-cyclopentyl methanamine | [C10H15NS + H]+ 182.1 182.1 | 3.3 g (93%); Colourless oil; free base |

Starting material: cyclopentyl-3-thienyl ketone (3.5 g, 19 mmol)
$^1$H NMR (400 MHz, DMSO-$d_6$) δ ppm 7.44-7.42 (m, 1H), 7.27 (t, J = 2 H$_z$, 1H), 7.412-7.10 (m, 1H), 3.74 (t, J = 8.4 H$_z$, 1H), 2.09-1.99 (m, 1H), 1.76-1.68 (m, 1H), 1.58-1.29 (m, 6H), 1.16-1.14 (m, 1H).

Synthesis of 1-cyclohexylpropan-1-amine

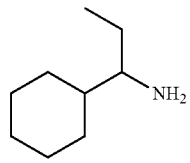

The mixture of 1-cyclohexylpropan-1-one (1.4 g, 10 mmols), NH$_4$OAc (9.25 g, 120 mmols), NaCNBH$_3$ (2.5 g, 40 mmols) in MeOH (80 mL) was refluxed overnight. The resulting reaction mixture was cooled down to rt and concentrated under reduced pressure. The residue was added 1 M NaOH (100 mL) and stirred for 20 min. The mixture was extracted with Et$_2$O. The combined organic layers were dried over Na$_2$SO$_4$ and concentrated under reduced pressure to provide the title compound as white crystals (380 mg, 27% yield). $^1$H NMR (400 MHz, CDCl$_3$) δ ppm 2.55-2.41 (dt, J=8.2, 4.1 Hz, 1H), 1.81-1.46 (m, 7H), 1.33-1.08 (m, 4H), 1.08-0.96 (m, 2H), 0.93 (t, J=8.2 Hz, 3H); MS ESI [M+H]+ 142.1, calcd for [C$_9$H$_{19}$N+H]+ 142.16.

(R,E)-N-(Cyclopentylmethylene)-2-methylpropane-2-sulfinamide

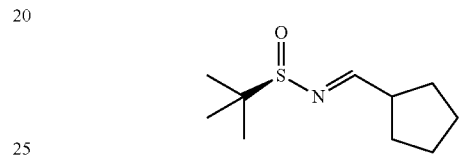

The title compound was synthesized according to General Method M utilizing cyclopentanecarboxaldehyde (15.0 g, 152.8 mmol, 1.0 eq.), (R)-t-butylsulfinylamide (24.1 g, 198.7 mmol, 1.3 eq.), and flame-dried CuSO$_4$ (73.2 g, 458.5 mmol, 3.0 eq.). The resulting mixture was stirred at rt for 71 h. The reaction mixture was filtered through a pad of Celite and the pad was rinsed with CH$_2$Cl$_2$ (5×100 mL). The combined organic extracts were concentrated under reduced pressure yielding a clear yellow oil (37.2 g). Purification by flash chromatography (SiO$_2$) using 1:9 EtOAc-cyclohexane as eluent gave the product (23.8 g, 78% isolated yield) as a clear pale yellow oil. $^1$H NMR (300 MHz, CDCl$_3$) δ ppm 7.99 (d, J=5.5 Hz, 1H), 3.02-2.87 (m, 1H), 1.97-1.78 (m, 2H), 1.78-1.55 (m, 6H), 1.18 (s, 9H).

The following sulfinamides were synthesized according to the synthesis of (R,E)-N-(cyclopentylmethylene)-2-methylpropane-2-sulfamide using General Method M:

| IUPAC name | Structure | MS calculated MS ESI [M + H]+ | Yield; Appearance; Salt form |
|---|---|---|---|
| (S,E)-N-(2-chlorobenzylidene)-2-methylpropane-2-sulfinamide | t-Bu-S(O)-N=CH-(2-Cl-C6H4) | [C11H14ClNOS + H]+ 244.1 N/A | 26.9 g (89%); pale yellow oil; Free base |

SMs: 2-chlorobenzaldehyde (20.9 g, 149 mmol), (S)-t-butylsulfinylamide (15.0 g, 124 mmol)
$^1$H NMR (300 MHz, CDCl$_3$) δ 9.05 (s, 1H), 8.06 (d, J = 7.5 Hz, 1H), 7.48-7.39 (m, 2H), 7.38-7.31 (m, 1H), 1.28 (s, 9H)

| (S,E)-2-methyl-N-(thiophen-3-ylmethylene)propane-2-sulfinamide | t-Bu-S(O)-N=CH-(thiophen-3-yl) | [C9H13NOS2 + H]+ 216.0 N/A | 20.2 g (76%); white solid; free base |

SMs: 3-thienylcarboxaldehyde (16.7 g, 149 mmol), (S)-t-butylsulfinylamide (15.0 g, 124 mmol)
$^1$H NMR (300 MHz, CDCl$_3$) δ 8.75 (s, 1H), 7.88-7.84 (m, 1H), 7.57 (d, J = 5.0 Hz, 1H), 7.40-7.34 (m, 1H), 1.25 (s, 9H)

Large Scale Asymmetric Synthesis of (S)-1-(Cyclopentyl)-1-(2-pyridinyl)methylamine HCl salt A. (R$_S$)-N-((S)-cyclopentyl(pyridin-2-yl)methyl)-2-methylpropane-2-sulfinamide

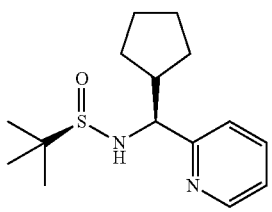 [SMILES: CC(C)(C)[S@@](=O)N[C@H](c1ccccn1)C1CCCC1]

A solution of 2-bromopyridine (11.8 mL, 19.5 g, 123.5 mmol in dry THF (50 mL) was added carefully to i-PrMgCl·LiCL (1.3 M in THF, 95.0 mL, 123.5 mmol). The resulting solution was stirred at rt for 3 h after which it was added dropwise, over 45 min, to a −48° C. solution of (R,E)-N-(cyclopentylmethylene)-2-methylpropane-2-sulfinamide (19.1 g, 95.0 mmol) in dry CH$_2$Cl$_2$ (250 mL). The resulting mixture was stirred at −48° C. for 1 h before being allowed to slowly warm up to rt over 16 h. The reaction was quenched by addition of saturated aq NH$_4$Cl (200 mL). H$_2$O (200 mL) was added and the mixture was extracted with CH$_2$Cl$_2$ (3×100 mL). The combined organic extracts were washed with brine (150 mL). The organic layer was dried (Na$_2$SO$_4$) and was concentrated under reduced pressure yielding the crude product (28.6 g, 5:1 d.r. (R$_S$,S)-(R$_S$,R)) as a clear red oil. The crude product was purified by repeated flash chromatography on silica gel using 1:19 MeOH-EtOAc as eluent in combination with trituration of the obtained solids with cyclohexane which eventually gave the pure product (8.80 g, 33%) as a white solid; $^1$H NMR (400 MHz, CDCl$_3$) δ ppm 8.56 (d, J=4.5 Hz, 1H), 7.63 (dt, J=1.0, 7.5 Hz, 1H), 7.22 (d, J=7.5 Hz, 1H), 7.16 (dd, J=4.5, 7.5 Hz, 1H), 4.26 (dd, J=5.0, 8.5 Hz, 1H), 3.95 (d, J=5.0 Hz, 1H), 2.44-2.31 (m, 1H), 1.94-1.83 (m, 1H), 1.68-1.44 (m, 5H), 1.44-1.32 (m, 1H), 1.30-1.17 (m, 1H), 1.13 (s, 9H).

B. (S)-1-(cyclopentyl)-1-(2-pyridinyl)methylamine HCl salt

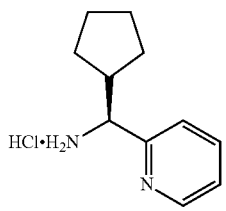

The title compound was synthesized according to General Method N utilizing HCl (2.0 M in Et$_2$O, 31.4 mL, 62.8 mmol) and a solution of (R$_S$)-N-((S)-cyclopentyl(pyridin-2-yl)methyl)-2-methylpropane-2-sulfinamide (8.8 g, 31.4 mmol) in MeOH (100 mL). After the addition was complete the cooling bath was removed and the mixture was stirred at rt for 1 h. The reaction mixture was concentrated under reduced pressure and the residue was suspended in Et$_2$O (125 mL). The precipitation was filtered off and washed with Et$_2$O (2×125 mL) and dried under reduced pressure yielding the crude product (7.7 g, 95.0% ee (S)) as a white solid. The crude product was recrystallised from t-BuOMe (150 mL), EtOH (200 mL) and MeOH (170 mL) at 80° C. The crystals formed after the solution cooled down were collected by filtration (3.3 g, 99.0% ee (S)) and the filtrate was concentrated under reduced pressure and was recrystallised again from t-BuOMe (100 mL) and MeOH (150 mL). The second crop of crystals were collected by filtration (1.3 g, 98.0% ee (S)) resulting in a combined yield of 4.6 g, 69% isolated yield). $^1$H NMR (400 MHz, D$_2$O+NaOH) δ ppm 8.81 (d, J=5.5 Hz, 1H), 8.55 (t, J=8.0 Hz, 1H), 8.06 (d, J=8.0 Hz, 1H), 7.99 (t, J=6.5 Hz, 1H), 4.53 (d, J=10.5 Hz, 1H), 2.63-2.50 (m, 1H), 2.11-2.01 (m, 1H), 1.84-1.40 (m, 6H), 1.24-1.12 (m, 1H). The ee of the compound was determined by acetylating small samples with AcCl (see example below for the synthesis) and analysing the products, (S)- and (R)-N-(Cyclopentyl(pyridin-2-yl)methyl)acetamides, by chiral HPLC: Daicel Chiralpak AD-H, 80:20 v/v heptane-EtOH (+0.2% Et$_3$N), 1.0 mL/min, λ=230 nm, R$_t$=9.5 min (R), R$_t$=25.4 min (S).

C. (rac)-N-(cyclopentyl(pyridin-2-yl)methyl)acetamide

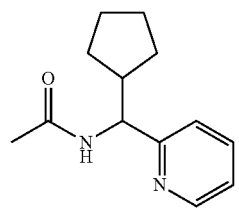 [SMILES: CC(=O)NC(c1ccccn1)C1CCCC1]

AcCl (0.10 g, 1.25 mmol) was added to a stirred suspension of Et$_3$N (0.35 mL, 0.25 g, 2.5 mmol, 2.2 eq.) and (rac)-1-cyclopentyl-1-(2-pyridinyl)methylamine HCl salt (0.25 g, 1.14 mmol) in CH$_2$Cl$_2$ (5 mL). The resulting mixture was stirred at rt for 2 h. The reaction mixture was washed with H$_2$O (10%, 3×3 mL) and was dried over Na$_2$SO$_4$ and was concentrated under reduced pressure yielding the crude product (0.20 g) as a clear yellow oil which quickly crystallized. $^1$H NMR (300 MHz, CDCl$_3$) δ ppm 8.53 (d, J=5.0 Hz, 1H), 7.62 (dt, J=1.5, 7.5 Hz, 1H), 7.28 (t, J=7.5 Hz, 1H), 7.16 (d, J=5.0 Hz, 1H), 6.72 (br d, J=7.0 Hz, 1H), 4.93 (t, J=9.0 Hz, 1H), 2.37-2.20 (m, 1H), 2.00 (s, 3H), 1.80-1.10 (m, 8H); HPLC: Daicel Chiralpak AD-H, 80:20 v/v heptane-EtOH (+0.2% Et$_2$NH), 1.0 mL min$^{-1}$, 210 nm, R$_t$=9.5 min, R$_t$=19.2 min.

Large Scale Asymmetric Synthesis of (S)-1-(2-chlorophenyl)-1-isopropylmethylamine HCl salt A. (S$_S$)-N-((S)-1-(2-chlorophenyl)-2-methylpropyl)-2-methylpropane-2-sulfinamide

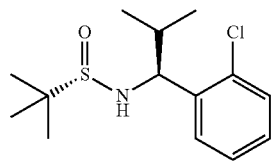 [SMILES: CC(C)[C@H](N[S@@](=O)C(C)(C)C)c1ccccc1Cl]

i-PrMgCl (2.0 M in THF, 46.2 mL, 92.3 mmol) was added carefully to stirred Me$_2$Zn (1.2 M in PhMe, 82 mL, 98.4 mmol) at rt. The resulting solution was stirred at rt for 30 min before being added dropwise, over 30 min, to a stirred −78° C. solution of (S,E)-N-(2-chlorobenzylidene)-2-methylpropane-2-sulfamide (15.0 g, 61.5 mmol) in dry THF (350 mL). After the addition was complete the reaction mixture was stirred at −78° C. for 3 h before being quenched by careful addition of satd aq NH₄Cl (200 mL). The mixture was extracted with Et₂O (3×100 mL). The combined organic extracts were washed with brine (100 mL) and were dried (Na₂SO₄). The organic layer was concentrated under reduced pressure yielding the crude product (17.9 g, quantitative yield, 16:1 d.r. (S_S,S)-(S_S,R) as a white solid which was used without any further purification. ¹H NMR (300 MHz, CDCl₃) δ ppm 7.38-7.15 (m, 4H), 4.46 (t, J=8.0 Hz, 1H), 3.75 (br d, J=8.0 Hz, 1H), 2.28-2.15 (m, 1H), 1.22 (s, 9H), 1.01 (d, J=6.5 Hz, 3H), 0.85 (d, J=6.5 Hz, 3H).

B. (S)-1-(2-chlorophenyl)-1-isopropylmethylamine HCl salt

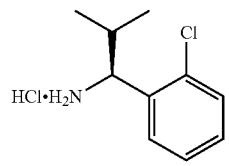

The title compound was synthesized according to General Method M utilizing HCl (2.0 M in Et₂O, 61.0 mL, 122.0 mmol) and a solution of (S_S)-N-((S)-1-(2-chlorophenyl)-2-methylpropyl)-2-methylpropane-2-sulfamide (17.8 g, 61.0 mmol) in MeOH (175 mL). After the addition was complete the cooling bath was removed and the mixture was stirred at rt for 1 h. The reaction mixture was concentrated under reduced pressure and Et₂O (250 mL) was added and a white precipitation formed. The precipitation was filtered off and washed with Et₂O (2×200 mL) and dried under reduced pressure yielding the crude product (11.8 g, 88.7% ee (S)) as a white solid. The crude product was recrystallised from t-BuOMe (300 mL) and MeOH (48 mL) at 80° C. After having cooled down over night only a small amount of crystals had been formed which were removed by filtration. The filtrate was concentrated under reduced pressure and after roughly half the volume had been removed a second crop of solids appeared which was also removed by filtration. The two crops of crystals were found to be racemic by chiral HPLC. The filtrate was concentrated to dryness and recrystallised again from t-BuOMe (300 mL) and MeOH (33 mL) at 80° C. Again only a small amount of crystals were formed as the solution cooled down which were removed by filtration, as was a second crop of solids formed when the solution was concentrated under reduced pressure. The remaining filtrate was concentrated to dryness and was suspended in t-BuOMe (200 mL) and filtered off. The resulting white solid was washed with Et₂O (3×150 mL) and was dried under reduced pressure yielding the purified product (9.0 g, 67% isolated yield, 97% ee (9) as a white solid. ¹H NMR (400 MHz, D₂O+NaOH) δ ppm 7.59-7.41 (m, 4H), 4.60 (d, J=9.5 Hz, 1H), 2.44-2.30 (m, 1H), 1.18 (d, J=6.5 Hz, 3H), 0.85 (d, J=6.5 Hz, 3H; HPLC: Daicel Chiralpak AD-H, 97:3 v/v heptane-EtOH (+0.1% Et3N), 1.0 mL/min, λ=280 nm, R_t=6.0 min (S), R_t=7.3 min (R).

Large Scale Asymmetric Synthesis of (S)-1-(cyclopentyl)-1-(3-thienyl)methylamine HCl salt A. (S_S)-N-((S)-cyclopentyl(thiophen-3-yl)methyl)-2-methylpropane-2-sulfamide

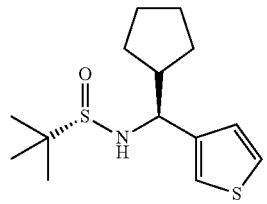 [SMILES: CC(C)(C)[S@](=O)N[C@H](c1ccsc1)C1CCCC1]

Cyclopentylmagnesium bromide (2.0 M in Et2O, 55.4 mL, 110.8 mmol) was added carefully to stirred dimethyl zinc (1.2 M in PhMe, 100 mL, 120 mmol) at rt. Dry THF (50 mL) was added and the mixture was stirred at rt for 30 min before being added slowly, dropwise over 30 min to a stirred −78° C. solution of (S,E)-N-(3-thienyl)-2-methylpropane-2-sulfinamide (19.9 g, 92.3 mmol) in dry THF (350 mL). Once the addition was complete the mixture was rapidly warmed up to −48° C. and was stirred at this temperature for 3 h. The reaction was quenched by addition of satd aq NH₄Cl (200 mL). H₂O (200 mL) was added and the mixture was extracted with Et₂O (3×100 mL). The combined organic extracts were washed with brine (100 mL), dried (Na₂SO₄) and concentrated under educed pressure yielding the crude product (31.4 g, 3:2 mixture of product and Me-added product, (S)-2-methyl-N-(1-(thiophen-3-yl)ethyl)propane-2-sulfinamide) as a clear yellow oil. The crude product was dissolved in 1:1 EtOAc-cyclohexane and was repeatedly columned through SiO₂ using 1:1 EtOAc/cyclohexane as eluent to yield the purified product (13.6 g, 52% isolated yield, >25:1 d.r. (S_S,S)-(S_S,R)) as a white solid. ¹H NMR (400 MHz, CDCl₃) δ ppm 7.28 (dd, J=2.5, 5.0 Hz, 1H), 7.19 (d, J=2.5 Hz, 1H), 7.10 (d, J=5.0 Hz, 1H), 4.28 (t, J=7.5 Hz, 1H), 3.35 (d, J=6.5 Hz, 1H), 2.47-2.35 (m, 1H), 1.92-1.82 (m, 1H), 1.65-1.46 (m, 5H), 1.40-1.30 (m, 1H), 1.28-1.16 (m, 1H), 1.2 (s, 9H).

B. (S)-1-(cyclopentyl)-1-(3-thienyl)methylamine HCl salt

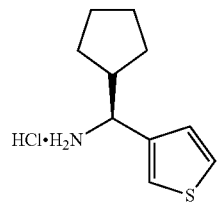

The title compound was synthesized according to General Method M utilizing HCl (2.0 M in Et₂O, 47.3 mL, 94.6 mmol) and a solution of (S_S)-N-((S)-cyclopentyl(thiophen-3-yl)methyl)-2-methylpropane-2-sulfinamide (13.5 g, 47.3 mmol) in MeOH (135 mL). After the addition was complete the cooling bath was removed and the mixture was stirred at rt for 1 h. The reaction mixture was concentrated under reduced pressure and the residue was suspended in Et₂O (200 mL). The precipitation was filtered off and washed with Et₂O (2×200 mL) and dried under reduced pressure yielding the crude product (9.0 g, 92.9% ee (S)) as a white solid. The compound was suspended in t-BuOMe (150 mL), filtered and washed with Et₂O (2×100 mL) and dried under reduced pressure yielding the product (8.4 g, 82% isolated yield, 94.5% ee (S)) as a white solid. ¹H NMR (400 MHz, D₂O+NaOH) δ ppm 7.57-7.52 (m, 2H), 7.23 (d, J=5.0 Hz, 1H), 4.31 (d, J=10.5 Hz, 1H), 2.56-2.43 (m, 1H), 2.04-1.94 (m, 1H), 1.80-1.48 (m, 5H), 1.46-1.34 (m, 1H), 1.24-1.09 (m, 1H); HPLC: Daicel Chiralcel OJ-H, 97:3 v/v heptane-EtOH (+0.2% Et₃N), 1.0 mL/min, λ=230 nm, R_t=7.6 min (R), R_t=8.3 min (S).

Synthesis of tert-butyl 1H-indazol-5-ylcarbamate

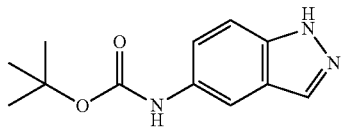 [SMILES: CC(C)(C)OC(=O)Nc1ccc2[nH]ncc2c1]

A DMF (15 mL) solution of aminoindazole (1.0 g, 7.5 mmol) and DIPEA (2.0 mL, 11 mmol) was treated with Boc₂O (1.7 g, 7.7 mmol) (50% added in one portion as a solid, and 50% as a solution in anh DMF (1 mL)) at 0° C. The reaction was stirred with the cooling for 1.5 h and then allowed to warm slowly to rt overnight. Later it was diluted with H₂O to ~100 mL. A tan precipitate was collected by filtration, washed with H₂O and dried to afford the product as a light tan solid (1.7 g, 94%). ¹H NMR (400 MHz, DMSO-d₆) δ ppm 12.90 (s., 1 H), 9.27 (s, 1 H), 7.94 (s, 1 H), 7.87 (br.s, 1 H), 7.41 (d, J=8.80 Hz, 1 H), 7.33 (d, J=9.2 Hz, 1 H), 1.47 (s, 9 H). MS ESI 233.9 [M+H]⁺, calcd for [C₁₂H₁₅N₃O₂+H]⁺ 234.0.

Synthesis of tert-butyl 3-iodo-1H-indazol-5-ylcarbamate

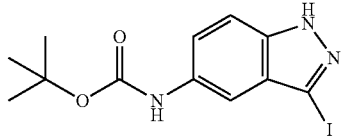 [SMILES: CC(C)(C)OC(=O)Nc1ccc2[nH]nc(I)c2c1]

To a cooled (0° C.) DMF (30 mL) solution t-butyl 1H-indazol-5-ylcarbamate (1.6 g, 6.9 mmol) and K₂CO₃ (3.8 g, 27.6 mmol) was added I₂ (1.8 g, 7.1 mmol) in one portion. The reaction was stirred with cooling for 3 h and then treated with 10% aq NaHSO₃ (50 mL) and subsequently with H₂O (150 mL). A filtration and washing (H₂O) of the ppt provided crude material which after purification by flash chromatography (SiO₂, 70 g, 0 to 6% MeOH in DCM) and recrystallization from EtOAc/hexanes yielded tert-butyl 3-iodo-1H-indazol-5-ylcarbamate (3) as an off-white solid (1.9 g, 78%). ¹H NMR (400 MHz, Acetone-d₆) δ ppm 12.54 (br. s., 1H), 8.51 (br. s., 1 H), 7.87 (br.s., 1 H), 7.24-7.66 (m, 2 H), 1.51 (s, 9 H); MS ESI [M+H]⁺ 359.9 (100) r, calcd for [C₁₂H₁₄IN₃O₂+H]⁺ 360.0.

Synthesis of (R)-N-(3-iodo-1H-indazol-5-yl)-2-methoxy-2-phenylacetamide

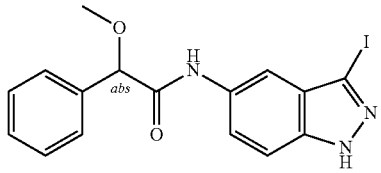 [SMILES: COC(C(=O)Nc1ccc2[nH]nc(I)c2c1)c1ccccc1]

A. (R)-N-(1H-indazol-5-yl)-2-methoxy-2-phenylacetamide was synthesized according to the General Method A utilizing 1H-indazol-5-amine (0.50 g, 3.76 mmol), (R)-2-methoxy-2-phenylacetic (0.65 g, 3.9 mmol), N-ethyl-N-isopropylpropan-2-amine (1.3 mL, 7.5 mmol) and TBTU (1.27 g, 3.9 mmol) in DMF (10 mL). The (R)-N-(1H-indazol-5-yl)-2-methoxy-2-phenylacetamide was precipitated by addition of H₂O, filtered and dried to provide a tan solid (0.81 g) which was used without further purification. MS ESI 282.1 [M+H]⁺, calcd for [C₁₆H₁₅N₃O₂:+H]⁺ 281.1.

B. (R)-N-(3-iodo-1H-indazol-5-yl)-2-methoxy-2-phenylacetamide was prepared according to the General method B using (0.81 g, 2.8 mmol), I2 (1.4 g, 5.7 mmol) and KOH (0.48 g, 8.5 mmol) in DMF (8 mL) to provide the desired compound as a white solid (0.58 g, 50%). MS ESI 408.1 [M+H]⁺, calcd for [C₁₆H₁₄IN₃O₂+H]⁺ 408.1.

Synthesis of 2-(pyrrolidin-1-yl)-2-(thiophen-3-yl)acetic acid

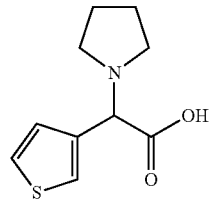 [SMILES: O=C(O)C(c1ccsc1)N1CCCC1]

The title compound was synthesized according to General Method D by using a glyoxylic acid monohydrate (10.79 g, 0.11 mol) and pyrrolidine (9.69 mL, 0.11 mol) was combined with DCM (375 mL) and sonicated for 15 min. Thiophene-3-boronic acid (15 g, 0.11 mol) was added and the mixture was stirred at room temperature for 24 h. the solid was filtered and washed with little DCM to gave 38 g crude product as crop-1. The mother liquor concentrated under reduced pressure to give an additional 4 g as crop-2. The combined crude product purified by Biotage SNAP 100 g silica column (gradient 0-50% MeOH in DCM) gave the title compound as a cream solid (21.7 g, 70%). ¹H NMR (400 MHz, CD₃OD) δ 7.66 (dd, J=2.8 Hz, J=1.2 Hz, 1H), 7.53 (dd, J=5.2 Hz, 2.8 Hz, 1H), 7.28 (dd, J=5.2 Hz, 1.2 Hz, 1H), 4.65 (s, 1H), 3.06 (br.s, 2H), 2.04-1.95 (br.s, 4H), 2H merged with solvent peak; MS ESI 212 [M+H]⁺, calcd for [C₁₀H₁₃NO₂S+H]⁺ 212.07.

Synthesis of N-(3-iodo-1H-indazol-5-yl)-2-(pyrrolidin-1-yl)-2-(thiophen-3-yl)acetamide

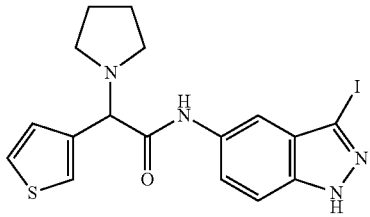 [SMILES: O=C(Nc1ccc2[nH]nc(I)c2c1)C(c1ccsc1)N1CCCC1]

Using method A, 3-iodo-1H-indazol-5-amine (2.53 g, 9.76 mmol) and 2-(pyrrolidin-1-yl)-2-(thiophen-3-yl)acetic acid (1.69 g, 8.0 mmol) in DMF (57.5 mL) were stirred at rt for 29 h. The reaction mixture was added dropwise into H$_2$O (400 mL) and the precipitate was collected by filtration, transferred using a mixture of acetone and EtOH, and concentrated to dryness. Purification on Biotage Isolera (silica, 60-90% EtOAc/Hexane) gave the title compound (1.61 g, 44%) which was used without further purification. $^1$H NMR (400 MHz, CD$_3$OD) δ ppm 7.83 (s, 1 H), 7.49-7.56 (m, 2 H), 7.44-7.48 (m, 1 H), 7.39-7.44 (m, 1 H), 7.33 (d, J=5.0 Hz, 1 H), 4.11 (s, 1 H), 2.67 (d, J=6.0 Hz, 2 H), 2.51 (d, J=5.8 Hz, 2H), 1.81-1.87 (m, 5 H).

Synthesis of N-(3-iodo-1H-indazol-5-yl)-2-(pyrrolidin-1-yl)-2-(thiophen-2-yl)acetamide A. 2-(pyrrolidin-1-yl)-2-(thiophen-2-yl)acetic acid

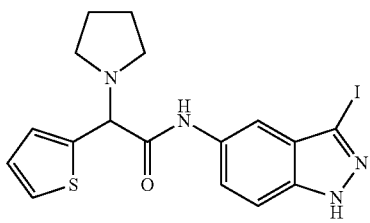 [SMILES: O=C(Nc1ccc2[nH]nc(I)c2c1)C(c1cccs1)N1CCCC1]

The title compound was synthesized according to General Method D by using a glyoxylic acid monohydrate (1.08 g, 11.7 mmol) and pyrrolidine (0.97 mL, 11.7 mol) was combined with DCM (45 mL) and sonicated for 15 min. Thiophene-2-boronic acid (1.5 g, 11.7 m mol) was added and the mixture was stirred at room temperature for 24 h. The solid was filtered and washed with DCM to give 2.2 g crude product. The crude product was purified by Biotage SNAP 50 g silica column (0-30% MeOH in DCM) gave the title compound as an off white solid (1.97 g, 79%). $^1$H NMR (400 MHz, CD$_3$OD) δ 7.54-7.53 (br.s, 1H), 7.35 (s, 1H), 7.07 (s, 1H), 3.42-3.35 (br.s, 2H), 3.13 (br.s, 2H), 2.02 (br.s, 4H), 1H merged with solvent peak; MS ESI 212 [M+H]$^+$, calcd for [C$_{10}$H$_{13}$NO$_2$S+H]$^+$ 212.07.

B. N-(1H-indazol-5-yl)-2-(pyrrolidin-1-yl)-2-(thiophen-2-yl)acetamide

To a cooled (0-5° C.) solution of 2-(pyrrolidin-1-yl)-2-(thiophen-2-yl)acetic acid (200 mg, 0.946 mmol) in DCM (8 mL) was added DMAP (10 mg) followed by TEA (0.53 mL, 3.79 mmol) and (CH$_3$)$_3$COCl (0.14 mL, 1.14 mmol) added slowly at the same temperature. After 1 h stirring at 0° C., 5-amino-1H-indazole (145 mg, 1.09 mmol) added and at rt for 24 h. The reaction was diluted with DCM (20 mL) washed with H$_2$O and dried (Na$_2$SO$_4$) and concentrated under reduced pressure to give the title compound as a brown oil. The crude product was purified by Biotage SNAP 25 g silica column (0-10% MeOH in DCM) to give the title compound as a brown solid (210 mg, 68%). $^1$H NMR (400 MHz, DMSO-d$_6$) δ ppm 12.96 (s, 1H), 10.08 (s, 1H), 8.07 (s, 1H), 7.98 (s, 1H), 7.46-7.41 (m, 3H), 7.12 (s, 1H), 6.95 (s, 1H), 4.33 (s, 1H), 1.69 (br.s, 4H), 4H merged with solvent peak; MS ESI 327 [M+H]$^+$, calcd for [C$_{17}$H$_{18}$N$_4$OS+H]$^+$ 327.1.

C. N-(3-iodo-1H-indazol-5-yl)-2-(piperidin-1-yl)-2-thiophen-3-yl)acetamide

The title compound was synthesized according to General Method B by using a solution of N-(1H-indazol-5-yl)-2-(piperidin-1-yl)-2-(thiophen-2-yl)acetamide (143 mg, 0.438 mmol) in DMF (2.14 mL) and K$_2$CO$_3$ (242 mg, 1.75 mmol) was added I$_2$ (122 mg, 0.481 mmol) in one portion. The reaction was stirred at rt for 24 h and then treated with 5% aq Na$_2$S$_2$O$_3$.5H$_2$O (20 mL). The product was extracted using EtOAc (25 mL) and washed with H$_2$O (5 mL) followed by brine (5 mL), dried (Na$_2$SO$_4$) and concentrated under vacuum to give brown oily residue. The crude product was purified by Biotage SNAP 25 g silica column (0-80% EtOAc in hexanes) to give a yellow solid (78 m g, 39%). $^1$H NMR (400 MHz, CDCl$_3$) δ ppm 11.06-10.88 (br.s, 1H), 9.14 (s, 1H), 7.74 (s, 1H), 7.62-7.60 (m, 1H), 7.42-7.40 (m, 1H), 7.26 (s, 1H), 7.12 (s, 1H), 6.97 (s, 1H), 4.31 (s, 1H), 2.70 (br.s, 2H), 2.62 (br.s, 2H), 1.86 (br.s, 4H); MS ESI 453.1 [M+H]$^+$, calcd for [C$_{17}$H$_{17}$IN$_4$OS+H]$^+$ 453.02.

Synthesis of N-(1-cyclohexylpropyl)-3-iodo-1H-indazole-5-carboxamide

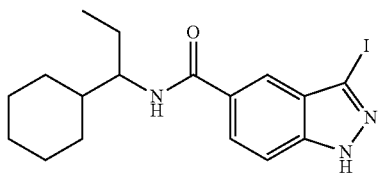 [SMILES: CCC(NC(=O)c1ccc2[nH]nc(I)c2c1)C1CCCCC1]

The mixture of 1-cyclohexylpropan-1-amine (380 mg, 2.69 mmol), 3-iodo-1H-indazole-5-carboxylic acid (774.9 mg, 2.69 mmol), DIPEA (1.33 mL, 8.07 mmols) in DMF (8 mL) was cooled down to 0° C. and added TBTU (864 mg, 2.69 mmol). After stirring at 0° C. for 1 h, H$_2$O was added followed by EtOAc. The organic layer was separated and washed with H$_2$O (3×), brine, dried over Na$_2$SO$_4$ and concentrated under reduced pressure to provide the title compound as a light yellow solid (418 mg, 38% yield). $^1$H NMR (400 MHz, CDCl$_3$) δ ppm 10.65 (s, 1H), 7.92 (m, 2H), 7.54 (d, J=8.8 Hz, 1H), 5.89 (d, J=4.1 Hz, 1H), 4.02 (m, 1H), 1.86-1.67 (m, 6H), 1.56-1.44 (m, 2H), 1.31-1.06 (m, 4H), 0.99 (t, J=8.2 Hz, 3H); MS ESI [M+H]$^+$ 412.3, calcd for [C$_{17}$H$_{22}$IN$_3$O+H]$^+$ 412.09.

Synthesis of 3-iodo-N-(2-methyl-2-morpholinopropyl)-1H-indazole-5-carboxamide

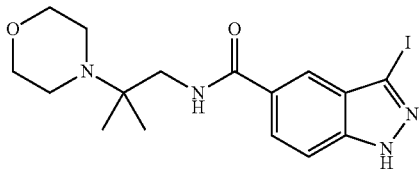 [SMILES: CC(C)(CNC(=O)c1ccc2[nH]nc(I)c2c1)N1CCOCC1]

The title compound was synthesized according to General Method A utilizing 2-methyl-2-morpholinopropan-1-amine and obtained as a white solid (65 mg, 15% yield). $^1$H NMR (400 MHz, CD$_3$OD) δ ppm 8.02 (s, 1 H), 7.93 (d, J=8.8 Hz, 1 H), 7.62 (d, J=8.3 Hz, 1 H), 3.72-3.78 (m, 4 H), 2.70 (br. s., 4 H), 1.15 (s, 6 H); MS ESI [M+H]$^+$ 429.0, calcd for [C$_{16}$H$_2$N$_4$O$_2$+H]$^+$ 429.08.

Synthesis of 3-iodo-N-(2-morpholino-2-(thiophen-3-yl)ethyl)-1H-indazole-5-carboxamide

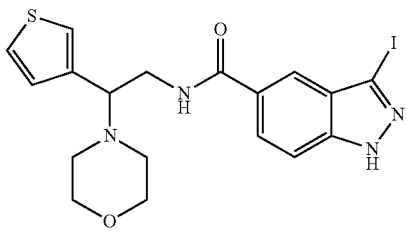 [SMILES: O=C(NCC(c1ccsc1)N1CCOCC1)c1ccc2[nH]nc(I)c2c1]

The title compound was synthesized according to General Method A utilizing 2-morpholino-2-(thiophen-3-yl)ethanamine and obtained as an off-white solid (180 mg, 37% yield). $^1$H NMR (400 MHz, CD$_3$OD) δ ppm 7.88 (s, 1 H), 7.83 (d, J=8.8 Hz, 1 H), 7.56 (d, J=8.8 Hz, 1 H), 7.43-7.48 (m, 1 H), 7.32 (m, J=2.5 Hz, 1 H), 7.15 (d, J=5.0 Hz, 1 H), 3.96-4.05 (m, 2 H), 3.64-3.76 (m, 5 H), 2.54-2.64 (m, 2 H), 2.51 (br. s., 2 H); MS ESI [M+H]$^+$ 483.1, calcd for [C$_{18}$H$_{19}$IN$_4$O$_2$S+H]$^+$ 483.04.

Synthesis of (S)-N-(1-cyclohexylethyl)-1H-indazole-5-carboxamide

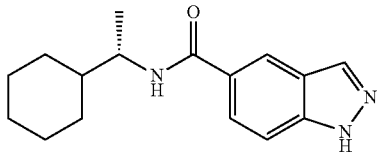 [SMILES: C[C@H](NC(=O)c1ccc2[nH]ncc2c1)C1CCCCC1]

The title compound was synthesized according to the General Method A utilizing 1H-indazole-5-carboxylic acid (500 mg, 3.1 mmol), (s)-(+)-1-cyclohexylethyl amine (349 mg, 3.1 mmol), TBTU (992 mg, 3.1 mmol), DIPEA (1.1 mL, 6.2 mmol), and DMF (15 mL) to give the title compound (off-white solid, 850 mg, 100%). $^1$H NMR (400 MHz, CD$_3$OD) δ ppm 8.29 (s, 1 H), 8.16 (s, 1 H), 7.85 (d, J=8.8 Hz, 1 H), 7.59 (d, J=9.0 Hz, 1 H), 3.92-4.01 (m, 1 H), 1.74-1.92 (m, 4 H), 1.64-1.71 (m, 1 H), 1.44-1.55 (m, 1 H), 1.22 (d, J=6.8 Hz, 6 H), 0.99-1.13 (m, 2 H); MS ESI 272.1 [M+H]$^+$, calcd for [C$_{16}$H$_{21}$N$_3$O+H]$^+$ 272.2.

Synthesis of (S)-N-(1-cyclohexylethyl)-3-iodo-1H-indazole-5-carboxamide

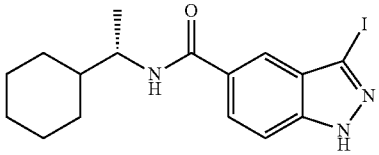 [SMILES: C[C@H](NC(=O)c1ccc2[nH]nc(I)c2c1)C1CCCCC1]

The title compound was synthesized according to the General Method B utilizing (S)-N-(1-cyclohexylethyl)-1H-indazole-5-carboxamide (850 mg, 3.2 mmol), I$_2$ (1.59 g, 6.4 mmol), K$_2$CO$_3$ (1.32 g, 9.6 mmol), and DMF (15 mL) to give the title compound (light orange solid, 846 mg, 67%). $^1$H NMR (400 MHz, CD$_3$OD) δ ppm 7.99-8.03 (m, 1 H), 7.86 (d, J=8.8 Hz, 1 H), 7.56 (d, J=8.0 Hz, 1 H), 3.91-4.02 (m, 1 H), 1.72-1.91 (m, 4 H), 1.61-1.72 (m, 1 H), 1.44-1.56 (m, 1 H), 1.13-1.34 (m, 6 H), 0.98-1.11 (m, 2 H); MS ESI 398.2 [M+H]$^+$, calcd for [C$_{16}$H$_{20}$IN$_3$O+H]$^+$ 398.1.

Synthesis of (S)-N-(cyclopropyl(phenyl)methyl)-3-iodo-1H-indazole-5-carboxamide

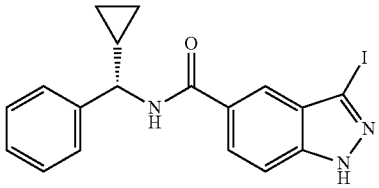 [SMILES: O=C(N[C@H](c1ccccc1)C1CC1)c1ccc2[nH]nc(I)c2c1]

The title compound was synthesized according to the General Method A utilizing 3-iodo-1H-indazole-5-carboxylic acid (79 mg, 0.79 mmol), (s)-cycloproylphenylmethylamine·HCl (50 mg, 0.27 mmol), TBTU (87 mg, 0.27 mmol), DIPEA (0.14 mL, 0.81 mmol), and DMF (4 mL) to give the title compound (orange solid, 110 mg, 98%). $^1$H NMR (400 MHz, CD$_3$OD) δ ppm 8.09 (s, 1 H), 7.95 (dd, J=8.9, 1.6 Hz, 1 H), 7.56 (d, J=8.8 Hz, 1 H), 7.43-7.50 (m, 2 H), 7.33 (t, J=7.6 Hz, 2 H), 7.24 (t, J=7.3 Hz, 1 H), 4.46 (d, J=9.5 Hz, 1 H), 1.34-1.46 (m, 1 H), 0.66 (d, J=8.0 Hz, 2 H), 0.48 (m, 2 H); MS ESI 418.1 [M+H]$^+$, calcd for [C$_{18}$H$_{16}$IN$_3$O+H]$^+$ 418.0.

Synthesis of (R)-N-(cyclopropyl(phenyl)methyl)-3-iodo-1H-indazole-5-carboxamide

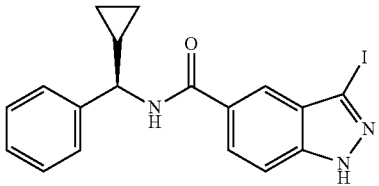 [SMILES: O=C(N[C@@H](c1ccccc1)C1CC1)c1ccc2[nH]nc(I)c2c1]

The title compound was synthesized according to the General Method A utilizing 3-iodo-1H-indazole-5-carboxylic acid (160 mg, 0.55 mmol), (R)-cycloproylphenylmethylamine. HCl (100 mg, 0.55 mmol), TBTU (177 mg, 0.55 mmol), DIPEA (0.29 mL, 1.65 mmol), and DMF (8 mL) to give the title compound (orange solid, 232 mg, 100%). $^1$H NMR (400 MHz, CD$_3$OD) δ ppm 8.09 (s, 1 H), 7.95 (dd, J=8.8, 1.51 Hz, 1 H), 7.55 (d, J=8.8 Hz, 1 H), 7.44-7.50 (m, 2 H), 7.32 (t, J=7.5 Hz, 2H), 7.22 (t, J=7.3 Hz, 1 H), 4.46 (d, J=9.5 Hz, 1H), 1.39 (br. s, 1 H), 0.61-0.68 (m, 2 H), 0.39-0.52 (m, 2 H); MS ESI 418.1 [M+H]$^+$, calcd for [C$_{18}$H$_{16}$IN$_3$O+H]$^+$ 418.0.

Synthesis of (R)-N-(1-cyclohexylethyl)-1H-indazole-5-carboxamide

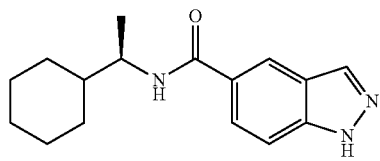 [SMILES: C[C@@H](NC(=O)c1ccc2[nH]ncc2c1)C1CCCCC1]

The title compound was synthesized according to the General Method A utilizing 1H-indazole-5 carboxylic acid (500 mg, 3.1 mmol), (R)-(−)-1-cyclohexylethylamine (392 mg, 3.1 mmol), TBTU (992 mg, 3.1 mmol), DIPEA (1.1 mL, 6.2 mmol), and DMF (15 mL) to give the title compound (off-white solid, 800 mg, 96%). MS ESI 272.2 [M+H]$^+$, calcd for [C$_{16}$H$_{21}$N$_3$O+H]$^+$ 272.2.

Synthesis of (R)-N-(1-cyclohexylethyl)-3-iodo-1H-indazole-5-carboxamide

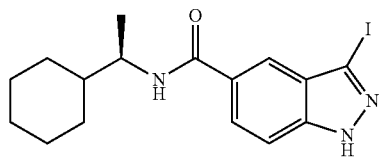 [SMILES: C[C@@H](NC(=O)c1ccc2[nH]nc(I)c2c1)C1CCCCC1]

The title compound was synthesized according to the General Method B utilizing (R)-N-(1-cyclohexylethyl)-1H-indazole-5-carboxamide (800 mg, 3.0 mmol), I$_2$ (1.5 g, 5.9 mmol), K$_2$CO$_3$ (1.22 g, 8.9 mmol), and DMF (15 mL) to give the title compound (pale yellow solid, 825 mg, 70%). $^1$H NMR (400 MHz, CD$_3$OD) δ ppm 8.02 (s, 1 H), 7.91 (dd, J=8.8, 1.5 Hz, 1 H), 7.56 (d, J=8.8 Hz, 1 H), 3.91-4.02 (m, 1 H), 1.73-1.91 (m, 4 H), 1.61-1.72 (m, 1 H), 1.45-1.56 (m, 1 H), 1.13-1.34 (m, 6 H), 0.98-1.12 (m, 2 H); MS ESI 398.2 [M+H]$^+$, calcd for [C$_{16}$H$_{20}$IN$_3$O+H]$^+$ 398.1.

Synthesis of (R)-3-iodo-N-(1-(thiophen-2-yl)ethyl)-1H-indazole-5-carboxamide

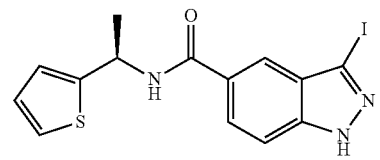 [SMILES: C[C@@H](NC(=O)c1ccc2[nH]nc(I)c2c1)c1cccs1]

The title compound was synthesized according to the General Method A utilizing 3-iodo-1H-indazole-5-carboxylic acid (86 mg, 0.30 mmol), (R)-1-(2-thienyl)ethylamine (50 mg, 0.30 mmol), TBTU (96 mg, 0.30 mmol), DIPEA (0.15 mL, 0.90 mmol), and DMF (5 mL). Purification by flash chromatography (SiO$_2$, Biotage 25 g, 5-25% MeOH in CH$_2$Cl$_2$) gave the title compound (yellow solid, 70 mg, 59%). $^1$H NMR (400 MHz, CD$_3$OD) δ ppm 8.06 (s, 1 H), 7.94 (dd, J=8.8, 1.5 Hz, 1 H), 7.56 (dd, J=8.8, 0.8 Hz, 1 H), 7.27 (dd, J=5.1, 1.1 Hz, 1 H), 7.05 (dt, J=3.5, 1.0 Hz, 1 H), 6.96 (dd, J=5.0, 3.5 Hz, 1 H), 5.57 (q, J=6.9 Hz, 1 H), 1.69 (d, J=7.0 Hz, 3 H); MS ESI 398.1 [M+H]$^+$, calcd for [C$_{14}$H$_{12}$IN$_3$OS+H]$^+$ 398.0.

Synthesis of (R)-3-iodo-N-(1-(thiophen-2-yl)propyl)-1H-indazole-5-carboxamide

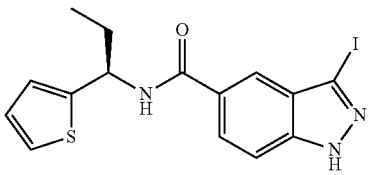 [SMILES: CC[C@@H](NC(=O)c1ccc2[nH]nc(I)c2c1)c1cccs1]

The title compound was synthesized according to the General Method A utilizing 3-iodo-1H-indazole-5-carboxylic acid (75 mg, 0.26 mmol), (R)-1-(2-thienyl)propylamine (50 mg, 0.26 mmol), TBTU (83 mg, 0.26 mmol), DIPEA (0.14 mL, 0.78 mmol), and DMF (4 mL) to give the title compound (yellow oil, 90 mg, 84%). $^1$H NMR (400 MHz, CD$_3$OD) δ ppm 8.07 (dd, J=1.8, 0.8 Hz, 1 H), 7.94 (dd, J=8.9, 1.6 Hz, 1 H), 7.57 (dd, J=8.9, 0.6 Hz, 1 H), 7.27 (dd, J=5.1, 1.1 Hz, 1H), 7.06 (dt, J=2.4, 1.1 Hz, 1 H), 6.97 (dd, J=5.3, 3.5 Hz, 1 H), 5.34 (t, J=7.5 Hz, 1 H), 2.01-2.12 (m, 2 H), 1.05 (t, J=7.3 Hz, 3 H); MS ESI 412.0 [M+H]$^+$, calcd for [C$_{15}$H$_{14}$IN$_3$OS+H]$^+$ 412.0.

Synthesis of (S)-N-(3-hydroxy-1-phenylpropyl)-3-iodo-1H-indazole-5-carboxamide

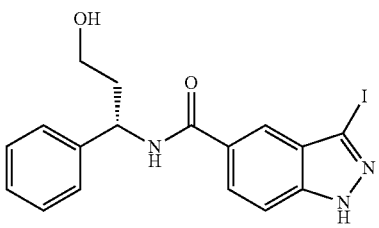 [SMILES: O=C(N[C@@H](CCO)c1ccccc1)c1ccc2[nH]nc(I)c2c1]

The title compound was synthesized according to the General Method A utilizing 3-iodo-1H-indazole-5-carboxylic acid (288 mg, 1 mmol), (S)-3-phenyl-beta-alaminol (151 mg, 1 mmol), TBTU (321 mg, 1 mmol), DIPEA (0.52 mL, 3 mmol), and DMF (15 mL) Purification by flash chromatography (SiO$_2$, Biotage 25 g, 0-25% MeOH in CH$_2$Cl$_2$) gave the title compound (white solid, 203 mg, 48%). $^1$H NMR (400 MHz, DMSO-d$_6$) δ ppm 13.70 (s, 1 H), 8.93 (d, J=8.0 Hz, 1 H), 8.07 (s, 1 H), 7.94 (d, J=8.3 Hz, 1 H), 7.59 (d, J=8.5 Hz, 1 H), 7.40 (d, J=7.5 Hz, 2 H), 7.33 (t, J=7.5 Hz, 2 H), 7.22 (t, J=7.0 Hz, 1 H), 5.15-5.23 (m, 1 H), 4.56-4.61 (m, 1 H), 3.39-3.52 (m, 2 H), 2.02-2.14 (m, 1 H), 1.86-1.98 (m, 1 H), 1.19-1.29 (m, 1 H); MS ESI 422.1 [M+H]$^+$, calcd for [C$_{17}$H$_{16}$IN$_3$O$_2$+H]$^+$ 422.0.

Synthesis of 3-iodo-N-(1-(2-methylbenzyl)cyclopropyl)-1H-indazole-5-carboxamide

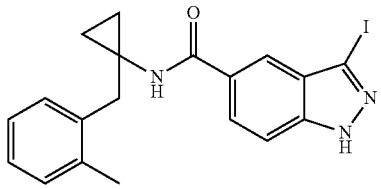 [SMILES: Cc1ccccc1CC1(NC(=O)c2ccc3[nH]nc(I)c3c2)CC1]

The title compound was synthesized according to the General Method A utilizing 3-iodo-1H-indazole-5-carboxylic acid (288 mg, 1 mmol), 1-(2-methylbenzyl)cyclopropanamine.HCl (197 mg, 1 mmol), TBTU (321 mg, 1 mmol), DIPEA (0.52 mL, 3 mmol), and DMF (15 mL). Purification by flash chromatography (SiO$_2$, Biotage 0-25% MeOH in CH$_2$Cl$_2$) gave the title compound (off-white solid, 193 mg, 45%); MS ESI 432.1 [M+H]$^+$, calcd for [C$_{19}$H$_{18}$IN$_3$O+H]$^+$ 432.1.

Synthesis of (R)-N-(3-hydroxy-1-phenylpropyl)-3-iodo-1H-indazole-5-carboxamide

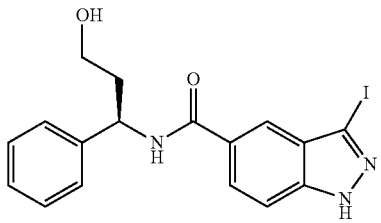 [SMILES: O=C(N[C@H](CCO)c1ccccc1)c1ccc2[nH]nc(I)c2c1]

The title compound was synthesized according to the General Method A utilizing 3-iodo-1H-indazole-5-carboxylic acid (288 mg, 1 mmol), (R)-3-phenyl-beta-alaminol (151 mg, 1 mmol), TBTU (321 mg, 1 mmol), DIPEA (0.52 mL, 3 mmol), and DMF (15 mL) Purification by flash chromatography (SiO$_2$, Biotage 25 g, 0-25% MeOH in CH$_2$Cl$_2$) gave the title compound (white solid, 247 mg, 59%). $^1$H NMR (400 MHz, DMSO-d$_6$) δ ppm 13.70 (s, 1 H), 8.93 (d, J=8.3 Hz, 1 H), 8.06 (s, 1 H), 7.94 (d, J=9.0 Hz, 1 H), 7.59 (d, J=8.5 Hz, 1 H), 7.40 (d, J=7.5 Hz, 2 H), 7.33 (t, J=7.5 Hz, 2 H), 7.22 (t, J=7.5 Hz, 1 H), 5.15-5.24 (m, 1 H), 4.59 (br. s., 1 H), 3.45 (br. s., 2 H), 2.02-2.15 (m, 1 H), 1.86-1.98 (m, 1 H), 1.22-1.29 (m, 1 H); MS ESI 422.1 [M+H]$^+$, calcd for [C$_{17}$H$_{16}$IN$_3$O$_2$+H]$^+$ 422.0.

Synthesis of 2-cyclopentyl-2-(2-methoxyphenyl)acetic acid

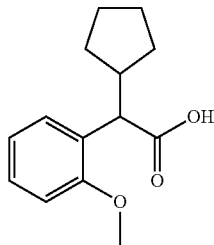 [SMILES: COc1ccccc1C(C(=O)O)C1CCCC1]

Methyl 2-(2-methoxyphenyl)acetate (900 mg, 5 mmol) and 60% NaH (240 mg, 6 mmol) were dissolved in DMF (25 mL) and cooled to 0° C. Cyclopentyl bromide (745 mg, 5 mmol) was added and the reaction was gradually warmed to rt. The reaction was stirred at rt for 16 h and then partitioned between EtOAc (100 mL) and NaHCO$_3$ (150 mL). The mixture was washed with brine (150 mL), dried over MgSO$_4$ and the solvent was removed under reduced pressure. Saponification was conducted by addition of 2 M NaOH (20 mL) and heating at 60° C. for 16 h. The mixture was then acidified with 2 M aq HCl and then extracted with EtOAc. The solution was dried over MgSO$_4$ and concentrated to give the title compound (yellow solid, 760 mg, 65%). $^1$H NMR (400 MHz, CDCl$_3$) δ ppm 7.39 (dd, J=7.6, 1.6 Hz, 1 H), 7.24 (td, J=7.8, 1.3 Hz, 1 H), 6.95 (m, 1 H), 6.89 (d, J=8.3 Hz, 1 H), 3.94 (d, J=11.0 Hz, 1 H), 3.84 (s, 3 H), 2.48-2.60 (m, 1 H), 1.93-2.04 (m, 1 H), 1.51-1.76 (m, 3 H), 1.39-1.51 (m, 2 H), 1.32-1.39 (m, 1 H), 0.97-1.07 (m, 1 H); MS ESI 235.1 [M+H]$^+$, calcd for [C$_{14}$H$_{18}$O$_3$+H]$^+$ 235.1.

Synthesis of 2-cyclopentyl-N-(3-iodo-1H-indazol-5-yl)-2-(2-methoxyphenyl)acetamide

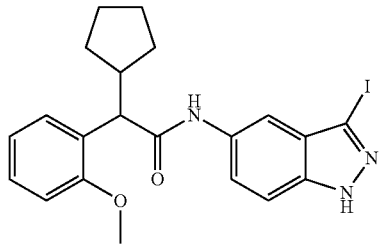 [SMILES: COc1ccccc1C(C(=O)Nc1ccc2[nH]nc(I)c2c1)C1CCCC1]

The title compound was synthesized according to the General Method A utilizing 3-iodo-1H-indazol-5-amine (221 mg, 0.85 mmol), 2-cyclopentyl-2-(2-methoxyphenyl)acetic acid (200 mg, 0.85 mmol), TBTU (273 mg, 0.85 mmol), DIPEA (0.44 mL, 2.55 mmol), and DMF (10 mL). Purification by flash chromatography (SiO$_2$, Biotage 25 g, 0-25% MeOH in CH$_2$Cl$_2$) gave the title compound (orange solid, 81 mg, 20%). MS ESI 476.2 [M+H]$^+$, calcd for [C$_{21}$H$_{22}$IN$_3$O$_2$+H]$^+$ 476.1.

Synthesis of N-(cyclopentyl(phenyl)methyl)-3-iodo-1H-indazole-5-carboxamide

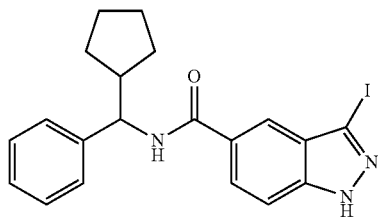 [SMILES: O=C(NC(c1ccccc1)C1CCCC1)c1ccc2[nH]nc(I)c2c1]

The title compound was synthesized according to the General Method A utilizing 3-iodo-1H-indazole-5-carboxylic acid (288 mg, 1 mmol), cyclopentyl(phenyl)methanamine (204 mg, 1 mmol), TBTU (321 mg, 1 mmol), DIPEA (0.52 mL, 3 mmol), and DMF (7 mL) to gave the title compound (yellow solid, 445 mg, 97%). $^1$H NMR (400 MHz, CD$_3$OD) δ ppm 8.03 (s, 1 H), 7.90 (dd, J=8.7, 1.6 Hz, 1 H), 7.56 (d, J=8.8 Hz, 1 H), 7.44 (d, J=7.3 Hz, 2 H), 7.33 (t, J=7.5 Hz, 2 H), 7.24 (t, J=7.5 Hz, 1 H), 4.83 (d, J=11.0 Hz, 1 H), 2.48-2.61 (m, 1 H), 1.95-2.07 (m, 1 H), 1.35-1.79 (m, 6 H), 1.14-1.26 (m, 1 H).

Synthesis of 2-cyclopentyl-2-(2-fluorophenyl)acetic acid

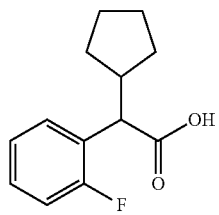 [SMILES: O=C(O)C(c1ccccc1F)C1CCCC1]

Ethyl (2-fluorophenyl)acetate (900 mg, 5 mmol) and 60% NaH (240 mg, 6 mmol) were dissolved in DMF (25 mL) and cooled to 0° C. Cyclopentyl bromide (745 mg, 5 mmol) was added and the reaction was gradually warmed to rt. Reaction was stirred at rt for 16 h and then partitioned between EtOAc (100 mL) and NaHCO$_3$ (150 mL). The reaction was washed with brine (150 mL), dried over MgSO$_4$ and solvent was removed under reduced pressure. Saponification was conducted by addition of 2 M NaOH (20 mL) and heating at 60° C. for 16 h. The mixture was then acidified with 2 M aq HCl and then extracted with EtOAc. The solution was dried over MgSO$_4$ and concentrated to give the title compound (yellow solid, 800 mg, 72%). $^1$H NMR (400 MHz, CDCl$_3$) δ ppm 7.46 (t, J=6.6 Hz, 1 H), 7.20-7.26 (m, 1 H), 7.12 (t, J=7.5 Hz, 1 H), 7.05 (t, J=9.2 Hz, 1 H), 3.78 (d, J=11.0 Hz, 1 H), 2.47-2.60 (m, 1 H), 1.93-2.04 (m, 1 H), 1.54-1.75 (m, 3 H), 1.41-1.54 (m, 2 H), 1.29-1.41 (m, 1 H), 0.98-1.12 (m, 1 H).

Synthesis of 2-cyclopentyl-2-(2-fluorophenyl)-N-(3-iodo-1H-indazol-5-yl)acetamide

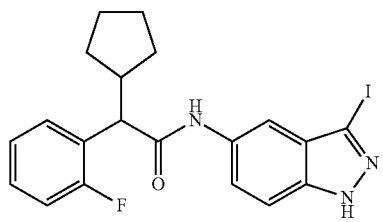 [SMILES: O=C(Nc1ccc2[nH]nc(I)c2c1)C(c1ccccc1F)C1CCCC1]

The title compound was synthesized according to the General Method A utilizing 3-iodo-1H-indazol-5-amine (518 mg, 2 mmol), 2-cyclopentyl-2-(2-fluorophenyl)acetic acid (444 mg, 2 mmol), TBTU (642 mg, 2 mmol), DIPEA (1 mL, 6 mmol), and DMF (10 mL) Purification by flash chromatography (SiO$_2$, Biotage 25 g, 0-25% MeOH in CH$_2$Cl$_2$) gave the title compound (yellow oil, 217 mg, 23%). Some di-acetylate by product was also collected as a yellow solid (201 mg, 15%). $^1$H NMR (400 MHz, CD$_3$OD) δ ppm 8.08 (d, J=9.0 Hz, 1 H), 7.54 (td, J=7.5, 1.6 Hz, 1 H), 7.20-7.27 (m, 1 H), 7.01-7.14 (m, 3 H), 6.66 (d, J=2.3 Hz, 1 H), 5.24 (d, J=11.3 Hz, 1 H), 2.68-2.82 (m, 1 H), 1.87-2.00 (m, 1 H), 1.59-1.78 (m, 3 H), 1.43-1.59 (m, 2 H), 1.20-1.36 (m, 2 H).

Synthesis of cyclohexyl(phenyl)methanamine

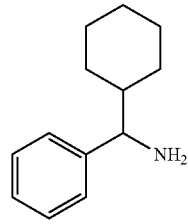 [SMILES: NC(c1ccccc1)C1CCCCC1]

The title compound was synthesized according to the General Method G, utilizing cyclohexylphenyl ketone (1.5 g, 8.0 mmol), NH$_4$OAc (7.4 g, 96 mmol), NaCNBH$_3$ (2 g, 32 mmol), and MeOH (30 mL) to give the title compound (clear oil, 1.41 g, 93%). $^1$H NMR (400 MHz, CDCl$_3$) δ ppm 7.27-7.39 (m, 3 H), 7.23 (d, J=7.3 Hz, 2 H), 4.24 (br. s., 2 H), 3.58 (d, J=8.3 Hz, 1 H), 1.83-1.98 (m, 1 H), 1.72-1.83 (m, 1 H), 1.63 (br. d, J=8.5 Hz, 3 H), 1.19-1.38 (m, 2 H), 1.11 (d, J=8.5 Hz, 2H), 0.91-1.05 (m, 1 H), 0.71-0.87 (m, 1 H).

Synthesis of N-(cyclohexyl(phenyl)methyl)-3-iodo-1H-indazole-5-carboxamide

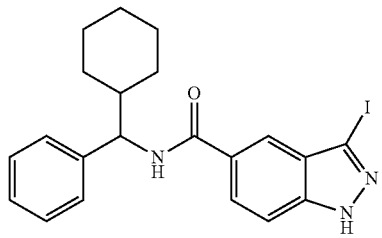 [SMILES: O=C(NC(c1ccccc1)C1CCCCC1)c1ccc2[nH]nc(I)c2c1]

The title compound was synthesized according to the General Method A utilizing 3-iodo-1H-indazole-5-carboxylic acid (576 mg, 2 mmol), cyclohexyl(phenyl)methanamine (378 mg, 2 mmol), TBTU (642 mg, 2 mmol), DIPEA (1 mL, 6 mmol), and DMF (6 mL) to gave the title compound (yellow solid, 917 mg, 100%). $^1$H NMR (400 MHz, CD$_3$OD) δ ppm 8.03 (s, 1 H), 7.90 (d, J=8.8 Hz, 1 H), 7.55 (d, J=9.0 Hz, 1 H), 7.40 (d, J=7.3 Hz, 2 H), 7.33 (s, 3 H), 4.79 (d, J=10.0 Hz, 1 H), 2.04-2.16 (m, 1 H), 1.59-2.01 (m, 4 H), 1.12-1.41 (m, 6 H), 0.86-1.02 (m, 1 H).

Synthesis of phenyl(tetrahydro-2H-pyran-4-yl)methanone

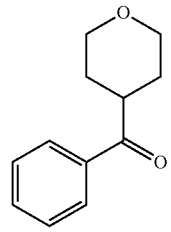

SOCl$_2$ (8 mL) was added to tetrahydro-2H-pyran-4-carboxylic acid (3.0 g, 23.1 mmol) and the resulting mixture was heated at 85° C. (oil temp.) for 1 h and cooled to rt. Removal of volatile materials gave crude acid chloride as pale yellow liquid. It was diluted with benzene (12 mL) and added slowly to a suspension of AlCl₃ (5.84 g, 43.8 mmol) in benzene (12 mL). After addition, the resulting mixture was heated at 75° C. for 1 h, cooled to rt, poured onto ice/H₂O, extracted with DCM and purified by flash chromatography (EtOAc/hex 20%) to give phenyl(tetrahydro-2H-pyran-4-yl)methanone (light yellow solid, 3.15 g, 72%). ¹H NMR (400 MHz, CDCl₃) δ 7.64 (d, J=7.6 Hz, 2H), 7.58 (t, J=7.4 Hz, 1H), 7.49 (t, J=7.6 Hz, 2H), 4.07 (tt, J=11.6 Hz, 2.8 Hz, 2H), 3.58 (dt, J=11.6 Hz, 2.5 Hz, 2H), 3.54-3.48 (m, 1H), 1.96-1.84 (m, 2H), 1.83-1.77 (m, 2H).

Synthesis of phenyl(tetrahydro-2H-pyran-4-yl)methanamine

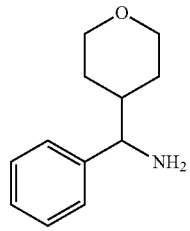 [SMILES: NC(c1ccccc1)C1CCOCC1]

A mixture of phenyl(tetrahydro-2H-pyran-4-yl)methanone (950 mg, 5 mmol), NH₄OAc (4.62 g, 60 mmol) and NaCNBH₃ (1.26 g, 20 mmol) in MeOH (30 mL) was heated O/N at 60° C. It was diluted with H₂O, extracted with DCM and purified by flash chromatography (MeOH/DCM 0-20%) to give phenyl(tetrahydro-2H-pyran-4-yl)methanamine (white solid, 262 mg, 42%). ¹H NMR (400 MHz, CD₃OD) δ 7.42-7.28 (m, 5H), 3.98 (dd, J=11.2 Hz, 3.6 Hz, 1H), 3.81 (dd, J=11.6 Hz, 2.8 Hz, 1H), 3.68 (d, J=8.8 Hz, 1H), 3.42 (dt, J=12.0 Hz, 2.0 Hz, 1H), 3.26 (dt, J=11.6 Hz, 2.8 Hz, 1H), 1.96-1.85 (m, 2H), 1.46-1.34 (m, 1H), 1.26-1.10 (m, 2H); MS ESI 175.0 [M+H]⁺, calcd for [C₁₂H₁₇NO−NH₃+H]⁺ 175.1.

Synthesis of 3-iodo-N-(phenyl(tetrahydro-2H-pyran-4-yl)methyl)-1H-indazole-5-carboxamide

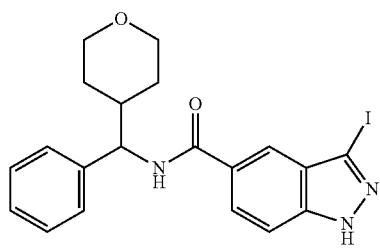 [SMILES: O=C(NC(c1ccccc1)C1CCOCC1)c1ccc2[nH]nc(I)c2c1]

To a solution of phenyl(tetrahydro-2H-pyran-4-yl)methanamine (262 mg, 1.37 mmol), 3-iodo-1H-indazole-5-carboxamide (395 mg, 1.37 mmol) in DMF (5 mL) at 0° C. was added TBTU (440 mg, 1.37 mmol), followed by iPr₂NEt (0.48 mL, 2.74 mmol). The resulting mixture was stirred at 0° C. for 30 min, quenched with H₂O and stirred for 10 min at rt. Suction filtration gave crude 3-iodo-N-(phenyl(tetrahydro-2H-pyran-4-yl)methyl)-1H-indazole-5-carboxamide (off white solid, 589 mg). MS ESI 462.1 [M+H]⁺, calcd for [C₂₀H₂₀IN₃O+H]⁺ 462.1.

Synthesis of N-(2-cyclopentyl-2-phenylethyl)-3-iodo-1H-indazole-5-carboxamide

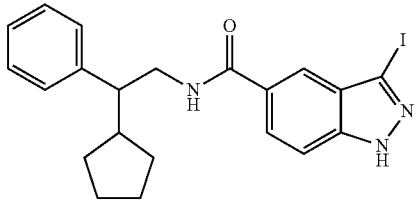 [SMILES: O=C(NCC(c1ccccc1)C1CCCC1)c1ccc2[nH]nc(I)c2c1]

The title compound was synthesized according to the General Method A utilizing 3-iodo-1H-indazole-5-carboxylic acid (500 mg, 1.74 mmol), 2-cyclopentyl-2-phenylethanamine (329 mg, 1.74 mmol), TBTU (559 mg, 1.74 mmol), DIPEA (0.90 mL, 5.21 mmol), and DMF (6 mL) to gave the title compound (yellow solid, 602 mg, 75%). ¹H NMR (400 MHz, CD₃OD) δ ppm 7.65-7.70 (m, 2 H), 7.49 (d, J=9.0 Hz, 1 H), 7.17-7.34 (m, 5 H), 3.80-3.91 (m, 1 H), 3.45-3.56 (m, 1 H), 2.80-2.85 (m, 1 H), 2.12-2.23 (m, 1 H), 2.00-2.12 (m, 1 H), 1.38-1.77 (m, 6 H), 0.99-1.11 (m, 1 H); MS ESI 460.2 [M+H]⁺, calcd for [C₂₁H₂₂IN₃O+H]⁺ 460.1.

Synthesis of cyclopentyl(pyridin-2-yl)methanamine

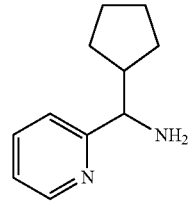 [SMILES: NC(c1ccccn1)C1CCCC1]

The title compound was synthesized according to the General Method G, utilizing cyclopentyl-2-pyridyl ketone (1 g, 5.7 mmol), NH₄OAc (5.3 g, 69 mmol), NaCNBH₃ (1.4 g, 23 mmol), and MeOH (20 mL) to give the title compound (clear oil, 931 mg, 93%). ¹H NMR (400 MHz, CD₃OD) δ ppm 8.50 (d, J=4.0 Hz, 1 H), 7.80 (t, J=7.9 Hz, 1 H), 7.41 (d, J=8.0 Hz, 1 H), 7.31 (t, J=5.0 Hz, 1 H), 3.76 (d, J=8.8 Hz, 1 H), 2.14-2.27 (m, 1 H), 1.88-1.99 (m, 1 H), 1.36-1.75 (m, 5 H), 1.25-1.35 (m, 1 H), 1.12-1.24 (m, 1 H).

Synthesis of N-(cyclopentyl(pyridin-2-yl)methyl)-3-iodo-1H-indazole-5-carboxamide

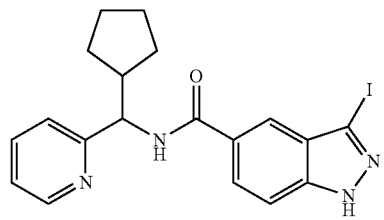 [SMILES: O=C(NC(c1ccccn1)C1CCCC1)c1ccc2[nH]nc(I)c2c1]

The title compound was synthesized according to the General Method A utilizing 3-iodo-1H-indazole-5-carboxylic acid (1.52 g, 5.28 mmol), cyclopentyl(pyridin-2-yl)methanamine (930 mg, 5.28 mmol), TBTU (1.69 mg, 5.28 mmol), DIPEA (2.75 mL, 15.8 mmol), and DMF (10 mL) to gave the title compound (pale yellow solid, 1.76 g, 75%). ¹H NMR (400 MHz, CD₃OD) δ ppm 8.50-8.57 (m, 1 H), 8.07

(s, 1 H), 7.93 (d, J=9.3 Hz, 1 H), 7.82 (t, J=7.4 Hz, 1 H), 7.57 (d, J=8.8 Hz, 1 H), 7.51 (d, J=7.5 Hz, 1 H), 7.32 (dd, J=6.6, 5.4 Hz, 1 H), 5.01 (d, J=9.8 Hz, 1 H), 2.48-2.62 (m, 1 H), 1.94-2.05 (m, 1 H), 1.48-1.78 (m, 5 H), 1.23-1.42 (m, 2 H); MS ESI 447.1 [M+H]$^+$, calcd for [C$_{19}$H$_{19}$IN$_4$O+H]$^+$ 447.1.

Synthesis of cyclobutyl(pyridin-2-yl)methanamine

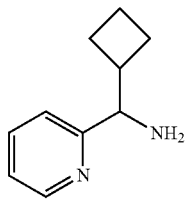 [SMILES: NC(c1ccccn1)C1CCC1]

The title compound was synthesized according to the General Method G, utilizing cyclobutyl-2-pyridyl ketone (1 g, 6.2 mmol), NH$_4$OAc (5.8 g, 74 mmol), NaCNBH$_3$ (1.6 g, 25 mmol), and MeOH (20 mL) to give the title compound (clear oil, 991 mg, 98%). $^1$H NMR (400 MHz, CD$_3$OD) δ ppm 8.49 (d, J=4.3 Hz, 1 H), 7.78 (td, J=7.6, 1.8 Hz, 1 H), 7.39 (d, J=7.8 Hz, 1 H), 7.26-7.32 (m, 1 H), 3.88 (d, J=9.3 Hz, 1 H), 2.55-2.65 (m, 1 H), 2.09-2.20 (m, 1 H), 1.64-2.01 (m, 6 H).

Synthesis of N-(cyclobutyl(pyridin-2-yl)methyl)-3-iodo-1H-indazole-5-carboxamide

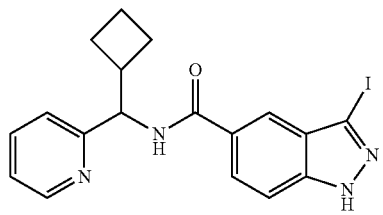 [SMILES: O=C(NC(c1ccccn1)C1CCC1)c1ccc2[nH]nc(I)c2c1]

The title compound was synthesized according to the General Method A utilizing 3-iodo-1H-indazole-5-carboxylic acid (1.76 g, 6.1 mmol), cyclobutyl(pyridin-2-yl)methanamine (990 mg, 6.1 mmol), TBTU (1.96 mg, 6.1 mmol), DIPEA (3.2 mL, 18 mmol), and DMF (10 mL) to give the title compound (pale yellow solid, 1.83 g, 69%). $^1$H NMR (400 MHz, CD$_3$OD) δ ppm 8.51 (d, J=4.8 Hz, 1 H), 8.08 (s, 1 H), 7.94 (dd, J=8.7, 0.9 Hz, 1 H), 7.80 (td, J=7.6, 1.4 Hz, 2 H), 7.57 (d, J=8.8 Hz, 1 H), 7.48 (d, J=8.0 Hz, 1 H), 7.27-7.32 (m, 1 H), 5.19 (d, J=10.3 Hz, 1 H), 2.86-2.97 (m, 1 H), 2.16-2.26 (m, 1 H), 1.77-2.05 (m, 5 H); MS ESI 433.1 [M+H]$^+$, calcd for [C$_{18}$H$_{17}$IN$_4$O+H]$^+$ 433.0.

Synthesis of (1-methylpiperidin-4-yl)(phenyl)methanone

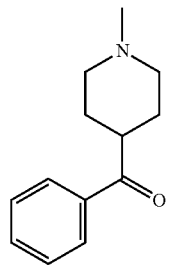

In a microwave vial, 4-benzylpiperidine.HCl (650 mg, 2.89 mmol) was dissolved in formic acid (3 mL) and formalin (937 μL, 11.6 mmol) was added. The vial was sealed and placed in microwave reactor and heated at 150° C. for 5 min. The mixture was concentrated and partitioned between EtOAc (20 mL) and 0.5 M NaOH (30 mL), washed with brine, dried using MgSO$_4$ and concentrated under reduced pressure to give the title compound (clear oil, 520 mg, 89%). $^1$H NMR (400 MHz, CD$_3$OD) δ ppm 7.97-8.06 (m, 2 H), 7.65 (t, J=7.5 Hz, 1 H), 7.54 (t, J=7.3 Hz, 2 H), 3.69-3.81 (m, 1 H), 3.61 (d, J=11.5 Hz, 2 H), 3.18 (t, J=13.6 Hz, 2 H), 2.92 (s, 3 H), 2.16 (d, J=14.8 Hz, 2 H), 1.92 (q, J=13.6 Hz, 2 H).

Synthesis of (1-methylpiperidin-4-yl)(phenyl)methanamine

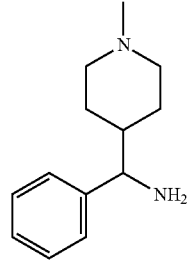

Using General Method G, (1-methylpiperidin-4-yl)(phenyl)methanone (520 mg, 2.56 mmol), MeOH (15 mL), NH$_4$OAc (2.37 g, 30 mmol), and NaCNBH$_3$ (645 mg, 10.2 mmol) gave the title compound (clear oil, 503 mg, 96%). MS ESI [M+H]$^+$ 205.1, calcd for [C$_{13}$H$_{20}$N$_2$+H]$^+$ 205.2.

Synthesis of N-(3-iodo-1-(tetrahydro-2H-pyran-2-yl)-1H-indazol-5-yl)-2-(pyrrolidin-1-yl)-2-(thiophen-3-yl)acetamide

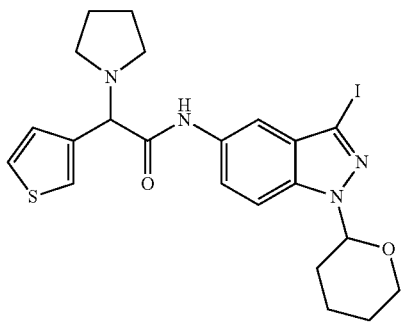 [SMILES: O=C(Nc1ccc2c(c1)c(I)nn2C1CCCCO1)C(c1ccsc1)N1CCCC1]

The title compound was synthesized according to the General Method A utilizing 3-iodo-1-(tetrahydro-2H-pyran-2-yl)-1H-indazol-5-amine (686 mg, 2 mmol), 2-(pyrrolidin-1-yl)-2-(thiophen-3-yl)acetic acid (422 mg, 2 mmol), TBTU (642 mg, 2 mmol), DIPEA (1 mL, 6 mmol), and DMF (10 mL). Purification by flash chromatography (SiO$_2$, Biotage 25 g, 0-30% MeOH in CH$_2$Cl$_2$) gave the title compound (yellow solid, 921 mg, 86%). NMR (400 MHz, CD$_3$OD) δ ppm 7.83 (s, 1 H), 7.62 (d, J=8.8 Hz, 1 H), 7.56 (d, J=8.5 Hz, 1 H), 7.50 (br. s, 1 H), 7.38-7.45 (m, 1 H), 7.30-7.36 (m, 1 H), 5.76 (d, J=7.3 Hz, 1 H), 4.11 (s, 1 H), 3.92-4.00 (m, 1 H), 3.72-3.82 (m, 1 H), 2.62-2.71 (m, 2 H), 2.38-2.55 (m, 3 H), 2.06-2.16 (m, 1 H), 1.95-2.05 (m, 1 H), 1.56-1.90 (m, 7 H), 1.24-1.35 (m, 1 H); MS ESI 537.2 [M+H]$^+$, calcd for [C$_{22}$H$_{25}$IN$_4$O$_2$S+H]$^+$ 537.1.

Synthesis of 2-cyclopentyl-N-(3-iodo-1-(tetrahydro-2H-pyran-2-yl)-1H-indazol-5-yl)-2-(thiophen-3-yl)acetamide

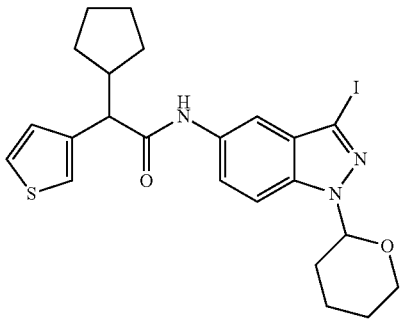 [SMILES: O=C(Nc1ccc2c(c1)c(I)nn2C1CCCCO1)C(c1ccsc1)C1CCCC1]

The title compound was synthesized according to the General Method A utilizing 3-iodo-1-(tetrahydro-2H-pyran-2-yl)-1H-indazol-5-amine (172 mg, 0.5 mmol), 2-(cyclopentyl)-2-(thiophen-3-yl)acetic acid (105 mg, 0.5 mmol), TBTU (160 mg, 0.5 mmol), DIPEA (0.26 mL, 1.5 mmol), and DMF (10 mL) Purification by flash chromatography (SiO$_2$, Biotage 25 g, 0-30% MeOH in CH$_2$Cl$_2$) gave the title compound (white solid, 260 mg, 97%). $^1$H NMR (400 MHz, CD$_3$OD) δ ppm 7.98 (s, 1 H), 7.84 (s, 1 H), 7.61 (d, J=9.0 Hz, 1 H), 7.49-7.54 (m, 1 H), 7.34-7.39 (m, 1 H), 7.28-7.31 (m, 1 H), 7.21 (d, J=5.0 Hz, 1 H), 5.73-5.78 (m, 1 H), 3.93-4.00 (m, 1 H), 3.74-3.82 (m, 1 H), 3.54 (d, J=11.0 Hz, 1 H), 2.61-2.70 (m, 1 H), 2.39-2.51 (m, 1 H), 2.07-2.15 (m, 1 H), 1.88-2.05 (m, 2 H), 1.77-1.86 (m, 1 H), 1.60-1.77 (m, 5 H), 1.50-1.59 (m, 2 H), 1.30-1.41 (m, 1 H), 1.09-1.22 (m, 1 H).

Synthesis of N-(1H-indazol-5-yl)-2-(piperidin-1-yl)-2-(thiophen-3-yl)acetamide

A. 2-(Piperidin-1-yl)-2-(thiophen-3-yl)acetic acid

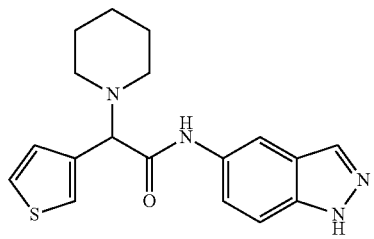 [SMILES: O=C(Nc1ccc2[nH]ncc2c1)C(c1ccsc1)N1CCCCC1]

The title compound was synthesized according to General Method D by using glyoxylic acid monohydrate (1.8 g, 19 mmol) and piperidine (1.93 mL, 19 mmol) in CH$_2$Cl$_2$ (75 mL) and sonicating for 15 min. Thiophene-3-boronic acid (2.5 g, 19 mmol) was added and the mixture was stirred at rt for 24 h. Purification by Biotage (50 g SiO2, 0-30% MeOH in DCM) gave the title compound (cream solid, 3.4 g, 77%). $^1$H NMR (400 MHz, CD$_3$OD) δ 7.58 (s, 1H), 7.33 (s, 2H), 4.70 (s, 1H), 3.71-3.63 (br.m, 2H), 3.17 (br.s, 2H), 1.94-1.93 (br.m, 2H), 1.83-1.80 (br.m, 2H), 1.55-1.53 (br.s, 2H); MS ESI 226.1 [M+H]$^+$, calcd for [C$_{11}$H$_{15}$NO$_2$S+H]$^+$ 226.1.

B. N-(1H-indazol-5-yl)-2-(piperidin-1-yl)-2-(thiophen-3-yl)acetamide (CH$_3$)$_3$COCl (1.82 mL, 0.014 mol) was added slowly to a cooled (0-5° C.) solution of 2-(piperidin-1-yl)-2-(thiophen-3-yl)acetic acid (3.0 g, 13 mmol), DMAP (81 mg) and TEA (7.5 mL, 53 mmol) in DCM (150 mL). After 1 h stirring at 0° C., 5-amino-1H-indazole (1.95 g, 14 mmol) added and the mixture was stirred at rt for 24 h. The reaction mixture was washed with H$_2$O, dried (Na$_2$SO$_4$) and concentrated under vacuum. The crude product was heated in 1:1 hexane-isopropyl alcohol (40 mL) at 75° C. for 30 min and the product filtered at rt to give the first crop of title compound (off white solid, 2.65 g). The filtrate concentrated under reduced pressure and purified by flash chromatography (SiO$_2$, 0-15% MeOH in DCM) to give the second crop (360 mg, combined yield 3.01 g, 66%). $^1$H NMR (400 MHz, CDCl$_3$) δ ppm 10.1 (br.s., 1H), 8.51 (br. s., 1H), 9.57 (s, 1H), 8.14 (s, 1H), 8.04 (d, J=0.8 Hz, 1H), 7.51-7.45 (m, 2H), 7.32-7.31 (m, 1H), 7.06 (dd, J=5.2 Hz, J=1.2 Hz, 1H), 4.22 (s, 1H), 2.49-2.40 (br.m, 4H), 1.67-1.61 (br.m, 6H); MS ESI 341.1 [M+H]$^+$, calcd for [C$_{18}$H$_{20}$N$_4$OS+H]$^+$ 341.4.

Synthesis of N-(3-iodo-1H-indazol-5-yl)-2-(piperidin-1-yl)-2-(thiophen-3-yl)acetamide

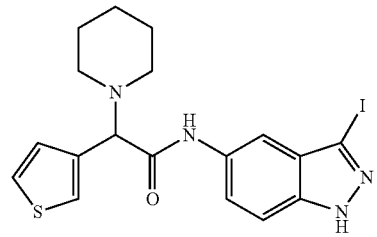 [SMILES: O=C(Nc1ccc2[nH]nc(I)c2c1)C(c1ccsc1)N1CCCCC1]

The title compound was synthesized according to General Method B from N-(1H-indazol-5-yl)-2-(piperidin-1-yl)-2-(thiophen-3-yl)acetamide (3.0 g, 8.8 mmol), K$_2$CO$_3$ (4.87 g, 8.8 mmol) and I$_2$ (2.45 g, 9.6 mmol) in DMF (24 mL). The reaction was stirred at rt for 24 h and then treated with 5% aq, Na$_2$S$_2$O$_3$.5H$_2$O (200 mL). The solid was filtered and washed with H$_2$O (4×25 mL) to give crude brown solid. The crude product was purified by flash chromatography (SiO$_2$, 0-80% EtOAc in Hexane) to give the title compound (pale yellow solid, 1.8 g, 44%). $^1$H NMR (400 MHz, CDCl$_3$) δ ppm 10.4 (s, 1H), 9.62 (s, 1H), 7.83 (d, J=1.2 Hz, 1H), 7.62 (dd, J=8.8 Hz, J=3.2 Hz, 1H), 7.44 (d, J=8.8 Hz, 1H), 7.34-7.32 (m, 1H), 7.07 (d, J=4 Hz, 1H), 4.25 (s, 1H), 2.49 (br.m, 4H), 1.69 (br.m, 4H), 1.48 (br.s., 2H); MS ESI 467.1 [M+H]$^+$, calcd for [C$_{18}$H$_{19}$IN$_4$OS+H]$^+$ 467.

Synthesis of N-(cyclopentyl(thiophen-3-yl)methyl)-3-iodo-1H-indazole-5-carboxamide

A. cyclopentyl(thiophen-3-yl)methanamine

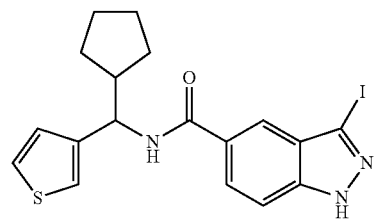 [SMILES: O=C(NC(c1ccsc1)C1CCCC1)c1ccc2[nH]nc(I)c2c1]

The title compound was prepared using General Method G from cyclopentyl-3-thienyl ketone (3.5 g, 19.4 mmol) at 60° C. for 24 h. Evaporation of MeOH and addition of 2 M NaOH (50 mL), extraction using EtOAc (2×100 mL), and purification by flash chromatography (SiO$_2$, 0-20% MeOH in DCM) gave the title compound (colorless oil, 3.25 g, 92.5%). $^1$H NMR (400 MHz, DMSO-d$_6$) δ ppm 7.44-7.42 (m, 1H), 7.27 (t, J=2 Hz, 1H), 7.12-7.10 (m, 1H), 3.74 (t, J=8.4 Hz, 1H), 2.09-1.99 (m, 1H), 1.76-1.68 (m, 1H), 1.58-1.29 (m, 6H), 1.16-1.14 (m, 1H).

B. N-(cyclopentyl(thiophen-3-yl)methyl)-3-iodo-1H-indazole-5-carboxamide

The title compound was prepared using General Method A by from cyclopentyl(thiophen-3-yl)methanamine (3.25 g, 17.9 mmol), 3-iodo-1H-indazol-5-carboxylic acid (5.16 g, 17.9 mmol), DIPEA (12.49 mL, 71.6 mmol) and TBTU (5.74 g, 17.9 mmol) in DMF (49 mL) at 20° C. for 4 h. The mixture was poured into H$_2$O (1.3 L) and the solid was collected by filtration and washed with H$_2$O to provide the title compound (cream color solid, 7.95 g, 98%). $^1$H NMR (400 MHz, DMSO-d$_6$) δ ppm 13.72 (br.s, 1H), 8.86 (t, J=8.8 Hz, 1H), 7.92-7.9 (m, 1H), 7.58 (t, J=8.8 Hz, 1H), 7.46-7.44 (m, 1H), 7.39-7.38 (m, 1H), 7.22 (d, J=4.8 Hz, 1H), 4.98 (t, J=9.6 Hz, 1H), 1.81-1.78 (m, 1H), 1.61-1.32 (m, 7H), 1.2-1.17 (m, 1H); MS ESI 452 [M+H]$^+$, calcd for [C$_{18}$H$_{18}$IN$_3$OS+H]$^+$ 452.

Synthesis of N-(1-(2-chlorophenyl)-2-methylpropyl)-3-iodo-1H-indazole-5-carboxamide

A. 1-(2-chlorophenyl)-2-methylpropan-1-ol

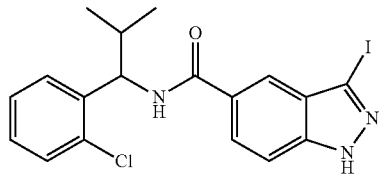 [SMILES: CC(C)C(NC(=O)c1ccc2[nH]nc(I)c2c1)c1ccccc1Cl]

A solution of 2-chlorobenzaldehyde (2.75 g) in Et$_2$O (30 mL) was slowly added to a solution of isopropyl magnesium bromide (obtained from 0.98 g of magnesium and 4.85 g 2-bromopropane in 70 mL anhydrous Et$_2$O) at 0° C. The reaction mixture was stirred for 1 h at 0° C., and then quenched with aq. 25% NH$_4$Cl (100 mL). The organic layer was separated and the aq. layer was extracted with EtOAc (50 mL). The combined organic layer was washed with H$_2$O and brine, dried (Na$_2$SO$_4$) and concentrated under vacuum. Purification by flash chromatography (SiO$_2$, 0-25% EtOAc in Hexane) gave the title compound (clear colorless oil, 1.5 g, 41%). $^1$H NMR (400 MHz, DMSO-d$_6$) δ 7.52 (d, J=7.2 Hz, 1H). 7.37-7.31 (m, 2H), 7.25-7.21 (m, 1H), 5.27 (d, J=4.4 Hz, 1H), 4.68 (dd, J=5.2 Hz, 1H), 1.88-1.80 (m, 1H), 0.86 (dd, J=17.2 Hz, J=6.8 Hz, 6H).

B. 1-(2-chlorophenyl)-2-methyl-propan-1-one

A solution of 1-(2-chlorophenyl)-2-methylpropan-1-ol (1.5 g in 15 mL DCM) was added to a suspension of PCC (2.62 g in 30 mL DCM) at 25° C., monitoring the reaction by TLC. The reaction was complete in 2 h. Et$_2$O (120 mL) was added and the reaction mixture was stirred for 15 min. The supernatent was decanted, dried (Na$_2$SO$_4$) and concentrated under vacuum. Purification by flash chromatography (SiO$_2$, 0-10% EtOAc in Hexane) gave the title compound (clear colorless oil, 1.24 g, 82%). $^1$H NMR (400 MHz, CDCl$_3$) δ 7.41-7.27 (m, 4H), 3.37-3.30 (m, 1H), 1.19 (d, J=6.8 Hz, 6H).

C. 1-(2-chlorophenyl)-2-methylpropan-1-amine

The title compound was prepared using General Method G from 1-(2-chlorophenyl)-2-methyl-propan-1-one (1.5 g, 8.2 mmol) at 65° C. for 24 h. Evaporation of MeOH and addition of 3M aq NaOH (100 mL), extraction using EtOAc (2×100 mL), and purification by flash chromatography (SiO$_2$, 0-25% DCM in MeOH) to give the title compound (colorless oil, 348 mg, 23%). $^1$H NMR (400 MHz, DMSO-d$_6$) δ ppm 7.38-7.21 (m, 4H), 4.87 (br.s, 2H), 4.16 (d, J=8.0 Hz, 1H), 2.12-2.04 (m, 1H), 1.02 (d, J J=6.4 Hz, 3H), 0.82 (d, J=6.8 Hz, 3H); MS ESI 184.08. [M+H]$^+$, calcd for [C$_{10}$H$_{14}$ClN+H]$^+$ 184.08.

D. N-(1-(2-chlorophenyl)-2-methylpropyl)-3-iodo-1H-indazole-5-carboxamide

The title compound was synthesized according to General Method A by using 1-(2-chlorophenyl)-2-methylpropan-1-amine (0.55 g, 2.99 mmol), DMF (11 mL), 3-iodo-1H-indazole-5-carboxylic acid (863 mg, 2.99 mmol), DIPEA (2.09 mL, 11.98 mmol) and TBTU (960 mg, 2.99 mmol). The resultant reaction mass stirred at 25° C. for 12 h and then quenched it in H$_2$O (440 mL). The solid collected by filtration and was washed with H$_2$O to provide the title compound (cream color solid, 1.29 g, 95%). $^1$H NMR (400 MHz, DMSO-d$_6$) δ 13.76 (s, 1H), 8.91 (d, J=8.8 Hz, 1H), 7.91 (d, J=9.2 Hz, 1H), 7.74-7.66 (m, 1H), 7.59 (d, J=8.8 Hz, 1H), 7.46-7.22 (m, 4H), 5.27 (t, J=9.2 Hz, 1H), 2.20-2.15 (m, 1H), 1.08 (d, J=6.0 Hz, 3H), 0.79 (d, J=6.8 Hz, 3H); MS ESI 454 [M+H]$^+$, calcd for [C$_{18}$H$_{17}$ClIN$_3$O+H]$^+$ 454.

Synthesis of N-(cyclobutyl(phenyl)methyl)-3-iodo-1H-indazole-5-carboxamide

A. cyclobutyl(phenyl)methanamine

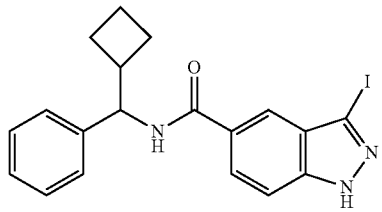 [SMILES: O=C(NC(c1ccccc1)C1CCC1)c1ccc2[nH]nc(I)c2c1]

Using General Method G, cyclobutyl(phenyl)methanone (1.06 mL, 13.9 mmol) gave the title compound (1.12 g, 100%) which was used crude. $^1$H NMR (400 MHz, CDCl$_3$) δ ppm 7.28-7.35 (m, 4 H), 7.21-7.27 (m, 1 H), 3.80 (d, J=9.3 Hz, 1 H), 2.46-2.56 (m, 1 H), 2.10-2.21 (m, 1 H), 1.67-1.93 (m, 5 H).

B. N-(cyclobutyl(phenyl)methyl)-3-iodo-1H-indazole-5-carboxamide

Using General Method A, 3-iodo-1H-indazole-5-carboxylic acid (285 mg, 0.99 mmol) and cyclobutyl(phenyl)methanamine (177 mg, 1.10 mmol) gave the title compound (brown solid, 334 mg, 78%) after purification on the Biotage (RPC18, 10-95% MeOH in 0.1% TFA-H$_2$O). $^1$H NMR (400 MHz, Acetone-d$_6$) δ ppm 12.89 (m, 0 H), 8.24 (d, J=7.8 Hz, 1 H), 8.09 (s, 1 H), 8.04 (dd, J=8.8, 1.3 Hz, 1 H), 7.64 (d, J=8.8 Hz, 1 H), 7.47 (d, J=7.5 Hz, 2 H), 7.33 (t, J=7.5 Hz, 2 H), 7.23 (t, J=7.5 Hz, 1 H), 5.21 (dd, J=10.2, 8.9 Hz, 1 H), 2.18 (d, J=5.3 Hz, 1 H), 1.94-2.03 (m, 1 H), 1.80-1.93 (m, 4 H). MS ESI 432.1 [M+H]$^+$, calcd for [C$_{19}$H$_{18}$IN$_3$O+H]$^+$ 432.06.

Synthesis of (R)-N-((3-chlorothiophen-2-yl)(cyclopropyl)methyl)-3-iodo-1H-indazole-5-carboxamide

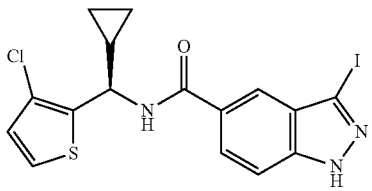 [SMILES: O=C(N[C@@H](c1sccc1Cl)C1CC1)c1ccc2[nH]nc(I)c2c1]

Using General Method A, 3-iodo-1H-indazole-5-carboxylic acid (161.0 mg, 0.56 mmol) and (R)-(3-chlorothiophen-2-yl)(cyclopropyl)methanamine hydrochloride (125.2 mg, 0.56 mmol) in DMF (6 mL) were stirred at rt for 29 h. The reaction mixture was added dropwise into $H_2O$ (70 mL) and the precipitate was collected by filtration, transferred using a mixture of acetone and EtOH, and concentrated to dryness. Purification by flash chromatography ($SiO_2$, 0-40% EtOAc/DCM) gave the title compound (light tan solid, 209.3 mg, 85% pure, 70%) which was used without further purification. $^1$H NMR (400 MHz, $CD_3OD$) δ ppm 8.08 (s, 1 H), 7.94 (dd, J=8.8, 1.5 Hz, 1 H), 7.58 (d, J=9.0 Hz, 1 H), 7.39 (d, j=5.5 Hz, 1 H), 6.94 (d, J=5.3 Hz, 1 H), 4.97 (d, J=9.0 Hz, 1 H), 1.51 (td, J=8.4, 3.8 Hz, 1 H), 0.62-0.74 (m, 2 H), 0.50-0.62 (m, 2 H).

Synthesis of (S)-N-((3-chlorothiophen-2-yl)(cyclopropyl)methyl)-3-iodo-1H-indazole-5-carboxamide

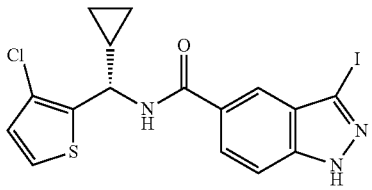 [SMILES: O=C(N[C@H](c1sccc1Cl)C1CC1)c1ccc2[nH]nc(I)c2c1]

Using General Method A following the work-up method for the corresponding (R) enantiomer, 3-iodo-1H-indazole-5-carboxylic acid (161.5 mg, 0.56 mmol) and (S)-(3-chlorothiophen-2-yl)(cyclopropyl)methanamine hydrochloride (125.2 mg, 0.56 mmol) gave the title compound (beige solid, 218 mg, 72%) which was used without further purification. $^1$H NMR (400 MHz, $CD_3OD$) δ ppm 8.08 (s, 1 H), 7.94 (dd, J=8.8, 1.5 Hz, 1 H), 7.58 (d, J=9.0 Hz, 1 H), 7.39 (d, J=5.5 Hz, 1 H), 6.94 (d, J=5.3 Hz, 1 H), 4.97 (d, J=9.0 Hz, 1 H), 1.51 (td, J=8.4, 3.8 Hz, 1 H), 0.62-0.74 (m, 2 H), 0.50-0.62 (m, 2 H).

Synthesis of (R)-N-(1-(2-chlorophenyl)propyl)-3-iodo-1H-indazole-5-carboxamide

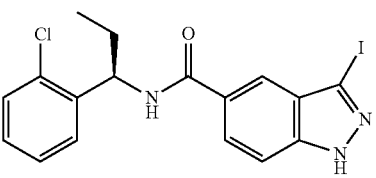 [SMILES: CC[C@@H](NC(=O)c1ccc2[nH]nc(I)c2c1)c1ccccc1Cl]

Using General Method A, 3-iodo-1H-indazole-5-carboxylic acid (489 mg, 1.7 mmol) and (R)-1-(2-chlorophenyl)propan-1-amine hydrochloride (349 mg, 1.7 mmol) gave the title compound (white solid, 650 mg, 95% pure, 83%) after aq. work-up with EtOAc and purification by flash chromatography ($SiO_2$, 5-30% EtOAc in DCM). $^1$H NMR (400 MHz, $CD_3OD$) δ ppm 8.11 (s, 1 H), 7.95 (dd, J=8.9, 1.6 Hz, 1 H), 7.59 (d, J=8.5 Hz, 1 H), 7.51 (dd, J=7.7, 1.4 Hz, 1 H), 7.41 (dd, J=7.8, 1.4 Hz, 1 H), 7.31 (td, J=7.5, 1.5 Hz, 1 H), 7.21-7.27 (m, 1 H), 5.46 (dd, J=8.9, 5.9 Hz, 1 H), 1.87-2.01 (m, 2 H), 1.09 (t, J=7.3 Hz, 3 H). MS ESI 440.2 [M+H]$^+$, calcd for [$C_{17}H_{15}ClIN_3O$+H]$^+$ 440.0.

Synthesis of (S)-N-(1-(2-chlorophenyl)propyl)-3-iodo-1H-indazole-5-carboxamide

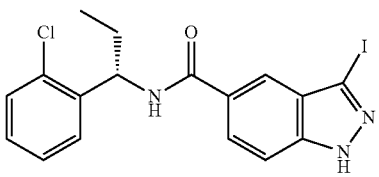 [SMILES: CC[C@H](NC(=O)c1ccc2[nH]nc(I)c2c1)c1ccccc1Cl]

Using General Method A, 3-iodo-1H-indazole-5-carboxylic acid (490 mg, 1.7 mmol) and (S)-1-(2-chlorophenyl)propan-1-amine hydrochloride (348 mg, 1.69 mmol) gave the title compound (white solid, 525 mg, 70%) after aq. work-up with EtOAc and purification by flash chromatography ($SiO_2$, 5-30% EtOAc in DCM). $^1$H NMR (400 MHz, Acetone-$d_6$) δ ppm 12.89 (s, 1 H), 8.39 (d, J=8.5 Hz, 1 H), 8.16 (s, 1 H), 8.07 (dd, J=8.8, 1.5 Hz, 1 H), 7.67 (s, 1 H), 7.65 (td, J=3.8, 1.6 Hz, 1 H), 7.43 (dd, J=7.5, 1.6 Hz, 1 H), 7.33 (td, J=7.5, 1.6 Hz, 1 H), 7.27 (td, J=7.5, 1.6 Hz, 1 H), 5.55 (td, J=8.2, 6.3 Hz, 1 H), 1.88-1.96 (m, 2 H), 1.08 (t, J=7.4 Hz, 3 H). MS ESI 440.2 [M+H]$^+$, calcd for [$C_{17}H_{15}ClIN_3O$+H]$^+$ 440.0.

Synthesis of (R)-N-(1-(2-fluorophenyl)ethyl)-3-iodo-1H-indazole-5-carboxamide

A. (R)-1-(2-fluorophenyl)ethanamine hydrochloride

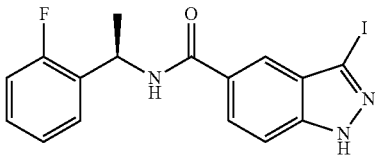 [SMILES: C[C@@H](NC(=O)c1ccc2[nH]nc(I)c2c1)c1ccccc1F]

To (R)-2-methylpropane-2-sulfinamide (121 mg, 1.0 mmol), Ti(OEt)$_4$ (0.41 mL, 2.0 mmol) in THF (2.0 mL) was added 1-(2-fluorophenyl)ethanone (0.15 mL, 1.2 mmol) and the mixture heated to 70° C. for 18 h. The reaction was then cooled to −48° C. and NaBH$_4$ (151 mg, 4.0 mmol) was added and the reaction was allowed to warm to rt and stir for 4 h at which time it was quenched with MeOH, brine was added (5 mL), and the resulting slurry was filtered through Celite washing with EtOAc. The resulting filtrate was extracted with EtOAc washing with brine and the material purified by column chromatography (silica gel, 98:2 CH$_2$Cl$_2$/MeOH) which gave 189 mg, 78% of (R)-N-((R)-1-(2-fluorophenyl)ethyl)-2-methylpropane-2-sulfinamide which was 58% de by NMR. This material was taken up in MeOH (3.5 mL) and HCl (1.6 mL of a 1.0M solution in Et$_2$O) was added and the reaction stirred for 1.5 h. The solvent was then removed and the product precipitated with Et$_2$O (10 mL) and filtered to give 109 mg, 62% (over the 2 steps) of a white solid (58% ee).

B. (R)-N-(1-(2-fluorophenyl)ethyl)-3-iodo-1H-indazole-5-carboxamide

General Method A was used except using (R)-1-(2-fluorophenyl)ethanamine hydrochloride (109 mg, 0.621 mmol), 3-iodo-1H-indazole-5-carboxylic acid (179 mg, 0.621 mmol), TBTU (209 mg, 0.652 mmol), DIPEA (0.44 mL, 2.5 mmol), and DMF (3.5 mL). The title compound was obtained as a white solid (120 mg, 47%). NMR (400 MHz, CD$_3$OD) δ ppm 8.09 (s, 1H), 7.94 (d, J=9.2 Hz, 1H), 7.57 (d, J=9.2 Hz, 1H), 7.45 (t, J=7.2 Hz, 1H), 7.30-7.25 (m, 1H), 7.16-7.07 (m, 2H), 5.51 (q, J=7.2 Hz, 1H), 1.60 (d, J=7.2 Hz, 3H); MS ESI 410.1 [M+H]$^+$, calcd for [C$_{16}$H$_{13}$FIN$_3$O+H]$^+$ 410.02.

Synthesis of (R)-N-(1-(2-chlorophenyl)propyl)-3-iodo-1H-indazole-5-carboxamide

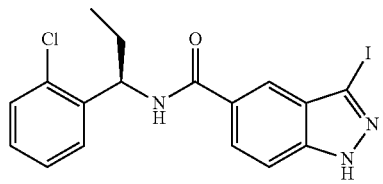 [SMILES: CC[C@@H](NC(=O)c1ccc2[nH]nc(I)c2c1)c1ccccc1Cl]

Prepared in the same way as (R)-N-(1-(2-fluorophenyl)ethyl)-3-iodo-1H-indazole-5-carboxamide except substituting 1-(2-chlorophenyl)propan-1-one. The ee was determined to be 36% using the method described for (R)-N-(1-(2-fluorophenyl)ethyl)-3-iodo-1H-indazole-5-carboxamide. MS ESI 440.0 [M+H]$^+$, calcd for [C$_{17}$H$_{15}$ClIN$_3$O+H]$^+$ 440.00.

Synthesis of (S)-N-(cyclopropyl(thiophen-2-yl)methyl)-3-iodo-1H-indazole-5-carboxamide

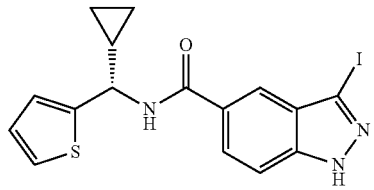 [SMILES: O=C(N[C@H](c1cccs1)C1CC1)c1ccc2[nH]nc(I)c2c1]

Prepared in the same way as (R)-N-(1-(2-fluorophenyl)ethyl)-3-iodo-1H-indazole-5-carboxamide except substituting cyclopropyl(thiophen-2-yl)methanone. The ee was determined to be 50% using the method described for (R)-N-(1-(2-fluorophenyl)ethyl)-3-iodo-1H-indazole-5-carboxamide. MS ESI 424.0 [M+H]$^+$, calcd for [C$_{16}$H$_{14}$IN$_3$OS+H]$^+$ 424.00.

Synthesis of (S)-3-iodo-N-(2-methoxy-1-phenylethyl)-1H-indazole-5-carboxamide

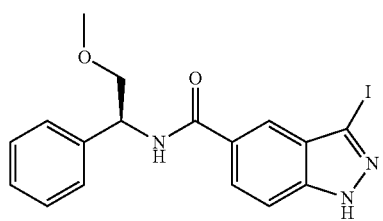 [SMILES: COC[C@@H](NC(=O)c1ccc2[nH]nc(I)c2c1)c1ccccc1]

General Method A was used except using (S)-2-methoxy-1-phenylethanamine (0.30 mL, 2.0 mmol), 3-iodo-1H-indazole-5-carboxylic acid (576 mg, 2.0 mmol), TBTU (640 mg, 2.0 mmol), DIPEA (1.4 mL, 8.0 mmol), and DMF (13 mL). The product was isolated as a white solid (575 mg, 68%). MS ESI 422.0 [M+H]$^+$, calcd for [C$_{17}$H$_{16}$IN$_3$O$_2$+H]$^+$ 422.04.

Synthesis of (R)-3-iodo-N-(1-(3-methoxyphenyl)propyl)-1H-indazole-5-carboxamide

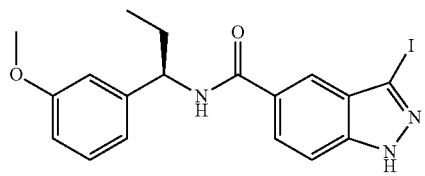 [SMILES: CC[C@@H](NC(=O)c1ccc2[nH]nc(I)c2c1)c1cccc(OC)c1]

General Method A was used except using (R)-1-(3-methoxyphenyl)propan-1-amine hydrochloride (202 mg, 1.0 mmol), 3-iodo-1H-indazole-5-carboxylic acid (288 mg, 1.0 mmol), TBTU (320 mg, 1.0 mmol), DIPEA (0.70 mL, 4.0 mmol), and DMF (6.0 mL). The product was isolated as a white solid (933 g mg, 77%). MS ESI 436.0 [M+H]$^+$, calcd for [C$_{18}$H$_{18}$IN$_3$O$_2$+H]$^+$ 436.05.

Synthesis of ethyl 2-cyclopentyl-2-(pyridin-2-yl)acetate

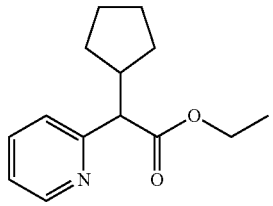 [SMILES: CCOC(=O)C(c1ccccn1)C1CCCC1]

The solution of ethyl 2-(pyridin-2-yl)acetate (2 g, 12.1 mmol) in anhydrous DMF (20 mL) was cooled down to 0° C. followed by adding of 60% NaH (581 mg, 14.5 mmol) in portions and bromocyclopentane (1.98 g, 13.3 mmol) dropwise. The resulting suspension was stirred at rt for 2 h before H$_2$O was added. The mixture was extracted with EtOAc. The organic layer was washed with H$_2$O for three times and brine, dried over Na$_2$SO$_4$ and concentrated under reduced pressure to give the title compound as a yellow oil (370 mg, 52% yield). $^1$H NMR (400 MHz, CDCl$_3$) δ ppm 8.55 (d, J=4.8 Hz, 1 H), 7.65 (td, J=7.7, 1.8 Hz, 1 H), 7.40 (d, J=8.0 Hz, 1 H), 7.17 (ddd, J=7.4, 5.0, 0.9 Hz, 1 H), 4.04-4.23 (m, 2 H), 3.58 (d, J=11.0 Hz, 1 H), 2.58-2.75 (m, 1 H), 1.88-2.01 (m, 1 H), 1.24-1.54 (m, 5 H), 1.22 (t, J=7.2 Hz, 3 H), 1.07 (dq, J=12.4, 8.2 Hz, 1 H), 0.79-0.92 (m, 1 H); MS ESI [M+H]$^+$ 234.0, calcd for [C$_{14}$H$_{19}$NO$_2$+H]$^+$ 234.15.

Synthesis of 2-cyclopentyl-2-(pyridin-2-yl)acetic acid

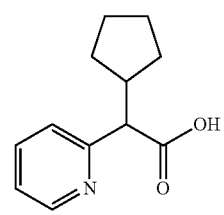 [SMILES: O=C(O)C(c1ccccn1)C1CCCC1]

The title compound was synthesized according to the method of 2-(4-(4-bromophenoxy)piperidin-1-yl)acetic acid utilizing ethyl 2-cyclopentyl-2-(pyridin-2-yl)acetate and obtained as a colourless gel (216 mg, 43% yield). $^1$H NMR (400 MHz, CD$_3$OD) δ ppm 8.75 (d, J=5.3 Hz, 1 H), 8.45-8.53 (m, 1 H), 8.08 (d, J=7.8 Hz, 1 H), 7.86-7.95 (m, 1 H), 3.85 (d, J=11.0 Hz, 1 H), 2.66 (m, 1 H), 1.99-2.10 (m, 1 H), 1.39-1.82 (m, 6 H), 1.04-1.16 (m, 1 H); MS ESI [M+H]$^+$ 206.1, calcd for [C$_{12}$H$_{15}$NO$_2$+H]$^+$ 206.12.

Synthesis of 2-cyclopentyl-N-(3-iodo-1-(tetrahydro-2H-pyran-2-yl)-1H-indazol-5-yl)-2-(pyridin-2-yl)acetamide

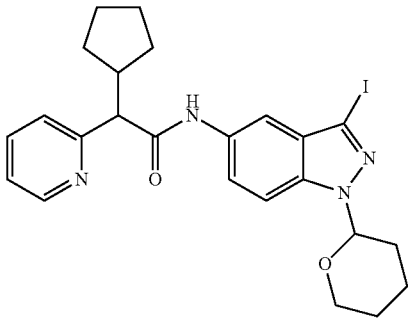 [SMILES: O=C(Nc1ccc2c(c1)c(I)nn2C1CCCCO1)C(c1ccccn1)C1CCCC1]

The title compound was synthesized according to General Method A utilizing 2-cyclopentyl-2-(pyridin-2-yl)acetic acid and 3-iodo-1-(tetrahydro-2H-pyran-2-yl)-1H-indazol-5-amine and obtained as a brown solid (178 mg, 23% yield). $^1$H NMR (400 MHz, CDCl$_3$) δ ppm 10.06 (br. s., 1 H), 8.63 (d, J=4.0 Hz, 1 H), 7.64-7.80 (m, 2 H), 7.43-7.58 (m, 2 H), 7.20-7.38 (m, 3 H), 5.64 (d, J=8.0 Hz, 1 H), 3.98 (d, J=10.5 Hz, 1 H), 3.70 (t, J=9.3 Hz, 1 H), 3.42-3.56 (m, 1 H), 2.60-2.75 (m, 1 H), 2.51 (d, J=9.5 Hz, 1 H), 1.88-2.21 (m, 3 H), 1.33-1.82 (m, 9 H), 1.00-1.15 (m, 1 H); MS ESI [M+H]$^+$ 531.2, calcd for [C$_{24}$H$_{27}$IN$_4$O$_2$+H]$^+$ 531.13.

Synthesis of 2-cyclopentyl-N-(3-iodo-1H-indazol-5-yl)-2-(pyridin-2-yl)acetamide

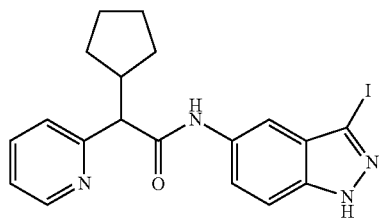 [SMILES: O=C(Nc1ccc2[nH]nc(I)c2c1)C(c1ccccn1)C1CCCC1]

The solution of 2-cyclopentyl-N-(3-iodo-1-(tetrahydro-2H-pyran-2-yl)-1H-indazol-5-yl)-2-(pyridin-2-yl)acetamide (178 mg, 0.34 mmol) and TsOH.H$_2$O (288 mg, 1.51 mmols) in MeOH (3 mL) was stirred at 125° C. for 3 h with microwave irradiation in a sealed vial before concentrated under reduced pressure. The residue was purified by flash chromatography (MeOH/DCM 0%-10%) to give the title compound as a light yellow solid (104 mg, 69% yield). $^1$H NMR (400 MHz, CD$_3$OD) δ ppm 8.48 (dd, J=4.9, 0.9 Hz, 1 H), 7.85 (d, J=1.3 Hz, 1 H), 7.76 (td, J=7.7, 1.8 Hz, 1 H), 7.60 (d, J=7.8 Hz, 1 H), 7.40-7.51 (m, 2 H), 7.27 (ddd, J=7.5, 5.0, 1.0 Hz, 1 H), 3.59 (d, J=11.0 Hz, 1 H), 2.68-2.84 (m, 1 H), 1.94 (dd, J=11.7, 4.6 Hz, 1 H), 1.35-1.76 (m, 6 H), 0.99-1.12 (m, 1 H); MS ESI [M+H]$^+$ 447.1, calcd for [C$_{19}$H$_{19}$IN$_4$O+H]$^+$ 447.07.

Synthesis of 2-cyclopropyl-N-(3-iodo-1-(tetrahydro-2H-pyran-2-yl)-1H-indazol-5-yl)-2-phenylacetamide

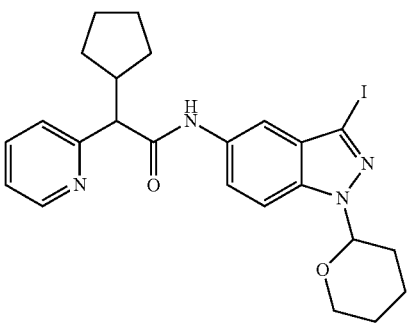 [SMILES: O=C(Nc1ccc2c(c1)c(I)nn2C1CCCCO1)C(c1ccccn1)C1CCCC1]

The title compound was synthesized according to General Method A utilizing 2-cyclopropyl-2-phenylacetic acid and 3-iodo-1-(tetrahydro-2H-pyran-2-yl)-1H-indazol-5-amine and obtained as a pale solid (120 mg, 70% yield). $^1$H NMR (400 MHz, CDCl$_3$) δ ppm 7.88 (s, 1 H), 7.70 (d, J=5.5 Hz, 1 H), 7.25-7.44 (m, 6 H), 5.59 (dd, J=9.3, 2.0 Hz, 1 H), 3.97 (d, J=11.5 Hz, 1 H), 3.64-3.74 (m, 1 H), 2.88 (d, J=9.8 Hz, 1 H), 2.40-2.54 (m, 1 H), 2.07-2.17 (m, 1 H), 1.95-2.04 (m, 1 H), 1.58-1.79 (m, 3 H), 1.48-1.58 (m, 1 H), 0.74-0.85 (m, 1 H), 0.56-0.69 (m, 1 H), 0.44-0.54 (m, 1 H), 0.24 (dq, J=9.5, 4.9 Hz, 1 H); MS ESI [M+H]$^+$ 502.2, calcd for [C$_{23}$H$_{24}$N$_3$O$_2$+H]$^+$ 502.10.

Synthesis of 2-cyclopropyl-N-(3-iodo-1H-indazol-5-yl)-2-phenylacetamide

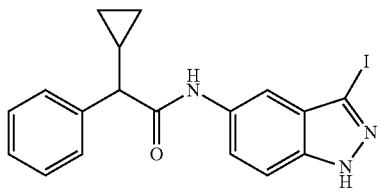 [SMILES: O=C(Nc1ccc2[nH]nc(I)c2c1)C(c1ccccc1)C1CC1]

The title compound was synthesized according to the method of 2-cyclopentyl-N-(3-iodo-1H-indazol-5-yl)-2-(pyridin-2-yl)acetamide utilizing 2-cyclopropyl-N-(3-iodo-1-(tetrahydro-2H-pyran-2-yl)-1H-indazol-5-yl)-2-phenylacetamide and obtained as a white solid (87 mg, 87% yield). $^1$H NMR (400 MHz, CDCl$_3$) δ ppm 7.80 (s, 1 H), 7.38-7.49 (m, 6 H), 7.33-7.37 (m, 1 H), 2.91 (d, J=9.3 Hz, 1 H), 0.82-0.91 (m, 1 H), 1.20-1.27 (m, 1 H), 0.63-0.71 (m, 1 H), 0.50-0.61 (m, 1 H), 0.27-0.34 (m, 1 H); MS ESI [M+H]$^+$ 418.1, calcd for [C$_{18}$H$_{16}$IN$_3$O+H]$^+$ 418.04.

Synthesis of (R)-2-cyclopropyl-N-(3-iodo-1H-indazol-5-yl)-2-(pyridin-2-yl)acetamide

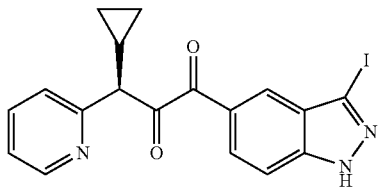 [SMILES: O=C(C(=O)[C@@H](c1ccccn1)C1CC1)c1ccc2[nH]nc(I)c2c1]

The title compound was synthesized according to General Method A utilizing (R)-cyclopropyl(pyridin-2-yl)methanamine and obtained as a light yellow solid (334 mg, 80% yield). ¹H NMR (400 MHz, CD₃OD) δ ppm 8.51-8.55 (m, 1 H), 8.13-8.16 (m, 1 H), 7.95-8.00 (m, 1 H), 7.81-7.86 (m, 1 H), 7.53-7.61 (m, 2 H), 7.30-7.36 (m, 1H), 4.49-4.53 (m, 1 H), 1.38-1.48 (m, 1 H), 0.68-0.75 (m, 1 H), 0.51-0.64 (m, 3 H); MS ESI [M+H]⁺ 419.0, calcd for [C₁₇H₁₅INO₄+H]⁺ 419.04.

Synthesis of (S)-2-cyclopropyl-N-(3-iodo-1H-indazol-5-yl)-2-(pyridin-2-yl)acetamide

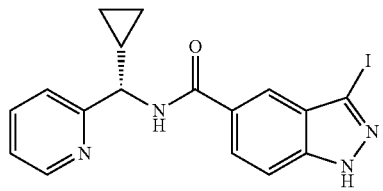 [SMILES: O=C(N[C@H](c1ccccn1)C1CC1)c1ccc2[nH]nc(I)c2c1]

The title compound was synthesized according to General Method A utilizing (S)-cyclopropyl(pyridin-2-yl)methanamine and obtained as a yellow solid (874 mg, 77% yield). ¹H NMR (400 MHz, CD₃OD) δ ppm 8.51-8.55 (m, 1 H), 8.13-8.16 (m, 1 H), 7.95-8.00 (m, 1 H), 7.81-7.86 (m, 1 H), 7.53-7.61 (m, 2 H), 7.30-7.36 (m, 1 H), 4.49-4.53 (m, 1 H), 1.38-1.48 (m, 1 H), 0.68-0.75 (m, 1 H), 0.51-0.64 (m, 3 H); MS ESI [M+H]⁺ 419.0, calcd for [C₁₇H₁₅INO₄+H]⁺ 419.04.

Synthesis of (R)-2-(3-chloropyridin-2-yl)-2-cyclopropyl-N-(3-iodo-1H-indazol-5-yl)acetamide

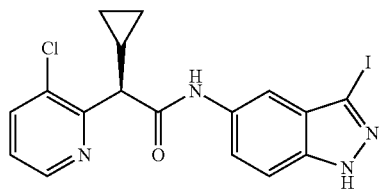 [SMILES: O=C(Nc1ccc2[nH]nc(I)c2c1)[C@@H](c1ncccc1Cl)C1CC1]

The title compound was synthesized according to General Method A utilizing (R)-(3-chloropyridin-2-yl)(cyclopropyl)methanamine and obtained as a white solid (322 mg, 78% yield). ¹H NMR (400 MHz, CDCl₃) δ ppm 13.10 (s, 1H), 8.49-8.50 (m, 1 H), 8.00-8.02 (d, J=9.6 Hz, 1 H), 7.95 (s, 1 H), 7.84-7.86 (dd, J=8.8, 0.8 Hz, 1 H), 7.67-7.69 (m, 1 H), 7.40-7.42 (d, J=8.8 Hz, 1 H), 7.16-7.19 (m, 1 H), 5.46-5.50 (t, J=8.0 Hz, 1 H), 1.37-1.45 (m, 1 H), 0.61-0.66 (m, 1 H), 0.47-0.58 (m, 3 H); MS ESI [M+H]⁺ 453.2, calcd for [C₁₇H₁₄ClINO₄+H]⁺ 453.00.

Synthesis of (S)-2-(3-chloropyridin-2-yl)-2-cyclopropyl-N-(3-iodo-1H-indazol-5-yl)acetamide

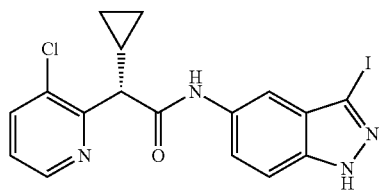 [SMILES: O=C(Nc1ccc2[nH]nc(I)c2c1)[C@H](c1ncccc1Cl)C1CC1]

The title compound was synthesized according to General Method A utilizing (S)-(3-chloropyridin-2-yl)(cyclopropyl)methanamine and obtained as a yellow solid (863 mg, 83% yield). ¹H NMR (400 MHz, CDCl₃) δ ppm 13.10 (s, 1H), 8.49-8.50 (m, 1 H), 8.00-8.02 (d, J=9.6 Hz, 1 H), 7.95 (s, 1 H), 7.84-7.86 (dd, J=8.8, 0.8 Hz, 1 H), 7.67-7.69 (m, 1 H), 7.40-7.42 (d, J=8.8 Hz, 1 H), 7.16-7.19 (m, 1 H), 5.46-5.50 (t, J=8.0 Hz, 1 H), 1.37-1.45 (m, 1 H), 0.61-0.66 (m, 1 H), 0.47-0.58 (m, 3 H); MS ESI [M+H]⁺ 453.2, calcd for [C₁₇H₁₄ClINO₄+H]⁺ 453.00.

Synthesis of 4-morpholinotetrahydro-2H-pyran-4-carbonitrile

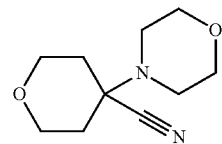 [SMILES: N#CC1(N2CCOCC2)CCOCC1]

To a suspension of anh MgSO₄ (3.61 g, 29.9 mmol) and 4-oxotetrahydropyran (1.0 g, 9.9 mmol) in anh DMA (10 mL) under Ar atmosphere was added acetone cyanohydrine (0.85 g, 9.9 mmol) and morpholine (1.77 g, 19.9 mmol) at rt. The reaction mixture was stirred for 48 h at 45° C. and quenched with H₂O (40 mL) and the product was with Et₂O (2×75 mL). The combined organic layers were washed with (H₂O, brine), dried (Na₂SO₄) and concentrated under vacuum to give white solid (1.58 g, 80%). ¹H NMR (400 MHz, CDCl₃) δ ppm 4.04 (dt, J=12.1, 3.4 Hz, 2 H), 3.73-3.82 (m, 4 H), 3.67 (td, J=12.2, 2.0 Hz, 2 H), 2.59-2.71 (m, 4 H), 2.08 (dd, J=13.3, 2.3 Hz, 2 H), 1.72 (dt, J=12.0, 3.2 Hz, 2 H); MS ESI 197.0 [M+H]⁺, calcd for [C₁₀H₁₆N₂O₂+H]⁺ 197.1

Synthesis of (2R,6S)-2,6-dimethyl-4-morpholinotetrahydro-2H-pyran-4-carbonitrile

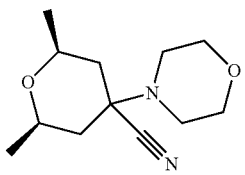 [SMILES: C[C@@H]1CC(C#N)(N2CCOCC2)C[C@H](C)O1]

The title compound was synthesized as 4-morpholinotetrahydro-2H-pyran-4-carbonitrile by utilizing (2R,6S)-2,6-dimethyldihydro-2H-pyran-4(3H)-one (325 mg, 2.53 mmol), anh MgSO₄ (916 mg, 7.60 mmol), acetone cyanohydrine (216 mg, 2.53 mmol), morpholine (442 mg, 5.07 mmol), anh DMA (3.25 mL) to give the title compound as a white solid (460 mg, 81%); NMR (400 MHz, CDCl₃) δ ppm 3.71-3.81 (m, 6 H), 2.62-2.69 (m, 4 H), 2.10 (d, J=12.5 Hz, 2 H), 1.51 (s, 2 H), 1.22-1.32 (m, 6 H); MS ESI 225.0 [M+H]⁺, calcd for [C₁₂H₂₀N₂O₂+H]⁺ 225.1.

Synthesis of 1-morpholino cyclobutanecarbonitrile

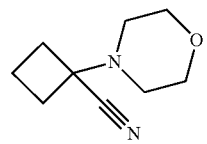 [SMILES: N#CC1(N2CCOCC2)CCC1]

To cooled acetic acid (10 mL) under Ar, morpholine (2.49 mL, 28.5 mmol) was added over 15 min followed by cyclobutanone (500 mg, 7.13 mmol) and TMSCN (2.17 mL, 17.1 mmol) at 0° C. The mixture was slowly warmed to it and stirred overnight. DCM (40 mL) was then added and the aqueous phase was basified to pH 8 with aq K₂CO₃. The organic layer was separated and washed (H₂O, brine), dried (Na₂SO₄) and concentrated under vacuum to give colorless thick oil (900 mg, 76%). ¹H NMR (400 MHz, CDCl₃) δ ppm 3.64-3.82 (m, 4 H), 2.33-2.52 (m, 6 H), 2.10-2.29 (m, 3 H), 1.87-1.99 (m, 1 H); MS ESI 167.0 [M+H]⁺, calcd for [C₉H₁₄N₂O+H]⁺ 167.1

Synthesis of (1-thiophen-3-yl)cyclohexanecarbonitrile

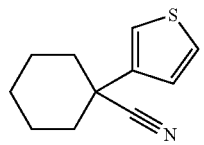 [SMILES: N#CC1(c2ccsc2)CCCCC1]

NaH (60% in mineral oil) (0.65 g, 16.2 mmol) under Ar was suspended in anh DMF (8 mL) at −5° C. To this suspension was added a solution of 3-thiopheneacetonitrile (1 g, 8.1 mmol) and 1,5-dibromopropane (1.96 g, 8.1 mmol) in anh DMF (4 mL) over 15 min. The mixture was stirred for 24 h at rt and quenched using 2 M aq HCl (20 mL). The product was extracted with EtOAc (2×20 mL) and the combined EtOAc layer washed (H₂O, brine), dried (Na₂SO₄) and concentrated under vacuum to give a crude brown thick oil. Purification by flash chromatography (Biotage Isolera, 25 g HP-SIL, 0-20% EtOAc in hexanes) afforded a clear colorless oil (670 mg, 43%). ¹H NMR (400 MHz, CDCl₃) δ ppm 7.36 (dd, J=5.0, 3.0 Hz, 1 H), 7.27-2.28 (m, H), 7.15 (dd, J=5.1, 1.4 Hz, 1 H), 2.23 (d, J=11.3 Hz, 2 H), 1.68-1.91 (m, 7 H), 1.22-1.35 (m, 1 H); MS ESI 192.0 [M+H]⁺, calcd for [C₁₁H₁₃NS+H]⁺ 192.1.

The following intermediates were synthesized according to synthetic method of (1-thiophen-3-yl)cyclohexanecarbonitrile

| IUPAC name | Structure | MS calculated MS ESI [M + H]⁺ | Yield; Appearance; Salt form |
|---|---|---|---|
| 4-(pyridin-4-yl)tetrahydro-2H-pyran-4-carbonitrile | 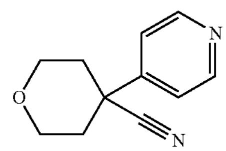 [SMILES: N#CC1(c2ccncc2)CCOCC1] | [C₁₁H₁₂N₂O + H]⁺ 189.1 189.0 | 853 mg (71%); reddish solid; free base |

SMs: 2-(pyridin-4-yl)acetonitrile (750 mg, 6.35 mmol), 1-bromo-2-(2-bromoethoxy)ethane (0.875 mL, 6.98 mmol), NaH (533 mg, 13.33 mmol), KI (1.16 g, 6.98 mmol), anh DMF (15 mL)
¹H NMR (400 MHz, CDCl₃) δ ppm 8.63-8.73 (m, 2 H), 7.35-7.47 (m, 2 H), 4.06-4.17 (m, 2 H), 3.91 (td, J = 12.2, 2.0 Hz, 2 H), 2.10-2.20 (m, 2 H), 1.97-2.08 (m, 2 H)

| 1-(pyridin-4-yl)cyclohexanecarbonitrile | | [C₁₂H₁₄N₂ + H]⁺ 187.1 187.0 | 600 mg (76%); pale yellow oil; free base |
|---|---|---|---|

SMs: 2-(pyridin-4-yl)acetonitrile (500 mg, 4.23 mmol), 1,5-dibromopentane (580 mL, 4.23 mmol), NaH (372 mg, 9.30 mmol), anh DMF (10 mL)
¹H NMR (400 MHz. CDCl₃) δ ppm 8.59-8.70 (m, 2 H), 7.33-7.46 (m, 2 H), 2.14 (d, J = 11.8 Hz, 2 H), 1.76-1.97 (m, 6 H). 1.25-1.37 (m, 1 H)

| 1-(pyridin-3-yl)cyclohexanecarbonitrile | | [C₁₂H₁₄N₂ + H]⁺ 187.1 187.0 | 625 mg (79%); pale yellow oil; free base |
|---|---|---|---|

SMs: 2-(pyridin-3-yl)acetonitrile (500 mg, 4.23 mmol), 1,5-dibromopentane (580 mL, 4.23 mmol), NaH (372 mg, 9.30 mmol), anh DMF (10 mL)
¹H NMR (400 MHz, CDCl₃) δ ppm 8.72-8.81 (m, 1 H), 8.59 (dd, J = 4.9, 1.6 Hz, 1 H), 7.74-7.90 (m, 1 H), 7.35 (ddd, J = 8.0, 4.8, 0.8 Hz, 1 H), 2.14-2.25 (m, 2 H), 1.75-1.98 (m, 7 H), 1.25-1.39 (m, 1 H)

| 1-(pyridin-2-yl)cyclopropanecarbonitrile | | [C₉H₈N₂ + H]⁺ 145.07 187.0 | 900 mg (74%); white solid; free base |
|---|---|---|---|

SMs: 2-(pyridin-2-yl)acetonitrile (1.0 g, 8.4 mmol), 1,5-dibromoethane (1.59 g, 8.4 mmol), NaH (0.81 g, 18.5 mmol), anh DMF(10 mL)
¹H NMR (400 MHz, CDCl₃) δ ppm 8.33-8.53 (m, 1 H) 7.63-7.77 (m, 2 H) 7.17 (ddd, J = 6.8, 4.9, 1.9 Hz, 1 H) 1.80-1.88 (m, 2 H) 1.67-1.76 (m, 2 H)

Synthesis of 1-(4-fluoropiperidin-1-yl)cyclohexanecarbonitrile

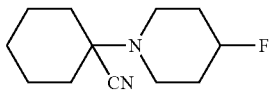

Cyclohexanone (0.50 g, 5.1 mmol), 4-fluoropiperidine hydrochloride (0.77 g, 5.5 mmol), KCN (0.35 g, 5.3 mmol) were stirred in EtOH (5 mL), H$_2$O (5 mL) for 20 h at rt. The reaction mixture was partitioned between Et$_2$O and H$_2$O. The organics were washed (H$_2$O 2×, brine), dried (Na$_2$SO$_4$) and concentrated under reduced pressure to afford the desired product as pale yellow oil (0.73 g) that was used directly without further purification. $^1$H NMR (400 MHz, CDCl$_3$) δ ppm 2.94-3.00 (m, 2 H), 2.74-2.85 (m, 2 H), 1.52-2.20 (m, 12 H), 1.18-1.39 (m, 2 H); MS ESI [M+H]$^+$ 211.0, calcd [C$_{12}$H$_{18}$F$_2$N$_2$+H]$^+$ 211.1.

The following intermediates were synthesized according to the synthesis of 4-morpholinotetrahydro-2H-pyran-4-carbonitrile using or 1-(4-fluoropiperidin-1-yl)cyclohexanecarbonitrile using TMSCN and KCN, respectively:

Synthesis of (1-(thiophen-3-yl)cyclohexyl)methanamine

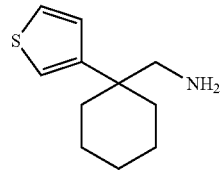 [SMILES: NCC1(c2ccsc2)CCCCC1]

LiAlH$_4$ (1M in THF, 4.4 mL, 4.4 mmol) was added over 15 min to a cooled (0-5° C.) solution of (1-thiophen-3-yl) cyclohexanecarbonitrile (670 mg, 3.5 mmol) in anh THF (6.7 mL) under Ar. The mixture was stirred at rt for 24 h and quenched by adding EtOAc (25 mL) and 2 M aq Na$_2$CO$_3$ (20 mL). The layers were separated and aq layer was extracted using EtOAc (20 mL). The combined organic layers were washed with H$_2$O, dried (Na$_2$SO$_4$) and concentrated under reduced pressure to give a crude oil. Purification by flash chromatography (Biotage Isolera, 25 g HP-SIL, 0-25% MeOH in DCM) gave the title compound as a clear colorless oil (340 mg, 49%). $^1$H NMR (400 MHz, CDCl$_3$) δ ppm 7.46 (dd, J=4.9, 2.9 Hz, 1 H), 7.15 (dd, J=2.9, 1.4 Hz, 1 H), 7.05 (dd, J=5.0, 1.3 Hz, 1 H), 3.33 (br. s, 2 H), 1.93 (d, J=8.3 Hz, 2 H), 1.37-1.56 (m, 5 H), 1.19-1.33 (m, 3 H), 0.94 (br. s, 2 H); MS ESI 195.1 [M+H]$^+$, calcd for [C$_{11}$H$_{17}$NS+H]$^+$ 195.1.

The following intermediates were synthesized according to synthetic method of (1-(thiophen-3-yl)cyclohexyl)methanamine

| IUPAC name | Structure | MS calculated MS ESI [M + H]$^+$ | Yield; Appearance; Salt form |
|---|---|---|---|
| 1-(4-fluoropiperidin-1-yl)cyclohexanecarbonitrile | 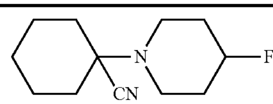 | [C$_{12}$H$_{19}$FN$_2$ + H]$^+$ 211.15 211.0 | 0.73 g (68%); pale yellow oil; free base |

SMs: cyclohexanone (0.50 g, 5.1 mmol), 4-fluoropiperidine hydrochloride (0.77 g, 5.5 mmol), KCN (0.35 g, 5.3 mmol)
$^1$H NMR (400 MHz, CDCl$_3$) δ ppm 4.70-4.87 (m, 0.5 H), 4.62 (m, 0.5 H), 2.85 (m, 2 H), 2.56 (m, 2 H), 1.52-2.20 (m, 12 H), 1.22-1.35 (m, 2 H)

| 1-(4,4-difluoropiperidin-1-yl)cyclohexanecarbonitrile | | [C$_{12}$H$_{18}$F$_2$N$_2$ + H]$^+$ 229.14 229.0 | 0.87 g (75 %); pale yellow oil, free base |

SMs: cyclohexanone (0.50 g, 5.1 mmol), 4,4-difluoropiperidine hydrochloride (0.87 g, 5.5 mmol), KCN (0.34 g, 5.3 mmol)
$^1$H NMR (400 MHz, CDCl$_3$) δ ppm 2.94-3.00 (m, 2 H), 2.74-2.85 (m, 2 H), 1.52-2.20 (m, 12 H), 1.18-1.39 (m, 2 H)

| 4,4-difluoro-1-morpholinocyclohexanecarbonitrile | | [C$_{11}$H$_{16}$F$_2$N$_2$O + H]$^+$ 231.12 231.1 | 0.66 g (77%), tan solid; free base |

SMs: 4,4-difluorocyclohexanone (0.50 g, 3.7 mmol), morpholine (0.64 mL, 7.5 mmol), (0.34 g, 5.3 mmol), 2-hydroxy-2-methylpropanenitrile (0.32 g, 3.7 mmol), MgSO$_4$ (1.35 g, 11.2 mmol)
$^1$H NMR (400 MHz, CDCl$_3$) δ ppm 3.78 (s, 4 H), 2.62-2.69 (m, 4 H), 1.77-2.26 (m, 8 H)

| IUPAC name | Structure | MS calculated MS ESI [M + H]+ | Yield; Appearance; Salt form |
|---|---|---|---|
| (1-morpholino-cyclobutyl)methanamine | 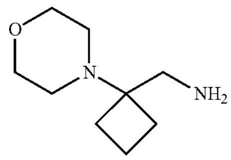 [SMILES: NCC1(N2CCOCC2)CCC1] | [C₉H₁₈N₂O + H]⁺ 171.1 171.0 | 275 mg (53%); colorless oil; free base |

SMs: 1-morpholinocyclobutanecarbonitrile (500 mg, 3.0 mmol), LiAlH₄ (1M in THF, 3.75 mL, 3.76 mmol), anh THF(3 mL)
¹H NMR (400 MHz, CDCl₃) δ ppm 3.69 (t, J = 4.8 Hz, 4 H), 2.80 (s, 2 H), 2.52 (t, J = 4.8 Hz, 4 H), 2.10-2.21 (m, 2 H), 1.65-1.77 (m, 2 H), 1.54-1.64 (m, 2 H), 1.32 (br. s, 2 H)

| (4-morpholinotetrahydro-2H-pyran-4-yl)methanamine | | [C₁₀H₂₀N₂O₂ + H]⁺ 201.1 201.0 | 432 mg (27%); colorless oil; free base |

SMs: 4-morpholinotetrahydro-2H-pyran-4-carbonitrile (1.58 g, 8.0 mmol), LiAlH₄ (1M in THF, 10 mL, 10 mmol), anh THF (16 mL)
¹H NMR (400 MHz, CDCl₃) δ ppm 3.80-3.90 (m, 2 H), 3.65-3.74 (m, 4 H), 3.59 (ddd, J = 11.2, 8.1, 3.0 Hz, 2 H), 2.83 (s, 2 H), 2.60-2.69 (m, 4 H), 1.73-1.85 (m, 2 H), 1.47-1.57 (m, 2 H), 1.32 (brs, 2 H)

| (1-(4-fluoropiperidin-1-yl)cyclohexyl)methanamine | | [C₁₂H₂₃FN₂ + H]⁺ 215.18 215.1 | 194 mg, crude 31% by wt; free base |

SMs: 1-(4-fluoropiperidin-1-yl)cyclohexanecarbonitrile (0.30 g, 1.4 mmol), LiAlH₄ (20 mL, 1M in THF, 20 mmol)

| (1-(4,4-difluoropiperidin-1-yl)cyclohexyl)methanamine | | [C₁₂H₂₂F₂N₂ + H]⁺ 233.18 233.0 | 0.22 g (72%) clear oil; free base |

SMs: 1-(4,4-difluoropiperidin-1-yl)cyclohexanecarbonitrile (0.30 g, 1.3 mmol), LiAlH₄ (10 mL, 1M in THF, 10 mmol)
¹H NMR (400 MHz, CDCl₃) δ ppm 2.73 (s, 2 H), 1.83-2.04 (m, 4 H), 1.11-1.71 (m, 12 H)

| (4,4-difluoro-1-morpholinocyclohexyl)methanamine | | [C₁₁H₂₀F₂N₂O + H]⁺ 235.15 235.0 | 0.15 g (44%); pale yellow solid, free base |

SMs: 4,4-difluoro-1-morpholinocyclohexanecarbonitrile (0.33 g, 1.4 mmol), LiAlH₄ (17 mL, 1M in THF, 17 mmol)
¹H NMR (400 MHz, CDCl₃) δ ppm 3.59-3.78 (m, 4 H), 2.75 (s, 2 H), 2.62-2.71 (m, 4 H), 1.73-2.18 (m, 6H), 1.53-1.70 (m, 2 H)

(4-(pyridin-4-yl)tetrahydro-2H-pyran-4-yl)methan-amine

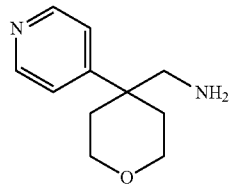 [SMILES: NCC1(c2ccncc2)CCOCC1]

To a solution of 4-(pyridin-4-yl)tetrahydro-2H-pyran-4-carbonitrile (100 mg, 0.53 mmol) in MeOH (5 mL) was added 2M NH$_3$ in MeOH (10 mL) and Ra—Ni (200 mg, 3.41 mmol) under Ar. Then reaction mixture stirred at rt under atmosphere of H$_2$ (1 atm) for 24 h. After reaction completion (by TLC) the catalyst was filtered under inert atmosphere and washed with MeOH. The combined filtrate was concentrated under pressure to give an oily residue. The residue was passed through PoraPak Rxn 20 cc column and the pure product was eluted using 2M NH$_3$ in MeOH to give a pale yellow oil (88 mg, 86%). $^1$H NMR (400 MHz, CDCl$_3$) δ ppm 8.53-8.65 (m, 2 H), 7.17-7.28 (m, 2 H), 3.81 (dt, J=12.0, 4.4 Hz, 2 H), 3.38-3.59 (m, 2 H), 2.83 (s, 2 H), 2.09-2.23 (m, 2 H), 1.87 (ddd, J=13.7, 9.6, 3.8 Hz, 2 H), 0.79-1.35 (m, 2 H); MS ESI 193.0 [M+H]$^+$, calcd for [C$_{11}$H$_{16}$N$_2$O+H]$^+$ 193.1.

The following intermediates were synthesized according to synthetic method of (4-(pyridin-4-yl)tetrahydro-2H-pyran-4-yl)methanamine

| IUPAC name | Structure | MS calculated MS ESI [M + H]$^+$ | Yield; Appearance; Salt form |
|---|---|---|---|
| (1-(pyridin-3-yl)cyclohexyl)methanamine | 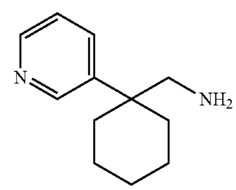 [SMILES: NCC1(c2cccnc2)CCCCC1] | [C$_{12}$H$_{18}$N$_2$ + H]$^+$ 191.1 191.0 | 150 mg (73%); cream solid; free base |

SMs: 1-(pyridin-3-yl)cyclohexanecarbonitrile (200 mg, 1.07 mmol), Ra—Ni (500 mg, 8.53 mmol), MeOH (4 mL), 2M NH$_3$—MeOH (10 mL)
$^1$H NMR (400 MHz, CDCl$_3$) δ ppm 8.61 (d, J = 2.3 Hz, 1 H), 8.46 (dd, J = 4.6, 1.4 Hz, 1 H), 7.65 (dd, J = 8.0, 1.8 Hz, 1 H), 7.22-7.33 (m, 1 H), 2.74 (s, 2 H), 2.09-2.23 (m, 2 H), 1.45-1.66 (m, 8 H), 1.25-1.44 (m, 2H)

| (1-(pyridin-4-yl)cyclohexyl)methanamine | | [C$_{12}$H$_{18}$N$_2$ + H]$^+$ 191.1 191.0 | 175 mg (86%); cream solid; free base |
|---|---|---|---|

SMs: 1-(pyridin-4-yl)cyclohexanecarbonitrile (200 mg, 1.07 mmol), Ra—Ni (500 mg, 8.53 mmol). MeOH (4 mL), 2M NH$_3$—MeOH (10 mL)
$^1$H NMR (400 MHz, CDCl$_3$) δ ppm 8.53-8.61 (m, 2 H), 7.22-7.28 (m, 2 H), 2.72 (s, 2 H), 2.08-2.19 (m, 2H), 1.69-1.93 (m, 8 H), 1.23-1.43 (m, 2 H)

| (1-(pyridin-2-yl)cyclopropyl)methanamine | | [C$_9$H$_{12}$N$_2$ + H]$^+$ 149.1 191.0 | 300 mg (42%); brown oil; free base |
|---|---|---|---|

SMs: 1-(pyridin-2-yl)cyclopropane carbonitrile (700 mg, 4.85 mmol), Ra—Ni (1.4 g, 24 mmol), MeOH (14 mL), 2M NH$_3$—MeOH (14 mL)
$^1$H NMR (400 MHz, CDCl$_3$) δ ppm 8.52 (d, J = 5.0 Hz, 1 H), 7.60 (td, J = 7.8, 1.8 Hz, 1 H), 7.18 (d, J = 8.0 Hz, 1 H), 7.08 (dd, J = 6.5, 5.0 Hz, 1 H), 3.09 (m, 2 H), 1.07-1.18 (m, 2 H), 0.88-0.96 (m, 2 H)

Synthesis of (S)-N-(cyclopropyl(2-fluorophenyl)methyl)-3-iodo-1H-indazole-5-carboxamide

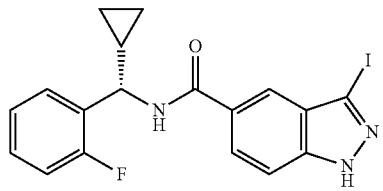 [SMILES: O=C(N[C@H](c1ccccc1F)C1CC1)c1ccc2[nH]nc(I)c2c1]

The title compound was synthesized according to General Method A utilizing 3-iodo-1H-indazole-5-carboxylic acid (358 mg, 1.23 mmol), (S)-cyclopropyl(2-fluorophenyl)methanamine hydrochloride (250 mg, 1.23 mmol), BOP-Cl (576 mg, 1.3 mmol), DIPEA (1.08 mL, 6.19 mmol) and DMF (5 mL) at 0° C. The reaction was stirred and slowly warmed to rt and stirred at 24° C. for 3 h. The reaction was concentrated and purified by flash chromatography (Biotage isolera 60 g C18-HS, 5-90% MeOH in 0.1% TFA.H$_2$O) to give the title compound as an off white solid (405 mg, 75%). NMR (400 MHz, CD$_3$OD) δ ppm 8.08 (s, 1 H), 7.95 (dd, J=8.8, 1.6 Hz, 1 H), 7.56-7.58 (m, 2 H), 7.26-7.31 (m, 1 H), 7.17 (t, J=7.6 Hz, 1 H), 7.09 (t, J=10 Hz, 1 H), 4.76 (d, J=9.2 Hz, 1 H), 1.41-1.50 (m, 1 H), 0.66-0.72 (m, 1 H), 0.58-0.62 (m, 1 H), 0.50-0.56 (m, 2 H); MS ESI 436.2 [M+H]$^+$, calcd for [C$_{18}$H$_{15}$FIN$_3$O+H]$^+$ 436.

Synthesis of (S)-N-(cyclopropyl(pyridin-2-yl)methyl)-6-fluoro-3-iodo-1H-indazole-5-carboxamide

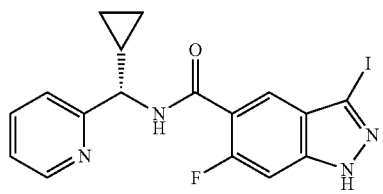 [SMILES: O=C(N[C@H](c1ccccn1)C1CC1)c1cc2c(I)n[nH]c2cc1F]

The title compound was synthesized according to General Method A utilizing 6-fluoro-3-iodo-1H-indazole-5-carboxylic acid (145 mg, 0.47 mmol), (S)-cyclopropyl(pyridin-2-yl)methanamine hydrochloride (88 mg, 0.47 mmol), BOP-Cl (230 mg, 0.52 mmol), DIPEA (0.41 mL, 2.36 mmol) and DMF (4 mL). The reaction was stirred at 24° C. for 3 h, concentrated in vacuo and purified by flash chromatography (Biotage isolera 60 g C18-HS, 5-90% MeOH in 0.1% TFA/H$_2$O) to give the title compound as a white solid (158 mg, 77%). $^1$H NMR (400 MHz, CD$_3$OD) δ ppm 8.8.61 (s, 1 H), 7.93 (d, J=6.4 Hz, 1 H), 7.83-7.87 (m, 1 H), 7.55 (d, J=7.6 Hz, 1 H), 7.33-7.39 (m, 2 H), 4.59 (d, J=8.8 Hz, 1 H), 1.32-1.40 (m, 1 H), 0.66-0.71 (m, 1 H), 0.58-0.65 (m, 3 H); MS ESI 437.1 [M+H]$^+$, calcd for [C$_{17}$H$_{14}$FIN$_4$O+H]$^+$ 437.

Synthesis of (S)-N-(1-(2-fluorophenyl)-3-methylbutyl)-3-iodo-1H-indazole-5-carboxamide

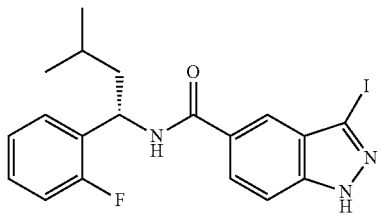 [SMILES: CC(C)C[C@H](NC(=O)c1ccc2[nH]nc(I)c2c1)c1ccccc1F]

The title compound was synthesized according to General Method A by utilizing (S)-1-(2-fluorophenyl)-3-methylbutan-1-amine HCl salt (1.0 g, 0.46 mmol), 3-iodo-1H-indazole-5-carboxylic acid (1.32 g, 0.46 mmol), TBTU (1.55 g, 0.48 mmol), DIPEA (3.01 mL, 1.84 mmol) and DMF (15 mL). After stirring for 4 h, the crude reaction was subsequently diluted with H$_2$O, filtered and washed with H$_2$O to give the title compound as a cream solid (1.8 g, 87%). $^1$H NMR (400 MHz, CD$_3$OD) δ ppm 8.95 (d, J=8.4 Hz, 1H), 8.08 (s, 1 H), 7.93 (d, J=8.8 Hz, 1H), (m, 1 H), 7.60-7.50 (m, 1 H), 7.47-7.56 (m, 1 H), 7.23-7.31 (m, 1 H), 7.13-7.21 (m, 2 H), 5.41-5.53 (m, 1 H), 1.84-1.92 (m, 1 H), 1.60-1.72 (m, 1 H), 1.47-1.58 (m, 1 H), 0.89-0.99 (m, 6 H); MS ESI 452.2 [M+H]$^+$, calcd for [C$_{19}$H$_{19}$FIN$_3$O+H]$^+$ 452.06.

The following intermediates were synthesized according to General Method A:

| IUPAC name | Structure | MS calculated MS ESI [M + H]$^+$ | Yield; Appearance; Salt form |
|---|---|---|---|
| 3-iodo-N-(3-methyl-1-(pyridin-2-yl)butyl)-1H-indazole-5-carboxamide | 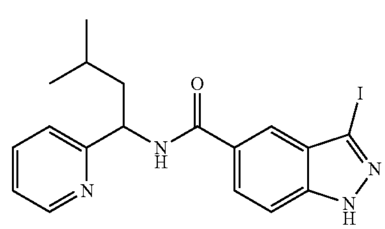 [SMILES: CC(C)CC(NC(=O)c1ccc2[nH]nc(I)c2c1)c1ccccn1] | [C$_{18}$H$_{19}$IN$_4$O + H]$^+$ 435.1 435.1 | 2.31 g (53%), beige solid; free base |

SMs: 3-methyl-1-(pyridin-2-yl)butan-1-amine (1.64 g, 10 mmol), 3-iodo-1H-indazole-5-carboxylic acid (2.88 g, 10 mmol)

| IUPAC name | Structure | MS calculated<br>MS ESI [M + H]⁺ | Yield;<br>Appearance;<br>Salt form |
|---|---|---|---|
| (S)-3-iodo-N-(1-phenylbutyl)-1H-indazole-5-carboxamide | | [C₁₈H₁₈IN₃O + H]⁺<br>420.0<br>420.1 | 3.15 g (75%),<br>beige solid;<br>free base |

SMs: (S)-1-phenylbutan-1-amine (1.49 g, 10 mmol), 3-iodo-1H-indazole-5-carboxylic acid (2.88 g, 10 mmol)
¹H NMR (400 MHz, DMSO-d₆) δ ppm 13.55 (brs, 1H), 8.91 (d, J = 8.4 Hz, 1H), 8.07 (s, 1H), 7.94 (dd, J = 8.8, 1.2 Hz, 1H), 7.58 (d, J = 8.8 Hz, 1H), 7.40 (d, J = 7.2 Hz, 2H), 7.32 (t, J = 7.8 Hz, 2H), 7.21 (t, J = 7.4 Hz, 1H), 5.09-5.01 (m, 1H), 1.96-1.85 (m, 1H), 1.79-1.69 (m, 1H), 1.46-1.25 (m, 2H), 0.91 (t, J = 7.2 Hz, 3H).

| | | | |
|---|---|---|---|
| 3-iodo-N-(3-methyl-1-phenylbutyl)-1H-indazole-5-carboxamide | | [C₁₉H₂₀IN₃O + H]⁺<br>434.1<br>434.1 | 1.66 g (76%),<br>off white solid;<br>free base |

SMs: 3-methyl-1-phenylbutan-1-amine (815 mg, 5 mmol), 3-iodo-1H-indazole-5-carboxylic acid (1.44 g, 5 mmol)
¹H NMR (400 MHz, CDCl₃) δ ppm ¹H NMR (400 MHz, DMSO-d₆) δ ppm 13.69 (s, 1H), 8.90 (d, J = 8.4 Hz, 1H), 8.07 (s, 1H), 7.97-7.83 (m, 1H), 7.58 (d, J = 8.8 Hz, 1H), 7.44-7.38 (m, 2H), 7.33 (t, J = 7.4 Hz, 2H), 7.22 (t, J = 7.2 Hz, 1H), 5.20-5.10 (m, 1H), 1.93-1.83 (m, 1H), 1.68-1.53 (m, 2H), 0.94 (t, J = 6.4 Hz, 6H).

| | | | |
|---|---|---|---|
| (R)-3-iodo-N-(3-methyl-1-(pyridin-2-yl)butyl)-1H-indazole-5-carboxamide | | [C₁₈H₁₉IN₄O + H]⁺<br>435.1<br>435.1 | 1.21 g,<br>yellow solid;<br>free base |

SMs: (R)-3-methyl-1-(pyridin-2-yl)butan-1-amine (705 mg), 3-iodo-1H-indazole-5-carboxylic acid (1.008 g, 3.5 mmol).
¹H NMR (400 MHz, DMSO-d₆) δ ppm 13.69 (s, 1H), 8.94 (d, J = 8.4 Hz, 1H), 8.53-8.50 (m, 1H), 8.14-8.12 (m, 1H), 7.98 (dd, J = 8.8, 1.6 Hz, 1H), 7.75 (dd, J = 7.6, 2.0 Hz, 1H), 7.59 (d, J = 8.8, Hz, 1H), 7.43 (d, J = 8.0 Hz, 1H), 7.27-7.22 (m, 1H), 5.26-5.16 (m, 1H), 1.91-1.83 (m, 1H), 1.76-1.65 (m, 2H), 0.95 (d, J = 6.8 Hz, 3H), 0.93 (d, J = 6.4 Hz, 3H).

| | | | |
|---|---|---|---|
| (S)-3-iodo-N-(3-methyl-1-phenylbutyl)-1H-indazole-5-carboxamide | | [C₁₉H₂₀IN₃O + H]⁺<br>434.1<br>434.3 | 424 mg (39%);<br>while solid;<br>free base |

SMs: 3-iodo-1H-indazole-5-carboxylic acid (0.721 g, 2.5 mmol), (S)-3-methyl-1-phenylbutan-1-amine HCl salt (0.5 g, 2.5 mmol)
¹H NMR (400 MHz, DMSO-d₆) δ ppm 13.68 (s, 1 H), 8.90 (d, J = 8.5 Hz, 1 H), 8.03-8.09 (m, 1 H), 7.94 (dd, J = 8.8, 1.5 Hz, 1 H), 7.58 (dd, J = 8.8, 0.8 Hz, 1 H), 7.38-7.43 (m, 2 H), 7.28-7.35 (m, 2 H), 7.18-7.24 (m, 1 H), 5.15 (dd, J = 8.7, 4.4 Hz, 1 H), 1.88 (dd, J = 10.0, 8.0 Hz, 1 H), 1.50-1.68 (m, 2 H), 0.93 (t, J = 6.5 Hz, 6 H)

| IUPAC name | Structure | MS calculated<br>MS ESI [M + H]+ | Yield;<br>Appearance;<br>Salt form |
|---|---|---|---|
| (S)-N-(3,3-dimethyl-1-phenylbutyl)-3-iodo-1H-indazole-5-carboxamide | 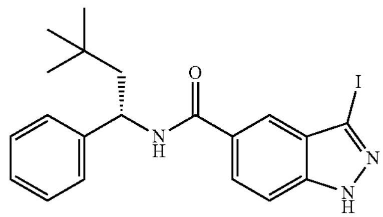 [SMILES: CC(C)(C)C[C@H](NC(=O)c1ccc2[nH]nc(I)c2c1)c1ccccc1] | [C$_{20}$H$_{22}$IN$_3$O + H]+<br>448.1<br>448.3 | 534 mg (51%);<br>off white solid;<br>free base |

SMs: 3-iodo-1H-indazole-5-carboxylic acid (647 mg, 2.3 mmol), (S)-3,3-dimethyl-1-phenylbutan-1-amine HCl salt (500 mg, 2.3 mmol)
$^1$H NMR (400 MHz, CD$_3$OD) δ ppm 8.06 (s, 1 H), 7.92 (d, J= 1.5 Hz, 1 H), 7.58 (d, J= 8.5 Hz, 1 H), 7.42 (d, J = 7.5 Hz, 2H), 7.33 (t, J = 7.7 Hz, 2 H), 7.23 (s, 1 H), 5.30-5.37 (m, 1 H), 2.03-2.13 (m, 1 H), 1.70-1.79 (m, 1 H), 1.05 (s, 9H)

| IUPAC name | Structure | MS calculated<br>MS ESI [M + H]+ | Yield;<br>Appearance;<br>Salt form |
|---|---|---|---|
| N-(cyclopentyl(pyrimidin-2-yl)methyl)-3-iodo-1H-indazole-5-carboxamide | | [C$_{18}$H$_{18}$IN$_5$O + H]+<br>448.06<br>448.1 | 0.38 g (75%);<br>off white solid;<br>free base |

SMs: 3-iodo-1H-indazole-5-carboxylic acid (325 mg, 1.1 mmol), cyclopentyl(pyrimidin-2-yl)methanamine (200 mg, 1.1 mmol)
$^1$H NMR (400 MHz, DMSO-d$_6$) δ ppm 13.67 (s, 1 H), 8.97 (d, J = 8.3 Hz, 1 H), 8.78 (d, J = 4.8 Hz, 2 H), 8.11 (s, 1 H), 7.94 (d, J = 8.8 Hz, 1 H), 7.57 (d, J = 8.5 Hz, 1 H), 7.38 (t, J = 4.9 Hz, 1 H), 5.01 (t, J= 8.78 Hz, 1 H), 2.52-2.63 (m, 1 H), 1.81-1.94 (m, 1 H), 1.38-1.71 (m, 5 H), 1.20-1.36 (m, 2 H)

| IUPAC name | Structure | MS calculated<br>MS ESI [M + H]+ | Yield;<br>Appearance;<br>Salt form |
|---|---|---|---|
| N-(2,2-dimethyl-1-(pyridin-2-yl)propyl)-3-iodo-1H-indazole-5-carboxamide | | [C$_{18}$H$_{19}$IN$_4$O + H]+<br>435.1;<br>435.1 | 1.19 g (45%);<br>light yellow solid;<br>free base |

SMs: 3-iodo-1H-indazole-5-carboxylic acid (1.8 g, 6.1 mmol) and 2,2-dimethyl-1-(pyridin-2-yl)propan-1-amine (1.0 g, 6.1 mmol)
$^1$H NMR (400 MHz, CD$_3$OD) δ ppm 8.54-8.59 (m, 1 H), 8.06 (s, 1 H), 7.94 (d, J = 9.3 Hz, 1 H), 7.77-7.84 (m, 1 H), 7.59 (d, J = 8.5 Hz, 1 H), 7.46-7.52 (m, 1 H), 7.31-7.37 (m, 1 H), 5.22 (d, J = 10.8 Hz, 1 H), 1.00-1.07 (m, 9 H)

| IUPAC name | Structure | MS calculated<br>MS ESI [M + H]+ | Yield;<br>Appearance;<br>Salt form |
|---|---|---|---|
| 3-iodo-N-(2-phenylbutyl)-1H-indazole-5-carboxamide | | [C$_{18}$H$_{18}$IN$_3$O + H]+<br>420.0;<br>420.2 | 936 mg (74%);<br>yellow oil;<br>free base |

SMs: 3-iodo-1H-indazole-5-carboxylic acid (864 mg, 3.00 mmol) and 2-phenylbutan-1-amine hydrochloride (558 mg, 3.00 mmol)
$^1$H NMR (400 MHz, CD$_3$OD) δ ppm 7.81 (s, 1 H), 7.78 (dd, J = 8.8, 1.5 Hz, 1 H), 7.52 (d, J = 8.8 Hz, 1 H), 7.28-7.35 (m, 2 H), 7.18-7.28 (m, 3 H), 3.64-3.72 (m, 1 H), 3.45-3.54 (m, 1 H), 2.88-2.98 (m, 1 H), 2.81 (s, 1 H), 1.78-1.91 (m, 1 H), 1.61-1.73 (m, 1 H), 0.83 (t, J = 7.4 Hz, 3 H)

| IUPAC name | Structure | MS calculated MS ESI [M + H]+ | Yield; Appearance; Salt form |
|---|---|---|---|
| N-(cyclohexyl (pyridin-2-yl)methyl)-3-iodo-1H-indazole-5-carboxamide | 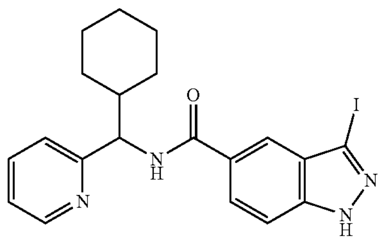 [SMILES: O=C(NC(c1ccccn1)C1CCCCC1)c1ccc2[nH]nc(I)c2c1] | [C20H21IN4O + H]+ 461.1; 461.1 | 1.34 g (55%); light yellow solid; free base |

SMs: 3-iodo-1H-indazole-5-carboxylic acid (1.52 g, 5.26 mmol) and cyclohexyl(pyridin-2-yl)methanamine (1.00 g, 5.26 mmol)

Synthesis of N-(1-(2-chlorophenyl)-3-methylbutyl)-3-iodo-1H-indazole-5-carboxamide

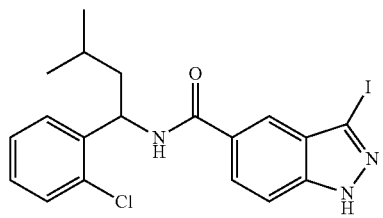 [SMILES: CC(C)CC(NC(=O)c1ccc2[nH]nc(I)c2c1)c1ccccc1Cl]

To a RBF charged with Mg powder (7.20 g, 300 mmol) in Et$_2$O (100 mL) was added i-BuBr (32.6 mL, 300 mmol) portionwise. After addition, it was stirred at rt for 1 h before 2-chlorobenzonitrile (20.63 g, 150 mmol) in PhMe (100 mL) was added slowly. The resulting mixture was refluxed (oil Temp 70° C.) for 3 h and cooled to rt. The mixture was added slowly to a cold solution of NaBH$_4$ in MeOH at −78° C. After addition, cold bath was removed and the mixture was stirred for 45 min before quenching at 0° C. with 2 M aq HCl and adjusting to pH 2 and diluting with H$_2$O. After extracting with EtOAc, the aqueous layer was basified with 4 M NaOH to pH 12 and extracted with DCM to give 1-(2-chlorophenyl)-3-methylbutan-1-amine as dark orange oil (12.90 g). MS ESI 181.0 [M+H]+, calcd for [C$_{11}$H$_{16}$ClN+H−NH$_3$]+ 181.1.

The title compound (2.78 g, pale yellow solid) was prepared using 1-(2-chlorophenyl)-3-methylbutan-1-amine (1.98 g, 10 mmol), 3-iodo-1H-indazole-5-carboxylic acid (2.88 g, 10 mmol) according to General Method A. $^1$H NMR (400 MHz, DMSO-d$_6$) δ ppm 13.70 (s, 1H), 9.01 (d, J=8.4 Hz, 1H), 8.12-8.09 (m, 1H), 7.96 (dd, J=8.8, 1.6 Hz, 1H), 7.62-7.57 (m, 2H), 7.41 (dd, J=8.0, 1.2 Hz, 1H), 7.34 (dt, J=8.0, 1.2 Hz, 1H), 7.24 (dt, J=7.6, 1.6 Hz, 1H), 5.60-5.52 (m, 1H), 1.88-1.72 (m, 2H), 1.49-1.41 (m, 1H), 0.97 (d, J=6.4 Hz, 3H), 0.95 (d, J=6.4 Hz, 3H). MS ESI 468.4 [M+H]+, calcd for [C$_{19}$H$_{19}$ClIN$_3$O+H]+ 468.0.

The following intermediates were synthesized according to the synthesis of N-(1-(2-chlorophenyl)-3-methylbutyl)-3-iodo-1H-indazole-5-carboxamide:

| IUPAC name | Structure | MS calculated MS ESI [M + H]+ | Yield; Appearance; Salt form |
|---|---|---|---|
| N-(2-ethyl-1-(pyridin-2-yl)butyl)-3-iodo-1H-indazole-5-carboxamide | 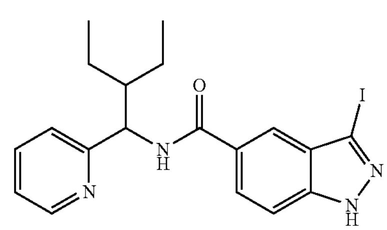 [SMILES: CCC(CC)C(NC(=O)c1ccc2[nH]nc(I)c2c1)c1ccccn1] | [C19H21IN4O + H]+ 449.1 449.1 | 2.06 g, yellow solid; free base |

SMs: 3-bromopentane (3.02 g, 20 mmol), Mg (480 mg, 20 mmol), picolinonitrile (1.05 g 10 mmol); NaBH$_4$ (760 mg, 20 mmol); 3-iodo-1H-indazole-5-carboxylic acid (1.73 g, 6 mmol).

$^1$H NMR (400 MHz, DMSO-d$_6$) δ ppm 13.69 (brs, 1H), 8.81 (d, J = 9.2 Hz, 1H), 8.55-8.52 (m, 1H), 8.07 (s, 1H), 7.93 (dd, J = 8.8, 1.2 Hz, 1H), 7.76 (dt, J = 7.6, 1.6 Hz, 1H), 7.57 (d, J = 8.8 Hz, 1H), 7.48 (d, J = 7.6 Hz, 1H), 7.25 (dd, J = 6.6, 5.0 Hz, 1H), 5.15 (t, J = 8.8 Hz, 1H), 2.10-2.02 (m, 1H), 1.56-1.42 (m, 2H), 1.13 (quintet, J = 6.9 Hz, 2H), 0.82 (t, J = 7.6 Hz, 3H), 0.77 (t, J = 7.4 Hz, 3H).

-continued

| IUPAC name | Structure | MS calculated MS ESI [M + H]⁺ | Yield; Appearance; Salt form |
|---|---|---|---|
| 3-iodo-N-(pyridin-2-yl(tetrahydro-2H-pyran-4-yl)methyl)-1H-indazole-5-carboxamide | 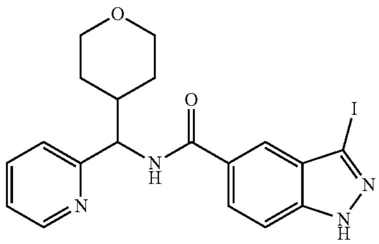 [SMILES: O=C(NC(c1ccccn1)C1CCOCC1)c1ccc2[nH]nc(I)c2c1] | [C$_{19}$H$_{19}$IN$_4$O$_2$ + H]⁺<br>463.1<br>463.2 | 400 mg,<br>yellow solid;<br>free base |

(activation was required for 4-bromotetrahydro-2H-pyran Grignard initiation); SMs: 4-bromotetrahydro-2H-pyran (1.65 g, 10 mmol), Mg (240 mg, 10 mmol), picolinonitrile (1.05 g 10 mmol); NaBH$_4$ (760 mg, 20 mmol); 3-iodo-1H-indazole-5-carboxylic acid (1.15 g, 4 mmol).
¹H NMR (400 MHz, DMSO-d$_6$) δ ppm 13.69 (s, 1H), 8.92 (d, J = 8.4 Hz, 1H), 8.54 (d, J = 4.4 Hz, 1H), 8.09 (s, 1H), 7.94 (d, J = 8.8 Hz, 1H), 7.77 (t, J = 7.6 Hz, 1H), 7.57 (d, J = 8.8 Hz, 1H), 7.47 (d, J = 7.6 Hz, 1H), 7.28-7.24 (m, 1H), 5.00-4.91 (m, 1H), 3.94-3.87 (m, 1H), 3.81-3.74 (m, 1H), 3.35-3.13 (m, 2H), 2.33-2.20(m, 1H), 1.83-1.77 (m, 1H), 1.40-1.20 (m, 2H), 1.09-1.00 (m, 1H).

| N-((2-chlorophenyl)(cyclobutyl)methyl)-3-iodo-1H-indazole-5-carboxamide | | [C$_{19}$H$_{17}$ClIN$_3$O + H]⁺<br>466.0<br>466.4 | 1.91 g,<br>beige solid;<br>free base |

SMs: bromocyclobutane (2.70 g, 20 mmol), Mg (480 mg, 20 mmol), picolinonitrile (1.05 g 10 mmol); NaBH$_4$ (760 mg, 20 mmol); 3-iodo-1H-indazole-5-carboxylic acid (1.152 g, 4 mmol).

| N-(1-(2-chlorophenyl)pent-4-en-1-yl)-3-iodo-1H-indazole-5-carboxamide | | [C$_{19}$H$_{17}$ClIN$_3$O + H]⁺<br>466.0<br>466.4 | 1.24 g,<br>beige solid;<br>free base |

SMs: (bromomethyl)cyclopropane (5.40 g, 40 mmol), Mg (960 mg, 40 mmol), 2-chloro-benzonitrile (2.75 g 20 mmol); NaBH$_4$ (1.52 g, 40 mmol); 3-iodo-1H-indazole-5-carboxylic acid (803 g, 2.5 mmol).
¹H NMR (400 MHz, DMSO-d$_6$) δ ppm 13.70 (brs, 1H), 9.04 (d, J = 8.0 Hz, 1H), 8.11 (s, 1H), 7.95 (dd, J = 8.8, 1.6 Hz, 1H), 7.60 (d, J = 8.8 Hz, 1H), 7.57 (dd, J = 7.8, 1.4 Hz, 1H), 7.41 (dd, J = 7.8, 1.0 Hz, 1H), 7.34 (dt, J = 7.2, 1.2 Hz, 1H), 7.25 (dt, J = 7.6, 1.6 Hz, 1H), 5.93-5.80 (m, 1H), 5.47-5.38 (m, 1H), 5.07-4.96 (m, 2H), 2.30-2.07 (m, 2H), 2.00-1.76 (m, 2H).

| N-(1-(2-fluorophenyl)-3,3-dimethylbutyl)-3-iodo-1H-indazole-5-carboxamide | | [C$_{20}$H$_{21}$FIN$_3$O + H]⁺<br>466.1<br>466.4 | 408 mg,<br>beige solid;<br>free base |

SMs: 1-bromo-2,2-dimethylpropane (6.04 g, 40 mmol), Mg (960 mg, 40 mmol), 2-fluoro-benzonitrile (2.46 g 20 mmol); NaBH$_4$ (1.52 g, 40 mmol); 3-iodo-1H-indazole-5-carboxylic acid (288 g, 1 mmol).

Synthesis of isobutyl 3-iodo-5-((2,2,2-trifluoro-1-phenylethyl)carbamoyl)-1H-indazole-1-carboxylate

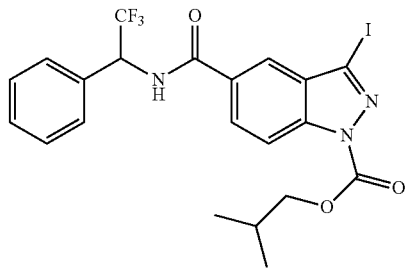 [SMILES: CC(C)COC(=O)n1nc(I)c2cc(C(=O)NC(c3ccccc3)C(F)(F)F)ccc21]

3-iodo-1H-indazole-5-carboxylic acid (1.73 g, 6.00 mmol), isobutyl chloroformate (1.57 mL, 12.0 mmol), DIPEA (2.09 mL, 1.80 mmol), and DMF (20 mL) were combined and cooled to 0° C. The reaction was stirred at 0° C. for 10 min at which point 2,2,2-trifluoro-1-phenylethanamine (1.27 mg, 6.00 mmol) was added. The mixture was warmed to rt and stirred for 1.5 h, The crude reaction was subsequently diluted with EtOAc and washed with aq NaHCO$_3$ and brine. The mixture was dried over MgSO$_4$ and the solvent was removed under reduced pressure to give the title compound as a beige solid (1.45 g, 44%). The product was used without further purification. MS ESI 546.1 [M+H]$^+$, calcd for [C$_{21}$H$_{19}$F$_3$IN$_3$O$_3$+H]$^+$ 546.0.

The following enantiomerically pure intermediates were prepared by separating racemic compounds using preparative chiral supercritical fluid chromatography (SFC):

| IUPAC name | Structure | MS calculated<br>MS ESI [M + H]$^+$ | Yield;<br>Appearance;<br>Salt form |
|---|---|---|---|
| (S)-N-(1-(2-chlorophenyl)-3-methylbutyl)-3-iodo-1H-indazole-5-carboxamide | | [C$_{19}$H$_{19}$ClIN$_3$O + H]$^+$<br>468.0<br>As racemate | 16.5 g (39%),<br>pale yellow solid;<br>free base |
| (R)-N-(1-(2-chlorophenyl)-3-methylbutyl)-3-iodo-1H-indazole-5-carboxamide | | [C$_{19}$H$_{19}$ClIN$_3$O + H]$^+$<br>468.0<br>As racemate | 17.0 g (40%),<br>pale yellow solid;<br>free base |
| (S)-N-(cyclopentyl(pyridin-2-yl)methyl)-3-iodo-1H-indazole-5-carboxamide | | [C$_{19}$H$_{19}$IN$_4$O + H]$^+$<br>447.1<br>447.1 | 3.6 g (46%);<br>yellow solid;<br>free base |

SMs: crude N-(1-(2-chlorophenyl)-3-methylbutyl)-3-iodo-1H-indazole-5-carboxamide (42.4 g)
Preparative HPLC method: OJ-H (2 × 25 cm); 30% EtOH (0.1% DEA)/CO$_2$, 100 bar; 70 mL/min, 220 nm
Analytic HPLC method: OJ-H (25 × 0.46 cm); 40% EtOH (DEA)/CO$_2$, 100 bar; 3 mL/min, 220 and 254 nm; R$_t$ 1.33 min, 100% ee SMs: crude N-(1-(2-chlorophenyl)-3-methylbutyl)-3-iodo-1H-indazole-5-carboxamide (42.4 g)
Preparative HPLC method: OJ-H (2 × 25 cm); 30% EtOH (0.1% DEA)/CO$_2$, 100 bar; 70 mL/min, 220 nm
Analytic HPLC method: OJ-H (25 × 0.46 cm); 40% EtOH (DEA)/CO$_2$, 100 bar; 3 mL/min, 220 and 254 nm; R$_t$ 2.67 min, 100% ee SMs: N-(cyclopentyl(pyridin-2-yl)methyl)-3-iodo-1H-indazole-5-carboxamide (7.9 g, 18 mmol)
Preparative HPLC method: AD-H (2 × 15 cm); 25% EtOH (0.1% DEA)/CO$_2$, 100 bar; 65 mL/min, 220 nm
Analytic HPLC method: AD-H (15 × 0.46 cm); 40% EtOH (DEA)/CO$_2$, 100 bar; 3 mL/min, 220, 254, and 280 nm; R$_t$ 2.14 min, >99% ee

| IUPAC name | Structure | MS calculated<br>MS ESI [M + H]+ | Yield;<br>Appearance;<br>Salt form |
|---|---|---|---|
| (R)-N-(cyclopentyl<br>(pyridin-2-yl)methyl)-<br>3-iodo-1H-indazole-5-<br>carboxamide | 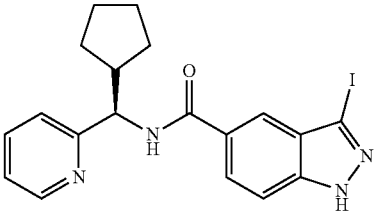 [SMILES: O=C(N[C@@H](c1ccccn1)C1CCCC1)c1ccc2[nH]nc(I)c2c1] | [C₁₉H₁₉IN₄O + H]+<br>447.1<br>447.1 | 3.5 g (44%);<br>yellow solid;<br>free base |

SMs: N-(cyclopentyl(pyridin-2-yl)methyl)-3-iodo-1H-indazole-5-carboxamide (7.9 g, 18 mmol)
Preparative HPLC method: AD-H (2 × 15 cm); 25% EtOH (0.1% DEA)/CO₂, 100 bar; 65 mL/min, 220 nm
Analytic HPLC method: AD-H (15 × 0.46 cm); 40% EtOH (DEA)/CO₂, 100 bar; 3 mL/min, 220, 254,
and 280 nm; R$_t$ 1.36 min, >99% ee

| (S)-N-(1-(2-<br>chlorophenyl)-2-<br>methylpropyl)-3-iodo-<br>1H-indazole-5-<br>carboxamide | 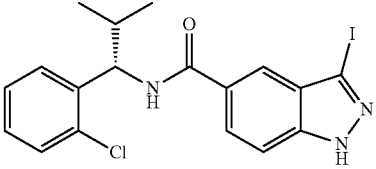 [SMILES: CC(C)[C@H](NC(=O)c1ccc2[nH]nc(I)c2c1)c1ccccc1Cl] | [C₁₈H₁₇ClIN₃O + H]+<br>454.0<br>454.0 | 454 mg (46%);<br>yellow solid;<br>free base |

SMs: N-(1-(2-chlorophenyl)-2-methylpropyl)-3-iodo-1H-indazole-5-carboxamide (1.0 g, 2.2 mmol)
Preparative HPLC method: IC (2 × 15 cm); 30% i-PrOH/CO₂, 100 bar; 65 mL/min, 220 nm
Analytic HPLC method: IC (15 × 0.46 cm); 30% i-PrOH (DEA)/CO₂, 100 bar; 3 mL/min, 220, 254, and
280 nm; R$_t$ 4.57 min, >99% ee

| (R)-N-(1-(2-<br>chlorophenyl)-2-<br>methylpropyl)-3-iodo-<br>1H-indazole-5-<br>carboxamide | 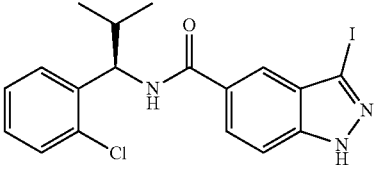 [SMILES: CC(C)[C@@H](NC(=O)c1ccc2[nH]nc(I)c2c1)c1ccccc1Cl] | [C₁₈H₁₇ClIN₃O + H]+<br>454.0<br>454.0 | 454 mg (46%);<br>yellow solid;<br>free base |

SMs: N-(1-(2-chlorophenyl)-2-methylpropyl)-3-iodo-1H-indazole-5-carboxamide (1.0 g, 2.2 mmol)
Preparative HPLC method: IC (2 × 15 cm); 30% i-PrOH/CO₂, 100 bar; 65 mL/min, 220 nm
Analytic HPLC method: IC (15 × 0.46 cm); 30% i-PrOH (DEA)/CO₂, 100 bar; 3 mL/min, 220, 254, and
280 nm; R$_t$ 6.32 min, >99% ee

| (S)-N-<br>(cyclopentyl(thiophen-<br>3-yl)methyl)-3-iodo-<br>1H-indazole-5-<br>carboxamide | 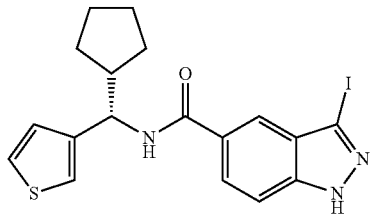 [SMILES: O=C(N[C@H](c1ccsc1)C1CCCC1)c1ccc2[nH]nc(I)c2c1] | [C₁₈H₁₈IN₃OS + H]+<br>452.0<br>452.0 | 1.1 g (42%);<br>yellow solid;<br>free base |

SMs: N-(cyclopentyl(thiophen-3-yl)methyl)-3-iodo-1H-indazole-5-carboxamide (2.6 g, 5.8 mmol)
Preparative HPLC method: OJ-H (3 × 15 cm); 35 methanol (0.1% DEA)/CO₂, 100 bar; 70 mL/min, 220 nm
Analytic HPLC method: OJ-H (10 × 0.46 cm); 30% methanol (DEA)/CO₂, 100 bar; 3 mL/min, 220,
254, and 280 nm; R$_t$ 2.83 min, >99% ee

| (R)-N-<br>(cyclopentyl(thiophen-<br>3-yl)methyl)-3-iodo-<br>1H-indazole-5-<br>carboxamide | 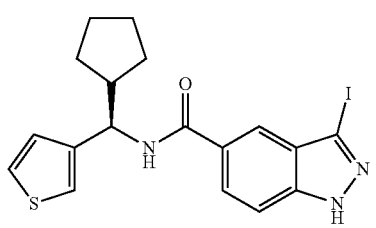 [SMILES: O=C(N[C@@H](c1ccsc1)C1CCCC1)c1ccc2[nH]nc(I)c2c1] | [C₁₈H₁₈IN₃OS + H]+<br>452.0<br>452.0 | 1.2 g (46%);<br>yellow solid;<br>free base |

SMs: N-(cyclopentyl(thiophen-3-yl)methyl)-3-iodo-1H-indazole-5-carboxamide (2.6 g, 5.8 mmol)
Preparative HPLC method: OJ-H (3 × 15 cm): 35 methanol (0.1% DEA)/CO₂, 100 bar: 70 mL/min, 220 nm
Analytic HPLC method: OJ-H (10 × 0.46 cm); 30% methanol (DEA)/CO₂, 100 bar; 3 mL/min, 220,
254, and 280 nm; R$_t$ 1.45 min, >99% ee -continued

| IUPAC name | Structure | MS calculated MS ESI [M + H]+ | Yield; Appearance; Salt form |
|---|---|---|---|
| (S)-N-(cyclopentyl (pyrimidin-2-yl)methyl)-3-iodo-1H-indazole-5-carboxamide | 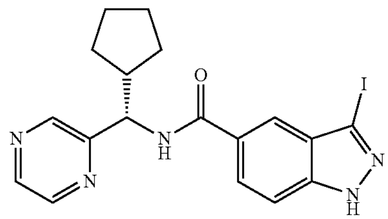 [SMILES: O=C(N[C@H](c1cnccn1)C1CCCC1)c1ccc2[nH]nc(I)c2c1] | [C$_{18}$H$_{18}$IN$_5$O + H]+ 448.1 448.1 | 468 mg (44%); yellow solid; free base |

SMs: N-(cyclopentyl(pyrimidin-2-yl)methyl)-3-iodo-1H-indazole-5-carboxamide (1.1 g, 2.4 mmol)
Preparative HPLC method: AD-H (2 × 25 cm); 30% EtOH (0.1% DEA)/CO$_2$, 100 bar; 65 mL/min, 220 nm
Analytic HPLC method: AD-H (25 × 0.46 cm); 40% EtOH(DEA)/CO:, 100 bar; 3 mL/min. 220 and 254 nm; R$_t$ 2.95 min, >99% ee

| IUPAC name | Structure | MS calculated MS ESI [M + H]+ | Yield; Appearance; Salt form |
|---|---|---|---|
| (R)-N-(cyclopenlyl (pyrimidin-2-yl)methyl)-3-iodo-1H-indazole-5-carboxamide | | [[C$_{18}$H$_{18}$IN$_5$O + H]+ 448.1 448.4 | 475 mg (45%); yellow solid; free base |

SMs: N-(cyclopentyl(pyrimidin-2-yl)methyl)-3-iodo-1H-indazole-5-carboxamide (1.1 g, 2.4 mmol)
Preparative HPLC method: AD-H (2 × 25 cm); 30% EtOH (0.1% DEA)/CO$_2$, 100 bar; 65 mL/min, 220 nm
Analytic HPLC method: AD-H (25 × 0.46 cm); 40% EtOH (DEA)/CO$_2$, 100 bar; 3 mL/min, 220 and 254 nm; R$_t$ 2.29 min, >99% ee The following intermediates were synthesized according to General Method A:

| IUPAC name | Structure | MS calculated MS ESI [M + H]+ | Yield; Appearance; Salt form |
|---|---|---|---|
| 3-iodo-N-((3-morpholino tetrahydro-2H-pyran-3-yl)methyl)-1H-indazole-5-carboxamide | 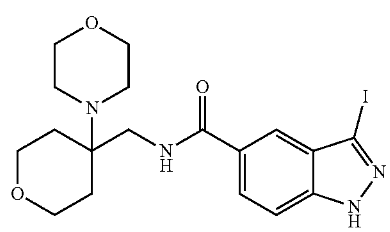 [SMILES: O=C(NCC1(N2CCOCC2)CCOCC1)c1ccc2[nH]nc(I)c2c1] | [C$_{18}$H$_{23}$IN$_4$O$_3$ + H]+ 471.1 471.1 | 824 mg (63%), white solid; free base |

SMs: (3-morpholinotetrahydro-2H-pyran-3-yl)methanamine (600 mg, 3 mmol), 3-iodo-1H-indazole-5-carboxylic acid (864 mg, 3 mmol)
$^1$H NMR (400 MHz, DMSO-d$_6$) δ ppm 13.70 (s, 1H), 8.19 (t, J = 6.0 Hz, 1H), 7.96 (s, 1H), 7.90 (d, J = 8.8 Hz, 1H), 7.61 (d, J = 8.8 Hz, 1H), 3.70-3.35 (m, 14H, partially buried in MeOH), 2.75-2.65 (m, 4H), 1.75-1.53 (m, 4H).

| IUPAC name | Structure | MS calculated MS ESI [M + H]+ | Yield; Appearance; Salt form |
|---|---|---|---|
| 3-iodo-N-((1-(morpholinomethyl)cyclopropyl)methyl)-1H-indazole-5-carboxamide | | [C$_{17}$H$_{21}$IN$_4$O$_2$ + H]+ 441.1 441.1 | 1.372 g (62%), light beige solid; free base |

SMs: (1-(morpholinomethyl)cyclopropyl)methanamine (850 mg, 5 mmol), 3-iodo-1H-indazole-5-carboxamide (1.44 g, 5 mmol)

| IUPAC name | Structure | MS calculated<br>MS ESI [M + H]+ | Yield;<br>Appearance;<br>Salt form |
|---|---|---|---|
| N-((2,2-dimethyl-1-phenylcyclopropyl)methyl)-3-iodo-1H-indazole-5-carboxamide | 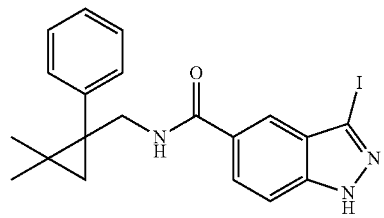 [SMILES: CC1(C)CC1(CNC(=O)c1ccc2[nH]nc(I)c2c1)c1ccccc1] | $[C_{20}H_{20}IN_3O + H]^+$<br>446.07<br>446.1 | 628 mg (92%);<br>cream solid |

SMs: (2,2-dimethyl-1-phenylcyclopropyl)methanamine (249 mg, 1.42 mmol), 3-iodo-1H-indazol-5-carboxylic acid (411 mg, 1.42 mmol), DIPEA (0.5 mL, 2.87 mmol), TBTU (461 mg, 1.44 mmol), anh DMF (5 mL)
$^1$H NMR (400 MHz, CD$_3$OD) δ ppm 7.67-7.70 (m, 2 H), 7.49 (d, J = 8.8 Hz, 1 H), 7.31-7.35 (m, 4 H), 7.21-7.24 (m, 1 H), 3.92 (d, J = 12.8 Hz, 1 H), 3.59-3.63 (m, 2 H), 1.43 (s, 3 H), 0.94-0.99 (m, 1 H), 0.80 (s, 3 H)

| IUPAC name | Structure | MS calculated<br>MS ESI [M + H]+ | Yield;<br>Appearance;<br>Salt form |
|---|---|---|---|
| 3-iodo-N-((1-morpholino cyclopentyl)methyl)-1H-indazole-5-carboxamide | 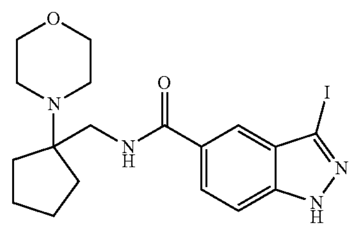 [SMILES: O=C(NCC1(N2CCOCC2)CCCC1)c1ccc2[nH]nc(I)c2c1] | $[C_{18}H_{23}IN_4O_2 + H]^+$<br>455.09<br>456.0 | 658 mg (86%);<br>off white solid<br>TFA salt |

SMs: (1-morpholinocyclopentyl)methanamine (390 mg, 1.35 mmol), 3-iodo-1H-indazol-5-carboxylic acid (299 mg, 1.35 mmol), DIPEA (0.47 mL, 2.71 mmol), TBTU (440 mg, 1.37 mmol), anh DMF (7 mL)
$^1$H NMR (400 MHz, CD$_3$OD) δ ppm 8.16 (s, 1 H), 8.02 (dd, J = 8.8, 1.3 Hz, 1 H), 7.63 (d, J = 8.8 Hz, 1 H), 4.14 (d, J = 12.5 Hz, 2 H), 3.76-3.91 (m, 4 H), 3.70 (d, J = 12.0 Hz, 2 H), 3.46 (br. s, 2 H), 2.07 (br. s, 4 H), 1.90 (d, J = 6.0 Hz, 4 H)

| IUPAC name | Structure | MS calculated<br>MS ESI [M + H]+ | Yield;<br>Appearance;<br>Salt form |
|---|---|---|---|
| 3-iodo-N-((1-morpholinocyclo-heptyl)methyl)-1H-indazole-5-carboxamide | 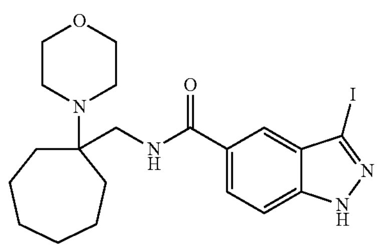 [SMILES: O=C(NCC1(N2CCOCC2)CCCCCC1)c1ccc2[nH]nc(I)c2c1] | $[C_{20}H_{27}IN_4O_2 + H]^+$<br>483.1<br>483.0 | 775 mg (86%);<br>off white solid<br>TFA salt |

SMs: (1-morpholinocycloheptyl)methanamine(288 mg, 1.36 mmol), 3-iodo-1H-indazol-5-carboxylic acid (390 mg, 1.36 mmol), DIPEA (0.47 mL, 2.71 mmol), TBTU (440 mg, 1.37 mmol), anh DMF (12 mL)
$^1$H NMR (400 MHz, CD$_3$OD) δ ppm 8.16 (s, 1 H), 8.02 (dd, J = 8.9, 1.4 Hz, 1 H), 7.63 (d, J = 8.8 Hz, 1 H), 4.18 (d, J = 12.3 Hz, 2 H), 3.85-3.98 (m, 2 H), 3.76 (s, 2 H), 3.68 (d, J = 11.8 Hz, 2 H), 3.36 (br. s, 2 H), 2.09-2.15 (m, 2 H), 1.87-2.00 (m, 2 H), 1.76 (br. s, 2 H), 1.65 (br. s, 6 H)

| IUPAC name | Structure | MS calculated<br>MS ESI [M + H]+ | Yield;<br>Appearance;<br>Salt form |
|---|---|---|---|
| 3-iodo-N-((4-(thiophen-2-yl)tetrahydro-2H-pyran-4-yl)methyl)-1H-indazole-5-carboxamide | 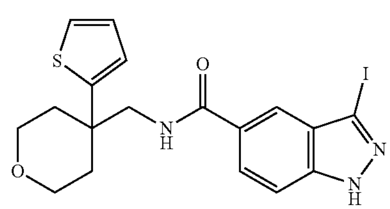 [SMILES: O=C(NCC1(c2cccs2)CCOCC1)c1ccc2[nH]nc(I)c2c1] | $[C_{18}H_{18}IN_3O_2S + H]^+$<br>468.02<br>468.1 | 430 mg (73%);<br>white solid,<br>free base |

SMs: (4-(thiophen-2-yl)tetrahydro-2H-pyran-4-yl)methanamine (250 mg, 1.3 mmol), 3-iodo-1H-indazole-5-carboxylic acid (366 mg, 1.3 mmol)
$^1$H NMR (400 MHz, CDCl$_3$) δ ppm 10.60 (br. s., 1 H), 7.72-7.90 (m, 2 H), 7.49 (d, J= 8.5 Hz, 1 H), 7.36 (d, J = 4.5 Hz, 1 H), 7.11-7.15 (m, 1 H), 6.99 (d, J = 3.5 Hz, 1 H), 6.03 (br. s., 1 H), 3.84-3.96 (m, 2 H), 3.69 (d, J = 6.5 Hz, 2 H), 3.60-3.67 (m, 2 H), 2.07-2.19 (m, 2 H), 1.97-2.07 (m, 2 H)

| IUPAC name | Structure | MS calculated<br>MS ESI [M + H]⁺ | Yield;<br>Appearance;<br>Salt form |
|---|---|---|---|
| N-((1-(cyclopentyloxy)cyclo-hexyl)methyl)-3-iodo-1H-indazole-5-carboxamide | | $[C_{20}H_{26}IN_3O_2 + H]^+$<br>468.11<br>468.1 | 1.4 g (60%);<br>white solid,<br>free base |

SMs: (1-(cyclopentyloxy)cyclohexyl)methanamine (1.0 g, 5.1 mmol) and 3-iodo-1H-indazole-5-carboxylic acid (1.5 g, 5.1 mmol)

$^1$H NMR (400 MHz, CDCl$_3$) δ ppm 10.57 (br. s, 1 H), 7.86-8.00 (m, 2 H), 7.52 (d, J = 8.5 Hz, 1 H), 6.54 (br. s., 1 H), 4.06-4.20 (m, 1 H), 3.57 (d, J = 4.5 Hz, 2 H), 1.87 (d, J = 4.8 Hz, 2 H), 1.67-1.82 (m, 4 H), 1.61 (br. s., 4 H), 1.36-1.57 (m, 8 H)

| IUPAC name | Structure | MS calculated<br>MS ESI [M + H]⁺ | Yield;<br>Appearance;<br>Salt form |
|---|---|---|---|
| N-(2-ethyl-2-phenylbutyl)-3-iodo-1H-indazole-5-carboxamide | 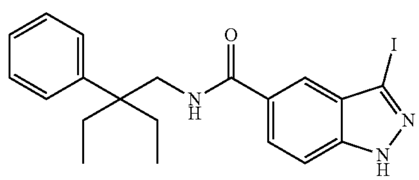 [SMILES: CCC(CC)(CNC(=O)c1ccc2[nH]nc(I)c2c1)c1ccccc1] | $[C_{20}H_{22}IN_3O + H]^+$<br>448.09<br>448.2 | 555 mg (73%);<br>white solid,<br>free base |

SMs: (1-(cyclopentyloxy)cyclohexyl)methanamine (1.0 g, 5.1 mmol) and 3-iodo-1H-indazole-5-carboxylic acid (1.5 g, 5.1 mmol)

$^1$H NMR (400 MHz, CD$_3$OD) δ ppm 7.67-7.79 (m, 2 H), 7.52 (d, J = 8.5 Hz, 1 H), 7.35-7.47 (m, 4 H), 7.24 (t, J = 6.8 Hz, 1 H), 3.74 (s, 2 H), 1.86 (q, J = 7.1 Hz, 4 H), 0.82 (t, J = 7.3 Hz, 6 H)

| IUPAC name | Structure | MS calculated<br>MS ESI [M + H]⁺ | Yield;<br>Appearance;<br>Salt form |
|---|---|---|---|
| 3-iodo-N-((1-phenylcyclo-hexyl)methyl)-1H-indazole-5-carboxamide | | $[C_{21}H_{22}IN_3O + H]^+$<br>460.08<br>460.3 | 13 g (80%);<br>cream solid |

SMs: 1-(1-phenylcyclohexyl)methanamine hydrochloride (1.0 g, 3.5 mmol), 3-iodo-1H-indazol-5-carboxylic acid (1.02 g, 3.5 mmol), DIPEA (2.96 mL, 17 mmol), TBTU (1.12 g, 3.5 mmol), anh DMF (15 mL)

$^1$H NMR (400 MHz, CDCl$_3$) δ ppm 10.70 (br. s, 1 H), 7.75-7.78 (m, 1 H), 7.68 (s, 1 H), 7.45-7.52 (m, 5 H), 7.30-7.34 (m, 1 H), 5.72-5.74 (br. s, 1 H), 3.60 (t, J = 6.0 Hz, 2 H), 2.17-2.20 (m, 2 H), 1.74-1.79 (m, 2 H), 1.61-1.67 (m, 3 H), 1.40-1.51 (m, 3 H)

| IUPAC name | Structure | MS calculated<br>MS ESI [M + H]⁺ | Yield;<br>Appearance;<br>Salt form |
|---|---|---|---|
| 3-iodo-N-((1-phenylcyclopropyl)methyl)-1H-indazole-5-carboxamide | 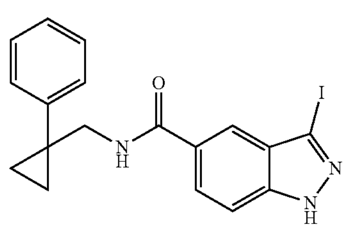 [SMILES: O=C(NCC1(c2ccccc2)CC1)c1ccc2[nH]nc(I)c2c1] | $[C_{18}H_{16}IN_3O + H]^+$<br>418.04<br>418.2 | 160 mg (70%);<br>cream solid |

SMs: (1-phenylcyclopropyl)methylamine hydrochloride (100 mg, 0.54 mmol), 3-iodo-1H-indazol-5-carboxylic acid (157 g, 0.54 mmol), DIPEA (0.47 mL, 2.72 mmol), TBTU (175 mg, 0.54 mmol), anh DMF (4 mL)

$^1$H NMR (400 MHz, CDCl$_3$) δ ppm 12.53 (brs, 1 H), 7.67-7.80 (m, 2 H), 7.30-7.47 (m, 5 H), 7.19-7.29 (m, 1 H), 6.52 (t, J = 5.5 Hz, 1 H), 3.70 (d, J = 5.5 Hz, 2 H), 0.98-1.07 (m, 2 H), 0.88-0.98 (m, 2 H)

| IUPAC name | Structure | MS calculated MS ESI [M + H]+ | Yield; Appearance; Salt form |
|---|---|---|---|
| 3-iodo-N-((1-(thiophen-3-yl)cyclohexyl)methyl)-1H-indazole-5-carboxamide | 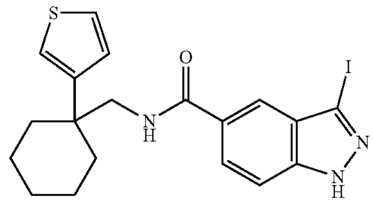 [SMILES: O=C(NCC1(c2ccsc2)CCCCC1)c1ccc2[nH]nc(I)c2c1] | [C$_{19}$H$_{20}$IN$_3$OS + H]+ 466.04 466.2 | 280 mg (94%); cream solid |

SMs: (1-(thiophen-3-yl)cyclohexyl) methanamine (125 mg, 0.64 mmol), 3-iodo-1H-indazol-5-carboxylic acid (184 mg, 0.64 mmol), DIPEA (0.56 mL, 3.19 mmol), TBTU (205 mg, 0.64 mmol), DMF (4 mL)
$^1$H NMR (400 MHz, CDCl$_3$) δ ppm 10.52-10.72 (m, 1 H), 7.79 (d, J = 8.8 Hz, 1 H), 7.72 (s, 1 H), 7.43 -7.51 (m, 2 H), 713-7.20 (m, 2 H), 5.82 (br. s, 1 H), 3.60 (d, J = 6.0 Hz, 2 H), 2.04-2.13 (m, 2 H), 1.60-1.81 (m, 4 H), 1.46 (d, J = 5.3 Hz, 4 H)

| 3-iodo-N-((4-phenyltetrahydro-2H-pyran-4-yl)methyl)-1H-indazole-5-carboxamide | | [C$_{20}$H$_{20}$IN$_3$O$_2$ + H]+ 462.06 462.2 | 520 mg (72%); cream solid |
|---|---|---|---|

SMs: 1-(4-phenyltetrahydro-2H-pyran-4-yl)methanamine (300 mg, 1.56 mmol), 3-iodo-1H-indazol-5-carboxylic acid (452 mg, 1.56 mmol), DIPEA (0.82 mL, 4.70 mmol), TBTU (504 mg, 1.56 mmol), DMF (6 mL)
$^1$H NMR (400 MHz, CDCl$_3$) δ ppm 10.95-11.11 (m, 1 H), 7.75 (dd, J = 8.8, 1.5 Hz, 1 H), 7.65 (dd, J = 1.5, 0.8 Hz, 1 H), 7.50-7.56 (m, 2 H), 7.42-7.49 (m, 3 H), 7.34-7.40 (m, 1 H), 5.78 (s, 1 H) 3.88-3.96 (m, 2 H), 3.75 (d, J = 6.3 Hz, 2 H), 3.68 (ddd, J = 11.5, 8.0, 3.0 Hz, 2 H), 2.17-2.25 (m, 2 H), 1.98-2.05 (m, 2 H)

| 3-iodo-N-((1-(pyridin-2-yl)cyclohexyl)methyl)1H-indazole-5-carboxamide | | [C$_{20}$H$_{21}$IN$_4$O + H]+ 461.08 461.1 | 229 mg (72%); cream solid free base |
|---|---|---|---|

SMs: (1-(pyridin-2-yl)cyclohexyl)methanamine, TsOH salt (250 mg, 0.69 mmol), 3-iodo-1H-indazol-5-carboxylic acid (199 mg, 0.69 mmol), DIPEA (0.48 mL, 2.76 mmol), TBTU (222 mg, 0.69 mmol), DMF (4 mL)
$^1$H NMR (400 MHz, CDCl$_3$) δ ppm 10.68 (br. s, 1 H), 8.79 (d, J = 4.0 Hz, 1 H), 7.87-7.99 (m, 2 H), 7.68-7.86 (m, 2 H), 7.49 (dd, J = 12.2, 8.2 Hz, 2 H), 7.22-7.24 (m, 1 H), 3.70 (d, J = 4.8 Hz, 2 H), 2.23 (br. s, 2 H), 1.66-1.85 (m, 4 H), 1.31-1.64 (m, 4 H)

| N-(((2R,6S)-2,6-dimethyl-4-morpholino tetrahydro-2H-pyran-4-yl) methyl)-3-iodo-1H-indazole-5-carboxamide | | [C$_{20}$H$_{27}$IN$_4$O$_3$ + H]+ 499.1 499.2 | 150 mg (37%); white solid TFA salt |
|---|---|---|---|

SMs: ((2R,6S)-2,6-dimethyl-4-morpholinotetrahydro-2H-pyran-4-yl)methanamine trifluoroacetate salt (150 mg, 0.65 mmol), 3-iodo-1H-indazol-5-carboxylic acid (189 mg, 0.65 mmol), DIPEA (0.46 mL, 2.63 mmol), TBTU (211 mg, 0.65 mmol), DMF (3 mL)
$^1$H NMR (400 MHz, CD$_3$OD) δ ppm 8.16 (d, J = 0.8 Hz, 1 H), 8.02 (dd, J = 8.8, 1.5 Hz, 1 H), 7.63 (d, J = 8.8 Hz, 1 H), 4.15 (d, J = 11.0 Hz, 2 H), 4.03 (s, 2 H), 3.88 (dd, J = 10.0, 5.3 Hz, 4 H), 3.67 (d, J = 9.5 Hz, 2 H), 3.43 (br. s, 2 H), 2.03 (d, J = 12.8 Hz, 2 H), 1.59 (t, J =11.9 Hz, 2 H), 1.28 (d, J = 6.0 Hz, 6 H)

| IUPAC name | Structure | MS calculated MS ESI [M + H]+ | Yield; Appearance; Salt form |
|---|---|---|---|
| N-((4-(2-fluorophenyl)tetrahydro-2H-pyran-4-yl)methyl)-3-iodo-1H-indazol-5-carboxamide | 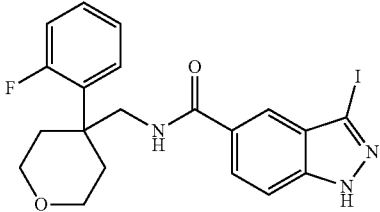 [SMILES: O=C(NCC1(c2ccccc2F)CCOCC1)c1ccc2[nH]nc(I)c2c1] | [C$_{20}$H$_{19}$FIN$_3$O$_2$ + H]$^+$ 480.05 480.1 | 1.02 g (89%); cream solid |

SMs: (4-(2-fluorophenyl)tetrahydro-2H-pyran-4-yl)methanamine (500 mg, 2.38 mmol), 3-iodo-1H-indazol-5-carboxylic acid (688 mg, 2.38 mmol), DIPEA (1.66 mL, 9.55 mmol), TBTU (767 mg, 2.38 mmol), DMF (6 mL)
$^1$H NMR (400 MHz, CDCl$_3$) δ ppm 7.72 (dd, J = 8.7, 1.4 Hz, 1 H), 7.59 (s, 1 H), 7.46 (d, J = 8.8 Hz, 1 H), 7.33-7.41 (m, 2H), 7.27-7.32 (m, 1 H), 7.17 (dd, J = 13.2, 8.2 Hz, 1 H), 5.83 (t, J = 6.4 Hz, 1 H), 3.89-4.01 (m, 4 H), 3.65-3.76 (m, 2 H), 2.31 (dd, J = 13.7, 3.9 Hz, 2 H), 2.03-2.14 (m, 2 H)

| | | | |
|---|---|---|---|
| 3-iodo-N-((4-(pyridin-4-yl)tetrahydro-2H-pyran-4-yl)methyl)-1H-indazol-5-carboxamide | 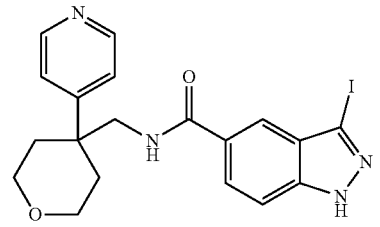 [SMILES: O=C(NCC1(c2ccncc2)CCOCC1)c1ccc2[nH]nc(I)c2c1] | [C$_{19}$H$_{19}$IN$_4$O$_2$ + H]$^+$ 463.06 463.1 | 520 mg (72%); cream solid free base |

SMs: (4-(pyridin-4-yl)tetrahydro-2H-pyran-4-yl)methanamine (380 mg, 1.97 mmol), 3-iodo-1H-indazol-5-carboxylic acid (569 mg, 1.97 mmol), DIPEA (1.38 mL, 7.9 mmol), TBTU (635 mg, 1.97 mmol), DMF(11.4 mL)
$^1$H NMR (400 MHz, DMSO-d$_6$) δ ppm 13.62-13.70 (m, 1 H), 8.52 (d, J = 6.0 Hz, 2 H), 7.85 (s, 1 H), 7.75-7.80 (m, 1 H), 7.52-7.60 (m, 2 H), 7.40 (d, J = 6.0 Hz, 2 H), 3.73-3.83 (m, 2 H), 2.03-2.14 (m, 3 H), 1.86-1.97 (m, 2 H), 2H merged with solvent peak

| | | | |
|---|---|---|---|
| 3-iodo-N-((1-morpholinocyclobutyl)methyl)-1H-indazol-5-carboxamide | 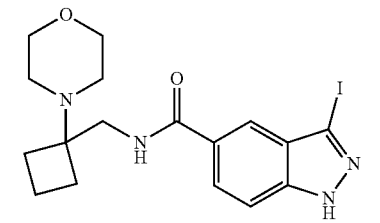 [SMILES: O=C(NCC1(N2CCOCC2)CCC1)c1ccc2[nH]nc(I)c2c1] | [C$_{17}$H$_{21}$IN$_4$O$_2$ + H]$^+$ 441.07 441.1 | 520 mg (73%); cream solid free base |

SMs: (1-morpholinocyclobutyl)methanamine (275 mg, 1.62 mmol), 3-iodo-1H-indazol-5-carboxylic acid (465 mg, 1.62 mmol), DIPEA (1.13 mL, 6.46 mmol), TBTU (520 mg, 1.62 mmol), DMF (4.4 mL)
$^1$H NMR (400 MHz, DMSO-d$_6$) δ ppm 13.73 (s, 1 H), 8.43-8.50 (m, 1 H), 8.00 (s, 1 H), 7.88-7.96 (m, 1 H), 7.56-7.64 (m, 1 H), 3.54 (d, J = 5.3 Hz, 6 H), 2.52-2.57 (m, 4 H), 1.86-2.01 (m, 4H), 1.63-1.75 (m, 2 H)

| | | | |
|---|---|---|---|
| 3-iodo-N-((1-(pyridin-4-yl)cyclohexyl)methyl)-1H-indazol-5-carboxamide | 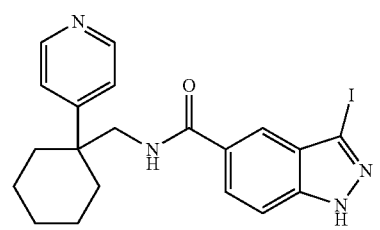 [SMILES: O=C(NCC1(c2ccncc2)CCCCC1)c1ccc2[nH]nc(I)c2c1] | [C$_{20}$H$_{21}$IN$_4$O + H]$^+$ 461.08 461.1 | 275 mg (76%); cream solid free base |

SMs: (1-(pyridin-4-yl)cyclohexyl)methanamine (175 mg, 0.92 mmol), 3-iodo-1H-indazol-5-carboxylic acid (225 mg, 0.92 mmol), DIPEA (0.55 mL, 3.67 mmol), TBTU (251 mg, 0.92 mmol), DMF (5 mL)
$^1$H NMR (400 MHz, DMSO-d$_6$) δ ppm 13.66 (m, 1 H), 8.47-8.54 (m, 2 H), 8.24-8.33 (m, 1 H), 7.82-7.87 (m, 1 H), 7.73-7.80 (m, 1 H), 7.52-7.59 (m, 1 H), 7.34-7.42 (m, 2 H), 2.13-2.24 (m, 2 H), 1.52-1.69 (m, 4 H), 1.40-1.51 (m, 1 H), 1.09-1.36 (m, 3 H)

| IUPAC name | Structure | MS calculated<br>MS ESI [M + H]+ | Yield;<br>Appearance;<br>Salt form |
|---|---|---|---|
| 3-iodo-N-((1-(pyridin-3-yl)cyclohexyl)methyl)-1H-indazole-5-carboxamide | 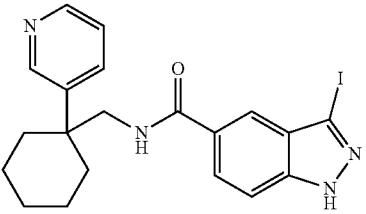 [SMILES: O=C(NCC1(c2cccnc2)CCCCC1)c1ccc2[nH]nc(I)c2c1] | [C$_{20}$H$_{21}$IN$_4$O + H]+<br>461.08<br>461.1 | 280 mg (77%);<br>cream solid<br>free base |

SMs: (1-(pyridin-3-yl)cyclohexyl)methanamine (150 mg, 0.78 mmol), 3-iodo-1H-indazol-5-carboxylic acid (192 mg, 0.78 mmol), DIPEA (0.47 mL, 3.15 mmol), TBTU (215 mg, 0.78 mmol), DMF (4.5 mL)
$^1$H NMR (400 MHz, DMSO-d$_6$) δ ppm 8.60 (br. s, 1 H), 8.25-8.45 (m, 2 H), 7.70-7.92 (m, 3 H), 7.54 (d, J = 8.8 Hz, 1 H), 7.32 (br. s, 1 H), 5.75 (brs, 1 H), 2.22 (brs, 2 H), 1.41-1.76 (m, 5 H), 1.19 (brs, 3 H)

| IUPAC name | Structure | MS calculated<br>MS ESI [M + H]+ | Yield;<br>Appearance;<br>Salt form |
|---|---|---|---|
| 3-iodo-N-((1-(pyridin-2-yl)cyclopropyl)methyl)-1H-indazole-5-carboxamide | 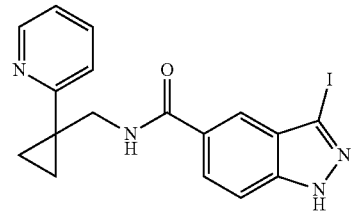 [SMILES: O=C(NCC1(c2ccccn2)CC1)c1ccc2[nH]nc(I)c2c1] | [C$_{17}$H$_{15}$IN$_4$O + H]+<br>419.03<br>419 | 601 mg (71%);<br>white solid;<br>free base |

SMs: (1-(pyridin-2-yl)cyclopropyl)methanamine (300 mg, 2.02 mmol), 3-iodo-1H-indazol-5-carboxylic acid (580 mg, 2.02 mmol), DIPEA (1.41 mL, 8.08 mmol), TBTU (648 mg, 2.02 mmol), DMF (6 mL)
$^1$H NMR (400 MHz, DMSO-d$_6$) δ ppm 13.68 (brs, 1 H), 8.62 (s, 1 H), 8.46 (d, J = 3.8 Hz, 1 H), 7.97 (s, 1 H), 7.91 (dd, J = 8.8, 1.5 Hz, 1 H), 7.67 (d, J = 1.5 Hz, 1 H), 7.57 (d, J = 8.8 Hz, 1 H), 7.48 (d, J = 8.0 Hz, 1 H), 7.09-7.19 (m, 1 H), 3.82 (d, J = 5.5 Hz, 2 H), 1.12-1.18 (m, 2 H), 1.09 (d, J = 5.3 Hz, 1 H)

| IUPAC name | Structure | MS calculated<br>MS ESI [M + H]+ | Yield;<br>Appearance;<br>Salt form |
|---|---|---|---|
| 3-iodo-N-((3-phenyloxetan-3-yl)methyl)-1H-indazole-5-carboxamide | 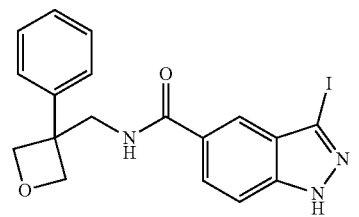 [SMILES: O=C(NCC1(c2ccccc2)COC1)c1ccc2[nH]nc(I)c2c1] | [C$_{18}$H$_{16}$IN$_3$O$_2$ + H]+<br>434.03<br>434.1 | 550 mg (83%);<br>white solid |

SMs: (3-phenyloxetan-3-yl)methanamine (250 mg, 1.53 mmol), 3-iodo-1H-indazol-5-carboxylic acid (441 mg, 1.53 mmol), DIPEA (1.07 mL, 6.12 mmol), TBTU (491 mg, 1.53 mmol), DMF (4 mL)
$^1$H NMR (400 MHz, DMSO-d$_6$) δ ppm 13.70 (br. s, 1 H), 8.77 (br. s, 1 H), 7.93 (s, 1 H), 7.85 (d, J = 8.5 Hz, 1 H), 7.58 (d, J = 8.5 Hz, 1 H), 7.36 (d, J = 7.0 Hz, 2 H), 7.26 (d, J = 6.0 Hz, 1 H), 7.19 (d, J = 7.5 Hz, 2 H), 4.90 (d, J = 6.0 Hz, 2 H), 4.80 (d, J = 5.5 Hz, 2 H), 3 75 (d, J = 5.0 Hz, 2 H)

| IUPAC name | Structure | MS calculated<br>MS ESI [M + H]+ | Yield;<br>Appearance;<br>Salt form |
|---|---|---|---|
| N-(3-iodo-1H-indazol-5-yl)-2-(1-morpholinocyclohexyl)acetamide | 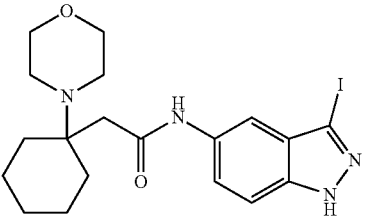 [SMILES: O=C(CC1(N2CCOCC2)CCCCC1)Nc1ccc2[nH]nc(I)c2c1] | [C$_{19}$H$_{25}$IN$_4$O$_2$ + H]+<br>469.1<br>469.2 | 130 mg (9%);<br>brown solid<br>TFA salt |

SMs: 2-(1-morpholinocyclohexyl)acetic acid hydrochloride (600 mg, 2.27 mmol), 3-iodo-1H-indazol-5-carboxylic acid (590 mg, 2.27 mmol), DIPEA (1.58 mL, 9.08 mmol), TBTU (728 mg, 2.27 mmol), DMF (10 mL)
$^1$H NMR (400 MHz, CD$_3$OD) δ 10.63 (br. s, 1 H), 7.97 (d, J = 3.0 Hz, 1 H), 7.45-7.58 (m, 2 H), 4.20 (d, J = 11.8 Hz, 2 H), 3.89 (t, J = 12.0 Hz, 2 H), 3.67 (d, J = 12.3 Hz, 2 H), 3.22 (s, 2 H), 1.74-2.00 (m, 9H), 1.50-1.70 (m, 2 H), 1.25-1.36 (m, 1 H)

| IUPAC name | Structure | MS calculated MS ESI [M + H]+ | Yield; Appearance; Salt form |
|---|---|---|---|
| 3-iodo-N-((4-morpholinotetrahydro-2H-pyran-4-yl)methyl)-1H-indazole-5-carboxamide | 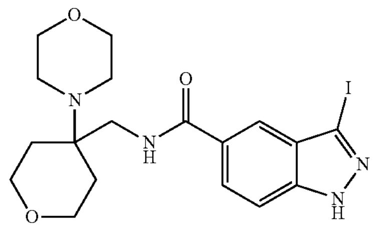 [SMILES: O=C(NCC1(N2CCOCC2)CCOCC1)c1ccc2[nH]nc(I)c2c1] | [$C_{18}H_{23}IN_4O_3$ + H]+<br>471.08<br>471.1 | 950 mg (88%);<br>cream solid;<br>free base |

SMs: (4-morpholinotetrahydro-2H-pyran-4-yl)methanamine (430 mg, 2.14 mmol), 3-iodo-1H-indazol-5-carboxylic acid (619 mg, 2.14 mmol), DIPEA (1.50 mL, 8.58 mmol), TBTU (690 mg, 2.14 mmol), DMF (6.5 mL)
$^1$H NMR (400 MHz, CDCl$_3$) δ ppm 11.17 (br. s, 1 H), 7.94 (dd, J = 4.5, 2.8 Hz, 2 H), 7.56 (d, J = 9.3 Hz, 1 H), 7.10-7.20 (m, 1 H), 3.92 (d, J = 11.8 Hz, 2 H), 3.78-3.86 (m, 4 H), 3.74 (s, 2 H), 3.64-3.72 (m, 2 H), 2.69-2.77 (m, 4 H), 1.95 (br. s, 2 H), 1.49 (d, J = 13.6 Hz, 2 H)

| 3-iodo-N-((1-methyl-4-phenylpiperidin-4-yl)methyl)-1H-indazole-5-carboxamide | | [$C_{21}H_{23}IN_4O$ + H]+<br>475.1<br>475.1 | 220 mg (76%);<br>cream solid;<br>free base |

SMs: (1-methyl-4-phenylpiperidin-4-yl)methanamine (125 mg, 0.61 mmol), 3-iodo-1H-indazol-5-carboxylic acid (177 mg, 0.60 mmol), DIPEA (400 mmL, 3.05 mmol), TBTU (196 mg, 0.61 mmol), DMF (3 mL)
$^1$H NMR (400 MHz, CDCl$_3$) δ ppm 7.67-7.69 (m, 1 H), 7.58 (s, 1 H), 7.45-7.51 (m, 4 H), 7.32-7.40 (m, 2 H), 5.82 (br. s, 1 H), 3.64 (d, J = 6.0 Hz, 2 H), 2.72 (br. s, 2 H), 2.49 (br. s, 2 H), 2.25 (br. m, 5 H), 2.25 (br. m, 2 H)

| 3-iodo-N-((1-(piperidin-1-yl)cyclohexyl)methyl)-1H-indazole-5-carboxamide | | [$C_{20}H_{27}IN_4O$ + H]+<br>467.12<br>467.2 | 0.14 g (93%);<br>colorless gum;<br>TFA salt |

SMs: 3-iodo-1H-indazole-5-carboxylic acid (0.075 g, 0.26 mmol) and (1-(piperidin-1-yl)cyclohexyl)methanamine (0.051 g, 0.26 mmol)
$^1$H NMR (400 MHz, CD$_3$OD) δ ppm 8.16 (d, J = 0.75 Hz, 1 H), 8.02 (dd, J = 8.9, 1.6 Hz, 1 H), 7.63 (d, J = 8.8 Hz, 1 H), 3.88-3.96 (m, 2 H), 3.79 (d, J = 11.5 Hz, 2 H), 3.07 (t, J = 11.3 Hz, 2 H), 1.45-2.11 (m, 14 H), 1.19-1.42 (m, 2 H)

| 3-iodo-N-((1-morpholinocyclohexyl)methyl)-1H-indazole-5-carboxamide | | [$C_{19}H_{25}IN_4O_2$ + H]+<br>469.10<br>469.2 | 148 mg (81%);<br>Colorless solid;<br>TFA salt |

SMs: 3-iodo-1H-indazole-5-carboxylic acid (0.090 g, 0.31 mmol) and (1-morpholinocyclohexyl)methanamine (62 mg, 0.31 mmol)
free base: $^1$H NMR (400 MHz, CD$_3$OD) δ ppm 8.01 (s, 1 H), 7.92 (d, J = 8.8 Hz, 1 H), 7.61 (d, J = 8.8 Hz, 1 H), 3.72 (br. s, 4 H), 3.52 (s, 2 H), 2.78 (br. s, 4 H), 1.45 (br. s, 10 H)

| IUPAC name | Structure | MS calculated<br>MS ESI [M + H]⁺ | Yield;<br>Appearance;<br>Salt form |
|---|---|---|---|
| 3-iodo-N-((1-(4-methylpiperazin-1-yl)cyclohexyl)methyl)-1H-indazole-5-carboxamide | 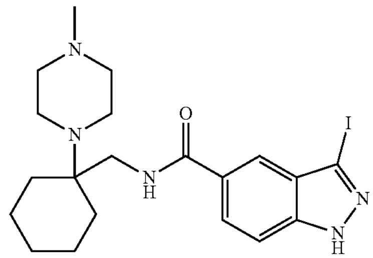 [SMILES: CN1CCN(C2(CNC(=O)c3ccc4[nH]nc(I)c4c3)CCCCC2)CC1] | [C$_{20}$H$_{28}$IN$_5$O + H]⁺<br>481.13<br>482.1 | 0.10 g (54%);<br>clear gum;<br>TFA |

SMs: 3-iodo-1H-indazole-5-carboxylic acid (0.090 g, 0.31 mmol) and (1-(4-methylpiperazin-1-yl)cyclohexyl)methanamine (66 mg, 0.31 mmol)

$^1$H NMR (400 MHz, CD$_3$OD) δ ppm 8.13 (s, 1 H), 8.00 (dd, J = 8.8, 1.51 Hz, 1 H), 7.62 (d, J = 9.0 Hz, 1 H), 3.73 (br. s., 2 H), 3.22-3.82 (br. s., 8H), 2.95 (s, 3 H), 1.21-1.98 (m, 10 H)

| IUPAC name | Structure | MS calculated<br>MS ESI [M + H]⁺ | Yield;<br>Appearance;<br>Salt form |
|---|---|---|---|
| N-((1-(dimethylamino)cyclohexyl)methyl)-3-iodo-1H-indazole-5-carboxamide | 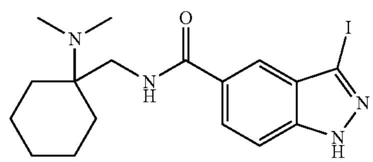 [SMILES: CN(C)C1(CNC(=O)c2ccc3[nH]nc(I)c3c2)CCCCC1] | [C$_{17}$H$_{23}$IN$_4$O + H]⁺<br>427.09<br>427.1 | 0.17 g (quant);<br>Clear gum<br>TFA salt |

SMs: 3-iodo-1H-indazole-5-carboxylic acid (0.090 g. 0.31 mmol) and 1-(aminomethyl)-N,N-dimethylcyclohexanamine (64 mg, 0.41 mmol)

$^1$H NMR (400 MHz, CD$_3$OD) δ ppm 8.16 (br.s., 1 H), 8.01 (dd, J = 8.9, 1.6 Hz, 1 H), 7.61 (dd, J = 8.9, 0.6 Hz, 1 H), 3.94 (s, 2 H), 2.98 (s, 6 H), 1.97-2.05 (m, 2 H), 1.58-1.91 (m, 7 H), 1.32-1.41 (m, 1 H)

| IUPAC name | Structure | MS calculated<br>MS ESI [M + H]⁺ | Yield;<br>Appearance;<br>Salt form |
|---|---|---|---|
| N-((1-((2S,6R)-2,6-dimethylmorpholino)cyclohexyl)methyl)-3-iodo-1H-indazole-5-carboxamide | 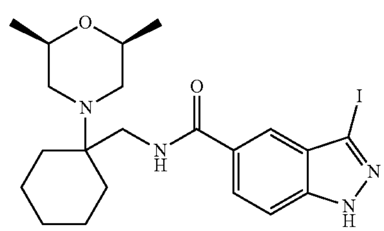 [SMILES: C[C@@H]1CN(C2(CNC(=O)c3ccc4[nH]nc(I)c4c3)CCCCC2)C[C@H](C)O1] | [C$_{21}$H$_{29}$IN$_4$O$_2$ + H]⁺<br>497.13<br>497.2 | 0.42 g (98%);<br>Clear gum;<br>TFA salt |

SMs: 3-iodo-1H-indazole-5-carboxylic acid (0.20 g, 0.70 mmol) and (1-((2S,6R)-2,6-dimethylmorpholino)cyclohexyl)methanamine (0.16 mg, 0.70 mmol)

$^1$H NMR (400 MHz, CD$_3$OD) δ ppm 8.16 (br. s, 1 H), 8.02 (dd, J = 8.8, 1.51 Hz, 1 H), 7.63 (dd, J = 8.8, 0.5 Hz, 1 H), 3.96-4.04 (m, 2 H), 3.94 (s, 2 H), 3.68 (d, J = 11.8 Hz, 2 H), 2.78-2.92 (m, 2 H), 1.57-2.04 (m, 9 H), 1.23-1.33 (m, 7 H)

| IUPAC name | Structure | MS calculated<br>MS ESI [M + H]⁺ | Yield;<br>Appearance;<br>Salt form |
|---|---|---|---|
| N-((1-(4-fluoropiperidin-1-yl)cyclohexyl)methyl)-3-iodo-1H-indazole-5-carboxamide | 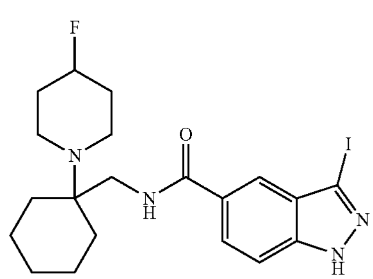 [SMILES: O=C(NCC1(N2CCC(F)CC2)CCCCC1)c1ccc2[nH]nc(I)c2c1] | [C$_{20}$H$_{26}$FIN$_4$O + H]⁺<br>485.11<br>485.1 | 86 mg (51%);<br>white solid;<br>TFA salt |

SMs: 3-iodo-1H-indazole-5-carboxylic acid (0.081 g, 0.28 mmol) and (1-(4-fluoropiperidin-1-yl)cyclohexyl)methanamine (60 mg, 0.28 mmol)

| IUPAC name | Structure | MS calculated<br>MS ESI [M + H]+ | Yield;<br>Appearance;<br>Salt form |
|---|---|---|---|
| N-((1-(4,4-difluoropiperidin-1-yl)cyclohexyl)methyl)-3-iodo-1H-indazole-5-carboxamide | 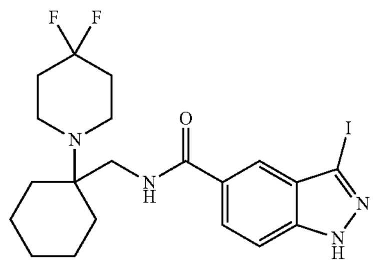 [SMILES: O=C(NCC1(N2CCC(F)(F)CC2)CCCCC1)c1ccc2[nH]nc(I)c2c1] | [C20H25F2IN4O + H]+<br>503.10<br>503.1 | 0.19 g (quant);<br>White foam;<br>TFA salt |

SMs: 3-iodo-1H-indazole-5-carboxylic acid (89 mg, 0.31 mmol), (1-(4,4-difluoropiperidin-1-yl)cyclohexyl)methanamine (0.11 g, 0.31 mmol)
$^1$H NMR (400 MHz, CD$_3$OD) δ ppm 8.18 (s, 1 H), 8.03 (d, J = 8.8 Hz, 1 H), 7.63 (d, J = 8.8 Hz, 1 H), 3.98 (s, 2 H), 2.30-2.53 (m, 4 H), 2.01-2.18 (m, 2 H), 1.58-1.95 (m., 10 H), 1.26-1.39 (m, 2 H)

| N-((4,4-difluoro-1-morpholinocyclohexyl)methyl)-3-iodo-1H-indazole-5-carboxamide | | [C19H23F2IN4O2 + H]+<br>505.08<br>505.1 | 0.33 g (quant);<br>beige solid;<br>free base |

SMs: 3-iodo-1H-indazole-5-carboxylic acid (184 mg, 0.641 mmol), (4,4-difluoro-1-morpholinocyclohexyl)methanamine (150, 0.64 mmol)
$^1$H NMR (400 MHz, CDCl$_3$) δ ppm 7.86-7.97 (m, 2 H), 7.55 (d, J = 9.0 Hz, 1 H), 3.78 (br. s., 4 H), 3.64 (d, J = 5.8 Hz, 2 H), 2.68-2.79 (m, 4 H), 1.85-2.20 (m, 6 H), 1.46-1.74 (m, 2 H)

| 3-iodo-N-((1-(pyridin-3-yl)cyclopropyl)methyl)-1H-indazole-5-carboxamide | | [C17H15IN4O + H]+<br>419.03<br>419.1 | 0.28 g (77%);<br>free base |

Starting Materials: 3-iodo-1H-indazole-5-carboxylic acid (248 mg, 0.86 mmol), (1-(pyridin-3-yl)cyclopropyl)methanamine (127 mg, 0.86 mmol)
$^1$H NMR (400 MHz, CD$_3$OD) δ ppm 8.57 (d, J = 1.5 Hz, 1 H), 8.37 (dd, J = 5.0, 1.5 Hz, 1 H), 7.92 (d, J = 0.8 Hz, 1 H), 7.87 (dt, J = 7.9, 1.8 Hz, 1 H), 7.81 (dd, J = 8.8, 1.5 Hz, 1 H), 7.54 (d, J = 8.8 Hz, 1 H), 7.37 (dd, J= 7.9, 4.9 Hz, 1 H), 3.66 (s, 2 H), 1.07-1.15 (m, 2 H), 0.88-0.97 (m, 2 H)

| N-(3-iodo-1H-indazol-5-yl)-2-(3-phenyloxetan-3-yl)acetamide | | [C18H16IN3O2 + H]+<br>434.03<br>434.1 | 81 mg (50%)<br>light tan solid;<br>free base |

Starting Materials: 2-(3-phenyloxetan-3-yl)acetic acid (0.19 g, 1.0 mmol) and 3-iodo-1H-indazol-5-amine*TFA (0.37 g, 1.0 mmol)

| IUPAC name | Structure | MS calculated MS ESI [M + H]⁺ | Yield; Appearance; Salt form |
|---|---|---|---|
| N-(2-ethyl-2-morpholinobutyl)-3-iodo-1H-indazole-5-carboxamide | 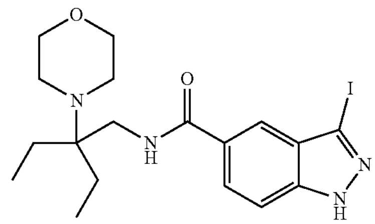 [SMILES: CCC(CC)(CNC(=O)c1ccc2[nH]nc(I)c2c1)N1CCOCC1] | [C$_{18}$H$_{25}$IN$_4$O$_2$ + H]⁺ 457.10 457.2 | 0.5 g (quant); pale yellow gum; free base |

Starting Materials: 3-iodo-1H-indazole-5-carboxylic acid (0.31 g, 1.06 mmol), 2-ethyl-2-morpholinobutan-1-amine (0.20 g, 1.06 mmol)
¹H NMR (400 MHz, CD$_3$OD) δ ppm7.93-8.02 (m, 2 H), 7.89 (dd, J = 8.8, 1.5 Hz, 1 H), 7.62 (d, J = 8.8 Hz, 1 H), 3.67-3.80 (m, 4 H), 3.44 (s, 2 H), 2.74-2.84 (m, 11 H),, 1.67 (dt, J = 14.6, 7.3 Hz, 3 H), 1.48-1.62 (m, 3H), 0.96 (m, 8 H)

| | | | |
|---|---|---|---|
| 3-iodo-N-((1-(pyridin-4-yl)cyclopropyl)methyl)-1H-indazole-5-carboxamide | | [C$_{17}$H$_{15}$IN$_4$O + H]⁺ 419.03 419.0 | 0.20 g (56%); while solid; free base |

Starting Materials: 3-iodo-1H-indazole-5-carboxylic acid (0.25 g, 0.85 mmol), (1-(pyridin-4-yl)cyclopropyl)methanamine hydrochloride (0.19 mmol, 0.86 mmol)
NMR (400 MHz, CD$_3$OD/CDCl$_3$) δ ppm 8.44-8.53 (m, 1 H), 8.42 (d, J = 5.5 Hz, 2 H), 7.92-7.98 (m, 1 H), 7.77-7.87 (m, 1 H), 7.49-7.55 (m, 1 H), 7.41 (d, J = 6.3 Hz, 2 H), 3.76 (m, 2 H), 1.18-1.25 (m, 2 H), 0.99-1.10 (s, 2 H)

| | | | |
|---|---|---|---|
| 3-iodo-N-((1-(4-methylpiperazin-1-yl)cyclopentyl)methyl)-1H-indazole-5-carboxamide | | [C$_{19}$H$_{26}$IN$_5$O + H]⁺ 468.12 468.3 | 0.6 g (quant); off white solid; TFA salt |

Starting Materials: 3-iodo-1H-indazole-5-carboxylic acid (0.30 g, 1.0 mmol), (1-(4-methylpiperazin-1-yl)cyclopentyl)methanamine (0.20 g, 1.0 mmol)
¹H NMR (400 MHz, CD$_3$OD) δ ppm 8.12 (dd, J = 1.8, 0.8 Hz, 1 H), 8.00 (dd, J = 8.9, 1.6 Hz, 1 H), 7.59 (dd, J = 8.8, 0.8 Hz, 1 H), 3.71-3.84 (m, 6 H), 3.63 (br. s., 4 H), 2.98 (s, 3 H), 1.98-2.10 (m, 4 H), 1.79-1.96 (m, 4 H)

| | | | |
|---|---|---|---|
| 3-iodo-N-((1-(morpholinomethyl)cyclohexyl)methyl)-1H-indazole-5-carboxamide | | [C$_{20}$H$_{27}$IN$_4$O$_2$ + H]⁺ 483.1 483.3 | 718 mg (63%); yellow solid; free base |

SMs: 3-iodo-1H-indazole-5-carboxylic acid (678 mg, 2.4 mmol), (1-(morpholinomethyl)cyclohexyl)methanamine (500 mg, 2.4 mmol)
¹H NMR (400 MHz, DMSO-d$_6$) δ ppm 13.71 (s, 1 H) 8.52-8.58 (m, 1 H) 7.86-7.92 (m, 2 H) 7.61 (d, J = 8.5 Hz, 1 H), 3.55-3.60 (m, 4 H), 3.36 (d, J = 5.5 Hz, 2 H), 2.49 (dt, J = 3.5, 1.8 Hz, 4 H), 2.31 (s, 2 H), 1.27-1.51 (m, 10 H)

| IUPAC name | Structure | MS calculated<br>MS ESI [M + H]⁺ | Yield;<br>Appearance;<br>Salt form |
|---|---|---|---|
| 3-iodo-N-((3-morpholinotetrahydro-2H-pyran-3-yl)methyl)-1H-indazole-5-carboxamide | 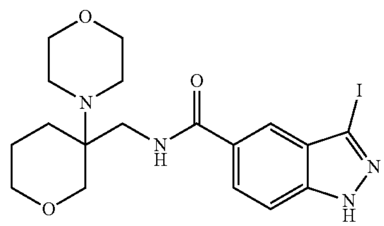 [SMILES: O=C(NCC1(N2CCOCC2)CCCOC1)c1ccc2[nH]nc(I)c2c1] | $[C_{18}H_{23}IN_4O_3 + H]^+$<br>471.1<br>471.1 | 824 mg (63%),<br>white solid;<br>free base |

SMs: (3-morpholinotetrahydro-2H-pyran-3-yl)methanamine (600 mg, 3 mmol), 3-iodo-1H-indazole-5-carboxylic acid (864 mg, 3 mmol)

¹H NMR (400 MHz, DMSO-$d_6$) δ ppm 13.70 (s, 1H), 8.19 (t, J = 6.0 Hz, 1H), 7.96 (s, 1H), 7.90 (d, J = 8.8 Hz, 1H), 7.61 (d, J = 8.8 Hz, 1H), 3.70-3.35 (m, 14H, partially buried in MeOH), 2.75-2.65 (m, 4H), 1.75-1.53 (m, 4H).

| IUPAC name | Structure | MS calculated<br>MS ESI [M + H]⁺ | Yield;<br>Appearance;<br>Salt form |
|---|---|---|---|
| 3-iodo-N-((1-(morpholinomethyl)cyclopropyl)methyl)-1H-indazole-5-carboxamide | 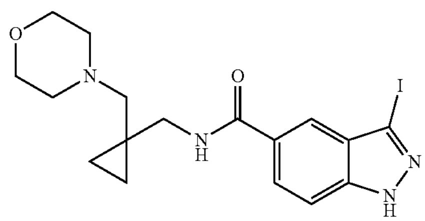 [SMILES: O=C(NCC1(CN2CCOCC2)CC1)c1ccc2[nH]nc(I)c2c1] | $[C_{17}H_{21}IN_4O_2 + H]^+$<br>441.1<br>441.1 | 1.372 g (62%),<br>light beige solid;<br>free base |

SMs: (1-(morpholinomethyl)cyclopropyl)methanamine (850 mg, 5 mmol), 3-iodo-1H-indazole-5-carboxamide (1.44 g, 5 mmol)

| IUPAC name | Structure | MS calculated<br>MS ESI [M + H]⁺ | Yield;<br>Appearance;<br>Salt form |
|---|---|---|---|
| (S)-N-(1-(3-fluoropyridin-2-yl)-2-methylpropyl)-3-iodo-1H-indazole-5-carboxamide | 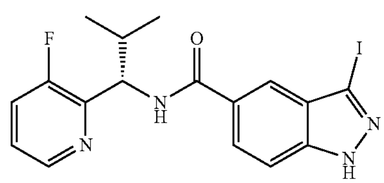 [SMILES: CC(C)[C@H](NC(=O)c1ccc2[nH]nc(I)c2c1)c1ncccc1F] | $[C_{17}H_{16}FIN_4O + H]^+$<br>439.04<br>439.1 | 750 mg (70%);<br>off white solid |

SMs: (S)-1-(3-fluoropyridin-2-yl)-2-methylpropan-1-amine hydrochloride (500 mg, 2.44 mmol), 3-iodo-1H-indazol-5-carboxylic acid (704 mg, 2.44 mmol), DIPEA (2.13 mL, 12.2 mmol), TBTU (785 mg, 2.44 mmol), anh DMF (10 mL)

¹H NMR (400 MHz, CD₃OD) δ ppm 8.44 (s, 1 H), 8.08 (s, 1 H), 7.59 (dd, J = 8.8, 1.6 Hz, 1 H), 7.57-7.64 (m, 2 H), 7.37-7.41 (m, 1 H), 5.37 (d, J = 8.8 Hz, 1 H), 2.31-2.40 (m, 1 H), 1.15 (d, J = 6.4 Hz, 3 H), 0.88 (d, J = 6.8 Hz, 3 H)

| IUPAC name | Structure | MS calculated<br>MS ESI [M + H]⁺ | Yield;<br>Appearance;<br>Salt form |
|---|---|---|---|
| (S)-N-(1-(2-fluorophenyl)-2-methylpropyl)-3-iodo-1H-indazole-5-carboxamide | 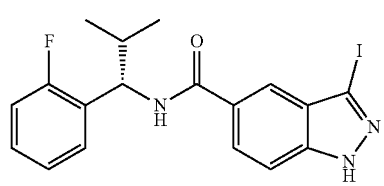 [SMILES: CC(C)[C@H](NC(=O)c1ccc2[nH]nc(I)c2c1)c1ccccc1F] | $[C_{18}H_{17}FIN_3O + H]^+$<br>438.04<br>438.2 | 940 mg (87.5%);<br>cream solid |

SMs: (S)-1-(2-fluorophenyl)-2-methylpropan-1-amine hydrochloride (500 mg, 2.45 mmol), 3-iodo-1H-indazol-5-carboxylic acid (707 mg, 2.45 mmol), DIPEA (2.14 mL, 12.25 mmol), TBTU (787 mg, 2.45 mmol), anh DMF (10 mL)

¹H NMR (400 MHz, CD₃OD) δ ppm 8.05 (s, 1 H), 7.89-7.92 (m, 1 H), 7.58 (d, J = 8.8 Hz, 1 H), (m, 1 H), 7.48-7.52 (m, 1 H), 7.26-7.31 (m, 1 H), 7.16-7.19 (m, 1 H), 7.07-7.12 (m, 1 H), 5.13 (d, J = 9.6 Hz, 1 H), 2.22-2.30 (m, 1 H), 1.17 (d, J = 6.4 Hz, 3 H), 0.86 (d, J = 6.4 Hz, 3 H)

| IUPAC name | Structure | MS calculated MS ESI [M + H]+ | Yield; Appearance; Salt form |
|---|---|---|---|
| (S)-N-(1-(2-chlorophenyl)-2-cyclopropylethyl)-3-iodo-1H-indazole-5-carboxamide | 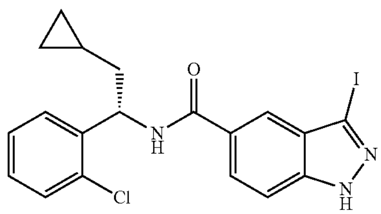 [SMILES: O=C(N[C@@H](CC1CC1)c1ccccc1Cl)c1ccc2[nH]nc(I)c2c1] | [C$_{19}$H$_{17}$ClIN$_3$O + H]+ 466.0 466.4 | 4.77 g (crude); yellow solid; free base |

SMs: (S)-1-(2-chlorophenyl)-2-cyclopropylethanamine hydrochloride (2.32 g, 10 mmol), 3-iodo-1H-indazole-5-carboxylic acid (2.88 g, 10 mmol).
$^1$H NMR (400 MHz, DMSO-d$_6$) δ ppm 13.71 (s, 1H), 9.06 (d, J = 8.0 Hz, 1H), 8.12 (s, 1H), 7.95 (dd, J = 8.8, 1.2 Hz, 1H), 7.60 (d, J = 8.8 Hz, 1H), 7.55 (dd, J = 7.6, 1.2 Hz, 1H), 7.40 (d, J = 8.0 Hz, 1H), 7.32 (t, J = 6.8 Hz, 1H), 7.24 (dt, J = 7.6, 1.2 Hz, 1H), 5.55-5.45 (m, 1H), 1.98-1.88 (m, 1H), 1.48-1.38 (m, 1H). 0.90-0.81 (m, 1H), 0.50-0.36 (m, 2H), 0.27-0.18 (m, 1H), 0.13-0.60 (m, 1H).

| (R)-N-(1-(2-chlorophenyl)-2-cyclopropylethyl)-3-iodo-1H-indazole-5-carboxamide | | [C$_{19}$H$_{17}$ClIN$_3$O + H]+ 466.0 466.4 | 4.74 g (crude); yellow solid; free base |

SMs: (R)-1-(2-chlorophenyl)-2-cyclopropylethanamine hydrochloride (2.32 g, 10 mmol), 3-iodo-1H-indazole-5-carboxylic acid (2.88 g, 10 mmol).
$^1$H NMR (400 MHz, DMSO-d$_6$) Spectral data was identical for that obtained in (S)-N-(1-(2-chlorophenyl)-2-cyclopropylethyl)-3-iodo-1H-indazole-5-carboxamide Synthesis of 3-(4-((1-methylpiperidin-4-yl)oxy)phenyl)-1H-indazol-5-amine

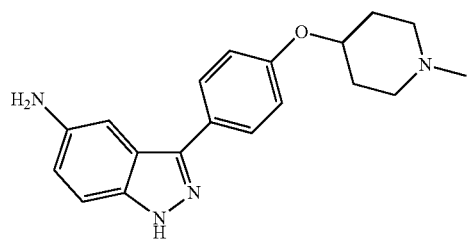 [SMILES: CN1CCC(Oc2ccc(-c3n[nH]c4ccc(N)cc34)cc2)CC1]

tert-Butyl(3-iodo-1H-indazol-5-yl)carbamate (398 mg, 1.11 mmol), 1-methyl-4-(4-(4,4,5,5-tetramethyl-1,3,2-dioxaborolan-2-yl)phenoxy)piperidine (530 mg, 1.67 mmol), and LiCl (141 mg, 3.33 mmol) were dissolved into dioxane (7.0 mL) and 2 M aq Na$_2$CO$_3$ (2.8 mL) in a microwave vial. The mixture was purged with Ar for 15 min at which time Pd(PPh$_3$)$_4$ (96 mg, 0.083 mmol) was added. The vial was sealed and heated in the microwave at 120° C. for 3 h. The reaction was cooled, the solvent removed and the residue purified by column chromatography (SiO$_2$, 90:10 CH$_2$Cl$_2$/MeOH) which gave 230 mg of BOC protected material which was dissolved into CH$_2$Cl$_2$ (5 mL) and TFA (0.5 mL) was added. The reaction was stirred for 3 h. The solvent was removed and product precipitated with Et$_2$O which gave after drying 235 mg, 38% of a brown solid as the di-TFA salt. $^1$H NMR (400 MHz, CD$_3$OD) δ ppm 8.01 (s, 1 H), 7.90-7.86 (m, 2H), 7.73 (d, J=8.8 Hz, 1H), 7.42 (d, J=9.0, 1H), 7.23-7.16 (m, 2H), 4.88 (bs, 1H), 3.66-3.39 (m, 2H), 3.39-3.00 (m, 2H), 2.95-2.89 (m, 3H), 2.46-2.29 (m, 2H), 2.17-1.90 (m, 21-1); MS ESI 323.1 [M+H]+, calcd for [C$_{19}$H$_{22}$N$_4$O+H]+ 323.19.

Synthesis of 3-(4-morpholinophenyl)-1H-indazol-5-amine

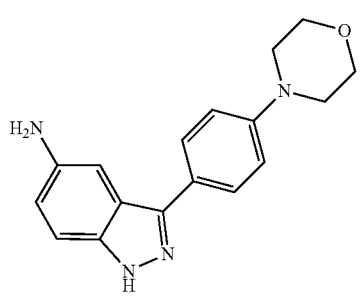 [SMILES: Nc1ccc2[nH]nc(-c3ccc(N4CCOCC4)cc3)c2c1]

The same procedure was followed as for 3-(4-((1-methylpiperidin-4-yl)oxy)phenyl)-1H-indazol-5-amine bis(2,2,2-trifluoroacetate) using tert-butyl(3-iodo-1H-indazol-5-yl)carbamate (359 mg, 1.0 mmol) and 4-(4-(4,4,5,5-tetramethyl-1,3,2-dioxaborolan-2-yl)phenyl)morpholine (434 mg, 1.5 mmol). Obtained 210 mg of an impure brown solid as the di-TFA salt which was used for subsequent synthetic steps; MS ESI 295.1 [M+H]$^+$, calcd for [$C_{17}H_{18}N_4O+H$]$^+$ 295.16.

Preparation of Exemplary Compounds of the Invention

Example A1

N-(3-(3-(morpholinomethyl)phenyl)-1H-indazol-5-yl)-2-(pyrrolidin-1-yl)-2-(thiophen-3-yl)acetamide

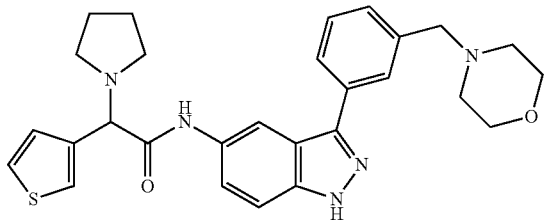 [SMILES: O=C(Nc1ccc2[nH]nc(-c3cccc(CN4CCOCC4)c3)c2c1)C(c1ccsc1)N1CCCC1]

To a mixture of N-(3-iodo-1H-indazol-5-yl)-2-(pyrrolidin-1-yl)-2-(thiophen-3-yl)acetamide (56.6 mg, 0.125 mmol) and 4-(3-(4,4,5,5-tetramethyl-1,3,2-dioxaborolan-2-yl)benzyl)morpholine (33.3 mg, 0.11 mmol) in PhCH$_3$/EtOH (1.5 mL/3 mL) was added 1 M aq Na$_2$CO$_3$ (0.3 mL, 0.3 mmol), followed by Pd(PPh$_3$)$_4$ (5.8 mg, 0.005 mmol). The resulting mixture was purged with Ar and microwaved 30 min at 125° C. After removal of solvents, it was purified by flash chromatography (EtOAc/hex 0 to 100%, then MeOH/DCM 5-15%) and then triturated with Et$_2$O to give the title compound as beige solid (15 mg, 27%). $^1$H NMR (400 MHz, CD$_3$OD) δ 8.37 (s, 1H), 7.91 (s, 1H), 7.83 (d, J=6.8 Hz, 1H), 7.55-7.47 (m, 4H), 7.45-7.39 (m, 2H), 7.35 (d, J=4.8 Hz, 1H), 4.15 (s, 1H), 3.72 (t, J=4.6 Hz, 4H), 3.65 (s, 2H), 2.75-2.65 (m, 2H), 2.60-2.50 (m, 6H), 1.90-1.85 (m, 4H); MS ESI 502.2 [M+H]$^+$, calcd for [$C_{28}H_{31}N_5O_2S+H$]$^+$ 502.2.

Example A2

N-(3-(4-(4-methylpiperazin-1-yl)phenyl)-1H-indazol-5-yl)-2-(pyrrolidin-1-yl)-2-(thiophen-3-yl)acetamide

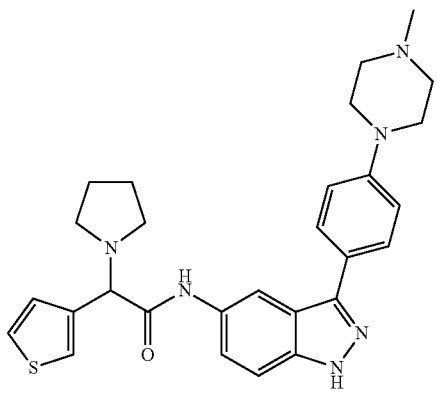 [SMILES: CN1CCN(c2ccc(-c3n[nH]c4ccc(NC(=O)C(c5ccsc5)N5CCCC5)cc34)cc2)CC1]

The title compound was synthesized according to General Method C by using a mixture of N-(3-iodo-1H-indazol-5-yl)-2-(pyrrolidin-1-yl)-2-(thiophen-3-yl)acetamide (50 mg, 0.11 mmol), 1-methyl-4-(4-(4,4,5,5-tetramethyl-1,3,2-dioxaborolan-2-yl)phenyl)piperazine (40 mg, 0.13 mmol), Pd(PPh$_3$)$_4$ (6.35 mg, 0.005 mmol) and 1 M aq Na$_2$CO$_3$ (0.22 mL) in PhMe/EtOH (2.25 mL, 2:1 mixture) in a vial under Ar that was heated under microwave irradiation at 125° C. for 2 h. The reaction mixture was diluted with EtOAc (10 mL) and washed with H$_2$O (5 mL) followed by brine (5 mL), dried (Na$_2$SO$_4$) and concentrated under vacuum to give brown oily residue. The crude product was purified by flash chromatography (100 g SiO$_2$ column, 0-10% 2 M NH$_3$-MeOH in DCM; then by RP HPLC C18 60 g column, 10-80% MeOH in 0.1% TFA-H$_2$O) to give the title compound as a TFA salt (pale yellow solid, 21 mg, 26%). $^1$H NMR (400 MHz, CD$_3$OD) δ 8.35 (s, 1H), 7.85-7.83 (m, 3H), 7.64 (br.s, 1H), 7.54-7.49 (m, 2H), 7.38 (dd, J=4.4 Hz, 1H), 7.19 (d, J=8.4 Hz, 2H), 5.26 (s, 1H), 3.98-3.86 (br.m, 3H), 3.67-3.60 (m, 2H), 3.17-3.11 (br.m, 4H), 3.00 (s, 3H), 2.26-2.14 (br.m, 3H), 2.02-2.01 (br.s, 1H), 2H merged with solvent peak, MS ESI 501.1[M+H]$^+$, calcd for [$C_{28}H_{32}N_6OS+H$]$^+$ 501.2.

Example A3

N-(3-(4-(morpholinomethyl)phenyl)-1H-indazol-5-yl)-2-(pyrrolidin-1-yl)-2-(thiophen-3-yl)acetamide

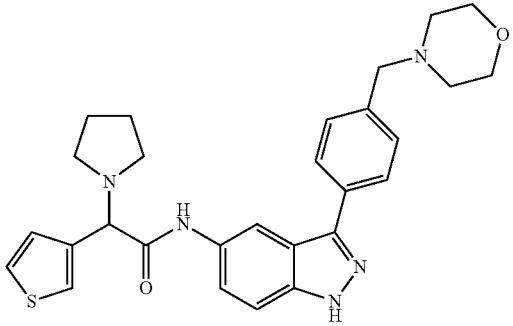 [SMILES: O=C(Nc1ccc2[nH]nc(-c3ccc(CN4CCOCC4)cc3)c2c1)C(c1ccsc1)N1CCCC1]

To a mixture of N-(3-iodo-1H-indazol-5-yl)-2-(pyrrolidin-1-yl)-2-(thiophen-3-yl)acetamide (181 mg, 0.4 mmol) and 4-(4-(4,4,5,5-tetramethyl-1,3,2-dioxaborolan-2-yl)benzyl)morpholine (121 mg, 0.4 mmol) in EtOH (10 mL) was added 1 M aq Na$_2$CO$_3$ (0.8 mL, 0.8 mmol), followed by Pd(PPh$_3$)$_4$ (23 mg, 0.02 mmol). The resulting mixture was purged with Ar and microwaved 1 h at 125° C. After removal of solvents, it was redissolved in DMF/MeOH/TFA (4 mL/1 mL/0.5 mL), filtered thru microfilter and purified by PREP-HPLC twice to give the title compound as a di-TFA salt (off white solid, 52 mg, 18%). $^1$H NMR (400 MHz, CD$_3$OD) δ 8.40 (s, 1H), 8.05 (d, J=8.0 Hz, 2H), 7.89-7.85 (m, 1H), 7.68 (d, J=8.0 Hz, 2H), 7.63 (dd, J=4.8 Hz, 2.8 Hz, 1H), 7.60-7.52 (m, 2H), 7.38 (dd, J=4.8 Hz, 0.8 Hz, 1H), 5.32 (s, 1H), 4.44 (s, 2H), 4.10-3.05 (m, 12H), 2.30-1.95 (m, 4H); MS ESI 502.1 [M+H]$^+$, calcd for [$C_{28}H_{31}H_5O_2S+H$]$^+$ 502.2.

Example A4

N-(3-(4-morpholinophenyl)-1H-indazol-5-yl)-2-(pyrrolidin-1-yl)-2-(thiophen-3-yl-acetamide

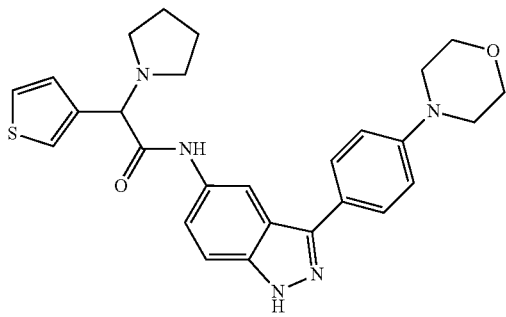 [SMILES: O=C(Nc1ccc2[nH]nc(-c3ccc(N4CCOCC4)cc3)c2c1)C(c1ccsc1)N1CCCC1]

Aq. Na$_2$CO$_3$ (2 M, 1.0 mL, 2.0 mmol) was added to a solution of N-(3-iodo-1H-indazol-5-yl)-2-(pyrrolidin-1-yl)-2-(thiophen-3-yl)acetamide (300.2 mg, 0.66 mmol), (4-morpholinophenyl)boronic acid (191.2 mg, 0.93 mmol) and PdCl$_2$(dppf).DCM (52.0 mg, 0.064 mmol) in 1:1 PhMe:EtOH (14 mL), and the mixture was heated in a microwave for 3 h at 120° C. The product was partitioned between EtOAc (250 mL) and H$_2$O (25 mL), and the aq layer was extracted with EtOAc (4×100 mL). The combined organic layers were washed sequentially with H$_2$O (25 mL) and brine (25 mL), dried (Na$_2$SO$_4$), filtered and evaporated in vacuo. Purification by flash chromatography (SiO$_2$, 0-10% MeOH in DCM; followed by RPC18, 10-80% MeOH in 0.1% TFA-H$_2$O) gave the title compound as the TFA salt (yellow powder, 265.1 mg, 56%). $^1$H NMR (400 MHz, CD$_3$OD) δ ppm 8.38 (d, J=1.25 Hz, 1 H), 7.87 (dd, J=3.01, 1.25 Hz, 1 H), 7.82 (d, J=8.78 Hz, 2 H), 7.67 (dd, J=5.02, 3.01 Hz, 1 H), 7.53 (d$_{AB}$, J=9.00 Hz, 1 H), 7.48 (d$_{AB}$d, J=9.00, 1.70 Hz, 1 H), 7.38 (dd, J=5.02, 1.25 Hz, 1 H), 7.16 (d, J=8.78 Hz, 2 H), 5.20 (s, 1 H), 3.87-3.92 (m, 4 H), 3.25-3.30 (m, 4 H), 3.13-3.24 (m, 1 H), 3.10 (br. s., 1 H), 2.20-2.29 (m, 1 H), 2.10-2.20 (m, 2 H), 2.01 (br. s., 1 H). MS ESI 488.3 [M+H]$^+$, calcd for [C$_{27}$H$_{29}$N$_5$O$_2$S+H]$^+$ 488.21.

Example A5

N-(3-(4-(2-(dimethylamino)ethoxy)phenyl)-1H-indazol-5-yl)-2-(pyrrolidin-1-yl)-2-(thiophen-3-yl)acetamide

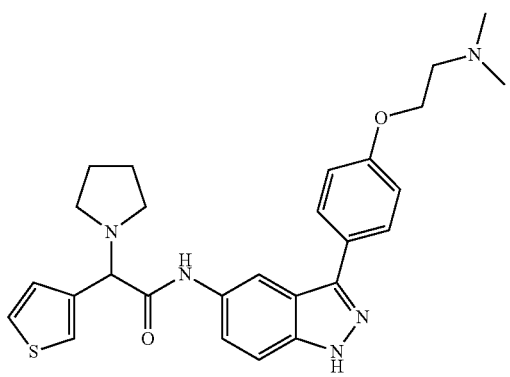 [SMILES: CN(C)CCOc1ccc(-c2n[nH]c3ccc(NC(=O)C(c4ccsc4)N4CCCC4)cc23)cc1]

To a mixture of N-(3-iodo-1H-indazol-5-yl)-2-(pyrrolidin-1-yl)-2-(thiophen-3-yl)acetamide (226 mg, 0.5 mmol) and N,N-dimethyl-2-(4-(4,4,5,5-tetramethyl-1,3,2-dioxaborolan-2-yl)phenoxy)ethanamine (146 mg, 0.5 mmol) in EtOH (10 mL) was added 1 M aq Na$_2$CO$_3$ (1 mL, 1 mmol), followed by Pd(PPh$_3$)$_4$ (23 mg, 0.02 mmol). The resulting mixture was purged with Ar and microwaved 1 h at 125° C. Additional Pd(PPh$_3$)$_4$ (11.6 mg, 0.01 mmol) was added and the reaction mixture was was purged with Ar and microwaved 2 h at 125° C. After removal of solvents, it was purified by flash chromatography (MeOH/DCM 5-15%, then pure MeOH) and prep-HPLC to give the title compound as a di-TFA salt (white solid, 114 mg, 32%). $^1$H NMR (400 MHz, CD$_3$OD) δ 8.34 (s, 1H), 7.88-7.83 (m, 3H), 7.59 (dd, J=4.8 Hz, 3.2 Hz, 1H), 7.53 (s, 2H), 7.38 (d, J=5.2 Hz, 1H), 7.13 (d, J=8.8 Hz, 2H), 5.35 (s, 1H), 4.38 (t, J=4.6 Hz, 2H), 3.83 (brs, 1H), 3.60 (t, J=4.6 Hz, 2H), 3.35-3.05 (m, 3H), 2.98 (s, 6H), 2.25-1.90 (m, 4H); MS ESI 490.2 [M+H]$^+$, calcd for [C$_{27}$H$_{31}$N$_5$O$_2$S+H]$^+$ 490.2.

Example A6

N-(3-(4-(2-morpholinoethyl)phenyl)-1H-indazol-5-yl)-2-(pyrrolidin-1-yl)-2-(thiophen-3-yl)acetamide

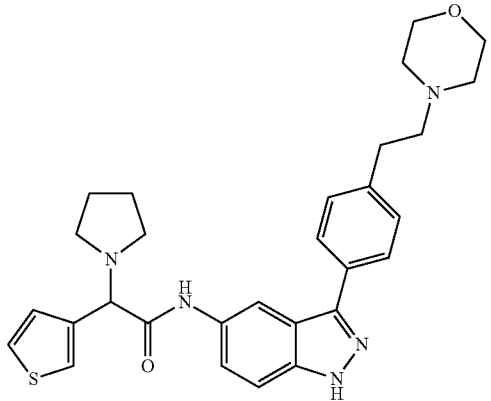 [SMILES: O=C(Nc1ccc2[nH]nc(-c3ccc(CCN4CCOCC4)cc3)c2c1)C(c1ccsc1)N1CCCC1]

To a mixture of N-(3-iodo-1H-indazol-5-yl)-2-(pyrrolidin-1-yl)-2-(thiophen-3-yl)acetamide (181 mg, 0.4 mmol) and 4-(4-(4,4,5,5-tetramethyl-1,3,2-dioxaborolan-2-yl)phenethyl)morpholine (127 mg, 0.4 mmol) in EtOH (10 mL) was added 1 M aq Na$_2$CO$_3$ (0.8 mL, 0.8 mmol), followed by Pd(PPh$_3$)$_4$ (23 mg, 0.02 mmol). The resulting mixture was purged with Ar and microwaved 2 h at 125° C. Additional Pd(PPh$_3$)$_4$ (11.6 mg, 0.01 mmol) was added and the reaction mixture was purged with Ar and microwaved 1 h at 125° C. After removal of solvents, it was purified by flash chromatography (MeOH/DCM 5-15%, then pure MeOH) and prep-HPLC to give the title compound as a di-TFA salt (white solid, 85 mg, 29%). $^1$H NMR (400 MHz, CD$_3$OD) δ 8.38 (s, 1H), 7.92-7.85 (m, 3H), 7.64-7.59 (m, 1H), 7.54 (s, 2H), 7.44 (d, J=8.0 Hz, 2H), 7.38 (d, J=4.4 Hz, 1H), 5.32 (s, 1H), 4.12-4.03 (m, 2H), 3.90-3.77 (m, 3H), 3.63-3.55 (m, 2H), 3.47-3.40 (m, 2H), 3.26-3.06 (m, 7H), 2.30-1.90 (m, 4H); MS ESI 516.2 [M+H]$^+$, calcd for [C$_{29}$H$_{33}$N$_5$O$_2$S+H]$^+$ 516.2.

Example A7

N-(3-(4-((1-methylpiperidin-4-yl)oxy)phenyl)-1H-indazol-5-yl)-2-(pyrrolidin-1-yl)-2-(thiophen-3-yl)acetamide

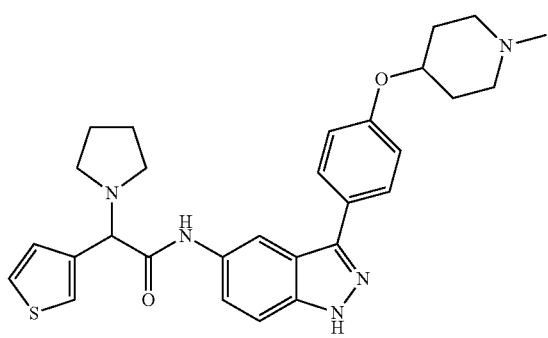 [SMILES: CN1CCC(Oc2ccc(-c3n[nH]c4ccc(NC(=O)C(c5ccsc5)N5CCCC5)cc34)cc2)CC1]

Using General Method C2, three vials each containing N-(3-iodo-1H-indazol-5-yl)-2-(pyrrolidin-1-yl)-2-(thiophen-3-yl)acetamide (400 mg, 0.882 mmol) and 1-methyl-4-(4-(4,4,5,5-tetramethyl-1,3,2-dioxaborolan-2-yl)phenoxy)piperidine (368 mg, 1.05 mmol) with 15% catalyst in PhMe:EtOH (8 mL:4 mL) were heated for 5 h at 125° C. in the microwave. The combined reactions were extracted with EtOAc, and purified by flash chromatography (SiO$_2$, 0-80% MeOH in DCM); followed by purification with prep HPLC and Biotage RPC18, 10-90% MeOH in 0.1% TFA-H$_2$O, the title compound was obtained as the TFA salt (off-white solid, 545 mg, 27.6%). $^1$H NMR (400 MHz, CD$_3$OD) δ ppm 8.36 (s, 1 H), 7.82-7.91 (m, 3 H), 7.64 (dd, J=5.0, 3.0 Hz, 1 H), 7.49-7.57 (m, 2 H), 7.38 (dd, J=5.1, 1.1 Hz, 1 H), 7.11-7.22 (m, 2 H), 5.29 (s, 1 H), 4.62-4.73 (m, 0.33 H), 3.87 (brs, 1 H), 3.60-3.69 (m, 0.67 H), 3.49-3.34 (m, 3.33 H), 3.02-3.27 (m, 3 H), 2.94, 2.93 (s, 3 H), 2.43 (d, J=14.3 Hz, 0.67 H), 1.86-2.34 (m, 8 H). MS ESI 516.2 [M+H]$^+$, calcd for [C$_{29}$H$_{33}$N$_5$O$_2$S+H]$^+$ 516.24.

Example A8

N-(3-(3-methoxy-4-(piperidin-4-yloxy)phenyl)-1H-indazol-5-yl)-2-(pyrrolidin-1-yl)-2-(thiophen-3-yl)acetamide

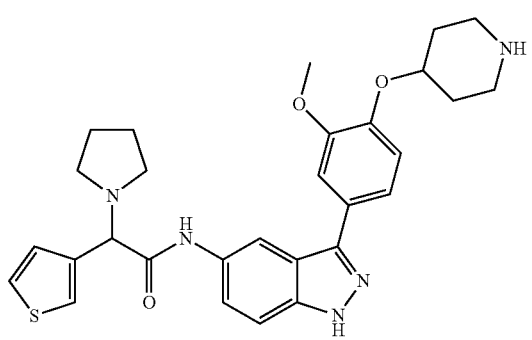 [SMILES: COc1cc(-c2n[nH]c3ccc(NC(=O)C(c4ccsc4)N4CCCC4)cc23)ccc1OC1CCNCC1]

The title compound was synthesized according to the General Method C, utilizing N-(3-iodo-1H-indazol-5-yl)-2-(pyrrolidin-1-yl)-2-(thiophen-3-yl)acetamide (50 mg, 0.11 mmol), 4-(1-boc-piperidin-4-yloxy)-3-methoxyphenyl boronic acid (46 mg, 0.13 mmol), PdCl$_2$dppf (4.5 mg, 0.0055 mmol), sat aq Na$_2$CO$_3$ (0.5 mL), and 1.5 mL of PhMe:EtOH (1:1). The vial was charged with Ar and heated in the microwave reactor at 125° C. for 2 h. The mixture was purified by RPHPLC, treated with using DCM/TFA for 1 h, followed by trituration with Et$_2$O to give the title compound as a TFA salt (beige solid, 54 mg, 65%). $^1$H NMR (400 MHz, CD$_3$OD) δ ppm 8.45 (s, 1 H), 7.86 (br. s, 1 H), 7.62-7.68 (m, 1 H), 7.44-7.59 (m, 4 H), 7.37 (d, J=5.0 Hz, 1 H), 7.21 (d, J=8.3 Hz, 1 H), 5.24 (s, 1 H), 4.71 (br. s, 1 H), 3.98 (s, 3 H), 3.80-3.92 (m, 1 H), 3.44-3.56 (m, 3 H), 3.02-3.28 (m, 5 H), 2.13 (br. s, 7 H), 1.90-2.05 (m, 1H); MS ESI 532.2 [M+H]$^+$, calcd for [C$_{29}$H$_{33}$N$_5$O$_3$S+H]$^+$ 532.2.

Example A9

N-(3-(4-(4-hydroxypiperidin-1-yl)phenyl)-1H-indazol-5-yl)-2-(pyrrolidin-1-yl)-2-(thiophen-3-yl)acetamide A. N-(3-(4-(4-oxopiperidin-1-yl)phenyl)-1H-indazol-5-yl)-2-(pyrrolidin-1-yl)-2-(thiophen-3-yl)acetamide

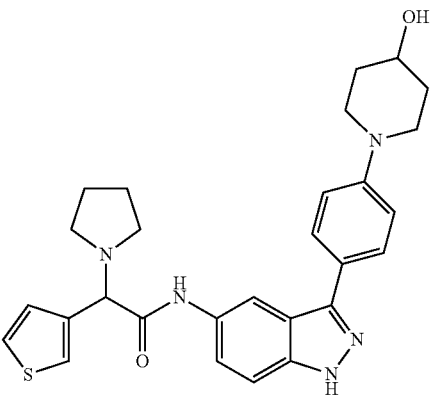 [SMILES: O=C(Nc1ccc2[nH]nc(-c3ccc(N4CCC(O)CC4)cc3)c2c1)C(c1ccsc1)N1CCCC1]

The title compound was synthesized according to General Method C by using a sealed degassed mixture of N-(3-iodo-1H-indazol-5-yl)-2-(pyrrolidin-1-yl)-2-(thiophen-3-yl)acetamide (700 mg, 1.54 mmol), 1-(4-(4,4,5,5-tetramethyl-1,3,2-dioxaborolan-2-yl)phenyl)piperidin-4-one (466 mg, 1.54 mmol), Pd(PPh$_3$)$_4$ (139 mg, 0.12 mmol), 1 M aq Na$_2$CO$_3$ (3.1 mL) in PhMe/EtOH (14 mL, 2:1 mixture) under Ar was heated under microwave irradiation at 125° C. for 3 h. The reaction mixture was diluted with EtOAc (42 mL) and washed it with of H$_2$O (2×15 mL) followed by brine (20 mL), dried (Na$_2$SO$_4$), and concentrated under vacuum. Purification by flash chromatography (100 g SiO$_2$, 0-10% MeOH in DCM; then 25 g SiO$_2$ column; 0-40% MeOH in DCM) gave the title compound (light brown solid, 300 mg, 39%). MS ESI 500.2 [M+H]$^+$, calcd for [C$_{28}$H$_{30}$N$_4$O$_3$S+H]$^+$ 500.6.

B. N-(3-(4-(4-hydroxypiperidin-1-yl)phenyl)-1H-indazol-5-yl)-2-(pyrrolidin-1-yl)-2-(thiophen-3-yl)acetamide To a solution of N-(3-(4-(4-oxopiperidin-1-yl)phenyl)-1H-indazol-5-yl)-2-(pyrrolidin-1-yl)-2-(thiophen-3-yl)acetamide (340 mg, 0.68 mmol) in a mixture of DCM (3.4 mL) and MeOH (6.8 mL) was added NaBH₄ (52 mg, 1.36 mmol) in two lots at rt. The reaction mixture was stirred at rt for 5 h, and then concentrated under reduced pressure. The residue treated with 25% aq NH₄Cl solution (10 mL) and the product was extracted with EtOAc (100 mL, 25 mL), washed with H₂O followed by brine, dried (Na₂SO₄), and concentrated under vacuum. Purification by RP HPLC provided the title compound as a TFA salt (yellow solid, 230 g, 46%). $^1$H NMR (400 MHz, CD$_3$OD) δ ppm 8.42 (m, 1H), 8.13 (dd, J=6.8 Hz, J=2 Hz, 2H), 7.89 (dd, J=2.8 Hz, J=1.2 Hz, 1H), 7.79 (s, 1H), 7.77 (s, 1H), 7.64-7.62 (m, 1H), 7.59-7.53 (m, 2H), 7.39 (dd, J=4.8 Hz, J=1.2 Hz, 1H), 5.36 (s, 1H), 4.12-4.1 (m, 1H), 3.90-3.85 (m, 3H), 3.66-3.61 (m, 2H), 3.30-3.05 (br.m, 2H), 2.29-2.01 (br.m, 8H), 1H merged with solvent peak; MS ESI 502.1 [M+H]$^+$, calcd for [C$_{28}$H$_{31}$N$_5$O$_2$S+H]$^+$ 502.2

Example A10

N-(3-(3-methoxy-4-(4-methylpiperazin-1-yl)phenyl)-1H-indazol-5-yl)-2-(pyrrolidin-1-yl)-2-(thiophen-3-yl)acetamide

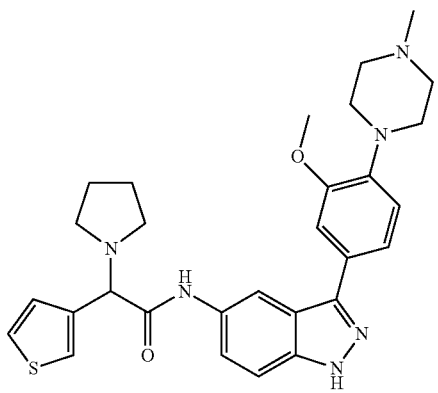 [SMILES: COc1cc(-c2n[nH]c3ccc(NC(=O)C(c4ccsc4)N4CCCC4)cc23)ccc1N1CCN(C)CC1]

The title compound was synthesized according to the General Method C, utilizing N-(3-iodo-1H-indazol-5-yl)-2-(pyrrolidin-1-yl)-2-(thiophen-3-yl)acetamide (50 mg, 0.11 mmol), 1-(2-methoxy-4-(4,4,5,5-tetramethyl-1,3,2-dioxaborolan-2-yl)phenyl)-4-methylpiperazine (43 mg, 0.13 mmol), PdCl₂dppf (4.5 mg, 0.0055 mmol), satd. aq Na₂CO₃ (0.5 mL), and 1.5 mL of PhMe:EtOH (1:1). The vial was charged with Ar and heated in the microwave reactor at 125° C. for 2 h. Purification by RP HPLC, followed by flash chromatography (SiO₂, Biotage 25 g, 5-25% MeOH in CH₂Cl₂) to give the title compound (white solid, 11 mg, 19%)$^1$H NMR (400 MHz, CD$_3$OD) δ ppm 8.40 (s, 1 H), 7.44-7.55 (m, 5 H), 7.39-7.44 (m, 1 H), 7.33 (d, J=5.3 Hz, 1 H), 7.09 (d, J=7.8 Hz, 1 H), 4.18 (s, 1H), 3.97 (s, 3 H), 3.08-3.24 (m, 4 H), 2.73 (br. s, 6 H), 2.49-2.59 (m, 2 H), 2.42 (s, 3 H), 1.86 (br. s, 4 H); MS ESI 531.4 [M+H]$^+$, calcd for [C$_{29}$H$_{34}$N$_6$O$_2$S+H]$^+$ 531.3.

Example A11

N-(3-(4-(4-methylpiperazin-1-yl)phenyl)-1H-indazol-5-yl)-1,2,3,4-tetrahydronaphthalene-1-carboxamide

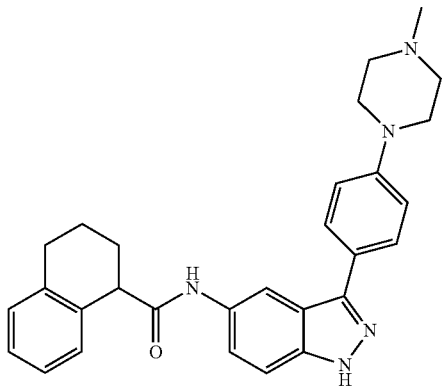 [SMILES: CN1CCN(c2ccc(-c3n[nH]c4ccc(NC(=O)C5CCCc6ccccc65)cc34)cc2)CC1]

To a mixture of N-(3-iodo-1H-indazol-5-yl)-1,2,3,4-tetrahydronaphthalene-1-carboxamide (167 mg, 0.4 mmol) and 1-methyl-4-(4-(4,4,5,5-tetramethyl-1,3,2-dioxaborolan-2-yl)phenyl)piperazine (121 mg, 0.4 mmol) in EtOH (12 mL) was added 1 M aq Na₂CO₃ (0.8 mL, 0.8 mmol), followed by Pd(PPh₃)₄ (23 mg, 0.02 mmol). The resulting mixture was purged with Ar and microwaved 3 h at 125° C. After removal of solvents, it was redissolved in DMF (5 mL), filtered and purified by prep -HPLC to give the title compound as white solid (135 mg, 59%) in TFA salt. $^1$H NMR (400 MHz, CD$_3$OD) δ 8.50 (s, 1H), 7.54 (d, J=8.0 Hz, 2H), 7.48 (s, 2H), 7.10 (d, J=7.2 Hz, 1H), 7.07-6.97 (m, 3H), 6.86 (d, J=8.4 Hz, 2H), 3.88 (t, J=6.6 Hz, 1H), 3.61 (d, J=11.2 Hz, 2H), 3.37 (d, J=10.0 Hz, 2H), 2.94 (quint, J=12.4 Hz, 4H), 2.80-2.63 (m, 5H; s, 3H at 2.75), 2.12-1.95 (m, 3H), 1.71-1.59 (m, 1H); MS ESI 466.3 [M+H]$^+$, calcd for [C$_{29}$H$_{31}$N$_5$O+H]$^+$ 466.3.

Example A12

N-(cyclopropyl(phenyl)methyl)-3-(4-morpholinophenyl)-1H-indazole-5-carboxamide

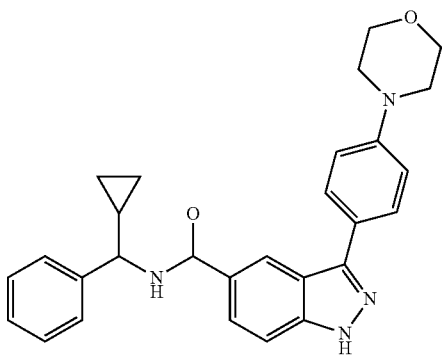 [SMILES: OC(NC(c1ccccc1)C1CC1)c1ccc2[nH]nc(-c3ccc(N4CCOCC4)cc3)c2c1]

The title compound was synthesized according to the General Method C, utilizing N-(cyclopropyl(phenyl)methyl)-3-iodo-1H-indazole-5-carboxamide (50 mg, 0.12 mmol), 4-morpholinophenylboronic acid pinacol ester (40 mg, 0.14 mmol), PdCl$_2$dppf (4.9 mg, 0.006 mmol), satd. aq Na$_2$CO$_3$ (0.5 mL), and 1.5 mL of PhMe:EtOH (1:1). The vial was charged with Ar and heated in the microwave reactor at 125° C. for 2 h. Purification by RP HPLC, followed by trituration with Et$_2$O gave the title compound as a TFA salt (beige solid, 11 mg, 16%). $^1$H NMR (400 MHz, CD$_3$OD) δ ppm 8.60 (s, 1 H), 7.87-7.98 (m, 3 H), 7.58 (d, J=8.8 Hz, 1 H), 7.47 (d, J=7.0 Hz, 2 H), 7.31 (t, J=7.2 Hz, 2 H), 7.22 (t, J=6.8 Hz, 1 H), 7.15 (d, J=7.8 Hz, 2 H), 4.48 (d, J=9.5 Hz, 1 H), 3.86 (br. s, 4 H), 3.25 (br. s, 4 H), 1.34-1.44 (m, 1 H), 0.64 (m, 2 H), 0.46 (m, 2 H); MS ESI 453.3 [M+H]$^+$, calcd for [C$_{28}$H$_{28}$N$_4$O$_2$+H]$^+$ 453.2.

Example A13

N-(cyclopropyl(phenyl)methyl)-3-(3-methoxy-4-(piperidin-4-yloxy)phenyl)-1H-indazole-5-carboxamide

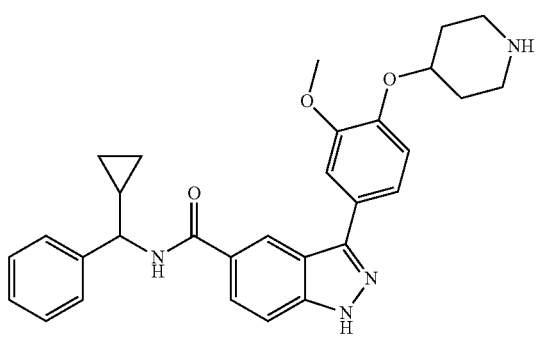 [SMILES: COc1cc(-c2n[nH]c3ccc(C(=O)NC(c4ccccc4)C4CC4)cc23)ccc1OC1CCNCC1]

The title compound was synthesized according to the General C, utilizing N-(cyclopropyl(phenyl)methyl)-3-iodo-1H-indazole-5-carboxamide (50 mg, 0.12 mmol), 4-(1-boc-piperidin-4-yloxy)-3-methoxyphenyl boronic acid (49 mg, 0.14 mmol), PdCl$_2$dppf (4.9 mg, 0.006 mmol), satd. aq Na$_2$CO$_3$ (0.5 mL), and 1.5 mL of PhMe:EtOH (1:1). The vial was charged with Ar and heated in the microwave reactor at 125° C. for 2 h. The mixture was purified by RPHPLC, treated with DCM/TFA for 1 h, followed by trituration with Et$_2$O to give the title compound as a TFA salt (white solid, 25 mg, 34%). $^1$H NMR (400 MHz, CD$_3$OD) δ ppm 8.59 (s, 1 H), 7.95 (d, J=8.5 Hz, 1 H), 7.54-7.66 (m, 3 H), 7.48 (d, J=7.3 Hz, 2 H), 7.33 (t, J=7.7 Hz, 2 H), 7.17-7.27 (m, 2 H), 4.69 (br. s, 1 H), 4.48 (d, J=9.5 Hz, 1 H), 3.96 (s, 3 H), 3.44-3.55 (m, 2 H), 3.18-3.27 (m, 2 H), 2.11 (m, 4 H), 1.34-1.46 (m, 1 H), 0.66 (d, J=8.3 Hz, 2 H), 0.41-0.54 (m, 2 H); MS ESI 497.4 [M+H]$^+$, calcd for [C$_{30}$H$_{32}$N$_4$O$_3$+H]$^+$ 497.3.

Example A14

N-(3-(benzo[d][1,3]dioxol-5-yl)-1H-indazol-5-yl)-2-(pyrrolidin-1-yl)-2-(thiophen-3-yl)acetamide

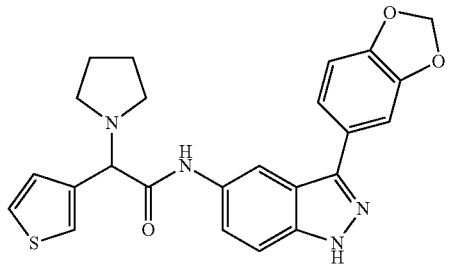 [SMILES: O=C(Nc1ccc2[nH]nc(-c3ccc4c(c3)OCO4)c2c1)C(c1ccsc1)N1CCCC1]

To a mixture of N-(3-iodo-1H-indazol-5-yl)-2-(pyrrolidin-1-yl)-2-(thiophen-3-yl)acetamide (90 mg, 0.2 mmol) and 2-(benzo[d][1,3]dioxol-5-yl)-HBpin (50 mg, 0.2 mmol) in EtOH (4.5 mL) was added 1 M aq Na$_2$CO$_3$ (0.4 mL, 0.4 mmol), followed by Pd(PPh$_3$)$_4$ (11.6 mg, 0.01 mmol). The resulting mixture was purged with Ar and microwaved 2.5 h at 125° C. After removal of solvents, it was redissolved in DMF (5 mL), filtered and purified by prep-HPLC twice to give the title compound as light brown solid (49.3 mg, 44%) in TFA salt. $^1$H NMR (400 MHz, CD$_3$OD) δ 8.35 (t, J=1.2 Hz, 1H), 7.87 (dd, J=2.8 Hz, 1.2 Hz, 1H), 7.63 (dd, J=5.0 Hz, 3.0 Hz, 1H), 7.54-7.47 (m, 2H), 7.39-7.36 (m, 2H), 7.34 (d, J=1.6 Hz, 1H), 6.95 (d, J=8.0 Hz, 1H), 6.01 (s, 2H), 5.28 (s, 1H), 3.87 (brs, 1H), 3.35-3.05 (m, 3H), 2.30-1.90 (m, 4H); MS ESI 447.2 [M+H]$^+$, calcd for [C$_{24}$H$_{22}$N$_4$O$_3$+H]$^+$ 447.1.

Example A15

N-(3-(2,3-dihydrobenzo[b][1,4]dioxin-6-yl)-1H-indazol-5-yl)-2-(pyrrolidin-1-yl)-2-(thiophen-3-yl)acetamide

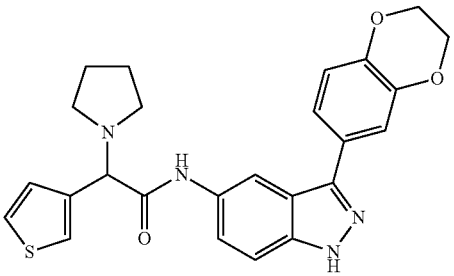 [SMILES: O=C(Nc1ccc2[nH]nc(-c3ccc4c(c3)OCCO4)c2c1)C(c1ccsc1)N1CCCC1]

To a mixture of N-(3-iodo-1H-indazol-5-yl)-2-(pyrrolidin-1-yl)-2-(thiophen-3-yl)acetamide (90 mg, 0.2 mmol) and 2-(2,3-dihydrobenzo[b][1,4]dioxin-6-yl)-HBpin (54 mg, 0.2 mmol) in EtOH (4.5 mL) was added 1 M aq Na$_2$CO$_3$ (0.4 mL, 0.4 mmol), followed by Pd(PPh$_3$)$_4$ (11.6 mg, 0.01 mmol). The resulting mixture was purged with Ar and microwaved 2.5 h at 125° C. After removal of solvents, it was redissolved in DMF (5 mL), filtered and purified by prep-HPLC to give the title compound as a TFA salt (light brown solid, 58.8 mg, 51%). $^1$H NMR (400 MHz, CD$_3$OD) δ 8.35 (t, J=0.8 Hz, 1H), 7.86 (dd, J=2.8 Hz, 1.2 Hz, 1H), 7.62 (dd, J=5.0 Hz, 3.0 Hz, 1H), 7.50 (s, 2H), 7.39-7.34 (m, 3H), 6.94 (d, J=8.8 Hz, 1H), 5.27 (s, 1H), 4.28 (s, 4H), 3.86 (brs, 1H), 3.35-3.05 (m, 3H), 2.30-1.90 (m, 4H); MS ESI 461.2 [M+H]$^+$, calcd for [C$_{25}$H$_{24}$N$_4$O$_3$S+H]$^+$ 461.2.

Example A16

N-(3-(1-methylindolin-5-yl)-1H-indazol-5-yl)-2-(pyrrolidin-1-yl)-2-(thiophen-3-yl)acetamide

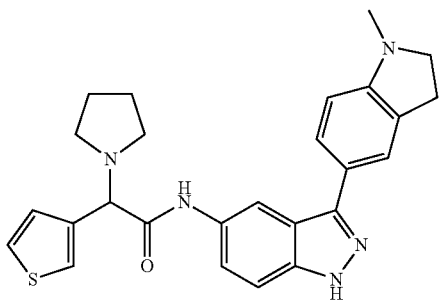 [SMILES: CN1CCc2cc(-c3n[nH]c4ccc(NC(=O)C(c5ccsc5)N5CCCC5)cc34)ccc21]

To a mixture of N-(3-iodo-1H-indazol-5-yl)-2-(pyrrolidin-1-yl)-2-(thiophen-3-yl)acetamide (90 mg, 0.2 mmol) and 1-methyl-5-(4,4,5,5-tetramethyl-1,3,2-dioxaborolan-2-yl)indoline (52 mg, 0.2 mmol) in EtOH (4.5 mL) was added 1 M aq Na$_2$CO$_3$ (0.4 mL, 0.4 mmol), followed by Pd(PPh$_3$)$_4$ (11.6 mg, 0.01 mmol). The resulting mixture was purged with Ar and microwaved 2.5 h at 125° C. After removal of solvents, it was redissolved in DMF (5 mL), filtered and purified by prep-HPLC to give the title compound as a TFA salt (brown solid, 27.2 mg, 24%). $^1$H NMR (400 MHz, CD$_3$OD) δ 8.36 (t, J=1.2 Hz, 1H), 7.88 (dd, J=2.8 Hz, 1.2 Hz, 1H), 7.83-7.79 (m, 2H), 7.64 (dd, J=5.2 Hz, 2.8 Hz, 1H), 7.55 (s, 2H), 7.38 (dd, J=4.8 Hz, 1.2 Hz, 1H), 7.18 (d, J=8.4 Hz, 1H), 5.28 (s, 1H), 3.88 (brs, 1H), 3.70 (t, J=7.6 Hz, 2H), 3.27-3.04 (m, 8H; s, 3H at 2.86), 2.30-1.90 (m, 4H); MS ESI 458.1 [M+H]$^+$, calcd for [C$_{26}$H$_{27}$N$_5$OS+H]$^+$ 458.2.

Example A17

N-(3-(4-methyl-3,4-dihydro-2H-benzo[b][1,4]oxazin-7-yl)-1H-indazol-5-yl)-2-(pyrrolidin-1-yl)-2-(thiophen-3-yl)acetamide

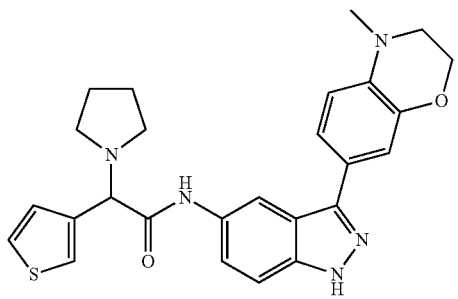 [SMILES: CN1CCOc2cc(-c3n[nH]c4ccc(NC(=O)C(c5ccsc5)N5CCCC5)cc34)ccc21]

To a mixture of N-(3-iodo-1H-indazol-5-yl)-2-(pyrrolidin-1-yl)-2-(thiophen-3-yl)acetamide (90 mg, 0.2 mmol) and 4-methyl-7-(4,4,5,5-tetramethyl-1,3,2-dioxaborolan-2-yl)-3,4-dihydro-2H-benzo[b][1,4]oxazine (55 mg, 0.2 mmol) in EtOH (4.5 mL) was added 1 M aq Na$_2$CO$_3$ (0.4 mL, 0.4 mmol), followed by Pd(PPh$_3$)$_4$ (11.6 mg, 0.01 mmol). The resulting mixture was purged with Ar and microwaved 2.5 h at 125° C. After removal of solvents, it was redissolved in DMF (5 mL), filtered and purified by prep-HPLC to give the title compound as a TFA salt (dark yellow solid, 37.4 mg, 32%) in TFA salt. $^1$H NMR (400 MHz, CD$_3$OD) δ 8.36 (s, 1H), 7.86 (d, J=2.0 Hz, 1H), 7.64 (dd, J=4.8 Hz, 2.8 Hz, 1H), 7.50 (s, 2H), 7.39-7.33 (m, 2H), 7.25 (d, J=1.6 Hz, 1H), 6.83 (d, J=8.4 Hz, 1H), 5.24 (s, 1H), 4.31 (t, J=4.2 Hz, 1H), 3.87 (brs, 1H), 3.35-3.05 (m, 5H), 2.95 (s, 3H), 2.27-1.92 (m, 4H); MS ESI 474.2 [M+H]$^+$, calcd for [C$_{26}$H$_{27}$N$_5$O$_2$S+H]$^+$ 474.2.

Example A18

N-(3-(4-((1-methylpiperidin-4-yl)oxy)phenyl)-1H-indazol-5-yl-1,2,3,4-tetrahydronaphthalene-1-carboxamide

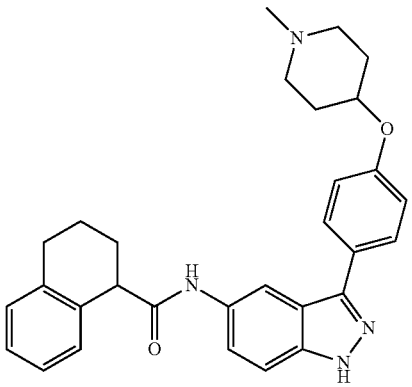 [SMILES: CN1CCC(Oc2ccc(-c3n[nH]c4ccc(NC(=O)C5CCCc6ccccc65)cc34)cc2)CC1]

To a mixture of N-(3-iodo-1H-indazol-5-yl)-1,2,3,4-tetrahydronaphthalene-1-carboxamide (167 mg, 0.4 mmol) and 1-methyl-4-(4-(4,4,5,5-tetramethyl-1,3,2-dioxaborolan-2-yl)phenoxy)piperidine (130 mg, 0.44 mmol) in EtOH (10 mL) was added 1 M aq Na$_2$CO$_3$ (0.8 mL, 0.8 mmol), followed by Pd(PPh$_3$)$_4$ (23 mg, 0.02 mmol). The resulting mixture was purged with Ar and microwaved 2 h at 130° C. After removal of solvents, it was redissolved in DMF/TFA (5 mL/0.5 mL), filtered and purified by prep-HPLC to give the title compound as a TFA salt (white solid, 130 mg, 55%). $^1$H NMR (400 MHz, CD$_3$OD) δ 8.49 (s, 1H), 7.85-7.77 (m, 2H), 7.54-7.46 (m, 2H), 7.16-6.97 (m, 6H), 4.65-4.61 (m, 0.7H), 4.50-4.42 (m, 0.3H), 3.91 (t, J=7.0 Hz, 1H), 3.50-3.44 (m, 0.7H), 3.30-3.17 (m, 2.8H; partially overlapped with CD$_3$OD solvent residue), 3.07-2.98 (m, 0.7H), 2.86-2.70 (m, 5.3H), 2.27-1.65 (m, 8H); MS ESI 481.3 [M+H]$^+$, calcd for [C$_{30}$H$_{32}$N$_4$O$_2$+H]$^+$ 481.3.

Example A19

N-(cyclopropyl(phenyl)methyl)-3-(3-methoxy-4-((1-methylpiperidin-4-yl)oxy)phenyl)-1H-indazole-5-carboxamide

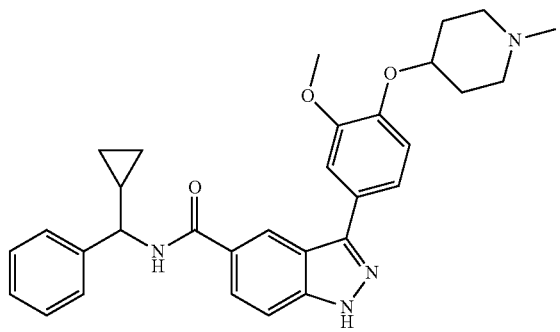 [SMILES: COc1cc(-c2n[nH]c3ccc(C(=O)NC(c4ccccc4)C4CC4)cc23)ccc1OC1CCN(C)CC1]

The title compound was synthesized according to the General Method C, utilizing N-(cyclopropyl(phenyl)methyl)-3-iodo-1H-indazole-5-carboxamide (70 mg, 0.17 mmol), 4-(2-methoxy-4-(4,4,5,5-tetramethyl-1,3,2-dioxaborolan-2-yl)phenoxy)-1-methylpiperidine (70 mg, 0.20 mmol), PdCl$_2$dppf (6.9 mg, 0.0085 mmol), satd. Na$_2$CO$_3$ (0.5 mL), and 1.5 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 26 mg, 25%). $^1$H NMR (400 MHz, CD$_3$OD) δ ppm 8.59 (s, 1 H), 7.95 (d, J=8.3 Hz, 1 H), 7.52-7.67 (m, 3 H), 7.48 (d, J=7.0 Hz, 2 H), 7.33 (t, J=7.0 Hz, 2 H), 7.13-7.28 (m, 2 H), 4.71 (br. s., 1 H), 4.51-4.59 (m, 0.3 H), 4.48 (br. t., J=8.2 Hz, 1 H), 3.90-4.02 (m, 3 H), 3.56-3.67 (m, 0.7 H), 3.37-3.52 (m, 1.3 H), 3.07-3.19 (m, 0.7 H), 2.84-2.97 (m, 3 H), 1.87-2.43 (m, 5 H), 1.35-1.45 (m, 1 H), 0.65 (d, J=7.8 Hz, 2 H), 0.37-0.54 (m, 2 H); MS ESI 511.6 [M+H]$^+$, calcd for [C$_{31}$H$_{34}$N$_4$O$_3$+H]$^+$ 511.3.

Example A20

N-(3-(3,4-dihydro-2H-benzo[b][1,4]dioxepin-7-yl)-1H-indazol-5-yl)-2-(pyrrolidin-1-yl)-2-(thiophen-3-yl)acetamide

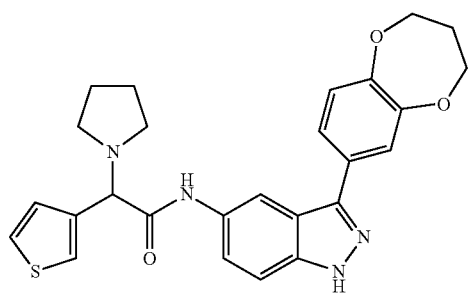 [SMILES: O=C(Nc1ccc2[nH]nc(-c3ccc4c(c3)OCCCO4)c2c1)C(c1ccsc1)N1CCCC1]

To a mixture of N-(3-iodo-1H-indazol-5-yl)-2-(pyrrolidin-1-yl)-2-(thiophen-3-yl)acetamide (90 mg, 0.2 mmol) and (3,4-dihydro-2H-benzo[b][1,4]dioxepin-7-yl)boronic acid (39 mg, 0.2 mmol) in EtOH (4.5 mL) was added 1 M aq Na$_2$CO$_3$ (0.4 mL, 0.4 mmol), followed by Pd(PPh$_3$)$_4$ (11.6 mg, 0.01 mmol). The resulting mixture was purged with Ar and microwaved 2.5 h at 125° C. After removal of solvents, it was redissolved in DMF (5 mL), filtered, purified by prep-HPLC twice and triturated with Et$_2$O to give the title compound as a TFA salt (light brown solid, 33.5 mg, 28%). $^1$H NMR (400 MHz, CD$_3$OD) δ 8.36 (s, 1H), 7.87 (dd, J=2.8 Hz, 1.2 Hz, 1H), 7.64 (dd, J=5.0 Hz, 3.0 Hz, 1H), 7.52 (d, J=1.2 Hz, 2H), 7.49 (d, J=2.0 Hz, 1H), 7.46 (dd, J=8.2 Hz, 2.2 Hz, 1H), 7.38 (dd, J=4.8 Hz, 1.2 Hz, 1H), 7.08 (d, J=8.4 Hz, 1H), 5.26 (s, 1H), 4.27-4.18 (m, 4H), 3.87 (brs, 1H), 3.35-3.05 (m, 3H), 2.25-1.93 (m, 6H); MS ESI 475.3 [M+H]$^+$, calcd for [C$_{26}$H$_{26}$N$_4$O$_3$S+H]$^+$ 475.2.

Example A21

N-(3-(3-methoxy-4-((1-methylpiperidin-4-yl)oxy)phenyl)-1H-indazol-5-yl)-2-(pyrrolidin-1-yl)-2-(thiophen-3-yl)acetamide

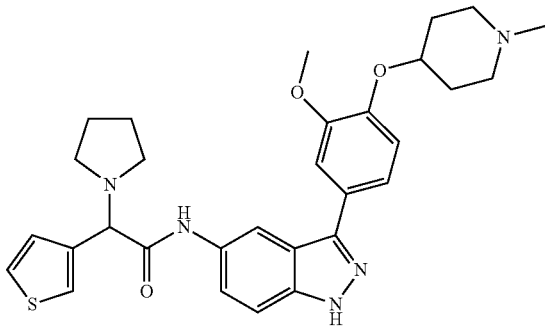

The title compound was synthesized according to the General Method C, utilizing N-(3-iodo-1H-indazol-5-yl)-2-(pyrrolidin-1-yl)-2-(thiophen-3-yl)acetamide (76 mg, 0.17 mmol), 4-(2-methoxy-4-(4,4,5,5-tetramethyl-1,3,2-dioxaborolan-2-yl)phenoxy)-1-methylpiperidine (70 mg, 0.20 mmol), PdCl$_2$dppf (6.9 mg, 0.0085 mmol), satd. aq Na$_2$CO$_3$ (0.5 mL), and 1.5 mL of PhMe:EtOH (1:1). The vial was charged with Ar and heated in the microwave reactor at 125° C. for 2 h. Purification by RPHPLC, followed by trituration with Et$_2$O gave the title compound as a bis-TFA salt (light brown solid, 41 mg, 31%). $^1$H NMR (400 MHz, CD$_3$OD) δ ppm 8.45 (s, 1 H), 7.87 (s, 1 H), 7.63 (br. s., 1 H), 7.42-7.59 (m, 4 H), 7.37 (d, J=4.8 Hz, 1 H), 7.20 (d, J=8.0 Hz, 1 H), 5.29 (s, 1 H), 4.65-4.76 (m, 1 H), 4.50-4.61 (m, 0.3 H), 3.98 (s, 3 H), 3.55-3.69 (m, 0.7 H), 3.37-3.54 (m, 4 H), 3.06-3.27 (m, 3 H), 2.93 (s, 3 H), 1.89-2.50 (m, 8 H); MS ESI 546.1 [M+H]$^+$, calcd for [C$_{30}$H$_{35}$N$_5$O$_3$S+H]$^+$ 546.3.

Example A22

N-(3-(4-morpholinophenyl)-1H-indazol-5-yl)-1,2,3,4-tetrahydronaphthalene-1-carboxamide

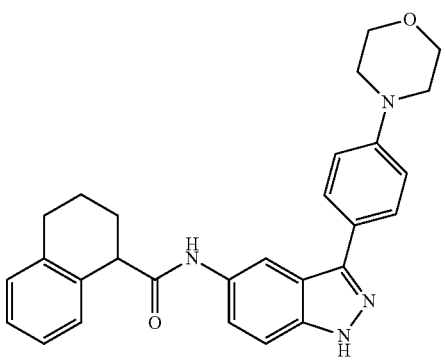 [SMILES: O=C(Nc1ccc2[nH]nc(-c3ccc(N4CCOCC4)cc3)c2c1)C1CCCc2ccccc21]

To a mixture of N-(3-iodo-1H-indazol-5-yl)-1,2,3,4-tetrahydronaphthalene-1-carboxamide (167 mg, 0.4 mmol) and (4-morpholinophenyl)boronic acid (91 mg, 0.44 mmol) in EtOH (12 mL) was added 1 M aq Na$_2$CO$_3$ (0.8 mL, 0.8 mmol), followed by Pd(PPh₃)₄ (23 mg, 0.02 mmol). The resulting mixture was purged with Ar and microwaved 2 h at 125° C. After removal of solvents, it was purified by flash chromatography (MeOH/DCM 0-10%) and RPHPLC to give the title compound as a TFA salt (light yellow solid, 59.8 mg, 26%). $^1$H NMR (400 MHz, CD₃OD) δ 8.49 (s, 1H), 8.43 (d, J=8.8 Hz, 2H), 7.49 (s, 2H), 7.16-7.02 (m, 6H), 3.90 (t, J=7.0 Hz, 1H), 3.81 (t, J=4.6 Hz, 4H), 3.19 (brs, 4H), 2.89-2.70 (m, 2H), 2.18-2.02 (m, 3H), 1.77-1.67 (m, 1H); MS ESI 453.3 [M+H]⁺, calcd for [C₂₈H₂₈N₄O₂+H]⁺ 453.2.

Example A23

N-(3-(4-(morpholinomethyl)phenyl)-1H-indazol-5-yl)-1,2,3,4-tetrahydronaphthalene-1-carboxamide

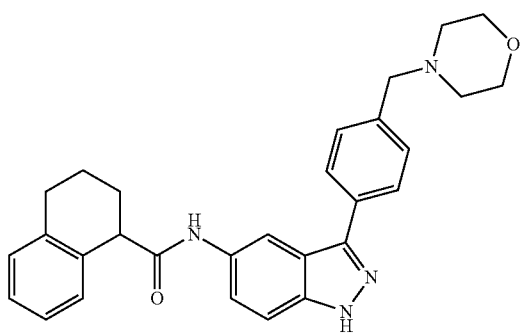 [SMILES: O=C(Nc1ccc2[nH]nc(-c3ccc(CN4CCOCC4)cc3)c2c1)C1CCCc2ccccc21]

To a mixture of N-(3-iodo-1H-indazol-5-yl)-1,2,3,4-tetrahydronaphthalene-1-carboxamide (167 mg, 0.4 mmol) and 4-(4-(4,4,5,5-tetramethyl-1,3,2-dioxaborolan-2-yl)benzyl)morpholine (121 mg, 0.4 mmol) in EtOH (12 mL) was added 1 M aq Na₂CO₃ (0.8 mL, 0.8 mmol), followed by Pd(PPh₃)₄ (23 mg, 0.02 mmol). The resulting mixture was purged with Ar and microwaved 2 h at 125° C. After removal of solvents, it was redissolved in DMF/TFA (6 mL/0.5 mL) and purified by prep-HPLC to give the title compound as a TFA salt (white solid, 135 mg, 58%). $^1$H NMR (400 MHz, CD₃OD) δ 8.50 (s, 1H), 7.98 (d, J=8.0 Hz, 2H), 7.56-7.47 (m, 4H), 7.15 (d, J=7.2 Hz, 1H), 7.12-7.03 (m, 3H), 4.26 (s, 2H), 3.98-3.88 (m, 3H), 3.67 (t, J=12.0 Hz, 2H), 3.28 (d, J=11.6 Hz, 2H), 3.08 (t, J=10.8 Hz, 2H), 2.86-2.69 (m, 2H), 2.20-2.02 (m, 3H), 1.77-1.67 (m, 1H); MS ESI 467.3 [M+H]⁺, calcd for [C₂₉H₃₀N₄O₂+H]⁺ 467.2.

Example A24

N-(cyclopropyl(phenyl)methyl)-3-(4-((1-methylpiperidin-4-yl)oxy)phenyl)-1H-indazole-5-carboxamide

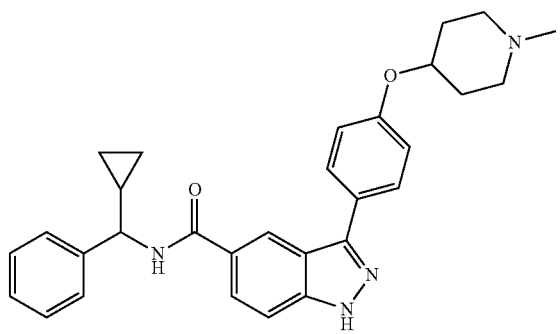 [SMILES: CN1CCC(Oc2ccc(-c3n[nH]c4ccc(C(=O)NC(c5ccccc5)C5CC5)cc34)cc2)CC1]

The title compound was synthesized according to the General Method C, utilizing N-(cyclopropyl(phenyl)methyl)-3-iodo-1H-indazole-5-carboxamide (200 mg, 0.48 mmol), (4-((1-methylpiperidin-4-yl)oxy)phenyl)boronic acid pinacol ester (152 mg, 0.48 mmol), PdCl₂dppf (20 mg, 0.024 mmol), satd. aq Na₂CO₃ (1.25 mL), and 3.75 mL of PhMe:EtOH (1:1). The vial was charged with Ar and heated in the microwave reactor at 125° C. for 2 h. Purification by RP HPLC, followed by flash chromatography (SiO₂, Biotage 25 g, 0-30% MeOH in CH₂Cl₂) gave the title compound (white solid, 80 mg, 35%). $^1$H NMR (400 MHz, CD₃OD) δ ppm 8.60 (s, 1 H), 7.95 (d, J=9.0 Hz, 1 H), 7.90 (d, J=8.8 Hz, 2 H), 7.59 (d, J=8.8 Hz, 1 H), 7.47 (d, J=7.5 Hz, 2 H), 7.31 (t, J=7.5 Hz, 2 H), 7.22 (t, J=7.5 Hz, 1 H), 7.08 (d, J=8.8 Hz, 2 H), 4.55 (br. s, 1 H), 4.47 (d, J=9.3 Hz, 1 H), 2.91-3.03 (m, 2 H), 2.63-2.76 (m, 2 H), 2.50 (s, 3 H), 2.02-2.14 (m, 2 H), 1.85-1.98 (m, 2 H), 1.34-1.44 (m, 1 H), 0.64 (d, J=8.3 Hz, 2 H), 0.45 (dd, J=9.5, 4.52 Hz, 2 H); MS ESI 481.4 [M+H]⁺, calcd for [C₃₀H₃₂N₄O₂+H]⁺ 481.3.

Example A25

N-(3-(4-((1-methylpiperidin-4-yl)amino)phenyl)-1H-indazol-5-yl)-2-yl)phenyl)piperidin-1-yl)-2-thiophen-3-yl)acetamide A. 1-methyl-N-(4-(4,4,5,5-tetramethyl-1,3,2-dioxaborolan-2-yl)phenyl)piperidin-4-amine

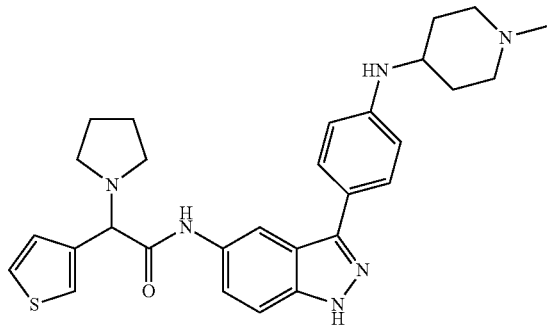 [SMILES: CN1CCC(Nc2ccc(-c3n[nH]c4ccc(NC(=O)C(c5ccsc5)N5CCCC5)cc34)cc2)CC1]

NaBH(OAc)₃ (290 mg, 1.36 mmol) was added to a solution of N-methyl-4-piperidone (155 mg, 1.36 mmol) in 1,2-dichloroethane (10 mL) at rt. Then 4-(4,4,5,5-tetramethyl-1,3,2-dioxaborolan-2-yl)aniline (200 mg, 0.912 mmol) and 2-3 drops of acetic acid under N₂ were added to the mixture at rt and stirring was continued for 18 h. Sat aq NaHCO₃ (10 mL) was added in one lot at the same temperature and the mixture was stirred for 15 min. DCM (10 mL) was then added and the layers were separated. The aq. layer was extracted using DCM (10 mL), and the combined organic layer was washed with brine and dried (Na₂SO₄). The solvent was removed under vacuum. The resultant oily residue purified by Biotage (25 g SiO₂ column, 0-50% MeOH in DCM) to give the title compound (cream solid, 84 mg, 29%). $^1$H NMR (400 MHz, CDCl₃) δ 7.63 (d, J=8.8 Hz, 2H), 6.58 (d, J=8.8 Hz, 2H), 3.77 (d, J=7.6 Hz, 1H), 3.35 (br.s, 1H), 2.82-2.79 (br.d, 1H), 2.30 (s, 3H), 2.14 (t, J=1.2 Hz, 2H), 2.07-2.03 (m, 2H), 1.66 (br.s, 1H), 1.54-1.45 (m, 2H), 1.32 (s, 12H); MS ESI 317.1[M+H]⁺, calcd for [C₁₈H₂₉BN₂O₂+H]⁺ 317.2.

B. N-(3-(4-((1-methylpiperidin-4-yl)amino)phenyl)-1H-indazol-5-yl)-2-(pyrrolidin-1-yl)-2-thiophen-3-yl)acetamide The title compound was synthesized according to General Method C by using a sealed degassed mixture of N-(3-iodo-1H-indazol-5-yl)-2-(pyrrolidin-1-yl)-2-(thiophen-3-yl)acetamide (50 mg, 0.11 mmol), 1-methyl-N-(4-(4,4,5,5-tetramethyl-1,3,2-dioxaborolan-2-yl)phenyl)piperidin-4-amine (42 mg, 0.13 mmol), Pd(PPh$_3$)$_4$ (7 mg, 0.005 mmol), 1 M aq Na$_2$CO$_3$ (0.22 mL) in PhMe/EtOH (2.25 mL, 1:0.5 mixture) under Ar was heated under microwave irradiation at 125° C. for 2 h. The reaction mixture was diluted with EtOAc (10 mL) and washed with H$_2$O and brine (5 mL each), dried (Na$_2$SO$_4$), and concentrated under vacuum to give brown oily residue. The crude product was purified by Biotage (100 g SiO$_2$, 0-10% 2 M NH$_3$-MeOH in DCM; then RP column C18 60 g, 10-80% MeOH in 0.1% TFA-H$_2$O) to give the title compound as a TFA salt (pale yellow solid, 9 mg, 11%). $^1$H NMR (400 MHz, CD$_3$OD) δ 8.34 (s, 1H), 7.87 (t, J=1.6 Hz, 1H), 7.72 (d, J=8.4 Hz, 2H), 7.66 (dd, J=3.2 Hz, J=5.2 Hz 1H), 7.53-7.50 (m, 2H), 7.38 (dd, J=4.8 Hz, J=1.2 Hz, 2H), 6.89-6.85 (m, 2H), 5.23 (s, 1H), 4.44 (t, J=4.8 Hz, 1H), 3.88-3.60 (br.m, 4H), 3.26-3.09 (br.m, 4H), 2.92 (s, 3H), 2.38-2.34 (br.m, 2H), 2.24-2.15 (br.m, 4H), 2.01-1.97 (br.m, 1H), 1.79-1.70 (br.m, 1H); MS ESI 515.1 [M+H]$^+$, calcd for [C$_{29}$H$_{34}$N$_6$OS+H]$^+$ 515.2.

Example A26

(R)-3-(4-((1-methylpiperidin-4-yl)oxy)phenyl)-N-(1,2,3,4-tetrahydronaphthalen-1-yl)-1H-indazole-5-carboxamide

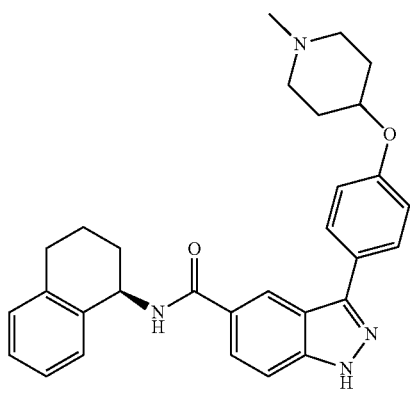 [SMILES: CN1CCC(Oc2ccc(-c3n[nH]c4ccc(C(=O)N[C@@H]5CCCc6ccccc65)cc34)cc2)CC1]

To a solution of (R)-1,2,3,4-tetrahydronaphthalen-1-amine (735 mg, 5 mmol), 1H-indazole-5-carboxylic acid (810 g, 5 mmol) in DMF (30 mL) was added $^i$Pr$_2$NEt (2.61 mL, 15 mmol), followed by TBTU (1.6 g, 5 mmol). The resulting mixture was stirred for 2 h at 0° C. Attempted iodination failed so was quenched with Na$_2$S$_2$O$_3$/H$_2$O to give (R)-N-(1,2,3,4-tetrahydronaphthalen-1-yl)-1H-indazole-5-carboxamide (orange solid, 1.64 g, may contain H$_2$O). $^1$H NMR (400 MHz, DMSO-d$_6$) δ 0.79 (s, 1H), 8.76 (d, J=8.4 Hz, 1H), 8.39 (s, 1H), 8.18 (s, 1H), 7.92 (dd, J=8.6 Hz, 1.4 Hz, 1H), 7.56 (d, J=8.8 Hz, 1H), 7.23-7.10 (m, 4H), 5.30-5.20 (m, 1H), 2.85-2.70 (m, 2H), 2.05-1.90 (m, 2H), 1.90-1.70 (m, 2H); MS ESI 292.1 [M+H]$^+$, calcd for [C$_{18}$H$_{17}$N$_3$O+H]$^+$ 292.1.

A solution of (R)-N-(1,2,3,4-tetrahydronaphthalen-1-yl)-1H-indazole-5-carboxamide (29.1 mg, 0.1 mmol), NBS (19.6 mg, 0.11 mmol) in EtOH (5 mL) was refluxed for 1 h. Additional (R)-N-(1,2,3,4-tetrahydronaphthalen-1-yl)-1H-indazole-5-carboxamide (582 mg, 2 mmol), NBS (392 mg, 2.2 mmol) and EtOH (30 mL) were added and it was refluxed for 4 h. After removal of solvents, it was purified by flash chromatography (MeOH/DCM 0-10%) to give crude (R)-3-bromo-N-(1,2,3,4-tetrahydronaphthalen-1-yl)-1H-indazole-5-carboxamide (dark beige solid, 0.77 g). MS ESI 370.0 [M+H]$^+$, calcd for [C$_{18}$H$_{16}$BrN$_3$O+H]$^+$ 370.0.

To a mixture of (R)-3-bromo-N-(1,2,3,4-tetrahydronaphthalen-1-yl)-1H-indazole-5-carboxamide (163 mg, 0.44 mmol) and 1-methyl-4-(4-(4,4,5,5-tetramethyl-1,3,2-dioxaborolan-2-yl)phenoxy)piperidine (127 mg, 0.4 mmol) in EtOH (12 mL) was added 1 M aq Na$_2$CO$_3$ (0.8 mL, 0.8 mmol), followed by Pd(PPh$_3$)$_4$ (23 mg, 0.02 mmol). The resulting mixture was purged with Ar and microwaved 2 h at 130° C. After removal of solvents, it was redissolved in DMF/TFA (6 mL/0.5 mL) and purified by prep-HPLC to give the title compound as a TFA salt (white solid, 85 mg, 36%). $^1$H NMR (400 MHz, CD$_3$OD) δ 8.59 (s, 1H), 7.97-7.88 (m, 3H), 7.58 (d, J=8.0 Hz, 1H), 727-7.23 (m, 1H), 7.14-7.05 (m, 5H), 5.35 (t, J=6.6 Hz, 1H), 4.80-4.76 (m, 0.7H), 4.65-4.56 (m, 0.3H), 3.64-3.57 (m, 0.7H), 3.43-3.28 (m, 2.6H; partially overlapped with CD$_3$OD solvent residue), 3.21-3.13 (m, 0.7H), 2.91 (s, 3H), 2.90-2.72 (m, 2H), 2.42-1.76 (m, 8H); MS ESI 481.4 [M+H]$^+$, calcd for [C$_{30}$H$_{32}$N$_4$O$_2$+H]$^+$ 481.3.

Example A27

(R)-2-methoxy-N-(3-(4-((1-methylpiperidin-4-yl)oxy)phenyl)-1H-indazol-5-yl)-2-phenylacetamide

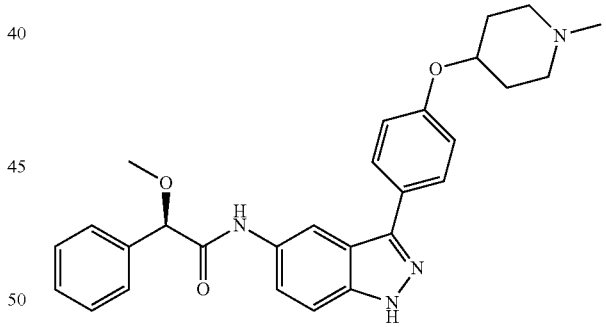

The title compound was synthesized according to the General Method General Method C utilizing ((R)-N-(3-iodo-1H-indazol-5-yl)-2-methoxy-2-phenylacetamide (0.060 g, 0.15 mmol), 1-methyl-4-(4-(4,4,5,5-tetramethyl-1,3,2-dioxaborolan-2-yl)phenoxy)piperidine (71 mg, 0.22 mmol), PdCl$_2$dppf.CH$_2$Cl$_2$ (7 mg, 0.09 mmol), satd aq Na$_2$CO$_3$ (0.5 mL) in PhMe (1.5 mL) and EtOH (1.5 mL) under microwave heating (130° C., 90 min). The title compound was isolated as a white powder (42.5 mg, 60%). $^1$H NMR (400 MHz, CD$_3$OD) δ ppm 8.36 (d, J=1.0 Hz, 1 H), 7.83 (d, J=8.8 Hz, 2 H), 7.47-7.59 (m, 4 H), 7.31-7.45 (m, 3 H), 7.07 (d, J=8.8 Hz, 2 H), 4.83 (s, 1 H), 4.52 (br. s., 1 H), 3.46 (s, 3 H), 2.85 (br. s., 2 H), 2.55 (br.s., 2 H), 2.42 (s, 3 H), 1.98-2.12 (m, 2 H), 1.93-1.82 (br.s, 2 H); MS ESI [M+H]$^+$ 471.3, calcd for [C$_{28}$H$_{30}$N$_4$O$_3$+H]$^+$ 471.2.

Example A28

N-(3-(4-(piperidin-4-yloxy)phenyl)-1H-indazol-5-yl)-2-(pyrrolidin-1-yl)-2-(thiophen-3-yl)acetamide A. tert-butyl 4-(4-(5-(2-(pyrrolidin-1-yl)-2-(thiophen-3-yl)acetamido)-1H-indazol-3-yl)phenoxy)piperidine-1-carboxylate

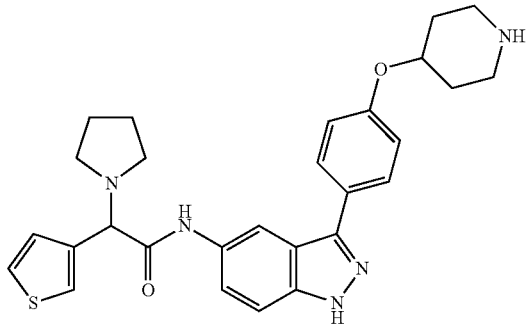 [SMILES: O=C(Nc1ccc2[nH]nc(-c3ccc(OC4CCNCC4)cc3)c2c1)C(c1ccsc1)N1CCCC1]

Using General Method C2, N-(3-iodo-1H-indazol-5-yl)-2-(pyrrolidin-1-yl)-2-(thiophen-3-yl)acetamide (132.8 mg, 0.294 mmol) and tert-butyl 4-(4-(4,4,5,5-tetramethyl-1,3,2-dioxaborolan-2-yl)phenoxy)piperidine-1-carboxylate (142.3 mg, 0.352 mmol) gave the title compound after 3 h at 120° C. in the microwave (102.7 mg, 58%) after work-up using a PoraPak Rxn CX followed by purification by flash chromatography (SiO$_2$, 50-100 EtOAc in DCM). $^1$H NMR (400 MHz, CDCl$_3$) δ ppm 8.42 (s, 1 H), 7.89 (d, J=8.8 Hz, 2 H), 7.47 (dd, J=8.8, 2.0 Hz, 1 H), 7.44 (d, J=8.8 Hz, 1 H), 7.34 (s, 1 H), 7.29-7.33 (m, 1 H), 7.15 (dd, J=5.0, 1.3 Hz, 1 H), 7.04 (d, J=8.8 Hz, 2 H), 4.54 (dt, J=7.1, 3.6 Hz, 1 H), 4.16 (s, 1 H), 3.70-3.79 (m, 2 H), 3.33-3.41 (m, 2 H), 2.67 (d, J=6.8 Hz, 2 H), 2.56 (d, J=6.0 Hz, 2 H), 1.96 (br. s., 2 H), 1.74-1.89 (m, 6 H), 1.49 (s, 9 H). MS ESI 602.4 [M+H]$^+$, calcd for [C$_{33}$H$_{39}$N$_5$O$_4$S+H]$^+$ 602.38.

B. N-(3-(4-(piperidin-4-yloxy)phenyl)-1H-indazol-5-yl)-2-(pyrrolidin-1-yl)-2-(thiophen-3-yl)acetamide tert-Butyl4-(4-(5-(2-(pyrrolidin-1-yl)-2-(thiophen-3-yl)acetamido)-1H-indazol-3-yl)phenoxy)piperidine-1-carboxylate (102 mg, 0.169 mmol) was dissolved in DCM (4 mL) and TFA (1 mL) was added. The resulting mixture was stirred at rt for 3 h. The crude reaction mixture was partitioned between EtOAc (150 mL) and sat aq NaHCO$_3$ (25 mL). The organic layer was washed with H$_2$O (25 mL) and brine (25 mL), dried (Na$_2$SO$_4$), filtered and concentrated to dryness. Purification by flash chromatography (SiO$_2$, 0-20% 2 M NH$_3$-MeOH in DCM) gave the title compound (beige solid, 26.8 mg, 31%). $^1$H NMR (400 MHz, CDCl$_3$) δ ppm 9.25 (s, 1 H), 8.41 (d, J=1.0 Hz, 1 H), 7.86 (d, J=8.8 Hz, 2 H), 7.44 (dd, J=9.0, 1.8 Hz, 1 H), 7.40 (d, J=8.6 Hz, 1 H), 7.32-7.35 (m, 1 H), 7.29-7.32 (m, 1 H), 7.15 (dd, J=4.9, 1.1 Hz, 1 H), 7.01 (d, J=8.8 Hz, 2 H), 4.45 (tt, J=7.7, 3.8 Hz, 1 H), 4.16 (s, 1 H), 3.15-3.23 (m, 2 H), 2.82 (ddd, J=12.4, 8.8, 3.4 Hz, 2 H), 2.63-2.71 (m, 2 H), 2.51-2.58 (m, 2 H), 2.06 (ddt, J=12.7, 6.4, 3.2, 3.2 Hz, 2 H), 1.84 (br. s., 4 H), 1.75 (dtd, J=12.8, 8.5, 8.5, 3.9 Hz, 2 H). MS ESI 502.2 [M+H]$^+$, calcd for [C$_{28}$H$_{31}$N$_5$O$_2$S+H]$^+$ 502.23.

Example A29

2-(pyrrolidin-1-yl)-N-(3-(4-((tetrahydro-2H-pyran-4-yl)oxy)phenyl)-1H-indazol-5-yl)-2-(thiophen-3-yl)acetamide

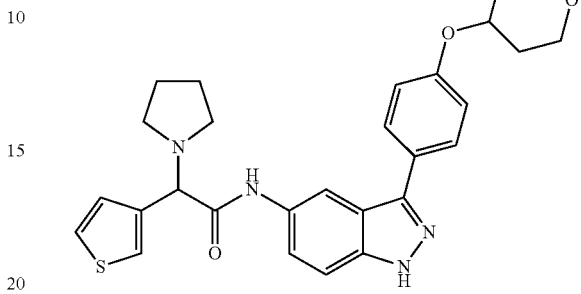

The title compound was synthesized according to General Method C by using a sealed degassed mixture of N-(3-iodo-1H-indazol-5-yl)-2-(pyrrolidin-1-yl)-2-(thiophen-3-yl)acetamide (800 mg, 1.76 mmol), 4,4,5,5-tetramethyl-2-(4-((tetrahydro-2H-pyran-4-yl)oxy)phenyl)-1,3,2-dioxaborolane (538 mg, 1.76 mmol), Pd(PPh$_3$)$_4$ (204 mg, 0.176 mmol), 1 M aq Na$_2$CO$_3$ (3.54 mL) in PhMe/EtOH (20 mL, 1:0.5 mixture) under Ar was heated under microwave irradiation at 125° C. for 4 h. The reaction mixture was diluted with EtOAc (120 mL) and washed with H$_2$O (20 mL) followed by brine (20 mL), dried (Na$_2$SO$_4$) and concentrated under vacuum to give brown oily residue. The crude product was purified by Biotage (100 g SiO2, 0-20% MeOH in DCM; then RP HPLC C18 60 g column, 10-80% MeOH in 0.1% TFA-H$_2$O) to give the title compound as a TFA salt (light brown solid, 355 mg, 32.5%). $^1$H NMR (400 MHz, CD$_3$OD) δ 8.38 (s, 1H), 7.87-7.80 (m, 3H), 7.64-7.62 (m, 1H), 7.54-7.48 (m, 2H), 7.38 (d, J=5.2 Hz, 1H), 7.09 (d, J=8.4 Hz, 2H), 5.26 (s, 1H), 4.65-4.59 (m, 1H), 3.99-3.86 (br.m, 3H), 3.63-3.57 (br.m, 2H), 3.21-3.08 (br.m, 2H), 2.16-2.03 (br.m, 7H) 1.78-1.72 (br.m, 2H); MS ESI 503.3 [M+H]$^+$, calcd for [C$_{28}$H$_{30}$N$_4$O$_3$S+H]$^+$ 503.6.

Example A30

N-(3-(4-((1-isopropylpiperidin-4-yl)oxy)phenyl)-1H-indazol-5-yl)-2-(pyrrolidin-1-yl)-2-(thiophen-3-yl)acetamide

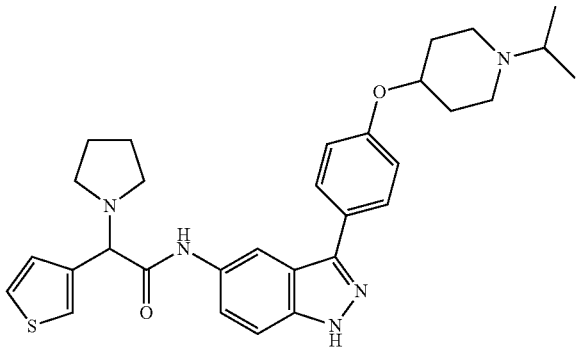 [SMILES: CC(C)N1CCC(Oc2ccc(-c3n[nH]c4ccc(NC(=O)C(c5ccsc5)N5CCCC5)cc34)cc2)CC1]

Using General Method C2, N-(3-iodo-1H-indazol-5-yl)-2-(pyrrolidin-1-yl)-2-(thiophen-3-yl)acetamide (53.1 mg, 0.117 mmol) and 1-isopropyl-4-(4-(4,4,5,5-tetramethyl-1,3,2-dioxaborolan-2-yl)phenoxy)piperidine (47 mg, 0.14 mmol) heated for 3 h at 120° C. in the microwave followed by work-up using a PoraPak RXn CX followed by purification by flash chromatography (RPC18, 10-80% MeOH in 0.1% TFA-H$_2$O; repeated PoraPak work-up; then SiO$_2$, 0-20% 2 M NH$_3$-MeOH in DCM) gave the title compound (beige solid, 14.0 mg, 22%). $^1$H NMR (400 MHz, CDCl$_3$) δ ppm 9.23 (s, 1 H), 8.39 (d, J=1.3 Hz, 1 H), 7.87 (d, J=8.8 Hz, 2 H), 7.47 (dd, J=9.0, 1.5 Hz, 1 H), 7.39 (d, J=9.0 Hz, 1 H), 7.32-7.35 (m, 1 H), 7.29-7.32 (m, 1 H), 7.15 (dd, J=4.9, 1.1 Hz, 1 H), 7.03 (d, J=8.8 Hz, 2 H), 4.39 (tt, J=7.3, 3.8 Hz, 1 H), 4.15 (s, 1 H), 2.77-2.90 (m, 3 H), 2.62-2.72 (m, 2 H), 2.42-2.59 (m, 4 H), 2.03-2.14 (m, 2 H), 1.87-1.95 (m, 2 H), 1.84 (br. s., 4 H), 1.11 (d, J=6.5 Hz, 6 H). MS ESI 544.2 [M+H]$^+$, calcd for [C$_{31}$H$_{37}$N$_5$O$_2$S+H]$^+$ 544.27.

Example A31

N-(3-(4-((1-methylpiperidin-4-yl)oxy)phenyl)-1H-indazol-5-yl)-2-(piperidin-1-yl)-2-(thiophen-3-yl)acetamide

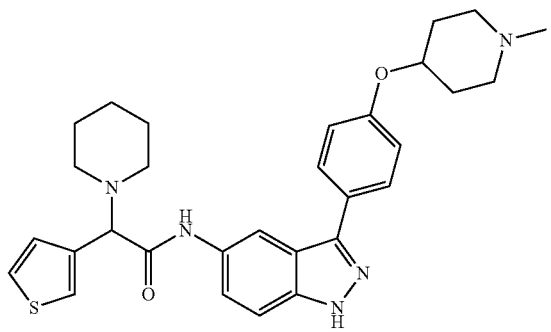 [SMILES: CN1CCC(Oc2ccc(-c3n[nH]c4ccc(NC(=O)C(c5ccsc5)N5CCCCC5)cc34)cc2)CC1]

The title compound was synthesized according to General Method C by using a mixture of N-(3-iodo-1H-indazol-5-yl)-2-(piperidin-1-yl)-2-(thiophen-3-yl)acetamide (125 mg, 0.268 mmol), 1-methyl-4-(4-(4,4,5,5-tetramethyl-1,3,2-dioxaborolan-2-yl)phenoxy)piperidine (103 mg, 0.324 mmol), Pd(PPh$_3$)$_4$ (15.5 mg, 0.0134 mmol) and 1 M aq Na$_2$CO$_3$ (0.54 mL) in PhMe/EtOH (3.75 mL, 2:1 mixture) in vial under Ar was heated under microwave irradiation at 125° C. for 2 h. The reaction mixture was diluted with EtOAc (10 mL) and washed it with of H$_2$O (5 mL) followed by brine (5 mL), dried (Na$_2$SO$_4$) and concentrated under vacuum. Purification by prep-HPLC gave the title compound as a TFA salt (off white solid, 27 mg, 16%). $^1$H NMR (400 MHz, CD$_3$OD) δ 8.37 (s, 1H), 7.88-7.84 (m, 3H), 7.67-7.65 (m, 1H), 7.55-7.49 (m, 2H), 7.39 (dd, J=5.2 Hz, J=1.2 Hz, 1H), 7.21 (d, J=9.2 Hz, 1H), 7.16 (d, J=8.4 Hz, 1H), 5.21 (s, 1H), 3.78-3.75 (m, 1H), 3.67-3.60 (br.m, 1H), 3.46-3.36 (br.m, 3H), 3.22-3.08 (br.m, 3H), 2.95 (s, 3H), 2.46-2.43 (br.m, 2H), 2.18-1.79 (br.m, 7H), 1.6-1.51 (br.m, 1H), 1H merged with solvent peak; MS ESI 530.2 [M+H]$^+$, calcd for [C$_{30}$H$_{35}$N$_5$O$_2$S+H]$^+$ 530.2.

Example A32

N-(3-(4-morpholinophenyl)-1H-indazol-5-yl)-2-(piperidin-1-yl)-2-(thiophen-3-yl)acetamide

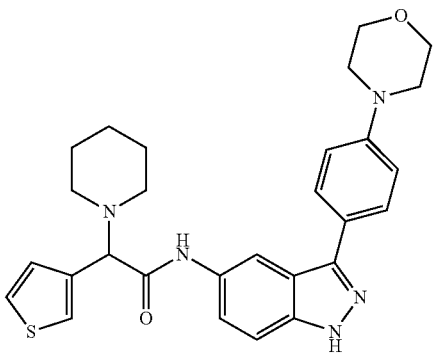 [SMILES: O=C(Nc1ccc2[nH]nc(-c3ccc(N4CCOCC4)cc3)c2c1)C(c1ccsc1)N1CCCCC1]

The title compound was synthesized according to General Method C by using a sealed degassed mixture of N-(3-iodo-1H-indazol-5-yl)-2-(piperidin-1-yl)-2-(thiophen-3-yl)acetamide (125 mg, 0.268 mmol), 4-(Morpholino)phenylboronic acid (67 mg, 0.268 mmol), Pd(PPh$_3$)$_4$ (15.5 mg, 0.013 mmol), 1 M aq Na$_2$CO$_3$ (0.80 mL) in PhMe/EtOH (3.75 mL, 1:0.5 mixture) under Ar was heated under microwave irradiation at 125° C. for 2 h. The reaction mixture was diluted with EtOAc (25 mL) and washed with H$_2$O followed by brine (10 mL each), dried (Na$_2$SO$_4$) and concentrated under vacuum. Purification by flash chromatography (SiO$_2$, 0-20% MeOH in DCM, then RP HPLC C18 60 g, 10-80% MeOH in 0.1% TFA-H$_2$O) gave the title compound as a TFA salt (yellow solid, 51 mg, 26%). $^1$H NMR (400 MHz, CD$_3$OD) δ 8.40 (s, 1H), 7.88-7.83 (m, 3H), 7.66-7.64 (m, 1H), 7.54-7.48 (m, 2H), 7.38 (dd, J=5.2 Hz, J=1.2 Hz, 1H), 7.20 (d, J=8.8 Hz, 2H), 5.20 (s, 1H), 3.89 (t, J=4.8 Hz, 4H), 3.78-3.75 (br.m, 1H), 3.35-3.77 (m, 4H), 3.19-3.07 (br.m, 2H), 2.94-2.88 (br.m, 1H) 2.02-1.82 (br.m, 5H), 1.56-1.54 (br.m, 1H); MS ESI 502.3 [M+H]$^+$, calcd for [C$_{28}$H$_{31}$N$_5$O$_2$S+H]$^+$ 502.2.

Example A33

N-(cyclopropyl(thiophen-3-yl)methyl)-3-(4-((1-methylpiperidin-4-yl)oxy)phenyl)-1H-indazole-5-carboxamide

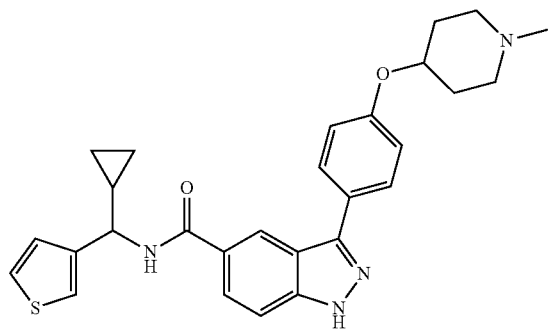 [SMILES: CN1CCC(Oc2ccc(-c3n[nH]c4ccc(C(=O)NC(c5ccsc5)C5CC5)cc34)cc2)CC1]

The title compound was synthesized according to the General Method C, utilizing N-(cyclopropyl(thiophen-3-yl)

methyl)-3-iodo-1H-indazole-5-carboxamide (100 mg, 0.24 mmol), (4-((1-methylpiperidin-4-yl)oxy)phenyl)boronic acid pinacol ester (75 mg, 0.24 mmol), PdCl$_2$dppf (10 mg, 0.012 mmol), satd. aq Na$_2$CO$_3$Na$_2$CO$_3$ (1 mL), and 3 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (beige solid, 70 mg, 49%). $^1$H NMR (400 MHz, CD$_3$OD) δ ppm 8.58 (s, 1 H), 7.95 (d, J=8.8 Hz, 3 H), 7.61 (d, J=8.8 Hz, 1 H), 7.33-7.39 (m, 2 H), 7.15-7.23 (m, 3 H), 4.74-4.86 (m, 2 H), 4.57-4.66 (m, 1 H), 3.33-3.50 (m, 3 H), 2.93 (s, 3 H), 2.04-2.33 (m, 4 H), 1.39-1.49 (m, 1 H), 0.68-0.76 (m, 1 H), 0.59-0.67 (m, 1 H), 0.43-0.53 (m, 2 H); MS ESI 487.4 [M+H]$^+$, calcd for [C$_{28}$H$_{30}$N$_4$O$_2$S+H]$^+$ 487.2.

Example A34

N-(3-(3-chloro-4-(piperidin-4-yloxy)phenyl)-1H-indazol-5-yl)-2-(pyrrolidin-1-yl)-2-(thiophen-3-yl)acetamide A. tert-butyl 4-(2-chloro-4-(5-(2-(pyrrolidin-1-yl)-2-(thiophen-3-yl)acetamido)-1H-indazol-3-yl)phenoxy)piperidine-1-carboxylate

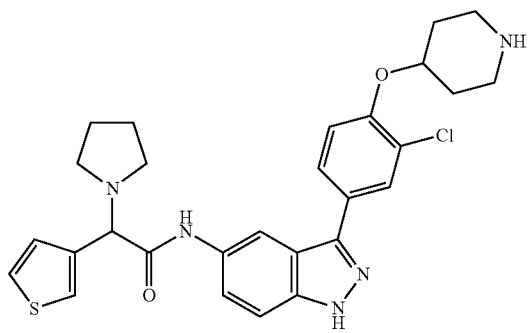 [SMILES: O=C(Nc1ccc2[nH]nc(-c3ccc(OC4CCNCC4)c(Cl)c3)c2c1)C(c1ccsc1)N1CCCC1]

Using General Method C2, N-(3-iodo-1H-indazol-5-yl)-2-(pyrrolidin-1-yl)-2-(thiophen-3-yl)acetamide (71.3 mg, 0.158 mmol) and tert-butyl 4-(2-chloro-4(4,4,5,5-tetramethyl-1,3,2-dioxaborolan-2-yl)phenoxy)piperidine-1-carboxylate (92.3 mg, 90% pure, 0.19 mmol) gave the title compound after 3 h at 120° C. in the microwave (68.4 mg, 68%) after aq. work-up using EtOAc followed by purification by flash chromatography (SiO$_2$, 50-100% EtOAc in DCM). $^1$H NMR (400 MHz, CDCl$_3$) δ ppm 9.26 (s, 1 H), 8.39 (s, 1 H), 7.98 (d, J=2.0 Hz, 1 H), 7.78 (dd, J=8.5, 2.0 Hz, 1 H), 7.48 (dd, J=9.0, 1.8 Hz, 1 H), 7.43 (d, J=9.0 Hz, 1 H), 7.33-7.35 (m, 1 H), 7.31 (dd, J=5.0, 3.0 Hz, 1 H), 7.16 (dd, J=4.8, 1.3 Hz, 1 H), 7.06 (d, J=8.8 Hz, 1 H), 4.60 (tt, J=6.2, 3.1 Hz, 1 H), 4.17 (s, 1 H), 3.65-3.73 (m, 2 H), 3.43-3.53 (m, 2 H), 2.68 (d, J=7.0 Hz, 2 H), 2.56 (d, J=6.0 Hz, 2 H), 1.88-1.99 (m, 4 H), 1.85 (br. s., 4 H), 1.49 (s, 9 H).

B. N-(3-(3-chloro-4-(piperidin-4-yloxy)phenyl)-1H-indazol-5-yl)-2-(pyrrolidin-1-yl)-2-(thiophen-3-yl)acetamide tert-Butyl-4-(2-chloro-4-(5-(2-(pyrrolidin-1-yl)-2-(thiophen-3-yl)acetamido)-1H-indazol-3-yl)phenoxy)piperidine-1-carboxylate (102 mg, 0.169 mmol) was dissolved in DCM (3 mL) and TFA (0.75 mL) was added. The resulting mixture was stirred at rt for 1 h, then the mixture was concentrated to dryness, and 2 M NH$_3$-MeOH was added and the mixture was concentrated to dryness. Purification by flash chromatography (SiO$_2$, 0-20% 2 M NH$_3$-MeOH in DCM) followed by PoraPak Rxn Cx work-up gave the title compound (beige solid, 48.3 mg, 85%). $^1$H NMR (400 MHz, CDCl$_3$) δ ppm 8.37 (d, J=1.3 Hz, 1 H), 7.98 (d, J=2.0 Hz, 1 H), 7.77 (dd, J=8.5, 2.0 Hz, 1 H), 7.47 (dd, J=9.0, 1.6 Hz, 1 H), 7.41 (d, J=9.0 Hz, 1 H), 7.33-7.36 (m, 1 H), 7.29-7.33 (m, 1 H), 7.16 (dd, J=5.0, 1.3 Hz, 1 H), 7.05 (d, J=8.5 Hz, 1 H), 4.45-4.53 (m, 1 H), 4.16 (s, 1 H), 3.16-3.27 (m, 2 H), 2.78 (ddd, J=12.4, 8.6, 3.4 Hz, 2 H), 2.63-2.72 (m, 2 H), 2.51-2.59 (m, 2 H), 2.04 (ddt, J=12.8, 6.5, 3.0, 3.0 Hz, 3 H), 1.75-1.89 (m, 6 H). MS ESI 536.1 [M+H]$^+$, calcd for [C$_{28}$H$_{30}$ClN$_5$O$_2$S+H]$^+$ 536.19.

Example A35

N-(cyclopropyl(thiophen-3-yl)methyl)-3-(4-morpholinophenyl)-1H-indazole-5-carboxamide

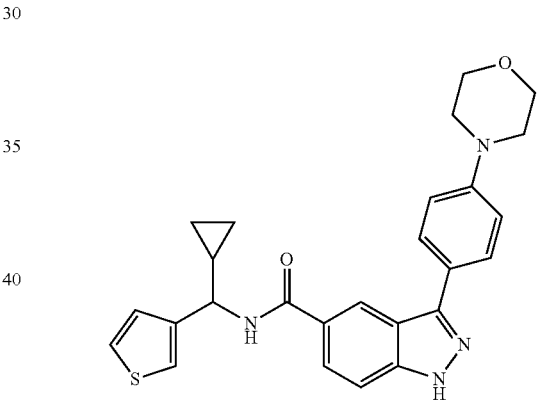

The title compound was synthesized according to the General Method C, utilizing N-(cyclopropyl(thiophen-3-yl)methyl)-3-iodo-1H-indazole-5-carboxamide (100 mg, 0.24 mmol), 4-morpholinophenylboronic acid pinacol ester (81 mg, 0.28 mmol), PdCl$_2$dppf (10 mg, 0.012 mmol), satd. Na$_2$CO$_{33}$ (0.5 mL), and 1.5 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 40 mg, 29%). $^1$H NMR (400 MHz, DMSO-d$_6$) δ ppm 13.25 (s, 1 H), 9.02 (d, J=8.8 Hz, 1 H), 8.57 (s, 1 H), 7.87-7.96 (m, 3 H), 7.58 (d, J=8.8 Hz, 1 H), 7.46-7.51 (m, 1 H), 7.40-7.44 (m, 1 H), 7.20 (d, J=5.8 Hz, 1 H), 7.12 (d, J=9.0 Hz, 2 H), 4.58 (t, J=9.3 Hz, 1 H), 3.74-3.80 (m, 4 H), 3.17-3.23 (m, 4 H), 1.33-1.44 (m, 1 H), 0.58-0.67 (m, 1 H), 0.48-0.57 (m, 1 H), 0.35-0.47 (m, 2 H); MS ESI 459.3 [M+H]$^+$, calcd for [C$_{26}$H$_{26}$N$_4$O$_2$S+H]$^+$ 459.2.

Example A36

2-cyclopentyl-N-(3-(4-((1-methylpiperidin-4-yl)oxy)phenyl)-1H-indazol-5-yl)-2-(thiophen-3-yl)acetamide A. ethyl 2-cyclopentyl-2-(thiophen-3-yl)acetate

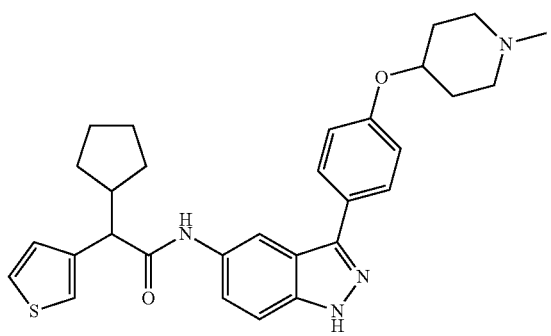

NaH (0.26 g, 6.5 mmol) was added portion wise to a solution of ethyl 3-thiophene acetate (0.88 mL, 5.8 mmol) in DMF (20 mL) at rt under Ar. After stirring for 5 min, cyclopentyl bromide (0.70 mL, 6.9 mmol) was added and stirring was continued for 18 h at 25° C. 20% NH$_4$Cl (50 mL) was added and the product was extracted using EtOAc (2×50 mL), and the combined EtOAc layer was washed with H$_2$O and brine and dried (Na$_2$SO$_4$) and concentrated under vacuum. Purification by flash chromatography (SiO$_2$, 0-25% EtOAc in hexane) gave the title compound (colorless oil, 1.04 g, 74%). $^1$H NMR (400 MHz, CDCl$_3$) δ 7.26-7.25 (m, 1H), 7.16-7.7.15 (m, 1H), 7.12 (dd, J=4.8 Hz, J=1.2 Hz, 1H), 4.18-4.06 (m, 2H), 3.45 (d, J=10.8 Hz, 1H), 2.51-2.49 (m, 1H), 1.86-1.83 (m, 1H), 1.46-1.49 (m, 6H), 1.24 (t, J=7.2 Hz, 3H), 1.12-1.05 (m, 1H).

B. 2-cyclopentyl-2-(thiophen-3-yl)acetic acid

NaOH (2 M, 5.45 mL, 10.9 mmol) was added to a solution of ethyl 2-cyclopentyl-2-(thiophen-3-yl)acetate (1.04 g, 4.3 mmol) in MeOH (10.4 mL) at rt. The reaction mixture was refluxed for 2.5 h, and then concentrated under reduced pressure. The residue was acidified to pH 2 using conc. HCl and the product was extracted using DCM (25 mL, 10 mL). The combined organic layer was washed with H$_2$O and brine, dried (Na$_2$SO$_4$) and concentrated under vacuum to give the title compound (off white solid, 0.89 g, 97%). $^1$H NMR (400 MHz, CDCl$_3$) δ 7.29-7.27 (m, 1H), 7.18-7.7.17 (m, 1H), 7.12-7.1 (m, 1H), 3.47 (d, J=10.8 Hz, 1H), 2.55-2.45 (m, 1H), 1.95-1.89 (m, 1H), 1.71-1.48 (m, 5H), 1.35-1.26 (m, 1H), 1.12-1.05 (m, 1H).

C. 2-cyclopentyl-N-(3-(4-((1-methylpiperidin-4-yl)oxy)phenyl)-1H-indazol-5-yl)-2-(thiophen-3-yl)acetamide The title compound was synthesized according to General Method A using 2-cyclopentyl-2-(thiophen-3-yl)acetic acid 19.1 mg, 0.09 mmol), DMF (1.5 mL), 3-(4-((1-methylpiperidin-4-yl)oxy)phenyl)-1H-indazol-5-amine trifluoroacetate (50 mg, 0.09 mmol), DIPEA (80 uL, 0.45 mmol) and TBTU (29.1 mg, 0.09 mmol). After 24 h at rt, direct purification by flash chromatography (SiO$_2$, 0-25% MeOH in DCM; then RP HPLC C18 60 g, 10-80% MeOH in 0.1% TFA-H$_2$O) gave the title compound as a TFA salt (off white solid, 31 mg, 54%). $^1$H NMR (400 MHz, CD$_3$OD) δ 10.08 (s, 1H), 8.43-8.42 (m, 1H), 7.88-7.8 (m, 2H), 7.52 (d, J=9.2 Hz, 1H), 7.40-7.35 (m, 2H), 7.31-7.3 (m, 1H), 7.22 (dd, J=5.2 Hz, J=1.2 Hz, 1H), 7.18-7.15 (m, 2H), 4.85 (s, 1H), 3.65-3.54 (m, 2H), 3.44-3.34 (br.m, 3H), 2.94 (d, J=4.4 Hz, 3H), 2.70-2.64 (m, 1H), 2.45-2.28 (m, 2H), 2.15-1.91 (br.m, 3H), 1.75-1.53 (br.m, 5H), 1.40-1.35 (m, 1H), 1.18-1.31 (m, 1H); MS ESI 515.1 [M+H]$^+$, calcd for [C$_{30}$H$_{34}$N$_4$O$_2$S+H]$^+$ 515.2.

Example A37

2-methoxy-N-(3-(4-((1-methylpiperidin-4-yl)oxy)phenyl)-1H-indazol-5-yl)-2-(thiophen-2-yl)acetamide

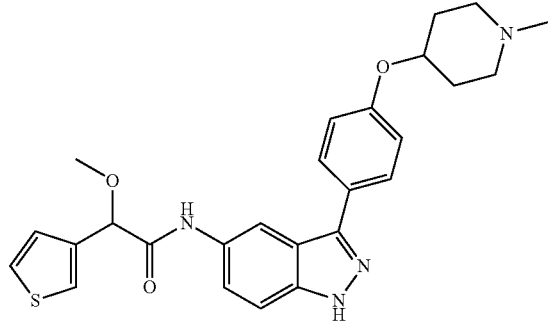 [SMILES: COC(C(=O)Nc1ccc2[nH]nc(-c3ccc(OC4CCN(C)CC4)cc3)c2c1)c1ccsc1]

The title compound was synthesized according to General Method A by using 2-methoxy-2-(thiophen-2-yl)acetic acid (15.6 mg, 0.09 mmol), DMF (1.5 mL), 3-(4-((1-methylpiperidin-4-yl)oxy)phenyl)-1H-indazol-5-amine trifluoroacetate (50 mg, 0.09 mmol), DIPEA (80 uL, 0.45 mmol) and TBTU (29.1 mg, 0.09 mmol). After 24 h at rt, direct purification by flash chromatography (SiO$_2$, 0-25% MeOH in DCM; then RP HPLC C18, 10-80% MeOH in 0.1% TFA-H$_2$O) gave the title compound as a TFA salt (off white solid, 27 mg, 50%). $^1$H NMR (400 MHz, CD$_3$OD) δ 8.41 (s, 1H), 7.89-7.85 (br.t, 2H), 7.55-7.52 (m, 3H), 7.45 (dd, J=4.8 Hz, 2.8 Hz, 1H), 7.23 (d, J=1.2 Hz, 1H), 7.19-7.11 (m, 2H), 4.95 (s, 1H), 3.65-3.6 (br.m, 1H), 3.38-3.58 (br.m, 1H), 3.48 (s, 3H), 3.62-3.41 (br.m, 3H), 2.94 (s, 3H), 2.45-28 (br.m, 2H), 2.14-1.88 (br.m, 2H); MS ESI 477.2 [M+H]$^+$, calcd for [C$_{26}$H$_{28}$N$_4$O$_3$S+H]$^+$ 477.2.

Example A38

(S)-N-(1-cyclohexylethyl)-3-(4-((1-methylpiperidin-4-yl)oxy)phenyl)-1H-indazole-5-carboxamide

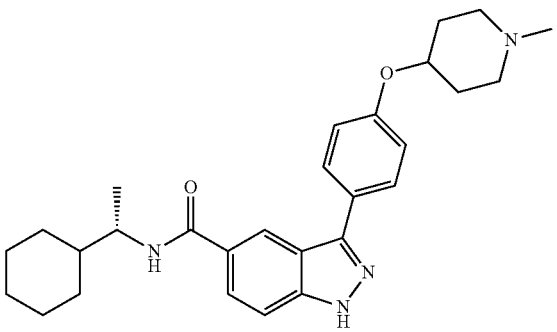 [SMILES: C[C@H](NC(=O)c1ccc2[nH]nc(-c3ccc(OC4CCN(C)CC4)cc3)c2c1)C1CCCCC1]

The title compound was synthesized according to the General Method C, utilizing (S)-N-(1-cyclohexylethyl)-3- iodo-1H-indazole-5-carboxamide (100 mg, 0.25 mmol), (4-((1-methylpiperidin-4-yl)oxy)phenyl)boronic acid pinacol ester (96 mg, 0.30 mmol), PdCl₂dppf (10 mg, 0.012 mmol), satd. aq Na₂CO₃ (1 mL), and 4 mL of PhMe:EtOH (1:1). The vial was charged with Ar and heated in the microwave reactor at 125° C. for 2 h. Purification by RPHPLC, followed by trituration with Et₂O gave the title compound as a TFA salt (white solid, 35 mg, 24%). ¹H NMR (400 MHz, CD₃OD) δ ppm 8.52 (s, 1 H), 7.87-7.99 (m, 3 H), 7.60 (d, J=8.5 Hz, 1 H), 7.14-7.25 (m, 2 H), 4.64-4.74 (m, 0.3 H), 3.93-4.05 (m, 1 H), 3.60-3.69 (m, 0.7 H), 3.34-3.49 (m, 2.7 H), 3.13-3.27 (m, 1.3 H), 2.95 (s, 3 H), 2.42-2.50 (m, 0.7 H), 2.27-2.38 (m, 1.3 H), 2.05-2.18 (m, 1.3 H), 1.73-1.97 (m, 4.7 H), 1.62-1.73 (m, 1 H), 1.44-1.57 (m, 1 H), 1.14-1.35 (m, 6 H), 1.01-1.14 (m, 2 H); MS ESI 461.4 [M+H]⁺, calcd for [$C_{28}H_{36}N_4O_2$+H]⁺ 461.3.

Example A39

2-methyl-N-(3-(4-((1-methylpiperidin-4-yl)oxy)phenyl)-1H-indazol-5-yl)-1,2,3,4-tetrahydroisoquinoline-1-carboxamide

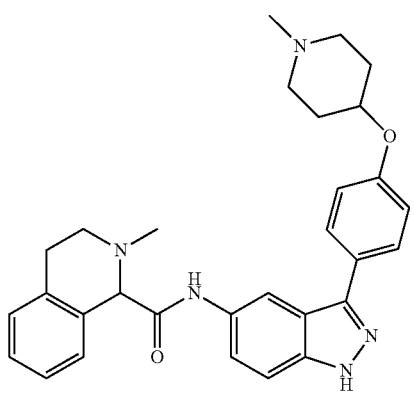 [SMILES: CN1CCC(Oc2ccc(-c3n[nH]c4ccc(NC(=O)C5c6ccccc6CCN5C)cc34)cc2)CC1]

To a mixture of 2-methyl-1,2,3,4-tetrahydroisoquinoline-1-carboxylic acid hydrochloride (25 mg, 0.1 mmol) and 3-(4-((1-methylpiperidin-4-yl)oxy)phenyl)-1H-indazol-5-amine di-trifluoroacetic acid (55 mg, 0.1 mmol) in DMF (5 mL) at 0° C. was added TBTU (32 mg, 0.1 mmol), followed by ⁱPr₂NEt (0.09 mL, 0.5 mmol). The resulting mixture was stirred for 30 min at 0° C. Additional 3-(4-((1-methylpiperidin-4-yl)oxy)phenyl)-1H-indazol-5-amine di-trifluoroacetic acid (5.5 mg, 0.01 mmol) and TBTU (3.2 mg, 0.01 mmol) were added and it was stirred for 30 min at 0° C. After removal of ⁱPr₂NEt, it was purified by prep-HPLC twice to give the title compound as a di-TFA salt (white solid, 51.3 mg, 71%). NMR (400 MHz, CD₃OD) δ 8.46 (t, J=0.8 Hz, 1H), 7.90-7.84 (m, 2H), 7.64 (dd, J=9.0 Hz, 1.8 Hz, 1H), 7.60 (d, J=9.2 Hz, 1H), 7.49 (d, J=7.2 Hz, 1H), 7.41-7.32 (m, 3H), 7.19-7.10 (m, 2H), 5.34 (s, 1H), 5.34-5.31 (m, 0.7H), 4.68-4.60 (m, 0.3H), 4.03 (brs, 0.8H), 3.65-3.58 (m, 1.7H), 3.45-3.33 (m, 3.4H; partially overlapped with CD₃OD solvent residue), 3.23-3.12 (m, 4.7H; s, 3H at 3.14), 2.92-2.91 (two s at 2.92 and 2.91, total 3H), 2.44-2.37 (m, 0.7H), 2.30-2.23 (m, 1.3H), 2.18-2.08 (m, 1.3H), 1.98-1.86 (m, 0.7H); MS ESI 496.2 [M+H]⁺, calcd for [$C_{30}H_{33}N_5O_2$+H]⁺ 496.3.

Example A40

(S)-N-(1-cyclohexylethyl)-3-(4-morpholinophenyl)-1H-indazole-5-carboxamide

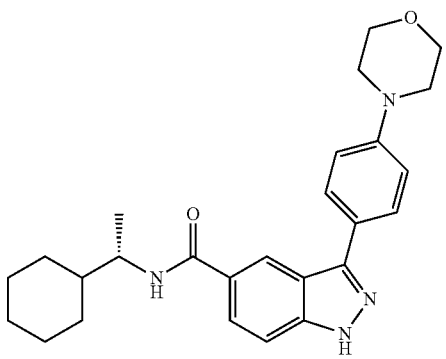 [SMILES: C[C@H](NC(=O)c1ccc2[nH]nc(-c3ccc(N4CCOCC4)cc3)c2c1)C1CCCCC1]

The title compound was synthesized according to the General Method C, utilizing (S)-N-(1-cyclohexylethyl)-3-iodo-1H-indazole-5-carboxamide (80 mg, 0.20 mmol), 4-morpholinophenylboronic acid pinacol ester (58 mg, 0.20 mmol), PdCl₂dppf (8 mg, 0.01 mmol), satd. aq Na₂CO₃ (0.5 mL), and 1.5 mL of PhMe:EtOH (1:1). The vial was charged with Ar and heated in the microwave reactor at 125° C. for 2 h. Purification by RPHPLC, followed by trituration with Et₂O gave the title compound (white solid, 18 mg, 21%). ¹H NMR (400 MHz, CD₃OD) δ ppm 8.55 (s, 1 H), 7.90 (d, J=8.8 Hz, 3 H), 7.58 (d, J=8.8 Hz, 1 H), 7.13 (d, J=8.5 Hz, 2 H), 3.92-4.03 (m, 1 H), 3.82-3.89 (m, 4 H), 3.24 (br. s, 4 H), 1.70-1.90 (m, 4 H), 1.61-1.69 (m, 1 H), 1.44-1.55 (m, 1 H), 1.22 (d, J=6.8 Hz, 6 H), 0.97-1.12 (m, 2 H); MS ESI 433.4 [M+H]⁺, calcd for [$C_{26}H_{32}N_4O_2$+H]⁺ 433.3.

Example A41

(S)-N-(3-(4-((1-methylpiperidin-4-yl)oxy)phenyl)-1H-indazol-5-yl)-2-((S)-2-methylpyrrolidin-1-yl)-2-(thiophen-3-yl)acetamide

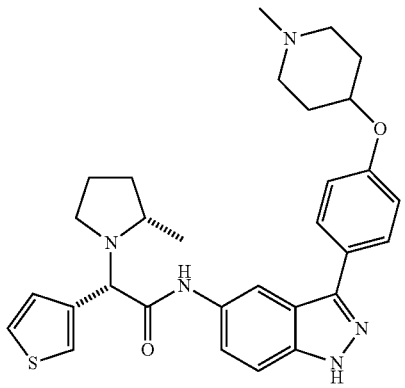

To a mixture of (S)-2-((S)-2-methylpyrrolidin-1-yl)-2-(thiophen-3-yl)acetic acid (22.5 mg, 0.1 mmol) and 3-(4-

((1-methylpiperidin-4-yl)oxy)phenyl)-1H-indazol-5-amine di-trifluoroacetic acid (55 mg, 0.1 mmol) in DMF (5 mL) at 0° C. was added TBTU (32.1 mg, 0.1 mmol), followed by iPr$_2$NEt (0.09 mL, 0.5 mmol). The resulting mixture was stirred for 10 min at 0° C. After removal of iPr$_2$NEt, it was purified by prep-HPLC to give the title compound as di-TFA salt (white solid, 31.1 mg, 71%). $^1$H NMR (400 MHz, CD$_3$OD) δ 8.35 (s, 1H), 7.91-7.93 (m, 3H), 7.64 (dd, J=5.0 Hz, 3.0 Hz, 1H), 7.54 (s, 2H), 7.41 (d, J=4.8 Hz, 1H), 7.21-7.13 (m, 2H), 5.33 (s, 1H), 4.89-4.85 (m, 0.7H), 4.72-4.64 (m, 0.3H), 3.84 (q, J=7.2 Hz, 1H), 3.68-3.62 (m, 0.7H), 3.48-3.12 (m, 5.3H; partially overlapped with CD$_3$OD solvent residue), 2.95-2.94 (two s at 2.95 and 2.94, total 3H), 2.48-2.26 (m, 3H), 2.20-1.82 (m, 5H), 1.53 (d, J=6.4 Hz, 3H); MS ESI 530.2 [M+H]$^+$, calcd for [C$_{30}$H$_{35}$N$_5$O$_2$S+H]$^+$ 530.3.

Example A42

(S)-N-(cyclopropyl(phenyl)methyl)-3-(4-((1-methyl-piperidin-4-yl)oxy)phenyl)-1H-indazole-5-carboxamide

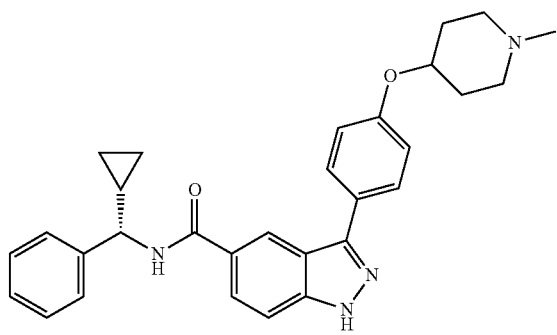 [SMILES: CN1CCC(Oc2ccc(-c3n[nH]c4ccc(C(=O)N[C@H](c5ccccc5)C5CC5)cc34)cc2)CC1]

The title compound was synthesized according to the General Method C, utilizing (S)-N-(cyclopropyl(phenyl)methyl)-3-iodo-1H-indazole-5-carboxamide (110 mg, 0.26 mmol), (4-((1-methylpiperidin-4-yl)oxy)phenyl)boronic acid pinacol ester (84 mg, 0.26 mmol), PdCl$_2$dppf (11 mg, 0.013 mmol), satd. aq Na$_2$CO$_3$ (1 mL), and 4 mL of PhMe:EtOH (1:1). The vial was charged with Ar and heated in the microwave reactor at 125° C. for 5 h. Purification by RPHPLC, followed by flash chromatography (SiO$_2$, Biotage 25 g, 5-25% MeOH in CH$_2$Cl$_2$) and trituration with Et$_2$O gave the title compound (white solid, 8.5 mg, 7%). $^1$H NMR (400 MHz, CD$_3$OD) δ ppm 8.60 (s, 1 H), 7.91 (m, 3 H), 7.59 (d, J=9.5 Hz, 1 H), 7.48 (d, J=7.3 Hz, 2 H), 7.32 (t, J=7.5 Hz, 2 H), 7.23 (t, J=7.3 Hz, 1 H), 7.10 (d, J=8.8 Hz, 2 H), 4.53 (br. s, 1 H), 4.47 (d, J=9.5 Hz, 1 H), 2.77-2.88 (m, 2 H), 2.45-2.59 (m, 2 H), 2.39 (s, 3 H), 2.01-2.13 (m, 2 H), 1.82-1.94 (m, 2 H), 1.34-1.45 (m, 1 H), 0.60-0.72 (m, 2 H), 0.39-0.53 (m, 2 H); MS ESI 481.4 [M+H]$^+$, calcd for [C$_{30}$H$_{32}$N$_4$O$_2$+H]$^+$ 481.3.

Example A43

N-(3-(4-(3-(dimethylamino)propoxy)phenyl)-1H-indazol-5-yl)-2-(pyrrolidin-1-yl)-2-(thiophen-3-yl)acetamide

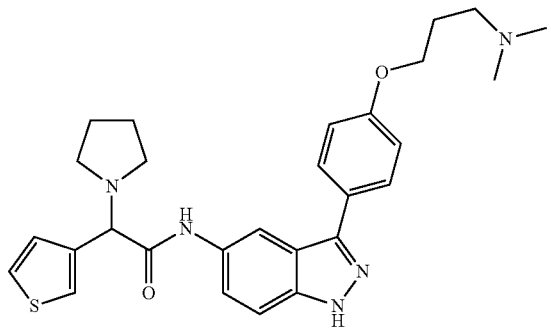 [SMILES: CN(C)CCCOc1ccc(-c2n[nH]c3ccc(NC(=O)C(c4ccsc4)N4CCCC4)cc23)cc1]

The title compound was synthesized according to General Method C by using a mixture of N-(3-iodo-1H-indazol-5-yl)-2-(pyrrolidin-1-yl)-2-(thiophen-3-yl)acetamide (75 mg, 0.165 mmol), N,N-dimethyl-3-(4-(4,4,5,5-tetramethyl-1,3,2-dioxaborolan-2-yl)phenoxy)propan-1-amine (60.7 mg, 0.198 mmol), PdCl$_2$dppf (11.6 mg, 0.016 mmol) and 1 M aq Na$_2$CO$_3$ (0.33 mL) in PhMe/EtOH (2.25 mL, 2:1 mixture) under Ar with heating under microwave irradiation at 130° C. for 2 h. The reaction mixture was diluted with EtOAc (22.5 mL) and washed with H$_2$O (10 mL) and brine (10 mL), dried (Na$_2$SO$_4$) and concentrated under vacuum and. Purification by flash chromatography (SiO$_2$, 0-10% 2 M NH$_3$-MeOH in DCM; then RP HPLC C18 60 g, 10-80° A MeOH in 0.1% TFA-H$_2$O) to give the title compound as a TFA salt (light pink solid, 20 mg, 17%). $^1$H NMR (400 MHz, CD$_3$OD) δ 8.35 (s, 1H), 7.88-7.83 (m, 3H), 7.66-7.64 (m, 1H), 7.55-7.49 (m, 2H), 7.38 (dd, J=5.2 Hz, J=1.2 Hz, 1H), 7.13 (d, J=6.8 Hz, 2H), 5.24 (s, 1H), 4.21 (t, J=5.6 Hz, 2H), 3.88-3.86 (br.m, 1H), 3.41 (t, J=7.6 Hz, 2H), 3.26-3.09 (br.m, 2H), 2.98 (s, 6H), 2.31-1.92 (br.m, 6H), 1H merged with solvent peak; MS ESI 504.2[M+H]$^+$, calcd for [C$_{28}$H$_{33}$N$_5$O$_2$S+H]$^+$ 504.2.

Example A44

2-(pyrrolidin-1-yl)-N-(3-(4-(2-(pyrrolidin-1-yl)ethoxy)phenyl)-1H-indazol-5-yl)-2-(thiophen-3-yl)acetamideamide

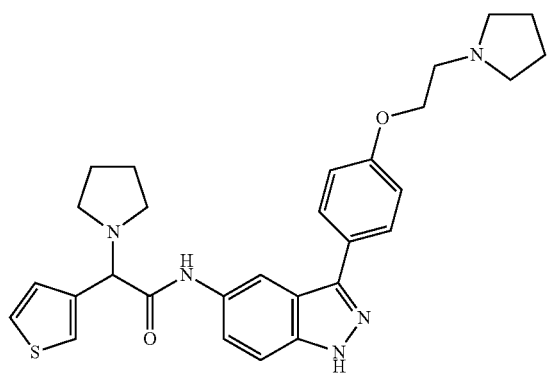 [SMILES: O=C(Nc1ccc2[nH]nc(-c3ccc(OCCN4CCCC4)cc3)c2c1)C(c1ccsc1)N1CCCC1]

Using General Method C2, N-(3-iodo-1H-indazol-5-yl)-2-(pyrrolidin-1-yl)-2-(thiophen-3-yl)acetamide (59.8 mg, 0.132 mmol) and (4-(2-(pyrrolidin-1-yl)ethoxy)phenyl)boronic acid (42.6 mg, 0.181 mmol) gave the title compound after 3 h at 120° C. in the microwave as the TFA salt (beige solid, 59.1 mg, 60%) after purification by flash chromatography (SiO$_2$, 0-20% 2 M NH$_3$-MeOH in DCM; followed by RP HPLC, 10-80% MeOH in 0.1% TFA-H$_2$O). $^1$H NMR (400 MHz, CD$_3$OD) δ ppm 8.36 (t, J=1.5 Hz, 1 H), 7.86-7.91 (m, 3 H), 7.65 (dd, J=5.0, 3.0 Hz, 1 H), 7.50-7.57 (m, 2 H), 7.38 (dd, J=5.1, 1.4 Hz, 1 H), 7.17-7.22 (m, 2 H), 5.28 (s, 1 H), 4.41-4.46 (m, 2 H), 3.88 (br. s., 1 H), 3.78 (dt, J=10.2, 5.1 Hz, 2 H), 3.67-3.75 (m, 2 H), 3.22-3.30 (m, 3 H), 3.19 (br. s., 1 H), 3.10 (br. s., 1 H), 2.05-2.28 (m, 7 H), 1.92-2.04 (m, 1 H). MS ESI 516.2 [M+H]$^+$, calcd for [C$_{29}$H$_{33}$N$_5$O$_2$S+H]$^+$ 516.24.

Example A45

N-(3-(4-(3-morpholinopropoxy)phenyl)-1H-indazol-5-yl)-2-(pyrrolidin-1-yl)-2-(thiophen-3-yl)acetamide

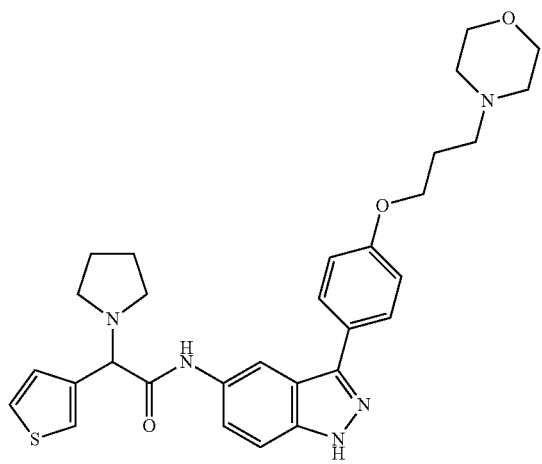 [SMILES: O=C(Nc1ccc2[nH]nc(-c3ccc(OCCCN4CCOCC4)cc3)c2c1)C(c1ccsc1)N1CCCC1]

Using General Method C2, N-(3-iodo-1H-indazol-5-yl)-2-(pyrrolidin-1-yl)-2-(thiophen-3-yl)acetamide (59.9 mg, 0.132 mmol) and (4-(3-(4-(4,4,5,5-tetramethyl-1,3,2-dioxaborolan-2-yl)phenoxy)propyl)morpholine (60.9 mg, 0.175 mmol) gave the title compound after 3 h at 12 0° C. in the microwave reactor as the TFA salt (off-white powder, 30.6 mg, 30%) after purification by flash chromatography (SiO$_2$, 5-15% MeOH in DCM; followed by RP HPLC, 10-80% MeOH in 0.1% TFA-H$_2$O). $^1$H NMR (400 MHz, CD$_3$OD) δ ppm 8.35-8.38 (m, 1 H), 7.88 (dd, J=2.9, 1.4 Hz, 1 H), 7.85 (d, J=8.8 Hz, 2 H), 7.63-7.67 (m, 1 H), 7.49-7.56 (m, 2 H), 7.38 (dd, J=5.3, 1.3 Hz, 1 H), 7.12 (d, J=8.8 Hz, 2 H), 5.27 (s, 1 H), 4.21 (t, J=5.6 Hz, 2 H), 4.11 (d, J=12.3 Hz, 2 H), 3.88 (br. s., 1 H), 3.81 (t, J=12.3 Hz, 2 H), 3.60 (d, J=12.3 Hz, 2 H), 3.40-3.48 (m, 2 H), 3.16-3.27 (m, 3 H), 3.10 (br. s., 1 H), 2.27-2.36 (m, 2 H), 2.23 (d, J=11.5 Hz, 1 H), 2.09-2.19 (m, 2 H), 2.01 (br. s., 1 H). MS ESI 546.3 [M+H]$^+$, calcd for [C$_{30}$H$_{35}$N$_5$O$_3$S+H]$^+$ 546.25.

Example A46

1-(2,6-diethylphenyl)-3-(3-(4-((1-methylpiperidin-4-yl)oxy)phenyl)-1H-indazol-5-yl)urea

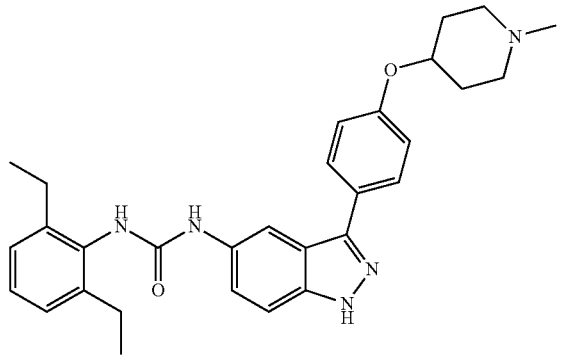 [SMILES: CCc1cccc(CC)c1NC(=O)Nc1ccc2[nH]nc(-c3ccc(OC4CCN(C)CC4)cc3)c2c1]

A solution of 3-(4-((1-methylpiperidin-4-yl)oxy)phenyl)-1H-indazol-5-amine bis(2,2,2-trifluoroacetate) (40 mg, 0.073 mmol), DIPEA (64 uL, 0.368 mmol), and DMF (1.0 mL) was cooled to 0° C. and then 1,3-diethyl-2-isocyanatobenzene (25 uL, 0.145 mmol) was added dropwise. The reaction was stirred for 2 h while warming to rt. A mixture of mono- and di-urea products were obtained which was treated directly with NaOMe (80 uL of a 25% wt solution in MeOH) and the mixture stirred for 15 min and then transferred to a separatory funnel with EtOAc (15 mL). The mixture was then washed with (satd. aq NaHCO$_3$ (2×10 mL), H$_2$O (1×10 mL), brine (1×10 mL)). The organic layer was dried over MgSO$_4$, filtered, and the solvent removed. The resulting residue was purified by prep-HPLC which gave 19 mg, 43% of the desired product isolated as its TFA salt (a white powder). $^1$H NMR (400 MHz, CD$_3$OD) δ ppm 8.26 (s, 1H), 7.87-7.83 (m, 2H), 7.49 (d, J=8.8 Hz, 1H), 7.30 (d, J=8.8 Hz, 1H), 7.22-7.09 (m, 5H), 4.83 (bs, 1H), 3.62-3.31 (m, 2H), 3.30-3.14 (m, 2H), 2.92-2.91 (m, 3H), 2.72-2.67 (m, 4H), 2.42-2.25 (m, 2H), 2.11-1.86 (m, 2H), 1.22 (t, J=7.6 Hz, 6H); MS ESI 498.5 [M+H]$^+$, calcd for [C$_{30}$H$_{35}$N$_5$O$_2$+H]$^+$ 498.29.

Example A47

(S)-2-((S)-2-methylpyrrolidin-1-yl)-N-(3-(4-morpholinophenyl)-1H-indazol-5-yl)-2-(thiophen-3-yl)acetamide

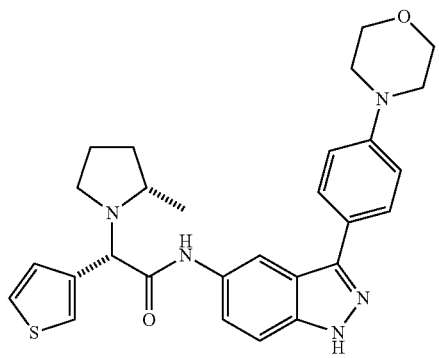

To a mixture of tert-butyl (3-iodo-1H-indazol-5-yl)carbamate (1.077 g, 3 mmol) and (4-morpholinophenyl)boronic acid (652 mg, 3.15 mmol) in EtOH (12 mL) was added 2 M Na$_2$CO$_3$ (3 mL, 6 mmol), followed by Pd(PPh$_3$)$_4$ (104 mg, 0.09 mmol). The resulting mixture was purged with Ar and microwaved 3 h at 125° C. Repeated this reaction twice on the same scale. All three reactions were combined, diluted with H$_2$O, extracted with EtOAc and purified by flash chromatography (MeOH/DCM 0-25%) to give 4.20 g of brown solid. It was redissolved in DCM (20 mL) and treated with TFA (10 mL). After stirring for 3 h at rt, it was concentrated and purified by Biotage RP column (5-90% MeOH in 0.1% TFA-H$_2$O) to give 3-(4-morpholinophenyl)-1H-indazol-5-amine as a di-TFA salt (light purple solid, 866 mg, 55%). $^1$H NMR (400 MHz, CD$_3$OD) δ 8.05 (s, 1H), 7.84 (d, J=7.2 Hz, 2H), 7.72 (d, J=8.0 Hz, 1H), 7.44 (d, J=8.4 Hz, 1H), 7.17 (d, J=7.2 Hz, 2H), 4.00-3.80 (m, 4H), 3.40-3.20 (m, 4H); MS ESI 295.0 [M+H]$^+$, calcd for [C$_{17}$H$_{18}$N$_4$O+H]$^+$ 295.1.

To a mixture of (S)-2-((S)-2-methylpyrrolidin-1-yl)-2-(thiophen-3-yl)acetic acid (22.5 mg, 0.1 mmol) and 3-(4-morpholinophenyl)-1H-indazol-5-amine di-trifluoroacetic acid (52.2 mg, 0.1 mmol) in DMF (5 mL) at 0° C. was added TBTU (32.1 mg, 0.1 mmol), followed by $^i$Pr$_2$NEt (0.07 mL). After stirring for 5 min at 0° C., additional $^i$Pr$_2$NEt (0.02 mL) was added and the resulting mixture was stirred for 30 min at 0° C. After removal of $^i$Pr$_2$NEt, it was purified by prep-HPLC to give the title compound as a di-TFA salt (white solid, 14.1 mg, 19%). $^1$H NMR (400 MHz, CD$_3$OD) δ 8.37 (t, J=1.6 Hz, 1H), 7.89 (d, J=1.6 Hz, 1H), 7.86 (d, J=8.8 Hz, 2H), 7.65 (dd, J=5.0 Hz, 3.0 Hz, 1H), 7.57-7.49 (m, 2H), 7.41 (d, J=4.8 Hz, 1H), 7.23 (d, J=8.4 Hz, 2H), 5.23 (s, 1H), 3.92 (t, J=4.8 Hz, 4H), 3.84 (q, J=6.7 Hz, 1H), 3.36-3.25 (m, 5H; partially buried under CD$_3$OD solvent residue), 3.20-3.12 (m, 1H), 2.46-2.36 (m, 1H), 2.06 (quint, J=7.1 Hz, 2H), 1.90-1.83 (m, 1H), 1.54 (d, J=6.4 Hz, 3H); MS ESI 502.3 [M+H]$^+$, calcd for [C$_{26}$H$_{28}$N$_6$O$_2$S+H]$^+$ 502.2.

Example A48

(R)-N-(1-cyclohexylethyl)-3-(4-morpholinophenyl)-1H-indazole-5-carboxamide

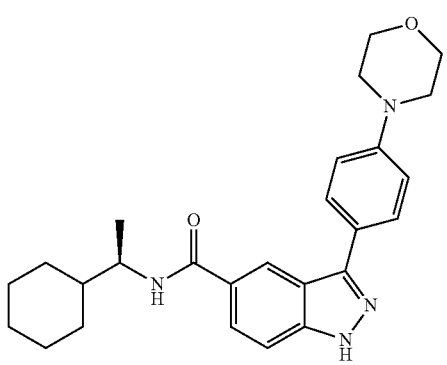 [SMILES: C[C@@H](NC(=O)c1ccc2[nH]nc(-c3ccc(N4CCOCC4)cc3)c2c1)C1CCCCC1]

The title compound was synthesized according to the 1 General Method C, utilizing (R)-N-(1-cyclohexylethyl)-3-iodo-1H-indazole-5-carboxamide (100 mg, 0.25 mmol), 4-morpholinophenylboronic acid pinacol ester (55 mg, 0.25 mmol), PdCl$_2$dppf (10 mg, 0.013 mmol), satd. aq Na$_2$CO$_3$ (1.5 mL), and 3.5 mL of PhMe:EtOH (1:1). The vial was charged with Ar and heated in the microwave reactor at 125° C. for 2 h. Purification by RP HPLC, followed by flash chromatography (SiO$_2$, Biotage 25 g, 5-25% MeOH in CH$_2$Cl$_2$), and passed through a PoraPak column to give the title compound (beige solid, 32 mg, 30%). $^1$H NMR (400 MHz, CD$_3$OD) δ ppm 8.55 (s, 1 H), 7.85-7.92 (m, 3 H), 7.57 (d, J=8.8 Hz, 1 H), 7.09 (d, J=8.8 Hz, 2 H), 3.93-4.02 (m, 1 H), 3.81-3.87 (m, 4 H), 3.17-3.23 (m, 4 H), 1.76 (br. s, 4 H), 1.61-1.69 (m, 1 H), 1.44-1.55 (m, 1 H), 1.22 (d, J=6.8 Hz, 6 H), 1.06 (d, J=2.5 Hz, 2 H); MS ESI 433.4 [M+H]$^+$, calcd for [C$_{26}$H$_{32}$N$_4$O$_2$+H]$^+$ 433.3.

Example A49

(S)-N-(cyclopropyl(phenyl)methyl)-3-(4-morpholinophenyl)-1H-indazole-5-carboxamide

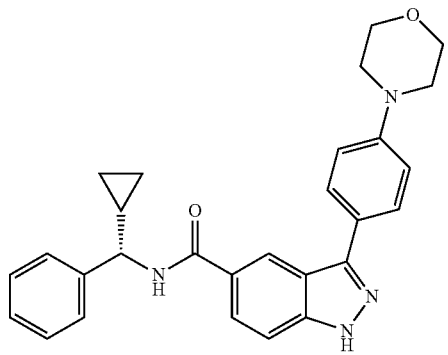 [SMILES: O=C(N[C@H](c1ccccc1)C1CC1)c1ccc2[nH]nc(-c3ccc(N4CCOCC4)cc3)c2c1]

The title compound was synthesized according to the General Method C, utilizing (S)-N-(cyclopropyl(phenyl)methyl)-3-iodo-1H-indazole-5-carboxamide (50 mg, 0.12 mmol), 4-morpholinophenylboronic acid pinacol ester (35 mg, 0.12 mmol), PdCl$_2$dppf (10 mg, 0.012 mmol), satd. aq Na$_2$CO$_3$ (1.5 mL), and 3.5 mL of PhMe:EtOH (1:1). The vial was charged with Ar and heated in the microwave reactor at 125° C. for 2 h. Purification by RP HPLC, followed by flash chromatography (SiO$_2$, Biotage 25 g, 5-25% MeOH in CH$_2$Cl$_2$) to give the title compound (beige solid, 13 mg, 24%). $^1$H NMR (400 MHz, CD$_3$OD) δ ppm 8.61 (s, 1 H), 7.91-7.98 (m, 3 H), 7.60 (d, J=8.8 Hz, 1 H), 7.48 (d, J=7.3 Hz, 2 H), 7.33 (t, J=7.5 Hz, 2 H), 7.20-7.28 (m, 3 H), 4.48 (d, J=9.5 Hz, 1 H), 3.86-3.93 (m, 4 H), 3.31-3.35 (m, 4 H), 1.35-1.46 (m, 1 H), 0.66 (d, J=8.0 Hz, 2 H), 0.41-0.53 (m, 2 H); MS ESI 453.3 [M+H]$^+$, calcd for [C$_{28}$H$_{28}$N$_4$O$_2$+H]$^+$ 453.2.

Example A50

N-(3-(4-((2S,6R)-2,6-dimethylmorpholino)phenyl)-1H-indazol-5-yl)-2-(pyrrolidin-1-yl)-2-(thiophen-3-yl)acetamide

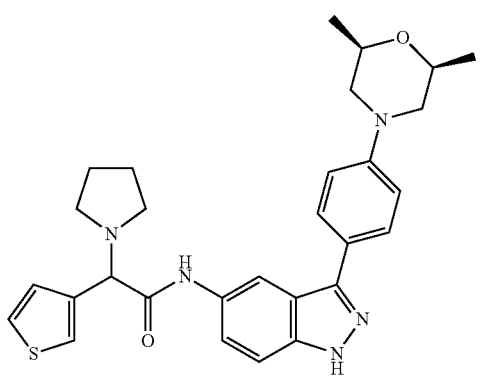 [SMILES: C[C@@H]1CN(c2ccc(-c3n[nH]c4ccc(NC(=O)C(c5ccsc5)N5CCCC5)cc34)cc2)C[C@H](C)O1]

The title compound was synthesized according to the General Method C2 utilizing N-(3-iodo-1H-indazol-5-yl)-2-(pyrrolidin-1-yl)-2-(thiophen-3-yl)acetamide (0.070 g, 0.15 mmol), (2S,6R)-2,6-dimethyl-4-(4-(4,4,5,5-tetramethyl-1,3,2-dioxaborolan-2-yl)phenyl)morpholine (0.064 g, 0.62 mmol) to provide the title compound as a white powder (7.2 mg, 9%). ¹H NMR (400 MHz, acetone-d₆) δ ppm 12.02-12.30 (br, 1 H), 9.59 (s, 1 H), 8.58 (s, 1 H), 7.89 (d, J=8.8 Hz, 2 H), 7.67 (d, J=8.8 Hz, 1 H), 7.50-7.59 (m, 2 H), 7.45 (dd, J=5.0, 3.0 Hz, 1 H), 7.34 (dd, J=4.9, 1.1 Hz, 1 H), 7.10 (d, J=9.0 Hz, 2 H), 4.12 (s, 1 H), 3.73-3.83 (m, 2 H), 3.69 (d, J=12.3 Hz, 2 H), 2.70-2.62 (m, 2 H), 2.45-2.56 (m, 2 H), 2.32-2.42 (m, 2 H), 1.81 (dt, J=6.3, 3.1 Hz, 4 H), 1.23 (d, J=6.3 Hz, 6 H); MS ESI 516.2 [M+H]⁺, calcd for [C₂₉H₃₃N₅O₂S+H]⁺ 516.2.

Example A51

(R)-N-(cyclopropyl(phenyl)methyl)-3-(4-morpholinophenyl)-1H-indazole-5-carboxamide

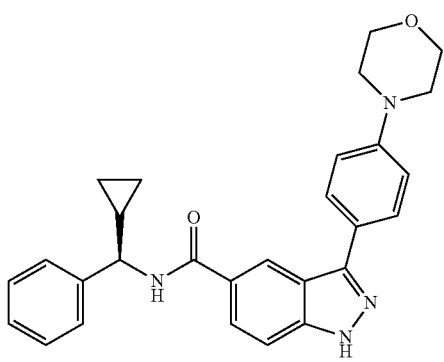 [SMILES: O=C(N[C@@H](c1ccccc1)C1CC1)c1ccc2[nH]nc(-c3ccc(N4CCOCC4)cc3)c2c1]

The title compound was synthesized according to the General Method C, utilizing (R)-N-(cyclopropyl(phenyl)methyl)-3-iodo-1H-indazole-5-carboxamide (60 mg, 0.14 mmol), 4-morpholinophenylboronic acid pinacol ester (42 mg, 0.14 mmol), PdCl₂dppf (11 mg, 0.014 mmol), satd. aq Na₂CO₃ (1.5 mL), and 3.5 mL of PhMe:EtOH (1:1). The vial was charged with Ar and heated in the microwave reactor at 125° C. for 2 h. Purification by RPHPLC, followed by passing through PoraPak column gave the title compound (beige solid, 18 mg, 28%). ¹H NMR (400 MHz, CD₃OD) δ ppm 8.61 (s, 1 H), 7.86-7.97 (m, 3 H), 7.59 (d, J=8.8 Hz, 1 H), 7.48 (d, J=7.3 Hz, 2 H), 7.33 (t, J=7.5 Hz, 2 H), 7.23 (t, J=7.3 Hz, 1 H), 7.13 (d, J=9.0 Hz, 2 H), 4.44-4.51 (m, 1 H), 3.86 (s, 4 H), 3.25 (s, 4 H), 1.36-1.45 (m, 1 H), 0.62-0.69 (m, 2 H), 0.42-0.52 (m, 2 H); MS ESI 453.4 [M+H]⁺, calcd for [C₂₈H₂₈N₄O₂+H]⁺ 453.2.

Example A52

N-(3-(6-morpholinopyridin-3-yl)-1H-indazol-5-yl)-2-(pyrrolidin-1-yl)-2-(thiophen-3-yl)acetamide

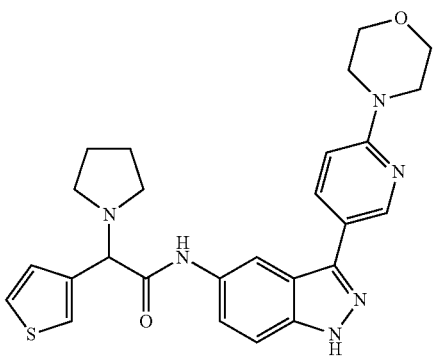 [SMILES: O=C(Nc1ccc2[nH]nc(-c3ccc(N4CCOCC4)nc3)c2c1)C(c1ccsc1)N1CCCC1]

To a mixture of N-(3-iodo-1H-indazol-5-yl)-2-(pyrrolidin-1-yl)-2-(thiophen-3-yl)acetamide (136 mg, 0.3 mmol) and 4-(5-(4,4,5,5-tetramethyl-1,3,2-dioxaborolan-2-yl)pyridin-2-yl)morpholine (87 mg, 0.3 mmol) in EtOH (4 mL) was added 1 M aq Na₂CO₃ (0.6 mL, 0.6 mmol), followed by Pd(PPh₃)₄ (17 mg, 0.015 mmol). The resulting mixture was purged with Ar and microwaved 2 h at 120° C. After removal of solvents, it was redissolved in DMF/TFA (5 mL/0.5 mL), filtered, purified by prep-HPLC, PoraPak and prep-HPLC to give the title compound as a di-TFA salt (light brownish white solid, 63.6 mg, 30%). ¹H NMR (400 MHz, CD₃OD) δ 8.59 (dd, J=9.6 Hz, 2.0 Hz, 1H), 8.48 (d, J=2.0 Hz, 1H), 8.32 (s, 1H), 7.89 (dd, J=3.2 Hz, 1.2 Hz, 1H), 7.64 (dd, J=5.0 Hz, 3.0 Hz, 1H), 7.61-7.55 (m, 2H), 7.46 (d, J=9.2 Hz, 1H), 7.40 (dd, J=4.8 Hz, 1.2 Hz, 1H), 5.36 (s, 1H), 3.93-3.83 (m, 5H), 3.73 (t, J=4.8 Hz, 4H), 3.38-3.06 (m, 3H), 2.30-1.95 (m, 4H); MS ESI 489.2 [M+H]⁺, calcd for [C₂₆H₂₈N₆O₂S+H]⁺ 489.2.

Example A53

(R)-3-(4-morpholinophenyl)-N-(1-(thiophen-2-yl)ethyl)-1H-indazole-5-carboxamide

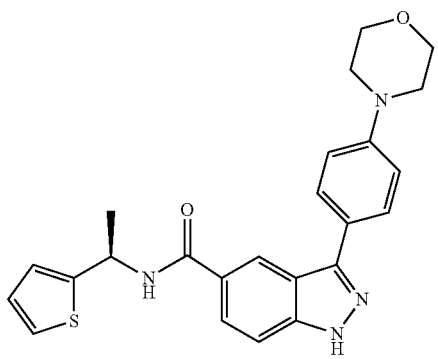 [SMILES: C[C@@H](NC(=O)c1ccc2[nH]nc(-c3ccc(N4CCOCC4)cc3)c2c1)c1cccs1]

The title compound was synthesized according to the General Method A, utilizing 3-(4-morpholinophenyl)-1H-indazole-5-carboxylic acid (98 mg, 0.30 mmol), (1R)-1-(2-thienyl)ethylamine.HCl (50 mg, 0.30 mmol), TBTU (96 mg, 0.30 mmol), DIPEA (0.16 mL, 0.90 mmol), and DMF (5 mL). Purification by RP HPLC, followed by passing through PoraPak column gave the title compound (white solid, 31 mg, 24%). NMR (400 MHz, CD$_3$OD) δ ppm 8.59 (s, 1 H), 7.86-7.96 (m, 3 H), 7.59 (d, J=8.5 Hz, 1 H), 7.25-7.30 (m, 1 H), 7.13 (d, J=8.8 Hz, 2 H), 7.04-7.08 (m, 1 H), 6.95-6.99 (m, 1 H), 5.56-5.64 (m, 1 H), 3.86 (s, 4 H), 3.21-3.26 (m, 4 H), 1.70 (d, J=7.0 Hz, 3 H); MS ESI 433.4 [M+H]$^+$, calcd for [C$_{24}$H$_{24}$N$_4$O$_2$S+H]$^+$ 433.2.

Example A54

N-(cyclopropyl(phenyl)methyl)-3-(6-morpholinopyridin-3-yl)-1H-indazole-5-carboxamide

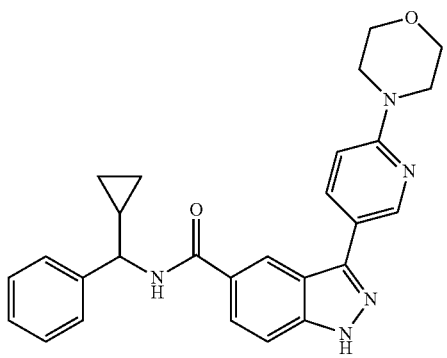 [SMILES: O=C(NC(c1ccccc1)C1CC1)c1ccc2[nH]nc(-c3ccc(N4CCOCC4)nc3)c2c1]

To a solution of K$_3$PO$_4$ (594 mg, 2.8 mmol) in H$_2$O (2 mL) was added 3-iodo-1H-indazole-5-carboxylic acid (202 mg, 0.7 mmol) and 4-(5-(4,4,5,5-tetramethyl-1,3,2-dioxaborolan-2-yl)pyridin-2-yl)morpholine (203 mg, 0.7 mmol), followed by DMF (8 mL) and Pd(PPh$_3$)$_4$ (41 mg, 0.035 mmol). The resulting mixture was purged with Ar, then microwaved 2 h at 110° C. It was purified by Biotage C-18 (0-80% MeOH in 0.1% TFA-H$_2$O), evaporated to dryness, triturated with MeOH (30 mL), filtered and dried to give crude 3-(6-morpholinopyridin-3-yl)-1H-indazole-5-carboxylic acid (light yellow oil, 110 mg). $^1$H NMR (400 MHz, CDCl$_3$) δ MS ESI 325.1 [M+H]$^+$, calcd for [C$_{17}$H$_{16}$N$_4$O$_3$+H]$^+$ 325.1.

To a mixture of the above crude 3-(6-morpholinopyridin-3-yl)-1H-indazole-5-carboxylic acid (110 mg, 0.25 mmol) and cyclopropyl(phenyl)methanamine (46 mg, 0.25 mmol) in DMF (5 mL) at 0° C. was added TBTU (80 mg, 0.25 mmol), followed by $^i$Pr$_2$NEt (0.26 mL, 1.5 mmol). The resulting mixture was stirred for 30 min at 0° C. After removal of iPr$_2$NEt, it was purified by prep-HPLC and PoraPak to give the title compound (white solid, 6.6 mg, 2% over 2 steps). $^1$H NMR (400 MHz, CD$_3$OD) δ 8.78 (d, J=2.0 Hz, 1H), 8.58 (t, J=0.8 Hz, 1H), 8.19 (dd, J=8.8 Hz, 2.4 Hz, 1H), 7.96 (dd, J=8.8 Hz, 1.6 Hz, 1H), 7.61 (dd, J=8.8 Hz, 0.8 Hz, 1H), 7.49 (d, J=7.2 Hz, 2H), 7.34 (t, J=7.6 Hz, 2H), 7.24 (tt, J=7.6 Hz, 1.2 Hz, 1H), 6.97 (d, J=8.4 Hz, 1H), 4.98 (d, J=9.6 Hz, 1H), 3.83 (t, J=4.8 Hz, 4H), 3.58 (t, J=4.8 Hz, 4H), 1.47-1.37 (m, 1H), 0.71-0.64 (m, 2H), 0.56-0.43 (m, 2H); MS ESI 454.3 [M+H]$^+$, calcd for [C$_{22}$H$_{22}$N$_5$O$_2$+H]$^+$ 454.2.

Example A55

(R)-3-(4-((1-methylpiperidin-4-yl)oxy)phenyl)-N-(1-(thiophen-2-yl)ethyl)-1H-indazole-5-carboxamide

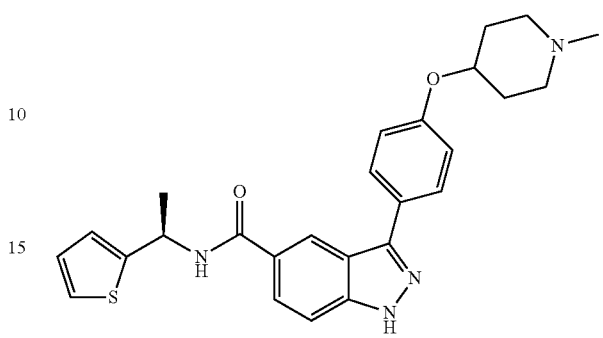

The title compound was synthesized according to the General Method C, utilizing (R)-3-iodo-N-(1-(thiophen-2-yl)ethyl)-1H-indazole-5-carboxamide (70 mg, 0.18 mmol), (4-((1-methylpiperidin-4-yl)oxy)phenyl)boronic acid pinacol ester (56 mg, 0.18 mmol), PdCl$_2$dppf (15 mg, 0.018 mmol), satd. aq Na$_2$CO$_3$ (1.5 mL), and 3.5 mL of PhMe:EtOH (1:1). The vial was charged with Ar and heated in the microwave reactor at 125° C. for 2 h. Purification by RP HPLC, followed by trituration with Et$_2$O gave the title compound as a TFA salt (white solid, 44 mg, 43%). $^1$H NMR (400 MHz, CD$_3$OD) δ ppm 8.57 (s, 1 H), 7.89-7.99 (m, 3 H), 7.60 (d, J=8.8 Hz, 1 H), 7.27 (d, J=4.8 Hz, 1 H), 7.11-7.22 (m, 2 H), 7.05 (br. s, 1 H), 6.96 (t, J=4.3 Hz, 1 H), 5.59 (s, 1 H), 4.58-4.72 (m, 0.3 H), 3.60-3.69 (m, 0.7 H), 3.33-3.47 (m, 3 H), 3.14-3.24 (m, 1 H), 2.93 (s, 3 H), 2.39-2.48 (m, 0.7 H), 2.23-2.35 (m, 1.3 H), 2.12 (br. s, 1.3 H), 1.83-1.98 (m, 0.7 H), 1.70 (d, J=6.8 Hz, 3 H); MS ESI 461.3 [M+H]$^+$, calcd for [C$_{26}$H$_{28}$N$_4$O$_2$S+H]$^+$ 461.2.

Example A56

1-(2-fluorophenyl)-3-(3-(4-((1-methylpiperidin-4-yl)oxy)phenyl)-1H-indazol-5-yl)urea

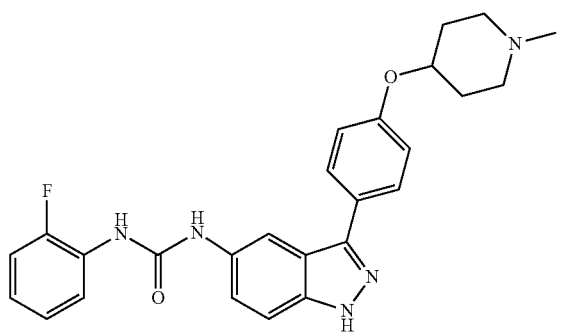

Using General Method J with 3-(4-((1-methylpiperidin-4-yl)oxy)phenyl)-1H-indazol-5-amine bis(2,2,2-trifluoroacetate) (96 mg, 0.174 mmol), 1-fluoro-2-isocyanatobenzene (39 uL, 0.348 mmol), DIPEA (150 uL, 0.87 mmol), and DMF (2.0 mL) gave the title compound as a TFA salt (17 mg, 21%, a tan solid). $^1$H NMR (400 MHz, CD$_3$OD) δ ppm 8.30 (s, 1H), 8.08 (t, J=7.6 Hz, 1H), 7.91-7.88 (m, 2H), 7.51 (d, J=9.0 Hz, 1H), 7.28 (d, J=8.6 Hz, 1H), 7.20-7.02 (m, 5H), 4.83 (bs, 1H), 3.64-3.41 (m, 2H), 3.30-2.93 (m, 2H), 2.93 (bs, 3H), 2.46-2.28 (m, 2H), 2.13-1.89 (m, 2H); MS ESI 460.3 [M+H]$^+$, calcd for [C$_{26}$H$_{26}$FN$_5$O$_2$+H]$^+$ 460.21.

Example A57

N-(3-(3-chloro-4-(1-methylpiperidin-4-yl)oxy)phenyl)-1H-indazol-5-yl)-2-(pyrrolidin-1-yl)-2-(thiophen-3-yl)acetamide

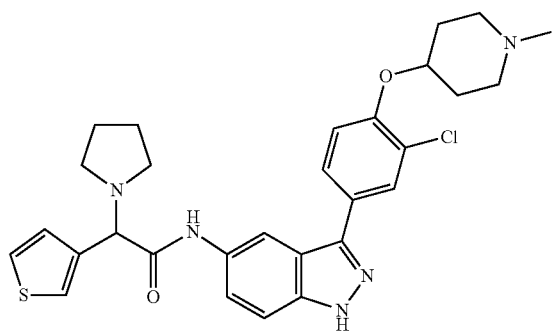 [SMILES: CN1CCC(Oc2ccc(-c3n[nH]c4ccc(NC(=O)C(c5ccsc5)N5CCCC5)cc34)cc2Cl)CC1]

Using General Method C2, N-(3-iodo-1H-indazol-5-yl)-2-(pyrrolidin-1-yl)-2-(thiophen-3-yl)acetamide (52.7 mg, 0.116 mmol) and 4-(2-chloro-4-(4,4,5,5-tetramethyl-1,3,2-dioxaborolan-2-yl)phenoxy)-1-methylpiperidine (61.8 mg, 80% pure, 0.14 mmol) were heated for 3 h at 125° C. in the microwave. Aq. work-up using EtOAc followed by purification by flash chromatography (RP HPLC, 10-80% MeOH in 0.1% TFA-H$_2$O; then SiO$_2$, 10-20% MeOH in DCM), gave the title compound (white solid, 15.4 mg, 24%). $^1$H NMR (400 MHz, CD$_3$OD) δ ppm 8.34 (m, J=1.0 Hz, 1 H), 7.92 (d, J=2.3 Hz, 1 H), 7.79 (dd, J=8.5, 2.3 Hz, 1 H), 7.49-7.56 (m, 3 H), 7.42 (dd, J=5.0, 3.0 Hz, 1 H), 7.34 (dd, J=5.0, 1.3 Hz, 1 H), 7.22 (d, J=8.5 Hz, 1 H), 4.60 (br. s., 1 H), 4.14 (s, 1 H), 2.75-2.84 (m, 2 H), 2.64-2.73 (m, 2 H), 2.47-2.57 (m, 4 H), 2.37 (s, 3 H), 2.00-2.10 (m, 2 H), 1.89-1.99 (m, 2 H), 1.85 (t, J=5.8 Hz, 4 H). MS ESI 550.1 [M+H]$^+$, calcd for [C$_{29}$H$_{32}$ClN$_5$O$_2$S+H]$^+$ 550.20.

Example A58

(R)-3-(4-morpholinophenyl)-N-(1-(thiophen-2-yl)propyl)-1H-indazole-5-carboxamide

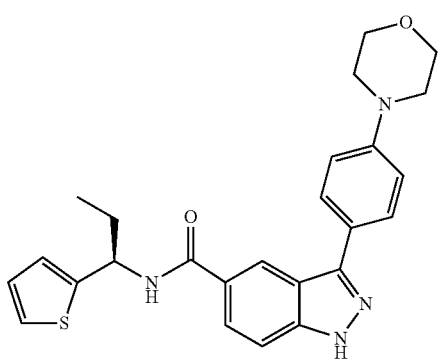 [SMILES: CC[C@@H](NC(=O)c1ccc2[nH]nc(-c3ccc(N4CCOCC4)cc3)c2c1)c1cccs1]

The title compound was synthesized according to the General Method A, utilizing 3-(4-morpholinophenyl)-1H-indazole-5-carboxylic acid (84 mg, 0.26 mmol), (1R)-1-(2-thienyl)propylamine HCl (50 mg, 0.26 mmol), TBTU (83 mg, 0.26 mmol), DIPEA (0.14 mL, 0.78 mmol), and DMF (5 mL). Purification by RP HPLC, followed by passing through PoraPak column gave the title compound (white solid, 34 mg, 29%). $^1$H NMR (400 MHz, CD$_3$OD) δ ppm 8.59 (s, 1 H), 7.82-7.95 (m, 3 H), 7.57 (d, J=8.8 Hz, 1 H), 7.26 (dd, J=5.0, 1.0 Hz, 1 H), 7.03-7.11 (m, 3 H), 6.95 (dd, J=4.9, 3.6 Hz, 1 H), 5.31-5.39 (m, 1 H), 3.80-3.87 (m, 4 H), 3.16-3.23 (m, 4 H), 2.06 (d, J=7.3 Hz, 2 H), 1.04 (t, J=7.3 Hz, 3H); MS ESI 447.3 [M+H]$^+$, calcd for [C$_{25}$H$_{26}$N$_4$O$_2$S+H]$^+$ 447.2.

Example A59

N-(3-(3-methyl-4-morpholinophenyl)-1H-indazol-5-yl)-2-(pyrrolidin-1-yl)-2-(thiophen-3-yl)acetamide

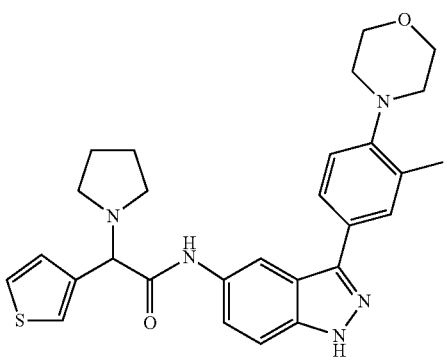 [SMILES: Cc1cc(-c2n[nH]c3ccc(NC(=O)C(c4ccsc4)N4CCCC4)cc23)ccc1N1CCOCC1]

To a mixture of N-(3-iodo-1H-indazol-5-yl)-2-(pyrrolidin-1-yl)-2-(thiophen-3-yl)acetamide (136 mg, 0.3 mmol) and (3-methyl-4-morpholinophenyl)boronic acid (73 mg, 0.33 mmol) in EtOH (4 mL) was added 1 M aq Na$_2$CO$_3$ (0.6 mL, 0.6 mmol), followed by Pd(PPh$_3$)$_4$ (17 mg, 0.015 mmol). The resulting mixture was purged with Ar and microwaved 2 h at 120° C. After removal of solvents, it was redissolved in DMF/TFA (6 mL/0.5 mL), purified by prep-HPLC, followed by PoraPak and acidification with TFA to give the title compound as a di-TFA salt (white solid, 162.4 mg, 74%). $^1$H NMR (400 MHz, CD$_3$OD) δ 8.38 (s, 1H), 7.87 (d, J=1.6 Hz, 1H), 7.81-7.76 (m, 2H), 7.61-7.52 (m, 3H), 7.42 (d, J=8.0 Hz, 1H), 7.38 (dd, J=5.2 Hz, 0.8 Hz, 1H), 5.35 (s, 1H), 4.02-3.96 (m, 4H), 3.90-3.80 (m, 1H), 3.35-3.25 (m, 5H), 3.20-3.04 (m, 2H), 2.48 (s, 3H), 2.25-1.93 (m, 4H); MS ESI 502.2 [M+H]$^+$, calcd for [C$_{28}$H$_{31}$N$_5$O$_2$S+H]$^+$ 502.2.

Example A60

N-(3-(3-fluoro-4-morpholinophenyl)-1H-indazol-5-yl)-2-(pyrrolidin-1-yl)-2-(thiophen-3-yl)acetamide

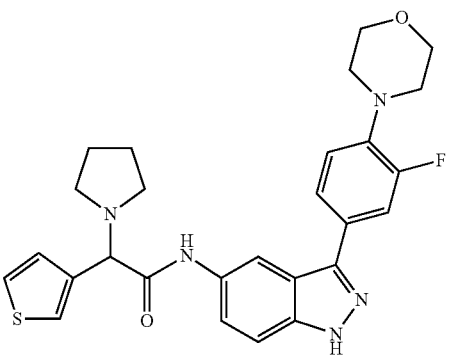 [SMILES: O=C(Nc1ccc2[nH]nc(-c3ccc(N4CCOCC4)c(F)c3)c2c1)C(c1ccsc1)N1CCCC1]

To a mixture of N-(3-iodo-1H-indazol-5-yl)-2-(pyrrolidin-1-yl)-2-(thiophen-3-yl)acetamide (136 mg, 0.3 mmol)

and (3-fluoro-4-morpholinophenyl)boronic acid (74 mg, 0.33 mmol) in EtOH (4 mL) was added 1 M aq $Na_2CO_3$ (0.6 mL, 0.6 mmol), followed by $Pd(PPh_3)_4$ (17 mg, 0.015 mmol). The resulting mixture was purged with Ar and microwaved 2 h at 120° C. After removal of solvents, it was redissolved in DMF/TFA (6 mL/0.5 mL), purified by prep-HPLC to give the title compound as a di-TFA salt (pale yellow solid, 84.3 mg, 38%). $^1$H NMR (400 MHz, $CD_3OD$) δ 8.40 (s, 1H), 7.87 (dd, J=2.8 Hz, 1.2 Hz, 1H), 7.65-7.61 (m, 2H), 7.57 (dd, J=13.8 Hz, 1.8 Hz, 1H), 7.52 (s, 2H), 7.38 (dd, J=5.2 Hz, 1.2 Hz, 1H), 7.07 (t, J=8.6 Hz, 1H), 5.31 (s, 1H), 3.92-3.78 (m, 5H), 3.35-3.25 (m, 1H), 3.22-3.03 (m, 6H), 2.25-1.92 (m, 4H); MS ESI 506.3 [M+H]$^+$, calcd for $[C_{27}H_{28}FN_5O_2S+H]^+$ 506.2.

Example A61

N-(cyclopropyl(phenyl)methyl)-3-(3-morpholino-phenyl)-1H-indazole-5-carboxamide

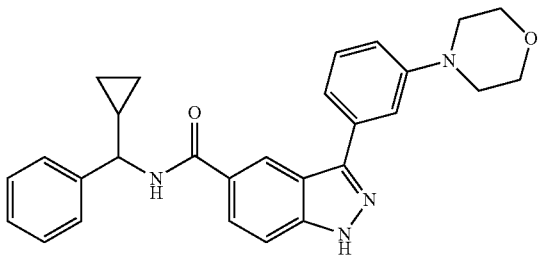 [SMILES: O=C(NC(c1ccccc1)C1CC1)c1ccc2[nH]nc(-c3cccc(N4CCOCC4)c3)c2c1]

The title compound was synthesized according to the General Method C, utilizing N-(cyclopropyl(phenyl) methyl)-3-iodo-1H-indazole-5-carboxamide (100 mg, 0.24 mmol), 3-(4-morpholino)phenylboronic acid pinacol ester (69 mg, 0.24 mmol), $Pd(PPh_3)_4$ (28 mg, 0.024 mmol), satd. aq $Na_2CO_3$ (1.25 mL), and 3.75 mL of PhMe:EtOH (1:1). The vial was charged with Ar and heated in the microwave reactor at 125° C. for 2 h. Purification by RPHPLC, followed by trituration with $Et_2O$ gave the title compound as beige solid (39 mg, 36%). $^1$H NMR (400 MHz, $CD_3OD$) δ ppm 8.58 (s, 1 H), 7.94 (dd, J=8.7, 1.4 Hz, 1 H), 7.62 (d, J=8.8 Hz, 1 H), 7.40-7.55 (m, 5 H), 7.34 (t, J=7.6 Hz, 2 H), 7.24 (t, J=7.3 Hz, 1 H), 7.05-7.10 (m, 1 H), 4.48 (t, J=8.5 Hz, 1 H), 3.84-3.89 (m, 4 H), 3.22-3.27 (m, 4 H), 1.33-1.44 (m, 1 H), 0.62-0.69 (m, 2 H), 0.41-0.54 (m, 2 H); MS ESI 453.4 [M+H]$^+$, calcd for $[C_{28}H_{28}N_4O_2+H]^+$ 453.2.

Example A62

1-(2-chlorophenyl)-3-(3-(4-((1-methylpiperidin-4-yl)oxy)phenyl)-1H-indazol-5-yl)urea

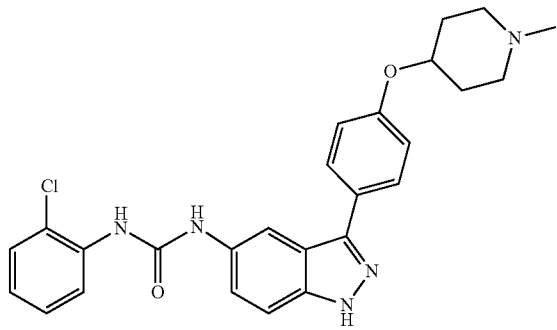 [SMILES: CN1CCC(Oc2ccc(-c3n[nH]c4ccc(NC(=O)Nc5ccccc5Cl)cc34)cc2)CC1]

Using General Method J, 3-(4-((1-methylpiperidin-4-yl)oxy)phenyl)-1H-indazol-5-amine bis(2,2,2-trifluoroacetate)

(111 mg, 0.202 mmol), 1-chloro-2-isocyanatobenzene (49 uL, 0.404 mmol) and DIPEA (180 uL, 1.01 mmol) in DMF (2.0 mL) gave the title compound as a TFA salt. (34 mg, 35%, an off-white solid). $^1$H NMR (400 MHz, $CD_3OD$) δ ppm 8.33 (s, 1H), 8.11 (d, J=7.3 Hz, 1H), 7.92-7.88 (m, 2H), 7.52 (d, J=8.8 Hz, 1H), 7.41 (d, J=8.4 Hz, 1H), 7.31-7.26 (m, 2H), 7.21-7.13 (m, 2H), 7.04 (t, J=7.9, 1H), 4.83 (bs, 1H), 3.66-3.39 (m, 2H), 3.30-3.18 (m, 2H), 2.95 (bs, 3H), 2.48-2.30 (m, 2H), 2.14-1.89 (m, 2H); MS ESI 476.4 [M+H]$^+$, calcd for $[C_{26}H_{26}ClN_5O_2+H]^+$ 476.19.

Example A63

(R)-3-(4-((1-methylpiperidin-4-yl)oxy)phenyl)-N-(1-(thiophen-2-yl)propyl)-1H-indazole-5-carboxamide

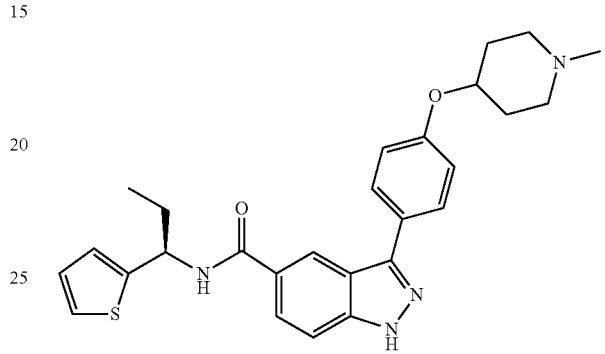

The title compound was synthesized according to the General Method C, utilizing (R)-3-iodo-N-(1-(thiophen-2-yl)propyl)-1H-indazole-5-carboxamide (90 mg, 0.22 mmol), (4-((1-methylpiperidin-4-yl)oxy)phenyl)boronic acid pinacol ester (69 mg, 0.22 mmol), $PdCl_2pddf$ (25 mg, 0.022 mmol), satd. aq $Na_2CO_3$ (1.25 mL), and 3.75 mL of PhMe: EtOH (1:1). The vial was charged with Ar and heated in the microwave reactor at 125° C. for 2 h. Purification by RPHPLC, followed by flash chromatography ($SiO_2$, Biotage 25 g, 0-40% MeOH in $CH_2Cl_2$) gave the title compound (white solid, 18 mg, 17%). $^1$H NMR (400 MHz, $CD_3OD$) δ ppm 8.58 (s, 1 H), 7.93 (dd, J=8.8, 1.5 Hz, 1 H), 7.88 (d, J=8.8 Hz, 2 H), 7.58 (d, J=8.8 Hz, 1 H), 7.25 (dd, J=5.0, 1.0 Hz, 1 H), 7.05 (s, 3 H), 6.94 (dd, J=5.0, 3.5 Hz, 1 H), 5.34 (t, J=7.5 Hz, 1 H), 4.45 (br. s, 1 H), 2.71 (br. s, 2 H), 2.36 (br. s, 2 H), 2.29 (s, 3 H), 1.95-2.12 (m, 4 H), 1.82 (br. d, J=7.5 Hz, 2 H), 1.03 (t, J=7.3 Hz, 3 H); MS ESI 475.3 [M+H]$^+$, calcd for $[C_{27}H_{30}N_4O_2S+H]^+$ 475.2.

Example A64

N-(cyclopropyl(phenyl)methyl)-3-(3-methyl-4-morpholinophenyl)-1H-indazole-5-carboxamide

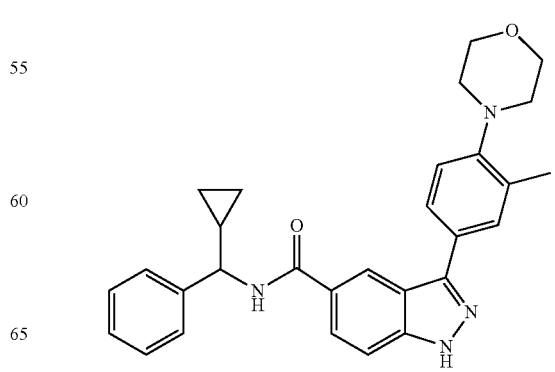

To a mixture of N-(cyclopropyl(phenyl)methyl)-3-iodo-1H-indazole-5-carboxamide (83.4 mg, 0.2 mmol) and (3-methyl-4-morpholinophenyl)boronic acid (44.2 mg, 0.2 mmol) in EtOH (4 mL) was added 1 M aq Na$_2$CO$_3$ (0.4 mL, 0.4 mmol), followed by Pd(PPh$_3$)$_4$ (11.6 mg, 0.01 mmol). The resulting mixture was purged with Ar and microwaved 2 h at 125° C. After removal of solvents, it was purified by flash chromatography (MeOH/DCM 0-15%), PoraPak and prep-HPLC to give the title compound as a TFA salt (light yellow solid, 36.3 mg, 31%). $^1$H NMR (400 MHz, CD$_3$OD) δ 8.06 (s, 1H), 7.96 (dd, J=8.8 Hz, 1.6 Hz, 1H), 7.85-7.80 (m, 2H), 7.60 (dd, J=8.8 Hz, 0.8 Hz, 1H), 7.49 (d, J=7.2 Hz, 2H), 7.36-7.30 (m, 2H), 7.28-7.21 (m, 2H), 4.48 (d, J=9.6 Hz, 1H), 3.90 (t, J=4.4 Hz, 4H), 3.06 (t, J=4.4 Hz, 4H), 2.44 (s, 3H), 1.46-1.36 (m, 1H), 1.20-1.13 (m, 2H), 1.03-0.93 (m, 2H); MS ESI 467.4 [M+H]$^+$, calcd for [C$_{29}$H$_{30}$N$_4$O$_2$+H]$^+$ 467.2.

Example A65

N-(cyclopropyl(phenyl)methyl)-3-(3-fluoro-4-morpholinophenyl)-1H-indazole-5-carboxamide

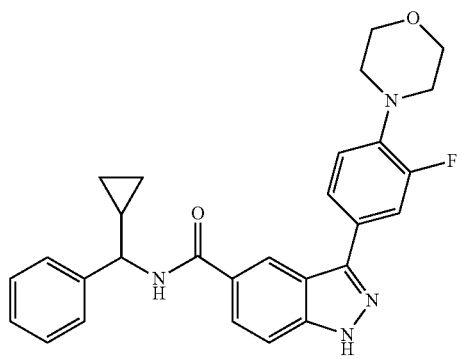 [SMILES: O=C(NC(c1ccccc1)C1CC1)c1ccc2[nH]nc(-c3ccc(N4CCOCC4)c(F)c3)c2c1]

To a mixture of N-(cyclopropyl(phenyl)methyl)-3-iodo-1H-indazole-5-carboxamide (83.4 mg, 0.2 mmol) and (3-fluoro-4-morpholinophenyl)boronic acid (45 mg, 0.2 mmol) in EtOH (4 mL) was added 1 M aq Na$_2$CO$_3$ (0.4 mL, 0.4 mmol), followed by Pd(PPh$_3$)$_4$ (11.6 mg, 0.01 mmol). The resulting mixture was purged with Ar and microwaved 2 h at 125° C. After removal of solvents, it was purified by flash chromatography (MeOH/DCM 0-15%), PoraPak and prep-HPLC to give the title compound as a TFA salt (yellowish white solid, 32.4 mg, 28%). $^1$H NMR (400 MHz, CD$_3$OD) δ 8.62 (s, 1H), 7.96 (dd, J=8.8 Hz, 1.6 Hz, 1H), 7.88 (d, J=8.4 Hz, 1H), 7.73 (dd, J=14.0 Hz, 2.0 Hz, 1H), 7.61 (d, J=8.8 Hz, 1H), 7.49 (d, J=7.6 Hz, 2H), 7.34 (t, J=7.6 Hz, 2H), 7.24 (t, J=7.4 Hz, 1H), 7.20-7.13 (m, 1H), 4.49 (d, J=9.2 Hz, 1H), 3.87 (t, J=4.6 Hz, 4H), 3.17-3.11 (m, 4H), 1.46-1.38 (m, 1H), 1.21-1.13 (m, 2H), 1.05-0.93 (m, 2H); MS ESI 471.4 [M+H]$^+$, calcd for [C$_{28}$H$_{27}$FN$_4$O$_2$+H]$^+$ 471.2.

Example A66

1-(2-chlorophenyl)-3-(3-(4-morpholinophenyl)-1H-indazol-5-yl)urea

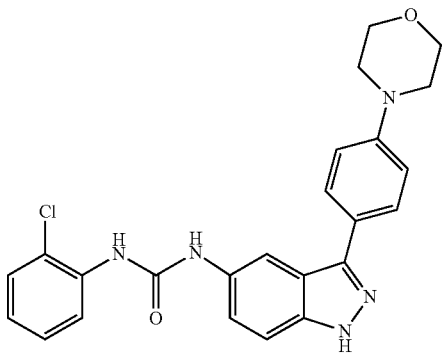 [SMILES: O=C(Nc1ccc2[nH]nc(-c3ccc(N4CCOCC4)cc3)c2c1)Nc1ccccc1Cl]

Using General Method J, 3-(4-morpholinophenyl)-1H-indazol-5-amine bis(2,2,2-trifluoroacetate) (69 mg, 0.234 mmol), 1-chloro-2-isocyanatobenzene (58 uL, 0.468 mmol) and DIPEA (160 uL, 0.936 mmol) in DMF (2.0 mL) gave the title compound as a TFA salt (7.6 mg, 7.2%, a white solid). 1H NMR (400 MHz, DMSO-d$_6$) δ ppm 12.96 (s, 1 H), 9.46-9.48 (m, 1 H), 8.28 (s, 2 H), 8.20 (dd, J=8.28, 1.51 Hz, 1 H), 7.79 (d, J=8.78 Hz, 2 H), 7.49 (dd, J=17.44, 8.41 Hz, 1 H), 7.28-7.33 (m, 2 H), 7.10 (d, J=8.78 Hz, 2 H), 7.00-7.05 (m, 1 H), 3.75-3.79 (m, 4 H), 3.17-3.21 (m, 4 H); MS ESI 448.4 [M+H]$^+$, calcd for [C$_{24}$H$_{22}$ClN$_5$O$_2$+H]$^+$ 448.15.

Example A67

N-(3-(4-((4-methylpiperazin-1-yl)methyl)phenyl)-1H-indazol-5-yl)-2-(pyrrolidin-1-yl)-2-(thiophen-3-yl)acetamide

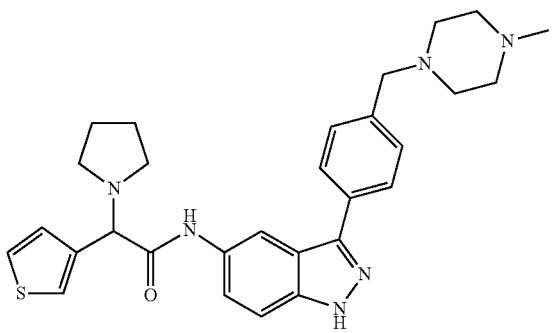 [SMILES: CN1CCN(Cc2ccc(-c3n[nH]c4ccc(NC(=O)C(c5ccsc5)N5CCCC5)cc34)cc2)CC1]

The title compound was synthesized according to General Method C by using a sealed degassed mixture of N-(3-iodo-1H-indazol-5-yl)-2-(pyrrolidin-1-yl)-2-(thiophen-3-yl)acetamide (75 mg, 0.165 mmol), 1-methyl-4-(4-(4,4,5,5-tetramethyl-1,3,2-dioxaborolan-2-yl)benzyl)piperazine (53 mg, 0.165 mmol), PdCl$_2$dppf (14 mg, 0.0165 mmol), 1 M aq Na$_2$CO$_3$ (0.17 mL) in PhMe/EtOH (3 mL, 1:0.5 mixture) under Ar with heating under microwave irradiation at 125° C. for 2.5 h. The reaction mixture was diluted with EtOAc (15 mL) and washed with H$_2$O (2×5 mL) and brine (5 mL), dried (Na$_2$SO$_4$) and concentrated under vacuum. Purification by flash chromatography (SiO$_2$, 0-80% MeOH in DCM) followed by RPHPLC gave the title compound as a TFA salt (light brown solid, 22 mg, 9%). $^1$H NMR (400 MHz, CD$_3$OD) δ 8.41 (s, 1H), 8.01 (d, J=8.0 Hz, 2H), 7.88-7.87 (m, 1H), 7.66-7.62 (m, 3H), 7.58-7.51 (m, 2H), 7.38-7.37 (m, 1H), 5.26 (s, 1H), 4.20 (s, 2H), 3.88-3.87 (br.s, 1H), 3.51 (brs, 4H), 3.13-3.10 (brm, 3H), 2.96 (s, 3H), 2.25-1.96 (brm, 5H), 3H merged with solvent peak, MS ESI 515.2 [M+H]$^+$, calcd for [C$_{29}$H$_{34}$N$_6$OS+H]$^+$ 515.2.

Example A68

N-(3-(4-(cyclohexylamino)phenyl)-1H-indazol-5-yl)-2-(pyrrolidin-1-yl)-2-(thiophen-3-yl)acetamide

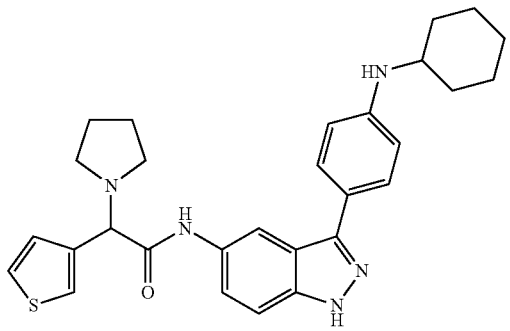 [SMILES: O=C(Nc1ccc2[nH]nc(-c3ccc(NC4CCCCC4)cc3)c2c1)C(c1ccsc1)N1CCCC1]

To a mixture of 4-(4,4,5,5-tetramethyl-1,3,2-dioxaborolan-2-yl)aniline (657 mg, 3 mmol) and cyclohexanone (0.31 mL, 3 mmol) in DCE (30 mL) was added NaBH(OAc)$_3$ (1.272 g, 6 mmol). The resulting mixture was cooled to 0° C. before HOAc (0.5 mL) was added. After stirring O/N at rt, it was quenched with satd aq NaHCO$_3$ (5 mL) and H$_2$O (30 mL), extracted with DCM and purified by flash chromatography (EtOAc/hex 0-45%) to give N-cyclohexyl-4-(4,4,5,5-tetramethyl-1,3,2-dioxaborolan-2-yl)aniline (off white solid, 705 mg, 78%). $^1$H NMR (400 MHz, CDCl$_3$) δ 7.62 (d, J=7.6 Hz, 2H), 6.56 (d, J=7.2 Hz, 2H), 3.35-3.25 (m, 1H), 2.12-2.02 (m, 2H), 1.72-1.62 (m, 2H), 4.45-1.10 (m, 18H); MS ESI 302.1 [M+H]$^+$, calcd for [C$_{18}$H$_{28}$BNO$_2$+H]$^+$ 302.1.

To a mixture of N-(3-iodo-1H-indazol-5-yl)-2-(pyrrolidin-1-yl)-2-(thiophen-3-yl)acetamide (136 mg, 0.3 mmol) and N-cyclohexyl-4-(4,4,5,5-tetramethyl-1,3,2-dioxaborolan-2-yl)aniline in EtOH (4 mL) was added 1 M aq Na$_2$CO$_3$ (0.6 mL, 0.6 mmol), followed by Pd(PPh$_3$)$_4$ (17.4 mg, 0.015 mmol). The resulting mixture was purged with Ar and microwaved 2 h at 120° C. Additional Pd(PPh$_3$)$_4$ (17.4 mg, 0.015 mmol) was added and the resulting mixture was purged with Ar and microwaved 2 h at 125° C. After removal of solvents, it was redissolved in DMF/TFA (6 mL/0.5 mL), purified by prep-HPLC and PoraPak to give the title compound (white solid, 52.3 mg, 35%). $^1$H NMR (400 MHz, CD$_3$OD) δ 8.33 (s, 1H), 7.65 (d, J=8.8 Hz, 2H), 7.51-7.43 (m, 3H), 7.38 (dd, J=9.0 Hz, 3.0 Hz, 1H), 7.30 (dd, J=5.2 Hz, 1.2 Hz, 1H), 6.72 (d, J=8.8 Hz, 2H), 4.08 (s, 1H), 3.29-3.21 (m, 1H), 2.68-2.58 (m, 2H), 2.50-2.42 (m, 2H), 2.07-1.98 (m, 2H), 1.85-1.72 (m, 6H), 1.68-1.62 (m, 1H), 1.45-1.32 (m, 2H), 1.30-1.12 (m, 3H); MS ESI 500.2 [M+H]$^+$, calcd for [C$_{29}$H$_{33}$N$_5$OS+H]$^+$ 500.2.

Example A69

N-(1-cyclohexylpropyl)-3-(4-((1-methylpiperidin-4-yl)oxy)phenyl)-1H-indazole-5-carboxamide

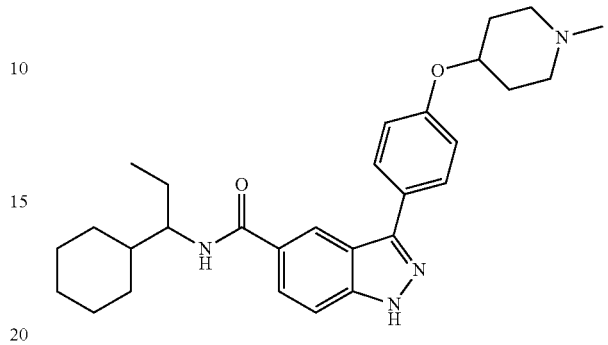

The title compound was synthesized according to General Method C3 utilizing N-(1-cyclohexylpropyl)-3-iodo-1H-indazole-5-carboxamide and 1-methyl-4-(4-(4,4,5,5-tetramethyl-1,3,2-dioxaborolan-2-yl)phenoxy)piperidine and obtained as a yellow solid (20 mg, 18% yield). $^1$H NMR (400 MHz, CD$_3$OD) δ ppm 8.57 (s, 1H), 7.92 (m, 3H), 7.60 (d, J=8.8 Hz, 1H), 7.08 (d, J=8.8 Hz, 2H), 4.47 (m, 1H), 3.87 (m, 1H), 2.72 (br, 2H), 2.37 (br, 2H), 2.30 (s, 3H), 2.05 (br, 2H), 1.83 (m, 3H), 1.74 (m, 3H), 1.65 (m, 1H), 1.51 (m, 2H), 1.22 (m, 4H), 1.08 (m, 2H), 0.95 (t, J=7.2 Hz, 3H); MS ESI [M+H]$^+$ 475.4, calcd for [C$_{29}$H$_{38}$N$_4$O$_2$+H]$^+$ 475.31.

Example A70

N-(3-(4-(cyclopentylamino)phenyl)-1H-indazol-5-yl)-2-(pyrrolidin-1-yl)-2-(thiophen-3-yl)acetamide

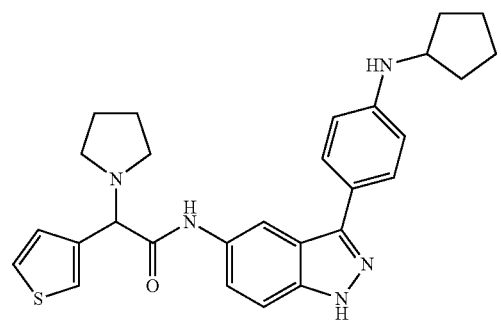 [SMILES: O=C(Nc1ccc2[nH]nc(-c3ccc(NC4CCCC4)cc3)c2c1)C(c1ccsc1)N1CCCC1]

To a mixture of 4-(4,4,5,5-tetramethyl-1,3,2-dioxaborolan-2-yl)aniline (876 mg, 4 mmol) and cyclopentanone (0.36 mL, 4 mmol) in DCE (30 mL) was added NaBH(OAc)$_3$ (1.484 g, 7 mmol), followed by HOAc (0.5 mL). The resulting mixture was stirred O/N at rt, quenched with satd aq NaHCO$_3$ (10 mL) and H$_2$O (30 mL), extracted with DCM and purified by flash chromatography (EtOAc/hex 0-45%) to give N-cyclopentyl-4-(4,4,5,5-tetramethyl-1,3,2-dioxaborolan-2-yl)aniline (off white solid, 393 mg, 34%). $^1$H NMR (400 MHz, CDCl$_3$) δ 7.63 (d, J=8.0 Hz, 2H), 6.58 (d, J=8.0 Hz, 2H), 3.82 (quint, J=6.2 Hz, 1H), 2.08-1.98 (m, 1H), 1.78-1.56 (m, 4H), 1.52-1.43 (m, 2H), 1.33 (s, 12H); MS ESI 288.1 [M+H]$^+$, calcd for [C$_{17}$H$_{26}$BNO$_2$+H]$^+$ 288.2.

To a mixture of N-(3-iodo-1H-indazol-5-yl)-2-(pyrrolidin-1-yl)-2-(thiophen-3-yl)acetamide (136 mg, 0.3 mmol) and N-cyclopentyl-4-(4,4,5,5-tetramethyl-1,3,2-dioxaborolan-2-yl)aniline (96 mg, 0.33 mmol) in EtOH (4 mL) was added 1 M aq Na$_2$CO$_3$ (0.6 mL, 0.6 mmol), followed by Pd(PPh$_3$)$_4$ (35 mg, 0.03 mmol). The resulting mixture was purged with Ar and microwaved 3 h at 125° C. After removal of solvents, it was purified by flash chromatography, PoraPak and prep-HPLC to give the title compound as a di-TFA salt (yellow solid, 51.9 mg, 24%). $^1$H NMR (400 MHz, CD$_3$OD) δ 8.43 (s, 1H), 8.08 (d, J=8.8 Hz, 2H), 7.87 (dd, J=3.0 Hz, 1.4 Hz, 1H), 7.64 (dd, J=5.0 Hz, 3.0 Hz, 1H), 7.60-7.52 (m, 4H), 7.39 (dd, J=5.2 Hz, 1.2 Hz, 1H), 5.33 (s, 1H), 4.02 (quint, J=6.7 Hz, 1H), 3.86 (brs, 1H), 3.35-3.05 (m, 3H), 2.30-1.95 (m, 6H), 1.93-1.67 (m, 6H); MS ESI 486.2 [M+H]$^+$, calcd for [C$_{28}$H$_{31}$N$_5$OS+H]$^+$ 486.2.

Example A71

2-(pyrrolidin-1-yl)-N-(3-(4-((tetrahydro-2H-pyran-4-yl)amino)phenyl)-1H-indazol-5-yl)-2-(thiophen-3-yl)acetamide

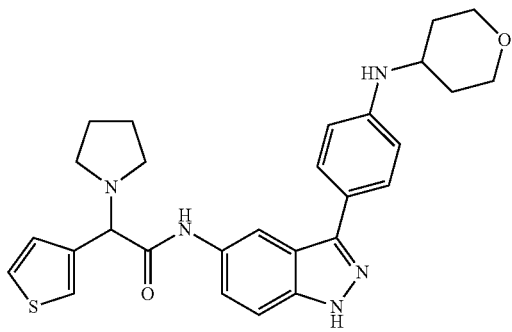

To a mixture of 4-(4,4,5,5-tetramethyl-1,3,2-dioxaborolan-2-yl)aniline (1.095 mg, 5 mmol), dihydro-2H-pyran-4(3H)-one (550 mg, 5 mmol) and NaBH(OAc)$_3$ (1.696 g, 8 mmol) in DCE (30 mL) was added HOAc (0.5 mL). The resulting mixture was stirred O/N at rt, quenched with satd aq NaHCO$_3$ (10 mL) and H$_2$O (30 mL), extracted with DCM and purified by flash chromatography (EtOAc/hex 0-45%) to give N-(4-(4,4,5,5-tetramethyl-1,3,2-dioxaborolan-2-yl)phenyl)tetrahydro-2H-pyran-4-amine (beige solid, 0.65 g, 43%). $^1$H NMR (400 MHz, CDCl$_3$) δ 7.64 (d, J=8.0 Hz, 2H), 6.60 (d, J=8.0 Hz, 2H), 4.01 (dt, J=12.0 Hz, 3.2 Hz, 2H), 3.60-3.45 (m, 3H), 2.08-2.00 (m, 2H), 1.60-1.44 (m, 2H), 1.33 (s, 12H); MS ESI 304.1 [M+H]$^+$, calcd for [C$_{17}$H$_{26}$BNO$_3$+H]$^+$ 304.2.

To a mixture of N-(3-iodo-1H-indazol-5-yl)-2-(pyrrolidin-1-yl)-2-(thiophen-3-yl)acetamide (136 mg, 0.3 mmol) and N-(4-(4,4,5,5-tetramethyl-1,3,2-dioxaborolan-2-yl)phenyl)tetrahydro-2H-pyran-4-amine (100 mg, 0.33 mmol) in EtOH (4 mL) was added 1 M aq Na$_2$CO$_3$ (0.6 mL, 0.6 mmol), followed by Pd(PPh$_3$)$_4$ (34.7 mg, 0.03 mmol). The resulting mixture was purged with Ar and microwaved 3 h at 125° C. After removal of solvents, it was purified by flash chromatography (MeOH/DCM 0-20%), PoraPak and prep-HPLC to give the title compound as a di-TFA salt (yellow solid, 21.9 mg, 10%). $^1$H NMR (400 MHz, CD$_3$OD) δ 8.42 (t, J=0.8 Hz, 1H), 8.03 (d, J=8.8 Hz, 2H), 7.88 (dd, J=3.2 Hz, 1.2 Hz, 1H), 7.65 (dd, J=5.2 Hz, 3.2 Hz, 1H), 7.57 (dd, J=8.8 Hz, 0.4 Hz, 1H), 7.54 (dd, J=8.4 Hz, 1.6 Hz, 1H), 7.43 (d, J=8.8 Hz, 2H), 7.38 (dd, J=8.8 Hz, 1.4 Hz, 1H), 5.23 (s, 1H), 4.08-4.00 (m, 2H), 3.93-3.72 (m, 2H), 3.48 (dt, J=11.8 Hz, 1.8 Hz, 2H), 3.35-3.05 (m, 3H), 2.28-2.09 (m, 3H), 2.06-1.95 (m, 3H), 1.80-1.69 (m, 2H); MS ESI 502.2 [M+H]$^+$, calcd for [C$_{28}$H$_{31}$H$_5$O$_2$S+H]$^+$ 502.2.

Example A72

1-ethyl-3-(3-(4-morpholinophenyl)-1H-indazol-5-yl)-1-phenylurea

A. 3-(4-morpholinophenyl)-1-(tetrahydro-2H-pyran-2-yl)-1H-indazol-5-amine

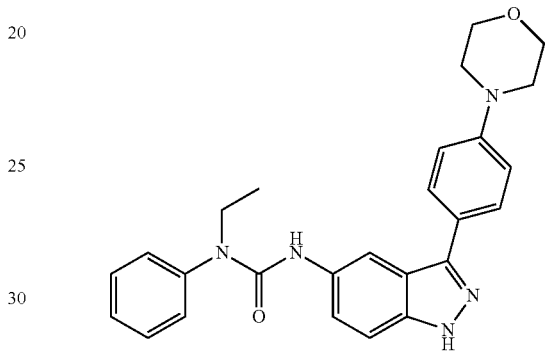

The same procedure was followed as for 3-(4-((1-methylpiperidin-4-yl)oxy)phenyl)-1H-indazol-5-amine bis(2,2,2-trifluoroacetate) instead using 3-iodo-1-(tetrahydro-2H-pyran-2-yl)-1H-indazol-5-amine (30 mg, 0.087 mmol) and 4-(4-(4,4,5,5-tetramethyl-1,3,2-dioxaborolan-2-yl)phenyl)morpholine (38 mg, 0.131 mmol). Obtained 36 mg of an impure product which was used for subsequent synthetic steps.

B. 1-ethyl-3-(3-(4-morpholinophenyl)-1H-indazol-5-yl)-1-phenylurea

To a solution of triphosgene (8 mg, 0.027 mmol) in CH$_2$Cl$_2$ (0.4 mL) cooled to 0° C. was added dropwise over 15 min a solution of 3-(4-morpholinophenyl)-1-(tetrahydro-2H-pyran-2-yl)-1H-indazol-5-amine (30 mg, 0.074 mmol) in DIPEA (28 uL, 0.16 mmol) and CH$_2$Cl$_2$ (0.6 mL). After stirring for an additional 15 min a solution of N-ethylaniline (10 uL, 0.074 mmol), DIPEA (13 uL, 0.074 mmol) and CH$_2$Cl$_2$ (0.5 mL) was added. After 3 h the reaction was quenched with MeOH (0.5 mL) and the solvent was removed. The residue was taken up in EtOH (0.4 mL) and HCl (0.1 mL of a 1 M solution in Et$_2$O) was added and the mixture heated to 50° C. for 2 h. The solvent was removed and the residue purified by prep-HPLC which gave 5.0 mg of the product isolated as its TFA salt (29%, a tan solid). $^1$H NMR (400 MHz, CDCl$_3$) δ ppm 8.03 (s, 1H), 7.84 (d, J=8.0 Hz, 2H), 7.51-7.17 (m, 6H), 7.02 (d, J=7.6 Hz, 2H), 6.14 (s, 1H), 3.92-3.82 (m, 6H), 3.24 (bs, 4H), 1.18 (bs, 3H); MS ESI 442.3 [M+H]$^+$, calcd for [C$_{26}$H$_{27}$N$_5$O$_2$+H]$^+$ 442.22.

Example A73

N-(3-(4-((1-methylpiperidin-4-yl)oxy)phenyl)-1H-indazol-5-yl)-3,4-dihydroquinoline-1(2H)-carboxamide

A. 3-(4-((1-methylpiperidin-4-yl)oxy)phenyl)-1-(tetrahydro-2H-pyran-2-yl)-1H-indazol-5-amine

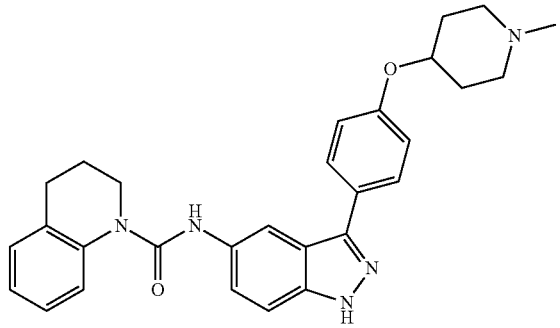 [SMILES: CN1CCC(Oc2ccc(-c3n[nH]c4ccc(NC(=O)N5CCCc6ccccc65)cc34)cc2)CC1]

The same procedure was followed as for 3-(4-((1-methylpiperidin-4-yl)oxy)phenyl)-1H-indazol-5-amine bis(2,2,2-trifluoroacetate) instead using 3-iodo-1-(tetrahydro-2H-pyran-2-yl)-1H-indazol-5-amine (300 mg, 0.874 mmol) and 1-methyl-4-(4-(4,4,5,5-tetramethyl-1,3,2-dioxaborolan-2-yl)phenoxy)piperidine (416 mg, 1.31 mmol). Obtained 130 mg of an impure product which was used for subsequent synthetic steps; MS ESI 407.1 [M+H]$^+$, calcd for [$C_{24}H_{30}N_4O_2$+H]$^+$ 407.24.

B. N-(3-(4-((1-methylpiperidin-4-yl)oxy)phenyl)-1H-indazol-5-yl)-3,4-dihydroquinoline-1(2H)-carboxamide To a solution of triphosgene (14 mg, 0.046 mmol) in $CH_2Cl_2$ (0.6 mL) cooled to 0° C. was added dropwise over 15 min a solution of 3-(4-((1-methylpiperidin-4-yl)oxy)phenyl)-1-(tetrahydro-2H-pyran-2-yl)-1H-indazol-5-amine (50 mg, 0.123 mmol) in DIPEA (47 uL, 0.271 mmol) and $CH_2Cl_2$ (0.9 mL). After stirring for an additional 15 min a solution of 1,2,3,4-tetrahydroquinoline (15 uL, 0.123 mmol), DIPEA (21 uL, 0.123 mmol) and $CH_2Cl_2$ (0.8 mL) was added. After 3 h the reaction was quenched with MeOH (0.5 mL) and the solvent was removed. The residue was taken up in EtOH (0.4 mL) and HCl (0.1 mL of a 1 M solution in $Et_2O$) was added and the mixture heated to 50° C. for 2 h. The solvent was removed and the residue purified by prep-HPLC which gave the product as its TFA salt (2.0 mg, 3.3%, a white film). $^1$H NMR (400 MHz, $CD_3OD$) δ ppm 8.14 (s, 1H), 7.90-7.86 (m, 2H), 7.49 (d, J=9.0 Hz, 1H), 7.43-7.36 (m, 2H), 7.21-7.11 (m, 4H), 7.05 (t, J=8.5 Hz, 1H), 4.83 (bs, 1H), 3.82-3.79 (m, 2H), 3.65-3.35 (m, 2H), 3.30-3.18 (m, 2H), 2.93 (bs, 3H), 2.82 (t, J=6.4 Hz, 2H), 2.45-2.28 (m, 2H), 2.14-1.88 (m, 4H); MS ESI 482.3 [M+H]$^+$, calcd for [$C_{29}H_{31}N_5O_2$+H]$^+$ 482.26.

Example A74

N-(2-methyl-2-morpholinopropyl)-3-(4-((1-methylpiperidin-4-yl)oxy)phenyl)-1H-indazole-5-carboxamide

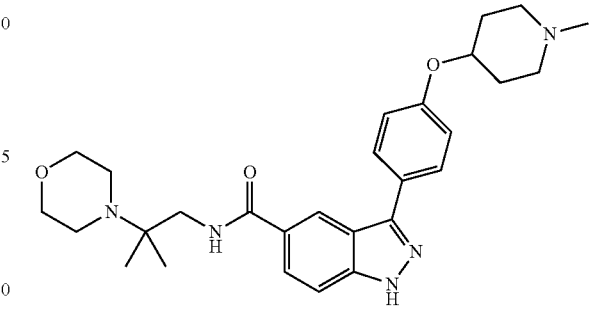

A TFA salt of the title compound was synthesized according to General Method C3 utilizing 3-iodo-N-(2-methyl-2-morpholinopropyl)-1H-indazole-5-carboxamide and 1-methyl-4-(4-(4,4,5,5-tetramethyl-1,3,2-dioxaborolan-2-yl)phenoxy)piperidine obtained as a white solid (38 mg, 35% yield). $^1$H NMR (400 MHz, $CD_3OD$) δ ppm 8.66 (s, 1H), 7.98 (m, 3H), 7.65 (d, J=8.8 Hz, 1H), 7.20 (m, 2H), 4.96, 4.86 (s, m, 1H), 4.13 (m, 2H), 3.86 (m, 2H), 3.70 (m, 4H), 3.60 (m, 1H), 3.33 (m, 4H), 2.93 (s, 3H), 2.42, 2.28 (m, 2H), 2.17, 1.95 (m, 2H), 1.48 (s, 6H); MS ESI [M+H]$^+$ 492.2, calcd for [$C_{28}H_{37}N_5O_3$+H]$^+$ 492.30.

Example A75

3-(4-((1-methylpiperidin-4-yl)oxy)phenyl)-N-(2-morpholino-2-(thiophen-3-yl)ethyl)-1H-indazole-5-carboxamide

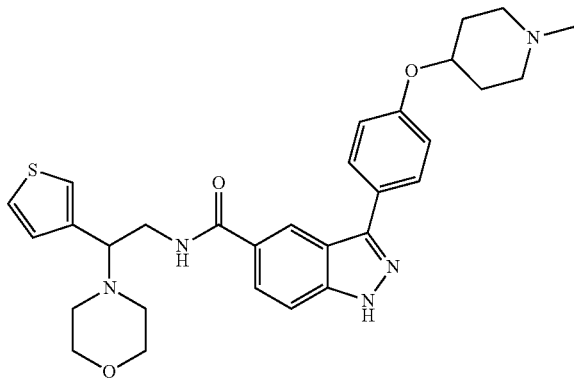 [SMILES: CN1CCC(Oc2ccc(-c3n[nH]c4ccc(C(=O)NCC(c5ccsc5)N5CCOCC5)cc34)cc2)CC1]

The title compound was synthesized according to General Method C3 utilizing 3-iodo-N-(2-morpholino-2-(thiophen-3-yl)ethyl)-1H-indazole-5-carboxamide and 1-methyl-4-(4-(4,4,5,5-tetramethyl-1,3,2-dioxaborolan-2-yl)phenoxy)piperidine and obtained as a white solid (19 mg, 15% yield). $^1$H NMR (400 MHz, $CD_3OD$) δ ppm 8.35 (s, 1 H), 7.87 (d, J=8.78 Hz, 2 H), 7.80 (dd, J=8.78, 1.51 Hz, 1 H), 7.57 (d, J=8.78 Hz, 1 H), 7.43 (dd, J=4.89, 2.89 Hz, 1 H), 7.27-7.32 (m, 1 H), 7.06-7.15 (m, 3 H), 4.52 (br. s., 1 H), 3.93-4.04 (m, 2 H), 3.63-3.74 (m, 5 H), 2.78 (br. s., 2 H), 2.39-2.62 (m, 6 H), 2.35 (s, 3 H), 2.07 (br. s., 2 H), 1.89 (br. s., 2 H); MS ESI [M+H]$^+$ 546.3, calcd for [C$_{30}$H$_{35}$N$_5$O$_3$S+H]$^+$ 546.25.

Example A76

1-(2,6-dichlorophenyl)-3-(3-(4-((1-methylpiperidin-4-yl)oxy)phenyl)-1H-indazol-5-yl)urea

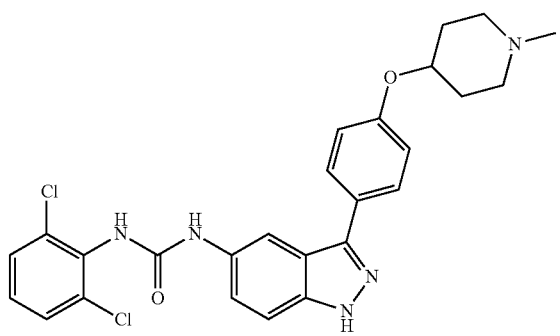 [SMILES: CN1CCC(Oc2ccc(-c3n[nH]c4ccc(NC(=O)Nc5c(Cl)cccc5Cl)cc34)cc2)CC1]

Using General Method J, 3-(4-((1-methylpiperidin-4-yl)oxy)phenyl)-1H-indazol-5-amine bis(2,2,2-trifluoroacetate) (50 mg, 0.11 mmol), 1,3-dichloro-2-isocyanatobenzene (43 mg, 0.23 mmol) and DIPEA (100 uL, 0.58 mmol) in DMF (1.2 mL) gave the title compound as a TFA salt (10 mg, 14%, a brown powder). $^1$H NMR (400 MHz, CD$_3$OD) δ ppm 8.25 (s, 1H), 7.89-7.86 (m, 2H), 7.52-7.41 (m, 3H), 7.34-7.25 (m, 2H), 7.17-7.10 (m, 2H), 4.84 (bs, 1H), 3.63-3.36 (m, 2H), 3.30-3.15 (m, 2H), 2.92 (bs, 3H), 2.43-2.26 (m, 2H), 2.11-1.87 (m, 21-1); MS ESI 510.3 [M+H]$^+$, calcd for [C$_{26}$H$_{25}$Cl$_2$N$_5$O$_2$+H]$^+$ 510.15.

Example A77

1-(2-chloro-4,6-dimethylphenyl)-3-(3-(4-((1-methylpiperidin-4-yl)oxy)phenyl)-1H-indazol-5-yl)urea

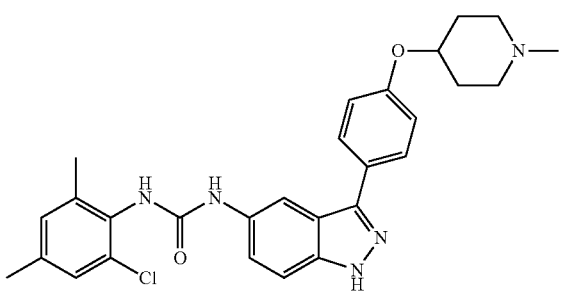

Using General Method J, 3-(4-((1-methylpiperidin-4-yl)oxy)phenyl)-1H-indazol-5-amine bis(2,2,2-trifluoroacetate) (50 mg, 0.11 mmol), 1-chloro-2-isocyanato-3,5-dimethylbenzene (42 mg, 0.23 mmol) and DIPEA (100 uL, 0.58 mmol) in DMF (1.2 mL) gave the title compound as a TFA salt (16 mg, 23%, brown powder). $^1$H NMR (400 MHz, CD$_3$OD) δ ppm 8.24 (s, 1H), 7.88-7.84 (m, 2H), 7.49 (d, J=8.9 Hz, 1H), 7.31 (d, J=8.9 Hz, 1H), 7.17-7.09 (m, 3H), 7.05 (s, 1H), 4.83 (bs, 1H), 3.63-3.33 (m, 2H), 3.30-3.15 (m, 2H), 2.92 (bs, 3H), 2.45-2.23 (m, 2H), 2.37 (s, 3H), 2.36 (s, 3H), 2.12-1.87 (m, 2H); MS ESI 504.3 [M+H]$^+$, calcd for [C$_{28}$H$_{30}$ClN$_5$O$_2$+H]$^+$ 504.22.

Example A78

N-(3-(4-(methyl(tetrahydro-2H-pyran-4-yl)amino)phenyl)-1H-indazol-5-yl)-2-(pyrrolidin-1-yl)-2-(thiophen-3-yl)acetamide

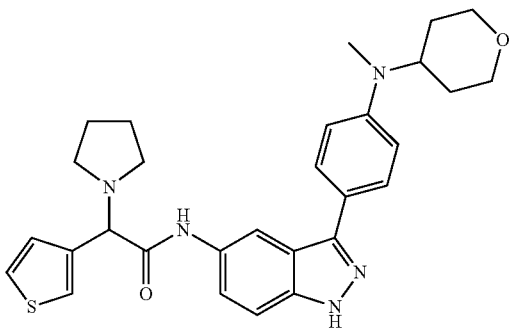 [SMILES: CN(c1ccc(-c2n[nH]c3ccc(NC(=O)C(c4ccsc4)N4CCCC4)cc23)cc1)C1CCOCC1]

To a solution of 37% formalin (0.21 mL, 3 mmol) in DCE/MeOH (20 mL/4 mL) was added N-(4-(4,4,5,5-tetramethyl-1,3,2-dioxaborolan-2-yl)phenyl)tetrahydro-2H-pyran-4-amine (303 mg, 1 mmol) and NaBH(OAc)$_3$ (424 mg, 2 mmol). Additional formalin (37% in H$_2$O, 0.21 mL, 3 mmol) and NaBH(OAc)$_3$ (424 mg, 2 mmol) were added and the reaction mixture was stirred for 2 h at rt, and then quenched with satd aq NaHCO$_3$ (10 mL) and H$_2$O (30 mL), extracted with DCM and purified by flash chromatography (0-45% MeOH/DCM) to give N-methyl-N-(4-(4,4,5,5-tetramethyl-1,3,2-dioxaborolan-2-yl)phenyl)tetrahydro-2H-pyran-4-amine (pink solid, 224 mg). $^1$H NMR (400 MHz, CDCl$_3$) δ MS ESI 318.1 [M+H]$^+$, calcd for [C$_{18}$H$_{28}$BNO$_3$+H]$^+$ 318.2.

To a mixture of N-(3-iodo-1H-indazol-5-yl)-2-(pyrrolidin-1-yl)-2-(thiophen-3-yl)acetamide (136 mg, 0.3 mmol) and N-methyl-N-(4-(4,4,5,5-tetramethyl-1,3,2-dioxaborolan-2-yl)phenyl)tetrahydro-2H-pyran-4-amine (100 mg, 0.315 mmol) in EtOH (4 mL) was added 1 M aq Na$_2$CO$_3$ (0.6 mL, 0.6 mmol), followed by Pd(PPh$_3$)$_4$ (69 mg, 0.06 mmol). The resulting mixture was purged with Ar and microwaved 3 h at 125° C. After removal of solvents, it was purified by flash chromatography (0-20% MeOH/DCM), prep-HPLC and PoraPak to give the title compound (white solid, 44.8 mg, 29%). $^1$H NMR (400 MHz, CD$_3$OD) δ 8.38 (s, 1H), 7.72 (d, J=8.8 Hz, 2H), 7.51-7.43 (m, 3H), 7.34 (dd, J=5.0 Hz, 3.0 Hz, 1H), 7.29 (dd, J=5.2 Hz, 0.8 Hz, 1H), 6.87 (d, J=8.8 Hz, 2H), 4.07 (s, 1H), 3.95 (dd, J=11.4 Hz, 4.2 Hz, 2H), 3.84 (tt, J=11.6 Hz, 3.8 Hz, 1H), 3.44 (t, J=11.0 Hz, 2H), 2.72 (s, 3H), 2.64-2.56 (m, 2H), 2.47-2.39 (m, 2H), 1.82-1.70 (m, 6H), 1.60-1.53 (m, 2H),; MS ESI 516.3 [M+H]$^+$, calcd for [C$_{29}$H$_{33}$N$_5$O$_2$S+H]$^+$ 516.2.

Example A79

(R)-2-((S)-2-methylpyrrolidin-1-yl)-N-(3-(4-morpholinophenyl)-1H-indazol-5-yl)-2-(thiophen-2-yl)acetamide A. (R)-2-((S)-2-methylpyrrolidin-1-yl)-2-(thiophen-2-yl)acetic acid

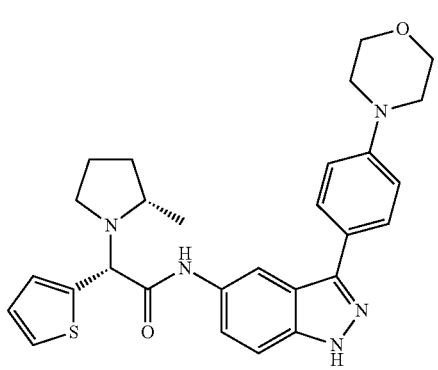 [SMILES: C[C@H]1CCCN1[C@H](C(=O)Nc1ccc2[nH]nc(-c3ccc(N4CCOCC4)cc3)c2c1)c1cccs1]

Using General Method D, (S)-2-methylpyrrolidine (0.135 mL, 1.57 mmol) and thiophen-2-ylboronic acid (201.1 mg, 1.57 mmol) gave the title compound (off-white solid, 330 mg, 93%) which was used without purification. NMR (400 MHz, CD$_3$OD) δ ppm 7.57 (d, J=4.5 Hz, 1 H), 7.36 (dd, J=3.5, 1.0 Hz, 1 H), 7.10 (dd, J=5.3, 3.5 Hz, 1 H), 3.63-3.73 (m, 1 H), 3.19-3.28 (m, 1 H), 2.24-2.39 (m, 1 H), 1.92-2.08 (m, 2 H), 1.74-1.85 (m, 1 H), 1.50 (d, J=6.53 Hz, 3 H).

B. (R)-2-((S)-2-methylpyrrolidin-1-yl)-N-(3-(4-morpholinophenyl)-1H-indazol-5-yl)-2-(thiophen-2-yl)acetamide (1-Cyano-2-ethoxy-2-oxoethylidenaminooxy)dimethylamino-morpholino-carbenium hexafluorophosphate (35.2 mg, 0.082 mmol) was added to an ice-cooled mixture of (R)-2-((S)-2-methylpyrrolidin-1-yl)-2-(thiophen-2-yl)acetic acid (16.5 mg, 0.073 mmol), 3-(4-morpholinophenyl)-1H-indazol-5-amine bis(2,2,2-trifluoroacetate) (39.9 mg, 0.076 mmol) and DIPEA (0.05 mL, 0.28 mmol) in DMF (1.0 mL) under Ar. The resulting mixture was stirred in ice bath for 1 h, then allowed to warm to rt and stirred for a further 22 h. The product was partitioned between EtOAc (200 mL) and satd aq NaHCO$_3$ (25 mL), and the aq. layer was extracted with EtOAc (2×25 mL). The combined organic layer was washed with H$_2$O (25 mL) and brine (25 mL), dried (Na$_2$SO$_4$), filtered, and concentrated to dryness. Purification by flash chromatography (SiO$_2$, 0-10% MeOH in DCM; followed by RP HPLC, 10-80% MeOH in 0.1% TFA-H$_2$O) followed by purification by another prep HPLC gave the title compound as the TFA salt (yellow solid film, 14.0 mg, 26%). $^1$H NMR (400 MHz, CD$_3$OD) δ ppm 8.38 (t, J=1.3 Hz, 1 H), 7.85 (d, J=8.3 Hz, 2 H), 7.71 (d, J=5.3 Hz, 1 H), 7.49-7.59 (m, 3 H), 7.20 (m, 3 H), 5.50 (s, 1 H), 3.90 (t, J=4.8 Hz, 4 H), 3.79-3.87 (m, 4 H), ~3.30 (4 H, obscured by solvent), 2.40 (dd, J=13.3, 7.8 Hz, 1 H), 2.06 (t, J=7.0 Hz, 2 H), 1.86 (dq, J=13.2, 6.5 Hz, 1 H), 1.52 (d, J=6.3 Hz, 3 H); MS ESI 502.3 [M+H]$^+$, calcd for [C$_{28}$H$_{31}$N$_5$O$_2$S+H]$^+$ 502.23.

Example A80

N-(3-(3-amino-4-((1-methylpiperidin-4-yl)oxy)phenyl)-1H-indazol-5-yl)-2-(pyrrolidin-1-yl)-2-(thiophen-3-yl)acetamide A. 1-methyl-4-(2-nitro-4-(4,4,5,5-tetramethyl-1,3,2-dioxaborolan-2-yl)phenoxy)piperidine

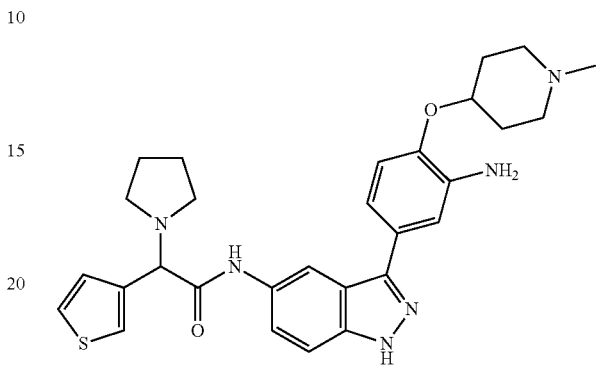

DIAD (0.25 mL, 1.26 mmol) was added drop-wise to a solution of PPh$_3$ (315 mg, 1.20 mmol), 2-nitro-4-(4,4,5,5-tetramethyl -1,3,2-dioxaborolan-2-yl)phenol (199.8 mg, 0.785 mmol) and 1-methylpiperidin-4-ol (138.3 mg, 1.20 mmol) in DCM (8 mL) under Ar and the reaction was stirred at rt for 3.5 d. Purification by flash chromatography without work-up or evaporation (SiO$_2$, 5-35% MeOH in DCM) gave the title compound (36.0 mg, 80% pure, 13%). $^1$H NMR (400 MHz, CDCl$_3$) δ ppm 8.25 (d, J=1.5 Hz, 1 H), 7.93 (dd, J=8.3, 1.5 Hz, 1 H), 7.63-7.71 (m, 1 H), 7.52-7.58 (m, 1 H), 7.43-7.50 (m, 1 H), 7.06 (d, J=8.5 Hz, 1 H), 4.82 (br. s., 1 H), 2.87-3.05 (m, 4 H), 2.61 (s, 3 H), 2.28-2.40 (m, 3 H), 2.09 (d, J=13.8 Hz, 2 H), 1.32-1.36 (m, 15 H). MS ESI 363.1 [M+H]$^+$, calcd for [C$_{18}$H$_{27}$BN$_2$O$_5$+H]$^+$ 363.21.

B. N-(3-(4-((1-methylpiperidin-4-yl)oxy)-3-nitrophenyl)-1H-indazol-5-yl)-2-(pyrrolidin-1-yl)-2-(thiophen-3-yl)acetamide Using General Method C2, N-(3-iodo-1H-indazol-5-yl)-2-(pyrrolidin-1-yl)-2-(thiophen-3-yl)acetamide (39.9 mg, 0.088 mmol) and 1-methyl-4-(2-nitro-4-(4,4,5,5-tetramethyl-1,3,2-dioxaborolan-2-yl)phenoxy)piperidine (35 mg, 80% pure, 0.077 mmol) gave the title compound after 3 h at 125° C. in the microwave (34.8 mg, 57%) after purification by flash chromatography (SiO$_2$, 15-30% MeOH in DCM; followed by RP HPLC, 10-80% MeOH in 0.1% TFA-H$_2$O). $^1$H NMR (400 MHz, CD$_3$OD) δ ppm 8.39-8.46 (m, 1.8H), 8.32-8.37 (m, 0.2 H), 8.16-8.25 (m, 1 H), 7.86-7.91 (m, 1 H), 7.62-7.68 (m, 1 H), 7.50-7.61 (m, 4 H), 7.34-7.43 (m, 1 H), 5.28-5.32 (m, 1 H), 5.12-5.18 (m, 1 H), 3.80-3.95 (m, 1.2 H), 3.64-3.73 (m, 0.8 H), 3.46-3.55 (m, 2 H), 3.33-3.42 (m, 2 H), 3.16-3.28 (m, 1 H), 3.03-3.15 (m, 1 H), 2.96 (s, 3 H), 2.43-2.53 (m, 0.8 H), 2.31-2.41 (m, 1.6 H), 2.10-2.29 (m, 5 H), 1.93-2.08 (m, 1 H). MS ESI 561.2 [M+H]$^+$, calcd for [C$_{29}$H$_{32}$N$_6$O$_4$S+H]$^+$ 561.23.

C. N-(3-(3-amino-4-((1-methylpiperidin-4-yl)oxy)phenyl)-1H-indazol-5-yl)-2-(pyrrolidin-1-yl)-2-(thiophen-3-yl)acetamide A mixture of Pd/C (10%, 18.1 mg, 0.017 mmol) and N-(3-(4-((1-methylpiperidin-4-yl)oxy)-3-nitrophenyl)-1H- indazol-5-yl)-2-(pyrrolidin-1-yl)-2-(thiophen-3-yl)acetamide (34.8 mg, 0.062 mmol) in MeOH (5 mL) was stirred at rt with $H_2$ balloon for 2.5 h, and then filtered through Celite, rinsing with MeOH (25 mL). After concentration to dryness, purification by RP HPLC (, 10-80% MeOH in 0.1% TFA-$H_2$O) followed by PoraPak Rxn Cx work-up gave the title compound (yellow solid, 6.5 mg, 20%). $^1$H NMR (400 MHz, $CD_3OD$) δ ppm 8.34 (s, 1 H), 7.47-7.52 (m, 3 H), 7.42 (dd, J=4.9, 2.9 Hz, 1 H), 7.32-7.35 (m, 2 H), 7.22 (dd, J=8.3, 2.0 Hz, 1 H), 6.98 (d, J=8.5 Hz, 1 H), 4.47 (br. s., 1 H), 4.11 (s, 1 H), 2.77 (br. s., 2 H), 2.67 (d, J=6.0 Hz, 3 H), 2.46-2.55 (m, 3 H), 2.40 (br. s., 2 H), 2.33 (s, 3 H), 2.06 (br. s., 2 H), 1.89 (d, J=9.5 Hz, 2 H), 1.84 (br. s., 4 H). MS ESI 531.1 $[M+H]^+$, calcd for $[C_{29}H_{34}N_6O_2S+H]^+$ 531.25.

Example A81

1-(4-methoxy-2-methylphenyl)-3-(3-(4-((1-methylpiperidin-4-yl)oxy)phenyl)-1H-indazol-5-yl)urea

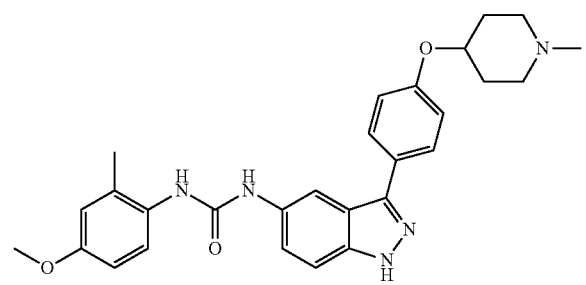

Using General Method J, 3-(4-((1-methylpiperidin-4-yl)oxy)phenyl)-1H-indazol-5-amine bis(2,2,2-trifluoroacetate) (50 mg, 0.11 mmol), 1-isocyanato-4-methoxy-2-methylbenzene (33 uL, 0.23 mmol) and DIPEA (100 uL, 0.58 mmol) in DMF (1.2 mL) gave the title compound as a TFA salt (25 mg, 36%, a beige powder). $^1$H NMR (400 MHz, $CD_3OD$) δ ppm 8.26 (s, 1H), 7.89-7.86 (m, 2H), 7.49 (d, J=8.8 Hz, 1H), 7.36 (d, J=8.8 Hz, 1H), 7.28 (d, J=8.9 Hz, 1H), 7.19-7.12 (m, 2H), 6.81 (d, J=2.6 Hz, 1H), 6.75 (dd, $J_1$=8.4 Hz, $J_2$=2.5 Hz, 1H), 4.83 (bs, 1H), 3.77 (s, 3H), 3.64-3.32 (m, 2H), 3.30-3.15 (m, 2H), 2.93 (bs, 3H), 2.47-2.29 (m, 2H), 2.29 (s, 3H), 2.14-1.91 (m, 2H); MS ESI 486.3 $[M+H]^+$, calcd for $[C_{28}H_{31}N_5O_3+H]^+$ 486.25.

Example A82

N-(3-(4-morpholinophenyl)-1H-indazol-5-yl)-2-(pyrrolidin-1-yl)-2-(thiophen-2-yl)acetamide

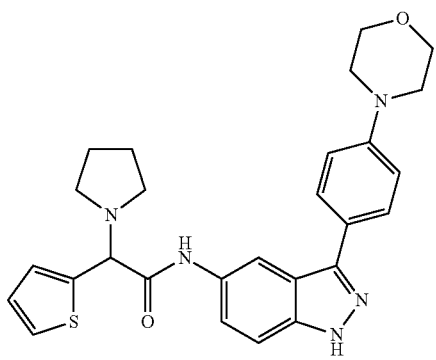 [SMILES: O=C(Nc1ccc2[nH]nc(-c3ccc(N4CCOCC4)cc3)c2c1)C(c1cccs1)N1CCCC1]

To a mixture of 2-(pyrrolidin-1-yl)-2-(thiophen-2-yl)acetic acid (85 mg, 0.4 mmol), 3-(4-morpholinophenyl)-1H-indazol-5-amine di-trifluoroacetic acid (229 mg, 0.44 mmol) and TBTU (128 mg, 0.4 mmol) in DMF (6 mL) at 0° C. was added $^i$Pr$_2$NEt (0.28 mL, 1.6 mmol). The resulting mixture was stirred for 1 h at 0° C. and purified by prep-HPLC to give the title compound as a di-TFA salt (yellow solid, 263 mg, 92%). $^1$H NMR (400 MHz, $CD_3OD$) δ 8.39 (s, 1H), 7.88 (d, J=8.4 Hz, 2H), 7.52 (d, J=4.8 Hz, 1H), 7.54 (s, 2H), 7.51 (dd, J=3.2 Hz, 0.8 Hz, 1H), 7.33-7.26 (m, 2H), 7.12 (dd, J=5.2 Hz, 3.6 Hz, 1H), 5.78 (s, 1H), 3.89 (t, J=4.6 Hz, 4H), 3.40-3.10 (m, 8H), 2.20-1.90 (m, 4H); MS ESI 488.3 $[M+H]^+$, calcd for $[C_{27}H_{32}N_5O_2S+H]^+$ 488.2.

Example A83

N-(3-(4-(4-hydroxypiperidin-1-yl)phenyl)-1H-indazol-5-yl)-2-(piperidin-1-yl)-2-(thiophen-3-yl)acetamide

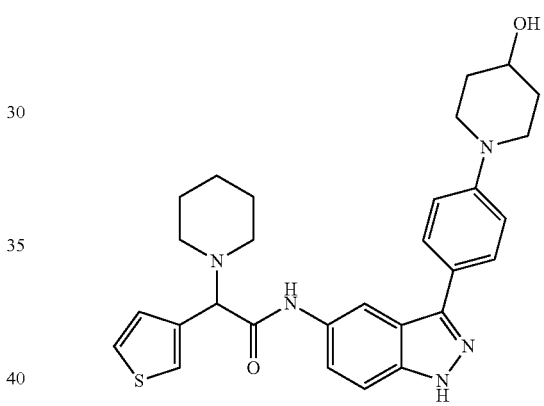

The title compound was synthesized according to General Method C by using a sealed degassed mixture of N-(3-iodo-1H-indazol-5-yl)-2-(piperidin-1-yl)-2-(thiophen-3-yl)acetamide (75 mg, 0.16 mmol), 1-(4-(4,4,5,5-tetramethyl-1,3,2-dioxaborolan-2-yl)phenyl)piperidin-4-ol (90 mg, 0.17 mmol), Pd(PPh$_3$)$_4$ (14 mg, 0.012 mmol), 1 M aq Na$_2$CO$_3$ (0.32 mL) in PhMe/EtOH (3 mL, 1:0.5 mixture) under Ar with heating under microwave irradiation at 130° C. for 3 h. The reaction mixture was diluted with EtOAc (20 mL) and washed with H$_2$O (2×10 mL) and brine (10 mL), dried (Na$_2$SO$_4$) and concentrated under vacuum. Purification by flash chromatography (SiO$_2$, 0-15% MeOH in DCM) followed by RPHPLC and passing through a PoraPak column with 1 M NH$_3$-MeOH to elute gave the title compound (off white solid, 36 mg, 43%). $^1$H NMR (400 MHz, $CD_3OD$) δ ppm 8.35 (m, 1H), 7.79 (d, J=8.8 Hz, 2H), 7.49 (s, 2H), 7.45-7.41 (m, 1H), 7.42-7.40 (m, 1H), 7.26 (dd, J=4.8 Hz, J=1.2 Hz, 1H), 7.10 (d, j=9.2 Hz, 2H), 4.14 (s, 1H), 3.79-3.74 (m, 1H), 3.68-3.63 (m, 2H), 2.97-2.91 (br.m, 2H), 2.45 (br.s, 4H), 2.04-1.96 (br.m, 2H), 1.70-1.61 (br.m, 6H), 1.49-1.47 (br.m, 2H); MS ESI 516.2 $[M+H]^+$, calcd for $[C_{29}H_{33}N_5O_2S+H]^+$ 516.2.

Example A84

N-(cyclopropyl(phenyl)methyl)-3-(4-(4-hydroxypiperidin-1-yl)phenyl)-1H-indazole-5-carboxamide

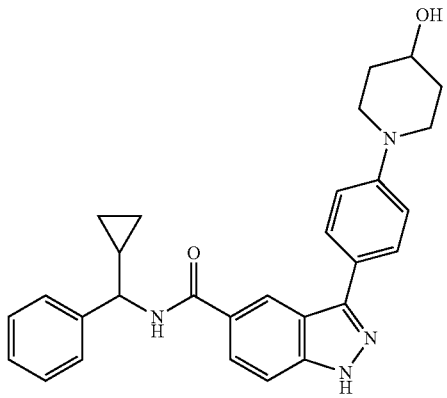 [SMILES: O=C(NC(c1ccccc1)C1CC1)c1ccc2[nH]nc(-c3ccc(N4CCC(O)CC4)cc3)c2c1]

Using General Method C2, N-(cyclopropyl(phenyl)methyl)-3-iodo-1H-indazole-5-carboxamide (51.3 mg, 0.12 mmol) and 1-(4-(4,4,5,5-tetramethyl-1,3,2-dioxaborolan-2-yl)phenyl)piperidin-4-ol (77.8 mg, 65% pure, 0.16 mmol) gave the title compound after 5 h at 125° C. in the microwave as the TFA salt (yellow solid film, 22.2 mg, 31%). $^1$H NMR (400 MHz, CD$_3$OD) δ ppm 8.63 (s, 1 H), 8.21 (d, J=8.8 Hz, 2 H), 7.99 (dd, J=8.8, 1.5 Hz, 1 H), 7.74 (d, J=8.5 Hz, 2 H), 7.66 (d, J=8.8 Hz, 1 H), 7.50 (d, J=7.3 Hz, 2 H), 7.34 (t, J=7.5 Hz, 2 H), 7.25 (t, J=7.3 Hz, 1 H), 4.50 (d, J=9.5 Hz, 1 H), 4.10 (tt, J=7.1, 3.6 Hz, 1 H), 3.89 (ddd, J=11.9, 8.3, 3.4 Hz, 2 H), 3.55-3.66 (m, 2 H), 2.18-2.31 (m, 2 H), 2.02 (dtd, J=14.3, 7.2, 7.2, 3.6 Hz, 2 H), 1.38-1.48 (m, 1 H), 0.62-0.75 (m, 2 H), 0.42-0.56 (m, 2 H). MS ESI 467.4 [M+H]$^+$, calcd for [C$_{29}$H$_{30}$N$_4$O$_2$+H]$^+$ 467.25.

Example A85

N-((1-methylpiperidin-4-yl)(phenyl)methyl)-3-(4-morpholinophenyl)-1H-indazole-5-carboxamide

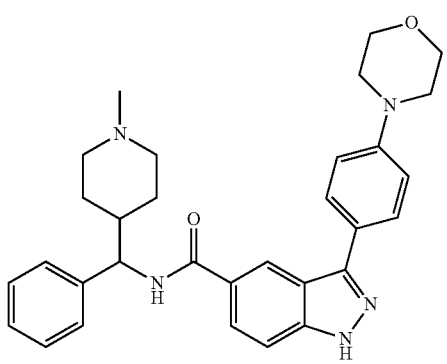 [SMILES: CN1CCC(C(NC(=O)c2ccc3[nH]nc(-c4ccc(N5CCOCC5)cc4)c3c2)c2ccccc2)CC1]

The title compound was synthesized according to the General Method A, utilizing 3-(4-morpholinophenyl)-1H-indazole-5-carboxylic acid (100 mg, 0.31 mmol), (1-methylpiperidin-4-yl)(phenyl)methanamine (63 mg, 0.31 mmol), TBTU (100 mg, 0.31 mmol), DIPEA (0.16 mL, 0.93 mmol), and DMF (5 mL). Purification by flash chromatography (SiO$_2$, Biotage 25 g, 5-75% MeOH in CH$_2$Cl$_2$) followed by RPHPLC, and trituration with Et$_2$O gave the title compound as a bis-TFA salt (light yellow solid, 18 mg, 8%). $^1$H NMR (400 MHz, CD$_3$OD) δ ppm 8.55 (s, 1 H), 7.87 (s, 3 H), 7.59 (d, J=8.53 Hz, 1 H), 7.46 (d, J=6.78 Hz, 2 H), 7.39 (t, J=7.53 Hz, 2 H), 7.30 (t, J=7.50 Hz, 1 H), 7.14 (d, J=8.78 Hz, 2 H), 4.92-4.96 (m, 1 H), 3.83-3.91 (m, 4 H), 3.55-3.62 (m, 1 H), 3.41-3.49 (m, 1 H), 3.21-3.27 (m, 4 H), 2.86-3.03 (m, 2 H), 2.85 (s, 3 H), 2.17-2.35 (m, 2 H), 1.40-1.72 (m, 3 H); MS ESI 511.2 [M+H]$^+$, calcd for [C$_{31}$H$_{35}$N$_5$O$_2$+H]$^+$ 510.3.

Example A86

1-(2,6-diethylphenyl)-3-(3-(4-morpholinophenyl)-1H-indazol-5-yl)urea

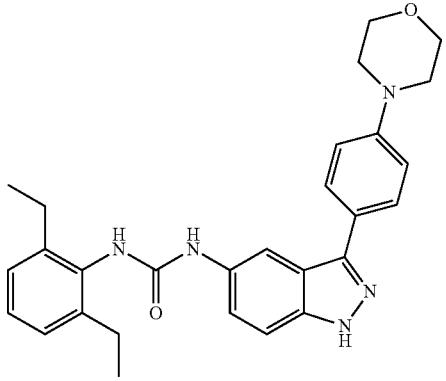 [SMILES: CCc1cccc(CC)c1NC(=O)Nc1ccc2[nH]nc(-c3ccc(N4CCOCC4)cc3)c2c1]

Using General Method J, 3-(4-morpholinophenyl)-1H-indazol-5-amine bis(2,2,2-trifluoroacetate) (78 mg, 0.150 mmol), 1,3-diethyl-2-isocyanatobenzene (52 uL, 0.30 mmol) and DIPEA (130 uL, 0.75 mmol) in DMF (1.5 mL) gave the title compound as a TFA salt (25 mg, 36%, a yellow solid). $^1$H NMR (400 MHz, DMSO-d$_6$) δ ppm 8.77 (s, 1H), 8.26 (s, 1H), 7.77 (d, J=8.8 Hz, 2H), 7.62 (s, 1H), 7.45 (d, J=8.5 Hz, 1H), 7.31 (d, J=8.2 Hz, 1H), 7.18-7.06 (m, 5H), 3.75 (bs, 4H), 3.16 (bs, 4H), 2.60 (q, J=8.0 Hz, 4H), 1.14 (t, J=7.2 Hz, 6H); MS ESI 470.3 [M+H]$^+$, calcd for [C$_{28}$H$_{31}$N$_5$O$_2$+H]$^+$ 470.26.

Example A87

N-(3-(4-(4-hydroxypiperidin-1-yl)phenyl)-1H-indazol-5-yl)-2-methoxy-2-(thiophen-3-yl)acetamide A. tert-butyl (3-(4-(4-hydroxypiperidin-1-yl)phenyl)-1H-indazol-5-yl)carbamate

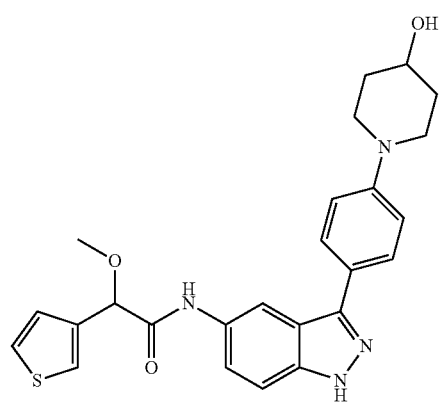 [SMILES: COC(C(=O)Nc1ccc2[nH]nc(-c3ccc(N4CCC(O)CC4)cc3)c2c1)c1ccsc1]

The title compound was synthesized according to General Method C from tert-butyl (3-iodo-1H-indazol-5-yl)carbamate (445 mg, 1.23 mmol) and 1-(4-(4,4,5,5-tetramethyl-1,3,2-dioxaborolan-2-yl)phenyl)piperidin-4-ol (376 mg, 1.23 mmol) with Pd(PPh$_3$)$_4$ (100 mg, 0.086 mmol) and 1 M aq Na$_2$CO$_3$ (3.0 mL) in PhMe/EtOH (8.9 mL, 2:1 mixture) under Ar with heating under microwave irradiation at 130° C. for 5 h. The reaction mixture was diluted with EtOAc (25 mL) and washed (H₂O (15 mL), brine (20 mL)), dried (Na₂SO₄) and concentrated under vacuum. Purification by flash chromatography (SiO₂, 0-20% MeOH in DCM) gave the title compound (185 mg). ¹H NMR (400 MHz, CDCl₃) δ 8.17 (s, 1H), 7.79 (d, J=8.4 Hz, 2H), 7.45 (d, J=8.8 Hz, 1H), 7.36 (d, J=9.2 Hz, 1H), 7.08 (d, J=8.8 Hz, 2H), 3.77-3.72 (m, 1H), 3.63-3.62 (br.m, 2H), 2.93-2.86 (m, 2H), 1.98-1.94 (br.m, 2H), 1.68-1.59 (br.m, 2H), 1.53 (s, 9H); MS ESI 409.3 [M+H]⁺, calcd for [C₂₃H₂₈N₄O₃+H]⁺ 409.2.

B. 1-(4-(5-amino-1H-indazol-3-yl)phenyl)piperidin-4-ol

CF₃COOH (3 mL) was added to a solution of tert-butyl (3-(4-(4-hydroxypiperidin-1-yl)phenyl)-1H-indazol-5-yl) carbamate (185 mg) in DCM (2 mL) at rt and the mixture was stirred for 24 h. Concentration under vacuum gave the title compound as a 2×TFA salt (brown solid, 167 mg, 25%, 2 steps). ¹H NMR (400 MHz, CD₃OD) δ 8.07 (d, J=1.2 Hz, 1H), 7.98 (d, J=8.8 Hz, 2H), 7.76 (d, J=8.8 Hz, 1H), 7.45-7.43 (m, 3H), 5.36-5.30 (m, 1H), 3.74-3.70 (m, 2H), 3.52-3.46 (m, 3H), 2.34-2.29 (m, 2H), 2.15-2.07 (m, 2H); MS ESI 309.1 [M+H]⁺, calcd for [C₁₈H₂₀N₄O+H]⁺ 309.1.

C. N-(3-(4-(4-hydroxypiperidin-1-yl)phenyl)-1H-indazol-5-yl)-2-methoxy-2-(thiophen-3-yl)acetamide The title compound was synthesized according to General Method A by using 2-methoxy-2-(thiophen-2-yl)acetic acid (30 mg, 0.172 mmol), DMF (3 mL), 1-(4-(5-amino-1H-indazol-3-yl)phenyl)piperidin-4-ol trifluoroactetate (94 mg, 0.175 mmol), DIPEA (152 uL, 0.80 mmol) and TBTU (56 mg, 0.174 mmol). After stirring for 24 h at rt and concentrated under reduced pressure, direct purification using Biotage (SiO₂, 0-25% MeOH in DCM; then RP HPLC C18 60 g, 10-80% MeOH in 0.1% TFA-H₂O) gave the title compound as a TFA salt (cream color solid, 38 mg, 54%). ¹H NMR (400 MHz, CD₃OD) δ ppm 8.48 (d, J=0.4 Hz, 1H), 8.16 (d, J=8.8 Hz, 2H), 7.77 (d, J=8.8 Hz, 2H), 7.59-7.53 (m, 3H), 7.45 (dd, J=5.2 Hz, J=3.2 Hz, 1H), 7.23 (dd, J=4.8 Hz, J=0.8 Hz, 1H), 4.96 (s, 1H), 4.15-4.09 (m, 1H), 3.91-3.85 (m, 2H), 3.68-3.62 (m, 2H), 3.48 (s, 3H), 2.29-2.23 (br.m, 2H), 2.08-2.201 (br.m, 2H); MS ESI 463.1[M+H]⁺, calcd for [C₂₅H₂₆N₄O₃S+H]⁺ 463.1

Example A88

N-(3-(4-(4-hydroxypiperidin-1-yl)phenyl)-1H-indazol-5-yl)-2-(pyrrolidin-1-yl)-2-(thiophen-2-yl)acetamide

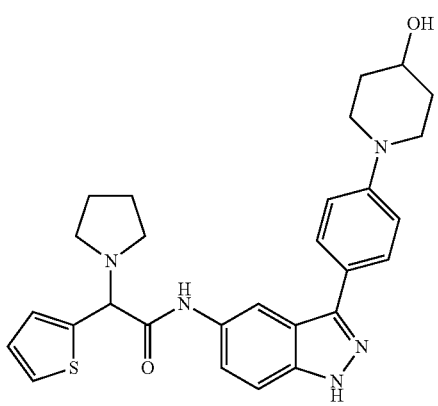 [SMILES: O=C(Nc1ccc2[nH]nc(-c3ccc(N4CCC(O)CC4)cc3)c2c1)C(c1cccs1)N1CCCC1]

To a mixture of 2-(pyrrolidin-1-yl)-2-(thiophen-2-yl)acetic acid (25.5 mg, 0.12 mmol), 1-(4-(5-amino-1H-indazol-3-yl)phenyl)piperidin-4-ol di-trifluoroacetic acid (64 mg, 0.12 mmol) and TBTU (39 mg, 0.12 mmol) in DMF (6 mL) at 0° C. was added ᶦPr₂NEt (0.084 mL, 0.48 mmol). The resulting mixture was sonicated to make a clear solution and stirred for 10 min at 0° C. It was quenched with H₂O (30 mL) and satd aq NaHCO₃ (10 mL), extracted with EtOAc and purified by prep-HPLC and PoraPak to give the title compound (white solid, 18.5 mg, 31%). ¹H NMR (400 MHz, CD₃OD) δ 8.33 (t, J=0.8 Hz, 1H), 7.77 (pseudo d, J=8.8 Hz, 2H), 7.53-7.47 (m, 2H), 7.39 (dd, J=5.0 Hz, 0.6 Hz, 1H), 7.21 (dd, J=3.6 Hz, 1.2 Hz, 1H), 7.09 (pseudo d, J=8.8 Hz, 2H), 6.99 (dd, J=5.2 Hz, 3.6 Hz, 1H), 4.31 (s, 1H), 3.77 (sept, J=4.4 Hz, 1H), 3.66 (tt, J=12.8 Hz, 4.0 Hz, 2H), 2.97-2.90 (m, 2H), 2.73-2.65 (m, 2H), 2.60-2.53 (m, 2H), 2.02-1.95 (m, 2H), 1.89-1.80 (m, 4H), 1.70-1.61 (m, 2H); MS ESI 502.2 [M+H]⁺, calcd for [C₂₈H₃₁N₅O₂S+H]⁺ 502.2.

Example A89

N-(3-(4-(4-hydroxy-4-methylpiperidin-1-yl)phenyl)-1H-indazol-5-yl)-2-(pyrrolidin-1-yl)-2-(thiophen-3-yl)acetamide

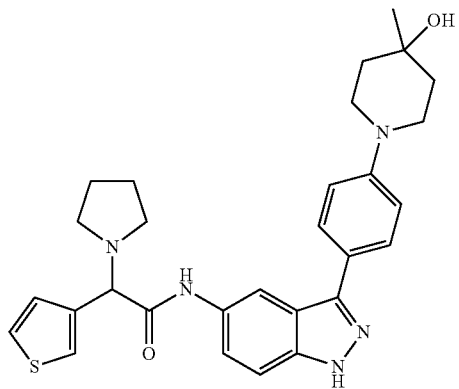 [SMILES: CC1(O)CCN(c2ccc(-c3n[nH]c4ccc(NC(=O)C(c5ccsc5)N5CCCC5)cc34)cc2)CC1]

The title compound was synthesized according to General Method C3 utilizing N-(3-iodo-1H-indazol-5-yl)-2-(pyrrolidin-1-yl)-2-(thiophen-3-yl)acetamide and 4-methyl-1-(4-(4,4,5,5-tetramethyl-1,3,2-dioxaborolan-2-yl)phenyl)piperidin-4-ol and obtained as a white solid (15 mg, 22% yield). ¹H NMR (400 MHz, CD₃OD) δ ppm 8.33 (s, 1H), 7.77 (d, J=8.8 Hz, 2H), 7.49 (m, 3H), 7.40 (m, 1H), 7.33 (dd, J=4.2 Hz, 1 Hz, 1H), 7.08 (d, J=8.8 Hz, 2H), 4.10 (s, 1H), 3.38 (m, 2H), 3.23 (m, 2H), 2.65 (br, 2H), 2.48 (br, 2H), 1.82 (m, 4H), 1.72 (m, 4H), 1.26 (s, 3H); MS ESI [M+H]⁺ 516.2, calcd for [C₂₉H₃₃N₅O₂S+H]⁺ 516.25.

Example A90

N-(3-(4-methyl-2,3,4,5-tetrahydrobenzo[f][1,4]oxazepin-7-yl)-1H-indazol-5-yl)-2-(pyrrolidin-1-yl)-2-(thiophen-3-yl)acetamide A. 7-bromo-4-methyl-2,3,4,5-tetrahydrobenzo[f][1,4]oxazepine

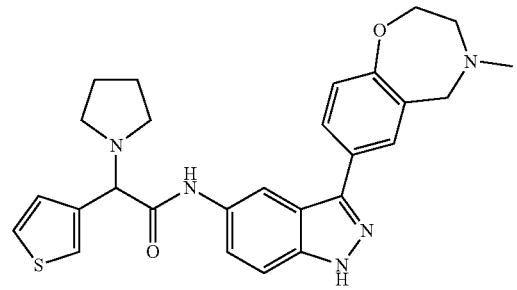 [SMILES: CN1CCOc2ccc(-c3n[nH]c4ccc(NC(=O)C(c5ccsc5)N5CCCC5)cc34)cc2C1]

tert-Butyl 7-bromo-2,3-dihydrobenzo[f][1,4]oxazepine-4(5H)-carboxylate (388 mg, 1.18 mmol) was dissolved into CH$_2$Cl$_2$ (6.0 mL) and TFA (0.6 mL) and the resulting solution stirred for 3 h and then the solvent was removed. The resulting residue was then dissolved into THF (3.0 mL) and formalin (48 uL, 0.644 mmol), and NaBH(OAc)$_3$ were added. The reaction was stirred for 2 h at which time the mixture was transferred to a separatory funnel with EtOAc (20 mL) and then washed with satd aq NaHCO$_3$ ((2×20 mL), and brine (1×20 mL). The organic layer was dried over MgSO$_4$ filtered and the solvent removed to give 82 mg, 58% of the product as a colourless oil. MS ESI 243.9 [M+H]$^+$, calcd for [C$_{10}$H$_{12}$BrNO+H]$^+$ 244.02.

B. 4-methyl-7-(4,4,5,5-tetramethyl-1,3,2-dioxaborolan-2-yl)-2,3,4,5-tetrahydrobenzo[f][1,4]oxazepine To a solution of 7-bromo-4-methyl-2,3,4,5-tetrahydrobenzo[f][1,4]oxazepine (82 mg, 0.340 mmol), TEA (140 uL, 1.02 mmol), dioxane (1.0 mL), and HBpin(74 uL, 0.510 mmol) under Ar was added S-Phos (6.0 mg, 0.014 mmol) and Cl$_2$Pd(CH$_3$CN)$_2$ (1.0 mg, 0.034 mmol) and the reaction heated to 110° C. for 2 h. The mixture was transferred to a separatory funnel with EtOAc (15 mL) and washed with NaHCO$_{3\,(satd)}$ (10 mL), H$_2$O (10 mL), and brine (10 mL). The organic layer was dried over MgSO$_4$, and the solvent removed to give 82 mg, 84% of the product as brown oil. MS ESI 290.1 [M+H]$^+$, calcd for [C$_{16}$H$_{24}$BNO$_3$+H]$^+$ 290.19.

C. N-(3-(4-methyl-2,3,4,5-tetrahydrobenzo[f][1,4]oxazepin-7-yl)-1H-indazol-5-yl)-2-(pyrrolidin-1-yl)-2-(thiophen-3-yl)acetamide A solution of 4-methyl-7-(4,4,5,5-tetramethyl-1,3,2-dioxaborolan-2-yl)-2,3,4,5-tetrahydrobenzo[f][1,4]oxazepine (75 mg, 0.259 mmol), N-(3-iodo-1H-indazol-5-yl)-2-(pyrrolidin-1-yl)-2-(thiophen-3-yl)acetamide (98 mg, 0.216 mmol), LiCl (27 mg, 0.648 mmol), Na$_2$CO$_3$ (0.54 ml, of a 2 M solution), and dioxane (1.5 mL) was purged with Ar for 15 min at which time Pd(PPh$_3$)$_4$ (13 mg, 0.011 mmol) was added and the reaction heated to 125° C. in a microwave reactor for 3 h. The solvent was then removed and the product purified by prep-HPLC which yielded 20 mg of the product as its bis-TFA salt (19%, a white powder). $^1$H NMR (400 MHz, CD$_3$OD) δ ppm 8.31 (s, 1H), 7.77-7.75 (m, 2H), 7.55-7.49 (m, 3H), 7.43-7.41 (m, 1H), 7.33 (d, J=5.1 Hz, 1H), 7.12 (d, J=7.9 Hz, 1H), 4.14-4.10 (m, 3H), 3.87 (s, 2H), 3.03-3.01 (m, 2H), 2.69-2.66 (m, 2H), 2.51-2.49 (m, 2H), 2.47 (s, 3H), 1.86-1.83 (m, 4H); MS ESI 488.1 [M+H]$^+$, calcd for [C$_{27}$H$_{29}$N$_5$O$_2$S+H]$^+$ 488.21.

Example A91

N-(3-(4-((1-methylpiperidin-4-yl)oxy)phenyl)-1H-indazol-5-yl)-2-(pyrrolidin-1-yl)-2-(thiophen-2-yl)acetamide

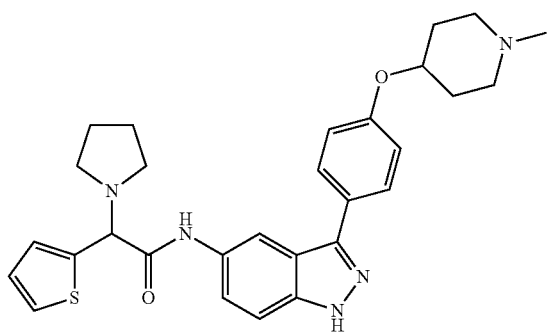 [SMILES: CN1CCC(Oc2ccc(-c3n[nH]c4ccc(NC(=O)C(c5cccs5)N5CCCC5)cc34)cc2)CC1]

To a mixture of crude N-(3-iodo-1H-indazol-5-yl)-2-(pyrrolidin-1-yl)-2-(thiophen-2-yl)acetamide (150 mg, assuming 0.3 mmol) and 1-methyl-4-(4-(4,4,5,5-tetramethyl-1,3,2-dioxaborolan-2-yl)phenoxy)piperidine (95 mg, 0.3 mmol) in EtOH (4 mL) was added 1 M aq Na$_2$CO$_3$ (0.6 mL, 0.6 mmol), followed by Pd(PPh$_3$)$_4$ (17 mg, 0.015 mmol). The resulting mixture was purged with Ar and microwaved 3 h at 125° C. After removal of solvents, it was purified by flash chromatography (EtOAc/hex 0-100%, then MeOH/DCM 0-20%, then 0.02 M NH$_3$ in MeOH) and prep-HPLC to give the title compound as a di-TFA salt (light brown solid, 25.1 mg, 11%). $^1$H NMR (400 MHz, CD$_3$OD) δ 8.37 (s, 1H), 7.90-7.83 (m, 2H), 7.69 (d, J=8.8 Hz, 1H), 7.58-7.51 (m, 3H), 7.22-7.14 (m, 3H), 5.50 (s, 1H), 4.90-4.87 (m, 0.7H), 4.73-4.65 (m, 0.3H), 4.00-3.10 (m, 8H), 2.95-2.94 (two s at 2.95 and 2.94, 3H), 2.47-1.88 (m, 8H); MS ESI 516.2 [M+H]$^+$, calcd for [C$_{29}$H$_{33}$N$_5$O$_2$S+H]$^+$ 516.2.

Example A92

N-(3-(4-(1-Methylpiperidin-4-yloxy)phenyl)-1H-indazol-5-yl)-2-o-tolylacetamide

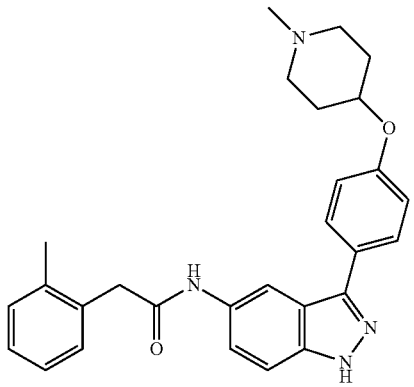 [SMILES: Cc1ccccc1CC(=O)Nc1ccc2[nH]nc(-c3ccc(OC4CCN(C)CC4)cc3)c2c1]

The title compound was synthesized according to General Method C, utilizing N-(3-iodo-1H-indazol-5-yl)-2-o-tolylacetamide (100 mg, 0.26 mmol), 1-methyl-4-(4-(4,4,5,5-tetramethyl-1,3,2-dioxaborolan-2-yl)phenoxy)piperidine (89 mg, 0.28 mmol), Pd(PPh$_3$)$_4$ (30 mg, 0.026 mmol), 2 M aq Na$_2$CO$_3$ (0.26 mL), PhMe (4 mL), and EtOH (2 mL). H$_2$O (30 mL) was added and the product was extracted into EtOAc (4×30 mL). The combined organic layers were dried over MgSO$_4$, filtered and evaporated in vacuo. Purification by flash chromatography (Biotage, 25 g HP-SIL, 100% EtOAc, then 2-30% MeOH in DCM) followed by RPHPLC gave the title compound as a white solid (163 mg, 11%). The title compound was isolated as a TFA salt. $^1$H NMR (400 MHz, CD$_3$OD) δ ppm 8.44 (d, J=1.2 Hz, 1 H), 7.87-7.83 (m, 2 H), 7.52 (d, J=8.9 Hz, 1 H), 7.43 (dd, J=8.9, 1.8 Hz, 1 H), 7.29-7.26 (m, 1 H), 7.21-7.09 (m, 5 H), 4.81 (m, 0.76 H), 4.60 (m, 0.38 H), 3.78 (s, 2 H), 3.60 (d, J=12 Hz, 0.71 H), 3.40-3.32 (m, 2.43 H), 3.16 (td, J=12.9, 2.3 Hz, 0.74 H), 2.91, 2.90 (2 s, 3 H), 2.41-2.38 (m, 3.6 H), 2.26 (d, J=16 Hz, 1.4 H), 2.13-2.04 (m, 1.4 H), 1.93-1.87 (m, 0.72 H); MS ESI 455.3 [M+H]$^+$, calcd for [C$_{28}$H$_{30}$N$_4$O$_2$+H]$^+$ 455.24.

Example A93

N-(3-(1,4-dimethyl-2,3,4,5-tetrahydro-1H-benzo[e][1,4]diazepin-7-yl)-1H-indazol-5-yl)-2-(pyrrolidin-1-yl)-2-(thiophen-3-yl)acetamide

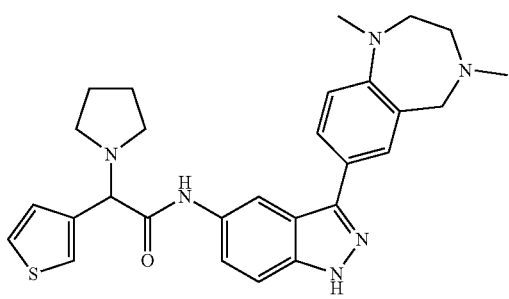 [SMILES: CN1CCN(C)c2ccc(-c3n[nH]c4ccc(NC(=O)C(c5ccsc5)N5CCCC5)cc34)cc2C1]

The title compound was prepared using General Method C3 from N-(3-iodo-1H-indazol-5-yl)-2-(pyrrolidin-1-yl)-2-(thiophen-3-yl)acetamide and tert-butyl 7-bromo-2,3-dihydro-1H-benzo[e][1,4]diazepine-4(5H)-carboxylate. The product was isolated as its bis-TFA salt (22%, pale-yellow solid). $^1$H NMR (400 MHz, CD$_3$OD) δ ppm 8.37 (s, 1H), 7.95 (d, J=8.3 Hz, 1H), 7.90 (s, 1H), 7.87 (s, 1H), 7.66-7.64 (m, 1H), 7.54 (s, 2H), 7.36 (d, J=4.0 Hz, 1H), 7.26 (d, J=8.4 Hz, 1H), 4.58-4.42 (m, 2H), 3.98-3.35 (m, 5H), 3.29-3.09 (m, 4H), 3.06 (s, 3H), 3.03 (s, 3H), 2.25-1.95 (m, 4H); MS ESI 501.2 [M+H]$^+$, calcd for [C$_{28}$H$_{32}$N$_6$OS+H]$^+$ 501.24.

Example A94

N-(3-(4-(4-Methyl-2-oxopiperazin-1-yl)phenyl)-1H-indazol-5-yl)-2-(pyrrolidin-1-yl)-2-(thiophen-3-yl)acetamide

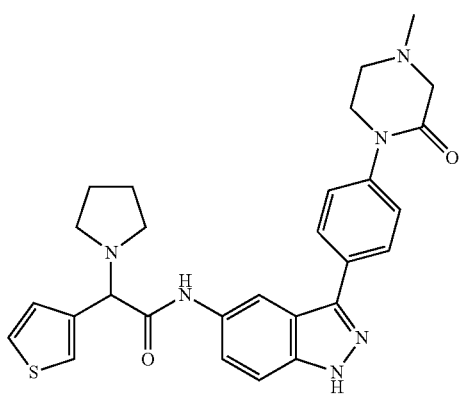 [SMILES: CN1CCN(c2ccc(-c3n[nH]c4ccc(NC(=O)C(c5ccsc5)N5CCCC5)cc34)cc2)C(=O)C1]

A. 1-(4-Iodophenyl)-4-methylpiperazin-2-one

CuI (0.081 g, 0.42 mmol) was added to an Ar-purged solution of 1,4-diiodobenzene (1.7 g, 5.1 mmol), 4-methyl-piperazin-2-one (0.50 g, 4.3 mmol), trans-N$^1$,N$^4$-dimethylcyclohexane-1,4-diamine (0.14 mL, 0.85 mmol), and K$_3$PO$_4$ (1.8 g, 8.5 mmol) in dioxane (10 mL). The resulting mixture was heated at 110° C. for 8 h in a Biotage microwave reactor. H$_2$O (30 mL) was added and the product was extracted into EtOAc (4×30 mL). The combined organic layers were dried over MgSO$_4$, filtered and evaporated in vacuo. Purification by flash chromatography (Biotage, 25 g HP-SIL, EtOAc then 2-10% MeOH in DCM) gave the title compound as a yellow solid (0.74 g, 55%). $^1$H NMR (400 MHz, CD$_3$OD) δ ppm 7.76 (d, J=8.6 Hz, 2 H), 7.11 (d, J=8.7 Hz, 2 H), 3.70 (t, J=5.4 Hz, 2 H), 3.24 (s, 2 H), 3.28 (t, J=5.6 Hz, 2 H), 2.40 (s, 3 H); MS ESI 316.9 [M+H]$^+$, calcd for [C$_{11}$H$_{13}$IN$_2$O+H]$^+$ 317.01.

B. 4-Methyl-1-(4-(4,4,5,5-tetramethyl-1,3,2-dioxaborolan-2-yl)phenyl)piperazin-2-one The title compound was synthesized according to General Method F, utilizing 1-(4-iodophenyl)-4-methylpiperazin-2-one (74 mg, 2.3 mmol), HBpin (0.44 mL, 3.0 mmol), Cl$_2$Pd(CH$_3$CN)$_2$ (3.0 mg, 0.012 mmol), SPhos (20 mg, 0.047 mmol), NEt$_3$ (1.0 mL, 7.0 mmol) and dioxane (1.0 mL). H$_2$O (30 mL) was added and the product was extracted into EtOAc (4×30 mL). The combined organic layers were dried over MgSO$_4$, filtered and evaporated in vacuo. Purification by flash chromatography (Biotage, 25 g HP-SIL, EtOAc then 2-20% MeOH in DCM) gave the title compound as a white solid (0.14 g, 20%). $^1$H NMR (400 MHz, CD$_3$OD) δ ppm 7.81 (d, J=8.4 Hz, 2 H), 7.33 (d, J=8.4 Hz, 2 H), 3.74 (t, J=5.2 Hz, 2 H), 3.27 (s, 2 H), 2.85 (t, J=5.5 Hz, 2 H), 2.42 (s, 3 H), 1.35 (s, 12 H); MS ESI 317.1 [M+H]$^+$, calcd for [C$_{17}$H$_{25}$BN$_2$O$_3$+H]$^+$ 317.20.

C. N-(3-(4-(4-Methyl-2-oxopiperazin-1-yl)phenyl)-1H-indazol-5-yl)-2-(pyrrolidin-1-yl)-2-(thiophen-3-yl)acetamide The title compound was synthesized according to General Method C, utilizing N-(3-iodo-1H-indazol-5-yl)-2-(pyrrolidin-1-yl)-2-(thiophen-3-yl)acetamide (182 mg, 0.40 mmol), 4-methyl-1-(4-(4,4,5,5-tetramethyl-1,3,2-dioxaborolan-2-yl)phenyl)piperazin-2-one (140 mg, 0.44 mmol), Pd(PPh$_3$)$_4$ (51 mg, 0.044 mmol), 2 M Na$_2$CO$_3$ (0.44 mL), PhMe (4 mL), and EtOH (2 mL). H$_2$O (30 mL) was added and the product was extracted into EtOAc (4×30 mL). The combined organic layers were dried over MgSO$_4$, filtered and evaporated in vacuo. Purification by flash chromatography (Biotage, 50 g HP-SIL, 100% EtOAc, then 2-20% MeOH in DCM) followed by RPHPLC gave the title compound as a white solid (111 mg, 33%). The title compound was isolated as a di-TFA salt. $^1$H NMR (400 MHz, CD$_3$OD) δ ppm 8.24 (d, J=1.0 Hz, 1 H), 8.03 (d, J=8.6 Hz, 2 H), 7.87 (dd, J=2.9, 1.2 Hz, 1 H), 7.66 (dd, J=5.1, 3.0 Hz, 1 H), 7.59-7.50 (m, 4 H), 7.38 (dd, J=5.0, 1.2 Hz, 1 H), 5.24 (s, 1 H), 4.18 (s, 2 H), 4.10 (t, J=5.4 Hz, 2 H), 3.87-3.83 (br m, 1 H), 3.82 (t, J=5.9 Hz, 2 H), 3.20-3.02 (br m, 2 H), 3.13 (s, 3 H), 2.26-1.97 (br m, 4 H); MS ESI 515.1 [M+H]$^+$, calcd for [C$_{28}$H$_{30}$N$_6$O$_2$S+H]$^+$ 515.22.

Example A95

N-(3-(4-(4-(hydroxymethyl)piperidin-1-yl)phenyl)-1H-indazol-5-yl)-2-(pyrrolidin-1-yl)-2-(thiophen-3-yl)acetamide

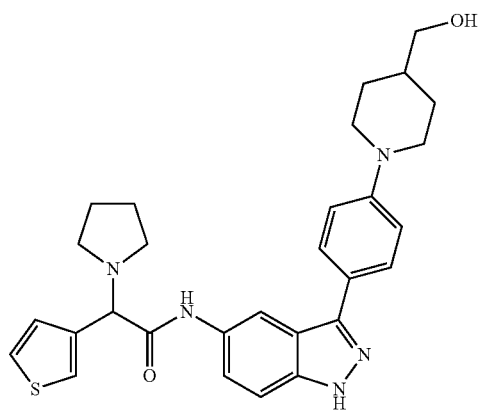 [SMILES: O=C(Nc1ccc2[nH]nc(-c3ccc(N4CCC(CO)CC4)cc3)c2c1)C(c1ccsc1)N1CCCC1]

The title compound was synthesized according to General Method C3 utilizing N-(3-iodo-1H-indazol-5-yl)-2-(pyrrolidin-1-yl)-2-(thiophen-3-yl)acetamide and (1-(4-(4,4,5,5-tetramethyl-1,3,2-dioxaborolan-2-yl)phenyl)piperidin-4-yl)methanol and obtained as a white solid (15 mg, 12% yield). $^1$H NMR (400 MHz, CD$_3$OD) δ ppm 8.34 (s, 1H), 7.76 (d, J=8.8 Hz, 2H), 7.49 (m, 3H), 7.39 (m, 1H), 7.33 (m, 1H), 7.06 (d, J=8.8 Hz, 2H), 4.10 (s, 1H), 3.77 (m, 2H), 3.44 (d, J=6.4 Hz, 2H), 2.68 (m, 4H), 2.48 (br, 2H), 1.83 (m, 6H), 1.62 (m, 1H), 1.37 (m, 2H); MS ESI [M+H]$^+$ 516.2, calcd for [C$_{29}$H$_{33}$N$_5$O$_2$S+H]$^+$ 516.24.

Example A96

N-(3-(3-(4-Methylpiperazine-1-carbonyl)phenyl)-1H-indazol-5-yl)-2-(pyrrolidin-1-yl)-2-(thiophen-3-yl)acetamide

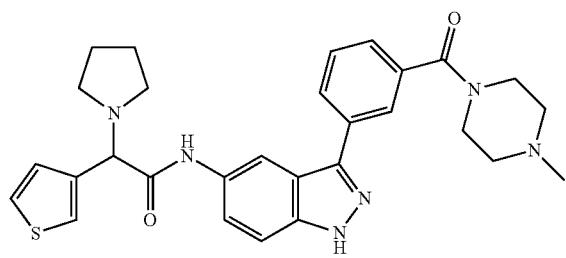 [SMILES: CN1CCN(C(=O)c2cccc(-c3n[nH]c4ccc(NC(=O)C(c5ccsc5)N5CCCC5)cc34)c2)CC1]

The title compound was synthesized according to General Method C, utilizing N-(3-iodo-1H-indazol-5-yl)-2-(pyrrolidin-1-yl)-2-(thiophen-3-yl)acetamide (200 mg, 0.44 mmol), (4-methylpiperazin-1-yl)(3-(4,4,5,5-tetramethyl-1,3,2-dioxaborolan-2-yl)phenyl)methanone (160 mg, 0.49 mmol), Pd(PPh$_3$)$_4$ (51 mg, 0.044 mmol), 2 M Na$_2$CO$_3$ (0.50 mL), PhMe (4 mL), and EtOH (2 mL). H$_2$O (30 mL) was added and the product was extracted into EtOAc (4×30 mL). The combined organic layers were dried over MgSO$_4$, filtered and evaporated in vacuo. Purification by flash chromatography (Biotage, 50 g HP-SIL, 100% EtOAc, then 2-25% MeOH in DCM) followed by RP HPLC gave the title compound as a light brown solid as isolated as a di-TFA salt (111 mg, 33%). $^1$H NMR (400 MHz, CD$_3$OD) δ ppm 8.41 (s, 1 H), 8.08 (d, J=7.9 Hz, 1 H), 8.03 (s, 1 H), 7.80 (dd, J=2.9, 1.2 Hz, 1 H), 7.69-7.64 (m, 2 H), 7.57-7.54 (m, 3 H), 7.38 (dd, J=5.1, 1.2 Hz, 1 H), 5.29 (s, 1 H), 3.89-3.36 (br m, 5 H), 3.31-3.13 (br m, 4 H), 2.96 (s, 3 H), 2.25-1.98 (br m, 4 H); MS ESI 529.1 [M+H]$^+$, calcd for [C$_{29}$H$_{32}$N$_6$O$_2$S+H]$^+$ 529.23.

Example A97

(R)-2-((R)-2-methylpyrrolidin-1-yl)-N-(3-(4-morpholinophenyl)-1H-indazol-5-yl)-2-(thiophen-3-yl)acetamide

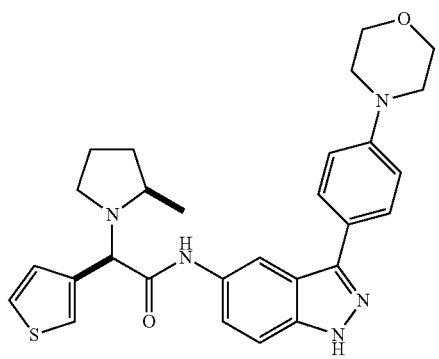 [SMILES: C[C@@H]1CCCN1[C@@H](C(=O)Nc1ccc2[nH]nc(-c3ccc(N4CCOCC4)cc3)c2c1)c1ccsc1]

To a mixture of (R)-2-((R)-2-methylpyrrolidin-1-yl)-2-(thiophen-3-yl)acetic acid (22.5 mg, 0.1 mmol), 3-(4-morpholinophenyl)-1H-indazol-5-amine di-trifluoroacetic acid (57.2 mg, 0.1 mmol) and COMU (47.1 mg, 0.11 mmol) in DMF (6 mL) at −20° C. was added $^i$Pr$_2$NEt (0.07 mL, 0.4 mmol). The resulting mixture was stirred for 1 h at −20° C. After removal of $^i$Pr$_2$NEt, it was purified by prep-HPLC, PoraPak and flash chromatography flash chromatography (EtOAc/hex 0-100%, then MeOH/DCM 10-20%) to give the title compound (pale yellow solid, 18.1 mg, 36%). $^1$H NMR (400 MHz, CD$_3$OD) δ 8.38 (s, 1H), 7.80 (d, J=8.8 Hz, 2H), 7.51 (s, 2H), 7.43 (dd, J=2.8 Hz, 1.2 Hz, 1H), 7.40 (dd, J=4.8 Hz, 2.8 Hz, 1H), 7.23 (dd, J=5.2 Hz, 1.2 Hz, 1H), 7.06 (d, J=8.8 Hz, 2H), 4.56 (s, 1H), 3.83 (t, J=4.8 Hz, 4H), 3.18 (t, J=4.8 Hz, 4H), 2.95-2.86 (m, 1H), 2.83-2.73 (m, 1H), 2.39 (dd, J=13.8 Hz, 8.2 Hz, 1H), 2.30-1.91 (m, 1H), 1.87-1.74 (m, 1H), 1.70-1.59 (m, 1H), 1.55-1.45 (m, 1H), 1.17 (d, J=6.4 Hz, 3H); MS ESI 502.3 [M+H]$^+$, calcd for [C$_{26}$H$_{28}$N$_6$O$_2$S+H]$^+$ 502.2.

Example A98

N-(cyclopropyl(phenyl)methyl)-3-(4-((1-(2-methoxyethyl)piperidin-4-yl)oxy)phenyl)-1H-indazole-5-carboxamide

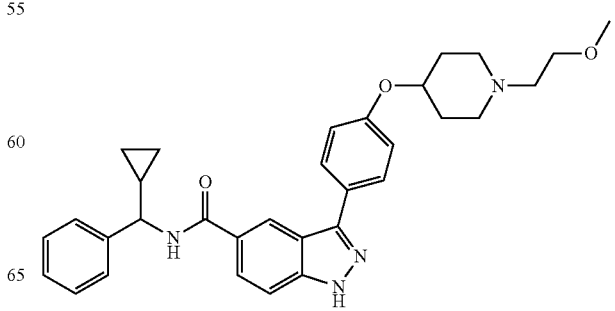

The title compound was prepared using General Method C3 from N-(cyclopropyl(phenyl)methyl)-3-iodo-1H-indazole-5-carboxamide (70 mg, 0.168 mmol) and 1-(2-methoxyethyl)-4-(4-(4,4,5,5-tetramethyl-1,3,2-dioxaborolan-2-yl)phenoxy)piperidine (79 mg, 0.218 mmol) which gave 42 mg of product isolated as its TFA salt (47%, a pale-yellow powder). $^1$H NMR (400 MHz, CD$_3$OD) δ ppm 8.58 (s, 1H), 7.97-7.93 (m, 3H), 7.61 (d, J=8.8 Hz, 1H), 7.48 (d, J=7.3 Hz, 2H), 7.35-7.31 (m, 2H), 7.26-7.15 (m, 3H), 4.87 (bs, 1H), 4.48 (d, J=9.6 Hz, 1H), 3.76-3.70 (m, 2H), 3.54-3.22 (m, 9H), 2.45-2.28 (m, 2H), 2.19-1.94 (m, 2H), 1.45-1.33 (m, 1H), 0.68-0.63 (m, 2H), 0.50-0.47 (m, 2H); MS ESI 525.4 [M+H]$^+$, calcd for [C$_{32}$H$_{36}$N$_4$O$_3$+H]$^+$ 525.29.

Example A99

N-(3-(3-((1-methylpiperidin-4-yl)oxy)phenyl)-1H-indazol-5-yl)-2-(pyrrolidin-1-yl)-2-(thiophen-3-yl)acetamide A. 4-(3-bromophenoxy)-1-methylpiperidine

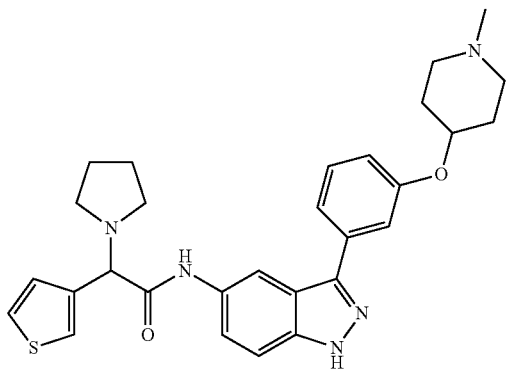 [SMILES: CN1CCC(Oc2cccc(-c3n[nH]c4ccc(NC(=O)C(c5ccsc5)N5CCCC5)cc34)c2)CC1]

To a solution of 4-(3-bromophenoxy)piperidine (500 mg, 1.7 mmol) in formic acid (13.11 mL) was added formalin (0.51 mL). The solution was heated to 150° C. for 15 min under microwave irradiation. The solvent was removed in vacuo. The residue was made alkaline using 50% KOH (10 mL) and the product was extracted using DCM (2×25 mL). The organic layer was washed with brine, dried (Na$_2$SO$_4$) and concentrated to give the title compound as a colorless thick oil (360 mg, 78%). $^1$H NMR (400 MHz, CDCl$_3$) δ 15-7.06 (m, 3H), 6.85-6.82 (m, 1H), 4.29 (br.m, 1H), 2.68 (br.s, 2H), 2.31 (br.s, 5H), 2.02-197 (br.m, 2H), 1.88-1.80 (br.m, 2H); MS ESI 272 [M+H]$^+$, calcd for [C$_{12}$H$_{16}$BrNO+H]$^+$ 270.

B. 1-methyl-4-(3-(4,4,5,5-tetramethyl-1,3,2-dioxaborolan-2-yl)phenoxy)piperidine The title compound was synthesized according to General Method E by using a solution of 4-(3-bromophenoxy)-1-methylpiperidine (350 mg, 1.29 mmol) in DMF (5.25 mL) was added B$_2$pin$_2$ (576 mg, 2.26 mmol), KOAc (381 mg, 3.88 mmol) and PdCl$_2$dppf (80 mg, 0.097 mmol) under Ar. The degassed suspension was sealed and heated in an oil bath at 125° C. for 3 h. The product was partitioned between EtOAc (50 mL) and H$_2$O (25 mL). The aq. layer was extracted with EtOAc (50 mL) and the combined EtOAc layer was washed with H$_2$O and brine, dried (Na$_2$SO$_4$) and concentrated under vacuum. Purification by flash chromatography (SiO$_2$, 0-50% DCM in MeOH) gave title compound (brown thick oil, 148 mg, 36%). $^1$H NMR (400 MHz, CDCl$_3$) δ 7.41 (d, J=7.2 Hz, 1H), 7.35 (d, J=2.0 Hz, 1H), 7.31-7.28 (m, 1H), 7.02 (dd, J=8.0 Hz, J=2.0 Hz, 1H), 4.47 (s, 1H), 2.78-2.76 (br.m, 2H), 2.53-2.48 (br.s, 2H), 2.41 (s, 3H), 2.12 (br.s, 2H), 1.98-1.92 (br.s, 2H), 1.35 (s, 12H); MS ESI 318.2 [M+H]$^+$, calcd for [C$_{18}$H$_{18}$BNO$_3$+H]$^+$ 318.2.

C. N-(3-(3-((1-methylpiperidin-4-yl)oxy)phenyl)-1H-indazol-5-yl)-2-(pyrrolidin-1-yl)-2-(thiophen-3-yl)acetamide The title compound was synthesized according to General Method C from N-(3-iodo-1H-indazol-5-yl)-2-(pyrrolidin-1-yl)-2-(thiophen-3-yl)acetamide (200 mg, 0.44 mmol), 1-methyl-4-(3-(4,4,5,5-tetramethyl-1,3,2-dioxaborolan-2-yl)phenoxy)piperidine (141 mg, 0.44 mmol) with PdCl$_2$dppf (72 mg, 0.088 mmol) min 1 M aq Na$_2$CO$_3$ (0.89 mL) in PhMe/EtOH (9 mL, 2:1 mixture) under Ar with heating under microwave irradiation at 125° C. for 5 h. The reaction mixture was diluted with EtOAc (40 mL) and washed with H$_2$O and brine, dried (Na$_2$SO$_4$) and concentrated under vacuum. Purification by flash chromatography (SiO$_2$, 0-20% 2 M-NH$_3$-MeOH in DCM), then by RPHPLC gave the title compound as a TFA salt (light brown solid, 31 mg, 9%). $^1$H NMR (400 MHz, CD$_3$OD) δ 8.41 (d, J=8.0 Hz, 1H), 7.88-7.87 (m, 1H), 7.66 (dd, J=5.2 Hz, J=3.2 Hz, 1H), 7.57-7.44 (m, 5H), 7.39 (dd, J=4.8 Hz, J=1.2 Hz, 1H), 7.13-7.05 (m, 1H), 5.27 (s, 1H), 4.7-4.69 (m, 0.39H), 3.88-3.84 (br.s, 1H), 3.67 (br.d, 1H), 3.43-3.37 (br.m, 3H), 3.24-3.11 (br.m, 3H), 2.95 (s, 3H), 2.48-1.89 (br.m, 9H), 0.61H merged with solvent peak, MS ESI 516.1[M+H]$^+$, calcd for [C$_{29}$H$_{33}$N$_5$O$_2$S+H]$^+$ 516.2.

Example A100

N-(cyclobutyl(phenyl)methyl)-3-(4-(4-hydroxypiperidin-1-yl)phenyl)-1H-indazole-5-carboxamide

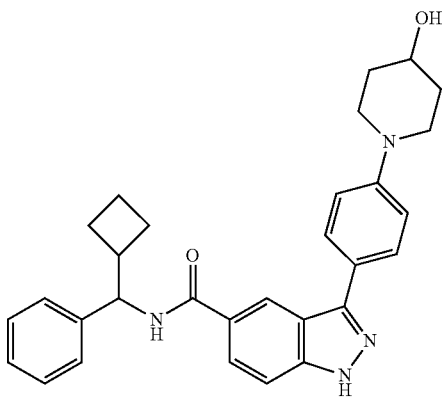 [SMILES: O=C(NC(c1ccccc1)C1CCC1)c1ccc2[nH]nc(-c3ccc(N4CCC(O)CC4)cc3)c2c1]

Using General Method C2, N-(cyclobutyl(phenyl)methyl)-3-iodo-1H-indazole-5-carboxamide (69.8 mg, 0.162 mmol) and 1-(4-(4,4,5,5-tetramethyl-1,3,2-dioxaborolan-2-yl)phenyl)piperidin-4-ol (73.1 mg, 80% pure, 0.19 mmol) gave the title compound as the TFA salt (pale pink solid, 42.2 mg, 49%) after heating in a sealed vial at 125° C. for 14 h and purification by flash chromatography (SiO$_2$, 10-50% acetone in DCM; followed by RP HPLC, 10-90% MeOH in 0.1% TFA-H$_2$O). $^1$H NMR (400 MHz, CD$_3$OD) δ ppm 8.83 (d, J=7.8 Hz, 0.2 H partially exchanged), 8.56 (s, 1 H), 8.18 (d, J=8.5 Hz, 2 H), 7.93 (d, J=8.8 Hz, 1 H), 7.73 (d, J=8.5 Hz, 2 H), 7.63 (d, J=9.0 Hz, 1 H), 7.41 (d, J=7.5 Hz, 2 H), 7.32 (t, J=7.5 Hz, 2 H), 7.20-7.26 (m, 1 H), 5.10 (d, J=10.5 Hz, 1 H), 4.05-4.14 (m, 1 H), 3.83-3.93 (m, 2 H), 3.54-3.67 (m, 2 H)

MS ESI 481.4 [M+H]⁺, calcd for $[C_{30}H_{32}N_4O_2+H]^+$ 481.26.

Example A101

N-(cyclopropyl(thiophen-3-yl)methyl)-3-(4-(4-hydroxypiperidin-1-yl)phenyl)-1H-indazole-5-carboxamide

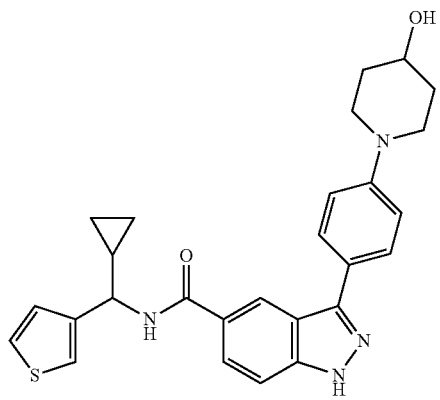 [SMILES: O=C(NC(c1ccsc1)C1CC1)c1ccc2[nH]nc(-c3ccc(N4CCC(O)CC4)cc3)c2c1]

Using General Method C2, N-(cyclopropyl(thiophen-3-yl)methyl)-3-iodo-1H-indazole-5-carboxamide (50.0 mg, 0.118 mmol) and 1-(4-(4,4,5,5-tetramethyl-1,3,2-dioxaborolan-2-yl)phenyl)piperidin-4-ol (53.7 mg, 80% pure, 0.14 mmol) gave the title compound as the TFA salt (pale pink solid, 26.8 mg, 39%) after heating in microwave at 125° C. for 3 h and purification by flash chromatography (SiO₂, 25-50% acetone in DCM; followed by RP HPLC, 10-90% MeOH in 0.1% TFA-H₂O). ¹H NMR (400 MHz, CD₃OD) δ ppm 8.63 (s, 1 H), 8.24 (d, J=8.8 Hz, 2 H), 7.99 (dd, J=8.9, 1.4 Hz, 1 H), 7.78 (d, J=8.8 Hz, 2 H), 7.67 (d, J=8.8 Hz, 1 H), 7.36-7.40 (m, 2 H), 7.21 (t, J=3.3 Hz, 1 H), 4.64 (d, J=9.3 Hz, 1 H), 4.11 (ft, J=7.0, 3.3 Hz, 1 H), 3.91 (ddd, J=12.0, 8.4, 3.4 Hz, 2 H), 3.65 (ddd, J=11.9, 7.7, 3.5 Hz, 2 H), 2.21-2.31 (m, 2 H), 2.04 (dtd, J=14.2, 7.2, 7.2, 3.5 Hz, 2 H), 1.41-1.51 (m, 1 H), 0.74 (td, J=8.3, 3.8 Hz, 1 H), 0.65 (td, J=8.3, 4.8 Hz, 1 H), 0.45-0.56 (m, 2 H). MS ESI 473.3 [M+H]⁺, calcd for $[C_{27}H_{28}N_4O_2S+H]^+$ 473.20.

Example A102

N-(3-(4-((1-(2-fluoroethyl)piperidin-4-yl)oxy)phenyl)-1H-indazol-5-yl)-2-(pyrrolidin-1-yl)-2-(thiophen-3-yl)acetamide

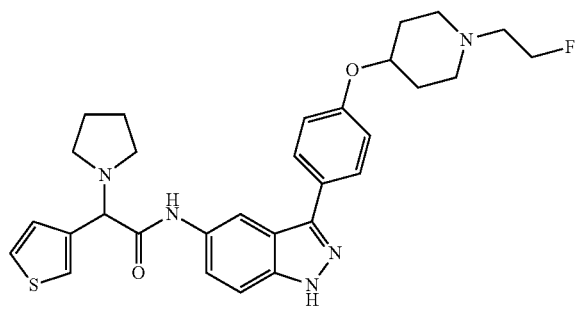 [SMILES: O=C(Nc1ccc2[nH]nc(-c3ccc(OC4CCN(CCF)CC4)cc3)c2c1)C(c1ccsc1)N1CCCC1]

The title compound was synthesized according to General Method C3 utilizing N-(3-iodo-1H-indazol-5-yl)-2-(pyrrolidin-1-yl)-2-(thiophen-3-yl)acetamide and 1-(2-fluoroethyl)-4-(4-(4,4,5,5-tetramethyl-1,3,2-dioxaborolan-2-yl)phenoxy) piperidine and obtained as a white solid (20 mg, 10% yield). ¹H NMR (400 MHz, CD₃OD) δ ppm 8.33 (s, 1H), 7.82 (d, J=8.8 Hz, 2H), 7.51 (m, 3H), 7.42 (m, 1H), 7.33 (dd, J=4.8 Hz, 0.8 Hz, 1H), 7.08 (d, J=8.8 Hz, 2H), 4.67 (t, J=4.8 Hz, 1H), 4.55 (t, J=4.8 Hz, 1H), 4.51 (m, 1H), 4.13 (s, 1H), 2.86 (m, 2H), 2.80 (t, J=4.8 Hz, 1H), 2.73 (t, J=4.8 Hz, 1H), 2.70 (m, 2H), 2.52 (m, 2H), 1.82 (m, 6H); MS ESI [M+H]⁺ 548.2, calcd for $[C_{30}H_{34}FN_5O_2S+H]^+$ 548.25.

Example A103

2-cyclopropyl-N-(3-(4-(4-hydroxypiperidin-1-yl)phenyl)-1H-indazol-5-yl)-2-phenylacetamide

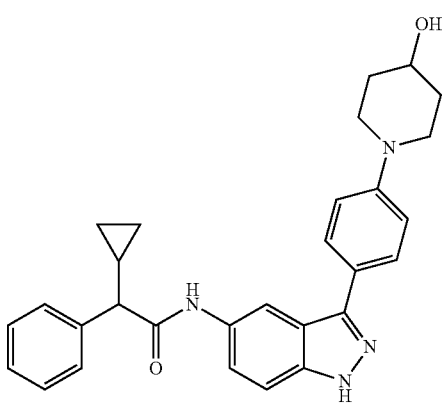 [SMILES: O=C(Nc1ccc2[nH]nc(-c3ccc(N4CCC(O)CC4)cc3)c2c1)C(c1ccccc1)C1CC1]

The title compound was synthesized according to General Method A by using 2-cyclopropyl-2-phenylacetic acid (16 mg, 0.09 mmol), DMF (2 mL), 1-(4-(5-amino-1H-indazol-3-yl)phenyl)piperidin-4-ol trifluoroacetate (48.7 mg, 0.0.9 mmol), DIPEA (80 uL, 0.55 mmol) and TBTU (29 mg, 0.09 mmol). After stirring for 24 h at rt, concentration under reduced pressure and direct purification using Biotage (SiO₂, 0-25% MeOH in DCM; then RP HPLC C18 60 g, 10-80% MeOH in 0.1% TFA-H₂O) gave the title compound as a TFA salt (beige color solid, 21 mg, 40%). ¹H NMR (400 MHz, CD₃OD)) δ ppm 8.50 (m, 1H), 8.16 (d, J=8.0 Hz, 2H), 7.77 (d, J=8.0 Hz, 2H), 7.57 (d, J=9.2 Hz, 1H), 7.51 (d, J=7.6 Hz, 2H), 7.42 (d, J=9.2 Hz, 1H), 7.37-7.33 (m, 2H), 7.28-7.25 (m, 1H), 4.11 (s, 1H), 3.98-3.87 (m, 2H), 3.65 (br.s, 2H), 2.94 (d, J=9.6 Hz, 1H), 2.25-2.23 (br.m, 2H), 2.05 (br.s, 2H), 1.6 (br.s, 1H), 0.70-0.62 (br.m, 2H), 0.48-0.28 (brm, 2H); MS ESI 467.4. [M+H]⁺, calcd for $[C_{29}H_{30}N_4O_2+H]^+$ 467.2

Example A104

N-(cyclopropyl(phenyl)methyl)-3-(4-((1-(2-hydroxyethyl)piperidin-4-yl)oxy)phenyl)-1H-indazole-5-carboxamide

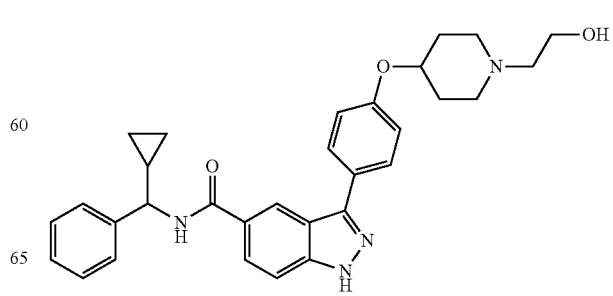

The title compound was prepared using General Method C3 from N-(cyclopropyl(phenyl)methyl)-3-iodo-1H-indazole-5-carboxamide (60 mg, 0.144 mmol) and 2-(4-(4-(4,4,5,5-tetramethyl-1,3,2-dioxaborolan-2-yl)phenoxy)piperidin-1-yl)EtOH (70 mg, 0.202 mmol) which gave 23 mg of product isolated as its TFA salt (31%, a white solid). $^1$H NMR (400 MHz, CD$_3$OD) δ ppm 8.58 (s, 1H), 7.97-7.93 (m, 3H), 7.61 (d, J=8.8 Hz, 1H), 7.48 (d, J=7.3 Hz, 2H), 7.36-7.32 (m, 2H), 7.26-7.16 (m, 3H), 4.87 (bs, 1H), 4.48 (d, J=9.5 Hz, 1H), 3.92-3.30 (m, 8H), 2.45-2.29 (m, 2H), 2.22-1.98 (m, 2H), 1.43-1.33 (m, 1H), 0.71-0.64 (m, 2H), 0.50-0.48 (m, 2H); MS ESI 511.5 [M+H]$^+$, calcd for [C$_{31}$H$_{34}$N$_4$O$_3$+H]$^+$ 511.27.

Example A105 rel-N-(3-(4-(((1r,4r)-4-hydroxycyclohexyl)amino)phenyl)-1H-indazol-5-yl)-2-(pyrrolidin-1-yl)-2-(thiophen-3-yl)acetamide

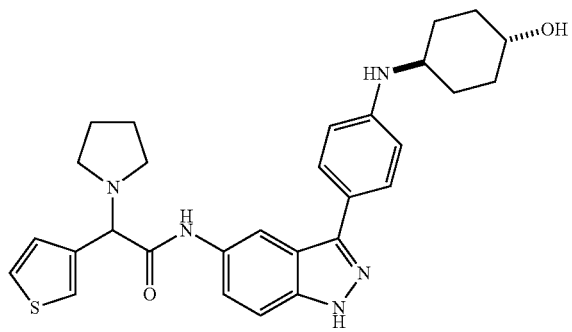

To a mixture of 1,4-diiodobenzene (3.299 g, 10 mmol), trans-4-aminocyclohexanol (1.15 g, 10 mmol), CuI (391 mg, 2 mmol), BINOL (572 mg, 2 mmol) and K$_3$PO$_4$ (4.24 g, 20 mmol) was added DMF (30 mL). The resulting mixture was purged with Ar and stirred at rt for 2 d. It was diluted with EtOAc (60 mL) and MeOH (30 mL), sonicated, filtered through Celite (rinsed with EtOAc/MeOH), concentrated and purified by flash chromatography (EtOAc/hex 0-100%) to give rel-(1r,4r)-4-((4-iodophenyl)amino)cyclohexanol as blackish white solid (2.367 g, 75%). $^1$H NMR (400 MHz, DMSO-d$_6$) δ 7.28 (d, J=8.8 Hz, 2H), 6.39 (d, J=8.8 Hz, 2H), 5.59 (d, J=8.0 Hz, 1H), 4.54 (br, s, 1H), 3.45-3.35 (m, 1H), 3.14-3.04 (m, 1H), 1.93-1.77 (m, 4H), 1.30-1.18 (m, 2H), 1.17-1.06 (m, 2H); MS ESI 318.0 [M+H]$^+$, calcd for [C$_{12}$H$_{16}$INO+H]$^+$ 318.0.

To a mixture of rel-(1r,4r)-4-((4-iodophenyl)amino)cyclohexanol (951 mg, 3 mmol), Pd(CH$_3$CN)$_2$Cl$_2$ (15.6 mg, 0.06 mmol) and dicyclohexyl(2',6'-dimethoxy-[1,1'-biphenyl]-2-yl)phosphine (98.5 mg, 0.24 mmol) in 1,4-dioxane (4.5 mL) was added Et$_3$N (1.3 mL, 9 mmol), followed by pinacolborane (1.74 mL, 12 mmol) slowly. After addition, the resulting mixture was purged with Ar and microwaved 2 h at 110° C. It was combined with a 0.4 mmol scale reaction. After removal of solvents, it was purified by flash chromatography (EtOAc/hex 0-100%) to give rel-(1r,4r)-4-(4-(4,4,5,5-tetramethyl-1,3,2-dioxaborolan-2-yl)phenyl)amino)cyclohexanol (white solid, 1.028 g, 95%). $^1$H NMR (400 MHz, CD$_3$OD) δ 7.52 (d, J=8.4 Hz, 2H), 6.55 (d, J=8.4 Hz, 2H), 3.61-3.52 (m, 1H), 3.28-3.19 (m, 1H), 2.09-1.92 (m, 4H), 1.46-1.33 (m, 2H), 1.29 (s, 12H), 1.25-1.15 (m, 2H); MS ESI 318.1 [M+H]$^+$, calcd for [C$_{18}$H$_{28}$BNO$_3$+H]$^+$ 318.2.

To a mixture of N-(3-iodo-1H-indazol-5-yl)-2-(pyrrolidin-1-yl)-2-(thiophen-3-yl)acetamide (181 mg, 0.4 mmol) and rel-(1r,4r)-4-((4-(4,4,5,5-tetramethyl-1,3,2-dioxaborolan-2-yl)phenyl)amino)cyclohexanol (127 mg, 0.4 mmol) in EtOH (10 mL) was added 1 M aq Na$_2$CO$_3$ (0.8 mL, 0.8 mmol), followed by Pd(PPh$_3$)$_4$ (23 mg, 0.02 mmol). The resulting mixture was purged with Ar and microwaved 3 h at 125° C. Additional Pd(PPh$_3$)$_4$ (23 mg, 0.02 mmol) was added and the reaction mixture was purged with Ar and microwaved 3 h at 125° C. After removal of solvents, it was purified by flash chromatography (MeOH/DCM 0-25%), Biotage RP column (MeOH/H$_2$O (1% TFA) 0-50%) and flash chromatography (EtOAc/hex 10-100%, then MeOH/DCM 0-20%) to give the title compound (light brown solid, 21.2 mg, 10%). $^1$H NMR (400 MHz, CD$_3$OD) δ 8.31 (s, 1H), 7.66 (d, J=8.4 Hz, 2H), 7.53-7.45 (m, 3H), 7.42 (dd, J=5.2 Hz, 2.8 Hz, 1H), 7.33 (dd, J=5.2 Hz, 1.2 Hz, 1H), 6.74 (d, J=8.4 Hz, 2H), 4.16 (s, 1H), 3.65-3.56 (m, 1H), 3.32-3.25 (m, 1H), 2.74-2.67 (m, 2H), 2.57-2.48 (m, 2H), 2.15-2.08 (m, 2H), 2.03-1.95 (m, 2H), 1.90-1.80 (m, 4H), 1.49-1.38 (m, 2H), 1.32-1.22 (m, 2H); MS ESI 516.3 [M+H]$^+$, calcd for [C$_{29}$H$_{33}$N$_5$O$_2$S+H]$^+$ 516.2.

Example A106 trans-N-(cyclopropyl(phenyl)methyl)-3-(4-(((1r,4r)-4-hydroxycyclohexyl)amino)phenyl)-1H-indazole-5-carboxamide

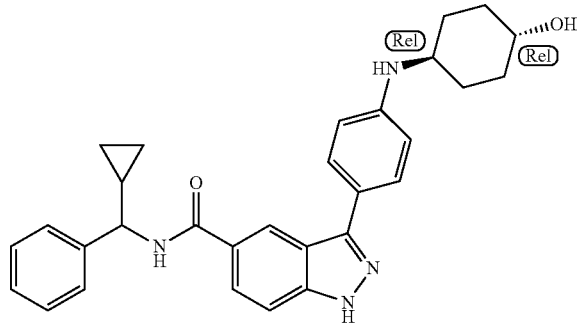 [SMILES: O=C(NC(c1ccccc1)C1CC1)c1ccc2[nH]nc(-c3ccc(N[C@H]4CC[C@H](O)CC4)cc3)c2c1]

To a mixture of N-(cyclopropyl(phenyl)methyl)-3-iodo-1H-indazole-5-carboxamide (167 mg, 0.4 mmol) and rel-(1r,4r)-4-((4-(4,4,5,5-tetramethyl-1,3,2-dioxaborolan-2-yl)phenyl)amino)cyclohexanol (127 mg, 0.4 mmol) in EtOH (10 mL) was added 1 M aq Na$_2$CO$_3$ (0.8 mL, 0.8 mmol), followed by Pd(PPh$_3$)$_4$ (46 mg, 0.04 mmol). The resulting mixture was purged with Ar and microwaved 5 h at 125° C. After removal of solvents, it was purified by flash chromatography (MeOH/DCM 0-20%), Biotage RP column (MeOH/H$_2$O (1% TFA) 0-100%), PoraPak, flash chromatography (EtOAc/hex 10-100%) and PoraPak to give the title compound (light yellow solid, 55.4 mg, 29%). $^1$H NMR (400 MHz, CD$_3$OD) δ 8.63 (s, 1H), 7.93 (dd, J=8.8 Hz, 1.6 Hz, 1H), 7.73 (d, J=8.4 Hz, 2H), 7.54 (d, J=9.2 Hz, 1H), 7.45 (d, J=7.2 Hz, 2H), 7.29 (t, J=7.6 Hz, 2H), 7.20 (t, J=7.6 Hz, 1H), 6.72 (d, J=8.8 Hz, 2H), 4.46 (d, J=8.8 Hz, 1H), 3.61-3.53 (m, 1H), 3.27-3.19 (m, 1H), 2.11-2.03 (m, 2H), 2.00-1.92 (m, 2H), 1.45-1.32 (m, 3H), 1.28-1.17 (m, 2H), 0.65-0.56 (m, 2H), 0.50-0.37 (m, 2H); MS ESI 481.5 [M+H]$^+$, calcd for [C$_{30}$H$_{32}$N$_4$O$_2$+H]$^+$ 481.3.

Example A107

(R)-2-methoxy-N-(3-(4-((1-(2-methoxyethyl)piperidin-4-yl)oxy)phenyl)-1H-indazol-5-yl)-2-phenylacetamide

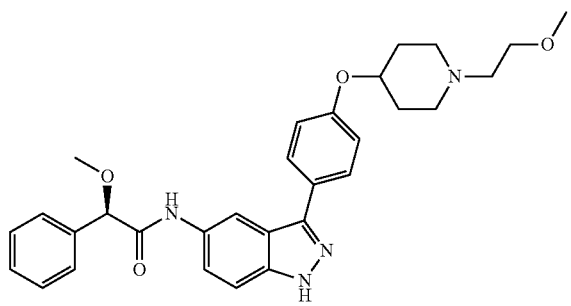 [SMILES: COCCN1CCC(Oc2ccc(-c3n[nH]c4ccc(NC(=O)[C@H](OC)c5ccccc5)cc34)cc2)CC1]

The title compound was prepared using General Method C3 from (R)-N-(3-iodo-1H-indazol-5-yl)-2-methoxy-2-phenylacetamide (60 mg, 0.147 mmol) and 1-(2-methoxyethyl)-4-(4-(4,4,5,5-tetramethyl-1,3,2-dioxaborolan-2-yl)phenoxy) piperidine (64 mg, 0.176 mmol) which gave 29 mg of product isolated as its TFA salt (38%, an off-white solid). $^{1}$H NMR (400 MHz, CD$_{3}$OD) δ ppm 8.40 (s, 1H), 7.87-7.83 (m, 2H), 7.54-7.48 (m, 4H), 7.42-7.33 (m, 3H), 7.18-7.11 (m, 2H), 4.87 (bs, 1H), 4.83 (s, 1H), 3.76-3.21 (m, 8H), 3.50 (s, 3H), 3.46 (s, 3H), 2.43-2.27 (m, 2H), 2.19-1.94 (m, 2H); MS ESI 515.4 [M+H]$^{+}$, calcd for [C$_{30}$H$_{34}$N$_{4}$O$_{4}$+H]$^{+}$ 515.27.

Example A108

3-(4-(1-Methylpiperidin-4-yloxy)phenyl)-N-(2-morpholinobenzyl)-1H-indazole-5-carboxamide

A. 3-Iodo-N-(2-morpholinobenzyl)-1H-indazole-5-carboxamide

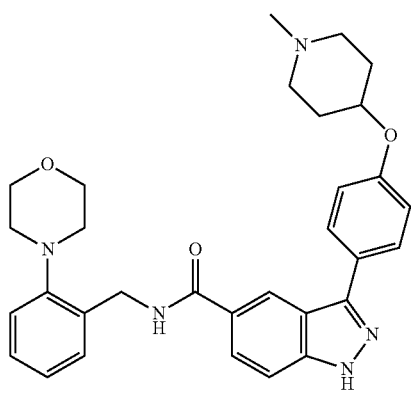 [SMILES: CN1CCC(Oc2ccc(-c3n[nH]c4ccc(C(=O)NCc5ccccc5N5CCOCC5)cc34)cc2)CC1]

The title compound was synthesized according to General Method A, utilizing 3-iodo-1H-indazole-5-carboxylic acid (150 mg, 0.52 mmol), (2-morpholinophenyl)methanamine (120 mg, 0.0.57 mmol), TBTU (184 mg, 0.57 mmol), DIPEA (0.36 mL, 2.1 mmol), and DMF (4 mL). H$_{2}$O (20 mL) was added and the product was extracted into EtOAc (4×20 mL). The combined organic layers were dried over MgSO$_{4}$, filtered and evaporated in vacuo. The residue was then dissolved in MeOH (20 mL) and poured into a preconditioned 20 mL PoraPak Rxn Cx cartridge. The MeOH (30 mL) rinse was discarded and the product was eluted with 2 M NH$_{3}$ in MeOH (30 mL). The solvent was removed in vacuo, and the product was used without further purification (99%, 240 mg). $^{1}$H NMR (400 MHz, CD$_{3}$OD) δ ppm 8.08 (s, 1 H), 7.98-7.96 (m, 1 H), 7.57 (d, J=8.9 Hz, 1 H), 7.37-7.32 (m, 1 H), 7.26 (t, J=7.5 Hz, 1H), 7.18 (d, J=7.8 Hz, 1 H), 7.10 (t, J=7.2 Hz, 1H), 4.76 (s, 2 H), 3.84 (br m, 4 H), 2.92-2.86 (br m, 4 H); MS ESI 463.1 [M+H]$^{+}$, calcd for [C$_{19}$H$_{19}$IN$_{4}$O$_{2}$+H]$^{+}$ 463.06.

B. 3-(4-(1-Methylpiperidin-4-yloxy)phenyl)-N-(2-morpholinobenzyl)-1H-indazole-5-carboxamide The title compound was synthesized according to General Method C, utilizing 3-iodo-N-(2-morpholinobenzyl)-1H-indazole-5-carboxamide (113 mg, 0.24 mmol), 1-methyl-4-(4-(4,4,5,5-tetramethyl-1,3,2-dioxaborolan-2-yl)phenoxy)piperidine (85 mg, 0.27 mmol), Pd(PPh$_{3}$)$_{4}$ (28 mg, 0.024 mmol), 2 M aq Na$_{2}$CO$_{3}$ (0.30 mL), PhMe (4 mL), and EtOH (2 mL). H$_{2}$O (30 mL) was added and the product was extracted into EtOAc (4×30 mL). The combined organic layers were dried over MgSO$_{4}$, filtered and evaporated in vacuo. Purification by flash chromatography (Biotage, 25 g HP-SIL, 2-30% MeOH in DCM) followed by RP HPLC (Biotage, 60 g C18-H, 0.1% TFA-H$_{2}$O in MeOH, 10-90%) gave the title compound as a white solid (45 mg, 29%). The title compound was isolated as a TFA salt. $^{1}$H NMR (400 MHz, CD$_{3}$OD) δ ppm 8.65 (s, 1 H), 8.01 (dd, J=8.8 Hz, 1.4 Hz, 1 H), 7.95 (t, J=8.6 Hz, 2 H), 7.72 (d, J=7.9 Hz, 1 H), 7.55-7.50 (m, 4 H), 7.23 (d, J=8.8 Hz, 1.3 H), 7.18 (d, J=8.8 Hz, 0.7 H), 4.89-4.85 (br m, 1 H), 4.77-4.67 (m, 2.4 H), 4.24 (br m, 4 H), 3.65-3.58 (br m, 4 H), 3.47-3.36 (m, 3 H), 3.23 (td, J=12.9, 2.8 Hz, 0.85 H), 2.94, 2.93 (2 s, 3 H), 2.47-2.43 (m, 0.7 H), 2.33-2.30 (m, 1.4 H), 2.20-2.12 (m, 1.4 H), 2.00-1.89 (m, 0.74 H); MS ESI 526.3 [M+H]$^{+}$, calcd for [C$_{31}$H$_{35}$N$_{5}$O$_{3}$+H]$^{+}$ 526.27.

Example A109

3-(4-(1-Methylpiperidin-4-yloxy)phenyl)-N-(2-(morpholinomethyl)benzyl)-1H-indazole-5-carboxamide

A. 3-Iodo-N-(2-(morpholinomethyl)benzyl)-1H-indazole-5-carboxamide

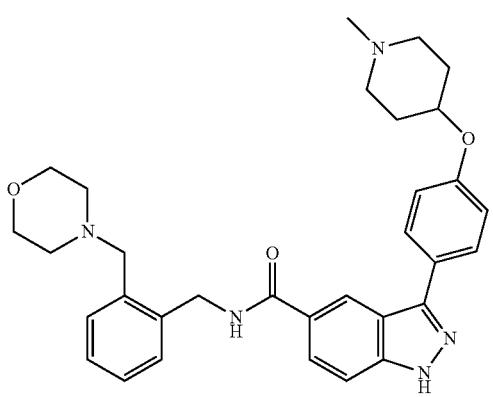 [SMILES: CN1CCC(Oc2ccc(-c3n[nH]c4ccc(C(=O)NCc5ccccc5CN5CCOCC5)cc34)cc2)CC1]

The title compound was synthesized according to General Method A, utilizing 3-iodo-1H-indazole-5-carboxylic acid (150 mg, 0.52 mmol), (2-(morpholinomethyl)phenyl)methanamine (118 mg, 0.0.57 mmol), TBTU (184 mg, 0.57 mmol), DIPEA (0.36 mL, 2.1 mmol), and DMF (4 mL). H₂O (20 mL) was added and the product was extracted into EtOAc (4×20 mL). The combined organic layers were dried over MgSO₄, filtered and evaporated in vacuo. The residue was then dissolved in MeOH (20 mL) and poured into a preconditioned 20 mL PoraPak Rxn Cx cartridge. The methanol (30 mL) rinse was discarded and the product was eluted with 2 M NH₃ in Methanol (30 mL). The solvent was removed in vacuo, and the product was used without further purification (220 mg, 89%). ¹H NMR (400 MHz, CD₃OD) δ ppm 8.01 (s, 1 H), 7.92 (dd, J=8.8, 1.6 Hz, 1 H), 7.61 (d, J=8.8 Hz, 1 H), 7.45 (d, J=7.5 Hz, 1 H), 7.34-7.25 (m, 4 H), 4.77 (s, 2 H), 3.64 (s, 2 H), 3.56 (t, J=4.7 Hz, 4 H), 2.47 (br m, 4 H); MS ESI 477.2 [M+H]⁺, calcd for [C₂₀H₂₁IN₄O₂+H]⁺ 477.07.

B. 3-(4-(1-Methylpiperidin-4-yloxy)phenyl)-N-(2-(morpholinomethyl)benzyl)-1H-indazole-5-carboxamide The title compound was synthesized according to General Method C, utilizing 3-iodo-N-(2-(morpholinomethyl)benzyl)-1H-indazole-5-carboxamide (110 mg, 0.23 mmol), 1-methyl-4-(4-(4,4,5,5-tetramethyl-1,3,2-dioxaborolan-2-yl)phenoxy)piperidine (81 mg, 0.25 mmol), Pd(PPh₃)₄ (27 mg, 0.023 mmol), 2 M aq Na₂CO₃ (0.30 mL), PhMe (4 mL), and EtOH (2 mL). H₂O (30 mL) was added and the product was extracted into EtOAc (4×30 mL). The combined organic layers were dried over MgSO₄, filtered and evaporated in vacuo. Purification by flash chromatography (Biotage, 25 g HP-SIL, EtOAc then 2-30% MeOH in DCM) followed by RP HPLC (Biotage, 60 g Rp-C18-H, 0.1% TFA-H₂O in MeOH, 10-90%) gave the title compound as a white solid (53 mg, 30%). The title compound was isolated as a di-TFA salt. ¹H NMR (400 MHz, CD₃OD) δ ppm 8.65 (s, 1 H), 8.00-7.94 (m, 3 H), 7.66-7.63 (m, 2 H), 7.54 (td, J=7.4, 1.1 Hz, 1 H), 7.46 (d, J=6.8 Hz, 1 H), 7.40 (t, J=7.4 Hz, 1 H), 7.25-7.18 (m, 2 H), 4.81-4.69 (m, 0.5 H), 4.64, 4.63 (2 s, 2 H), 4.13-4.11 (m, 2 H), 4.00 (t, J=11.9 Hz, 2 H), 3.67-3.65 (m, 0.68 H), 3.53-3.40 (m, 5 H), 3.24 (td, J=12.7, 2.4 Hz, 1 H), 2.96, 2.95 (2 s, 3 H), 2.47-2.44 (m, 0.65 H), 2.34-2.30 (m, 1.3 H), 2.21-2.14 (m, 1.4 H), 2.00-1.90 (m, 0.71 H); MS ESI 540.3 [M+H]⁺, calcd for [C₃₂H₃₇N₅O₃+H]⁺ 540.29.

Example A110

N-(cyclopentyl(thiophen-3-yl)methyl)-3-(4-((1-methylpiperidin-4-yl)oxy)phenyl)-1H-indazol-5-carboxamide

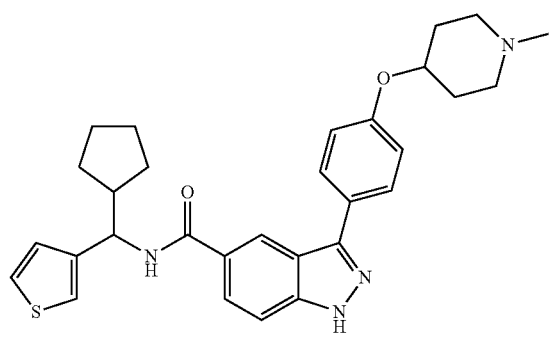 [SMILES: CN1CCC(Oc2ccc(-c3n[nH]c4ccc(C(=O)NC(c5ccsc5)C5CCCC5)cc34)cc2)CC1]

The title compound was synthesized according to General Method C from N-(cyclopentyl(thiophen-3-yl)methyl)-3-iodo-1H-indazole-5-carboxamide (150 mg, 0.332 mmol) and 1-methyl-4-(4-(4,4,5,5-tetramethyl-1,3,2-dioxaborolan-2-yl)phenoxy)piperidine (106 mg, 0.334 mmol) with PdCl₂dppf (35 mg, 0.042 mmol) and 1 M aq Na₂CO₃ (0.64 mL) in PhMe/EtOH (3.75 mL, 2:1 mixture) under Ar with heating under microwave irradiation at 125° C. for 4 h. The reaction mixture was diluted with EtOAc (25 mL) and washed with H₂O (10 mL) and brine (10 mL), dried (Na₂SO₄) and concentrated under vacuum. Purification by flash chromatography (SiO2, 0-20% 2 M NH₃-MeOH in DCM; then RP HPLC C18 60 g, 10-80% MeOH in 0.1% TFA-H₂O) gave the title compound as a TFA salt (off white solid, 60 mg, 28%). ¹H NMR (400 MHz, CD₃OD). δ 8.52 (s, 1H), 7.94-7.88 (m, 3H), 7.6 (d, J=8.8 Hz, 1H), 7.36-7.32 (m, 2H), 7.20-7.13 (m, 3H), 5.08 (d, J=6.0 Hz, 1H), 4.85 (s, 1H), 3.66 (t, J=13.6 Hz, 1H), 3.44-3.32 (m, 5H), 3.23 (br.m, 1H), 2.59-2.53 (br.m, 1H), 2.45-2.27 (m, 2H), 2.16-1.87 (m, 3H), 1.74-1.44 (br.m, 6H), 1.28-1.25 (m, 1H); MS ESI 515.4[M+H]⁺, calcd for [C₃₀H₃₄N₄O₂S+H]⁺ 515.2.

Example A111

N-(3-(4-(4-(2-hydroxypropan-2-yl)piperidin-1-yl)phenyl)-1H-indazol-5-yl)-2-(pyrrolidin-1-yl)-2-(thiophen-3-yl)acetamide

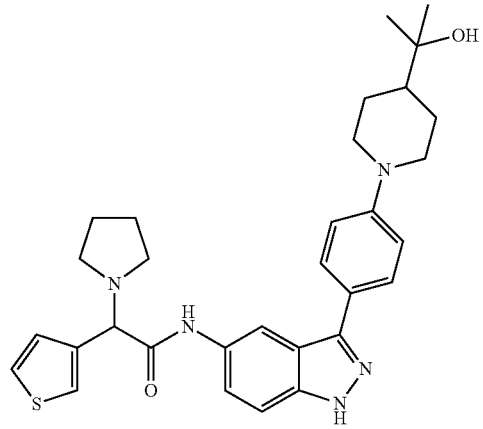 [SMILES: CC(C)(O)C1CCN(c2ccc(-c3n[nH]c4ccc(NC(=O)C(c5ccsc5)N5CCCC5)cc34)cc2)CC1]

The title compound was synthesized according to General Method C3 utilizing N-(3-iodo-1H-indazol-5-yl)-2-(pyrrolidin-1-yl)-2-(thiophen-3-yl)acetamide and 2-(1-(4-(4,4,5,5-tetramethyl-1,3,2-dioxaborolan-2-yl)phenyl)piperidin-4-yl)propan-2-ol and obtained as a white solid (21 mg, 23% yield). ¹H NMR (400 MHz, CD₃OD) δ ppm 8.43 (s, 1H), 8.15 (d, J=8.8 Hz, 2H), 7.88 (m, 1H), 7.83 (d, J=8.8 Hz, 2H), 7.65 (m, 1H), 7.58 (m, 2H), 7.38 (d, J=5.2 Hz, 1H), 5.31 (s, 1H), 3.83 (m, 3H), 3.70 (m, 2H), 3.33 (m, 2H), 3.15 (m, 2H), 2.16 (m, 5H), 1.92 (m, 3H), 1.27 (s, 6H); MS ESI [M+H]⁺ 544.2, calcd for [C₃₁H₃₇N₅O₂S+H]⁺ 544.27.

Example A112

N-(cyclopropyl(phenyl)methyl)-3-(4-(4-(2-hydroxypropan-2-yl)piperidin-1-yl)phenyl)-1H-indazole-5-carboxamide

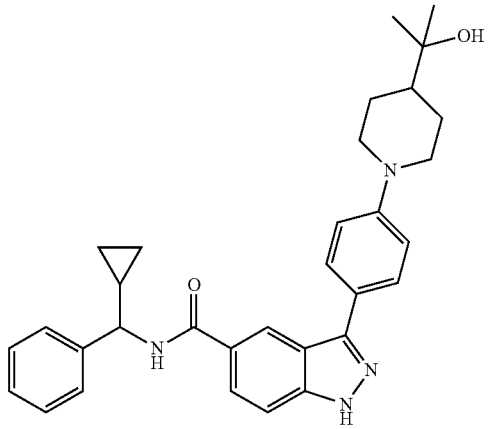

The title compound was synthesized according to General Method C3 utilizing N-(cyclopropyl(phenyl)methyl)-3-iodo-1H-indazole-5-carboxamide and 2-(1-(4-(4,4,5,5-tetramethyl-1,3,2-dioxaborolan-2-yl)phenyl)piperidin-4-yl)propan-2-ol and obtained (white solid, 21 mg, 22% yield). $^1$H NMR (400 MHz, CD$_3$OD) δ ppm 8.63 (s, 1 H), 7.95 (dd, J=8.78, 1.51 Hz, 1 H), 7.85 (d, J=8.78 Hz, 2 H), 7.58 (d, J=8.78 Hz, 1 H), 7.48 (d, J=7.28 Hz, 2 H), 7.32 (t, J=7.53 Hz, 2 H), 7.23 (m, J=7.28 Hz, 1 H), 7.09 (d, J=8.78 Hz, 2 H), 5.49 (s, 1 H), 4.48 (d, J=9.54 Hz, 1 H), 3.84 (d, J=12.30 Hz, 2 H), 2.66 (t, J=11.04 Hz, 2 H), 1.87 (d, J=9.29 Hz, 2 H), 1.46 (d, J=3.51 Hz, 3 H), 1.18 (s, 6 H), 0.65 (d, J=8.28 Hz, 2 H), 0.46 (d, J=15.31 Hz, 2 H); MS ESI [M+H]$^+$ 509.5, calcd for [C$_{32}$H$_{36}$N$_4$O$_2$+H]$^+$ 509.29.

Example A113

N-(3-(3-(dimethylamino)-4-((1-methylpiperidin-4-yl)oxy)phenyl)-1H-indazol-5-yl)-2-(pyrrolidin-1-yl)-2-(thiophen-3-yl)acetamide

A. 4-(4-bromo-2-nitrophenoxy)-1-methylpiperidine

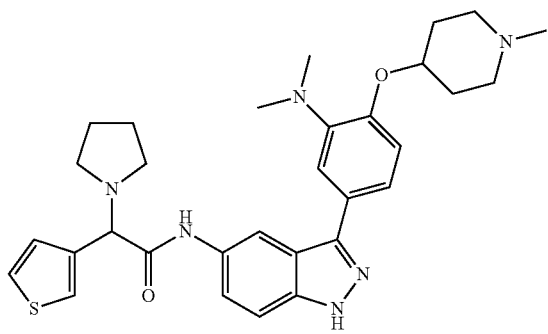 [SMILES: CN1CCC(Oc2ccc(-c3n[nH]c4ccc(NC(=O)C(c5ccsc5)N5CCCC5)cc34)cc2N(C)C)CC1]

NaH (0.54 g, 13 mmol) was added portion wise to a solution of N-methyl-4-piperidinol (1.13 g, 11 mmol) in DMF (14 mL) at rt under Ar, followed by a solution of 4-bromo-1-fluoro-2-nitrobenzene (2.0 g, 9 mmol) in DMF (6 mL). The reaction mixture was heated at 75° C. for 16 h. The product was partitioned between 20% NaCl and EtOAc (2×300 mL), and the combined EtOAc layer was washed with H$_2$O and brine, dried (Na$_2$SO$_4$) and concentrated under vacuum to give the title compound (yellowish orange oil, 2.78 g, 97%). $^1$H NMR (400 MHz, CDCl$_3$) 7.94 (d, J=2.4 Hz, 1H), 7.60 (dd, J=8.8 Hz, J=2.4 Hz, 1H), 6.98 (d, J=9.2 Hz, 1H), 4.52 (s, 1H), 2.60 (br.s, 2H), 2.40 (br.s, 2H), 2.31 (s, 3H), 2.03-1.89 (m, 4H); MS ESI 316.9 [M+H]$^+$, calcd for [C$_{12}$H$_{15}$BrN$_2$O$_3$+H]$^+$ 315.

B. 5-bromo-2-((1-methylpiperidin-4-yl)oxy)aniline

1 M aq HCl (10 mL) was added slowly over 15 min to a suspension 4-(4-bromo-2-nitrophenoxy)-1-methylpiperidine (2.75 g, 8.7 mmol) and iron powder (9.75 g, 174 mmol) in PhMe (30 mL) and EtOH (10 mL) at 60° C. The reaction mixture was gradually heated to 100° C. and stirred for 4 h. The solid sludge was filtered through SiO2 pad at 90° C. and washed with hot EtOAc. The organic layer was washed with 1 M aq Na$_2$CO$_3$ (50 mL) and brine and dried (Na$_2$SO$_4$) and concentrated under vacuum. Purification by flash chromatography (SiO$_2$, 0-75% MeOH in DCM) gave the title compound (brown solid, 1.0 g, 40%). $^1$H NMR (400 MHz, CDCl$_3$)) δ ppm 6.85 (d, J=2.0 Hz, 1H), 6.79 (dd, J=8.8 Hz, J=2.4 Hz, 1H), 6.66 (d, J=8.8 Hz, 1H), 4.28 (s, 1H), 3.86 (s, 2H), 2.69-2.66 (br.s, 2H), 2.31 (s, 5H), 2.06-2.02 (br.m, 2H), 1.91-1.83 (br.m, 2H); MS ESI 287 [M+H]$^+$, calcd for [C$_{12}$H$_{17}$BrN$_2$O+H]$^+$ 285.

C. 5-bromo-N,N-dimethyl-2-((1-methylpiperidin-4-yl)oxy)aniline

NaBH(OAc)$_3$ (3.3 g, 15.5 mmol) was added to an ice cooled solution of 5-bromo-2-((1-methylpiperidine-4-yl)oxy)aniline (0.74 g, 2.6 mmol) and 37% aq. solution of formaldehyde (2.11 g, 26 mmol) in MeCN (22.2 mL). The reaction mixture was stirred overnight at rt and then concentrated under vacuum. The product was partitioned between 2 M Na$_2$CO$_3$ and EtOAc. The aq. layer was extracted with EtOAc and the combined EtOAc layer was washed with H$_2$O and brine, dried (Na$_2$SO$_4$) and concentrated under vacuum. Purification by flash chromatography (SiO$_2$, 0-25% DCM in MeOH) gave the title compound (thick brown oil, 0.65 g, 80%). $^1$H NMR (400 MHz, CDCl$_3$) δ ppm 6.99-6.97 (t, 0.1=2.4 Hz, 2H), 6.73 (d, J=9.2 Hz, 1H), 4.30 (br.t, 1H), 2.80 (s, 6H), 2.76-2.73 (br.s, 2H), 2.31 (s, 3H), 2.29-2.65 (br.m, 2H), 2.05-2.0 (br.m, 2H), 1.92-1.84 (m, 2H); MS ESI 313 [M+H]$^+$, calcd for [C$_{14}$H$_{21}$BrN$_2$O+H]$^+$ 313.1.

D. N,N-dimethyl-2-((1-methylpiperidin-4-yl)oxy)-5-(4,4,5,5-tetramethyl-1,3,2-dioxaborolan-2-yl)aniline Using General Method E with 5-bromo-N,N-dimethyl-2-((1-methylpiperidin-4-yl)oxy)aniline (200 mg, 0.638 mmol) in DMF (3 mL) at 125° C. for 4 h, aq. work-up and purification by flash chromatography (SiO2, 0-30% 2 M NH₃-MeOH in DCM) gave the title compound (brown color solid, 74 mg, 32%). ¹H NMR (400 MHz, CDCl₃) δ ppm 7.41-7.36 (m, 2H), 6.86 (d, J=8 Hz, 1H), 4.44 (br.d, 1H), 2.82 (s, 6H), 2.75-2.73 (br.s, 2H), 2.32 (br.d, 5H), 2.09-2.05 (br.m, 2H), 1.97-1.89 (br.m, 2H), 1.33 (s, 12H); MS ESI 361.2 [M+H]⁺, calcd for [C₂₀H₃₃BN₂O₃+H]⁺ 361.2.

E. N-(3-(3-(dimethylamino)-4-((1-methylpiperidin-4-yl)oxy)phenyl)-1H-indazol-5-yl)-2-(pyrrolidin-1-yl)-2-(thiophen-3-yl)acetamide According to General Method C2, N-(3-iodo-1H-indazol-5-yl)-2-(pyrrolidin-1-yl)-2-(thiophen-3-yl)acetamide (90 mg, 0.195 mmol) and N,N-dimethyl-2-((1-methylpiperidin-4-yl)oxy)-5-(4,4,5,5-tetramethyl-1,3,2-dioxaborolan-2-yl)aniline (72 mg, 0.98 mmol) were heated under microwave irradiation at 125° C. for 4 h in PhMe/EtOH (2.7 mL, 2:1 mixture). Purification by flash chromatography (SiO₂, 0-50% 2 M NH₃-MeOH in DCM; then RP HPLC Cl₈RP HPLC C18 60 g, 10-80% MeOH in 0.1% TFA-H₂O) gave the title compound as a TFA salt (off white solid, 30 mg, 19%). ¹H NMR (400 MHz, CD₃OD). ¹H NMR (400 MHz, CD₃OD). δ 8.44 (d, J=12.4 Hz, 1H), 8.26 (s, 1H), 80.8-80.5 (m, 1H), 7.88 (t, J=2.0 Hz, 1H), 7.66 (dd, J=5.2 Hz, J=3.2 Hz, 1H), 7.58-7.54 (m, 3H), 7.39 (d, J=8.0 Hz, 1H), 5.30 (s, 1H), 5.11 (s, 0.6H), 3.87 (br.s, 1H), 3.75-3.71 (br.m, 1H), 3.60-3.57 (br.m, 2H), 3.43 (d, J=16.8 Hz, 6H), 3.28-3.1 (br.m, 3H), 2.97 (s, 3H), 2.56-2.53 (br.m, 1H), 2.46-2.42 (br.m, 1H), 2.31-1.99 (br.m, 6H), 1H merged with solvent peak; MS ESI 559.2 [M+H]⁺, calcd for [C₃₁H₃₈N₆O₂S+H]⁺ 559.3.

Example A114

1-(2,6-diethylphenyl)-3-(3-(4-methyl-2,3,4,5-tetrahydrobenzo[f][1,4]oxazepin-7-yl)-1H-indazol-5-yl)urea

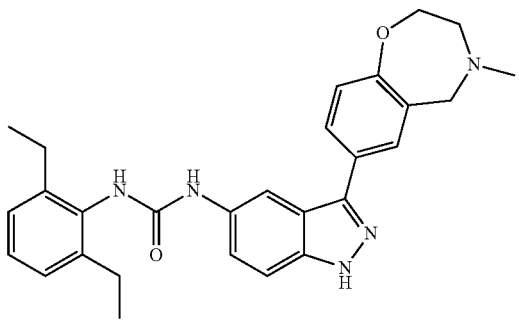 [SMILES: CCc1cccc(CC)c1NC(=O)Nc1ccc2[nH]nc(-c3ccc4c(c3)CN(C)CCO4)c2c1]

Using General Method J, 3-(4-methyl-2,3,4,5-tetrahydrobenzo[f][1,4]oxazepin-7-yl)-1H-indazol-5-amine bis(2,2,2-trifluoroacetate) (74 mg, 0.152 mmol), 1,3-diethyl-2-isocyanatobenzene (52 uL, 0.300 mmol) and DIPEA (130 uL, 0.750 mmol) in DMF (1.5 mL) gave the title compound as a TFA salt (29 mg, 41%, brown solid). ¹H NMR (400 MHz, CD₃OD) δ ppm 8.39 (s, 1H), 7.99-7.96 (m, 2H), 7.52 (d, J=8.8 Hz, 1H), 7.28-7.10 (m, 5H), 4.62 (s, 2H), 4.54-4.51 (bs, 1H), 4.18-4.10 (bs, 1H), 3.73 (bs, 2H), 3.08-3.03 (m, 3H), 2.71 (q, J=7.2 Hz, 4H), 1.24 (t, J=7.6 Hz, 6H); MS ESI 470.4 [M+H]⁺, calcd for [C₂₈H₃₁N₅O₂+H]⁺ 470.26.

Example A115 tert-butyl 4-(4-(5-(2-(pyrrolidin-1-yl)-2-(thiophen-3-yl)acetamido)-1H-indazol-3-yl)phenoxy)piperidine-1-carboxylate

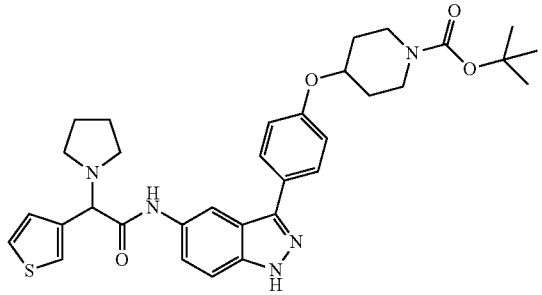 [SMILES: CC(C)(C)OC(=O)N1CCC(Oc2ccc(-c3n[nH]c4ccc(NC(=O)C(c5ccsc5)N5CCCC5)cc34)cc2)CC1]

The title compound was synthesized according to General Method C3 utilizing N-(3-iodo-1H-indazol-5-yl)-2-(pyrrolidin-1-yl)-2-(thiophen-3-yl)acetamide and tert-butyl 4-(4-(4,4,5,5-tetramethyl-1,3,2-dioxaborolan-2-yl)phenoxy)piperidine-1-carboxylate and obtained as a pale white solid (14 mg, 21% yield). ¹H NMR (400 MHz, CD₃OD) δ ppm 8.33 (s, 1H), 7.81 (d, J=8.8 Hz, 2H), 7.50 (m, 3H), 7.42 (dd, J=4.8 Hz, 2.8 Hz, 1H), 7.33 (m, 1H), 7.07 (d, J=8.8 Hz, 2H), 4.63 (m, 1H), 4.14 (s, 1H), 3.73 (m, 2H), 3.33 (m, 2H), 2.69 (m, 2H), 2.51 (m, 2H), 1.90 (m, 2H), 1.70 (m, 4H), 1.48 (s, 9H); MS ESI [M+H]⁺ 602.4, calcd for [C₃₃H₃₉H₅O₄S+H]⁺ 602.28.

Example A116

N-(3-(4-(4-methoxypiperidin-1-yl)phenyl)-1H-indazol-5-yl)-2-(pyrrolidin-1-yl)-2-(thiophen-3-yl)acetamide

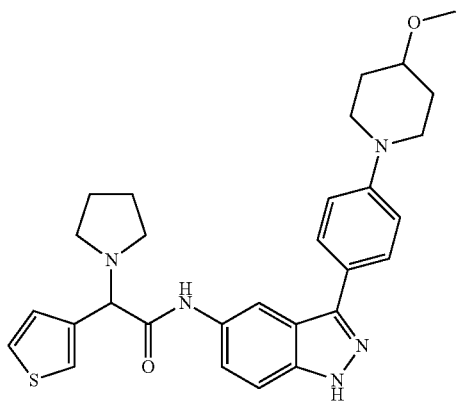 [SMILES: COC1CCN(c2ccc(-c3n[nH]c4ccc(NC(=O)C(c5ccsc5)N5CCCC5)cc34)cc2)CC1]

To a solution of 1-(4-(4,4,5,5-tetramethyl-1,3,2-dioxaborolan-2-yl)phenyl)piperidin-4-ol (152 mg, 0.5 mmol) in DMF (5 mL) at rt was added 60% NaH (40 mg, 1 mmol). The resulting mixture was stirred at rt for 10 min before MeI (0.031 mL, 0.5 mmol) was added. After addition, the resulting mixture was stirred O/N at rt. This reaction was repeated on 1 mmol scale (rt, 2 h). Both reactions were combined, quenched with satd aq NH₄Cl (5 mL) and H₂O (100 mL), extracted with EtOAc and purified by flash chromatography (EtOAc/hex 0-30%) to give 4-methoxy-1-(4-(4,4,5,5-tetramethyl-1,3,2-dioxaborolan-2-yl)phenyl)piperidine (white solid, 95 mg, 20%). MS ESI 318.1 [M+H]⁺, calcd for [C₁₈H₂₈BNO₃+H]⁺ 318.2.

To a mixture of N-(3-iodo-1H-indazol-5-yl)-2-(pyrrolidin-1-yl)-2-(thiophen-3-yl)acetamide (136 mg, 0.3 mmol) and 4-methoxy-1-(4-(4,4,5,5-tetramethyl-1,3,2-dioxaborolan-2-yl)phenyl)piperidine (95 mg, 0.3 mmol) in EtOH (4 mL) was added 1 M aq Na₂CO₃ (0.6 mL, 0.6 mmol), followed by Pd(PPh₃)₄ (17.4 mg, 0.015 mmol). The resulting mixture was purged with Ar and microwaved 4 h at 125° C. After removal of solvents, it was purified by flash chromatography (EtOAc/hex 0-100%, then MeOH/DCM 15%), Biotage RP column (MeOH/H₂O (1% TFA) 0-100%) to give the title compound as a di-TFA salt (light yellow solid, 57.6 mg, 26%). ¹H NMR (400 MHz, CD₃OD) δ 8.42 (s, 1H), 8.11 (d, J=8.4 Hz, 2H), 7.88 (dd, J=2.8 Hz, 1.2 Hz, 1H), 7.74 (br d, J=8.0 Hz, 2H), 7.64 (dd, J=5.0 Hz, 3.0 Hz, 1H), 7.60-7.53 (m, 2H), 7.39 (dd, J=4.8 Hz, 1.2 Hz, 1H), 5.33 (s, 1H), 3.90-3.77 (m, 3H), 3.71-3.64 (m, 1H), 3.62-3.53 (m, 2H), 3.44 (s, 3H), 3.35-3.05 (m, 3H), 2.31-1.93 (m, 8H); MS ESI 516.2 [M+H]⁺, calcd for [C₂₂H₃₂N₅O₂S+H]⁺ 516.2.

Example A117

N-(cyclopropyl(thiophen-3-yl)methyl)-3-(4-((1-(2-hydroxyethyl)piperidin-4-yl)oxy)phenyl)-1H-indazole-5-carboxamide

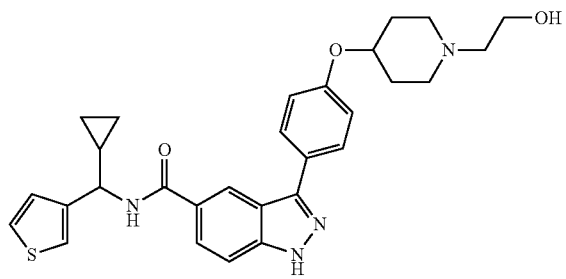 [SMILES: O=C(NC(c1ccsc1)C1CC1)c1ccc2[nH]nc(-c3ccc(OC4CCN(CCO)CC4)cc3)c2c1]

The title compound was prepared using General Method C3 from N-(cyclopropyl(thiophen-3-yl)methyl)-3-iodo-1H-indazole-5-carboxamide (40 mg, 0.095 mmol) and 2-(4-(4-(4,4,5,5-tetramethyl-1,3,2-dioxaborolan-2-yl)phenoxy)piperidin-1-yl)ethanol (43 mg, 0.124 mmol) which gave 14 mg of product isolated as its TFA salt (23%, white solid). ¹H NMR (400 MHz, CD₃OD) δ ppm 9.04 (bs, 1H), 8.58 (s, 1H), 7.96-7.94 (m, 3H), 7.61 (d, J=8.8 Hz, 1H), 7.37 (bs, 2H), 7.22-7.15 (m, 3H), 4.87 (bs, 1H), 4.65-4.61 (m, 1H), 3.91-3.28 (m, 12H), 2.45-2.29 (m, 2H), 2.21-1.95 (m, 2H), 1.44-1.40 (m, 1H), 0.73-0.63 (m, 2H), 0.50-0.48 (m, 2H); MS ESI 517.3 [M+H]⁺, calcd for [C₂₉H₃₂N₄O₃S+H]⁺ 517.23.

Example A118

N-(3-(4-((1-formylpiperidin-4-yl)oxy)phenyl)-1H-indazol-5-yl)-2-(pyrrolidin-1-yl)-2-(thiophen-3-yl)acetamide

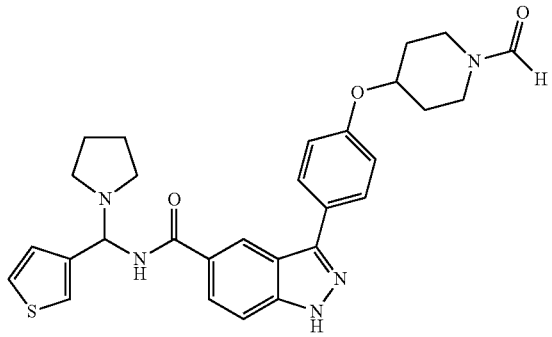 [SMILES: O=CN1CCC(Oc2ccc(-c3n[nH]c4ccc(C(=O)NC(c5ccsc5)N5CCCC5)cc34)cc2)CC1]

The title compound was synthesized according to General Method C3 utilizing N-(3-iodo-1H-indazol-5-yl)-2-(pyrrolidin-1-yl)-2-(thiophen-3-yl)acetamide and 4-(4-(4,4,5,5-tetramethyl-1,3,2-dioxaborolan-2-yl)phenoxy)piperidine-1-carbaldehyde and obtained as a yellow solid (39 mg, 35% yield). ¹H NMR (400 MHz, CD₃OD) δ ppm 8.35 (s, 1H), 8.04 (s, 1H), 7.82 (d, J=8.8 Hz, 2H), 7.50 (m, 3H), 7.40 (m, 1H), 7.33 (m, 1H), 7.08 (d, J=8.8 Hz, 2H), 4.72 (m, 1H), 4.16 (s, 1H), 3.75 (m, 2H), 3.67 (m, 2H), 3.52 (m, 2H), 3.41 (m, 2H), 2.67 (m, 2H), 2.51 (m, 2H), 1.98 (m, 2H), 1.80 (m, 6H); MS ESI [M+H]⁺ 530.4, calcd for [C₂₉H₃₁N₅O₃S+H]⁺ 530.22.

Example A119

N-(cyclopropyl(o-tolyl)methyl)-3-(4-morpholinophenyl)-1H-indazole-5-carboxamide

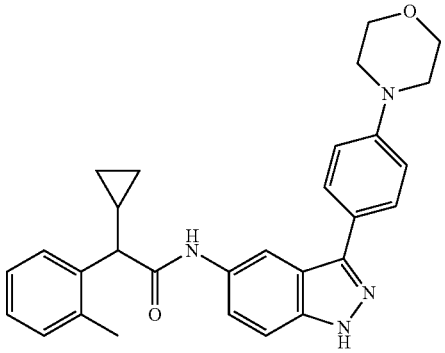 [SMILES: Cc1ccccc1C(C(=O)Nc1ccc2[nH]nc(-c3ccc(N4CCOCC4)cc3)c2c1)C1CC1]

To a 20 mL microwave vial charged with Mg powder (240 mg, 10 mmol), THF (10 mL) was added bromocyclopropane (1.21 g, 10 mmol). The resulting mixture was stirred for 30 min at rt before 2-methylbenzonitrile (468 mg, 4 mmol) was added. It was microwaved 10 min at 100° C., cooled to rt and added dropwise to a cold solution of NaBH₄ (380 mg, 10 mmol) in MeOH (25 mL) at 0° C. The resulting mixture was stirred for 15 min at rt, concentrated and purified by flash chromatography (MeOH/DCM 0-20%) to give cyclopropyl (o-tolyl)methanamine (yellow oil which solidified upon standing, 0.70 g, 87%). $^1$H NMR (400 MHz, CD$_3$OD) δ 8.49 (d, J=7.6 Hz, 1H), 7.27-7.22 (m, 1H), 7.20-7.17 (m, 2H), 3.75 (d, J=8.4 Hz, 1H), 2.35 (s, 3H), 1.37-1.27 (m, 1H), 0.71-0.63 (m, 1H), 0.53-0.46 (m, 1H), 0.38-0.31 (m, 1H), 0.29-0.33 (m, 1H); MS ESI 145.0 [M+H]$^+$, calcd for [C$_{11}$H$_{15}$N NH$_3$+H]$^+$ 145.1.

To a solution of 3-iodo-1H-indazole-5-carboxylic acid (1.44 g, 5 mmol) and (4-morpholinophenyl)boronic acid (1.09 g, 5.25 mmol) in DMF (10 mL) was added a solution of K$_3$PO$_4$ (3.18 g, 15 mmol) in H$_2$O (4 mL), followed by Pd(PPh$_3$)$_4$ (116 mg, 0.1 mmol). The resulting mixture was purged with Ar and microwaved 5 h at 120° C. Repeated this reaction on the same scale and the two reactions were combined. After separation of DMF layer, the aq. layer was extracted with EtOAc. The combined organic layers were concentrated to dryness, suspended in MeOH (60 mL), treated with 4 mL of TFA, sonicated and filtered to give 3-(4-morpholinophenyl)-1H-indazole-5-carboxylic acid (yellow solid, 1.162 g, 36%). $^1$H NMR (400 MHz, DMSO-d$_6$) δ 13.4 (s, 1H), 12.8 (br, s, 1H), 8.61 (s, 1H), 7.94 (dd, J=8.8 Hz, 1H), 7.83 (d, J=8.8 Hz, 2H), 7.61 (d, J=8.8 Hz, 1H), 7.13 (d, J=8.8 Hz, 2H), 3.77 (t, J=4.8 Hz, 4H), 3.20 (t, J=4.8 Hz, 4H); MS ESI 324.1 [M+H]$^+$, calcd for [C$_{18}$H$_{17}$N$_3$O$_3$+H]$^+$ 324.1.

To a solution of cyclopropyl(o-tolyl)methanamine (80.5 mg, 0.5 mmol), 3-(4-morpholinophenyl)-1H-indazole-5-carboxylic acid (194 mg, 0.6 mmol) and TBTU (160.5 mg, 0.5 mmol) in DMF (6 mL) was added iPr$_2$NEt (0.174 mL, 1 mmol). The resulting mixture was stirred for 30 min at rt. After removal of iPr$_2$NEt, it was purified by prep-HPLC, PoraPak and flash chromatography (MeOH/DCM 10-20%) to give the title compound (white solid, 88.7 mg, 38%). $^1$H NMR (400 MHz, CD$_3$OD) δ 8.99 (d, J=8.0 Hz, 0.5H, NH), 8.58 (s, 1H), 7.91 (d, J=8.8 Hz, 1H), 7.78 (d, J=8.4 Hz, 2H), 7.56 (d, J=7.6 Hz, 1H; partially overlapped with the peak at 7.53), 7.53 (d, J=8.8 Hz, 1H; partially overlapped with the peak at 7.56), 7.14-7.04 (m, 3H), 6.92 (d, J=8.8 Hz, 2H), 4.90-4.86 (m, 1H; partially buried under H$_2$O peak), 3.74 (t, J=4.6 Hz, 4H), 3.05 (t, J=4.8 Hz, 4H), 2.37 (s, 3H), 1.45-1.35 (m, 1H), 0.63-0.42 (m, 3H), 0.33-0.27 (m, 1H); MS ESI 467.5 [M+H]$^+$, calcd for [C$_{29}$H$_{30}$N$_4$O$_2$+H]$^+$ 467.2.

Example A120

N-(3-(4-(3-Hydroxyazetidin-1-yl)phenyl)-1H-indazol-5-yl)-2-(pyrrolidin-1-yl)-2-(thiophen-3-yl)acetamide A. Azetidin-3-ol

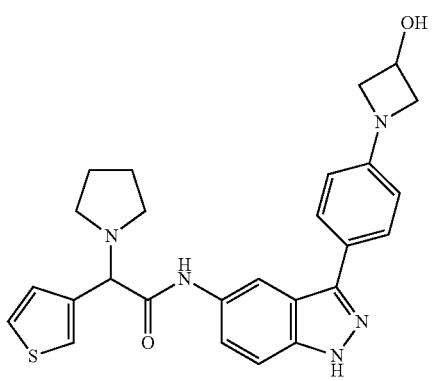 [SMILES: O=C(Nc1ccc2[nH]nc(-c3ccc(N4CC(O)C4)cc3)c2c1)C(c1ccsc1)N1CCCC1]

A solution of tert-butyl 3-hydroxyazetidine-1-carboxylate (1.0 g, 5.84 mmol) and TFA (5 mL) in DCM (10 mL) was stirred at rt for 1 h. The solvent was removed in vacuo. The residue was then dissolved in MeOH (20 mL) and poured into a preconditioned 20 mL PoraPak Rxn Cx cartridge. The MeOH (30 mL) rinse was discarded and the product was eluted with 2 M NH$_3$ in MeOH (30 mL). The solvent was removed in vacuo, and the product was used without further purification. $^1$H NMR (400 MHz, CD$_3$OD) δ ppm 4.56 (quint, J=6.8 Hz, 1 H), 3.64 (t, J=7.0 Hz, 2 H), 3.50 (t, J=7.0 Hz, 2 H); MS ESI 74.2 [M+H]$^+$, calcd for [C$_c$H$_7$NO+H]$^+$ 74.05.

B. 1-(4-Iodophenyl)azetidin-3-ol

The title compound was synthesized according to General Method I, utilizing 1,4-diiodobenzene (470 mg, 1.4 mmol), azetidin-3-ol (125 mg, 1.7 mmol), CuI (54 mg, 0.29 mmol), BINOL (82 mg, 0.29 mmol), and K$_3$PO$_4$ (610 mg, 2.9 mmol) in DMF (5 mL). The mixture was diluted with EtOAc, filtered through a cake of Celite and the filtrate was concentrated to give the crude product. Purification by flash chromatography (Biotage, 25 g HP-SIL, 20-100% EtOAc in Hexanes) gave the title compound as a white solid (262 mg, 67%). $^1$H NMR (400 MHz, CD$_3$OD) δ ppm 7.43 (d, J=8.8 Hz, 2 H), 6.27 (d, J=8.8 Hz, 2 H), 4.65 (quint, J=4.9 Hz, 1 H), 4.10 (t, J=7.4 Hz, 2 H), 3.57 (dd, J=8.4, 4.9 Hz, 2 H); MS ESI 275.9 [M+H]$^+$, calcd for [C$_9$H$_{10}$INO+H]$^+$ 275.98.

C. 1-(4-(4,4,5,5-Tetramethyl-1,3,2-dioxaborolan-2-yl)phenyl)azetidin-3-ol

The title compound was synthesized according to General Method E, utilizing 1-(4-iodophenyl)azetidin-3-ol (290 mg, 0.96 mmol), bis(pinacolato)diboron (366 mg, 1.4 mmol), PdCl$_2$(dppf) (39 mg, 0.048 mmol), KOAc (280 mg, 2.9 mmol) and DMSO (4.0 mL). The reaction was quenched with satd aq NaHCO$_3$ solution, extracted with EtOAc, dried over MgSO$_4$, filtered, and concentrated to dryness. Purification by flash chromatography (Biotage, 50 g HP-SIL, 10-50% EtOAc in hexanes) gave the title compound as a yellow oil (260 mg, 100%). $^1$H NMR (400 MHz, CDCl$_3$) δ ppm 7.65 (d, J=8.4 Hz, 2 H), 6.40 (d, J=8.4 Hz, 2 H), 4.98 (quint, J=4.8 Hz, 1 H), 4.18 (dd, J=15, 8.0 Hz, 2 H), 3.76 (dd, J=8.4, 4.6 Hz, 2 H), 1.31 (s, 12 H); MS ESI 276.0 [M+H]$^+$, calcd for [C$_{15}$H$_{22}$BNO$_3$+H]$^+$ 276.17.

D. N-(3-(4-(3-hydroxyazetidin-1-yl)phenyl)-1H-indazol-5-yl)-2-(pyrrolidin-1-yl)-2-(thiophen-3-yl)acetamide The title compound was synthesized according to General Method C, utilizing N-(3-iodo-1H-indazol-5-yl)-2-(pyrrolidin-1-yl)-2-(thiophen-3-yl)acetamide (360 mg, 0.79 mmol), 1-(4-(4,4,5,5-tetramethyl-1,3,2-dioxaborolan-2-yl)phenyl)azetidin-3-ol (240 mg, 0.87 mmol), Pd(PPh$_3$)$_4$ (92 mg, 0.079 mmol), 2 M Na$_2$CO$_3$ (0.80 mL), PhMe (4 mL), and EtOH (2 mL). H$_2$O (30 mL) was added and the product was extracted into EtOAc (4×30 mL). The combined organic layers were dried over MgSO$_4$, filtered and evaporated in vacuo. Purification by flash chromatography (Biotage, 50 g HP-SIL, 20-100% EtOAc in hexanes, then 2-15% MeOH in DCM) followed by RPHPLC gave the title compound as a bright yellow solid (90 mg, 16%).

The title compound was isolated as a di-TFA salt. $^1$H NMR (400 MHz, CD$_3$OD) δ ppm 8.37 (s, 1 H), 7.87 (dd, J=2.9, 1.3 Hz, 2 H), 7.80 (d, J=8.6 Hz, 2 H), 7.63 (dd, J=5.1, 3.0 Hz, 1 H), 7.52 (d, J=1.1 Hz, 2 H), 7.38 (dd, J=5.1, 1.2 Hz, 1 H), 6.84 (br d, J=7.4 Hz, 2 H), 5.27 (s, 1 H), 4.74 (quint, J=5.1 Hz, 1 H), 4.39-4.34 (br m, 2 H), 3.90-3.78 (br m, 3 H), 3.30-3.02 (br m, 3 H), 3.13 (s, 3 H), 2.16-1.90 (br m, 4 H); MS ESI 474.1 [M+H]+, calcd for [C$_{26}$H$_{27}$H$_{5}$O$_{2}$S+H]+ 474.19.

Example A121

N-(cyclobutyl(thiophen-3-yl)methyl)-3-(4-((1-methylpiperidin-4-yl)oxy)phenyl)-1H-indazole-5-carboxamide

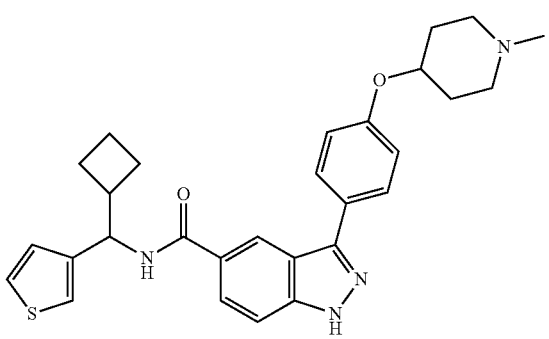 [SMILES: CN1CCC(Oc2ccc(-c3n[nH]c4ccc(C(=O)NC(c5ccsc5)C5CCC5)cc34)cc2)CC1]

A mixture of cyclobutyl(thiophen-3-yl)methanone (1.04 g, 6.27 mmol), NH$_4$OAc (5.85 g, 75.24 mmol) and NaCNBH$_3$ (1.58 g, 25.08 mmol) in MeOH (30 mL) was heated at 65° C. for 3 h, then left O/N at 65° C. After removal of solvent, it was purified by flash chromatography (MeOH/DCM 0-30%) to give cyclobutyl(thiophen-3-yl)methanamine (colorless oil, 1.194 g). $^1$H NMR (400 MHz, CD$_3$OD) δ 7.55-7.50 (m, 2H), 7.17 (dd, J=4.8 Hz, 1.2 Hz, 1H), 4.37 (d, J=10.0 Hz, 1H), 2.93-2.82 (m, 1H), 2.29-2.19 (m, 1H), 2.05-1.75 (m, 5H); MS ESI 151.0 [M+H]+, calcd for [C$_9$H$_{13}$NS−NH$_3$+H]+ 151.1.

To a solution of cyclobutyl(thiophen-3-yl)methanamine (1.194 g, 6.27 mmol), 3-iodo-1H-indazole-5-carboxamide (1.81 g, 6.27 mmol) in DMF (20 mL) at 0° C. was added TBTU (2.01 g, 6.27 mmol), followed by $^i$Pr$_2$NEt (2.18 mL, 12.54 mmol). The resulting mixture was stirred at 0° C. for 1 h, quenched with H$_2$O (70 mL) and stirred for 1.5 h at rt. Suction filtration gave crude N-(cyclobutyl(thiophen-3-yl)methyl)-3-iodo-1H-indazole-5-carboxamide (light beige solid, 2.512 g). $^1$H NMR (400 MHz, DMSO-d$_6$) δ 13.69 (s, 1H), 8.75 (d, J=8.8 Hz, 1H), 8.04 (s, 1H), 7.94 (dd, J=4.6 Hz, 1.4 Hz, 1H), 7.58 (d, J=8.8 Hz, 1H), 7.45 (dd, J=4.8 Hz, 2.8 Hz, 1H), 7.35 (d, J=3.2 Hz, 1H), 7.14 (dd, J=4.8 Hz, 0.8 Hz, 1H), 5.19 (t, J=9.4 Hz, 1H), 2.10-2.00 (m, 1H), 2.00-1.88 (m, 1H), 1.86-1.70 (m, 5H); MS ESI 438.0 [M+H]+, calcd for [C$_{17}$H$_{16}$IN$_3$OS+H]+ 438.0.

To a mixture of crude N-(cyclobutyl(thiophen-3-yl)methyl)-3-iodo-1H-indazole-5-carboxamide (262 mg, 0.6 mmol) and 1-methyl-4-(4-(4,4,5,5-tetramethyl-1,3,2-dioxaborolan-2-yl)phenoxy)piperidine (159 mg, 0.5 mmol) in EtOH (15 mL) was added 1 M aq Na$_2$CO$_3$ (1 mL, 1 mmol), followed by Pd(PPh$_3$)$_4$ (29 mg, 0.025 mmol). The resulting mixture was purged with Ar and microwaved 4 h at 125° C. After removal of solvents, it was purified by flash chromatography (MeOH/DCM 0-100%, then 0.05 NH$_3$ in MeOH/DCM 20%), PoraPak and prep-HPLC to give the title compound as a TFA salt (light yellow solid, 65.8 mg, 21%). $^1$H NMR (400 MHz, CD$_3$OD) δ 8.55 (s, 1H), 7.94-7.88 (m, 3H), 7.59 (d, J=8.8 Hz, 1H), 7.33 (dd, J=5.0 Hz, 3.0 Hz, 1H), 7.26 (d, J=3.2 Hz, 1H), 7.17-7.10 (m, 3H), 5.26 (d, J=6.4 Hz, 1H), 4.83-4.78 (m, 0.7H), 4.68-4.58 (m, 0.3H), 3.66-3.58 (m, 0.7H), 3.45-3.33 (m, 2.6H), 3.23-3.15 (m, 0.7H), 2.98-2.87 (m, 4H; s, 3H at 2.93), 2.45-1.80 (m, 10H); MS ESI 501.5 [M+H]+, calcd for [C$_{29}$H$_{32}$N$_4$O$_2$S+H]+ 501.2.

Example A122

N-(cyclopropyl(phenyl)methyl)-3-(4-((1-(2-fluoroethyl)piperidin-4-yl)oxy)phenyl)-1H-indazole-5-carboxamide

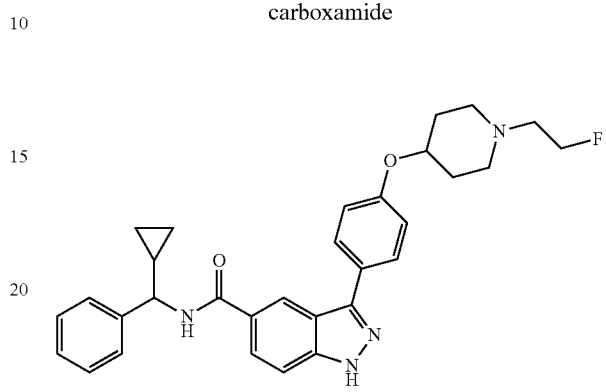

The title compound was synthesized according to General Method C3 utilizing N-(cyclopropyl(phenyl)methyl)-3-iodo-1H-indazole-5-carboxamide and 1-(2-fluoroethyl)-4-(4-(4,4,5,5-tetramethyl-1,3,2-dioxaborolan-2-yl)phenoxy)piperidine and obtained (white solid, 8 mg, 11% yield). $^1$H NMR (400 MHz, CD$_3$OD) δ ppm 8.61 (s, 1H), 7.96 (dd, J=8.8 Hz, 1.6 Hz, 1H), 7.91 (d, J=8.8 Hz, 2H), 7.60 (d, J=8.8 Hz, 1H), 7.49 (d, J=7.2 Hz, 2H), 7.34 (m, 2H), 7.24 (m, 1H), 7.12 (d, J=8.8 Hz, 2H), 4.66 (t, J=4.8 Hz, 1H), 4.54 (t, J=4.8 Hz, 1H), 4.48 (d, J=9.6 Hz, 1H), 2.87 (m, 2H), 2.80 (t, J=4.8 Hz, 1H), 2.73 (t, J=4.8 Hz, 1H), 2.51 (t, J=8.8 Hz, 1H), 2.08 (m, 2H), 1.87 (m, 2H), 1.41 (m, 2H), 0.66 (m, 2H), 0.47 (m, 2H); MS ESI [M+H]+ 513.4, calcd for [C$_{31}$H$_{33}$FN$_4$O$_2$+H]+ 513.27.

Example A123

N-(cyclobutyl(thiophen-3-yl)methyl)-3-(4-morpholinophenyl)-1H-indazole-5-carboxamide

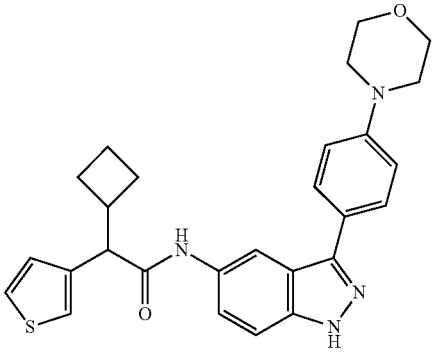 [SMILES: O=C(Nc1ccc2[nH]nc(-c3ccc(N4CCOCC4)cc3)c2c1)C(c1ccsc1)C1CCC1]

To a mixture of crude N-(cyclobutyl(thiophen-3-yl)methyl)-3-iodo-1H-indazole-5-carboxamide (262 mg, 0.6 mmol) and (4-morpholinophenyl)boronic acid (104 mg, 0.5 mmol) in EtOH (15 mL) was added 1 M aq Na$_2$CO$_3$ (1 mL, 1 mmol), followed by Pd(PPh$_3$)$_4$ (29 mg, 0.025 mmol). The resulting mixture was purged with Ar and microwaved 4 h at 125° C. It was diluted with H$_2$O, extracted with DCM and purified by flash chromatography (MeOH/DCM 0-20%), PoraPak, prep-HPLC, flash chromatography (EtOAc/hex 0-95%) and trituration with MeOH to give the title compound (white solid, 57.1 mg, 24%). $^1$H NMR (400 MHz, CDCl$_3$) δ 11.14 (s, 1H, NH), 8.49 (s, 1H), 7.87 (d, J=8.0 Hz, 2H), 7.74 (d, J=8.4 Hz, 1H), 7.36 (d, J=8.8 Hz, 1H), 7.17 (s, 1H), 7.09 (d, J=4.4 Hz, 1H), 7.01 (d, J=8.4 Hz, 2H), 6.40 (d, J=8.8 Hz, 1H), 5.40 (t, J=8.6 Hz, 1H), 3.89 (s, 4H), 3.22 (s, 4H), 2.91-2.80 (m, 1H), 2.20-1.75 (m, 8H); MS ESI 473.4 [M+H]$^+$, calcd for [C$_{27}$H$_{28}$N$_4$O$_2$S+H]$^+$ 473.2.

Example A124

1-(2,6-diethylphenyl)-3-(3-(4-(4-methylmorpholin-2-yl)phenyl)-1H-indazol-5-yl)urea

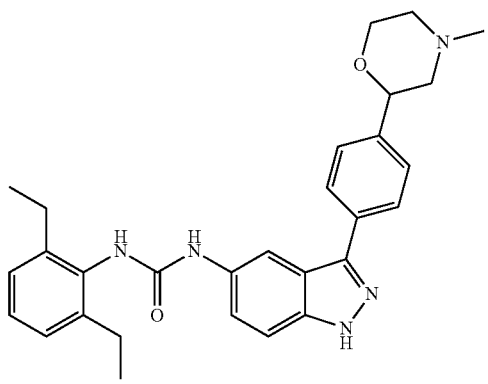 [SMILES: CCc1cccc(CC)c1NC(=O)Nc1ccc2[nH]nc(-c3ccc(C4CN(C)CCO4)cc3)c2c1]

A. 2-(4-bromophenyl)-4-tolylmorpholine

To an ice-cooled solution of 2-amino-1-(4-bromophenyl)ethanol (500 mg, 2.31 mmol) in NEt$_3$ (0.48 mL, 3.47 mmol) and CH$_2$Cl$_2$ (10 mL) was added tosyl chloride (440 mg, 2.31 mmol) and the reaction stirred for 18 h. The mixture was diluted with CH$_2$Cl$_2$ (100 mL), washed with brine (2×50 mL) and the organic layer dried over MgSO$_4$. The organic layer was filtered and the solvent removed to give the intermediate N-(2-(4-bromophenyl)-2-hydroxyethyl)-4-methylbenzenesulfonamide which was dissolved into CH$_2$Cl$_2$ (15 mL). The solution was cooled to 0° C., NaH (245 mg of 60% wt suspension) was added, the mixture stirred for 5 min and then (2-bromoethyl)diphenylsulfonium trifluoromethanesulfonate (931 mg, 2.10 mmol) was added and the reaction was allowed to warm to rt overnight. The reaction was then quenched with H$_2$O (2 mL) and extracted with CH$_2$Cl$_2$ (50 mL) and the organic layer washed with brine (1×25 mL). The solvent was removed and the residue titurated with 9:1 hexanes/Et$_2$O which gave after drying 613 mg, 88% of the product as a white solid. MS ESI 396.7 [M+H]$^+$, calcd for [C$_{17}$H$_{18}$BrNO$_3$S+H]$^+$ 396.03.

B. 2-(4-bromophenyl)-4-methylmorpholine 2-(4-Bromophenyl)-4-tolylmorpholine (509 mg, 1.28 mmol), phenol (242 mg, 2.57 mmol) were dissolved into HBr (33% wt solution in AcOH) and the mixture heated to 55° C. for 3 h. The reaction was cooled and the product precipitated with Et2O and filtered washing with Et2O to give the de-protected material which was then dissolved into THF (7.5 mL) and then formalin (0.24 mL, 3.26 mmol) followed by NaBH(OAc)$_3$ (752 mg, 3.55 mmol) were added and the mixture stirred for 18 h. The reaction was poured into a separatory funnel containing NaHCO$_3$ (50 mL) and then extracted with EtOAc (2×50 mL). The organic layers were separated and washed with brine (1×50 mL), dried over MgSO$_4$ and the solvent removed to give the 243 mg, 64% of the product as a brown oil. MS ESI 257.9 [M+H]$^+$, calcd for [C$_{11}$H$_{14}$BrNO+H]$^+$ 258.03.

C. 3-(4-(4-methylmorpholin-2-yl)phenyl)-1H-indazol-5-amine bis(2,2,2-trifluoroacetate)

The boronic ester was prepared from 2-(4-bromophenyl)-4-methylmorpholine using General Method F which was used directly in the Suzuki-Miyaura coupling. The same procedure was then followed as for 3-(4-((1-methylpiperidin-4-yl)oxy)phenyl)-1H-indazol-5-amine bis(2,2,2-trifluoroacetate) using tert-butyl (3-iodo-1H-indazol-5-yl)carbamate (112 mg, 0.312 mmol) and 4-methyl-2-(4-(4,4,5,5-tetramethyl-1,3,2-dioxaborolan-2-yl)phenyl)morpholine (123 mg, 0.406 mmol). Obtained 45 mg of an impure brown solid which was used for subsequent synthetic steps; MS ESI 309.1 [M+H]$^+$, calcd for [C$_{18}$H$_{20}$N$_4$O+H]$^+$ 309.17.

D. 1-(2,6-diethylphenyl)-3-(3-(4-(4-methylmorpholin-2-yl)phenyl)-1H-indazol-5-yl)urea Using General Method J, 3-(4-(4-methylmorpholin-2-yl)phenyl)-1H-indazol-5-amine bis(2,2,2-trifluoroacetate) (45 mg, 0.085 mmol), 1,3-diethyl-2-isocyanatobenzene (29 uL, 0.168 mmol) and DIPEA (73 uL, 0.42 mmol) in DMF (0.5 mL) gave the title compound as a TFA salt (23 mg, 56%, a white solid). $^1$H NMR (400 MHz, CD$_3$OD) δ ppm 8.29 (s, 1H), 7.97 (d, J=8.3 Hz, 2H), 7.56-7.51 (m, 3H), 7.31 (d, J=8.8 Hz, 1H), 7.21-7.16 (m, 3H), 4.78-4.75 (m, 1H), 4.34-4.30 (m, 1H), 4.00-3.94 (m, 1H), 3.70-3.67 (m, 1H), 3.56-3.52 (m, 1H), 3.31-3.28 (m, 1H), 3.17-3.13 (m, 1H), 2.97 (s, 3H), 2.70 (q, J=7.6 Hz, 4H), 1.23 (t, J=7.6 Hz, 6H); MS ESI 484.5 [M+H]$^+$, calcd for [C$_{29}$H$_{33}$N$_5$O$_2$+H]$^+$ 484.27.

Example A125

(S)-N-(3-hydroxy-1-phenylpropyl)-3-(4-((1-methylpiperidin-4-yl)oxy)phenyl)-1H-indazole-5-carboxyamide

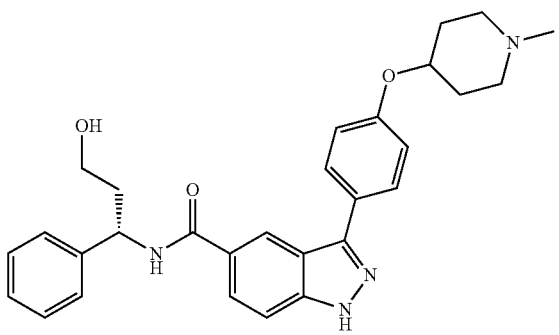 [SMILES: CN1CCC(Oc2ccc(-c3n[nH]c4ccc(C(=O)N[C@@H](CCO)c5ccccc5)cc34)cc2)CC1]

The title compound was synthesized according to the General Method C, utilizing (S)-N-(3-hydroxy-1-phenylpropyl)-3-iodo-1H-indazole-5-carboxamide (50 mg, 0.11 mmol), (4-((1-methylpiperidin-4-yl)oxy)phenyl)boronic acid pinacol ester (41 mg, 0.13 mmol), Pd(PPh$_3$)$_4$ (6.4 mg, 0.0055 mmol), satd. aq Na$_2$CO$_3$ (1.5 mL), and 3.5 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 20 mg, 30%). $^1$H NMR (400 MHz, CD$_3$OD) δ ppm 8.56 (s, 1 H), 7.87-7.97 (m, 3 H), 7.61 (d, J=8.5 Hz, 1 H), 7.44 (d, J=7.8 Hz, 2 H), 7.34 (t, J=7.5 Hz, 1 H), 7.12-7.27 (m, 3 H), 5.29-5.38 (m, 1 H), 4.62-4.73 (m, 0.3 H), 3.58-3.73 (m, 2.7 H), 3.34-3.49 (m, 3 H), 3.15-3.27 (m, 1 H), 2.94 (s, 3 H), 2.39-2.50 (m, 0.7 H), 2.25-2.35 (m, 1.3 H), 2.05-2.22 (m, 3.3 H), 1.83-1.98 (m, 0.7 H); MS ESI 485.4 [M+H]+, calcd for [$C_{29}H_{32}N_4O_3$+H]+ 485.3.

Example A126

N-(cyclopropyl(phenyl)methyl)-3-(4-((1-formylpiperidin-4-yl)oxy)phenyl)-1H-indazole-5-carboxamide

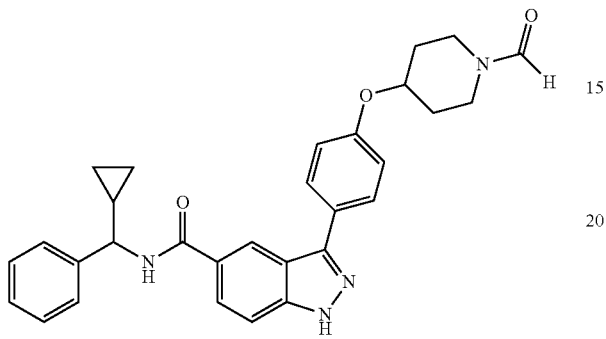

The title compound was synthesized according to General Method C3 utilizing N-(cyclopropyl(phenyl)methyl)-3-iodo-1H-indazole-5-carboxamide and 4-(4-(4,4,5,5-tetramethyl-1,3,2-dioxaborolan-2-yl)phenoxy)piperidine-1-carbaldehyde and obtained as a yellow solid (14 mg, 27% yield). $^1$H NMR (400 MHz, CD$_3$OD) δ ppm 8.61 (s, 1 H), 8.03 (s, 1 H), 7.89-7.98 (m, 3 H), 7.59 (d, J=8.78 Hz, 1 H), 7.48 (d, J=7.28 Hz, 2 H), 7.32 (t, J=7.53 Hz, 2 H), 7.23 (m, J=7.53 Hz, 1 H), 7.12 (d, J=8.78 Hz, 2 H), 4.69-4.77 (m, 1 H), 4.45-4.51 (m, 1 H), 3.62-3.79 (m, 2 H), 3.49-3.58 (m, 1 H), 3.37-3.46 (m, 1 H), 1.91-2.08 (m, 2 H), 1.72-1.91 (m, 2 H), 1.34-1.46 (m, 1 H), 0.65 (d, J=8.28 Hz, 2 H), 0.41-0.53 (m, 2 H); MS ESI [M+H]+ 495.3, calcd for [$C_{30}H_{30}N_4O_3$+H]+ 495.24.

Example A127

N-(1-(2-methylbenzyl)cyclopropyl)-3-(4-((1-methylpiperidin-4-yl)oxy)phenyl)-1H-indazole-5-carboxamide

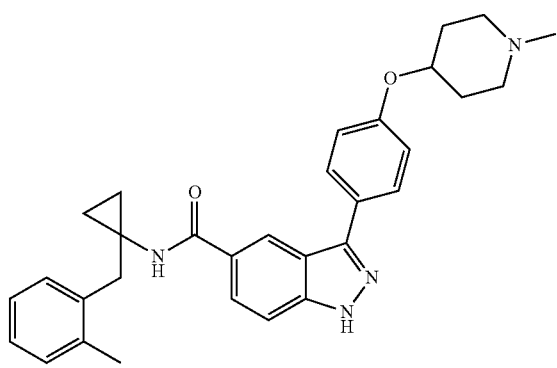 [SMILES: Cc1ccccc1CC1(NC(=O)c2ccc3[nH]nc(-c4ccc(OC5CCN(C)CC5)cc4)c3c2)CC1]

The title compound was synthesized according to the General Method C, utilizing 3-iodo-N-(1-(2-methylbenzyl)cyclopropyl)-1H-indazole-5-carboxamide (50 mg, 0.12 mmol), (4-((1-methylpiperidin-4-yl)oxy)phenyl)boronic acid pinacol ester (37 mg, 0.12 mmol), Pd(PPh$_3$)$_4$ (7 mg, 0.0058 mmol), satd. aq Na$_2$CO$_3$ (1.5 mL), and 3.5 mL of PhMe:EtOH (1:1). The vial was charged with Ar and heated in the microwave reactor at 125° C. for 2 h. Purification by RPHPLC gave the title compound as a TFA salt (white solid, 19 mg, 26%). $^1$H NMR (400 MHz, CD$_3$OD) δ ppm 8.36 (s, 1 H), 7.86-7.95 (m, 2 H), 7.78 (dd, J=8.8, 1.2 Hz, 1 H), 7.52-7.58 (m, 1 H), 7.05-7.27 (m, 6 H), 4.65-4.74 (m, 0.3 H), 3.61-3.70 (m, 0.7 H), 3.34-3.49 (m, 2.7 H), 3.18-3.27 (m, 1.3 H), 3.16 (s, 2 H), 2.92-2.98 (s, 3 H), 2.41-2.52 (m, 0.7 H), 2.27-2.38 (m, 4.3 H), 2.06-2.18 (m, 1.3 H), 1.86-1.99 (m, 0.7 H), 0.85 (m, J=4.0 Hz, 4 H); MS ESI 495.3 [M+H]+, calcd for [$C_{31}H_{34}N_4O_2$+H]+ 495.3.

Example A128

(R)-N-(1-(2-chlorophenyl)propyl)-3-(4-((1-(2-methoxyethyl)piperidin-4-yl)oxy)phenyl)-1H-indazole-5-carboxamide

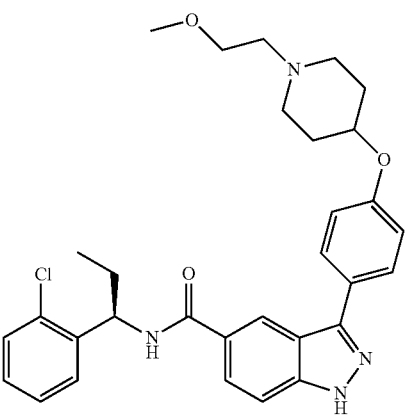 [SMILES: CC[C@@H](NC(=O)c1ccc2[nH]nc(-c3ccc(OC4CCN(CCOC)CC4)cc3)c2c1)c1ccccc1Cl]

Using General Method C3, (R)-N-(1-(2-chlorophenyl)propyl)-3-iodo-1H-indazole-5-carboxamide (66 mg, 0.150 mmol) and 1-(2-methoxyethyl)-4-(4-(4,4,5,5-tetramethyl-1,3,2-dioxaborolan-2-yl)phenoxy)piperidine (69 mg, 0.190 mmol) gave the title compound as a TFA salt (10 mg, 12%, a pale-yellow solid). $^1$H NMR (400 MHz, CD$_3$OD) δ ppm 8.88 (bs, 1H), 8.57 (s, 1H), 7.96-7.93 (m, 3H), 7.62 (d, J=8.0 Hz, 1H), 7.49 (d, J=6.0 Hz, 1H), 7.42-7.16 (m, 4H), 5.47-5.45 (m, 1H), 4.87 (bs, 1H), 3.76-3.70 (m, 3H), 3.54-3.30 (m, 9H), 2.44-2.29 (m, 2H), 2.18-1.90 (m, 4H), 1.05 (t, J=7.5 Hz, 3H); MS ESI 547.7 [M+H]+, calcd for [$C_{31}H_{35}ClN_4O_3$+H]+ 547.25.

Example A129

(R)-N-(1-(2-fluorophenyl)ethyl)-3-(4-((1-(2-methoxyethyl)piperidin-4-yl)oxy)phenyl)-1H-indazole-5-carboxamide

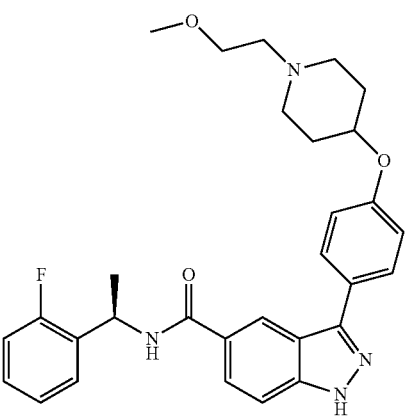 [SMILES: COCCN1CCC(Oc2ccc(-c3n[nH]c4ccc(C(=O)N[C@H](C)c5ccccc5F)cc34)cc2)CC1]

Using General Method C3, (R)-N-(1-(2-fluorophenyl)ethyl)-3-iodo-1H-indazole-5-carboxamide (61 mg, 0.150 mmol) and 1-(2-methoxyethyl)-4-(4-(4,4,5,5-tetramethyl-1,3,2-dioxaborolan-2-yl)phenoxy)piperidine (69 mg, 0.190 mmol) gave the title compound as a TFA salt (24 mg, 31% a white solid). $^1$H NMR (400 MHz, CD$_3$OD) δ ppm 8.57 (s, 1H), 7.97-7.93 (m, 3H), 7.61 (d, J=8.8 Hz, 1H), 7.47-7.43 (m, 1H), 7.29-7.06 (m, 5H), 5.55-5.50 (m, 1H), 4.87 (bs, 1H), 3.77-3.70 (m, 3H), 3.54-3.22 (m, 8H), 2.45-2.28 (m, 2H), 2.17-1.97 (m, 2H), 1.60 (d, J=7.2 Hz, 3H); MS ESI 517.4 [M+H]$^+$, calcd for [C$_{30}$H$_{33}$FN$_4$O$_3$+H]$^+$ 517.26.

Example A130

N-(cyclopropyl(phenyl)methyl)-3-(4-((1-(2-(dimethylamino)acetyl)piperidin-4-yl)oxy)phenyl)-1H-indazole-5-carboxamide

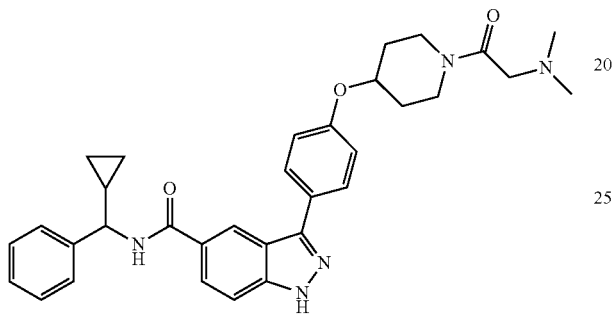

The title compound was synthesized according to General Method C3 utilizing N-cyclopropyl(phenyl)methyl)-3-iodo-1H-indazole-5-carboxamide and 2-(dimethylamino)-1-(4-(4-(4,4,5,5-tetramethyl-1,3,2-dioxaborolan-2-yl)phenoxy)piperidin-1-yl)ethanone and obtained as a pale yellow solid (66 mg, 56% yield). $^1$H NMR (400 MHz, CD$_3$OD) δ ppm 8.60 (s, 1 H), 7.95 (m, J=8.5 Hz, 3 H), 7.61 (d, J=8.8 Hz, 1 H), 7.50 (d, J=7.0 Hz, 2 H), 7.35 (t, J=7.6 Hz, 2 H), 7.25 (m, J=7.3 Hz, 1 H), 7.16 (d, J=8.8 Hz, 2 H), 4.73-4.80 (m, 1 H), 4.49 (d, J=9.5 Hz, 1 H), 3.74-3.92 (m, 2 H), 3.67 (s, 3 H), 3.47-3.55 (m, 1 H), 2.58 (s, 6 H), 1.96-2.14 (m, 2 H), 1.76-1.93 (m, 2 H), 1.37-1.47 (m, 1 H), 0.64-0.70 (m, 2 H), 0.44-0.53 (m, 2 H); MS ESI [M+H]$^+$ 552.5, calcd for [C$_{33}$H$_{37}$N$_5$O$_3$+H]$^+$ 552.30.

Example A131

(R)-N-(1-(2-chlorophenyl)propyl)-3-(4-((1-methylpiperidin-4-yl)oxy)phenyl)-1H-indazole-5-carboxamide

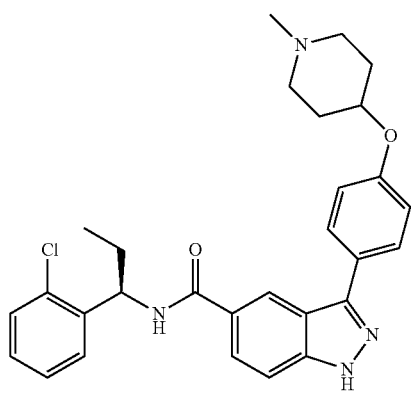 [SMILES: CC[C@@H](NC(=O)c1ccc2[nH]nc(-c3ccc(OC4CCN(C)CC4)cc3)c2c1)c1ccccc1Cl]

The title compound was prepared using General Method C3 from (R)-N-(1-(2-chlorophenyl)propyl)-3-iodo-1H-indazole-5-carboxamide (58 mg, 0.132 mmol) and 1-methyl-4-(4-(4,4,5,5-tetramethyl-1,3,2-dioxaborolan-2-yl)phenoxy)piperidine (55 mg, 0.172 mmol) which gave 39 mg of product isolated as its TFA salt (59%, orange solid). $^1$H NMR (400 MHz, CD$_3$OD) δ ppm 8.57 (s, 1H), 7.95-7.91 (m, 3H), 7.61 (d, J=8.8 Hz, 1H), 7.55 (d, J=7.0 Hz, 1H), 7.39 (d, J=8.0 Hz, 1H), 7.30-7.14 (m, 4H), 5.47-5.43 (m, 1H), 4.87 (bs, 1H), 3.65-3.17 (m, 4H), 2.93-2.92 (m, 3H), 2.44-2.27 (m, 2H), 2.15-1.86 (m, 4H), 1.07 (t, J=7.2 Hz, 3H); MS ESI 503.5 [M+H]$^+$, calcd for [C$_{29}$H$_{31}$ClN$_4$O$_2$+H]$^+$ 503.22.

Example A132

N-(cyclopropyl(o-tolyl)methyl)-3-(4-((1-methylpiperidin-4-yl)oxy)phenyl)-1H-indazole-5-carboxamide

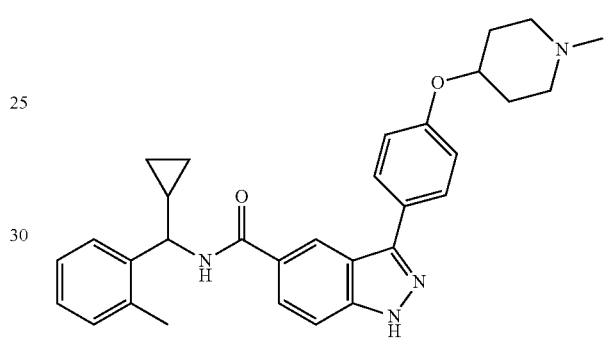

To a solution of cyclopropyl(o-tolyl)methanamine (2.82 g, 17.5 mmol), 3-iodo-1H-indazole-5-carboxamide (5.04 g, 17.5 mmol) in DMF (20 mL) at 0° C. was added TBTU (5.62 g, 17.5 mmol), followed by iPr$_2$NEt (6.08 mL, 35 mmol). The resulting mixture was stirred at 0° C. for 30 min, quenched with H$_2$O till total volume about 250 mL and stirred for 30 min at rt. Suction filtration gave crude N-(cyclopropyl(o-tolyl)methyl)-3-iodo-1H-indazole-5-carboxamide (beige solid, 7.53 g). MS ESI 432.1 [M+H]$^+$, calcd for [C$_{19}$H$_{18}$IN$_3$O+H]$^+$ 432.0.

To a mixture of crude N-(cyclopropyl(o-tolyl)methyl)-3-iodo-1H-indazole-5-carboxamide (190 mg, 0.44 mmol) and 1-methyl-4-(4-(4,4,5,5-tetramethyl-1,3,2-dioxaborolan-2-yl)phenoxy)piperidine (127 mg, 0.4 mmol) in EtOH (12 mL) was added 1 M aq Na$_2$CO$_3$ (0.8 mL, 0.8 mmol), followed by Pd(dppf)Cl$_2$—CH$_2$Cl$_2$ (33 mg, 0.04 mmol). The resulting mixture was purged with Ar and microwaved 4 h at 125° C. It was diluted with H$_2$O, extracted with DCM and purified by flash chromatography (MeOH/DCM 0-100%, then 0.05 NH$_3$ in MeOH), Biotage RP column (MeOH/H$_2$O (1% TFA) 5-80%) and prep-HPLC to give the title compound as a TFA salt (white solid, 24.0 mg, 10%). $^1$H NMR (400 MHz, CD$_3$OD) δ 8.54 (s, 1H), 7.98-7.90 (m, 3H), 7.61 (d, J=7.6 Hz, 1H; partially overlapped with the peak at 7.59), 7.59 (d, J=8.8 Hz, 1H; partially overlapped with the peak at 7.61), 7.22-7.12 (m, 5H), 4.90 (1H, buried under H$_2$O peak), 4.88-4.85 (m, 0.7H; partially buried under H$_2$O peak), 4.71-4.62 (m, 0.3H), 3.67-3.62 (m, 0.7H), 3.47-3.34 (m, 2.6H), 3.25-3.17 (m, 0.7H), 2.95-2.94 (two s at 2.95 and 2.94, 3H), 2.47-2.38 (m, 3.7H; s, 3H at 2.42), 2.33-2.26 (m, 1.3H), 2.17-2.07 (m, 1.3H), 1.98-1.86 (0.7H), 1.52-1.42 (m, 1H), 0.71-0.64 (m, 1H), 0.63-0.56 (m, 1H), 0.55-0.46 (m, 1H), 0.40-0.33 (m, 1H); MS ESI 495.4 [M+H]$^+$, calcd for [C$_{31}$H$_{34}$N$_4$O$_2$+H]$^+$ 495.4.

Example A133

N-(3-(4-((1-methylpiperidin-4-yl)oxy)phenyl)-1H-indazol-5-yl)-2-(pyrrolidin-1-yl)-2-(o-tolyl)acetamide

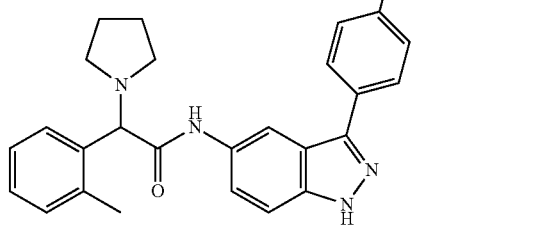

To a solution of 2-(pyrrolidin-1-yl)-2-(o-tolyl)acetic acid (3.00 g, assuming 10 mmol), 3-iodo-1H-indazol-5-amine hydrochloride salt (2.94 g, 10 mmol) in DMF (40 mL) at 0° C. was added TBTU (3.21 g, 10 mmol), followed by iPr$_2$NEt (5.22 mL, 30 mmol). The resulting mixture was stirred at 0° C. for 2 h, quenched with H$_2$O (300 mL) and stirred for 30 min at rt. Suction filtration gave crude N-(3-iodo-1H-indazol-5-yl)-2-(pyrrolidin-1-yl)-2-(o-tolyl)acetamide (brown solid, 3.19 g). LC-MS indicated a mixture of desired product N-(3-iodo-1H-indazol-5-yl)-2-(pyrrolidin-1-yl)-2-(o-tolyl)acetamide and di-acylated byproduct. MS ESI 461.1 [M+H]$^+$, calcd for [C$_{20}$H$_{21}$IN$_4$O+H]$^+$ 461.1.

To a mixture of crude N-(3-iodo-1H-indazol-5-yl)-2-(pyrrolidin-1-yl)-2-(o-tolyl)acetamide (213 mg, assuming 0.4 mmol) and 1-methyl-4-(4-(4,4,5,5-tetramethyl-1,3,2-dioxaborolan-2-yl)phenoxy)piperidine (127 mg, 0.4 mmol) in EtOH (12 mL) was added 1 M aq Na$_2$CO$_3$ (1.0 mL, 1.0 mmol), followed by Pd(dppf)Cl$_2$—CH$_2$Cl$_2$ (33 mg, 0.04 mmol). The resulting mixture was purged with Ar and microwaved 4 h at 125° C. It was diluted with H$_2$O, extracted with DCM and purified by flash chromatography (MeOH/DCM 0-100%, then 0.05 NH$_3$ in MeOH), Biotage RP column (MeOH/H$_2$O (1% TFA) 5-60%) and prep-HPLC to give the title compound as a TFA salt (light brown solid, 56 mg, 19%). $^1$H NMR (400 MHz, CD$_3$OD) δ 8.23 (s, 1H), 7.88-7.83 (m, 2H), 7.76 (d, J=7.6 Hz, 1H), 7.54 (t, J=9.0 Hz, 2H), 7.43-7.34 (m, 3H), 7.20-7.13 (m, 2H), 5.45 (s, 1H), 4.90-4.85 (m, 0.7H), 4.72-4.64 (m, 0.3H), 3.92 (br s, 0.7H), 3.58-3.52 (m, 0.7H), 3.50-2.98 (m, 6.4H), 2.95-2.94 (two s at 2.95 and 2.94, 3H), 2.67 (s, 3H), 2.47-1.88 (m, 8H); MS ESI 524.2 [M+H]$^+$, calcd for [C$_{32}$H$_{37}$N$_5$O$_2$+H]$^+$ 524.3.

Example A134

(R)-N-(1-(2-fluorophenyl)ethyl)-3-(4-((1-methylpiperidin-4-yl)oxy)phenyl)-1H-indazole-5-carboxamide

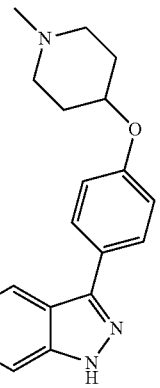

The title compound was prepared using General Method C3 from (R)-N-(1-(2-fluorophenyl)ethyl)-3-iodo-1H-indazole-5-carboxamide (47 mg, 0.115 mmol) and 1-methyl-4-(4-(4,4,5,5-tetramethyl-1,3,2-dioxaborolan-2-yl)phenoxy)piperidine (48 mg, 0.150 mmol) which gave 23 mg of product isolated as its TFA salt (43%, white solid). $^1$H NMR (400 MHz, CD$_3$OD) δ ppm 8.57 (s, 1H), 7.97-7.93 (m, 3H), 7.61 (d, J=8.8 Hz, 1H), 7.47-7.43 (m, 1H), 7.28-7.07 (m, 5H), 5.55-5.50 (m, 1H), 4.87 (bs, 1H), 3.66-3.20 (m, 4H), 2.95-2.94 (m, 3H), 2.48-2.30 (m, 2H), 2.15-1.89 (m, 2H), 1.60 (d, J=6.8 Hz, 3H); MS ESI 473.4 [M+H]$^+$, calcd for [C$_{28}$H$_{29}$FN$_4$O$_2$+H]$^+$ 473.24.

Example A135

(R)-N-(3-(4-(((3S,4R)-3-fluoro-1-methylpiperidin-4-yl)oxy)phenyl)-1H-indazol-5-yl)-2-methoxy-2-phenylacetamide

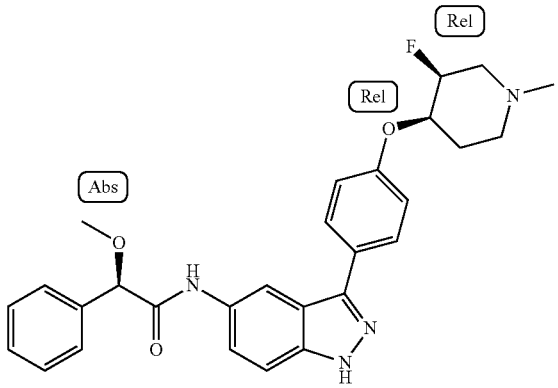

The title compound was synthesized according to the General Method C2 utilizing ((R)-N-(3-iodo-1H-indazol-5-yl)-2-methoxy-2-phenylacetamide (0.14 g, 0.34 mmol), a crude mixture of (4-((3-fluoro-1-methylpiperidin-4-yl)oxy)phenyl)boronic acid and diisopropyl (4-((cis-3-fluoro-1-methylpiperidin-4-yl)oxy)phenyl)boronate diisopropyl (0.16 g, ~0.48 mmol) to provide the title compound as a white powder (22 mg, 13%). $^1$H NMR (400 MHz, acetone-d$_6$) δ ppm 11.82-12.49 (br.s., 1 H), 9.43 (br. s., 1 H), 8.63 (d, J=1.51 Hz, 1 H), 7.94 (d, J=9.03 Hz, 2 H), 7.74 (dd, J=8.9, 1.9 Hz, 1 H), 7.51-7.59 (m, 3 H), 7.30-7.44 (m, 3 H), 7.16 (d, J=9.0 Hz, 2 H), 4.91-4.98 (m, 0.5 H), 4.85 (s, 1 H), 4.80-4.83 (m, 0.5 H), 4.69 (br. s., 1 H), 3.47 (s, 3 H), 2.94 (br. s., 1 H), 2.46-2.74 (m, 2 H), 2.40-2.31 (m., 1 H), 2.29 (s, 3 H), 1.99-2.18 (m, 1 H), 1.84-1.99 (m, 1 H); MS ESI 489.3 [M+H]$^+$, calcd for [C$_{28}$H$_{29}$FN$_4$O$_3$+H]$^+$ 489.2.

Example A136

N-(cyclopropyl(2-fluorophenyl)methyl)-3-(4-((1-methylpiperidin-4-yl)oxy)phenyl)-1H-indazole-5-carboxamide

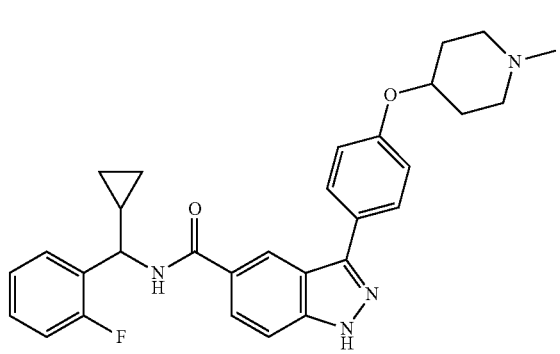 [SMILES: Cc1ccccc1C(NC(=O)c1ccc2[nH]nc(-c3ccc(OC4CCN(C)CC4)cc3)c2c1)C1CC1]

To a 20 mL microwave vial charged with Mg powder (480 mg, 20 mmol), THF (15 mL) was added bromocyclopropane (2.42 g, 20 mmol). The resulting mixture was stirred for 30 min at rt before 2-fluorobenzonitrile (1.21 g, 10 mmol) was added. It was microwaved 20 min at 100° C., cooled to rt and added dropwise to a cold solution of NaBH$_4$ (760 mg, 20 mmol) in MeOH (60 mL) at 0° C. The resulting mixture was stirred for 30 min at rt, quenched with H$_2$O, extracted with DCM and purified by flash chromatography (MeOH/DCM 0-20%) to give cyclopropyl(2-fluorophenyl)methanamine (yellow oil, 843 mg, 51%). $^1$H NMR (400 MHz, CDCl$_3$) δ 7.52 (dt, J=7.4 Hz, 1H), 7.31-7.24 (m, 1H), 7.18 (t, J=7.6 Hz, 1H), 7.10-7.04 (m, 1H), 3.45 (d, J=9.2 Hz, 1H), 1.25-1.16 (m, 1H), 0.67-0.60 (m, 1H), 0.49-0.37 (m, 2H), 0.29-0.22 (m, 1H); MS ESI 149.0 [M+H]$^+$, calcd for [C$_{10}$H$_{12}$FN–NH$_3$+H]$^+$ 149.1.

To a solution of cyclopropyl(2-fluorophenyl)methanamine (828 mg, 5.02 mmol), 3-iodo-1H-indazole-5-carboxamide (1.45 g, 5.02 mmol) in DMF (20 mL) at 0° C. was added TBTU (1.62 g, 5.02 mmol), followed by $^i$Pr$_2$NEt (1.75 mL, 10.05 mmol). The resulting mixture was stirred at 0° C. for 30 min, quenched with H$_2$O to a total volume of about 130 mL and stirred for 15 min at rt. Suction filtration gave crude N-(cyclopropyl(2-fluorophenyl)methyl)-3-iodo-1H-indazole-5-carboxamide (pale yellow solid, 2.068 g). ESI 436.1 [M+H]$^+$, calcd for [C$_{18}$H$_{15}$FIN$_3$O+H]$^+$ 436.0.

To a mixture of crude N-(cyclopropyl(2-fluorophenyl)methyl)-3-iodo-1H-indazole-5-carboxamide (218 mg, 0.5 mmol) and 1-methyl-4-(4-(4,4,5,5-tetramethyl-1,3,2-dioxaborolan-2-yl)phenoxy)piperidine (127 mg, 0.4 mmol) in EtOH (12 mL) was added 1 M aq Na$_2$CO$_3$ (0.8 mL, 0.8 mmol), followed by Pd(PPh$_3$)$_4$ (46 mg, 0.04 mmol). The resulting mixture was purged with Ar and microwaved 4 h at 125° C. After removal of solvents, it was purified by prep-HPLC to give the title compound as a TFA salt (off white solid, 69.4 mg, 28%). $^1$H NMR (400 MHz, CD$_3$OD) δ 8.56 (s, 1H), 7.96-7.88 (m, 3H), 7.61-7.53 (m, 2H), 7.28-7.22 (m, 1H), 7.16-7.04 (m, 4H), 4.81-4.78 (m, 0.7H; partially overlapped with the peak at 4.76), 4.76 (d, J=9.6 Hz, 1H; partially overlapped with the peak at 4.81-4.78), 4.66-4.58 (m, 0.3H), 3.65-3.58 (m, 0.7H), 3.43-3.28 (m, 2.6H), 3.22-3.13 (m, 0.7H), 2.91 (s, 3H), 2.41-2.35 (m, 0.7H), 2.27-2.20 (m, 1.3H), 2.15-2.05 (m, 1.3H), 1.96-1.85 (m, 0.7H), 1.48-1.38 (m, 1H), 1.22-1.13 (m, 1H), 1.10-1.03 (m, 1H), 1.02-0.90 (m, 2H); MS ESI 499.4 [M+H]$^+$, calcd for [C$_{30}$H$_{31}$FN$_4$O$_2$+H]$^+$ 499.2.

Example A137

(R)-N-(3-hydroxy-1-phenylpropyl)-3-(4-((1-methylpiperidin-4-yl)oxy)phenyl)-1H-indazole-5-carboxamide

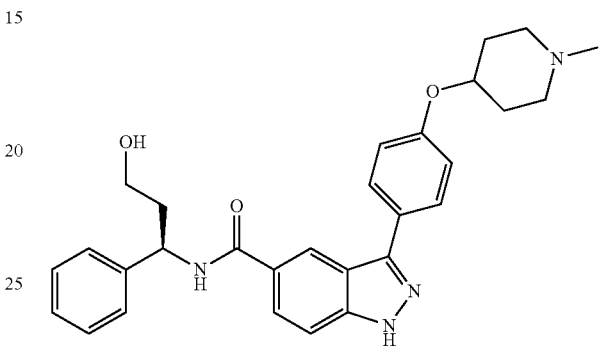

The title compound was synthesized according to the General Method C, utilizing (R)-N-(3-hydroxy-1-phenylpropyl)-3-iodo-1H-indazole-5-carboxamide (50 mg, 0.11 mmol), (4-((1-methylpiperidin-4-yl)oxy)phenyl)boronic acid pinacol ester (41 mg, 0.13 mmol), Pd(PPh$_3$)$_4$ (6.4 mg, 0.0055 mmol), satd. aq Na$_2$CO$_3$ (1.5 mL), and 3.5 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 23 mg, 35%). $^1$H NMR (400 MHz, CD$_3$OD) δ ppm 8.56 (s, 1 H), 7.89-7.97 (m, 3 H), 7.61 (d, J=9.0 Hz, 1 H), 7.44 (d, J=7.0 Hz, 2 H), 7.34 (t, J=7.6 Hz, 2 H), 7.13-7.27 (m, 3 H), 5.29-5.38 (m, 1 H), 4.63-4.73 (m, 0.3 H), 3.59-3.75 (m, 2.7 H), 3.33-3.52 (m, 3 H), 3.15-3.27 (m, 1 H), 2.91-2.97 (m, 3 H), 2.40-2.49 (m, 0.7 H), 2.26-2.36 (m, 1.3 H), 2.05-2.21 (m, 3.3 H), 1.85-1.98 (m, 0.7 H); MS ESI 485.4 [M+H]$^+$, calcd for [C$_{29}$H$_{32}$N$_4$O$_3$+H]$^+$ 485.3.

Example A138

2-cyclopropyl-N-(3-(4-((1-methylpiperidin-4-yl)oxy)phenyl)-1H-indazol-5-yl)-2-phenylacetamide

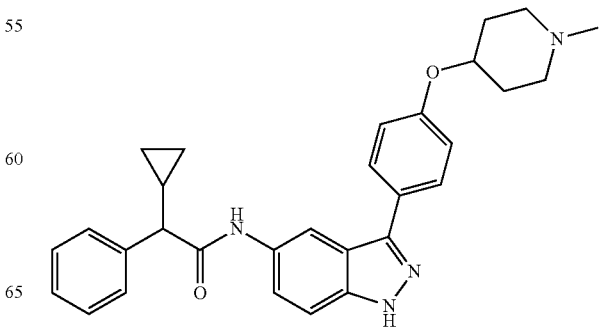

To a solution of 2-cyclopropyl-2-phenylacetic acid (20 mg, 0.113 mmol) in DMF (2 mL) was added 3-(4-((1-methylpiperidin-4-yl)oxy)phenyl)-1H-indazol-5-amine trifluoroacetate (62.5 mg, 0.113 mmol), DIPEA (102 uL, 0.565 mmol) and TBTU (36 mg, 0.113 mmol). The reaction mass was stirred for 24 h at rt and concentrated under reduced pressure. Purification by flash chromatography (SiO$_2$, 0-40% 2 M NH$_3$-MeOH in DCM; then RP HPLC C$_{18}$RP 60 g, 10-80% MeOH in 0.1% TFA-H$_2$O) followed by passing through a PoraPak column with 2 M NH$_3$-MeOH to elute gave the title compound (white solid, 29 mg, 51%). $^1$H NMR (400 MHz, CD$_3$OD) δ 8.45 (d, J=1.2 Hz, 1H), 7.88-7.84 (m, 2H), 7.52-7.48 (m, 3H), 7.43-7.42 (m, 1H), 7.41-7.40 (m, 2H), 7.36-7.32 (m, 1H), 7.17-7.10 (m, 2H), 4.83 (s, 1H), 3.64 (m, 1H), 3.42-3.37 (m, 3H), 3.21-3.19 (br.m, 1H), 2.93-2.90 (m, 3H), 2.43-2.26 (m, 2H), 2.14-2.10 (m, 2H), 1.60-1.57 (br.m, 1H), 0.71-0.61 (m, 2H), 0.48-0.44 (m, 1H), 0.27-0.23 (m, 1H); MS ESI 481.4. [M+H]$^+$, calcd for [C$_{30}$H$_{32}$N$_4$O$_2$+H]$^+$ 481.6.

Example A139

N-(cyclopropyl(phenyl)methyl)-3-(4-(4-methylmorpholin-2-yl)phenyl)-1H-indazole-5-carboxamide

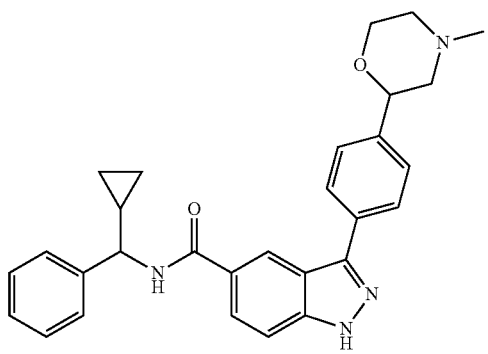 [SMILES: CN1CCOC(c2ccc(-c3n[nH]c4ccc(C(=O)NC(c5ccccc5)C5CC5)cc34)cc2)C1]

The title compound was prepared using General Method C3 from N-(cyclopropyl(phenyl)methyl)-3-iodo-1H-indazole-5-carboxamide (65 mg, 0.155 mmol) and 4-methyl-2-(4-(4,4,5,5-tetramethyl-1,3,2-dioxaborolan-2-yl)phenyl)morpholine (61 mg, 0.201 mmol) which gave 36 mg of product isolated as its TFA salt (50%, a white solid). $^1$H NMR (400 MHz, CD$_3$OD) δ ppm 8.61 (s, 1H), 8.06 (d, J=8.3 Hz, 2H), 7.97 (d, J=8.8 Hz, 1H), 7.64-7.59 (m, 3H), 7.48 (d, J=7.5 Hz, 2H), 7.36-7.22 (m, 3H), 4.89 (bs, 1H), 4.49 (d, J=9.6 Hz, 1H), 4.34-4.31 (m, 1H), 4.03-3.98 (m, 1H), 3.72-3.69 (m, 1H), 3.57-3.54 (m, 1H), 3.31-3.13 (m, 2H), 2.98 (s, 3H), 1.44-1.34 (m, 1H), 0.71-0.64 (m, 2H), 0.52-0.48 (m, 2H); MS ESI 467.4 [M+H]$^+$, calcd for [C$_{29}$H$_{30}$N$_4$O$_2$+H]$^+$ 467.24.

Example A140

N-(cyclopropyl(phenyl)methyl)-3-(4-(2-morpholinoethoxy)phenyl)-1H-indazole-5-carboxamide

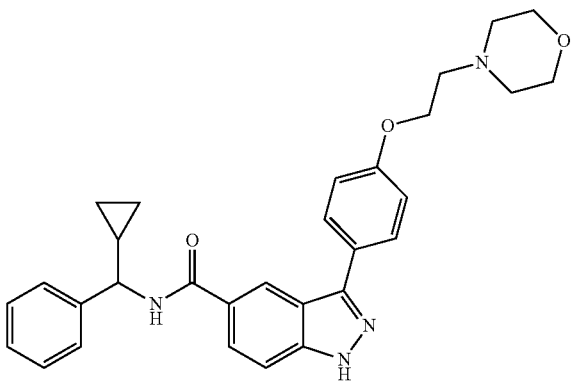 [SMILES: O=C(NC(c1ccccc1)C1CC1)c1ccc2[nH]nc(-c3ccc(OCCN4CCOCC4)cc3)c2c1]

A TFA salt of the title compound was synthesized according to General Method C3 utilizing N-(cyclopropyl(phenyl)methyl)-3-iodo-1H-indazole-5-carboxamide and 4-(2-(4-(4,4,5,5-tetramethyl-1,3,2-dioxaborolan-2-yl)phenoxy)ethyl)morpholine without running through PoraPak and obtained as a white solid (56 mg, 77% yield). NMR (400 MHz, CD$_3$OD) δ ppm 8.59 (s, 1H), 7.96 (d, J=8.78 Hz, 3H), 7.61 (d, J=8.78 Hz, 1H), 7.49 (d, J=7.28 Hz, 2H), 7.33 (t, J=7.53 Hz, 2H), 7.21-7.28 (m, 1H), 7.17 (d, J=8.78 Hz, 2H), 4.40-4.53 (m, 3H), 3.96-4.15 (m, 2H), 3.86 (br. s., 2H), 3.51-3.71 (m, 4H), 3.32 (br. s, 2H), 1.34-1.47 (m, 1H), 0.66 (d, J=8.03 Hz, 2H), 0.42-0.53 (m, 2H); MS ESI [M+H]$^+$ 497.4, calcd for [C$_{30}$H$_{32}$N$_4$O$_3$+H]$^+$ 497.26.

Example A141

N-(cyclopropyl(o-tolyl)methyl)-3-(4-(3-hydroxyazetidin-1-yl)phenyl)-1H-indazole-5-carboxamide

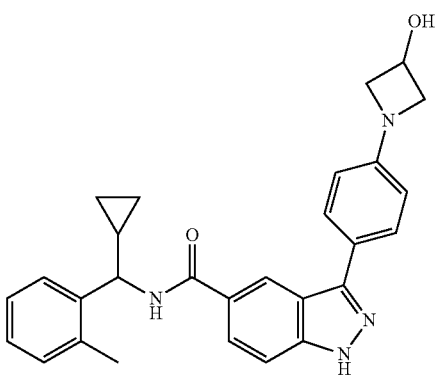 [SMILES: Cc1ccccc1C(NC(=O)c1ccc2[nH]nc(-c3ccc(N4CC(O)C4)cc3)c2c1)C1CC1]

The title compound was synthesized according to General Method C, utilizing N-(cyclopropyl(o-tolyl)methyl)-3-iodo- 1H-indazole-5-carboxamide (142 mg, 0.33 mmol), 1-(4-(4, 4,5,5-tetramethyl-1,3,2-dioxaborolan-2-yl)phenyl)azetidin-3-ol (100 mg, 0.36 mmol), Pd(PPh$_3$)$_4$ (38 mg, 0.033 mmol), 2 M aq Na$_2$CO$_3$ (0.40 mL), PhMe (4 mL), and EtOH (2 mL). H$_2$O (30 mL) was added and the product was extracted into EtOAc (4×30 mL). The combined organic layers were dried over MgSO$_4$, filtered and evaporated in vacuo. Purification by flash chromatography (Biotage, 50 g HP-SIL, 20-100% EtOAc in hexanes) followed by RP flash chromatography (Biotage, 60 g RP HPLC C18-, 0.1% TFA-H$_2$O in MeOH, 10-90%) gave the title compound as a yellow solid (44 mg, 23%). The title compound was isolated as a TFA salt. $^1$H NMR (400 MHz, CD$_3$OD) δ ppm 8.54 (s, 1 H), 7.90 (dd, J=8.8, 1.5 Hz, 1 H), 7.86 (d, J=8.5 Hz, 2 H), 7.61 (d, J=7.6 Hz, 1 H), 7.56 (d, J=8.8 Hz, 1 H), 7.21-7.13 (m, 3 H), 6.78 (d, J=8.5 Hz, 2 H), 4.89-4.84 (m, 1 H), 4.72 (quint, J=5.4 Hz, 1 H), 4.30 (t, J=7.9 Hz, 2 H), 7.79 (dd, J=8.7, 5.0 Hz, 2 H), 2.41 (s, 3 H), 1.48-1.41 (br m, 1 H), 0.69-0.63 (br m, 1 H), 0.61-0.54 (br m, 1 H), 0.52-0.46 (br m, 1 H), 0.38-0.32 (br m, 1 H); MS ESI 453.2 [M+H]$^+$, calcd for [C$_{28}$H$_{28}$N$_4$O$_2$+H]$^+$ 453.22.

Example A142

N-(2-(hydroxymethyl)benzyl)-3-(4-((1-methylpiperidin-4-yl)oxy)phenyl)-1H-indazole-5-carboxamide

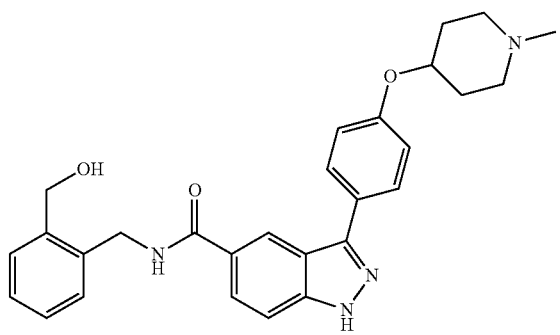 [SMILES: CN1CCC(Oc2ccc(-c3n[nH]c4ccc(C(=O)NCc5ccccc5CO)cc34)cc2)CC1]

The title compound was synthesized according to the General Method A utilizing 3-(4-((1-methylpiperidin-4-yl)oxy)phenyl)-1H-indazole-5-carboxylic acid (34 mg, 0.1 mmol), (2-aminomethyl-phenyl)-Methanol (14 mg, 0.1 mmol), TBTU (32 mg, 0.1 mmol), DIPEA (52 μL, 0.3 mmol), and DMF (4 mL). Purification by RPHPLC, followed by trituration with Et$_2$O gave the title compound as a TFA salt (white solid, 50 mg, 86%). $^1$H NMR (400 MHz, CD$_3$OD) δ ppm 8.58 (s, 1 H), 7.89-7.97 (m, 3 H), 7.60 (d, J=8.8 Hz, 1 H), 7.37-7.44 (m, 2 H), 7.24-7.31 (m, 2 H), 7.17 (d, J=8.8 Hz, 2 H), 4.78 (s, 2 H), 4.72 (s, 2 H), 3.44 (br. s, 2 H), 3.32 (br. s, 2 H), 2.92 (s, 3H), 2.06-2.32 (m, 4 H); MS ESI 471.3 [M+H]$^+$, calcd for [C$_{28}$H$_{30}$N$_4$O$_3$+H]$^+$ 471.2.

Example A143

N-(2-methyl-1-(o-tolyl)propyl)-3-(4-((1-methylpiperidin-4-yl)oxy)phenyl)-1H-indazole-5-carboxamide

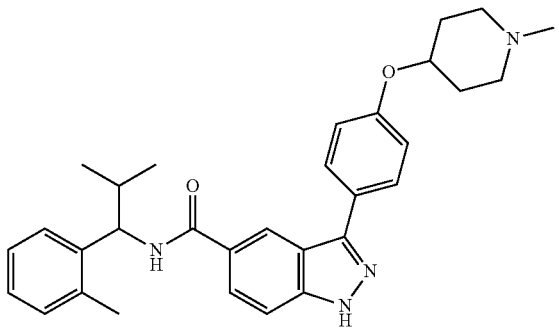 [SMILES: Cc1ccccc1C(NC(=O)c1ccc2[nH]nc(-c3ccc(OC4CCN(C)CC4)cc3)c2c1)C(C)C]

To a 20 mL microwave vial charged with Mg powder (240 mg, 20 mmol), THF (15 mL) was added 2-bromopropane (2.46 g, 20 mmol). The resulting mixture was stirred for 30 min at rt before 2-methylbenzonitrile (1.21 g, 10 mmol) was added. It was microwaved 15 min at 100° C., cooled to rt and added dropwise to a cold solution of NaBH$_4$ (760 mg, 20 mmol) in MeOH (45 mL) at 0° C. The resulting mixture was stirred for 30 min at rt, quenched with H$_2$O, extracted with DCM and purified by flash chromatography (MeOH/DCM 0-20%) to give crude 2-methyl-1-(o-tolyl)propan-1-amine (yellow oil, 167 mg). $^1$H NMR (400 MHz, CDCl$_3$) δ 7.37 (d, J=7.6 Hz, 1H), 7.23-7.18 (m, 1H), 7.12 (d, J=4.0 Hz, 2H), 3.88 (d, J=7.6 Hz, 1H), 2.34 (s, 3H), 1.95-1.85 (m, 1H), 1.02 (d, J=6.4 Hz, 3H), 0.81 (d, J=6.8 Hz, 3H); MS ESI 147.0 [M+H]$^+$, calcd for [C$_{11}$H$_{17}$N+H]$^+$ 147.1.

To a solution of 3-iodo-1H-indazole-5-carboxylic acid (576 g, 2 mmol) and 1-methyl-4-(4-(4,4,5,5-tetramethyl-1,3,2-dioxaborolan-2-yl)phenoxy)piperidine (634 mg, 2) in DMF (9 mL) was added a solution of K$_3$PO$_4$ (1.272 g, 6 mmol) in H$_2$O (3 mL), followed by Pd(dppf)Cl$_2$—CH$_2$Cl$_2$ (82 mg, 0.1 mmol). The resulting mixture was purged with Ar and microwaved 5 h at 120° C. The DMF layer was separated, concentrated and purified by flash chromatography (MeOH/DCM 0-100% then 0.05 M NH$_3$ in MeOH) to give 3-(4-((1-methylpiperidin-4-yl)oxy)phenyl)-1H-indazole-5-carboxylic acid (brown solid, 140 mg, 20%). $^1$H NMR (400 MHz, DMSO-d$_6$) δ 13.4 (s, 1H), 8.60 (s, 1H), 7.96 (dd, J=8.8 Hz, 1.2 Hz, 1H), 7.87 (d, J=8.8 Hz, 2H), 7.60 (d, J=8.8 Hz, 1H), 7.13 (d, J=8.8 Hz, 2H), 4.48-4.40 (m, 1H), 2.70-2.55 (m, 2H), 2.25-2.10 (m, 5H; s, 3H at 2.20), 2.05-1.90 (m, 2H), 1.74-1.60 (m, 2H); MS ESI 352.2 [M+H]$^+$, calcd for [C$_{20}$H$_{21}$N$_3$O$_3$+H]$^+$ 352.2.

To a flask charged with crude 2-methyl-1-(o-tolyl)propan-1-amine (32 mg, 0.2 mmol) and TBTU (32 mg, 0.1 mmol) was added a solution of 3-(4-((1-methylpiperidin-4-yl)oxy)phenyl)-1H-indazole-5-carboxylic acid (33 mg, 0.1 mmol) in DMF (2.5 mL) followed by iPr$_2$NEt (0.05 mL, 0.3 mmol). The resulting mixture was stirred for 30 min at rt and purified by prep-HPLC and PoraPak to give the title compound (pale yellow solid, 24.2 mg, 49%). $^1$H NMR (400 MHz, CD$_3$OD) δ 8.52 (s, 1H), 7.90-7.93 (m, 3H), 7.56 (d, J=8.8 Hz, 1H), 7.44 (d, J=7.6 Hz, 1H), 7.18-7.07 (m, 3H), 7.05 (d, J=8.8 Hz, 2H), 5.10 (d, J=10.4 Hz, 1H), 4.50-4.42 (m, 1H), 2.77-2.68 (m, 2H), 2.53 (s, 3H), 2.44-2.33 (m, 2H), 2.32 (s, 3H), 2.28-2.18 (m, 1H), 2.07-1.99 (m, 2H), 1.87-

1.78 (m, 2H), 1.18 (d, J=6.4 Hz, 3H), 0.80 (d, J=6.8 Hz, 3H); MS ESI 497.4 [M+H]+, calcd for [C31H36N4O2+H]+ 497.3.

Example A144

N-(1-(2-chlorophenyl)-2-methylpropyl)-3-(4-((1-methylpiperidin-4-yl)oxy)phenyl)-1H-indazole-5-carboxamide

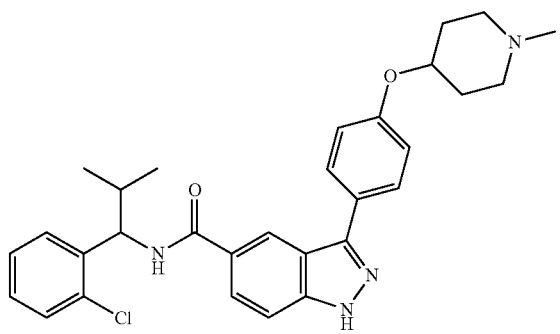 [SMILES: CC(C)C(NC(=O)c1ccc2[nH]nc(-c3ccc(OC4CCN(C)CC4)cc3)c2c1)c1ccccc1Cl]

Method 1:

A. 1-(2-chlorophenyl)-2-methylpropan-1-amine

To a 20 mL microwave vial charged with Mg powder (240 mg, 20 mmol), THF (15 mL) was added 2-bromopropane (2.46 g, 20 mmol). The resulting mixture was stirred for 30 min at rt before 2-chlorobenzonitrile (1.10 g, 8 mmol) was added. It was microwaved 15 min at 100° C., cooled to rt and added dropwise to a cold solution of NaBH4 (760 mg, 20 mmol) in MeOH (45 mL) at 0° C. The resulting mixture was stirred for 20 min at rt, quenched with H2O, extracted with DCM and purified by flash chromatography (MeOH/DCM 0-20%) to give crude 1-(2-chlorophenyl)-2-methylpropan-1-amine (brown oil, 543 mg). 1H NMR (400 MHz, CDCl3) δ 7.48 (dd, J=7.6 Hz, 1.6 Hz, 1H), 7.38 (dd, J=8.0 Hz, 1.2 Hz, 1H), 7.33 (dt, J=7.6 Hz, 1.2 Hz, 1H), 7.23 (dt, J=7.6 Hz, 1.4 Hz, 1H), 4.13 (d, J=7.2 Hz, 1H), 2.03-1.95 (m, 1H), 1.02 (d, J=6.4 Hz, 3H), 0.83 (d, J=6.8 Hz, 3H); MS ESI 166.9 [M+H]+, calcd for [C10H14ClN−NH3+H]+ 167.1.

B. N-(1-(2-chlorophenyl)-2-methylpropyl)-3-(4-((1-methylpiperidin-4-yl)oxy)phenyl)-1H-indazole-5-carboxamide To a flask charged with crude 1-(2-chlorophenyl)-2-methylpropan-1-amine (36 mg, 0.2 mmol) and TBTU (32 mg, 0.1 mmol) was added a solution of 3-(4-((1-methylpiperidin-4-yl)oxy)phenyl)-1H-indazole-5-carboxylic acid (33 mg, 0.1 mmol) in DMF (2.5 mL) followed by iPr2NEt (0.05 mL, 0.3 mmol). The resulting mixture was stirred for 30 min at rt and purified by prep-HPLC to give the title compound as a TFA salt (light brown solid, 36.8 mg, 58%). 1H NMR (400 MHz, CD3OD) δ 8.85 (d, J=8.0 Hz, 0.2H, NH), 8.52 (s, 1H), 7.93-7.87 (m, 3H), 7.59 (d, J=8.8 Hz, 1H), 7.55 (dd, J=7.8 Hz, 1.4 Hz, 1H), 7.39 (dd, J=8.0 Hz, 1.2 Hz, 1H), 7.30 (dd, J=7.6 Hz, 1.2 Hz, 1H), 7.22 (dt, J=7.6 Hz, 1.6 Hz, 1H), 7.19-7.12 (m, 2H), 5.38 (d, J=9.6 Hz, 1H), 4.87-4.82 (m, 0.7H), 4.70-4.62 (m, 0.3H), 3.67-3.62 (m, 0.7H), 3.46-3.33 (m, 2.6H), 3.25-3.17 (m, 0.7H), 2.94-2.93 (two s at 2.94 and 2.93, 3H), 2.47-2.38 (m, 0.7H), 2.33-2.24 (m, 2.3H), 2.18- 2.07 (m, 1.3H), 1.98-1.87 (m, 0.7H), 1.17 (d, J=6.8 Hz, 3H), 0.87 (d, J=6.8 Hz, 3H); MS ESI 517.5 [M+H]+, calcd for [C30H33ClN4O2+H]+ 517.2.

Method 2:

The title compound was synthesized according to General Method C2 using N-(1-(2-chlorophenyl)-2-methylpropyl)-3-iodo-1H-indazol-5-carboxamide (400 mg, 0.88 mmol) and 1-methyl-4-(4-(4,4,5,5-tetramethyl-1,3,2-dioxaborolan-2-yl)phenoxy)piperidine (280 mg, 0.88 mmol) with PdCl2dppf (68 mg, 0.083 mmol) and 1 M aq Na2CO3 (1.76 mL, 1.76 mmol) in PhMe/EtOH (13 mL, 1:1 mixture) with heating under microwave irradiation at 125° C. for 3.5 h. The product was extracted with EtOAc (50 mL), washed with H2O (15 mL) and brine (15 mL), dried (Na2SO4) and concentrated under vacuum. Purification by flash chromatography (SiO2, 0-50% 1 M NH3-MeOH in DCM; then RP HPLC C18 120 g, 10-80% MeOH 0.1% TFA-H2O) gave the title compound as a TFA salt (light brown solid, 231 mg, 41.6%). 1H NMR and MS ESI were identical to that obtained in Method 1.

Example A145

(R)-2-methoxy-N-(3-(4-((1-methylpiperidin-4-yl)methoxy)phenyl)-1H-indazol-5-yl)-2-phenylacetamide

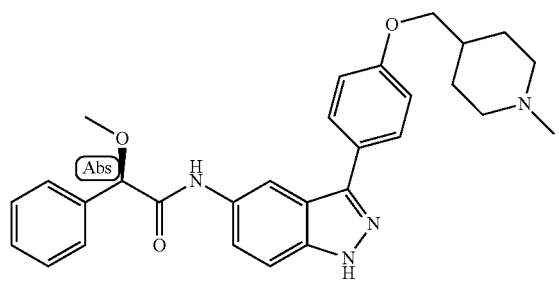 [SMILES: CO[C@@H](C(=O)Nc1ccc2[nH]nc(-c3ccc(OCC4CCN(C)CC4)cc3)c2c1)c1ccccc1]

A. 4-((4-iodophenoxy)methyl)-1-methylpiperidine was synthesized according to General Method H utilizing 1-fluoro-4-iodobenzene (0.70 g, 3.1 mmol), ((1-methylpiperidin-4-yl)methanol (0.41 g, 3.1 mmol) and NaH (60% in oil, 0.15 g, 3.7 mmol (3.7) in DMF (10 mL) as a light orange solid (0.82 g, 79%). NMR (400 MHz, CDCl3) δ ppm 7.53 (d, J=7.5 Hz, 2 H), 6.65 (d, J=7.5 Hz, 2 H), 3.75 (d, J=6.3 Hz, 2 H), 2.88 (d, J=11.5 Hz, 2 H), 2.28 (s, 3 H), 1.95 (td, J=11.8, 2.3 Hz, 2 H), 1.69-1.86 (m, 3 H), 1.33-1.47 (m, 2 H); MS ESI [M+H]+ 332.0, calcd for [C13H18INO+H]+ 332.0.

B. A stirred solution of 4-((4-iodophenoxy)methyl)-1-methylpiperidine (0.40 g, 1.2 mmol) in anh THF (10 mL) under Ar was treated with n-BuLi (1.6 M in hexanes, 1.5 mL, 2.4 mmol) dropwise at 78° C. After 20 min of stirring at the temperature, B(Oi-Pr)3 (2.8 mL, 12.0 mmol) was added rapidly. After additional 1 h at the temperature, the reaction was removed from the cooling bath and stirred for 1 h at rt before it was concentrated under reduced pressure to afford a crude mixture of the title compound and (4-((1-methylpiperidin-4-yl)methoxy)phenyl)boronic acid as a light orange solid (1.0 g) that was used without further purification. MS ESI 250.0 [M+H]+, calcd for [C13H20BNO3:+H]+ 250.1.

C. (R)-2-methoxy-N-(3-(4-((1-methylpiperidin-4-yl)methoxy)phenyl)-1H-indazol-5-yl)-2-phenylacetamide was synthesized according to the General Method C2 utilizing ((R)-N-(3-iodo-1H-indazol-5-yl)-2-methoxy-2-phenylacetamide (0.14 g, 0.34 mmol), a crude mixture of diisopropyl (4-((1-methylpiperidin-4-yl)methoxy)phenyl)boronate (0.33 g, ~0.4 mmol) to provide the title compound as a TFA salt: a white powder (30 mg, 25%). $^1$H NMR (400 MHz, CD$_3$OD) δ ppm 8.39 (s, 1 H), 7.84 (d, J=8.8 Hz, 2 H), 7.49-7.58 (m, 4 H), 7.30-7.45 (m, 3 H), 7.07 (d, J=8.8 Hz, 2 H), 4.84 (s, 1 H), 3.98 (d, J=5.3 Hz, 2 H), 3.63-3.53 (m, 2 H), 3.47 (s, 3 H), 3.11-3.01 (br. m., 2 H), 2.89 (s, 3 H), 2.20-2.09 (m, 3 H), 1.76-1.61 (br. m., 2 H); MS ESI 485.3 [M+H]$^+$, calcd for [C$_{29}$H$_{32}$N$_4$O$_3$+H]$^+$ 485.2.

Example A146

N-(3-(4-(1-Methylpiperidin-4-yloxy)phenyl)-1H-indazol-5-yl)isochroman-1-carboxamide

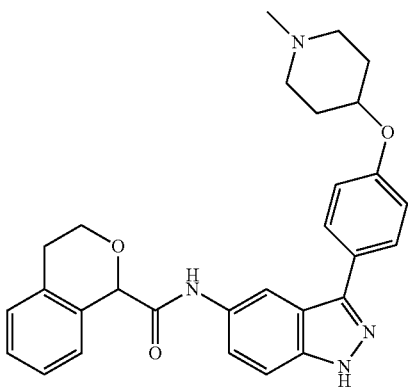 [SMILES: CN1CCC(Oc2ccc(-c3n[nH]c4ccc(NC(=O)C5OCCc6ccccc65)cc34)cc2)CC1]

A. Isochroman-1-carboxylic acid

A mixture of 2-phenylethanol (4 mL, 33 mmol) and glyoxylic acid hydrate (3.4 g, 37 mmol) in TFA (15 mL) was heated in a microwave reactor at 120° C. for 16 h. The solvent was removed in vacuo. The residue was then dissolved in H$_2$O and aq NH$_4$OH was added until the pH of the solution was over 7. The aq layer was washed with EtOAc (3×40 mL). 2 M aq HCl was added to the aq layer until the pH of the solution was less than 3. The product was extracted into EtOAc (4×40 mL). The combined organic layers were dried over MgSO$_4$, filtered and evaporated in vacuo. Trituration with hexanes provided the title compound as a yellow solid (4.4 g, 74%). $^1$H NMR (400 MHz, CDCl$_3$) δ ppm 7.56-7.54 (m, 2 H), 7.27-7.22 (m, 2 H), 7.17-7.15 (m, 1 H), 5.39 (s, 1 H), 4.34-4.28 (m, 1 H), 4.05-3.99 (m, 1 H), 2.98-2.84 (m, 2 H); MS ESI 178.9 [M+H]$^+$, calcd for [C$_{10}$H$_{10}$O$_3$+H]$^+$ 179.06.

B. N-(3-Iodo-1-(isochroman-1-carbonyl)-1H-indazol-5-yl)isochroman-1-carboxamide

The title compound was synthesized according to General Method A, utilizing 3-iodo-1H-indazol-5-amine (400 mg, 1.5 mmol), isochroman-1-carboxylic acid (300 mg, 1.7 mmol), TBTU (545 mg, 1.7 mmol), DIPEA (1.1 mL, 6.2 mmol), and DMF (8 mL). H$_2$O (20 mL) was added and the precipitate was collected, rinsing with H$_2$O (10 mL×3). Purification by flash chromatography (Biotage, 25 g HP-SIL, 10-50% EtOAc in hexanes) gave the title compound as a light yellow solid (270 mg, 30%). $^1$H NMR (400 MHz, CDCl$_3$) δ ppm 8.71 (s, 1 H), 8.33 (d, J=8.9 Hz, 1 H), 8.09 (dd, J=4.4, 1.9 Hz, 1 H), 7.85-7.82 (m, 1 H), 7.62-7.58 (m, 1 H), 7.29-7.08 (m, 5 H), 6.78 (s, 1 H), 5.38 (s, 1 H), 4.54-4.49 (m, 1 H), 4.37-4.33 (m, 1 H), 4.11-4.05 (m, 1 H), 4.01-3.95 (m, 1 H), 3.19-3.13 (m, 1 H), 3.01-2.95 (m, 2 H), 2.83-2.78 (m, 1 H); MS ESI 580.1 [M+H]$^+$, calcd for [C$_{27}$H$_{22}$IN$_3$O$_4$+H]$^+$ 580.07.

C. N-(3-(4-(1-methylpiperidin-4-yloxy)phenyl)-1H-indazol-5-yl)isochroman-1-carboxamide The title compound was synthesized according to General Method C, utilizing N-(3-iodo-1-(isochroman-1-carbonyl)-1H-indazol-5-yl)isochroman-1-carboxamide (120 mg, 0.21 mmol), 1-methyl-4-(4-(4,4,5,5-tetramethyl-1,3,2-dioxaborolan-2-yl)phenoxy)piperidine (72 mg, 0.23 mmol), Pd(PPh$_3$)$_4$ (24 mg, 0.021 mmol), 2 M aq Na$_2$CO$_3$ (0.4 mL), PhMe (4 mL), and EtOH (2 mL). H$_2$O (30 mL) was added and the product was extracted into EtOAc (4×30 mL). The combined organic layers were dried over MgSO$_4$, filtered and evaporated in vacuo. Purification by flash chromatography (Biotage, 25 g HP-SIL, 100% EtOAc, then 2-10% MeOH in DCM) followed by RPHPLC gave the title compound as a TFA salt. The salt was then dissolved in MeOH (20 mL) and poured into a preconditioned 20 mL PoraPak Rxn Cx cartridge. The Methanol (30 mL) rinse was discarded and the product was eluted with 2 M NH3 in Methanol (30 mL). The solvent was removed in vacuo to afford the title compound as a white solid (32 mg, 32%). $^1$H NMR (400 MHz, CD$_3$OD) δ ppm 8.34 (s, 1 H), 7.81 (d, J=8.6 Hz, 2 H), 7.55-7.48 (m, 3 H), 7.23-7.15 (m, 3 H), 7.03 (d, J=8.6 Hz, 2 H), 5.33 (s, 1 H), 4.50-4.40 (m, 1 H), 4.33-4.28 (m, 1 H), 3.94-3.88 (m, 1 H), 3.17-3.09 (m, 1 H), 2.78-2.70 (m, 3 H), 2.40-2.29 (m, 1 H), 2.10-1.90 (m, 2 H), 1.85-1.75 (m, 2 H); MS ESI 483.4 [M+H]$^+$, calcd for [C$_{29}$H$_{30}$N$_4$O$_3$+H]$^+$ 483.23.

Example A147

N-(cyclopropyl(thiophen-2-yl)methyl)-3-(4-((1-methylpiperidin-4-yl)oxy)phenyl)-1H-indazole-5-carboxamide

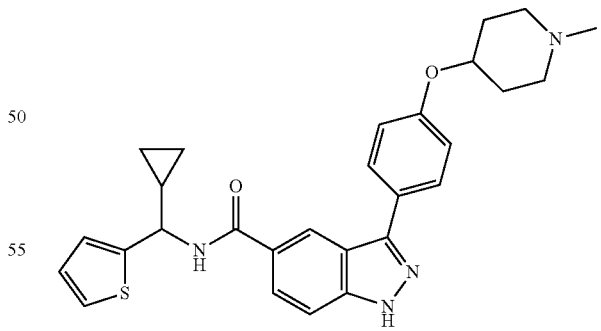

A mixture of cyclopropyl(thiophen-2-yl)methanone (3.04 g, 10 mmol), Na$_4$OAc (18.48 g, 240 mmol) and NaCNBH$_3$ (5.04 g, 80 mmol) in MeOH (60 mL) was heated at 65° C., O/N. After removal of solvent, it was purified by flash chromatography (MeOH/DCM 0-20%) to give cyclopropyl (thiophen-2-yl)methanamine (colorless oil, 876 mg, 42%). $^1$H NMR (400 MHz, CDCl$_3$) δ 7.33 (d, J=5.2 Hz, 1H), 7.20 (d, J=7.6 Hz, 1H), 7.04 (dd, J=5.2 Hz, 3.8 Hz, 1H), 3.78 (d, J=10.0 Hz, 1H), 1.50-1.38 (m, 1H), 0.90-0.75 (m, 2H), 0.67-0.60 (m, 1H), 0.52-0.43 (m, 1H); MS ESI 137.0 [M+H]$^+$, calcd for [C$_8$H$_{11}$NS-NH$_3$+H]$^+$ 137.0.

To a flask charged with crude cyclopropyl(thiophen-2-yl)methanamine (30 mg, 0.2 mmol) and TBTU (32 mg, 0.1 mmol) was added a solution of 3-(4-((1-methylpiperidin-4-yl)oxy)phenyl)-1H-indazole-5-carboxylic acid (33 mg, 0.1 mmol) in DMF (2.5 mL) followed by iPr$_2$NEt (0.05 mL, 0.3 mmol). The resulting mixture was stirred for 30 min at rt and purified by prep-HPLC, PoraPak, flash chromatography (MeOH/CM 0-100%, then 0.05 M NH$_3$ in MeOH) and prep-HPLC to give the title compound as a TFA salt (white solid, 7.9 mg, 13%). $^1$H NMR (400 MHz, CD$_3$OD) δ 8.61 (s, 1H), 8.00-7.94 (m, 3H), 7.63 (d, J=8.8 Hz, 1H), 7.29 (d, J=5.2 Hz, 1H), 7.23-7.13 (m, 3H), 6.98 (t, J=4.2 Hz, 1H), 4.85-4.65 (m, 2H; 1H, J=5.6 Hz at 4.77), 3.68-3.18 (m, 4H), 2.95-2.94 (two s at 2.95 and 2.94, 3H), 2.49-2.28 (m, 2H), 2.18-1.87 (m, 2H), 1.57-1.47 (m, 1H), 0.82-0.75 (m, 1H), 0.71-0.62 (m, 1H), 0.60-0.50 (m, 2H); MS ESI 487.4 [M+H]$^+$, calcd for [C$_{28}$H$_{30}$N$_4$O$_2$S+H]$^+$ 487.2.

Example A148

2-cyclopentyl-N-(3-(4-((1-methylpiperidin-4-yl)oxy)phenyl)-1H-indazol-5-yl)-2-phenylacetamide

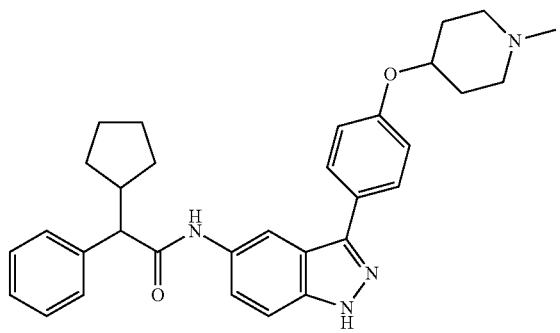

To a mixture of 2-cyclopentyl-2-phenylacetic acid (1.02 g, 5 mmol), 3-iodo-1H-indazol-5-amine (1.30 g, 5 mmol) in DMF (10 mL) at 0° C. was added TBTU (1.61 g, 5 mmol), followed by iPr$_2$NEt (1.74 mL, 10 mmol). The resulting mixture was stirred at rt for 2 h, quenched with H$_2$O, extracted with EtOAc and purified by flash chromatography (EtOAc.hex 0-100%) to give N-(cyclopentyl(phenyl)methyl)-3-iodo-1H-indazole-5-carboxamide (light brown solid, 422 mg, 19%). $^1$H NMR (400 MHz, DMSO-d$_6$) δ 13.40 (s, 1H), 7.92 (s, 1H), 7.47-7.41 (m, 4H), 7.32 (t, J=7.4 Hz, 2H), 7.24 (d, J=8.0 Hz, 1H), 2.70-2.50 (m, 1H), 1.90-0.95 (m, 8H).

To a mixture of N-(cyclopentyl(phenyl)methyl)-3-iodo-1H-indazole-5-carboxamide (214 mg, 0.5 mmol) and 1-methyl-4-(4-(4,4,5,5-tetramethyl-1,3,2-dioxaborolan-2-yl)phenoxy)piperidine (127 mg, 0.4 mmol) in EtOH (12 mL) was added 1 M aq Na$_2$CO$_3$ (0.8 mL, 0.8 mmol), followed by Pd(PPh$_3$)$_4$ (46 mg, 0.04 mmol). The resulting mixture was purged with Ar and microwaved 4 h at 125° C. After removal of solvents, it was purified by prep-HPLC and PoraPak to give the title compound (light brown solid, 60.2 mg, 30%). $^1$H NMR (400 MHz, CD$_3$OD) δ 8.38 (s, 1H), 7.76 (d, J=8.8 Hz, 2H), 7.48-7.45 (m, 4H), 7.27 (t, J=7.4 Hz, 2H), 7.20 (d, J=7.2 Hz, 1H), 6.95 (d, J=8.8 Hz, 2H), 4.38-4.31 (m, 1H), 3.39 (d, J=7.2 Hz, 1H), 2.78-2.60 (m, 3H), 2.36-2.23 (m, 5H; s, 3H at 2.26), 2.00-1.90 (m, 3H), 1.81-1.32 (m, 8H), 1.10-1.00 (m, 1H); MS ESI 509.5 [M+H]$^+$, calcd for [C$_{32}$H$_{36}$N$_4$O$_2$+H]$^+$ 509.3.

Example A150

N-((2-chlorophenyl)(cyclopropyl)methyl)-3-(4-((1-methylpiperidin-4-yl)oxy)phenyl)-1H-indazole-5-carboxamide

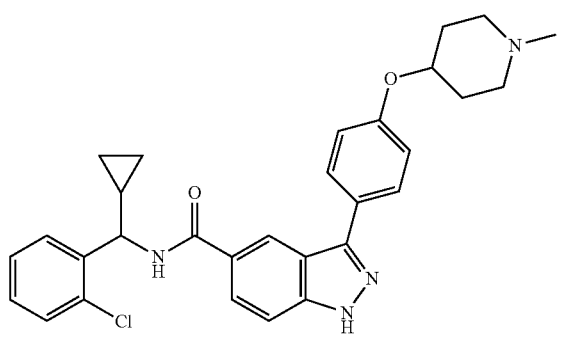

To a 20 mL microwave vial charged with Mg powder (480 mg, 20 mmol), THF (15 mL) was added bromocyclopropane (2.42 g, 20 mmol). The resulting mixture was stirred for 30 min at rt before 2-chlorobenzonitrile (1.10 g, 8 mmol) was added. It was microwaved 15 min at 100° C., cooled to rt and added dropwise to a cold solution of NaBH$_4$ (760 mg, 20 mmol) in MeOH (45 mL) at 0° C. The resulting mixture was stirred for 20 min at rt, quenched with H$_2$O, extracted with DCM and purified by flash chromatography (MeOH/DCM 0-20%) to give cyclopropyl(2-chlorophenyl)methanamine (light orange oil, 1.12 g, 77%). $^1$H NMR (400 MHz, CD$_3$OD) δ 7.62 (dd, J=8.0 Hz, 1.6 Hz, 1H), 7.37 (dd, J=8.0 Hz, 1.2 Hz, 1H), 7.33 (dt, J=7.6 Hz, 1.2 Hz, 1H), 7.23 (dd, J=7.6 Hz, 1.6 Hz, 1H), 3.74 (d, J=8.8 Hz, 1H), 1.28-1.19 (m, 1H), 0.67-0.60 (m, 1H), 0.48-0.35 (m, 2H), 0.32-0.26 (m, 1H); MS ESI 164.9 [M+H]$^+$, calcd for [C$_{10}$H$_{12}$ClN-NH$_3$+H]$^+$ 165.0.

To a solution of cyclopropyl(2-chlorophenyl)methanamine (1.12 g, 6.17 mmol), 3-iodo-1H-indazole-5-carboxamide (1.68 g, 5.85 mmol) in DMF (30 mL) was added TBTU (1.88 g, 5.85 mmol), followed by $^i$Pr$_2$NEt (2.03 mL, 11.7 mmol). The resulting mixture was stirred at rt for 30 min, quenched with H$_2$O and stirred for 30 min at rt. Suction filtration gave crude N-((2-chlorophenyl)(cyclopropyl)methyl)-3-iodo-1H-indazole-5-carboxamide (pale yellow solid, 2.582 g). MS ESI 452.2 [M+H]$^+$, calcd for [C$_{18}$H$_{15}$ClIN$_3$O+H]$^+$ 452.0.

To a mixture of crude N-((2-chlorophenyl)(cyclopropyl)methyl)-3-iodo-1H-indazole-5-carboxamide (226 mg, 0.5 mmol) and 1-methyl-4-(4-(4,4,5,5-tetramethyl-1,3,2-dioxaborolan-2-yl)phenoxy)piperidine (127 mg, 0.4 mmol) in EtOH (10 mL) was added 1 M aq Na$_2$CO$_3$ (1 mL, 1 mmol), followed by Pd(PPh$_3$)$_4$ (46 mg, 0.04 mmol). The resulting mixture was purged with Ar and microwaved 4 h at 125° C. After removal of solvents, it was purified by prep-HPLC and PoraPak to give the title compound (white solid, 59.0 mg, 29%). $^1$H NMR (400 MHz, CD$_3$OD) δ 8.58 (s, 1H), 7.92 (dd, J=9.0 Hz, 1.4 Hz, 1H), 7.84 (d, J=8.4 Hz, 2H), 7.63 (dd, J=7.8 Hz, 1.4 Hz, 1H), 7.55 (d, J=8.8 Hz, 1H), 7.32 (dd, J=8.0 Hz, 0.8 Hz, 1H), 7.23 (t, J=7.6 Hz, 1H), 7.16 (dt, J=7.6 Hz, 1.6 Hz, 1H), 6.99 (d, J=8.8 Hz, 2H), 4.99 (d, J=8.8 Hz, 1H), 4.40-4.30 (m, 1H), 2.71-2.62 (m, 2H), 2.37-2.25 (m, 5H; s, 3H at 2.27), 2.02-1.93 (m, 2H), 1.83-1.73 (m, 2H), 1.45-1.35 (m, 1H), 0.67-0.60 (m, 1H), 0.55-0.45 (m, 3H); MS ESI 515.4 [M+H]$^+$, calcd for [C$_{30}$H$_{31}$ClN$_4$O$_2$+H]$^+$ 515.2.

Example A151

N-(cyclopropyl(2-methoxyphenyl)methyl)-3-(4-((1-methylpiperidin-4-yl)oxy)phenyl)-1H-indazole-5-carboxamide

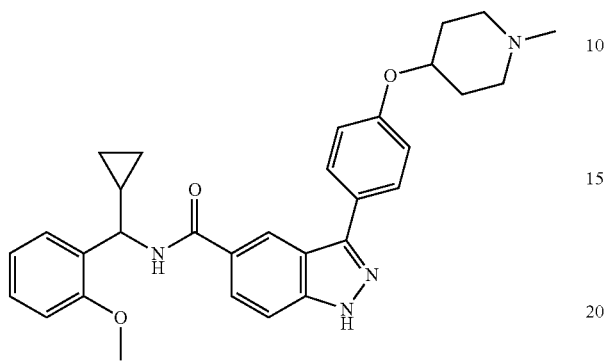

To a 20 mL microwave vial charged with Mg powder (480 mg, 20 mmol), THF (15 mL) was added bromocyclopropane (2.42 g, 20 mmol). The resulting mixture was stirred for 30 min at rt before 2-methoxybenzonitrile (1.064 g, 8 mmol) was added. It was microwaved 15 min at 100° C., cooled to rt and added dropwise to a cold solution of NaBH$_4$ (760 mg, 20 mmol) in MeOH (45 mL) at 0° C. The resulting mixture was stirred for 20 min at rt, quenched with H$_2$O, extracted with DCM and purified by flash chromatography (MeOH/DCM 0-20%) to give cyclopropyl(2-methoxyphenyl)methanamine (light orange oil which partially solidified upon standing, 933 mg, 77%). $^1$H NMR (400 MHz, CD$_3$OD) δ 7.36 (dd, J=7.4 Hz, 1.4 Hz, 1H), 7.25 (dt, J=7.4 Hz, 1.6 Hz, 1H), 6.98 (d, J=8.4 Hz, 1H), 6.94 (dt, J=7.4 Hz, 1.0 Hz, 1H), 3.86 (s, 3H), 3.76 (d, J=9.2 Hz, 1H), 1.34-1.24 (m, 1H), 0.66-0.59 (m, 1H), 0.49-0.41 (m, 1H), 0.40-0.33 (m, 1H), 0.23-0.16 (m, 1H); MS ESI 161.0 [M+H]$^+$, calcd for [C$_{11}$H$_{15}$NO NH$_3$+H]$^+$ 161.1.

To a solution of cyclopropyl(2-methoxyphenyl)methanamine (933 mg, 5.27 mmol), 3-iodo-1H-indazole-5-carboxamide (1.44 g, 5 mmol) in DMF (25 mL) was added TBTU (1.61 g, 5 mmol), followed by $^i$Pr$_2$NEt (2.03 mL, 11.7 mmol). The resulting mixture was stirred at rt for 30 min, quenched with H$_2$O and stirred for 30 min at rt. Suction filtration gave crude N-(cyclopropyl(2-methoxyphenyl)methyl)-3-iodo-1H-indazole-5-carboxamide (off white solid, 2.068 g). MS ESI 448.1 [M+H]$^+$, calcd for [C$_{19}$H$_{18}$IN$_3$O$_2$+H]$^+$ 448.0.

To a mixture of crude N-(cyclopropyl(2-methoxyphenyl)methyl)-3-iodo-1H-indazole-5-carboxamide (224 mg, 0.5 mmol) and 1-methyl-4-(4-(4,4,5,5-tetramethyl-1,3,2-dioxaborolan-2-yl)phenoxy)piperidine (127 mg, 0.4 mmol) in EtOH (10 mL) was added 1 M aq Na$_2$CO$_3$ (1 mL, 1 mmol), followed by Pd(PPh$_3$)$_4$ (46 mg, 0.04 mmol). The resulting mixture was purged with Ar and microwaved 4 h at 125° C. After removal of solvents, it was purified by prep-HPLC and PoraPak to give the title compound (white solid, 53.7 mg, 26%). $^1$H NMR (400 MHz, CD$_3$OD) δ 8.55 (s, 1H), 7.90 (dd, J=8.8 Hz, 1.6 Hz, 1H), 7.86 (d, J=8.8 Hz, 2H), 7.56 (d, J=8.8 Hz, 1H), 7.40 (dd, J=7.6 Hz, 1.6 Hz, 1H), 7.19 (dt, J=7.8 Hz, 1.6 Hz, 1H), 7.02 (d, J=8.8 Hz, 2H), 6.94 (d, J=8.8 Hz, 1H), 6.89 (t, J=7.4 Hz, 1H), 4.83 (d, J=9.2 Hz, 1H), 4.43-4.35 (m, 1H), 3.84 (s, 3H), 2.73-2.64 (m, 2H), 2.37-2.25 (m, 5H; s, 3H at 2.27), 2.03-1.94 (m, 2H), 1.85-1.74 (m, 2H), 1.49-1.39 (m, 1H), 0.62-0.52 (m, 1H), 0.50-0.38 (m, 3H); MS ESI 511.4 [M+H]$^+$, calcd for [C$_{31}$H$_{34}$N$_4$O$_3$+H]$^+$ 511.3.

Example A153

3-(4-((1-(2-methoxyethyl)piperidin-4-yl)oxy)phenyl)-N-(1-phenylpropyl)-1H-indazole-5-carboxamide

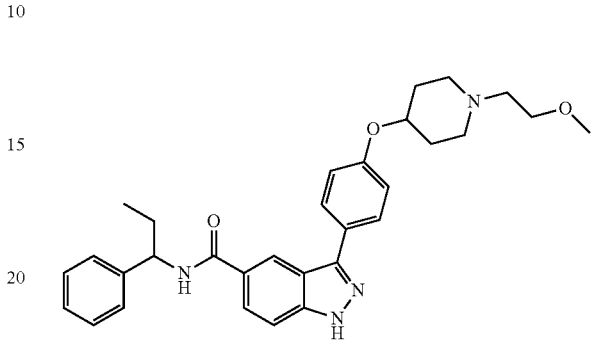

The title compound was synthesized according to General Method C3 utilizing 3-iodo-N-(1-phenylpropyl)-1H-indazole-5-carboxamide and 1-(2-methoxyethyl)-4-(4-(4,4,5,5-tetramethyl-1,3,2-dioxaborolan-2-yl)phenoxy)piperidine and obtained as a yellow solid (30 mg, 32% yield). $^1$H NMR (400 MHz, CD$_3$OD) δ ppm 8.58 (s, 1H), 7.94 (dd, J=8.8, 1.51 Hz, 1H), 7.90 (d, J=8.5 Hz, 2H), 7.59 (d, J=8.8 Hz, 1H), 7.41 (d, J=7.5 Hz, 2H), 7.32 (t, J=7.5 Hz, 2H), 7.19-7.25 (m, 1H), 7.10 (d, J=8.8 Hz, 2H), 5.03 (t, J=7.5 Hz, 1H), 4.58 (br. s., 1H), 3.62 (t, J=5.4 Hz, 2H), 3.38 (s, 3H), 3.08 (t, J=8.2 Hz, 2H), 2.92 (t, J=5.0 Hz, 2H), 2.82 (br. s., 2H), 2.05-2.16 (m, 2H), 1.85-2.04 (m, 4H), 1.00 (t, J=7.3 Hz, 3H); MS ESI [M+H]$^+$ 513.5, calcd for [C$_{31}$H$_{36}$N$_4$O$_3$+H]$^+$ 513.29.

Example A154

(S)-N-(cyclopropyl(thiophen-3-yl)methyl)-3-(4-((1-(2-methoxyethyl)piperidin-4-yl)oxy)phenyl)-1H-indazole-5-carboxamide

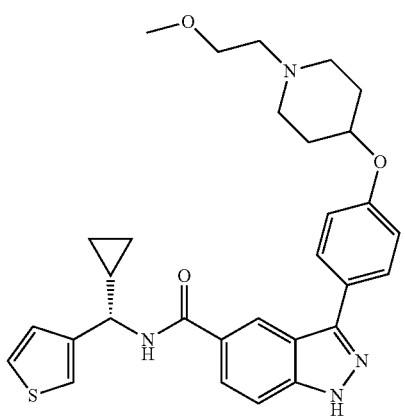 [SMILES: COCCN1CCC(Oc2ccc(-c3n[nH]c4ccc(C(=O)N[C@H](c5ccsc5)C5CC5)cc34)cc2)CC1]

The title compound was prepared using General Method C3 from (S)-N-(cyclopropyl(thiophen-3-yl)methyl)-3-iodo-1H-indazole-5-carboxamide (60 mg, 0.142 mmol) and 1-(2-methoxyethyl)-4-(4-(4,4,5,5-tetramethyl-1,3,2-dioxaborolan-2-yl)phenoxy)piperidine (67 mg, 0.185 mmol) which gave 48 mg of product isolated as its TFA salt (64%, pale-yellow solid). $^1$H NMR (400 MHz, CD$_3$OD) δ ppm 8.58 (s, 1H), 7.98-7.94 (m, 3H), 7.61 (d, J=8.7 Hz, 1H), 7.38-7.36 (m, 2H), 7.22-7.16 (m, 3H), 4.87 (bs, 1H), 4.61 (d, J=9.6 Hz, 1H), 3.76-3.22 (m, 11H), 2.46-2.29 (m, 2H), 2.20-1.97 (m, 2H), 1.48-1.43 (m, 1H), 0.76-0.64 (m, 2H), 0.55-0.47 (m, 2H); MS ESI 531.4 [M+H]$^+$, calcd for [C$_{30}$H$_{34}$N$_4$O$_3$S+H]$^+$ 531.24.

Example A155

N-(cyclopentyl(thiophen-3-yl)methyl)-3-(4-((1-(2-methoxyethyl)piperidin-4-yl)oxy)phenyl)-1H-indazole-5-carboxamide

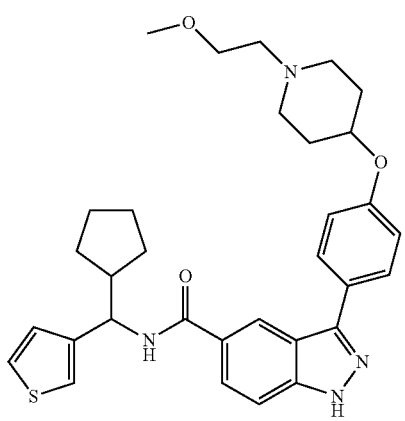 [SMILES: COCCN1CCC(Oc2ccc(-c3n[nH]c4ccc(C(=O)NC(c5ccsc5)C5CCCC5)cc34)cc2)CC1]

The title compound was prepared using General Method C3 from N-(cyclopentyl(thiophen-3-yl)methyl)-3-iodo-1H-indazole-5-carboxamide (75 mg, 0.166 mmol) and 1-(2-methoxyethyl)-4-(4-(4,4,5,5-tetramethyl-1,3,2-dioxaborolan-2-yl)phenoxy)piperidine (78 mg, 0.216 mmol) which gave 34 mg of product isolated as its TFA salt (37%, a pale-yellow solid). $^1$H NMR (400 MHz, CD$_3$OD) δ ppm 8.51 (s, 1H), 7.95-7.88 (m, 3H), 7.60 (d, J=8.8 Hz, 1H), 7.37-7.32 (m, 2H), 7.22-7.15 (m, 3H), 5.05 (d, J=10.4 Hz, 1H), 4.87 (bs, 1H), 3.77-3.19 (m, 11H), 2.59-1.92 (m, 6H), 1.69-1.23 (m, 7H); MS ESI 559.4 [M+H]$^+$, calcd for [C$_{32}$H$_{38}$N$_4$O$_3$S+H]$^+$ 559.27.

Example A156

2-cyclopentyl-2-(2-methoxyphenyl)-N-(3-(4-((1-methylpiperidin-4-yl)oxy)phenyl)-1H-indazol-5-yl)acetamide

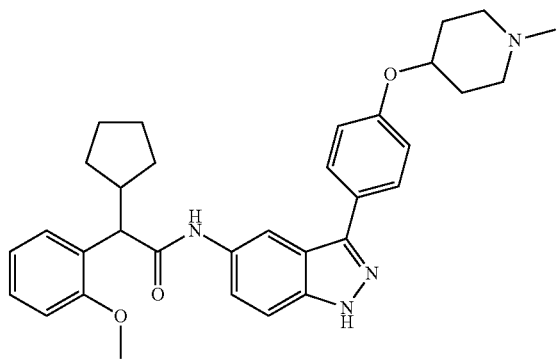 [SMILES: COc1ccccc1C(C(=O)Nc1ccc2[nH]nc(-c3ccc(OC4CCN(C)CC4)cc3)c2c1)C1CCCC1]

The title compound was synthesized according to the General Method C, utilizing 2-cyclopentyl-N-(3-iodo-1H-indazol-5-yl)-2-(2-methoxyphenyl)acetamide (50 mg, 0.10 mmol), (4-((1-methylpiperidin-4-yl)oxy)phenyl) boronic acid pinacol ester (33 mg, 0.1 mmol), Pd(PPh$_3$)$_4$ (6 mg, 0.005 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (beige solid, 16 mg, 25%). $^1$H NMR (400 MHz, CD$_3$OD) δ ppm 8.40 (s, 1 H), 7.81-7.89 (m, 2 H), 7.55 (dd, J=7.8, 1.5 Hz, 1 H), 7.49 (d, J=9.3, 1 H), 7.38 (dd, J=8.9, 1.9 Hz, 1 H), 7.08-7.25 (m, 3 H), 6.91-7.00 (m, 2 H), 4.57-4.69 (m, 0.3 H), 4.01 (d, J=11.0 Hz, 1 H), 3.89 (s, 3 H), 3.57-3.65 (m, 0.7 H), 3.32-3.47 (m, 3 H), 3.13-3.25 (m, 0.7 H), 2.89-2.96 (m, 3 H), 2.66-2.79 (m, 1 H), 2.37-2.48 (m, 0.7 H), 2.23-2.34 (m, 1.3 H), 2.03-2.16 (m, 1.3 H), 1.82-2.00 (m, 1.3 H), 1.70-1.81 (m, 1 H), 1.40-1.70 (m, 5.7 H), 1.03-1.16 (m, 1 H); MS ESI 539.4 [M+H]$^+$, calcd for [C$_{33}$H$_{38}$N$_4$O$_3$+H]$^+$ 539.3.

Example A157

N-(cyclopropyl(phenyl)methyl)-3-(4-((1-(oxetan-3-yl)piperidin-4-yl)oxy)phenyl)-1H-indazole-5-carboxamide

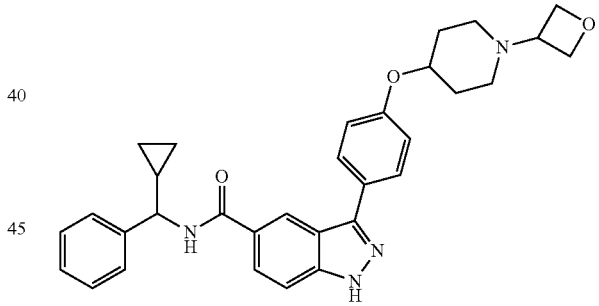

The title compound was synthesized according to General Method C3 utilizing N-(cyclopropyl(phenyl)methyl)-3-iodo-1H-indazole-5-carboxamide and 1-(oxetan-3-yl)-4-(4-(4,4,5,5-tetramethyl-1,3,2-dioxaborolan-2-yl)phenoxy)piperidine and obtained as a yellow solid (38 mg, 38% yield). $^1$H NMR (400 MHz, CD$_3$OD) δ ppm 8.62 (s, 1 H), 7.96 (dd, J=8.8, 1.51 Hz, 1 H), 7.89 (d, J=8.8 Hz, 2 H), 7.59 (d, J=8.8 Hz, 1 H), 7.47 (d, J=7.3 Hz, 2 H), 7.27-7.33 (t, J=7.6 Hz, 2 H), 7.18-7.24 (m, 1 H), 7.03 (d, J=8.8 Hz, 2 H), 4.69 (t, J=6.3 Hz, 2 H), 4.58 (t, J=6.3 Hz, 2 H), 4.47 (d, J=9.5 Hz, 1 H), 4.39-4.45 (m, 1 H), 3.47 (quin, J=6.5 Hz, 1 H), 2.55 (br. s., 2 H), 2.20 (d, J=7.8 Hz, 2 H), 1.96-2.06 (m, 2 H), 1.74-1.86 (m, 2 H), 1.33-1.44 (m, 1 H), 0.58-0.68 (m, 2 H), 0.39-0.51 (m, 2 H); MS ESI [M+H]$^+$ 523.3, calcd for [C$_{32}$H$_{34}$H$_4$O$_3$+H]$^+$ 523.27.

Example A158

N-(cyclopropyl(phenyl)methyl)-3-(4-((1-(2-(dimethylamino)-2-oxoethyl)piperidin-4-yl)oxy)phenyl)-1H-indazole-5-carboxamide

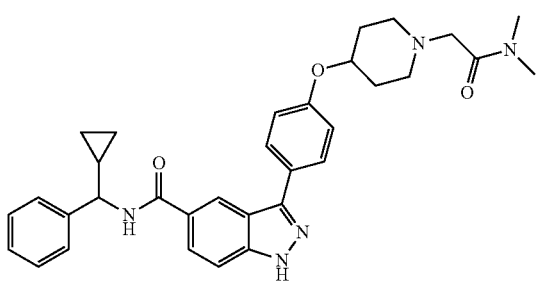 [SMILES: CN(C)C(=O)CN1CCC(Oc2ccc(-c3n[nH]c4ccc(C(=O)NC(c5ccccc5)C5CC5)cc34)cc2)CC1]

The title compound was synthesized according to General Method C3 utilizing N-(cyclopropyl(phenyl)methyl)-3-iodo-1H-indazole-5-carboxamide and N,N-dimethyl-2-(4-(4-(4,4,5,5-tetramethyl-1,3,2-dioxaborolan-2-yl)phenoxy)piperidin-1-yl)acetamide and obtained as a white solid (28 mg, 27% yield). $^1$H NMR (400 MHz, CD$_3$OD) δ ppm 8.61 (s, 1 H), 7.96 (dd, J=8.8, 1.51 Hz, 1 H), 7.91 (d, J=8.8 Hz, 2 H), 7.60 (d, J=8.8 Hz, 1 H), 7.48 (d, j=7.3 Hz, 2 H), 7.32 (t, J=7.5 Hz, 2 H), 7.19-7.26 (m, 1 H), 7.09 (d, J=8.8 Hz, 2 H), 4.43-4.59 (m, 2 H), 3.55 (br. s., 2 H), 3.07 (s, 3 H), 3.01 (m, J=7.0 Hz, 2 H), 2.96 (s, 3 H), 2.73 (br. s., 2 H), 2.06-2.16 (m, 2 H), 1.95 (br. s., 2 H), 1.40 (m, J=8.7, 4.14 Hz, 1 H), 0.65 (d, J=8.8 Hz, 2 H), 0.47 (dd, J=9.4, 4.6 Hz, 2 H); MS ESI [M+H]$^+$ 552.4, calcd for [C$_{33}$H$_{37}$N$_5$O$_3$+H]$^+$ 552.30.

Example A159

N-(cyclopentyl(phenyl)methyl)-3-(4-((1-methylpiperidin-4-yl)oxy)phenyl)-1H-indazole-5-carboxamide

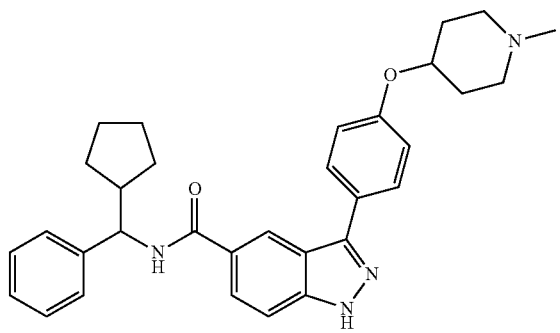 [SMILES: CN1CCC(Oc2ccc(-c3n[nH]c4ccc(C(=O)NC(c5ccccc5)C5CCCC5)cc34)cc2)CC1]

The title compound was synthesized according to the General Method C, utilizing N-(cyclopentyl(phenyl)methyl)-3-iodo-1H-indazole-5-carboxamide (100 mg, 0.21 mmol), (4-((1-methylpiperidin-4-yl)oxy)phenyl)boronic acid pinacol ester (67 mg, 0.21 mmol), Pd(PPh$_3$)$_4$ (12 mg, 0.010 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (light yellow solid, 44 mg, 34%). $^1$H NMR (400 MHz, CD$_3$OD) δ ppm 8.51 (s, 1 H), 7.86-7.95 (m, 3 H), 7.58 (d, J=8.8 Hz, 1 H), 7.44 (d, J=7.3 Hz, 2 H), 7.32 (t, J=7.5 Hz, 2 H), 7.11-7.25 (m, 3 H), 4.83 (d, J=10.8 Hz, 1 H), 4.60-4.72 (m, 0.3 H), 3.59-3.67 (m, 0.7 H), 3.33-3.47 (m, 2.7 H), 3.14-3.25 (m, 0.7 H), 2.91-2.96 (m, 3 H), 2.47-2.59 (m, 1 H), 2.38-2.47 (m, 0.7 H), 2.24-2.33 (m, 1.3 H), 2.04-2.18 (m, 1.3 H), 1.84-2.04 (m, 1.7 H), 1.58-1.78 (m, 3.3 H), 1.36-1.58 (m, 3.3 H), 1.13-1.26 (m, 1 H); MS ESI 509.4 [M+H]$^+$, calcd for [C$_{32}$H$_{36}$N$_4$O$_2$+H]$^+$ 509.3.

Example A160

N-(cyclopropyl(pyridin-2-yl)methyl)-3-(4-((1-formylpiperidin-4-yl)oxy)phenyl)-1H-indazole-5-carboxamide

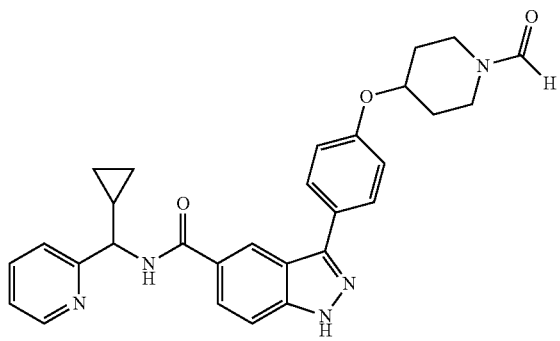 [SMILES: O=CN1CCC(Oc2ccc(-c3n[nH]c4ccc(C(=O)NC(c5ccccn5)C5CC5)cc34)cc2)CC1]

The title compound was synthesized according to General Method C3 utilizing N-(cyclopropyl(pyridin-2-yl)methyl)-3-iodo-1H-indazole-5-carboxamide and 4-(4-(4,4,5,5-tetramethyl-1,3,2-dioxaborolan-2-yl)phenoxy)piperidine-1-carbaldehyde and obtained as a white solid (36 mg, 29% yield). $^1$H NMR (400 MHz, CD$_3$OD) δ ppm 8.77 (dd, J=5.7, 0.7 Hz, 1 H), 8.70 (s, 1 H), 8.56 (t, J=7.1 Hz, 1 H), 8.20 (d, J=8.0 Hz, 1 H), 7.90-8.01 (m, 4 H), 7.63 (d, J=8.8 Hz, 1 H), 7.15 (d, J=8.8 Hz, 2 H), 4.72-4.80 (m, 1 H), 4.49 (d, J=10.0 Hz, 1 H), 3.64-3.82 (m, 2 H), 3.39-3.58 (m, 2 H), 1.92-2.10 (m, 2 H), 1.71-1.90 (m, 2 H), 1.45-1.58 (m, 1 H), 0.84-0.95 (m, 1 H), 0.58-0.81 (m, 3H); MS ESI [M+H]$^+$ 496.3, calcd for [C$_{29}$H$_{29}$N$_5$O$_3$+H]$^+$ 496.23.

Example A161

N-(cyclopentyl(phenyl)methyl)-3-(4-((1-(2-methoxyethyl)piperidin-4-yl)oxy)phenyl)-1H-indazole-5-carboxamide

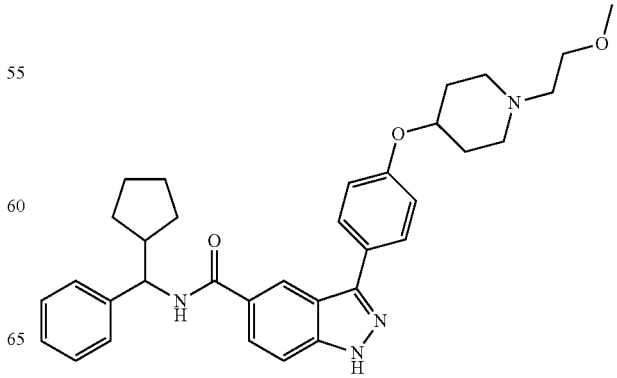

The title compound was synthesized according to the General Method C, utilizing N-(cyclopentyl(phenyl)methyl)-3-iodo-1H-indazole-5-carboxamide (100 mg, 0.21 mmol), (4-((1-(2-methoxyethyl)-piperidin-4-yl)oxy)phenyl)boronic acid pinacol ester (76 mg, 0.21 mmol), Pd(PPh$_3$)$_4$ (12 mg, 0.010 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 42 mg, 30%). $^1$H NMR (400 MHz, CD$_3$OD) δ ppm 8.51 (s, 1 H), 7.86-7.94 (m, 3 H), 7.58 (d, J=8.5 Hz, 1 H), 7.43 (d, J=7.3 Hz, 2 H), 7.31 (t, J=7.5 Hz, 2 H), 7.10-7.25 (m, 3 H), 4.83 (d, J=8.3 Hz, 1 H), 4.60-4.71 (m, 0.3 H), 3.66-3.77 (m, 2.7 H), 3.45-3.56 (m, 1.3 H), 3.43 (s, 3 H), 3.31-3.43 (m, 3.3 H), 3.14-3.27 (m, 1 H), 2.46-2.59 (m, 1 H), 2.34-2.45 (m, 0.7 H), 2.10-2.32 (m, 3 H), 1.90-2.05 (m, 1.7 H), 1.35-1.77 (m, 6 H), 1.12-1.25 (m, 1 H); MS ESI 554.2 [M+H]$^+$, calcd for [C$_{34}$H$_{40}$N$_4$O$_3$+H]$^+$ 553.3.

Example A162

2-cyclopentyl-2-(2-fluorophenyl)-N-(3-(4-((1-methylpiperidin-4-yl)oxy)phenyl)-1H-indazol-5-yl)acetamide

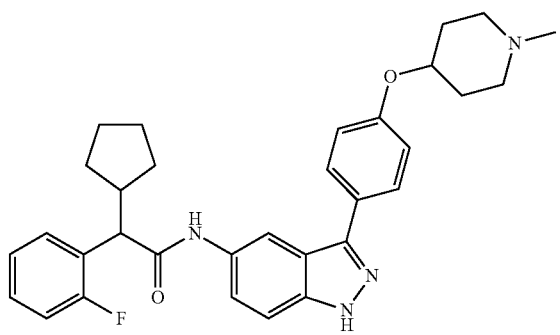 [SMILES: CN1CCC(Oc2ccc(-c3n[nH]c4ccc(NC(=O)C(c5ccccc5F)C5CCCC5)cc34)cc2)CC1]

The title compound was synthesized according to the General Method C, utilizing 2-cyclopentyl-N-(1-(2-cyclopentyl-2-(2-fluorophenyl)acetyl)-3-(4-((1-methylpiperidin-4-yl)oxy)phenyl)-1H-indazol-5-yl)-2-(2-fluorophenyl)acetamide (100 mg, 0.15 mmol), (4-((1-methylpiperidin-4-yl)oxy)phenyl)boronic acid pinacol ester (48 mg, 0.15 mmol), Pd(PPh$_3$)$_4$ (9 mg, 0.0075 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 38 mg, 40%). $^1$H NMR (400 MHz, CD$_3$OD) δ ppm 8.40 (dd, J=4.8, 1.2 Hz, 1 H), 7.82-7.89 (m, 2 H), 7.66-7.73 (m, 1 H), 7.50 (d, J=9.0 Hz, 1 H), 7.37-7.43 (m, 1 H), 7.23-7.30 (m, 1 H), 7.05-7.20 (m, 4 H), 4.59-4.71 (m, 0.3 H), 3.88 (m, J=11.3, 1 H), 3.58-3.67 (m, 0.7 H), 3.33-3.47 (m, 3 H), 3.13-3.26 (m, 0.7 H), 2.89-2.96 (m, 3 H), 2.64-2.77 (m, 1 H), 2.37-2.48 (m, 0.7 H), 2.23-2.35 (m, 1.3 H), 2.03-2.16 (m, 1.3 H), 1.84-2.00 (m, 1.7 H), 1.40-1.81 (m, 6.3 H), 1.05-1.18 (m, 1 H); MS ESI 527.4 [M+H]$^+$, calcd for [C$_{32}$H$_{35}$FN$_4$O$_2$+H]$^+$ 527.3.

Example A163

(S)-N-(cyclopropyl(thiophen-2-yl)methyl)-3-(4-((1-(2-methoxyethyl)piperidin-4-yl)oxy)phenyl)-1H-indazole-5-carboxamide

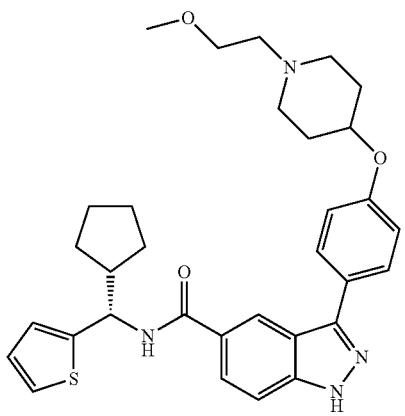 [SMILES: COCCN1CCC(Oc2ccc(-c3n[nH]c4ccc(C(=O)N[C@H](c5cccs5)C5CCCC5)cc34)cc2)CC1]

The title compound was prepared using General Method C3 from (S)-N-(cyclopropyl(thiophen-2-yl)methyl)-3-iodo-1H-indazole-5-carboxamide (110 mg, 0.260 mmol) and 1-(2-methoxyethyl)-4-(4-(4,4,5,5-tetramethyl-1,3,2-dioxaborolan-2-yl)phenoxy)piperidine (122 mg, 0.338 mmol) which gave 77 mg of product isolated as its TFA salt (56%, an off-white solid). $^1$H NMR (400 MHz, CD$_3$OD) δ ppm 8.60 (s, 1H), 7.97-7.94 (m, 3H), 7.61 (d, J=8.9 Hz, 1H), 7.27 (d, J=5.3 Hz, 1H), 7.20-7.12 (m, 3H), 6.98-6.96 (m, 1H), 4.87 (bs, 1H), 4.75 (d, J=9.6 Hz, 1H), 3.76-3.19 (m, 11H), 2.42-1.95 (m, 4H), 1.54-1.48 (m, 1H), 0.80-0.67 (m, 2H), 0.55-0.49 (m, 2H); MS ESI 531.5 [M+H]$^+$, calcd for [C$_{30}$H$_{34}$N$_4$O$_3$S+H]$^+$ 531.24.

Example A164

(S)-N-(2-methoxy-1-phenylethyl)-3-(4-((1-(2-methoxyethyl)piperidin-4-yl)oxy)phenyl)-1H-indazole-5-carboxamide

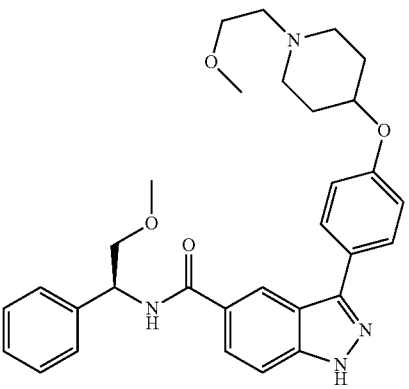 [SMILES: COCCN1CCC(Oc2ccc(-c3n[nH]c4ccc(C(=O)N[C@H](COC)c5ccccc5)cc34)cc2)CC1]

The title compound was prepared using General Method C3 from (S)-3-iodo-N-(2-methoxy-1-phenylethyl)-1H-indazole-5-carboxamide (110 mg, 0.260 mmol) and 1-(2-methoxyethyl)-4-(4-(4,4,5,5-tetramethyl-1,3,2-dioxaborolan-2-yl)phenoxy)piperidine (122 mg, 0.338 mmol) which gave 97 mg of product isolated as its TFA salt (71%, off white solid). ¹H NMR (400 MHz, CD₃OD) δ ppm 8.58 (s, 1H), 7.96-7.93 (m, 3H), 7.61 (d, J=8.8 Hz, 1H), 7.43 (d, J=7.6 Hz, 2H), 7.28-7.15 (m, 5H), 5.42-5.38 (m, 1H), 4.87 (bs, 1H), 3.84-3.68 (m, 5H), 3.53-3.19 (m, 11H), 2.43-2.27 (m, 2H), 2.19-1.96 (m, 2H); MS ESI 529.5 [M+H]⁺, calcd for [C₃₁H₃₆N₄O₄+H]⁺ 529.28.

Example A165

3-(4-(2-(1H-imidazol-1-yl)ethoxy)phenyl)-N-(cyclopropyl(phenyl)methyl)-1H-indazole-5-carboxamide

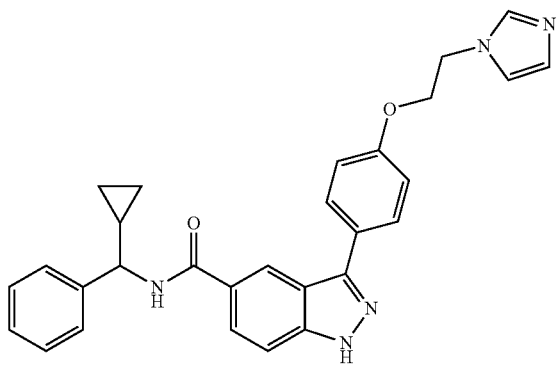 [SMILES: O=C(NC(c1ccccc1)C1CC1)c1ccc2[nH]nc(-c3ccc(OCCn4ccnc4)cc3)c2c1]

The title compound was synthesized according to the General Method C, utilizing N-(cyclopropyl(phenyl) methyl)-3-iodo-1H-indazole-5-carboxamide (100 mg, 0.22 mmol), 4-(2-(1H-imidazol-1-yl)ethoxy)phenyl boronic acid (51 mg, 0.22 mmol), Pd(PPh₃)₄ (13 mg, 0.011 mmol), satd. aq Na₂CO₃ (1.25 mL), and 3.75 mL of PhMe:EtOH (1:1). The vial was charged with Ar and heated in the microwave reactor at 125° C. for 2 h. Purification by RPHPLC, followed by trituration with Et₂O gave the title compound as a TFA salt (white solid, 70 mg, 54%). ¹H NMR (400 MHz, CD₃OD) δ ppm 9.09 (s, 1 H), 8.56 (s, 1 H), 7.94 (t, J=8.5 Hz, 3 H), 7.79 (s, 1 H), 7.57-7.63 (m, 2 H), 7.48 (d, J=7.8 Hz, 2 H), 7.34 (t, J=7.6 Hz, 2 H), 7.24 (t, J=7.5 Hz, 1 H), 7.12 (d, J=8.5 Hz, 2 H), 4.73 (t, J=4.8 Hz, 2 H), 4.42-4.52 (m, 3 H), 1.35-1.46 (m, 1 H), 0.62-0.70 (m, 2 H), 0.42-0.53 (m, 2 H); MS ESI 478.3 [M+H]⁺, calcd for [C₂₉H₂₇N₅O₂+H]⁺ 478.2.

Example A166

(R)-N-((3-chlorothiophen-2-yl)(cyclopropyl) methyl)-3-(4-((1-methylpiperidin-4-yl)oxy)phenyl)-1H-indazole-5-carboxamide

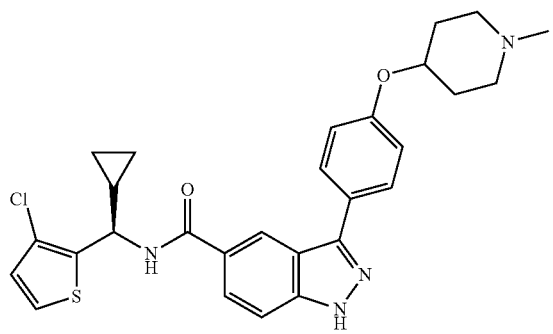

Using General Method C2, (R)-N-((3-chlorothiophen-2-yl)(cyclopropyl)methyl)-3-iodo-1H-indazole-5-carboxamide (76.6 mg, 85% pure, 0.142 mmol) and 1-methyl-4-(4-(4,4,5,5-tetramethyl-1,3,2-dioxaborolan-2-yl)phenoxy) piperidine (46.1 mg, 0.145 mmol) for 2 h at 125° C. in the microwave, the mixture was passed through a PoraPak Rxn Cx with acetone/MeOH and the product was eluted with 2 M NH₃-MeOH. Purification by flash chromatography (SiO₂, 5-25% MeOH in DCM, then 25% 2 M NH₃-MeOH in DCM; followed by RP HPLC, 10-90% MeOH in 0.1% TFA-H₂O) gave the title compound as the TFA salt (beige solid, 28.9 mg, 32%). ¹H NMR (400 MHz, CD₃OD) δ ppm 9.15 (d, J=7.5 Hz, 0.2 H partially exchanged), 8.57 (s, 1 H), 7.88-7.98 (m, 3 H), 7.61 (d, J=9.0 Hz, 1 H), 7.38 (d, J=5.3 Hz, 1 H), 7.11-7.23 (m, 2 H), 6.94 (s, 1 H), 4.97 (d, J=8.8 Hz, 1 H), 4.61-4.72 (m, 0.3 H), 3.65 (d, J=12.5 Hz, 0.7 H), 3.34-3.48 (m, 3 H), 3.16-3.26 (m, 0.7 H), 2.95, 2.94 (2-s, 3 H), 2.44 (d, J=14.6 Hz, 0.7 H), 2.26-2.35 (m, 1.3 H), 2.06-2.19 (m, 1.3 H), 1.86-1.99 (m, 0.7 H), 1.45-1.56 (m, 1 H), 0.61-0.73 (m, 2 H), 0.50-0.61 (m, 2 H). MS ESI 521.4 [M+H]⁺, calcd for [C₂₈H₂₉ClN₄O₂S+H]⁺ 521.18.

Example A167

(S)-N-((3-chlorothiophen-2-yl)(cyclopropyl)methyl)-3-(4-((1-methylpiperidin-4-yl)oxy)phenyl)-1H-indazole-5-carboxamide

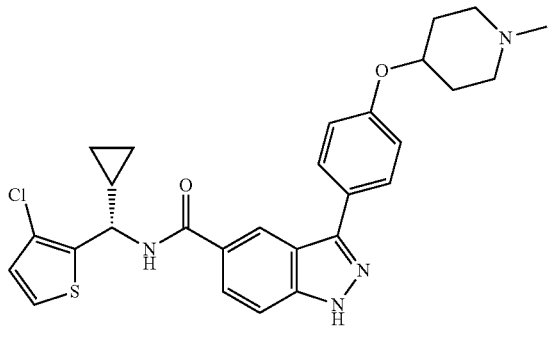 [SMILES: CN1CCC(Oc2ccc(-c3n[nH]c4ccc(C(=O)N[C@H](c5sccc5Cl)C5CC5)cc34)cc2)CC1]

Using General Method C2, (S)-N-((3-chlorothiophen-2-yl)(cyclopropyl)methyl)-3-iodo-1H-indazole-5-carboxamide (102.1 mg, 85% pure, 0.19 mmol) and 1-methyl-4-(4-(4,4,5,5-tetramethyl-1,3,2-dioxaborolan-2-yl)phenoxy) piperidine (60.4 mg, 0.19 mmol) for 2 h at 130° C. in the microwave, the mixture was passed through a PoraPak Rxn Cx with acetone/MeOH and the product was eluted with 2 M NH₃-MeOH. Purification by flash chromatography (SiO₂, 15% MeOH in DCM, then 15-35% 2 M NH₃-MeOH in DCM; followed by RP HPLC, 10-90% MeOH in 0.1% TFA-H₂O) gave the title compound as the TFA salt (beige solid, 31.8 mg, 26%). ¹H NMR (400 MHz, CD₃OD) δ ppm 9.15 (d, J=7.5 Hz, 0.2 H partially exchanged), 8.57 (s, 1 H), 7.88-7.98 (m, 3 H), 7.61 (d, J=9.0 Hz, 1 H), 7.38 (d, J=5.3 Hz, 1 H), 7.11-7.23 (m, 2 H), 6.94 (s, 1 H), 4.97 (d, J=8.8 Hz, 1 H), 4.61-4.72 (m, 0.35 H), 3.65 (d, J=12.5 Hz, 0.65 H), 3.34-3.48 (m, 3 H), 3.16-3.26 (m, 0.7 H), 2.95, 2.94 (2-s, 3 H), 2.44 (d, J=14.6 Hz, 0.7 H), 2.26-2.35 (m, 1.3 H), 2.06-2.19 (m, 1.3 H), 1.86-1.99 (m, 0.7 H), 1.45-1.56 (m, 1 H), 0.61-0.73 (m, 2 H), 0.50-0.61 (m, 2 H). MS ESI 521.4 [M+H]⁺, calcd for [C₂₈H₂₉ClN₄O₂S+H]⁺ 521.18.

Example A169

(R)-N-(3-(4-((1-formylpiperidin-4-yl)oxy)phenyl)-1H-indazol-5-yl)-2-methoxy-2-phenylacetamide

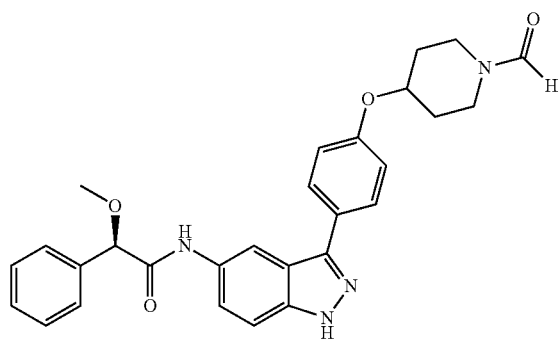 [SMILES: CO[C@@H](C(=O)Nc1ccc2[nH]nc(-c3ccc(OC4CCN(C=O)CC4)cc3)c2c1)c1ccccc1]

The title compound was synthesized according to General Method C3 utilizing (R)-N-(3-iodo-1H-indazol-5-yl)-2-methoxy-2-phenylacetamide and 4-(4-(4,4,5,5-tetramethyl-1,3,2-dioxaborolan-2-yl)phenoxy)piperidine-1-carbaldehyde and obtained as an off-white solid (59 mg, 50% yield). $^1$H NMR (400 MHz, CD$_3$OD) δ ppm 8.39 (d, J=1.0 Hz, 1 H), 7.95 (s, 1 H), 7.78 (d, J=8.8 Hz, 2 H), 7.44-7.56 (m, 4 H), 7.25-7.38 (m, 3 H), 6.96 (d, J=8.8 Hz, 2 H), 4.80 (s, 1 H), 4.54 (dt, J=6.5, 3.5 Hz, 1 H), 3.59-3.69 (m, 1 H), 3.47-3.57 (m, 1 H), 3.37-3.45 (m, 4 H), 3.20-3.30 (m, 1 H), 1.75-1.92 (m, 2 H), 1.57-1.74 (m, 2 H); MS ESI [M+H]$^+$ 485.4, calcd for [C$_{28}$H$_{28}$N$_4$O$_4$+H]$^+$ 485.22.

Example A170

N-(cyclohexyl(phenyl)methyl)-3-(4-((1-methylpiperidin-4-yl)oxy)phenyl)-1H-indazole-5-carboxamide

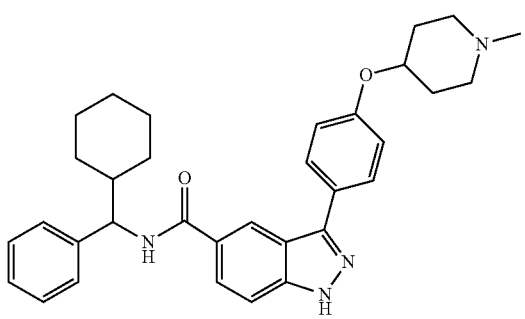 [SMILES: CN1CCC(Oc2ccc(-c3n[nH]c4ccc(C(=O)NC(c5ccccc5)C5CCCCC5)cc34)cc2)CC1]

The title compound was synthesized according to the General Method C, utilizing N-(cyclohexyl(phenyl)methyl)-3-iodo-1H-indazole-5-carboxamide (100 mg, 0.22 mmol), (4-((1-methylpiperidin-4-yl)oxy)phenyl)boronic acid pinacol ester (70 mg, 0.22 mmol), Pd(PPh$_3$)$_4$ (13 mg, 0.01 mmol), satd. aq Na$_2$CO$_3$ (1.25 mL), and 3.75 mL of PhMe: EtOH (1:1). The vial was charged with Ar and heated in the microwave reactor at 125° C. for 2 h. Purification by RPHPLC gave the title compound as a TFA salt (white solid, 46 mg, 33%). $^1$H NMR (400 MHz, CD$_3$OD) δ ppm 8.51 (s, 1 H), 7.85-7.96 (m, 3 H), 7.58 (d, J=8.8 Hz, 1 H), 7.40 (d, J=7.3 Hz, 2 H), 7.32 (t, J=7.6 Hz, 2 H), 7.10-7.26 (m, 3 H), 4.81 (d, J=10.0 Hz, 1 H), 4.60-4.70 (m, 0.3 H), 3.59-3.68 (m, 0.7 H), 3.33-3.47 (m, 3 H), 3.13-3.25 (m, 0.7 H), 2.89-2.96 (m, 3 H), 2.37-2.45 (m, 0.7 H), 2.23-2.33 (m, 1.3 H), 2.03-2.17 (m, 2.4 H), 1.84-1.97 (m, 1.7 H), 1.74-1.84 (m, 1 H), 1.60-1.71 (m, 2 H), 1.08-1.39 (m, 6.3 H), 0.86-0.99 (m, 1 H); MS ESI 523.5 [M+H]$^+$, calcd for [C$_{33}$H$_{38}$N$_4$O$_2$+H]$^+$ 523.3.

Example A171

N-(cyclopropyl(pyridin-2-yl)methyl)-3-(4-((1-(oxetan-3-yl)piperidin-4-yl)oxy)phenyl)-1H-indazole-5-carboxamide

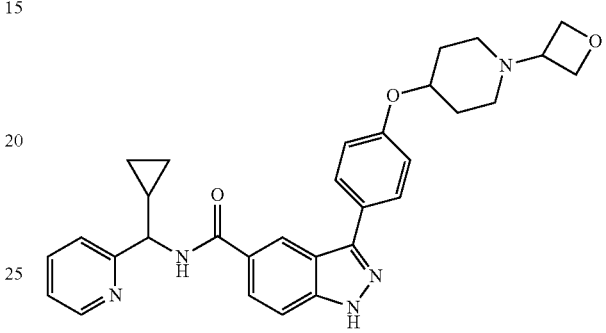

The title compound was synthesized according to General Method C3 utilizing N-(cyclopropyl(pyridin-2-yl)methyl)-3-iodo-1H-indazole-5-carboxamide and 1-(oxetan-3-yl)-4-(4-(4,4,5,5-tetramethyl-1,3,2-dioxaborolan-2-yl)phenoxy)piperidine and obtained as a white solid (23 mg, 23% yield). $^1$H NMR (400 MHz, CD$_3$OD) δ ppm 8.65 (s, 1 H), 8.52 (d, J=4.0 Hz, 1 H), 7.96 (dd, J=8.9, 1.3 Hz, 1 H), 7.92 (d, J=8.5 Hz, 2 H), 7.81 (td, J=7.6, 1.7 Hz, 1 H), 7.60 (d, J=9.2 Hz, 1 H), 7.53 (d, J=8.0 Hz, 1 H), 7.27-7.34 (m, 1 H), 7.09 (d, J=8.8 Hz, 2 H), 4.65-4.74 (m, 2 H), 4.61 (t, J=6.2 Hz, 2 H), 4.51 (d, J=9.5 Hz, 2 H), 3.52 (quin, J=6.4 Hz, 1 H), 2.61 (br. s., 2 H), 2.25 (br. s., 2 H), 2.01-2.11 (m, 2 H), 1.78-1.90 (m, 2 H), 1.35-1.46 (m, 1 H), 0.69 (br. s., 1 H), 0.48-0.63 (m, 3 H); MS ESI [M+H]$^+$ 524.2, calcd for [C$_{31}$H$_{33}$N$_5$O$_3$+H]$^+$ 524.27.

Example A172

2-(azetidin-1-yl)-N-(3-(4-morpholinophenyl)-1H-indazol-5-yl)-2-(thiophen-3-yl)acetamide

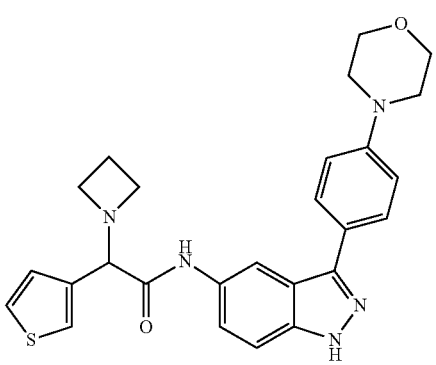 [SMILES: O=C(Nc1ccc2[nH]nc(-c3ccc(N4CCOCC4)cc3)c2c1)C(c1ccsc1)N1CCC1]

A mixture of thiophen-3-ylboronic acid (5.61 g, 43.9 mmol) and glyoxylic acid monohydrate (4.04 g, 43.9 mmol)

in DCM (200 mL) was stirred for 5 min at rt before azetidine (2.50 g, 43.9 mmol) was added. The resulting mixture was stirred O/N at rt. White precipitates formed were collected by suction filtration, rinsed with DCM and dried to give 2-(azetidin-1-yl)-2-(thiophen-3-yl)acetic acid as a $H_3BO_3$ salt (light beige solid, 10.96 g). $^1$H NMR (400 MHz, $CD_3OD$) δ 7.64 (s, 1H), 7.52 (t, 1H), 7.19 (d, J=4.8 Hz, 1H), 4.45-3.50 (m, 4H), 2.60-2.30 (m, 2H); MS ESI 197.9 [M+H]$^+$, calcd for [$C_9H_{11}NO_2S$+H]$^+$ 198.0.

To a mixture of 2-(azetidin-1-yl)-2-(thiophen-3-yl)acetic acid $H_3BO_3$ salt (52 mg, 0.2 mmol), 3-(4-morpholinophenyl)-1H-indazol-5-amine di-trifluoroacetic acid (259 mg, 90% pure, 0.2 mmol) in DMF (5 mL) at 0° C. was added TBTU (65 mg, 0.2 mmol), followed by $^iPr_2NEt$ (0.14 mL, 0.8 mmol). The resulting mixture was stirred for 30 min at 0° C. It was purified by prep-HPLC and PoraPak to give the title compound (pale yellow solid, 8.0 mg, 8%). $^1$H NMR (400 MHz, $CD_3OD$) δ 8.32 (s, 1H), 7.80 (d, J=8.8 Hz, 2H), 7.52-7.49 (m, 3H), 7.41 (dd, J=8.6 Hz, 3.0 Hz, 1H), 7.25 (d, J=4.8 Hz, 1H), 7.09 (d, J=8.8 Hz, 2H), 4.21 (s, 1H), 3.86 (t, J=4.8 Hz, 4H), 3.40 (q, J=6.8 Hz, 2H), 3.27-3.18 (m, 6H), 2.15 (quint, 7.0 Hz, 2H); MS ESI 474.2 [M+H]$^+$, calcd for [$C_{26}H_{27}N_5O_2S$+H]$^+$ 474.2.

Example A173

(S)-N-(2-methoxy-1-phenylethyl)-3-(4-((1-methylpiperidin-4-yl)oxy)phenyl)-5-carboxamide

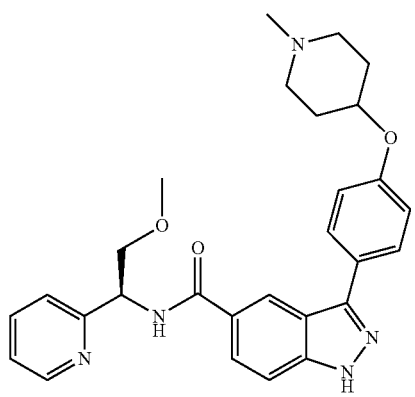 [SMILES: COC[C@@H](NC(=O)c1ccc2[nH]nc(-c3ccc(OC4CCN(C)CC4)cc3)c2c1)c1ccccn1]

The title compound was prepared using General Method C3 from (S)-3-iodo-N-(2-methoxy-1-phenylethyl)-1H-indazole-5-carboxamide (68 mg, 0.166 mmol) and 1-methyl-4-(4-(4,4,5,5-tetramethyl-1,3,2-dioxaborolan-2-yl)phenoxy)piperidine (70 mg, 0.216 mmol) which gave product as a white solid (34 mg, 43% yield) isolated as its TFA salt. $^1$H NMR (400 MHz, $CD_3OD$) δ ppm 8.58 (s, 1H), 7.97-7.93 (m, 3H), 7.62 (d, J=8.8 Hz, 1H), 7.44 (d, J=7.6 Hz, 2H), 7.28-7.15 (m, 5H), 5.42-5.39 (m, 1H), 4.87 (bs, 1H), 3.84-3.68 (m, 3H), 3.42-3.30 (m, 6H), 2.95-2.93 (m, 3H), 2.47-2.30 (m, 2H), 2.15-2.10 (m, 2H); MS ESI 485.4 [M+H]$^+$, calcd for [$C_{29}H_{32}N_4O_3$+H]$^+$ 485.26.

Example A174

(R)-N-(1-(3-methoxyphenyl)propyl)-3-(4-((1-methylpiperidin-4-yl)oxy)phenyl)-1H-indazole-5-carboxamide

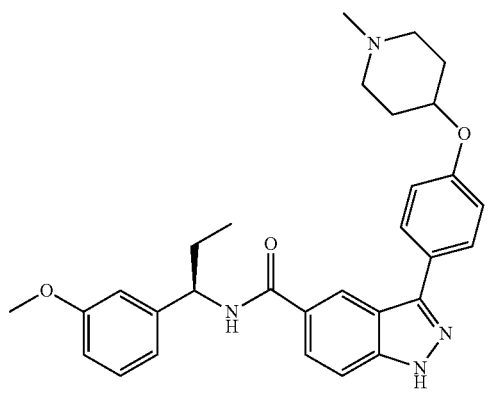 [SMILES: CC[C@@H](NC(=O)c1ccc2[nH]nc(-c3ccc(OC4CCN(C)CC4)cc3)c2c1)c1cccc(OC)c1]

The title compound was prepared using General Method C3 from (R)-3-iodo-N-(1-(3-methoxyphenyl)propyl)-1H-indazole-5-carboxamide (70 mg, 0.161 mmol) and 1-methyl-4-(4-(4,4,5,5-tetramethyl-1,3,2-dioxaborolan-2-yl)phenoxy)piperidine (66 mg, 0.209 mmol) which gave of product (26 mg) isolated as its TFA salt (gave 26 mg, 33%, white solid). $^1$H NMR (400 MHz, $CD_3OD$) δ ppm 8.55 (s, 1H), 7.95-7.91 (m, 3H), 7.60 (d, J=8.8 Hz, 1H), 7.26-7.13 (m, 3H), 6.99-6.87 (m, 2H), 6.79 (m, 1H), 5.01-4.97 (m, 1H), 4.87 (bs, 1H), 3.97 (s, 3H), 3.65-3.17 (m, 4H), 2.94-2.93 (m, 3H), 2.45-2.27 (m, 2H), 2.15-1.89 (m, 2H), 1.00 (t, J=7.2 Hz, 3H); MS ESI 500.2 [M+H]$^+$, calcd for [$C_{30}H_{34}N_4O_3$+H]$^+$ 499.27.

Example A175

N-(3-(4-((1-(2-methoxyethyl)piperidin-4-yl)oxy)phenyl)-1H-indazol-5-yl)-2-(pyrrolidin-1-yl)-2-(thiophen-3-yl)acetamide

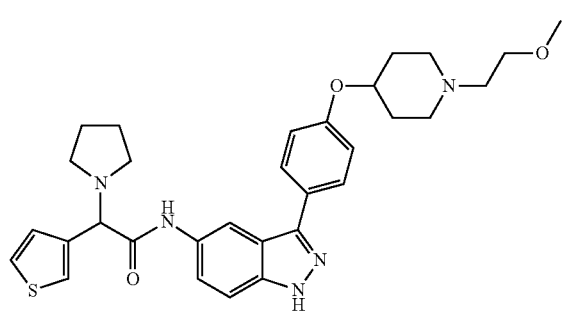 [SMILES: COCCN1CCC(Oc2ccc(-c3n[nH]c4ccc(NC(=O)C(c5ccsc5)N5CCCC5)cc34)cc2)CC1]

The title compound was prepared using General Method C3 from N-(3-iodo-1H-indazol-5-yl)-2-(pyrrolidin-1-yl)-2-(thiophen-3-yl)acetamide (42 mg, 0.093 mmol) and 1-(2-methoxyethyl)-4-(4-(4,4,5,5-tetramethyl-1,3,2-dioxaborolan-2-yl)phenoxy)piperidine (44 mg, 0.121 mmol) which gave 10 mg of product isolated as its di-TFA salt (10 mg, 19%, a white solid). $^1$H NMR (400 MHz, $CD_3OD$) δ ppm 8.35 (s, 1H), 7.87-7.83 (m, 3H), 7.66-7.64 (m, 1H), 7.55-7.48 (m, 2H), 7.37 (d, J=5.1 Hz, 1H), 7.21-7.14 (m, 2H), 5.21 (bs, 1H), 4.87 (bs, 1H), 3.89-3.71 (m, 4H), 3.55-3.05

Example A176

2-cyclopentyl-N-(3-(4-((1-formylpiperidin-4-yl)oxy)phenyl)-1H-indazol-5-yl)-2-(pyridin-2-yl)acetamide

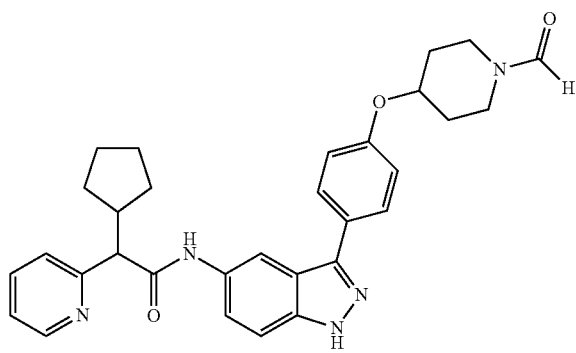 [SMILES: O=CN1CCC(Oc2ccc(-c3n[nH]c4ccc(NC(=O)C(c5ccccn5)C5CCCC5)cc34)cc2)CC1]

The mixture of 2-cyclopentyl-N-(3-iodo-1H-indazol-5-yl)-2-(pyridin-2-yl)acetamide (50 mg, 0.112 mmol), 4-(4-(4,4,5,5-tetramethyl-1,3,2-dioxaborolan-2-yl)phenoxy)piperidine-1-carbaldehyde (41 mg, 0.123 mmol), Pd(PPh$_3$)$_4$ (13 mg, 0.011 mmol), LiCl (14 mg, 0.336 mmol), 2 M aq Na$_2$CO$_3$ solution (0.28 mL, 0.56 mmol) in dioxane (1 mL) was stirred at 125° C. for 3 h with microwave irradiation under Ar. The resulting reaction mixture was filtered through Celite and the filtrate was concentrated under reduced pressure. The residue was purified by prep HPLC followed by running through PoraPak to give the title compound as a peach solid (39 mg, 67% yield). $^1$H NMR (400 MHz, CD$_3$OD) δ ppm 8.48 (d, J=5.0 Hz, 1 H), 8.41 (s, 1 H), 8.00 (s, 1 H), 7.79 (d, J=8.3 Hz, 2 H), 7.75 (td, J=7.8, 1.7 Hz, 1 H), 7.62 (d, J=8.0 Hz, 1 H), 7.43-7.51 (m, 2 H), 7.23-7.29 (m, 1 H), 7.01 (d, J=8.8 Hz, 2 H), 4.62 (tt, J=6.8, 3.4 Hz, 1 H), 3.69 (td, J=8.5, 4.0 Hz, 1 H), 3.56-3.65 (m, 2 H), 3.40-3.49 (m, 1 H), 3.28-3.38 (m, 1 H), 2.79 (m, J=10.9 Hz, 1 H), 1.82-2.01 (m, 3 H), 1.36-1.79 (m, 8 H), 1.08 (dd, J=12.3, 8.0 Hz, 1 H); MS ESI [M+H]$^+$ 524.4, calcd for [C$_{31}$H$_{33}$N$_5$O$_3$+H]$^+$ 524.27.

Example A177

3-(4-((1-methylpiperidin-4-yl)oxy)phenyl)-N-(phenyl(tetrahydro-2H-pyran-4-yl)methyl)-1H-indazole-5-carboxamide

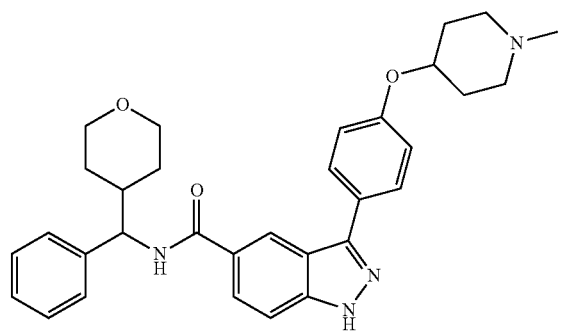 [SMILES: CN1CCC(Oc2ccc(-c3n[nH]c4ccc(C(=O)NC(c5ccccc5)C5CCOCC5)cc34)cc2)CC1]

The title compound was synthesized according to the General Method C, utilizing 3-iodo-N-(phenyl(tetrahydro-2H-pyran-4-yl)methyl)-1H-indazole-5-carboxamide (100 mg, 0.22 mmol), (4-((1-methylpiperidin-4-yl)oxy)phenyl) boronic acid pinacol ester (70 mg, 0.22 mmol), Pd(PPh$_3$)$_4$ (13 mg, 0.01 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 25 mg, 18%). $^1$H NMR (400 MHz, CD$_3$OD) δ ppm 8.52 (s, 1 H), 7.90 (dd, J=8.9, 2.9 Hz, 3 H), 7.58 (d, J=8.8 Hz, 1 H), 7.42 (d, J=6.8 Hz, 2 H), 7.33 (t, J=7.5 Hz, 2 H), 7.25 (d, J=7.3 Hz, 1 H), 7.09-7.18 (m, 2 H), 4.85 (d, J=10.5 Hz, 1 H), 4.59-4.69 (m, 0.3 H), 3.94-4.02 (m, 1 H), 3.81-3.89 (m, 1 H), 3.57-3.67 (m, 0.7 H), 3.34-3.46 (m, 3.7 H), 3.28 (d, J=2.0 Hz, 0.7 H), 2.89-2.95 (m, 3 H), 2.34-2.45 (m, 0.7 H), 2.24 (br. s., 1.5 H), 2.04-2.21 (m, 2.7 H), 1.84-2.00 (m, 1.7 H), 1.38-1.53 (m, 1 H), 1.12-1.31 (m, 3 H); MS ESI 525.4 [M+H]$^+$, calcd for [C$_{32}$H$_{36}$N$_4$O$_3$+H]$^+$ 525.3.

Example A178

N-(cyclopropyl(phenyl)methyl)-3-(4-((1R,3R,5S)-8-methyl-8-azabicyclo[3.2.1]octan-3-yl)oxy)phenyl)-1H-indazole-5-carboxamide

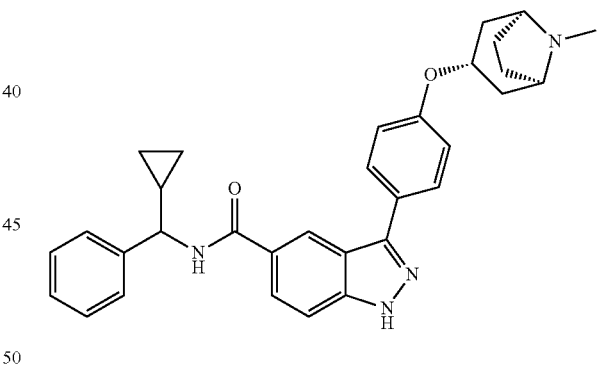

The title compound was synthesized according to the General Method C2 utilizing 2-cyclopropyl-N-(3-iodo-1H-indazol-5-yl)-2-phenylacetamide (90 mg, 0.22 mmol) and (1R,3R,5S)-8-methyl-3-(4-(4,4,5,5-tetramethyl-1,3,2-dioxaborolan-2-yl)phenoxy)-8-azabicyclo[3.2.1]octane (0.14 g, ~0.31 mmol) to afford the title compound as a white powder (7.5 mg, 7%). NMR (400 MHz, CD$_3$OD) δ ppm 8.61 (s, 1 H), 7.89-8.00 (m, 3 H), 7.61 (d, J=8.8 Hz, 1 H), 7.49 (d, J=7.2 Hz, 2 H), 7.33 (t, J=7.5 Hz, 2 H), 7.24 (t, J=7.3 Hz, 1 H), 7.04 (d, J=8.8 Hz, 2 H), 4.69 (t, J=4.7 Hz, 1 H), 4.48 (d, J=9.2 Hz, 1 H), 3.44 (br. s., 2 H), 2.50 (s, 3 H), 2.02-2.37 (m, 8 H), 1.48-1.37 (m, 1 H), 0.70-0.62 (m, 2 H), 0.52-0.42 (m, 2 H); MS ESI 507.3 [M+H]$^+$, calcd for [C$_{32}$H$_{34}$N$_4$O$_2$+H]$^+$ 507.3.

(starting partial from previous page) (m, 11H), 2.44-2.28 (m, 2H), 2.18-1.95 (m, 2H); MS ESI 560.2 [M+H]$^+$, calcd for [C$_{31}$H$_{37}$N$_5$O$_3$S+H]$^+$ 560.27.

Example A179

2-cyclopentyl-N-(3-(4-((1-methylpiperidin-4-yl)oxy)phenyl)-1H-indazol-5-yl)-2-(pyridin-2-yl)acetamide

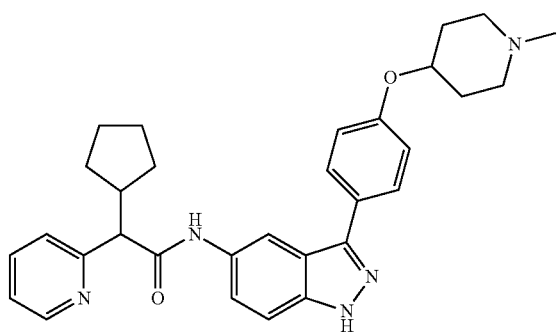 [SMILES: CN1CCC(Oc2ccc(-c3n[nH]c4ccc(NC(=O)C(c5ccccn5)C5CCCC5)cc34)cc2)CC1]

The title compound was synthesized according to General Method C3 utilizing 2-cyclopentyl-N-(3-iodo-1-(tetrahydro-2H-pyran-2-yl)-1H-indazol-5-yl)-2-(pyridin-2-yl)acetamide and 1-methyl-4-(4-(4,4,5,5-tetramethyl-1,3,2-dioxaborolan-2-yl)phenoxy)piperidine and obtained as a white solid (18 mg, 32% yield). $^1$H NMR (400 MHz, CD$_3$OD) δ ppm 8.47-8.53 (m, 1 H), 8.37 (d, J=1.0 Hz, 1 H), 7.75-7.85 (m, 3 H), 7.64 (d, J=8.0 Hz, 1 H), 7.43-7.52 (m, 2 H), 7.31 (ddd, J=7.2, 5.0, 1.0 Hz, 1 H), 7.05 (d, J=8.8 Hz, 2 H), 4.46 (br. s., 1 H), 3.61 (d, J=11.0 Hz, 1 H), 2.64-2.87 (m, 3 H), 2.39 (br. s., 2 H), 2.27-2.33 (m, 3 H), 1.90-2.09 (m, 3 H), 1.40-1.89 (m, 8 H), 1.11 (m, J=12.5, 8.0 Hz, 1 H); MS ESI [M+H]$^+$ 510.2, calcd for [C$_{31}$H$_{35}$N$_5$O$_2$+H]$^+$ 510.29.

Example A180

N-(cyclopropyl(pyridin-2-yl)methyl)-3-(4-(4-(2-hydroxypropan-2-yl)piperidin-1-yl)phenyl)-1H-indazole-5-carboxamide

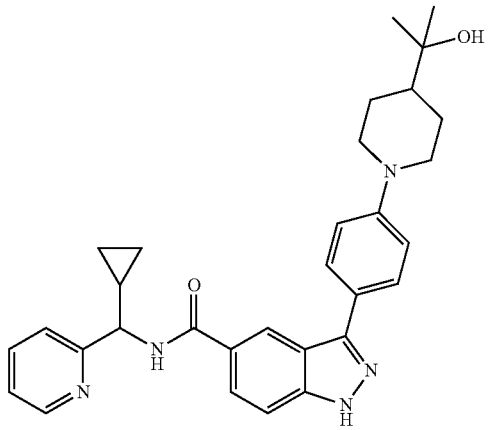 [SMILES: CC(C)(O)C1CCN(c2ccc(-c3n[nH]c4ccc(C(=O)NC(c5ccccn5)C5CC5)cc34)cc2)CC1]

The title compound was synthesized according to General Method C3 utilizing N-(cyclopropyl(pyridin-2-yl)methyl)-3-iodo-1H-indazole-5-carboxamide and 2-(1-(4-(4,4,5,5-tetramethyl-1,3,2-dioxaborolan-2-yl)phenyl)piperidin-4-yl)propan-2-ol and obtained as a white solid (16 mg, 16% yield). $^1$H NMR (400 MHz, CD$_3$OD) δ ppm 8.67 (s, 1 H), 8.51 (d, J=4.7 Hz, 1 H), 7.95 (dd, J=8.8, 1.5 Hz, 1 H), 7.86 (d, J=8.8 Hz, 2 H), 7.79 (td, J=7.8, 1.7 Hz, 1 H), 7.58 (d, J=8.8 Hz, 1 H), 7.52 (d, J=7.8 Hz, 1 H), 7.29 (ddd, J=6.9, 5.6, 1.0 Hz, 1 H), 7.09 (d, J=9.0 Hz, 2 H), 4.50 (d, J=9.2 Hz, 1 H), 3.84 (d, J=12.0 Hz, 2 H), 2.65 (t, J=11.2 Hz, 2 H), 1.86 (d, J=9.7 Hz, 2 H), 1.34-1.54 (m, 4 H), 1.17 (s, 6 H), 0.67 (m, J=8.0 Hz, 1 H), 0.47-0.61 (m, 3 H); MS ESI [M+H]$^+$ 510.2, calcd for [C$_{31}$H$_{35}$N$_5$O$_2$+H]$^+$ 510.29.

Example A181

2-ethoxy-N-(3-(4-((1-methylpiperidin-4-yl)oxy)phenyl)-1H-indazol-5-yl)-2-phenylacetamide

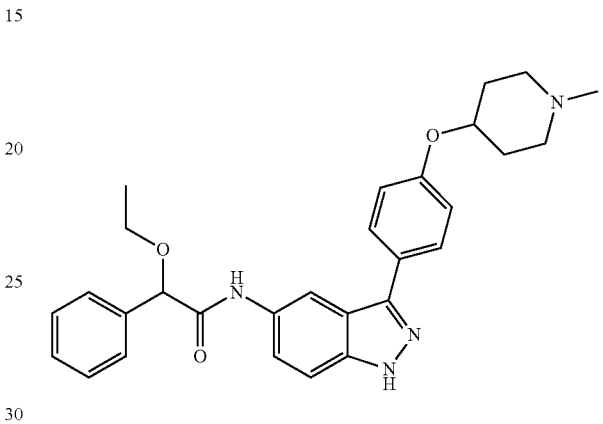

A. 2-Ethoxy-N-(3-iodo-1H-indazol-5-yl)-2-phenylacetamide was synthesized according to General Method A utilizing 3-iodo-1H-indazol-5-amine (200 mg, 0.77 mmol) and 2-ethoxy-2-phenylacetic acid (155 mg, 0.86 mmol), TBTU (250 mg, 0.78 mmol) and DIPEA (0.36 mL, 2.3 mmol) in DMF (5 mL). The crude material was precipitated by adding H$_2$O, collected by filtration, dried and taken into MeOH (5 mL). Heating with MeONa (1.3 mL, 25 wt % in MeOH, 6.0 mmol) at 50° C. for 45 min, cooling to rt, concentration to dryness followed by flash chromatography (SiO$_2$, 2-25% MeOH in DCM) provided 2-ethoxy-N-(3-iodo-1H-indazol-5-yl)-2-phenylacetamide as an off-white solid (121 mg, 37%). MS ESI 422.1 [M+H]$^+$, calcd for [C$_{17}$H$_{16}$IN$_3$O+H]$^+$ 422.0.

B. 2-Ethoxy-N-(3-(4-((1-methylpiperidin-4-yl)oxy)phenyl)-1H-indazol-5-yl)-2-phenylacetamide synthesized according to the General Method C2 utilizing 2-ethoxy-N-(3-iodo-1 H-indazol-5-yl)-2-phenylacetamide (63 mg, 0.15 mmol), 1-methyl-4-(4-(4,4,5,5-tetramethyl-1,3,2-dioxaborolan-2-yl)phenoxy)piperidine (62 mg, 0.19 mmol), PdCl$_2$dppf.CH$_2$Cl$_2$ (7 mg, 0.009 mmol), satd aq Na$_2$CO$_3$ (0.5 mL) in PhMe (1.5 mL) and EtOH (1.5 mL) under microwave heating (130° C., 2 h). The title compound was isolated after flash chromatography (SiO$_2$, 0-60% MeOH-DCM) followed by four separate purifications using: (a) RP HPLC (Biotage C18 column, MeOH—H$_2$O+0.1% TFA), (b) PoraPak, (c) prep-TLC (SiO$_2$, 10% 7M NH$_3$/MeOH in DCM) and (d) trituration with hexanes; as a white powder (9.6 mg, 13%). $^1$H NMR (400 MHz, CD$_3$OD) δ ppm 8.35 (d, J=1.0 Hz, 1H), 7.84 (d, J=8.8 Hz, 2H), 7.48-7.59 (m, 4H), 7.30-7.44 (m, 3H), 7.09 (d, J=8.8 Hz, 2H), 4.94 (s, 1H), 4.55 (br. s., 1H), 3.56-3.75 (m, 2H), 2.88 (br. s., 2H), 2.57 (br. s., 2H), 2.43 (s, 3H), 2.07 (br.s., 2H), 1.92 (br. s., 2H), 1.33 (t, J=7.0 Hz, 3H); MS ESI [M+H]$^+$ 485.3, calcd for [C$_{29}$H$_{32}$N$_4$O$_3$+H]$^+$ 485.2.

Example A182

N-(cyclopropyl(2-fluorophenyl)methyl)-3-(4-((1-formylpiperidin-4-yl)phenyl)-1H-indazole-5-carboxamide

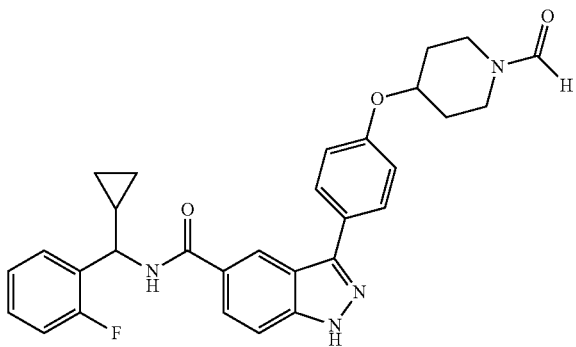 [SMILES: O=CN1CCC(Oc2ccc(-c3n[nH]c4ccc(C(=O)NC(c5ccccc5F)C5CC5)cc34)cc2)CC1]

The title compound was synthesized according to General Method C3 utilizing N-(cyclopropyl(2-fluorophenyl)methyl)-3-iodo-1H-indazole-5-carboxamide and 4-(4-(4,4,5,5-tetramethyl-1,3,2-dioxaborolan-2-yl)phenoxy)piperidine-1-carbaldehyde and obtained as a white solid (10 mg, 14% yield). NMR (400 MHz, CD$_3$OD) δ ppm 8.59 (s, 1 H), 8.04 (s, 1 H), 7.88-7.96 (m, 3 H), 7.52-7.62 (m, 2 H), 7.26 (m, J=7.8 Hz, 1 H), 7.02-7.19 (m, 4 H), 4.69-4.79 (m, 2 H), 3.76 (s, 2 H), 3.47-3.56 (m, 1 H), 3.38-3.46 (m, 1 H), 1.91-2.08 (m, 2 H), 1.78 (br. s., 2 H), 1.38-1.49 (m, 1 H), 0.67 (d, J=4.0 Hz, 1 H), 0.38-0.62 (m, 3 H); MS ESI [M+H]$^+$ 513.4, calcd for [C$_{30}$H$_{29}$FN$_4$O$_3$+H]$^+$ 513.23.

Example A183

2-(cyclopentyloxy)-N-(3-(4-((1-methylpiperidin-4-yl)oxy)phenyl)-1H-indazol-5-yl)-2-phenylacetamide

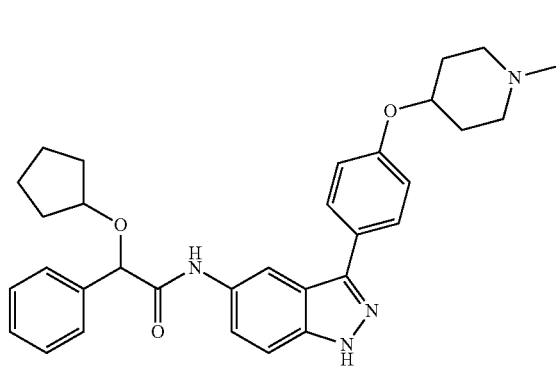 [SMILES: CN1CCC(Oc2ccc(-c3n[nH]c4ccc(NC(=O)C(OC5CCCC5)c5ccccc5)cc34)cc2)CC1]

A. To a DCM (20 mL) solution of tert-butyl (3-iodo-1H-indazol-5-yl)carbamate (200 mg, 0.56 mmol) was added TFA (2 mL) dropwise at rt. The reaction was stirred to 70 min before more TFA (1 mL). The stirring was continued overnight. The reaction mixture was concentrated to dryness under reduced pressure to provide 3-iodo-1H-indazol-5-amine 2,2,2-trifluoroacetate. The light brown residue was taken into anh. DMF (8 mL) and subjected to the conditions described by method A utilizing tert-butyl (3-iodo-1H-indazol-5-yl)carbamate (200 mg, 0.56 mmol) and sodium 2-(cyclopentyloxy)-2-phenylacetate (0.28 mg, 1.2 mmol), TBTU (0.51 g, 2.8 mmol) and DIPEA (0.5 mL, 3.2 mmol) in DMF (5 mL). The crude material was precipitated by adding H$_2$O, collected by filtration, dried (0.29 g, brown solid) and taken into MeOH (20 mL). The reaction was heated with MeONa (1.0 mL, 25%, in MeOH, 4.6 mmol) at 50° C. for 1 h and left standing at rt overnight. Concentration to dryness under reduced pressure, followed by flash chromatography (SiO$_2$, 0-20% MeOH in DCM) followed by RP HPLC (Biotage C18, 10-90% MeOH—H$_2$O+0.1% TFA) provided 2-(cyclopentyloxy)-N-(3-iodo-1H-indazol-5-yl)-2-phenylacetamide (71 mg, 28%) as a light tan solid. MS ESI 462.2 [M+H]$^+$, calcd for [C$_{20}$H$_{20}$IN$_3$O$_2$+H]$^+$ 462.1.

B. 2-(Cyclopentyloxy)-N-(3-(4-((1-methylpiperidin-4-yl)oxy)phenyl)-1H-indazol-5-yl)-2-phenylacetamide was synthesized according to the General Method C2 utilizing 2-(cyclopentyloxy)-N-(3-iodo-1H-indazol-5-yl)-2-phenylacetamide (71 mg, 0.15 mmol), 1-methyl-4-(4-(4,4,5,5-tetramethyl-1,3,2-dioxaborolan-2-yl)phenoxy)piperidine (68 mg, 0.21 mmol), PdCl$_2$dppf.CH$_2$Cl$_2$ (6.3 mg, 0.0077 mmol), satd aq Na$_2$CO$_3$ (0.5 mL) in PhMe (1.5 mL) and EtOH (1.5 mL) under microwave heating (130° C., 2H). A TFA salt of the title compound was isolated after flash chromatography (SiO$_2$, 0-60% MeOH-DCM) followed by RP HPLC (Biotage C18 column, MeOH—H$_2$O+0.1% TFA) as a white powder (36.8 mg, 38%). $^1$H NMR (400 MHz, CD$_3$OD) δ ppm 8.35 (s, 1 H), 7.82 (d, J=8.8 Hz, 2 H), 7.48-7.58 (m, 4 H), 7.37 (d, J=7.8 Hz, 3 H), 7.05 (d, J=8.8 Hz, 2 H), 4.98 (s, 1 H), 4.38-4.54 (m, 1 H), 4.11 (br. s., 1 H), 2.73 (br. s., 2 H), 2.39 (br. s., 2 H), 2.31 (s, 3 H), 2.03 (br. s., 2 H), 1.70-1.96 (m, 8 H), 1.58 (dd, J=7.5, 4.7 Hz, 2 H); MS ESI [M+H]$^+$ 524.4, calcd for [C$_{32}$H$_{36}$N$_4$O$_3$+H]$^+$ 524.3.

Example A184

N-(3-(4-((1-(oxetan-3-yl)piperidin-4-yl)oxy)phenyl)-1H-indazol-5-yl)-2-(pyrrolidin-1-yl)-2-(thiophen-3-yl)acetamide

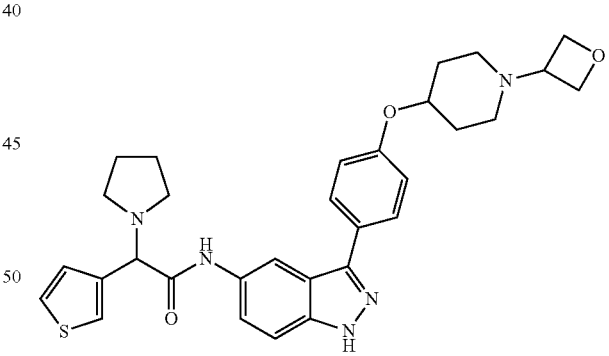

The title compound was synthesized according to General Method C3 utilizing N-(3-iodo-1H-indazol-5-yl)-2-(pyrrolidin-1-yl)-2-(thiophen-3-yl)acetamide and 1-(oxetan-3-yl)-4-(4-(4,4,5,5-tetramethyl-1,3,2-dioxaborolan-2-yl)phenoxy)piperidine and obtained as a pale solid (20 mg, 20% yield). $^1$H NMR (400 MHz, CD$_3$OD) δ ppm 8.36 (s, 1 H), 7.81 (d, J=8.8 Hz, 2 H), 7.46-7.52 (m, 3 H), 7.35-7.42 (m, 1 H), 7.29-7.35 (m, 1 H), 7.02 (d, J=8.8 Hz, 2 H), 4.66 (m, J=13.3 Hz, 2 H), 4.57 (t, J=6.2 Hz, 2 H), 4.37-4.47 (m, 1 H), 4.10 (s, 1 H), 3.41-3.50 (m, 1 H), 2.59-2.69 (m, 2 H), 2.44-2.59 (m, 4 H), 2.12-2.23 (m, 2 H), 1.95-2.05 (m, 2 H), 1.82 (br. s., 6 H); MS ESI [M+H]$^+$ 558.2, calcd for [C$_{31}$H$_{35}$N$_5$O$_3$S+H]$^+$ 558.25.

Example A185

2-cyclopropyl-N-(3-(4-((1-(oxetan-3-yl)piperidin-4-yl)oxy)phenyl)-1H-indazol-5-yl)-2-phenylacetamide

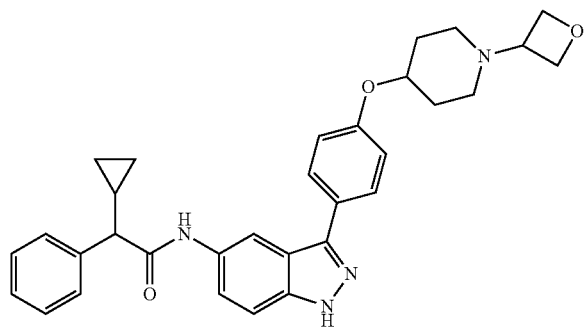 [SMILES: O=C(Nc1ccc2[nH]nc(-c3ccc(OC4CCN(C5COC5)CC4)cc3)c2c1)C(c1ccccc1)C1CC1]

The title compound was synthesized according to General Method C3 utilizing 2-cyclopropyl-N-(3-iodo-1H-indazol-5-yl)-2-phenylacetamide and 1-(oxetan-3-yl)-4-(4-(4,4,5,5-tetramethyl-1,3,2-dioxaborolan-2-yl)phenoxy)piperidine and obtained as a pale solid (21 mg, 42% yield). $^1$H NMR (400 MHz, CD$_3$OD) δ ppm 8.42 (s, 1 H), 7.80 (d, J=8.8 Hz, 2 H), 7.48 (dd, J=7.2, 3.0 Hz, 4 H), 7.28-7.35 (m, 2 H), 7.24 (m, J=7.2 Hz, 1 H), 7.01 (d, J=8.8 Hz, 2 H), 4.62-4.69 (m, 2 H), 4.57 (t, J=6.2 Hz, 2 H), 4.37-4.46 (m, 1 H), 3.46 (quin, J=6.6 Hz, 1 H), 2.91 (d, J=10.0 Hz, 1 H), 2.50-2.59 (m, 2 H), 2.12-2.23 (m, 2 H), 1.94-2.05 (m, 2 H), 1.73-1.85 (m, 2 H), 1.53-1.63 (m, 1 H), 0.55-0.73 (m, 2 H), 0.39-0.50 (m, 1 H), 0.18-0.28 (m, 1 H); MS ESI [M+H]$^+$ 523.4, calcd for [C$_{32}$H$_{34}$N$_4$O$_3$+H]$^+$ 523.27.

Example A186

N-(cyclopropyl(thiophen-3-yl)methyl)-3-(4-((1-formylpiperidin-4-yl)oxy)phenyl)-1H-indazole-5-carboxamide

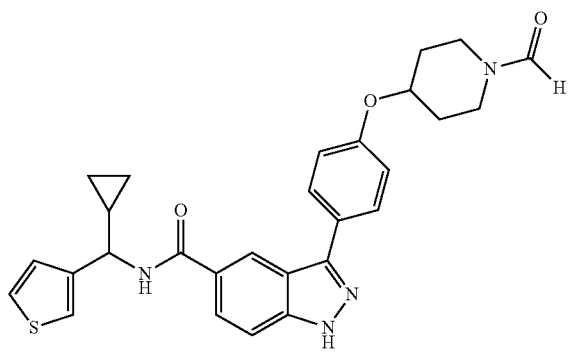 [SMILES: O=CN1CCC(Oc2ccc(-c3n[nH]c4ccc(C(=O)NC(c5ccsc5)C5CC5)cc34)cc2)CC1]

The title compound was synthesized according to General Method C3 utilizing N-(cyclopropyl(thiophen-3-yl)methyl)-3-iodo-1H-indazole-5-carboxamide and 4-(4-(4,4,5,5-tetramethyl-1,3,2-dioxaborolan-2-yl)phenoxy)piperidine-1-carbaldehyde and obtained as a pale solid (18 mg, 31% yield). $^1$H NMR (400 MHz, CD$_3$OD) δ ppm 8.61 (s, 1 H), 8.02 (s, 1 H), 7.96 (dd, J=8.8, 1.51 Hz, 1 H), 7.90 (d, J=8.5 Hz, 2 H), 7.59 (d, J=8.8 Hz, 1 H), 7.31-7.36 (m, 2 H), 7.15-7.21 (m, 1 H), 7.08 (d, J=8.8 Hz, 2 H), 4.69 (dt, J=6.8, 3.4 Hz, 1 H), 4.62 (d, J=9.5 Hz, 1 H), 3.60-3.77 (m, 2 H), 3.44-3.53 (m, 1 H), 3.36-3.43 (m, 1 H), 1.89-1.99 (m, 2 H), 1.67-1.84 (m, 2 H), 1.42 (dd, J=9.1, 4.6 Hz, 1 H), 0.70 (dd, J=8.8, 4.5 Hz, 1 H), 0.61 (dd, J=8.0, 4.2 Hz, 1 H), 0.47 (td, J=8.4, 4.7 Hz, 2 H); MS ESI [M+H]$^+$ 501.3, calcd for [C$_{28}$H$_{28}$N$_4$O$_3$S+H]$^+$ 501.20.

Example A187

2-isopropoxy-N-(3-(4-((1-methylpiperidin-4-yl)oxy)phenyl)-1H-indazol-5-yl)-2-phenylacetamide

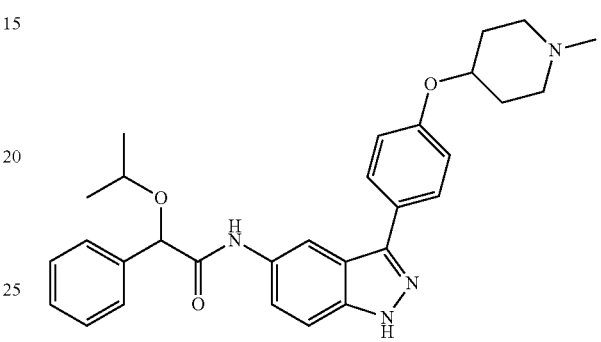

N-(3-iodo-1H-indazol-5-yl)-2-isopropoxy-2-phenylacetamide was synthesized according to General Method A utilizing 3-iodo-1H-indazol-5-amine 2,2,2-trifluoroacetate (300 mg, 0.80 mmol), and 2-isopropoxy-2-phenylacetic acid (312 mg, 1.6 mmol), TBTU (516 mg, 1.6 mmol) and DIPEA (0.50 mL, 3.2 mmol) in DMF (5 mL). The crude material was partitioned between H$_2$O and EtOAc. The organic layer was washed (satd aq NaHCO$_3$, H$_2$O), dried (Na$_2$SO$_4$) and concentrated under reduced pressure. The resultant pale orange oil (0.55 g) was taken into MeOH (20 mL) and heated with MeONa (2.0 mL, 25 wt %, in MeOH, 9.2 mmol) at 50° C. for 2 h. Later the reaction mixture was cooled to rt, concentrated under reduced pressure and purified by flash chromatography (SiO$_2$, 0-10% MeOH in DCM) provided N-(3-iodo-1H-indazol-5-yl)-2-isopropoxy-2-phenylacetamide as a light tan foam (141 mg, 40%). NMR (400 MHz, CD$_3$OD) δ ppm 7.83 (s, 1 H), 7.54-7.61 (m, 3 H), 7.50 (d, J=7.5 Hz, 1 H), 7.26-7.44 (m, 3 H), 5.06 (s, 1 H), 3.71-3.86 (m, 1 H), 1.33 (d, J=6.0 Hz, 3 H), 1.26 (d, J=6.0 Hz, 3 H); MS ESI 436.1 [M+H]$^+$, calcd for [C$_{18}$H$_{18}$I N$_3$O$_2$+H]$^+$ 436.0.

2-isopropoxy-N-(3-(4-((1-methylpiperidin-4-yl)oxy)phenyl)-1H-indazol-5-yl)-2-phenylacetamide was synthesized according to the General Method C2 utilizing N-(3-iodo-1H-indazol-5-yl)-2-isopropoxy-2-phenylacetamide (100 mg, 0.23 mmol), 1-methyl-4-(4-(4,4,5,5-tetramethyl-1,3,2-dioxaborolan-2-yl)phenoxy)piperidine (94.7 mg, 0.30 mmol), PdCl$_2$dppf.CH$_2$Cl$_2$ (9.4 mg, 0.011 mmol), satd aq Na$_2$CO$_3$ (0.5 mL) in PhMe (1.5 mL) and EtOH (1.5 mL) under microwave heating (130° C., 2 h). A TFA salt of 2-isopropoxy-N-(3-(4-((1-methylpiperidin-4-yl)oxy)phenyl)-1H-indazol-5-yl)-2-phenylacetamide was isolated after flash chromatography (SiO$_2$, 5-90% MeOH-DCM) followed by RP HPLC (Biotage C18 column, MeOH—H$_2$O+0.1% TFA) as a white powder (39.3 mg, 28%). $^1$H NMR (400 MHz, CD$_3$OD) δ ppm 8.34 (s, 1 H), 7.82 (d, J=8.8 Hz, 2 H), 7.46-7.60 (m, 4 H), 7.27-7.42 (m, 3 H), 7.07 (d, J=8.8 Hz, 2 H), 5.05 (s, 1 H), 4.48 (br. s., 1 H), 3.79 (spt, J=6.3 Hz, 1 H), 2.74 (br. s., 2 H), 2.40 (br. s., 2 H), 2.32 (s, 3 H), 2.04

(br. s., 2 H), 1.85 (br. s., 2 H), 1.32 (d, J=6.0 Hz, 3 H), 1.25 (d, J=6.2 Hz, 3 H); MS ESI [M+H]$^+$ 499.4, calcd for [C$_{30}$H$_{34}$N$_4$O$_3$+H]$^+$ 499.3.

Example A188

3-(3-chloro-4-((1-methylpiperidin-4-yl)oxy)phenyl)-N-(cyclopropyl(phenyl)methyl)-1H-indazole-5-carboxamide

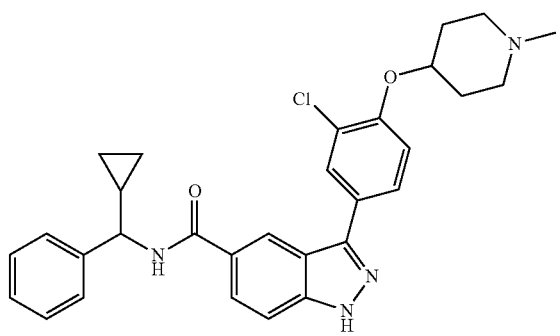

The title compound was synthesized according to the General Method C, utilizing N-(cyclopropyl(phenyl)methyl)-3-iodo-1H-indazole-5-carboxamide (100 mg, 0.24 mmol), 4-(2-chloro-4-(4,4,5,5-tetramethyl-1,3,2-dioxaborolan-2-yl)phenoxy)-1-methylpiperidine (84 mg, 0.24 mmol), Pd(PPh$_3$)$_4$ (14 mg, 0.012 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 58 mg, 38%). $^1$H NMR (400 MHz, CD$_3$OD) δ ppm 8.57 (s, 1 H), 8.04-8.09 (m, 1 H), 7.91-7.99 (m, 2 H), 7.63 (d, J=8.5 Hz, 1 H), 7.49 (d, J=7.5 Hz, 2 H), 7.30-7.39 (m, 3 H), 7.25 (t, J=7.5 Hz, 1 H), 4.68-4.78 (m, 0.3 H), 4.46-4.53 (m, 1 H), 3.62-3.70 (m, 0.7 H), 3.35-3.53 (m, 3 H), 3.14-3.26 (m, 1 H), 2.91-2.98 (m, 3 H), 2.42-2.51 (m, 0.7 H), 2.29-2.38 (m, 1.3 H), 2.08-2.20 (m, 1.3 H), 1.92-2.06 (m, 0.7 H), 1.36-1.46 (m, 1 H), 0.63-0.71 (m, 2 H), 0.43-0.54 (m, 2 H); MS ESI 515.5 [M+H]$^+$, calcd for [C$_{30}$H$_{31}$ClN$_4$O$_2$+H]$^+$ 515.2.

Example A189

N-(3-(4-((1-(oxetan-3-yl)azetidin-3-yl)oxy)phenyl)-1H-indazol-5-yl)-2-(pyrrolidin-1-yl)-2-(thiophen-3-yl)acetamide

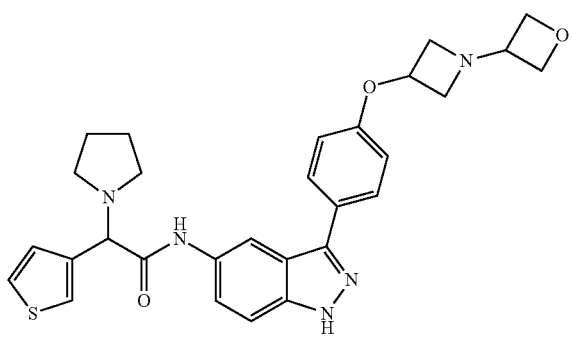 [SMILES: O=C(Nc1ccc2[nH]nc(-c3ccc(OC4CN(C5COC5)C4)cc3)c2c1)C(c1ccsc1)N1CCCC1]

To a solution of tert-butyl 3-hydroxyazetidine-1-carboxylate (8.65 g, 50 mmol) in DMF (100 mL) at rt was added NaH (60% in mineral oil, 2.20 g, 55 mmol). After stirring for 5 min at rt, 1-fluoro-4-iodobenzene (11.10 g, 50 mmol) was added and the resulting mixture was heated at 85° C. (oil temp.) for 5 h, then O/N at 80° C. (oil temp.). After cooling to rt, it was quenched with H$_2$O (350 mL) and stirred for 15 min at rt. The resulting precipitates were collected by suction filtration, washed with H$_2$O and dried to give tert-butyl 3-(4-iodophenoxy)azetidine-1-carboxylate (yellow solid, 12.792 g, 68%). $^1$H NMR (400 MHz, CDCl$_3$) δ 7.56 (d, J=9.2 Hz, 2H), 6.53 (d, J=8.8 Hz, 2H), 4.87-4.80 (m, 1H), 4.29 (dd, J=7.4 Hz, 2.6 Hz, 2H), 4.99 (dd, J=9.8 Hz, 4.2 Hz, 2H), 4.46 (s, (H); MS ESI 319.9 [M+1-1]$^+$, calcd for [C$_{14}$H$_{18}$INO$_3$–C$_4$H$_9$+H]$^+$ 320.0.

To a solution of tert-butyl 3-(4-iodophenoxy)azetidine-1-carboxylate (2.66 g, 7.10 mmol) in DCM (30 mL) was added TFA (10 mL). The resulting mixture was stirred O/N at rt. After removal of solvents, it was basified with satd aq NaHCO$_3$ (50 mL), extracted with DCM and evaporated to give 3-(4-iodophenoxy)azetidine (off white solid, 1.87 g, 96%). $^1$H NMR (400 MHz, DMSO-d$_6$) δ 7.61 (d, J=8.8 Hz, 2H), 6.90 (d, J=8.8 Hz, 2H), 5.00 (quint, J=5.6 Hz, 1H), 4.18-4.40 (m, 2H), 3.80-3.74 (m, 2H); MS ESI 275.8 [M+H]$^+$, calcd for [C$_9$H$_{10}$INO+H]$^+$ 276.0.

To a suspension of 3-(4-iodophenoxy)azetidine (2.20 g, 8 mmol) in DCE (100 mL) was added oxetan-3-one (860 mg, 12 mmol), followed by NaBH(OAc)$_3$ (3.40 g, 16 mmol) and HOAc (0.2 mL). The resulting mixture was stirred O/N at rt. Additional oxetan-3-one (126 mg, 3 mmol) and NaBH(OAc)$_3$ (850 mg g, 4 mmol) and the resulting mixture was stirred for 3 h at rt. It was quenched with satd aq NaHCO$_3$ (30 mL) and H$_2$O (30 mL), extracted with DCM and evaporated to give crude 3-(4-iodophenoxy)-1-(oxetan-3-yl)azetidine (light yellow solid, 2.34 g). $^1$H NMR (400 MHz, DMSO-d$_6$) δ 7.58 (d, J=8.8 Hz, 2H), 6.68 (d, J=8.8 Hz, 2H), 4.81 (quint, J=5.6 Hz, 1H), 4.55 (t, J=6.6 Hz, 2H), 4.33 (t, J=5.8 Hz, 2H), 3.78-3.68 (m, 3H), 3.13-3.07 (m, 2H); MS ESI 331.9 [M+H]$^+$, calcd for [C$_{12}$H$_{14}$IN$_2$O+H]$^+$ 332.0.

To a mixture of crude 3-(4-iodophenoxy)-1-(oxetan-3-yl)azetidine (1.17 g, 3.53 mmol), B$_2$pin$_2$ (988 mg, 3.89 mmol), KOAc (1.04 g, 10.6 mmol) was added DMF (10 mL), followed by Pd(dppf)Cl$_2$—CH$_2$Cl$_2$ (86 mg, 3 mol %). The resulting mixture was purged with Ar and microwaved 2 h at 85° C. This reaction was repeated on the same scale, combined, diluted with H$_2$O, extracted with EtOAc and purified by flash chromatography (MeOH/DCM 0-15%) twice to give crude 1-(oxetan-3-yl)-3-(4-(4,4,5,5-tetramethyl-1,3,2-dioxaborolan-2-yl)phenoxy)azetidine (brown oil, 1.996 g). $^1$H NMR (400 MHz, CDCl$_3$) δ 8.02 (s, 1H), 7.74 (d, J=8.4 Hz, 2H), 6.77 (d, J=8.4 Hz, 2H), 4.93-4.86 (quint, 1H), 4.73 (t, J=6.8 Hz, 2H), 4.57 (t, J=6.0 Hz, 2H), 3.92-3.85 (m, 3H), 3.33-3.28 (m, 2H), 1.33 (s, 12H); MS ESI 332.1 [M+H]$^+$, calcd for [C$_{18}$H$_{26}$BNO$_4$+H]$^+$ 332.2.

To a mixture of N-(3-iodo-1H-indazol-5-yl)-2-(pyrrolidin-1-yl)-2-(thiophen-3-yl)acetamide (181 mg, 0.4 mmol) and 1-(oxetan-3-yl)-3-(4-(4,4,5,5-tetramethyl-1,3,2-dioxaborolan-2-yl)phenoxy)azetidine (125 mg, 0.38 mmol) in EtOH (10 mL) was added 1 M aq Na$_2$CO$_3$ (0.8 mL, 0.8 mmol), followed by Pd(PPh$_3$)$_4$ (23 mg, 0.02 mmol). The resulting mixture was purged with Ar and microwaved 3 h at 125° C. After removal of solvents, it was purified by prep-HPLC, PoraPak and flash chromatography (MeOH/DCM 0-20%) to give the title compound (white solid, 54.5 mg, 26%). $^1$H NMR (400 MHz, CD$_3$OD) δ 8.34 (s, 1H), 7.80 (d, J=8.8 Hz, 2H), 7.51-7.47 (m, 3H), 7.38 (dd, J=8.8 Hz, 2.8 Hz, 1H), 7.31 (dd, J=9.0 Hz, 1.0 Hz, 1H), 6.88 (d, J=8.8 Hz, 2H), 4.85 (quint, J=5.6 Hz, 1H), 4.72 (t, J=6.8 Hz, 2H), 4.48 (dd, J=6.8 Hz, 5.2 Hz, 2H), 4.13 (s, 1H), 3.85-3.77 (m, 3H), 3.29 (dd, J=9.2 Hz, 5.2 Hz, 2H), 2.70-2.62 (m, 2H), 2.53-2.45 (m, 2H), 1.85-1.76 (m, 4H); MS ESI 530.2 [M+H]$^+$, calcd for [C$_{29}$H$_{31}$N$_5$O$_3$S+H]$^+$ 530.2.

Example A190

N-(cyclopropyl(phenyl)methyl)-3-(4-((1-(oxetan-3-yl)azetidin-3-yl)oxy)phenyl)-1H-indazole-5-carboxamide

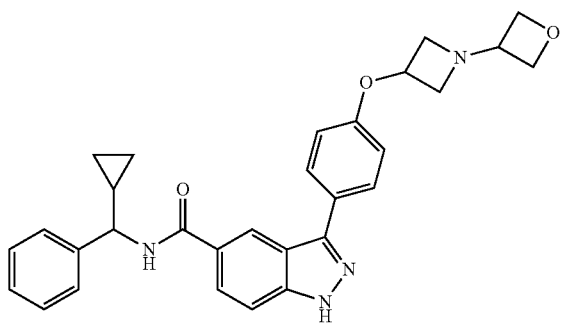 [SMILES: O=C(NC(c1ccccc1)C1CC1)c1ccc2[nH]nc(-c3ccc(OC4CN(C5COC5)C4)cc3)c2c1]

To a mixture of N-(cyclopropyl(phenyl)methyl)-3-iodo-1H-indazole-5-carboxamide (168 mg, 0.4 mmol) and 1-(oxetan-3-yl)-3-(4-(4,4,5,5-tetramethyl-1,3,2-dioxaborolan-2-yl)phenoxy)azetidine (125 mg, 0.38 mmol) in EtOH (10 mL) was added 1 M aq Na$_2$CO$_3$ (0.8 mL, 0.8 mmol), followed by Pd(PPh$_3$)$_4$ (23 mg, 0.02 mmol). The resulting mixture was purged with Ar and microwaved 3 h at 125° C. After removal of solvents, it was purified by prep-HPLC, PoraPak and flash chromatography (MeOH/DCM 0-20%) to give the title compound (white solid, 43.6 mg, 22%). $^1$H NMR (400 MHz, CD$_3$OD) δ 8.61 (s, 1H), 7.96 (d, J=8.8 Hz, 1H), 7.90 (d, J=8.8 Hz, 2H), 7.59 (d, J=8.8 Hz, 1H), 7.47 (d, J=7.6 Hz, 2H), 7.31 (t, J=7.4 Hz, 2H), 7.22 (t, J=7.2 Hz, 1H), 6.93 (d, J=8.8 Hz, 2H), 4.90-4.86 (m, 1H, partially buried by H$_2$O peak), 4.74 (t, J=6.8 Hz, 2H), 4.45-4.45 (m, 3H), 3.89-3.80 (m, 3H), 3.35-3.28 (m, 2H; overlapped with CD$_3$OD solvent residue), 1.44-1.34 (m, 1H), 0.68-0.59 (m, 2H), 0.51-0.39 (m, 2H); MS ESI 495.4 [M+H]$^+$, calcd for [C$_{30}$H$_{30}$N$_4$O$_3$+H]$^+$ 495.2.

Example A191

2-(azetidin-1-yl)-N-(3-(4-((1-methylpiperidin-4-yl)oxy)phenyl)-1H-indazol-5-yl)-2-(thiophen-3-yl)acetamide

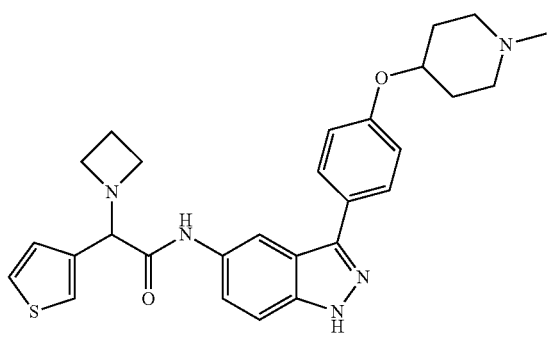 [SMILES: CN1CCC(Oc2ccc(-c3n[nH]c4ccc(NC(=O)C(c5ccsc5)N5CCC5)cc34)cc2)CC1]

A suspension of 2-(azetidin-1-yl)-2-(thiophen-3-yl)acetic acid H$_3$BO$_3$ salt (2.59 g, 10 mmol) and 3-iodo-1H-indazol-5-amine (2.59 g, 10 mmol) in DMF (50 mL) was sonicated and stirred for 15 min at rt until a homogeneous suspension was obtained. TBTU (3.21 g, 10 mmol) was added at 0° C., followed by $^i$Pr$_2$NEt (5.2 mL, 30 mmol). The resulting mixture was stirred for 1 h at 0° C., quenched with H$_2$O (200 mL), stirred for 10 min at rt, suction filtered and dried to give crude 2-(azetidin-1-yl)-N-(3-iodo-1H-indazol-5-yl)-2-(thiophen-3-yl)acetamide (brown solid, 2.973 g). LC-MS indicated a mixture of desired product 2-(azetidin-1-yl)-N-(3-iodo-1H-indazol-5-yl)-2-(thiophen-3-yl)acetamide and di-acylated byproduct. $^1$H NMR (400 MHz, CDCl$_3$) 8 MS ESI 439.0 [M+H]$^+$, calcd for [C$_{16}$H$_{15}$IN$_4$OS+H]$^+$ 439.0.

To a mixture of crude 2-(azetidin-1-yl)-N-(3-iodo-1H-indazol-5-yl)-2-(thiophen-3-yl)acetamide (290 mg, assuming 0.5 mmol) and 1-methyl-4-(4-(4,4,5,5-tetramethyl-1,3,2-dioxaborolan-2-yl)phenoxy)piperidine (158 mg, 0.5 mmol) in EtOH (12 mL) was added 1 M aq Na$_2$CO$_3$ (1.5 mL, 1.5 mmol), followed by Pd(PPh$_3$)$_4$ (58 mg, 0.05 mmol). The resulting mixture was purged with Ar and microwaved 4 h at 125° C. After removal of solvents, it was purified by prep-HPLC, PoraPak, flash chromatography (MeOH/DCM 0-100%), Biotage RP column (MeOH/H$_2$O (1% TFA) 5-80%) and PoraPak to give the title compound (white solid, 35 mg, 14%). $^1$H NMR (400 MHz, CD$_3$OD) δ 8.33 (s, 1H), 7.81 (d, J=8.8 Hz, 2H), 7.52-7.47 (m, 3H), 7.39 (dd, J=9.0 Hz, 3.0 Hz, 1H), 7.24 (dd, J=5.0 Hz, 1.0 Hz, 1H), 7.03 (d, J=8.8 Hz, 2H), 4.47-4.40 (m, 1H), 4.18 (s, 1H), 3.37 (q, J=7.1 Hz, 2H), 3.20 (q, J=7.1 Hz, 2H), 2.76-2.66 (m, 2H), 2.42-2.32 (m, 2H), 2.29 (s, 3H), 2.12 (quint, J=7.2 Hz, 2H), 2.06-1.97 (m, 2H), 1.86-1.76 (m, 2H); MS ESI 502.2 [M+H]$^+$, calcd for [C$_{28}$H$_{31}$N$_5$O$_2$S+H]$^+$ 502.2.

Example A192

(R)-N-(1-(2-chlorophenyl)propyl)-3-(4-((1-(oxetan-3-yl)piperidin-4-yl)oxy)phenyl)-1H-indazole-5-carboxamide

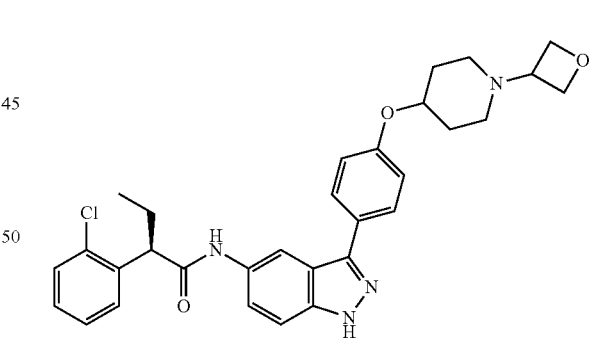

Using General Method C2, (R)-N-(1-(2-chlorophenyl)propyl)-3-iodo-1H-indazole-5-carboxamide (45.1 mg, 95% pure, 0.097 mmol) and 1-(oxetan-3-yl)-4-(4-(4,4,5,5-tetramethyl-1,3,2-dioxaborolan-2-yl)phenoxy)piperidine (39.4 mg, 80% pure, 0.088 mmol) gave the title compound (off-white solid, 18.8 mg, 39%) after 14 h at 125° C. in reaction block with purification by flash chromatography (SiO$_2$, 50-100% EtOAc in DCM, then 0-15% MeOH in EtOAc; followed by RP HPLC, 10-75% MeOH in 0.1% TFA-H$_2$O) and PoraPak RXn Cx work-up. $^1$H NMR (400 MHz, CD$_3$OD) δ ppm 8.60 (s, 1 H), 7.87-7.96 (m, 3 H), 7.47-7.52 (m, 1 H), 7.39 (d, J=7.8 Hz, 1 H), 7.25-7.31 (m, 1 H), 7.18-7.24 (m, 1 H), 7.09 (d, J=8.8 Hz, 2 H), 5.46 (dd, J=9.0, 5.8 Hz, 1 H), 4.67-4.73 (m, 2 H), 4.62 (t, J=6.3 Hz, 2 H), 4.51 (br. s., 1 H), 3.53 (quin, J=6.5 Hz, 1 H), 2.55-2.67 (m, 2 H), 2.19-2.31 (m, 2 H), 2.01-2.11 (m, 2 H), 1.79-2.00 (m, 4 H), 1.07 (t, J=7.4 Hz, 3 H). MS ESI 545.4 [M+H]$^+$, calcd for [C$_{31}$H$_{33}$ClN$_4$O$_3$+H]$^+$ 545.23.

Example A193

(S)-N-(1-(2-chlorophenyl)propyl)-3-(4-((1-(oxetan-3-yl)piperidin-4-yl)oxy)phenyl)-1H-indazole-5-carboxamide

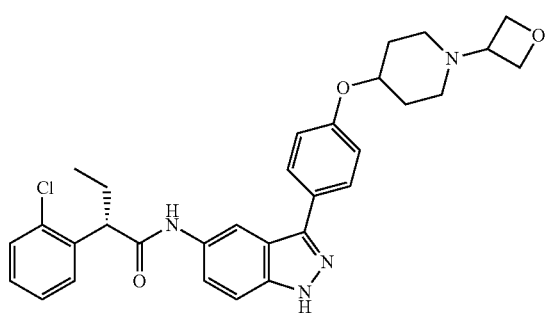 [SMILES: CC[C@H](C(=O)Nc1ccc2[nH]nc(-c3ccc(OC4CCN(C5COC5)CC4)cc3)c2c1)c1ccccc1Cl]

Using General Method C2, (S)-N-(1-(2-chlorophenyl)propyl)-3-iodo-1H-indazole-5-carboxamide (45.3 mg, 0.103 mmol) and 1-(oxetan-3-yl)-4-(4-(4,4,5,5-tetramethyl-1,3,2-dioxaborolan-2-yl)phenoxy)piperidine (39.4 mg, 80% pure, 0.088 mmol) gave the title compound (off-white solid, 19.8 mg, 42%) after 14 h at 125° C. in reaction block with purification by flash chromatography (SiO2, 100% EtOAc, then 0-100% DCM, then 0-10% MeOH in DCM; followed by RP HPLC, 10-90% MeOH in 0.1% TFA-H$_2$O) and PoraPak RXn Cx work-up. $^1$H NMR (400 MHz, CD$_3$OD) δ ppm 8.60 (s, 1 H), 7.87-7.96 (m, 3 H), 7.47-7.52 (m, 1 H), 7.39 (d, J=7.8 Hz, 1 H), 7.25-7.31 (m, 1 H), 7.18-7.24 (m, 1 H), 7.09 (d, J=8.8 Hz, 2 H), 5.46 (dd, J=9.0, 5.8 Hz, 1 H), 4.67-4.73 (m, 2 H), 4.62 (t, J=6.3 Hz, 2 H), 4.51 (br. s., 1 H), 3.53 (quin, J=6.5 Hz, 1 H), 2.55-2.67 (m, 2 H), 2.19-2.31 (m, 2 H), 2.01-2.11 (m, 2 H), 1.79-2.00 (m, 4 H), 1.07 (t, J=7.4 Hz, 3 H). MS ESI 545.4 [M+H]$^+$, calcd for [C$_{31}$H$_{33}$ClN$_4$O$_3$+H]$^+$ 545.23.

Example A194

N-(cyclopropyl(phenyl)methyl)-3-(3-methoxy-4-((1-(oxetan-3-yl)piperidin-4-yl)oxy)phenyl)-1H-indazole-5-carboxamide

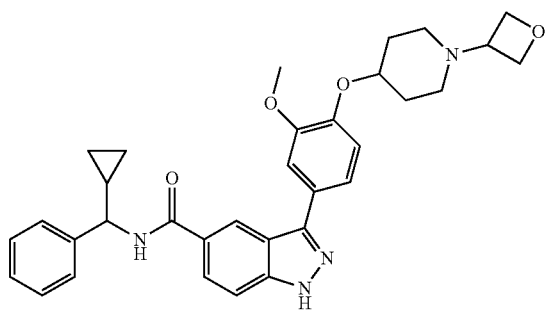 [SMILES: COc1cc(-c2n[nH]c3ccc(C(=O)NC(c4ccccc4)C4CC4)cc23)ccc1OC1CCN(C2COC2)CC1]

The title compound was synthesized according to the General Method C, utilizing N-(cyclopropyl(phenyl)methyl)-3-iodo-1H-indazole-5-carboxamide (50 mg, 0.12 mmol), 4-(2-methoxy-4-(4,4,5,5-tetramethyl-1,3,2-dioxaborolan-2-yl)phenoxy)-1-(oxetan-3-yl)piperidine (46 mg, 0.12 mmol), Pd(PPh$_3$)$_4$ (7 mg, 0.006 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by trituration with Et$_2$O gave the title compound as a TFA salt (white solid, 30 mg, 38%). $^1$H NMR (400 MHz, CD$_3$OD) δ ppm 8.58 (s, 1 H), 7.96 (d, J=8.8 Hz, 1 H), 7.54-7.66 (m, 3 H), 7.49 (d, J=7.8 Hz, 2 H), 7.34 (t, J=7.4 Hz, 2 H), 7.25 (t, J=7.8 Hz, 2 H), 4.89-4.95 (m, 2 H), 4.79-4.86 (m, 2 H), 4.44-4.53 (m, 2 H), 3.97 (s, 3 H), 3.44-3.52 (m, 1 H), 3.35-3.44 (m, 2 H), 2.21-2.45 (m, 2 H), 1.96-2.20 (m, 2 H), 1.34-1.46 (m, 1 H), 0.62-0.70 (m, 2 H), 0.41-0.54 (m, 2 H); MS ESI 553.5 [M+H]$^+$, calcd for [C$_{33}$H$_{36}$N$_4$O$_4$+H]$^+$ 553.3.

Example A195

N-(cyclopropyl(pyridin-2-yl)methyl)-3-(3-methoxy-4-((1-(oxetan-3-yl)piperidin-4-yl)oxy)phenyl)-1H-indazole-5-carboxamide

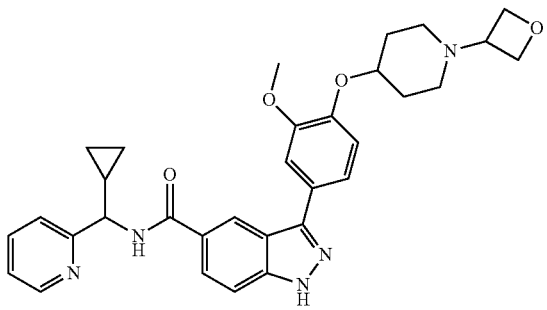 [SMILES: COc1cc(-c2n[nH]c3ccc(C(=O)NC(c4ccccn4)C4CC4)cc23)ccc1OC1CCN(C2COC2)CC1]

The title compound was synthesized according to the General Method C, utilizing N-(cyclopropyl(pyridin-2-yl)methyl)-3-iodo-1H-indazole-5-carboxamide (50 mg, 0.12 mmol), 4-(2-methoxy-4-(4,4,5,5-tetramethyl-1,3,2-dioxaborolan-2-yl)phenoxy)-1-(oxetan-3-yl)piperidine (46 mg, 0.12 mmol), Pd(PPh$_3$)$_4$ (7 mg, 0.006 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by flash chromatography (SiO$_2$, Biotage 25 g, 0-30% MeOH in CH$_2$Cl$_2$) and trituration with Et$_2$O gave the title compound (white solid, 23 mg, 35%). $^1$H NMR (400 MHz, CD$_3$OD) δ ppm 8.65 (s, 1 H), 8.49 (d, J=4.0 Hz, 1 H), 7.95 (d, J=9.0 Hz, 1 H), 7.78 (t, J=7.6 Hz, 1 H), 7.46-7.63 (m, 4 H), 7.28 (t, J=6.0 Hz, 1 H), 7.06 (d, J=8.0 Hz, 1 H), 4.66 (t, J=6.3 Hz, 2 H), 4.58 (t, J=6.0 Hz, 2 H), 4.50 (d, J=9.3 Hz, 1 H), 4.33-4.42 (m, 1 H), 3.91 (s, 3 H), 3.48 (m, 1 H), 2.60 (br. s, 2 H), 2.16 (br. s, 2 H), 1.97 (br. s, 2 H), 1.84 (br. s, 2 H), 1.32-1.44 (m, 1 H), 0.60-0.70 (m, 1 H), 0.45-0.59 (m, 3 H); MS ESI 554.2 [M+H]$^+$, calcd for [C$_{32}$H$_{35}$N$_5$O$_4$+H]$^+$ 554.3.

Example A196

(R)-N-(cyclopropyl(pyridin-2-yl)methyl)-3-(4-((1-(oxetan-3-yl)piperidin-4-yl)oxy)phenyl)-1H-indazole-5-carboxamide

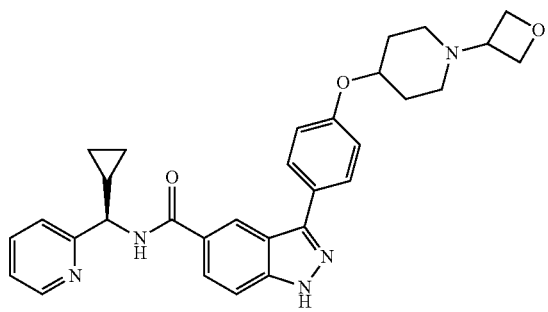 [SMILES: O=C(N[C@@H](c1ccccn1)C1CC1)c1ccc2[nH]nc(-c3ccc(OC4CCN(C5COC5)CC4)cc3)c2c1]

The title compound was synthesized according to General Method C3 utilizing (R)-2-cyclopropyl-N-(3-iodo-1H-indazol-5-yl)-2-(pyridin-2-yl)acetamide and 1-(oxetan-3-yl)-4-(4-(4,4,5,5-tetramethyl-1,3,2-dioxaborolan-2-yl)phenoxy)piperidine and obtained as a white solid (42 mg, 42% yield). $^1$H NMR (400 MHz, CD$_3$OD) δ ppm 8.67 (s, 1 H), 8.49 (d, J=4.7 Hz, 1 H), 7.96 (dd, J=8.8, 1.2 Hz, 1 H), 7.89 (d, J=8.8 Hz, 2 H), 7.75 (td, J=7.7, 1.6 Hz, 1 H), 7.58 (d, J=8.8 Hz, 1 H), 7.49 (d, J=8.0 Hz, 1 H), 7.22-7.29 (m, 1 H), 7.00 (d, J=8.8 Hz, 2 H), 4.59-4.67 (m, 2 H), 4.55 (t, J=6.1 Hz, 2 H), 4.50 (d, J=9.5 Hz, 1 H), 4.34-4.43 (m, 1 H), 3.42 (quin, J=6.4 Hz, 1 H), 2.51 (br. s., 2 H), 2.12 (d, J=7.5 Hz, 2 H), 1.96 (br. s., 2 H), 1.76 (d, J=8.2 Hz, 2 H), 1.30-1.43 (m, 1 H), 0.58-0.69 (m, 1 H), 0.44-0.58 (m, 3 H); MS ESI [M+H]$^+$ 524.2, calcd for [C$_{31}$H$_{33}$N$_5$O$_3$+H]$^+$ 524.27.

Example A197

(S)-N-(cyclopropyl(pyridin-2-yl)methyl)-3-(4-((1-(oxetan-3-yl)piperidin-4-yl)oxy)phenyl)-1H-indazole-5-carboxamide

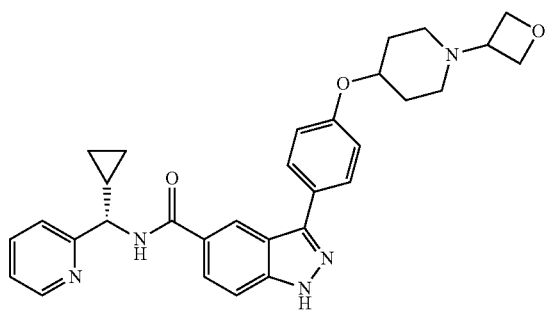 [SMILES: O=C(N[C@H](c1ccccn1)C1CC1)c1ccc2[nH]nc(-c3ccc(OC4CCN(C5COC5)CC4)cc3)c2c1]

The title compound was synthesized according to General Method C3 utilizing (S)-2-cyclopropyl-N-(3-iodo-1H-indazol-5-yl)-2-(pyridin-2-yl)acetamide and 1-(oxetan-3-yl)-4-(4-(4,4,5,5-tetramethyl-1,3,2-dioxaborolan-2-yl)phenoxy)piperidine and obtained as a white solid (44 mg, 44% yield). $^1$H NMR (400 MHz, CD$_3$OD) δ ppm 8.67 (s, 1 H) 8.49 (d, J=4.7 Hz, 1 H), 7.96 (dd, J=8.8, 1.2 Hz, 1 H), 7.89 (d, J=8.8 Hz, 2 H), 7.75 (td, J=7.7, 1.6 Hz, 1 H), 7.58 (d, J=8.8 Hz, 1 H), 7.49 (d, J=8.0 Hz, 1 H), 7.22-7.29 (m, 1 H), 7.00 (d, J=8.8 Hz, 2 H), 4.59-4.67 (m, 2 H), 4.55 (t, J=6.1 Hz, 2 H), 4.50 (d, J=9.5 Hz, 1 H), 4.34-4.43 (m, 1 H), 3.42 (quin, J=6.4 Hz, 1 H), 2.51 (br. s., 2 H), 2.12 (d, J=7.5 Hz, 2 H), 1.96 (br. s., 2 H), 1.76 (d, J=8.8 Hz, 2 H), 1.30-1.43 (m, 1 H), 0.58-0.69 (m, 1 H), 0.44-0.58 (m, 3 H); MS ESI [M+H]$^+$ 524.2, calcd for [C$_{31}$H$_{33}$N$_5$O$_3$+H]$^+$ 524.27.

Example A198

3-(3-chloro-4-((1-methylpiperidin-4-yl)oxy)phenyl)-N-(cyclopropyl(pyridin-2-yl)methyl)-1H-indazole-5-carboxamide

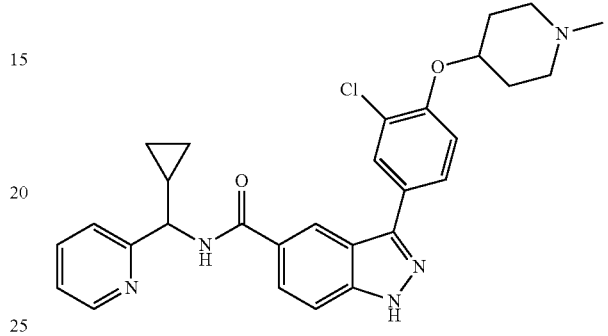

The title compound was synthesized according to the General Method C, utilizing N-(cyclopropyl(pyridin-2-yl)methyl)-3-iodo-1H-indazole-5-carboxamide (100 mg, 0.24 mmol), 4-(2-chloro-4-(4,4,5,5-tetramethyl-1,3,2-dioxaborolan-2-yl)phenoxy)-1-methylpiperidine (84 mg, 0.24 mmol), Pd(PPh$_3$)$_4$ (14 mg, 0.012 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by flash chromatography (SiO$_2$, Biotage 25 g, 0-30% MeOH in CH$_2$Cl$_2$) gave the title compound (white solid, 35 mg, 28%). $^1$H NMR (400 MHz, CD$_3$OD) δ ppm 8.61 (s, 1 H), 8.51 (d, J=4.8 Hz, 1 H), 8.00 (d, J=2.3 Hz, 1 H), 7.95 (dd, J=8.8, 1.2 Hz, 1 H), 7.88 (dd, J=8.5, 2.3 Hz, 1 H), 7.80 (td, J=7.7, 1.6 Hz, 1 H), 7.59 (d, J=8.8 Hz, 1 H), 7.53 (d, J=8.0 Hz, 1 H), 7.30 (dd, J=6.9, 5.4 Hz, 1 H), 7.23 (d, J=8.8 Hz, 1 H), 4.61 (br. s., 1 H), 4.50 (d, J=9.5 Hz, 1 H), 2.80-2.92 (m, 2 H), 2.54 (br. s, 2 H), 2.37 (s, 3 H), 2.00-2.09 (m, 2 H), 1.88-1.99 (m, 2 H), 1.35-1.45 (m, 1 H), 0.65-0.72 (m, 1 H), 0.49-0.62 (m, 3 H); MS ESI 516.2 [M+H]$^+$, calcd for [C$_{29}$H$_{30}$ClN$_5$O$_2$+H]$^+$ 516.2.

Example A199

N-((2-chlorophenyl)(cyclopentyl)methyl)-3-(4-((1-methylpiperidin-4-yl)oxy)phenyl)-1H-indazole-5-carboxamide

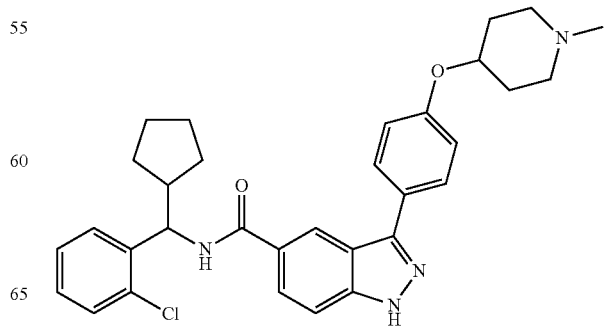

A mixture of (2-chlorophenyl)(cyclopentyl)methanone (2.085 g, 10 mmol), NH$_4$OAc (9.24 g, 120 mmol) and NaCNBH$_3$ (2.52 g, 40 mmol) in MeOH (60 mL) was heated at 65° C. for 1 h, then left O/N at 60° C. After removal of solvent, it was purified by flash chromatography (MeOH/DCM 0-20%) to give (2-chlorophenyl)(cyclopentyl)methanamine (colorless oil, 876 mg, 42%). $^1$H NMR (400 MHz, CD$_3$OD) δ 7.58 (dd, J=7.6 Hz, 1.6 Hz, 1H), 7.54 (dd, J=7.8 Hz, 1.4 Hz, 1H), 7.48 (dt, J=7.6 Hz, 1.6 Hz, 1H), 7.43 (dt, J=7.8 Hz, 1.8 Hz, 1H), 2.58-2.46 (m, 1H), 2.10-2.01 (m, 1H), 1.90-1.78 (m, 1H), 1.77-1.64 (m, 2H), 1.63-1.40 (m, 3H), 1.25-1.14 (m, 1H); MS ESI 193.0 [M+H]$^+$, calcd for [C$_{12}$H$_{16}$ClN–NH$_3$+H]$^+$ 193.1.

To a solution of (2-chlorophenyl)(cyclopentyl)methanamine (876 mg, 4.18 mmol), 3-iodo-1H-indazole-5-carboxamide (1.20 g, 4.18 mmol) in DMF (10 mL) at 0° C. was added TBTU (1.34 g, 4.18 mmol), followed by $^i$Pr$_2$NEt (1.45 mL, 8.36 mmol). The resulting mixture was stirred at 0° C. for 30 min, quenched with H$_2$O and stirred for 10 min at rt. Suction filtration gave crude N-((2-chlorophenyl)(cyclopentyl)methyl)-3-iodo-1H-indazole-5-carboxamide (light beige solid, 1.796 g). $^1$H NMR (400 MHz, CDCl$_3$) 5 MS ESI 480.2 [M+H]$^+$, calcd for [C$_{20}$H$_{19}$ClN$_3$O+H]$^+$ 480.0.

To a mixture of crude N-((2-chlorophenyl)(cyclopentyl) methyl)-3-iodo-1H-indazole-5-carboxamide (241 mg, 0.5 mmol) and 1-methyl-4-(4-(4,4,5,5-tetramethyl-1,3,2-dioxaborolan-2-yl)phenoxy)piperidine (158 mg, 0.5 mmol) in EtOH (12 mL) was added 1 M aq Na$_2$CO$_3$ (1 mL, 1 mmol), followed by Pd(PPh$_3$)$_4$ (29 mg, 0.025 mmol). The resulting mixture was purged with Ar and microwaved 3 h at 125° C. After removal of solvents, it was purified by flash chromatography (MeOH/DCM 0-20%), prep-HPLC and PoraPak to give the title compound (white solid, 14.4 mg, 5%). $^1$H NMR (400 MHz, CD$_3$OD) δ 8.53 (s, 1H), 7.88 (d, J=8.4 Hz, 3H), 7.60-7.55 (m, 2H), 7.38 (dd, J=7.8 Hz, 2.8 Hz, 1H), 7.29 (dt, J=7.6 Hz, 0.8 Hz, 1H), 7.20 (dt, J=7.8 Hz, 1.5 Hz, 1H), 7.08 (d, J=8.8 Hz, 2H), 5.44 (d, J=10.8 Hz, 1H), 4.53-4.46 (m, 1H), 2.80-2.70 (m, 2H), 2.65-2.52 (m, 1H), 2.47-2.36 (m, 2H), 2.33 (s, 3H), 2.10-1.94 (m, 3H), 1.90-1.50 (m, 7H), 1.45-1.38 (m, 2H); MS ESI 543.5 [M+H]$^+$, calcd for [C$_{32}$H$_{35}$ClN$_4$O$_2$+H]$^+$ 543.2.

Example A200

2-(azetidin-1-yl)-N-(3-(4-(4-hydroxypiperidin-1-yl) phenyl)-1H-indazol-5-yl)-2-(thiophen-3-yl)acetamide

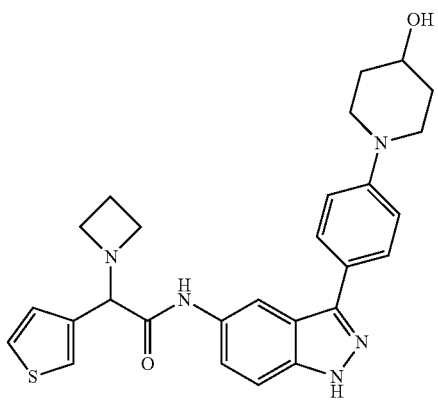 [SMILES: O=C(Nc1ccc2[nH]nc(-c3ccc(N4CCC(O)CC4)cc3)c2c1)C(c1ccsc1)N1CCC1]

To a mixture of 2-(azetidin-1-yl)-2-(thiophen-3-yl)acetic acid H$_3$BO$_3$ salt (34 mg, 0.13 mmol), 1-(4-(5-amino-1H-indazol-3-yl)phenyl)piperidin-4-ol di-trifluoroacetic acid (70 mg, 0.13 mmol) in DMF (5 mL) at 0° C. was added TBTU (42 mg, 0.13 mmol), followed by $^i$Pr$_2$NEt (0.16 mL, 0.91 mmol). The resulting mixture was stirred for 1 h at 0° C. It was purified by prep-HPLC and PoraPak to give the title compound (white solid, 30.2 mg, 31%). $^1$H NMR (400 MHz, CD$_3$OD) δ 8.32 (s, 1H), 7.76 (d, J=8.8 Hz, 2H), 7.52-7.46 (m, 3H), 7.39 (dd, J=5.0 Hz, 3.0 Hz, 1H), 7.24 (d, J=4.8 Hz, 1H), 7.07 (d, J=8.4 Hz, 2H), 4.18 (s, 1H), 3.80-3.72 (m, 1H), 3.68-3.60 (m, 2H), 3.37 (q, J=6.9 Hz, 2H), 3.20 (q, J=6.9 Hz, 2H), 2.96-2.87 (m, 2H), 2.12 (quint, J=7.1 Hz, 2H), 2.00-1.92 (m, 2H), 1.70-1.59 (m, 2H); MS ESI 488.2 [M+H]$^+$, calcd for [C$_{27}$H$_{29}$N$_5$O$_2$S+H]$^+$ 488.2.

Example A201

2-(azetidin-1-yl)-N-(3-(4-(4-(2-hydroxypropan-2-yl) piperidin-1-yl)phenyl)-1H-indazol-5-yl)-2-(thiophen-3-yl)acetamide

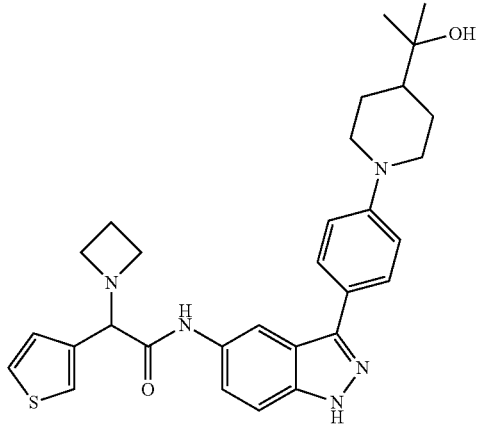 [SMILES: CC(C)(O)C1CCN(c2ccc(-c3n[nH]c4ccc(NC(=O)C(c5ccsc5)N5CCC5)cc34)cc2)CC1]

A di-TFA salt of the title compound was synthesized according to General Method C3 utilizing 2-(azetidin-1-yl)-N-(3-iodo-1H-indazol-5-yl)-2-(thiophen-3-yl)acetamide and 2-(1-(4-(4,4,5,5-tetramethyl-1,3,2-dioxaborolan-2-yl) phenyl)piperidin-4-yl)propan-2-ol obtained as an off-white solid (22 mg, 24% yield). $^1$H NMR (400 MHz, CD$_3$OD) δ ppm 8.41 (d, J=1.2 Hz, 1 H), 8.15 (d, J=8.8 Hz, 2 H), 7.86-7.90 (m, 1 H), 7.84 (d, J=8.8 Hz, 2 H), 7.64 (dd, J=5.1, 2.9 Hz, 1 H), 7.56-7.61 (m, 1 H), 7.49-7.55 (m, 1 H), 7.30 (dd, J=5.0, 1.2 Hz, 1 H), 5.51 (s, 1 H), 4.27 (br. s., 3 H), 3.63-3.87 (m, 5 H), 2.53-2.71 (m, 1 H), 2.36-2.53 (m, 1 H), 2.21 (d, J=13.8 Hz, 2 H), 1.87-2.03 (m, 2 H), 1.84 (d, J=12.0 Hz, 1 H), 1.23-1.31 (m, 6 H); MS ESI [M+H]$^+$ 530.2, calcd for [C$_{31}$H$_{33}$N$_5$O$_3$+H]$^+$ 530.26.

Example A202

(R)-3-(3-chloro-4-((1-methylpiperidin-4-yl)oxy)phenyl)-N-(3-hydroxy-1-phenylpropyl)-1H-indazole-5-carboxamide

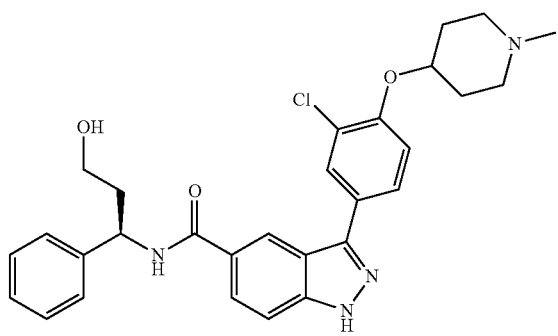 [SMILES: CN1CCC(Oc2ccc(-c3n[nH]c4ccc(C(=O)N[C@H](CCO)c5ccccc5)cc34)cc2Cl)CC1]

The title compound was synthesized according to the General Method C, utilizing (R)-N-(3-hydroxy-1-phenylpropyl)-3-iodo-1H-indazole-5-carboxamide (60 mg, 0.14 mmol), 4-(2-chloro-4-(4,4,5,5-tetramethyl-1,3,2-dioxaborolan-2-yl)phenoxy)-1-methylpiperidine (50 mg, 0.14 mmol), Pd(PPh$_3$)$_4$ (8 mg, 0.007 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by flash chromatography (SiO$_2$, Biotage 25 g, 0-30% MeOH in CH$_2$Cl$_2$) gave the title compound (white solid, 22 mg, 30%). $^1$H NMR (400 MHz, CD$_3$OD) δ ppm 8.54 (s, 1 H), 7.99 (d, J=2.0 Hz, 1 H), 7.82-7.94 (m, 2 H), 7.59 (d, J=8.8 Hz, 1 H), 7.44 (d, J=7.8 Hz, 2 H), 7.34 (t, J=7.8 Hz, 2 H), 7.20-7.27 (m, 2 H), 5.34 (dd, J=8.0, 6.8 Hz, 1 H), 4.59 (br. s, 1 H), 3.59-3.72 (m, 2 H), 2.73 (br. s, 2 H), 2.45 (br. s, 2 H), 2.32 (s, 3 H), 2.09-2.21 (m, 2 H), 2.03 (d, J=3.5 Hz, 2 H), 1.86-1.97 (m, 2 H); MS ESI 519.5 [M+H]$^+$, calcd for [C$_{29}$H$_{31}$ClN$_4$O$_3$+H]$^+$ 519.2.

Example A203

(R)-N-(cyclopropyl(pyridin-2-yl)methyl)-3-(4-((1-formylpiperidin-4-yl)oxy)phenyl)-1H-indazole-5-carboxamide

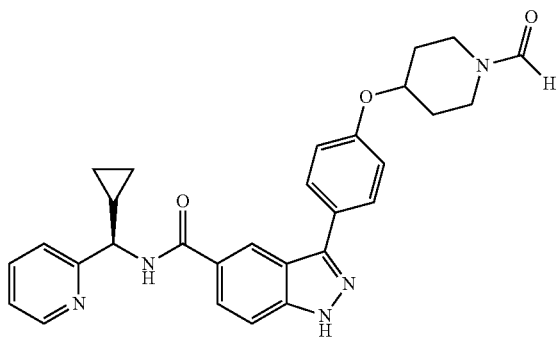 [SMILES: O=CN1CCC(Oc2ccc(-c3n[nH]c4ccc(C(=O)N[C@@H](c5ccccn5)C5CC5)cc34)cc2)CC1]

A TFA salt of the title compound was synthesized according to General Method C3 utilizing (R)-2-cyclopropyl-N-(3-iodo-1H-indazol-5-yl)-2-(pyridin-2-yl)acetamide and 4-(4-(4,4,5,5-tetramethyl-1,3,2-dioxaborolan-2-yl)phenoxy)piperidine-1-carbaldehyde obtained as a white solid (33 mg, 38% yield). $^1$H NMR (400 MHz, CD$_3$OD) δ ppm 8.77 (dd, J=5.7, 0.7 Hz, 1 H), 8.70 (s, 1 H), 8.56 (t, J=7.1 Hz, 1 H), 8.20 (d, J=8.0 Hz, 1 H), 7.90-8.01 (m, 4 H), 7.63 (d, J=8.8 Hz, 1 H), 7.15 (d, J=8.8 Hz, 2 H), 4.72-4.80 (m, 1 H), 4.49 (d, J=10.0 Hz, 1 H), 3.64-3.82 (m, 2 H), 3.39-3.58 (m, 2 H), 1.92-2.10 (m, 2 H), 1.71-1.90 (m, 2 H), 1.45-1.58 (m, 1 H), 0.84-0.95 (m, 1 H), 0.58-0.81 (m, 3 H); MS ESI [M+H]$^+$ 496.3, calcd for [C$_{29}$H$_{29}$N$_5$O$_3$+H]$^+$ 496.23.

Example A204

(S)-N-(cyclopropyl(pyridin-2-yl)methyl)-3-(4-((1-formylpiperidin-4-yl)oxy)phenyl)-1H-indazole-5-carboxamide

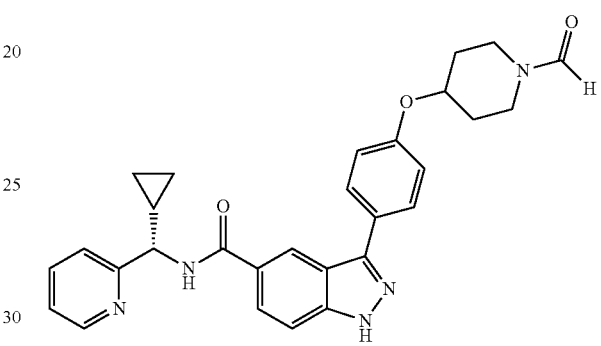

A TFA salt of the title compound was synthesized according to General Method C3 utilizing (S)-2-cyclopropyl-N-(3-iodo-1H-indazol-5-yl)-2-(pyridin-2-yl)acetamide and 4-(4-(4,4,5,5-tetramethyl-1,3,2-dioxaborolan-2-yl)phenoxy)piperidine-1-carbaldehyde and obtained as a white solid (32 mg, 38% yield). $^1$H NMR (400 MHz, CD$_3$OD) δ ppm 8.77 (dd, J=5.7, 0.7 Hz, 1 H), 8.70 (s, 1 H), 8.56 (t, J=7.1 Hz, 1 H), 8.20 (d, J=8.0 Hz, 1 H), 7.90-8.01 (m, 4 H), 7.63 (d, J=8.8 Hz, 1 H), 7.15 (d, J=8.8 Hz, 2 H), 4.72-4.80 (m, 1 H), 4.49 (d, J=10.0 Hz, 1 H), 3.64-3.82 (m, 2 H), 3.39-3.58 (m, 2 H), 1.92-2.10 (m, 2 H), 1.71-1.90 (m, 2 H), 1.45-1.58 (m, 1 H), 0.84-0.95 (m, 1 H), 0.58-0.81 (m, 3H); MS ESI [M+H]$^+$ 496.3, calcd for [C$_{29}$H$_{29}$N$_5$O$_3$+H]$^+$ 496.23.

Example A205

N-(cyclopropyl(phenyl)methyl)-3-(4-((1-formylpiperidin-4-yl)oxy)-3-methoxyphenyl)-1H-indazole-5-carboxamide

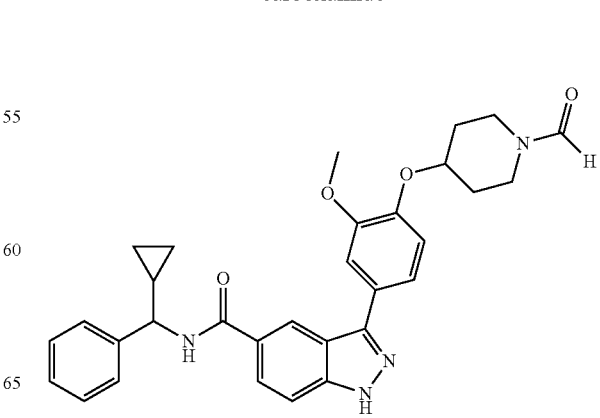

The title compound was synthesized according to the General Method C, utilizing N-(cyclopropyl(phenyl)methyl)-3-iodo-1H-indazole-5-carboxamide (100 mg, 0.24 mmol), 4-(2-methoxy-4-(4,4,5,5-tetramethyl-1,3,2-dioxaborolan-2-yl)phenoxy)piperidine-1-carbaldehyde (86 mg, 0.24 mmol), Pd(PPh$_3$)$_4$ (14 mg, 0.012 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC, followed by flash chromatography (SiO$_2$, Biotage 25 g, 0-30% MeOH in CH$_2$Cl$_2$, twice) gave the title compound (white solid, 25 mg, 20%). $^1$H NMR (400 MHz, CD$_3$OD) δ ppm 8.61 (s, 1 H), 8.01 (s, 1 H), 7.94 (d, J=8.8 Hz, 1 H), 7.50-7.61 (m, 3 H), 7.46 (d, J=7.3 Hz, 2 H), 7.31 (t, J=7.5 Hz, 2 H), 7.22 (t, J=7.3 Hz, 1 H), 7.10 (d, J=8.0 Hz, 1 H), 4.61 (br. s, 1 H), 4.47 (d, J=9.3 Hz, 1 H), 3.91 (s, 3 H), 3.63-3.78 (m, 2 H), 3.44-3.53 (m, 1 H), 3.33-3.41 (m, 1 H), 1.69-1.99 (m, 4 H), 1.32-1.43 (m, 1 H), 0.56-0.72 (m, 2 H), 0.39-0.53 (m, 2 H); MS ESI 525.3 [M+H]$^+$, calcd for [C$_{31}$H$_{32}$N$_4$O$_4$+H]$^+$ 525.2.

Example A206

N-(cyclopropyl(pyridin-2-yl)methyl)-3-(4-((1-formylpiperidin-4-yl)oxy)-3-methoxyphenyl)-1H-indazole-5-carboxamide

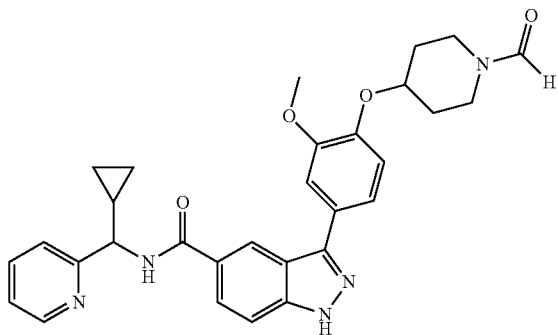 [SMILES: COc1cc(-c2n[nH]c3ccc(C(=O)NC(c4ccccn4)C4CC4)cc23)ccc1OC1CCN(C=O)CC1]

The title compound was synthesized according to the General Method C, utilizing N-(cyclopropyl(pyridin-2-yl)methyl)-3-iodo-1H-indazole-5-carboxamide (100 mg, 0.24 mmol), 4-(2-methoxy-4-(4,4,5,5-tetramethyl-1,3,2-dioxaborolan-2-yl)phenoxy)piperidine-1-carbaldehyde (86 mg, 0.24 mmol), Pd(PPh$_3$)$_4$ (14 mg, 0.012 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC and trituration with Et$_2$O gave the title compound (white solid, 43 mg, 34%). $^1$H NMR (400 MHz, CD$_3$OD) δ ppm 8.73 (d, J=5.5 Hz, 1 H), 8.68 (s, 1 H), 8.41-8.49 (m, 1 H), 8.10 (d, J=8.0 Hz, 1 H), 8.04 (s, 1 H), 7.98 (dd, J=8.9, 1.4 Hz, 1 H), 7.85 (t, J=6.8 Hz, 1 H), 7.63 (d, J=9.0 Hz, 1 H), 7.54-7.60 (m, 2 H), 7.17 (d, J=8.3 Hz, 1 H), 4.63-4.70 (m, 1 H), 4.49 (d, J=10.0 Hz, 1 H), 3.68-3.80 (m, 2 H), 3.48-3.57 (m, 1 H), 3.41 (d, J=4.8 Hz, 1 H), 1.73-2.03 (m, 4 H), 1.43-1.54 (m, 1 H), 0.81-0.90 (m, 1 H), 0.58-0.77 (m, 3 H); MS ESI 526.4 [M+H]$^+$, calcd for [C$_{30}$H$_{31}$N$_5$O$_4$+H]$^+$ 526.2.

Example A207

N-(2-cyclopentyl-2-phenylethyl)-3-(4-((1-methylpiperidin-4-yl)oxy)phenyl)-1H-indazole-5-carboxamide

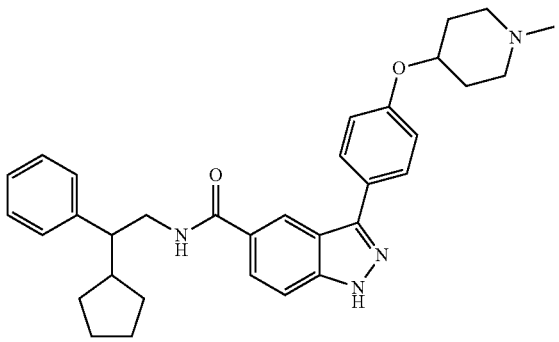 [SMILES: CN1CCC(Oc2ccc(-c3n[nH]c4ccc(C(=O)NCC(c5ccccc5)C5CCCC5)cc34)cc2)CC1]

The title compound was synthesized according to the General Method C, utilizing N-(2-cyclopentyl-2-phenylethyl)-3-iodo-1H-indazole-5-carboxamide (50 mg, 0.11 mmol), (4-((1-methylpiperidin-4-yl)oxy)phenyl)boronic acid pinacol ester (35 mg, 0.11 mmol), Pd(PPh$_3$)$_4$ (6 mg, 0.0055 mmol), satd. aq Na$_2$CO$_3$ (0.5 mL), and 1.5 mL of PhMe:EtOH (1:1). The vial was charged with Ar and heated in the microwave reactor at 125° C. for 2 h. Purification by RPHPLC gave the title compound as a TFA salt (white solid, 24 mg, 34%). $^1$H NMR (400 MHz, CD$_3$OD) δ ppm 8.19 (s, 1 H), 7.85 (t, J=8.3 Hz, 2 H), 7.64 (d, J=8.8 Hz, 1 H), 7.51 (d, J=8.8 Hz, 1 H), 7.21-7.31 (m, 4 H), 7.11-7.21 (m, 3 H), 4.63-4.73 (m, 0.3 H), 3.85-3.93 (m, 1 H), 3.62-3.69 (m, 0.7 H), 3.34-3.56 (m, 4 H), 3.15-3.27 (m, 1 H), 2.91-2.97 (m, 3 H), 2.75-2.86 (m, 1 H), 2.40-2.48 (m, 0.7 H), 2.23-2.37 (m, 1.3 H), 2.01-2.20 (m, 3.3 H), 1.87-2.00 (m, 0.7 H), 1.35-1.77 (m, 6 H), 0.96-1.10 (m, 1 H); MS ESI 523.4 [M+H]$^+$, calcd for [C$_{33}$H$_{38}$N$_4$O$_2$+H]$^+$ 523.3.

Example A208

N-(cyclopentyl(pyridin-2-yl)methyl)-3-(4-((1-methylpiperidin-4-yl)oxy)phenyl)-1H-indazole-5-carboxamide

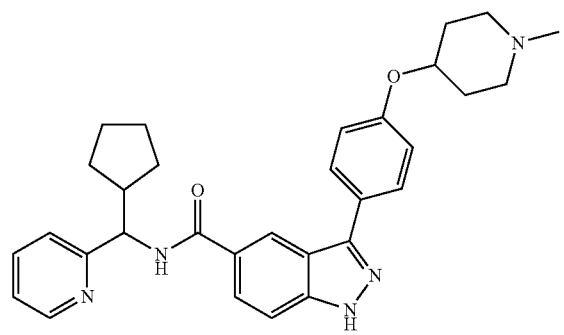 [SMILES: CN1CCC(Oc2ccc(-c3n[nH]c4ccc(C(=O)NC(c5ccccn5)C5CCCC5)cc34)cc2)CC1]

The title compound was synthesized according to the General Method C, utilizing N-(cyclopentyl(pyridin-2-yl)methyl)-3-iodo-1H-indazole-5-carboxamide (100 mg, 0.22 mmol), (4-((1-methylpiperidin-4-yl)oxy)phenyl)boronic acid pinacol ester (70 mg, 0.22 mmol), Pd(PPh$_3$)$_4$ (13 mg, 0.011 mmol), satd. aq Na$_2$CO$_3$ (1.25 mL), and 3.75 mL of PhMe:EtOH (1:1). The vial was charged with Ar and heated in the microwave reactor at 125° C. for 2 h. Purification by RPHPLC followed by flash chromatography (SiO$_2$, Biotage 25 g, 0-30% MeOH in CH$_2$Cl$_2$) gave the title compound (white solid, 43 mg, 38%). NMR (400 MHz, CD$_3$OD) δ ppm 8.57 (s, 1 H), 8.51 (d, J=4.3 Hz, 1 H), 7.86-7.94 (m, 3 H), 7.79 (t, J=7.6 Hz, 1 H), 7.59 (d, J=8.8 Hz, 1 H), 7.49 (d, J=7.8 Hz, 1 H), 7.29 (dd, J=7.0, 5.0 Hz, 1 H), 7.10 (d, J=8.5 Hz, 2 H), 5.01 (d, J=10.3 Hz, 1 H), 4.52 (br. s, 1 H), 2.82 (br. s, 2 H), 2.46-2.58 (m, 3 H), 2.39 (s, 3 H), 1.81-2.12 (m, 5 H), 1.45-1.76 (m, 5 H), 1.20-1.41 (m, 2 H); MS ESI 510.2 [M+H]$^+$, calcd for [C$_{31}$H$_{35}$N$_5$O$_2$+H]$^+$ 510.3.

Example A209

N-(cyclopropyl(pyridin-2-yl)methyl)-3-(4-((1-(oxetan-3-yl)azetidin-3-yl)oxy)phenyl)-1H-indazole-5-carboxamide

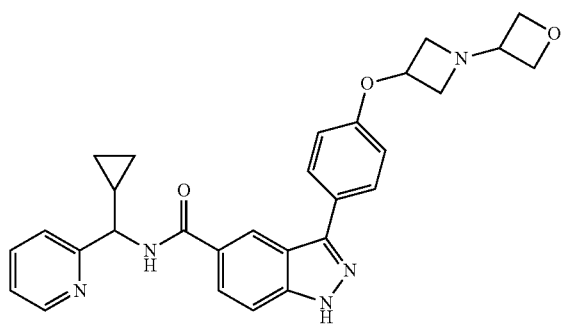 [SMILES: O=C(NC(c1ccccn1)C1CC1)c1ccc2[nH]nc(-c3ccc(OC4CN(C5COC5)C4)cc3)c2c1]

To a 20 mL microwave vial charged with Mg powder (240 mg, 10 mmol), THF (10 mL) was added bromocyclopropane (1.21 g, 10 mmol). The resulting mixture was stirred for 30 min at rt before a solution of picolinonitrile (520 mg, 5 mmol) in THF (3 mL) was added. It was microwaved 10 min at 100° C., cooled to rt and added dropwise to a cold solution of NaBH$_4$ (380 mg, 10 mmol) in MeOH (30 mL) at 0° C. The resulting mixture was stirred for 15 min at rt, quenched with H$_2$O, extracted with DCM and purified by flash chromatography (MeOH/DCM 0-30%) to give cyclopropyl(pyridin-2-yl)methanamine (light brown oil, 590 mg). $^1$H NMR (400 MHz, CDCl$_3$) δ 8.52 (d, J=4.0 Hz, 1H), 7.82 (dt, J=7.6 Hz, 1.6 Hz, 1H), 7.50 (d, J=8.0 Hz, 1H), 7.34-7.39 (m, 1H), 3.25 (d, J=8.8 Hz, 1H), 1.18-1.10 (m, 1H), 0.70-0.62 (m, 1H), 0.54-0.42 (m, 2H), 0.40-0.34 (m, 1H); MS ESI 132.0 [M+H]$^+$, calcd for [C$_9$H$_{12}$N$_2$–NH$_3$+H]$^+$ 132.1.

To a solution of cyclopropyl(pyridin-2-yl)methanamine (575 mg, 3.94 mmol), 3-iodo-1H-indazole-5-carboxamide (1.14 g, 3.94 mmol) in DMF (15 mL) at 0° C. was added TBTU (1.27 g, 3.94 mmol), followed by $^i$Pr$_2$NEt (1.37 mL, 7.88 mmol). The resulting mixture was stirred at rt for 30 min, quenched with H$_2$O till total volume about 100 mL and stirred for 10 min at rt. Suction filtration gave crude N-(cyclopropyl(pyridin-2-yl)methyl)-3-iodo-1H-indazole-5-carboxamide (off white solid, 1.290 g). MS ESI 419.0 [M+H]$^+$, calcd for [C$_{17}$H$_{15}$IN$_4$O+H]$^+$ 419.0.

To a mixture of crude N-(cyclopropyl(pyridin-2-yl)methyl)-3-iodo-1H-indazole-5-carboxamide (209 mg, 0.5 mmol) and 1-(oxetan-3-yl)-3-(4-(4,4,5,5-tetramethyl-1,3,2-dioxaborolan-2-yl)phenoxy)azetidine (166 mg, 0.5 mmol) in EtOH (12 mL) was added 1 M aq Na$_2$CO$_3$ (1 mL, 1 mmol), followed by Pd(PPh$_3$)$_4$ (29 mg, 0.025 mmol). The resulting mixture was purged with Ar and microwaved 4 h at 125° C. After removal of solvents, it was purified by flash chromatography (MeOH/DCM 0-20%), prep-HPLC and PoraPak to give the title compound (white solid, 40.0 mg, 16%). $^1$H NMR (400 MHz, CD$_3$OD) δ 8.64 (s, 1H), 8.51 (d, J=4.4 Hz, 1H), 7.96 (dd, J=9.0 Hz, 1.4 Hz, 1H), 7.92 (d, J=8.8 Hz, 2H), 7.80 (dt, J=7.8 Hz, 1.6 Hz, 1H), 7.60 (d, J=8.8 Hz, 1H), 7.52 (d, J=8.0 Hz, 1H), 7.32-7.27 (m, 1H), 6.96 (d, J=8.8 Hz, 2H), 4.96-4.90 (m, 1H, partially buried under H$_2$O peak), 4.75 (t, J=6.6 Hz, 2H), 4.53-4.47 (m, 3H), 3.90-3.83 (m, 3H), 3.38-3.33 (m, 2H, partially overlapped with CD$_3$OD solvent residue), 1.45-1.35 (m, 1H), 0.72-0.65 (m, 1H), 0.62-0.50 (m, 3H); MS ESI 496.2 [M+H]$^+$, calcd for [C$_{29}$H$_{29}$N$_5$O$_3$+H]$^+$ 496.2.

Example A210

N-(cyclobutyl(pyridin-2-yl)methyl)-3-(4-((1-methylpiperidin-4-yl)oxy)phenyl)-1H-indazole-5-carboxamide

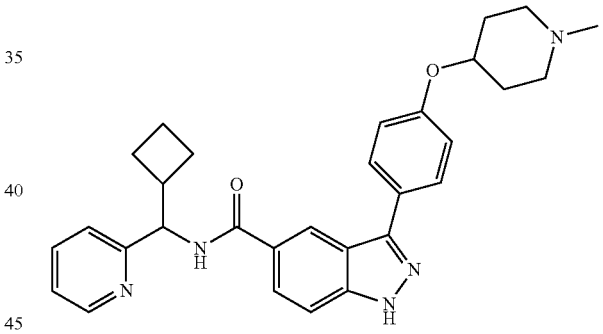

The title compound was synthesized according to the General Method C, utilizing N-(cyclobutyl(pyridin-2-yl)methyl)-3-iodo-1H-indazole-5-carboxamide (200 mg, 0.46 mmol), (4-((1-methylpiperidin-4-yl)oxy)phenyl)boronic acid pinacol ester (147 mg, 0.46 mmol), Pd(PPh$_3$)$_4$ (27 mg, 0.023 mmol), satd. aq Na$_2$CO$_3$ (1.25 mL), and 3.75 mL of PhMe:EtOH (1:1). The vial was charged with Ar and heated in the microwave reactor at 125° C. for 3 h. Purification by RPHPLC followed by flash chromatography (SiO$_2$, Biotage 25 g, 0-30% MeOH in CH$_2$Cl$_2$) gave the title compound (white solid, 70 mg, 31%). $^1$H NMR (400 MHz, CD$_3$OD) δ ppm 8.58 (s, 1 H), 8.51 (d, J=4.3 Hz, 1 H), 7.93 (d, J=8.5 Hz, 3 H), 7.80 (td, J=7.8, 1.5 Hz, 1 H), 7.60 (d, J=8.8 Hz, 1 H), 7.48 (d, J=8.0 Hz, 1 H), 7.27-7.33 (m, 1 H), 7.14 (d, J=8.5 Hz, 2 H), 5.19 (d, J=10.3 Hz, 1 H), 4.60 (br. s, 1 H), 2.86-2.98 (m, 3 H), 2.65 (br. s, 2 H), 2.48 (s, 3 H), 2.16-2.25 (m, 1 H), 2.05-2.16 (m, 2 H), 1.86-2.04 (m, 6 H), 1.76-1.86 (m, 1 H); MS ESI 496.2 [M+H]$^+$, calcd for [C$_{30}$H$_{33}$N$_5$O$_2$+H]$^+$ 496.3.

Example A211

(R)-N-((3-chloropyridin-2-yl)(cyclopropyl)methyl)-3-(4-((1-formylpiperidin-4-yl)oxy)phenyl)-1H-indazole-5-carboxamide

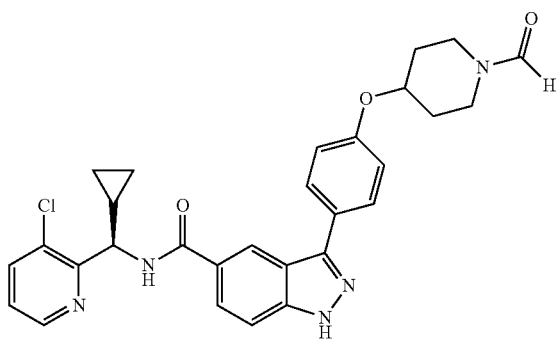 [SMILES: O=CN1CCC(Oc2ccc(-c3n[nH]c4ccc(C(=O)N[C@@H](c5ncccc5Cl)C5CC5)cc34)cc2)CC1]

A TFA salt of the title compound was synthesized according to General Method C3 utilizing (R)-2-(3-chloropyridin-2-yl)-2-cyclopropyl-N-(3-iodo-1H-indazol-5-yl)acetamide and 4-(4-(4,4,5,5-tetramethyl-1,3,2-dioxaborolan-2-yl)phenoxy)piperidine-1-carbaldehyde obtained as a light yellow solid (42 mg, 48% yield). $^1$H NMR (400 MHz, CD$_3$OD) δ ppm 8.64 (s, 1 H), 8.53 (d, J=3.5 Hz, 1 H), 8.04 (s, 1 H), 7.93 (t, J=9.1 Hz, 4 H), 7.59 (d, J=9.0 Hz, 1 H), 7.36 (dd, J=8.1, 4.9 Hz, 1 H), 7.10 (d, J=8.8 Hz, 2 H), 5.13 (d, J=9.0 Hz, 1 H), 4.71 (br. s., 1 H), 3.62-3.80 (m, 2 H), 3.46-3.58 (m, 1 H), 3.36-3.46 (m, 1 H), 1.97 (d, J=13.3 Hz, 2 H), 1.69-1.86 (m, 2 H), 1.51 (d, J=6.2 Hz, 1 H), 0.46-0.74 (m, 4 H); MS ESI [M++H]$^+$ 530.4, calcd for [C$_{29}$H$_{28}$ClN$_5$O$_3$+H]$^+$ 530.20.

Example A212

(S)-N-((3-chloropyridin-2-yl)(cyclopropyl)methyl)-3-(4-((1-formylpiperidin-4-yl)oxy)phenyl)-1H-indazole-5-carboxamide

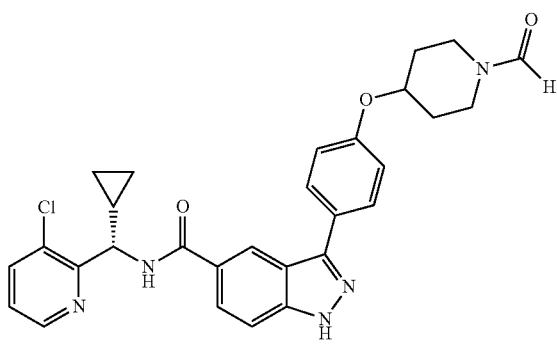 [SMILES: O=CN1CCC(Oc2ccc(-c3n[nH]c4ccc(C(=O)N[C@H](c5ncccc5Cl)C5CC5)cc34)cc2)CC1]

The title compound was synthesized according to General Method C3 utilizing (S)-2-(3-chloropyridin-2-yl)-2-cyclopropyl-N-(3-iodo-1H-indazol-5-yl)acetamide and 4-(4-(4,4,5,5-tetramethyl-1,3,2-dioxaborolan-2-yl)phenoxy)piperidine-1-carbaldehyde and obtained as a light yellow solid (36 mg, 49% yield). $^1$H NMR (400 MHz, CD$_3$OD) δ ppm 8.63 (s, 1 H), 8.46 (d, J=4.52 Hz, 1 H), 8.00 (s, 1 H), 7.93 (dd, J=8.8, 1.2 Hz, 1 H), 7.87 (d, J=8.2 Hz, 2 H), 7.79 (d, J=8.2 Hz, 1 H), 7.56 (d, J=8.8 Hz, 1 H), 7.20-7.28 (m, 1 H), 6.97-7.06 (m, 2 H), 5.19 (d, J=9.0 Hz, 1 H), 4.62 (m, J=3.3 Hz, 1 H), 3.65-3.75 (m, 1 H), 3.55-3.65 (m, 1 H), 3.41-3.51 (m, 1 H), 3.28-3.39 (m, 1 H), 1.92 (br. s., 2 H), 1.71 (br. s., 2 H), 1.40-1.53 (m, 1 H), 0.54-0.66 (m, 2 H), 0.50 (d, J=6.0 Hz, 2 H); MS ESI [M+H]$^+$ 530.4, calcd for [C$_{29}$H$_{28}$ClN$_5$O$_3$+H]$^+$ 530.20.

Example A213

N-((S)-cyclopropyl(pyridin-2-yl)methyl)-3-(4-(((1R,3R,5S)-8-methyl-8-azabicyclo[3.2.1]octan-3-yl)oxy)phenyl)-1H-indazole-5-carboxamide

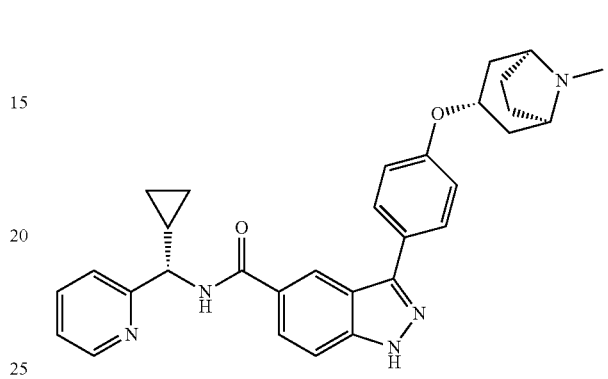

The title compounds was synthesized according to the General Method C2 utilizing (S)-N-(cyclopropyl(pyridin-2-yl)methyl)-3-iodo-1H-indazole-5-carboxamide (60 mg, 0.14 mmol) and (1R,3R,5S)-8-methyl-3-(4-(4,4,5,5-tetramethyl-1,3,2-dioxaborolan-2-yl)phenoxy)-8-azabicyclo[3.2.1]octane (33 mg, 0.099 mmol) to afford N-((S)-cyclopropyl(pyridin-2-yl)methyl)-3-(4-(((1R,3R,5S)-8-methyl-8-azabicyclo[3.2.1]octan-3-yl)oxy)phenyl)-1H-indazole-5-carboxamide as a white powder (14.3 mg, 28%). $^1$H NMR (400 MHz, CD$_3$OD) δ ppm 8.66 (s, 1 H), 8.53 (d, J=4.0 Hz, 1 H), 7.89-8.01 (m, 3 H), 7.79-7.87 (m, 1 H), 7.61 (d, J=8.8 Hz, 1 H), 7.54 (s, 1 H), 7.32 (dd, J=6.9, 5.4 Hz, 1 H), 7.04 (d, J=8.5 Hz, 2 H), 4.61-4.72 (m, 1 H), 4.50 (d, J=9.5 Hz, 1 H), 3.21 (br. s., 2 H), 2.34 (s, 3 H), 1.98-2.26 (m, 8 H), 1.34-1.48 (m, 1 H), 0.67-0.77 (m, 1 H), 0.46-0.65 (m, 3 H); MS ESI 508.2 [M+H]$^+$, calcd for [C$_{31}$H$_{33}$N$_5$O$_2$+H]$^+$ 508.2.

Example A214

(S)-N-(cyclopropyl(pyridin-2-yl)methyl)-3-(4-((1-methylpiperidin-4-yl)oxy)phenyl)-1H-indazole-5-carboxamide

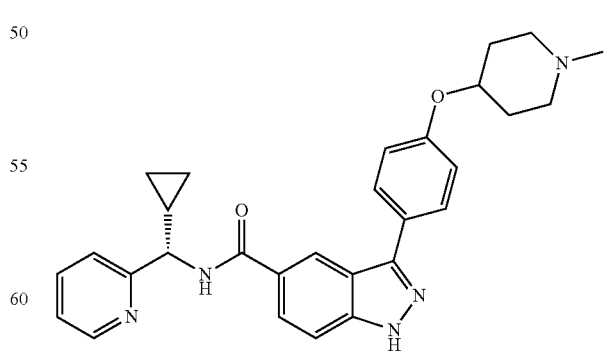

The title compound was synthesized according to the General Method C, utilizing (S)-N-(cyclopropyl(pyridin-2-yl)methyl)-3-iodo-1H-indazole-5-carboxamide (50 mg, 0.12 mmol), (4-((1-methylpiperidin-4-yl)oxy)phenyl)boronic acid pinacol ester (38 mg, 0.12 mmol), Pd(PPh$_3$)$_4$ (7 mg, 0.006 mmol), satd. aq Na$_2$CO$_3$ (1.25 mL), and 3.75 mL of PhMe:EtOH (1:1). The vial was charged with Ar and heated in the microwave reactor at 125° C. for 3 h. Purification by RPHPLC followed by flash chromatography (SiO$_2$, Biotage 25 g, 0-30% MeOH in CH$_2$Cl$_2$) gave the title compound (white solid, 21 mg, 36%). $^1$H NMR (400 MHz, CD$_3$OD) δ ppm 8.64 (s, 1 H), 8.52 (d, J=4.8 Hz, 1 H), 7.94 (s, 3 H), 7.82 (td, J=7.6, 1.8 Hz, 1 H), 7.60 (d, J=8.8 Hz, 1 H), 7.54 (d, J=7.8 Hz, 1 H), 7.29-7.35 (m, 1 H), 7.12 (d, J=8.8 Hz, 2 H), 4.53 (br. s, 1 H), 4.50 (d, 19.5 Hz, 1 H), 2.76 (br. s, 2 H), 2.43 (br. s, 2 H), 2.33 (s, 3 H), 2.02-2.11 (m, 2 H), 1.81-1.91 (m, 2 H), 1.35-1.46 (m, 1 H), 0.65-0.74 (m, 1 H), 0.49-0.62 (m, 3 H); MS ESI 482.2 [M+H]$^+$, calcd for [C$_{29}$H$_{31}$N$_5$O$_2$+H]$^+$ 482.3.

Example A215

(R)-N-((3-chloropyridin-2-yl)(cyclopropyl)methyl)-3-(4-((1-(oxetan-3-yl)piperidin-4-yl)oxy)phenyl)-1H-indazole-5-carboxamide

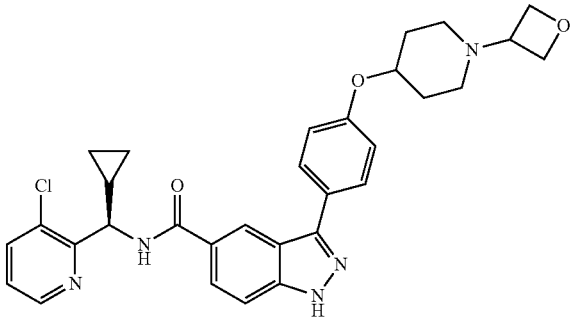 [SMILES: O=C(N[C@@H](c1ncccc1Cl)C1CC1)c1ccc2[nH]nc(-c3ccc(OC4CCN(C5COC5)CC4)cc3)c2c1]

The title compound was synthesized according to General Method C3 utilizing (R)-2-(3-chloropyridin-2-yl)-2-cyclopropyl-N-(3-iodo-1 H-indazol-5-yl)acetamide and 1-(oxetan-3-yl)-4-(4-(4,4,5,5-tetramethyl-1,3,2-dioxaborolan-2-yl)phenoxy)piperidine and obtained as a white solid (30 mg, 48% yield). $^1$H NMR (400 MHz, CD$_3$OD) δ ppm 8.65 (s, 1 H), 8.47 (dd, 14.6, 1.3 Hz, 1 H), 7.94 (dd, J=8.8, 1.5 Hz, 1 H), 7.88 (d, J=8.5 Hz, 2 H), 7.81 (dd, J=8.1, 1.3 Hz, 1 H), 7.57 (d, J=8.8 Hz, 1 H), 7.25 (dd, J=8.1, 4.6 Hz, 1 H), 7.01 (d, J=8.8 Hz, 2 H), 5.19 (d, J=9.0 Hz, 1 H), 4.60-4.68 (m, 2 H), 4.56 (t, J=6.2 Hz, 2 H), 4.35-4.45 (m, 1 H), 3.44 (quin, J=6.4 Hz, 1 H), 2.53 (br. s., 2 H), 2.15 (br. s., 2 H), 1.97 (br. s., 2 H), 1.78 (d, J=8.5 Hz, 2 H), 1.40-1.53 (m, 1 H), 0.55-0.66 (m, 2 H), 0.43-0.55 (m, 2 H); MS ESI [M+H]$^+$ 558.4, calcd for [C$_{31}$H$_{32}$ClN$_5$O$_3$+H]$^+$ 558.23.

Example A216

(S)-N-((3-chloropyridin-2-yl)(cyclopropyl)methyl)-3-(4-((1-(oxetan-3-yl)piperidin-4-yl)oxy)phenyl)-1H-indazole-5-carboxamide

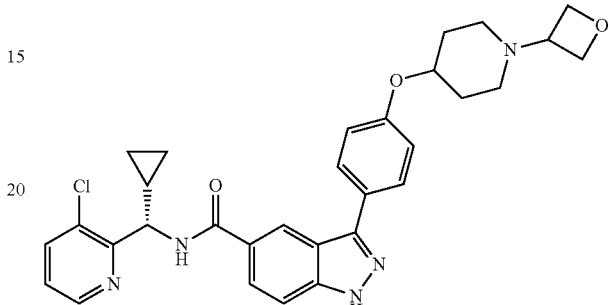

The title compound was synthesized according to General Method C3 utilizing (S)-2-(3-chloropyridin-2-yl)-2-cyclopropyl-N-(3-iodo-1H-indazol-5-yl)acetamide and 1-(oxetan-3-yl)-4-(4-(4,4,5,5-tetramethyl-1,3,2-dioxaborolan-2-yl)phenoxy)piperidine and obtained as a white solid (26 mg, 42% yield). $^1$H NMR (400 MHz, CD$_3$OD) δ ppm 8.65 (s, 1 H), 8.47 (dd, J=4.6, 1.3 Hz, 1 H), 7.94 (dd, J=8.8, 1.5 Hz, 1 H), 7.88 (d, J=8.5 Hz, 2 H), 7.81 (dd, J=8.1, 1.3 Hz, 1 H), 7.57 (d, J=8.8 Hz, 1 H), 7.25 (dd, J=8.1, 4.6 Hz, 1 H), 7.01 (d, J=8.8 Hz, 2 H), 5.19 (d, J=9.0 Hz, 1 H), 4.60-4.68 (m, 2 H), 4.56 (t, J=6.2 Hz, 2 H), 4.35-4.45 (m, 1 H), 3.44 (quin, J=6.4 Hz, 1 H), 2.53 (brs, 2 H), 2.15 (brs, 2 H), 1.97 (brs, 2 H), 1.78 (d, J=8.5 Hz, 2 H), 1.40-1.53 (m, 1 H), 0.55-0.66 (m, 2 H), 0.43-0.55 (m, 2 H); MS ESI [M+H]$^+$ 558.4, calcd for [C$_{31}$H$_{32}$ClN$_5$O$_3$+H]$^+$ 558.23.

The following final compounds were synthesized according to the synthesis of Example A1 using General Methods C, C2 or C3:

| Example/IUPAC name | Structure | MS calculated MS ESI [M + H]$^+$ | Yield; Appearance; Salt form |
|---|---|---|---|
| A217: (S)-N-(cyclopropyl(pyridin-2-yl)methyl)-3-(4-((1-(2-hydroxy-2-methylpropyl)piperidin-4-yl)oxy)phenyl)-1H-indazole-5-carboxamide | 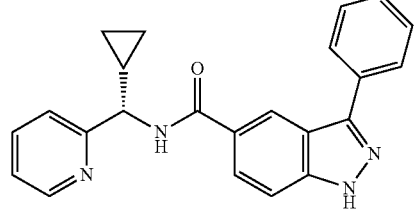 | [C$_{32}$H$_{37}$N$_5$O$_3$ + H]$^+$ 540.30 540.3 | 10 mg (13%); brown solid; free base |

SMs: (S)-N-(cyclopropyl(pyridin-2-yl)methyl)-3-iodo-1H-indazole-5-carboxamide (60 mg, 0.14 mmol), 2-methyl-1-(4-(4-(4,4,5,5-tetramethyl-1,3,2-dioxaborolan-2-yl)phenoxy)piperidin-1-yl)propan-2-ol (70 mg, 0.19 mmol)
$^1$H NMR (400 MHz, CD$_3$OD) δ ppm 8.64 (s, 1H), 8.51 (d, J = 4.5 Hz, 1H), 7.96-7.91 (m, 3H), 7.82 (t, J = 7.4 Hz, 1H), 7.59 (d, J = 8.8 Hz, 1H), 7.53 (d, J = 8.8 Hz, 1H), 7.33-7.30 (m, 1H), 7.10 (d, J = 8.6 Hz, 2H), 4.51-4.44 (m, 2H) 2.94-2.91 (m, 2H), 2.54-2.50 (m, 2H), 2.36 (s, 2H), 2.07-2.03 (m, 2H), 1.85-1.82 (m, 2H), 1.42-1.40 (m, 1H), 1.20 (s, 6H), 0.70-0.68 (m, 1H), 0.59-0.53 (m, 3H)

| Example/IUPAC name | Structure | MS calculated MS ESI [M + H]+ | Yield; Appearance; Salt form |
|---|---|---|---|
| A218: (S)-N-(cyclopropyl(thiophen-3-yl)methyl)-3-(4-((1-(2-hydroxy-2-methylpropyl)piperidin-4-yl)oxy)phenyl)-1H-indazole-5-carboxamide | 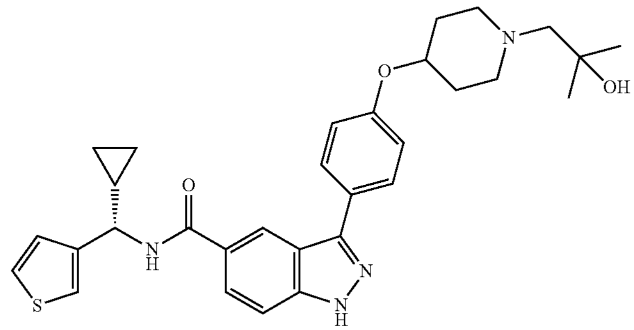 [SMILES: CC(C)(O)CN1CCC(Oc2ccc(-c3n[nH]c4ccc(C(=O)N[C@H](c5ccsc5)C5CC5)cc34)cc2)CC1] | [C$_{31}$H$_{36}$N$_4$O$_3$S + H]$^+$ 545.26 545.4 | 15 mg (19%); brown solid; free base |

SMs: (S)-N-(cyclopropyl(thiophen-3-yl)methyl)-3-iodo-1H-indazole-5-carboxamide (60 mg, 0.14 mmol), 2-methyl-1-(4-(4-(4,4,5,5-tetramethyl-1,3,2-dioxaborolan-2-yl)phenoxy)piperidin-1-yl)propan-2-ol (69 mg, 0.19 mmol)
$^1$H NMR (400 MHz, CD$_3$OD) δ ppm 8.61 (s, 1H), 7.97-7.91 (m, 3H), 7.60 (d, J = 8.8 Hz, 1H), 7.28 (d, J = 5.2 Hz, 1H), 7.13-7.09 (m, 3H), 6.98-6.96 (m, 1H), 4.75 (d, J = 9.2 Hz, 1H), 4.67-4.64 (m, 1H), 2.96-2.92 (m, 2H), 2.56-2.51 (m, 2H), 2.37 (s, 2H), 2.05-2.01 (m, 2H), 1.85-1.82 (m, 2H), 1.53-1.50 (m, 1H), 1.21 (s, 6H) 0.78-0.76 (m, 1H), 0.68-0.66 (m, 1H), 0.56-0.53 (m, 2H)

| | | | |
|---|---|---|---|
| A219: (R)-N-(cyclopentyl(thiophen-3-yl)methyl)-3-(4-((1-(2-hydroxyethyl)piperidin-4-yl)oxy)phenyl)-1H-indazole-5-carboxamide | | [C$_{31}$H$_{36}$N$_4$O$_3$S + H]$^+$ 545.26 545.4 | 41 mg (37%); brown solid; TFA salt |

SMs: (R)-N-(cyclopentyl(thiophen-3-yl)methyl)-3-iodo-1H-indazole-5-carboxamide (93 mg, 0.21 mmol), 2-(4-(4-(4,4,5,5-tetramethyl-1,3,2-dioxaborolan-2-yl)phenoxy)piperidin-1-yl)ethanol (93 mg, 0.27 mmol)
$^1$H NMR (400 MHz, CD$_3$OD) δ ppm 8.52 (s, 1 H), 7.95-7.87 (m, 3H), 7.59 (d, J = 8.6 Hz, 1 H), 7.36-7.32 (m, 2H), 7.21-7.15 (m, 3H), 5.05 (d, J = 10 Hz, 1H), 4.87 (bs, 1H), 3.98-3.91 (m, 2H), 3.77-3.54 (m, 2H), 3.44-3.21 (m, 2H), 2.60-2.15 (m, 5H), 2.01-1.92 (m, 2H), 1.70-1.43 (m, 7H), 1.31-1.20 (m, 1H)

| | | | |
|---|---|---|---|
| A220: N-((S)-cyclopropyl(thiophen-3-yl)methyl)-3-(4-((1-((R)-2-hydroxypropyl)piperidin-4-yl)oxy)phenyl)-1H-indazole-5-carboxamide | | [C$_{30}$H$_{34}$N$_4$O$_3$S + H]$^+$ 531.24 531.5 | 47 mg (51%); white solid; TFA salt |

SMs: (S)-N-(cyclopropyl(thiophen-3-yl)methyl)-3-iodo-1H-indazole-5-carboxamide (60 mg, 0.14 mmol), (R)-1-(4-(4-(4,4,5,5-tetramethyl-1,3,2-dioxaborolan-2-yl)phenoxy)piperidin-1-yl)propan-2-ol (67 mg, 0.19 mmol)
$^1$H NMR (400 MHz, CD$_3$OD) δ ppm 8.60 (s, 1H), 7.97-7.94 (m, 3H), 7.62 (d, J = 8.8 Hz, 1H), 7.28 (d, J = 4.8 Hz, 1H), 7.22-7.13 (m, 3H), 6.99-6.97 (m, 1H), 4.76 (d, J = 10 Hz, 1H), 4.87 (bs, 1H), 4.23-4.21 (m, 1H), 3.75-3.20 (m, 5H), 3.09-3.03 (m, 1H), 2.42-2.15 (m, 4H), 1.53-1.49 (m, 1H), 1.25 (d, J = 6.0 Hz, 3H), 0.80-0.76 (m, 1H), 0.68-0.65 (m, 1H), 0.59-0.45 (m, 2H)

| Example/IUPAC name | Structure | MS calculated MS ESI [M + H]⁺ | Yield; Appearance; Salt form |
|---|---|---|---|
| A221: N-((S)-cyclopropyl(pyridin-2-yl)methyl)-3-(4-((1-((R)-2-hydroxy-propyl)piperidin-4-yl)oxy)phenyl)-1H-indazole-5-carboxamide | 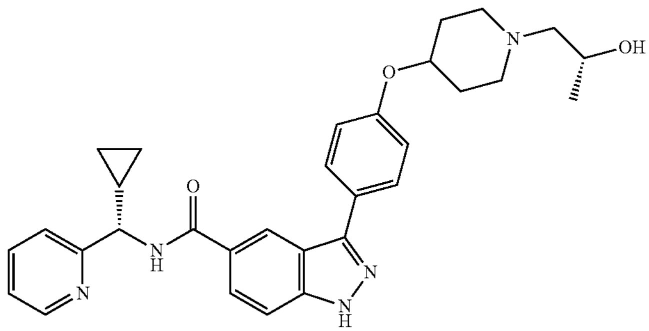 [SMILES: C[C@@H](O)CN1CCC(Oc2ccc(-c3n[nH]c4ccc(C(=O)N[C@H](c5ccccn5)C5CC5)cc34)cc2)CC1] | [C₃₁H₃₅N₅O₃ + H]⁺ 526.28 526.2 | 27 mg (51%); white solid; 2 × TFA salt |

SMs: (S)-N-(cyclopropyl(pyridin-2-yl)methyl)-3-iodo-1H-indazole-5-carboxamide (59 mg, 0.14 mmol), (R)-1-(4-(4-(4,4,5,5-tetramethyl-1,3,2-dioxaborolan-2-yl)phenoxy)piperidin-1-yl)propan-2-ol (67 mg, 0.19 mmol)
¹H NMR (400 MHz, CD₃OD) δ ppm 8.72 (d, J = 5.7 Hz, 1H), 8.66 (s, 1H), 8.44 (t, J = 8.7 Hz, 1H), 8.08 (d, J = 8.5 Hz, 1H), 8.00-7.95 (m, 3H), 7.86-7.82 (m, 1H), 7.63 (d, J = 8.9 Hz, 1H), 7.23-7.17 (m, 2H), 4.87 (bs, 1H), 4.48 (d, J = 10 Hz, 1H), 4.23-4.20 (m, 1H), 3.61-3.22 (m, 4H), 3.09-3.03 (m, 1H), 2.42-2.00 (m, 5H), 1.53-1.46 (m, 1H), 1.26 (d, J = 6.0 Hz, 3H), 0.90-0.84 (m, 1H), 0.75-0.67 (m, 3H)

| Example/IUPAC name | Structure | MS calculated MS ESI [M + H]⁺ | Yield; Appearance; Salt form |
|---|---|---|---|
| A222: N-((R)-cyclopentyl(thiophen-3-yl)methyl)-3-(4-((1-((R)-2-hydroxy-propyl)piperidin-4-yl)oxy)phenyl)-1H-indazole-5-carboxamide | 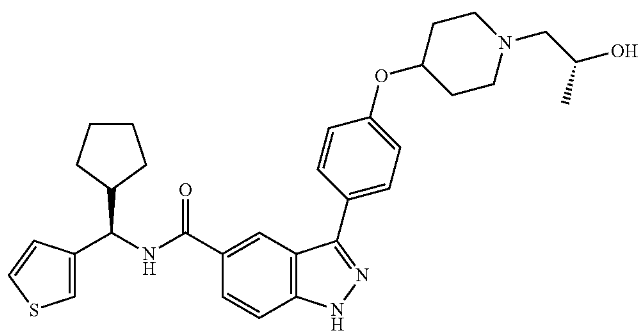 [SMILES: C[C@@H](O)CN1CCC(Oc2ccc(-c3n[nH]c4ccc(C(=O)N[C@@H](c5ccsc5)C5CCCC5)cc34)cc2)CC1] | [C₃₂H₃₈N₄O₃S + H]⁺ 559.27 559.6 | 46 mg (44%); white solid; TFA salt |

SMs: (R)-N-(cyclopentyl(thiophen-3-yl)methyl)-3-iodo-1H-indazole-5-carboxamide (61 mg, 0.14 mmol), (R)-1-(4-(4-(4,4,5,5-tetramethyl-1,3,2-dioxaborolan-2-yl)phenoxy)piperidin-1-yl)propan-2-ol (68 mg, 0.19 mmol)
¹H NMR (400 MHz, CD₃OD) δ ppm 8.52 (s, 1H), 7.95-7.88 (m, 3H), 7.60 (d, J = 8.7 Hz, 1H), 7.37-7.32 (m, 2H), 7.22-7.16 (m, 3H), 5.05 (d, J = 10 Hz, 1H), 4.87 (bs, 1H), 4.23-4.20 (m, 1H), 3.75-3.22 (m, 4H), 3.09-3.03 (m, 1H), 2.60-2.53 (m, 1H), 2.42-1.40 (m, 11H), 1.25 (d, J = 6.4 Hz)

| Example/IUPAC name | Structure | MS calculated MS ESI [M + H]⁺ | Yield; Appearance; Salt form |
|---|---|---|---|
| A223: N-((S)-cyclopropyl(thiophen-3-yl)methyl)-3-(4-((1-((R)-3,3,3-trifluoro-2-hydroxy-propyl)piperidin-4-yl)oxy)phenyl)-1H-indazole-5-carboxamide | 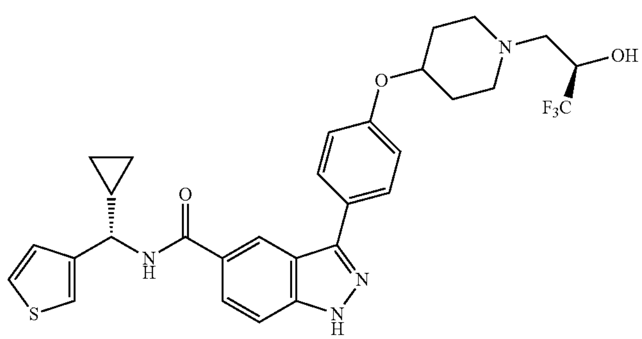 [SMILES: O=C(N[C@H](c1ccsc1)C1CC1)c1ccc2[nH]nc(-c3ccc(OC4CCN(C[C@@H](O)C(F)(F)F)CC4)cc3)c2c1] | [C₃₀H₃₁F₃N₄O₃S + H]⁺ 585.21 585.3 | 18 mg (16%); white solid; TFA salt |

SMs: (S)-N-(cyclopropyl(thiophen-3-yl)methyl)-3-iodo-1H-indazole-5-carboxamide (70 mg, 0.17 mmol), (R)-1,1,1-trifluoro-3-(4-(4-(4,4,5,5-tetramethyl-1,3,2-dioxaborolan-2-yl)phenoxy)piperidin-1-yl)propan-2-ol (89 mg, 0.22 mmol)
¹H NMR (400 MHz, CD₃OD) δ ppm 8.60 (s, 1H), 7.97-7.94 (m, 3H), 7.62 (d, J = 8.7 Hz, 1H), 7.28 (d, J = 4.7 Hz, 1H), 7.23-7.16 (m, 2H), 7.13 (m, 1H), 6.99-6.97 (m, 1H), 4.80-4.75 (m, 3H), 3.62-3.32 (m, 6H), 2.32-2.16 (m, 4H), 1.53-1.49 (m, 1H), 0.80-0.76 (m, 1H), 0.68-0.65 (m, 1H), 0.54-0.49 (m, 2H)

| Example/IUPAC name | Structure | MS calculated MS ESI [M + H]⁺ | Yield; Appearance; Salt form |
|---|---|---|---|
| A224: N-((R)-cyclopropyl(thiophen-3-yl)methyl)-3-(4-((1-((R)-3,3,3-trifluoro-2-hydroxy-propyl)piperidin-4-yl)oxy)phenyl)-1H-indazole-5-carboxamide | 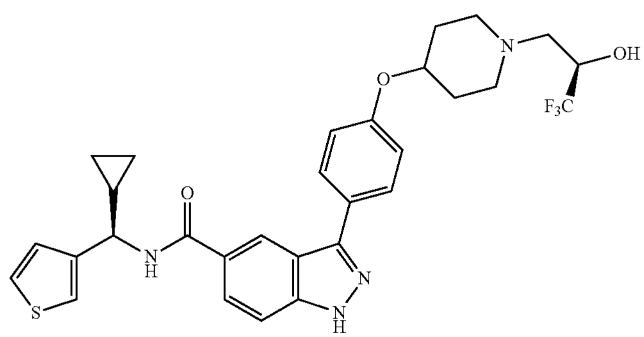 [SMILES: O=C(N[C@@H](c1ccsc1)C1CC1)c1ccc2[nH]nc(-c3ccc(OC4CCN(C[C@@H](O)C(F)(F)F)CC4)cc3)c2c1] | [$C_{30}H_{31}F_3N_4O_3S$ + H]⁺ 585.21 585.3 | 30 mg (26%); white solid; TFA salt |

SMs: (R)-N-(cyclopropyl(thiophen-3-yl)methyl)-3-iodo-1H-indazole-5-carboxamide (70 mg, 0.17 mmol), (R)-1,1,1-trifluoro-3-(4-(4-(4,4,5,5-tetramethyl-1,3,2-dioxaborolan-2-yl)phenoxy)piperidin-1-yl)propan-2-ol (89 mg, 0.22 mmol)
¹H NMR (400 MHz, CD₃OD) δ ppm 8.60 (s, 1H), 7.97-7.94 (m, 3H), 7.62 (d, J = 8.7 Hz, 1H), 7.28 (d, J = 4.7 Hz, 1H), 7.23-7.16 (m, 2H), 7.13 (m, 1H), 6.99-6.97 (m, 1H), 4.78 (bs, 1H), 4.76 (d, J = 9.6 Hz, 1H), 4.66-4.63 (bs, 1H), 3.62-3.32 (m, 6H), 2.32-2.16 (m, 4H), 1.53-1.49 (m, 1H), 0.80-0.76 (m, 1H), 0.68-0.65 (m, 1H), 0.54-0.49 (m, 2H)

| Example/IUPAC name | Structure | MS calculated MS ESI [M + H]⁺ | Yield; Appearance; Salt form |
|---|---|---|---|
| A225: N-((S)-cyclopropyl(pyridin-2-yl)methyl)-3-(4-((1-((R)-3,3,3-trifluoro-2-hydroxy-propyl)piperidin-4-yl)oxy)phenyl)-1H-indazole-5-carboxamide | 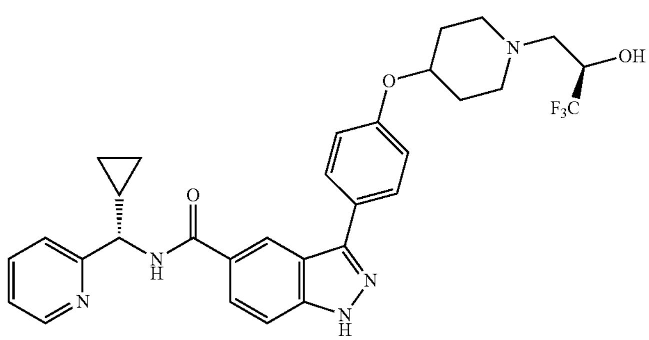 [SMILES: O=C(N[C@H](c1ccccn1)C1CC1)c1ccc2[nH]nc(-c3ccc(OC4CCN(C[C@@H](O)C(F)(F)F)CC4)cc3)c2c1] | [$C_{31}H_{32}F_3N_5O_3$ + H]⁺ 580.25 580.4 | 30 mg (24%); white solid; 2 × TFA salt |

SMs: (S)-N-(cyclopropyl(pyridin-2-yl)methyl)-3-iodo-1H-indazole-5-carboxamide (65 mg, 0.16 mmol), (R)-1,1,1-trifluoro-3-(4-(4-(4,4,5,5-tetramethyl-1,3,2-dioxaborolan-2-yl)phenoxy)piperidin-1-yl)propan-2-ol (84 mg, 0.20 mmol)
¹H NMR (400 MHz, CD₃OD) δ ppm 8.74 (d, J = 5.6 Hz, 1H), 8.67 (s, 1H), 8.51 (t, J = 8.8 Hz, 1H), 8.14 (d, J = 8.5 Hz, 1H), 8.00-7.96 (m, 3H), 7.91-7.88 (m, 1H), 7.63 (d, J = 8.8 Hz, 1H), 7.23-7.18 (m, 2H), 4.87 (bs, 1H), 4.67-4.64 (m, 1H), 4.49 (d, J = 10.4 Hz, 1H), 3.60-3.33 (m, 6H), 2.43-2.13 (m, 4H), 1.52-1.49 (m, 1H), 0.91-0.88 (m, 1H), 0.78-0.60 (m, 3H)

| Example/IUPAC name | Structure | MS calculated MS ESI [M + H]⁺ | Yield; Appearance; Salt form |
|---|---|---|---|
| A226: N-(2,2-difluoro-1-phenylethyl)-3-(4-((1-(oxetan-3-yl)piperidin-4-yl)oxy)phenyl)-1H-indazole-5-carboxamide | 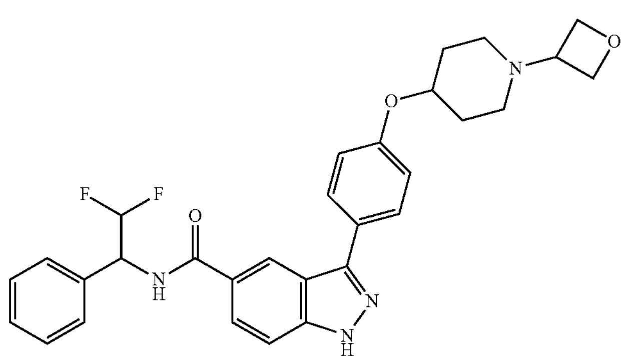 [SMILES: O=C(NC(c1ccccc1)C(F)F)c1ccc2[nH]nc(-c3ccc(OC4CCN(C5COC5)CC4)cc3)c2c1] | [$C_{30}H_{30}F_2N_4O_3$ + H]⁺ 533.24 533.4 | 12 mg (23%); pale-yellow solid; free base |

SMs: N-(2,2-difluoro-1-phenylethyl)-3-iodo-1H-indazole-5-carboxamide (42 mg, 0.098 mmol), 1-(oxetan-3-yl)-4-(4-(4,4,5,5-tetramethyl-1,3,2-dioxaborolan-2-yl)phenoxy)piperidine (46 mg, 0.13 mmol)
¹H NMR (400 MHz, CD₃OD) δ ppm 8.61 (s, 1H), 7.97-7.91 (m, 3H), 7.63-7.59 (m, 1H), 7.55-7.52 (m, 1H), 7.43-7.34 (m, 3H), 7.13-7.10 (m, 2H), 6.25 (t, J = 52 Hz, 1H), 5.63-5.56 (m, 1H), 4.87 (bs, 1H), 4.73-4.70 (m, 2H), 4.64-4.61 (m, 2H), 4.55 (bs, 1H), 3.64-3.60 (m, 1H), 2.65-2.60 (m, 2H), 2.30-2.26 (m, 2H), 2.10-2.06 (m, 2H), 1.89-1.85 (m, 2H)

| Example/IUPAC name | Structure | MS calculated MS ESI [M + H]+ | Yield; Appearance; Salt form |
|---|---|---|---|
| A227: N-(2,2-difluoro-1-phenylethyl)-3-(4-(((1R,3R,5S)-8-methyl-8-azabicyclo[3.2.1]octan-3-yl)oxy)phenyl)-1H-indazole-5-carboxamide | 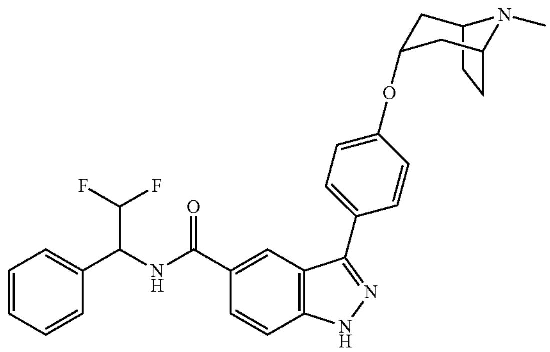 [SMILES: CN1C2CCC1CC(Oc1ccc(-c3n[nH]c4ccc(C(=O)NC(c5ccccc5)C(F)F)cc34)cc1)C2] | [C30H30F2N4O2 + H]+ 517.24 517.3 | 18 mg (22%); white solid; TFA salt |

SMs: N-(2,2-difluoro-1-phenylethyl)-3-iodo-1H-indazole-5-carboxamide (56 mg, 0.13 mmol), (1R,3R,5S)-8-methyl-3-(4-(4,4,5,5-tetramethyl-1,3,2-dioxaborolan-2-yl)phenoxy)-8-azabicyclo[3.2.1]octane (58 mg, 0.17 mmol)
$^1$H NMR (400 MHz, CD$_3$OD) δ ppm 8.61 (s, 1H), 7.97-7.91 (m, 3H), 7.61 (d, J = 6.5 Hz, 1H), 7.52 (d, J = 7.4 Hz, 2H), 7.44-7.33 (m, 3H), 7.04 (d, J = 8.7 Hz, 2H), 6.23 (td, J = 52 Hz, 4.4 Hz, 1H), 5.58 (td, J = 14 Hz, 4.4 Hz, 1H), 4.69-4.66 (m, 1H), 3.33-3.26 (bs, 2H), 2.38 (s, 3H), 2.22-2.02 (m, 8H)

| Example/IUPAC name | Structure | MS calculated MS ESI [M + H]+ | Yield; Appearance; Salt form |
|---|---|---|---|
| A228: N-((S)-1-(2-chlorophenyl)-2-methylpropyl)-3-(4-((1-((R)-3,3,3-trifluoro-2-hydroxypropyl)piperidin-4-yl)oxy)phenyl)-1H-indazole-5-carboxamide | | [C33H36ClF3N4O3 + H]+ 615.23 615.3 | 34 mg (30%); white solid; TFA salt |

SMs: (S)-N-(1-(2-chlorophenyl)-2-methylpropyl)-3-iodo-1H-indazole-5-carboxamide (70 mg, 0.15 mmol), (R)-1,1,1-trifluoro-3-(4-(4-(4,4,5,5-tetramethyl-1,3,2-dioxaborolan-2-yl)phenoxy)piperidin-1-yl)propan-2-ol (83 mg, 0.20 mmol)
$^1$H NMR (400 MHz, CD$_3$OD) δ ppm 8.50 (s, 1H), 7.94-7.86 (m, 3H), 7.61-7.52 (m, 2H), 7.40-7.37 (m, 1H), 7.32-7.19 (m, 4H), 5.39-5.34 (m, 1H), 4.65-4.60 (bs, 1H), 3.98 (s, 1H), 3.55-3.32 (m, 6H), 2.31-2.15 (m, 5H), 1.17-1.14 (m, 3H), 0.88-0.85 (m, 3H)

| Example/IUPAC name | Structure | MS calculated MS ESI [M + H]+ | Yield; Appearance; Salt form |
|---|---|---|---|
| A229: N((S)-cyclopentyl(pyridin-2-yl)methyl)-3-(4-((1-((R)-3,3,3-trifluoro-2-hydroxypropyl)piperidin-4-yl)oxy)phenyl)-1H-indazole-5-carboxamide | | [C33H36F3N5O3 + H]+ 608.28 608.3 | 39 mg (34%); white solid; 2 × TFA salt |

SMs: (S)-N-(cyclopentyl(pyridin-2-yl)methyl)-3-iodo-1H-indazole-5-carboxamide (70 mg, 0.16 mmol), (R)-1,1,1-trifluoro-3-(4-(4-(4,4,5,5-tetramethyl-1,3,2-dioxaborolan-2-yl)phenoxy)piperidin-1-yl)propan-2-ol (85 mg, 0.20 mmol)
$^1$H NMR (400 MHz, CD$_3$OD) δ ppm 8.80 (d, J = 5.2 Hz, 1H), 8.60-8.55 (m, 2H), 8.13 (d, J = 7.6 Hz, 1H), 7.96-7.92 (m, 4H), 7.61 (d, J = 8.8 Hz, 1H), 7.23-7.18 (m, 2H), 5.03 (d, J = 10.8 Hz, 1H), 4.87 (bs, 1H), 4.68-4.65 (bs, 1H), 3.98 (s, 2H), 3.57-3.33 (m, 4H), 2.66-2.60 (m, 1H), 2.33-2.19 (m, 4H), 1.82-1.51 (m, 6H), 1.50-1.38 (m, 1H), 1.31-1.21 (m, 1H)

| Example/IUPAC name | Structure | MS calculated MS ESI [M + H]+ | Yield; Appearance; Salt form |
|---|---|---|---|
| A230: N-((S)-cyclopentyl(pyridin-2-yl)methyl)-3-(4-((1-((R)-2-hydroxypropyl)piperidin-4-yl)oxy)phenyl)-1H-indazole-5-carboxamide | | [C₃₃H₃₉N₅O₃ + H]⁺ 554.31 554.3 | 56 mg (53%); beige solid; 2 × TFA salt |

SMs: (S)-N-(cyclopentyl(pyridin-2-yl)methyl)-3-iodo-1H-indazole-5-carboxamide (70 mg, 0.16 mmol), (R)-1-(4-(4-(4,4,5,5-tetramethyl-1,3,2-dioxaborolan-2-yl)phenoxy)piperidin-1-yl)propan-2-ol (74 mg, 0.20 mmol)
¹H NMR (400 MHz, CD₃OD) δ ppm 8.75 (d, J = 6.0 Hz, 1H), 8.58 (s, 1H), 8.44 (t, J = 8.4 Hz, 1H), 8.01-7.91 (m, 4H), 7.86-7.83 (m, 1H), 7.62 (d, J = 8.8 Hz, 1H), 7.22-7.16 (m, 2H), 5.01 (d, J = 10 Hz, 1H), 4.87 (bs, 1H), 4.23-4.20 (m, 1H), 3.75-3.22 (m, 4H), 3.09-3.04 (m, 1H), 2.64-2.57 (m, 1H), 2.42-1.95 (m, 6H), 1.79-1.35 (m, 6H), 1.24 (d, J = 6.5 Hz, 3H)

| Example/IUPAC name | Structure | MS calculated MS ESI [M + H]+ | Yield; Appearance; Salt form |
|---|---|---|---|
| A231: (S)-N-(cyclopentyl(pyridin-2-yl)methyl)-3-(4-((1-(2-hydroxy-2-methylpropyl)piperidin-4-yl)oxy)phenyl)-1H-indazole-5-carboxamide | 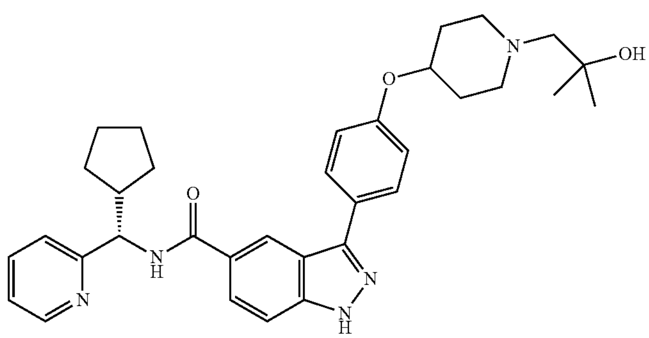 [SMILES: CC(C)(O)CN1CCC(Oc2ccc(-c3n[nH]c4ccc(C(=O)N[C@H](c5ccccn5)C5CCCC5)cc34)cc2)CC1] | [C₃₄H₄₁N₅O₃ + H]⁺ 568.33 568.4 | 62 mg (50%); brown-yellow solid; 2 × TFA salt |

SMs: (S)-N-(cyclopentyl(pyridin-2-yl)methyl)-3-iodo-1H-indazole-5-carboxamide (70 mg, 0.16 mmol), 2-methyl-1-(4-(4-(4,4,5,5-tetramethyl-1,3,2-dioxaborolan-2-yl)phenoxy)piperidin-1-yl)propan-2-ol (77 mg, 0.20 mmol)
¹H NMR (400 MHz, CD₃OD) δ ppm 8.72 (d, J = 5.3 Hz, 1H), 8.57 (s, 1H), 8.33 (t, J = 6.6 Hz, 1H), 7.96-7.91 (m, 4H), 7.77-7.74 (m, 1H), 7.62 (d, J = 8.7 Hz, 1H), 7.22-7.16 (m, 2H), 5.01 (d, J = 10 Hz, 1H), 4.87 (bs, 1H), 3.81-3.34 (m, 4H), 3.32-3.25 (bs, 2H), 2.61-2.57 (m, 1H), 2.30-2.09 (m, 6H), 1.75-1.35 (m, 6H), 1.38 (s, 6H)

| Example/IUPAC name | Structure | MS calculated MS ESI [M + H]+ | Yield; Appearance; Salt form |
|---|---|---|---|
| A232: (S)-N-(1-(2-chlorophenyl)-2-methylpropyl)-3-(4-((1-(2-hydroxyethyl)piperidin-4-yl)oxy)phenyl)-1H-indazole-5-carboxamide | | [C₃₁H₃₅ClN₄O₃ + H]⁺ 547.25 547.3 | 56 mg (55%); brown solid; TFA salt |

SMs: (S)-N-(1-(2-chlorophenyl)-2-methylpropyl)-3-iodo-1H-indazole-5-carboxamide (70 mg, 0.15 mmol), 2-(4-(4-(4,4,5,5-tetramethyl-1,3,2-dioxaborolan-2-yl)phenoxy)piperidin-1-yl)ethanol (71 mg, 0.20 mmol)
¹H NMR (400 MHz, CD₃OD) δ ppm 8.52 (s, 1H), 7.96-7.89 (m, 3H), 7.60 (d, J = 8.8 Hz, 1H), 7.53 (d, J = 7.2 Hz, 1H), 7.40 (d, J = 8.4 Hz, 1H), 7.33-7.16 (m, 4H), 5.39-5.35 (m, 1H), 4.87 (bs, 1H), 3.98-3.91 (m, 2H), 3.74-3.33 (m, 4H), 3.33-3.29 (m, 2H), 2.33-2.00 (m, 5H), 1.16 (d, J = 6.4 Hz, 3H), 0.87 (d, J = 6.8 Hz, 3H)

| Example/IUPAC name | Structure | MS calculated MS ESI [M + H]+ | Yield; Appearance; Salt form |
|---|---|---|---|
| A233: (S)-N-(cyclopentyl(pyridin-2-yl)methyl)-3-(4-((1-(2-hydroxy-ethyl)piperidin-4-yl)oxy)phenyl)-1H-indazole-5-carboxamide | 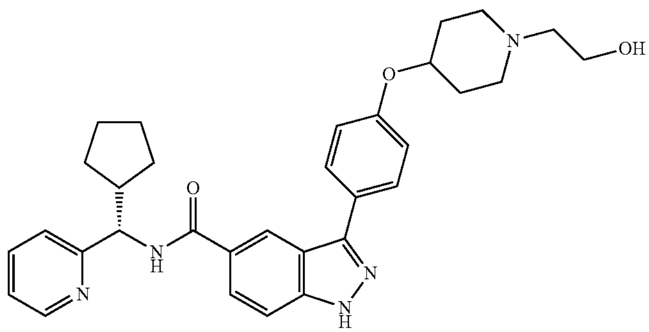 [SMILES: O=C(N[C@H](c1ccccn1)C1CCCC1)c1ccc2[nH]nc(-c3ccc(OC4CCN(CCO)CC4)cc3)c2c1] | [C$_{32}$H$_{37}$N$_5$O$_3$ + H]+ 540.30 540.4 | 50 mg (49%); brown-yellow solid; 2 × TFA salt |

SMs: (S)-N-(cyclopentyl(pyridin-2-yl)methyl)-3-iodo-1H-indazole-5-carboxamide (70 mg, 0.16 mmol), 2-(4-(4-(4,4,5,5-tetramethyl-1,3,2-dioxaborolan-2-yl)phenoxy)piperidin-1-yl)ethanol (71 mg, 0.20 mmol)
$^1$H NMR (400 MHz, CD$_3$OD) δ ppm 8.73 (d, J = 4.8 Hz, 1H), 8.58 (s, 1H), 8.40 (t, J = 6.6 Hz, 1H), 7.98-7.91 (m, 4H), 7.82-7.79 (m, 1H), 7.62 (d, J = 8.8 Hz, 1H), 7.23-7.17 (m, 2H), 5.02 (d, J = 10.8 Hz, 1H), 4.87 (bs, 1H), 3.93-3.90 (m, 2H), 3.78-3.16 (m, 6H), 2.62-2.58 (m, 1H), 2.45-1.97 (m, 5H), 1.77-1.45 (m, 7H)

| | | | |
|---|---|---|---|
| A234: N-((R)-(2-chlorophen-yl)(cycloprop-yl)methyl)-3-(4-(((1R,3R,5S)-8-methyl-8-azabi-cyclo[3.2.1]octan-3-yl)oxy)phenyl)-1H-indazole-5-carboxamide | | [C$_{32}$H$_{33}$ClN$_4$O$_2$ + H]+ 541.23 541.5 | 49 mg (37%); white solid; TFA salt |

SMs: (R)-N-((2-chlorophenyl)(cyclopropyl)methyl)-3-iodo-1H-indazole-5-carboxamide (91 mg, 0.20 mmol), (1R,3R,5S)-8-methyl-3-(4-(4,4,5,5-tetramethyl-1,3,2-dioxaborolan-2-yl)phenoxy)-8-azabicyclo[3.2.1]octane (71 mg, 0.21 mmol)
$^1$H NMR (400 MHz, CD$_3$OD) δ ppm 9.09 (d, J = 7.0 Hz, 0.2 H), 8.56 (s, 1 H), 7.88-7.97 (m, 3 H), 7.67 (d, J = 7.5 Hz, 1 H), 7.60 (d, J = 8.8 Hz, 1 H), 7.39 (d, J = 7.8 Hz, 1 H), 7.27-7.35 (m, 1 H), 7.20-7.27 (m, 1 H), 7.09 (d, J = 8.8 Hz, 2 H), 5.01 (d, J = 8.8 Hz, 1 H), 4.80 (brs, 1 H), 3.93 (brs, 2 H), 2.96-3.04 (m, 1 H), 2.84 (s, 4 H), 2.27-2.59 (m, 8 H), 1.38-1.51 (m, 1 H), 0.64-0.73 (m, 1 H), 0.46-0.61 (m, 3 H)

| | | | |
|---|---|---|---|
| A235: N-((S)-(2-chlorophen-yl)(cycloprop-yl)methyl)-3-(4-(((1R,3R,5S)-8-methyl-8-azabi-cyclo[3.2.1]octan-3-yl)oxy)phenyl)-1H-indazole-5-carboxamide | | [C$_{32}$H$_{33}$ClN$_4$O$_2$ + H]+ 541.23 541.5 | 58 mg (45%); white solid; TFA salt |

SMs: (S)-N-((2-chlorophenyl)(cyclopropyl)methyl)-3-iodo-1H-indazole-5-carboxamide (90 mg, 0.20 mmol), (1R,3R,5S)-8-methyl-3-(4-(4,4,5,5-tetramethyl-1,3,2-dioxaborolan-2-yl)phenoxy)-8-azabicyclo[3.2.1]octane (71 mg, 0.21 mmol)
$^1$H NMR data was identical for that obtained in example A234

| Example/IUPAC name | Structure | MS calculated MS ESI [M + H]+ | Yield; Appearance; Salt form |
|---|---|---|---|
| A236: (S)-N-(cyclopropyl(pyridin-2-yl)methyl)-3-(2,2-dimethyl-4-oxochroman-6-yl)-1H-indazole-5-carboxamide | 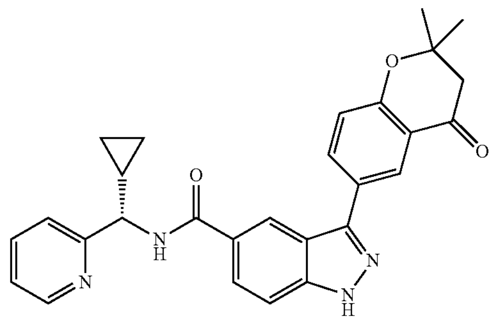 [SMILES: CC1(C)CC(=O)c2cc(-c3n[nH]c4ccc(C(=O)N[C@H](c5ccccn5)C5CC5)cc34)ccc2O1] | [C₂₈H₂₆N₄O₂ + H]+ 467.2 467.3 | 71 mg (51%); pale yellow solid; TFA salt |

SMs: (S)-N-(cyclopropyl(pyridin-2-yl)methyl)-3-iodo-1H-indazole-5-carboxamide (100 mg, 0.24 mmol), 2,2-dimethyl-6-(4,4,5,5-tetramethyl-1,3,2-dioxaborolan-2-yl)chroman-4-one (73 mg, 0.24 mmol), Pd(PPh₃)₄ (13 mg, 0.01 mmol)
¹H NMR (400 MHz, CD₃OD) δ ppm 8.78 (dd, J = 5.8, 0.8 Hz, 1 H), 8.68 (s, 1 H), 8.58 (d, J = 1.3 Hz, 1 H), 8.41 (d, J = 2.3 Hz, 1 H), 8.15-8.26 (m, 2 H), 7.92-8.01 (m, 2 H), 7.63 (d, J = 9.0 Hz, 1 H), 7.13 (d, J = 8.8 Hz, 1 H), 4.51 (d, J = 10.0 Hz, 1 H), 2.85 (s, 2 H), 1.53-1.59 (m, 1 H), 1.49-1.53 (m, 6 H), 0.87-0.96 (m, 1 H), 0.61-0.82 (m, 3 H)

| Example/IUPAC name | Structure | MS calculated MS ESI [M + H]+ | Yield; Appearance; Salt form |
|---|---|---|---|
| A237: (S)-N-(cyclopropyl(pyridin-2-yl)methyl)-3-(2,2,4-trimethyl-2H-chromen-6-yl)-1H-indazole-5-carboxamide | | [C₂₉H₂₈N₄O₂ + H]+ 465.2 465.3 | 65 mg (47%); while solid TFA salt |

SMs: (S)-N-(cyclopropyl(pyridin-2-yl)methyl)-3-iodo-1H-indazole-5-carboxamide (100 mg, 0.24 mmol), 4,4,5,5-tetramethyl-2-(2,2,4-trimethyl-2H-chromen-6-yl)-1,3,2-dioxaborolane (72 mg, 0.24 mmol), Pd(PPh₃)₄ (13 mg, 0.01 mmol)
¹H NMR (400 MHz, CD₃OD) δ ppm 8.70-8.76 (m, 1 H), 8.65 (d, J = 0.8 Hz, 1 H), 8.39-8.49 (m, 1 H), 8.11 (s, 1 H), 7.97 (dd, J = 8.8, 1.5 Hz, 1 H), 7.82-7.89 (m, 1 H), 7.77 (dd, J = 4.4, 2.4 Hz, 2 H), 7.58-7.65 (m, 1 H), 6.91 (d, J = 8.8 Hz, 1 H), 5.58 (d, J = 1.5 Hz, 1 H), 4.50 (d, J = 10.0 Hz, 1 H), 2.10 (d, J = 1.5 Hz, 3 H), 1.45-1.54 (m, 1 H), 1.42 (s, 6 H), 0.82-0.90 (m, 1 H), 0.59-0.77 (m, 3 H)

| Example/IUPAC name | Structure | MS calculated MS ESI [M + H]+ | Yield; Appearance; Salt form |
|---|---|---|---|
| A238: (S)-N-(cyclopropyl(pyridin-2-yl)methyl)-3-1,4-dimethyl-2-oxo-1,2-dihydroquinolin-6-yl)-1H-indazole-5-carboxamide | | [C₂₈H₂₅N₅O₂ +H]+ 464.2 464 | 45 mg (32%); light pink solid; TFA salt |

SMs: (S)-N-(cyclopropyl(pyridin-2-yl)methyl)-3-iodo-1H-indazole-5-carboxamide (100 mg, 0.24 mmol), 1,4-dimethyl-6-(4,4,5,5-tetramethyl-1,3,2-dioxaborolan-2-yl)quinolin-2(1H)-one (72 mg, 0.24 mmol), Pd(PPh₃)₄ (13 mg, 0.011 mmol)
¹H NMR (400 MHz, CD₃OD) δ ppm 8.79 (dd, J = 5.8, 0.8 Hz, 1 H), 8.68 (d, J = 0.8 Hz, 1 H), 8.57 (td, J = 7.9, 1.5 Hz, 1 H), 8.31 (d, J = 2.0 Hz, 1 H), 8.17-8.27 (m, 2 H), 7.92-8.02 (m, 2 H), 7.63 (dd, J = 8.9, 5.9 Hz, 2 H), 6.56 (d, J = 1.0 Hz, 1 H), 4.54 (d, J = 10.0 Hz, 1 H), 3.70 (s, 3 H), 2.54 (d, J = 1.0 Hz, 3 H), 1.49-1.60 (m, 1 H), 0.90 (s, 1 H), 0.63-0.82 (m, 3 H)

| Example/IUPAC name | Structure | MS calculated MS ESI [M + H]+ | Yield; Appearance; Salt form |
|---|---|---|---|
| A239: (S)-N-(cyclopentyl(pyridin-2-yl)methyl)-3-(1,4-dimethyl-2-oxo-1,2-dihydroquinolin-6-yl)-1H-indazole-5-carboxamide | | [C$_{30}$H$_{29}$N$_5$O$_2$ + H]+ 492.2 492.3 | 8 mg (8.5%); light brown solid; TFA salt |

SMs: (S)-N-(cyclopentyl(pyridin-2-yl)methyl)-3-iodo-1H-indazole-5-carboxamide (70 mg, 0.15 mmol), 1,4-dimethyl-6-(4,4,5,5-tetramethyl-1,3,2-dioxaborolan-2-yl)quinolin-2(1H)-one (47 mg, 0.15 mmol), Pd(PPh$_3$)$_4$ (9 mg, 0.007 mmol)
$^1$H NMR (400 MHz, CD$_3$OD) δ ppm 8.76 (d, J = 4.8 Hz, 1 H), 8.66 (s, 1 H), 8.40-8.44 (m, 2 H), 8.30-8.33 (m, 1 H), 7.97-8.01 (m, 1 H), 7.91-7.96 (m, 1 H), 7.81-7.87 (m, 1 H), 7.74 (d, J = 12 Hz, 1 H), 7.67 (d, J = 8.8 Hz, 1 H), 6.65 (s, 1 H), 5.04 (d, J = 10.8 Hz, 1 H), 3.79 (s, 3 H), 2.63 (d, J = 1.0 Hz, 4 H), 2.11-2.23 (m, 1 H), 1.71-1.84 (m, 3 H), 1.56-1.69 (m, 2 H), 1.41-1.51 (m, 1 H), 1.23-1.34 (m, 1 H)

| Example/IUPAC name | Structure | MS calculated MS ESI [M + H]+ | Yield; Appearance; Salt form |
|---|---|---|---|
| A240: (S)-N-(cyclopentyl(pyridin-2-yl)methyl)-3-(1-methyl-4-oxo-1,4-dihydroquinolin-6-yl)-1H-indazole-5-carboxamide | 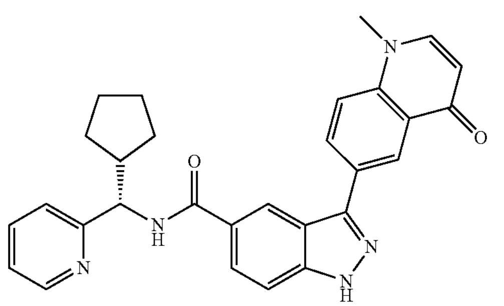 [SMILES: Cn1ccc(=O)c2cc(-c3n[nH]c4ccc(C(=O)N[C@H](c5ccccn5)C5CCCC5)cc34)ccc21] | [C$_{29}$H$_{27}$N$_5$O$_2$ + H]+ 478.2 478.4 | 19 mg (20%); cream solid; TFA salt |

SMs: (S)-N-(cyclopentyl(pyridin-2-yl)methyl)-3-iodo-1H-indazole-5-carboxamide (90 mg, 0.20 mmol), 1-methyl-6-(4,4,5,5-tetramethyl-1,3,2-dioxaborolan-2-yl)quinolin-4(1H)-one (86 mg, 0.24 mmol), PdCl$_2$dppf*CH$_2$Cl$_2$(16 mg, 0.02 mmol)
$^1$H NMR (400 MHz, CD$_3$OD) δ ppm 9.03 (d, J = 2.0 Hz, 1 H), 8.82 (dd, J = 1.5, 1.0 Hz, 2 H), 8.60 (s, 2 H), 8.30 (d, J = 7.5 Hz, 1 H), 8.12-8.18 (m, 1 H), 8.05 (d, J = 8.8 Hz, 1 H), 7.94 (dd, J = 9.0, 1.5 Hz, 2 H), 7.67 (dd, J = 8.8, 0.8 Hz, 1 H), 6.63 (d, J = 7.3 Hz, 1 H), 5.08 (d, J = 10.4 Hz, 1 H), 4.14 (s, 3 H), 2.63-2.67 (m, 1 H), 2.18-2.28 (m, 1 H), 1.70-1.84 (m, 3 H), 1.56-1.68 (m, 2 H), 1.41-1.52 (m, 1 H), 1.20-1.32 (m, 1 H)

| Example/IUPAC name | Structure | MS calculated MS ESI [M + H]+ | Yield; Appearance; Salt form |
|---|---|---|---|
| A241: (S)-N-(cyclopropyl(pyridin-2-yl)methyl)-3-4-oxochroman-6-yl)-1H-indazole-5-carboxamide | | [C$_{26}$H$_{22}$N$_4$O$_3$ + H]+ 439.1 439.3 | 24 mg (24%); cream solid; TFA salt |

SMs: (S)-N-(cyclopropyl(pyridin-2-yl)methyl)-3-iodo-1H-indazole-5-carboxamide (75 mg, 0.18 mmol), 6-(4,4,5,5-tetramethyl-1,3,2-dioxaborolan-2-yl)chroman-4-one (50 mg, 0.18 mmol), Pd(PPh$_3$)$_4$ (15 mg, 0.013 mmol)
$^1$H NMR (400 MHz, CD$_3$OD) δ ppm 8.76-8.80 (m, 1 H), 8.69 (dd, J = 1.5, 0.8 Hz, 1 H), 8.56-8.63 (m, 1 H), 8.46 (d, J = 2.0 Hz, 1 H), 8.18-8.25 (m, 2 H), 7.93-8.00 (m, 2 H), 7.64 (dd, J = 8.8, 0.8 Hz, 1 H), 7.17-7.23 (m, 1 H), 4.63 (t, J = 6.0 Hz, 2 H), 4.52 (d, J = 10.0 Hz, 1 H), 2.90 (t, J = 6.8 Hz, 2 H), 1.48-1.58 (m, 1 H), 0.87-0.96 (m, 1 H), 0.61-0.82 (m, 3 H)

| Example/IUPAC name | Structure | MS calculated MS ESI [M + H]⁺ | Yield; Appearance; Salt form |
|---|---|---|---|
| A242: (S)-N-(cyclopentyl(pyridin-2-yl)methyl)-3-(1-methyl-4-oxo-1,2,3,4-tetrahydroquinolin-6-yl)-1H-indazole-5-carboxamide | 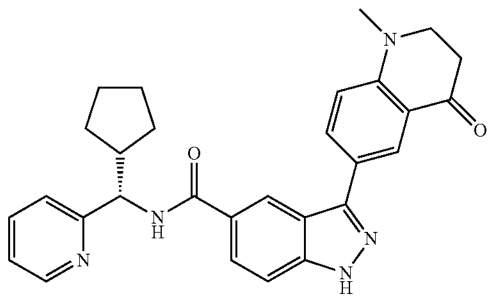 [SMILES: CN1CCC(=O)c2cc(-c3n[nH]c4ccc(C(=O)N[C@H](c5ccccn5)C5CCCC5)cc34)ccc21] | [C$_{29}$H$_{29}$N$_5$O$_2$ + H]⁺ 480.2 480.4 | 35 mg (29%); yellow solid; TFA salt |

SMs: (S)-N-(cyclopentyl(pyridin-2-yl)methyl)-3-iodo-1H-indazole-5-carboxamide (90 mg, 0.20 mmol), 1-methyl-6-(4,4,5,5-tetramethyl-1,3,2-dioxaborolan-2-yl)-2,3-dihydroquinolin-4(1H)-one (64 mg, 0.22 mmol), PdCl$_2$dppf*CH$_2$Cl$_2$ (16 mg, 0.02 mmol)
¹H NMR (400 MHz, CD$_3$OD) δ ppm 8.79 (dd, J = 5.8, 0.8 Hz, 1 H), 8.62 (s, 1 H), 8.55 (d, J = 1.5 Hz, 1 H), 8.43 (d, J = 2.3 Hz, 1 H), 8.06-8.14 (m, 2 H), 7.86-7.97 (m, 2 H), 7.60 (d, J = 8.8 Hz, 1 H), 7.02 (d, J = 9.0 Hz, 1 H), 5.03 (d, J = 10.5 Hz, 1 H), 3.58 (t, J = 7.2 Hz, 2 H), 3.10 (s, 3 H), 2.76-2.83 (m, 2 H), 2.58-2.71 (m, 1 H), 2.16-2.27 (m, 1 H), 1.70-1.85 (m, 3 H), 1.62 (br. s, 2 H) 1.40-1.51 (m, 1 H), 1.20-1.31 (m, 1 H)

| Example/IUPAC name | Structure | MS calculated MS ESI [M + H]⁺ | Yield; Appearance; Salt form |
|---|---|---|---|
| A243: N-(cyclopropyl(pyridin-2-yl)methyl)-3-(3-(methylsulfonyl)-4-(piperidin-4-yloxy)phenyl)-1H-indazole-5-carboxamide | 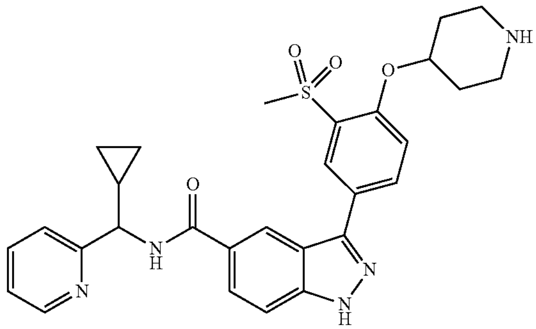 [SMILES: CS(=O)(=O)c1cc(-c2n[nH]c3ccc(C(=O)NC(c4ccccn4)C4CC4)cc23)ccc1OC1CCNCC1] | [C$_{29}$H$_{31}$N$_5$O$_4$S + H]⁺ 546.2 546.2 | 94 mg (51%); white solid; 2TFA salt |

SMs: N-(cyclopropyl(pyridin-2-yl)methyl)-3-iodo-1H-indazole-5-carboxamide (100 mg, 0.23 mmol), tert-butyl 4-(2-(methylsulfonyl)-4-(4,4,5,5-tetramethyl-1,3,2-dioxaborolan-2-yl)phenoxy)piperidine-1-carboxylate (127 mg, 0.26 mmol), PdCl$_2$dppf*CH$_2$Cl$_2$ (19 mg, 0.023 mmol)
¹H NMR (400 MHz, CD$_3$OD) δ ppm 8.8 (d, J = 5.8 Hz, 1 H), 8.67-8.55 (m, 3 H), 8.34 (dd, J = 8.8 Hz, 2.3 Hz, 1 H), 8.25 (d, J = 8 Hz, 1 H), 7.99-7.96 (m, 2 H), 7.65 (d, J = 9 Hz, 1 H), 7.5 (d, J = 8.8 Hz, 1 H), 5.19 (br.s, 1 H), 4.53 (d, J = 10.3 Hz, 1 H), 3.60-3.50 (m, 2 H), 2.35-2.15 (m, 4 H), 1.59-1.49 (m, 1 H), 0.95-0.85 (m, 1 H), 0.62-0.80 (m, 3 H), 5H merged with solvent peak.

| Example/IUPAC name | Structure | MS calculated MS ESI [M + H]⁺ | Yield; Appearance; Salt form |
|---|---|---|---|
| A244: N-(cyclopentyl(pyridin-2-yl) methyl)-3-(4-(((1R,3R,5S)-8-methyl-8-azabicyclo[3.2.1]octan-3-yl)oxy)phenyl)-1H-indazole-5-carboxamide | | [C$_{33}$H$_{37}$N$_5$O$_2$ + H]⁺ 536.3 536.3 | 65 mg (50%); white solid; 2TFA salt |

SMs: N-(cyclopentyl(pyridin-2-yl)methyl)-3-iodo-1H-indazole-5-carboxamide (75 mg, 0.16 mmol), (1R,3R,5S)-8-methyl-3-(4-(4,4,5,5-tetramethyl-1,3,2-dioxaborolan-2-yl)phenoxy)-8-azabicyclo[3.2.1]octane (60 mg, 0.17 mmol), PdCl$_2$dppf*CH$_2$Cl$_2$ (13 mg, 0.016 mmol)
¹H NMR (400 MHz, CD$_3$OD) δ ppm 8.80 (d, J = 5.3 Hz, 1 H), 8.48-8.65 (m, 2 H), 8.12 (d, J = 8.0 Hz, 1 H) 7.83-8.02 (m, 4 H), 7.62 (d, J = 8.5 Hz, 1 H), 7.13(d, J = 8.3 Hz, 2 H), 5.04 (d, J = 10.8 Hz, 1 H), 4.83 (br.s, 1 H), 3.95 (br. s, 2 H), 2.84 (s, 3 H), 2.31-2.69 (m, 9 H), 1.66-1.84 (m, 3 H), 1.52-1.67 (m, 2 H), 1.42 (br. s., 1 H) 1.26 (d, J = 8.5 Hz, 1 H), 1H merged with solvent peak.

| Example/IUPAC name | Structure | MS calculated MS ESI [M + H]+ | Yield; Appearance; Salt form |
|---|---|---|---|
| A245: N-(cyclopropyl(pyridin-2-yl)methyl)-3-(4-((1-methylpiperidin-4-yl)oxy)-3-(methylsulfonyl)phenyl)-1H-indazole-5-carboxamide | 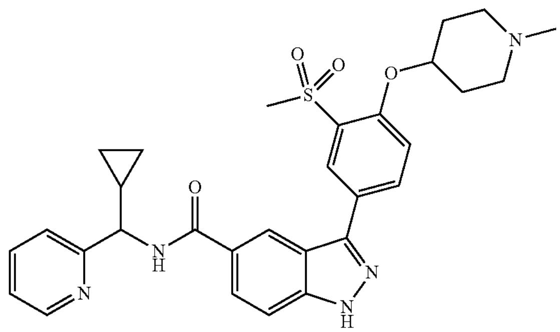 [SMILES: CN1CCC(Oc2ccc(-c3n[nH]c4ccc(C(=O)NC(c5ccccn5)C5CC5)cc34)cc2S(C)(=O)=O)CC1] | [$C_{30}H_{33}N_5O_4S$ + H]+ 560.2 560.2 | 28 mg (20%); white solid; 2TFA salt |

SMs: N-(cyclopropyl(pyridin-2-yl)methyl)-3-iodo-1H-indazole-5-carboxamide (75 mg, 0.17 mmol), 1-methyl-4-(2-(methylsulfonyl)-4-(4,4,5,5-tetramethyl-1,3,2-dioxaborolan-2-yl)phenoxy)piperidine (106 mg, 0.26 mmol), PdCl$_2$dppf*CH$_2$Cl$_2$ (15 mg, 0.017 mmol)
$^1$H NMR (400 MHz, CD$_3$OD) δ ppm 8.74-8.82 (m, 1 H), 8.64-8.72 (m, 1 H), 8.58 (s, 2 H) 8.34-8.44 (m, 1 H), 8.15-8.27 (m, 1 H), 7.90-8.05 (m, 2 H), 7.63-7.74 (m, 1 H), 7.46-7.60 (m, 1 H), 5.17-5.31 (m, 1 H), 4.46-4.58 (m, 1 H), 3.48-3.59 (m, 2 H), 3.40-3.49 (m, 2 H), 2.92 (s, 3 H), 2.41-2.55 (m, 2 H) 2.11-2.28 (m, 2 H), 1.44-1.59 (m, 1 H), 0.84-0.97 (m, 1 H), 0.60-0.82 (m, 3 H), 3H merged with solvent peak.

| | | | |
|---|---|---|---|
| A246: N-(cyclopropyl(phenyl)methyl)-3-(4-((1-methylpiperidin-4-yl)oxy)-3-(methylsulfonyl)phenyl)-1H-indazole-5-carboxamide | | [$C_{31}H_{34}N_4O_4S$ + H]+ 559.2 559.2 | 28 mg (21%); white solid; 2TFA salt |

SMs: N-(cyclopropyl(phenyl)methyl)-3-methyl-1H-indazole-5-carboxamide (80 mg, 0.19 mmol), 1-methyl-4-(2-(methylsulfonyl)-4-(4,4,5,5-tetramethyl-1,3,2-dioxaborolan-2-yl)phenoxy)piperidine (114 mg, 0.28 mmol), PdCl$_2$dppf*CH$_2$Cl$_2$ (15 mg, 0.019 mmol)
$^1$H NMR (400 MHz, CD$_3$OD) δ ppm 8.49-8.64 (m, 2 H), 8.28-8.43 (m, 1 H), 7.90-8.02 (m, 1 H), 7.60-7.72 (m, 1 H),7.45-7.56 (m, 3 H), 7.32-7.41 (m, 2 H), 7.18-7.32 (m, 1 H), 5.17-5.30 (m, 1 H), 4.41-4.57 (m, 1 H), 3.47-3.61 (m, 2 H), 3.39-3.48 (m, 2 H), 2.92 (s, 3 H), 2.37-2.54 (m, 2 H), 2.03-2.26 (m, 2 H), 1.30-1.50 (m, 1 H), 0.60-0.76 (m, 2 H), 0.40-0.58 (m, 2 H), 3H merged with solvent peak.

| | | | |
|---|---|---|---|
| A247: N-((R)-cyclopentyl(thiophen-3-yl)methyl)-3-(4-(((1R,3R,5S)-8-methyl-8-azabicyclo[3.2.1]octan-3-yl)oxy)phenyl)-1H-indazole-5-carboxamide | | [$C_{32}H_{36}N_4O_2S$ + H]+ 541.2 541.2 | 55 mg (51%); white solid; TFA salt |

SMs: (R)-N-(cyclopentyl(thiophen-3-yl)methyl)-3-iodo-1H-indazole-5-carboxamide (75 mg, 0.16 mmol), (1R,3R,5S)-8-methyl-3-(4-(4,4,5,5-tetramethyl-1,3,2-dioxaborolan-2-yl) phenoxy)-8-azabicyclo[3.2.1]octane (75 mg, 0.21 mmol), PdCl$_2$dppf*CH$_2$Cl$_2$ (14 mg, 0.016 mmol)
$^1$H NMR (400 MHz, CD$_3$OD) δ ppm 8.53 (s, 1 H), 7.84-8.00 (m, 3 H), 7.60 (d, J = 8.8 Hz, 1 H), 7.28-7.41 (m, 2 H), 7.20 (d, J = 4.8 Hz, 2 H), 7.10 (d, J = 8.8 Hz, 1 H), 5.06 (d, J = 10.3 Hz, 1H), 4.74-4.85 (m, 1 H), 3.94 (br. s, 2 H), 2.84 (s, 3 H), 2.57-2.50 (m, 3 H), 2.49-2.21 (m, 6 H), 2.01-1.87 (m, 1 H), 1.70-1.40 (m, 6 H), 1 29 (br. s, 1 H)

| Example/IUPAC name | Structure | MS calculated MS ESI [M + H]+ | Yield; Appearance; Salt form |
|---|---|---|---|
| A248: N-((S)-cyclopentyl(thiophen-3-yl)methyl)-3-(4-(((1R,3R,5S)-8-methyl-8-azabicyclo[3.2.1]octan-3-yl)oxy)phenyl)-1H-indazole-5-carboxamide | 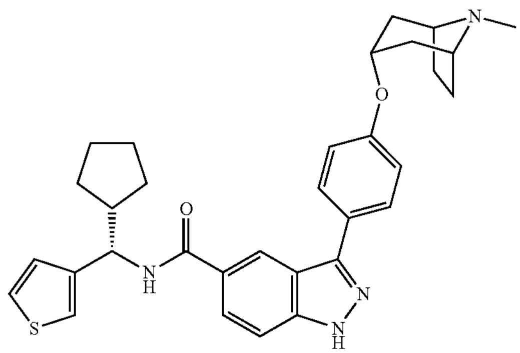 [SMILES: CN1C2CCC1CC(Oc1ccc(-c3n[nH]c4ccc(C(=O)N[C@H](c5ccsc5)C5CCCC5)cc34)cc1)C2] | [C$_{32}$H$_{36}$N$_4$O$_2$S + H]+ 541.2 541.2 | 30 mg (26%); light brown solid; TFA salt |

SMs: (S)-N-(cyclopentyl(thiophen-3-yl)methyl)-3-iodo-1H-indazole-5-carboxamide (75 mg, 0.16 mmol), (1R,3R,5S)-8-methyl-3-(4-(4,4,5,5-tetramethyl-1,3,2-dioxaborolan-2-yl) phenoxy)-8-azabicyclo[3.2.1]octane (75 mg, 0.21 mmol), PdCl$_2$dppf*CH$_2$Cl$_2$ (10 mg, 0.012 mmol)

$^1$H NMR (400 MHz, CD$_3$OD) δ ppm 8.53 (s, 1 H), 7.84-8.00 (m, 3 H), 7.60 (d, J = 8.8 Hz, 1 H), 7.28-7.41 (m, 2 H), 7.20 (d, J = 4.8 Hz, 2 H), 7.10 (d, J = 8.8 Hz, 1 H), 5.06 (d, J = 10.3 Hz, 1H), 4.74-4.85 (m, 1 H), 3.94 (br. s, 2 H), 2.84 (s, 3 H), 2.57-2.50 (m, 3 H), 2.49-2.21 (m, 6 H), 2.01-1.87 (m, 1 H), 1.70-1.40 (m, 6 H), 1.29 (br. s, 1 H)

| Example/IUPAC name | Structure | MS calculated MS ESI [M + H]+ | Yield; Appearance; Salt form |
|---|---|---|---|
| A249: (S)-N-(cyclopropyl(phenyl)methyl)-3-(1'-methylspiro[chroman-2,4'-piperidin]-6-yl)-1H-indazole-5-carboxamide | 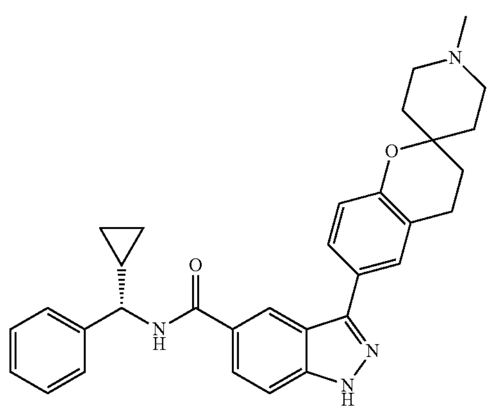 [SMILES: CN1CCC2(CCc3cc(-c4n[nH]c5ccc(C(=O)N[C@H](c6ccccc6)C6CC6)cc45)ccc3O2)CC1] | [C$_{32}$H$_{34}$N$_4$O$_2$ + H]+ 507.2 507.5 | 36 mg (30%); white solid; TFA salt |

SMs: (S)-N-(cyclopropyl(phenyl)methyl)-3-iodo-1H-indazole-5-carboxamide (100 mg, 0.24 mmol), 1'-methyl-6-(4,4,5,5-tetramethyl-1,3,2-dioxaborolan-2-yl)spiro[chroman-2,4'-piperidine] (90 mg, 0.26 mmol), PdCl$_2$dppf*CH$_2$Cl$_2$ (16 mg, 0.019 mmol)

$^1$H NMR (400 MHz, CD$_3$OD) δ ppm 8.58 (s, 1 H), 7.95 (dd, J = 8.8, 1.5 Hz, 1 H), 7.66-7.76 (m, 2 H), 7.59 (d, J = 8.8 Hz, 1 H), 7.50 (s, 2 H), 7.33 (d, J = 14.8 Hz, 2 H), 7.24 (s, 1 H), 6.94 (d, J = 8.3 Hz, 1 H), 4.49 (d, J = 9.5 Hz, 1 H), 2.90 (t, J = 6.7 Hz, 2 H), 2.68 (br. s, 2 H), 2.55 (br. s, 2 H), 2.36 (s, 3 H), 1.78-1.96 (m, 4 H), 1.65-1.81 (m, 2 H), 1.32-1.47 (m, 1 H), 0.66 (d, J = 8.0 Hz, 2 H), 0.39-0.57 (m, 2 H)

| Example/IUPAC name | Structure | MS calculated MS ESI [M + H]+ | Yield; Appearance; Salt form |
|---|---|---|---|
| A250: (S)-N-(1-(2-chlorophenyl)-2-methylpropyl)-3-(1'-methylspiro[chroman-2,4'-piperidin]-6-yl)-1H-indazole-5-carboxamide | 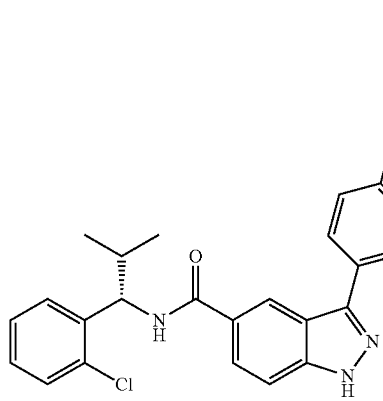 | [$C_{32}H_{35}ClN_4O_2$ + H]+ 543.2 543.6 | 45 mg (37%); white solid; TFA |

SMs: (S)-N-(1-(2-chlorophenyl)-2-methylpropyl)-3-iodo-1H-indazole-5-carboxamide (100 mg, 0.22 mmol), 1'-methyl-6-(4,4,5,5-tetramethyl-1,3,2-dioxaborolan-2-yl)spiro[chroman-2,4'-piperidine] (76 mg, 0.22 mmol), PdCl$_2$dppf*CH$_2$Cl$_2$ (15 mg, 0.018 mmol)

$^1$H NMR (400 MHz, CD$_3$OD) δ ppm 8.5 (s, 1 H), 7.86 (dd, J = 8.8 Hz, 1.5 Hz, 1 H), 7.68-7.65 (m, 2 H), 7.56-7.53 (m, 2 H), 7.39 (dd, J = 7.1 Hz, 1.8 Hz, 1 H), 7.29 (m, 1 H), 7.23 (dd, J = 7.8 Hz, 1.8 Hz, 1 H), 6.92 (d, J = 8.3 Hz, 1 H), 5.37(d, J = 9.6 Hz, 1 H), 2.87 (t, J = 6.8 Hz, 2 H), 2.68 (d, J = 11.3 Hz, 2 H), 2.55 (br.t, J = 10 Hz, 2 H), 2.35 (s, 3 H), 2.31-2.25 (m, 1 H), 1.89-1.84 (m, 4 H), 1.76-1.68 (m, 2 H), 1.16 (d, J = 6.4 Hz, 3 H), 0.87 (d, J = 6.8 Hz, 3 H)

| Example/IUPAC name | Structure | MS calculated MS ESI [M + H]+ | Yield; Appearance; Salt form |
|---|---|---|---|
| A251: (S)-N-(cyclopropyl(phenyl)methyl)-3-(1'-methyl-4-oxospiro[chroman-2,4'-piperidin]-6-yl)-1H-indazole-5-carboxamide | 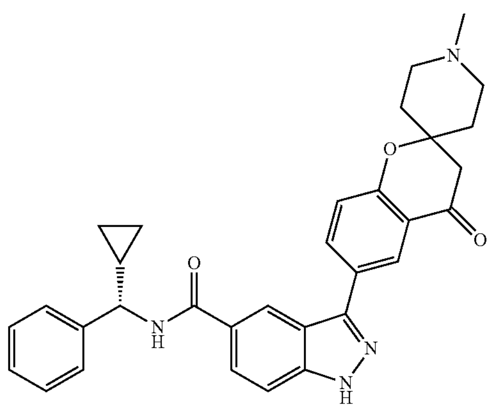 [SMILES: CN1CCC2(CC1)CC(=O)c1cc(-c3n[nH]c4ccc(C(=O)N[C@H](c5ccccc5)C5CC5)cc34)ccc1O2] | [$C_{32}H_{32}N_4O_3$ + H]+ 521.2 521.5 | 45 mg (48%); white solid; TFA |

SMs: (S)-N-(cyclopropyl(phenyl)methyl)-3-iodo-1H-indazole-5-carboxamide (75 mg, 0.18 mmol), 1'-methyl-6-(4,4,5,5-tetramethyl-1,3,2-dioxaborolan-2-yl)spiro[chroman-2,4'-piperidin]-4-one (65 mg, 0.18 mmol), PdCl$_2$dppf*CH$_2$Cl$_2$ (12 mg, 0.014 mmol)

$^1$H NMR (400 MHz, CD$_3$OD) δ ppm 8.59 (s, 1 H), 8.41 (d, J = 2.0 Hz, 1 H), 8.19 (dd, J = 8.7 Hz, 2.4 Hz, 1 H), 7.95 (dd, J = 8.8 Hz, 1.5 Hz, 1 H), 7.61 (d, J = 8.8 Hz, 1 H), 7.5 (d, J = 7 Hz, 2 H), 7.34 (t, J = 7.5 Hz, 2 H), 7.25-7.22 (m, 1 H), 7.18 (d, J = 8.4 Hz, 1 H), 4.50 (d, J = 9.6 Hz, 1 H), 2.83 (s, 2 H), 2.69-2.66 (m, 2 H), 2.52 (br.t, J = 11.2 Hz, 2 H), 2.35 (s, 3 H), 2.11-2.08 (br.d, 2 H), 1.84-1.76 (m, 2 H), 1.45-1.37 (m, 1 H), 0.68-0 62 (m, 2 H), 0.52-0.44 (m, 2 H)

-continued

| Example/IUPAC name | Structure | MS calculated MS ESI [M + H]+ | Yield; Appearance; Salt form |
|---|---|---|---|
| A252: N-((S)-cyclopentyl(pyridin-2-yl)methyl)-3-(4-(((1R,3R,5S)-8-methyl-8-azabicyclo[3.2.1]octan-3-yl)oxy)phenyl)-1H-indazole-5-carboxamide | 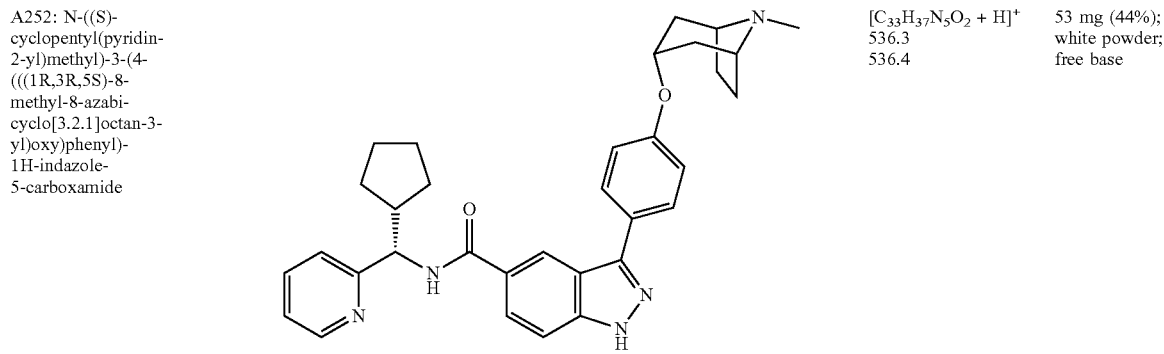 | [$C_{33}H_{37}N_5O_2$ + H]+ 536.3 536.4 | 53 mg (44%); white powder; free base |

SMs: (S)-N-(cyclopentyl(pyridin-2-yl)methyl)-3-iodo-1H-indazole-5-carboxamide (100 mg, 0.22 mmol), (1R,3R,5S)-8-methyl-3-(4-(4,4,5,5-tetramethyl-1,3,2-dioxaborolan-2-yl)phenoxy)-8-azabicyclo[3.2.1]octane (81 mg, 0.23 mmol), PdCl$_2$dppf*CH$_2$Cl$_2$ (14 mg, 0.018 mmol)

$^1$H NMR (400 MHz, CD$_3$OD) δ ppm 8.59 (s, 1 H), 8.53 (d, J = 4.5 Hz, 1 H), 7.85-8.00 (m, 3 H), 7.80 (td, J = 7.8, 1.5 Hz, 1 H), 7.59 (d, J = 8.8 Hz, 1 H), 7.50 (d, J = 7.8 Hz, 1 H), 7.30 (dd, J = 6.8, 5.3 Hz, 1 H), 7.00 (d, J = 8.8 Hz, 2 H), 5.02 (d, J = 10.3 Hz, 1 H), 4.63 (t, J = 4.6 Hz, 1 H), 3.17 (br. s, 2 H), 2.55 (d, J = 8.5 Hz, 1 H), 2.32 (s, 3 H), 2.05-2.24 (m, 6 H), 1.99 (d, J = 14.3 Hz, 3 H), 1.46-1.79 (m, 5 H), 1.21-1.43 (m, 2 H)

| A253: (S)-N-(cyclopentyl(pyridin-2-yl)methyl)-3-(1'-methylspiro[chroman-2,4'-piperidin]-6-yl)-1H-indazole-5-carboxamide | 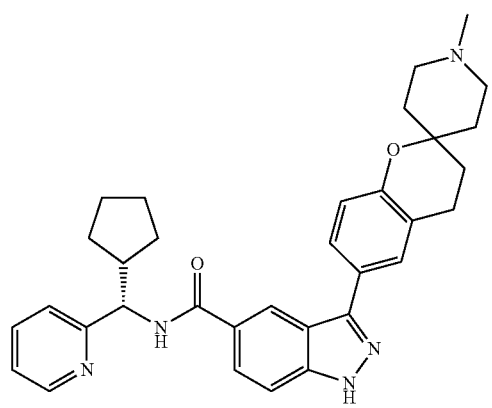 [SMILES: CN1CCC2(CCc3cc(-c4n[nH]c5ccc(C(=O)N[C@H](c6ccccn6)C6CCCC6)cc45)ccc3O2)CC1] | [$C_{33}H_{37}N_5O_2$ + H]+ 536.3 536.3 | 54 mg (45%); white powder; free base |

SMs: (S)-N-(cyclopentyl(pyridin-2-yl)methyl)-3-iodo-1H-indazole-5-carboxamide (100 mg, 0.22 mmol), 1'-methyl-6-(4,4,5,5-tetramethyl-1,3,2-dioxaborolan-2-yl)spiro[chroman-2,4'-piperidine] (77 mg, 0.22 mmol), PdCl$_2$dppf*CH$_2$Cl$_2$ (18 mg, 0.022 mmol)

$^1$H NMR (400 MHz, CD$_3$OD) δ ppm 8.43-8.62 (m, 2 H), 7.91 (dd, J = 8.8, 1.5 Hz, 1 H), 7.80 (td, J = 7.7, 1.8 Hz, 1 H), 7.61-7.72 (m, 2 H), 7.58 (d, J = 9.0 Hz, 1 H), 7.49 (d, J = 7.8 Hz, 1 H), 7.23-7.37 (m, 1 H), 6.93 (d, J = 8.3 Hz, 1 H), 5.02 (d, J = 10.3 Hz, 1 H), 2.89 (t, J = 6.8 Hz, 2 H), 2.68 (d, J = 11.5 Hz, 2 H), 2.42-2.61 (m, 3 H), 2.35 (s, 3 H), 1.93-2.04 (m, 1 H), 1.46-1.92 (m, 11 H), 1.22-1.44 (m, 2 H)

| Example/IUPAC name | Structure | MS calculated MS ESI [M + H]+ | Yield; Appearance; Salt form |
|---|---|---|---|
| A254: (S)-N-(cyclopropyl(phenyl)methyl)-3-(1-methyl-4'-oxospiro[azetidine-3,2'-chroman]-6'-yl)-1H-indazole-5-carboxamide | 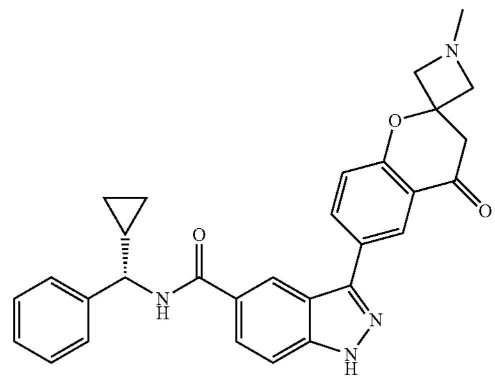 [SMILES: CN1CC2(CC(=O)c3cc(-c4n[nH]c5ccc(C(=O)N[C@H](c6ccccc6)C6CC6)cc45)ccc3O2)C1] | [$C_{30}H_{28}N_4O_3$ + H]+<br>493.2<br>493.2 | 73 mg (28%); white solid; TFA |

SMs: (S)-N-(cyclopropyl(phenyl)methyl)-3-iodo-1H-indazole-5-carboxamide (175 mg, 0.41 mmol), 1-methyl-6'-(4,4,5,5-tetramethyl-1,3,2-dioxaborolan-2-yl)spiro[azetidine-3,2'-chroman]-4'-one (152 mg, 0.46 mmol), PdCl$_2$dppf*CH$_2$Cl$_2$ (34 mg, 0.041 mmol)
$^1$H NMR (400 MHz, CD$_3$OD) δ ppm 8.56 (s, 1 H), 8.44 (s, 1 H), 8.29 (dd, J = 8.5, 2.0 Hz, 1 H), 7.90-8.03 (m, 1 H), 7.63 (d, J = 8.8 Hz, 1 H), 7.50 (d, J = 1.5 Hz, 2 H), 7.18-7.43 (m, 4 H), 4.24-4.75 (m, 5 H), 3.04 (br. s, 3 H), 1.35-1.49 (m, 1 H), 0.68 (d, J = 7.8 Hz, 2 H), 0.49 (dd, J = 9.0, 5.0 Hz, 2 H), 2H merged with solvent peak.

| A255: (S)-N-(1-(2-chlorophenyl)-2-methylpropyl)-3-(1-methyl-4'-oxospiro[azetidine-3,2'-chroman]-6'-yl)-1H-indazole-5-carboxamide | | [$C_{30}H_{29}ClN_4O_3$ + H]+<br>529.2<br>529.2 | 50 mg (35%); cream solid; TFA |

SMs: (S)-N-(1-(2-chlorophenyl)-2-methylpropyl)-3-iodo-1H-indazole-5-carboxamide (100 mg, 0.22 mmol), 1-methyl-6'-(4,4,5,5-tetramethyl-1,3,2-dioxaborolan-2-yl)spiro[azetidine-3,2'-chroman]-4'-one (73 mg, 0.22 mmol), PdCl$_2$dppf*CH$_2$Cl$_2$ (18 mg, 0.022 mmol)
$^1$H NMR (400 MHz, CD$_3$OD) δ ppm 8.85 (d, J = 8.4 Hz, 0.54 H), 8.49 (s, 1 H), 8.45 (s, 1H), 8.28 (dd, J = 8.4 Hz, 2.0 Hz, 1 H), 7.88 (m, 1 H), 7.62-7.56 (m, 2 H), 7.41-7.32 (m, 3 H), 7.26-7.21 (m, 1 H), 5.40-5.36 (m, 1 H), 4.63-4.30 (br.m, 4 H), 3.06 (br.s, 3 H), 2.34-2.25 (m, 1 H), 1.18 (d, J = 6.4 Hz, 3 H), 0.89 (d, J = 6.8 Hz, 3 H)

| A256: N-((S)-cyclopropyl(phenyl)methyl)-3-(4'-hydroxy-1-methylspiro(azetidine-3,2-chroman]-6'-yl)-1H-indazole-5-carboxamide | | [$C_{30}H_{30}N_4O_3$ + H]+<br>495.2<br>495.2 | 26 mg (58%); white solid; TFA |

SMs: (S)-N-(cyclopropyl(phenyl)methyl)-3-(1-methyl-4'-oxospiro[azetidine-3,2'-chroman]-6'-yl)-1H-indazole-5-carboxamide (45 mg, 0.074 mmol), NaBH$_4$ (16 mg, 0.14 mmol)
$^1$H NMR (400 MHz, CD$_3$OD) δ ppm 8.61 (s, 1 H), 8.11-7.97 (m, 3 H), 7.63 (d, J = 8.5 Hz 1 H), 7.50 (d, J = 7.5 Hz, 2 H), 7.30-7.40 (m, 2 H), 7.21-7.30 (m, 1 H), 7.09-7.22 (m, 1 H), 4.65-4.74 (m, 1 H), 4.48 (br. s, 3 H), 3.15 (s, 1 H), 2.93 (s, 2 H), 4.09-4.43 (m, 2 H), 2.50-2.62 (m, 1 H), 2.26-2.39 (m, 1 H), 1.35-1.49 (m, 1 H), 0.68 (d, J = 8.3 Hz, 2 H), 0.40-0.58 (m, 2 H)

| Example/IUPAC name | Structure | MS calculated MS ESI [M + H]+ | Yield; Appearance; Salt form |
|---|---|---|---|
| A257: (S)-N-(cyclopropyl(pyridin-2-yl)methyl)-3-(1'-methyl-4-oxospiro[chroman-2,4'-piperidin]-6-yl)-1H-indazole-5-carboxamide | 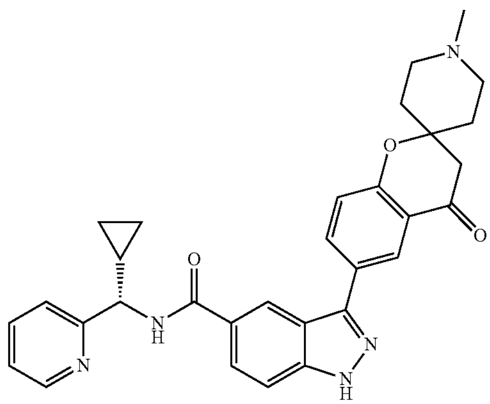 [SMILES: CN1CCC2(CC1)CC(=O)c1cc(-c3n[nH]c4ccc(C(=O)N[C@H](c5ccccn5)C5CC5)cc34)ccc1O2] | [C31H31N5O3 + H]+ 522.2 522.3 | 37 mg (29%); yellow powder; free base |

SMs: (S)-N-(cyclopropyl(pyridin-2-yl)methyl)-3-iodo-1H-indazole-5-carboxamide (100 mg, 0.23 mmol), 1'-methyl-6-(4,4,5,5-tetramethyl-1,3,2-dioxaborolan-2-yl)spiro[chroman-2,4'-piperidin]-4-one (85 mg, 0.23 mmol), PdCl2dppf*CH2Cl2 (19 mg, 0.023 mmol)
1H NMR (400 MHz, CD3OD) δ ppm 8.62 (s, 1 H), 8.54 (d, J = 4.3 Hz, 1 H), 8.41 (d, J = 2.0 Hz, 1 H), 8.20 (dd, J = 8.5, 2.3 Hz, 1 H), 7.91-7.99 (m, 1 H), 7.83 (d, J = 1.5 Hz, 1 H), 7.61 (d, J = 8.8 Hz, 1 H), 7.55 (d, J = 8.0 Hz, 1 H), 7.27-7.35 (m, 1 H), 7.19 (d, J = 8.8 Hz, 1 H), 4.54 (d, J = 9.3 Hz, 1 H), 2.84 (s, 2 H), 2.69 (d, J = 11.0 Hz, 2 H), 2.48-2.61 (m, 2 H), 2.36 (s, 3 H), 2.11 (d, J = 13.6 Hz, 2 H), 1.82 (br. s, 2 H), 1.37-1.48 (m, 1 H), 0.65-0.74 (m, 1 H), 0.49-0.64 (m, 3 H)

| Example/IUPAC name | Structure | MS calculated MS ESI [M + H]+ | Yield; Appearance; Salt form |
|---|---|---|---|
| A258: (S)-N-(1-(2-chlorophenyl)-2-methylpropyl)-3-(1',4-dimethylspiro[chromene-2,4'-piperidin]-6-yl)-1H-indazole-5-carboxamide | 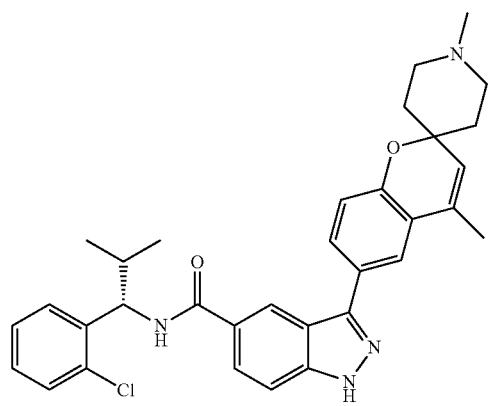 [SMILES: CC1=CC2(CCN(C)CC2)Oc2ccc(-c3n[nH]c4ccc(C(=O)N[C@H](c5ccccc5Cl)C(C)C)cc34)cc21] | [C33H35ClN4O2 + H]+ 555.2 555.6 | 39 mg (43%); white powder; free base |

SMs: (S)-N-(1-(2-chlorophenyl)-2-methylpropyl)-3-iodo-1H-indazole-5-carboxamide (75 mg, 0.16 mmol), 1',4-dimethyl-6-(4,4,5,5-tetramethyl-1,3,2-dioxaborolan-2-yl)spiro[chromene-2,4'-piperidine] (58 mg, 0.16 mmol), PdCl2dppf*CH2Cl2 (13 mg, 0.023 mmol)
1H NMR (400 MHz, CD3OD) δ ppm 8.52 (s, 1 H), 7.87 (d, J = 9.0 Hz, 1 H), 7.73-7.83 (m, 2 H), 7.49-7.61 (m, 2 H), 7.39 (d, J = 7.8 Hz, 1 H), 7.26-7.33 (m, 1 H), 7.17-7.26 (m, 1 H), 6.97 (d, J = 8.0 Hz, 1 H), 5.76 (s, 0.15 H), 5.56 (s. 0.85 H), 5.38 (d, J = 9.5 Hz, 1H), 2.47-2.71 (m, 4 H), 2.35 (s, 3 H), 2.21-2.32 (m, 1 H), 2.13 (s, 3 H), 2.02 (d, J = 14.1 Hz, 2 H), 1.74-1.79 (br. s, 2H), 1.16 (d, J = 6.5 Hz, 3 H), 0.87 (d, J = 6.8 Hz, 3 H)

| Example/IUPAC name | Structure | MS calculated MS ESI [M + H]+ | Yield; Appearance; Salt form |
|---|---|---|---|
| A259: (S)-N-(1-(2-chlorophenyl)-2-methylpropyl)-3-(4-((1-methyl piperidin-4-yl)oxy)-3-(methylsulfonyl)phen-yl)-1H-indazole-5-carboxamide | | [C31H35ClN4O4S + H]+ 596.2 595.6 | 45 mg (14%); cream solid; TFA |

SMs: (S)-N-(1-(2-chlorophenyl)-2-methylpropyl)-3-iodo-1H-indazole-5-carboxamide (75 mg, 0.16 mmol), 1-methyl-4-(2-(methylsulfonyl)-4-(4,4,5,5-tetramethyl-1,3,2-dioxaborolan-2-yl)phenoxy)piperidine (85 mg, 0.21 mmol), PdCl$_2$dppf*CH$_2$Cl$_2$ (13 mg, 0.015 mmol)

$^1$H NMR (400 MHz, CD$_3$OD) δ ppm 8.55 (d, J = 2.0 Hz, 1 H), 8.48 (s, 1 H), 8.29 (dd, J = 8.7, 2.1 Hz, 1 H), 7.82-7.93 (m, 1 H), 7.53-7.66 (m, 2 H), 7.36-7.52 (m, 2 H), 7.29-7.37 (m, 1 H), 7.24 (d, J = 6.5 Hz, 1 H), 5.39-5.40 (m, 1 H), 5.39 (d, J = 9.5 Hz, 1 H), 5.21 (br. s, 1 H), 3.37-3.58 (m, 4 H), 2.84-3.00 (m, 3 H), 2.42 (d, J = 14.8 Hz, 2 H), 2.19 (br. s, 4 H), 1.17 (d, J = 6.5 Hz, 3 H), 0.89 (d, J = 6.5 Hz, 3 H), 1H merged with solvent peak.

| Example/IUPAC name | Structure | MS calculated MS ESI [M + H]+ | Yield; Appearance; Salt form |
|---|---|---|---|
| A260: (S)-N-(cyclopropyl(pyridin-2-yl)methyl)-3-(1',4-dimethyl-spiro[chromene-2,4'-piperidin]-6-yl)-1H-indazole-5-carboxamide | 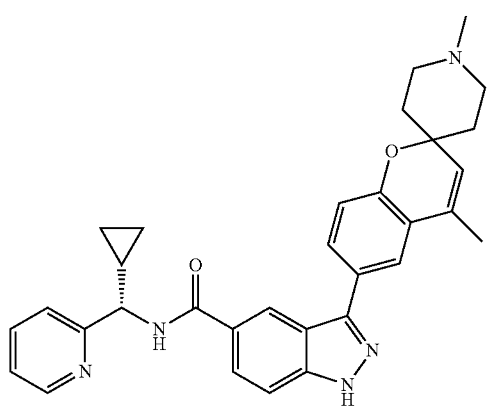 [SMILES: CC1=CC2(CCN(C)CC2)Oc2ccc(-c3n[nH]c4ccc(C(=O)N[C@H](c5ccccn5)C5CC5)cc34)cc21] | [C32H33N5O2 + H]+ 520.2 520.3 | 40 mg (32%); white powder; free base |

SMs: (S)-N-(cyclopropyl(pyridin-2-yl)methyl)-3-iodo-1H-indazole-5-carboxamide (100 mg, 0.23 mmol), 1',4-dimethyl-6-(4,4,5,5-tetramethyl-1,3,2-dioxaborolan-2-yl)spiro[chromene-2,4'-piperidine] (85 mg, 0.23 mmol), PdCl$_2$dppf*CH$_2$Cl$_2$ (19 mg, 0.023 mmol)

$^1$H NMR (400 MHz, CD$_3$OD) δ ppm 8.63 (s, 1 H), 8.52 (d, J = 4.3 Hz, 1 H), 7.95 (dd, J = 8.9, 1.4 Hz, 1 H), 7.76-7.87 (m, 3 H), 7.61 (d, J = 8.8 Hz, 1 H), 7.54 (d, J = 7.8 Hz, 1 H), 7.32 (s, 1 H), 7.00 (d, J = 8.8 Hz, 1 H), 5.79 (s, 0.15 H), 5.56 (s, 0.85 H), 4.52 (d, J = 9.3 Hz, 1 H), 2.48-2.72 (m, 4 H), 2.35 (s, 3 H), 2.13 (s, 3 H), 2.02 (d, J = 12.8 Hz, 2 H), 1.74-1.79 (m, 2 H), 1.37-1.42 (m, 1 H), 0.66-0.71 (m, 1 H), 0.49-0.63 (m, 3 H)

| Example/IUPAC name | Structure | MS calculated MS ESI [M + H]+ | Yield; Appearance; Salt form |
|---|---|---|---|
| A261: (S)-N-(cyclopentyl(pyridin-2-yl)methyl)-3-(1',4-dimethyl-spiro[chromene-2,4'-piperidin]-6-yl)-1H-indazole-5-carboxamide | 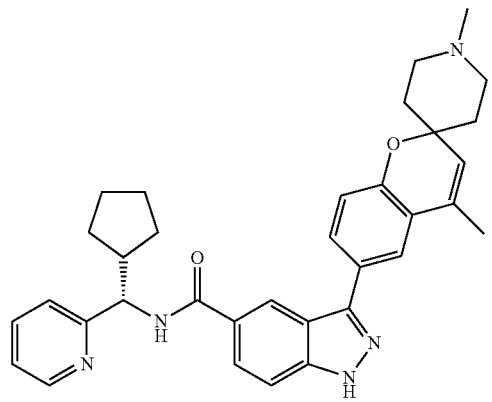 [SMILES: CC1=CC2(CCN(C)CC2)Oc2ccc(-c3n[nH]c4ccc(C(=O)N[C@H](c5ccccn5)C5CCCC5)cc34)cc21] | [C$_{34}$H$_{37}$N$_5$O$_2$ + H]+ 548.3 548.3 | 60 mg (46%); cream solid; HCl salt |

SMs: (S)-N-(cyclopentyl(pyridin-2-yl)methyl)-3-iodo-1H-indazole-5-carboxamide (100 mg, 0.22 mmol), 1',4-dimethyl-6-(4,4,5,5-tetramethyl-1,3,2-dioxaborolan-2-yl)spiro[chromene-2,4'-piperidine] (80 mg, 0.22 mmol), PdCl$_2$dppf*CH$_2$Cl$_2$ (13 mg, 0.011 mmol)
$^1$H NMR (400 MHz, CD$_3$OD) δ ppm 8.83 (d, J = 4.8 Hz, 1 H), 8.58-8.70 (m, 2 H), 8.23 (d, J = 7.3 Hz, 1 H), 7.95-8.08 (m, 2 H), 7.81-7.94 (m, 2 H), 7.65 (d, J = 9.0 Hz, 1 H), 7.18 (d, J = 8.3 Hz, 1 H), 5.87 (s, 0.24 H), 5.60 (s, 0.76 H), 5.05 (d, J = 10.8 Hz, 1 H), 3.45-3.72 (m, 3 H), 2.97 (s, 3 H), 2.68-2.73 (m, 1 H), 2.13-2.29 (m, 5 H), 2.02-2.13 (m, 2 H), 1.62-1.87 (m, 5 H), 1.20-1.44 (m, 2 H)

| Example/IUPAC name | Structure | MS calculated MS ESI [M + H]+ | Yield; Appearance; Salt form |
|---|---|---|---|
| A262: (S)-N-(cyclopropyl(pyridin-2-yl)methyl)-3-(4-oxo-2',3',5',6'-tetrahydrospiro[chroman-2,4'-pyran]-6-yl)-1H-indazole-5-carboxamide | 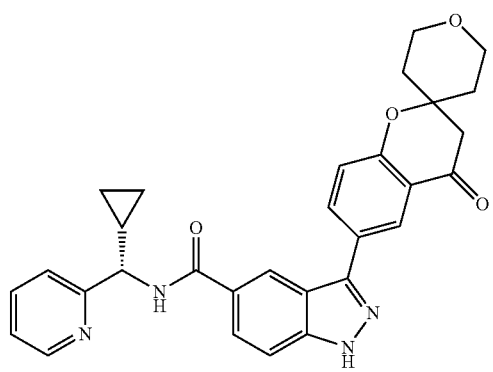 [SMILES: O=C(N[C@H](c1ccccn1)C1CC1)c1ccc2[nH]nc(-c3ccc4c(c3)C(=O)CC3(CCOCC3)O4)c2c1] | [C$_{30}$H$_{28}$N$_4$O$_4$ + H]+ 509.2 509.4 | 83 mg (56%); white solid; TFA salt |

SMs: (S)-N-(cyclopropyl(pyridin-2-yl)methyl)-3-iodo-1H-indazole-5-carboxamide (100 mg, 0.23 mmol), 6-(4,4,5,5-tetramethyl-1,3,2-dioxaborolan-2-yl)-2',3',5',6'-tetrahydrospiro[chroman-2,4'-pyran]-4-one (83 mg, 0.23 mmol), PdCl$_2$dppf*CH$_2$Cl$_2$ (13 mg, 0.011 mmol)
$^1$H NMR (400 MHz, CD$_3$OD) δ ppm 8.73-8.81 (m, 1 H), 8.64-8.70 (m, 1 H), 8.55 (td, J = 8.0, 1.6 Hz, 1 H), 8.41 (d, J = 2.5 Hz, 1 H), 8.16-8.25 (m, 2 H), 7.97 (dd, J = 8.9, 1.6 Hz, 1 H), 7.92 (ddd, J = 7.5, 6.0, 1.1 Hz, 1 H), 7.63 (dd, J = 8.8, 0.5 Hz, 1 H), 7.24 (d, J = 8.5 Hz, 1H), 4.51 (d, J = 10.0 Hz, 1 H), 3.83-3.93 (m, 2 H), 3.74-3.82 (m, 2 H), 2.88 (s, 2 H), 1.96-2.06 (m, 2 H), 1.79-1.91 (m, 2 H), 1.46-1.60 (m, 1 H), 0.85-0.95 (m, 1 H), 0.60-0.80 (m, 3 H)

| Example/IUPAC name | Structure | MS calculated MS ESI [M + H]+ | Yield; Appearance; Salt form |
|---|---|---|---|
| A263: (S)-N-(cyclopropyl(pyridin-2-yl)methyl)-3-(1'-formyl-4-oxospiro[chroman-2,4'-piperidin]-6-yl)-1H-indazole-5-carboxamide | 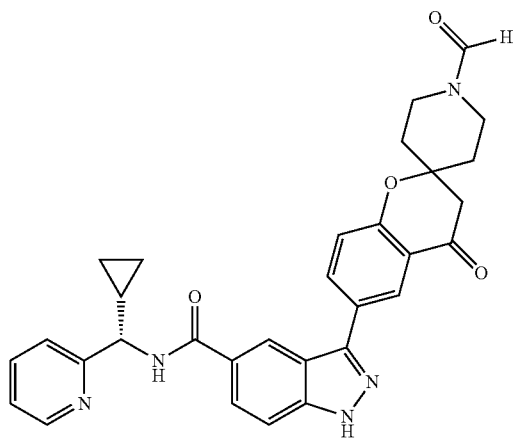 [SMILES: O=CN1CCC2(CC1)CC(=O)c1cc(-c3n[nH]c4ccc(C(=O)N[C@H](c5ccccn5)C5CC5)cc34)ccc1O2] | [C₃₁H₂₉N₅O₄ + H]+ 536.2 536.4 | 79 mg (51%); cream solid; TFA salt |

SMs: (S)-N-(cyclopropyl(pyridin-2-yl)methyl)-3-iodo-1H-indazole-5-carboxamide (100 mg, 0.23 mmol), 4-oxo-6-(4,4,5,5-tetramethyl-1,3,2-dioxaborolan-2-yl)spiro[chroman-2,4'-piperidine]-1'-carbaldehyde (89 mg, 0.23 mmol), PdCl₂dppf*CH₂Cl₂ (13 mg, 0.011 mmol)

¹H NMR (400 MHz, CD₃OD) δ ppm 8.78 (dq, J = 5.8 Hz, 0.8 Hz, 1 H), 8.68 (dd, J = 1.6 Hz, 0.9 Hz, 1 H), 8.58 (td, J = 7.9 Hz, 1.5 Hz, 1 H), 8.58 (s, 1 H), 8.24-8.18 (m, 2 H), 8.05 (s, 1 H), 7.99-7.90 (m, 2 H), 7.64 (dd, J = 8.8 Hz, 0.8 Hz, 1 H),7.25 (d, J = 8.5 Hz, 1 H), 4.52 (d, J = 10 Hz, 1 H), 4.19-4.15 (br.d, 1 H), 3.61-3.57(m, 2 H), 3.56-3.14 (br.t, 1 H), 2.88 (s, 2 H) 2.19-2.12 (br.t, 2 H), 1.70-1.80 (m, 2 H), 1.52-1.68 (m, 1 H), 0.92-0.86 (m, 1 H), 0.61-0.64 (m, 3 H)

| Example/IUPAC name | Structure | MS calculated MS ESI [M + H]+ | Yield; Appearance; Salt form |
|---|---|---|---|
| A264: (S)-N-(cyclopropyl(pyridin-2-yl)methyl)-3-(1'-(oxetan-3-yl)-4-oxospiro[chroman-2,4'-piperidin]-6-yl)-1H-indazole-5-carboxamide | 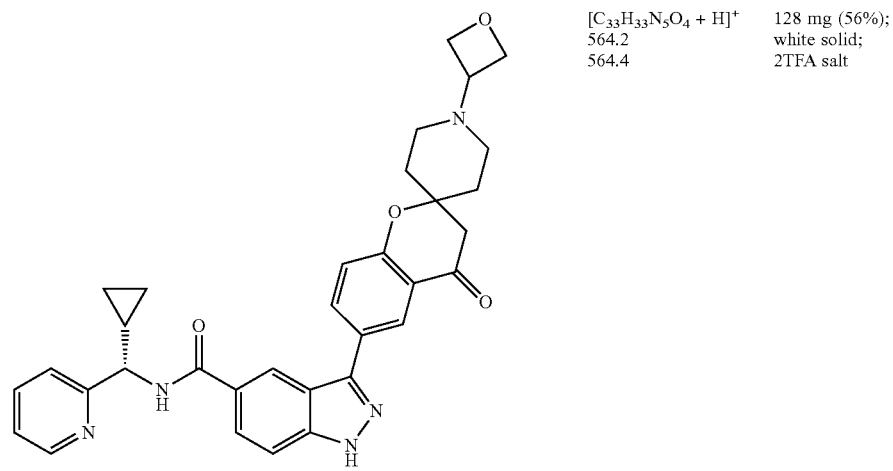 | [C₃₃H₃₃N₅O₄ + H]+ 564.2 564.4 | 128 mg (56%); white solid; 2TFA salt |

SMs: (S)-N-(cyclopropyl(pyridin-2-yl)methyl)-3-iodo-1H-indazole-5-carboxamide (125 mg, 0.29 mmol), 1'-(oxetan-3-yl)-6-(4,4,5,5-tetramethyl-1,3,2-dioxaborolan-2-yl)spiro[chroman-2,4'-piperidin]-4-one (131 mg, 0.32 mmol), PdCl₂dppf*CH₂Cl₂ (24 mg, 0.029 mmol)

¹H NMR (400 MHz, CD₃OD) δ ppm 8.78 (dd, J = 5.8, 1.0 Hz, 1 H), 8.65 (d, J = 0.5 Hz, 1 H), 8.56 (td, J = 8.0, 1.0 Hz, 1 H), 8.41 (d, J = 2.3 Hz, 1 H), 8.22 (m, 2H), 7.95 (m, 2 H), 7.63 (m, 1 H), 7.29 (d, J = 8.5 Hz, 1 H), 4.89-4.87 (m, 4 H), 4.58 (m, 1 H), 4.53 (d, J = 10 Hz, 1 H), 3.43 (m, 2 H), 2.96 (s, 2 H), 2.41 (d, J = 14.8 Hz, 2 H), 2.17-2.09 (m, 2 H), 1.58-1.49 (m, 1 H), 0.92-0.85 (m, 1H), 0.78-0.62 (m, 3H), 1H-merged with solvent peak.

-continued

| Example/IUPAC name | Structure | MS calculated MS ESI [M + H]+ | Yield; Appearance; Salt form |
|---|---|---|---|
| A265: N-((S)-cyclopropyl(2-fluorophenyl)methyl)-3-(4-((1R,3R,5S)-3-hydroxy-8-azabicyclo[3.2.1]octan-8-yl)phenyl)-1H-indazole-5-carboxamide | 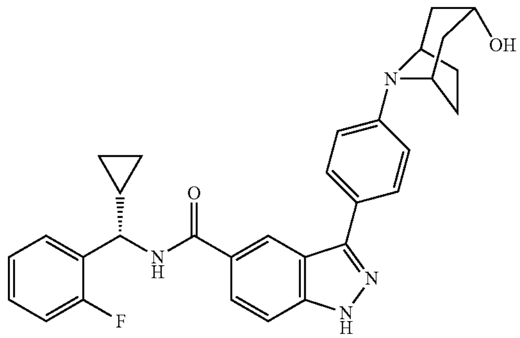 [SMILES: O=C(N[C@H](c1ccccc1F)C1CC1)c1ccc2[nH]nc(-c3ccc(N4C5CCC4CC(O)C5)cc3)c2c1] | [C$_{31}$H$_{31}$FN$_4$O$_2$ + H]$^+$ 511.2 511.4 | 38 mg (40%); yellow solid; HCl salt |

SMs: (S)-N-(cyclopropyl(2-fluorophenyl)methyl)-3-iodo-1H-indazole-5-carboxamide (75 mg, 0.17 mmol), (1R,3R,5S)-8-(4-(4,4,5,5-tetramethyl-1,3,2-dioxaborolan-2-yl)phenyl)-8-azabicyclo[3.2.1]octan-3-ol (57 mg, 0.17 mmol), Pd(PPh$_3$)$_4$ (15 mg, 0.012 mmol)
$^1$H NMR (400 MHz, CD$_3$OD) δ ppm 8.60 (s, 1 H), 8.27 (d, J = 8.4 Hz, 2 H), 7.98 (d, J = 8.8 Hz, 1 H), 7.58 (d, J = 8.4 Hz, 2 H), 7.67 (d, J = 8.4 Hz, 1 H), 7.58 (t, J = 7.2 Hz, 1 H), 7.26-7.31 (m, 1 H), 7.17 (t, J = 7.6 Hz, 1 H), 7.06-7.11 (m, 1 H), 4.77 (d, J = 9.6 Hz, 1 H), 4.71 (br.s, 2 H), 4.17 (s, 1 H), 2.71-2.73 (m, 2 H), 2.63-2.59 (m, 2 H), 2.23-2.27 (m, 4 H), 1.46-1.48 (br. m, 1 H), 0.62-0.69 (br. m, 1 H), 0.56-0.60 (m, 1 H), 0.45-0.54 (m, 2 H)

| | | | |
|---|---|---|---|
| A266: N-((R)-cyclopropyl(2-fluorophenyl)methyl)-3-(4-((1R,3R,5S)-3-hydroxy-8-azabicyclo[3.2.1]octan-8-yl)phenyl)-1H-indazole-5-carboxamide | | [C$_{31}$H$_{31}$FN$_4$O$_2$ + H]$^+$ 511.2 511.4 | 20 mg (40%); yellow powder; TFA salt |

SMs: (R)-N-(cyclopropyl(2-fluorophenyl)methyl)-3-iodo-1H-indazole-5-carboxamide (40 mg, 0.09 mmol), (1R,3R,5S)-8-(4-(4,4,5,5-tetramethyl-1,3,2-dioxaborolan-2-yl)phenyl)-8-azabicyclo[3.2.1]octan-3-ol (36 mg, 0.1 mmol), Pd(PPh$_3$)$_4$ (5 mg, 0.009 mmol)
$^1$H NMR (400 MHz, CD$_3$OD) δ 8.61 (s, 1 H), 8.09 (d, J = 8.5 Hz, 2 H), 8.02-7.91 (m, 1 H), 7.63 (d, J = 8.8 Hz, 1 H), 7.57 (t, J = 6.8 Hz, 1 H), 7.48 (d, J = 7.5 Hz, 2 H), 7.34-7.22 (m, 1 H), 7.22-7.12 (m, 1 H), 7.12-7.00 (m, 1 H), 4.76 (d, J = 9.5 Hz, 1 H), 4.53 (br. s., 2 H), 4.08 (br. s., 1 H), 2.59 (d, J = 7.8 Hz, 2 H), 2.48-2.39 (m, 2 H), 2.19-2.10 (m, 2 H), 2.05-1.97 (m, 2 H), 1.54-1.33 (m, 1 H), 0.75-0.63 (m, 1 H) 0.61-0.54 (m, 1 H), 0.53-0.38 (m, 2 H)

| | | | |
|---|---|---|---|
| A267: 3-(4-((1R,5S)-3-oxa-8-azabicyclo[3.2.1]octan-8-yl)phenyl)-N-((S)-cyclopropyl(2-fluorophenyl)methyl)-1H-indazole-5-carboxamide | | [C$_{30}$H$_{29}$FN$_4$O$_2$ +H]$^+$ 497.2 497.4 | 54 mg (59%); yellow solid; HCl salt |

SMs: (S)-N-(cyclopropyl(2-fluorophenyl)methyl)-3-iodo-1H-indazole-5-carboxamide (75 mg, 0.17 mmol), (1R,5S)-8-(4-(4,4,5,5-tetramethyl-1,3,2-dioxaborolan-2-yl)phenyl)-3-oxa-8-azabicyclo[3.2.1]octane (55 mg, 0.17 mmol), Pd(PPh$_3$)$_4$ (15 mg, 0.012 mmol)
$^1$H NMR (400 MHz, CD$_3$OD) δ ppm 8.62 (s, 1 H), 8.27 (d, J = 8.4 Hz, 2 H), 7.99 (d, J = 8.8 Hz, 1 H), 7.81 (d, J = 8.4 Hz, 2 H), 7.68 (d, J = 8.4 Hz, 1 H), 7.58 (t, J = 6.4 Hz, 1 H), 7.26-7.31 (m, 1 H), 7.17 (t, J = 7.6 Hz, 1 H), 7.06-7.11 (m, 1 H), 4.77 (d, J = 9.6 Hz, 1 H), 4.71 (br.s, 2 H), 4.25 (d, J = 12.4 Hz, 2 H), 3.99 (d, J = 12.8 Hz, 2 H), 2.35-2.37 (m, 2 H), 2.19-2.22 (m, 2 H), 1.46-1.48 (m, 1 H), 0.70-0.73 (br. m, 1 H), 0.59-0.69 (m, 1 H), 0.45-0.54 (m, 2 H)

| Example/IUPAC name | Structure | MS calculated MS ESI [M + H]+ | Yield; Appearance; Salt form |
|---|---|---|---|
| A268: 3-(4-((1R,5S)-3-oxa-8-azabi-cyclo[3.2.1]octan-8-yl)phenyl)-N-((R)-cyclopropyl(2-fluorophenyl)methyl)-1H-indazole-5-carboxamide | | [C₃₀H₂₉FN₄O₂ + H]+ 497.2 497.4 | 13 mg (12%); yellow solid; TFA salt |

SMs: (R)-N-(cyclopropyl(2-fluorophenyl)methyl)-3-iodo-1H-indazole-5-carboxamide (80 mg, 0.18 mmol), (1R,5S)-8-(4-(4,4,5,5-tetramethyl-1,3,2-dioxaborolan-2-yl)phenyl)-3-oxa-8-azabicyclo[3.2.1]octane (65 mg, 0.2 mmol), Pd(PPh₃)₄ (10 mg, 0.009 mmol)
¹H NMR (400 MHz, CD₃OD) δ ppm 8.61 (s, 1 H), 7.97-7.84 (m, 3 H), 7.63-7.50 (m, 2 H), 7.31-7.22 (m, 1 H), 7.16 (t, J = 7.2 Hz, 1 H), 7.12-7.03 (m, 2 H), 4.75 (d, J = 9.5 Hz, 1 H), 4.24 (br. s., 2 H), 3.93 (d, J = 11.0 Hz, 2 H), 3.57 (br. s., 2 H), 2.15-1.97 (m, 4 H), 1.48-1.40 (m, 1 H), 0.72-0.62 (m, 1 H), 0.62-0.53 (m, 1 H), 0.53-0.38 (m, 2 H)

| Example/IUPAC name | Structure | MS calculated MS ESI [M + H]+ | Yield; Appearance; Salt form |
|---|---|---|---|
| A269: (S)-N-(cyclo-propyl(2-fluoro-phenyl)methyl)-3-(4-(4-(oxetan-3-yl)piperazin-1-yl)phenyl)-1H-indazole-5-carboxamide | | [C₃₁H₃₂FN₅O₂ + H]+ 526.2 526.8 | 60 mg (54%); off-white solid; TFA salt |

SMs: (S)-N-(cyclopropyl(2-fluorophenyl)methyl)-3-iodo-1H-indazole-5-carboxamide (75 mg, 0.17 mmol), 1-(oxetan-3-yl)-4-(4-(4,4,5,5-tetramethyl-1,3,2-dioxaborolan-2-yl)phenyl)piperazine (60 mg, 0.17 mmol), Pd(PPh₃)₄ (15 mg, 0.012 mmol)
¹H NMR (400 MHz, CD₃OD) δ ppm 8.58 (d, J = 0.4 Hz, 1 H), 7.95 (dd, J = 8.8, 2.4 Hz, 3 H), 7.54-7.61 (m, 2 H), 7.25-7.30 (m, 1 H), 7.11-7.25 (m, 3 H), 7.06-7.09 (m, 1 H), 4.76 (d, J = 9.6 Hz, 1 H), 4.48-7.51 (m, 1 H), 3.58 (br.s, 4 H), 3.40 (br.s, 4 H), 1.41-1.47 (m, 1 H), 0.65-0.72 (m, 1 H), 0.53-0.61 (m, 1 H), 0.42-0.51 (m, 2 H), 4H-merged with solvent peak.

| Example/IUPAC name | Structure | MS calculated MS ESI [M + H]+ | Yield; Appearance; Salt form |
|---|---|---|---|
| A270: (R)-N-(cyclopropyl(2-fluorophenyl)methyl)-3-(4-(4-(oxelan-3-yl)piperazin-1-yl)phenyl)-1H-indazole-5-carboxamide | 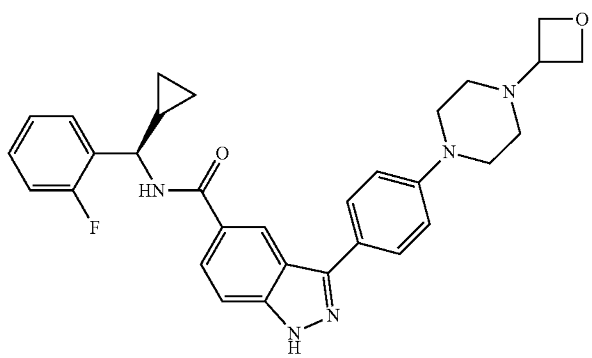 [SMILES: O=C(N[C@@H](c1ccccc1F)C1CC1)c1ccc2[nH]nc(-c3ccc(N4CCN(C5COC5)CC4)cc3)c2c1] | [C₃₁H₃₂FN₅O₂ + H]+ 526.2 526.8 | 20 mg (18%); yellow powder; TFA salt |

SMs: (R)-N-(cyclopropyl(2-fluorophenyl)methyl)-3-iodo-1H-indazole-5-carboxamide (80 mg, 0.18 mmol), 1-(oxetan-3-yl)-4-(4-(4,4,5,5-tetramethyl-1,3,2-dioxaborolan-2-yl)phenyl)piperazine (65 mg, 0.2 mmol), Pd(PPh₃)₄ (15 mg, 0.012 mmol)
¹H NMR (400 MHz, CD₃OD): Identical to the spectrum for Example A269.

| Example/IUPAC name | Structure | MS calculated MS ESI [M + H]+ | Yield; Appearance; Salt form |
|---|---|---|---|
| A271: N-((S)-cyclopropyl(pyridin-2-yl)methyl)-6-fluoro-3-(4-((1R,3R,5S)-3-hydroxy-8-azabicyclo[3.2.1]octan-8-yl)phenyl)-1H-indazole-5-carboxamide | 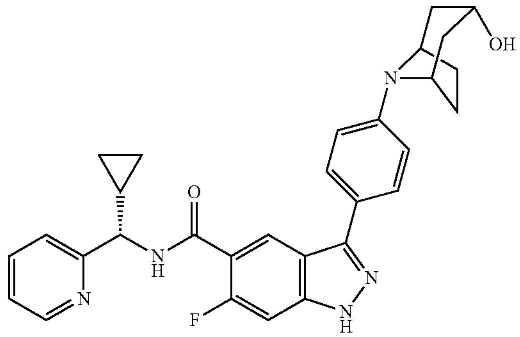 [SMILES: O=C(N[C@H](c1ccccn1)C1CC1)c1cc2c(-c3ccc(N4C5CCC4CC(O)C5)cc3)n[nH]c2cc1F] | [C30H30FN5O2 + H]+ 512.2 512.2 | 49 mg (52%); yellow solid; 2HCl salt |

SMs: (S)-N-(cyclopropyl(pyridin-2-yl)methyl)-6-fluoro-3-iodo-1H-indazole-5-carboxamide (70 mg, 0.16 mmol), (1R,3R,5S)-8-(4-(4,4,5,5-tetramethyl-1,3,2-dioxaborolan-2-yl)phenyl)-8-azabicyclo[3.2.1]octan-3-ol (53 mg, 0.16 mmol), Pd(PPh3)4 (14 mg, 0.012 mmol)
1H NMR described as a free base (400 MHz, CD3OD) δ ppm 8.53-54 (m, 1 H), 8.48 (d, J = 6.8 Hz, 1 H), 7.77-7.84 (m, 3 H), 7.53 (d, J = 8.0 Hz, 1 H), 7.29-7.34 (m, 2 H), 6.95 (d, J = 8.8 Hz, 2 H), 4.61 (d, J = 92 Hz, 1 H), 4.20 (br.s, 2 H), 3.93-3.95 (m, 1 H), 2.34-2.39 (m, 2 H), 2.20-2.23 (m, 2 H), 2.02-2.05 (m, 2 H), 1.62-1.66 (m, 2 H), 1.32-1.38 (m, 1 H), 0.64-0.69 (m, 1 H), 0.51-0.61 (m, 3 H)

| Example/IUPAC name | Structure | MS calculated MS ESI [M + H]+ | Yield; Appearance; Salt form |
|---|---|---|---|
| A272: 3-(4-((1R,5S)-3-oxa-8-azabicyclo[3.2.1]octan-8-yl)phenyl)-N-((S)-cyclopropyl(pyridin-2-yl)methyl)-6-fluoro-1H-indazole-5-carboxamide | 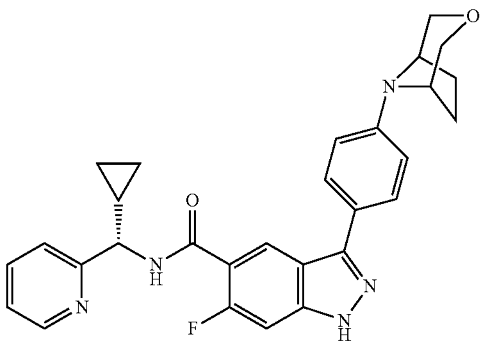 [SMILES: O=C(N[C@H](c1ccccn1)C1CC1)c1cc2c(-c3ccc(N4C5CCC4COC5)cc3)n[nH]c2cc1F] | [C29H29FN5O2 + H]+ 498.2 498.3 | 47 mg (60%); yellow solid; 2HCl salt |

SMs: (S)-N-(cyclopropyl(pyridin-2-yl)methyl)-6-fluoro-3-iodo-1H-indazole-5-carboxamide (60 mg, 0.13 mmol), (1R,5S)-8-(4-(4,4,5,5-tetramethyl-1,3,2-dioxaborolan-2-yl)phenyl)-3-oxa-8-azabicyclo[3.2.1]octane (43 mg, 0.13 mmol), Pd(PPh3)4 (12 mg, 0.01 mmol)
1H NMR described as a free base (400 MHz, CD3OD) δ ppm 8.53-54 (m, 1 H), 8.48 (d, J = 6.8 Hz, 1 H), 7.79-7.84 (m, 3 H), 7.54 (d, J = 8.0 Hz, 1 H), 7.30-7.33 (m, 2 H), 7.01 (d, J = 7.2 Hz, 2 H), 4.61 (d, J = 8.8 Hz, 1 H), 4.20 (s, 2 H), 3.92 (d, J = 10.8 Hz, 2 H), 3.54 (d, J = 11.2 Hz, 2 H), 2.02-2.11 (m, 4 H), 1.31-1.39 (m, 1 H), 0.64-0.70 (m, 1 H), 0.51-0.61 (m, 3 H), 1H-merged with solvent peak.

| Example/IUPAC name | Structure | MS calculated MS ESI [M + H]+ | Yield; Appearance; Salt form |
|---|---|---|---|
| A273: (S)-N-(1-(2-chlorophenyl)-2-methylpropyl)-3-(4-((1-methylpiperidin-4-yl)oxy)phenyl)-1H-indazole-5-carboxamide | 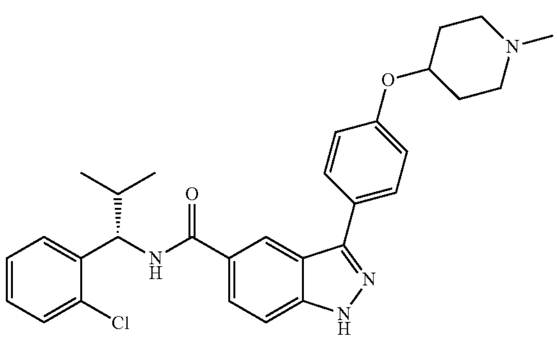 [SMILES: CC(C)[C@H](NC(=O)c1ccc2[nH]nc(-c3ccc(OC4CCN(C)CC4)cc3)c2c1)c1ccccc1Cl] | [C30H33ClN4O2 + H]+ 517.2 517.5 | 110 mg (52%); Light brown solid; TFA salt |

SMs: (S)-N-(1-(2-chlorophenyl)-2-methylpropyl)-3-iodo-1H-indazole-5-carboxamide (150 mg, 0.33 mmol), 1-methyl-4-(4-(4,4,5,5-tetramethyl-1,3,2-dioxaborolan-2-yl)phenoxy)piperidine (115 mg, 0.36 mmol), PdCl2dppf*CH2Cl2 (24 mg, 0.024 mmol)
1H NMR (400 MHz, CD3OD) δ ppm 8.87 (d, J = 8.5 Hz, 1 H), 8.50 (s, 1 H), 7.89 (t, J = 7.9 Hz, 3 H), 7.56 (t, J = 9.2 Hz, 2 H), 7.38 (d, J = 7.8 Hz, 1 H), 7.25-7.32 (m, 1 H) 7.18-7.24 (m, 1 H), 7.07-7.18 (m, 2 H), 5.32-5.44 (m, 1 H), 5.33-5.42 (m, 1 H), 4.82 (br. s, 0.7 H), 4.61-4.70 (m, 0.3 H), 3.63 (d, J = 13.1 Hz, 0.5 H), 3.34-3.47 (m, 3 H), 3.20 (br. s, 0.5 H), 2.93 (s, 3 H), 2.33-2.4 (m, 0.5 H), 2.21-2.33 (m, 2 H), 2.13 (d, J = 13.1 Hz, 1 H), 1.84-1.97 (m, 0.5 H), 1.16 (d, J = 6.5 Hz, 3 H), 0.87 (d, J = 6.8 Hz, 3 H),

| Example/IUPAC name | Structure | MS calculated MS ESI [M + H]+ | Yield; Appearance; Salt form |
|---|---|---|---|
| A274: (R)-N-(1-(2-chlorophenyl)-2-methylpropyl)-3-(4-((1-methylpiperidin-4-yl)oxy)phenyl)-1H-indazole-5-carboxamide | 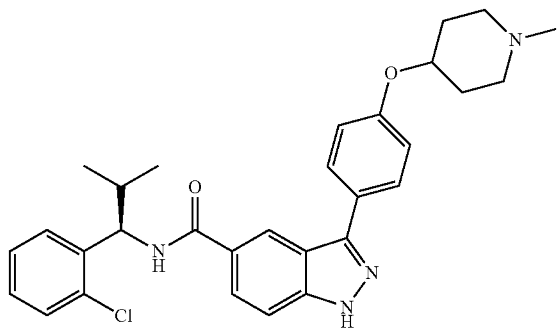 [SMILES: CC(C)[C@@H](NC(=O)c1ccc2[nH]nc(-c3ccc(OC4CCN(C)CC4)cc3)c2c1)c1ccccc1Cl] | [C$_{29}$H$_{29}$FN$_5$O$_2$ + H]+ 517.2 517.5 | 120 mg (61%); light brown solid; TFA salt |

SMs: (S)-N-(1-(2-chlorophenyl)-2-methylpropyl)-3-iodo-1H-indazole-5-carboxamide (140 mg, 0.30 mmol), 1-methyl-4-(4-(4,4,5,5-tetramethyl-1,3,2-dioxaborolan-2-yl)phenoxy)piperidine (108 mg, 0.33 mmol), PdCl$_2$dppf*CH$_2$Cl$_2$ (20 mg, 0.024 mmol)
$^1$H NMR (400 MHz, CD$_3$OD) δ ppm 8.87 (d, J = 8.5 Hz, 1 H), 8.50 (s, 1 H), 7.89 (t, J = 7.9 Hz, 3 H), 7.56 (t, J = 9.2 Hz, 2 H), 7.38 (d, J = 7.8 Hz, 1 H), 7.25-7.32 (m, 1 H) 7.18-7.24 (m, 1 H), 7.07-7.18 (m, 2 H), 5.32-5.44 (m, 1 H), 5.33-5.42 (m, 1 H), 4.82 (brs, 0.7 H), 4.61-4.70 (m, 0.3 H), 3.63 (d, J = 13.1 Hz, 0.5 H), 3.34-3.47 (m, 3 H), 3.20 (br s, 0.5 H), 2.93 (s, 3 H), 2.33-2.40 (m, 0.5 H), 2.21-2.33 (m, 2 H), 2.13 (d, J = 13.1 Hz, 1 H), 1.84-1.97 (m, 0.5 H), 1.16 (d, J = 6.5 Hz, 3 H), 0.87 (d, J = 6.8 Hz, 3 H).

| Example/IUPAC name | Structure | MS calculated MS ESI [M + H]+ | Yield; Appearance; Salt form |
|---|---|---|---|
| A275: (S)-N-(1-(2-fluorophenyl)-3-methylbutyl)-3-(4-(4-(oxetan-3-yl)piperazin-1-yl)phenyl)-1H-indazole-5-carboxamide | 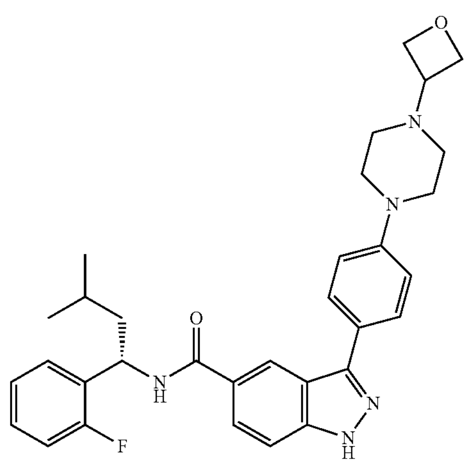 [SMILES: CC(C)C[C@H](NC(=O)c1ccc2[nH]nc(-c3ccc(N4CCN(C5COC5)CC4)cc3)c2c1)c1ccccc1F] | [C$_{32}$H$_{36}$FN$_5$O$_2$ + H]+ 542.2 542.5 | 82 mg (56%); yellow solid; TFA salt |

SMs: (S)-N-(1-(2-fluorophenyl)-3-methylbutyl)-3-iodo-1H-indazole-5-carboxamide (100 mg, 0.22 mmol), 1-(oxetan-3-yl)-4-(4-(4 4,5,5-tetramethyl-1,3,2-dioxaborolan-2-yl)phenyl)piperazine (76 mg, 0.22 mmol), Pd(PPh$_3$)$_4$ (13 mg, 0.011 mmol)
$^1$H NMR (400 MHz, CD$_3$OD) δ ppm 8.58 (s, 1 H), 7.91-7.95 (m, 3 H), 7.59-7.62 (m, 1 H), 7.44-7.48 (m, 1 H), 7.25-7.29 (m, 1 H) 7.06-7.18 (m, 4 H), 5.55-5.59 (m, 1 H), 4.46-4.53 (m, 1 H), 3.57 (br. s, 4 H), 3.40 (br. s, 4 H), 1.89-1.96 (m, 1 H), 1.63-1.75 (m, 2 H), 1.02 (d, J = 5.6 Hz, 6 H), 4H merged with solvent peak.

| Example/IUPAC name | Structure | MS calculated MS ESI [M + H]+ | Yield; Appearance; Salt form |
|---|---|---|---|
| A276: (S)-N-(1-(2-fluorophenyl)-3-methylbutyl)-3-(4-(3-morpholinoazetidin-1-yl)phenyl)-1H-indazole-5-carboxamide | 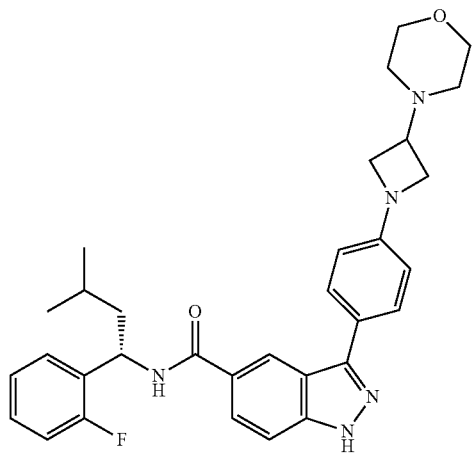 [SMILES: CC(C)C[C@H](NC(=O)c1ccc2[nH]nc(-c3ccc(N4CC(N5CCOCC5)C4)cc3)c2c1)c1ccccc1F] | [$C_{32}H_{36}FN_5O_2$ + H]+ 542.2 542.8 | 63 mg (43%); yellow solid; TFA salt |

SMs: (S)-N-(1-(2-fluorophenyl)-3-methylbutyl)-3-iodo-1H-indazole-5-carboxamide (100 mg, 0.22 mmol), 4-(1-(4-(4,4,5,5-tetramethyl-1,3,2-dioxaborolan-2-yl)phenyl)azetidin-3-yl)morpholine (76 mg, 0.22 mmol), Pd(PPh$_3$)$_4$ (13 mg, 0.011 mmol)

$^1$H NMR (400 MHz, CD$_3$OD) δ ppm 8.54 (s, 1 H), 7.85-7.94 (m, 3 H), 7.60 (d, J = 8.8 Hz, 1 H), 7.44-7.48 (m, 1 H), 7.24-7.29 (m, 1 H) 7.06-7.17 (m, 2 H), 6.69 (d, J = 8.8 Hz, 2 H), 5.55-5.59 (m, 1 H), 4.22-4.25 (m, 3 H), 3.70-4.20 (br. s, 6 H), 3.40-3.71 (br. s, 3 H), 1.89-1.94 (m, 1 H), 1.64-1.75 (m, 2 H), 1.02 (d, J = 5.6 Hz, 6 H), 1H Merged with solvent peak.

| Example/IUPAC name | Structure | MS calculated MS ESI [M + H]+ | Yield; Appearance; Salt form |
|---|---|---|---|
| A279: N-(1-(2-chlorophenyl)-2-methylpropyl)-3-(4-(((1R,3R,5S)-8-methyl-8-azabicyclo[3.2.1]octan-3-yl)oxy)phenyl)-1H-indazole-5-carboxamide | 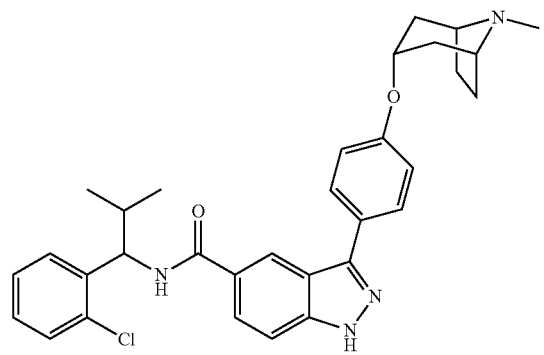 | [$C_{32}H_{35}ClN_4O_2$ + H]+ 543.2 543.5 | 51 mg (24%), white solid; free base |

SMs: N-(1-(2-chlorophenyl)-2-methylpropyl)-3-iodo-1H-indazole-5-carboxamide (218 mg, 0.48 mmol), (1R,3R,5S)-8-methyl-3-(4-(4,4,5,5-tetramethyl-1,3,2-dioxaborolan-2-yl)phenoxy)-8-azabicyclo[3.2.1]octane (137 mg, 0.4 mmol)

$^1$H NMR (400 MHz, DMSO-d$_6$) δ ppm 8.54 (s, 1H), 7.88 (d, J = 8.8 Hz, 1H), 7.82 (d, J = 7.6 Hz, 2H), 7.57-7.50 (m, 2H), 7.34 (d, J = 8.0 Hz, 1H), 7.23 (t, J = 7.6 Hz, 1H), 7.17 (t, J = 7.6 Hz, 1H), 6.89 (d, J = 8.0 Hz, 2H), 5.39 (d, J = 10.4 Hz, 1H), 4.55-4.48 (m, 1H), 3.15-3.05 (m, 2H), 2.30-2.15 (m, 4H; s, 3H at 2.28), 2.15-1.95 (m, 6H), 1.91 (d, J = 15.2 Hz, 2H), 1.15 (d, J = 6.4 Hz, 3H), 0.84 (d, J = 6.4 Hz, 3H).

| Example/IUPAC name | Structure | MS calculated MS ESI [M + H]+ | Yield; Appearance; Salt form |
|---|---|---|---|
| A280: N-((2-chlorophenyl)(cyclopropyl)methyl)-3-(4-(((1R,3R,5S)-8-methyl-8-azabicyclo[3.2.1]octan-3-yl)oxy)phenyl)-1H-indazole-5-carboxamide | | [C$_{32}$H$_{33}$ClN$_4$O$_2$ + H]+ 541.2 541.5 | 66 mg (31%), white solid; free base |

SMs: N-((2-chlorophenyl)(cyclopropyl)methyl)-3-iodo-1H-indazole-5-carboxamide (217 mg, 0.48 mmol), (1R,3R,5S)-8-methyl-3-(4-(4,4,5,5-tetramethyl-1,3,2-dioxaborolan-2-yl)phenoxy)-8-azabicyclo[3.2.1]octane (137 mg, 0.4 mmol)
$^1$H NMR (400 MHz, DMSO-d$_6$) δ ppm 8.59 (s, 1H), 7.92 (dd, J = 8.8, 1.2 Hz, 1H), 7.82 (d, J = 8.8 Hz, 2H), 7.62 (dd, J = 7.6, 1.6 Hz, 1H), 7.54 (d, J = 8.8 Hz, 1H), 7.30 (dd, J = 8.0, 1.2 Hz, 1H), 7.21 (dt, J = 7.6, 1.2 Hz, 1H), 7.14 (dt, J = 7.6, 1.6 Hz, 1H), 6.85 (d, J = 8.8 Hz, 2H), 5.00 (d, J = 8.8 Hz, 1H), 4.47 (t, J = 4.8 Hz, 1H), 3.10-3.05 (m, 2H), 2.24 (s, 3H), 2.10-1.93 (m, 6H), 1.86 (d, J = 14.4 Hz, 2H), 1.45-1.35 (m, 1H), 0.66-0.58 (m, 1H), 0.53-0.43 (m, 3H).

| Example/IUPAC name | Structure | MS calculated MS ESI [M + H]+ | Yield; Appearance; Salt form |
|---|---|---|---|
| A281: N-(1-(2-fluorophenyl)-2-methylpropyl)-3-(4-(((1R,3R,5S)-8-methyl-8-azabicyclo[3.2.1]octan-3-yl)oxy)phenyl)-1H-indazole-5-carboxamide | 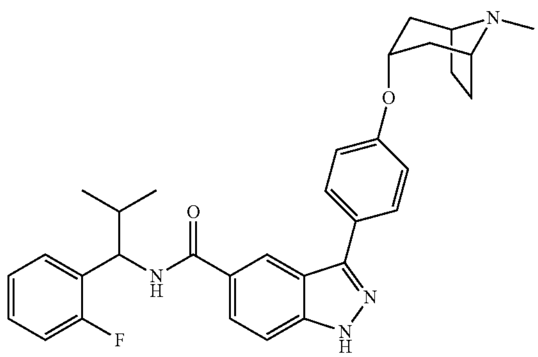 [SMILES: CC(C)C(NC(=O)c1ccc2[nH]nc(-c3ccc(OC4CC5CCC(C4)N5C)cc3)c2c1)c1ccccc1F] | [C$_{32}$H$_{35}$FN$_4$O$_2$ + H]+ 527.3 527.5 | 52 mg (24%), white solid; free base |

SMs: N-(1-(2-fluorophenyl)-2-methylpropyl)-3-iodo-1H-indazole-5-carboxamide (210 mg, 0.48 mmol), (1R,3R,5S)-8-methyl-3-(4-(4,4,5,5-tetramethyl-1,3,2-dioxaborolan-2-yl)phenoxy)-8-azabicyclo[3.2.1]octane (137 mg, 0.4 mmol)
$^1$H NMR (400 MHz, CD$_3$OD) δ ppm 8.53 (s, 1H), 7.89 (dd, J = 8.8, 1.2 Hz, 1H), 7.81 (d, J = 8.8 Hz, 2H), 7.58 (d, J = 8.8 Hz, 1H), 7.48 (t, J = 7.6 Hz, 1H), 7.25-7.18 (m, 1H), 7.08 (t, J = 7.4 Hz, 1H), 7.03 (t, J = 9.4 Hz, 1H), 6.88 (d, J = 8.8 Hz, 2H), 5.13 (d, J = 10.0 Hz, 1H), 4.60-4.54 (m, 1H), 3.50-3.42 (m, 2H), 2.55 (s, 3H), 2.44-2.33 (m, 2H), 2.30-2.08 (m, 5H), 2.02 (d, J = 15.2 Hz, 2H), 1.12 (d, J = 6.4 Hz, 3H), 0.81 (d, J = 6.4 Hz, 3H).

| Example/IUPAC name | Structure | MS calculated MS ESI [M + H]+ | Yield; Appearance; Salt form |
|---|---|---|---|
| A282: N-(cyclopropyl(2-fluorophenyl)methyl)-3-(4-(((1R,3R,5S)-8-methyl-8-azabicyclo[3.2.1]octan-3-yl)oxy)phenyl)-1H-indazole-5-carboxamide | | [C$_{32}$H$_{33}$FN$_4$O$_2$ + H]+ 525.3 525.4 | 54 mg (26%), white solid; free base |

SMs: N-(cyclopropyl(2-fluorophenyl)methyl)-3-iodo-1H-indazole-5-carboxamide (209 mg, 0.48 mmol), (1R,3R,5S)-8-methyl-3-(4-(4,4,5,5-tetramethyl-1,3,2-dioxaborolan-2-yl)phenoxy)-8-azabicyclo[3.2.1]octane (137 mg, 0.4 mmol)
$^1$H NMR (400 MHz, CD$_3$OD) δ ppm 8.59 (s, 1H), 7.93 (d, J = 8.4 Hz, 3H), 7.62-7.55 (m, 2H), 7.32-7.25 (m, 1H), 7.17 (t, J = 7.2 Hz, 1H), 7.13-7.03 (m, 3H), 4.76 (d, J = 9.2 Hz, 1H), 4.68 (t, 1H), 3.35-3.25 (m, 2H, partially buried in MeOH), 2.40 (s, 3H), 2.30-2.09 (m, 6H), 2.05 (d, J = 14.4 Hz, 2H), 1.50-1.40 (m, 1H), 0.74-0.66 (m, 1H), 0.64-0.56 (m, 1H), 0.56-0.43 (m, 2H).

| Example/IUPAC name | Structure | MS calculated MS ESI [M + H]+ | Yield; Appearance; Salt form |
|---|---|---|---|
| A283: N-(cyclobutyl(thiophen-3-yl)methyl)-3-(4-(((1R,3R,5S)-8-methyl-8-azabicyclo[3.2.1]octan-3-yl)oxy)phenyl)-1H-indazole-5-carboxamide | 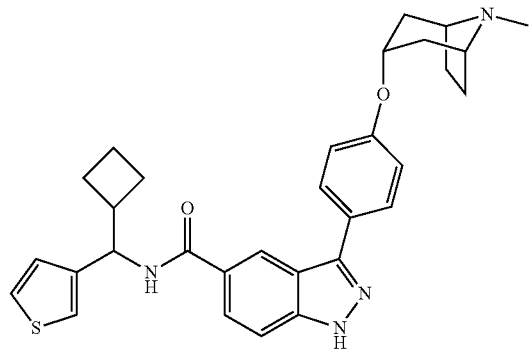 [SMILES: CN1C2CCC1CC(Oc1ccc(-c3n[nH]c4ccc(C(=O)NC(c5ccsc5)C5CCC5)cc34)cc1)C2] | [C₃₁H₃₄N₄O₂S + H]⁺ 527.2 527.4 | 39 mg (19%), white solid; free base |

SMs: N-(cyclobutyl(thiophen-3-yl)methyl)-3-iodo-1H-indazole-5-carboxamide (209 mg, 0.48 mmol), (1R,,5S)-8-methyl-3-(4-(4,4,5,5-tetramethyl-1,3,2-dioxaborolan-2-yl)phenoxy)-8-azabi-cyclo[3.2.1]octane (137 mg, 0.4 mmol)
¹H NMR (400 MHz, CD₃OD) δ ppm 8.56 (s, 1H), 7.92 (dd, J = 8.8, 1.6 Hz, 1H), 7.85 (d, J = 8.8 Hz, 2H), 7.59 (d, J = 9.2 Hz, 1H), 7.29 (dd, J = 9.0, 3.0 Hz, 1H), 7.24-7.21 (m, 1H), 7.11 (dd, J = 8.8, 0.8 Hz, 1H), 6.91 (d, J = 8.8 Hz, 2H), 5.25 (d, J = 10.4 Hz, 1H), 4.57 (t, J = 4.8 Hz, 1H), 3.41-3.35 (m, 2H), 2.98-2.87 (m, 1H), 2.48 (s, 3H), 2.35-2.26 (m, 2H), 2.25-2.05 (m, 5H), 2.05-1.77 (m, 7H).

| Example/IUPAC name | Structure | MS calculated MS ESI [M + H]+ | Yield; Appearance; Salt form |
|---|---|---|---|
| A284: N-((2-chlorophenyl)(cyclopentyl)methyl)-3-(4-(((1R,3R,5S)-8-methyl-8-azabicyclo[3.2.1]octan-3-yl)oxy)phenyl)-1H-indazole-5-carboxamide | | [C₃₄H₃₇ClN₄O₂ + H]⁺ 569.3 569.5 | 13 mg (6%), white solid; free base |

SMs: N-((2-chlorophenyl)(cyclopentyl)methyl)-3-iodo-1H-indazole-5-carboxamide (240 mg, 0.5 mmol), (1R,3R,5S)-8-methyl-3-(4-(4,4,5,5-tetramethyl-1,3,2-dioxaborolan-2-yl)phenoxy)-8-azabicyclo[3.2.1]octane (137 mg, 0.4 mmol)
¹H NMR (400 MHz, CD₃OD) δ ppm 8.54 (s, 1H), 7.90-7.85 (m, 3H), 7.60-7.55 (m, 2H), 7.36 (dd, J = 8.0, 1.2 Hz, 1H), 7.27 (dt, J = 7.6, 1.2 Hz, 1H), 7.20 (dt, J = 7.6, 1.6 Hz, 1H), 6.97 (d, J = 8.8 Hz, 2H), 5.45 (d, J = 10.8 Hz, 1H), 4.61 (t, J = 4.8 Hz, 1H), 3.21-3.14 (m, 2H), 2.63-2.42 (m, 1H), 2.33 (s, 3H), 2.20-2.03 (m, 6H), 2.02-1.94 (m, 3H), 1.80-1.50 (m, 5H), 1.45-1.37 (m, 2H).

| Example/IUPAC name | Structure | MS calculated MS ESI [M + H]+ | Yield; Appearance; Salt form |
|---|---|---|---|
| A285: N-(2-methyl-1-phenylpropyl)-3-(4-(((1R,3R,5S)-8-methyl-8-azabicyclo[3.2.1]octan-3-yl)oxy)phenyl)-1H-indazole-5-carboxamide | | [C₃₂H₃₆N₄O₂ + H]⁺ 509.3 509.4 | 42 mg (21%), white solid; free base |

SMs: 3-iodo-N-(2-methyl-1-phenylpropyl)-1H-indazole-5-carboxamide (210 mg, 0.5 mmol), (1R,3R,5S)-8-methyl-3-(4-(4,4,5,5-tetramethyl-1,3,2-dioxaborolan-2-yl)phenoxy)-8-azabicyclo[3.2.1]octane (137 mg, 0.4 mmol)
¹H NMR (400 MHz, CD₃OD) δ ppm 8.55 (s, 1H), 7.90 (dd, J = 8.8, 1.2 Hz, 1H), 7.84 (d, J = 8.8 Hz, 2H), 7.55 (d, J = 8.8 Hz, 1H), 7.41 (d, J = 8.8 Hz, 2H), 7.29 (t, J = 7.4 Hz, 2H), 7.21 (t, J = 7.2 Hz, 1H), 6.91 (d, J = 8.4 Hz, 2H), 4.76 (d, J = 10.0 Hz, 1H), 4.54 (t, J = 4.8 Hz, 1H), 3.14-3.08 (m, 2H), 2.30-2.17 (m, 4H; s, 3H at 2.28), 2.15-1.97 (m, 6H), 1.92 (d, J = 14.4 Hz, 2H), 1.12 (d, J = 6.4 Hz, 3H), 0.78 (d, J = 6.4 Hz, 3H).

| Example/IUPAC name | Structure | MS calculated MS ESI [M + H]+ | Yield; Appearance; Salt form |
|---|---|---|---|
| A286: N-(cyclopropyl(phenyl)methyl)-3-(4-(((1R,3S,5S)-8-methyl-8-azabicyclo[3.2.1]octan-3-yl)oxy)phenyl)-1H-indazole-5-carboxamide | 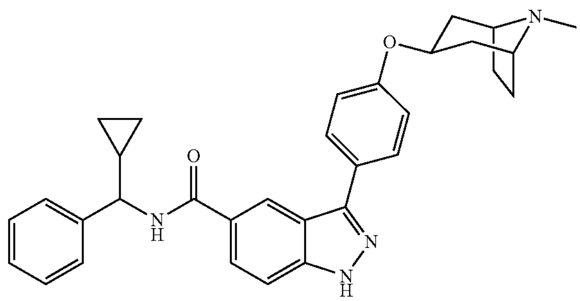 [SMILES: CN1C2CCC1CC(Oc1ccc(-c3n[nH]c4ccc(C(=O)NC(c5ccccc5)C5CC5)cc34)cc1)C2] | [C₃₂H₃₄N₄O₂ + H]+ 507.3 507.4 | 29 mg (14%), white solid; free base |

SMs: N-(cyclopropyl(phenyl)methyl)-3-iodo-1H-indazole-5-carboxamide (208 mg, 0.5 mmol), (1R,3S,5S)-8-methyl-3-(4-(4,4,5,5-tetramethyl-1,3,2-dioxaborolan-2-yl)phenoxy)-8-azabicyclo[3.2.1]octane (137 mg, 0.4 mmol)
$^1$H NMR (400 MHz, CD$_3$OD) δ ppm 8.62 (s, 1H), 7.96 (dd, J = 8.8, 1.6 Hz, 1H), 7.89 (d, J = 8.4 Hz, 2H), 7.59 (d, J = 8.8 Hz, 1H), 7.47 (d, J = 7.2 Hz, 2H), 7.32 (t, J = 7.6 Hz, 2H), 7.22 (t, J = 7.2 Hz, 1H), 7.05 (d, J = 8.8 Hz, 2H), 4.70-4.60 (m, 1H), 4.48 (d, J = 9.6 Hz, 1H), 3.30-3.23 (m, 2H), 2.33 (s, 3H), 2.17-2.04 (m, 4H), 1.85-1.74 (m, 4H), 1.45-1.35 (m, 1H), 0.68-0.60 (m, 2H), 0.52-0.40 (m, 2H).

| Example/IUPAC name | Structure | MS calculated MS ESI [M + H]+ | Yield; Appearance; Salt form |
|---|---|---|---|
| A287: N-((S)-1-(2-chlorophenyl)-2-methylpropyl)-3-(4-(((1R,3R,5S)-8-methyl-8-azabicyclo[3.2.1]octan-3-yl)oxy)phenyl)-1H-indazole-5-carboxamide | 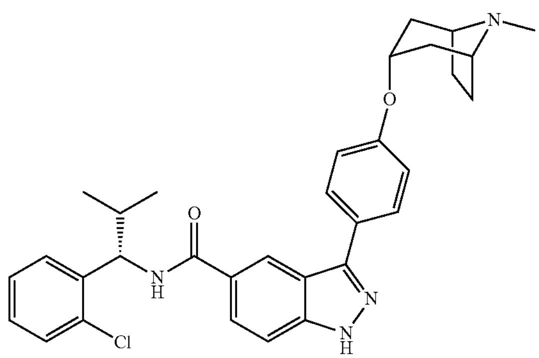 [SMILES: CC(C)[C@H](NC(=O)c1ccc2[nH]nc(-c3ccc(OC4CC5CCC(C4)N5C)cc3)c2c1)c1ccccc1Cl] | [C₃₂H₃₅ClN₄O₂ + H]+ 543.2 543.5 | 76 mg (47%), white solid; free base |

SMs: (S)-N-(1-(2-chlorophenyl)-2-methylpropyl)-3-iodo-1H-indazole-5-carboxamide (136 mg, 0.3 mmol), (1R,3R,5S)-8-methyl-3-(4-(4,4,5,5-tetramethyl-1,3,2-dioxaborolan-2-yl)phenoxy)-8-azabicyclo[3.2.1]octane (121 mg, 0.3 mmol)
Spectral data was identical for that obtained in racemic N-(1-(2-chlorophenyl)-2-methylpropyl)-3-(4-(((1R,3R,5S)-8-methyl-8-azabicyclo[3.2.1]octan-3-yl)oxy)phenyl)-1H-indazole-5-carboxamide.

| Example/IUPAC name | Structure | MS calculated MS ESI [M + H]+ | Yield; Appearance; Salt form |
|---|---|---|---|
| A288: N-((R)-1-(2-chlorophenyl)-2-methylpropyl)-3-(4-(((1R,3R,5S)-8-methyl-8-azabicyclo[3.2.1]octan-3-yl)oxy)phenyl)-1H-indazole-5-carboxamide | 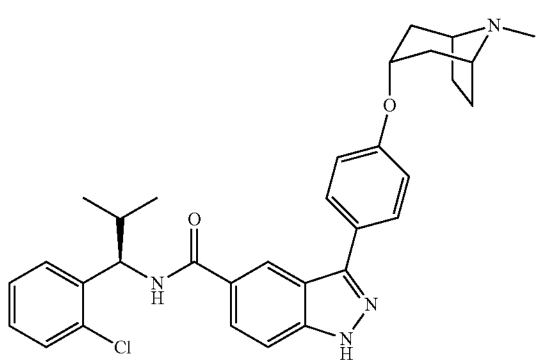 [SMILES: CC(C)[C@@H](NC(=O)c1ccc2[nH]nc(-c3ccc(OC4CC5CCC(C4)N5C)cc3)c2c1)c1ccccc1Cl] | [C₃₂H₃₅ClN₄O₂ + H]+ 543.2 543.6 | 66 mg (41%), white solid; free base |

SMs: (R)-N-(1-(2-chlorophenyl)-2-methylpropyl)-3-iodo-1H-indazole-5-carboxamide (136 mg, 0.3 mmol), (1R,3R,5S)-8-methyl-3-(4-(4,4,5,5-tetramethyl-1,3,2-dioxaborolan-2-yl)phenoxy)-8-azabicyclo[3.2.1]octane (121 mg, 0.3 mmol)
Spectral data was identical for that obtained in racemic N-(1-(2-chlorophenyl)-2-methylpropyl)-3-(4-(((1R,3r,5S)-8-methyl-8-azabicyclo[3.2.1]octan-3-yl)oxy)phenyl)-1H-indazole-5-carboxamide.

| Example/IUPAC name | Structure | MS calculated MS ESI [M + H]+ | Yield; Appearance; Salt form |
|---|---|---|---|
| A289: N-(1-(2-chlorophenyl)-2-methylpropyl)-3-(4-((1-methylazetidin-3-yl)oxy)phenyl)-1H-indazole-5-carboxamide | 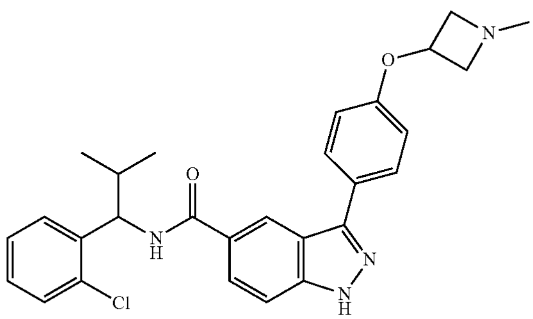 [SMILES: CC(C)C(NC(=O)c1ccc2[nH]nc(-c3ccc(OC4CN(C)C4)cc3)c2c1)c1ccccc1Cl] | [$C_{28}H_{29}ClN_4O_2$ + H]+ 489.2 489.5 | 5 mg (3%), white solid; free base |

SMs: N-(1-(2-chlorophenyl)-2-methylpropyl)-3-iodo-1H-indazole-5-carboxamide (181 mg, 0.4 mmol), 1-methyl-3-(4-(4,4,5,5-tetramethyl-1,3,2-dioxaborolan-2-yl)phenoxy)azetidine (120 mg, 0.38 mmol)
$^1$H NMR (400 MHz, CD$_3$OD) δ ppm 8.51 (s, 1H), 7.92 (d, J = 9.2 Hz, 2H, partially overlapping with the peak at 7.89), 7.89 (d, J = 9.2 Hz, 1H, partially overlapping with the peak at 7.92), 7.59 (d, J = 8.8 Hz, 1H), 7.55 (d, J = 7.6 Hz, 1H), 7.40 (d, J = 7.6 Hz, 1H), 7.31 (t, J = 7.4 Hz, 1H), 7.24 (t, J = 7.0 Hz, 1H), 6.99 (d, J = 8.4 Hz, 2H), 5.38 (d, J = 9.6 Hz, 1H), 5.00-4.85 (m, 2H, partially buried under H$_2$O), 3.91-3.86 (m, 2H), 2.46 (s, 3H), 2.34-2.24 (m, 1H), 1.17 (d, J = 6.4 Hz, 3H), 0.88 (d, J = 6.8 Hz, 3H).

| Example/IUPAC name | Structure | MS calculated MS ESI [M + H]+ | Yield; Appearance; Salt form |
|---|---|---|---|
| A290: N-(3-methyl-1-phenylbutyl)-3-(4-((1-(oxetan-3-yl)piperidin-4-yl)oxy)phenyl)-1H-indazole-5-carboxamide | 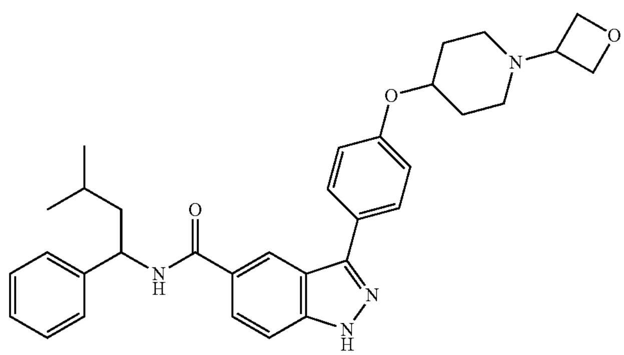 [SMILES: CC(C)CC(NC(=O)c1ccc2[nH]nc(-c3ccc(OC4CCN(C5COC5)CC4)cc3)c2c1)c1ccccc1] | [$C_{33}H_{38}N_4O_3$ + H]+ 539.3 539.5 | 67 mg (62%), white solid; free base |

SMs: 3-iodo-N-(3-methyl-1-phenylbutyl)-1H-indazole-5-carboxamide (95 mg, 0.22 mmol), 1-(oxetan-3-yl)-4-(4-(4,4,5,5-tetramethyl-1,3,2-dioxaborolan-2-yl)phenoxy)piperidine (72 mg, 0.2 mmol)
$^1$H NMR (400 MHz, CD$_3$OD) δ ppm 8.60 (s, 1H), 7.93 (dd, J = 8.8, 1.2 Hz, 1H), 7.86 (d, J = 8.4 Hz, 2H), 7.56 (d, J = 8.8 Hz, 1H), 7.40 (d, J = 7.6 Hz, 2H), 7.29 (t, J = 7.4 Hz, 2H), 7.19 (t, J = 7.2 Hz, 1H), 7.00 (d, J = 8.8 Hz, 2H), 5.26 (dd, J = 9.4, 5.8 Hz, 1H), 4.64 (t, J = 6.6 Hz, 2H), 4.56 (t, J = 5.8 Hz, 2H), 4.42-4.35 (m, 1H), 3.43 (quintet, J = 6.6 Hz, 1H), 2.57-2.47 (m, 2H), 2.20-2.10 (m, 2H), 2.02-1.84 (m, 3H), 1.82-1.72 (m, 2H), 1.72-1.62 (m, 2H), 0.96 (d, J = 6.4 Hz, 6H).

| Example/IUPAC name | Structure | MS calculated MS ESI [M + H]+ | Yield; Appearance; Salt form |
|---|---|---|---|
| A291: N-(3-methyl-1-(pyridin-2-yl)butyl)-3-(4-((1-(oxetan-3-yl)piperidin-4-yl)oxy)phenyl)-1H-indazole-5-carboxamide | 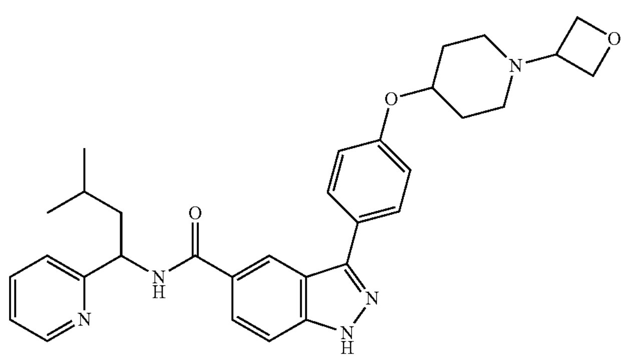 [SMILES: CC(C)CC(NC(=O)c1ccc2[nH]nc(-c3ccc(OC4CCN(C5COC5)CC4)cc3)c2c1)c1ccccn1] | [$C_{32}H_{37}N_5O_3$ + H]+ 540.3 540.3 | 44 mg (41%), white solid; free base |

SMs: 3-iodo-N-(3-methyl-1-(pyridin-2-yl)butyl)-1H-indazole-5-carboxamide (95 mg, 0.22 mmol), 1-(oxetan-3-yl)-4-(4-(4,4,5,5-tetramethyl-1,3,2-dioxaborolan-2-yl)phenoxy)piperidine (72 mg, 0.2 mmol)
$^1$H NMR (400 MHz, CD$_3$OD) δ ppm 8.64 (s, 1H), 8.51 (d, J = 4.0 Hz, 1H), 7.96 (dd, J = 8.8, 1.6 Hz, 1H), 7.90 (d, J = 8.8 Hz, 2H), 7.77 (dt, J = 7.6, 1.6 Hz, 1H), 7.60 (d, J = 8.8 Hz, 1H), 7.47 (d, J = 8.0 Hz, 1H), 7.30-7.25 (m, 1H), 7.05 (d, J = 8.8 Hz, 2H), 5.39-5.32 (m, 1H), 4.67 (t, J = 6.6 Hz, 2H), 4.58 (t, J = 6.4 Hz, 2H), 4.50-4.42 (m, 1H), 3.48 (quintet, J = 6.5 Hz, 1H), 2.62-2.52 (m, 2H), 2.27-2.16 (m, 2H), 2.07-1.97 (m, 2H), 1.95-1.67 (m, 5H), 1.03-0.98 (m, 6H).

| Example/IUPAC name | Structure | MS calculated MS ESI [M + H]+ | Yield; Appearance; Salt form |
| --- | --- | --- | --- |
| A292: N-(2-ethyl-1-(pyridin-2-yl)butyl)-3-(4-((1-(oxetan-3-yl)piperidin-4-yl)oxy)phenyl)-1H-indazole-5-carboxamide | 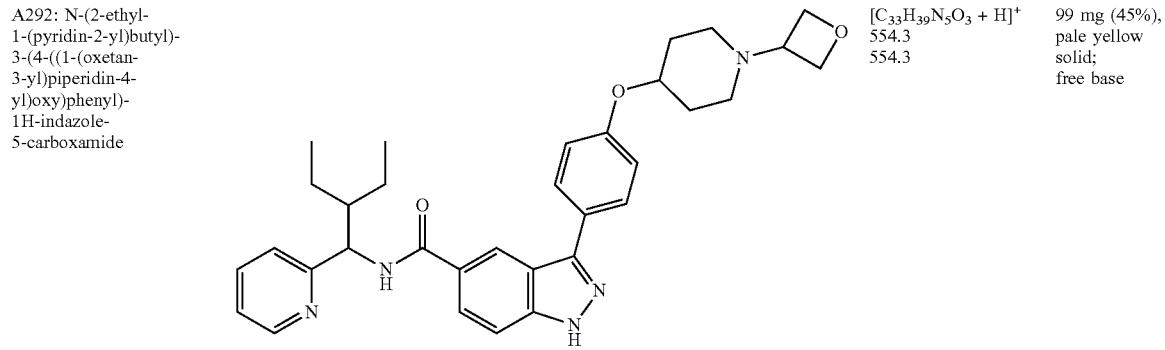 | [$C_{33}H_{39}N_5O_3$ + H]+ 554.3 554.3 | 99 mg (45%), pale yellow solid; free base |

SMs: N-(2-ethyl-1-(pyridin-2-yl)butyl)-3-iodo-1H-indazole-5-carboxamide (179 mg, 0.4 mmol), 1-(oxetan-3-yl)-4-(4-(4,4,5,5-tetramethyl-1,3,2-dioxaborolan-2-yl)phenoxy)piperidine (144 mg, 0.4 mmol)
$^1$H NMR (400 MHz, CD$_3$OD) δ ppm 8.60 (s, 1H), 8.52 (d, J = 4.0 Hz, 1H), 7.93 (dd, J = 8.8, 1.2 Hz, 1H), 7.87 (d, J = 8.8 Hz, 2H), 7.73 (dt, J = 7.8, 1.5 Hz, 1H), 7.58 (d, J = 8.8 Hz, 1H), 7.45 (d, J = 7.6 Hz, 1H), 7.25 (dd, J = 6.8, 5.2 Hz, 1H), 7.00 (d, J = 8.8 Hz, 1H), 5.28 (d, J = 8.8 Hz, 1H), 4.60 (t, J = 6.8 Hz, 2H), 4.54 (t, J = 6.4 Hz, 2H), 4.41-4.33 (m, 1H), 3.40 (quintet, J = 6.6 Hz, 1H), 2.55-2.45 (m, 2H), 2.17-1.92 (m, 5H), 1.81-1.70 (m, 2H), 1.66-1.47 (m, 2H), 1.21 (quintet, J = 7.0 Hz, 2H), 0.89 (t, J = 7.4 Hz, 3H), 0.82 (t J = 7.4 Hz, 3H).

| A293: 3-(4-((1-(oxetan-3-yl)piperidin-4-yl)oxy)phenyl)-N-(pyridin-2-yl(tetrahydro-2H-pyran-4-yl)methyl)-1H-indazole-5-carboxamide | 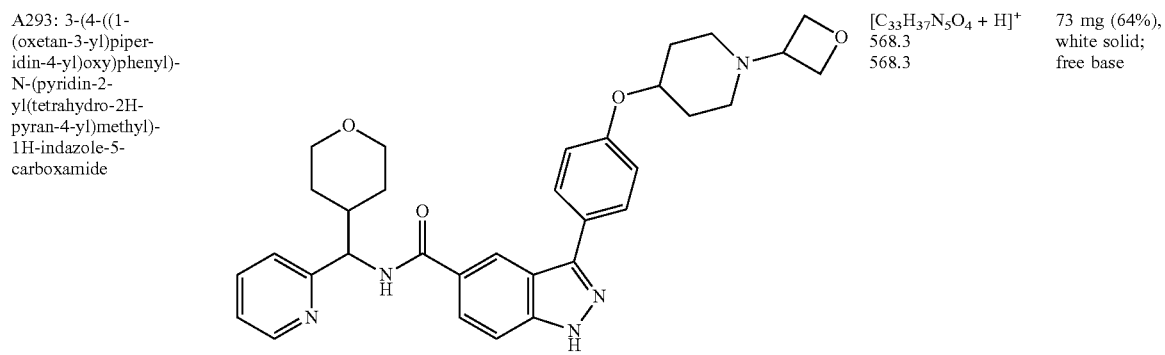 | [$C_{33}H_{37}N_5O_4$ + H]+ 568.3 568.3 | 73 mg (64%), white solid; free base |

SMs: 3-iodo-N-(pyridin-2-yl(tetrahydro-2H-pyran-4-yl)methyl)-1H-indazole-5-carboxamide (92 mg, 0.2 mmol), 1-(oxetan-3-yl)-4-(4-(4,4,5,5-tetramethyl-1,3,2-dioxaborolan-2-yl)phenoxy)piperidine (79 mg, 0.22 mmol)
$^1$H NMR (400 MHz, CD$_3$OD) δ ppm 8.62 (s, 1H), 8.55 (d, J = 4.4 Hz, 1H), 7.94 (dd, J = 8.8, 1.2 Hz, 1H), 7.88 (d, J = 8.8 Hz, 2H), 7.76 (dt, J = 7.6, 1.6 Hz, 1H), 7.59 (d, J = 8.8 Hz, 1H), 7.45 (d, J = 7.6 Hz, 1H), 7.28 (dd, J = 6.8, 1.2 Hz, 1H), 7.02 (d, J = 8.8 Hz, 2H), 5.06 (d, J = 9.2 Hz, 1H), 4.65 (t, J = 6.6 Hz, 2H), 4.57 (t, J = 6.2 Hz, 2H), 4.46-4.38 (m, 1H), 3.98-3.90 (m, 1H), 3.78-3.72 (m, 1H), 3.45 (quintet, J = 6.4 Hz, 1H), 3.37 (t, J = 10.4 Hz, 1H), 3.27 (t, J = 11.0 Hz, 1H), 2.60-2.48 (m, 2H), 2.31-2.10 (m, 3H), 2.04-1.96 (m, 2H), 1.90-1.74 (m, 3H), 1.55-1.32 (m, 2H), 1.13 (d, J = 12.8 Hz, 1H).

| Example/IUPAC name | Structure | MS calculated MS ESI [M + H]+ | Yield; Appearance; Salt form |
|---|---|---|---|
| A294: (S)-N-(1-(2-chlorophenyl)-2-methylpropyl)-3-(6-((1-(oxetan-3-yl)piperidin-4-yl)oxy)pyridin-3-yl)-1H-indazole-5-carboxamide | 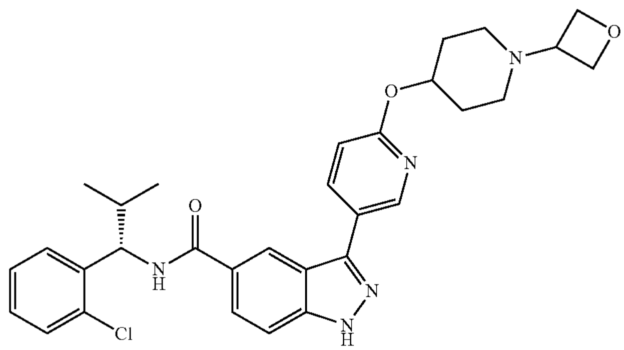 [SMILES: CC(C)[C@H](NC(=O)c1ccc2[nH]nc(-c3ccc(OC4CCN(C5COC5)CC4)nc3)c2c1)c1ccccc1Cl] | [C₃₁H₃₄ClN₅O₃ + H]+ 560.2 560.5 | 60 mg (54%), white solid; free base |

SMs: (S)-N-(1-(2-chlorophenyl)-2-methylpropyl)-3-iodo-1H-indazole-5-carboxamide (91 mg, 0.2 mmol), 2-((1-(oxetan-3-yl)piperidin-4-yl)oxy)-5-(4,4,5,5-tetramethyl-1,3,2-dioxaborolan-2-yl)pyridine (72 mg, 0.2 mmol)
$^1$H NMR (400 MHz, CD$_3$OD) δ ppm 8.71 (d, J = 1.6 Hz, 1H), 8.50 (s, 1H), 8.20 (dd, J = 8.4, 2.0 Hz, 1H), 7.88 (d, J = 8.8 Hz, 1H), 7.57 (d, J = 8.8 Hz, 1H), 7.53 (d, J = 8.4 Hz, 1H), 7.36 (d, J = 8.0 Hz, 1H), 7.26 (t, J = 7.0 Hz, 1H), 7.19 (t, J = 7.0 Hz, 1H), 6.86 (d, J = 8.4 Hz, 1H), 5.38 (d, J = 10.4 Hz, 1H), 5.15-5.06 (m, 1H), 4.68 (t, J = 6.8 Hz, 2H), 4.60 (t, J = 6.2 Hz, 2H), 3.51 (quintet, J = 6.4 Hz, 1H), 2.76-2.57 (m, 2H), 2.32-2.15 (m, 3H), 2.12-2.03 (m, 2H), 1.90-1.78 (m, 2H), 1.14 (d, J = 6.4 Hz, 3H), 0.85 (d, J = 6.8 Hz, 3H).

| Example/IUPAC name | Structure | MS calculated MS ESI [M + H]+ | Yield; Appearance; Salt form |
|---|---|---|---|
| A295: (S)-N-(cyclopentyl(pyridin-2-yl)methyl)-3-(4-((1-methylazetidin-3-yl)oxy)phenyl)-1H-indazole-5-carboxamide | 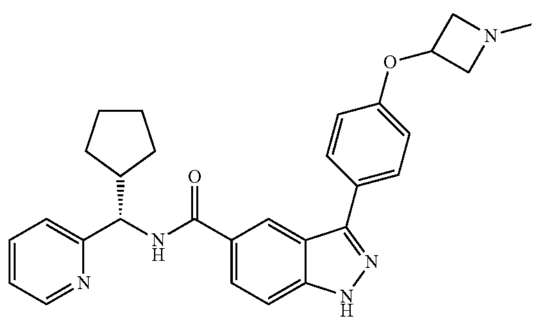 [SMILES: CN1CC(Oc2ccc(-c3n[nH]c4ccc(C(=O)N[C@H](c5ccccn5)C5CCCC5)cc34)cc2)C1] | [C₂₉H₃₁N₅O₂ + H]+ 482.2 482.2 | 63 mg (33%), white solid; free base |

SMs: (S)-N-(cyclopentyl(pyridin-2-yl)methyl)-3-iodo-1H-indazole-5-carboxamide (180 mg, 0.4 mmol), 1-methyl-3-(4-(4,4,5,5-tetramethyl-1,3,2-dioxaborolan-2-yl)phenoxy)azetidine (179 mg, about 67% pure, 0.4 mmol)
$^1$H NMR (400 MHz, CD$_3$OD) δ ppm 8.56 (s, 1H), 8.51 (d, J = 4.8 Hz, 1H), 7.93-7.85 (m, 3H), 7.75 (t, dt, J = 7.6, 0.8 Hz, 1H), 7.57 (d, J = 8.8 Hz, 1H), 7.46 (d, J = 8.0 Hz, 1H), 7.26 (dd, J = 6.8, 5.6 Hz, 1H), 6.92 (d, J = 8.8 Hz, 2H), 5.03 (d, J = 10.4 Hz, 1H), 4.83 (qintet, J = 5.4 Hz, 1H), 3.80 (dd, J = 8.4, 6.4 Hz, 2H), 3.25 (dd, J = 8.4, 5.2 Hz, 2H), 2.60-2.48 (m, 1H), 2.41 (s, 3H), 1.98-1.88 (m, 1H), 1.73-1.46 (m, 5H), 1.42-1.32 (m, 2H).

| Example/IUPAC name | Structure | MS calculated MS ESI [M + H]+ | Yield; Appearance; Salt form |
|---|---|---|---|
| A296: (S)-N-(1-(2-chlorophenyl)-2-methylpropyl)-3-(4-((1-(oxetan-3-yl)azetidin-3-yl)oxy)phenyl)-1H-indazole-5-carboxamide | 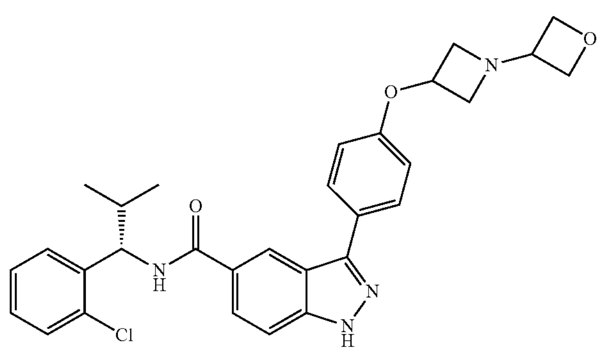 [SMILES: CC(C)[C@H](NC(=O)c1ccc2[nH]nc(-c3ccc(OC4CN(C5COC5)C4)cc3)c2c1)c1ccccc1Cl] | [C₃₀H₃₁ClN₄O₃ + H]+ 531.2 531.6 | 43 mg (41%), white solid; free base |

SMs: (S)-N-(1-(2-chlorophenyl)-2-methylpropyl)-3-iodo-1H-indazole-5-carboxamide (91 mg, 0.2 mmol), 1-(oxetan-3-yl)-3-(4-(4,4,5,5-tetramethyl-1,3,2-dioxaborolan-2-yl)phenoxy)azetidine (120 mg, 0.36 mmol)
$^1$H NMR (400 MHz, CD$_3$OD) δ ppm 8.51 (s, 1H), 7.90-7.82 (m, 3H), 7.55 (d, J = 8.8 Hz, 2H), 7.37 (d, J = 7.6 Hz, 1H), 7.27 (t, J = 7.2 Hz, 1H), 7.20 (t, J = 7.2 Hz, 1H), 6.92 (d, J = 8.4 Hz, 2H), 5.38 (d, J = 9.6 Hz, 1H), 4.94-4.86 (m, 1H, partially buried in H$_2$O peak), 4.75 (t, J = 6.6 Hz, 2H), 4.51 (t, J = 5.8 Hz, 2H), 3.90-3.78 (m, 3H), 3.37-3.28 (m, 2H, partially buried in MeOH peak), 2.32-2.32 (m, 1H), 1.15 (d, J = 6.4 Hz, 3H), 0.85 (d, J = 6.4 Hz, 3H).

| Example/IUPAC name | Structure | MS calculated MS ESI [M + H]+ | Yield; Appearance; Salt form |
|---|---|---|---|
| A297: N-((2-chlorophen-yl)(cyclobutyl)meth-yl)-3-(4-(4-(oxetan-3-yl)piperazin-1-yl)phenyl)-1H-indazole-5-carboxamide | | [C$_{32}$H$_{34}$ClN$_5$O$_2$ + H]+ 556.2 556.6 | 150 mg (68%), light yellow solid; free base |

SMs: N-((2-chlorophenyl)(cyclobutyl)methyl)-3-iodo-1H-indazole-5-carboxamide (186 mg, 0.4 mmol), 1-(oxetan-3-yl)-4-(4-(4,4,5,5-tetramethyl-1,3,2-dioxaborolan-2-yl)phenyl)piperazine (138 mg, 0.4 mmol)

$^1$H NMR (400 MHz, CD$_3$OD) δ ppm 8.57 (s, 1H), 7.89 (d, J = 8.8 Hz, 1H), 7.78 (d, J = 8.4 Hz, 2H), 7.52 (d, J = 8.8 Hz, 1H), 7.47 (d, J = 7.6 Hz, 1H), 7.30 (d, J = 7.6 Hz, 1H), 7.18 (t, J = 7.2 Hz, 1H), 7.12 (t, J = 7.6 Hz, 1H), 6.91 (d, J = 8.8 Hz, 2H), 5.65 (d, J = 10.0 Hz, 1H), 4.64 (t, J = 6.6 Hz, 2H), 4.56 (t, J = 6.0 Hz, 2H), 3.41 (qintet, J = 6.4 Hz, 1H), 3.17-3.05 (m, 4H), 3.00-2.87 (m, 1H), 2.40-2.27 (m, 4H), 2.23-2.12 (m, 1H), 2.06-1.94 (m, 1H), 1.92-1.75 (m 4H).

| Example/IUPAC name | Structure | MS calculated MS ESI [M + H]+ | Yield; Appearance; Salt form |
|---|---|---|---|
| A298: N-(1-(2-chlorophenyl)-3-methylbutyl)-3-(4-(4-(oxetan-3-yl)piperazin-1-yl)phenyl)-1H-indazole-5-carboxamide | 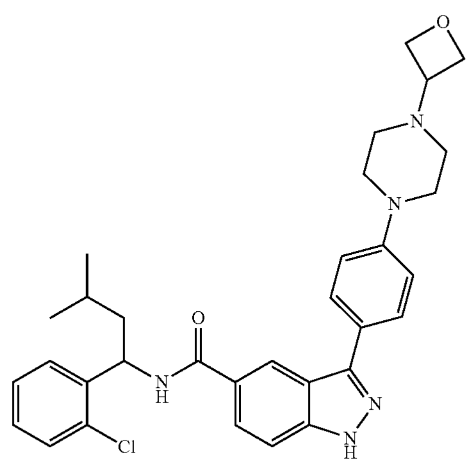 | [C$_{32}$H$_{36}$ClN$_5$O$_2$ + H]+ 558.3 558.6 | 115 mg (52%), light yellow solid; free base |

SMs: N-(1-(2-chlorophenyl)-3-methylbutyl)-3-iodo-1H-indazole-5-carboxamide (187 mg, 0.4 mmol), 1-(oxetan-3-yl)-4-(4-(4,4,5,5-tetramethyl-1,3,2-dioxaborolan-2-yl)phenyl)piperazine (138 mg, 0.4 mmol)

$^1$H NMR (400 MHz, CD$_3$OD) δ ppm 8.66 (s, 1H), 7.97 (dd, J = 9.0, 1.0 Hz, 1H), 7.79 (d, J = 8.4 Hz, 2H), 7.54 (d, J = 8.0 Hz, 1H), 7.49 (dd, J = 7.6, 1.2 Hz, 1H), 7.28 (dd, J = 7.8, 1.0 Hz, 1H), 7.17 (t, J = 7.2 Hz, 1H), 7.11 (dt, J = 7.8, 1.5 Hz, 1H), 6.87 (d, J = 8.8 Hz, 2H), 5.74-5.67 (m, 1H), 4.60 (t, J = 6.6 Hz, 2H), 4.52 (t, J = 6.2 Hz, 2H), 3.40-3.30 (m, 1H), 3.12-3.00 (m, 4H), 2.35-2.24 (m, 4H), 1.87-1.72 (m, 2H), 1.63-1.52 (m, 1H), 0.98 (d, J = 6.4 Hz, 3H), 0.92 (t, J = 6.4 Hz, 3H).

| Example/IUPAC name | Structure | MS calculated MS ESI [M + H]+ | Yield; Appearance; Salt form |
|---|---|---|---|
| A299: (S)-N-(1-(2-chlorophenyl)-3-methylbutyl)-3-(4-(4-(oxetan-3-yl)piperazin-1-yl)phenyl)-1H-indazole-5-carboxamide | 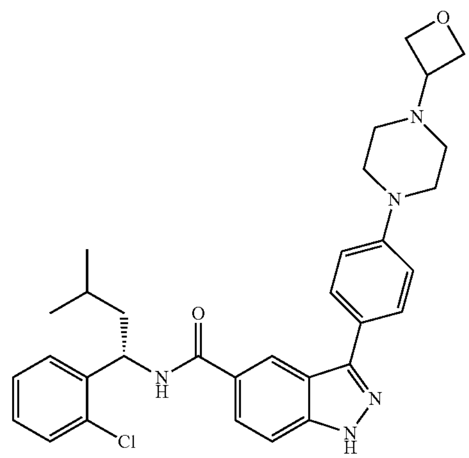 [SMILES: CC(C)C[C@H](NC(=O)c1ccc2[nH]nc(-c3ccc(N4CCN(C5COC5)CC4)cc3)c2c1)c1ccccc1Cl] | [C$_{33}$H$_{36}$ClN$_5$O$_2$ + H]+ 558.3 558.6 | 368 mg (68%), yellow solid; TFA salt |

SMs: (S)-N-(1-(2-chlorophenyl)-3-methylbutyl)-3-iodo-1H-indazole-5-carboxamide (374 mg, 0.8 mmol), 1-(oxetan-3-yl)-4-(4-(4,4,5,5-tetramethyl-1,3,2-dioxaborolan-2-yl)phenyl)piperazine (276 mg, 0.8 mmol)

Spectral data was identical for that obtained in racemic N-(1-(2-chlorophenyl)-3-methylbutyl)-3-(4-(4-(oxetan-3-yl)piperazin-1-yl)phenyl)-1H-indazole-5-carboxamide

| Example/IUPAC name | Structure | MS calculated MS ESI [M + H]+ | Yield; Appearance; Salt form |
|---|---|---|---|
| A300: (R)-N-(1-(2-chlorophenyl)-3-methylbutyl)-3-(4-(4-(oxetan-3-yl)piperazin-1-yl)phenyl)-1H-indazole-5-carboxamide | 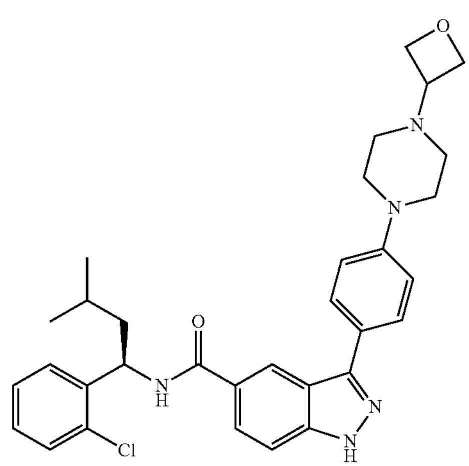 [SMILES: CC(C)C[C@@H](NC(=O)c1ccc2[nH]nc(-c3ccc(N4CCN(C5COC5)CC4)cc3)c2c1)c1ccccc1Cl] | [C$_{32}$H$_{36}$ClN$_5$O$_2$ + H]+ 558.3 559.5 | 6.508 g (60%), yellow solid; TsOH salt |

SMs: (R)-N-(1-(2-chlorophenyl)-3-methylbutyl)-3-iodo-1H-indazole-5-carboxamide (7.02 g, 15 mmol), 1-(oxetan-3-yl)-4-(4-(4,4,5,5-tetramethyl-1,3,2-dioxaborolan-2-yl)phenyl)piperazine (5.16 g, 15 mmol)

$^1$H NMR (400 MHz, CD$_3$OD) δ ppm 8.59 (s, 1H), 7.90-7.50 (m, 1H), 7.93 (d, J = 8.4 Hz, 2H), 7.72 (d, J = 8.4 Hz, 2H), 7.62 (d, J = 8.8 Hz, 1H), 7.80-7.40 (m, 1H), 7.39 (d, J = 8.0 Hz, 1H), 7.29 (t, J = 7.2 Hz, 1H), 7.25-7.19 (m, 3H), 7.16 (d, J = 8.4 Hz, 2H), 5.71 (dd, J = 10.0, 4.8 Hz, 1H), 4.96-4.85 (m, 4H, partially buried in H$_2$O), 4.31 (quintet, J = 6.0 Hz, 1H), 4.10-3.10 (m, 8H), 2.34 (s, 3H), 1.91-1.78 (m, 2H), 1.68-1.58 (m, 2H), 1.06 (d, J = 6.4 Hz, 3H), 1.01 (d, J = 6.4 Hz, 3H).

-continued

| Example/IUPAC name | Structure | MS calculated MS ESI [M + H]+ | Yield; Appearance; Salt form |
|---|---|---|---|
| A301: 3-(4-((1R,3S,5S)-3-hydroxy-8-azabicyclo[3.2.1]octan-8-yl)phenyl)-N-((S)-3-methyl-1-(pyridin-2-yl)butyl)-1H-indazole-5-carboxamide | 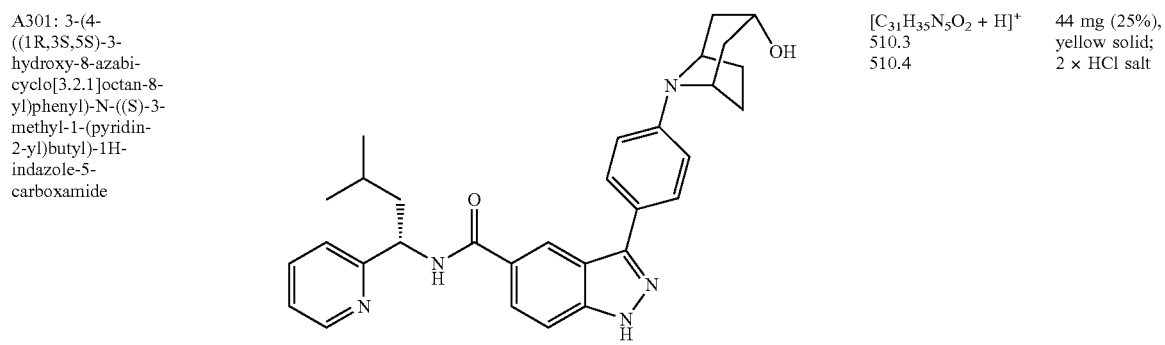 | [C$_{31}$H$_{35}$N$_5$O$_2$ + H]+ 510.3 510.4 | 44 mg (25%), yellow solid; 2 × HCl salt |

SMs: (S)-3-iodo-N-(3-methyl-1-(pyridin-2-yl)butyl)-1H-indazole-5-carboxamide (133 mg, 0.3 mmol), (1R,3R,5S)-8-(4-(4,4,5,5-tetramethyl-1,3,2-dioxaborolan-2-yl)phenyl)-8-azabicyclo[3.2.1]octan-3-ol (120 mg, 0.36 mmol)

Spectral data was identical for that obtained in 3-(4-((1R,3S,5S)-3-hydroxy-8-azabicyclo[3.2.1]octan-8-yl)phenyl)-N-((R)-3-methyl-1-(pyridin-2-yl)butyl)-1H-indazole-5-carboxamide.

| | | | |
|---|---|---|---|
| A302: N-(1-(2-chlorophenyl)pent-4-en-1-yl)-3-(4-(4-(oxetan-3-yl)piperazin-1-yl)phenyl)-1H-indazole-5-carboxamide |  | [C$_{32}$H$_{34}$ClN$_4$O$_2$ + H]+ 556.2 556.6 | 125 mg (47%), light yellow solid; TFA salt |

SMs: N-(1-(2-chlorophenyl)pent-4-en-1-yl)-3-iodo-1H-indazole-5-carboxamide (186 mg, 0.4 mmol), 1-(oxetan-3-yl)-4-(4-(4,4,5,5-tetramethyl-1,3,2-dioxaborolan-2-yl)phenyl)piperazine (138 mg, 0.4 mmol)

$^1$H NMR (400 MHz, CD$_3$OD) δ ppm 8.56 (s, 1H), 7.94 (dd, J = 8.8, 1.6 Hz, 1H), 7.86 (d, J = 8.4 Hz, 2H), 7.58 (d, J = 8.8 Hz, 1H), 7.51 (dd, J = 7.6, 1.2 Hz, 1H), 7.34 (dd, J = 7.8, 1.4 Hz, 1H), 7.24 (t, J = 7.6 Hz, 1H), 7.17 (dt, J = 7.4, 1.5 Hz, 1H), 7.04 (d, J = 8.8 Hz, 2H), 5.93-5.83 (m, 1H), 5.57 (dd, J = 8.8, 6.0 Hz, 1H), 5.10-4.84 (m, 6H), 4.45 (quintet, J = 6.4 Hz, 1H), 3.70-3.25 (m, 8H), 2.33-2.12 (m, 2H), 2.05-1.90 (m, 2H).

| Example/IUPAC name | Structure | MS calculated MS ESI [M + H]+ | Yield; Appearance; Salt form |
|---|---|---|---|
| A303: 3-(4-((1R,5S)-3-oxa-8-azabicyclo[3.2.1]octan-8-yl)phenyl)-N-((S)-3-methyl-1-(pyridin-2-yl)butyl)-1H-indazole-5-carboxamide | 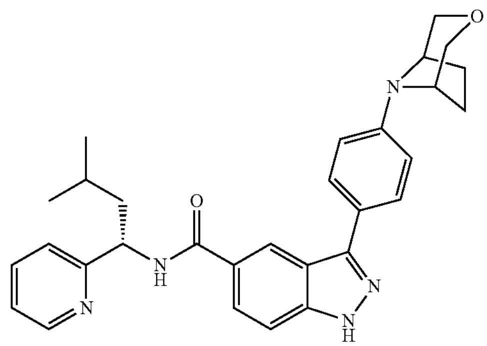 [SMILES: CC(C)C[C@H](NC(=O)c1ccc2[nH]nc(-c3ccc(N4C5CCC4COC5)cc3)c2c1)c1ccccn1] | [$C_{30}H_{33}N_5O_2$ + H]+ 496.3 496.3 | 79 mg (46%), yellow solid; 2 × HCl salt |

SMs: (S)-3-iodo-N-(3-methyl-1-(pyridin-2-yl)butyl)-1H-indazole-5-carboxamide (130 mg, 0.3 mmol), (1R,5S)-8-(4-(4,4,5,5-tetramethyl-1,3,2-dioxaborolan-2-yl)phenyl)-3-oxa-8-azabicyclo[3.2.1]octane (95 mg, 0.3 mmol)
$^1$H NMR (free base, 400 MHz, CD$_3$OD) δ ppm 8.68 (s, 1H), 8.51-8.48 (m, 1H), 7.97 (dd, J = 8.8, 1.2 Hz, 1H), 7.82 (d, J = 8.8 Hz, 2H), 7.74 (dt, J = 7.6, 1.6 Hz, 1H), 7.58 (d, J = 8.8 Hz, 1H), 7.46 (d, J = 8.0 Hz, 1H), 7.27-7.22 (m, 1H), 6.89 (d, J = 8.8 Hz, 2H), 5.37-5.32 (m, 1H), 4.12-4.02 (m, 2H), 3.81 (d, J = 10.8 Hz, 2H), 3.44 (d, J = 10.8 Hz, 2H), 2.03-1.85 (m, 5H), 1.78-1.65 (m, 2H), 0.97 (t, J = 5.6 Hz, 6H).

| Example/IUPAC name | Structure | MS calculated MS ESI [M + H]+ | Yield; Appearance; Salt form |
|---|---|---|---|
| A304: 3-(4-((1R,3S,5S)-3-hydroxy-9-azabicyclo[3.3.1]nonan-9-yl)phenyl)-N-((S)-3-methyl-1-(pyridin-2-yl)butyl)-1H-indazole-5-carboxamide | | [$C_{32}H_{37}N_5O_2$ + H]+ 524.3 524.3 | 36 mg (20%), yellow solid; 2 × HCl salt |

SMs: (S)-3-iodo-N-(3-methyl-1-(pyridin-2-yl)butyl)-1H-indazole-5-carboxamide (130 mg, 0.3 mmol), (1R,3R,5S)-9-(4-(4,4,5,5-tetramethyl-1,3,2-dioxaborolan-2-yl)phenyl)-9-azabicyclo[3.3.1]nonan-3-ol (113 mg, 0.33 mmol)
$^1$H NMR (free base, 400 MHz, CD$_3$OD) δ ppm 8.66 (d, J = 0.4 Hz, 1H), 8.52-8.48 (m, 1H), 7.95 (dd, J = 9.0, 1.4 Hz, 1H), 7.80 (d, J = 8.4 Hz, 2H), 7.76 (dd, J = 7.8, 1.8 Hz, 1H), 7.58 (d, J = 8.8 Hz, 1H), 7.48 (d, J = 7.6 Hz, 1H), 7.29-7.25 (m, 1H), 7.98 (d, J = 8.8 Hz, 2H), 5.38-5.32 (m, 1H), 4.35-4.27 (m, 2H), 3.75-3.66 (m, 1H), 2.47-2.37 (m, 2H), 2.30-2.15 (m, 1H), 1.95-1.85 (m, 1H), 1.85-1.77 (m, 4H), 1.68-1.40 (m, 5H), 1.05-0.97 (m, 6H).

| Example/IUPAC name | Structure | MS calculated MS ESI [M + H]+ | Yield; Appearance; Salt form |
|---|---|---|---|
| A305: 3-(4-((1R,3S,5S)-3-hydroxy-8-azabicyclo[3.2.1]octan-8-yl)phenyl)-N-((R)-3-methyl-1-(pyridin-2-yl)butyl)-1H-indazole-5-carboxamide | | [$C_{31}H_{35}N_5O_2$ + H]+ 510.3 510.3 | 52 mg (30%), yellow solid; 2 × HCl salt |

SMs: (R)-3-iodo-N-(3-methyl-1-(pyridin-2-yl)butyl)-1H-indazole-5-carboxamide (130 mg, 0.3 mmol), (1R,3R,5S)-8-(4-(4,4,5,5-tetramethyl-1,3,2-dioxaborolan-2-yl)phenyl)-8-azabicyclo[3.2.1]octan-3-ol (109 mg, 0.33 mmol)
$^1$H NMR (free base, 400 MHz, CD$_3$OD) δ ppm 8.66 (d, J = 0.8 Hz, 1H), 8.52-8.49 (m, 1H), 7.95 (dd, J = 8.8, 1.6 Hz, 1H), 7.82 (d, J = 8.8 Hz, 2H), 7.77 (dt, J = 7.6, 1.7 Hz, 1H), 7.57 (d, J = 8.8 Hz, 1H), 7.48 (d, J = 8.0 Hz, 1H), 7.29-7.25 (m, 1H), 6.91 (d, J = 8.8 Hz, 2H), 5.35 (dd, J = 10.0, 5.2 Hz, 1H), 4.25-4.18 (m, 2H), 3.91 (t, J = 4.6 Hz, 1H), 2.38-2.31 (m, 2H), 2.23-2.16 (m, 2H), 2.06-1.98 (m, 2H), 1.96-1.85 (m, 1H), 1.80-1.66 (m, 2H), 1.61 (d, J = 14.4 Hz, 2H), 1.02-0.97 (m, 6H).

| Example/IUPAC name | Structure | MS calculated MS ESI [M + H]+ | Yield; Appearance; Salt form |
|---|---|---|---|
| A306: 3-(4-((1R,5S,7R)-7-hydroxy-3-oxa-9-azabi-cyclo[3.3.1]nonan-9-yl)phenyl)-N-((S)-3-methyl-1-(pyridin-2-yl)butyl)-1H-indazole-5-carboxamide | 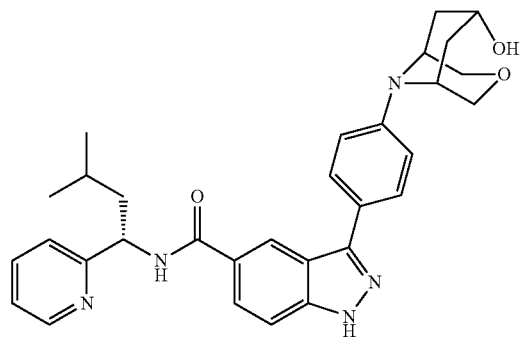 [SMILES: CC(C)C[C@H](NC(=O)c1ccc2[nH]nc(-c3ccc(N4C5COCC4CC(O)C5)cc3)c2c1)c1ccccn1] | [C₃₁H₃₅N₅O₃ + H]+ 526.3 526.4 | 59 mg (33%), yellow solid; 2 × HCl salt |

SMs: (S)-3-iodo-N-(3-methyl-1-(pyridin-2-yl)butyl)-1H-indazole-5-carboxamide (130 mg, 0.3 mmol), (1R,5S,7R)-9-(4-(4,4,5,5-tetramethyl-1,3,2-dioxaborolan-2-yl)phenyl)-3-oxa-9-azabi-cyclo[3.3.1]nonan-7-ol (99 mg, 0.3 mmol)

¹H NMR (400 MHz, CD₃OD) δ ppm 8.88 (s, 1H), 8.32 (d, J = 4.8 Hz, 1H), 8.70-8.62 (m, 1H), 8.28 (d, J = 6.4 Hz, 1H), 8.20 (d, J = 8.8 Hz, 1H), 8.08-7.98 (m, 3H), 7.76 (d, J = 8.8 Hz, 1H), 7.22 (d, J = 6.4 Hz, 2H), 5.53-5.45 (m, 1H), 4.19 (brs, 2H), 4.07-3.95 (m, 4H), 3.92-3.87 (m, 1H), 2.40-2.31 (m, 3H), 1.91-1.78 (m, 4H), 1.08 (d, J = 5.2 Hz, 3H), 1.06 (d, J = 5.2 Hz, 3H).

| Example/IUPAC name | Structure | MS calculated MS ESI [M + H]+ | Yield; Appearance; Salt form |
|---|---|---|---|
| A307: N-((S)-cycloprop-yl(pyridin-2-yl)methyl)-3-(4-((1R,3R,5S)-3-hydroxy-8-azabi-cyclo[3.2.1]octan-8-yl)phenyl)-1H-indazole-5-carboxamide | 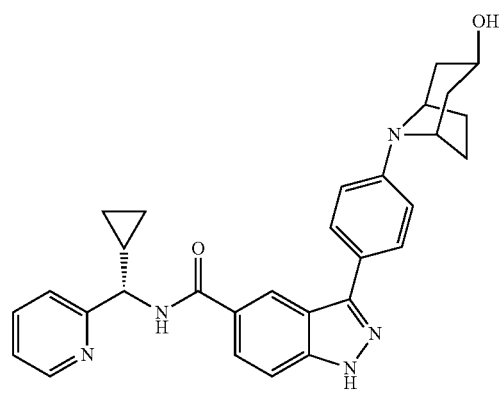 [SMILES: O=C(N[C@H](c1ccccn1)C1CC1)c1ccc2[nH]nc(-c3ccc(N4C5CCC4CC(O)C5)cc3)c2c1] | [C₃₀H₃₁N₅O₂ + H]+ 494.2 494.3 | 65 mg (38%), yellow solid; 2 × HCl salt |

SMs: (S)-N-(cyclopropyl(pyridin-2-yl)methyl)-3-iodo-1H-indazole-5-carboxamide (125 mg, 0.3 mmol), (1R,3S,5S)-8-(4-(4,4,5,5-tetramethyl-1,3,2-dioxaborolan-2-yl)phenyl)-8-azabicyclo[3.2.1]octan-3-ol (99 mg, 0.3 mmol)

¹H NMR (free base, 400 MHz, CD₃OD) δ ppm 8.67 (s, 1H), 8.51 (d, J = 4.8 Hz, 1H), 7.95 (dd, J = 8.8, 1.2 Hz, 1H), 7.86 (d, J = 8.8 Hz, 2H), 7.79 (dt, J = 8.0, 1.7 Hz, 1H), 7.57 (d, J = 7.2 Hz, 1H), 7.52 (d, J = 8.0 Hz, 1H), 7.29 (dd, J = 7.4, 5.0 Hz, 1H), 6.96 (d, J = 8.8 Hz, 2H), 4.51 (d, J = 8.8 Hz, 1H), 4.33 (s, 2H), 4.20-4.08 (m, 1H), 2.14-1.97 (m, 2H), 1.90-1.68 (m, 6H), 1.45-1.35 (m, 1H), 1.22-1.12 (m, 1H), 1.10-0.97 (m, 3H).

| Example/IUPAC name | Structure | MS calculated MS ESI [M + H]+ | Yield; Appearance; Salt form |
| --- | --- | --- | --- |
| A308: N-(1-(2-fluorophenyl)-3,3-dimethylbutyl)-3-(4-(4-(oxetan-3-yl)piperazin-1-yl)phenyl)-1H-indazole-5-carboxamide | 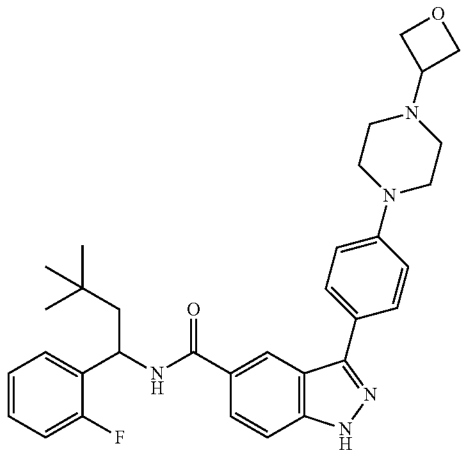 [SMILES: CC(C)(C)CC(NC(=O)c1ccc2[nH]nc(-c3ccc(N4CCN(C5COC5)CC4)cc3)c2c1)c1ccccc1F] | [$C_{33}H_{38}FN_5O_2$ + H]+ 556.3 556.5 | 103 mg (38%), yellow solid; TFA salt |

SMs: N-(1-(2-fluorophenyl)-3,3-dimethylbutyl)-3-iodo-1H-indazole-5-carboxamide (233 mg, 0.5 mmol), 1-(oxetan-3-yl)-4-(4-(4,4,5,5-tetramethyl-1,3,2-dioxaborolan-2-yl)phenyl)piperazine (138 mg, 0.4 mmol)

$^1$H NMR (400 MHz, CD$_3$OD) δ ppm 8.55 (d, J = 0.4 Hz, 1H), 7.91 (dd, J = 8.8, 1.6 Hz, 1H), 7.87 (d, J = 8.8 Hz, 2H), 7.58 (d, J = 8.8 Hz, 1H), 7.46 (dt, J = 8.0, 1.2 Hz, 1H), 7.26-7.19 (m, 1H), 7.13-7.03 (m, 4H), 5.66 (dd, J = 9.0, 3.0 Hz, 1H), 4.92-4.85 (m, 4H), 4.47 (quintet, J = 6.4 Hz, 1H), 3.70-3.25 (m, 8H), 2.04 (dd, J = 14.6, 9.4 Hz, 1H), 1.68 (dd, J = 14.6 Hz 3.0 Hz, 1H), 1.03 (s, 9H).

| Example/IUPAC name | Structure | MS calculated MS ESI [M + H]+ | Yield; Appearance; Salt form |
| --- | --- | --- | --- |
| A309: (S)-N-(cyclopentyl(pyridin-2-yl)methyl)-3-(4-(3-(oxetan-3-yl)azetidin-1-yl)phenyl)-1H-indazole-5-carboxamide | 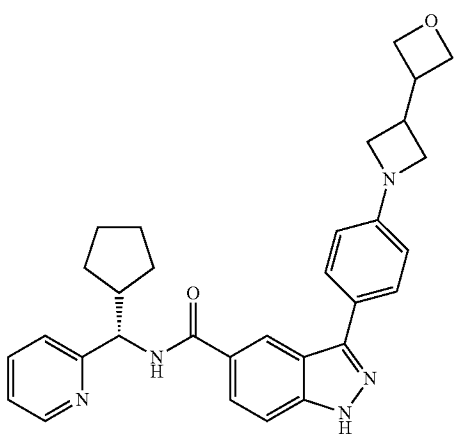 [SMILES: O=C(N[C@H](c1ccccn1)C1CCCC1)c1ccc2[nH]nc(-c3ccc(N4CC(C5COC5)C4)cc3)c2c1] | [$C_{31}H_{33}N_5O_2$ + H]+ 508.26 508.4 | 32 mg (22%); white solid; free base |

SMs: (S)-N-(cyclopentyl(pyridin-2-yl)methyl)-3-iodo-1H-indazole-5-carboxamide (130 mg, 0.29 mmol), 3-(oxetan-3-yl)-1-(4-(4,4,5,5-tetramethyl-1,3,2-dioxaborolan-2-yl)phenyl)azetidine (100 mg, 0.29 mmol)

$^1$H NMR (400 MHz, CD$_3$OD) δ ppm 8.56 (s, 1 H), 8.52 (d, J = 4.0 Hz, 1 H), 7.89 (dd, J = 8.8, 1.5 Hz, 1 H), 7.76-7.84 (m, 3 H), 7.56 (d, J = 8.8 Hz, 1 H), 7.49 (d, J = 7.8 Hz, 1 H), 7.26-7.33 (m, 1 H), 6.61 (d, J = 8.8 Hz, 2 H), 5.01 (d, J = 10.3 Hz, 1 H), 4.89 (dd, J = 7.8, 6.3 Hz, 2 H), 4.50 (t, J = 6.0 Hz, 2 H), 4.05 (t, J = 7.7 Hz, 2 H), 3.69 (dd, J = 7.4, 5.1 Hz, 2 H), 3.33-3.41 (m, 1 H), 3.05-3.15 (m, 1 H), 2.47-2.62 (m, 1 H), 1.92-2.03 (m, 1 H), 1.46-1.78 (m, 5 H), 1.22-1.42 (m, 2 H)

| Example/IUPAC name | Structure | MS calculated MS ESI [M + H]+ | Yield; Appearance; Salt form |
|---|---|---|---|
| A310: (S)-N-(1-(2-chlorophenyl)-2-methylpropyl)-3-(4-(3-(oxetan-3-yl)azetidin-1-yl)phenyl)-1H-indazole-5-carboxamide | 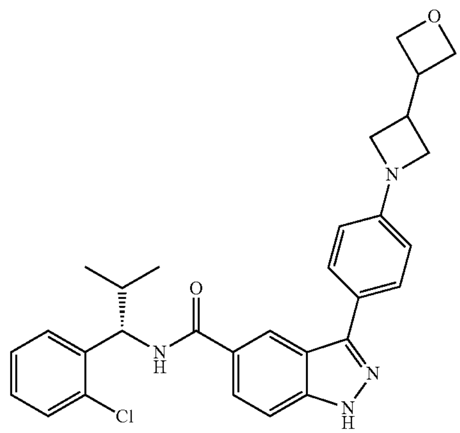 [SMILES: CC(C)[C@H](NC(=O)c1ccc2[nH]nc(-c3ccc(N4CC(C5COC5)C4)cc3)c2c1)c1ccccc1Cl] | [C$_{30}$H$_{31}$ClN$_4$O$_2$ + H]+ 515.21 515.6 | 67 mg (45%); yellow powder; free base |

SMs: (S)-N-(1-(2-chlorophenyl)-2-methylpropyl)-3-iodo-1H-indazole-5-carboxamide (133 mg, 0.29 mmol), 3-(oxetan-3-yl)-1-(4-(4,4,5,5-tetramethyl-1,3,2-dioxaborolan-2-yl)phenyl)azetidine (100 mg, 0.29 mmol)

$^1$H NMR (400 MHz, CDCl$_3$) δ ppm 11.46 (br. s., 1 H), 8.53 (d, J = 0.8 Hz, 1 H), 7.84 (d, J = 8.5 Hz, 2 H), 7.73 (dd, J = 8.7, 1.6 Hz, 1 H), 7.32-7.40 (m, 2 H), 7.29 (d, J = 8.8 Hz, 1 H), 7.20 (m, 2 H), 7.01 (d, J = 8.8 Hz, 1 H), 6.55 (d, J = 8.5 Hz, 2 H), 5.27 (t, J = 8.8 Hz, 1 H), 4.91 (dd, J = 7.7, 6.4 Hz, 2 H), 4.51 (t, J = 6.0 Hz, 2 H), 4.08 (t, J = 7.7 Hz, 2 H), 3.66-3.74 (m, 2 H), 3.30-3.41 (m, 1 H), 3.11 (m, 1 H), 2.38-2.42 (m, 1 H), 1.11 (d J = 6.5 Hz, 3 H), 0.90 (d, J = 6.8 Hz, 3 H)

| Example/IUPAC name | Structure | MS calculated MS ESI [M + H]+ | Yield; Appearance; Salt form |
|---|---|---|---|
| A311: (S)-N-(cyclopropyl(pyridin-2-yl)methyl)-3-(4-(3-(oxetan-3-yl)azetidin-1-yl)phenyl)-1H-indazole-5-carboxamide | 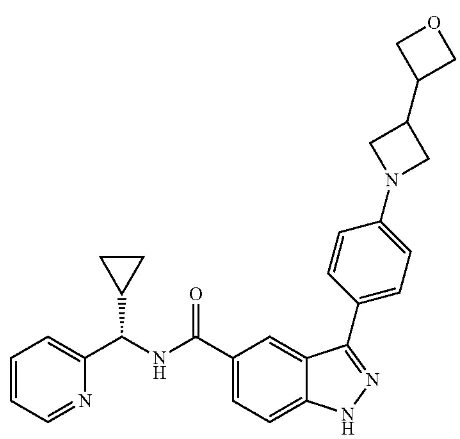 [SMILES: O=C(N[C@H](c1ccccn1)C1CC1)c1ccc2[nH]nc(-c3ccc(N4CC(C5COC5)C4)cc3)c2c1] | [C$_{29}$H$_{29}$N$_5$O$_2$ + H]+ 480.23 480.4 | 58 mg (31%); yellow solid; PTSA salt |

SMs: (S)-N-(cyclopropyl(pyridin-2-yl)methyl)-3-iodo-1H-indazole-5-carboxamide (122 mg, 0.29 mmol), 3-(oxetan-3-yl)-1-(4-(4,4,5,5-tetramethyl-1,3,2-dioxaborolan-2-yl)phenyl)azetidine (100 mg, 0.29 mmol)

$^1$H NMR (400 MHz, CDCl$_3$) δ 9.34 (d, J = 6.5 Hz, 1 H), 8.77 (d, J = 5.3 Hz, 1 H), 8.51 (s, 1 H), 8.33 (d, J = 7.8 Hz, 1 H), 8.04 (d, J = 7.8 Hz, 1 H), 7.90 (dd, J = 8.8, 1.3 Hz, 1 H), 7.73 (dd, J = 15.8, 8.5 Hz, 5 H), 7.21 (d, J = 8.8 Hz, 1 H), 7.08 (d, J = 8.0 Hz, 2 H), 6.45 (d, J = 8.5 Hz, 2 H), 4.89 (dd, J = 7.8, 6.3 Hz, 2 H), 4.58 (dd, J = 10.2, 6.9 Hz, 1 H), 4.48 (td, J = 6.0, 3.5 Hz, 2 H), 4.02 (td, J = 7.7, 2.6 Hz, 2 H), 3.65-3.67 (m, 2 H), 3.28-3.39 (m, 1 H), 3.04-3.14 (m, 1 H), 2.30 (s, 3 H), 1.90-2.01 (m, 1 H), 0.81-0.93 (m, 1 H), 0.71-0.80 (m, 1 H), 0.61-0.71 (m, 1 H), 0.47 (s, 1 H)

| Example/IUPAC name | Structure | MS calculated MS ESI [M + H]+ | Yield; Appearance; Salt form |
|---|---|---|---|
| A312: (R)-N-(cyclopent-yl(pyrimidin-2-yl)methyl)-3-(4-(3-(oxetan-3-yl)azetidin-1-yl)phenyl)-1H-indazole-5-carboxamide | 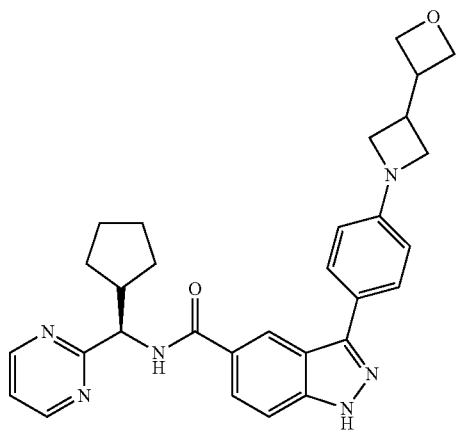 [SMILES: O=C(N[C@@H](c1ncccn1)C1CCCC1)c1ccc2[nH]nc(-c3ccc(N4CC(C5COC5)C4)cc3)c2c1] | $[C_{30}H_{32}N_6O_2 + H]^+$ 509.26 509.4 | 49 mg (60%); yellow solid; free base |

SMs: (R)-N-(cyclopentyl(pyrimidin-2-yl)methyl)-3-iodo-1H-indazole-5-carboxamide (71 mg, 0.16 mmol), 3-(oxetan-3-yl)-1-(4-(4,4,5,5-tetramethyl-1,3,2-dioxaborolan-2-yl)phenyl)azetidine (54 mg, 0.16 mmol)

$^1$H NMR (400 MHz, CD$_3$OD) δ 8.78 (d, J = 4.8 Hz, 2 H), 8.59 (s, 1 H), 7.91 (dd, J = 8.8, 1.3 Hz, 1 H), 7.83 (d, J = 8.8 Hz, 2 H), 7.58 (d, J = 8.8 Hz, 1 H), 7.37 (t, J = 4.9 Hz, 1 H), 6.62 (d, J = 8.5 Hz, 2 H), 5.18 (d, J = 9.5 Hz, 1 H), 4.90 (dd, J = 7.8, 6.3 Hz, 2 H), 4.51 (t, J = 6.0 Hz, 2 H), 4.06 (t, J = 7.7 Hz, 2 H), 3.70 (dd, J = 7.5, 5.0 Hz, 2 H), 3.33-3.43 (m, 1 H), 3.03-3.18 (m, 1 H), 2.50-2.67 (m, 1 H), 1.87-2.00 (m, 1 H), 1.50-1.78 (m, 51-I), 1.36-1.47 (m, 2 H)

| Example/IUPAC name | Structure | MS calculated MS ESI [M + H]+ | Yield; Appearance; Salt form |
|---|---|---|---|
| A313: (S)-N-(1-(2-chlorophenyl)-2-methylpropyl)-3-(4-(3-morpholinoazetidin-1-yl)phenyl)-1H-indazole-5-carboxamide | 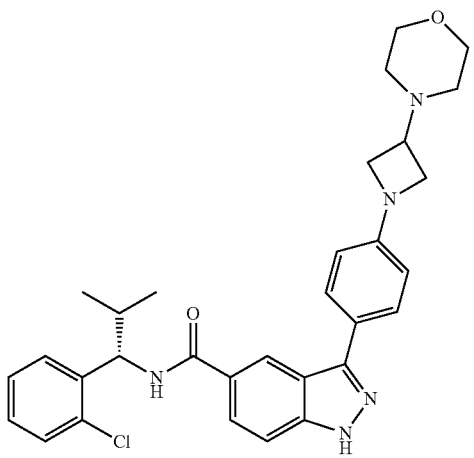 [SMILES: CC(C)[C@H](NC(=O)c1ccc2[nH]nc(-c3ccc(N4CC(N5CCOCC5)C4)cc3)c2c1)c1ccccc1Cl] | $[C_{31}H_{34}ClN_5O_2 + H]^+$ 544.24 544.4 | 79 mg (50%); yellow solid; TFA salt |

SMs: (S)-N-(1-(2-chlorophenyl)-2-methylpropyl)-3-iodo-1H-indazole-5-carboxamide (110 mg, 0.24 mmol), 4-(1-(4-(4,4,5,5-tetramethyl-1,3,2-dioxaborolan-2-yl)phenyl)azetidin-3-yl)morpholine (100 mg, 0.24 mmol)

$^1$H NMR (400 MHz, CD$_3$OD) δ 8.84 (d, J = 8.5 Hz, 1 H), 8.49 (dd, J = 1.5, 0.8 Hz, 1 H), 7.78-7.91 (m, 3 H), 7.49-7.63 (m, 2 H), 7.40 (dd, J = 7.9, 1.4 Hz, 1 H), 7.30 (td, J = 7.5, 1.3 Hz, 1 H), 7.19-7.27 (m, 1 H), 6.65 (d, J = 9.0 Hz, 2 H), 5.34-5.42 (m, 1 H), 4.19-4.30 (m, 3 H), 4.05-4.15 (m, 4 H), 3.99 (s, 2 H), 3.07-3.67 (m, 4 H), 2.22-2.35 (m, 1 H), 1.17 (d, J = 6.5 Hz, 3H), 0.88 (d, J = 6.8 Hz, 3 H)

| Example/IUPAC name | Structure | MS calculated MS ESI [M + H]⁺ | Yield; Appearance; Salt form |
|---|---|---|---|
| A314: ((S)-N-(cyclopentyl(pyridin-2-yl)methyl)-3-(4-(3-morpholinoazetidin-1-yl)phenyl)-1H-indazole-5-carboxamide | 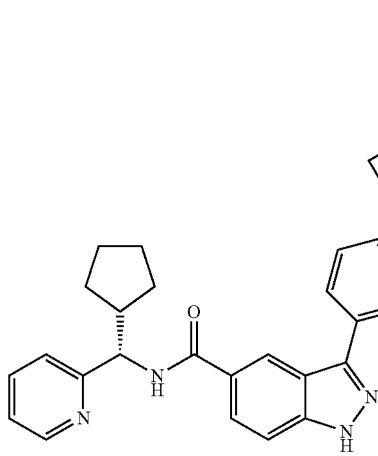 | $[C_{32}H_{36}N_6O_2 + H]^+$ 537.29 537.3 | 86 mg (46%); yellow powder; di-2 × TFA salt |

SMs: (S)-N-(cyclopentyl(pyridin-2-yl)methyl)-3-iodo-1H-indazole-5-carboxamide (110 mg, 0.24 mmol), 4-(1-(4-(4,4,5,5-tetramethyl-1,3,2-dioxaborolan-2-yl)phenyl)azetidin-3-yl)morpholine (100 mg, 0.24 mmol)

$^1$H NMR (400 MHz, CDCl$_3$) δ ppm 9.82 (d, J = 7.3 Hz, 1 H), 8.76 (d, J = 5.5 Hz, 1 H), 8.67 (s, 1 H), 8.32 (td, J = 7.8, 1.4 Hz, 1 H), 7.96-8.09 (m, 2 H), 7.86 (d, J = 8.5 Hz, 2 H), 7.69-7.80 (m, 1 H), 7.51 (d, J = 8.8 Hz, 1 H), 6.58 (d, J = 8.5 Hz, 2 H), 5.82-6.70 (m, 4 H), 5.14 (dd, J = 11.4, 7.7 Hz, 1 H), 4.22-4.31 (m, 2 H), 4.16 (t, J = 7.4 Hz, 2 H), 4.05 (d, J = 4.5 Hz, 4 H), 3.27 (br. s., 3 H), 2.69-2.86 (m, 1 H), 2.14-2.26 (m, 1 H), 1.49-1.81 (m, 4 H), 1.40 (d, J = 7.3 Hz, 1 H), 1.05-1.21 (m, 1 H)

| Example/IUPAC name | Structure | MS calculated MS ESI [M + H]⁺ | Yield; Appearance; Salt form |
|---|---|---|---|
| A315: (S)-N-(1-(2-chlorophenyl)-3-methylbutyl)-3-(4-(3-morpholinoazetidin-1-yl)phenyl)-1H-indazole-5-carboxamide | 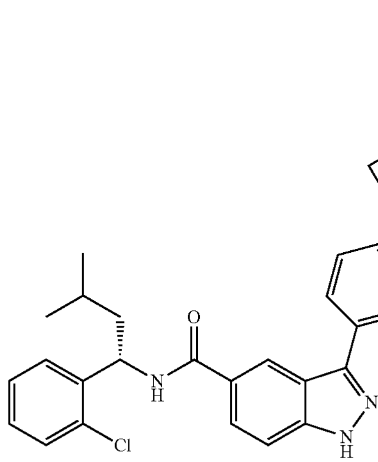 | $[C_{32}H_{36}ClN_5O_2 + H]^+$ 558.26 558.5 | 44 mg (30%); yellow solid; TFA salt |

SMs: (S)-N-(1-(2-chlorophenyl)-3-methylbutyl)-3-iodo-1H-indazole-5-carboxamide (100 mg, 0.22 mmol), 4-(1-(4-(4,4,5,5-tetramethyl-1,3,2-dioxaborolan-2-yl)phenyl)azetidin-3-yl)morpholine (90 mg, 0.22 mmol)

| Example/IUPAC name | Structure | MS calculated MS ESI [M + H]+ | Yield; Appearance; Salt form |
|---|---|---|---|
| A316: (R)-N-(cyclopropyl(pyridin-2-yl)methyl)-3-(4-(3-morpholinoazetidin-1-yl)phenyl)-1H-indazole-5-carboxamide | 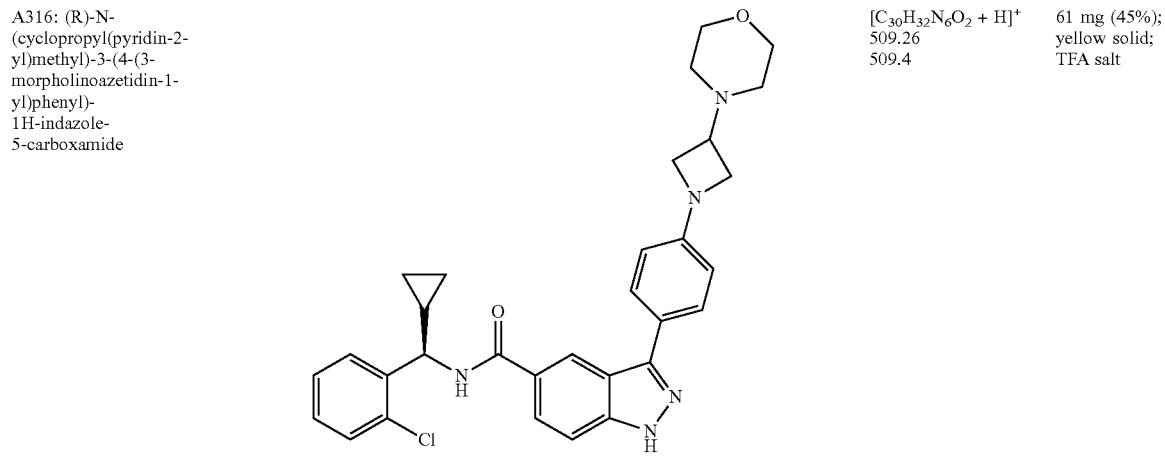 | [C30H32N6O2 + H]+ 509.26 509.4 | 61 mg (45%); yellow solid; TFA salt |

SMs: (R)-N-(cyclopropyl(pyridin-2-yl)methyl)-3-iodo-1H-indazole-5-carboxamide (91 mg, 0.22 mmol), 4-(1-(4-(4,4,5,5-tetramethyl-1,3,2-dioxaborolan-2-yl)phenyl)azetidin-3-yl)morpholine (90 mg, 0.22 mmol)

$^1$H NMR (400 MHz, CDCl$_3$) δ ppm 9.79 (d, J = 6.8 Hz, 1 H), 8.79 (d, J = 5.5 Hz, 1 H), 8.65 (s, 1 H), 8.35 (t, J = 7.7 Hz, 1 H), 8.04 (d, J = 8.8 Hz, 1 H), 7.97 (d, J = 8.0 Hz, 1 H), 7.82 (d, J = 8.3 Hz, 2 H), 7.77 (d, J = 7.3 Hz, 1 H), 7.50 (d, J = 9.0 Hz, 1 H), 6.56 (d, J = 8.3 Hz, 2 H), 4.53 (dd, J = 10.7, 6.9 Hz, 2 H), 4.26 (dd, J = 8.9, 4.6 Hz, 3 H), 4.16 (t, J = 8.2 Hz, 2 H), 4.04 (br. s., 4 H), 3.23 (br. s., 3 H), 1.59-1.91 (m, 1 H), 0.82-0.99 (m, 1 H), 0.59-0.78 (m, 2 H), 0.32-0.50 (m, 1 H) 3Hs too many? One too few Ar H?

| Example/IUPAC name | Structure | MS calculated MS ESI [M + H]+ | Yield; Appearance; Salt form |
|---|---|---|---|
| A317 (R)-N-(1-(2-chlorophenyl)-2-methylpropyl)-3-(4-(3-morpholinoazetidin-1-yl)phenyl)-1H-indazole-5-carboxamide | 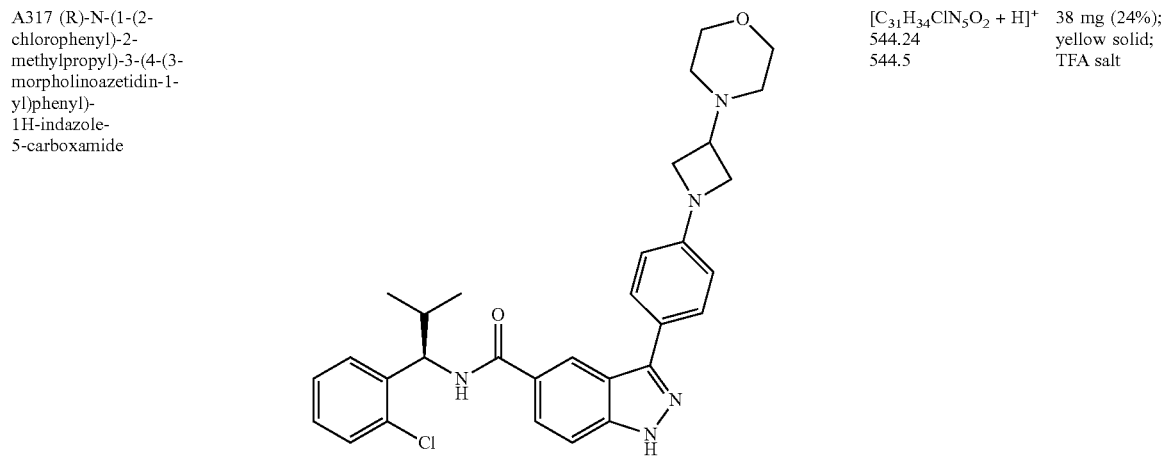 | [C31H34ClN5O2 + H]+ 544.24 544.5 | 38 mg (24%); yellow solid; TFA salt |

SMs: (R)-N-(1-(2-chlorophenyl)-2-methylpropyl)-3-iodo-1H-indazole-5-carboxamide (110 mg, 0.24 mmol), 4-(1-(4-(4,4,5,5-tetramethyl-1,3,2-dioxaborolan-2-yl)phenyl)azetidin-3-yl)morpholine (100 mg, 0.24 mmol)

$^1$H NMR (400 MHz, CD$_3$OD) δ ppm 8.83 (d, J = 8.7 Hz, 1 H), 8.49 (s, 1 H), 7.88-7.84 (m, 3 H), 7.59-7.54 (m, 2 H), 7.40 (d, J = 7.8 Hz, 1 H), 7.3 (t, J = 7.5 Hz, 1 H), 7.23 (t, J = 7.6 Hz, 1 H), 6.68 (d, J = 8.6 Hz, 2 H), 5.40-5.36 (m, 1 H), 4.86-3.90 (br m, 13 H), 2.31-2.26 (m, 1 H), 1.17 (d, J = 6.6 Hz, 3 H), 0.88 (d, J = 6.7 Hz, 3 H)

| Example/IUPAC name | Structure | MS calculated MS ESI [M + H]+ | Yield; Appearance; Salt form |
|---|---|---|---|
| A318: (1R,3R,5S)-tert-butyl cyclopropyl(pyridin-2-yl)methyl)carbamoyl)-1H-indazol-3-yl)phenoxy)-8-azabicyclo[3.2.1]octane-8-carboxylate | 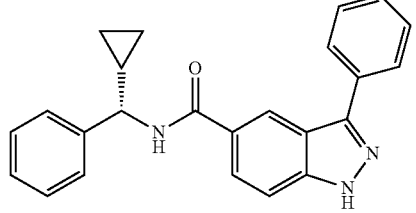 | [C35H39N5O4 + H]+ 593.7 594.4 | 10 mg (19%); white solid; free base |

SMs: (S)-N-(yclopropyl(pyridin-2-yl)methyl)-3-iodo-1H-indazole-5-carboxamide (0.052 g, 0.12 mmol), (1R,3R,5S)-tert-butyl 3-(4-(4,4,5,5-tetramethyl-1,3,2-dioxaborolan-2-yl)phenoxy)-8-azabicyclo[3.2.1]octane-8-carboxylate (0.050 g, 0.12 mmol)

$^1$H NMR (400 MHz, CDCl$_3$) δ ppm 8.61 (d, J = 4.0 Hz, 1 H), 8.56 (s, 1 H), 7.92 (d, J = 7.5 Hz, 1 H), 7.79-7.89 (m, 3 H), 7.66-7.74 (m, 1 H), 7.40 (d, J = 8.5 Hz, 1 H), 7.35 (d, J = 7.8 Hz, 1 H), 7.24 (dd, J = 6.9, 5.4 Hz, 1 H), 6.91 (d, J = 8.8 Hz, 2 H), 4.80 (t, J = 8.2 Hz, 1 H), 4.68 (br. s., 1 H), 4.13-4.35 (m, 2 H), 2.17 (br. s., 4 H), 2.00 (d, J = 15.3 Hz, 4 H), 1.50 (s, 9 H), 1.38 (d, J = 8.3 Hz, 1 H), 0.40-0.78 (m, 4 H)

| Example/IUPAC name | Structure | MS calculated MS ESI [M + H]+ | Yield; Appearance; Salt form |
|---|---|---|---|
| A319: N-(cyclopentyl(pyridin-2-yl)methyl)-3-(4-((1-(oxetan-3-yl)piperidin-4-yl)oxy)phenyl)-1H-indazole-5-carboxamide | 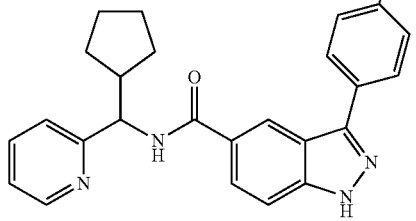 | [C33H37N5O3 + H]+ 552.3 552.3 | 12 mg (19%); white solid; free base |

SMs: N-(cyclopentyl(pyridin-2-yl)methyl)-3-iodo-1H-indazole-5-carboxamide (0.05 g, 0.11 mmol), 1-(oxetan-3-yl)-4-(4-(4,4,5,5-tetramethyl-1,3,2-dioxaborolan-2-yl)phenoxy)piperidine (0.044 g, 0.123 mmol)

$^1$H NMR (400 MHz, CD$_3$OD) δ ppm 8.59 (s, 1 H), 8.51 (d, J = 5.0 Hz, 1 H), 7.85-7.95 (m, 3 H), 7.77 (td, J = 7.7, 1.6 Hz, 1 H), 7.59 (d, J = 8.8 Hz, 1 H), 7.48 (d, J = 7.8 Hz, 1 H), 7.22-7.32 (m, 1 H), 7.05 (d, J = 18.5 Hz, 2 H), 5.01 (d, J = 10.3 Hz, 1 H), 4.64-4.71 (m, 2 H), 4.59 (t, J = 6.1 Hz, 2 H), 4.46 (d, J = 3.3 Hz, 1 H), 3.49 (quin, J = 6.4 Hz, 1 H), 2.45-2.63 (m, 3 H), 2.21 (br. s., 2 H), 1.90-2.07 (m, 3 H), 1.76-1.88 (m, 2 H), 1.43-1.74 (m, 5 H), 1.16-1.41 (m, 2 H)

| Example/IUPAC name | Structure | MS calculated MS ESI [M + H]+ | Yield; Appearance; Salt form |
|---|---|---|---|
| A320: N-((S)-cyclopropyl(pyridin-2-yl)methyl)-3-(4-(((1R,3R,5S)-8-(oxetan-3-yl)-8-azabicyclo[3.2.1]octan-3-yl)oxy)phenyl)-1H-indazole-5-carboxamide | 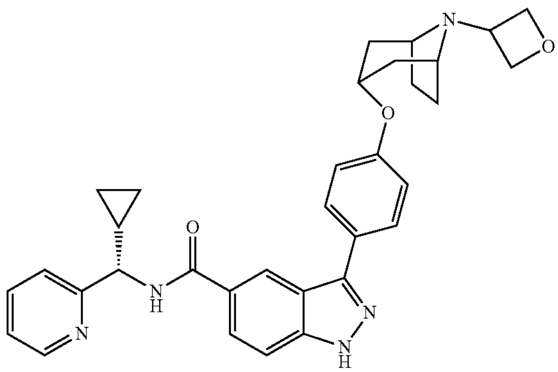 [SMILES: O=C(N[C@H](c1ccccn1)C1CC1)c1ccc2[nH]nc(-c3ccc(OC4CC5CCC(C4)N5C4COC4)cc3)c2c1] | [$C_{33}H_{35}N_5O_3$ + H]+ 550.3 550.2 | 12 mg (23%); white solid; free base |

SMs: (S)-N-(yclopropyl(pyridin-2-yl)methyl)-3-iodo-1H-indazole-5-carboxamide (39 mg, 0.094 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (40 mg, 0.104 mmol)

$^1$H NMR (400 MHz, CD$_3$OD) δ 8.66 (s, 1 H), 8.51 (d, J = 5.0 Hz, 1H), 7.96 (dd, J = 8.9, 1.4 Hz, 1H), 7.91 (d, J = 8.5 Hz, 2H), 7.80 (td, J = 7.7, 1.6 Hz, 1H), 7.59 d, J = 8.8 Hz, 1H), 7.52 (d, J = 7.8 Hz, 1H), 7.30 (dd, J = 7.0, 5.5 Hz, 1H), 6.97 (d, J = 8.8 Hz, 2H), 4.71 (t, J = 6.4 Hz, 2H), 4.63 (t, J = 4.6 Hz, 1H), 4.44-4.56 (m, 3 H), 3.76 (t, J = 6.0 Hz, 1H) 3.08 (br. s., 2H) 2.06-2.20 (m, 4H) 1.85-2.02 (m, 4H) 1.32-1.48 (m, 1H) 0.66 (d, J = 8.3 Hz, 1H) 0.46-0.61 (m, 3H)

| Example/IUPAC name | Structure | MS calculated MS ESI [M + H]+ | Yield; Appearance; Salt form |
|---|---|---|---|
| A321: N-(cyclopropyl(phenyl)methyl)-3-(4-(((1R,3R,5S)-8-(oxetan-3-yl)-8-azabicyclo[3.2.1]octan-3-yl)oxy)phenyl)-1H-indazole-5-carboxamide | 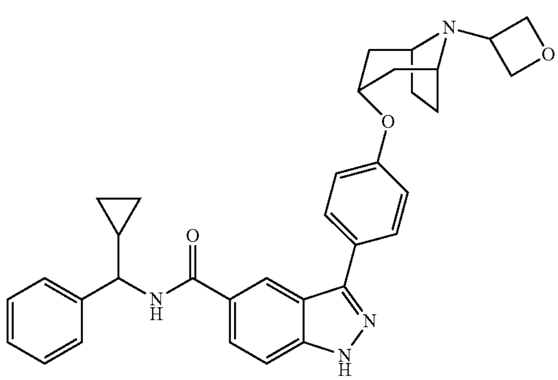 | [$C_{34}H_{36}N_4O_3$ + H]+ 549.3 549.4 | 41 mg (65%); white solid; free base |

SMs: N-(cyclopropyl(phenyl)methyl)-3-iodo-1H-indazole-5-carboxamide (39 mg, 0.094 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane(40 mg, 0.104 mmol)

$^1$H NMR (400 MHz, CD$_3$OD) δ 8.62 (s, 1 H), 7.96 (d, J = 8.8 Hz, 1H), 7.89 (d, J = 7.8 Hz, 2H), 7.59 (d, J-9.0 Hz, 1H), 7.48 (d, 7 = 7.8 Hz, 2H), 7.31 (t, J = 1.5 Hz, 2H), 7.23 (d, J = 7.5 Hz, 1H), 6.96 (d, J = 7.8 Hz, 2H), 4.71 (t, J = 6.1 Hz, 2H), 4.62 (br. s., 1H), 4.44 -4.55 (m, 3H), 3.71-3.81 (m, 1H), 3.08 (br. s., 2H), 2.07-2.19 (m, 4H), 1.84-2.03 (m, 4H), 1.33-1.45 (m, 1H), 0.64 (d, J = 8.3 Hz, 1H), 0.46 (d, J = 13.1 Hz, 2H)

| Example/IUPAC name | Structure | MS calculated MS ESI [M + H]+ | Yield; Appearance; Salt form |
| --- | --- | --- | --- |
| A322: N-((S)-cyclopropyl(pyridin-2-yl)methyl)-3-(4-(((1R,3R,5S)-8-formyl-8-azabi-cyclo[3.2.1]octan-3-yl)oxy)phenyl)-1H-indazole-5-carboxamide | | $[C_{31}H_{31}N_5O_3 + H]^+$ 522.3 522.4 | 32 mg (36%); white solid; free base |

SMs: (S)-N-(yclopropyl(pyridin-2-yl)methyl)-3-iodo-1H-indazole-5-carboxamide (72 mg, 0.173 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde(68 mg, 0.190 mmol)

$^1$H NMR (400 MHz, CD$_3$OD) δ ppm 8.66 (s, 1H), 8.50 (d, J = 4.5 Hz, 1H), 8.09 (s, 1H), 7.96 (d, J = 1.0 Hz, 1H) 7.90 (d, J = 8.5 Hz, 2H) 7.73-7.81 (m, 1H), 7.58 (d, J = 8.8 Hz, 1H), 7.51 (d, J = 7.8 Hz, 1H), 7.27 (dd, J = 7.5, 5.0 Hz, 1H), 6.95 (d, J = 8.5 Hz, 2H), 4.70 (br. s., 1H), 4.51 (d, J = 9.3 Hz, 2H), 4.12 (br. s., 1H), 2.17-2.29 (m, 2 H), 1.82-2.16 (m, 6 H), 1.31-1.46 (m, 1H), 0.59-0.69 (m, 1H), 0.46-0.58 (m, 3 H)

| Example/IUPAC name | Structure | MS calculated MS ESI [M + H]+ | Yield; Appearance; Salt form |
| --- | --- | --- | --- |
| A323: (1R,3R,5S)-tert-butyl 3-(4-(5-((cyclopropyl(phen-yl)methyl)carbamoyl)-1H-indazol-3-yl)phenoxy)-8-azabi-cyclo[3.2.1]octane-8-carboxylate | | $[C_{36}H_{40}N_4O_4 + H]^+$ 593.7 593.4 | 35 mg (42%); while solid; free base |

SMs: N-(cyclopropyl(phenyl)methyl)-3-iodo-1H-indazole-5-carboxamide (0.059 g, 0.14 mmol), (1R,3R,5S)-tert-butyl 3-(4-(4,4,5,5-tetramethyl-1,3,2-dioxaborolan-2-yl)phenoxy)-8-azabicyclo[3.2.1]octane-8-carboxylate (0.066 g, 0.15 mmol)

$^1$H NMR (400 MHz, CDCl$_3$) δ ppm 8.52 (s, 1 H), 7.86 (d, J = 8.5 Hz, 2 H), 7.78 (d, J = 8.8 Hz, 1 H), 7.46 (d, J = 7.5 Hz, 2 H), 7.28-7.36 (m, 2 H), 7.22-7.28 (m, 1 H), 6.96 (d, J = 7.8 Hz, 1 H), 6.88 (d, J = 8.8 Hz, 2 H), 4.57-4.71 (m, 2 H), 3.99-4.33 (m, 3 H), 2.12 (d, J = 5.0 Hz, 4 H), 1.96 (br. s., 4 H), 1.51 (s, 9 H), 0.51-0.72 (m, 3 H), 0.40-0.50 (m, 1 H)

| Example/IUPAC name | Structure | MS calculated MS ESI [M + H]+ | Yield; Appearance; Salt form |
|---|---|---|---|
| A324: N-(1-(2-chlorophenyl)-2-methylpropyl)-3-(4-(((1R,3R,5S)-8-(oxetan-3-yl)-8-azabicyclo[3.2.1]octan-3-yl)oxy)phenyl)-1H-indazole-5-carboxamide | 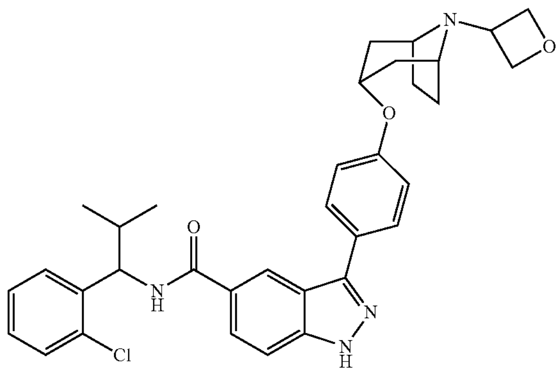 | [C₃₄H₃₇ClN₄O₃ + H]+ 585.3 585.5 | 34 mg (45%); white solid; TFA salt |

SMs: N-(1-(2-chlorophenyl)-2-methylpropyl)-3-iodo-1H-indazole-5-carboxamide (50 mg, 0.11 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane(47 mg, 0.12 mmol)

$^1$H NMR (400 MHz, CD$_3$OD) δ 8.50 (s, 1 H), 7.88 (d, J = 8.8 Hz, 3H), 7.56 (d, J = 8.8 Hz, 2H), 7.37 (d, J = 7.8 Hz, 1H), 7.23-7.30 (m, 1 H), 7.16-7.23 (m, 1 H), 7.01 (d, J = 8.5 Hz, 2H), 5.39 (d, J = 9.5 Hz, 1H), 4.90 (t, J = 7.5 Hz, 2H), 4.79 ( dd, J = 7.8, 5.3 Hz, 3H), 4.44 (br. s., 1H), 3.91 (br. s., 2H), 2.47 (d, J = 8.5 Hz, 4H), 2.14-2.39 (m, 5 H), 1.16 (d, J = 6.5 Hz, 3H), 0.86 (d, J = 6.5 Hz, 3H)

| Example/IUPAC name | Structure | MS calculated MS ESI [M + H]+ | Yield; Appearance; Salt form |
|---|---|---|---|
| A325: N-(2-methyl-1-(pyridin-2-yl)propyl)-3-(4-(((1R,3R,5S)-8-(oxetan-3-yl)-8-azabicyclo[3.2.1]octan-3-yl)oxy)phenyl)-1H-indazole-5-carboxamide | 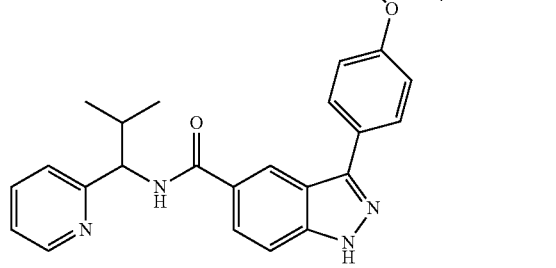 | [C₃₃H₃₇N₅O₃ + H]+ 552.3 552.3 | 25 mg (38%); white solid; free base |

SMs: 3-iodo-N-(2-methyl-1-(pyridin-2-yppropyl)-1H-indazole-5-carboxamide (0.05 g, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane(0.05 g, 0.13 mmol)

$^1$H NMR (400 MHz, CD$_3$OD) δ ppm 8.60 (s, 1 H), 8.54 (d, J = 4.8 Hz, 1H), 7.85-7.97 (m, 3H), 7.79 (m, 1H), 7.60 (d, J = 8.8 Hz, 1H), 7.48 (d, J = 7.8 Hz, 1H), 7.27-7.34 (m, 1 H), 6.99 (d, J = 8.8 Hz, 2H), 4.98 (d, J = 8.8 Hz, 1H), 4.71 (t, J = 6.4 Hz, 2H), 4.65 ( br. s., 1H), 4.52 (t, J = 5.9 Hz, 2H), 3.71-3.82 (m, 1 H), 3.09 (br. s., 2H), 2.26-2.38 (m, 1 H), 2.07-2.20 (m, 4 H), 1.85-2.02 (m, 4 H), 1.11 (d, J = 6.8 Hz, 3H), 0.83 (d, J = 6.8 Hz, 3H)

| Example/IUPAC name | Structure | MS calculated MS ESI [M + H]+ | Yield; Appearance; Salt form |
|---|---|---|---|
| A326: N-(cyclobutyl(thiophen-3-yl)methyl)-3-(4-(((1R,3R,5S)-8-(oxetan-3-yl)-8-azabi-cyclo[3.2.1]octan-3-yl)oxy)phenyl)-1H-indazole-5-carboxamide | 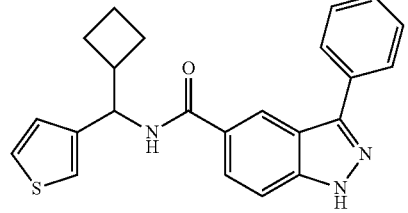 | [C₃₃H₃₆N₄O₃S + H]+ 569.3 569.4 | 19 mg (28%); white solid; free base |

SMs: N-(cyclobutyl(thiophen-3-yl)methyl)-3-iodo-1H-indazole-5-carboxamide (0.052 g, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane(0.05 g, 0.13 mmol)

$^1$H NMR (400 MHz, CD$_3$OD) δ ppm 8.56 (s, 1 H), 7.83-7.96 (m, 3 H), 7.58 (d, J = 9.0 Hz, 1H), 7.33 (dd, J = 4.9, 2.9 Hz, 1H), 7.26 (s, 1 H), 7.13 (d, J = 5.0 Hz, 1H), 6.97 (d, J = 8.8 Hz, 2H), 5.27 (d, J = 10.5 Hz, 1H), 4.59-4.76 (m, 3 H), 4.53 (t, J = 5.8 Hz, 2H), 3.77 (t, J = 5.9 Hz, 1H), 3.08 (br. s., 2H), 2.93 (br. s., 1H), 2.07-2.22 (m, 5 H), 1.80-2.06 (m, 9 H)

| Example/IUPAC name | Structure | MS calculated MS ESI [M + H]+ | Yield; Appearance; Salt form |
|---|---|---|---|
| A327: N-(2-methyl-1-(pyridin-2-yl)propyl)-3-(4-((1-(oxetan-3-yl)piperidin-4-yl)oxy)phenyl)-1H-indazole-5-carboxamide | 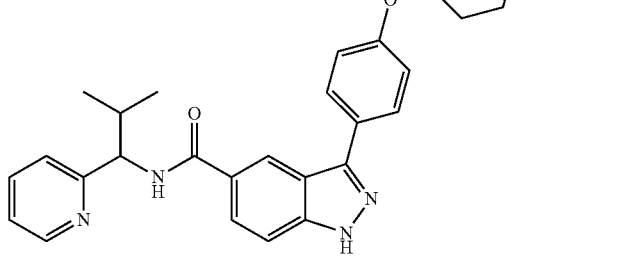 | [C₃₁H₃₅N₅O₃ + H]+ 526.3 526.2 | 36 mg (55%); white solid; free base |

SMs: 3-iodo-N-(2-methyl-1-(pyridin-2-yl)propyl)-1H-indazole-5-carboxamide (0.053 g, 0.13 mmol), 1-(oxetan-3-yl)-4-(4-(4,4,5,5-tetramethyl-1,3,2-dioxaborolan-2-yl)phenoxy)piperidine (0.05 g, 0.14 mmol)

$^1$H NMR (400 MHz, CD$_3$OD) δ 8.60 (s, 1 H), 8.53 (d, J = 4.8 Hz, 1H), 7.85-7.97 (m, 3H), 7.78 (td, J = 7.7, 1.5 Hz, 1H), 7.60 (d, J = 8.8 Hz, 1H), 7.47 (d,J = 7.8 Hz, 1H), 7.29 (dd, J = 7.5, 5.0 Hz, 1H), 7.06 (d, J = 8.5 Hz, 2H), 4.98 (d, J = 8.8 Hz, 1H), 4.67 (t, J = 1.0 Hz, 2H), 4.58 (t, J = 1.0 Hz, 2H), 4.46 (br. s., 1H), 3.48 (t, J = 6.5 Hz, 1H), 2.57 (br. s., 2H), 2.25-2.38 (m, 1H), 2.20 (br. s., 2H), 2.03 (dd, J = 12.7, 3.6 Hz, 2H), 1.74-1.88 (m, 2 H), 1.11 (d, J = 6.5 Hz, 3H), 0.82 (d, J = 6.8 Hz, 3H)

| Example/IUPAC name | Structure | MS calculated MS ESI [M + H]+ | Yield; Appearance; Salt form |
|---|---|---|---|
| A328: N-((S)-cyclopropyl(phenyl)methyl)-3-(4-(((1R,3R,5S)-8-formyl-8-azabicyclo[3.2.1]octan-3-yl)oxy)phenyl)-1H-indazole-5-carboxamide | 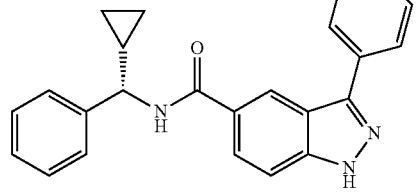 | [C32H32N4O3 + H]+ 521.3 521.3 | 20 mg (30%); white solid; free base |

SMs: (S)-N-(cyclopropyl(phenyl)methyl)-3-iodo-1H-indazole-5-carboxamide (53 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.63 (s, 1 H), 8.10 (s, 1 H), 7.97 (d, J = 9.0 Hz, 1 H), 7.89 (d, J = 8.5 Hz, 2 H), 7.59 (d, J = 8.8 Hz, 1 H), 7.47 (d, J = 1.5 Hz, 2 H), 7.31 (t, J = 7.5 Hz, 2 H), 7.21 (t, J = 1.0 Hz, 1 H), 6.97 (d, J = 8.5 Hz, 2 H), 4.72 (br. s, 1 H), 4.50-4.56 (m, 1 H), 4.47 (d, J = 9.5 Hz, 1 H), 4.14 (br. s, 1 H), 2.20-2.31 (m, 2 H), 2.02-2.19 (m, 4 H), 1.83-2.02 (m, 2 H), 1.32-1.44 (m, 1 H), 0.56-0.68 (m, 2 H), 0.37-0.50 (m, 2 H)

| Example/IUPAC name | Structure | MS calculated MS ESI [M + H]+ | Yield; Appearance; Salt form |
|---|---|---|---|
| A329: N-(cyclobutyl(thiophen-3-yl)methyl)-3-(4-(((1R,3R,5S)-8-formyl-8-azabicyclo[3.2.1]octan-3-yl)oxy)phenyl)-1H-indazole-5-carboxamide | 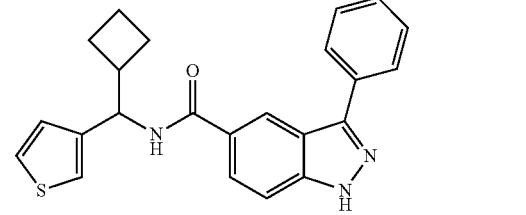 | [C31H32N4O3S + H]+ 541.2 541.3 | 17 mg (25%); white solid: free base |

SMs: N-(cyclobutyl(thiophen-3-yl)methyl)-3-iodo-1H-indazole-5-carboxamide (0.056 g, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (0.050 g, 0.14 mmol)

$^1$H NMR (400 MHz, CD$_3$OD) δ 8.56 (s, 1 H), 8.10 (s, 1 H), 7.85-7.95 (m, 3 H), 7.58 (d, J = 8.8 Hz, 1 H), 7.32 (dd, J = 4.8, 3.0 Hz, 1 H), 7.26 (s, 1 H), 7.12 (d, J = 5.0 Hz, 1 H), 6.98 (d, 7 = 8.8 Hz, 2 H), 5.27 (d, J = 10.5 Hz, 1 H), 4.74 (br. s., 1 H), 4.45-4.57 (m, 1 H), 4.15 (br. s., 1 H), 2.93 (d, J = 9.8 Hz, 1 H), 1.74-2.34 (m, 14 H)

| Example/IUPAC name | Structure | MS calculated MS ESI [M + H]+ | Yield; Appearance; Salt form |
|---|---|---|---|
| A330: N-(cyclobutyl(thiophen-3-yl)methyl)-3-(4-((1-formylpiperidin-4-yl)oxy)phenyl)-1H-indazole-5-carboxamide | | [$C_{29}H_{30}N_4O_3S$ + H]+ 515.2 515.3 | 19 mg (27%); white solid; free base |

SMs: N-(cyclobutyl(thiophen-3-yl)methyl)-3-iodo-1H-indazole-5-carboxamide (60 mg, 0.14 mmol), 4-(4-(4,4,5,5-tetramethyl-1,3,2-dioxaborolan-2-yl)phenoxy)piperidine-1-carbaldehyde (50 mg, 0.15 mmol)
$^1$H NMR (400 MHz, CD$_3$OD) δ 8.56 (d, J = 0.5 Hz, 1 H), 8.03 (s, 1 H), 7.85-7.94 (m, 4 H), 7.58 (d, J = 8.8 Hz, 1 H), 7.33 (dd, J = 4.9, 2.9 Hz, 1 H), 7.26 (d, J = 2.3 Hz, 1 H), 7.05-7.15 (m, 3 H), 5.27 (d, J = 10.3 Hz, 1 H), 4.71 (dt, J = 6.8, 3.5 Hz, 1 H), 3.61-3.80 (m, 2 H), 3.46-3.55 (m, 1 H), 3.36-3.45 (m, 1 H), 2.85-3.01 (m, 1 H), 2.08-2.23 (m, 1 H), 1.65-2.07 (m, 8 H)

| Example/IUPAC name | Structure | MS calculated MS ESI [M + H]+ | Yield; Appearance; Salt form |
|---|---|---|---|
| A331: N-(cyclobutyl(thiophen-3-yl)methyl)-3-(4-((1-(oxetan-3-yl)piperidin-4-yl)oxy)phenyl)-1H-indazole-5-carboxamide | | [$C_{31}H_{34}N_4O_3S$ +H]+ 543.3 543.4 | 16 mg (23%); white solid; free base |

SMs: N-(cyclobutyl(thiophen-3-yl)methyl)-3-iodo-1H-indazole-5-carboxamide (55 mg, 0.13 mmol), 1-(oxetan-3-yl)-4-(4-(4,4,5,5-tetramethyl-1,3,2-dioxaborolan-2-yl)phenoxy)piperidine (50 mg, 0.14 mmol)
$^1$H NMR (400 MHz, CD$_3$OD) δ ppm 8.56 (s, 1 H), 7.84-7.95 (m, 3 H), 7.58 (d, J = 8.8 Hz, 1 H), 7.32 (dd, J = 4.9, 2.9 Hz, 1 H), 7.25 (d, J = 1.8 Hz, 1 H), 7.12(dd, J = 5.0, 1.0 Hz, 1 H), 7.05(d, J = 8.8 Hz, 2 H), 5.26 (d, J = 10.3 Hz, 1 H), 4.64-4.72 (m, 2 H), 4.55-4.62 (m, 2 H), 4.46 (m, J = 3.3 Hz, 1 H), 3.49 (t, J = 6.4 Hz, 1 H), 2.86-3.01 (m, 1 H), 2.58 (br. s., 2 H), 2.10-2.27 (m, 3 H), 1.74-2.09 (m, 9 H)

| Example/IUPAC name | Structure | MS calculated MS ESI [M + H]+ | Yield; Appearance; Salt form |
|---|---|---|---|
| A332: (S)-N-(1-(2-chlorophenyl)-2-methylpropyl)-3-(4-((1-(oxetan-3-yl)piperidin-4-yl)oxy)phenyl)-1H-indazole-5-carboxamide | 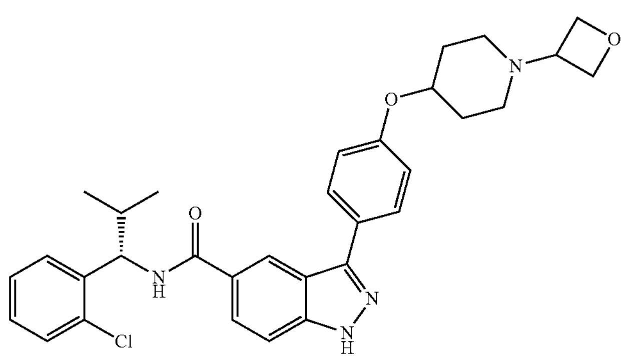 [SMILES: CC(C)[C@H](NC(=O)c1ccc2[nH]nc(-c3ccc(OC4CCN(C5COC5)CC4)cc3)c2c1)c1ccccc1Cl] | [$C_{32}H_{35}ClN_4O_3$ + H]+ 559.3 559.5 | 26 mg (39%); white solid; free base |

SMs: (S)-N-(1-(2-chlorophenyl)-2-methylpropyl)-3-iodo-1H-indazole-5-carboxamide (58 mg, 0.13 mmol), 1-(oxetan-3-yl)-4-(4-(4,4,5,5-tetramethyl-1,3,2-dioxaborolan-2-yl)phenoxy)piperidine (50 mg, 0.14 mmol)
$^1$H NMR (400 MHz, CD$_3$OD) δ 8.53 (s, 1 H), 7.76-7.90 (m, 3 H), 7.49-7.57 (m, 2 H), 7.36 (dd, J = 7.9, 1.1 Hz, 1 H), 7.14-7.29 (m, 2 H), 7.00 (d, J = 8.8 Hz, 2 H), 5.38 (d, J = 9.5 Hz, 1 H), 4.67 (t, J = 6.7 Hz, 2 H), 4.55-4.61 (m, 2H), 4.43 (d, J = 3.3 Hz, 1 H), 3.42-3.53 (m, 1 H), 2.55 (br. s., 2 H), 2.13-2.33 (m, 3 H), 2.00 (br. s., 2 H), 1.81 (br. s., 2 H), 1.14 (d, J = 6.8 Hz, 3 H), 0.85 (d, J = 6.8 Hz, 3 H)

| Example/IUPAC name | Structure | MS calculated MS ESI [M + H]+ | Yield; Appearance; Salt form |
|---|---|---|---|
| A333: N-((S)-1-2-chlorophenyl)-2-methylpropyl)-3-(4-(((1R,3R,5S)-8-formyl-8-azabicyclo[3.2.1]octan-3-yl)oxy)phenyl)-1H-indazole-5-carboxamide | 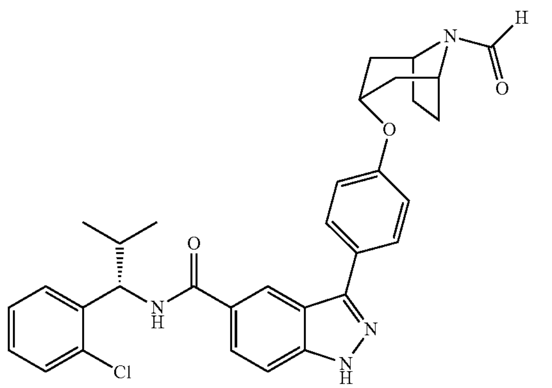 [SMILES: CC(C)[C@H](NC(=O)c1ccc2[nH]nc(-c3ccc(OC4CC5CCC(C4)N5C=O)cc3)c2c1)c1ccccc1Cl] | [C$_{32}$H$_{33}$ClN$_4$O$_3$ + H]+ 557.2 557.4 | 14 mg (%); white solid; free base |

SMs: (S)-N-(1-(2-chlorophenyl)-2-methylpropyl)-3-iodo-1H-indazole-5-carboxamide (58 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.53 (s, 1 H), 8.08 (s, 1 H), 7.88 (dd, J = 8.8, 1.5 Hz, 1 H), 7.81 (dd, J = 8.7, 1.4 Hz, 2 H), 7.50-7.58 (m, 2 H), 7.34 (dd, J = 8.0, 1.0 Hz, 1 H), 7.21-7.27 (m, 1 H), 7.13-7.20 (m, 1 H), 6.88 (dd, J = 8.9, 2.1 Hz, 2 H), 5.39 (d, J = 9.8 Hz, 1 H), 4.65 (br. s., 1 H), 4.49 (d, J = 3.0 Hz, 1 H), 4.10 (d, J = 3.0 Hz, 1 H), 1.78-2.34 (m, 9 H), 1.13 (d, J = 6.5 Hz, 3 H), 0.83 (d, J = 6.8 Hz, 3H)

| Example/IUPAC name | Structure | MS calculated MS ESI [M + H]+ | Yield; Appearance; Salt form |
|---|---|---|---|
| A334: (S)-N-(1-(2-chlorophenyl)-2-methylpropyl)-3-(4-((1-formylpiperidin-4-yl)oxy)phenyl)-1H-indazole-5-carboxamide | 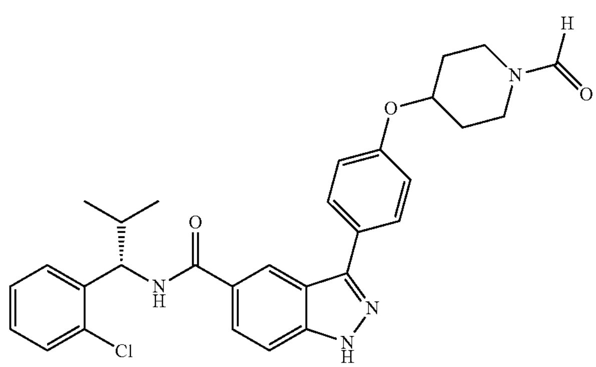 [SMILES: CC(C)[C@H](NC(=O)c1ccc2[nH]nc(-c3ccc(OC4CCN(C=O)CC4)cc3)c2c1)c1ccccc1Cl] | [C$_{30}$H$_{31}$ClN$_4$O$_3$ + H]+ 531.2 531.4 | 28 mg (38%); white solid; free base |

SMs: (S)-N-(1-(2-chlorophenyl)-2-methylpropyl)-3-iodo-1H-indazole-5-carboxamide (62 mg, 0.14 mmol), 4-(4-(4,4,5,5-tetramethyl-1,3,2-dioxaborolan-2-yl)phenoxy)piperidine-1-carbaldehyde (50 mg, 0.15 mmol)

$^1$H NMR (400 MHz, CD$_3$OD) δ ppm 8.51 (s, 1 H), 8.00 (s, 1 H), 7.77-7.90 (m, 3 H), 7.49-7.58 (m, 2 H), 7.34 (d, J = 7.8 Hz, 1 H), 7.20-7.28 (m, 1 H), 7.14-7.20 (m, 1 H), 7.01 (d, J = 8.3 Hz, 2 H), 5.39 (d, J = 9.8 Hz, 1 H), 4.63 (dt, J = 6.6, 3.4 Hz, 1 H), 3.56-3.74 (m, 2 H), 3.43-3.52 (m, 1 H), 3.34-3.40 (m, 1 H), 2.26 (dt, J = 9.5, 6.8 Hz, 1 H), 1.82-2.00 (m, 2 H), 1.62-1.81 (m, 2 H), 1.14 (d, J = 6.8 Hz, 3 H), 0.84 (d, J = 6.8 Hz, 3 H)

| Example/IUPAC name | Structure | MS calculated MS ESI [M + H]+ | Yield; Appearance; Salt form |
|---|---|---|---|
| A335: N-((S)-1-2-chlorophenyl)-2-methylpropyl)-3-(4-(((1R,3R,5S)-8-(oxetan-3-yl)-8-azabicyclo[3.2.1]octan-3-yl)oxy)phenyl)-1H-indazole-5-carboxamide | 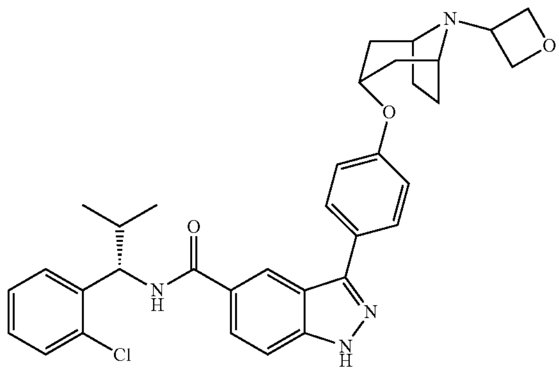 | [C$_{34}$H$_{37}$ClN$_4$O$_3$ + H]$^+$ 585.3 585.5 | 24 mg (38%); white solid; free base |

SMs: (S)-N-(1-(2-chlorophenyl)-2-methylpropyl)-3-iodo-1H-indazole-5-carboxamide (54 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

$^1$H NMR (400 MHz, CD$_3$OD) δ 8.54 (s, 1 H), 7.88 (dd, J = 8.9, 1.4 Hz, 1 H), 7.83 (d, J = 8.8 Hz, 2 H), 7.51-7.60 (m, 2 H), 7.36 (dd, J = 7.8, 1.0 Hz, 1 H), 7.23-7.30 (m, 1 H), 7.16-7.22 (m, 1 H), 6.90 (d, J = 8.8 Hz, 2 H), 5.38 (d, J = 9.8 Hz, 1 H), 4.70 (t, J = 6.4 Hz, 2 H), 4.58 (t, J = 4.6 Hz, 1 H), 4.51 (t, J = 5.8 Hz, 2 H), 3.74 (t, J = 6.0 Hz, 1 H), 3.05 (br. s., 2 H), 2.26 (dt, J = 9.8, 6.7 Hz, 1 H), 2.04-2.16 (m, 4 H), 1.82-1.98 (m, 4 H), 1.14 (d, J = 6.5 Hz, 3 H), 0.85 (d, J = 6.8 Hz, 3 H)

| Example/IUPAC name | Structure | MS calculated MS ESI [M + H]+ | Yield; Appearance; Salt form |
|---|---|---|---|
| A336: N-((S)-cyclopropyl(phenyl)methyl)-3-(4-(((1R,3R,5S)-8-(oxetan-3-yl)-8-azabicyclo[3.2.1]octan-3-yl)oxy)phenyl)-1H-indazole-5-carboxamide | 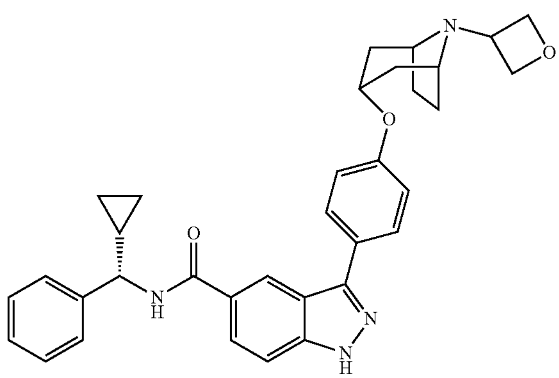 [SMILES: O=C(N[C@H](c1ccccc1)C1CC1)c1ccc2[nH]nc(-c3ccc(OC4CC5CCC(C4)N5C4COC4)cc3)c2c1] | [C$_{34}$H$_{36}$N$_4$O$_3$ + H]$^+$ 549.3 549.4 | 18 mg (28%); white solid; free base |

SMs: (S)-N-(cyclopropyl(phenyl)methyl)-3-iodo-1H-indazole-5-carboxamide (49 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

$^1$H NMR (400 MHz, CD$_3$OD) δ ppm 8.64 (s, 1 H), 7.97 (dd, J = 8.8, 1.5 Hz, 1 H), 7.87 (d, J = 8.8 Hz, 2 H), 7.58 (d, J = 8.8 Hz, 1 H), 7.46 (d, J = 7.5 Hz, 2 H), 7.29 (t, J = 7.5 Hz, 2 H), 7.16-7.24 (m, 1 H), 6.90 (d, J = 8.8 Hz, 2 H), 4.68 (t, J = 6.4 Hz, 2 H), 4.55 (t, J = 4.8 Hz, 1 H), 4.43-4.51 (m, 3 H), 3.70 (quin, J = 6.0 Hz, 1 H), 3.02 (br. s., 2 H), 2.02-2.14 (m, 4 H), 1.81-1.95 (m, 4 H), 1.37 (ddd, J = 12.7, 8.1, 4.5 Hz, 1 H), 0.54-0.68 (m, 2 H), 0.34-0.50 (m, 2 H)

| Example/IUPAC name | Structure | MS calculated MS ESI [M + H]⁺ | Yield; Appearance; Salt form |
|---|---|---|---|
| A337: N-((S)-1-(2-chlorophenyl)-2-methylpropyl)-3-(4-(((1R,3R,5S)-8-(2-hydroxyethyl)-8-azabicyclo[3.2.1]octan-3-yl)oxy)phenyl)-1H-indazole-5-carboxamide | 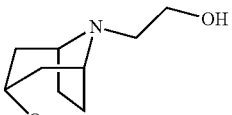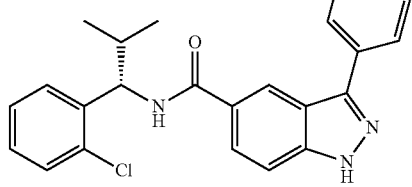 | [C₃₃H₃₇ClN₄O₃ + H]⁺ 573.3 573.5 | 28 mg (29%); white solid; free base |

SMs: (S)-N-(1-(2-chlorophenyl)-2-methylpropyl)-3-iodo-1H-indazole-5-carboxamide (77 mg, 0.17 mmol), 2-((1R,3R,5S)-3-(4-(4,4,5,5-tetramethyl-1,3,2-dioxaborolan-2-yl)phenoxy)-8-azabicyclo[3.2.1]octan-8-yl)EtOH (70 mg, 0.19 mmol)

¹H NMR (400 MHz, CD₃OD) δ ppm 8.53 (s, 1 H), 7.87 (dd, J = 8.8, 1.5 Hz, 1 H), 7.81 (d, J = 8.8 Hz, 2 H) 7.48-7.59 (m, 2 H), 7.35 (dd, J = 8.0, 1.0 Hz, 1 H), 7.21-7.29 (m, 1 H), 7.12-7.21 (m, 1 H), 6.88 (d, J = 8.8 Hz, 2 H), 5.38 (d, J = 9.8 Hz, 1 H), 4.55 (t, J = 4.9 Hz, 1 H), 3.68 (t, J = 6.3 Hz, 2 H), 3.26 (br. s., 2 H), 2.57 (t, J = 6.1 Hz, 2 H), 2.19-2.32 (m, 1 H), 2.05 -2.18 (m, 4H), 1.80-2.01 (m, 4 H), 1.13 (d, J = 6.8 Hz, 3 H), 0.84 (d, J = 6.8 Hz, 3 H)

| Example/IUPAC name | Structure | MS calculated MS ESI [M + H]⁺ | Yield; Appearance; Salt form |
|---|---|---|---|
| A338: N-(3-methyl-1-phenylbutyl)-3-(4-(((1R,3R,5S)-8-(oxetan-3-yl)-8-azabicyclo[3.2.1]octan-3-yl)oxy)phenyl)-1H-indazole-5-carboxamide | 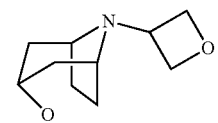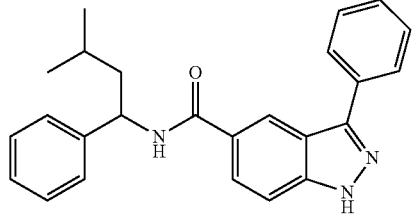 | [C₃₅H₄₀N₄O₃ + H]⁺ 565.3 565.5 | 27 mg (40%); white solid; free base |

SMs: 3-iodo-N-(3-methyl-1-phenylbutyl)-1H-indazole-5-carboxamide (51 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

¹H NMR (400 MHz, CD₃OD) δ ppm 8.59 (s, 1 H), 7.93 (dd, J = 8.8, 1.5 Hz, 1 H), 7.86 (d, J = 8.8 Hz, 2 H), 7.56 (d, J = 8.8 Hz, 1 H), 7.41 (d, J = 7.3 Hz, 2 H), 7.29 (t, J = 7.5 Hz, 2 H), 7.14-7.24 (m, 1 H), 6.91 (d, J = 8.8 Hz, 2 H), 5.26 (dd, J = 9.3, 5.5 Hz, 1 H), 4.68 (t, J = 6.4 Hz, 2 H), 4.56 (t, J = 4.8 Hz, 1 H), 4.49 (t, J = 5.8 Hz, 2 H), 3.71 (t, J = 6.1 Hz, 1 H), 3.02 (br. s., 2 H), 2.01-2.15 (m, 4 H), 1.79-1.96 (m, 5 H), 1.56-1.73 (m, 2 H), 0.97 (d, J = 6.0 Hz, 6 H)

| Example/IUPAC name | Structure | MS calculated MS ESI [M + H]+ | Yield; Appearance; Salt form |
|---|---|---|---|
| A339: 3-(4-(((1R,3R,5S)-8-formyl-8-azabicyclo[3.2.1]octan-3-yl)oxy)phenyl)-N-(3-methyl-1-(pyridin-2-yl)butyl)-1H-indazole-5-carboxamide | 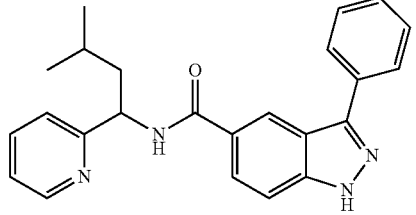 | $[C_{32}H_{35}N_5O_3 + H]^+$ 538.3 538.4 | 32 mg (47%); white solid; free base |

SMs: 3-iodo-N-(3-methyl-1-(pyridin-2-yl)butyl)-1H-indazole-5-carboxamide (55 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.65 (s, 1 H), 8.49 (d, J = 5.0 Hz, 1 H), 8.08 (s, 1 H), 7.97 (dd, J = 8.8, 1.5 Hz, 1 H), 7.86-7.90 (m, 2 H), 7.71-7.78 (m, 1 H), 7.59 (d, J = 8.8 Hz, 1 H), 7.47 (d, J = 7.8 Hz, 1 H), 7.20-7.29 (m, 1 H), 6.86-6.98 (m, 2 H), 5.36 (dd, J = 9.8, 5.3 Hz, 1 H), 4.68 (br. s., 1 H), 4.50 (br. s., 1 H), 4.11 (br. s., 1 H), 2.15-2.29 (m, 2 H), 1.97-2.15 (m, 4 H), 1.81-1.97 (m, 3 H), 1.62-1.81 (m, 2 H), 0.91-1.06 (m, 6 H)

| Example/IUPAC name | Structure | MS calculated MS ESI [M + H]+ | Yield; Appearance; Salt form |
|---|---|---|---|
| A340: 3-(4-(((1R,3R,5S)-8-formyl-8-azabicyclo[3.2.1]octan-3-yl)oxy)phenyl)-N-(3-methyl-1-phenylbutyl)-1H-indazole-5-carboxamide | 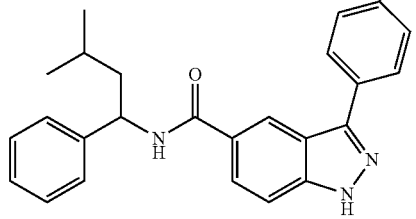 | $[C_{33}H_{36}N_4O_3 + H]^+$ 537.3 537.5 | 33 mg (49%); white solid; free base |

SMs: 3-iodo-N-(3-methyl-1-phenylbutyl)-1H-indazole-5-carboxamide (55 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.59 (s, 1 H), 8.07 (s, 1 H), 7.93 (dd, J = 8.8, 1.3 Hz, 1 H), 7.85 (d, J = 8.5 Hz, 2 H), 7.56 (d, J = 9.0 Hz, 1 H), 7.41 (d, J = 7.5 Hz, 2 H), 7.28 (t, J = 7.7 Hz, 2 H), 7.14-7.22 (m, 1 H), 6.91 (d, J = 8.5 Hz, 2 H), 5.26 (dd, J = 9.2, 5.6 Hz, 1 H), 4.65 (br. s., 1 H), 4.45-4.53 (m, 1 H), 4.09 (br. s., 1 H), 2.15-2.27 (m, 2 H), 1.80-2.14 (m, 7 H), 1.57-1.73 (m, 2 H), 0.96 (d, J = 5.8 Hz, 6 H)

| Example/IUPAC name | Structure | MS calculated MS ESI [M + H]+ | Yield; Appearance; Salt form |
|---|---|---|---|
| A341: N-(2-ethyl-1-(pyridin-2-yl)butyl)-3-(4-(((1R,3R,5S)-8-(oxetan-3-yl)-8-azabicyclo[3.2.1]octan-3-yl)oxy)phenyl)-1H-indazole-5-carboxamide | 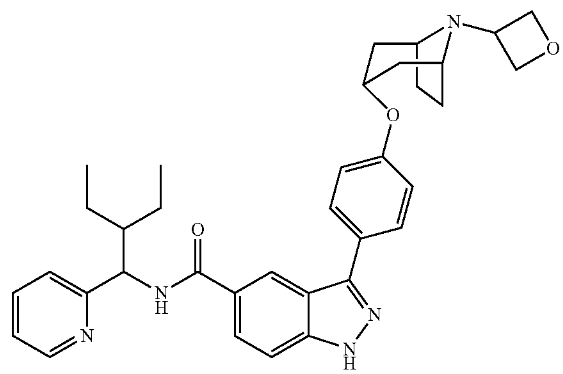 [SMILES: CCC(CC)C(NC(=O)c1ccc2[nH]nc(-c3ccc(OC4CC5CCC(C4)N5C4COC4)cc3)c2c1)c1ccccn1] | [C$_{35}$H$_{41}$N$_5$O$_3$ + H]+ 580.3 580.3 | 27 mg (40%); white solid; free base |

SMs: N-(2-ethyl-1-(pyridin-2-yl)butyl)-3-iodo-1H-indazole-5-carboxamide (53 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

$^1$H NMR (400 MHz, CD$_3$OD) δ ppm 8.59 (s, 1 H), 8.53 (d, J = 4.0 Hz, 1 H), 7.92 (dd, J = 8.8, 1.5 Hz, 1 H), 7.87 (d, J = 8.5 Hz, 2 H), 7.75 (td, J = 7.7, 1.8 Hz, 1 H), 7.59 (d, J = 9.0 Hz, 1 H), 7.47 (d, J = 7.8 Hz, 1 H), 7.27 (dd, J = 6.9, 5.1 Hz, 1 H), 6.93 (d, J = 8.8 Hz, 2 H), 5.28 (d, J = 8.8 Hz, 1 H), 4.67 (t, J = 6.3 Hz, 2 H), 4.58 (t, J = 4.8 Hz, 1 H), 4.48 (t, J = 5.8 Hz, 2 H), 3.70 (quin, J = 6.0 Hz, 1 H), 3.02 (br. s., 2 H), 1.99-2.14 (m, 5 H), 1.79-1.96 (m, 4 H), 1.46-1.69 (m, 2 H), 1.16-1.28 (m, 2 H), 0.90 (t, J = 7.4 Hz, 3 H), 0.84 (t, J = 7.4 Hz, 3 H)

| Example/IUPAC name | Structure | MS calculated MS ESI [M + H]+ | Yield; Appearance; Salt form |
|---|---|---|---|
| A342: N-(2-ethyl-1-(pyridin-2-yl)butyl)-3-(4-(((1R,3R,5S)-8-formyl-8-azabicyclo[3.2.1]octan-3-yl)oxy)phenyl)-1H-indazole-5-carboxamide | 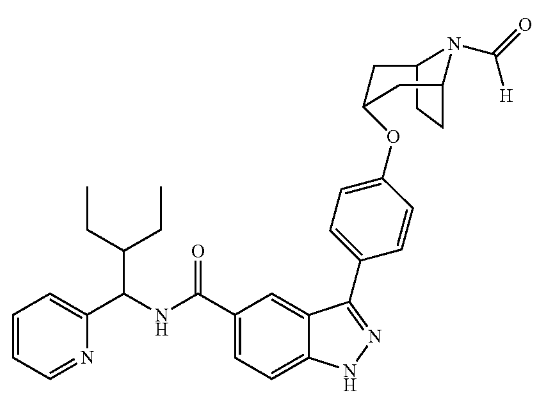 [SMILES: CCC(CC)C(NC(=O)c1ccc2[nH]nc(-c3ccc(OC4CC5CCC(C4)N5C=O)cc3)c2c1)c1ccccn1] | [C$_{33}$H$_{37}$N$_5$O$_3$ + H]+ 552.3 552.5 | 30 mg (43%); white solid; free base |

SMs: N-(2-ethyl-1-(pyridin-2-yl)butyl)-3-iodo-1H-indazole-5-carboxamide (57 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.59 (s, 1 H), 8.53 (d, J = 5.0 Hz, 1 H), 8.09 (s, 1 H), 7.85-7.96 (m, 3 H), 7.77 (td, J = 7.7, 1.6 Hz, 1 H), 7.59 (d, J = 8.8 Hz, 1 H), 7.48 (d, J = 7.8 Hz, 1 H), 7.28 (dd, J = 7.5, 5.0 Hz, 1 H), 6.98 (d, J = 8.8 Hz, 2 H), 5.28 (d, J = 8.8 Hz, 1 H), 4.72 (br. s., 1 H), 4.47-4.56 (m, 1 H), 4.14 (br. s., 1 H), 2.19-2.32 (m, 2 H), 1.99-2.18 (m, 5 H), 1.83-1.99 (m, 2 H), 1.43-1.70 (m, 2 H), 1.14-1.30 (m, 2 H), 0.91 (t, J = 7.4 Hz, 3 H) 0.85 (t, J = 7.4 Hz, 3 H)

| Example/IUPAC name | Structure | MS calculated MS ESI [M + H]+ | Yield; Appearance; Salt form |
|---|---|---|---|
| A343: 3-(4-(((1R,3R,5S)-8-formyl-8-azabicyclo[3.2.1]octan-3-yl)oxy)phenyl)-N-((S)-1-phenylbutyl)-1H-indazole-5-carboxamide | 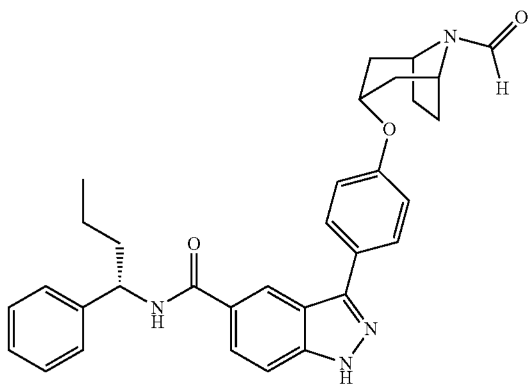 [SMILES: CCC[C@H](NC(=O)c1ccc2[nH]nc(-c3ccc(OC4CC5CCC(C4)N5C=O)cc3)c2c1)c1ccccc1] | [C₃₂H₃₄N₄O₃ + H]+ 523.3 523.5 | 27 mg (41%); white solid; free base |

SMs: (S)-3-iodo-N-(1-phenylbutyl)-1H-indazole-5-carboxamide (53 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

¹H NMR (400 MHz, CD₃OD) δ ppm 8.60 (s, 1 H), 8.07 (s, 1 H), 7.94 (dd, J = 8.8, 1.5 Hz, 1 H), 7.85 (d, J = 8.5 Hz, 2 H), 7.56 (d, J = 9.0 Hz, 1 H), 7.40 (d, J = 7.3 Hz, 2 H), 7.28 (t, J = 7.5 Hz, 2 H), 7.16-7.22 (m, 1 H), 6.91 (d, J = 8.5 Hz, 2 H), 5.13 (dd, J = 8.7, 6.7 Hz, 1 H), 4.65 (br. s., 1 H), 4.49 (d, J = 3.8 Hz, 1 H), 4.10(br. s., 1 H),2.21 (t, J = 7.4 Hz, 2 H), 1.74-2.14 (m, 8 H), 1.22- 1.52 (m, 2 H), 0.89-0.96 (m, 3 H)

| Example/IUPAC name | Structure | MS calculated MS ESI [M + H]+ | Yield; Appearance; Salt form |
|---|---|---|---|
| A344: 3-(4-(((1R,3R,5S)-8-(oxetan-3-yl)-8-azabicyclo[3.2.1]octan-3-yl)oxy)phenyl)-N-((S)-1-phenylbutyl)-1H-indazole-5-carboxamide | 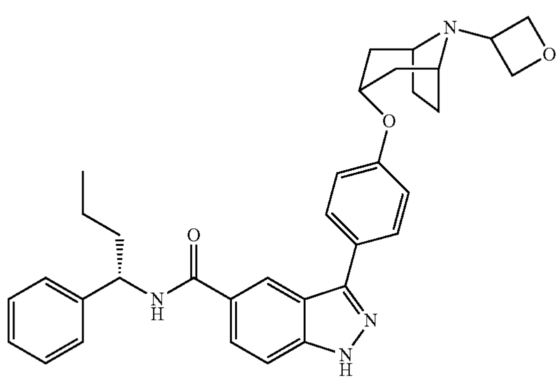 [SMILES: CCC[C@H](NC(=O)c1ccc2[nH]nc(-c3ccc(OC4CC5CCC(C4)N5C4COC4)cc3)c2c1)c1ccccc1] | [C₃₄H₃₈N₄O₃ + H]+ 551.3 551.5 | 27 mg (42%); white solid; free base |

SMs: (S)-3-iodo-N-(1-phenylbutyl)-1H-indazole-5-carboxamide (49 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

¹H NMR (400 MHz, CD₃OD) δ ppm 8.62 (s, 1 H), 7.94 (d, J = 8.8 Hz, 1 H), 7.84 (d, J = 8.5 Hz, 2 H), 7.55 (d, J = 8.8 Hz, 1 H), 7.39 (d, J = 1.5 Hz, 2 H), 7.28 (t, J = 7.5 Hz, 2 H), 7.15-7.22 (m, 1 H), 6.86 (d, J = 8.5 Hz, 2 H), 5.13 (t, J = 7.7 Hz, 1 H), 4.65 (t, J = 6.4 Hz, 2 H), 4.40-4.54 (m, 3 H), 3.67 (quin, J = 5.9Hz, 1 H), 2.98 (br. s., 2 H), 1.99-2.09 (m, 4 H), 1.71-1.98 (m, 6 H), 1.21-1.51 (m, 2 H), 0.92 (t, J = 7.3 Hz, 3 H)

| Example/IUPAC name | Structure | MS calculated MS ESI [M + H]+ | Yield; Appearance; Salt form |
|---|---|---|---|
| A345: N-(cyclobutyl(phenyl)methyl)-3-(4-(((1R,3R,5S)-8-(oxetan-3-yl)-8-azabicyclo[3.2.1]octan-3-yl)oxy)phenyl)-1H-indazole-5-carboxamide | 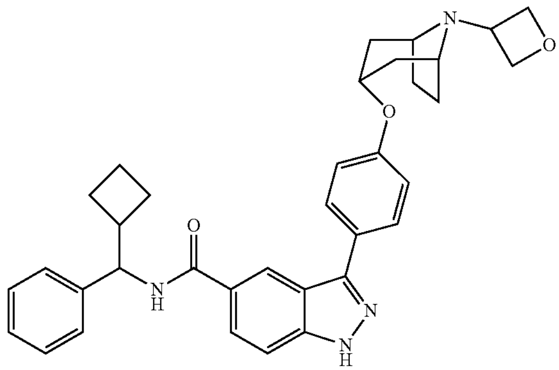 [SMILES: O=C(NC(c1ccccc1)C1CCC1)c1ccc2[nH]nc(-c3ccc(OC4CC5CCC(C4)N5C4COC4)cc3)c2c1] | [C$_{35}$H$_{38}$N$_4$O$_3$ + H]+ 563.3 563.5 | 31 mg (47%); white solid; free base |

SMs: N-(cyclobutyl(phenyl)methyl)-3-iodo-1H-indazole-5-carboxamide (51 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

$^1$H NMR (400 MHz, CD$_3$OD) δ ppm 8.58 (s, 1 H), 7.92 (dd, J = 8.8, 1.5 Hz, 1 H), 7.83 (d, J = 8.5 Hz, 2 H), 7.55 (d, J = 9.0 Hz, 1 H), 7.37 (d, J = 7.3 Hz, 2 H), 7.25 (t, J = 7.5 Hz, 2 H), 7.11-7.20 (m, 1 H), 6.85 (d, J = 8.8 Hz, 2 H), 5.08 (d, J = 10.8 Hz, 1 H), 4.66 (t, J = 6.4 Hz, 2 H), 4.42-4.55 (m, 3 H), 3.67 (quin, J = 6.0 Hz, 1 H), 2.98 (br. s., 2 H), 2.80-2.93 (m, 1 H), 2.11-2.21 (m, 1 H), 1.98-2.09 (m, 4 H), 1.69-1.95 (m, 9H)

| Example/IUPAC name | Structure | MS calculated MS ESI [M + H]+ | Yield; Appearance; Salt form |
|---|---|---|---|
| A346: N-(cyclobutyl(phenyl)methyl)-3-(4-(((1R,3R,5S)-8-formyl-8-azabicyclo[3.2.1]octan-3-yl)oxy)phenyl)-1H-indazole-5-carboxamide | 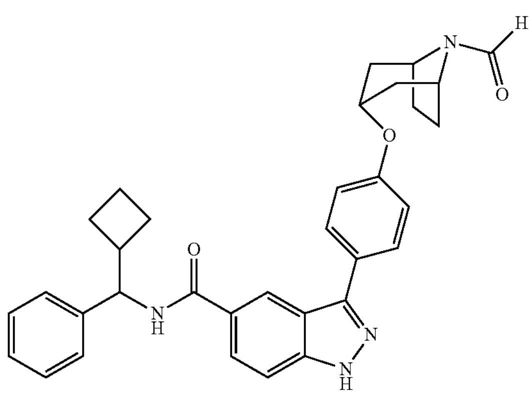 [SMILES: O=CN1C2CCC1CC(Oc1ccc(-c3n[nH]c4ccc(C(=O)NC(c5ccccc5)C5CCC5)cc34)cc1)C2] | [C$_{33}$H$_{34}$N$_4$O$_3$ + H]+ 535.3 535.3 | 26 mg (43%); white solid; free base |

SMs: N-(cyclobutyl(phenyl)methyl)-3-iodo-1H-indazole-5-carboxamide (55 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.57 (s, 1 H), 8.07 (s, 1 H), 7.92 (dd, J = 8.8, 1.3 Hz, 1 H), 7.84 (d, J = 8.5 Hz, 2 H), 7.56 (d, J = 8.8 Hz, 1 H), 7.38 (d, J = 7.5 Hz, 2 H), 7.26 (t, J = 1.5 Hz, 2 H), 7.12-7.22 (m, 1 H), 6.91 (d, J = 8.5 Hz, 2 H), 5.08 (d, J = 10.5 Hz, 1 H), 4.66 (br. s., 1 H), 4.44-4.53 (m, 1 H), 4.10 (br. s., 1 H), 2.80-2.95 (m, 1 H), 1.65-2.29 (m, 14 H)

| Example/IUPAC name | Structure | MS calculated MS ESI [M + H]+ | Yield; Appearance; Salt form |
|---|---|---|---|
| A347: N-((S)-cyclopentyl(pyridin-2-yl)methyl)-3-(4-(((1R,3R,5S)-8-(oxetan-3-yl)-8-azabi-cyclo[3.2.1]octan-3-yl)oxy)phenyl)-1H-indazole-5-carboxamide | 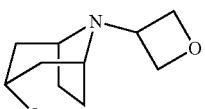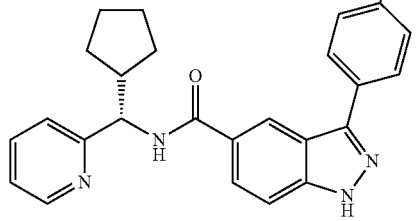 | [C35H39N5O3 + H]+ 578.3 578.4 | 36 mg (53%); white solid; free base |

SMs: (S)-N-(cyclopentyl(pyridin-2-yl)methyl)-3-iodo-1H-indazole-5-carboxamide (53 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

$^1$H NMR (400 MHz, CD$_3$OD) δ ppm 8.63 (s, 1 H), 8.49 (d, J = 4.8 Hz, 1 H), 7.93 (d, J = 8.8 Hz, 1 H), 7.84 (d, J = 8.8 Hz, 2 H), 7.72 (t, J = 7.7 Hz, 1 H), 7.56 (d, J = 8.8 Hz, 1 H), 7.46 (d, J = 7.8 Hz, 1 H), 7.24 (dd, J = 7.4, 5.1 Hz, 1 H), 6.85 (d, J = 8.8 Hz, 2 H), 5.01 (d, J = 10.3 Hz, 1 H), 4.64 (t, J = 6.4 Hz, 2 H), 4.40-4.54 (m, 3 H), 3.65 (quin, J = 6.0 Hz, 1 H), 2.96 (br. s., 2 H), 2.51 (dq, J = 16.9, 8.3 Hz, 1 H), 1.74-2.08 (m, 9 H), 1.40-1.69 (m, 5 H), 1.14-1.36 (m, 2 H)

| Example/IUPAC name | Structure | MS calculated MS ESI [M + H]+ | Yield; Appearance; Salt form |
|---|---|---|---|
| A348: N-((S)-cyclopentyl(pyridin-2-yl)methyl)-3-(4-(((1R,3R,5S)-8-formyl-8-azabi-cyclo[3.2.1]octan-3-yl)oxy)phenyl)-1H-indazole-5-carboxamide | 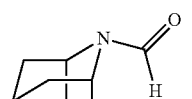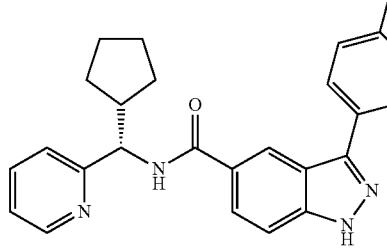 | [C33H35N5O3 + H]+ 550.3 550.3 | 42 mg (60%); while solid; free base |

SMs: (S)-N-(cyclopentyl(pyridin-2-yl)methyl)-3-iodo-1H-indazole-5-carboxamide (57 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.62 (s, 1 H), 8.50 (d, J = 4.5 Hz, 1 H), 8.06 (s, 1 H), 7.93 (dd, J = 8.8, 1.3 Hz, 1 H), 7.84 (d, J = 8.8 Hz, 2 H), 7.73 (td, J = 7.7, 1.6 Hz, 1 H), 7.57 (d, J = 8.8 Hz, 1 H), 7.47 (d, J = 7.8 Hz, 1 H), 7.24 (dd, J = 6.5, 5.0 Hz, 1 H), 6.88 (d, J = 8.5 Hz, 2 H), 5.02 (d, J = 10.3 Hz, 1 H), 4.63 (br. s., 1 H), 4.48 (d, J = 3.3 Hz, 1 H), 4.08 (br. s., 1 H), 2.59-2.43 (m, 1 H), 2.12-2.25 (m, 2 H), 1.79-2.11 (m, 7 H), 1.40-1.70 (m, 5 H), 1.12-1.37 (m, 2 H)

| Example/IUPAC name | Structure | MS calculated MS ESI [M + H]+ | Yield; Appearance; Salt form |
| --- | --- | --- | --- |
| A349: N-((S)-(2-chlorophenyl)(cyclo-propyl)methyl)-3-(4-(((1R,3R,5S)-8-(oxetan-3-yl)-8-azabicyclo[3.2.1]octan-3-yl)oxy)phenyl)-1H-indazole-5-carboxamide | | [C₃₄H₃₅ClN₄O₃ +H]+ 583.3 583.3 | 17 mg (25%); white solid; free base |

SMs: (S)-N-((2-chlorophenyl)(cyclopropyl)methyl)-3-iodo-1H-indazole-5-carboxamide (53 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)
$^1$H NMR (400 MHz, CD$_3$OD) δ ppm 8.58 (s, 1H), 7.92 (dd, J = 8.9, 1.1 Hz, 1H), 7.86 (d, J = 8.8 Hz, 2 H), 7.65 (d, J = 6.3 Hz, 1H), 7.57(d, J = 8.8 Hz, 1H), 7.35(d, J = 7.5 Hz, 1H), 7.24-7.30 (m, 1H,) 7.16-7.23 (m, 1H), 6.93 (d, J = 8.8 Hz, 2H), 5.00 (d, J = 8.8 Hz, 1H), 4.71 (t, J = 6.4 Hz, 2H), 4.59 (t, J = 4.6 Hz, 1H), 4.51 (t, J = 5.8 Hz, 2H), 3.75 (quin, J = 6.0 Hz, 1H), 3.06 (br. s., 2H), 2.04-2.17 (m, 4H), 1.83-1.98 (m, 4H), 1.41 (td, J = 8.4, 4.5 Hz, 1H), 0.60-0.69 (m, 1H), 0.45-0.57 (m, 3H)

| Example/IUPAC name | Structure | MS calculated MS ESI [M + H]+ | Yield; Appearance; Salt form |
| --- | --- | --- | --- |
| A350: N-((S)-(2-chlorophenyl)(cyclo-propyl)methyl)-3-(4-(((1R,3R,5S)-8-formyl-8-azabicyclo[3.2.1]octan-3-yl)oxy)phenyl)-1H-indazole-5-carboxamide | | [C₃₂H₃₁ClN₄O₃ + H]+ 555.2 555.4 | 20 mg (28%); white solid; free base |

SMs: (S)-N-((2-chlorophenyl)(cyclopropyl)methyl)-3-iodo-1H-indazole-5-carboxamide (58 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)
$^1$H NMR (400 MHz, CD$_3$OD) δ ppm 8.59 (s, 1 H), 8.07 (s, 1 H), 7.93 (dd, J = 8.8, 1.3 Hz, 1 H), 7.83 (d, J = 8.8 Hz, 2 H), 7.63 (d, J = 6.8 Hz, 1 H), 7.55 (d, J = 8.8 Hz, 1 H), 7.31 (d, J = 7.8 Hz, 1 H), 7.20-7.26 (m, 1 H), 7.11-7.19 (m, 1 H), 6.88 (d, J = 8.8 Hz, 2 H), 5.00 (d, J = 9.0 Hz, 1 H), 4.63 (br. s., 1 H), 4.43-4.53 (m, 1 H), 4.09 (br. s., 1 H), 2.14-2.26 (m, 2 H), 1.76-2.13 (m, 6 H), 1.31-1.48 (m, 1 H), 0.57-0.66 (m, 1 H), 0.40-0.55 (m, 3 H)

| Example/IUPAC name | Structure | MS calculated MS ESI [M + H]+ | Yield; Appearance; Salt form |
|---|---|---|---|
| A351: (S)-N-(cyclopropyl(pyridin-2-yl)methyl)-3-(4-(4-(2-hydroxypropan-2-yl)piperidin-1-yl)phenyl)-1H-indazole-5-carboxamide | 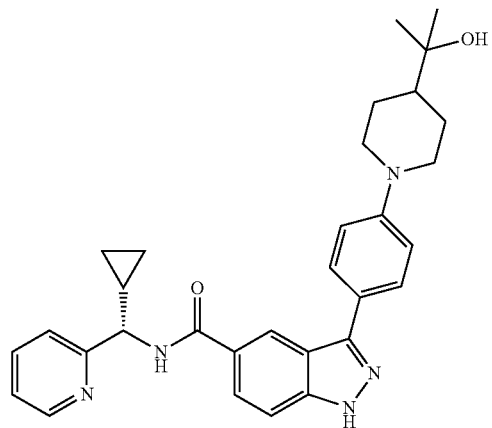 | [C31H35N5O2 + H]+ 510.3 510.4 | 34 mg (60%); white solid; TFA salt |

SMs: (S)-N-(yclopropyl(pyridin-2-yl)methyl)-3-iodo-1H-indazole-5-carboxamide (47 mg, 0.112 mmol), 4-(tert-butyl)-1-(4-(4,4,5,5-tetramethyl-1,3,2-dioxaborolan-2-yl)phenyl)piperidine (42 mg, 0.123 mmol)

$^1$H NMR (400 MHz, CD$_3$OD) δ ppm 8.79 (d, J = 5.8 Hz, 1 H), 8.75 (s, 1 H), 8.53-8.62 (m, 1 H), 8.18-8.31 (m, 3 H), 8.02 (dd, J = 8.9, 1.1 Hz, 1 H), 7.96 (t, J = 6.5 Hz, 1 H),7.85 (d, J = 8.8 Hz, 2 H), 7.68 (d, J = 8.8 Hz, 1 H),4.52 (d, J = 10.3 Hz, 1 H), 3.77-3.87 (m, 2 H), 3.63-3.76 (m, 2 H), 2.20 (d, J = 13.8 Hz, 2 H), 1.74-2.02 (m, 3 H), 1.46-1.62 (m, 1 H), 1.26 (s, 6 H), 0.85-0.96 (m, 1 H), 0.60-0.81 (m, 3 H)

| Example/IUPAC name | Structure | MS calculated MS ESI [M + H]+ | Yield; Appearance; Salt form |
|---|---|---|---|
| A352: N-((R)-cyclopropyl(pyridin-2-yl)methyl)-3-(4-(((1R,3R,5S)-8-(oxetan-3-yl)-8-azabicyclo[3.2.1]octan-3-yl)oxy)phenyl)-1H-indazole-5-carboxamide | 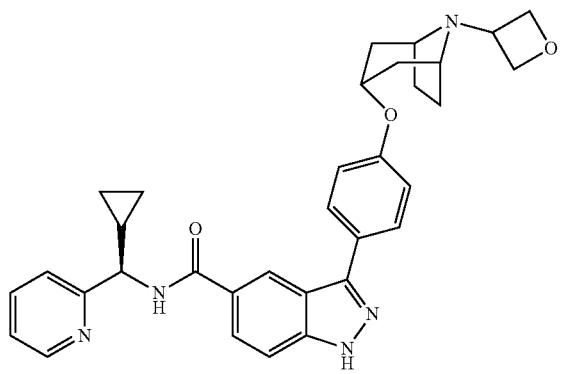 [SMILES: O=C(N[C@@H](c1ccccn1)C1CC1)c1ccc2[nH]nc(-c3ccc(OC4CC5CCC(C4)N5C4COC4)cc3)c2c1] | [C33H35N5O3 + H]+ 550.3 550.3 | 21 mg (32%); white solid; free base |

SMs: (R)-N-(cyclopropyl(pyridin-2-yl)methyl)-3-iodo-1H-indazole-5-carboxamide (49 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)

$^1$H NMR (400 MHz, CD$_3$OD) δ ppm 8.66 (s, 1 H), 8.50 (d, J = 4.3 Hz, 1 H), 7.96 (dd, J = 8.9, 1.1 Hz, 1 H), 7.90 (d, J = 8.5 Hz, 2 H), 7.78 (d, J = 1.5 Hz, 1 H), 7.58 (d, J = 8.5 Hz, 1 H), 7.51 (d, J = 7.8 Hz, 1 H), 7.28 (d, J = 1.3 Hz, 1 H), 6.95 (d, J = 8.5 Hz, 2 H), 4.69 (t, J = 6.4 Hz, 2 H), 4.60 (br. s., 1 H), 4.45-4.54 (m, 3 H), 3.73 (m, J = 6.0, 6.0 Hz, 1 H), 3.05 (br. s., 2 H), 2.04-2.17 (m, 4 H), 1.80-1.99 (m, 4 H), 1.31-1.47 (m, 1 H), 0.62-0.70 (m, 1 H), 0.46-0.60 (m, 3 H)

| Example/IUPAC name | Structure | MS calculated MS ESI [M + H]+ | Yield; Appearance; Salt form |
|---|---|---|---|
| A353: N-((R)-cyclopropyl(pyridin-2-yl)methyl)-3-(4-(((1R,3R,5S)-8-formyl-8-azabi-cyclo[3.2.1]octan-3-yl)oxy)phenyl)-1H-indazole-5-carboxamide | 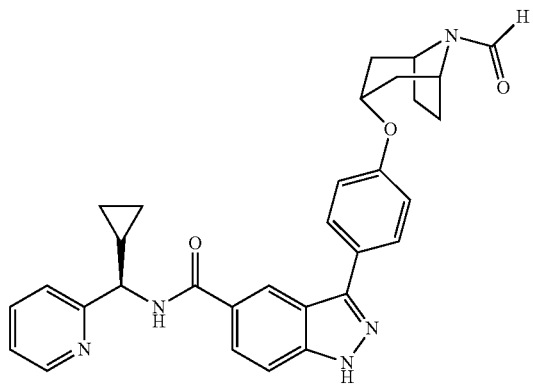 [SMILES: O=CN1C2CCC1CC(Oc1ccc(-c3n[nH]c4ccc(C(=O)N[C@@H](c5ccccn5)C5CC5)cc34)cc1)C2] | [C$_{31}$H$_{31}$N$_5$O$_3$ + H]+ 522.3 522.3 | 14 mg (20%); white solid; free base |

SMs: (R)-N-(cyclopropyl(pyridin-2-yl)methyl)-3-iodo-1H-indazole-5-carboxamide (53 mg, 0.13 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.66 (s, 1 H), 8.52 (d, J = 4.3 Hz, 1 H), 8.12 (s, 1 H), 7.89-7.99 (m, 3 H), 7.80 (td, J = 7.7, 1.8 Hz, 1 H), 7.60 (d, J = 8.8 Hz, 1 H), 7.53 (d, J = 8.0 Hz, 1 H), 7.30 (dd, J = 6.4, 5.1 Hz, 1 H), 7.02 (d, J = 8.5 Hz, 2 H), 4.78 (br. s., 1 H), 4.46-4.59 (m, 2 H), 4.17 (br. s., 1 H), 2.23-2.35 (m, 2 H), 2.07-2.23 (m, 4 H), 1.86-2.06 (m, 2 H), 1.40 (dt, J = 8.5, 4.4 Hz, 1 H), 0.64-0.73 (m, 1 H), 0.46-0.62 (m, 3 H)

| Example/IUPAC name | Structure | MS calculated MS ESI [M + H]+ | Yield; Appearance; Salt form |
|---|---|---|---|
| A354: N-((S)-1-(2-chlorophenyl)-2-methylpropyl)-3-(6-(((1R,3R,5S)-8-formyl-8-azabi-cyclo[3.2.1]octan-3-yl)oxy)pyridin-3-yl)-1H-indazole-5-carboxamide | 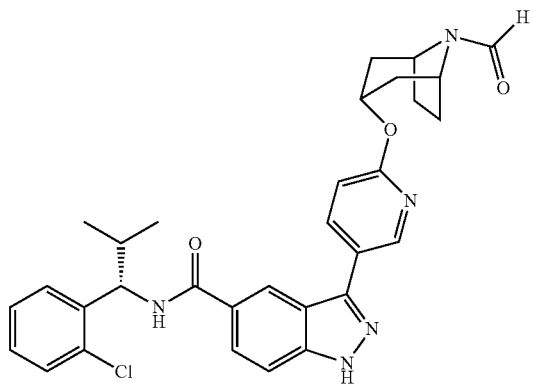 | [C$_{31}$H$_{32}$ClN$_5$O$_3$ + H]+ 558.2 558.6 | 25 mg (32%); white solid; free base |

SMs: (S)-N-(1-(2-chlorophenyl)-2-methylpropyl)-3-iodo-1H-indazole-5-carboxamide (63 mg, 0.14 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (50 mg, 0.14 mmol)

$^1$H NMR (400 MHz, CD$_3$OD) δ ppm 8.72 (d, J = 2.5 Hz, 1 H), 8.47-8.53 (m, 1 H), 8.23 (dd, J = 8.5, 2.5 Hz, 1 H), 8.12 (s, 1 H), 7.89 (dd, J = 8.8, 1.5 Hz, 1 H), 7.52-7.62 (m, 2 H), 7.37 (dd, J = 8.0, 1.3 Hz, 1 H), 7.28 (td, J = 7.5, 1.3 Hz, 1 H), 7.15-7.23 (m, 1 H), 6.88 (d, J = 8.8 Hz, 1 H), 5.33-5.47 (m, 2 H), 4.51-4.61 (m, 1 H), 4.09-4.25 (m, 1 H), 2.22-2.35 (m, 3 H), 1.82-2.21 (m, 6 H), 1.15 (d, J = 6.5 Hz, 3 H), 0.86 (d, J = 6.8 Hz, 3 H)

| Example/IUPAC name | Structure | MS calculated MS ESI [M + H]+ | Yield; Appearance; Salt form |
|---|---|---|---|
| A355: N-(1-(2-chlorophenyl)-3-methylbutyl)-3-(4-((1-(oxetan-3-yl)piperidin-4-yl)oxy)phenyl)-1H-indazole-5-carboxamide | 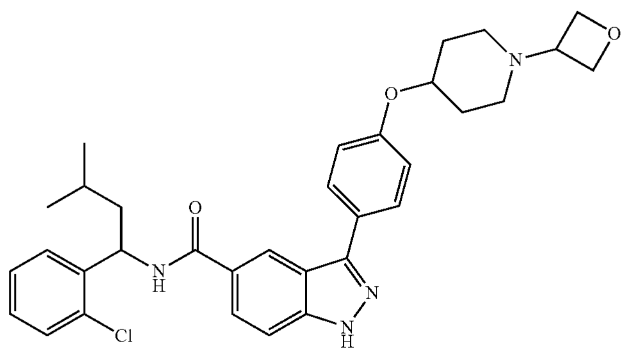 [SMILES: CC(C)CC(NC(=O)c1ccc2[nH]nc(-c3ccc(OC4CCN(C5COC5)CC4)cc3)c2c1)c1ccccc1Cl] | [C$_{33}$H$_{37}$ClN$_4$O$_3$ + H]$^+$ 573.3 573.6 | 23 mg (32%); white solid; free base |

SMs: N-(1-(2-chlorophenyl)-3-methylbutyl)-3-iodo-1H-indazole-5-carboxamide (55 mg, 0.13 mmol), 1-(oxetan-3-yl)-4-(4-(4,4,5,5-tetramethyl-1,3,2-dioxaborolan-2-yl)phenoxy)piperidine (50 mg, 0.14 mmol)
$^1$H NMR (400 MHz, CD$_3$OD) δ ppm 8.61 (dd, J = 1.5, 0.8 Hz, 1 H), 7.94 (dd, J = 8.9, 1.6 Hz, 1 H), 7.83-7.90 (m, 2 H), 7.58 (dd, J = 8.8, 0.8 Hz, 1 H), 7.50 (dd, J = 7.8, 1.8 Hz, 1 H), 7.34 (dd, J = 7.8, 1.3 Hz, 1 H), 7.24 (td, J = 7.5, 1.4 Hz, 1 H), 7.14-7.20 (m, 1 H), 6.96-7.06 (m, 2 H), 5.60-5.77 (m, 1 H), 4.63-4.70 (m, 2 H), 4.54-4.61 (m, 2 H), 4.37-4.46 (m, 1 H), 3.47 (quin, J = 6.4 Hz, 1 H), 2.55 (br. s., 2 H), 2.18 (t, J = 8.5 Hz, 2 H), 1.94-2.06 (m, 2 H), 1.72-1.90 (m, 4 H), 1.54-1.66 (m, 1 H), 1.03 (d, J = 6.5 Hz, 3 H), 0.98 (d, J = 6.5 Hz, 3 H)

| Example/IUPAC name | Structure | MS calculated MS ESI [M + H]+ | Yield; Appearance; Salt form |
|---|---|---|---|
| A356: N-((S)-1-(2-chlorophenyl)-2-methylpropyl)-3-(4-((1R,3S,5S)-3-hydroxy-8-azabicyclo[3.2.1]octan-8-yl)phenyl)-1H-indazole-5-carboxamide | | [C$_{31}$H$_{33}$ClN$_4$O$_2$ + H]$^+$ 529.2 529.6 | 15 mg (19%); yellow solid; free base |

SMs: (S)-N-(1-(2-chlorophenyl)-2-methylpropyl)-3-iodo-1H-indazole-5-carboxamide (69 mg, 0.15 mmol), (1R,3R,5S)-8-(4-(4,4,5,5-tetramethyl-1,3,2-dioxaborolan-2-yl)phenyl)-8-azabicyclo[3.2.1]octan-3-ol (50 mg, 0.15 mmol)
$^1$H NMR (400 MHz, CD$_3$OD) δ ppm 8.55 (dd, J = 1.6, 0.9 Hz, 1 H), 7.87 (dd, J = 8.8, 1.5 Hz, 1 H), 7.78 (d, J = 8.8 Hz, 2 H), 7.50-7.58 (m, 2 H), 7.36 (dd, J = 8.0, 1.3 Hz, 1 H), 7.23-7.30 (m, 1 H), 7.20 (dd, J = 8.0, 1.8 Hz, 1 H), 6.89 (d, J = 8.8 Hz, 2 H), 5.38 (d, J = 9.8 Hz, 1 H), 4.21 (br. s., 2 H), 3.91 (s, 1 H), 2.35 (d, J = 7.0 Hz, 2H), 2.23-2.31 (m, 1 H), 2.19 (d, J = 14.8 Hz, 2 H), 1.98-2.06 (m, 2 H), 1.61 (d, J = 14.6 Hz, 2 H), 1.14 (d, J = 6.5 Hz, 3 H), 0.85 (d, J = 6.8 Hz, 3 H)

| Example/IUPAC name | Structure | MS calculated MS ESI [M + H]+ | Yield; Appearance; Salt form |
|---|---|---|---|
| A357: N-(1-(2-chlorophenyl)-3-methylbutyl)-3-(4-((1-(oxetan-3-yl)azetidin-3-yl)oxy)phenyl)-1H-indazole-5-carboxamide | | [C$_{31}$H$_{33}$ClN$_4$O$_3$ + H]$^+$ 546.0 546.6 | 84 mg (39%); white solid; free base |

SMs: N-(1-(2-chlorophenyl)-3-methylbutyl)-3-iodo-1H-indazole-5-carboxamide (187 mg, 0.4 mmol), 1-(oxetan-3-yl)-3-(4-(4,4,5,5-tetramethyl-1,3,2-dioxaborolan-2-yl)phenoxy)azetidine (166 mg, 0.5 mmol)
$^1$H NMR (400 MHz, CD$_3$OD) δ ppm 8.59 (dd, J = 1.5, 0.8 Hz, 1 H), 7.85-7.98 (m, 3 H), 7.59 (dd, J = 8.9, 0.6 Hz, 1 H), 7.50 (dd, J = 7.5, 1.8 Hz, 1 H), 7.37 (dd, J = 7.9, 1.4 Hz, 1 H), 7.26 (td, J = 7.5, 1.4 Hz, 1 H), 7.17-7.22 (m, 1 H), 6.89-7.00 (m, 2 H), 5.61-5.76 (m, 1 H), 4.92 (m, 1 H) 4.75 (t, J = 6.8 Hz, 2 H), 4.51 (dd, J = 6.8, 5.0 Hz, 2 H), 3.78-3.94 (m, 3 H), 3.33-3.38 (m, 2 H), 1.74-1.92 (m, 2 H), 1.57-1.68 (m, 1 H), 1.05 (d, J = 6.5 Hz, 3 H), 1.00 (d, J = 6.5 Hz, 3 H)

| Example/IUPAC name | Structure | MS calculated MS ESI [M + H]+ | Yield; Appearance; Salt form |
|---|---|---|---|
| A358: 3-(4-(((1R,3R,5S)-8-formyl-8-azabi-cyclo[3.2.1]octan-3-yl)oxy)phenyl)-N-((S)-3-methyl-1-(pyridin-2-yl)butyl)-1H-indazole-5-carboxamide | | [$C_{32}H_{35}N_5O_3$ + H]+ 538.3 538.4 | 65 mg (49%); white solid; free base |

SMs: (S)-3-iodo-N-(3-methyl-1-(pyridin-2-yl)butyl)-1H-indazole-5-carboxamide (110 mg, 0.25 mmol), (1R,3R,5S)-3-(4-(4,4,5,5-tetramethyl-1,3,2-dioxaborolan-2-yl)phenoxy)-8-azabicyclo[3.2.1]octane-8-carbaldehyde (100 mg, 0.28 mmol)

$^1$H NMR (400 MHz, CD$_3$OD) δ ppm 8.64 (dd, J = 1.5, 1.0 Hz, 1 H), 8.48-8.52 (m, 1 H), 8.08 (s, 1 H), 7.97 (dd, J = 8.8, 1.5 Hz, 1 H), 7.86-7.92 (m, 2 H), 7.75 (td, J = 7.7, 1.8 Hz, 1 H), 7.59 (dd, J = 8.8, 0.8 Hz, 1 H), 7.48 (d, J = 8.0 Hz, 1 H), 7.25 (ddd, J = 7.6, 5.0, 1.3 Hz, 1 H), 6.88-6.99 (m, 2 H), 5.36 (dd, J = 9.9, 5.4 Hz, 1 H), 4.69 (br. s., 1 H), 4.48-4.53 (m, 1 H), 4.12 (d, J = 3.0 Hz, 1 H), 2.17-2.29 (m, 2 H), 2.00-2.16 (m, 4 H), 1.81-1.99 (m, 3 H), 1.61-1.81 (m, 2 H), 0.91-1.04 (m, 6 H)

| Example/IUPAC name | Structure | MS calculated MS ESI [M + H]+ | Yield; Appearance; Salt form |
|---|---|---|---|
| A359: (S)-N-(3-methyl-1-(pyridin-2-yl)butyl)-3-(4-(4-(oxetan-3-yl)piperazin-1-yl)phenyl)-1H-indazole-5-carboxamide | 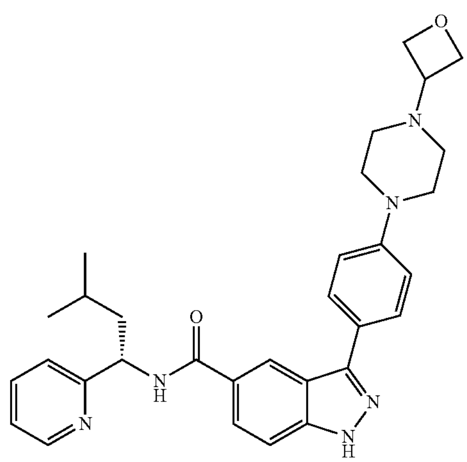 [SMILES: CC(C)C[C@H](NC(=O)c1ccc2[nH]nc(-c3ccc(N4CCN(C5COC5)CC4)cc3)c2c1)c1ccccn1] | [$C_{31}H_{36}N_6O_2$ + H]+ 525.3 525.3 | 70 mg (51%); yellow solid; free base |

SMs: (S)-3-iodo-N-(3-methyl-1-(pyridin-2-yl)butyl)-1H-indazole-5-carboxamide (115 mg, 0.26 mmol), 1-(oxetan-3-yl)-4-(4-(4,4,5,5-tetramethyl-1,3,2-dioxaborolan-2-yl)phenyl)piperazine (100 mg, 0.58 mmol)

$^1$H NMR (400 MHz, CD$_3$OD) δ ppm 8.64-8.70 (m, 1 H), 8.46-8.51 (m, 1 H), 7.94-8.01 (m, 1 H), 7.83 (d, J = 8.8 Hz, 2 H), 7.72 (td, J = 7.8, 1.8 Hz, 1 H), 7.58 (dd, J = 8.9, 0.6 Hz, 1 H), 7.46 (d, J = 7.8 Hz, 1 H), 7.23 (ddd, J = 7.5, 4.9, 1.1 Hz, 1 H), 6.94 (d, J = 9.0 Hz, 2 H), 5.36 (dd, J = 9.9, 5.4 Hz, 1 H), 4.59-4.68 (m, 2 H), 4.50-4.58 (m, 2 H), 3.36-3.43 (m, 1 H), 3.04-3.19 (m, 4 H), 2.21-2.48 (m, 4 H), 1.82-1.95 (m, 1 H), 1.60-1.80 (m, 2 H), 0.89-1.01 (m, 6 H)

| Example/IUPAC name | Structure | MS calculated MS ESI [M + H]+ | Yield; Appearance; Salt form |
|---|---|---|---|
| A360: N-((S)-cyclopentyl(pyridin-2-yl)methyl)-3-(4-((1R,3S,5S)-3-hydroxy-8-azabicyclo[3.2.1]octan-8-yl)phenyl)-1H-indazole-5-carboxamide | 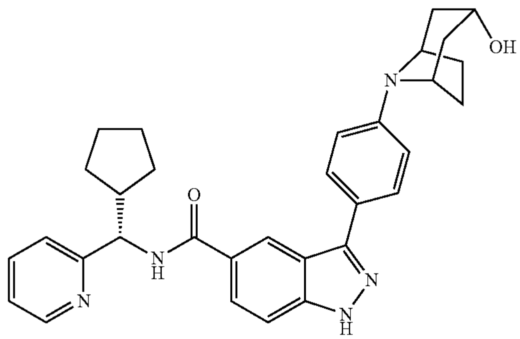 [SMILES: O=C(N[C@H](c1ccccn1)C1CCCC1)c1ccc2[nH]nc(-c3ccc(N4C5CCC4CC(O)C5)cc3)c2c1] | [$C_{32}H_{35}N_5O_2$ + H]+ 522.3 522.3 | 33 mg (33%); white solid; free base |

SMs: (S)-N-(cyclopentyl(pyridin-2-yl)methyl)-3-iodo-1H-indazole-5-carboxamide (86 mg, 0.19 mmol), (1R,3R,5S)-8-(4-(4,4,5,5-tetramethyl-1,3,2-dioxaborolan-2-yl)phenyl)-8-azabicyclo[3.2.1]octan-3-ol (70 mg, 0.21 mmol)
$^1$H NMR (400 MHz, CD$_3$OD) δ ppm 8.61 (dd, J = 1.5, 0.8 Hz, 1 H), 8.48-8.54 (m, 1 H), 7.91 (dd, J = 8.8, 1.5 Hz, 1 H), 7.73-7.84 (m, 3 H), 7.56 (dd, J = 8.9, 0.6 Hz, 1 H), 7.45-7.50 (m, 1 H), 7.28 (ddd, J = 7.5, 5.0, 1.3 Hz, 1 H), 6.90 (d, J = 8.8 Hz, 2 H), 5.01 (d, J = 10.3 Hz, 1 H), 4.22 (br. s., 2 H), 3.91 (t, J = 4.5 Hz, 1 H), 2.53 (m, J = 9.8 Hz, 1 H), 2.29-2.40 (m, 2 H), 2.19 (d, J = 11.0 Hz, 2 H), 1.88-2.07 (m, 3 H), 1.43-1.74 (m, 7 H), 1.19-1.40 (m, 2 H)

| Example/IUPAC name | Structure | MS calculated MS ESI [M + H]+ | Yield; Appearance; Salt form |
|---|---|---|---|
| A361: N-((S)-cyclopropyl(pyridin-2-yl)methyl)-3-(4-((1R,3S,5S)-3-hydroxy-8-azabicyclo[3.2.1]octan-8-yl)phenyl)-1H-indazole-5-carboxamide | 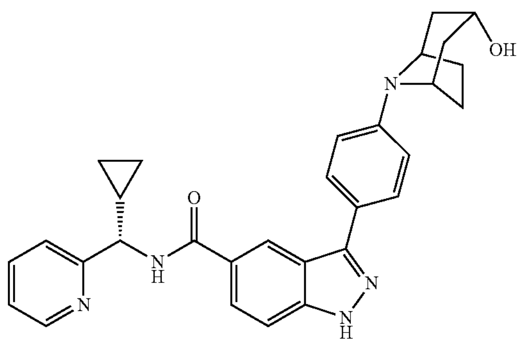 [SMILES: O=C(N[C@H](c1ccccn1)C1CC1)c1ccc2[nH]nc(-c3ccc(N4C5CCC4CC(O)C5)cc3)c2c1] | [$C_{30}H_{31}N_5O_2$ + H]+ 494.3 494.2 | 13 mg (10%); yellow solid; free base |

SMs: (S)-N-(yclopropyl(pyridin-2-yl)methyl)-3-iodo-1H-indazole-5-carboxamide (106 mg, 0.25 mmol), (1R,3R,5S)-8-(4-(4,4,5,5-tetramethyl-1,3,2-dioxaborolan-2-yl)phenyl)-8-azabicyclo[3.2.1]octan-3-ol (100 mg, 0.3 mmol)
$^1$H NMR (400 MHz, CD$_3$OD) δ ppm 8.67 (d, J = 0.8 Hz, 1 H), 8.51 (d, J = 4.0 Hz, 1 H), 7.95 (dd, J = 8.8, 1.5 Hz, 1 H), 7.76-7.88 (m, 3 H), 7.57 (d, J = 8.5 Hz, 1 H), 7.53 (d, J = 8.0 Hz, 1 H), 7.25-7.33 (m, 1 H), 6.94 (d, J = 8.8 Hz, 2 H), 4.51 (d, J = 9.5 Hz, 1 H), 4.25 (br. s., 2 H), 3.93 (s, 1 H), 2.36 (d, J = 7.3 Hz, 2 H), 2.22 (d, J = 14.3 Hz, 2 H), 2.00-2.09 (m, 2 H), 1.63 (d, J = 14.6 Hz, 2 H), 1.34-1.49 (m, 1 H), 0.63-0.72 (m, 1 H), 0.45-0.61 (m, 3 H)

| Example/IUPAC name | Structure | MS calculated MS ESI [M + H]+ | Yield; Appearance; Salt form |
|---|---|---|---|
| A362: N-((S)-cyclopropyl(phenyl)methyl)-3-(4-((1R,3S,5S)-3-hydroxy-8-azabicyclo[3.2.1]octan-8-yl)phenyl)-1H-indazole-5-carboxamide | 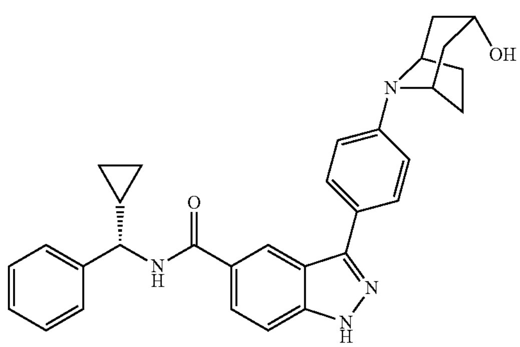 [SMILES: O=C(N[C@H](c1ccccc1)C1CC1)c1ccc2[nH]nc(-c3ccc(N4C5CCC4CC(O)C5)cc3)c2c1] | [$C_{31}H_{32}N_4O_2$ + H]+ 493.3 493.5 | 40 mg (29%); yellow solid; free base |

SMs: (S)-N-(cyclopropyl(phenyl)methyl)-3-iodo-1H-indazole-5-carboxamide (115 mg, 0.28 mmol), (1R,3R,5S)-8-(4-(4,4,5,5-tetramethyl-1,3,2-dioxaborolan-2-yl)phenyl)-8-azabicyclo[3.2.1]octan-3-ol (100 mg, 0.3 mmol)
$^1$H NMR (400 MHz, CD$_3$OD) δ ppm 8.64 (d, J = 0.8 Hz, 1 H), 7.95 (dd, J = 8.9, 1.4 Hz, 1 H), 7.82 (d, J = 8.5 Hz, 2 H), 7.56 (d, J = 8.8 Hz, 1 H), 7.47 (d, J = 7.5 Hz, 2 H), 7.30 (t, J = 7.5 Hz, 2 H), 7.21 (m, J = 7.5 Hz, 1 H), 6.90 (d, J = 8.8 Hz, 2 H), 4.47 (d, J = 9.5 Hz, 1 H), 4.20 (br. s., 2 H), 3.87-3.92 (m, 1 H), 2.34 (m, J = 7.0 Hz, 2 H), 2.13-2.23 (m, 2 H), 1.97-2.06 (m, 2 H), 1.60 (d, J = 14.3 Hz, 2 H), 1.31-1.45 (m, 1 H), 0.56-0.67 (m, 2 H), 0.36-0.51 (m, 2 H)

| Example/IUPAC name | Structure | MS calculated MS ESI [M + H]+ | Yield; Appearance; Salt form |
|---|---|---|---|
| A363: N-((R)-cyclopropyl(pyridin-2-yl)methyl)-3-(4-((1R,3R,5S)-3-hydroxy-8-azabicyclo[3.2.1]octan-8-yl)phenyl)-1H-indazole-5-carboxamide | 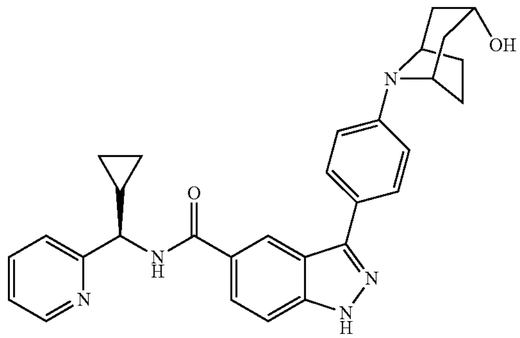 [SMILES: O=C(N[C@@H](c1ccccn1)C1CC1)c1ccc2[nH]nc(-c3ccc(N4C5CCC4CC(O)C5)cc3)c2c1] | [C$_{30}$H$_{31}$N$_5$O$_2$ + H]+ 494.4 494.4 | 13 mg (10%); white solid; free base |

SMs: (R)-N-(cyclopropyl(pyridin-2-yl)methyl)-3-iodo-1H-indazole-5-carboxamide (106 mg, 0.25 mmol), (1R,3R,5S)-8-(4-(4,4,5,5-tetramethyl-1,3,2-dioxaborolan-2-yl)phenyl)-8-azabicyclo[3.2.1]octan-3-ol (100 mg, 0.3 mmol)
$^1$H NMR (400 MHz, CD$_3$OD) δ ppm 8.68 (d, J = 0.8 Hz, 1H), 8.45-8.51 (m, 1H), 7.95 (dd, J = 8.8, 1.8 Hz, 1H), 7.82 (d, J = 8.8 Hz, 2H), 7.76 (td, J = 7.8, 1.8 Hz, 1H), 7.55 (dd, J = 8.8, 0.5 Hz, 1H), 7.50 (d, J = 8.0 Hz, 1H), 7.26 (ddd, J = 7.5, 4.9, 1.1 Hz, 1H), 6.87 (d, J = 8.8 Hz, 2H), 4.51 (d, J = 9.5 Hz, 1H), 4.18 (brs., 2H), 3.89 (t, J = 4.5 Hz, 1H), 2.28-2.36 (m,2H), 2.16 (d,J = 15.1 Hz, 2H), 1.93-2.04 (m, 2H), 1.59 (d, J = 14.6 Hz, 2H), 1.28-1.44 (m, 1H), 0.60-0.68 (m, 1H), 0.42-0.58 (m, 3H)

| Example/IUPAC name | Structure | MS calculated MS ESI [M + H]+ | Yield; Appearance; Salt form |
|---|---|---|---|
| A364: N-((R)-cyclopentyl(pyridin-2-yl)methyl)-3-(4-((1R,3R,5S)-3-hydroxy-8-azabicyclo[3.2.1]octan-8-yl)phenyl)-1H-indazole-5-carboxamide | 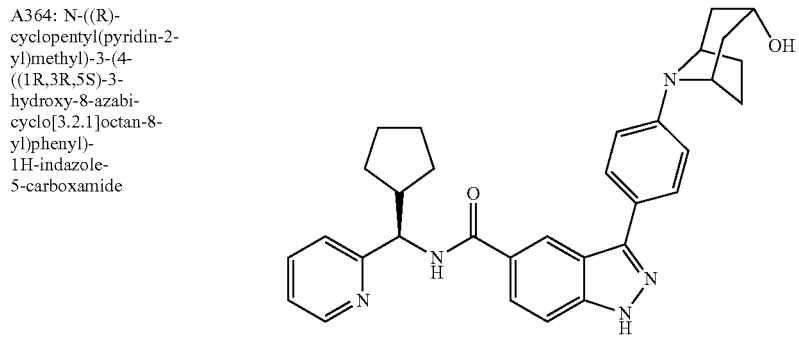 | [C$_{32}$H$_{35}$N$_5$O$_2$ + H]+ 522.3 522.5 | 34 mg (24%); yellow solid; free base |

SMs: (R)-N-(cyclopentyl(pyridin-2-yl)methyl)-3-iodo-1H-indazole-5-carboxamide (123 mg, 0.28 mmol), (1R,3R,5S)-8-(4-(4,4,5,5-tetramethyl-1,3,2-dioxaborolan-2-yl)phenyl)-8-azabicyclo[3.2.1]octan-3-ol (100 mg, 0.3 mmol)
$^1$H NMR (400 MHz, CD$_3$OD) δ ppm 8.61 (dd, J = 1.5, 0.8 Hz, 1 H), 8.48-8.54 (m, 1 H), 7.91 (dd, J = 8.8, 1.5 Hz, 1 H), 7.73-7.85 (m, 3 H), 7.56 (dd, J = 8.8, 0.5 Hz, 1 H), 7.48 (d, J = 7.8 Hz, 1 H), 7.28 (ddd, J = 7.5, 4.9, 1.1 Hz, 1 H), 6.90 (d, J = 8.8 Hz, 2 H), 5.01 (d, J = 10.3 Hz, 1 H), 4.22 (br. s., 2 H), 3.91 (t, J = 4.5 Hz, 1 H), 2.53 (m, J = 9.5 Hz, 1 H), 2.30-2.40 (m, 2 H), 2.12-2.23 (m, 2 H), 1.84-2.06 (m, 3 H), 1.43-1.76 (m, 7 H), 1.19-1.41 (m, 2 H)

| Example/IUPAC name | Structure | MS calculated MS ESI [M + H]+ | Yield; Appearance; Salt form |
|---|---|---|---|
| A365: N-((S)-cyclopropyl(thiophen-3-yl)methyl)-3-(4-((1R,3S,5S)-3-hydroxy-8-azabicyclo[3.2.1]octan-8-yl)phenyl)-1H-indazole-5-carboxamide | 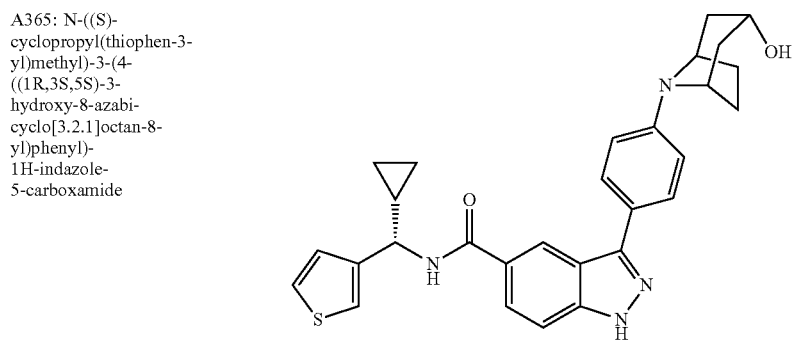 | [C$_{29}$H$_{30}$N$_4$O$_2$S + H]+ 499.2 499.4 | 30 mg (25%); yellow solid; free base |

SMs: (S)-N-(cyclopropyl(thiophen-3-yl)methyl)-3-iodo-1H-indazole-5-carboxamide (100 mg, 0.24 mmol), (1R,3R,5S)-8-(4-(4,4,5,5-tetramethyl-1,3,2-dioxaborolan-2-yl)phenyl)-8-azabicyclo[3.2.1]octan-3-ol (78 mg, 0.24 mmol)
$^1$H NMR (400 MHz, CD$_3$OD) δ ppm 8.64 (d, J = 0.8 Hz, 1 H), 7.95 (dd, J = 8.8, 1.5 Hz, 1 H), 7.84 (d, J = 8.8 Hz, 2H), 7.58 (d, J = 8.8 Hz, 1 H), 7.27 (dd, J = 5.1, 1.1 Hz, 1 H), 7.12 (dt, J = 3.5, 1.1 Hz, 1 H), 6.88-7.00 (m, 3 H), 4.76 (d, J = 9.5 Hz, 1 H), 4.24 (br. s., 2 H), 3.93 (s, 1 H), 2.36 (d, J = 7.0 Hz, 2 H), 2.17-2.25 (m, 2 H), 1.99-2.09 (m, 2 H), 1.63 (d, J = 14.6 Hz, 2H), 1.44-1.57 (m, 1 H), 0.71-0.81 (m, 1 H), 0.59-0.70 (m, 1 H), 0.42-0.58 (m, 2 H)

| Example/IUPAC name | Structure | MS calculated MS ESI [M + H]+ | Yield; Appearance; Salt form |
|---|---|---|---|
| A366: N-((R)-cyclopentyl(pyrimidin-2-yl)methyl)-3-(4-((1R,3R,5S)-3-hydroxy-8-azabi-cyclo[3.2.1]octan-8-yl)phenyl)-1H-indazole-5-carboxamide | 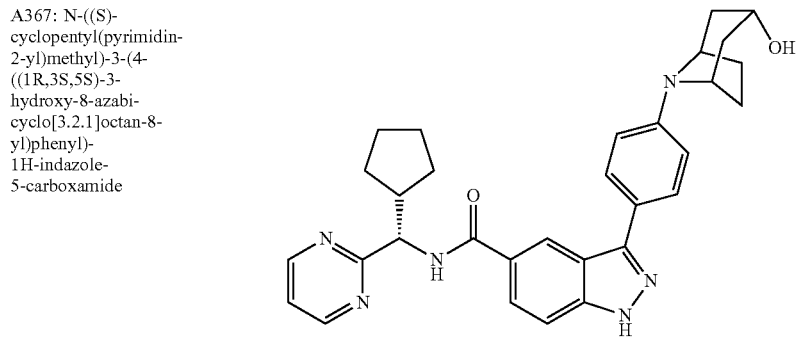 | [C$_{31}$H$_{34}$N$_6$O$_2$ + H]+ 523.27 523.5 | 19 mg (23%); yellow solid; free base |

SMs: (R)-N-(cyclopentyl(pyrimidin-2-yl)methyl)-3-iodo-1H-indazole-5-carboxamide (70 mg, 0.16 mmol), (1R,3R,5S)-8-(4-(4,4,5,5-tetramethyl-1,3,2-dioxaborolan-2-yl)phenyl)-8-azabicyclo[3.2.1]octan-3-ol (52 mg, 0.16 mmol)
$^1$H NMR (400 MHz, CD$_3$OD) δ ppm 8.76 (d, J = 5.0 Hz, 2 H), 8.63 (d, J = 0.5 Hz, 1 H), 7.92 (dd, J = 8.9, 1.6 Hz, 1 H), 7.83 (d, J = 8.8 Hz, 2 H), 7.57 (d, J = 8.8 Hz, 1 H), 7.35 (t, J = 4.9 Hz, 1 H), 6.93 (d, J = 8.8 Hz, 2 H), 5.18 (d, J = 9.5 Hz, 1 H), 4.24 (br. s., 2 H), 3.92 (t, J = 4.4 Hz, 1 H), 2.57 (m, J = 9.0 Hz, 1 H), 2.31-2.40 (m, 2 H), 2.21 (d, J = 15.1 Hz, 2 H), 2.00-2.08 (m, 2 H), 1.92 (d, J = 7.3 Hz, 1 H), 1.47-1.75 (m, 7 H), 1.36-1.45 (m, 2 H)

| A367: N-((S)-cyclopentyl(pyrimidin-2-yl)methyl)-3-(4-((1R,3S,5S)-3-hydroxy-8-azabi-cyclo[3.2.1]octan-8-yl)phenyl)-1H-indazole-5-carboxamide | 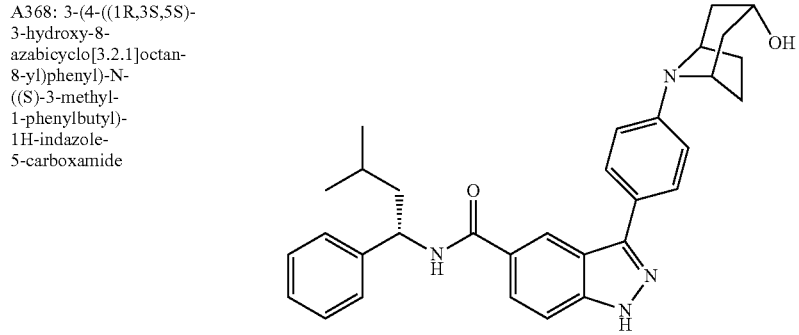 | [C$_{31}$H$_{34}$N$_6$O$_2$ + H]+ 523.3 523.4 | 30 mg (37%); yellow solid; free base |

SMs: (S)-N-(cyclopentyl(pyrimidin-2-yl)methyl)-3-iodo-1H-indazole-5-carboxamide (70 mg, 0.16 mmol), (1R,3R,5S)-8-(4-(4,4,5,5-tetramethyl-1,3,2-dioxaborolan-2-yl)phenyl)-8-azabicyclo[3.2.1]octan-3-ol (52 mg, 0.16 mmol)
$^1$H NMR (400 MHz, CD$_3$OD) δ ppm 8.72-8.80 (m, 2 H), 8.60-8.65 (m, 1 H), 7.92 (dd, J = 8.8, 1.5 Hz, 1 H), 7.84 (d, J = 8.8 Hz, 2 H), 7.57 (d, J = 8.8 Hz, 1 H), 7.36 (t, J = 4.9 Hz, 1 H), 6.94 (d, J = 8.8 Hz, 2H), 5.18 (d, J = 9.8 Hz, 1 H), 4.25 (br. s., 2 H), 3.93 (s, 1 H), 2.48-2.66 (m, 1 H), 2.36 (d, J = 7.3 Hz, 2H), 2.21 (d, J = 14.6 Hz, 2H), 2.00-2.08 (m, 2 H), 1.88-1.98 (m, 1 H), 1.47-1.75 (m, 7 H), 1.33-1.46 (m, 2 H)

| A368: 3-(4-((1R,3S,5S)-3-hydroxy-8-azabicyclo[3.2.1]octan-8-yl)phenyl)-N-((S)-3-methyl-1-phenylbutyl)-1H-indazole-5-carboxamide | | [C$_{33}$H$_{36}$N$_4$O$_2$ + H]+ 509.3 509.4 | 83 mg (77%); yellow solid; free base |

SMs: (S)-3-iodo-N-(3-methyl-1-phenylbutyl)-1H-indazole-5-carboxamide (92 mg, 0.21 mmol), (1R,3R,5S)-8-(4-(4,4,5,5-tetramethyl-1,3,2-dioxaborolan-2-yl)phenyl)-8-azabicyclo[3.2.1]octan-3-ol (70 mg, 0.21 mmol)
$^1$H NMR (400 MHz, CD$_3$OD) δ ppm 8.62 (s, 1 H), 7.92 (dd, J = 8.8, 1.3 Hz, 1 H), 7.80 (d, J = 8.5 Hz, 2 H), 7.54 (d, J = 8.8 Hz, 1 H), 7.41 (d, J = 7.3 Hz, 2 H), 7.30 (t, J = 7.7 Hz, 2 H), 7.21 (d, J = 7.5 Hz, 1 H), 6.88 (d, J = 8.8 Hz, 2 H), 5.18-5.29 (m, 1 H), 4.19 (br. s., 2 H), 3.90 (br. s., 1 H), 2.33 (d, J = 7.0 Hz, 2 H), 2.12-2.23 (m, 2H), 1.97-2.06 (m, 2 H), 1.83-1.96 (m, 1 H), 1.50-1.72 H), 0.96 (d, J = 6.3 Hz, 6 H)

| Example/IUPAC name | Structure | MS calculated MS ESI [M + H]+ | Yield; Appearance; Salt form |
|---|---|---|---|
| A369: (S)-N-(1-(2-chlorophenyl)-2-methylpropyl)-3-(4-(4-(oxetan-3-yl)-1,4-diazepan-1-yl)phenyl)-1H-indazole-5-carboxamide | 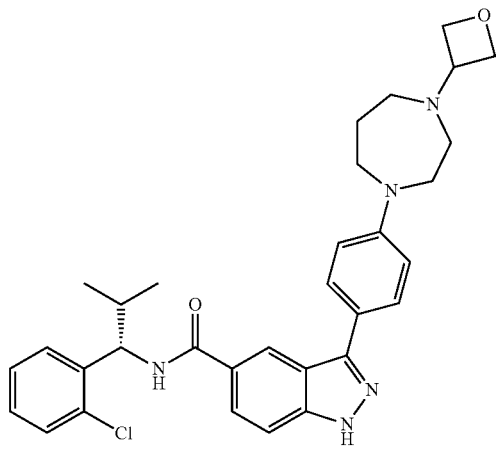 [SMILES: CC(C)[C@H](NC(=O)c1ccc2[nH]nc(-c3ccc(N4CCCN(C5COC5)CC4)cc3)c2c1)c1ccccc1Cl] | [C32H36ClN5O2 + H]+ 558.3 558.5 | 89 mg (57%); yellow solid; free base |

SMs: (S)-N-(1-(2-chlorophenyl)-2-methylpropyl)-3-iodo-1H-indazole-5-carboxamide (127 mg, 0.28 mmol), 1-(oxetan-3-yl)-4-(4-(4,4,5,5-tetramethyl-1,3,2-dioxaborolan-2-yl)phenyl)-1,4-diazepane (116 mg, 0.28 mmol)

$^1$H NMR (400 MHz, CD$_3$OD) δ ppm 8.57 (s, 1 H), 7.88 (d, J = 8.8 Hz, 1 H), 7.77 (d, J = 8.8 Hz, 2 H), 7.50-7.59 (m, 2 H), 7.37 (d, J = 7.8 Hz, 1 H), 7.24-7.30 (m, 1 H), 7.21 (dd, J = 7.7, 1.4 Hz, 1 H), 6.79 (d, J = 8.8 Hz, 2 H), 5.38 (d, J = 9.8 Hz, 1 H), 4.59-4.67 (m, 2 H), 4.52 (t, J = 6.3 Hz, 2 H), 3.46-3.68 (m, 5 H), 2.48-2.57 (m, 2 H), 2.30-2.37 (m, 2 H), 2.19-2.29 (m, 1 H), 1.92-2.04 (m, 2 H), 1.14 (d, J = 6.5 Hz, 3 H), 0.85 (d, J = 6.8 Hz, 3 H)

| Example/IUPAC name | Structure | MS calculated MS ESI [M + H]+ | Yield; Appearance; Salt form |
|---|---|---|---|
| A370: (S)-N-(cyclopentyl(pyridin-2-yl)methyl)-3-(4-(4-(oxetan-3-yl)-1,4-diazepan-1-yl)phenyl)-1H-indazole-5-carboxamide | 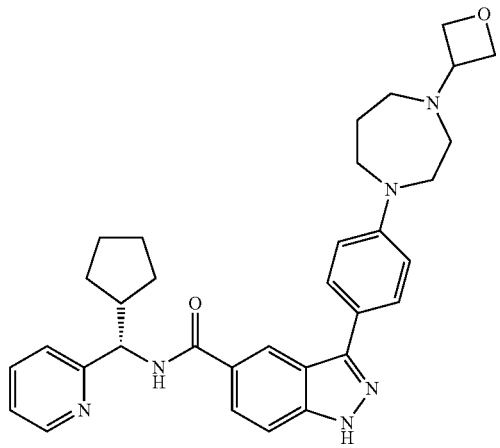 [SMILES: O=C(N[C@H](c1ccccn1)C1CCCC1)c1ccc2[nH]nc(-c3ccc(N4CCCN(C5COC5)CC4)cc3)c2c1] | [C33H38N6O2 + H]+ 551.3 551.6 | 71 mg (58%); yellow solid; free base |

SMs: (S)-N-(cyclopentyl(pyridin-2-yl)methyl)-3-iodo-1H-indazole-5-carboxamide (100 mg, 0.22 mmol), 1-(oxetan-3-yl)-4-(4-(4,4,5,5-tetramethyl-1,3,2-dioxaborolan-2-yl)phenyl)-1,4-diazepane (100 mg, 0.25 mmol)

$^1$H NMR (400 MHz, CD$_3$OD) δ ppm 8.64 (s, 1 H), 8.51 (d, J = 4.5 Hz, 1 H), 7.92 (dd, J = 8.8, 1.3 Hz, 1 H), 7.69-7.84 (m, 3 H), 7.56 (d, J = 8.8 Hz, 1 H), 7.48 (d, J = 7.8 Hz, 1 H), 7.27 (dd, J = 7.5, 5.0 Hz, 1 H), 6.77 (d, J = 9.0 Hz, 2 H), 5.01 (d, J = 10.3 Hz, 1 H), 4.61 (t, J = 6.7 Hz, 2 H), 4.50 (t, J = 6.1 Hz, 2 H), 3.48-3.62 (m, 5 H), 2.41-2.61 (m, 3 H), 2.23-2.33 (m, 2 H), 1.88-2.00 (m, 3 H), 1.41-1.76 (m, 5 H), 1.19-1.40 (m, 2 H)

| Example/IUPAC name | Structure | MS calculated MS ESI [M + H]+ | Yield; Appearance; Salt form |
|---|---|---|---|
| A371: (S)-N-(3-methyl-1-phenylbutyl)-3-(4-(4-(oxetan-3-yl)piperazin-1-yl)phenyl)-1H-indazole-5-carboxamide | 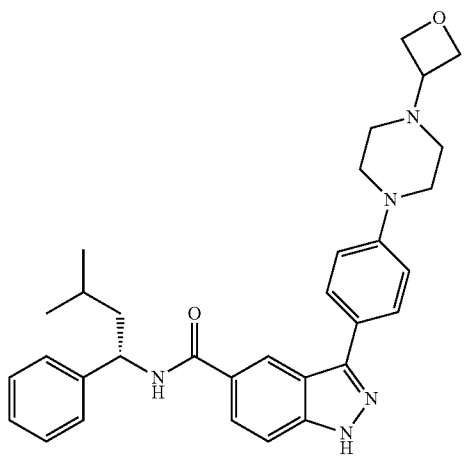 [SMILES: CC(C)C[C@H](NC(=O)c1ccc2[nH]nc(-c3ccc(N4CCN(C5COC5)CC4)cc3)c2c1)c1ccccc1] | [C₃₂H₃₇N₅O₂ + H]+ 524.3 524.5 | 62 mg (69%); white solid; free base |

SMs: (S)-3-iodo-N-(3-methyl-1-phenylbutyl)-1H-indazole-5-carboxamide (75 mg, 0.17 mmol), 1-(oxetan-3-yl)-4-(4-(4,4,5,5-tetramethyl-1,3,2-dioxaborolan-2-yl)phenyl)piperazine (60 mg, 0.17 mmol)

¹H NMR (400 MHz, CD₃OD) δ ppm 8.64 (s, 1 H), 7.95 (dd, J = 8.8, 1.5 Hz, 1 H), 7.81 (d, J = 8.8 Hz, 2 H), 7.55 (d, J = 8.8 Hz, 1 H), 7.40 (d, J = 7.3 Hz, 2 H), 7.27 (t, J = 7.5 Hz, 2 H), 7.12-7.22 (m, 1 H), 6.91 (d, J = 8.8 Hz, 2 H), 5.26 (dd, J = 9.1, 5.8 Hz, 1 H), 4.57-4.67 (m, 2 H), 4.48-4.56 (m, 2 H), 3.34-3.42 (m, 1 H), 3.02-3.17 (m, 4 H), 2.25-2.40 (m, 4 H), 1.76-1.96 (m, 1 H), 1.54-1.71 (m, 2 H), 0.83-1.01 (m, 6 H)

| Example/IUPAC name | Structure | MS calculated MS ESI [M + H]+ | Yield; Appearance; Salt form |
|---|---|---|---|
| A372: (S)-N-(3,3-dimethyl-1-phenylbutyl)-3-(4-(4-(oxetan-3-yl)piperazin-1-yl)phenyl)-1H-indazole-5-carboxamide | 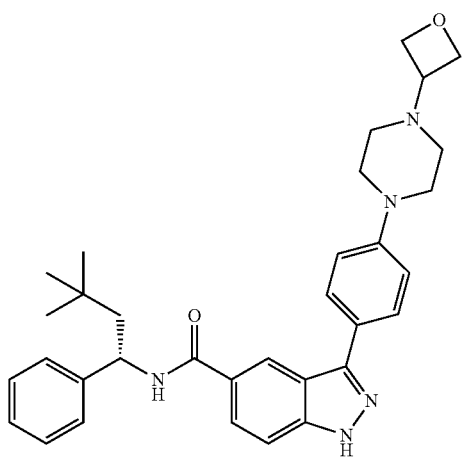 [SMILES: CC(C)(C)C[C@H](NC(=O)c1ccc2[nH]nc(-c3ccc(N4CCN(C5COC5)CC4)cc3)c2c1)c1ccccc1] | [C₃₃H₃₉N₅O₂ + H]+ 538.3 538.6 | 72 mg (64%); white solid; free base |

SMs: (S)-N-(3,3-dimethyl-1-phenylbutyl)-3-iodo-1H-indazole-5-carboxamide (95 mg, 0.21 mmol), 1-(oxetan-3-yl)-4-(4-(4,4,5,5-tetramethyl-1,3,2-dioxaborolan-2-yl)phenyl)piperazine (80 mg, 0.23 mmol)

¹H NMR (400 MHz, CD₃OD) δ ppm 8.58 (s, 1 H), 7.91 (d, J = 8.8 Hz, 1 H), 7.86 (d, J = 4.5 Hz, 2 H), 7.57 (d, J = 8.8 Hz, 1 H), 7.41 (d, J = 7.8 Hz, 2 H), 7.31 (t, J = 6.9 Hz, 2 H), 7.16-7.25 (m, 1 H), 6.98-7.13 (m, 2 H), 5.35 (dd, J = 9.5, 3.3 Hz, 1 H), 4.71 (d, J = 6.3 Hz, 2 H), 4.59-4.66 (m, 2 H), 3.52 (br. s., 1 H), 3.27 (br. s., 4 H), 2.49 (br. s., 4 H), 2.07 (dd, J = 14.4, 9.4 Hz, 1 H), 1.73 (dd, J = 14.3, 2.8 Hz, 1 H), 0.98-1 07 (m, 9 H)

| Example/IUPAC name | Structure | MS calculated MS ESI [M + H]+ | Yield; Appearance; Salt form |
|---|---|---|---|
| A373: N-(3-methyl-1-(pyridin-2-yl)butyl)-3-(4-(((1R,3R,5S)-8-(oxetan-3-yl)-8-azabicyclo[3.2.1]octan-3-yl)oxy)phenyl)-1H-indazole-5-carboxamide | 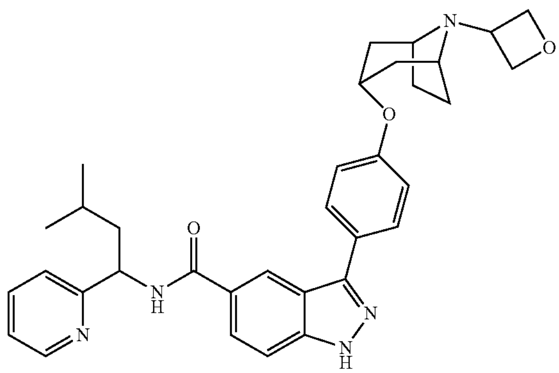 [SMILES: CC(C)CC(NC(=O)c1ccc2[nH]nc(-c3ccc(OC4CC5CCC(C4)N5C4COC4)cc3)c2c1)c1ccccn1] | $[C_{34}H_{39}N_5O_3 + H]^+$ 566.3 566.3 | 33 mg (49%): white solid; free base |

SMs: 3-iodo-N-(3-methyl-1-(pyridin-2-yl)butyl)-1H-indazole-5-carboxamide (51 mg, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (50 mg, 0.13 mmol)
$^1$H NMR (400 MHz, CD$_3$OD) δ ppm 8.65 (s, 1 H), 8.47-8.53 (m, 1 H), 7.96 (dd, J = 8.9, 1.4 Hz, 1 H), 7.88 (d, J = 8.5 Hz, 2 H), 7.75 (td, J = 7.7, 1.6 Hz, 1 H), 7.59 (d, J = 8.8 Hz, 1 H), 7.47 (d, J = 7.8 Hz, 1 H), 7.26 (dd, J = 7.0, 5.5 Hz, 1 H), 6.93 (d, J = 8.8 Hz, 2 H), 5.35 (dd, J = 9.8, 5.3 Hz, 1 H,), 4.68 (t, J = 6.4 Hz, 2 H), 4.58 (t, J = 4.8 Hz, 1 H), 4.49 (t, J = 5.9 Hz, 2 H), 3.71 (t, J = 6.0 Hz, 1 H), 3.03 (br. s., 2 H), 2.02-2.15 (m, 4 H), 1.81-1.97 (m, 5 H), 1.65-1.80 (m, 2 H), 0.99 (dd, J = 6.3, 3.5 Hz, 6 H)

Example A374

Synthesis of 3-(4-((1R,3R,5S)-8-azabicyclo[3.2.1]octan-3-yloxy)phenyl)-N-((S)-cyclopropyl(pyridin-2-yl)methyl)-1H-indazole-5-carboxamide

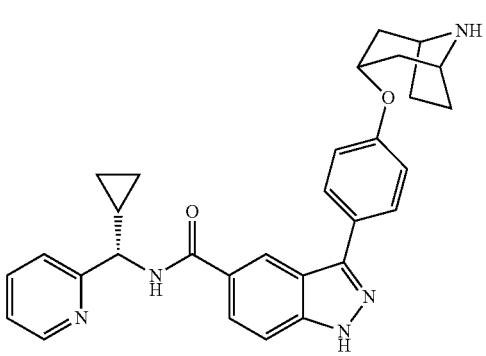 [SMILES: O=C(N[C@H](c1ccccn1)C1CC1)c1ccc2[nH]nc(-c3ccc(OC4CC5CCC(C4)N5)cc3)c2c1]

The solution of (1R,3R,5S)-tert-butyl 3-(4-(5-(((S)-cyclopropyl(pyridin-2-yl)methyl)carbamoyl)-1H-indazol-3-yl)phenoxy)-8-azabicyclo[3.2.1]octane-8-carboxylate (14 mg, 0.024 mmol), TFA (1 mL) in DCM (1 mL) was stirred at rt for 2 h. The solvents were removed under reduced pressure. The residue was run through PoraPak cation exchange resin. The solvent was removed under reduced pressure to give the title compound as a white solid (2.5 mg, 21%). $^1$H NMR (400 MHz, CD$_3$OD) δ ppm 8.65 (s, 1H), 8.53 (d, J=4.5 Hz, 1H), 7.90-7.99 (m, 3H), 7.83 (td, J=7.7, 1.5 Hz, 1H), 7.60 (d, J=8.8 Hz, 1 H), 7.54 (d, J=8.0 Hz, 1H), 7.32 (dd, J=6.9, 5.6 Hz, 1H), 7.03 (d, J=8.8 Hz, 2H), 4.73 (brs, 1H), 4.51 (d, J=9.3 Hz, 1H), 3.55 (br, 2H), 2.21-2.30 (m, 2H), 1.99-2.17 (m, 4H), 1.83-1.93 (m, 2H), 1.35-1.49 (m, 1H), 0.69 (d, J=8.3 Hz, 1H), 0.49-0.63 (m, 3H); MS ESI [M+H]$^+$ 494.2, calcd for [C$_{30}$H$_{31}$N$_5$O$_2$+H]$^+$ 494.3.

Example A375

Synthesis of 3-(4-((1R,3R,5S)-8-azabicyclo[3.2.1]octan-3-yloxy)phenyl)-N-(cyclopropyl(phenyl)methyl)-1H-indazole-5-carboxamide

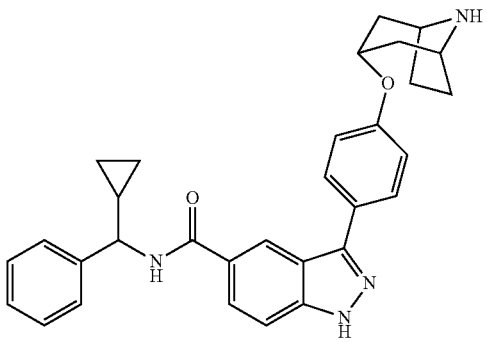 [SMILES: O=C(NC(c1ccccc1)C1CC1)c1ccc2[nH]nc(-c3ccc(OC4CC5CCC(C4)N5)cc3)c2c1]

The solution of (1R,3R,5S)-tert-butyl 3-(4-(5-((cyclopropyl(phenyl)methyl)carbamoyl)-1H-indazol-3-yl)phenoxy)-8-azabicyclo[3.2.1]octane-8-carboxylate (46 mg, 0.077 mmol), TFA (8 drops) in DCM (1 mL) was stirred at rt for 1 h. The solvents were removed under reduced pressure. The residue was purified by prep. HPLC to give the title compound as a white solid (TFA salt) (32 mg, 68%). $^1$H NMR (400 MHz, CD$_3$OD) δ ppm 8.60 (1 H, s), 7.88-8.01 (3 H, m), 7.60 (1 H, d, J=8.8 Hz), 7.48 (2 H, d, J=7.3 Hz), 7.32 (2 H, t, J=7.5 Hz), 7.18-7.26 (1 H, m), 7.05 (2 H, d, J=8.5 Hz), 4.77 (1 H, br. s.), 4.48 (1 H, d, J=9.3 Hz), 4.04 (2 H, br. s.), 2.41-2.52 (2 H, m), 2.18-2.38 (4 H, m), 2.07-2.18 (2 H, m), 1.33-1.47 (1 H, m), 0.60-0.70 (2 H, m), 0.39-0.53 (2 H, m); MS ESI [M+H]$^+$ 493.4, calcd for [C$_{30}$H$_{32}$N$_4$O$_2$+H]$^+$ 493.3.

The following final compounds were synthesized according to the synthesis of Example A1 using General Methods C, C2 or C3:

| Example/IUPAC name | Structure | MS calculated MS ESI [M + H]+ | Yield; Appearance Salt form |
|---|---|---|---|
| A376: N-((S)-cyclopropyl(phenyl)methyl)-3-(4-(((1R,3R,5S)-8-methyl-8-azabicyclo[3.2.1]octan-3-yl)oxy)phenyl)-1H-indazole-5-carboxamide | 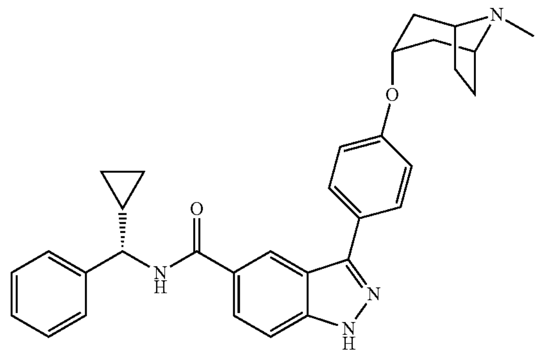 [SMILES: CN1C2CCC1CC(Oc1ccc(-c3n[nH]c4ccc(C(=O)N[C@H](c5ccccc5)C5CC5)cc34)cc1)C2] | [C₃₂H₃₄N₄O₂ + H]+ 507.27 507.4 | 20 mg (15%); white powder; HCl salt |

SMs: (S)-N-(cyclopropyl(phenyl)methyl)-3-iodo-1H-indazole-5-carboxamide (100 mg, 0.24 mmol), (1R,3R,5S)-8-methyl-3-(4-(4,4,5,5-tetramethyl-1,3,2-dioxaborolan-2-yl)phenoxy)-8-azabicyclo[3.2.1]octane (90 mg, 0.26 mmol)
¹H NMR (400 MHz, CD₃OD) δ ppm 8.62 (s, 1 H), 7.96 (dd, J = 8.8, 1.5 Hz, 1 H), 7.92 (d, J = 8.8 Hz, 2 H), 7.60 (d, J = 8.8 Hz, 1 H), 7.49 (d, J = 7.3 Hz, 2 H), 7.33 (t, J = 7.6 Hz, 2 H), 7.24 (t, J = 7.3 Hz, 1 H), 7.01 (d, J = 8.8 Hz, 2 H), 4.64 (t, J = 4.9 Hz, 1 H), 4.48 (d, J = 9.5 Hz, 1 H), 3.19 (br. s., 2 H), 2.33 (s, 3 H), 1.94-2.22 (m, 8H), 1.34-1.46 (m, 1H), 0.66 (d, J = 8.0 Hz, 2H), 0.40-0.53 (m, 2H)

| Example/IUPAC name | Structure | MS calculated MS ESI [M + H]+ | Yield; Appearance Salt form |
|---|---|---|---|
| A377: N-((S)-cyclopropyl(phenyl)methyl)-3-(4-((1-((S)-2-hydroxypropanoyl)piperidin-4-yl)oxy)phenyl)-1H-indazole-5-carboxamide | | [C₃₂H₃₄N₄O₂ + H]+ 539.26 539.4 | 32 mg (30%); white powder; free base |

SMs: (S)-N-(cyclopropyl(phenyl)methyl)-3-iodo-1H-indazole-5-carboxamide (82 mg, 0.20 mmol), (S)-2-hydroxy-1-(4-(4-(4,4,5,5-tetramethyl-1,3,2-dioxaborolan-2-yl)phenoxy)piperidin-1-yl)propan-1-one (83 mg, 0.22 mmol)
¹H NMR (400 MHz, CD₃OD) δ ppm 8.61 (s, 1 H), 7.93 (m, 3 H), 7.61 (d, J = 9.3 Hz, 1 H), 7.49 (d, J = 7.8 Hz, 2 H), 7.34 (t, J = 7.5 Hz, 2 H), 7.24 (t, J = 7.3 Hz, 1 H), 7.14 (d, J = 8.5 Hz, 2 H), 4.68-4.79 (m. 1 H), 4.62 (q, J = 6.3 Hz, 1 H), 4.48 (d, J = 9.5 Hz, 1 H), 3.76-3.99 (m, 2 H), 3.46-3.73 (m, 2 H), 1.93-2.13 (m, 2 H), 1.71-1.91 (m, 2 H), 1.37-1.48 (m, 1 H), 1.34 (d, J = 6.5 Hz, 3 H), 0.67 (d, J = 8.5 Hz, 2 H). 0.41-0.56 (m, 2 H)

| Example/IUPAC name | Structure | MS calculated MS ESI [M + H]+ | Yield; Appearance Salt form |
|---|---|---|---|
| A378: N-((R)-cyclopropyl(phenyl)methyl)-3-(4-(((1R,3R,5S)-8-methyl-8-azabicyclo[3.2.1]octan-3-yl)oxy)phenyl)-1H-indazole-5-carboxamide | | [C₃₂H₃₄N₄O₂ + H]+ 507.27 507.4 | 20 mg (12%); white powder; TFA salt |

SMs: (R)-N-(cyclopropyl(phenyl)methyl)-3-iodo-1H-indazole-5-carboxamide (114 mg, 0.27 mmol), (1R,3R,5S)-8-methyl-3-(4-(4,4,5,5-tetramethyl-1,3,2-dioxaborolan-2-yl)phenoxy)-8-azabicyclo[3.2.1]octane (118 mg, 0.34 mmol)
¹H NMR (400 MHz, CD₃OD) δ ppm 8.60 (s, 1 H), 7.88-8.04 (m, 3 H), 7.62 (d, J = 8.8 Hz, 1 H), 7.49 (d, J = 7.8 Hz, 2 H), 7.34 (t, J = 7.5 Hz, 2 H), 7.24 (t, J = 7.5 Hz, 1 H), 7.09 (d, J = 8.8 Hz, 2 H), 4.8 (br. s., 1 H), 4.48 (d, J = 9.5 Hz, 1 H), 3.93 (br. s., 2 H), 2.83 (s, 3 H), 2.27-2.59 (m, 8 H), 1.34-1.49 (m, 1 H), 0.32-0.71 (m, 2 H), 0.40-0.55 (m, 2 H)

-continued

| Example/IUPAC name | Structure | MS calculated MS ESI [M + H]+ | Yield; Appearance Salt form |
|---|---|---|---|
| A379: N-((S)-cyclopropyl(phenyl)methyl)-3-(4-((1-((R)-2-hydroxypropanoyl)piperidin-4-yl)oxy)phenyl)-1H-indazole-5-carboxamide | 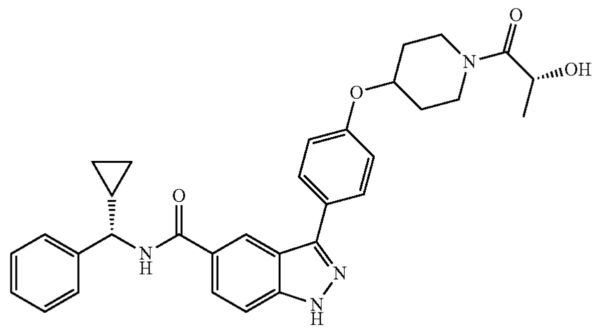 [SMILES: C[C@@H](O)C(=O)N1CCC(Oc2ccc(-c3n[nH]c4ccc(C(=O)N[C@H](c5ccccc5)C5CC5)cc34)cc2)CC1] | [C$_{32}$H$_{34}$N$_4$O$_4$ + H]+ 539.26 539.4 | 50 mg (49%); white solid; free base |

SMs: (S)-N-(cyclopropyl(phenyl)methyl)-3-iodo-1H-indazole-5-carboxamide (80 mg, 0.19 mmol), (R)-2-hydroxy-1-(4-(4-(4,4,5,5-tetramethyl-1,3,2-dioxaborolan-2-yl)phenoxy)piperidin-1-yl)propan-1-one (90 mg, 0.24 mmol)
$^1$H NMR (400 MHz, CD$_3$OD) δ ppm 8.61 (s, 1 H), 7.88-8.01 (m, 3 H), 7.61 (d, J = 9.3 Hz, 1 H), 7.50 (d, J = 7.8 Hz, 2 H), 7.35 (t, J = 7.5 Hz, 2 H), 7.22-7.28 (m, 1 H), 7.16 (d, J = 8.5 Hz, 2 H), 4.69-4.80 (br. s., 1 H), 4.56-4.67 (m, 1 H), 4.49 (d, J = 9.8 Hz, 1 H), 3.75-4.02 (m, 2 H), 3.44-3.75 (m, 2 H), 1.94-2.17 (m, 2 H), 1.71-1.94 (m, 2 H), 1.38-1.48 (m, 1 H), 1.35 (d, J = 6.5 Hz, 3 H), 0.68 (d, J = 8.3 Hz, 2 H), 0.39-0.56 (m, 2 H)

| Example/IUPAC name | Structure | MS calculated MS ESI [M + H]+ | Yield; Appearance Salt form |
|---|---|---|---|
| A380: N-((R)-cyclopropyl(pyridin-2-yl)methyl)-3-(4-(((1R,3R,5S)-8-methyl-8-azabicyclo[3.2.1]octan-3-yl)oxy)phenyl)-1H-indazole-5-carboxamide | 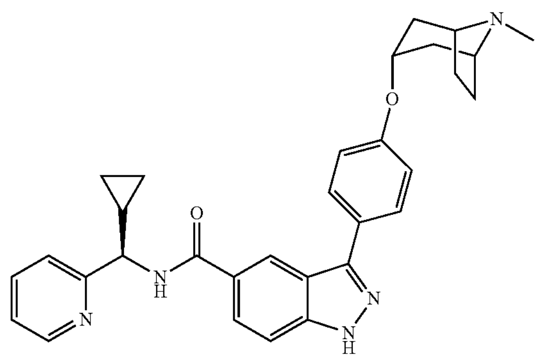 [SMILES: CN1C2CCC1CC(Oc1ccc(-c3n[nH]c4ccc(C(=O)N[C@@H](c5ccccn5)C5CC5)cc34)cc1)C2] | [C$_{31}$H$_{33}$N$_5$O$_2$ + H]+ 508.26 508.2 | 13.5 mg (10%); white powder; 2 × HCl salt |

SMs: (R)-N-(cyclopropyl(pyridin-2-yl)methyl)-3-iodo-1H-indazole-5-carboxamide (100 mg, 0.24 mmol), (1R,3R,5S)-8-methyl-3-(4-(4,4,5,5-tetramethyl-1,3,2-dioxaborolan-2-yl)phenoxy)-8-azabicyclo[3.2.1]octane (89 mg, 0.26 mmol)
$^1$H NMR (400 MHz, CD$_3$OD) δ ppm 8.79 (d, J = 7.0 Hz, 1 H), 8.70 (s, 1 H), 8.63 (t, J = 8.8 Hz, 1 H), 8.26 (d, J = 9.0 Hz, 1 H), 7.96-8.06 (m, 4 H), 7.65 (d, J = 9.3 Hz, 1 H), 7.15 (d, J = 8.8 Hz, 2 H), 4.49 (d, J = 10.3 Hz, 1 H), 3.86-4.02 (m, 2 H), 2.85 (s, 2 H), 2.28-2.61 (m, 7 H), 1.46-1.64 (m, 1 H), 0.59-1.00 (m, 5 H)** 1H is obscured by the signal due to H$_2$O

| Example/IUPAC name | Structure | MS calculated MS ESI [M + H]+ | Yield; Appearance Salt form |
|---|---|---|---|
| A381: (S)-N-(cyclopropyl(phenyl)methyl)-3-(4-((1-(2-hydroxy-2-methylpropanoyl)piperidin-4-yl)oxy)phenyl)-1H-indazole-5-carboxamide | 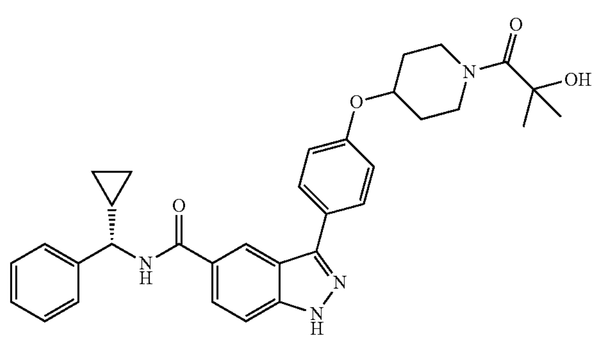 [SMILES: CC(C)(O)C(=O)N1CCC(Oc2ccc(-c3n[nH]c4ccc(C(=O)N[C@H](c5ccccc5)C5CC5)cc34)cc2)CC1] | [C$_{33}$H$_{36}$N$_4$O$_4$ + H]+ 553.27 553.4 | 49.1 mg (48%); white powder; free base |

SMs: (S)-N-(cyclopropyl(phenyl)methyl)-3-iodo-1H-indazole-5-carboxamide (77 mg, 0.18 mmol), 2-hydroxy-2-methyl-1-(4-(4-(4,4,5,5-tetramethyl-1,3,2-dioxaborolan-2-yl)phenoxy)piperidin-1-yl)propan-1-one (86 mg, 0.22 mmol)
$^1$H NMR (400 MHz, CD$_3$OD) δ ppm 8.62 (s, 1 H), 7.97 (dd, J = 8.8, 1.51 Hz, 1 H), 7.91 (d, J = 8.5 Hz, 2 H), 7.60 (d, J = 8.8 Hz, 1 H), 7.48 (d, J = 7.3 Hz, 2 H), 7.32 (t, J = 7.5 Hz, 2 H), 7.23 (t, J = 7.3 Hz, 1 H), 7.11 (d, J = 8.8 Hz, 2 H), 4.63-4.73 (m, 1 H), 4.48 (d, J = 9.5 Hz, 1 H), 3.40-4.40 (br.m, 4 H), 2.02 (br. s., 2 H), 1.79 (br. s., 2 H), 1.45 (s, 6 H), 1.32-1.45 (m, 1 H), 0.65 (d, J = 8.0 Hz, 2 H), 0.47 (dd, J = 8.4, 4.1 Hz, 2 H)

| Example/IUPAC name | Structure | MS calculated MS ESI [M + H]+ | Yield; Appearance Salt form |
|---|---|---|---|
| A382: (S)-N-(cyclopropyl(phenyl)methyl)-3-(4-((1-(2-hydroxyacetyl)piperidin-4-yl)oxy)phenyl)-1H-indazole-5-carboxamide | 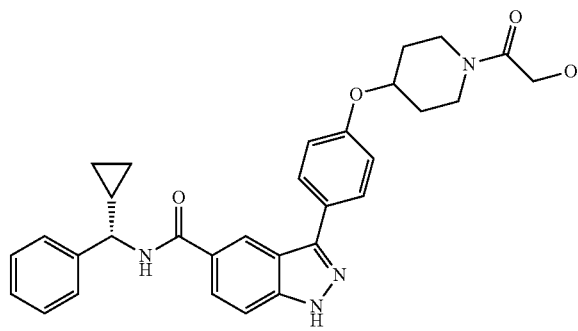 | [$C_{31}H_{32}N_4O_4$ + H]+ 525.24 525.4 | 34 mg (27%); white powder; free base |

SMs: (S)-N-(cyclopropyl(phenyl)methyl)-3-iodo-1H-indazole-5-carboxamide (100 mg, 0.24 mmol), 2-hydroxy-1-(4-(4-(4,4,5,5-tetramethyl-1,3,2-dioxaborolan-2-yl)phenoxy)piperidin-1-yl)ethanone (103 mg, 0.28 mmol)

$^1$H NMR (400 MHz, CD$_3$OD) δ ppm 8.61 (s, 1 H), 7.94 (m, J = 8.8 Hz, 3 H), 7.61 (d, J = 8.8 Hz, 1 H), 7.49 (d, J = 7.3 Hz, 2 H), 7.34 (t, J = 7.6 Hz, 2 H), 7.25 (t, J = 7.3 Hz, 1 H), 7.15 (d, J = 9.0 Hz, 2 H), 4.69-4.79 (m, 1 H), 4.49 (d, J = 9.3 Hz, 1 H), 4.27 (s, 2 H), 3.81-3.94 (m, 1 H), 3.55-3.75 (m, 2 H), 3.30-3.46 (m, 1 H), 1.97-2.12 (m, 2 H), 1.73-1.92 (m, 2 H), 1.34-1.50 (m, 1 H), 0.67 (d, J = 8.0 Hz, 2 H), 0.40-0.57 (m, 2 H)

| Example/IUPAC name | Structure | MS calculated MS ESI [M + H]+ | Yield; Appearance Salt form |
|---|---|---|---|
| A383: N-(cyclopropyl(pyridin-2-yl)methyl)-3-(4-morpholinophenyl)-1H-indazole-5-carboxamide | 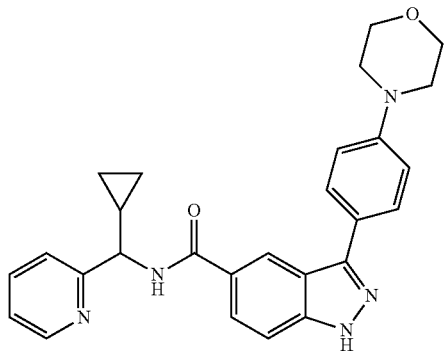 [SMILES: O=C(NC(c1ccccn1)C1CC1)c1ccc2[nH]nc(-c3ccc(N4CCOCC4)cc3)c2c1] | [$C_{27}H_{27}N_5O_2$ + H]+ 454.22 454.2 | 18.6 mg (17%); white powder; free base |

SMs: N-(cyclopropyl(pyridine-2-yl)methyl)-3-iodo-1H-indazole-5-carboxamide (100 mg, 0.24 mmol) and (4-morpholinophenyl)boronic acid (59 mg, 0.28 mmol)

$^1$H NMR (400 MHz, CD$_3$OD) δ ppm 8.66 (s, 1 H), 8.53 (d, J = 4.8 Hz, 1 H), 7.95 (dd, J = 8.8, 1.25 Hz, 1 H), 7.91 (d, J = 8.8 Hz, 2 H), 7.82 (td, J = 7.7, 1.63 Hz, 1 H), 7.60 (d, J = 8.8 Hz, 1 H), 7.54 (d, J = 8.0 Hz, 1 H), 7.32 (dd, J = 6.5, 5.0 Hz, 1 H), 7.13 (d, J = 8.8 Hz, 2 H), 4.51 (d, J = 9.5 Hz, 1 H), 3.81-3.91 (m, 4 H), 3.18-3.27 (m, 4 H), 1.34-1.48 (m, 1 H), 0.49-0.74 (m, 4 H)

| Example/IUPAC name | Structure | MS calculated MS ESI [M + H]⁺ | Yield; Appearance Salt form |
|---|---|---|---|
| A384: N-(cyclopropyl(pyridin-2-yl)methyl)-3-(4-(4-(2-hydroxyethyl)piperazin-1-yl)phenyl)-1H-indazole-5-carboxamide | 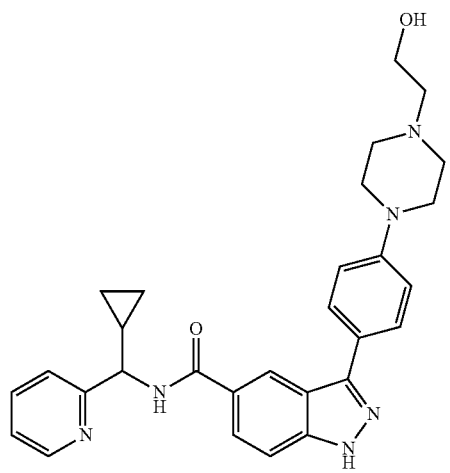 [SMILES: O=C(NC(c1ccccn1)C1CC1)c1ccc2[nH]nc(-c3ccc(N4CCN(CCO)CC4)cc3)c2c1] | $[C_{29}H_{32}N_6O_2 + H]^+$ 497.26 497.2 | 51 mg (45%); pale yellow gum; free base |

SMs: N-(cyclopropyl(pyridine-2-yl)methyl)-3-iodo-1H-indazole-5-carboxamide (100 mg, 0.24 mmol) and 2-(4-(4-(4,4,5,5-tetramethyl-1,3,2-dioxaborolan-2-yl)phenyl)piperazin-1-yl)EtOH (95 mg, 0.29 mmol)

¹H NMR (400 MHz, CD₃OD) δ ppm 8.76 (d, J = 6.3 Hz, 1 H), 8.69 (s, 1 H), 8.53 (t, J = 8.0 Hz, 1 H), 8.16 (d, J = 8.3 Hz, 1 H), 7.94-8.02 (m, 3 H), 7.91 (t, J = 6.8 Hz, 1 H), 7.64 (d, J = 8.3 Hz, 1 H), 7.22 (d, J = 8.8 Hz, 2 H), 4.50 (d, J = 10.0 Hz, 1 H), 3.91-4.01 (m, 4 H), 3.65-3.85 (br.s., 2 H), 3.37-3.41 (m, 4 H), 3.15-3.37 (br.s. 2 H), 1.45-1.58 (m, 1 H), 0.83-0.96 (m, 1 H), 0.60-0.80 (m, 3 H)

| Example/IUPAC name | Structure | MS calculated MS ESI [M + H]⁺ | Yield; Appearance Salt form |
|---|---|---|---|
| A385: N-(cyclopentyl(pyrimidin-2-yl)methyl)-3-(4-(((1R,3R,5S)-8-methyl-8-azabicyclo[3.2.1]octan-3-yl)oxy)phenyl)-1H-indazole-5-carboxamide | 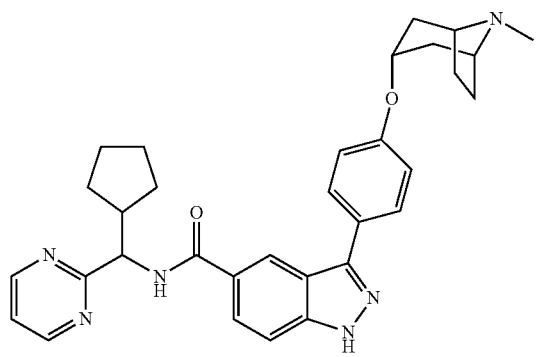 [SMILES: CN1C2CCC1CC(Oc1ccc(-c3n[nH]c4ccc(C(=O)NC(c5ncccn5)C5CCCC5)cc34)cc1)C2] | $[C_{32}H_{36}N_6O_2 + H]^+$ 537.29 537.4 | 11 mg (10%); white powder; free base |

SMs: (1R,3r,5S)-8-methyl-3(4-(4,4,5,5-tetramethyl-1,3,2-dioxaborolan-2-yl)phenoxy)-8-azabicyclo[3.2.1]octane (90 mg) and (1R,3R,5S)-8-methyl-3-(4-(4,4,5,5-tetramethyl-1,3,2-dioxaborolan-2-yl)phenoxy)-8-azabicyclo[3.2.1]octane (83 mg, 0.24 mmol)

¹H NMR (400 MHz, CD₃OD) δ ppm 8.78 (d, J = 5.0 Hz, 2 H), 8.61 (s, 1 H), 7.93 (d, J = 8.5 Hz, 3 H), 7.60 (d, J = 8.8 Hz, 1 H), 7.38 (t, J = 4.9 Hz, 1 H), 7.03 (d, J = 8.8 Hz, 2 H, 5.18 (d, J = 9.5 Hz, 1 H), 4.61-4.70 (m, 1 H), 3.22 (br. s., 2 H), 2.55-2.64 (m, 1 H), 2.35 (s, 3 H), 1.85-2.25 (m, 9 H), 1.49-1.84 (m, 5 H), 1.26-1.49 (m, 2 H)

| Example/IUPAC name | Structure | MS calculated MS ESI [M + H]⁺ | Yield; Appearance Salt form |
|---|---|---|---|
| A386: (R)-3-(3-chloro-4-((1-methylpiperidin-4-yl)oxy)phenyl)-N-(cyclopropyl(pyridin-2-yl)methyl)-1H-indazole-5-carboxamide | 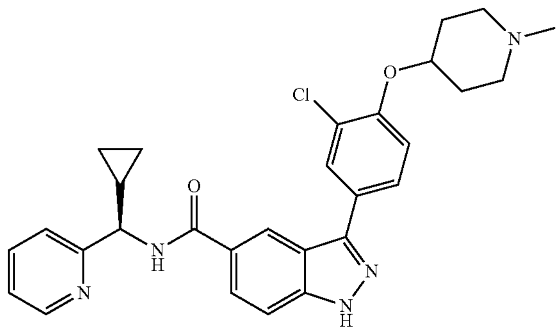 [SMILES: CN1CCC(Oc2ccc(-c3n[nH]c4ccc(C(=O)N[C@@H](c5ccccn5)C5CC5)cc34)cc2Cl)CC1] | [C$_{29}$H$_{30}$ClN$_5$O$_2$ + H]⁺ 516.2 516.2 | 21 mg (29%); white solid; free base |

SMs: (R)-N-(cyclopropyl(pyridin-2-yl)methyl)-3-iodo-1H-indazole-5-carboxamide (60 mg, 0.14 mmol), 4-(2-chloro-4-(4,4,5,5-tetramethyl-1,3,2-dioxaborolan-2-yl)phenoxy)-1-methylpiperidine (50 mg, 0.14 mmol)
¹H NMR (400 MHz, CD$_3$OD) δ ppm 8.62 (s, 1 H), 8.50-8.55 (m, 1 H), 8.02 (s, 1 H), 7.88-7.98 (m, 2 H), 7.82 (t, J = 7.7 Hz, 1 H), 7.61 (d, J = 9.3 Hz, 1 H), 7.54 (d, J = 7.8 Hz, 1 H), 7.24-7.35 (m, 2 H), 4.59-4.67 (m, 1 H), 4.51 (d, J = 9.0 Hz, 1 H), 2.71-2.82 (m, 2 H), 2.43-2.54 (m, 2 H), 2.34 (s, 3 H), 2.01-2.11 (m, 2 H), 1.89-1.99 (m, 2 H), 1.36-1.47 (m, 1 H), 0.66-0.74 (m, 1 H), 0.50-0.63 (m, 3 H)

| Example/IUPAC name | Structure | MS calculated MS ESI [M + H]⁺ | Yield; Appearance Salt form |
|---|---|---|---|
| A387: N-(cyclopropyl(phenyl)methyl)-3-(4-(((1R,5S,7s)-9-methyl-3-oxa-9-azabicyclo[3.3.1]nonan-7-yl)oxy)phenyl)-1H-indazole-5-carboxamide | 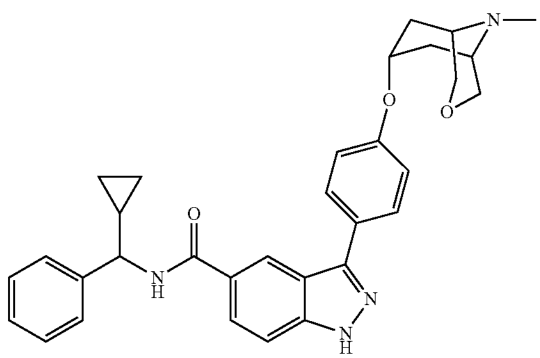 [SMILES: CN1C2COCC1CC(Oc1ccc(-c3n[nH]c4ccc(C(=O)NC(c5ccccc5)C5CC5)cc34)cc1)C2] | [C$_{32}$H$_{34}$N$_4$O$_3$ + H]⁺ 523.3 523.4 | 43 mg (27%); white solid; free base |

SMs: N-(cyclopropyl(phenyl)methyl)-3-iodo-1H-indazole-5-carboxamide (127 mg, 0.31 mmol), (1R,5S,7s)-9-methyl-7-(4-(4,4,5,5-tetramethyl-1,3,2-dioxaborolan-2-yl)phenoxy)-3-oxa-9-azabicyclo[3.3.1]nonane (110 mg, 0.31 mmol)
¹H NMR (400 MHz, CD$_3$OD) δ ppm 8.61(s, 1 H), 7.92-7.98 (m, 1 H), 7.89 (d, J = 8.8 Hz, 2 H), 7.59 (d, J = 8.8 Hz, 1 H), 7.47 (d, J = 7.3 Hz, 2 H), 7.32 (t, J = 7.5 Hz, 2 H), 7.22 (t, J = 7.3 Hz, 1 H), 7.07 (d, J = 8.8 Hz, 2 H), 4.74-4.80 (m, 1 H), 4.62 (br. s., 1 H), 4.47 (d, J = 9.5 Hz, 1 H), 3.94 (d, J = 10.3 Hz, 2 H), 3.64 (d, J = 11.3 Hz, 2 H), 2.67-2.73 (m, 2 H), 2.53 (s, 3 H), 2.42-2.52 (m, 2 H), 1.82 (d, J = 15.3 Hz, 2 H), 1.34-1.45 (m, 1 H), 0.65 (d, J = 8.0 Hz, 2 H), 0.40-0.52 (m, 2 H)

| Example/IUPAC name | Structure | MS calculated MS ESI [M + H]⁺ | Yield; Appearance Salt form |
|---|---|---|---|
| A388: N-(2,2-dimethyl-1-(pyridin-2-yl)propyl)-3-(4-((1-methylpiperidin-4-yl)oxy)phenyl)-1H-indazole-5-carboxamide | | [C$_{30}$H$_{35}$N$_5$O$_2$ + H]⁺ 498.3 498.2 | 42 mg (37%); white solid; free base |

SMs: N-(2,2-dimethyl-1-(pyridin-2-yl)propyl)-3-iodo-1H-indazole-5-carboxamide (100 mg, 0.23 mmol), 1-methyl-4-(4-(4,4,5,5-tetramethyl-1,3,2-dioxaborolan-2-yl)phenoxy)piperidine (73 mg, 0.23 mmol)
¹H NMR (400 MHz, CD$_3$OD) δ ppm 8.53-8.58 (m, 2 H), 7.86-7.95 (m, 3 H), 779 (t, J = 7.4 Hz, 1 H), 7.62 (d, J = 8.8 Hz, 1 H), 7.47 (d, J = 7.8 Hz, 1 H), 7.29-7.36 (m, 1 H), 7.10 (d, J = 8.5 Hz, 2 H), 5.22 (s, 1 H), 4.50 (br. s., 1 H), 2.67-2.78 (m, 2 H), 2.34-2.45 (m, 2 H), 2.30 (s, 3 H), 1.99-2.10 (m, 2 H), 1.77-1.89 (m, 2 H), 1.03 (s, 9 H)

| Example/IUPAC name | Structure | MS calculated MS ESI [M + H]+ | Yield; Appearance Salt form |
|---|---|---|---|
| A389: N-((S)-cyclopropyl(pyridin-2-yl)methyl)-3-(4-(((1R,5S,7s)-9-methyl-3-oxa-9-azabicyclo[3.3.1]nonan-7-yl)oxy)phenyl)-1H-indazole-5-carboxamide | 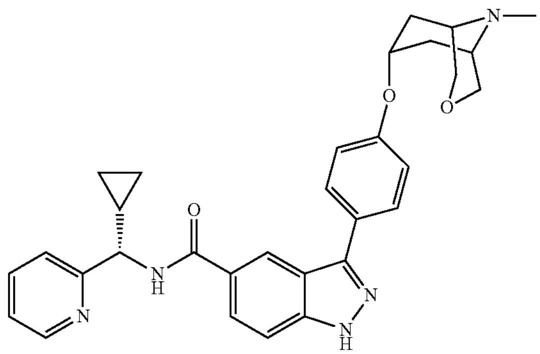 [SMILES: CN1C2COCC1CC(Oc1ccc(-c3n[nH]c4ccc(C(=O)N[C@H](c5ccccn5)C5CC5)cc34)cc1)C2] | [C$_{31}$H$_{33}$N$_5$O$_3$ + H]+ 524.3 524.2 | 33 mg (33%); white solid; free base |

SMs: (S)-N-(cyclopropyl(pyridin-2-yl)methyl)-3-iodo-1H-indazole-5-carboxamide (82 mg, 0.19 mmol), (1R,5S,7s)-9-methyl-7-(4-(4,4,5,5-tetramethyl-1,3,2-dioxaborolan-2-yl)phenoxy)-3-oxa-9-azabicyclo[3.3.1]nonane (70 mg, 0.19 mmol)

$^1$H NMR (400 MHz, CD$_3$OD) δ ppm 8.65 (s, 1 H), 8.51 (d, J = 5.0 Hz, 1 H), 7.88-7.98 (m, 3 H), 7.78-7.85 (m, 1 H), 7.60 (d, J = 8.8 Hz, 1 H), 7.53 (d, J = 7.8 Hz, 1 H), 7.28-7.34 (m, 1 H), 7.10 (d, J = 8.8 Hz, 2 H), 4.77-4.84 (m, 1 H), 4.62 (br. s., 1 H), 4.49 (d, J = 9.5 Hz, 1 H), 3.95 (d, J= 12.3 Hz, 2 H), 3.65 (d, J = 11.3 Hz, 2 H), 2.67-2.76 (m, 2 H), 2.54 (s, 3 H), 2.44-2.53 (m, 2 H), 1.85 (d, J = 15.8 Hz, 2 H), 1.35-1.45 (m, 1 H), 0.64-0.73 (m, 1 H), 0.48-0.62 (m, 3 H)

| Example/IUPAC name | Structure | MS calculated MS ESI [M + H]+ | Yield; Appearance Salt form |
|---|---|---|---|
| A390: N-(cyclopropyl(phenyl)methyl)-3-(4-(((1R,3R,5S)-9-methyl-9-azabicyclo[3.3.1]nonan-3-yl)oxy)phenyl)-1H-indazole-5-carboxamide | 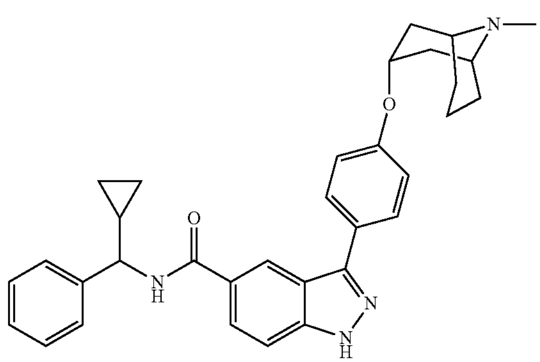 | [C$_{33}$H$_{36}$N$_4$O$_2$ + H]+ 521.3 521.4 | 58 mg (40%); white solid; free base |

SMs: N-(cyclopropyl(phenyl)methyl)-3-iodo-1H-indazole-5-carboxamide (117 mg, 0.28 mmol), (1R,3R,5S)-9-methy-3-(4-(4,4,5,5-tetramethyl-1,3,2-dioxaborolan-2-yl)phenoxy)-9-azabicyclo[3.3.1]nonane (100 mg, 0.28 mmol)

$^1$H NMR (400 MHz, CD$_3$OD) δ ppm 8.62 (s, 1 H), 7.95 (dd, J = 8.8, 1.5 Hz, 1 H), 7.90 (d, J = 8.8 Hz, 2 H), 7.59 (d, J = 8.8 Hz, 1 H), 7.47 (d, J = 7.3 Hz, 2 H), 7.31 (t, J = 7.4 Hz, 2 H), 7.22 (t, J = 7.3 Hz, 1 H), 7.02 (d, J = 8.8 Hz, 2 H), 4.69-4.75 (m, 1 H), 4.47 (d, J = 9.5 Hz, 1 H), 2.93 (br. s., 2 H), 2.56-2.70 (m, 1 H), 2.42-2.53 (m, 5 H), 2.01 (s, 2 H), 1.70 (d, J = 15.3 Hz, 2 H), 1.34-1.51 (m, 4 H), 0.64 (d, J = 8.0 Hz, 2 H), 0.39-0.51 (m, 2 H)

| Example/IUPAC name | Structure | MS calculated MS ESI [M + H]+ | Yield; Appearance Salt form |
|---|---|---|---|
| A391: N-(cyclopentyl(pyridin-2-yl)methyl)-3-(4-(((1R,3R,5S)-9-methyl-9-azabicyclo[3.3.1]nonan-3-yl)oxy)phenyl)-1H-indazole-5-carboxamide | 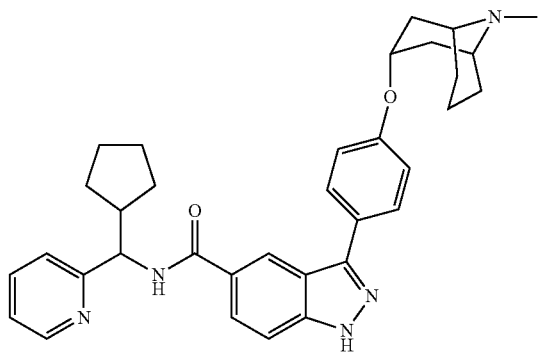 | [C$_{34}$H$_{39}$N$_5$O$_2$ + H]+ 550.3 550.3 | 32 mg (32%); white solid; free base |

SMs: N-(cyclopentyl(pyridin-2-yl)methyl)-3-iodo-1H-indazole-5-carboxamide (124 mg, 0.28 mmol), (1R,3R,5S)-9-methyl-3-(4-(4,4,5,5-tetramethyl-1,3,2-dioxaborolan-2-yl)phenoxy)-9-azabicyclo[3.3.1]nonane (100 mg, 0.28 mmol)

$^1$H NMR (400 MHz, CD$_3$OD) δ ppm 8.59 (s, 1 H), 8.51 (d, J = 4.3 Hz, 1 H), 7.86-7.95 (m, 3 H), 7.78 (td, J = 6.3, 1.8 Hz, 1 H), 7.59 (d, J = 8.8 Hz, 1 H), 7.48 (d, J = 7.8 Hz, 1 H), 7.26-7.31 (m, 1 H), 7.03 (d, J = 8.8 Hz, 2 H), 5.00 (d, J = 10.3 Hz, 1 H), 4.69-4.77 (m, 1 H), 2.92 (br. s., 1 H), 2.57-2.70 (m, 1 H), 2.43-2.54 (m, 6 H), 1.91-2.07 (m, 3 H), 1.21-1.75 (m, 12 H)

| Example/IUPAC name | Structure | MS calculated MS ESI [M + H]+ | Yield; Appearance Salt form |
|---|---|---|---|
| A392: N-(cyclopentyl (pyridin-2-yl)methyl)-3-(4-(((1R,5S,7s)-9-methyl-3-oxa-9-azabicyclo[3.3.1]nonan-7-yl)oxy)phenyl)-1H-indazole-5-carboxamide | 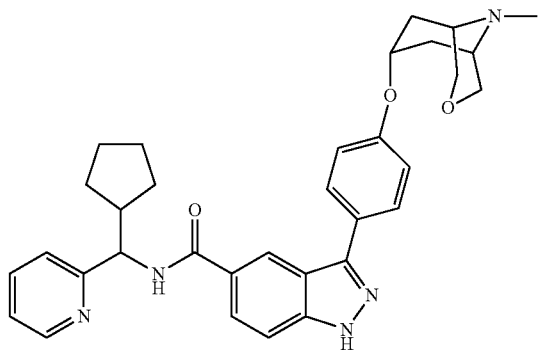 [SMILES: CN1C2COCC1CC(Oc1ccc(-c3n[nH]c4ccc(C(=O)NC(c5ccccn5)C5CCCC5)cc34)cc1)C2] | [C$_{33}$H$_{37}$N$_5$O$_3$ + H]+ 552.3 552.3 | 25 mg (28%); white solid; free base |

Starting materials N-(cyclopentyl(pyridin-2-yl)methyl)-3-iodo-1H-indazole-5-carboxamide (70 mg, 0.16 mmol), (1R,5S,7s)-9-methyl-7-(4-(4,4,5,5-tetramethyl-1,3,2-dioxaborolan-2-yl)phenoxy)-3-oxa-9-azabicyclo[3.3.1]nonane (57 mg, 0.16 mmol)

$^1$H NMR (400 MHz, CD$_3$OD) δ ppm 8.58 (s, 1 H), 8.52 (d, J = 5.8 Hz, 1 H), 7.90 (s, 3 H), 7.79 (t, J = 7.8 Hz, 1 H), 7.59 (d, J = 8.8 Hz, 1 H), 7.49 (d, J = 7.8 Hz, 1 H), 7.27-7.33 (m, 1 H), 7.09 (d, J = 8.8 Hz, 2 H), 5.01 (d, J = 10.3 Hz, 1 H), 4.77-4.83 (m, 1 H), 3.95 (d, J = 10.3 Hz, 2 H), 3.65 (d, J = 11.3 Hz, 2 H), 2.68-2.75 (m, 2 H), 2.44-2.58 (m, 6 H), 1.93-2.03 (m, 1 H), 1.84 (d, J = 15.6 Hz, 2 H), 1.46-1.77 (m, 5 H), 1.22-1.41 (m, 2 H)

-continued

| Example/IUPAC name | Structure | MS calculated MS ESI [M + H]⁺ | Yield; Appearance Salt form |
|---|---|---|---|
| A393: N-(1-(2-chlorophenyl)-2-methylpropyl)-3-(4-(((1R,5S,7s)-9-methyl-3-oxa-9-azabicyclo[3.3.1]nonan-7-yl)oxy)phenyl)-1H-indazole-5-carboxamide | | [C₃₂H₃₅ClN₄O₃ + H]⁺ 559.2 559.5 | 42 mg (50%); white solid; free base |

Starting materials N-(1-(2-chlorophenyl)-2-methylpropyl)-3-iodo-1H-indazole-5-carboxamide (70 mg, 0.15 mmol), (1R,5S,7s)-9-methyl-7-(4-(4,4,5,5-tetramethyl-1,3,2-dioxaborolan-2-yl)phenoxy)-3-oxa-9-azabicyclo[3.3.1]nonane (55 mg, 0.15 mmol)
¹H NMR (400 MHz, CD₃OD) δ ppm 8.54 (s, 1 H), 7.84-7.91 (m, 3 H), 7.51-7.59 (m, 2 H), 7.38 (dd, J = 8.3, 1.3 Hz, 1 H), 7.28 (t, J = 6.5 Hz, 1 H), 7.18-7.24 (m, 1 H), 7.06 (d, J = 8.8 Hz, 2 H), 5.37 (d, J = 9.8 Hz, 1 H), 4.74-4.81 (m, 1 H), 3.95 (d, J = 10.0 Hz, 2 H), 3.64 (d, J = 11.0 Hz, 2 H), 2.71 (d, J = 5.5 Hz, 2 H), 2.54 (s, 3 H), 2.42-2.53 (m, 2 H), 2.21-2.32 (m, 1 H), 1.83 (d, J = 15.6 Hz, 2 H), 1.16 (d, J = 6.5 Hz, 3 H), 0.86 (d, J = 6.8 Hz, 3 H).

| | | | |
|---|---|---|---|
| A394: N-(1-(2-chlorophenyl)-2-methylpropyl)-3-(4-(((1R,3R,5S)-9-methyl-9-azabicyclo[3.3.1]nonan-3-yl)oxy)phenyl)-1H-indazole-5-carboxamide | | [C₃₂H₃₇ClN₄O₂ + H]⁺ 557.3 557.6 | 56 mg (33%); white solid; free base |

Starting materials N-(1-(2-chlorophenyl)-2-methylpropyl)-3-iodo-1H-indazole-5-carboxamide (140 mg, 0.30 mmol), (1R,3R,5S)-9-methyl-3-(4-(4,4,5,5-tetramethyl-1,3,2-dioxaborolan-2-yl)phenoxy)-9-azabicyclo[3.3.1]nonane (110 mg, 0.30 mmol)
¹H NMR (400 MHz, CD₃OD) δ ppm 8.54 (s, 1 H), 7.81-7.99 (m, 3 H), 7.55 (t, J = 7.0 Hz, 2 H), 7.37 (d, J = 7.0 Hz, 1 H), 7.26 J = 8.0 Hz, 1 H), 7.20 (t, J = 8.0 Hz, 1 H), 7.00 (d, J = 8.8 Hz, 2 H), 5.37 (d, J = 9.8 Hz, 1 H), 4.71 (br. s., 1 H), 2.92 (br. s., 2 H), 2.55-2.71 (m, 1 H), 2.39-2.54 (m, 5 H), 2.21-2.33 (m, 1 H), 1.93-2.08 (m, 2 H), 1.69 (d, J = 15.8 Hz, 2 H), 1.32-1.51 (m, 3 H), 1.15 (d, J = 6.5 Hz, 3 H), 0.85 (d, J = 6.5 Hz, 3 H)

| | | | |
|---|---|---|---|
| A395: N-(2-methyl-1-(pyridin-2-yl)propyl)-3-(4-((8-methyl-8-azabicyclo[3.2.1]octan-3-yl)oxy)phenyl)-1H-indazole-5-carboxamide | | [C₃₁H₃₅N₅O₂ + H]⁺ 510.3 510.2 | 74 mg (40%); white solid; free base |

Starting materials 3-iodo-N-(2-methyl-1-(pyridin-2-yl)propyl)-1H-indazole-5-carboxamide (150 mg, 0.36 mmol), endo-8-methyl-3-(4-(4,4,5,5-tetramethyl-1,3,2-dioxaborolan-2-yl)phenoxy)-8-azabicyclo[3.2.1]octane (123 mg, 0.36 mmol)
¹H NMR (400 MHz, CD₃OD) δ ppm 8.58 (s, 1 H), 8.54 (d, J = 4.8 Hz, 1 H), 7.87-7.96 (m, 3 H), 7.80 (t, J = 7.7 Hz, 1 H), 7.59 (d, J = 8.8 Hz, 1 H), 7.48 (d, J = 7.8 Hz, 1 H), 7.31 (dd, J = 7.5, 5.0 Hz, 1 H), 7.01 (d, J = 8.5 Hz, 2 H), 4.97 (d, J = 8.8 Hz, 1 H), 4.64 (t, J = 4.8 Hz, 1 H), 3.18 (br. s., 2 H), 2.24-2.38 (m, 4 H), 1.93-2.21 (m, 8 H), 1.11 (d, J = 6.5 Hz, 3 H), 0.83 (d, J = 6.8 Hz, 3 H)

-continued

| Example/IUPAC name | Structure | MS calculated MS ESI [M + H]⁺ | Yield; Appearance Salt form |
|---|---|---|---|
| A396: N-(2-methyl-1-(pyridin-2-yl)propyl)-3-(4-((8-methyl-8-azabicyclo[3.2.1]octan-3-yl)oxy)phenyl)-1H-indazole-5-carboxamide | 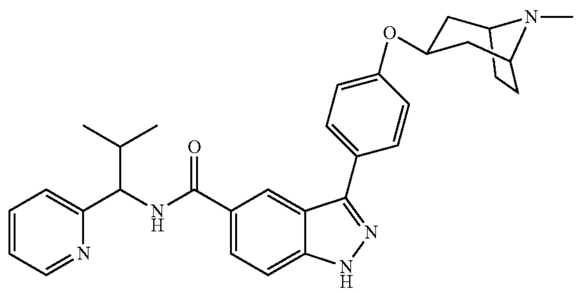 [SMILES: CC(C)C(NC(=O)c1ccc2[nH]nc(-c3ccc(OC4CC5CCC(C4)N5C)cc3)c2c1)c1ccccn1] | [C₃₁H₃₅N₅O₂ + H]⁺ 510.3 510.2 | 102 mg (56%); white solid; free base |

Starting materials 3-iodo-N-(2-methyl-1-(pyridin-2-yl)propyl)-1H-indazole-5-carboxamide (150 mg, 0.36 mmol), exo-8-methyl-3-(4-(4,4,5,5-tetramethyl-1,3,2-dioxaborolan-2-yl)phenoxy)-8-azabicyclo[3.2.1]octane (123 mg, 0.36 mmol)
¹H NMR (400 MHz, CD₃OD) δ ppm 8.58 (s, 1 H), 8.52 (d, J = 4.3 Hz, 1 H), 7.92 (dd, J = 8.9, 1.4 Hz, 1 H), 7.87 (d, J = 8.8 Hz, 2 H), 7.77 (td, J = 7.7, 1.5 Hz, 1 H), 7.58 (d, J = 8.8 Hz, 1 H), 7.45 (d, J = 7.8 Hz, 1 H), 7.28 (dd, J = 6.9, 5.1 Hz, 1 H), 7.05 (d, J = 8.8 Hz, 2 H), 4.97 (d, J = 9.0 Hz, 1 H), 4.58-4.70 (m, 1 H), 3.25 (br. s., 2 H), 2.23-2.37 (m, 4 H), 1.99-2.16 (m, 4 H), 1.69-1.85 (m, 4 H), 1.10 (d, J = 6.5 Hz, 3 H), 0.81 (d, J = 6.8 Hz, 3 H)

| A397: N-((S)-cyclopropyl(pyridin-2-yl)methyl)-3-(4-((8-methyl-8-azabicyclo[3.2.1]octan-3-yl)oxy)phenyl)-1H-indazole-5-carboxamide | 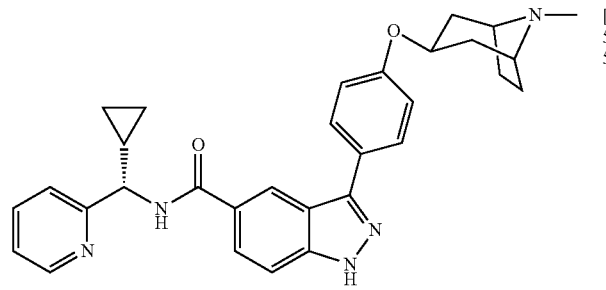 | [C₃₁H₃₂N₅O₂ + H]⁺ 508.3 508.2 | 73 mg (60%); white solid; free base |

Starting materials (S)-N-(cyclopropyl(pyridin-2-yl)methyl)-3-iodo-1H-indazole-5-carboxamide (100 mg, 0.24 mmol), exo-8-methyl-3-(4-(4,4,5,5-tetramethyl-1,3,2-dioxaborolan-2-yl)phenoxy)-8-azabicyclo[3.2.1]octane (82 mg, 0.24 mmol)
¹H NMR (400 MHz, CD₃OD) δ ppm 8.65 (s, 1H), 8.50 (d, J = 4.3 Hz, 1H), 7.95 (dd, J = 8.8, 1.5 Hz, 1 H), 7.89 (d, J = 8.8 Hz, 2H), 7.79 (td, J = 7.7, 1.6 Hz, 1H), 7.58 (d, J = 8.8 Hz, 1H), 7.51 (d, J = 7.8 Hz, 1 H), 7.26-7.33 (m, 1H), 7.06 (d, J = 8.8 Hz, 2H), 4.66 (s, 1H), 4.49 (d, J = 9.5 Hz, 1H), 3.26 (br, 2H), 2.32 (s, 3H), 2.00-2.16 (m, 4H), 1.70-1.86 (m, 4H), 1.33-1.44 (m, 1H), 0.66 (s, 1H), 0.46-0.60 (m, 3H)

| A398: N-(cyclopentyl(pyridin-2-yl)methyl)-3-(4-((8-methyl-8-azabicyclo[3.2.1]octan-3-yl)oxy)phenyl)-1H-indazole-5-carboxamide | 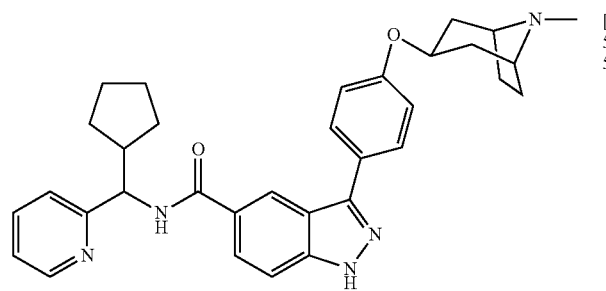 | [C₃₃H₃₇N₅O₂ + H]⁺ 536.3 536.2 | 43 mg (36%); white solid; free base |

Starting materials N-cyclopentyl(pyridin-2-yl)methyl)-3-iodo-1H-indazole-5-carboxamide (100 mg, 0.22 mmol), exo-8-methyl-3-(4-(4,4,5,5-tetramethyl-1,3,2-dioxaborolan-2-yl)phenoxy)-8-azabicyclo[3.2.1]octane (75 mg, 0.22 mmol)
¹H NMR (400 MHz, CD₃OD) δ ppm 8.57 (s, 1 H), 8.52 (d, J = 4.8 Hz, 1 H), 7.85-7.94 (m, 3 H), 7.75-7.82 (m, 1 H), 7.59 (d, J = 9.0 Hz, 1 H), 7.49 (d, J = 7.8 Hz, 1 H), 7.30 (dd, J = 6.9, 5.4 Hz, 1 H), 7.08 (d, J = 8.8 Hz, 2 H), 5.01 (d, J = 10.5 Hz, 1 H), 4.63-4.74 (m, 1 H), 3.29 (br. s., 2 H), 2.46-2.61 (m, 1 H), 2.34 (s, 3 H), 2.04-2.19 (m, 4 H), 1.92-2.03 (m, 1 H), 1.46-1.87 (m, 9 H), 1.20-1.41 (m, 2 H)

| Example/IUPAC name | Structure | MS calculated MS ESI [M + H]+ | Yield; Appearance Salt form |
|---|---|---|---|
| A399: (S)-N-(cyclopropyl(phenyl)methyl)-3-(4-(4-(oxetan-3-yl)piperazin-1-yl)phenyl)-1H-indazole-5-carboxamide | 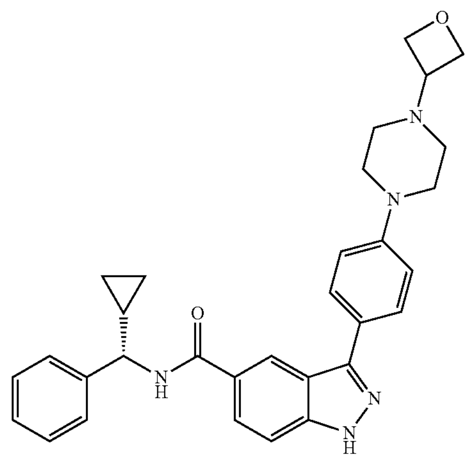 [SMILES: O=C(N[C@H](c1ccccc1)C1CC1)c1ccc2[nH]nc(-c3ccc(N4CCN(C5COC5)CC4)cc3)c2c1] | [$C_{31}H_{33}N_5O_2$ + H]+ 508.3 508.4 | 50 mg (52%); white solid; free base |

SMs: (S)-N-(cyclopropyl(phenyl)methyl)-3-iodo-1H-indazole-5-carboxamide (78 mg, 0.19 mmol), 1-(oxetan-3-yl)-4-(4-(4,4,5,5-tetramethyl-1,3,2-dioxaborolan-2-yl)phenyl)piperazine (64 mg, 0.19 mmol)

1H NMR (400 MHz, CD$_3$OD) δ ppm 8.62 (s, 1 H), 7.91-7.98 (m, 1 H), 7.87 (d, J = 8.8 Hz, 2 H), 7.59 (s, 1 H), 7.47 (d, J = 7.3 Hz, 2 H), 7.31 (t, J = 7.5 Hz, 2 H), 7.22 (t, J = 7.5 Hz, 1 H), 7.07 (d, J = 8.8 Hz, 2 H), 4.71 (t, J = 6.8 Hz, 2 H), 4.63 (t, J = 6.3 Hz, 2 H), 4.47 (d, J = 9.5 Hz, 1 H), 3.48-3.56 (m, 1 H), 3.23-3.29 (m, 4 H), 2.45-2.54 (m, 4 H), 1.33-1.45 (m, 1 H), 0.64 (d, J = 8.0 Hz, 2 H), 0.39-0.51 (m, 2 H)

| Example/IUPAC name | Structure | MS calculated MS ESI [M + H]+ | Yield; Appearance Salt form |
|---|---|---|---|
| A400: (3-(4-((8-methyl-8-azabicyclo[3.2.1]octan-3-yl)oxy)phenyl)-N-(2,2,2-trifluoro-1-phenylethyl)-1H-indazole-5-carboxamide | 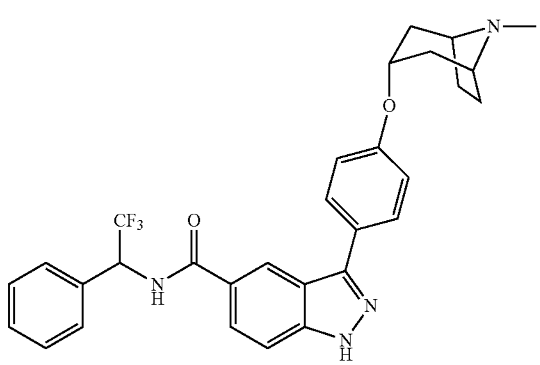 [SMILES: CN1C2CCC1CC(Oc1ccc(-c3n[nH]c4ccc(C(=O)NC(c5ccccc5)C(F)(F)F)cc34)cc1)C2] | [$C_{30}H_{29}F_3N_4O_2$ + H]+ 535.3 535.3 | 16 mg (17%); white solid; free base |

SMs: isobutyl 3-iodo-5-((2,2,2-trifluoro-1-phenylethyl)carbamoyl)-1H-indazole-1-carboxylate (100 mg, 0.18 mmol), 8-methyl-3-(4-(4,4,5,5-tetramethyl-1,3,2-dioxaborolan-2-yl)phenoxy)-8-azabicyclo[3.2.1]octane (62 mg, 0.18 mmol)

1H NMR (400 MHz, CD$_3$OD) δ ppm 8.61 (s, 1 H), 7.87-7.98 (m, 3 H), 7.61 (d, J = 8.0 Hz, 3 H), 7.38-7.46 (m, 3 H), 7.03 (d, J = 8.8 Hz, 2 H), 6.03 (q, J = 8.2 Hz, 1 H), 4.66 (t, J = 4.8 Hz, 1 H), 3.20 (br. s., 2 H), 2.33 (s, 3 H), 1.97-2.22 (m, 8 H)

| Example/IUPAC name | Structure | MS calculated MS ESI [M + H]$^+$ | Yield; Appearance Salt form |
|---|---|---|---|
| A401: (S)-N-(cyclopropyl(pyridin-2-yl)methyl)-3-(4-(4-(oxetan-3-yl)piperazin-1-yl)phenyl)-1H-indazole-5-carboxamide | 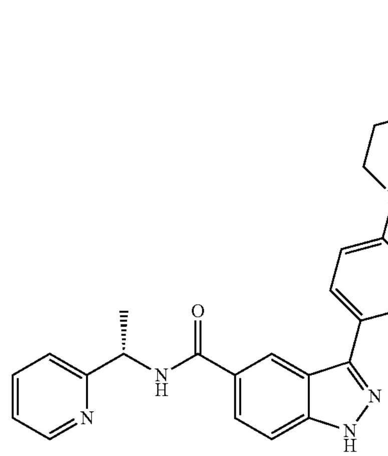 | [C$_{30}$H$_{32}$N$_6$O$_2$ + H]$^+$ 509.3 509.2 | 26 mg (20%); white solid; free base |

SMs: (S)-N-(cyclopropyl(pyridin-2-yl)methyl)-3-iodo-1H-indazole-5-carboxamide (103 mg, 0.25 mmol), 1-(oxetan-3-yl)-4-(4-(4,4,5,5-tetramethyl-1,3,2-dioxaborolan-2-yl)phenyl)piperazine (85 mg, 0.25 mmol)

$^1$H NMR (400 MHz, CD$_3$OD) δ ppm 8.66 (s, 1 H), 8.50 (d, J = 4.0 Hz, 1 H), 7.95 (dd, J = 8.9, 1.4 Hz, 1 H), 7.88 (d, J = 8.8 Hz, 2 H), 7.76-7.82 (m, 1 H), 7.58 (d, J = 8.8 Hz, 1 H), 7.52 (d, J = 7.8 Hz, 1 H), 7.26-7.32 (m, 1 H), 7.07 (d, J = 8.8 Hz, 2 H), 4.70 (t, J = 6.5 Hz, 2 H), 4.62 (t, J = 5.8 Hz, 2 H), 4.50 (d, J = 9.5 Hz, 1 H), 3.51 (quin, J = 6.3 Hz, 1 H), 3.23-3.29 (m, 4 H), 2.45-2.51 (m, 4 H), 1.33-1.45 (m, 1 H), 0.63-0.71 (m, 1 H), 0.48-0.60 (m, 3 H)

| Example/IUPAC name | Structure | MS calculated MS ESI [M + H]$^+$ | Yield; Appearance Salt form |
|---|---|---|---|
| A402: N-(cyclopentyl(pyridin-2-yl)methyl)-3-(4-(4-(oxetan-3-yl)piperazin-1-yl)phenyl)-1H-indazole-5-carboxamide | 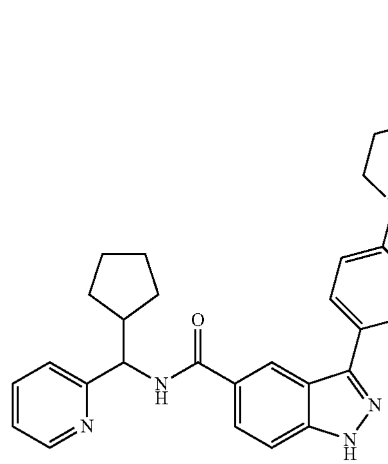 | [C$_{32}$H$_{36}$N$_6$O$_2$ + H]$^+$ 537.3 537.3 | 10.3 mg (8%); brown solid; free base |

SMs: N-(cyclopentyl(pyridin-2-yl)methyl)-3-iodo-1H-indazole-5-carboxamide (112 mg, 0.25 mmol), 1-(oxetan-3-yl)-4-(4-(4,4,5,5-tetramethyl-1,3,2-dioxaborolan-2-yl)phenyl)piperazine (85 mg, 0.25 mmol)

$^1$H NMR (400 MHz, CD$_3$OD) δ ppm 8.58 (s, 1 H), 8.52 (d, J = 5.0 Hz, 1 H), 7.86-7.93 (m, 3 H), 7.76-7.83 (m, 1 H), 7.58 (d, J = 8.5 Hz, 1 H), 7.50 (d, J = 7.8 Hz, 1 H), 7.27-7.33 (m, 1 H), 7.13 (d, J = 8.8 Hz, 2 H), 5.01 (d, J = 10.3 Hz, 1 H), 4.74 (t, J = 6.5 Hz, 2 H), 4.66 (t, J = 6.0 Hz, 2 H), 3.53-3.60 (m, 1 H), 3.32-3.37 (m, 4 H), 2.49-2.59 (m, 5 H), 1.92-2.05 (m, 1 H), 1.46-1.78 (m, 5 H), 1.21-1.42 (m, 2 H)

| Example/IUPAC name | Structure | MS calculated MS ESI [M + H]⁺ | Yield; Appearance Salt form |
|---|---|---|---|
| A403: (S)-N-(cyclopropyl(phenyl)methyl)-3-(4-(4-(oxetan-3-yl)piperidin-1-yl)phenyl)-1H-indazole-5-carboxamide | 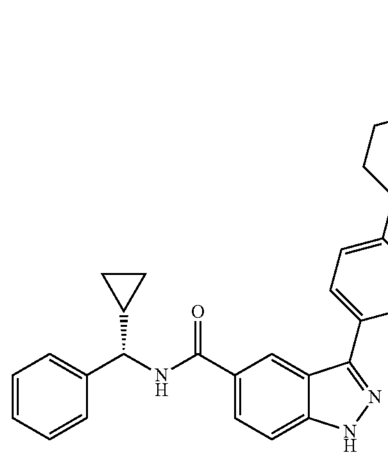 | $[C_{32}H_{34}N_4O_2 + H]^+$<br>507.3<br>507.4 | 70 mg (58%); white solid; free base |

SMs: (S)-N-(cyclopropyl(phenyl)methyl)-3-iodo-1H-indazole-5-carboxamide (100 mg, 0.24 mmol), 1-(oxetan-3-yl)-4-(4-(4,4,5,5-tetramethyl-1,3,2-dioxaborolan-2-yl)phenyl)piperidine (82 mg, 0.24 mmol)
¹H NMR (400 MHz, CD₃OD) δ ppm 8.63 (s, 1 H), 7.89-7.99 (m, 3 H), 7.61 (d, J = 8.8 Hz, 1 H), 7.48 (d, J =7.5 Hz, 2 H), 7.40 (d, J = 8.3 Hz, 2 H), 7.32 (t, J = 7.4 Hz, 2 H), 7.23 (t, J = 7.3 Hz, 1 H), 4.71 (t, J = 5.5 Hz, 2 H), 4.63 (t, J = 6.0 Hz, 2 H), 4.48 (d, J = 9.5 Hz, 1 H), 3.48-3.56 (m, 1 H), 2.91 (d, J = 11.3 Hz, 2 H), 2.57-2.68 (m, 1 H), 1.94-2.04 (m, 2 H), 1.87 (d, J = 3.0 Hz, 4 H), 1.34-1.46 (m, 1 H), 0.59-0.70 (m, 2 H), 0.39-0.53 (m, 2 H)

| Example/IUPAC name | Structure | MS calculated MS ESI [M + H]⁺ | Yield; Appearance Salt form |
|---|---|---|---|
| A404: (S)-N-(cyclopropyl(pyridin-2-yl)methyl)-3-(4-(4-(oxetan-3-yl)piperidin-1-yl)phenyl)-1H-indazole-5-carboxamide | 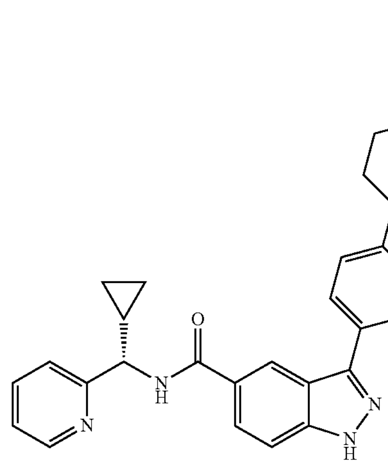 | $[C_{31}H_{33}N_5O_2 + H]^+$<br>508.3<br>508.2 | 26 mg (20%); white solid; free base |

SMs: (S)-N-(cyclopropyl(pyridin-2-yl)methyl)-3-iodo-1H-indazole-5-carboxamide (100 mg, 0.24 mmol), 1-(oxetan-3-yl)-4-(4-(4,4,5,5-tetramethyl-1,3,2-dioxaborolan-2-yl)phenyl)piperidine (82 mg, 0.24 mmol)
¹H NMR (400 MHz, CD₃OD) δ ppm 8.67 (s, 1 H), 8.51 (d, J = 4.5 Hz, 1 H), 7.90-8.00 (m, 3 H), 7.77-7.83 (m, 1 H), 7.61 (d, J = 8.8 Hz, 1 H), 7.53 (d, J = 7.8 Hz, 1 H), 7.40 (d, J = 8.3 Hz, 2 H), 7.26-7.33 (m, 1 H), 4.70 (t, J = 7.0 Hz, 2 H), 4.63 (t, J = 6.0 Hz, 2 H), 4.50 (d, J = 9.5 Hz, 1 H), 3.51 (quin, J = 6.3 Hz, 1H), 2.90 (d, J = 11.5 Hz, 2 H), 2.55-2.67 (m, 1 H), 1.98 (td, J = 11.5, 2.8 Hz, 2 H), 1.76-1.91 (m, 4 H), 1.34-1.47 (m, 1 H), 0.64-0.72 (m, 1 H), 0.53 (s, 3 H)

| Example/IUPAC name | Structure | MS calculated MS ESI [M + H]+ | Yield; Appearance Salt form |
|---|---|---|---|
| A405: (S)-N-(1-(2-chlorophenyl)-2-methylpropyl)-3-(4-(4-(oxetan-3-yl)piperazin-1-yl)phenyl)-1H-indazole-5-carboxamide | 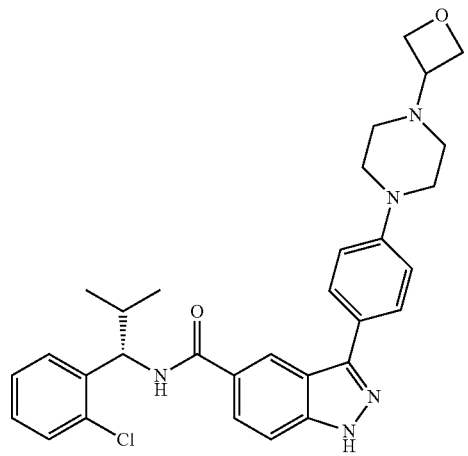 [SMILES: CC(C)[C@H](NC(=O)c1ccc2[nH]nc(-c3ccc(C4CCN(C5COC5)CC4)cc3)c2c1)c1ccccc1Cl] | [C31H34ClN5O2 + H]+ 544.2 544.5 | 51 mg (43%); white solid; free base |

SMs: (S)-N-(1-(2-chlorophenyl)-2-methylpropyl)-3-iodo-1H-indazole-5-carboxamide (100 mg, 0.22 mmol), 1-(oxetan-3-yl)-4-(4-(4,4,5,5-tetramethyl-1,3,2-dioxaborolan-2-yl)phenyl)piperazine (76 mg, 0.22 mmol)
$^1$H NMR (400 MHz, CD$_3$OD) δ ppm 8.54 (s, 1 H), 7.81-7.90 (m, 3 H), 7.51-7.58 (m, 2 H), 7.37 (dd, J = 7.8, 1.0 Hz, 1 H), 7.25-7.31 (m, 1 H), 7.18-7.23 (m, 1 H), 7.06 (d, J = 8.8 Hz, 2 H), 5.37 (d, J = 9.8 Hz, 1 H), 4.72 (t, J = 6.8 Hz, 2 H), 4.63 (t, J = 6.3 Hz, 2 H), 3.49-3.57 (m, 1 H), 3.25-3.30 (m, 4 H), 2.47-2.53 (m, 4 H), 2.21-2.33 (m, 1 H), 1.15 (d, J = 6.8 Hz, 3 H), 0.86 (d, J = 6.5 Hz, 3 H)

| Example/IUPAC name | Structure | MS calculated MS ESI [M + H]+ | Yield; Appearance Salt form |
|---|---|---|---|
| A406: (S)-N-(1-(2-chlorophenyl)-2-methylpropyl)-3-(4-(4-(oxelan-3-yl)piperidin-1-yl)phenyl)-1H-indazole-5-carboxamide | 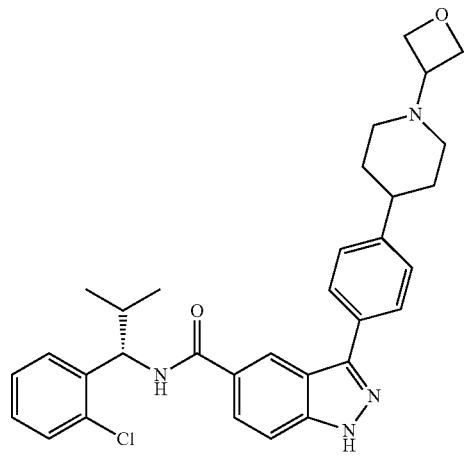 | [C32H35ClN4O2 + H]+ 43.2 543.6 | 54 mg (45%); beige solid; free base |

SMs: (S)-N-(1-(2-chlorophenyl)-2-methylpropyl)-3-iodo-1H-indazole-5-carboxamide (100 mg, 0.22 mmol), 1-(oxetan-3-yl)-4-(4-(4,4,5,5-tetramethyl-1,3,2-dioxaborolan-2-yl)phenyl)piperidine (76 mg, 0.22 mmol)
$^1$H NMR (400 MHz, DMSO-d$_6$) δ ppm 13.38 (s, 1 H), 8.83 (d, J = 8.0 Hz, 1 H), 8.52 (s, 1 H), 7.85-7.97 (m, 3 H), 7.64-7.70 (m, 1 H), 7.61 (d, J = 8.8 Hz, 1 H), 7.39-7.48 (m, 3 H), 7.35 (t, J = 7.5 Hz, 1 H), 7.21-7.27 (m, 1 H), 5.27 (t, J = 8.8 Hz, 1 H), 4.55 (t, J = 6.0 Hz, 2 H), 4.46 (t, J = 5.8 Hz, 2 H), 3.38-3.46 (m, 1 H), 2.83 (d, J = 11.3 Hz, 2 H), 2.53-2.62 (m, 1 H), 2.11-2.24 (m, 1 H), 1.66-1.94 (m, 6 H), 1.08 (d, J = 6.5 Hz, 3 H), 0.79 (d, J = 6.8 Hz, 3 H)

| Example/IUPAC name | Structure | MS calculated MS ESI [M + H]⁺ | Yield; Appearance Salt form |
|---|---|---|---|
| A407: 3-(4-morpholinophenyl)-N-(2-phenylbutyl)-1H-indazole-5-carboxamide | 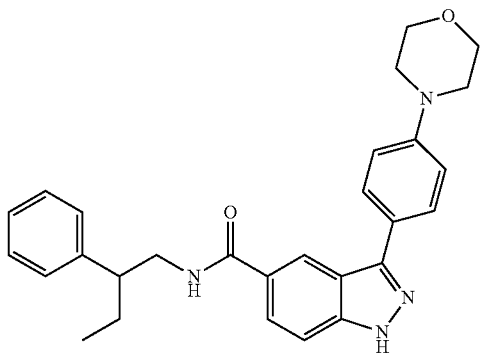 [SMILES: CCC(CNC(=O)c1ccc2[nH]nc(-c3ccc(N4CCOCC4)cc3)c2c1)c1ccccc1] | [C$_{28}$H$_{30}$N$_4$O$_2$ + H]⁺ 455.2 455.4 | 58 mg (53%); white solid; free base |

SMs: 3-iodo-N-(2-phenylbutyl)-1H-indazole-5-carboxamide (100 mg, 0.24 mmol), 4-(4-(4,4,5,5-tetramethyl-1,3,2-dioxaborolan-2-yl)phenyl)morpholine (69 mg, 0.24 mmol)
$^1$H NMR (400 MHz, CD$_3$OD) δ ppm 8.32 (s, 1 H), 7.80 (d, J = 8.8 Hz, 2 H), 7.75 (dd, J = 8.8, 1.5 Hz, 1 H), 7.52 (d, J = 8.8 Hz, 1 H), 7.26-7.33 (m, 2 H), 7.15-7.25 (m, 3 H), 7.06 (d, J = 9.0 Hz, 2 H), 3.80-3.87 (m, 4 H), 3.64-3.72 (m, 1 H), 3.43-3.51 (m, 1 H), 3.16-3.23 (m, 4 H), 2.87-2.96 (m, 1 H), 1.77-1.88 (m, 1 H), 1.59-1.71 (m, 1 H), 0.81 (t, J = 7.4 Hz, 3 H)

| Example/IUPAC name | Structure | MS calculated MS ESI [M + H]⁺ | Yield; Appearance Salt form |
|---|---|---|---|
| A408: 3-(4-((1-methylpiperidin-4-yl)oxy)phenyl)-N-(2-phenylbutyl)-1H-indazole-5-carboxamide | 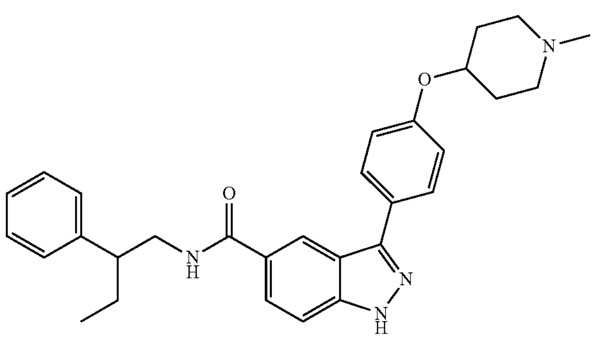 [SMILES: CCC(CNC(=O)c1ccc2[nH]nc(-c3ccc(OC4CCN(C)CC4)cc3)c2c1)c1ccccc1] | [C$_{30}$H$_{34}$N$_4$O$_2$ + H]⁺ 483.3 483.4 | 49 mg (42%); white solid; free base |

SMs: 3-iodo-N-(2-phenylbutyl)-1H-indazole-5-carboxamide (100 mg, 0.24 mmol), 1-methyl-4-(4-(4,4,5,5-tetramethyl-1,3,2-dioxaborolan-2-yl)phenoxy)piperidine (76 mg, 0.24 mmol)
$^1$H NMR (400 MHz, CD$_3$OD) δ ppm 8.30 (s, 1 H), 7.83 (d, J = 8.5 Hz, 2 H), 7.75 (dd, J = 8.9, 1.1 Hz, 1 H), 7.53 (d, J = 8.8 Hz, 1 H), 7.26-7.32 (m, 2 H), 7.16-7.26 (m, 3 H), 7.07 (d, J = 8.8 Hz, 2 H), 4.48 (br. s., 1 H), 3.69 (dd, J = 13.1, 6.8 Hz, 1 H), 3.47 (dd, J = 13.3, 8.5 Hz, 1 H), 2.91 (br. s., 1 H), 2.73 (br. s., 2 H), 2.39 (br. s., 2 H), 2.31 (s, 3 H), 2.04 (br. s., 2 H), 1.77-1.90 (m, 3 H), 1.58-1.71 (m, 1H), 0.81 (t, J = 7.3 Hz, 3 H)

| Example/IUPAC name | Structure | MS calculated MS ESI [M + H]⁺ | Yield; Appearance Salt form |
|---|---|---|---|
| A409: N-(cyclohexyl(pyridin-2-yl)methyl)-3-(4-((1-methylpiperidin-4-yl)oxy)phenyl)-1H-indazole-5-carboxamide | 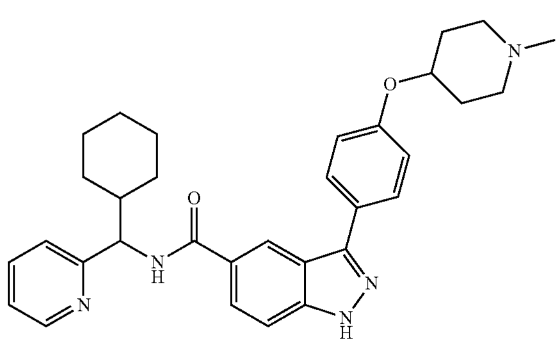 [SMILES: CN1CCC(Oc2ccc(-c3n[nH]c4ccc(C(=O)NC(c5ccccn5)C5CCCCC5)cc34)cc2)CC1] | [C$_{32}$H$_{37}$N$_5$O$_2$ + H]⁺ 524.3 524.3 | 43 mg (37%); white solid; free base |

SMs: N-(cyclohexyl(pyridin-2-yl)methyl)-3-iodo-1H-indazole-5-carboxamide (100 mg, 0.22 mmol), 1-methyl-4-(4-(4,4,5,5-tetramethyl-1,3,2-dioxaborolan-2-yl)phenoxy)piperidine (70 mg, 0.22 mmol)
$^1$H NMR (400 MHz, CD$_3$OD) δ ppm 8.57 (s, 1 H), 8.54 (d, J = 3.8 Hz, 1 H), 7.87-7.95 (m, 3 H), 7.77-7.83 (m, 1 H), 7.60 (d, J = 8.8 Hz, 1 H), 7.46 (d, J = 7.8 Hz, 1 H), 7.27-7.34 (m, 1 H), 7.11 (d, J = 8.8 Hz, 2 H), 5.01 (d, J = 9.0 Hz, 1 H), 4.52 (br. s., 1 H), 2.70-2.82 (m, 2 H), 2.37-2.47 (m, 2 H), 2.33 (s, 3 H), 1.96-2.12 (m, 3 H), 1.76-1.92 (m, 3 H), 1.63-1.72 (m, 2 H), 1.12-1.38 (m, 6 H), 0.96-1.09 (m, 1 H)

| Example/IUPAC name | Structure | MS calculated MS ESI [M + H]+ | Yield; Appearance Salt form |
| --- | --- | --- | --- |
| A410: (S)-N-(cyclopentyl(pyridin-2-yl)methyl)-3-(4-(4-(oxetan-3-yl)piperazin-1-yl)phenyl)-1H-indazole-5-carboxamide | 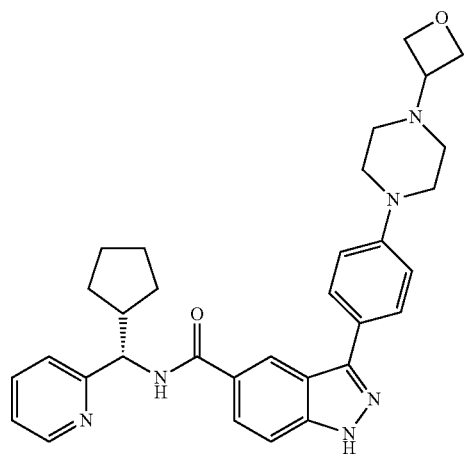 [SMILES: O=C(N[C@H](c1ccccn1)C1CCCC1)c1ccc2[nH]nc(-c3ccc(N4CCN(C5COC5)CC4)cc3)c2c1] | [C32H36N6O2 + H]+ 537.3 537.3 | 49 mg (42%); white solid; free base |

SMs: (S)-N-(cyclopentyl(pyridin-2-yl)methyl)-3-iodo-1H-indazole-5-carboxamide (100 mg, 0.22 mmol), 1-(oxetan-3-yl)-4-(4-(4,4,5,5-tetramethyl-1,3,2-dioxaborolan-2-yl)phenyl)piperazine (76 mg, 0.22 mmol)
$^1$H NMR (400 MHz, CD$_3$OD) δ ppm 8.60 (s, 1 H), 8.52 (d, J = 4.3 Hz, 1 H), 7.92 (d, J = 8.8 Hz, 1 H), 7.87 (d, J = 8.3 Hz, 2 H), 7.79 (t, J = 7.8 Hz, 1 H), 7.59 (d, J = 8.8 Hz, 1 H), 7.50 (d, J = 7.3 Hz, 1 H), 7.25-7.33 (m, 1 H), 7.07 (d, J = 8.3 Hz, 2 H), 5.02 (d, J = 10.3 Hz, 1 H), 4.72 (t, J = 6.5 Hz, 2 H), 4.63 (t, J = 6.0 Hz, 2 H), 3.45-3.56 (m, 1 H), 3.28 (br. s., 4 H), 2.42-2.59 (m, 5 H), 1.91-2.02 (m, 1 H), 1.45-1.77 (m, 5 H), 1.23-1.40 (m, 2 H)

| Example/IUPAC name | Structure | MS calculated MS ESI [M + H]+ | Yield; Appearance Salt form |
| --- | --- | --- | --- |
| A411: (R)-N-(cyclopentyl(pyridin-2-yl)methyl)-3-(4-(4-(oxetan-3-yl)piperazin-1-yl)phenyl)-1H-indazole-5-carboxamide | 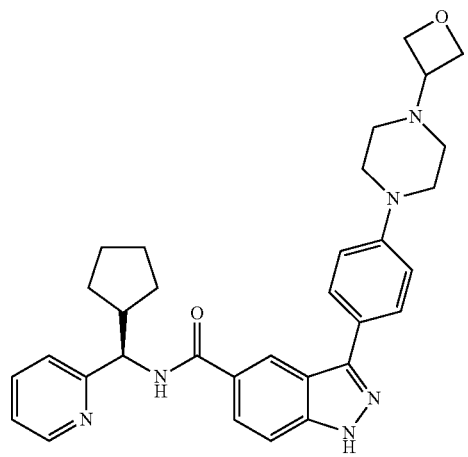 [SMILES: O=C(N[C@@H](c1ccccn1)C1CCCC1)c1ccc2[nH]nc(-c3ccc(N4CCN(C5COC5)CC4)cc3)c2c1] | [C32H36N6O2 + H]+ 537.3 537.3 | 52 mg (44%); white solid; free base |

SMs: (R)-N-(cyclopentyl(pyridin-2-yl)methyl)-3-iodo-1H-indazole-5-carboxamide (100 mg, 0.22 mmol), 1-(oxetan-3-yl)-4-(4-(4,4,5,5-tetramethyl-1,3,2-dioxaborolan-2-yl)phenyl)piperazine (76 mg, 0.22 mmol)
$^1$H NMR (400 MHz, CD$_3$OD) δ ppm 8.59 (s, 1 H), 8.52 (d, J = 4.0 Hz, 1 H), 7.91 (dd, J = 9.0, 1.3 Hz, 1 H), 7.86 (d, J = 8.8 Hz, 2 H), 7.75-7.82 (m, 1 H), 7.58 (d, J = 8.8 Hz, 1 H), 7.49 (d, J = 8.0 Hz, 1 H), 7.25-7.32 (m, 1 H), 7.08 (d, J = 8.8 Hz, 2 H), 5.01 (d, J = 10.0 Hz, 1 H), 4.72 (t, J = 6.5 Hz, 2 H), 4.63 (t, J = 6.0 Hz, 2 H), 3.49-3.57 (m, 1 H), 3.28 (s, 4 H), 2.46-2.58 (m, 5 H), 1.92-2.01 (m, 1 H), 1.46-1.75 (m, 5 H), 1.23-1.40 (m, 2 H)

| Example/IUPAC name | Structure | MS calculated MS ESI [M + H]+ | Yield; Appearance Salt form |
|---|---|---|---|
| A412: (R)-N-(1-(2-chlorophenyl)-2-methylpropyl)-3-(4-(4-(oxetan-3-yl)piperazin-1-yl)phenyl)-1H-indazole-5-carboxamide | 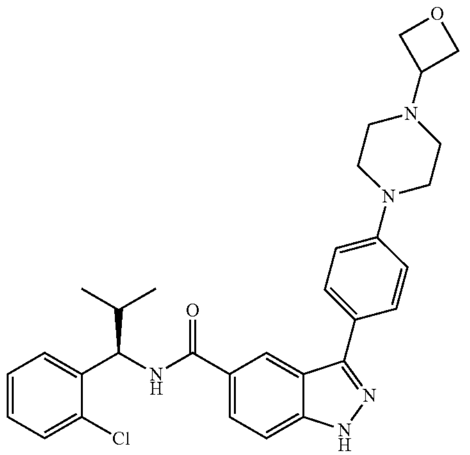 [SMILES: CC(C)[C@@H](NC(=O)c1ccc2[nH]nc(-c3ccc(N4CCN(C5COC5)CC4)cc3)c2c1)c1ccccc1Cl] | [C₃₁H₃₄ClN₅O₂ + H]+ 544.2 544.4 | 278 mg (51%); yellow solid; HCl salt |

SMs: (R)-N-(1-(2-chlorophenyl)-2-methylpropyl)-3-iodo-1H-indazole-5-carboxamide (453 mg, 1 mmol), 1-(oxetan-3-yl)-4-(4-(4,4,5,5-tetramethyl-1,3,2-dioxaborolan-2-yl)phenyl)piperazine (344 mg, 1 mmol)
¹H NMR (400 MHz, CD₃OD) δ ppm 8.52 (s, 1 H), 7.87-7.95 (m, 3 H), 7.59 (d, J = 8.8 Hz, 1 H), 7.52-7.57 (m, 1 H), 7.37-7.41 (m, 1 H), 7.27-7.33 (m, 1 H), 7.20-7.25 (m, 1 H), 7.19 (d, J = 8.8 Hz, 2 H), 5.37 (d, J = 9.5 Hz, 1 H), 4.88-4.97 (m, 4 H), 4.48-4.56 (m, 1 H), 3.98 (br. s, 2 H), 3.62 (br. s., 2 H), 3.24 (br. s., 4 H), 2.22-2.35 (m, 1 H), 1.16 (d, J = 7.3 Hz, 3 H), 0.87 (d, J = 6.8 Hz, 3 H)

| Example/IUPAC name | Structure | MS calculated MS ESI [M + H]+ | Yield; Appearance Salt form |
|---|---|---|---|
| A413: 3-(4-((1R,5S)-3-oxa-8-azabicyclo[3.2.1]octan-8-yl)phenyl)-N-((S)-(2-chlorophenyl)-3-methylbutyl)-1H-indazole-5-carboxamide | | [C₃₁H₃₃ClN₄O₂ 529.2 529.5 | 53 mg (39%); yellow solid; TFA salt |

SMs: (S)-N-(1-(2-chlorophenyl)-3-methylbutyl)-3-iodo-1H-indazole-5-carboxamide (100 mg, 0.21 mmol), 8-(4-(4,4,5,5-tetramethyl-1,3,2-dioxaborolan-2-yl)phenyl)-3-oxa-8-azabicyclo[3.2.1]octane (66 mg, 0.21 mmol)
¹H NMR (400 MHz, CD₃OD) δ ppm 8.61 (s, 1 H), 7.89-7.98 (m, 3 H), 7.60 (d, J = 8.8 Hz, 1 H), 7.50 (dd, J = 7.8, 1.8 Hz, 1 H), 7.37 (dd, J = 7.8, 1.5 Hz, 1 H), 7.27 (td, J = 7.3, 1.5 Hz, 1 H), 7.20 (td, J = 7.5, 1.8 Hz, 1 H), 7.16 (br. s., 2 H), 5.66-5.73 (m, 1 H), 4.28 (br. s., 2 H), 3.95 (d, J = 11.0 Hz, 2 H), 3.57-3.66 (m, 2 H), 2.01-2.16 (m, 4 H), 1.77-1.88 (m, 2 H), 1.62 (s, 1 H), 1.04 (d, J = 6.5 Hz, 3 H), 1.00 (d, J = 6.5 Hz, 3 H)

| Example/IUPAC name | Structure | MS calculated MS ESI [M + H]+ | Yield; Appearance Salt form |
|---|---|---|---|
| A414: 3-(4-((1R,5S)-3-oxa-8-azabicyclo[3.2.1]octan-8-yl)phenyl)-N-((S)-cyclopropyl(pyridin-2-yl)methyl)-1H-indazole-5-carboxamide | | [C₂₉H₂₉N₅O₂ + H]+ 480.2 480.2 | 64 mg (38%); yellow solid; 2TFA salt |

SMs: (S)-N-(cyclopropyl(pyridin-2-yl)methyl)-3-iodo-1H-indazole-5-carboxamide (100 mg, 0.24 mmol), 8-(4-(4,4,5,5-tetramethyl-1,3,2-dioxaborolan-2-yl)phenyl)-3-oxa-8-azabicyclo[3.2.1]octane (76 mg, 0.24 mmol)
¹H NMR (400 MHz, CD₃OD) δ ppm 8.64-8.73 (m, 2 H), 8.40 (td, J = 7.9, 1.8 Hz, 1 H), 8.05 (d, J = 8.0 Hz, 1 H), 7.96 (dd, J = 8.8, 1.5 Hz, 1 H), 7.87 (d, J = 8.0 Hz, 1 H), 7.77-7.83 (m, 1 H), 7.60 (d, J = 8.8 Hz, 1 H), 7.02 (br. s., 2 H), 4.48 (d, J = 10.0 Hz, 1 H), 4.19 (br. s., 2 H), 3.90 (d, J = 10.8 Hz, 2 H), 3.53 (br. s., 2 H), 1.96-2.12 (m, 4 H), 1.42-1.54 (m, 1 H), 0.80-0.89 (m, 1 H), 0.56-0.75 (m, 3 H)

| Example/IUPAC name | Structure | MS calculated MS ESI [M + H]⁺ | Yield; Appearance Salt form |
|---|---|---|---|
| A415: 3-(4-((1R,5S)-3-oxa-8-azabicyclo[3.2.1]octan-8-yl)phenyl)-N-((S)-1-(2-chlorophenyl)-2-methylpropyl)-1H-indazole-5-carboxamide | 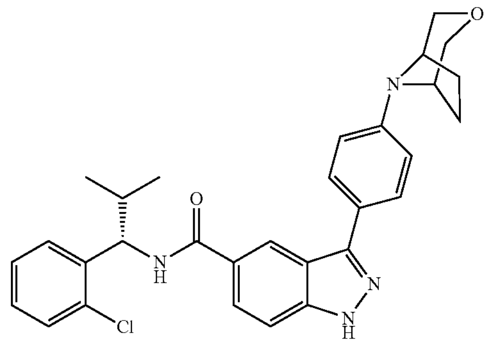 [SMILES: CC(C)[C@H](NC(=O)c1ccc2[nH]nc(-c3ccc(N4C5CCC4COC5)cc3)c2c1)c1ccccc1Cl] | $[C_{30}H_{31}ClN_4O_2 + H]^+$ 515.2 515.6 | 51 mg (37%); yellow solid; TFA salt |

SMs: (S)-N-(1-(2-chlorophenyl)-2-methylpropyl)-3-iodo-1H-indazole-5-carboxamide (100 mg, 0.22 mmol), 8-(4-(4,4,5,5-tetramethyl-1,3,2-dioxaborolan-2-yl)phenyl)-3-oxa-8-azabicyclo[3.2.1]octane (69 mg, 0.22 mmol)
$^1$H NMR (400 MHz, CD$_3$OD) δ ppm 8.54 (s, 1 H), 7.93 (br. s., 2 H), 7.86-7.90 (m, 1 H), 7.58 (d, J = 8.5 Hz, 1 H), 7.54 (dd, J = 7.7, 1.6 Hz, 1 H), 7.38 (dd, J = 7.9, 1.4 Hz, 1 H), 7.27-7.32 (m, 1 H), 7.13-7.25 (m, 3 H), 5.37 (d, J = 9.8 Hz, 1 H), 4.32 (br. s., 2 H), 3.95-4.0 (m, 2 H), 3.64 (br. s., 2 H), 2.22-2.33 (m, 1 H), 2.02-2.18 (m, 4 H), 1.16 (d, J = 6.8 Hz, 3 H), 0.86 (d, J = 6.5 Hz, 3 H)

| Example/IUPAC name | Structure | MS calculated MS ESI [M + H]⁺ | Yield; Appearance Salt form |
|---|---|---|---|
| A416: 3-(4-((1R,5S)-3-oxa-8-azabicyclo[3.2.1]octan-8-yl)phenyl)-N-((S)-cyclopentyl(pyridin-2-yl)methyl)-1H-indazole-5-carboxamide | 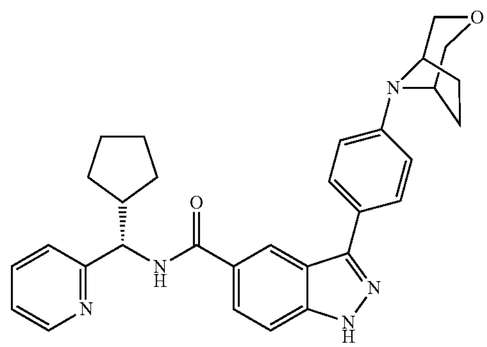 [SMILES: O=C(N[C@H](c1ccccn1)C1CCCC1)c1ccc2[nH]nc(-c3ccc(N4C5CCC4COC5)cc3)c2c1] | $[C_{31}H_{33}N_5O_2 + H]^+$ 508.3 508.4 | 32 mg (20%); yellow solid; 2TFA salt |

SMs: (S)-N-(cyclopentyl(pyridin-2-yl)methyl)-3-iodo-1H-indazole-5-carboxamide (100 mg, 0.22 mmol), 8-(4-(4,4,5,5-tetramethyl-1,3,2-dioxaborolan-2-yl)phenyl)-3-oxa-8-azabicyclo[3.2.1]octane (69 mg, 0.22 mmol)
$^1$H NMR (400 MHz, CD$_3$OD) δ ppm 8.78 (d, J = 6.0 Hz, 1 H), 8.61 (s, 1 H), 8.55 (t, J = 7.9 Hz, 1 H), 8.09 (d, J = 8.0 Hz, 1 H), 7.81-7.98 (m, 4 H), 7.60 (d, J = 8.3 Hz, 1 H), 7.08 (br. s., 2 H), 5.01 (d, J = 0.8 Hz, 1 H), 4.25 (br. s., 2 H), 3.94 (d, J = 11.0 Hz, 2 H), 3.58 (br. s., 2 H), 2.55-2.68 (m, 1 H), 2.15-2.26 (m, 1 H), 2.00-2.14 (m, 4 H), 1.67-1.84 (m, 3 H), 1.53-1.67 (m, 2 H), 1.39-1.49 (m, 1 H), 1.18-1.29 (m, 1 H)

| Example/IUPAC name | Structure | MS calculated MS ESI [M + H]⁺ | Yield; Appearance Salt form |
|---|---|---|---|
| A417: 3-(4-((1R,5S)-3-oxa-9-azabicyclo[3.3.1]nonan-9-yl)phenyl)-N-((S)-(2-chlorophenyl)-3-methylbutyl)-1H-indazole-5-carboxamide | 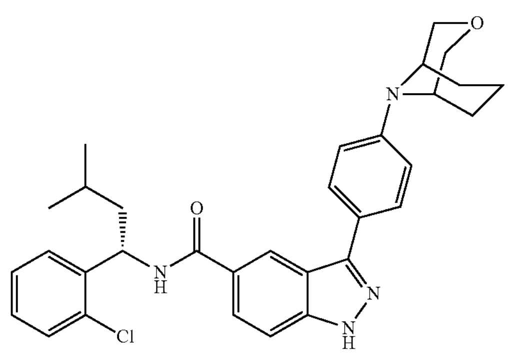 [SMILES: CC(C)C[C@H](NC(=O)c1ccc2[nH]nc(-c3ccc(N4C5CCCC4COC5)cc3)c2c1)c1ccccc1Cl] | $[C_{32}H_{35}ClN_4O_2 + H]^+$ 543.2 543.7 | 22 mg (16%); yellow solid; TFA salt |

SMs: (S)-N-(1-(2-chlorophenyl)-3-methylbutyl)-3-iodo-1H-indazole-5-carboxamide (100 mg, 0.21 mmol), (1R,5S)-9-(4-(4,4,5,5-tetramethyl-1,3,2-dioxaborolan-2-yl)phenyl)-3-oxa-9-azabicyclo[3.3.1]nonane (69 mg, 0.21 mmol)
$^1$H NMR (400 MHz, CD$_3$OD) δ ppm 8.63 (s, 1 H), 7.94 (dd, J = 8.8, 1.5 Hz, 1 H), 7.88 (d, J = 8.5 Hz, 2 H), 7.60 (d, J = 8.5 Hz, 1 H), 7.50 (dd, J = 7.9, 1.6 Hz, 1 H), 7.38 (d, J = 6.5 Hz, 1 H), 7.25-7.31 (m, 1 H), 7.18-7.24 (m, 1 H), 6.99-7.13 (m, 2 H), 5.65-5.72 (m, 1 H), 3.95-4.09 (m, 4 H), 3.92 (br. s., 2 H), 2.57-2.71 (m, 1 H), 1.99-2.12 (m, 2 H), 1.70-1.90 (m, 4 H), 1.57-1.67 (m, 2 H), 1.05 (d, J = 6.5 Hz, 3 H), 1.01 (d, J = 6.5 Hz, 3 H)

| Example/IUPAC name | Structure | MS calculated MS ESI [M + H]⁺ | Yield; Appearance Salt form |
|---|---|---|---|
| A418: 3-(4-((1R,5S)-3-oxa-9-azabicyclo[3.3.1]nonan-9-yl)phenyl)-N-((S)-cyclopentyl(pyridin-2-yl)methyl)-1H-indazole-5-carboxamide | 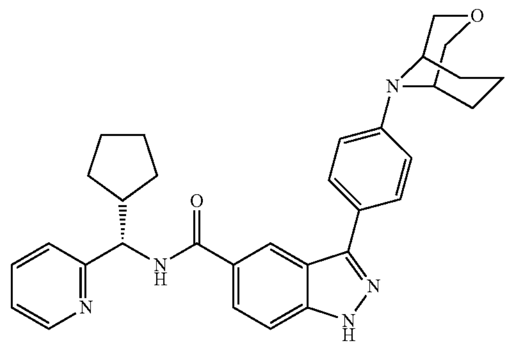 [SMILES: O=C(N[C@H](c1ccccn1)C1CCCC1)c1ccc2[nH]nc(-c3ccc(N4C5CCCC4COC5)cc3)c2c1] | $[C_{32}H_{35}N_5O_2 + H]^+$ 522.3 522.4 | 49 mg (30%); yellow solid; 2 × TFA salt |

SMs: (S)-N-(cyclopentyl(pyridin-2-yl)methyl)-3-iodo-1H-indazole-5-carboxamide (100 mg, 0.22 mmol), (1R,5S)-9-(4-(4,4,5,5-tetramethyl-1,3,2-dioxaborolan-2-yl)phenyl)-3-oxa-9-azabicyclo[3.3.1]nonane (74 mg, 0.22 mmol)
¹H NMR (400 MHz, CD₃OD) δ ppm 8.78 (d, J = 5.8 Hz, 1 H), 8.61 (s, 1 H), 8.56 (t, J = 7.3 Hz, 1 H), 8.09 (d, J = 8.0 Hz, 1 H), 7.95 (t, J = 6.8 Hz, 1 H), 7.82-7.92 (m, 3 H), 7.59 (d, J = 8.8 Hz, 1 H), 7.04 (d, J = 8.5 Hz, 2 H), 5.01 (d, J = 10.8 Hz, 1 H), 4.05 (d, J = 11.0 Hz, 2 H), 3.98 (d, J = 11.3 Hz, 2 H), 3.92 (br. s., 2 H), 2.55-2.70 (m, 2 H), 2.15-2.25 (m, 1 H), 1.99-2.12 (m, 2 H), 1.69-1.84 (m, 5 H), 1.54-1.67 (m, 3 H), 1.39-1.49 (m, 1 H), 1.16-1.30 (m, 1 H)

| Example/IUPAC name | Structure | MS calculated MS ESI [M + H]⁺ | Yield; Appearance Salt form |
|---|---|---|---|
| A419: 3-(4-((1R,5S)-3-oxa-8-azabicyclo[3.2.1]octan-8-yl)phenyl)-N-((R)-cyclopentyl(pyridin-2-yl)methyl)-1H-indazole-5-carboxamide | | $[C_{31}H_{33}N_5O_2 + H]^+$ 508.3 508.3 | 93 mg (58%); yellow solid; 2TFA salt |

SMs: (R)-N-(cyclopentyl(pyridin-2-yl)methyl)-3-iodo-1H-indazole-5-carboxamide (100 mg, 0.22 mmol), 8-(4-(4,4,5,5-tetramethyl-1,3,2-dioxaborolan-2-yl)phenyl)-3-oxa-8-azabicyclo[3.2.1]octane (69 mg, 0.22 mmol)
¹H NMR (400 MHz, CD₃OD) δ ppm 8.76 (d, J = 6.0 Hz, 1 H), 8.60 (s, 1 H), 8.46-8.53 (m, 1 H), 8.05 (d, J = 8.3 Hz, 1 H), 7.83-7.93 (m, 4 H), 7.60 (d, J = 8.8 Hz, 1 H), 7.01-7.10 (m, 2 H), 5.01 (d, J = 10.8 Hz, 1 H), 4.24 (br. s., 2 H), 3.93 (d, J = 11.3 Hz, 2 H), 3.57 (d, J = 11.5 Hz, 2 H), 2.55-2.66 (m, 1 H), 2.13-2.23 (m, 1 H), 2.10 (br. s., 4 H), 1.67-1.84 (m, 3 H), 1.54-1.67 (m, 2 H), 1.38-1.48 (m, 1 H), 1.19-1.30 (m, 1 H)

| Example/IUPAC name | Structure | MS calculated MS ESI [M + H]⁺ | Yield; Appearance Salt form |
|---|---|---|---|
| A420: N-((S)-cyclopentyl(pyridin-2-yl)methyl)-3-(4-((1R,5S,7R)-7-hydroxy-3-oxa-9-azabicyclo[3.3.1]nonan-9-yl)phenyl)-1H-indazole-5-carboxamide | | $[C_{32}H_{35}N_5O_3 + H]^+$ 538.3 538.5 | 68 mg (40%); yellow solid; 2TFA salt |

SMs: (S)-N-(cyclopentyl(pyridin-2-yl)methyl)-3-iodo-1H-indazole-5-carboxamide (100 mg, 0.22 mmol), (1R,5S,7r)-9-(4-(4,4,5,5-tetramethyl-1,3,2-dioxaborolan-2-yl)phenyl)-3-oxabicyclo[3.3.1]nonan-7-ol (76 mg, 0.22 mmol)
¹H NMR (400 MHz, CD₃OD) δ ppm 8.76 (d, J = 5.0 Hz, 1 H), 8.60 (s, 1 H), 8.48 (td, J = 7.9, 1.5 Hz, 1 H), 8.04 (d, J = 8.0 Hz, 1 H), 7.84-7.93 (m, 4 H), 7.59 (d, J = 8.8 Hz, 1 H), 7.05 (d, J = 8.5 Hz, 2 H), 5.01 (d, J = 10.8 Hz, 1 H), 4.03-4.09 (m, 2 H), 3.91-4.02 (m, 4 H), 3.88 (br. s., 1 H), 2.54-2.66 (m, 1 H), 2.27-2.37 (m, 2 H), 2.13-2.22 (m, 1 H), 1.67-1.82 (br. m, 5 H), 1.53-1.66 (m, 2 H), 1.38-1.48 (m, 1 H), 1.18-1.29 (m, 1 H)

| Example/IUPAC name | Structure | MS calculated MS ESI [M + H]⁺ | Yield; Appearance Salt form |
|---|---|---|---|
| A421: N((S)-1-(2-chlorophenyl)-2-methylpropyl)-3-(4-((1R,5S,7R)-7-hydroxy-3-oxa-9-azabicyclo[3.3.1]nonan-9-yl)phenyl)-1H-indazole-5-carboxamide | 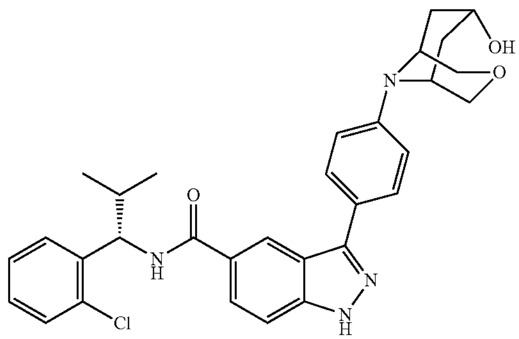 [SMILES: CC(C)[C@H](NC(=O)c1ccc2[nH]nc(-c3ccc(N4C5COCC4CC(O)C5)cc3)c2c1)c1ccccc1Cl] | $[C_{31}H_{33}ClN_4O_3 + H]^+$ 545.2 545.6 | 68 mg (47%); yellow solid; TFA salt |

SMs: (S)-N-(1-(2-chlorophenyl)-2-methylpropyl)-3-iodo-1H-indazole-5-carboxamide (100 mg, 0.22 mmol), (1R,5S,7R)-9-(4-(4,4,5,5-tetramethyl-1,3,2-dioxaborolan-2-yl)phenyl)-3-oxabicyclo[3.3.1]nonan-7-ol (76 mg, 0.22 mmol)
¹H NMR (400 MHz, CD₃OD) δ ppm 8.55 (s, 1 H), 7.81-7.91 (m, 3 H), 7.52-7.59 (m, 2 H), 7.38 (dd, J = 7.8, 1.3 Hz, 1 H), 7.29 (td, J = 7.5, 1.4 Hz, 1 H), 7.21 (td, J = 7.7, 1.6 Hz, 1 H), 7.02 (br. s., 2 H), 5.34-5.40 (m, 1 H), 3.82-4.07 (m, 7 H), 2.21-2.37 (m, 3 H), 1.74 (d, J = 15.6 Hz, 2 H), 1.15 (d, J = 6.5 Hz, 3 H), 0.86 (d, J = 6.8 Hz, 3 H)

| Example/IUPAC name | Structure | MS calculated MS ESI [M + H]⁺ | Yield; Appearance Salt form |
|---|---|---|---|
| A422: 3-(4-((1R,5S)-3-oxa-8-azabicyclo[3.2.1]octan-8-yl)phenyl)-N-((R)-cyclopropyl(pyridin-2-yl)methyl)-1H-indazole-5-carboxamide | | $[C_{29}H_{29}N_5O_2 + H]^+$ 480.2 480.2 | 68 mg (51%); yellow solid; 2HCl salt |

SMs: (R)-N-(cyclopropyl(pyridin-2-yl)methyl)-3-iodo-1H-indazole-5-carboxamide (100 mg, 0.24 mmol), 8-(4-(4,4,5,5-tetramethyl-1,3,2-dioxaborolan-2-yl)phenyl)-3-oxa-8-azabicyclo[3.2.1]octane (76 mg, 0.24 mmol)
¹H NMR (400 MHz, CD₃OD) δ ppm 8.78-8.83 (m, 2 H), 8.66 (t, J = 8.4 Hz, 1 H), 8.32 (d, J = 8.0 Hz, 1 H), 8.28 (d, J = 8.5 Hz, 2 H), 8.00-8.05 (m, 2 H), 7.75 (d, J = 8.5 Hz, 2 H), 7.69 (d, J = 8.8 Hz, 1 H), 4.68 (br. s, 2 H), 4.51 (d, J = 10.3 Hz, 1 H), 4.21 (d, J = 12.5 Hz, 2 H), 3.93 (d, J = 12.0 Hz, 2 H), 2.30-2.38 (m, 2 H), 2.16-2.24 (m, 2 H), 1.56-1.65 (m, 1 H), 0.89-0.98 (m, 1 H), 0.62-0.82 (m, 3 H)

| Example/IUPAC name | Structure | MS calculated MS ESI [M + H]⁺ | Yield; Appearance Salt form |
|---|---|---|---|
| A423: 3-(4-((1R,5S)-3-oxa-8-azabicyclo[3.2.1]octan-8-yl)phenyl)-N-((R)-3-hydroxy-1-phenylpropyl)-1H-indazole-5-carboxamide | | $[C_{29}H_{30}N_4O_3 + H]^+$ 483.2 483.4 | 48 mg (39%); yellow solid; HCl salt |

SMs: (R)-N-(3-hydroxy-1-phenylpropyl)-3-iodo-1H-indazole-5-carboxamide (100 mg, 0.24 mmol), 8-(4-(4,4,5,5-tetramethyl-1,3,2-dioxaborolan-2-yl)phenyl)-3-oxa-8-azabicyclo[3.2.1]octane (75 mg, 0.24 mmol)
¹H NMR (400 MHz, CD₃OD) δ ppm 8.61 (s, 1 H), 8.25 (d, J = 8.5 Hz, 2 H), 7.96 (dd, J = 8.9, 1.1 Hz, 1 H), 7.79 (d, J = 7.0 Hz, 2 H), 7.67 (d, J = 9.0 Hz, 1 H), 7.45 (d, J = 7.5 Hz, 2 H), 7.35 (t, J = 7.7 Hz, 2 H), 7.25 (t, J = 7.3 Hz, 1 H), 5.31-5.37 (m, 1 H), 4.71 (br. s, 2 H), 4.21 (d, J = 12.0 Hz, 2 H), 3.97 (d, J = 12.8 Hz, 2 H), 3.60-3.72 (m, 2 H), 2.32-2.40 (m, 2 H), 2.10-2.24 (m, 4 H)

| Example/IUPAC name | Structure | MS calculated MS ESI [M + H]⁺ | Yield; Appearance Salt form |
|---|---|---|---|
| A424: N-((S)-1-(2-chlorophenyl)-3-methylbutyl)-3-(4-((1R,5S,7R)-7-hydroxy-3-oxa-9-azabicyclo[3.3.1]nonan-9-yl)phenyl)-1H-indazole-5-carboxamide | 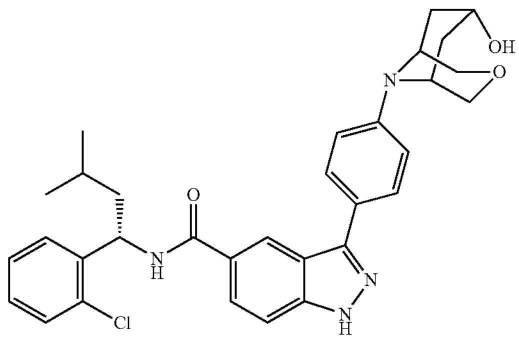 [SMILES: CC(C)C[C@H](NC(=O)c1ccc2[nH]nc(-c3ccc(N4C5COCC4CC(O)C5)cc3)c2c1)c1ccccc1Cl] | [C$_{32}$H$_{35}$ClN$_4$O$_3$ + H]⁺ 559.2 559.6 | 28 mg (34%); yellow solid; HCl salt |

SMs: (S)-N-(1-(2-chlorophenyl)-3-methylbutyl)-3-iodo-1H-indazole-5-carboxamide (68 mg, 0.14 mmol), (1R,5S,7R)-9-(4-(4,4,5,5-tetramethyl-1,3,2-dioxaborolan-2-yl)phenyl)-3-oxabicyclo[3.3.1]nonan-7-ol (50 mg, 0.14 mmol)
¹H NMR (400 MHz, CD$_3$OD) δ ppm 8.68 (s, 1 H), 8.09 (d, J = 8.8 Hz, 1 H), 7.91 (d, J = 8.8 Hz, 2 H), 7.70 (d, J = 9.0 Hz, 1 H), 7.50 (d, J = 7.5 Hz, 1 H), 7.38 (d, J = 7.8 Hz, 1 H), 7.28 (t, J = 7.8 Hz, 1 H), 7.22 (t, J = 6.3 Hz, 1 H), 7.12 (d, J = 9.0 Hz, 2 H), 5.66-5.73 (m, 1 H), 4.12 (br. s., 2 H), 3.92-4.05 (m, 4 H), 3.86-3.91 (m, 1 H), 2.27-2.37 (m, 2 H), 1.75-1.89 (m, 4 H), 1.59-1.68 (m, 1 H), 1.05 (d, J = 6.3 Hz, 3 H), 1.01 (d, J = 6.3 Hz, 3 H)

| Example/IUPAC name | Structure | MS calculated MS ESI [M + H]⁺ | Yield; Appearance Salt form |
|---|---|---|---|
| A425: N-((R)-cyclopentyl(pyridin-2-yl)methyl)-3-(4-((1R,5S,7R)-7-hydroxy-3-oxa-9-azabicyclo[3.3.1]nonan-9-yl)phenyl)-1H-indazole-5-carboxamide | | [C$_{32}$H$_{35}$N$_5$O$_3$ + H]⁺ 538.3 538.4 | 55 mg (56%); yellow solid; 2 × HCl salt |

SMs: (R)-N-(cyclopentyl(pyridin-2-yl)methyl)-3-iodo-1H-indazole-5-carboxamide (70 mg, 0.16 mmol), (1R,5S,7R)-9-(4-(4,4,5,5-tetramethyl-1,3,2-dioxaborolan-2-yl)phenyl)-3-oxabicyclo[3.3.1]nonan-7-ol (54 mg, 0.16 mmol)
¹H NMR (400 MHz, CD$_3$OD) δ ppm 8.81 (d, J = 6.0 Hz, 1 H), 8.73 (s, 1 H), 8.65 (t, J = 7.8 Hz, 1 H), 8.23 (d, J = 7.8 Hz, 1 H), 7.99-8.08 (m, 2 H), 7.96 (d, J = 8.3 Hz, 1 H), 7.69 (d, J = 8.8 Hz, 1 H), 7.16 (d, J = 8.0 Hz, 2 H), 5.04 (d, J = 10.8 Hz, 1 H), 4.15 (br. s., 2 H), 3.93-4.05 (m, 4 H), 3.90 (br. s., 1 H), 2.65-2.77 (m, 1 H), 2.29-2.41 (m, 2 H), 2.17-2.28 (m, 1 H), 1.69-1.88 (m, 5 H), 1.53-1.68 (m, 2 H), 1.39-1.50 (m, 1 H), 1.17-1.30 (m, 1 H)

| Example/IUPAC name | Structure | MS calculated MS ESI [M + H]⁺ | Yield; Appearance Salt form |
|---|---|---|---|
| A426: N-((S)-3,3-dimethyl-1-phenylbutyl)-3-(4-((1R,5S,7R)-7-hydroxy-3-oxa-9-azabicyclo[3.3.1]nonan-9-yl)phenyl)-1H-indazole-5-carboxamide | | [C$_{33}$H$_{38}$N$_4$O$_3$ + H]⁺ 539.3 539.5 | 38 mg (41%); yellow solid; HCl salt |

SMs: (S)-N-(3,3-dimethyl-1-phenylbutyl)-3-iodo-1H-indazole-5-carboxamide (70 mg, 0.16 mmol), (1R,5S,7R)-9-(4-(4,4,5,5-tetramethyl-1,3,2-dioxaborolan-2-yl)phenyl)-3-oxabicyclo[3.3.1]nonan-7-ol (54 mg, 0.16 mmol)
¹H NMR (400 MHz, CD$_3$OD) δ ppm 8.63 (s, 1 H), 8.05 (dd, J = 9.0, 1.5 Hz, 1 H), 7.89 (d, J = 8.8 Hz, 2 H), 7.67 (d, J = 8.8 Hz, 1 H), 7.41 (d, J = 7.3 Hz, 2 H), 7.32 (t, J = 7.5 Hz, 2 H), 7.21 (t, J = 7.5 Hz, 1 H), 7.11 (d, J = 8.8 Hz, 2 H), 5.34 (dd, J = 9.5, 3.5 Hz, 1 H), 4.11 (br. s., 2 H), 3.91-4.03 (m, 4 H), 3.86-3.90 (m, 1 H), 2.27-2.37 (m, 2 H), 2.02-2.11 (m, 1 H), 1.70-1.84 (m, 3 H), 1.03 (s, 9 H)

| Example/IUPAC name | Structure | MS calculated MS ESI [M + H]⁺ | Yield; Appearance Salt form |
|---|---|---|---|
| A427 3-(4-(4-hydroxypiperidin-1-yl)phenyl)-N-((1-morpholinocyclohexyl)methyl)-1H-indazole-5-carboxamide | 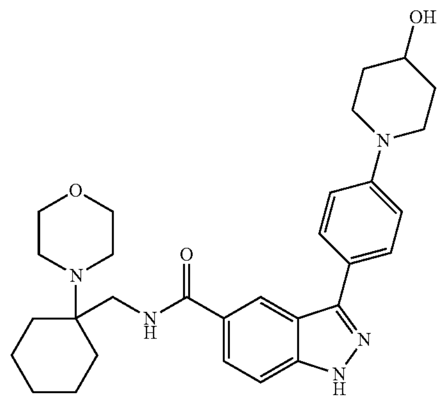 [SMILES: O=C(NCC1(N2CCOCC2)CCCCC1)c1ccc2[nH]nc(-c3ccc(N4CCC(O)CC4)cc3)c2c1] | [$C_{30}H_{39}N_5O_3$ + H]⁺ 518.3 518.2 | 30.5 mg (30%); pale yellow solid; 2TFA salt |

SMs: 3-iodo-N-((1-morpholinocyclohexyl)methyl)-1H-indazole-5-carboxamide TFA salt (79.5 mg, 0.13 mmol), 1-(4-(4,4,5,5-tetramethyl-1,3,2-dioxaborolan-2-yl)phenyl) piperidin-4-ol (69.8 mg, 0.18 mmol), PdCl₂dppf*CH₂Cl₂ (18 mg, 0.015 mmol)
¹H NMR (400 MHz, CD₃OD) δ ppm 8.74 (s, 1 H), 8.26 (d, J = 8.8 Hz, 2 H), 8.05 (dd, J = 8.8, 1.5 Hz, 1 H), 7.83 (d, J = 8.8 Hz, 2 H), 7.71 (d, J = 8.8 Hz, 1 H), 4.09-4.22 (m, 3 H), 3.85-3.99 (m, 6 H), 3.63-3.74 (m, 4 H), 2.67 (s, 2 H), 2.24-2.35 (m, 2 H), 2.00 (d, J = 11.5 Hz, 4 H0, 1.88 (br. s, 2 H), 1.78 (d, J = 3.5 Hz, 5 H), 1.25-1.39 (m, 1 H)

| A428: 3-(4-((1-methylpiperidin-4-yl)oxy)phenyl)-N-((1-morpholinocyclopentyl)methyl)-1H-indazole-5-carboxamide | | [$C_{30}H_{39}N_5O_3$ + H]⁺ 518.3 518.2 | 31.5 mg (36%); yellow solid; free base |

SMs: 3-iodo-N-((1-morpholinocyclopentyl)methyl)-1H-indazole-5-carboxamide TFA salt (95.6 mg, 0.16 mmol), 1-methyl-4-(4-(4,4,5,5-tetramethyl-1,3,2-dioxaborolan-2-yl)phenoxy)piperidine (71 mg, 0.22 mmol), PdCl₂dppf*CH₂Cl₂(13.5 mg, 0.016 mmol)
¹H NMR (400 MHz, CD₃OD) δ ppm 8.50 (s, 1H), 7.83-7.95 (m, 3H), 7.62 (d, J = 8.8 Hz, 1H), 7.10 (d, J = 8.8 Hz, 2H), 4.44-4.56 (m, 1H), 3.64-3.75 (m, 4H), 3.54 (s, 2H), 2.65-2.83 (m, 6H), 2.40 (br, 2H), 2.32 (s, 3H), 2.05 (br, 2H), 1.77-1.92 (m, 4H), 1.70 (t, J = 6.9 Hz, 4H), 1.53-1.64 (m, 2H)

| A429: 3-(4-((1-methylpiperidin-4-yl)oxy)phenyl)-N-((1-morpholinocycloheptyl)methyl)-1H-indazole-5-carboxamide | | [$C_{32}H_{43}N_5O_3$ + H]⁺ 546.3 546.3 | 27.3 mg (29%); white solid; free base |

SMs: 3-iodo-N-((1-morpholinocycloheptyl)methyl)-1H-indazole-5-carboxamide TFA salt (100.4 mg, 0.16 mmol), 1-methyl-4-(4-(4,4,5,5-tetramethyl-1,3,2-dioxaborolan-2-yl)phenoxy)piperidine (71 mg, 0.22 mmol), PdCl₂dppf*CH₂Cl₂ (13.5 mg, 0.016 mmol)
¹H NMR (400 MHz, CD₃OD) δ ppm 8.48 (s, 1H), 7.82-7.95 (m, 3H), 7.62 (d, J = 8.8 Hz, 1H), 7.10 (d, J = 8.8 Hz, 2H), 4.44-4.55 (m, 1H), 3.63-3.76 (m, 4 H), 3.47 (s, 2 H), 2.63-2.81 (m, 6 H), 2.40 (br. s, 2 H), 2.32 (s, 3 H), 2.05 (d, J = 3.3 Hz, 2 H), 1.79-1.95 (m, 4 H), 1.45-1.70 (m, 10 H)

| Example/IUPAC name | Structure | MS calculated MS ESI [M + H]+ | Yield; Appearance Salt form |
|---|---|---|---|
| A430: (4-(((2R,4R,6S)-2,6-dimethyltetrahydro-2H-pyran-4-yl)oxy)phenyl)-N-((1-morpholino cyclopentyl)methyl)-1H-indazole-5-carboxamide | 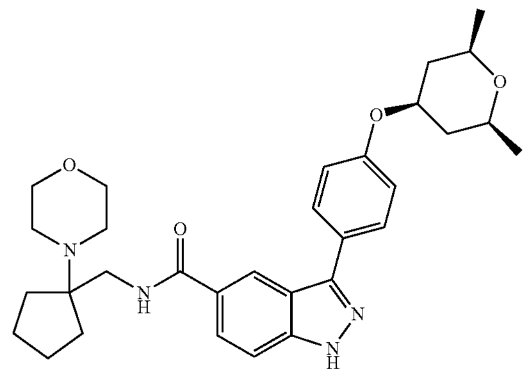 [SMILES: C[C@@H]1C[C@H](Oc2ccc(-c3n[nH]c4ccc(C(=O)NCC5(N6CCOCC6)CCCC5)cc34)cc2)C[C@H](C)O1] | $[C_{31}H_{40}N_4O_4 + H]^+$ 533.3 533.5 | 38.7 mg (42%); off white solid; TFA salt |

SMs: 3-iodo-N-((1-morpholinocyclopentyl)methyl)-1H-indazole-5-carboxamide TFA salt (80.5 mg, 0.14 mmol), 2-(4-(((2R,4R,6S)-2,6-dimethyltetrahydro-2H-pyran-4-yl)oxy)phenyl)-HBpin (51 mg, 0.15 mmol), PdCl$_2$dppf*CH$_2$Cl$_2$ (12 mg, 0.014 mmol)
$^1$H NMR (400 MHz, CD$_3$OD) δ ppm 8.65 (s, 1 H), 7.99 (dd, J = 8.8, 1.5 Hz, 1 H), 7.92 (d, J = 8.8 Hz, 2 H), 7.65 (d, J = 8.8 Hz, 1 H), 7.13 (d, J = 8.8 Hz, 2 H), 4.60 (s, 1 H), 4.12 (d, J = 12.3 Hz, 2 H), 3.74-3.92 (m, 4 H), 3.58-3.73 (m, 4 H), 3.46 (d, J = 12.0 Hz, 2 H), 2.17 (dd, J = 12.2, 4.1 Hz, 2 H), 2.05 (br. s, 4 H), 1.82-1.96 (m, 4 H), 1.24 (d, J = 6.3 Hz, 8 H).

| Example/IUPAC name | Structure | MS calculated MS ESI [M + H]+ | Yield; Appearance Salt form |
|---|---|---|---|
| A431: N-((2,2-dimethyl-1-phenylcyclopropyl)methyl)-3-(4-((1-methylpiperidin-4-yl)oxy)phenyl)-1H-indazole-5-carboxamide | 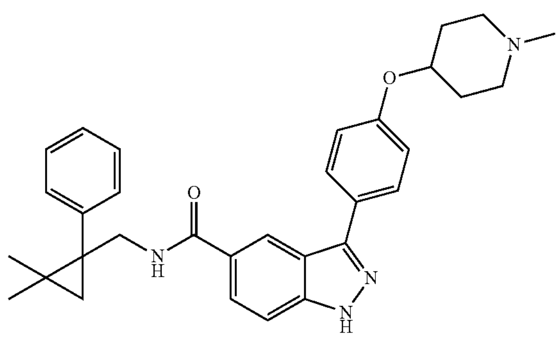 | $[C_{32}H_{36}N_4O_2 + H]^+$ 509.2 509.3 | 67.6 mg (53%); beige solid; TFA salt |

SMs: N-((2,2-dimethyl-1-phenylcyclopropyl)methyl)-3-iodo-1H-indazole-5-carboxamide (95.8 mg, 0.20 mmol), 1-methyl-4-(4-(4,4,5,5-tetramethyl-1,3,2-dioxaborolan-2-yl)phenoxy)piperidine (75.6 mg, 0.23 mmol), PdCl$_2$dppf*CH$_2$Cl$_2$ (17.7 mg, 0.016 mmol)
$^1$H NMR (400 MHz, CD$_3$OD) δ ppm 8.21 (d, J = 1.0 Hz, 1 H), 7.84-7.93 (m, 2 H), 7.66 (dd, J = 8.9, 1.4 Hz, 1 H), 7.53 (d, J = 8.8 Hz, 1 H), 7.25-7.38 (m, 4 H), 7.13-7.25 (m, 3 H), 4.69-4.70 (m, 0.40 H), 3.91-3.94 (m, 2 H), 3.60-3.67 (m, 1.80 H), 3.40-3.46 (m, 2.70 H), 2.94 (m, 3 H), 2.43-2.47 (m, 0.70 H), 2.29-2.33 (m, 1.30 H), 2.11-2.19 (m, 1.30 H), 1.89-1.99 (m, 0.70 H), 1.43 (s, 3 H), 0.91-1.01 (m, 2 H), 0.79 (s, 3 H), 1H merged with solvent peak.

| Example/IUPAC name | Structure | MS calculated MS ESI [M + H]+ | Yield; Appearance Salt form |
|---|---|---|---|
| A432: 3-(4-((1-(2-hydroxyethyl)piperidin-4-yl)oxy)phenyl)-N-((1-morpholinocyclohexyl)methyl)-1H-indazole-5-carboxamide | 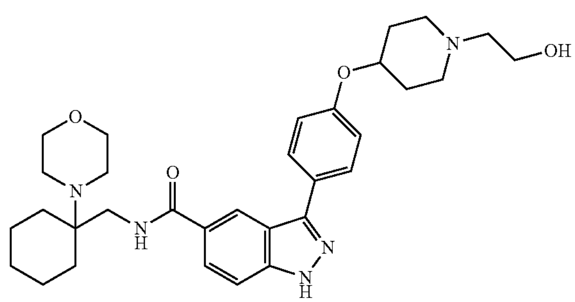 [SMILES: O=C(NCC1(N2CCOCC2)CCCCC1)c1ccc2[nH]nc(-c3ccc(OC4CCN(CCO)CC4)cc3)c2c1] | $[C_{32}H_{43}N_5O_4 + H]^+$ 562.34 562.3 | 60 mg (51%); white solid; TFA salt |

SMs: 3-iodo-N-((1-morpholinocyclohexyl)methyl)-1H-indazole-5-carboxamide (96 mg, 0.21 mmol), 2-(4-(4-(4,4,5,5-tetramethyl-1,3,2-dioxaborolan-2-yl)phenoxy)piperidin-1-yl)EtOH (93 mg, 0.27 mmol)
$^1$H NMR (400 MHz, CD$_3$OD) δ ppm 8.68 (s, 1H), 8.02-7.96 (m, 3H), 7.65 (d, J = 8.8 Hz, 1H), 7.24-7.18 (m, 2H), 4.87 (bs, 1H), 4.24-4.14 (m, 2H), 3.98-3.86 (m, 7H), 3.78-3.22 (m, 6H), 2.44-2.17 (m, 4H), 2.07-1.55 (m, 12H), 1.39-1.22 (m, 1H)

| Example/IUPAC name | Structure | MS calculated MS ESI [M + H]+ | Yield; Appearance Salt form |
|---|---|---|---|
| A433: 3-(4-((1-(oxetan-3-yl)piperidin-4-yl)oxy)phenyl)-N-((4-(thiophen-2-yl)tetrahydro-2H-pyran-4-yl)methyl)-1H-indazole-5-carboxamide | 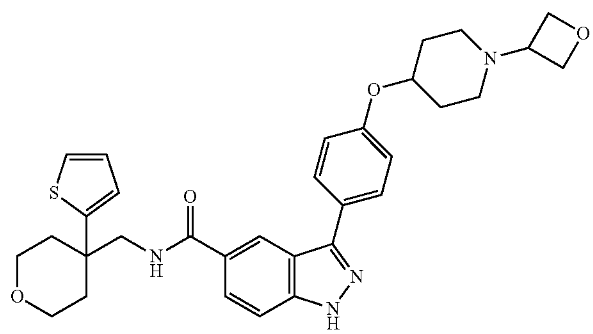 [SMILES: O=C(NCC1(c2cccs2)CCOCC1)c1ccc2[nH]nc(-c3ccc(OC4CCN(C5COC5)CC4)cc3)c2c1] | [C$_{32}$H$_{36}$N$_4$O$_4$S + H]+ 573.25 573.5 | 71 mg (83%); orange solid; free base |

SMs: 3-iodo-N-((4-(thiophen-2-yl)tetrahydro-2H-pyran-4-yl)methyl)-1H-indazole-5-carboxamide (70 mg, 0.15 mmol), 1-(oxetan-3-yl)-4-(4-(4,4,5,5-tetramethyl-1,3,2-dioxaborolan-2-yl)phenoxy)piperidine (72 mg, 0.20 mmol)
$^1$H NMR (400 MHz, CD$_3$OD) δ ppm 8.43 (s, 1H), 7.88 (d, J = 8.6 Hz, 2H), 7.82 (d, J = 8.8 Hz, 1H), 7.57 (d, J = 8.8 Hz, 1H), 7.37 (d, J = 5.0 Hz, 1H), 7.12 (d, J = 8.6 Hz, 2H), 7.07-7.02 (m, 2H), 4.87 (bs, 1H), 4.71 (t, J = 6.8 Hz, 2H), 4.63 (t, J = 6.8 Hz, 2H), 4.61-4.56 (bs, 1H), 3.87-3.83 (m, 2H), 3.66-3.54 (m, 4H), 2.66-2.64 (m, 2H), 2.32-2.29 (m, 2H), 2.14-1.98 (m, 6H), 1.90-1.85 (m, 2H)

| Example/IUPAC name | Structure | MS calculated MS ESI [M + H]+ | Yield; Appearance Salt form |
|---|---|---|---|
| A434: N-((1-(cyclopentyloxy)cyclohexyl)methyl)-3-(4-((1-(oxetan-3-yl)piperidin-4-yl)oxy)phenyl)-1H-indazole-5-carboxamide | 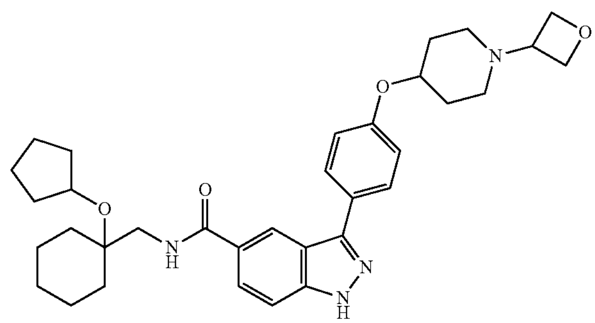 [SMILES: O=C(NCC1(OC2CCCC2)CCCCC1)c1ccc2[nH]nc(-c3ccc(OC4CCN(C5COC5)CC4)cc3)c2c1] | [C$_{34}$H$_{44}$N$_4$O$_4$ + H]+ 573.34 573.5 | 45 mg (52%); colourless solid; free base |

SMs: N-((1-(cyclopentyloxy)cyclohexyl)methyl)-3-iodo-1H-indazole-5-carboxamide (70 mg, 0.15 mmol), 1-(oxetan-3-yl)-4-(4-(4,4,5,5-tetramethyl-1,3,2-dioxaborolan-2-yl)phenoxy)piperidine (72 mg, 0.20 mmol)
$^1$H NMR (400 MHz, CD$_3$OD) δ ppm 8.49 (s, 1H), 7.91-7.85 (m, 3H), 7.61 (d, J = 8.9 Hz, 1H), 7.11 (d, J = 8.7 Hz, 2H), 4.87 (bs, 1H), 4.71 (t, J = 6.8 Hz, 2H), 4.62 (t, J = 6.8 Hz, 2H), 4.61-4.55 (bs, 1H), 4.46-4.22 (m, 1H), 3.57-3.53 (m, 2H), 2.66-2.64 (m, 2H), 2.30-2.28 (m, 2H), 2.10-2.06 (m, 2H), 1.87-1.29 (m, 20H)

| Example/IUPAC name | Structure | MS calculated MS ESI [M + H]+ | Yield; Appearance Salt form |
|---|---|---|---|
| A435: N-((1-(cyclopentyloxy)cyclohexyl)methyl)-3-(4-morpholinophenyl)-1H-indazole-5-carboxamide | 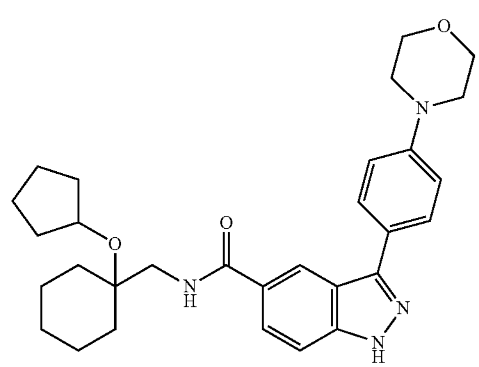 [SMILES: O=C(NCC1(OC2CCCC2)CCCCC1)c1ccc2[nH]nc(-c3ccc(N4CCOCC4)cc3)c2c1] | [C$_{30}$H$_{38}$N$_4$O$_3$ + H]+ 503.30 503.5 | 61 mg (66%); orange solid; TFA salt |

SMs: N-((1-(cyclopentyloxy)cyclohexyl)methyl)-3-iodo-1H-indazole-5-carboxamide (70 mg, 0.15 mmol), (4-morpholinophenyl)boronic acid (41 mg, 0.20 mmol)
$^1$H NMR (400 MHz, CD$_3$OD) δ ppm 8.51 (s, 1H), 7.93 (d, J = 8.8 Hz, 2H), 7.86 (d, J = 8.8 Hz, 1H), 7.61 (d, J = 9.0 Hz, 1H), 7.22 (d, J = 8.6 Hz, 2H), 4.24-4.22 (m, 1H), 3.91-3.88 (m, 4H), 3.53 (s, 2H), 3.35-3.31 (m, 4H), 1.91-1.86 (m, 2H), 1.80-1.41 (m, 16H)

| Example/IUPAC name | Structure | MS calculated MS ESI [M + H]⁺ | Yield; Appearance Salt form |
| --- | --- | --- | --- |
| A436: 3-(4-morpholinophenyl)-N-((4-(thiophen-2-yl)tetrahydro-2H-pyran-4-yl)methyl)-1H-indazole-5-carboxamide | | [$C_{28}H_{30}N_4O_3S$ + H]⁺<br>503.21<br>503.5 | 64 mg (66%); pale-orange solid; TFA salt |
| SMs: 3-iodo-N-((4-(thiophen-2-yl)tetrahydro-2H-pyran-4-yl)methyl)-1H-indazole-5-carboxamide (70 mg, 0.15 mmol), (4-morpholinophenyl)boronic acid (41 mg, 0.20 mmol)<br>¹H NMR (400 MHz, CD₃OD) δ ppm 8.46 (s, 1H), 7.96 (d, J = 8.8 Hz, 2H), 7.81 (d, J = 8.8 Hz, 1H), 7.58 (d, J = 8.8 Hz, 1H), 7.37 (d, J = 5.0 Hz, 1H), 7.30 (d, J = 7.4 Hz, 2H), 7.07-7.02 (m, 2H), 3.95-3.92 (m, 4H), 3.87-3.84 (m, 2H), 3.60-3.55 (m, 4H), 3.42-3.36 (m, 4H), 2.15-2.11 (m, 2H), 2.05-1.99 (m, 2H) | | | |
| A437: N-(2-ethyl-2-phenylbutyl)-3-(4-morpholinophenyl)-1H-indazole-5-carboxamide | | [$C_{30}H_{34}N_4O_2$ + H]⁺<br>483.28<br>483.4 | 63 mg (63%); orange solid; TFA salt |
| SMs: N-(2-ethyl-2-phenylbutyl)-3-iodo-1H-indazole-5-carboxamide (75 mg, 0.17 mmol), 4-(4-(4,4,5,5-tetramethyl-1,3,2-dioxaborolan-2-yl)phenyl)morpholine (63 mg, 0.23 mmol)<br>¹H NMR (400 MHz, CD₃OD) δ ppm 8.25 (s, 1H), 7.87 (d, J = 8.8 Hz, 2H), 7.67 (d, J = 7.4 Hz, 1H), 7.52 (d, J = 8.8 Hz, 1H), 7.40 (d, J = 7.4 Hz, 2H), 7.34 (t, J = 7.4 Hz, 2H), 7.26-7.19 (m, 3H), 3.92-3.88 (m, 4H), 3.71 (s, 2H), 3.34-3.30 (m, 4H), 1.82 (q, J = 7.2 Hz, 4H), 0.79 (t, J = 7.2 Hz, 6H) | | | |
| A438: N-((1-(cyclopentyloxy)cyclohexyl)methyl])-3-(4-(((1R,3R,5S)-8-methyl-8-azabicyclo[3.2.1]octan-3-yl)oxy)pheny])-1H-indazole-5-carboxamide | | [$C_{34}H_{44}N_4O_3$ + H]⁺<br>557.35<br>557.4 | 38 mg (44%); white solid; TFA salt |
| SMs: N-((1-(cyclopentyloxy)cyclohexyl)methyl)-3-iodo-1H-indazole-5-carboxamide (60 mg, 0.13 mmol), (1R,3R,5S)-8-methyl-3-(4-(4,4,5,5-tetramethyl-1,3,2-dioxaborolan-2-yl)phenoxy)-8-azabicyclo[3.2.1]octane (56 mg, 0.17 mmol)<br>¹H NMR (400 MHz, CD₃OD) δ ppm 8.50 (s, 1H), 7.94 (d, J = 8.8 Hz, 2H), 7.87 (d, J = 7.7 Hz, 1H), 7.62 (d, J = 8.9 Hz, 1H), 7.08 (d, J = 8.7 Hz, 2H), 4.77-4.75 (bs, 1H), 4.25-4.22 (m, 1H), 3.64-3.60 (bs, 2H), 3.54 (s, 2H), 2.63 (s, 3H), 2.40-2.24 (m, 8H), 1.91-1.53 (m, 18H) | | | |

| Example/IUPAC name | Structure | MS calculated MS ESI [M + H]+ | Yield; Appearance Salt form |
|---|---|---|---|
| A439: N-(2-ethyl-2-phenylbutyl)-3-(4-((1-(oxetan-3-yl)piperidin-4-yl)oxy)phenyl)-1H-indazole-5-carboxamide | 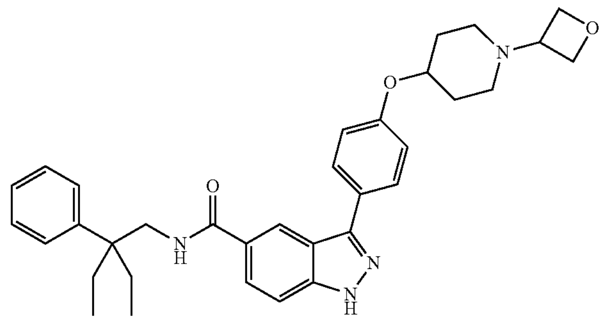 [SMILES: CCC(CC)(CNC(=O)c1ccc2[nH]nc(-c3ccc(OC4CCN(C5COC5)CC4)cc3)c2c1)c1ccccc1] | [C₃₄H₄₀N₄O₃ + H]+ 553.32 553.4 | 36 mg (56%); pink solid; TFA salt |

SMs: N-(2-ethyl-2-phenylbutyl)-3-iodo-1H-indazole-5-carboxamide (43 mg, 0.096 mmol), 1-(oxetan-3-yl)-4-(4-(4,4,5,5-tetramethyl-1,3,2-dioxaborolan-2-yl)phenoxy)piperidine (45 mg, 0.13 mmol)
¹H NMR (400 MHz, CD₃OD) δ ppm 8.26 (s, 1H), 7.89 (d, J = 8.4 Hz, 2H), 7.67 (d, J = 7.4 Hz, 1H), 7.55 (d, J = 8.7 Hz, 1H), 7.44 (d, J = 7.4 Hz, 2H), 7.37 (t, J = 7.4 Hz, 2H), 7.25-7.19 (m, 3H), 4.90-4.80 (m, 5H), 4.54-4.51 (m, 1H), 3.75 (s, 2H), 3.49-3.31 (m, 4H), 2.38-2.17 (m, 4H), 1.85 (q, J = 7.2 Hz, 4H), 0.82 (t, J = 7.2 Hz, 6H)

| Example/IUPAC name | Structure | MS calculated MS ESI [M + H]+ | Yield; Appearance Salt form |
|---|---|---|---|
| A440: N-(2-ethyl-2-phenylbutyl)-3-(4-((1-methylpiperidin-4-yl)oxy)phenyl)-1H-indazole-5-carboxamide | 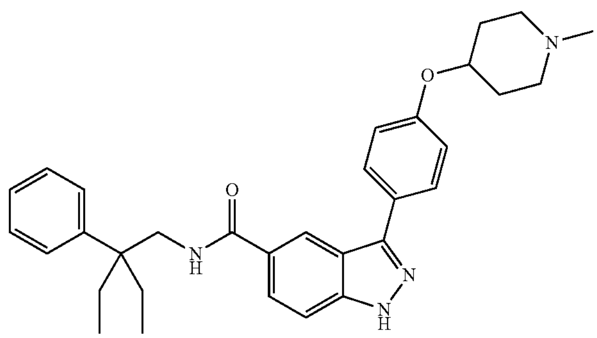 [SMILES: CCC(CC)(CNC(=O)c1ccc2[nH]nc(-c3ccc(OC4CCN(C)CC4)cc3)c2c1)c1ccccc1] | [C₃₂H₃₈N₄O₂ + H]+ 511.31 511.4 | 24 mg (29%); pink solid; TFA salt |

SMs: N-(2-ethyl-2-phenylbutyl)-3-iodo-1H-indazole-5-carboxamide (60 mg, 0.13 mmol), 1-methyl-4-(4-(4,4,5,5-tetramethyl-1,3,2-dioxaborolan-2-yl)phenoxy)piperidine (55 mg, 0.17 mmol)
¹H NMR (400 MHz, CD₃OD) δ ppm 8.26 (s, 1H), 7.90-7.86 (m, 2H), 7.68 (d, J = 7.5 Hz, 1H), 7.55 (d, J = 8.8 Hz, 1H), 7.44 (d, J = 7.4 Hz, 2H), 7.37 (t, J = 7.4 Hz, 2H), 7.24-7.17 (m, 3H), 4.90-4.87 (m, 1H), 3.76 (s, 2H), 3.68-3.20 (m. 4H), 2.98-2.95 (m, 3H), 2.45-1.95 (m, 4H), 1.85 (q, J = 7.2 Hz, 4H), 0.82 (t, J = 7.2 Hz, 6H)

| Example/IUPAC name | Structure | MS calculated MS ESI [M + H]+ | Yield; Appearance Salt form |
|---|---|---|---|
| A441: N-(2-ethyl-2-phenylbutyl)-3-(4-(4-methylpiperazin-1-yl)phenyl)-1H-indazole-5-carboxamide | 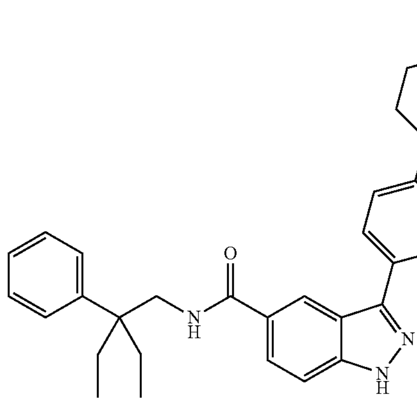 | [C₃₁H₃₇N₅O + H]+ 496.31 496.4 | 23 mg (29%); yellow solid; free base |

SMs: N-(2-ethyl-2-phenylbutyl)-3-iodo-1H-indazole-5-carboxamide (70 mg, 0.16 mmol), 1-methyl-4-(4-(4,4,5,5-tetramethyl-1,3,2-dioxaborolan-2-yl)phenyl)piperazine (62 mg, 0.20 mmol)
¹H NMR (400 MHz, CD₃OD) δ ppm 8.23 (s, 1H), 7.79 (d, J = 8.8 Hz, 2H), 7.68 (d, J = 7.6 Hz, 1H), 7.53 (d, J = 8.6 Hz, 1H), 7.44 (d, J = 7.5 Hz, 2H), 7.37 (t, J = 7.4 Hz, 2H), 7.23 (t, J = 7.6 Hz, 1H), 7.14 (d, J = 8.8 Hz, 2H), 3.74 (s, 2H), 3.36-3.33 (m, 4H), 2.70-2.66 (m, 4H), 2.39 (s, 3H), 1.85 (q, J = 7.2 Hz, 4H), 0.82 (t, J = 7.2 Hz, 6H)

| Example/IUPAC name | Structure | MS calculated MS ESI [M + H]⁺ | Yield; Appearance Salt form |
|---|---|---|---|
| A442: N-((1-(cyclopentyloxy)cyclohexyl)methyl)-3-(4-((1-methylpiperidin-4-yl)oxy)phenyl)-1H-indazole-5-carboxamide | 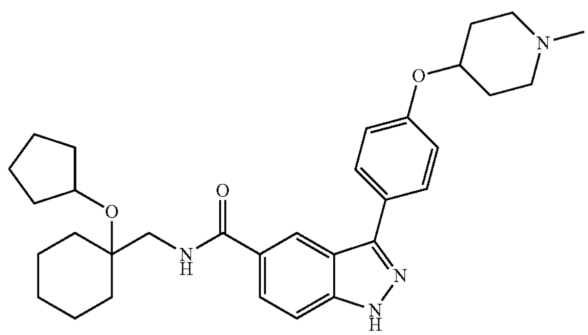 [SMILES: CN1CCC(Oc2ccc(-c3n[nH]c4ccc(C(=O)NCC5(OC6CCCC6)CCCCC5)cc34)cc2)CC1] | [C$_{32}$H$_{42}$N$_4$O$_3$ + H]⁺ 531.33 531.3 | 29 mg (43%); brown solid; free base |

SMs: N-((1-(cyclopentyloxy)cyclohexyl)methyl)-3-iodo-1H-indazole-5-carboxamide (60 mg, 0.13 mmol), 1-methyl-4-(4-(4,4,5,5-tetramethyl-1,3,2-dioxaborolan-2-yl)phenoxy)piperidine (52 mg, 0.17 mmol)
¹H NMR (400 MHz, CD$_3$OD) δ ppm 8.49 (s, 1H), 7.91-7.85 (m, 3H), 7.61 (d, J = 8.7 Hz, 1H), 7.10 (d, J = 8.7 Hz, 2H), 4.52-4.50 (bs, 1H), 4.25-4.23 (m, 1H), 3.53 (s, 2H), 2.77-2.74 (m, 2H), 2.44-2.41 (m, 2H), 2.33 (s, 3H), 2.09-2.04 (m, 2H), 1.90-1.36 (m, 20H)

| Example/IUPAC name | Structure | MS calculated MS ESI [M + H]⁺ | Yield; Appearance Salt form |
|---|---|---|---|
| A443: (R)-N-(2-ethyl-2-phenylbutyl)-3-(4-((1-(2-hydroxypropyl)piperidin-4-yl)oxy)phenyl)-1H-indazole-5-carboxamide | 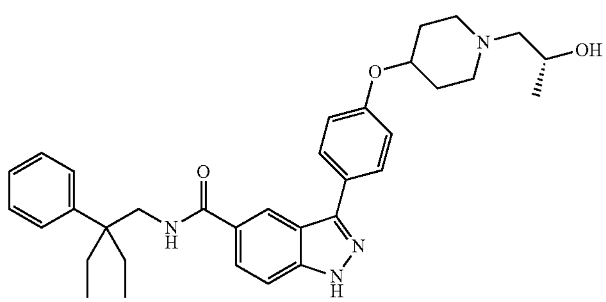 [SMILES: CCC(CC)(CNC(=O)c1ccc2[nH]nc(-c3ccc(OC4CCN(C[C@@H](C)O)CC4)cc3)c2c1)c1ccccc1] | [C$_{34}$H$_{42}$N$_4$O$_3$ + H]⁺ 555.33 555.3 | 20 mg (19%); white solid; TFA salt |

SMs: N-(2-ethyl-2-phenylbutyl)-3-iodo-1H-indazole-5-carboxamide (70 mg, 0.16 mmol), (R)-1-(4-(4-(4,4,5,5-tetramethyl-1,3,2-dioxaborolan-2-yl)phenoxy)piperidin-1-yl)propan-2-ol (74 mg, 0.20 mmol)
¹H NMR (400 MHz, CD$_3$OD) δ ppm 8.26 (s, 1H), 7.90-7.87 (m, 2H), 7.68 (d, J = 7.5 Hz, 1H), 7.55 (d, J = 8.5 Hz, 1H), 7.44 (d, J = 7.5 Hz, 2H), 7.37 (t, J = 7.4 Hz, 2H), 7.24-7.17 (m, 3H), 4.87 (bs, 1H), 4.28-4.15 (m, 1H), 3.75 (s, 2H), 3.62-3.25 (m, 4H), 3.11-3.07 (m, 1H), 2.48-1.98 (m, 4H), 1.85 (q, J = 7.2 Hz, 4H), 1.25 (d, J = 6.4 Hz, 3H), 0.82 (t, J = 7.2 Hz, 6H)

| Example/IUPAC name | Structure | MS calculated MS ESI [M + H]⁺ | Yield; Appearance Salt form |
|---|---|---|---|
| A444: (R)-N-((1-(cyclopentyloxy)cyclohexyl)methyl)-3-(4-((1-(2-hydroxypropyl)piperidin-4-yl)oxy)phenyl)-1H-indazole-5-carboxamide | 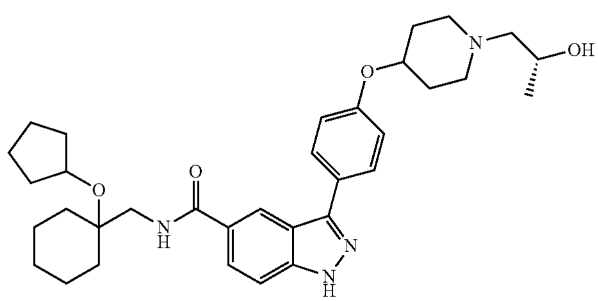 [SMILES: C[C@@H](O)CN1CCC(Oc2ccc(-c3n[nH]c4ccc(C(=O)NCC5(OC6CCCC6)CCCCC5)cc34)cc2)CC1] | [C$_{34}$H$_{46}$N$_4$O$_4$ + H]⁺ 575.36 575.4 | 32 mg (31%); yellow solid; TFA salt |

SMs: N-((1-(cyclopentyloxy)cyclohexyl)methyl)-3-iodo-1H-indazole-5-carboxamide (70 mg, 0.15 mmol), (R)-1-(4-(4-(4,4,5,5-tetramethyl-1,3,2-dioxaborolan-2-yl)phenoxy)piperidin-1-yl)propan-2-ol (72 mg, 0.20 mmol)
¹H NMR (400 MHz, CD$_3$OD) δ ppm 8.50 (s, 1H), 7.97-7.93 (m, 2H), 7.86 (d, J = 9.2 Hz, 1H), 7.67-7.62 (m, 2H), 7.22-7.16 (m, 2H), 4.87 (bs, 1H), 4.26-4.21 (m, 2H), 4.52-4.50 (bs, 1H), 3.75-3.31 (m, 6H), 3.53 (s, 2H), 3.09-3.03 (m, 1H), 2.46-2.16 (m, 4H), 1.91-1.37 (s, 18H), 1.25 (d, J = 6.4 Hz, 3H)

| Example/IUPAC name | Structure | MS calculated MS ESI [M + H]+ | Yield; Appearance Salt form |
|---|---|---|---|
| A445: 3-(4-(((1R,3R,5S)-8-methyl-8-azabicyclo[3.2.1]octan-3-yl)oxy)phenyl)-N-((4-(thiophen-2-yl)tetrahydro-2H-pyran-4-yl)methyl)-1H-indazole-5-carboxamide | 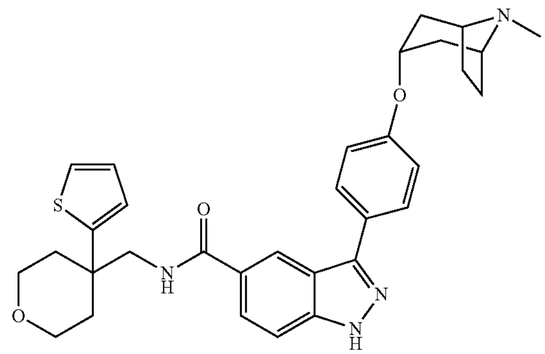 [SMILES: CN1C2CCC1CC(Oc1ccc(-c3n[nH]c4ccc(C(=O)NCC5(c6cccs6)CCOCC5)cc34)cc1)C2] | [$C_{32}H_{36}N_4O_3S$ + H]+ 557.26 557.3 | 34 mg (40%); white solid; TFA salt |

SMs: 3-iodo-N-((4-thiophen-2-yl)tetrahydro-2H-pyran-4-yl)methyl)-1H-indazole-5-carboxamide (60 mg, 0.13 mmol), (1R,3r,5S)-8-methyl-3-(4-(4,4,5,5-tetramethyl-1,3,2-dioxaborolan-2-yl)phenoxy)-8-azabicyclo[3.2.1]octane (56 mg, 0.17 mmol)
$^1$H NMR (400 MHz, CD$_3$OD) δ ppm 8.45 (s, 1H), 8.27-8.24 (m, 1H), 7.95 (d, J = 8.8 Hz, 2H), 7.81 (d, J = 7.6 Hz, 1H), 7.59 (d, J = 9.0 Hz, 1H), 7.37 (d, J = 5.0 Hz, 1H), 7.14 (d, J = 8.7 Hz, 2H), 7.08-7.02 (m, 2H), 4.87 (bs, 1H), 3.98-3.95 (m, 2H), 3.87-3.84 (m, 2H), 3.59-3.55 (m, 4H), 2.84 (s, 3H), 2.58-2.55 (m, 2H), 2.42-2.35 (m, 5H), 2.15-2.03 (m, 4H)

| A446: 3-(4-morpholinophenyl)-N-((1-(piperidin-1-yl)cyclohexyl)methyl)-1H-indazole-5-carboxamide | | [$C_{30}H_{39}N_5O_2$ + H]+ 502.31 502.5 | 29.5 mg (40%); off white solid; free base |

SMs: 3-iodo-N-((1-(piperidin-1-yl)cyclohexyl)methyl)-1H-indazole-5-carboxamide*TFA (70 mg, 0.12 mmol), (4-morpholinophenyl)boronic acid (35 mg, 0.17 mmol)
$^1$H NMR (400 MHz, CD$_3$OD) δ ppm 8.54 (s, 1 H), 7.89 (d, J = 9.0 Hz, 3 H), 7.63 (d, J = 8.8 Hz, 1 H), 7.13 (d, J = 9.0 Hz, 2 H), 3.79-3.90 (m, 4 H), 3.45-3.71 (br. m, 2 H), 3.17-3.28 (m, 4 H), 2.56-2.97 (br.m, 2 H), 1.25-1.84 (m, 16 H)

| A447: N-((1-morpholinocyclohexyl)methyl)-3-(4-morpholinophenyl)-1H-indazole-5-carboxamide | | [$C_{29}H_{37}N_5O_3$ + H]+ 504.29 504.3 | 45.9 mg (74%); pale yellow solid; TFA salt |

SMs: 3-iodo-N-((1-morpholinocyclohexyl)methyl)-1H-indazole-5-carboxamide*TFA (70 mg, 0.12 mmol), (4-morpholinophenyl)boronic acid (35 mg, 0.17 mmol)
$^1$H NMR (400 MHz, CD$_3$OD) δ ppm 8.69 (d, J = 0.8 Hz, 1 H), 8.01 (dd, J = 8.8, 1.5 Hz, 1 H), 7.96 (d, J = 8.8 Hz, 2 H), 7.65 (d, J = 8.8 Hz, 1 H), 7.26 (d, J = 9.0 Hz, 2 H), 4.15 (d, J = 11.5 Hz, 2 H), 3.81-3.98 (m, 8 H), 3.66 (d, J = 12.0 Hz, 2 H), 3.23-3.38 (m, 6 H), 1.49-2.04 (m, 9 H), 1.16-1.39 (m, 1 H)

| Example/IUPAC name | Structure | MS calculated MS ESI [M + H]+ | Yield; Appearance Salt form |
|---|---|---|---|
| A448: N-((1-(4-methylpiperazin-1-yl)cyclohexyl)methyl)-3-(4-morpholinophenyl)-1H-indazole-5-carboxamide | 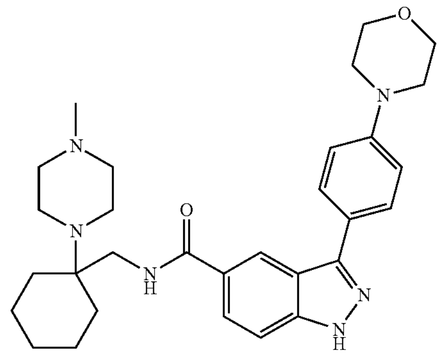 [SMILES: CN1CCN(C2(CNC(=O)c3ccc4[nH]nc(-c5ccc(N6CCOCC6)cc5)c4c3)CCCCC2)CC1] | [C₃₀H₄₀N₆O₂ + H]+ 517.32 517.3 | 22 mg (32%); off white powder; TFA salt |

SMs: 3-iodo-N-((1-(4-methylpiperazin-1-yl)cyclohexyl)methyl)-1H-indazole-5-carboxamide (70 mg, 0.12 mmol), (4-morpholinophenyl)boronic acid (35 mg, 0.17 mmol)
¹H NMR (400 MHz, CD₃OD) δ ppm 8.61 (s, 1 H), 7.84-7.98 (m, 3 H), 7.63 (d, J = 8.8 Hz, 1 H), 7.20 (d, J = 8.8 Hz, 2 H), 3.85-3.94 (m, 4 H), 3.64 (br.s, 2 H), 3.00-3.50 (br.s. 8 H), 3.26-3.40 (m, 4 H), 2.91 (s, 3 H), 1.47-1.95 (br. m., 10 H)

| Example/IUPAC name | Structure | MS calculated MS ESI [M + H]+ | Yield; Appearance Salt form |
|---|---|---|---|
| A449: 3-(4-((1-methylpiperidin-4-yl)oxy)phenyl)-N-((1-morpholinocyclohexyl)methyl)-1H-indazole-5-carboxamide | | [C₃₁H₄₁N₅O₃ + H]+ 532.32 532.3 | 41.3 mg (52%); white powder; free base |

SMs: 3-iodo-N-((1-morpholinocyclohexyl)methyl)-1H-indazole-5-carboxamide*TFA (69 mg, 0.12 mmol), 1-methy-4-(4-(4,4,5,5-tetramethyl-1,3,2-dioxaborolan-2-yl)phenoxy)piperidine (65 mg, 0.21 mmol)
¹H NMR (400 MHz, CD₃OD) δ ppm 8.51 (d, J = 0.5 Hz, 1 H), 7.84-7.94 (m, 3 H), 7.63 (dd, J = 8.8, 0.5 Hz, 1 H), 7.12 (d, J = 8.8 Hz, 2 H), 4.54 (br. s, 1 H), 3.66-3.76 (m, 4 H), 3.52 (s, 2 H), 2.69-2.87 (m, 6 H), 2.47 (br. s, 2 H), 2.36 (s, 3 H), 2.08 (br. s, 2 H), 1.60-1.96 (m, 6 H), 1.34-1.58 (m, 6 H)

| Example/IUPAC name | Structure | MS calculated MS ESI [M + H]+ | Yield; Appearance Salt form |
|---|---|---|---|
| A450: N-((1-(dimethylamino)cyclohexyl)methyl)-3-(4-morpholinophenyl)-1H-indazole-5-carboxamide | | [C₂₇H₃₅N₅O₂ + H]+ 462.28 462.3 | 48 mg (61%); white solid; free base |

SMs: N-((1-(dimethylamino)cyclohexyl)methyl)-3-iodo-1H-indazole-5-carboxamide*TFA (90 mg, 0.17 mmol), (4-morpholinophenyl)boronic acid (48 mg, 0.23 mmol)
¹H NMR (400 MHz, Acetone-d₆) δ ppm 8.63 (s, 1 H), 7.96 (d, J = 8.8 Hz, 2 H), 7.92 (dd, J = 8.8, 1.5 Hz, 1 H), 7.64 (dd, J = 8.8, 0.8 Hz, 1 H), 7.56 (br.s., 1H), 7.12 (d, J = 8.8 Hz, 2 H), 3.79-3.85 (m, 4 H), 3.53-3.58 (m, 2 H), 3.20-3.27 (m, 4 H), 2.37 (s, 6 H), 1.68-1.81 (m, 2 H), 1.62 (d, J = 6.8 Hz, 2 H), 1.31-1.56 (m, 6H)

| Example/IUPAC name | Structure | MS calculated MS ESI [M + H]+ | Yield; Appearance Salt form |
|---|---|---|---|
| A451: N((1-((2S,6R)-2,6-dimethylmorpholino)cyclohexyl)methyl)-3-(4-morpholinophenyl)-1H-indazole-5-carboxamide | 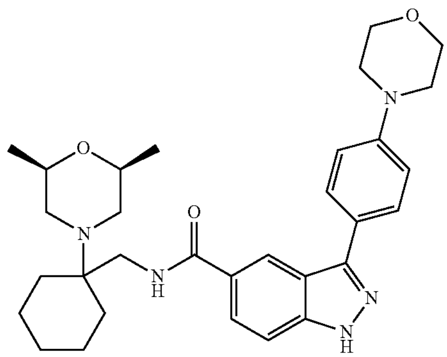 [SMILES: C[C@@H]1CN(C2(CNC(=O)c3ccc4[nH]nc(-c5ccc(N6CCOCC6)cc5)c4c3)CCCCC2)C[C@H](C)O1] | [C₃₁H₄₁N₅O₃ + H]+ 532.32 532.4 | 103 mg (81%) pale yellow solid; TFA salt |

SMs: N-((1-((2S,6R)-2,6-dimethylmorpholino)cyclohexyl)methyl)-3-iodo-1H-indazole-5-carboxamide*TFA (0.12 g, 0.20 mmol), (4-morpholinophenyl)boronic acid (57 mg, 0.27 mmol)
¹H NMR (400 MHz, CD₃OD) δ ppm 8.68 (d, J = 0.5 Hz, 1 H), 8.00 (dd, J = 8.9, 1.6 Hz, 1 H), 7.95 (d, J = 8.8 Hz, 2 H), 7.66 (d, J = 8.8 Hz, 1 H), 7.25 (d, J = 9.0 Hz, 2 H), 3.96-4.06 (m, 2 H), 3.86-3.95 (m, 6 H), 3.67 (d, J = 12.0 Hz, 2 H), 3.25-3.37 (m, 4 H), 2.84 (t, J = 11.3 Hz, 2 H), 1.54-2.03 (m, 9H), 1.30 (m, 7 H)

| A452: N-((1-((2S,6R)-2,6-dimethylmorpholino)cyclohexyl)methyl)-3-(4-((1-methylpiperidin-4-yl)oxy)phenyl)-1H-indazole-5-carboxamide | | [C₃₃H₄₅N₅O₃ + H]+ 560.35 560.3 | 50 mg (45%); white solid; free base |

SMs: N-((1-((2S,6R)-2,6-dimethylmorpholino)cyclohexyl)methyl)-3-iodo-1H-indazole-5-carboxamide*TFA (0.12 g, 0.20 mmol), ), 1-methyl-4-(4-(4,4,5,5-tetramethyl-1,3,2-dioxaborolan-2-yl)phenoxy)piperidine (87 mg, 0.21 mmol)
¹H NMR (400 MHz, CD₃OD) δ ppm 8.48 (s, 1 H), 7.78-7.94 (m, 3 H), 7.62 (d, J = 8.8 Hz, 1 H), 7.11 (d, J = 8.8 Hz, 2 H), 4.53 (br. s., 1 H), 3.57-3.71 (m, 2 H), 3.50 (s, 2 H), 2.91 (d, J = 11.3 Hz, 2 H), 2.79 (br. s., 2 H), 2.46 (br. s., 2 H), 2.36 (s, 3 H), 2.00-2.21 (m, 4H), 1.83-1.92 (m, 2 H), 1.72-1.82 (br. m., 2 H), 1.61-1.70 (br. m., 2 H), 1.35-1.51 (m, 6 H), 1.15 (d, J = 6.30 Hz, 6 H)

| A453: 3-(4-(4-methylpiperazin-1-yl)phenyl)-N-((1-morpholinocyclohexyl)methyl)-1H-indazole-5-carboxamide | | [C₃₀H₄₀N₆O₂ + H]+ 517.32 517.3 | 84 mg (83%) white solid TFA salt |

SMs: SMs: 3-iodo-N-((1-morpholinocyclohexyl)methyl)-1H-indazole-5-carboxamide*TFA (95 mg, 0.16 mmol), 1-methyl-4-(4-(4,4,5,5-tetramethyl-1,3,2-dioxaborolan-2-yl)phenyl)piperazine (65 mg, 0.21 mmol),
¹H NMR (400 MHz, CD₃OD) δ ppm 8.70 (s, 1 H), 8.01 (dd, J = 8.9, 1.6 Hz, 1 H), 7.96 (d, J = 8.8 Hz, 2 H), 7.66 (d, J = 8.8 Hz, 1 H), 7.23 (d, J = 8.8 Hz, 2 H), 4.12-4.21 (m, 2 H), 3.96-4.04 (m, 2 H), 3.94 (s, 2 H), 3.83-3.94 (m, 2 H), 3.64-3.71 (m, 4 H), 3.28-3.38 (m, 4 H), 3.08-3.22 (m, 2 H), 3.01 (s, 3 H), 1.55-2.05 (br. m, 9 H), 1.22-1.40 (m, 1 H)

| Example/IUPAC name | Structure | MS calculated MS ESI [M + H]+ | Yield; Appearance Salt form |
|---|---|---|---|
| A454: 3-(4-((2S,6R)-2,6-dimethylmorpholino)phenyl)-N-((1-morpholinocyclohexyl)methyl)-1H-indazole-5-carboxamide | 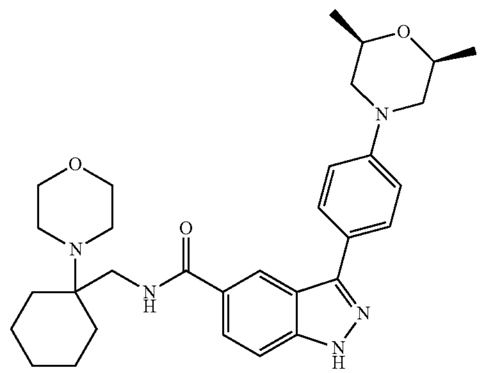 [SMILES: C[C@@H]1CN(c2ccc(-c3n[nH]c4ccc(C(=O)NCC5(N6CCOCC6)CCCCC5)cc34)cc2)C[C@H](C)O1] | [C₃₁H₄₁N₅O₃ + H]+ 532.32 532.3 | 43 mg (44%); off white solid; TFA salt |

SMs: 3-iodo-N-((1-morpholinocyclohexyl)methyl)-1H-indazole-5-carboxamide*TFA (90 mg, 0.15 mmol), (2S,6R)-2,6-dimethyl-4-(4-(4,4,5,5-tetramethyl-1,3,2-dioxaborolan-2-yl)phenyl)morpholine (63 mg, 0.20 mmol)
$^1$H NMR (400 MHz, CD$_3$OD) δ ppm 8.69 (s, 1 H), 8.01 (dd, J = 8.8, 1.5 Hz, 1 H), 7.94 (d, J = 8.5 Hz, 2 H), 7.66 (d, J = 8.8 Hz, 1 H), 7.24 (d, J = 8.8 Hz, 2 H), 4.12-4.22 (m, 2 H), 3.93 (s, 2 H), 3.81-3.91 (m, 4 H), 3.68 (d, J = 11.8 Hz, 4 H), 3.22-3.40 (m, 2 H), 2.55 (t, J = 11.4 Hz, 2 H), 1.58-2.04 (m, 9H), 1.28 (m, 7 H)

| Example/IUPAC name | Structure | MS calculated MS ESI [M + H]+ | Yield; Appearance Salt form |
|---|---|---|---|
| A455: 3-(4-(((3S,4R)-3-fluoro-1-methylpiperidin-4-yl)oxy)phenyl)-N-((1-morpholinocyclohexyl)methyl)-1H-indazole-5-carboxamide | 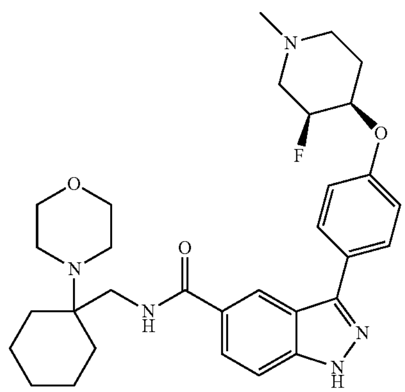 [SMILES: CN1CC[C@@H](Oc2ccc(-c3n[nH]c4ccc(C(=O)NCC5(N6CCOCC6)CCCCC5)cc34)cc2)[C@@H](F)C1] | [C₃₁H₄₀FN₅O₃ + H]+ 550.31 550.2 | 42 mg (22%); white powder; free base; |

SMs: 3-iodo-N-((1-morpholinocyclohexyl)methyl)-1H-indazole-5-carboxamide*TFA (160 mg, 0.27 mmol), diisopropyl (4-((3R,4S)-3-fluoro-1-methylpiperidin-4-yl)oxy)phenyl)boronate compound with diisopropyl (4-(((3S,4R)-3-fluoro-1-methylpiperidin-4-yl)oxy)phenyl)boronate, a 1:1 mixture (0.16 g, 0.48 mmol)
$^1$H NMR (400 MHz, CD$_3$OD) δ ppm 8.50 (s, 1 H), 7.81-7.97 (m, 3 H), 7.62 (d, J = 8.8 Hz, 1 H), 7.15 (d, J = 8.8 Hz, 2 H), 4.90 (d, J = 50.9 Hz, 1 H), 4.49-4.68 (br. m, 1 H), 3.63-3.73 (m, 4 H), 3.49 (s, 2 H), 2.94-3.13 (m, 1 H), 2.42-2.83 (m, 6 H), 2.26-2.43 (m, 1 H), 2.34 (s, 3 H), 2.07-2.19 (m, 1 H), 1.87-2.01 (m, 1 H), 1.55-1.83 (m, 4 H), 1.31-1.52 (m, 6 H)

| Example/IUPAC name | Structure | MS calculated MS ESI [M + H]+ | Yield; Appearance Salt form |
|---|---|---|---|
| A456: N-((1-(4-fluoropiperidin-1-yl)cyclohexyl)methyl)-3-(4-morpholinophenyl)-1H-indazole-5-carboxamide | 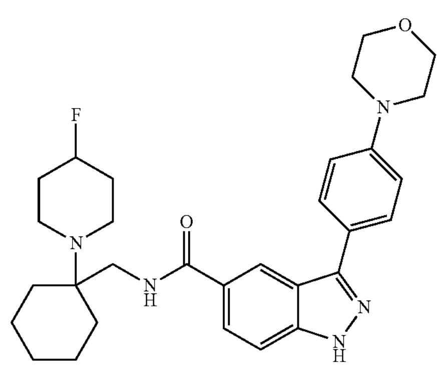 [SMILES: O=C(NCC1(N2CCC(F)CC2)CCCCC1)c1ccc2[nH]nc(-c3ccc(N4CCOCC4)cc3)c2c1] | [C₃₀H₃₈FN₅O₂ + H]+ 520.30 520.4 | 45 mg (60%); white powder, free base |

SMs: N-((1-(4-fluoropiperidin-1-yl)cyclohexyl)methyl)-3-iodo-1H-indazole-5-carboxamide (86 mg, 0.14 mmol), (4-morpholinophenyl)boronic acid (45 mg, 0.21 mmol)
$^1$H NMR (400 MHz, CD$_3$OD) δ 12.38 (br. s., 1 H), 8.50 (s, 1 H), 7.73-8.14 (m, 3 H), 7.54 (d, J = 8.8 Hz, 2 H), 6.99 (d, J = 9.0 Hz, 2 H), 4.53 (d, J = 49.4 Hz, 1 H), 3.63-3.75 (m, 4 H), 3.35-3.57 (m, 2 H), 3.06-3.14 (m, 4 H), 2.40-2.98 (m, 4 H), 1.08-1.93 (m, 14 H)

| Example/IUPAC name | Structure | MS calculated MS ESI [M + H]+ | Yield; Appearance Salt form |
|---|---|---|---|
| A457: N-((1-(4,4-difluoropiperidin-1-yl)cyclohexyl)methyl)-3-(4-morpholinophenyl)-1H-indazole-5-carboxamide | 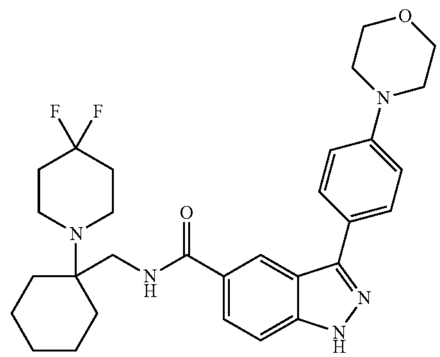 [SMILES: O=C(NCC1(N2CCC(F)(F)CC2)CCCCC1)c1ccc2[nH]nc(-c3ccc(N4CCOCC4)cc3)c2c1] | [C$_{30}$H$_{37}$F$_2$N$_5$O$_2$ + H]+ 538.29 538.4 | 39 mg (48%), white powder; free base |

SMs: N-((1-(4,4-difluoropiperidin-1-yl)cyclohexyl)methyl)-3-iodo-1H-indazole-5-carboxamide*TFA (91 mg, 0.15 mmol), (4-morpholinophenyl)boronic acid (45 mg, 0.21 mmol)
$^1$H NMR (400 MHz, CD$_3$OD) δ ppm 8.50 (s, 1 H), 7.87 (d, J = 8.8 Hz, 3 H), 7.60 (d, J = 8.8 Hz, 1 H), 7.11 (d, J = 8.8 Hz, 2 H), 3.78-3.98 (m, 4 H), 3.47 (s, 2 H), 3.06-3.27 (m, 4 H), 2.78-3.03 (m, 4 H), 1.81-2.04 (m, 4 H), 1.22-1.73 (m, 10 H).

| Example/IUPAC name | Structure | MS calculated MS ESI [M + H]+ | Yield; Appearance Salt form |
|---|---|---|---|
| A458: N-((4,4-difluoro-1-morpholinocyclohexyl)methyl)-3-(4-((1-methylpiperidin-4-yl)oxy)phenyl)-1H-indazole-5-carboxamide | 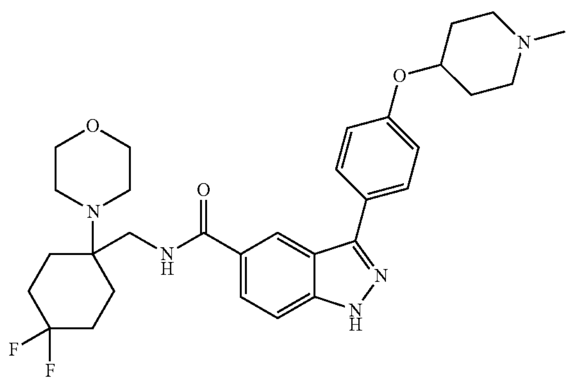 [SMILES: CN1CCC(Oc2ccc(-c3n[nH]c4ccc(C(=O)NCC5(N6CCOCC6)CCC(F)(F)CC5)cc34)cc2)CC1] | [C$_{31}$H$_{39}$F$_2$N$_5$O$_3$ + H]+ 568.30 568.3 | 38 mg (33%), white powder, free base |

SMs: N-((4,4-difluoro-1-morpholinocyclohexyl)methyl)-3-iodo-1H-indazole-5-carboxamide (100 mg, 0.20), 1-methyl-4-(4-(4,4,5,5-tetramethyl-1,3,2-dioxaborolan-2-yl)phenoxy)piperidine (82 mg, 0.26 mmol)
$^1$H NMR (400 MHz, CD$_3$OD) δ ppm 8.52 (s, 1 H), 7.84-7.95 (m, 3 H), 7.62 (d, J = 8.8 Hz, 1 H), 7.12 (d, J = 8.8 Hz, 2 H), 4.56 (br. s., 1 H), 3.69 (br. s., 4 H), 3.51 (s, 2 H), 2.90 (br. s., 2 H), 2.74-2.83 (m, 4 H), 2.60 (br. s., 2 H), 2.45 (s, 3 H), 1.71-2.19 (m, 10 H), 1.63 (t, J = 14.3 Hz, 2 H).

| Example/IUPAC name | Structure | MS calculated MS ESI [M + H]+ | Yield; Appearance Salt form |
|---|---|---|---|
| A459: 3-(4-(4-(2-hydroxyethyl)piperazin-1-yl)phenyl)-N-((1-morpholinocyclohexyl)methyl)-1H-indazole-5-carboxamide | 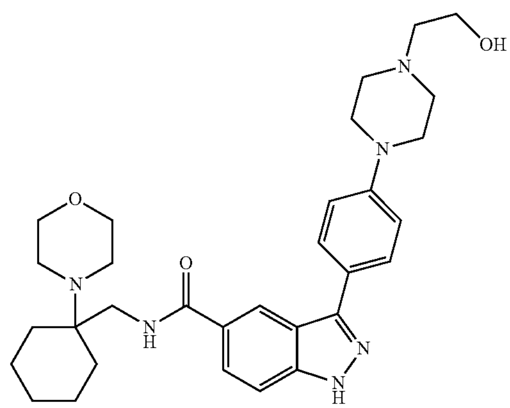 [SMILES: O=C(NCC1(N2CCOCC2)CCCCC1)c1ccc2[nH]nc(-c3ccc(N4CCN(CCO)CC4)cc3)c2c1] | [C$_{31}$H$_{42}$N$_6$O$_3$ + H]+ 547.33 547.3 | 14 mg (12%); white powder; free base |

SMs: 3-iodo-N-((1-morpholinocyclohexyl)methyl)-1H-indazole-5-carboxamide*TFA (100 mg, 0.21 mmol), 2-(4-(4-(4,4,5,5-tetramethyl-1,3,2-dioxaborolan-2-yl)phenyl)piperazin-1-yl)EtOH (85 mg, 0.26 mmol)
$^1$H NMR (400 MHz, CD$_3$OD) δ ppm 8.52 (s, 1 H), 7.89 (d, J = 8.3 Hz, 3 H), 7.62 (d, J = 9.3 Hz, 1 H), 7.15 (d, J = 1.8 Hz, 2 H), 6.66-3.80 (m., 6 H), 3.53 (s, 2 H), 2.76 (br. s., 8 H), 2.63 (t, J = 5.5 Hz, 2 H), 1.62-1.86 (m, 4 H), 1.34-1.55 (m, 6 H); *4H are obscured by the signal due to CD$_3$OD at 3.31 ppm.

| Example/IUPAC name | Structure | MS calculated MS ESI [M + H]+ | Yield; Appearance Salt form |
|---|---|---|---|
| A460: N-((4,4-difluoro-1-morpholinocyclohexyl)methyl)-3-(4-morpholinophenyl)-1H-indazole-5-carboxamide | 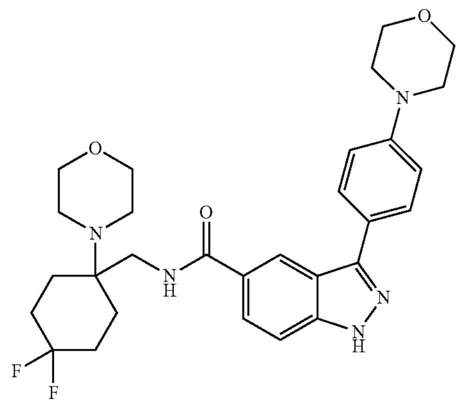 [SMILES: O=C(NCC1(N2CCOCC2)CCC(F)(F)CC1)c1ccc2[nH]nc(-c3ccc(N4CCOCC4)cc3)c2c1] | [C$_{29}$H$_{35}$F$_2$N$_5$O$_3$ + H]+ 540.27 540.4 | 9 mg (8%); pale yellow solid; 2 × HCl |

SMs: SMs: N-((4,4-difluoro-1-morpholinocyclohexyl)methyl)-3-iodo-1H-indazole-5-carboxamide (95 mg, 0.19 mmol), (4-morpholinophenyl)boronic acid (53 mg, 0.26 mmol)
$^1$H NMR (400 MHz, CD$_3$OD) δ ppm 8.76 (s, H), 8.13 (d, J = 9.0 Hz, 2H), 8.05 (d, J = 10.3 Hz, 1 H), 7.70 (d, J = 8.3 Hz, 1H), 7.55 (d, J = 10.3 Hz, 2H), 4.13-4.23 (m, 2H), 3.98-4.07 (m, 6 H), 3.87-3.97 (m, 2 H), 3.68-3.77 (m, 2 H), 3.56 (br. s., 4 H), 3.38-3.49 (m, 2 H), 2.07-2.37 (m, 8 H)

| A461: 3-(4-morpholinophenyl)-N-((1-(pyridin-3-yl)cyclopropyl)methyl)-1H-indazole-5-carboxamide | | [C$_{27}$H$_{27}$N$_5$O$_2$ + H]+ 454.22 454.2 | 79.4 mg (81%); light yellow powder; free base |

SMs: SMs: 3-iodo-N-((1-(pyridin-3-yl)cyclopropyl)methyl)-1H-indazole-5-carboxamide (90 mg, 0.17 mmol), (4-morpholinophenyl)boronic acid (54 mg, 0.26 mmol)
$^1$H NMR (400 MHz, CD$_3$OD) δ ppm 8.96 (s, 1 H), 8.72 (d, J = 5.8 Hz, 1 H), 8.66 (d, J = 8.0 Hz, 1 H), 8.54 (s, 1 H), 8.18 (d, J = 8.8 Hz, 2 H), 8.01 (dd, J = 8.2, 5.9 Hz, 1 H), 7.85 (dd, J = 8.8, 1.3 Hz, 1 H), 7.76 (d, J = 8.5 Hz, 2 H), 7.63 (d, J = 8.8 Hz, 1 H), 4.04-4.19 (m, 4 H), 3.78 (s, 2 H), 3.62-3.73 (m, 4 H), 1.24-1.37 (m, 2 H), 1.06-1.19 (m, 2 H)

| A462: N-(3-(4-((1-(oxetan-3-yl)piperidin-4-yl)oxy)phenyl)-1H-indazol-5-yl)-2-(3-phenyloxetan-3-yl)acetamide | | [C$_{32}$H$_{34}$N$_4$O$_4$ + H]+ 539.26 539.2 | 25 mg (26%); white powder; free base |

SMs: N-(3-iodo-1H-indazol-5-yl)-2-(3-phenyloxetan-3-yl)acetamide (77 mg, 0.18 mmol), 1-(oxetan-3-yl)-4-(4-(4,4,5,5-tetramethyl-1,3,2-dioxaborolan-2-yl)phenoxy)piperidine (83 mg, 0.23 mmol)
$^1$H NMR (400 MHz, CD$_3$OD) δ ppm 8.12 (s, 1H), 7.86 (d, J = 8.5 Hz, 2H), 7.69 (dd, J = 9.0, 1.8 Hz, 1H), 7.61 (d, J = 9.3 Hz, 1H), 7.24-7.44 (m, 5H), 7.11 (d, J = 8.8 Hz, 2H), 4.72 (t, J = 6.5 Hz, 2H), 4.63 (t, J = 6.5 Hz, 2H), 4.54 (br. s, 1H), 4.32 (s, 2H), 3.75 (s, 2H), 3.53-3.67 (m, 1H), 2.95-3.11 (m, 2 H), 2.59-2.71 (m, 2 H), 2.25-2.36 (m, 2 H), 2.03-2.15 (m, 2 H), 1.80-1.95 (m, 2 H)

| Example/IUPAC name | Structure | MS calculated MS ESI [M + H]⁺ | Yield; Appearance Salt form |
|---|---|---|---|
| A463: N-(2-ethyl-2-morpholinobutyl)-3-(4-morpholinophenyl)-1H-indazole-5-carboxamide | 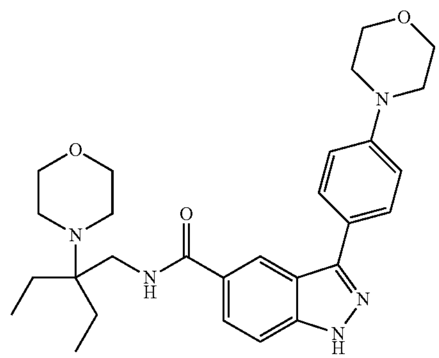 [SMILES: CCC(CC)(CNC(=O)c1ccc2[nH]nc(-c3ccc(N4CCOCC4)cc3)c2c1)N1CCOCC1] | [C$_{28}$H$_{37}$N$_5$O$_3$ + H]⁺ 492.29 492.4 | 99 mg (90%); pale yellow gum; TFA salt |

SMs: N-(2-ethyl-2-morpholinobutyl)-3-iodo-1H-indazole-5-carboxamide (82 mg, 0.18 mmol), 4-morpholinophenyl)boronic acid (51 mg, 0.25 mmol)
¹H NMR (400 MHz, CD$_3$OD) δ ppm 8.68 (d, J = 0.8 Hz, 1 H), 7.94-8.02 (m, 3 H), 7.66 (d, J = 8.8 Hz, 1 H), 7.27 (d, J = 8.8 Hz, 2 H), 4.08-4.22 (m, 2 H), 3.89-3.99 (m, 6 H), 3.77 (s, 2 H), 3.64-3.74 (m, 2 H), 3.38-3.48 (m, 2 H), 3.34-3.37 (m, 4 H), 1.97-2.06 (m, 2 H), 1.80-1.90 (m, 2 H), 1.13 (t, J = 7.5 Hz, 6 H)

| Example/IUPAC name | Structure | MS calculated MS ESI [M + H]⁺ | Yield; Appearance Salt form |
|---|---|---|---|
| A464: 3-(4-morpholinophenyl)-N-((1-(pyridin-4-yl)cyclopropyl)methyl)-1H-indazole-5-carboxamide | 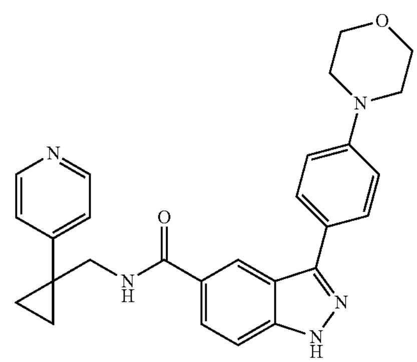 [SMILES: O=C(NCC1(c2ccncc2)CC1)c1ccc2[nH]nc(-c3ccc(N4CCOCC4)cc3)c2c1] | [C$_{27}$H$_{27}$N$_5$O$_2$ + H]⁺ 453.22 454.3 | 105 mg (86%); pale yellow solid; TFA salt |

SMs: 3-iodo-N-((1-(pyridin-4-yl)cyclopropyl)methyl)-1H-indazole-5-carboxamide (90 mg, 0.21 mmol), 4-morpholinophenyl)boronic acid (54 mg, 0.26 mmol)
¹H NMR (400 MHz, CD$_3$OD) δ ppm 8.64 (d, J = 7.0 Hz, 2 H), 8.54 (s, 1 H), 7.98 (d, J = 6.8 Hz, 2 H), 7.94 (d, J = 8.5 Hz, 2 H), 7.88 (dd, J = 8.8, 1.2 Hz, 1 H), 7.59 (d, J = 8.8 Hz, 1 H), 7.28 (d, J = 8.0 Hz, 2 H), 3.33 (br. s, 2 H), 1.50-1.56 (m, 2 H), 1.32-1.38 (m, 2 H)

| Example/IUPAC name | Structure | MS calculated MS ESI [M + H]⁺ | Yield; Appearance Salt form |
|---|---|---|---|
| 465: N-(2-ethyl-2-morpholinobutyl)-3-(4-(4-methylpiperazin-1-yl)phenyl)-1H-indazole-5-carboxamide | 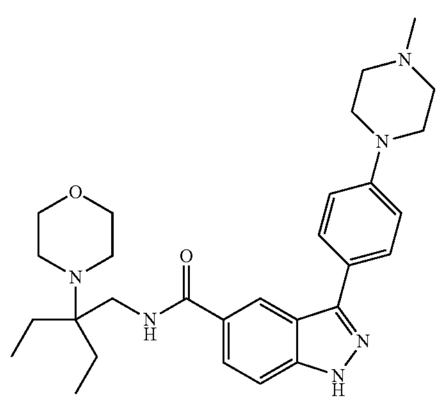 [SMILES: CCC(CC)(CNC(=O)c1ccc2[nH]nc(-c3ccc(N4CCN(C)CC4)cc3)c2c1)N1CCOCC1] | [C$_{29}$H$_{40}$N$_6$O$_2$ + H]⁺ 505.32 505.3 | 9.2 mg (9%); white powder; free base |

SMs: N-(2-ethyl-2-morpholinobutyl)-3-iodo-1H-indazole-5-carboxamide (94 mg, 0.21 mmol), 1-methyl-4-(4-(4,4,5,5-tetramethyl-1,3,2-dioxaborolan-2-yl)phenyl)piperazine (87 mg, 0.29 mmol)
¹H NMR (400 MHz, CD$_3$OD) δ ppm 8.47 (s, 1 H), 7.81-7.92 (m, 3 H), 7.63 (d, J = 8.8 Hz, 1 H), 7.14 (d, J = 8.8 Hz, 2 H), 3.64-3.74 (m, 4 H), 3.43 (s, 2 H), 2.73-2.95 (m, 4 H), 2.57-2.73 (m, 4 H), 2.38 (s, 3 H), 1.62-1.78 (m, 2 H), 1.47-1.60 (m, 2 H), 0.95 (t, J = 7.5 Hz, 6 H)

| Example/IUPAC name | Structure | MS calculated MS ESI [M + H]+ | Yield; Appearance Salt form |
|---|---|---|---|
| A466: N-(2-ethyl-2-morpholinobutyl)-3-(4-((1-(oxetan-3-yl)piperidin-4-yl)oxy)phenyl)-1H-indazole-5-carboxamide | 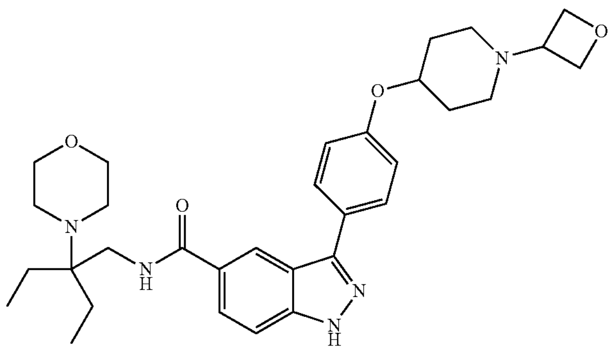 [SMILES: CCC(CC)(CNC(=O)c1ccc2[nH]nc(-c3ccc(OC4CCN(C5COC5)CC4)cc3)c2c1)N1CCOCC1] | [C₃₂H₄₃N₅O₄ + H]+ 562.33 562.4 | 68 mg (55%); white powder; free base |

SMs: N-(2-ethyl-2-morpholinobutyl)-3-iodo-1H-indazole-5-carboxamide (100 mg, 0.0.22 mmol),
1-(oxetan-3-yl)-4-(4-(4,4,5,5-tetramethyl-1,3,2-dioxaborolan-2-yl)phenoxy)piperidine (95 mg, 0.26 mmol)
¹H NMR (400 MHz, CDCl₃/CD₃OD) δ ppm 8.45 (s, 1 H), 7.86 (d, J = 8.3 Hz, 2 H), 7.80 (d, J = 9.0 Hz, 1 H), 7.54 (d, J = 8.8 Hz, 1 H), 7.04 (d, J = 8.0 Hz, 2 H), 4.59-4.72 (m, 4 H), 4.46 (br. s., 1 H), 3.72 (br. s., 4 H), 3.48-3.57 (m, 1 H), 3.39 (s, 2 H), 2.72 (br. s., 4 H), 2.57 (br. s., 2 H), 2.17-2.33 (m, 2 H), 1.97-2.10 (m, 2 H), 1.92 (br. s., 2 H), 1.58-1.73 (m, 2 H), 1.39-1.55 (m, 2 H), 0.92 (t, J = 7.4 Hz, 6 H)

| A467: N-((1-(4-methylpiperazin-1-yl)cyclopentyl)methyl)-3-(4-morpholinophenyl)-1H-indazole-5-carboxamide | | [C₂₉H₃₈N₆O₂ + H]+ 503.31 503.5 | 104 mg (77%); light yellow powder; TFA salt |

SMs: 3-iodo-N-((1-(4-methylpiperazin-1-yl)cyclopentyl)methyl)-1H-indazole-5-carboxamide (130 mg, 0.22 mmol), 4-morpholinophenyl)boronic acid (50 mg, 0.24 mmol)
¹H NMR (400 MHz, CD₃OD) δ ppm 8.67 (d, J = 0.8 Hz, 1H), 8.06 (d, J = 8.8 Hz, 2H), 8.02 (dd, J = 8.9, 1.6 Hz, 1H), 7.64 (d, J = 8.5 Hz, 1H), 7.46 (d, J = 8.5 Hz, 2H), 3.96-4.01 (m, 4H), 3.93 (br, 4H), 3.81 (s, 2H), 3.75 (br, 4H), 3.48 (br, 4H), 3.01 (s, 3H), 2.09 (d, J = 6.3 Hz, 4H), 1.84-1.93 (m, 4H)

| A468: 3-(4-((1R,5S)-3-oxa-8-azabicyclo[3.2.1]octan-8-yl)phenyl)-N-((1-methyl-4-phenylpiperidin-4-yl)methyl)-1H-indazole-5-carboxamide | | [C₃₃H₃₇N₅O₂ + H]+ 535.29 536.8 | 20 mg (16%); light yellow solid 2 × HCl; |

SMs: 3-iodo-N-((1-methyl-4-phenylpiperidin-4-yl)methyl)-1H-indazole-5-carboxamide (100 mg, 0.21 mmol), (1R,5S)-8-(4-(4,4,5,5-tetramethyl-1,3,2-dioxaborolan-2-yl)phenyl)-3-oxa-8-azabicyclo[3.2.1]octane (103 mg, 0.33 mmol)
¹H NMR (400 MHz, CD₃OD) δ ppm 8.35 (s, 1 H), 7.81 (d, J = 8.8 Hz, 2 H), 7.76 (dd, J = 8.8, 1.0 Hz, 1 H), 7.54 (d, J = 8.8 Hz, 1 H), 7.36-7.48 (m, 4 H), 7.25 (t, J = 7.3 Hz, 1 H), 7.02 (d, J = 8.8 Hz, 2 H), 4.23 (br. s., 2 H), 3.93 (d, J = 10.8 Hz, 2 H), 3.52-3.59 (m, 4 H), 2.64-2.77 (m, 2 H), 2.28 (br. s., 3 H), 2.19 (s, 3 H), 1.94-2.14 (m, 7 H)

| Example/IUPAC name | Structure | MS calculated MS ESI [M + H]⁺ | Yield; Appearance Salt form |
|---|---|---|---|
| A469: 3-(4-morpholinophenyl)-N-((1-phenylcyclohexyl)methyl)-1H-indazole-5-carboxamide | 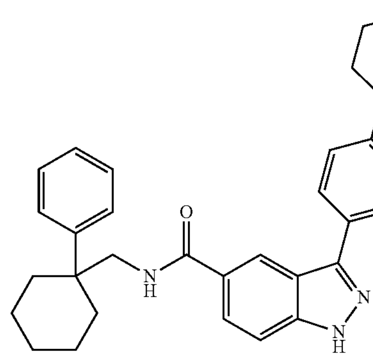 | [C$_{31}$H$_{34}$N$_4$O$_2$ + H]⁺ 495.2 495.5 | 72 mg (43%); yellow solid; TFA salt |

SMs: 3-iodo-N-((1-phenylcyclohexyl)methyl)-1H-indazole-5-carboxamide (125 mg, 0.27 mmol), (4-morpholinophenyl)boronic acid (57 mg, 0.27 mmol), Pd(PPh$_3$)$_4$ (32 mg, 0.027 mmol)
$^1$H NMR (400 MHz, CD$_3$OD) δ ppm 8.32 (s, 1 H), 7.91 (d, J = 8.5 Hz, 2 H), 7.73 (dd, J = 8.8, 1.5 Hz, 1 H), 7.55 (d, J = 8.8 Hz, 1 H), 7.47 (d, J = 7.5 Hz, 2 H), 7.37 (t, J = 7.8 Hz, 2 H), 7.20-7.32 (m, 3 H), 3.87-3.96 (m, 4 H), 3.45-3.52 (m, 2 H), 3.27-3.40 (m, 4 H), 2.27 (d, J = 13.1 Hz, 2 H), 1.47-1.76 (m, 5 H), 1.30-1.45 (m, 3 H)

| Example/IUPAC name | Structure | MS calculated MS ESI [M + H]⁺ | Yield; Appearance Salt form |
|---|---|---|---|
| A470: 3-(4-((1-methylpiperidin-4-yl)oxy)phenyl)-N-((1-phenylcyclohexyl)methyl)-1H-indazole-5-carboxamide | 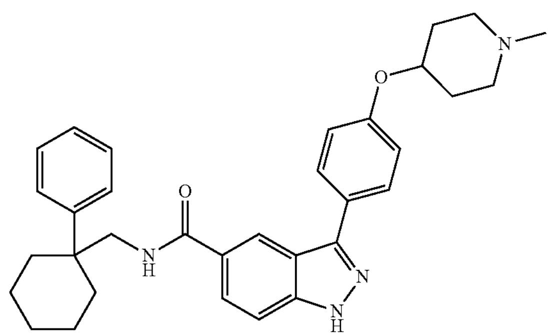 [SMILES: CN1CCC(Oc2ccc(-c3n[nH]c4ccc(C(=O)NCC5(c6ccccc6)CCCCC5)cc34)cc2)CC1] | [C$_{33}$H$_{38}$N$_4$O$_2$ + H]⁺ 523.3 523.5 | 52 mg (30%); light brown solid; TFA salt |

SMs: 3-iodo-N-((1-phenylcyclohexyl)methyl)-1H-indazole-5-carboxamide (125 mg, 0.27 mmol), 1-methyl-4-(4-(4,4,5,5-tetramethyl-1,3,2-dioxaborolan-2-yl)phenoxy)piperidine (87 mg, 0.27 mmol), PdCl$_2$dppf*CH$_2$Cl$_2$ (34 mg, 0.014 mmol)
$^1$H NMR (400 MHz, CD$_3$OD) δ ppm 8.28-8.33 (m, 1 H), 7.90 (s, 3 H), 7.70-7.76 (m, 1 H), 7.54-7.60 (m, 1 H), 7.47 (s, 2 H), 7.38 (s, 2 H), 7.23 (d, J = 8.8 Hz, 3 H), 4.64-4.76 (m, 1H), 3.61-3.70 (m, 1 H), 3.34-3.53 (m, 4 H), 3.18-3.29 (m, 1 H), 2.92-2.98 (m, 3 H), 2.43-2.51 (m, 1 H), 2.25-2.37 (m, 3 H), 1.90-2.21 (m, 2 H), 1.51-1.77 (m, 5 H) 1.32-1.46 (m, 3 H), 2H merged with solvent peak.

| Example/IUPAC name | Structure | MS calculated MS ESI [M + H]⁺ | Yield; Appearance Salt form |
|---|---|---|---|
| A471: 3-(4-((1-methylpiperidin-4-yl)oxy)phenyl)-N-((1-phenylcyclopropyl)methyl)-1H-indazole-5-carboxamide | 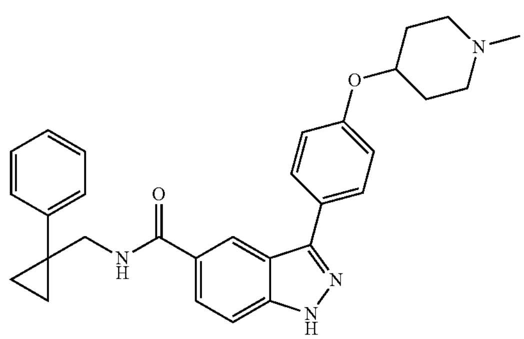 [SMILES: CN1CCC(Oc2ccc(-c3n[nH]c4ccc(C(=O)NCC5(c6ccccc6)CC5)cc34)cc2)CC1] | [C$_{30}$H$_{32}$N$_4$O$_2$ + H]⁺ 481.2 481.4 | 24 mg (22%); off white solid; TFA salt |

SMs: 3-iodo-N-((1-phenylcyclopropyl)methyl)-1H-indazole-5-carboxamide (75 mg, 0.18 mmol), 1-methyl-4-(4-(4,4,5,5-tetramethyl-1,3,2-dioxaborolan-2-yl)phenoxy)piperidine (57 mg, 0.18 mmol), Pd(PPh$_3$)$_4$ (21 mg, 0.019 mmol)
$^1$H NMR (400 MHz, CD$_3$OD) δ ppm 8.40 (s, 1 H), 7.88-7.97 (m, 2 H), 7.79 (d, J = 8.8 Hz, 1 H), 7.57 (d, J = 8.8 Hz, 2 H), 7.42 (d, J = 7.5 Hz, 2 H), 7.29 (t, J = 7.7 Hz, 2 H), 7.14-7.24 (m, 3 H), 4.64-4.76 (m, 1H), 3.65 (s, 2 H), 3.36-3.50 (m, 3 H), 3.18-3.28 (m, 1 H), 2.91-2.99 (m, 3 H), 2.41-2.50 (m, 0.7 H), 2.28-2.36 (m, 1.3 H), 2.10-2.21 (m, 1.3 H), 1.86-2.01 (m, 0.7 H), 0.98-1.05 (m, 2 H), 0.84-0.91 (m, 2 H)

| Example/IUPAC name | Structure | MS calculated MS ESI [M + H]+ | Yield; Appearance Salt form |
|---|---|---|---|
| A472: 3-(4-((1-methylpiperidin-4-yl)oxy)phenyl)-N-((1-(thiophen-3-yl)cyclohexyl)methyl)-1H-indazole-5-carboxamide | 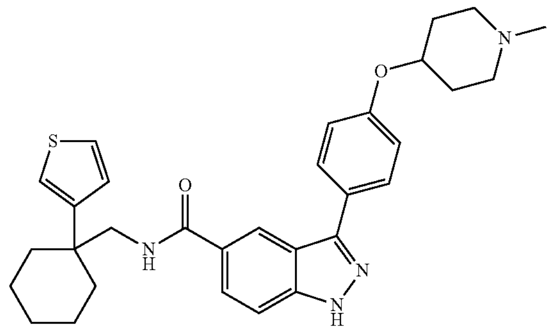 [SMILES: CN1CCC(Oc2ccc(-c3n[nH]c4ccc(C(=O)NCC5(c6ccsc6)CCCCC5)cc34)cc2)CC1] | [$C_{31}H_{36}N_4O_2$ + H]+ 529.2 529.4 | 38 mg (27%); light brown solid; TFA salt |

SMs: 3-iodo-N-((1-(thiophen-3-yl)cyclohexyl)methyl)-1H-indazole-5-carboxamide (100 mg, 0.21 mmol), 1-methyl-4-(4-(4,4,5,5-tetramethyl-1,3,2-dioxaborolan-2-yl)phenoxy)piperidine (68 mg, 0.21 mmol), PdCl$_2$dppf*CH$_2$Cl$_2$ (26 mg, 0.032 mmol)
$^1$H NMR (400 MHz, CD$_3$OD) δ ppm 8.34 (br. s, 1 H), 7.93 (br. s, 2 H), 7.75 (d, J = 6.3 Hz, 1 H), 7.61-7.70 (m, 1 H), 7.58 (br. s, 1 H), 7.42 (br. s, 1 H), 7.14-7.29 (m, 3 H), 4.67-4.78 (m, 0.40 H), 3.63-3.72 (m, 0.70 H), 3.37-3.53 (m, 4.7 H), 3.18-3.29 (m, 0.80 H), 2.96 (br. s, 3 H), 2.43-2.53 (m, 0.70 H), 2.32 (br. s, 1.37 H), 2.17 (d, J = 11.5 Hz, 3.33 H), 1.89-2.03 (m, 0.80 H), 1.61-1.78 (m, 3.9 H), 1.40 (br. s, 4.3 H), 1H merged with solvent peak.

| A473: 3-(4-((1-methylpiperidin-4-yl)oxy)phenyl)-N-((4-phenyltetrahydro-2H-pyran-4-yl)methyl)-1H-indazole-5-carboxamide | | [$C_{32}H_{36}N_4O_3$ + H]+ 525.2 525.4 | 13 mg (9%); white solid; TFA salt |

SMs: 3-iodo-N-((4-phenyltetrahydro-2H-pyran-4-yl)methyl)-1H-indazole-5-carboxamide(100 mg, 0.21 mmol), 1-methyl-4-(4-(4,4,5,5-tetramethyl-1,3,2-dioxaborolan-2-yl)phenoxy)piperidine 69 mg, 0.21 mmol), Pd(PPh$_3$)$_4$ (19 mg, 0.016 mmol)
$^1$H NMR (400 MHz, CD$_3$OD) δ ppm 8.30-8.36 (m, 1 H), 8.05-8.11 (m, 1 H), 7.80-7.91 (m, 2 H), 7.72-7.78 (m, 1 H), 7.55-7.60 (m, 1 H), 7.42-7.51 (m, 2 H), 7.39-7.44 (m, 2 H) 7.27-7.33 (m, 1 H), 7.16-7.26 (m, 2 H), 4.65-4.78 (m, 0.45 H), 3.84-3.92 (m, 2 H), 3.51-3.72 (m, 4.9 H), 3.37-3.51 (m, 2.86 H), 3.20-3.29 (m, 0.85 H), 2.94-2.99 (m, 3 H), 2.44-2.53 (m, 0.7 H), 2.31-2.39 (m, 0.9 H), 2.21-2.28 (m, 2 H), 2.08-2.20 (m, 1.49 H), 1.90-2.08 (m, 2.88 H)

| A474: 3-(4-((1-methylpiperidin-4-yl)oxy)phenyl)-N-((1-(pyridin-2-yl)cyclohexyl)methyl)-1H-indazole-5-carboxamide | | [$C_{32}H_{37}N_5O_2$ + H]+ 524.3 524.3 | 30 mg (18%); off white solid; TFA salt |

SMs: 3-iodo-N-((1-(pyridin-2-yl)cyclohexyl)methyl)-1H-indazole-5-carboxamide (100 mg, 0.21 mmol), 1-methyl-4-(4-(4,4,5,5-tetramethyl-1,3,2-dioxaborolan-2-yl)phenoxy)piperidine (69 mg, 0.21 mmol), PdCl$_2$dppf*CH$_2$Cl$_2$ (27 mg, 0.032 mmol)
$^1$H NMR (400 MHz, CD$_3$OD) δ ppm 8.69-8.76 (m, 1 H), 8.47-8.53 (m, 1 H), 8.39 (s, 1 H), 8.16 (s, 1 H), 7.93 (d, J = 8.3 Hz, 3 H), 7.68 (s, 1 H), 7.56 (d, J = 8.8 Hz, 1 H), 7.22 (d, J = 8.5 Hz, 1 H), 7.14-7.20 (m, 1 H), 3.71 (s, 3 H), 3.44 (br. s, 4 H), 3.18-3.28 (m, 1 H), 2.91-3.00 (m, 3 H), 2.41-2.56 (m, 3 H), 2.28-2.37 (m, 1 H), 2.10-2.22 (m, 1 H), 1.94 (br. s, 3 H), 1.77-1.87 (m, 2 H), 1.52-1.69 (m, 2 H), 1.26-1.42 (m, 2 H)

| Example/IUPAC name | Structure | MS calculated MS ESI [M + H]⁺ | Yield; Appearance Salt form |
|---|---|---|---|
| A475: N-(((2R,6S)-2,6-dimethyl-4-morpholinotetrahydro-2H-pyran-4-yl)methyl)-3-(4-((1-methylpiperidin-4-yl)oxy)phenyl)-1H-indazole-5-carboxamide | 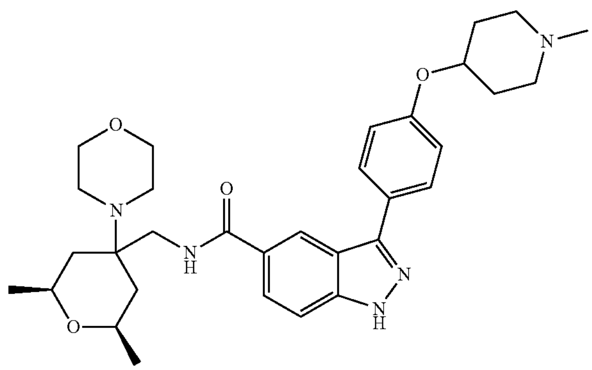 | $[C_{32}H_{43}N_5O_4 + H]^+$ 562.3 562.3 | 36 mg (28%); white solid; 2TFA salt |

SMs: N-(((2R,6S)-2,6-dimethyl-4-morpholinotetrahydro-2H-pyran-4-yl)methyl)-3-iodo-1H-indazole-5-carboxamide (100 mg, 0.16 mmol), 1-methyl-4-(4-(4,4,5,5-tetramethyl-1,3,2-dioxaborolan-2-yl)phenoxy)piperidine (55 mg, 0.17 mmol), PdCl₂dppf*CH₂Cl₂ (20 mg, 0.024 mmol)
¹H NMR (400 MHz, CD₃OD) δ ppm 8.63-8.68 (m, 1 H), 7.96 (s, 3 H), 7.64-7.69 (m, 1 H), 7.17-7.27 (m, 2 H), 4.11-4.24 (m, 2 H), 4.03 (s, 2 H), 3.81-3.94 (m, 4 H), 3.59-3.74 (m, 3 H), 3.36-3.51 (m, 5 H), 3.15-3.28 (m, 1 H), 2.91-2.99 (m, 3 H), 2.26-2.51 (m, 2 H), 2.10-2.22 (m, 1 H), 1.89-2.07 (m, 3 H), 1.54-1.65 (m, 2 H), 1.28 (d, J = 6.0 Hz, 6 H)

| Example/IUPAC name | Structure | MS calculated MS ESI [M + H]⁺ | Yield; Appearance Salt form |
|---|---|---|---|
| A476: N-((4-(2-fluorophenyl)tetrahydro-2H-pyran-4-yl)methyl)-3-(4-((1-methylpiperidin-4-yl)oxy)phenyl)-1H-indazole-5-carboxamide | | $[C_{32}H_{35}FN_4O_3 + H]^+$ 543.2 543.4 | 42 mg (25%); off white solid; TFA salt |

SMs: N-((4-(2-fluorophenyl)tetrahydro-2H-pyran-4-yl)methyl)-3-iodo-1H-indazole-5-carboxamide (150 mg, 0.31 mmol), 1-methyl-4-(4-(4,4,5,5-tetramethyl-1,3,2-dioxaborolan-2-yl)phenoxy)piperidine (100 mg, 0.31 mmol), PdCl₂dppf*CH₂Cl₂ (38 mg, 0.046 mmol)
¹H NMR (400 MHz, CD₃OD) δ ppm 8.25 (s, 1 H), 7.84 (d, J = 8.8 Hz, 2 H), 7.70 (d, J = 1.5 Hz, 1 H), 7.53 (d, J = 8.8 Hz, 1 H), 7.36-7.42 (m, 1 H), 7.29-7.35 (m, 1 H), 7.11 (d, J = 8.8 Hz, 4 H), 4.50-4.58 (m, 1 H), 3.87-3.96 (m, 2 H), 3.81 (s, 2 H), 3.60 (br. s, 2 H), 2.71-2.83 (m, 2 H), 2.40-2.50 (m, 2 H), 2.34 (s, 5 H), 2.00-2.14 (m, 4 H), 1.81-1.94 (m, 2 H)

| Example/IUPAC name | Structure | MS calculated MS ESI [M + H]⁺ | Yield; Appearance Salt form |
|---|---|---|---|
| A477: N-((1-morpholinocyclopentyl)methyl)-3-(4-((tetrahydro-2H-pyran-4-yl)oxy)phenyl)-1H-indazole-5-carboxamide | | $[C_{29}H_{36}N_4O_4 + H]^+$ 505.2 505.4 | 61 mg (56%); cream solid; TFA salt |

SMs: 3-iodo-N-((1-morpholinocyclopentyl)methyl)-1H-indazole-5-carboxamide (100 mg, 0.17 mmol), 4,4,5,5-tetramethyl-2-(4-((tetrahydro-2H-pyran-4-yl)oxy)phenyl)-1,3,2-dioxaborolane (54 mg, 0.17 mmol), PdCl₂dppf*CH₂Cl₂ (21 mg, 0.026 mmol)
¹H NMR (400 MHz, CD₃OD) δ ppm 8.65 (s, 1 H), 8.00 (dd, J = 8.9, 1.6 Hz, 1 H), 7.90-7.96 (m, 2 H), 7.65 (d, J = 9.0 Hz, 1 H), 7.15 (d, J = 8.8 Hz, 2 H), 4.68 (s, 1 H), 4.12 (br. s, 2 H), 3.95-4.04 (m, 2 H), 3.76-3.90 (m, 4 H), 3.59-3.74 (m, 4 H), 3.39-3.52 (m, 2 H), 2.01-2.14 (m, 6 H), 1.84-1.97 (m, 4 H), 1.79 (dd, J = 8.8, 4.3 Hz, 2 H), 2H merged with solvent peak.

| Example/IUPAC name | Structure | MS calculated MS ESI [M + H]+ | Yield; Appearance Salt form |
|---|---|---|---|
| A478: 3-(4-((1-methylpiperidin-4-yl)oxy)phenyl)-N-((4-(pyridin-4-yl)tetrahydro-2H-pyran-4-yl)methyl)-1H-indazole-5-carboxamide | 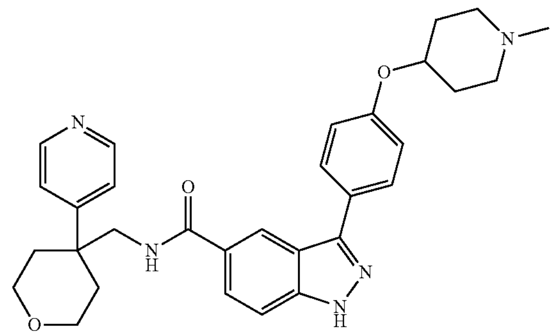 [SMILES: CN1CCC(Oc2ccc(-c3n[nH]c4ccc(C(=O)NCC5(c6ccncc6)CCOCC5)cc34)cc2)CC1] | [C31H35N5O3 + H]+ 526.2 546.2 | 10 mg (9%); white solid; free base |

SMs: 3-iodo-N-((4-(pyridin-4-yl)tetrahydro-2H-pyran-4-yl)methyl)-1H-indazole-5-carboxamide (125 mg, 0.21 mmol), 1-methyl-4-(4-(4,4,5,5-tetramethyl-1,3,2-dioxaborolan-2-yl)phenoxy)piperidine (69 mg, 0.21 mmol), PdCl2dppf*CH2Cl2 (26 mg, 0.031 mmol)
$^1$H NMR (400 MHz, CD3OD) δ ppm 8.53 (d, J = 6.0 Hz, 2 H), 8.28-8.36 (m, 1 H), 7.87 (d, J = 8.8 Hz, 2 H), 7.71-7.78 (m, 1 H), 7.53 (d, J = 6.0 Hz, 3 H), 7.14 (d, J = 8.8 Hz, 2 H), 4.52-4.61 (m, 1 H), 3.87-3.95 (m, 2 H), 3.66 (s, 2 H), 3.48-3.59 (m, 2 H), 2.72-2.83 (m, 2 H), 2.40-2.51 (m, 2 H), 2.34 (s, 3 H), 2.18-2.27 (m, 2 H), 2.01-2.15 (m, 4 H), 1.83-1.96 (m, 2 H),

| Example/IUPAC name | Structure | MS calculated MS ESI [M + H]+ | Yield; Appearance Salt form |
|---|---|---|---|
| A479: 3-(4-((1-methylpiperidin-4-yl)oxy)phenyl)-N-((1-morpholinocyclobutyl)methyl)-1H-indazole-5-carboxamide | 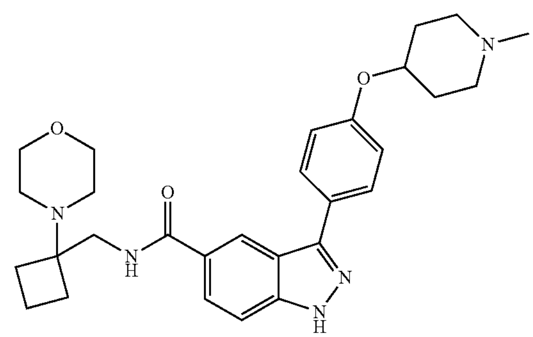 [SMILES: CN1CCC(Oc2ccc(-c3n[nH]c4ccc(C(=O)NCC5(N6CCOCC6)CCC5)cc34)cc2)CC1] | [C29H37N5O3 + H]+ 504.2 504.2 | 50 mg (36%); white solid; free base |

SMs: 3-iodo-N-((1-morpholinocyclobutyl)methyl)-1H-indazole-5-carboxamide (125 mg, 0.27 mmol), 1-methyl-4-(4-(4,4,5,5-tetramethyl-1,3,2-dioxaborolan-2-yl)phenoxy)piperidine (86 mg, 0.27 mmol), PdCl2dppf*CH2Cl2 (33 mg, 0.04 mmol)
$^1$H NMR (400 MHz, CD3OD) δ ppm 8.52 (s, 1 H), 7.82-7.95 (m, 3 H), 7.61 (d, J = 8.8 Hz, 1 H), 7.09 (d, J = 8.8 Hz, 2 H), 4.49 (br. s, 1 H), 3.26-3.34 (m, 2 H), 2.57-2.82 (m, 6 H), 2.40 (br. s, 2 H), 2.32 (s, 3 H), 1.99-2.20 (m, 4 H), 1.74-1.97 (m, 6 H), 4H merged with solvent peak.

| Example/IUPAC name | Structure | MS calculated MS ESI [M + H]+ | Yield; Appearance Salt form |
|---|---|---|---|
| A480: 3-(4-((1-methylpiperidin-4-yl)oxy)phenyl)-N-((1-(pyridin-4-yl)cyclohexyl)methyl)-1H-indazole-5-carboxamide | 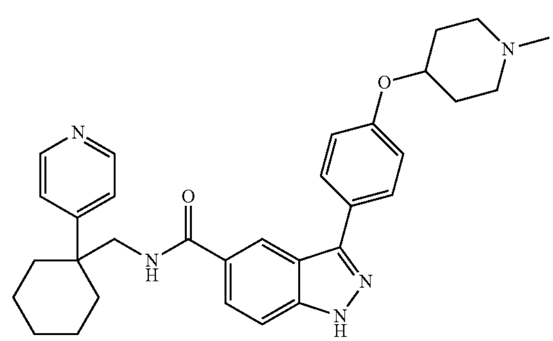 [SMILES: CN1CCC(Oc2ccc(-c3n[nH]c4ccc(C(=O)NCC5(c6ccncc6)CCCCC5)cc34)cc2)CC1] | [C32H37N5O2 + H]+ 524.3 524.3 | 55 mg (34%); white solid; 2TFA salt |

SMs: 3-iodo-N-((1-(pyridin-4-yl)cyclohexyl)methyl)-1H-indazole-5-carboxamide (100 mg, 0.21 mmol), 1-methyl-4-(4-(4,4,5,5-tetramethyl-1,3,2-dioxaborolan-2-yl)phenoxy)piperidine (69 mg, 0.21 mmol), PdCl2dppf*CH2Cl2 (27 mg, 0.033 mmol)
$^1$H NMR (400 MHz, CD3OD) δ ppm 8.73 (d, J = 6.3 Hz, 2H), 8.58-8.64 (m, 1H), 8.41 (s, 1H), 8.20 (d, J = 6.8 Hz, 2H), 7.87-7.97 (m, 2 H), 7.73 (d, J = 9.0 Hz, 1 H), 7.57 (d, J = 8.8 Hz, 1 H), 7.14-7.26 (m, 2 H), 4.62-4.77 (m, 1 H), 3.61-3.70 (m, 2.6 H), 3.34-3.50 (m, 2.70 H), 3.16-3.28 (m, 0.7 H), 2.91-2.99 (m, 3 H), 2.45 (d, J = 14.1 Hz, 2.6 H), 2.29 (br. s, 1.4 H), 2.08-2.23 (m, 1.3 H), 1.71-2.01 (m, 4.7 H), 1.44-1.66 (m, 2 H), 1.31 (br. s, 2 H), 1H merged with solvent peak.

| Example/IUPAC name | Structure | MS calculated MS ESI [M + H]+ | Yield; Appearance Salt form |
|---|---|---|---|
| A481: (R)-3-(4-((1-methylpyrrolidin-3-yl)oxy)phenyl)-N-((1-morpholinocyclohexyl)methyl)-1H-indazole-5-carboxamide | 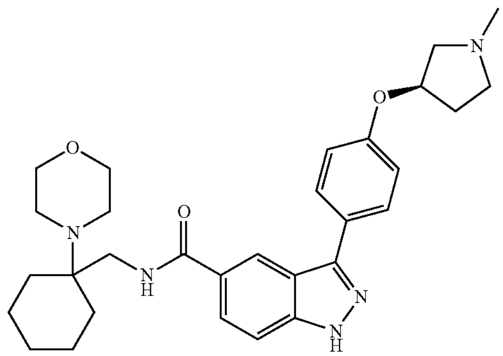 [SMILES: CN1CC[C@@H](Oc2ccc(-c3n[nH]c4ccc(C(=O)NCC5(N6CCOCC6)CCCCC5)cc34)cc2)C1] | [$C_{30}H_{39}N_5O_3$ + H]+ 518.3 518.3 | 36 mg (28%); white solid; 2TFA salt |

SMs: 3-iodo-N-((1-morpholinocyclohexyl)methyl)-1H-indazole-5-carboxamide (80 mg, 0.17 mmol), (R)-1-methyl-3-(4-(4,4,5,5-tetramethyl-1,3,2-dioxaborolan-2-yl)phenoxy)pyrrolidine (65 mg, 0.17 mmol), PdCl$_2$dppf*CH$_2$Cl$_2$ (21 mg, 0.025 mmol)
$^1$H NMR (400 MHz, CD$_3$OD) δ ppm 8.69 (s, 1 H), 7.99 (d, J = 8.5 Hz, 3 H), 7.68 (s, 1 H), 7.19 (s, 2 H), 5.28-5.37 (m, 1 H), 4.13-4.21 (m, 2 H), 3.94 (s, 5 H), 3.64-3.72 (m, 2 H), 3.36-3.52 (m, 2 H), 3.04 (br. s, 3 H), 2.66-2.82 (m, 0.7 H), 2.24-2.53 (m, 1.3 H), 1.95-2.04 (m, 2 H), 1.86-1.95 (m, 2 H), 1.58-1.85 (m, 5 H), 1.25-1.40 (m, 1 H), 3H merged with solvent peak.

| Example/IUPAC name | Structure | MS calculated MS ESI [M + H]+ | Yield; Appearance Salt form |
|---|---|---|---|
| A482: 3-(4-((1-methylpiperidin-4-yl)oxy)phenyl)-N-((1-(pyridin-3-yl)cyclohexyl)methyl)-1H-indazole-5-carboxamide | 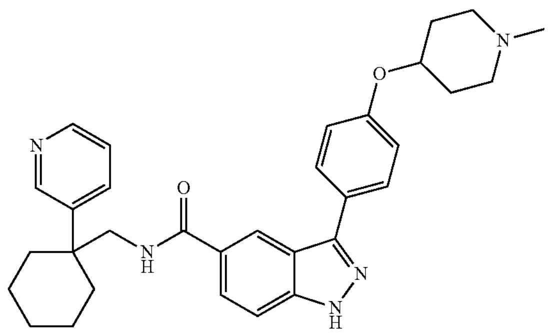 [SMILES: CN1CCC(Oc2ccc(-c3n[nH]c4ccc(C(=O)NCC5(c6cccnc6)CCCCC5)cc34)cc2)CC1] | [$C_{32}H_{37}N_5O_2$ + H]+ 524.3 524.2 | 67 mg (47%); white solid; 2TFA salt |

SMs: 3-iodo-N-((1-(pyridin-3-yl)cyclohexyl)methyl)-1H-indazole-5-carboxamide (100 mg, 0.21 mmol), 1-methyl-4-(4-(4,4,5,5-tetramethyl-1,3,2-dioxaborolan-2-yl)phenoxy)piperidine (69 mg, 0.21 mmol), PdCl$_2$dppf*CH$_2$Cl$_2$ (27 mg, 0.033 mmol)
$^1$H NMR (400 MHz, CD$_3$OD) δ ppm 8.93 (s, 1 H), 8.69 (q, J = 5.3 Hz, 3 H), 8.39 (s, 1 H), 7.99 (dd, J = 7.9, 6.1 Hz, 1H), 7.86-7.95 (m, 2H), 7.70 (d, J = 8.8 Hz, 1H), 7.56 (d, J = 8.8 Hz, 1 H), 7.15-7.25 (m, 2 H), 4.66-4.77 (m, 0.4 H), 3.62 (d, J = 5.8 Hz, 2.60 H), 3.42 (m, 2.7 H), 3.18-3.28 (m, 0.3 H), 2.90-2.99 (m, 3 H), 2.25-2.50 (m, 4 H), 2.16 (br. s, 1.4 H), 1.89 (t, J = 11.2 Hz, 2.6 H), 1.68-1.82 (m, 2H), 1.60 (br. s, 2 H), 1.33 (d, J = 11.0 Hz, 2 H), 1H merged with solvent peak.

| Example/IUPAC name | Structure | MS calculated MS ESI [M + H]+ | Yield; Appearance Salt form |
|---|---|---|---|
| A483: 3-(4-(8-oxa-3-azabicyclo[3.2.1]octan-3-yl)phenyl)-N-((1-morpholinocyclohexyl)methyl)-1H-indazole-5-carboxamide | | [$C_{31}H_{39}N_5O_3$ + H]+ 530.3 530.4 | 36 mg (31%); yellow solid; 2TFA salt |

SMs: 3-iodo-N-((1-morpholinocyclohexyl)methyl)-1H-indazole-5-carboxamide (80 mg, 0.17 mmol), 2-(4-((1R,3R,5S)-8-oxabicyclo[3.2.1]octan-3-yl)phenyl)-HBpin (54 mg, 0.17 mmol), PdCl$_2$dppf*CH$_2$Cl$_2$ (14 mg, 0.017 mmol)
$^1$H NMR (400 MHz, CD$_3$OD) δ ppm 8.68 (s, 1 H), 8.00 (d, J = 9.3 Hz, 1 H), 7.87 (d, J = 8.3 Hz, 2 H), 7.64 (d, J = 8.8 Hz, 1 H), 7.03 (d, J = 8.0 Hz, 2 H), 4.51 (br. s, 2 H), 4.16 (d, J = 12.8 Hz, 2 H), 3.82-3.98 (m, 4 H), 3.66 (d, J = 12.3 Hz, 2 H), 3.51 (d, J = 11.5 Hz, 2 H), 2.98 (d, J = 11.5 Hz, 2 H), 1.85-2.06 (m, 9 H), 1.55-1.84 (m, 6 H), 1.24-1.39 (m, 1 H), 3H merged with solvent peak.

| Example/IUPAC name | Structure | MS calculated MS ESI [M + H]+ | Yield; Appearance Salt form |
|---|---|---|---|
| A484: 3-(4-(((1R,3R, 5S)-8-methyl-8-azabicyclo [3.2.1]octan-3-yl)oxy)phenyl)-N-((4-phenyl tetrahydro-2H-pyran-4-yl)methyl)-1H-indazole-5-carboxamide | 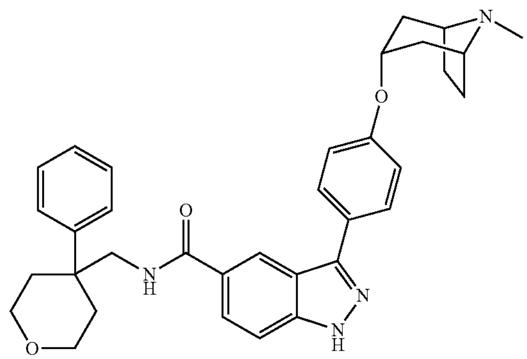 [SMILES: CN1C2CCC1CC(Oc1ccc(-c3n[nH]c4ccc(C(=O)NCC5(c6ccccc6)CCOCC5)cc34)cc1)C2] | [$C_{34}H_{38}N_4O_3$ + H]+ 551.3 551.4 | 52 mg (36%); white solid; TFA salt |

SMs: 3-iodo-N-((4-phenyltetrahydro-2H-pyran-4-yl)methyl)-1H-indazole-5-carboxamide (100 mg, 0.21 mmol), (1R,3R,5S)-8-methyl-3-(4-(4,4,5,5-tetramethyl-1,3,2-dioxaborolan-2-yl)phenoxy)-8-azabicyclo[3.2.1]octane (82 mg, 0.21 mmol), PdCl$_2$dppf*CH$_2$Cl$_2$ (13 mg, 0.016 mmol)
$^1$H NMR (400 MHz, CD$_3$OD) δ ppm 8.33 (s, 1 H), 8.06 (br. s, 1 H), 7.92 (d, J = 8.8 Hz, 2 H), 7.75 (dd, J = 8.8, 1.5 Hz, 1 H), 7.57 (d, J = 8.8 Hz, 1 H), 7.44-7.50 (m, 2 H), 7.37-7.44 (m, 2 H), 7.29 (d, J = 7.3 Hz, 1 H), 7.13 (d, J = 8.8 Hz, 2 H), 3.96 (br. s, 2 H), 3.87 (dt, J = 12.0, 4.2 Hz, 3 H), 3.51-3.65 (m, 4 H), 2.85 (s, 3 H), 2.57 (d, J = 8.5 Hz, 2 H), 2.31-2.52 (m, 6 H), 2.23 (d, J = 13.8 Hz, 2H), 1.97-2.08 (m, 2 H)

| Example/IUPAC name | Structure | MS calculated MS ESI [M + H]+ | Yield; Appearance Salt form |
|---|---|---|---|
| A485: N-(3-(4-((1-methylpiperidin-4-yl)oxy) phenyl)-1H-indazol-5-yl)-2-(1-morpholino cyclohexyl)acetamide | 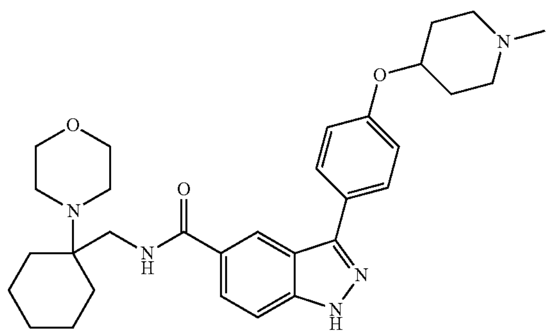 [SMILES: CN1CCC(Oc2ccc(-c3n[nH]c4ccc(C(=O)NCC5(N6CCOCC6)CCCCC5)cc34)cc2)CC1] | [$C_{31}H_{41}N_5O_3$ + H]+ 532.3 532.3 | 37 mg (51%); off white solid; free base |

SMs: N-(3-iodo-1H-indazol-5-yl)-2-(1-morpholinocyclohexyl)acetamide (125 g, 0.21 mmol), 1-methyl-4-(4-(4,4,5,5-tetramethyl-1,3,2-dioxaborolan-2-yl)phenoxy)piperidine (80 g, 0.25 mmol), PdCl$_2$dppf*CH$_2$Cl$_2$ (17 mg, 0.021 mmol)
$^1$H NMR (400 MHz, CD$_3$OD) δ ppm 8.38 (s, 1 H), 7.84 (d, J = 8.8 Hz, 2 H), 7.43-7.57 (m, 2 H), 7.07 (d, J = 8.5 Hz, 2 H), 4.44-4.54 (m, 1 H), 3.73 (d, J = 3.8 Hz, 4 H), 2.60-2.84 (m, 6 H), 2.38-2.54 (m, 4 H), 2.33 (s, 3 H), 2.04 (br. s, 2 H), 1.65-1.95 (m, 6 H), 1.30-1.64 (m, 6 H)

| Example/IUPAC name | Structure | MS calculated MS ESI [M + H]+ | Yield; Appearance Salt form |
|---|---|---|---|
| A486: 3-(4-((4-(hydroxylmethyl)-1-methylpiperidin-4-yl)methyl)phenyl)-N-((1-morpholinocyclohexyl) methyl)-1H-indazole-5-carboxamide | 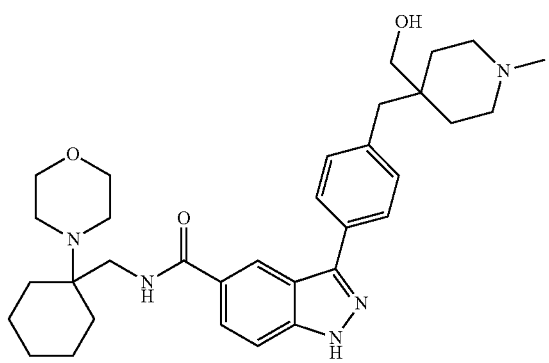 [SMILES: CN1CCC(CO)(Cc2ccc(-c3n[nH]c4ccc(C(=O)NCC5(N6CCOCC6)CCCCC5)cc34)cc2)CC1] | [$C_{33}H_{45}N_5O_3$ + H]+ 560.3 560.3 | 15 mg (51%); white solid; free base |

SMs: 3-iodo-N-((1-morpholinocyclohexyl)methyl)-1H-indazole-5-carboxamide (40.8 mg, 0.087 mmol), (1-methyl-4-(4-(4,4,5,5-tetramethyl-1,3,2-dioxaborolan-2-yl)benzyl)piperidin-4-yl)methanol (66 mg, 0.087 mmol), Pd(PPh$_3$)$_4$ (11 mg, 0.09 mmol)
$^1$H NMR (400 MHz, CD$_3$OD) δ ppm 8.53 (s, 1 H), 7.87-7.97 (m, 3 H), 7.64 (d, J = 8.8 Hz, 1 H), 7.41 (d, J = 8.0 Hz, 2 H), 3.71 (br. s, 4 H), 3.52 (s, 2 H), 3.36 (d, J = 4.5 Hz, 3 H), 2.78 (m, 6 H), 2.58-2.67 (m, 2 H), 2.46-2.55 (m, 2 H), 2.32 (s, 3 H), 1.64-1.85 (m, 4 H), 1.38-1.62 (m, 10 H)

| Example/IUPAC name | Structure | MS calculated MS ESI [M + H]⁺ | Yield; Appearance Salt form |
| --- | --- | --- | --- |
| A487: 3-(4-((1-(oxetan-3-yl)piperidin-4-yl)oxy)phenyl)-N-((3-phenyloxetan-3-yl)methyl)-1H-indazole-5-carboxamide | 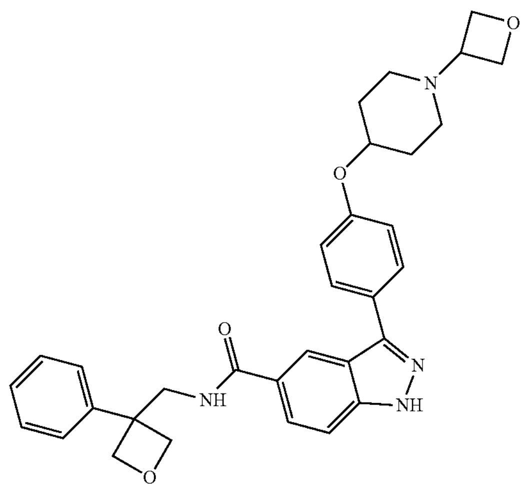 [SMILES: O=C(NCC1(c2ccccc2)COC1)c1ccc2[nH]nc(-c3ccc(OC4CCN(C5COC5)CC4)cc3)c2c1] | [C$_{32}$H$_{34}$N$_4$O$_4$ + S + H]⁺ 539.2 539.2 | 15 mg (16%); white solid; free base |

SMs: 3-iodo-N-((3-phenyloxetan-3-yl)methyl)-1H-indazole-5-carboxamide (75 mg, 0.17 mmol), 1-(axetan-3-yl)-4-(4-(4,4,5,5-tetramethyl-1,3,2-dioxaborolan-2-yl)phenoxy)piperidine (62 mg, 0.17 mmol), PdCl$_2$dppf*CH$_2$Cl$_2$ (11 mg, 0.013 mmol)

¹H NMR (400 MHz, CD$_3$OD) δ ppm 8.50 (s, 1 H), 7.83-7.95 (m, 3 H), 7.52 (d, J = 8.8 Hz, 1 H), 7.47 (d, J = 1.5 Hz, 2 H), 7.36 (t, J = 7.8 Hz, 2 H), 7.24 (s, 1 H), 7.10 (d, J = 8.8 Hz, 2 H), 4.67-4.77 (m, 4 H), 4.59-4.66 (m, 3 H), 4.48-4.56 (m, 1 H), 3.90 (d, J = 5.8 Hz, 2 H), 3.79 (s, 2 H), 3.49-3.58 (m, 1 H), 2.57-2.68 (m, 2 H), 2.21-2.32 (m, 2 H), 2.02-2.14 (m, 2 H), 1.81-1.94 (m, 2 H)

| Example/IUPAC name | Structure | MS calculated MS ESI [M + H]⁺ | Yield; Appearance Salt form |
| --- | --- | --- | --- |
| A488: 3-(4-(((1R,3R,5S)-8-methyl-8-azabicyclo[3.2.1]octan-3-yl)oxy)pheny])-N-((1-(pyridine-2-yl)cyclopropyl)methyl)-1H-indazole-5-carboxamide | | [C$_{31}$H$_{33}$N$_5$O$_2$ + H]⁺ 508.2 508.3 | 23 mg (15%); beige solid; TFA salt |

SMs: 3-iodo-N-((1-(pyridin-2-yl)cyclopropyl)methyl)-1H-indazole-5-carboxamide (100 mg, 0.23 mmol), (1R,3R,5S)-8-methyl-3-(4-(4,4,5,5-tetramethyl-1,3,2-dioxaborolan-2-yl)phenoxy)-8-azabicyclo[3.2.1]octane (82 mg, 0.23 mmol), PdCl$_2$dppf*CH$_2$Cl$_2$ (19 mg, 0.023 mmol)

¹H NMR (400 MHz, CD$_3$OD) δ ppm 8.72-8.79 (m, 1 H), 8.50 (s, 2 H), 7.95 (d, J = 8.8 Hz, 4 H), 7.79-7.85 (m, 1 H), 7.61 (s, 1 H), 7.14 (d, J = 8.8 Hz, 2 H), 3.89-4.00 (m, 2 H), 3.82 (s, 2 H), 2.85 (s, 3 H), 2.32-2.62 (m, 8 H), 1.41 (s, 2 H), 1.32 (s, 2 H), 1H merged with solvent peak.

| Example/IUPAC name | Structure | MS calculated MS ESI [M + H]+ | Yield; Appearance Salt form |
|---|---|---|---|
| A489: 3-(1',4-dimethylspiro[chromene-2,4'-piperidin]-6-yl)-N-((1-morpholinocyclohexyl)methyl)-1H-indazole-5-carboxamide | 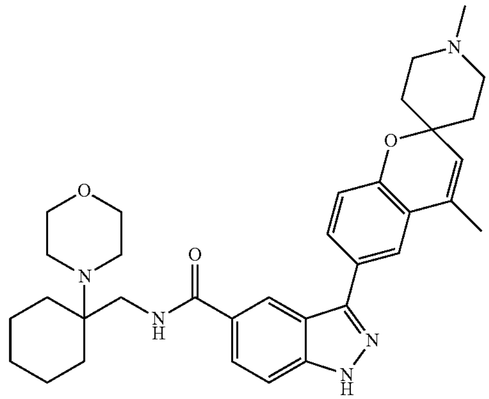 [SMILES: CC1=CC2(CCN(C)CC2)Oc2ccc(-c3n[nH]c4ccc(C(=O)NCC5(N6CCOCC6)CCCCC5)cc34)cc21] | [C₃₄H₄₃N₅O₃ + H]+ 570.3 570.3 | 60 mg (46%); cream solid; HCl salt |

SMs: 3-iodo-N-((1-morpholinocyclohexyl)methyl)-1H-indazole-5-carboxamide (100 mg, 0.21 mmol), 1',4-dimethyl-6-(4,4,5,5-tetramethyl-1,3,2-dioxaborolan-2-yl)spiro [chromene-2,4'-piperidine] (76 mg, 0.21 mmol), PdCl₂dppf*CH₂Cl₂ (12 mg, 0.010 mmol)
¹H NMR (400 MHz, CD₃OD) δ ppm 8.71 (s, 1H), 8.07 (d, J = 9.0 Hz, 1H), 7.90-7.96 (m, 1H), 7.87 (s, 1H), 7.69 (d, J = 8.8 Hz, 1H), 7.17-7.24 (m, 1H), 5.88 (s, 0.16H), 5.60 (s, 0.84H), 4.15 (d, J = 12.0 Hz, 2H), 3.88-4.03 (m, 4.4H), 3.68 (d, J = 11.5 Hz, 2.6H), 3.39-3.55 (m, 4.30H), 2.92-3.05 (m, 3 H), 2.16-2.33 (m, 5 H), 1.96-2.15 (m, 4.70H), 1.62-1.94 (m, 8 H), 1.23-1.45 (m, 1H)

| A490: 3-(2,2-dimethyl-4-oxochroman-6-yl)-N-((1-morpholinocyclohexyl)methyl)-1H-indazole-5-carboxamide | | [C₃₀H₃₆N₄O₄ + H]+ 517.2 517.4 | 86 mg (64%); Yellow solid; TFA salt |

SMs: 3-iodo-N-((1-morpholinocyclohexyl)methyl)-1H-indazole-5-carboxamide (100 mg, 0.21 mmol), 2,2-dimethyl-6-(4,4,5,5-tetramethyl-1,3,2-dioxaborolan-2-yl)chroman-4-one (64 mg, 0.21 mmol), Pd(PPh₃)₄ (12 mg, 0.01 mmol)
¹H NMR (400 MHz, CD₃OD) δ ppm 8.64 (d, J = 0.8 Hz, 1 H), 8.39 (d, J = 2.3 Hz, 1 H), 8.18 (dd, J = 8.8, 2.3 Hz, 1 H), 8.00 (dd, J = 8.8, 1.5 Hz, 1 H), 7.66 (dd, J = 8.9, 0.6 Hz, 1 H), 7.14 (d, J = 8.5 Hz, 1 H), 4.12-4.23 (m, 2 H), 3.94 (s, 4 H), 3.63-3.75 (m, 2 H), 2.86 (s, 2 H), 1.97-2.06 (m, 2 H), 1.85-1.95 (m, 2 H), 1.78 (br. s, 5 H), 1.51 (s, 6 H), 1.30-1.39 (m, 1 H), 2H merged with solvent peak

| A491: 3-(1,4-dimethyl-2-oxo-1,2-dihydroquinolin-6-yl)-N-((1-morpholinocyclohexyl)methyl)-1H-indazole-5-carboxamide | | [C₃₀H₃₅N₅O₃ + H]+ 514.2 514.4 | 28 mg (30%); Cream solid; TFA salt |

SMs: 3-iodo-N-((1-morpholinocyclohexyl)methyl)-1H-indazole-5-carboxamide (70 mg, 0.15 mmol), 1,4-dimethyl-6-(4,4,5,5-tetramethyl-1,3,2-dioxaborolan-2-yl)quinolin-2-(1H)-one (45 mg, 0.15 mmol), Pd(PPh₃)₄ (9 mg, 0.008 mmol)
¹H NMR (400 MHz, CD₃OD) δ ppm 8.68-8.77 (m, 1 H), 8.39 (d, J = 1.8 Hz, 1 H), 8.26-8.34 (m, 1 H), 8.02 (d, J = 1.5 Hz, 1 H), 7.66-7.77 (m, 2 H), 6.62 (d, J = 1.0 Hz, 1 H), 4.14-4.23 (m, 2 H), 3.96 (s, 4 H), 3.76 (s, 3 H), 3.65-3.73 (m, 2 H), 2.60 (d, J = 1.0 Hz, 3 H), 1.96-2.05 (m, 2 H), 1.87-1.95 (m, 2 H), 1.59-1.85 (m, 5 H), 1.26-1.40 (m, 1 H), 2H merged with solvent peak

| Example/IUPAC name | Structure | MS calculated MS ESI [M + H]⁺ | Yield; Appearance Salt form |
|---|---|---|---|
| A492: 3-(4-((1R,3R,5S)-3-hydroxy-8-azabicyclo[3.2.1]octan-8-yl)phenyl)-N-((4-phenyltetrahydro-2H-pyran-4-yl)methyl)-1H-indazole-5-carboxamide | 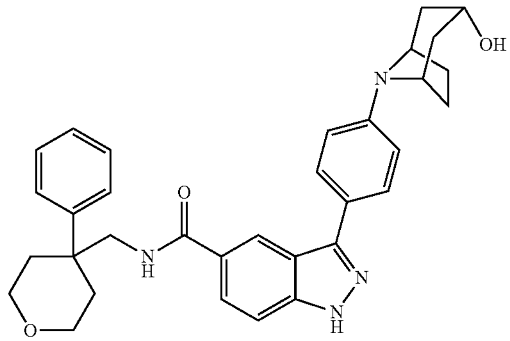 [SMILES: O=C(NCC1(c2ccccc2)CCOCC1)c1ccc2[nH]nc(-c3ccc(N4C5CCC4CC(O)C5)cc3)c2c1] | [C$_{33}$H$_{36}$N$_4$O$_3$ + H]⁺ 537.2 537.4 | 44 mg (36%); Yellow solid; HCl salt |

SMs: 3-iodo-N-((4-phenyltetrahydro-2H-pyran-4-yl)methyl)-1H-indazole-5-carboxamide (100 mg, 0.21 mmol), (1R,3R,5S)-8-(4-(4,4,5,5-tetramethyl-1,3,2-dioxaborolan-2-yl)phenyl)-8-azabicyclo[3.2.1]octan-3-ol (89 mg, 0.21 mmol), Pd(PPh$_3$)$_4$ (12 mg, 0.01 mmol)
¹H NMR (400 MHz, CD$_3$OD) δ ppm 8.40 (s, 1 H), 8.22 (d, J = 8.3 Hz, 2 H), 7.85 (d, J = 8.5 Hz, 2 H), 7.77 (dd, J = 8.8, 1.3 Hz, 1 H), 7.62 (d, J = 8.8 Hz, 1 H), 7.45-7.51 (m, 2 H), 7.37-7.44 (m, 2 H), 7.25-7.32 (m, 1 H), 4.73 (br. s, 2 H), 4.19 (br. s, 1 H), 3.87 (dt, J = 11.8, 3.9 Hz, 2 H), 3.62 (s, 2 H), 3.55 (t, J = 9.7 Hz, 2 H), 2.74 (d, J = 8.5 Hz, 2 H), 2.65 (d, J = 15.8 Hz, 2 H), 2.16-2.33 (m, 6 H), 1.97-2.10 (m, 2 H), 1H merged with solvent peak

| Example/IUPAC name | Structure | MS calculated MS ESI [M + H]⁺ | Yield; Appearance Salt form |
|---|---|---|---|
| A493: 3-(4-((1R,3R,5S)-3-hydroxy-8-azabicyclo[3.2.1]octan-8-yl)phenyl)-N-((4-morpholinotetrahydro-2H-pyran-4-yl)methyl)-1H-indazole-5-carboxamide | | [C$_{31}$H$_{39}$N$_5$O$_4$ + H]⁺ 546.3 546.5 | 44 mg (37%); yellow solid; 2HCl salt |

SMs: 3-iodo-N-((4-morpholinotetrahydro-2H-pyran-4-yl)methyl)-1H-indazole-5-carboxamide (90 mg, 0.19 mmol), (1R,3R,5S)-8-(4-(4,4,5,5-tetramethyl-1,3,2-dioxaborolan-2-yl)phenyl)-8-aza bicyclo[3.2.1]octan-3-ol (63 mg, 0.19 mmol), Pd(PPh$_3$)$_4$ (16 mg, 0.014 mmol)
¹H NMR (400 MHz, CD$_3$OD) δ ppm 8.84 (s, 1 H), 8.35 (d, J = 8.3 Hz, 2 H), 8.07 (s, 1 H), 7.88 (d, J = 8.3 Hz, 2 H), 7.72 (d, J = 9.0 Hz, 1 H), 4.74 (br. s, 2 H), 4.10-4.22 (m, 5 H), 4.02-4.09 (m, 2 H), 3.96 (s, 2 H), 3.79-3.88 (m, 2 H), 3.64-3.74 (m, 2 H), 3.41-3.52 (m, 2 H), 2.74 (d, J = 8.5 Hz, 2 H), 2.58-2.69 (m, 2 H), 2.26 (m, 4 H), 2.08-2.18 (m, 2 H), 1.94-2.03 (m, 2 H), 1H merged with solvent peak

| Example/IUPAC name | Structure | MS calculated MS ESI [M + H]⁺ | Yield; Appearance Salt form |
|---|---|---|---|
| A494: N-((1-(morpholinomethyl)cyclopropyl)methyl)-3-(4-morpholinophenyl)-1H-indazole-5-carboxamide | | [C$_{27}$H$_{29}$N$_5$O$_2$S + H]⁺ 476.2 476.3 | 205 mg (68%), white solid; 2TFA salt |

SMs: (1-(morpholinomethyl)cyclopropyl)methanamine (101 mg, 0.6 mmol), 3-(4-morpholinophenyl)-1H-indazole-5-carboxylic acid (162 mg, 0.5 mmol)
¹H NMR (400 MHz, CD$_3$OD) δ ppm 8.68 (s, 1H), 8.03 (d, J = 8.8 Hz, 1H), 7.93 (d, J = 8.8 Hz, 2H), 7.65 (d, J = 8.8 Hz, 1H), 7.21 (d, J = 8.4 Hz, 2H), 4.15 (d, J = 12.8 Hz, 2H), 3.97 (t, J = 12.0 Hz, 2H), 3.90 (t, J = 4.4 Hz, 4H), 3.65 (d, J = 12.8 Hz, 2H), 3.45 (s, 2H), 3.34-3.23 (m, 4H), 3.18 (t, J = 11.6 Hz, 2H), 3.12 (s, 2H), 0.90-0.85 (m, 2H), 0.78-0.72 (m, 2H).

| Example/IUPAC name | Structure | MS calculated MS ESI [M + H]+ | Yield; Appearance Salt form |
|---|---|---|---|
| A495: 3-(4-((1R,3R,5S)-3-hydroxy-8-azabicyclo[3.2.1]octan-8-yl)phenyl)-N-((3-morpholinotetrahydro-2H-pyran-3-yl)methyl)-1H-indazole-5-carboxamide | | [$C_{31}H_{39}N_5O_4$ + H]+ 546.3 546.3 | 57 mg (46%), yellow solid; 2 × HCl salt |

SMs: 3-iodo-N-((3-morpholinotetrahydro-2H-pyran-3-yl)methyl)-1H-indazole-5-carbox-amide (94 mg, 0.2 mmol), (1R,3R,5S)-8-(4-(4,4,5,5-tetramethyl-1,3,2-dioxaborolan-2-yl)phenyl)-8-azabicyclo[3.2.1]octan-3-ol (73 mg, 0.22 mmol)
$^1$H NMR (400 MHz, CD$_3$OD) δ ppm 8.50 (d, J = 0.4 Hz, 1H), 7.87 (dd, J = 8.8 Hz, 1.2 Hz, 1H), 7.82 (d, J = 8.4 Hz, 2H), 7.58 (d, J = 8.8 Hz, 1H), 6.93 (d, J = 8.8 Hz, 2H), 4.23 (brs, 2H), 3.93 (t, J = 4.6 Hz, 1H), 3.75-3.58 (m, 8H), 3.56-3.48 (m, 2H), 2.75 (t, J = 4.4 Hz, 4H), 2.36 (dd, J = 7.2, 6.0 Hz, 2H), 2.25-2.17 (m, 2H), 2.07-1.98 (m, 2H), 1.86-1.75 (m, 1H), 1.75-1.60 (m, 5H).

| | | | |
|---|---|---|---|
| A496: rel-3-(4-(((1R,3S)-3-hydroxycyclohexyl)oxy)phenyl)-N-((1-morpholinocyclopentyl)methyl)-1H-indazole-5-carboxamide | | [$C_{30}H_{38}N_4O_4$ + H]+ 519.3 519.4 | 115 mg (56%), white solid; free base |

SMs: 3-iodo-N-((1-morpholinocyclopentyl)methyl)-1H-indazole-5-carboxamide TFA salt (227 mg, 0.4 mmol), rel-(1R,3S)-3-(4-(4,4,5,5-tetramethyl-1,3,2-dioxaborolan-2-yl)phenoxy)cyclohexanol (175 mg, 0.45 mmol)
$^1$H NMR (400 MHz, CD$_3$OD) δ ppm 8.48 (s, 1H), 7.88-7.84 (m, 3H), 7.58 (d, J = 8.8 Hz, 1H), 7.04 (d, J = 8.8 Hz, 2H), 4.34-4.26 (m, 1H), 3.70-3.60 (m, 5H), 3.49 (s, 2H), 2.66 (t, J = 4.2 Hz, 4H), 2.46-2.40 (m, 1H), 2.13-2.07 (m, 1H), 1.97-1.90 (m, 1H), 1.85-1.73 (m, 3H), 1.70-1.60 (m, 4H), 1.58-1.50 (m, 2H), 1.42-1.17 (m, 4H).

| | | | |
|---|---|---|---|
| A497: cis-3-(4-(((1R,3S)-3-hydroxycyclohexyl)oxy)phenyl)-N-((1-morpholinocyclohexyl)methyl)-1H-indazole-5-carboxamide | | [$C_{31}H_{40}N_4O_4$ + H]+ 533.3 533.4 | 76 mg (36%), white solid; free base |

SMs: 3-iodo-N-((1-morpholinocyclohexyl)methyl)-1H-indazole-5-carboxamide (187 mg, 0.4 mmol), cis-3-(4-(4,4,5,5-tetramethyl-1,3,2-dioxaborolan-2-yl)phenoxy)cyclohexanol (175 mg, 0.45 mmol)
$^1$H NMR (400 MHz, CD$_3$OD) δ ppm 8.49 (s, 1H), 7.90-7.85 (m, 3H), 7.59 (d, J = 8.8 Hz, 1H), 7.04 (d, J = 8.4 Hz, 2H), 4.35-4.25 (m, 1H), 3.70-3.60 (m, 5H), 3.45 (S, 2H), 2.68 (t, J = 4.2 Hz, 4), 2.46-2.40 (m, 1H), 2.13-2.07 (m, 1H), 1.98-1.92 (m, 1H), 1.85-1.78 (m, 1H), 1.75-1.57 (m, 4H), 1.45-1.16 (m, 10H).

| Example/IUPAC name | Structure | MS calculated MS ESI [M + H]+ | Yield; Appearance Salt form |
|---|---|---|---|
| A498: 3-(4-((1-methylpiperidin-4-yl)oxy)phenyl)-N-((1-(morpholinomethyl)cyclopropyl)methyl)-1H-indazole-5-carboxamide | 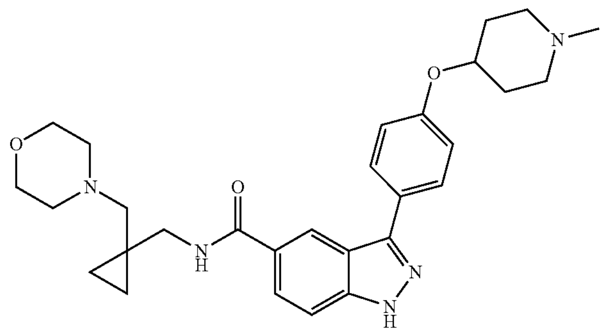 [SMILES: CN1CCC(Oc2ccc(-c3n[nH]c4ccc(C(=O)NCC5(CN6CCOCC6)CC5)cc34)cc2)CC1] | [C29H37N5O3 + H]+ 504.3 504.3 | 29 mg (14%), yellow solid; free base |

SMs: 3-iodo-N-((1-(morpholinomethyl)cyclopropyl)methyl)-1H-indazole-5-carboxamide (176 mg, 0.4 mmol), 1-methyl-4-(4-(4,4,5,5-tetramethyl-1,3,2-dioxaborolan-2-yl)phenoxy)piperidine (127 mg, 0.4 mmol)
$^1$H NMR (400 MHz, CD$_3$OD) δ ppm 8.51 (s, 1H), 7.93-7.87 (m, 3H), 7.62 (d, J = 8.8 Hz, 1H), 7.10 (d, J = 8.8 Hz, 2H), 4.53-4.45 (m, 1H), 3.59 (t, J = 4.6 Hz, 4H), 3.48 (s, 2H), 2.80-2.69 (m, 2H), 2.55-2.28 (m, 11H), 2.10-2.00 (m, 2H), 1.90-1.80 (m, 2H), 0.64 (t, J = 5.2 Hz, 2H), 0.39 (t, J = 5.2 Hz, 2H).

| A499: 3-(4-(3-morpholinoazetidin-1-yl)phenyl)-N-((4-phenyltetrahydro-2H-pyran-4-yl)methyl)-1H-indazole-5-carboxamide | | [C33H37N5O3 + H]+ 552.29 552.5 | 73 mg (46%); Yellow solid; TFA salt |

Starting materials: 3-iodo-N-((4-phenyltetrahydro-2H-pyran-4-yl)methyl)-1H-indazole-5-carboxamide (110 mg, 0.24 mmol), 4-(1-(4-(4,4,5,5-tetramethyl-1,3,2-dioxaborolan-2-yl)phenyl)azetidin-3-yl)morpholine (100 mg, 0.24 mmol)

| A500: N-((1-morpholinocyclohexyl)methyl)-3-(4-(4-(oxetan-3-yl)piperazin-1-yl)phenyl)-1H-indazole-5-carboxamide | | [C32H42N6O3 + H]+ 559.3 559.3 | 65 mg (55%); white solid; free base |

SMs: 3-iodo-N-((1-morpholinocyclohexyl)methyl)-1H-indazole-5-carboxamide (100 mg, 0.21 mmol), 1-(oxetan-3-yl)-4-(4-(4,4,5,5-tetramethyl-1,3,2-dioxaborolan-2-yl)phenyl)piperazine (74 mg, 0.21 mmol)
$^1$H NMR (400 MHz, CD$_3$OD) δ ppm 8.52 (s, 1 H), 7.81-7.91 (m, 3 H), 7.60 (d, J = 8.8 Hz, 1 H), 7.07 (d, J = 8.8 Hz, 2 H), 4.71 (t, J = 6.5 Hz, 2 H), 4.62 (t, J = 6.1 Hz, 2 H), 3.67 (br. s., 4 H), 3.52 (s, 1 H), 3.48 (s, 2 H), 3.22-3.29 (m, 4 H), 2.71 (br. s., 4 H), 2.43-2.52 (m, 4 H), 1.70-1.81 (m, 2 H), 1.60-1.70 (m, 2 H), 1.33-1.48 (m, 6 H)

| Example/IUPAC name | Structure | MS calculated MS ESI [M + H]+ | Yield; Appearance Salt form |
|---|---|---|---|
| A501: 3-(4-((1R,5S)-3-oxa-8-azabicyclo[3.2.1]octan-8-yl)phenyl)-N-((1-morpholinocyclohexyl)methyl)-1H-indazole-5-carboxamide | 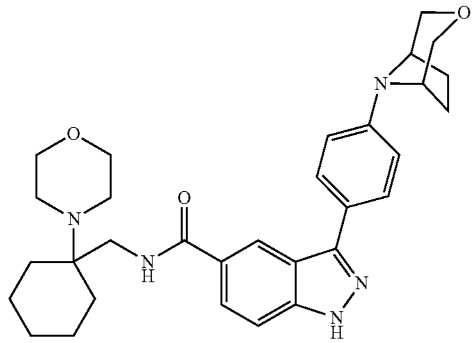 [SMILES: O=C(NCC1(N2CCOCC2)CCCCC1)c1ccc2[nH]nc(-c3ccc(N4C5CCC4COC5)cc3)c2c1] | [C₃₁H₃₉N₅O₃ + H]+ 530.3 530.5 | 70 mg (44%); yellow solid; 2 × TFA salt |

SMs: 3-iodo-N-((1-morpholinocyclohexyl)methyl)-1H-indazole-5-carboxamide (100 mg, 0.21 mmol), 8-(4-(4,4,5,5-tetramethyl-1,3,2-dioxaborolan-2-yl)phenyl)-3-oxa-8-azabicyclo[3.2.1]octane (67 mg, 0.21 mmol)
$^1$H NMR (400 MHz, CD$_3$OD) δ ppm 8.67 (s, 1 H), 7.99 (dd, J = 8.9, 1.6 Hz, 1 H), 7.86 (d, J = 8.8 Hz, 1 H), 7.63 (dd, J = 8.9, 0.6 Hz, 1 H), 7.03 (d, J = 8.5 Hz, 2 H), 4.21 (br. s., 2 H), 4.15 (d, J = 12.5 Hz, 2 H), 3.82-3.95 (m, 6 H), 3.65 (d, J = 11.8 Hz, 2 H), 3.54 (d, J = 10.8 Hz, 2 H), 3.30-3.33 (m, 2 H), 2.00-2.13 (m, 4 H), 1.92-1.99 (m, 2 H), 1.84-1.92 (m, 2 H), 1.70-1.83 (m, 3 H), 1.55-1.69 (m, 2 H), 1.23-1.36 (m, 1 H)

| Example/IUPAC name | Structure | MS calculated MS ESI [M + H]+ | Yield; Appearance Salt form |
|---|---|---|---|
| A502: 3-(4-((1R,5S)-3-oxa-8-azabicyclo[3.2.1]octan-8-yl)phenyl)-N-((4-phenyltetrahydro-2H-pyran-4-yl)methyl)-1H-indazole-5-carboxamide | | [C₃₂H₃₄N₄O₃ + H]+ 523.3 523.8 | 55 mg (39%); yellow solid; TFA salt |

SMs: 3-iodo-N-((4-phenyltetrahydro-2H-pyran-4-yl)methyl)-1H-indazole-5-carboxamide (100 mg, 0.22 mmol), 8-(4-(4,4,5,5-tetramethyl-1,3,2-dioxaborolan-2-yl)phenyl)-3-oxa-8-azabicyclo[3.2.1]octane (69 mg, 0.22 mmol)
$^1$H NMR (400 MHz, CD$_3$OD) δ ppm 8.33 (s, 1 H), 8.03 (t, J = 6.1 Hz, 1 H), 7.78-7.91 (m, 2 H), 7.74 (dd, J = 8.9, 1.4 Hz, 1 H), 7.54 (d, J = 8.5 Hz, 1 H), 7.35-7.47 (m, 4 H), 7.26 (t, J = 7.3 Hz, 1 H), 7.12 (br. s., 1 H), 4.27 (br. s., 2 H), 3.95 (d, J = 10.5 Hz, 2 H), 3.80-3.88 (m, 2 H), 3.49-3.64 (m, 4 H), 2.20 (d, J = 14.3 Hz, 2 H), 1.95-2.16 (m, 6 H)

| Example/IUPAC name | Structure | MS calculated MS ESI [M + H]+ | Yield; Appearance Salt form |
|---|---|---|---|
| A503: 3-(4-((1R,5S,7S)-7-hydroxy-3-oxa-9-azabicyclo[3.3.1]nonan-9-yl)phenyl)-N-((4-phenyltetrahydro-2H-pyran-4-yl)methyl)-1H-indazole-5-carboxamide | | [C₃₃H₃₆N₄O₄ + H]+ 553.3 553.5 | 23 mg (23%); yellow solid; HCl salt |

SMs: 3-iodo-N-((4-phenyltetrahydro-2H-pyran-4-yl)methyl)-1H-indazole-5-carboxamide (80 mg, 0.17 mmol), (1R,5S,7R)-9-(4-(4,4,5,5-tetramethyl-1,3,2-dioxaborolan-2-yl)phenyl)-3-oxabicyclo[3.3.1]nonan-7-ol (60 mg, 0.17 mmol)
$^1$H NMR (400 MHz, CD$_3$OD) δ ppm 8.33 (s, 1 H), 7.83 (d, J = 8.0 Hz, 2 H), 7.75 (d, J = 8.8 Hz, 1 H), 7.54 (d, J = 8.5 Hz, 1 H), 7.45-7.49 (m, 2 H), 7.42 (t, J = 7.8 Hz, 2 H), 7.28 (t, J = 7.3 Hz, 1 H), 7.07 (d, J = 8.3 Hz, 2 H), 4.10 (br. s., 2 H), 4.00 (s, 4 H), 3.83-3.93 (m, 3 H), 3.51-3.64 (m, 4 H), 2.31-2.41 (m, 2 H), 2.18-2.27 (m, 2 H), 1.97-2.07 (m, 2 H), 1.79 (d, J = 14.6 Hz, 2 H)

| Example/IUPAC name | Structure | MS calculated MS ESI [M + H]+ | Yield; Appearance Salt form |
|---|---|---|---|
| A504: 3-(4-((1-formylpiperidin-4-yl)oxy)phenyl)-N-((1-morpholinocyclohexyl)methyl)-1H-indazole-5-carboxamide | 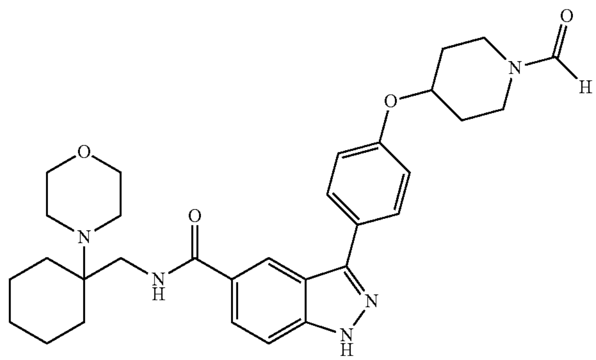 [SMILES: O=CN1CCC(Oc2ccc(-c3n[nH]c4ccc(C(=O)NCC5(N6CCOCC6)CCCCC5)cc34)cc2)CC1] | [C$_{31}$H$_{39}$N$_5$O$_4$ + H]+ 546.4 546.3 | 35 mg (50%); yellow solid; free base |

SMs: 3-iodo-N-((1-morpholinocyclohexyl)methyl)-1H-indazole-5-carboxamide (60 mg, 0.13 mmol), 4-(4-(4,4,5,5-tetramethyl-1,3,2-dioxaborolan-2-yl)phenoxy)piperidine-1-carbaldehyde (47 mg, 0.14 mmol)
$^1$H NMR (400 MHz, CD$_3$OD) δ ppm 8.51 (s, 1 H), 8.03 (1 H, s), 7.85-7.94 (m, 3 H), 7.62 (d,, J = 8.8 Hz, 1H), 7.11 (d, J = 8.8 Hz, 2H), 4.71 (dt, J = 6.9, 3.6 Hz, 1H), 3.73 (dd, J = 7.9, 4.1 Hz, 1H), 3.62-3.70 (m, 5H), 3.45-3.53 (m, 3H), 3.37-3.45 (m, 1H), 2.64-2.76 (m, 4H), 1.90-2.07 (m, 2H), 1.57-1.86 (m, 6H), 1.32-1.52 (m, 6H)

| Example/IUPAC name | Structure | MS calculated MS ESI [M + H]+ | Yield; Appearance Salt form |
|---|---|---|---|
| A505: N-((1-morpholinocyclohexyl)methyl)-3-(4-(piperazin-1-yl)phenyl)-1H-indazole-5-carboxamide | | [C$_{29}$H$_{38}$N$_6$O$_3$ + H]+ 503.3 503.3 | 3 mg (5%); white solid; free base |

SMs: 3-iodo-N-((1-morpholinocyclohexyl)methyl)-1H-indazole-5-carboxamide (60 mg, 0.13 mmol), 1-(4-(4,4,5,5-tetramethyl-1,3,2-dioxaborolan-2-yl)phenyl)piperazine (41 mg, 0.14 mmol)
$^1$H NMR (400 MHz, CD$_3$OD) δ ppm 8.52 (s, 1H), 7.82-7.92 (m, 3H), 7.61 (d, J = 8.8 Hz, 1H), 7.10 (d, J = 8.8 Hz, 2H), 3.69 (br. s., 4H), 3.49 (s, 2H), 3.19-3.27 (m, 4H), 2.95-3.06 (m, 4H), 2.73 (d, J = 3.8 Hz,4H), 1.59-1.82 (m, 4H), 1.43 (m, 6H)

| Example/IUPAC name | Structure | MS calculated MS ESI [M + H]+ | Yield; Appearance Salt form |
|---|---|---|---|
| A506: N-((1-morpholinocyclohexyl)methyl)-3-(4-((1-(oxetan-3-yl)piperidin-4-yl)oxy)phenyl)-1H-indazole-5-carboxamide | | [C$_{33}$H$_{43}$N$_5$O$_4$ + H]+ 574.3 574.3 | 22 mg (30%); white solid; free base |

SMs: 3-iodo-N-((1-morpholinocyclohexyl)methyl)-1H-indazole-5-carboxamide (0.059 g, 0.13 mmol), 1-(oxetan-3-yl)-4-(4-(4,4,5,5-tetramethyl-1,3,2-dioxaborolan-2-yl)phenoxy)piperidine(0.050 g, 0.14 mmol)
$^1$H NMR (400 MHz, CD$_3$OD) δ ppm 8.51 (s, 1 H), 7.86-7.92 (m, 3 H), 7.61 (d, J = 8.8 Hz, 1 H), 7.07 (d, J = 8.8 Hz, 2 H), 4.68 (t, J = 1.0 Hz, 2 H), 4.59 (t, J = 1.0 Hz, 2 H), 4.47 (br. s., 1 H), 3.67 (br. s., 4 H), 3.44-3.54 (m, 3 H), 2.71 (d, J = 4.0 Hz, 4 H), 2.58 (br. s., 2 H), 2.21 (br. s., 2 H), 2.04 (dd, J = 12.8, 3.5 Hz, 2 H), 1.59-1.87 (m, 6 H), 1.31-1.49 (m, 6 H)

| Example/IUPAC name | Structure | MS calculated MS ESI [M + H]+ | Yield; Appearance Salt form |
|---|---|---|---|
| A507: N-((1-morpholinocyclohexyl)methyl)-3-(4-(((1R,3R,5S)-8-(oxetan-3-yl)-8-azabicyclo[3.2.1]octan-3-yl)oxy)phenyl)-1H-indazole-5-carboxamide | 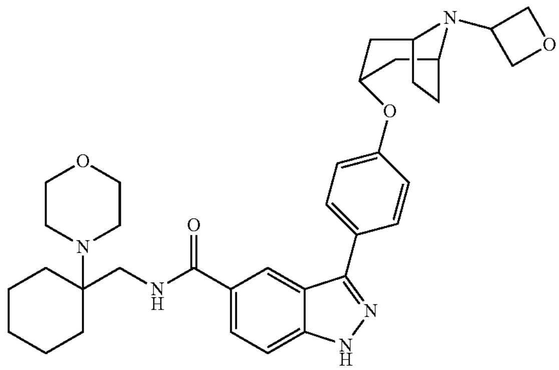 [SMILES: O=C(NCC1(N2CCOCC2)CCCCC1)c1ccc2[nH]nc(-c3ccc(OC4CC5CCC(C4)N5C4COC4)cc3)c2c1] | [$C_{35}H_{45}N_5O_4$ + H]+ 600.4 600.3 | 29 mg (41%); white solid; free base |

SMs: 3-iodo-N-((1-morpholinocyclohexyl)methyl)-1H-indazole-5-carboxamide (0.050 g, 0.12 mmol), (1R,3R,5S)-8-(oxetan-3-yl)-3-(4-(4,4,5,5-tetramethyl-1,3,2-dioxaborolan-2-yl)phenoxy)-8-azabicyclo[3.2.1]octane (0.050 g, 0.13 mmol)
$^1$H NMR (400 MHz, CD$_3$OD) δ ppm 8.51 (s, 1 H), 7.89 (d, J = 8.8 Hz, 3 H), 7.61 (d, J = 8.8 Hz, 1 H), 6.96 (d, J = 8.8 Hz, 2 H), 4.69 (t, J = 6.4 Hz, 2 H), 4.61 (t, J = 4.6 Hz, 1 H), 4.50 (t, J = 5.8 Hz, 2 H), 3.74 (t, J = 6.0 Hz, 1 H), 3.66 (br. s., 4 H), 3.47 (s, 2 H), 3.06 (br. s., 2 H), 2.70 (br. s., 4 H), 2.05-2.18 (m, 4 H), 1.84-2.00 (m, 4 H), 1.56-1.78 (m, 4 H), 1.32-1.50 (m, 6 H)

| Example/IUPAC name | Structure | MS calculated MS ESI [M + H]+ | Yield; Appearance Salt form |
|---|---|---|---|
| A508: 3-(4-((1R,3R,5S)-3-hydroxy-8-azabicyclo[3.2.1]octan-8-yl)phenyl)-N-((1-morpholinocyclohexyl)methyl)-1H-indazole-5-carboxamide | 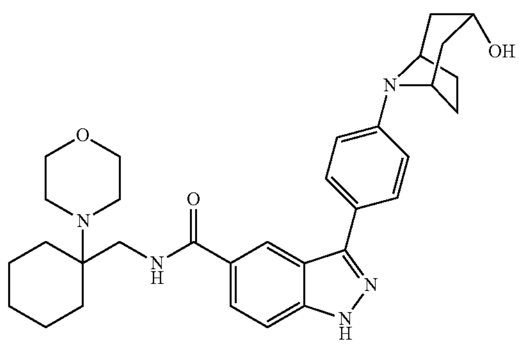 [SMILES: O=C(NCC1(N2CCOCC2)CCCCC1)c1ccc2[nH]nc(-c3ccc(N4C5CCC4CC(O)C5)cc3)c2c1] | [$C_{32}H_{41}N_5O_3$ + H]+ 544.3 544.3 | 48 mg (35%); yellow solid; free base |

SMs: 3-iodo-N-((1-morpholinocyclohexyl)methyl)-1H-indazole-5-carboxamide (118 mg, 0.25 mmol), (1R,3R,5S)-8-(4-(4,4,5,5-tetramethyl-1,3,2-dioxaborolan-2-yl)phenyl)-8-azabicyclo[3.2.1]octan-3-ol (100 mg, 0.3 mmol)
$^1$H NMR (400 MHz, CD$_3$OD) δ ppm 8.51 (d, J = 0.8 Hz, 1 H), 7.87 (dd, J = 8.8, 1.5 Hz, 1 H), 7.81 (d, J = 8.8 Hz, 2 H), 7.58 (d, J = 8.8 Hz, 1 H), 6.90 (d, J = 8.8 Hz, 2 H), 4.20 (br. s., 2 H), 3.91 (t, J = 4.4 Hz, 1 H), 3.60-3.70 (m, 4 H), 3.46 (s, 2 H), 2.63-2.73 (m, 4 H), 2.30-2.38 (m, 2 H), 2.19 (dt, J = 14.6, 3.9 Hz, 2 H), 1.95-2.07 (m, 2 H), 1.70 (d, J = 13.1 Hz, 2 H), 1.61 (d, J = 14.3 Hz, 4 H), 1.31-1.48 (m, 6 H)

| Example/IUPAC name | Structure | MS calculated MS ESI [M + H]+ | Yield; Appearance Salt form |
|---|---|---|---|
| A509: N-((1-(morpholinomethyl)cyclohexyl)methyl)-3-(4-morpholinophenyl)-1H-indazole-5-carboxamide | 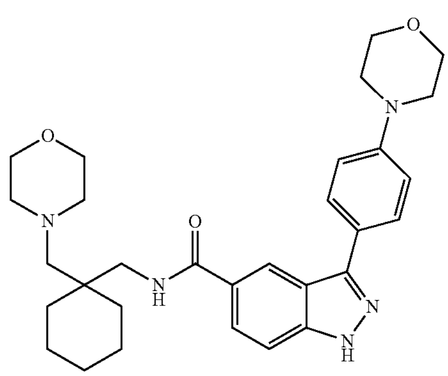 [SMILES: O=C(NCC1(CN2CCOCC2)CCCCC1)c1ccc2[nH]nc(-c3ccc(N4CCOCC4)cc3)c2c1] | [$C_{30}H_{39}N_5O_3$ + H]+ 518.3 518.5 | 114 mg (63%); white solid; free base |

SMs: 3-iodo-N-((1-(morpholinomethyl)cyclohexyl)methyl)-1H-indazole-5-carboxamide (168 mg, 0.35 mmol), (4-morpholinophenyl)boronic acid (80 mg, 0.39 mmol)
$^1$H NMR (400 MHz, CD$_3$OD) δ ppm 8.48 (s, 1 H), 7.86 (d, J = 8.5 Hz, 3 H), 7.63-7.68 (m, 1 H), 7.15 (d, J = 8.8 Hz, 2 H), 3.84-3.91 (m, 4 H), 3.48-3.55 (m, 6 H), 3.23-3.28 (m, 4 H), 2.57 (br. s., 4 H), 2.43 (s, 2 H), 1.55 (br. s., 7 H), 1.34-1.47 (m, 3 H)

| Example/IUPAC name | Structure | MS calculated MS ESI [M + H]+ | Yield; Appearance Salt form |
|---|---|---|---|
| A510: 3-(4-((1R,5S)-3-oxa-8-azabicyclo[3.2.1]octan-8-yl)phenyl)-N-((1-(morpholinomethyl)cyclohexyl)methyl)-1H-indazole-5-carboxamide | 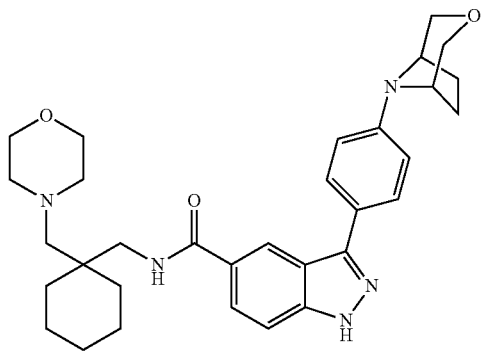 [SMILES: O=C(NCC1(CN2CCOCC2)CCCCC1)c1ccc2[nH]nc(-c3ccc(N4C5CCC4COC5)cc3)c2c1] | $[C_{32}H_{41}N_5O_3 + H]^+$ 544.3 544.5 | 62 mg (51%); Light yellow solid; free base |

SMs: 3-iodo-N-((1-(morpholinomethyl)cyclohexyl)methyl)-1H-indazole-5-carboxamide (107 mg, 0.22 mmol), (1R,5S)-8-(4-(4,4,5,5-tetramethyl-1,3,2-dioxaborolan-2-yl)phenyl)-3-oxa-8-azabicyclo[3.2.1]octane (80 mg, 0.25 mmol)

$^1$H NMR (400 MHz, CD$_3$OD) δ ppm 8.49 (s, 1 H), 7.88 (dd, J = 8.7, 1.4 Hz, 1H), 7.81 (d, J = 8.8 Hz, 2H), 7.64 (d, J = 8.8 Hz, 1H), 7.01 (d, J = 8.8 Hz, 2H), 4.19 (br, 2 H), 3.90 (d, J = 10.8 Hz, 2H), 3.45-3.57 (m, 8H), 2.53 (br, 4H), 2.39 (s, 2H), 1.95-2.12 (m, 4H), 1.44-1.58 (m, 7H), 1.37 (m, 3H)

| Example/IUPAC name | Structure | MS calculated MS ESI [M + H]+ | Yield; Appearance Salt form |
|---|---|---|---|
| A511: (S)-N-(1-(2-chlorophenyl)-3-methylbutyl)-3-(4-((1-(oxetan-3-yl)piperidin-4-yl)oxy)phenyl)-1H-indazole-5-carboxamide | 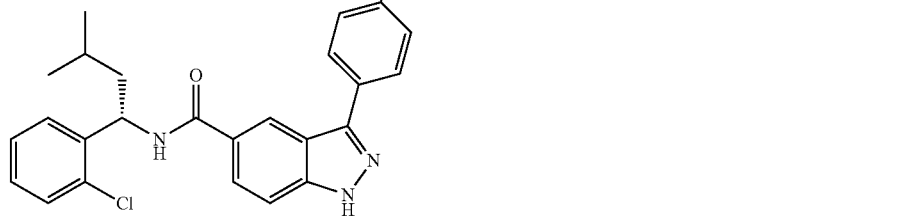 | $[C_{33}H_{37}ClN_4O_3 + H]^+$ 573.3 573.5 | 77 mg (63%); white solid; free base |

SMs: (S)-N-(1-(2-chlorophenyl)-3-methylbutyl)-3-(4-((1-(oxetan-3-yl)piperidin-4-yl)oxy)phenyl)-1H-indazole-5-carboxamide (0.099 g, 0.21 mmol), 1-(oxetan-3-yl)-4-(4-(4,4,5,5-tetramethyl-1,3,2-dioxaborolan-2-yl)phenoxy)piperidine (0.080 g, 0.22 mmol)

$^1$H NMR (400 MHz, CD$_3$OD) δ ppm 8.62 (s, 1 H), 7.95 (d, J = 9.5 Hz, 1 H), 7.84 (d, J = 8.5 Hz, 2 H), 7.56 (d, J = 8.8 Hz, 1 H), 7.45-7.52 (m, 1 H), 7.31 (d, J = 7.8 Hz, 1 H), 7.17-7.24 (m, 1 H), 7.11-7.17 (m, 1 H), 6.96 (d, J = 8.8 Hz, 2 H), 5.70 (dd, J = 10.0, 4.5 Hz, 1 H), 4.59-4.66 (m, 2 H), 4.49-4.58 (m, 2 H), 4.33 (d, J = 3.0 Hz, 1 H), 3.41 (quin, J = 6.5 Hz, 1 H), 2.49 (br. s., 2 H), 2.05-2.18 (m, 2 H), 1.93 (br. s., 2 H), 1.68-1.87 (m, 4 H), 1.51-1.64 (m, 1 H), 0.99 (d, J = 6.5 Hz, 3 H), 0.93 (d, J = 6.3 Hz, 3 H)

| Example/IUPAC name | Structure | MS calculated MS ESI [M + H]+ | Yield; Appearance Salt form |
|---|---|---|---|
| A512: N-((R-cyclopropyl(pyridin-2-yl)methyl)-3-(4-((1R,3S,5S)-3-hydroxy-8-azabicyclo[3.2.1]octan-8-yl)phenyl)-1H-indazole-5-carboxamide | 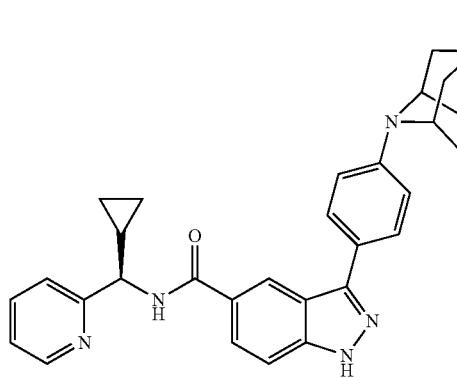 | [C$_{30}$H$_{31}$N$_5$O$_2$ + H]+ 494.4 494.5 | 58 mg (53%); yellow solid; free base |

SMs: (R)-N-(cyclopropyl(pyridin-2-yl)methyl)-3-iodo-1H-indazole-5-carboxamide (0.092 g, 0.22 mmol), (1R,3S,5S)-8-(4-(4,4,5,5-tetramethyl-1,3,2-dioxaborolan-2-yl)phenyl)-8-azabicyclo[3.2.1]octan-3-ol (0.080 g, 0.24 mmol)

$^1$H NMR (400 MHz, CD$_3$OD) δ ppm 8.68 (d, J = 0.8 Hz, 1 H), 8.45-8.53 (m, 1 H), 7.95 (dd, J = 8.9, 1.4 Hz, 1 H), 7.84 (d, J = 8.5 Hz, 2 H), 7.76 (td, J = 7.8, 1.8 Hz, 1 H), 7.56 (d, J = 8.8 Hz, 1 H), 7.50 (d, J = 7.8 Hz, 1 H), 7.26 (ddd, J = 7.5, 5.0, 1.0 Hz, 1 H), 6.92 (d, J = 8.8 Hz, 2 H), 4.51 (d, J = 9.3 Hz, 1 H), 4.29 (br. s., 2 H), 4.04-4.19 (m, 1 H), 1.97-2.07 (m, 2 H), 1.65-1.84 (m, 6 H), 1.28-1.48 (m, 1 H), 0.62-0.70 (m, 1 H), 0.46-0.59 (m, 3 H)

| Example/IUPAC name | Structure | MS calculated MS ESI [M + H]+ | Yield; Appearance Salt form |
|---|---|---|---|
| A513: N-((S)-cyclopentyl)(pyridin-2-yl)methyl)-3-(4-((1R,3R,5S)-3-hydroxy-8-azabicyclo[3.2.1]octan-8-yl)phenyl)-1H-indazole-5-carboxamide | 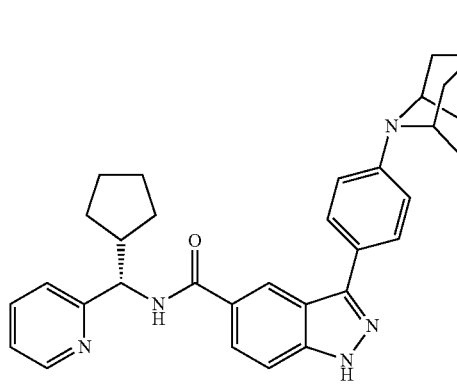 | [C$_{32}$H$_{35}$N$_5$O$_2$ + H]+ 522.3 522.5 | 66 mg (57%); yellow solid; free base |

SMs: (S)-N-(cyclopentyl(pyridin-2-yl)methyl)-3-iodo-1H-indazole-5-carboxamide (0.099 g, 0.22 mmol), (1R,3S,5S)-8-(4-(4,4,5,5-tetramethyl-1,3,2-dioxaborolan-2-yl)phenyl)-8-azabicyclo[3.2.1]octan-3-ol (0.080 g, 0.24 mmol)

$^1$H NMR (400 MHz, CD$_3$OD) δ ppm 8.59 (s, 1 H), 8.53 (d, J = 4.0 Hz, 1 H), 7.91 (d, J = 8.8 Hz, 1 H), 7.86 (d, J = 8.8 Hz, 2 H), 7.80 (m, J = 1.8 Hz, 1 H), 7.58 (d, J = 8.8 Hz, 1 H), 7.51 (d, J = 7.8 Hz, 1 H), 7.27-7.35 (m, 1 H), 7.01 (d, J = 8.8 Hz, 2 H), 5.02 (d, J = 10.3 Hz, 1 H), 4.38 (br. s., 1 H), 4.10-4.23 (m, 1 H), 2.47-2.64 (m, 1 H), 2.09 (d, J = 5.5 Hz, 2 H), 1.93-2.04 (m, 1 H), 1.48-1.89 (m, 12 H), 1.24-1.43 (m, 2 H)

| Example/IUPAC name | Structure | MS calculated MS ESI [M + H]+ | Yield; Appearance Salt form |
|---|---|---|---|
| A514: N-((S)-1-(2-chlorophenyl)-2-methylpropyl)-3-(4-((1R,3R,5S)-3-hydroxy-8-azabicyclo[3.2.1]octan-8-yl)phenyl)-1H-indazole-5-carboxamide | 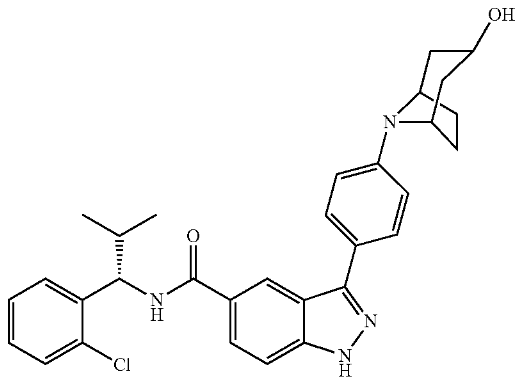 [SMILES: CC(C)[C@H](NC(=O)c1ccc2[nH]nc(-c3ccc(N4C5CCC4CC(O)C5)cc3)c2c1)c1ccccc1Cl] | [C$_{31}$H$_{33}$ClN$_4$O$_2$ + H]+ 529.2 529.6 | 70 mg (60%); yellow solid; free base |

SMs: (S)-N-(1-(2-chlorophenyl)-2-methylpropyl)-3-iodo-1H-indazole-5-carboxamide (0.100 g, 0.22 mmol), (1R,3S,5S)-8-(4-(4,4,5,5-tetramethyl-1,3,2-dioxaborolan-2-yl)phenyl)-8-azabicyclo[3.2.1]octan-3-ol (0.080 g, 0.24 mmol)
$^1$H NMR (400 MHz, CD$_3$OD) δ ppm 8.55 (s, 1 H), 7.79-7.91 (m, 3 H), 7.56 (d, J = 8.3 Hz, 2 H), 7.39 (dd, J = 7.8, 1.3 Hz, 1 H), 7.27-7.34 (m, 1 H), 7.22 (m, J = 7.8, 1.8 Hz, 1 H), 7.00 (d, J = 9.0 Hz, 2 H), 5.32-5.44 (m, 1 H), 4.38 (br. s., 2 H), 4.08-4.23 (m, 1 H), 2.21-2.34 (m, 1 H), 2.04-2.13 (m, 2 H), 1.70-1.89 (m, 6 H), 1.17 (d, J = 6.8 Hz, 3 H), 0.87 (d, J = 6.8 Hz, 3 H)

| | | | |
|---|---|---|---|
| A515: 3-(4-morpholinophenyl)-N-((3-morpholinotetrahydro-2H-pyran-3-yl)methyl)-1H-indazole-5-carboxamide | | [C$_{28}$H$_{35}$N$_5$O$_4$ + H]+ 506.3 506.4 | 96 mg (86%); yellow solid; free base |

SMs: 3-iodo-N-((3-morpholinotetrahydro-2H-pyran-3-yl)methyl)-1H-indazole-5-carboxamide (0.103 g, 0.22 mmol), (4-morpholinophenyl)boronic acid (0.050 g, 0.24 mmol)
$^1$H NMR (400 MHz, CD$_3$OD) δ ppm 8.49 (s, 1 H), 7.81-7.91 (m, 3 H), 7.60 (d, J = 8.8 Hz, 1 H), 7.08 (td, J = 4.5, 2.6 Hz, 2 H), 3.80-3.87 (m, 4 H), 3.57-3.77 (m, 9 H), 3.52 (dd, J = 13.7, 2.6 Hz, 2 H), 3.14-3.23 (m, 4 H), 2.76 (d, J = 3.0 Hz, 4 H), 1.76-1.88 (m, 1 H), 1.71 (br. s., 2 H)

| | | | |
|---|---|---|---|
| A516: 3-(4-((1R,3S,5S)-3-hydroxy-8-azabicyclo[3.2.1]octan-8-yl)phenyl)-N-((3-morpholinotetrahydro-2H-pyran-3-yl)methyl)-1H-indazole-5-carboxamide | | [C$_{31}$H$_{39}$N$_5$O$_4$ + H]+ 546.3 546.3 | 102 mg (84%); White solid; free base |

SMs: 3-iodo-N-((3-morpholinotetrahydro-2H-pyran-3-yl)methyl)-1H-indazole-5-carboxamide (0.121 g, 0.22 mmol), (1R,3S,5S)-8-(4-(4,4,5,5-tetramethyl-1,3,2-dioxaborolan-2-yl)phenyl)-8-azabicyclo[3.2.1]octan-3-ol (0.080 g, 0.24 mmol)
$^1$H NMR (400 MHz, CD$_3$OD) δ ppm 8.51 (d, J = 0.8 Hz, 1 H), 7.82-7.91 (m, 3 H), 7.60 (d, J = 8.5 Hz, 1 H), 7.00 (dd, J = 8.8, 2.0 Hz, 2 H), 4.37 (br. s., 2 H), 4.07-4.23 (m, 1 H), 3.59-3.78 (m, 8 H), 3.48-3.58 (m, 2 H), 2.78 (br. s., 4 H), 2.07 (br. s., 2 H), 1.66-1.91 (m, 10 H)

| Example/IUPAC name | Structure | MS calculated MS ESI [M + H]+ | Yield; Appearance Salt form |
|---|---|---|---|
| A517: 3-(4-((1R,5S)-3-oxa-8-azabicyclo[3.2.1]octan-8-yl)phenyl)-N-((3-morpholinotetrahydro-2H-pyran-3-yl)methyl)-1H-indazole-5-carboxamide | 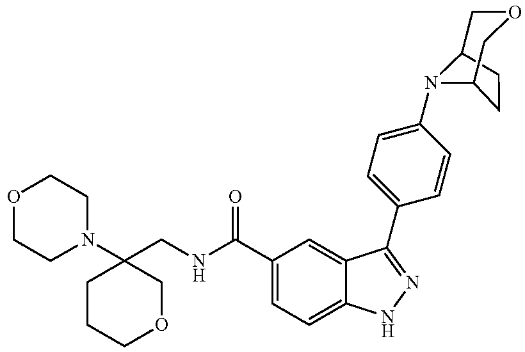 [SMILES: O=C(NCC1(N2CCOCC2)CCCOC1)c1ccc2[nH]nc(-c3ccc(N4C5CCC4COC5)cc3)c2c1] | [C30H37N5O4 + H]+ 532.3 532.4 | 62 mg (67%); yellow solid; free base |

SMs: 3-iodo-N-((3-morpholinotetrahydro-2H-pyran-3-yl)methyl)-1H-indazole-5-carboxamide (0.080 g, 0.173 mmol), (1R,5S)-8-(4-(4,4,5,5-tetramethyl-1,3,2-dioxaborolan-2-yl)phenyl)-3-oxa-8-azabicyclo[3.2.1]octane (0.060 g, 0.19 mmol)
$^1$H NMR (400 MHz, CD$_3$OD) δ ppm 8.51 (s, 1 H), 7.79-7.92 (m, 3 H), 7.60 (d, J = 8.8 Hz, 1 H), 6.99 (d, J = 8.8 Hz, 2 H), 4.17 (br. s., 2 H), 3.89 (d, J = 10.8 Hz, 2 H), 3.58-3.77 (m, 8 H), 3.45-3.57 (m, 4 H), 2.76 (br. s.,4 H), 1.97-2.11 (m, 4 H), 1.82 (d, J = 9.3 Hz, 1 H), 1.71 (br. s., 3 H)

| A518: N-((S)-1-(2-fluorophenyl)-3-methylbutyl)-3-(4-((1R,3S,5S)-3-hydroxy-8-azabicyclo[3.2.1]octan-8-yl)phenyl)-1H-indazole-5-carboxamide | | [C32H35FN4O2 + H]+ 527.28 527.5 | 31 mg (25%); Yellow solid; HCl salt |

SMs: (S)-N-(1-(2-fluorophenyl)-3-methylbutyl)-3-iodo-1H-indazole-5-carboxamide (100 mg, 0.22 mmol), (1R,3R,5S)-8-(4-(4,4,5,5-tetramethyl-1,3,2-dioxaborolan-2-yl)phenyl)-8-azabicyclo [3.2.1]octan-3-ol (73 mg, 0.22 mmol), Pd(PPh$_3$)$_4$ (13 mg, 0.011 mmol)
$^1$H NMR (400 MHz, CD$_3$OD) δ ppm 8.61 (s, 1H), 8.25 (br. s, 2H), 7.98 (d, J = 8.8 Hz, 1H), 7.83 (br. s, 2 H), 7.67 (d, J = 8.4 Hz, 1 H), 7.46-7.49 (m, 1H), 7.24-7.29 (m, 1 H), 7.14-7.17 (m, 1 H), 7.06-7.11 (m, 1 H), 5.57-5.59 (m, 1 H), 4.71 (br. s, 2 H), 4.16 (s, 1 H), 2.71-2.73 (br. m, 2 H), 2.58-2.62 (br. m, 2 H), 2.23-2.26 (br. m, 4 H), 1.92-1.96 (m, 1 H), 1.70 (br. m, 2 H), 1.02 (d, J = 5.6 Hz, 6 H)

| A519: 3-(4-((1R,5S)-3-oxa-8-azabicyclo[3.2.1]octan-8-yl)phenyl)-N-((S)-1-(2-fluorophenyl)-3-methylbutyl)-1H-indazole-5-carboxamide | | [C31H33FN4O2 + H]+ 513.26 513.5 | 43 mg (35%); yellow solid; HCl salt |

SMs: (S)-N-(1-(2-fluorophenyl)-3-methylbutyl)-3-iodo-1H-indazole-5-carboxamide (100 mg, 0.22 mmol), (1R,5S)-8-(4-(4,4,5,5-tetramethyl-1,3,2-dioxaborolan-2-yl)phenyl)-3-oxa-8-azabicyclo [3.2.1]octane (69.6 mg, 0.22 mmol), Pd(PPh$_3$)$_4$ (13 mg, 0.011 mmol)
$^1$H NMR (400 MHz, CD$_3$OD) δ ppm 8.61 (s, 1 H), 8.20 (br. s, 2 H), 7.98 (d, J = 8.4 Hz, 1 H), 7.64-7.71 (m, 3 H), 7.45-7.49 (m, 1 H), 7.24-7.29 (m, 1 H), 7.06-7.17 (m, 2 H), 5.57-5.59 (m, 1 H), 4.67 (br. s, 2 H), 4.16-4.17 (br. m, 2 H), 3.91-3.92 (br. s, 2 H), 2.32-2.33 (m, 2 H), 2.19 (br. s, 2 H), 1.92-1.96 (m, 1 H), 1.65-1.70 (m, 2 H), 1.02 (d, J = 6.0 Hz, 6 H)

| Example/IUPAC name | Structure | MS calculated MS ESI [M + H]+ | Yield; Appearance Salt form |
|---|---|---|---|
| A520: (S)-N-(3,3-dimethyl-1-phenylbutyl)-3-(4-(3-morpholinoazetidin-1-yl)phenyl)-1H-indazole-5-carboxamide | 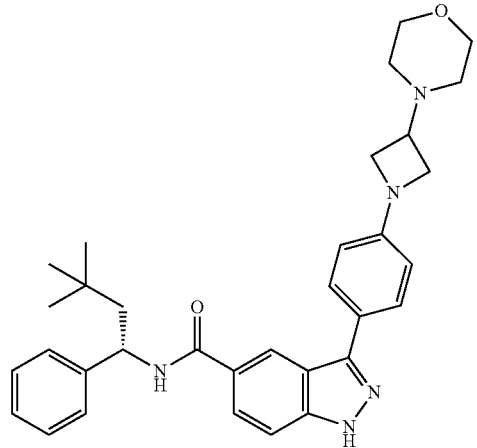 [SMILES: CC(C)(C)C[C@H](NC(=O)c1ccc2[nH]nc(-c3ccc(N4CC(N5CCOCC5)C4)cc3)c2c1)c1ccccc1] | [C33H39N5O2 + H]+ 538.3 538.6 | 67 mg (51%), yellow solid; TFA salt |

SMs: (S)-N-(3,3-dimethyl-1-phenylbutyl)-3-iodo-1H-indazole-5-carboxamide (89.4 mg, 0.2 mmol), 4-(1-(4-(4,4,5,5-tetramethyl-1,3,2-dioxaborolan-2-yl)phenyl)azetidin-3-yl)morpholine (68.8 mg, 0.2 mmol)
$^1$H NMR (400 MHz, CD$_3$OD) δ ppm 8.53 (s, 1H), 7.90 (dd, J = 9.0, 1.4 Hz, 1H), 7.84 (d, J = 8.4 Hz, 1H), 7.38 (d, J = 8.8 Hz, 1H), 7.42 (d, J = 7.6 Hz, 2H), 7.32 (t, J = 7.6 Hz, 2H), 7.21 (t, J = 7.2 Hz, 1H), 6.65 (d, J = 8.8 Hz, 2H), 5.34 (dd, J = 9.4, 5.4 Hz, 1H), 4.24-4.18 (m, 3H), 4.15-2.95 (m, 10H), 2.07 (dd, J = 14.4, 9.6 Hz, 1H), 1.73 (dd, J = 14.6, 3.4 Hz, 1H), 1.03 (s, 9H).

| Example/IUPAC name | Structure | MS calculated MS ESI [M + H]+ | Yield; Appearance Salt form |
|---|---|---|---|
| A521: (S)-N-(3-methyl-1-phenylbutyl)-3-(4-(3-morpholinoazetidin-1-yl)phenyl)-1H-indazole-5-carboxamide | 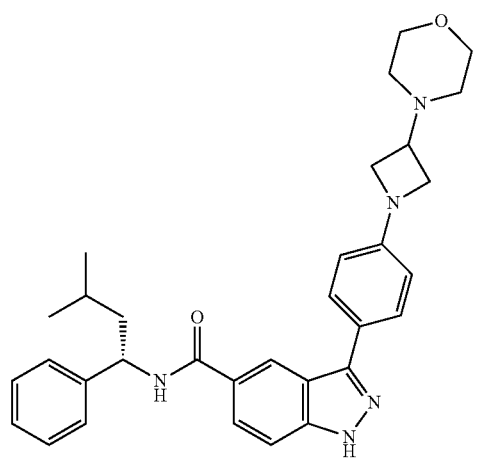 [SMILES: CC(C)C[C@H](NC(=O)c1ccc2[nH]nc(-c3ccc(N4CC(N5CCOCC5)C4)cc3)c2c1)c1ccccc1] | [C32H37N5O2 + H]+ 524.3 524.5 | 51 mg (40%), yellow solid; TFA salt |

SMs: (S)-3-iodo-N-(3-methyl-1-phenylbutyl)-1H-indazole-5-carboxamide (86.6 mg, 0.2 mmol), 4-(1-(4-(4,4,5,5-tetramethyl-1,3,2-dioxaborolan-2-yl)phenyl)azatidin-3-yl)morpholine (68.8 mg, 0.2 mmol)
$^1$H NMR (400 MHz, CD$_3$OD) δ ppm 8.55 (d, J = 0.4 Hz, 1H), 7.92 (dd, J = 8.8, 1.6 Hz, 1H), 7.85 (d, J = 8.4 Hz, 2H), 7.59 (d, J = 8.8 Hz, 1H), 7.43 (d, J = 7.6 Hz, 2H), 7.33 (t, J = 7.6 Hz, 2H), 7.23 (t, J = 7.4 Hz, 1H), 6.65 (d, J = 8.4 Hz, 2H), 5.26 (dd, J = 9.4, 5.4 Hz, 1H), 4.27-4.18 (m, 3H), 4.15-2.95 (m, 10H), 1.97-1.87 (m, 1H), 1.73-1.65 (m, 1H), 1.00 (d, J = 5.2 Hz, 6H).

| Example/IUPAC name | Structure | MS calculated MS ESI [M + H]+ | Yield; Appearance Salt form |
|---|---|---|---|
| A522: (S)-N-(1-(3-fluoropyridin-2-yl)-2-methylpropyl)-3-(4-(3-morpholinoazetidin-1-yl)phenyl)-1H-indazole-5-carboxamide | 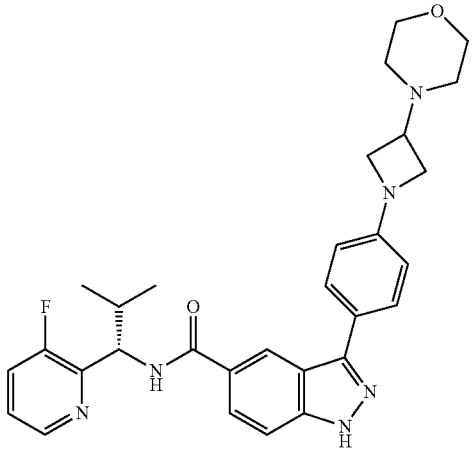 [SMILES: CC(C)[C@H](NC(=O)c1ccc2[nH]nc(-c3ccc(N4CC(N5CCOCC5)C4)cc3)c2c1)c1ncccc1F] | [C30H33FN6O2 + H]+ 529.27 529.5 | 52 mg (30%); yellow solid; 2TFA salt |

SMs: (S)-N-(1-(3-fluoropyridin-2-yl)-2-methylpropyl)-3-iodo-1H-indazole-5-carboxamide (100 mg, 0.22 mmol), 4-(1-(4-(4,4,5,5-tetramethyl-1,3,2-dioxaborolan-2-yl)phenyl)azetidin-3-yl)morpholine (79 mg, 0.22 mmol), Pd(PPh3)4 (13 mg, 0.011 mmol)

$^1$H NMR (400 MHz, CD$_3$OD) δ ppm 8.56 (s, 1 H), 8.44 (d, J = 4.8 Hz, 1 H), 7.87-7.93 (m, 3 H), 7.59-7.63 (m, 2 H), 738-7.42 (m, 1 H), 6.73 (d, J = 8.8 Hz, 2 H), 5.38 (d, J = 9.2 Hz, 1 H), 4.24-4.31 (br. m, 3 H), 3.84-4.13 (br. m, 5 H), 2.3-2.39 (m, 1 H), 1.15 (d, J = 6.4 Hz, 3 H), 0.88 (d, J = 5.8 Hz, 3 H), 6H merged with solvent peak.

| Example/IUPAC name | Structure | MS calculated MS ESI [M + H]+ | Yield; Appearance Salt form |
|---|---|---|---|
| A523: (S)-N-(1-(3-fluoropyridin-2-yl)-2-methylpropyl)-3-(4-(3-morpholinoazetidin-1-yl)phenyl)-1H-indazole-5-carboxamide | 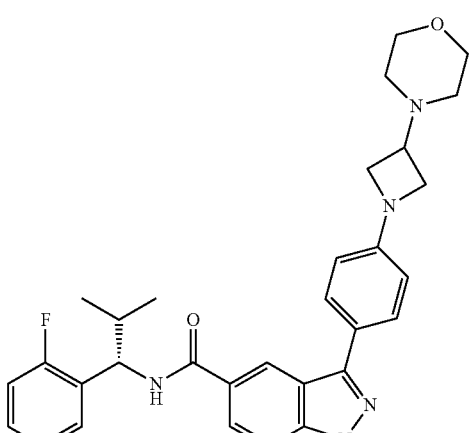 | [C31H34FN5O2 + H]+ 528.27 528.3 | 90 mg (70%); yellow solid TFA salt |

SMs: (S)-N-(1-(2-fluorophenyl)-2-methylpropyl)-3-iodo-1H-indazole-5-carboxamide (100 mg, 0.22 mmol), 4-(1-(4-(4,4,5,5-tetramethyl-1,3,2-dioxaborolan-2-yl)phenyl)azetidin-3-yl)morpholine (79 mg, 0.22 mmol), Pd(PPh3)4 (13 mg, 0.011 mmol)

$^1$H NMR (400 MHz, CD$_3$OD) δ ppm 8.50 (s, 1 H), 7.83-7.89 (m, 3 H), 7.59 (d, J = 8.8 Hz, 1 H), 7.47-7.51 (m, 1 H), 7.25-7.30 (m, 1 H), 7.14-7.18 (m, 1 H), 7.06-7.11 (m, 1 H), 6.80 (d, J = 8.8 Hz, 2 H), 5.10-5.15 (m, 1 H), 4.22-4.24 (br. m, 3 H), 4.09-4.11 (br. m, 3 H), 3.98-3.49 (br. m, 4 H), 2.21-2.30 (m, 1 H), 1.17 (d, J = 6.8 Hz, 3 H), 0.86 (d, J = 6.8 Hz, 3 H), 3H merged with solvent peak

| Example/IUPAC name | Structure | MS calculated MS ESI [M + H]+ | Yield; Appearance Salt form |
|---|---|---|---|
| A524: (S)-N-(1-(2-chlorophenyl)-2-cyclopropylethyl)-3-(4-(4-(oxetan-3-yl)piperazin-1-yl)phenyl)-1H-indazole-5-carboxamide | 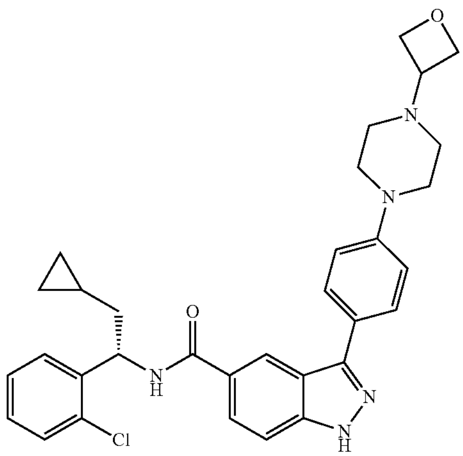 [SMILES: O=C(N[C@@H](CC1CC1)c1ccccc1Cl)c1ccc2[nH]nc(-c3ccc(N4CCN(C5COC5)CC4)cc3)c2c1] | [C$_{32}$H$_{34}$ClN$_5$O$_2$ + H]+ 556.2 556.7 | 100 mg (37%), yellow solid; TFA salt |

SMs: (S)-N-(1-(2-chlorophenyl)-2-cyclopropylethyl)-3-iodo-1H-indazole-5-carboxamide (187 mg, 0.4 mmol), 1-(oxetan-3-yl)-4-(4-(4,4,5,5-tetramethyl-1,3,2-dioxaborolan-2-yl)phenyl)piperazine (138 mg, 0.4 mmol)
$^1$H NMR (400 MHz, CD$_3$OD) δ ppm 8.59 (d, J = 0.4 Hz, 1H), 7.94 (dd, J = 8.8, 1.6 Hz, 1H), 7.86 (d, J = 8.8 Hz, 2H), 7.58 (d, J = 8.8 Hz, 1H), 7.51 (dd, J = 7.6, 1.6 Hz, 1H), 7.34 (dd, J = 7.6, 1.2 Hz, 1H), 7.23 (dt, J = 7.2, 1.2 Hz, 1H), 7.19 (dt, J = 7.6, 1.6 Hz, 1H), 7.02 (d, J = 8.8 Hz, 2H), 5.66 (dd, J = 9.2, 5.2 Hz, 1H), 4.93-4.84 (m, 4H), 4.45 (quintet, J = 6.4 Hz, 1H), 3.70-3.10 (m, 8H), 1.95-1.86 (m, 1H), 1.66-1.58 (m, 1H), 0.89-0.78 (m, 1H), 0.50-0.38 (m, 2H), 0.24-0.17 (m, 1H), 0.13-0.50 (m, 1H).

| Example/IUPAC name | Structure | MS calculated MS ESI [M + H]+ | Yield; Appearance Salt form |
|---|---|---|---|
| A525: (R)-N-(1-(2-chlorophenyl)-2-cyclopropylethyl)-3-(4-(4-(oxetan-3-yl)piperazin-1-yl)phenyl)-1H-indazole-5-carboxamide | | [C$_{32}$H$_{34}$ClN$_5$O$_2$ + H]+ 556.2 556.7 | 116 mg (43%), yellow solid; TFA salt |

SMs: (R)-N-(1-(2-chlorophenyl)-2-cyclopropylethyl)-3-iodo-1H-indazole-5-carboxamide (187 mg, 0.4 mmol), 1-(oxetan-3-yl)-4-(4-(4,4,5,5-tetramethyl-1,3,2-dioxaborolan-2-yl)phenyl)piperazine (138 mg, 0.4 mmol)
$^1$H NMR (400 MHz, CD$_3$OD) Spectral data was identical for that obtained in (S)-N-(1-(2-chlorophenyl)-2-cyclopropylethyl)-3-(4-(4-(oxetan-3-yl)piperazin-1-yl)phenyl)-1H-indazole-5-carboxamide

Example B

TTK Inhibition Assay

Active TTK was purchased from Invitrogen as an amino terminal GST fusion of full length human TTK. Amino terminal 6 histidine, sumo tagged human TTK (residues 1-275) was expressed in *E. coli*, and purified to >95% homogeneity by Ni$^{2+}$ agarose, gel filtration, and ion exchange chromatography.

TTK activity was measured using an indirect ELISA detection system. GST-TTK (0.68 nM) was incubated in the presence of 16 μM ATP (Sigma cat# A7699), 50 mM Hepes pH 7.2, 1 mM EGTA, 10 mM MgCl$_2$, and 0.1% Pluronic in a 96 well microtitre plate pre-coated with amino terminal 6 histidine, sumo tagged TTK (amino acid residues 1-275). The reaction was allowed to proceed for 30 minutes, followed by 5 washes of the plate with Wash Buffer (phosphate buffered saline supplemented with 0.2% Tween 20), and incubation for 30 minutes with a 1:3000 dilution of primary antibody (Cell Signaling cat# 9381). The plate was washed 5 times with Wash Buffer, incubated for 30 minutes in the presence of secondary antibody coupled to horse radish peroxidase (BioRad cat# 1721019, 1:3000 concentration), washed an additional 5 times with Wash Buffer, and incubated in the presence of TMB substrate (Sigma cat# T0440).

The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 µM) or at a variable inhibitor concentration (typically 0.5 µM to 0.001 µM in a 10 point dose response titration). Compounds were pre-incubated in the presence of enzyme for 5 minutes prior to addition of ATP and the activity remaining quantified using the above described activity assay. The % Inhibition of a compound was determined using the following formula: % Inhibition=100×(1−(experimental value−background value)/(high activity control−background value)). The $IC_{50}$ value was determined using a non-linear 4 point logistic curve fit (XLfit4, IDBS) with the formula: $(A+(B/(1+((x/C)^D))))$, where A=background value, B=range, C=inflection point, D=curve fit parameter.

In Table 1 below, $IC_{50}$ value ranges for exemplary compounds are given. The $IC_{50}$ ranges are indicated as "A," "B," and "C," for values less than or equal to 0.1 µM; those greater than 0.1 µM and less than or equal to 0.5 µM; and those greater than 0.5 µM, respectively.

Example C

Cancer Cell Line Data on Exemplary Compounds of the Invention

Breast cancer cells (MDA-MB-231), colon cancer cells (HCT116) and ovarian cancer cells (PA-1) were seeded (1000 to 4000 in 80 µl per well depending on the cell growth rate) into 96 well plates 24 hours before compound overlay. Compounds were prepared as 10 mM stock solutions in 100% DMSO which were diluted with DMEM (Dulbecco's Modified Eagle's Medium) cell growth Medium (Invitrogen, Burlington, ON, Canada) containing 10% FBS (Fetal Bovine Serum) to concentrations ranging from 50 nM to 250 µM. Aliquots (20 µl) from each concentration were overlaid to 80 µl of the pre-seeded cells in the 96 well plates to make final concentrations of 10 nM to 50 µM. The cells were cultured for 5 days before the Sulforhodamine B assay (SRB) was performed to determine the compound's cell growth inhibition activity.

Sulforhodamine B (purchased from Sigma, Oakville, ON, Canada) is a water-soluble dye that binds to the basic amino acids of the cellular proteins. Thus, colorimetric measurement of the bound dye provides an estimate of the total protein mass that is related to the cell number. the cells are fixed in situ by gently aspirating off the culture media and adding 50 µl ice cold 10% Trichloroacetic Acid (TCA) per well and incubate at 4° C. for 30-60 min. The plates are washed with $H_2O$ five times and allowed to air dry for 5 min. Addition of 50 µl 0.4% (w/v) SRB solution in 1% (v/v) acetic acid to each well and incubation for 30 min at RT completes the staining reaction. Following staining, plates are washed four times with 1% acetic acid to remove unbound dye and then allowed to air dry for 5 min. The stain is solubilized with 100 µl of 10 mM Tris pH 10.5 per well. Absorbance is read at 570 nm.

The percentage (%) of relative growth inhibition was calculated by comparing to DMSO treated only cells (100%). $GI_{50}$'s were determined for compounds with cytotoxic activity. The $GI_{50}$ was calculated using GraphPad PRISM software (GraphPad Software, Inc., San Diego, Calif., USA). $GI_{50}$ (growth inhibition) is the compound concentration that causes 50% inhibition of cell growth.

In Table 1 below, $GI_{50}$ value ranges for compound examples against breast cancer cell lines (MDA-MB-231), colon cancer cell lines (HCT116) and ovarian cancer cell lines (PA-1) are given. The example compounds demonstrated varying growth inhibition/cell killing activity against cells of breast cancer, colon cancer, and ovarian cancer. The $GI_{50}$ ranges are indicated as "A," "B," and "C," for values less than or equal to 0.1 µM; those greater than 0.1 µM and less than or equal to 0.5 µM; and those greater than 0.5 µM, respectively.

Example D

Colon and Ovarian Cancer Tumor-Initiating Cell Data of Exemplary Compounds

Materials and Methods: Non-tissue or tissue cultured treated T-75 flask and 96-well plates were purchased from VWR. Vitamin B-27 supplement, MEM NEAA (minimum essential medium non essential amino acids), sodium pyruvate, L-glutamine, N2 supplement, penicillin-streptomycin and fungizone/amphotericin B were obtained from Invitrogen. Lipid mixture, heparin and EGF were purchased from Sigma; bFGF from BD Biosciences. Tumor Initiating Cells (TICs) from colon were routinely maintained using non-tissue cultured treated T-75 flasks in DMEM:F12 medium containing 0.2×B-27 supplement, 4 ug/ml heparin, 1×MEM NEAA, 1× sodium pyruvate, 1 mM glutamine, 10 pg/ul bFGF, 20 pg/ul EGF, 1×N2 supplement, lipid mixture, penicillin-streptomycin and fungizone/amphotericin B. Ovarian TICs were routinely maintained using tissue cultured treated T-75 flasks in DMEM:F12 medium containing 1×B-27 supplement, 4 ug/ml heparin, 20 pg/ul bFGF, 20 pg/ul EGF and penicillin-streptomycin.

Assay Protocol: Compounds described herein were dissolved in DMSO and further diluted in cell culture medium for $GI_{50}$ determination. Colon TICs were trypsinized and seeded into non-tissue cultured treated 96-well plates with 4,000 cells/well. After 24 h, compound was added into the cell culture at different concentrations, and the final concentration of DMSO was adjusted to 0.1%. Cells were then cultured at 37° C. for 9 days. Ovarian TICs were trypsinized and seeded into tissue cultured treated 96-well plates with 1,000 cells/well. After 24 h, compound was added into the cell culture at different concentrations, and the final concentration of DMSO was adjusted to 0.1%. Cells were then cultured at 37° C. for 6 days. Cell viability was assessed by Alamar Blue assay: 10 ul of Alamar Blue was added into each well. After 4 hours incubation at 37° C., fluorescence was recorded at excitation 544 and emission 590. $GI_{50}$ (Growth inhibition) was calculated using GraphPad Prism 4.0 software. Cell growth inhibition data for compounds described herein is tabulated below.

In Table 1 below, $GI_{50}$ value ranges for compound examples against TICs (Colon 12 and Ovarian 2393A) are given. The $GI_{50}$ ranges are indicated as "A," "B," and "C," for values less than or equal to 0.1 µM; those greater than 0.1 µM and less than or equal to 0.5 µM; and those greater than 0.5 µM, respectively.

TABLE 1

In vitro activity of Compound Examples

| Example # | TTK IC$_{50}$ Range | Cancer Cell Line GI$_{50}$ Range | | | Tumor Initiating Cell GI$_{50}$ Range | |
|---|---|---|---|---|---|---|
| | | HCT116 | MDA-MB-468 | PA-1 | Ovarain 2393A | Colon 12 |
| A1 | A | C | C | NA | NA | NA |
| A2 | A | A | C | NA | NA | NA |
| A3 | A | B | C | NA | NA | NA |
| A4 | A | A | C | NA | B | A |
| A5 | A | A | C | NA | NA | NA |
| A6 | A | B | C | NA | NA | NA |
| A7 | A | A | C | A | A | B |
| A8 | A | A | C | NA | NA | NA |
| A9 | A | A | C | NA | B | B |
| A10 | A | B | C | NA | NA | NA |
| A11 | A | B | C | NA | NA | NA |
| A12 | A | A | NA | NA | B | C |
| A13 | A | B | C | NA | NA | NA |
| A14 | A | C | C | NA | NA | NA |
| A15 | A | C | C | NA | NA | NA |
| A16 | A | B | C | NA | NA | NA |
| A17 | A | C | C | NA | NA | NA |
| A18 | A | B | C | B | NA | NA |
| A19 | A | B | C | NA | NA | NA |
| A20 | A | B | C | NA | NA | NA |
| A21 | A | A | C | NA | NA | NA |
| A22 | A | B | C | NA | NA | NA |
| A23 | B | C | C | NA | NA | NA |
| A24 | A | A | C | A | A | A |
| A446 | B | B | C | NA | NA | NA |
| A447 | A | A | A | A | A | A |
| A25 | A | A | C | NA | A | B |
| A26 | A | B | C | NA | NA | NA |
| A27 | A | A | C | NA | B | B |
| A28 | A | A | C | NA | NA | NA |
| A29 | A | A | C | NA | B | A |
| A30 | A | A | C | NA | NA | NA |
| A31 | A | A | C | NA | NA | NA |
| A32 | A | A | C | NA | NA | NA |
| A33 | A | A | C | NA | B | B |
| A448 | A | B | C | NA | NA | NA |
| A34 | A | A | C | NA | NA | NA |
| A35 | A | A | B | NA | B | C |
| A36 | A | A | B | NA | NA | NA |
| A37 | A | A | NA | NA | NA | NA |
| A38 | A | A | C | NA | NA | NA |
| A39 | A | A | NA | NA | NA | NA |
| A40 | A | B | C | NA | NA | NA |
| A449 | A | A | B | NA | B | A |
| A41 | A | A | NA | NA | A | B |
| A42 | A | A | C | NA | NA | NA |
| A450 | C | C | C | NA | NA | NA |
| A43 | A | A | C | NA | NA | NA |
| A44 | A | A | C | NA | NA | NA |
| A45 | A | A | C | NA | NA | NA |
| A46 | A | A | B | NA | B | C |
| A47 | A | B | NA | NA | NA | NA |
| A48 | A | C | C | NA | NA | NA |
| A49 | A | B | NA | NA | NA | NA |
| A50 | A | A | NA | NA | NA | NA |
| A51 | A | B | NA | NA | NA | NA |
| A52 | A | B | NA | NA | NA | NA |
| A53 | A | B | C | NA | NA | NA |
| A54 | A | C | C | NA | NA | NA |
| A55 | A | A | C | NA | NA | NA |
| A56 | B | C | C | NA | NA | NA |
| A57 | A | B | C | NA | NA | NA |
| A58 | A | B | C | NA | NA | NA |
| A59 | B | C | C | NA | NA | NA |
| A60 | A | B | C | NA | NA | NA |
| A61 | B | C | C | NA | NA | NA |
| A451 | B | C | C | NA | NA | NA |
| A62 | A | C | C | NA | NA | NA |
| A452 | A | C | C | NA | NA | NA |
| A63 | A | A | C | NA | NA | NA |
| A64 | B | C | C | NA | NA | NA |
| A65 | B | C | C | NA | NA | NA |
| A66 | C | C | C | NA | NA | NA |
| A67 | A | B | C | NA | NA | NA |
| A68 | A | C | C | NA | NA | NA |
| A69 | A | B | C | NA | NA | NA |
| A70 | A | B | NA | NA | NA | NA |
| A71 | A | A | NA | NA | NA | NA |
| A72 | C | NA | NA | NA | NA | NA |
| A74 | A | C | C | NA | NA | NA |
| A73 | A | C | C | NA | NA | NA |
| A75 | A | B | C | NA | NA | NA |
| A76 | A | A | NA | NA | NA | NA |
| A77 | A | B | C | NA | NA | NA |
| A78 | A | A | NA | NA | NA | NA |
| A79 | A | A | NA | NA | NA | NA |
| A80 | A | A | NA | NA | NA | NA |
| A81 | B | B | C | B | NA | NA |
| A82 | A | A | NA | A | NA | NA |
| A83 | A | A | NA | B | NA | NA |
| A84 | A | A | NA | B | NA | NA |
| A85 | A | A | A | A | NA | NA |
| A86 | A | A | B | B | NA | NA |
| A87 | A | B | NA | B | NA | NA |
| A88 | A | A | NA | A | NA | NA |
| A89 | A | A | NA | A | B | B |
| A90 | A | B | C | C | NA | NA |
| A91 | A | A | C | A | A | B |
| A92 | A | A | C | B | NA | NA |
| A93 | A | C | C | C | NA | NA |
| A94. | C | NA | NA | NA | NA | NA |
| A95 | A | A | NA | A | NA | NA |
| A453 | A | A | A | A | B | A |
| A96 | C | C | C | C | NA | NA |
| A97 | A | B | NA | B | NA | NA |
| A98 | A | A | B | A | B | B |
| A99 | A | C | C | C | NA | NA |
| A427 | A | A | B | A | NA | NA |
| A100 | A | A | B | A | NA | NA |
| A101 | A | A | NA | A | NA | NA |
| A102 | A | A | NA | A | NA | NA |
| A454 | A | B | B | B | NA | NA |
| A103 | A | A | B | A | NA | NA |
| A104 | A | A | B | A | NA | NA |
| A105 | A | A | NA | A | NA | NA |
| A106 | A | A | NA | A | NA | NA |
| A469 | A | B | B | B | NA | NA |
| A470 | A | B | B | B | NA | NA |
| A107 | A | B | C | B | NA | NA |
| A108. | A | B | C | B | NA | NA |
| A.109 | A | C | C | B | NA | NA |
| A110 | A | A | A | A | B | A |
| A111 | A | A | NA | A | NA | NA |
| A112 | A | B | B | B | NA | NA |
| A113 | A | A | B | A | NA | NA |
| A114 | A | C | C | C | NA | NA |
| A428 | A | B | C | B | NA | NA |
| A429 | A | A | B | B | NA | NA |
| A455 | A | A | B | B | B | B |
| A115 | B | C | C | C | NA | NA |
| A116 | A | B | C | B | NA | NA |
| A117 | A | A | NA | A | NA | NA |
| A118 | A | A | NA | A | A | B |
| A471 | A | B | C | B | NA | NA |
| A472 | A | B | C | B | NA | NA |
| A119 | A | B | NA | B | NA | NA |
| A473 | A | B | NA | B | NA | NA |
| A120. | A | A | NA | A | NA | NA |
| A121 | A | A | NA | A | NA | NA |
| A122 | A | B | NA | B | NA | NA |
| A123 | A | B | NA | A | NA | NA |
| A124 | A | B | C | B | NA | NA |

TABLE 1-continued

In vitro activity of Compound Examples

| Example # | TTK IC$_{50}$ Range | Cancer Cell Line GI$_{50}$ Range | | | Tumor Initiating Cell GI$_{50}$ Range Ovarain | |
|---|---|---|---|---|---|---|
| | | HCT116 | MDA-MB-468 | PA-1 | 2393A | Colon 12 |
| A474 | A | B | C | B | NA | NA |
| A125 | A | B | C | B | NA | NA |
| A456 | B | NA | NA | NA | NA | NA |
| A457 | B | NA | NA | NA | NA | NA |
| A126 | A | B | B | B | NA | NA |
| A127 | A | B | C | B | NA | NA |
| A128 | A | A | B | B | B | A |
| A129 | A | B | C | B | NA | NA |
| A475 | B | NA | NA | NA | NA | NA |
| A130 | A | A | B | B | B | A |
| A131 | A | A | B | A | B | A |
| A132 | A | A | B | A | B | A |
| A133 | A | A | C | A | B | A |
| A134 | A | A | C | B | C | B |
| A135 | A | B | C | B | NA | NA |
| A476 | A | B | C | B | NA | NA |
| A477 | B | NA | NA | NA | NA | NA |
| A458 | A | B | C | B | NA | NA |
| A136 | A | A | A | A | A | C |
| A137 | A | A | C | B | B | C |
| A138 | A | A | C | A | B | A |
| A139 | A | B | C | B | NA | NA |
| A140 | A | B | B | B | NA | NA |
| A141 | A | B | B | B | NA | NA |
| A142 | A | B | C | C | NA | NA |
| A143 | A | B | C | B | NA | NA |
| A144 | A | A | B | A | A | A |
| A496 | A | B | C | B | NA | NA |
| A497 | A | B | B | B | NA | NA |
| A145 | A | B | C | B | NA | NA |
| A146 | A | C | C | B | NA | NA |
| A430 | B | NA | NA | NA | NA | NA |
| A147 | A | A | C | A | A | B |
| A148 | A | B | C | B | NA | NA |
| A150 | A | A | B | A | A | A |
| A151 | A | A | C | B | B | B |
| A478 | A | C | C | C | NA | NA |
| A431 | A | B | C | B | NA | NA |
| A153 | A | B | C | B | NA | NA |
| A154 | A | A | B | B | A | A |
| A155 | A | B | B | B | NA | NA |
| A156 | A | B | C | C | NA | NA |
| A157 | A | B | B | B | B | B |
| A158 | A | B | B | B | NA | NA |
| A1159 | A | B | C | B | NA | NA |
| A160 | A | A | B | B | B | B |
| A479 | B | NA | NA | NA | NA | NA |
| A161 | A | B | C | B | NA | NA |
| A162 | A | B | C | B | NA | NA |
| A504 | A | A | B | B | B | B |
| A163 | A | A | A | A | B | B |
| A164 | A | B | C | B | NA | NA |
| A165 | A | C | C | C | NA | NA |
| A480 | A | B | C | B | NA | NA |
| A166 | A | A | B | A | A | A |
| A167 | A | A | NA | B | A | A |
| A481 | A | B | C | B | NA | NA |
| A168 | B | B | B | B | NA | NA |
| A482 | A | B | C | B | C | C |
| A169 | A | B | NA | B | C | C |
| A170 | A | C | C | C | C | C |
| A171 | A | A | NA | A | A | B |
| A172 | A | A | NA | A | A | A |
| A173 | A | B | C | B | B | C |
| A174 | A | A | C | B | B | B |
| A175 | A | A | B | B | A | B |
| A176 | A | B | B | B | B | B |
| A177 | A | A | B | B | B | B |
| A178 | A | A | B | A | B | B |
| A179 | A | A | B | B | B | B |
| A180 | A | A | NA | B | B | B |
| A181 | A | B | C | B | C | B |
| A182 | A | A | NA | A | A | A |
| A183 | A | B | C | B | C | C |
| A184 | A | A | C | A | A | B |
| A185 | A | B | NA | B | B | B |
| A186 | A | A | NA | A | A | A |
| A187 | A | A | C | A | C | B |
| A188 | A | B | C | B | C | C |
| A189 | A | A | C | A | C | C |
| A190 | A | B | NA | B | B | B |
| A191 | A | A | C | A | A | B |
| A192 | A | B | NA | B | NA | NA |
| A193 | A | A | A | A | B | A |
| A194 | A | B | C | B | NA | NA |
| A195 | A | B | NA | B | NA | NA |
| A196 | A | A | NA | A | NA | NA |
| A197 | A | A | NA | A | A | A |
| A198 | A | A | B | B | B | B |
| A199 | A | B | B | B | NA | NA |
| A200 | A | A | NA | A | A | B |
| A201 | A | A | NA | A | A | A |
| A494 | A | C | NA | C | NA | NA |
| A202 | A | A | C | A | B | B |
| A498 | B | NA | NA | NA | NA | NA |
| A203 | A | B | NA | B | NA | NA |
| A204 | A | A | NA | A | A | A |
| A205 | A | B | NA | B | NA | NA |
| A206 | A | B | NA | B | NA | NA |
| A207 | A | B | C | B | NA | NA |
| A208 | A | A | NA | A | A | B |
| A209 | A | B | NA | B | NA | NA |
| A210 | A | A | NA | A | B | B |
| A211 | A | B | NA | B | NA | NA |
| A212 | A | A | NA | A | A | B |
| A505 | A | A | B | A | B | C |
| A213 | A | A | NA | A | A | C |
| A214 | A | A | NA | A | A | C |
| A215 | A | A | NA | A | B | A |
| A216 | A | A | NA | A | A | A |
| A217 | A | A | NA | A | B | B |
| A218 | A | B | B | B | NA | NA |
| A279 | A | A | A | A | B | B |
| A243 | A | C | C | C | NA | NA |
| A386 | A | B | C | B | C | B |
| A374 | A | A | NA | A | B | C |
| A219 | A | B | B | A | NA | NA |
| A432 | A | A | NA | A | NA | NA |
| A319 | A | B | NA | A | NA | NA |
| A483 | A | B | NA | B | NA | NA |
| A280 | A | A | B | A | NA | NA |
| A320 | A | A | NA | A | B | A |
| A244 | A | A | B | A | B | B |
| A281 | A | A | B | A | NA | NA |
| A282 | A | A | B | A | NA | NA |
| A283 | A | A | B | A | B | B |
| A220 | A | B | B | B | NA | NA |
| A221 | A | A | NA | A | B | B |
| A245 | A | B | C | B | C | C |
| A246 | A | B | C | A | C | C |
| A234 | A | A | B | A | B | B |
| A277 | A | A | B | A | B | B |
| A235 | A | A | A | A | A | A |
| A278 | A | A | A | A | A | A |
| A321 | A | B | B | B | B | A |
| A247 | A | B | B | B | B | B |
| A322 | A | A | NA | A | A | A |
| A387 | A | A | C | A | NA | NA |
| A388 | A | B | C | B | NA | NA |
| A222 | A | A | B | A | B | A |
| A376 | A | A | B | A | B | B |
| A389 | A | A | NA | A | NA | NA |

TABLE 1-continued

In vitro activity of Compound Examples

| Example # | TTK IC$_{50}$ Range | Cancer Cell Line GI$_{50}$ Range | | | Tumor Initiating Cell GI$_{50}$ Range Ovarain | |
|---|---|---|---|---|---|---|
| | | HCT116 | MDA-MB-468 | PA-1 | 2393A | Colon 12 |
| A375 | A | A | B | A | NA | NA |
| A223 | A | B | C | B | NA | NA |
| A224 | A | B | C | B | NA | NA |
| A390 | A | A | B | A | NA | NA |
| A484 | A | A | B | A | B | B |
| A248 | A | B | B | B | NA | NA |
| A391 | A | A | B | A | B | A |
| A284 | A | B | B | B | NA | NA |
| A285 | A | A | B | A | NA | NA |
| A286 | A | A | A | A | NA | NA |
| A392 | A | A | NA | A | NA | NA |
| A393 | A | A | NA | A | NA | NA |
| A324 | A | B | B | B | NA | NA |
| A225 | A | A | B | A | NA | NA |
| A287 | A | A | A | A | B | B |
| A288 | A | A | B | B | B | B |
| A377 | A | B | NA | B | NA | NA |
| A394 | A | A | B | B | B | B |
| A378 | A | A | B | A | B | B |
| A289 | A | B | C | B | NA | NA |
| A273 | A | A | A | A | A | A |
| A274 | A | B | C | B | B | B |
| A485 | A | A | C | A | B | B |
| A486 | A | B | C | B | NA | NA |
| A325 | A | B | B | B | B | A |
| A395 | A | A | A | A | B | A |
| A396 | A | A | NA | A | NA | NA |
| A379 | A | B | NA | B | B | A |
| A380 | A | A | B | A | NA | NA |
| A326 | A | B | B | B | A | A |
| A327 | A | A | NA | A | NA | NA |
| A397 | A | A | NA | A | NA | NA |
| A398 | A | A | A | A | NA | NA |
| A459 | A | A | B | A | B | B |
| A328 | A | A | NA | A | B | A |
| A381 | A | B | NA | B | NA | NA |
| A399 | A | A | NA | B | NA | NA |
| A460 | A | C | C | C | NA | NA |
| A400 | A | B | C | B | NA | NA |
| A506 | A | A | NA | A | NA | NA |
| A507 | A | B | B | B | NA | NA |
| A329 | A | A | NA | A | A | A |
| A401 | A | A | NA | A | NA | NA |
| A226 | A | B | NA | B | NA | NA |
| A433 | A | B | NA | B | NA | NA |
| A434 | A | C | C | C | NA | NA |
| A382 | A | A | NA | A | NA | NA |
| A402 | A | A | NA | A | A | A |
| A403 | A | C | NA | C | NA | NA |
| A330 | A | A | NA | A | NA | NA |
| A331 | A | A | NA | A | NA | NA |
| A332 | A | A | NA | A | A | A |
| A461 | A | C | C | C | NA | NA |
| A404 | A | C | NA | C | NA | NA |
| A333 | A | A | NA | A | A | A |
| A436 | A | B | NA | B | NA | NA |
| A435 | A | C | NA | C | NA | NA |
| A462 | B | C | NA | C | NA | NA |
| A334 | A | A | NA | A | A | A |
| A487 | A | C | C | C | NA | NA |
| A335 | A | A | B | A | A | A |
| A405 | A | A | A | A | A | A |
| A406 | A | C | C | C | NA | NA |
| A437 | A | B | NA | B | NA | NA |
| A336 | A | B | NA | B | NA | NA |
| A383 | A | B | NA | B | NA | NA |
| A384 | A | B | NA | B | NA | NA |
| A227 | A | A | C | B | NA | NA |
| A407 | A | C | NA | C | NA | NA |
| A463 | A | B | B | A | NA | NA |
| A408 | A | NA | NA | NA | NA | NA |
| A445 | A | A | B | A | NA | NA |
| A438 | A | B | C | B | NA | NA |
| A337 | A | A | A | A | A | A |
| A373 | A | B | B | B | NA | NA |
| A249 | A | B | B | B | NA | NA |
| A250 | A | A | B | A | NA | NA |
| A409 | A | B | B | B | NA | NA |
| A439 | A | B | B | B | NA | NA |
| A440 | A | B | B | B | NA | NA |
| A385 | A | A | NA | A | A | B |
| A338 | A | B | B | B | NA | NA |
| A290 | A | B | NA | B | NA | NA |
| A251 | A | B | B | B | NA | NA |
| A291 | A | A | NA | A | NA | NA |
| A339 | A | A | A | A | A | A |
| A441 | A | B | B | B | NA | NA |
| A292 | A | A | A | A | NA | NA |
| A340 | A | B | B | A | NA | NA |
| A341 | A | B | B | B | NA | NA |
| A252 | A | A | A | A | NA | NA |
| A464 | B | C | C | B | NA | NA |
| A342 | A | A | A | A | NA | NA |
| A343 | A | A | B | A | B | A |
| A253 | A | A | B | A | NA | NA |
| A465 | A | B | B | A | NA | NA |
| A344 | A | C | C | B | NA | NA |
| A345 | A | B | B | B | NA | NA |
| A346 | A | B | B | B | NA | NA |
| A488 | A | C | C | C | NA | NA |
| A442 | A | C | C | C | NA | NA |
| A466 | A | B | NA | A | NA | NA |
| A347 | A | A | B | B | NA | NA |
| A348 | A | A | A | A | NA | NA |
| A443 | A | B | C | B | NA | NA |
| A444 | A | C | C | C | NA | NA |
| A349 | A | A | NA | A | A | A |
| A350 | A | A | NA | A | A | A |
| A351 | A | A | NA | A | NA | NA |
| A254 | A | B | C | B | NA | NA |
| A255 | A | B | B | B | NA | NA |
| A293 | A | B | NA | B | NA | NA |
| A256 | B | C | C | C | NA | NA |
| A257 | A | A | B | A | B | B |
| A258 | A | A | A | A | A | A |
| A500 | A | A | NA | A | A | A |
| A410 | A | A | NA | A | A | A |
| A294 | A | B | NA | B | NA | NA |
| A295 | A | A | B | A | NA | NA |
| A228 | A | B | B | B | B | C |
| A229 | A | B | B | B | NA | NA |
| A259 | A | A | A | A | A | B |
| A352 | A | B | NA | B | NA | NA |
| A353 | A | A | NA | A | NA | NA |
| A260 | A | A | A | A | A | B |
| A296 | A | A | NA | A | NA | NA |
| A230 | A | A | NA | A | NA | NA |
| A231 | A | A | NA | A | NA | NA |
| A232 | A | A | NA | A | NA | NA |
| A233 | A | A | NA | A | NA | NA |
| A297 | A | A | A | A | NA | NA |
| A298 | A | A | A | A | A | A |
| A411 | A | A | A | A | A | A |
| A261 | A | A | A | A | A | B |
| A489 | A | A | A | A | A | A |
| A354 | A | B | B | B | NA | NA |
| A355 | A | B | B | B | NA | NA |
| A356 | A | A | A | A | A | A |
| A262 | A | B | B | B | NA | NA |
| A357 | A | B | B | B | NA | NA |
| A358 | A | A | A | A | A | A |
| A359 | A | A | A | A | NA | NA |

TABLE 1-continued

In vitro activity of Compound Examples

| Example # | TTK IC$_{50}$ Range | Cancer Cell Line GI$_{50}$ Range | | | Tumor Initiating Cell GI$_{50}$ Range Ovarian | |
|---|---|---|---|---|---|---|
| | | HCT116 | MDA-MB-468 | PA-1 | 2393A | Colon 12 |
| A309 | A | A | A | A | A | A |
| A360 | A | A | A | A | A | A |
| A263 | A | B | B | A | NA | NA |
| A310 | A | A | A | A | A | A |
| A299 | A | A | A | A | A | A |
| A300 | A | A | A | A | B | A |
| A236 | A | C | C | C | NA | NA |
| A508 | A | A | A | A | A | A |
| A237 | A | C | C | C | NA | NA |
| A361 | A | A | NA | A | A | A |
| A238 | A | B | C | B | NA | NA |
| A362 | A | A | A | A | A | A |
| A363 | A | A | A | A | A | A |
| A264 | A | A | A | A | B | B |
| A490 | B | C | C | C | NA | NA |
| A311 | A | A | A | A | A | A |
| A467 | B | C | C | C | NA | NA |
| A301 | A | A | A | A | A | A |
| A364 | A | A | A | A | NA | A |
| A491 | A | C | C | C | NA | NA |
| A239 | A | C | C | C | NA | NA |
| A312 | A | A | A | A | NA | NA |
| A492 | A | A | A | A | NA | A |
| A365 | A | A | A | A | NA | NA |
| A366 | A | A | A | A | NA | A |
| A367 | A | A | A | A | NA | A |
| A412 | A | A | B | A | NA | NA |
| A413 | A | A | B | A | NA | NA |
| A501 | A | A | A | A | NA | A |
| A493 | A | B | C | B | NA | NA |
| A414 | A | A | A | A | NA | A |
| A302 | A | A | B | A | NA | NA |
| A313 | A | A | A | A | NA | A |
| A314 | A | A | A | A | NA | A |
| A240 | A | C | C | C | NA | NA |
| A499 | A | B | B | B | NA | NA |
| A241 | A | C | C | C | NA | NA |
| A315 | A | A | B | A | B | A |
| A316 | A | B | B | B | NA | NA |
| A242 | A | C | C | B | NA | NA |
| A502 | A | A | A | A | A | A |
| A415 | A | A | A | A | A | A |
| A416 | A | A | A | A | A | A |
| A417 | A | B | B | B | NA | NA |
| A303 | A | A | A | A | A | A |
| A304 | A | B | B | B | NA | NA |
| A305 | A | A | A | A | A | A |
| A306 | A | A | A | A | NA | NA |
| A368 | A | A | B | B | B | A |
| A265 | A | A | A | A | A | A |
| A267 | A | A | A | A | A | A |
| A369 | A | A | NA | A | A | A |
| A418 | A | A | A | A | A | A |
| A419 | A | A | A | A | A | A |
| A509 | A | C | C | C | NA | NA |
| A510 | A | B | B | B | NA | NA |
| A420 | A | A | A | A | A | A |
| A266 | A | A | A | A | A | A |
| A268 | A | A | A | A | A | A |
| A370 | A | A | A | A | B | A |
| A371 | A | A | B | A | NA | NA |
| A270 | A | A | B | A | NA | NA |
| A269 | A | A | A | A | A | A |
| A421 | A | A | A | A | A | A |
| A372 | A | A | B | A | NA | NA |
| A271 | A | C | C | B | NA | NA |
| A272 | A | B | C | B | NA | NA |
| A422 | A | A | NA | A | B | A |
| A495 | A | B | B | A | NA | NA |
| A307 | A | A | A | A | B | B |
| A468 | A | B | C | B | NA | NA |
| A503 | A | A | B | A | NA | NA |
| A423 | A | A | A | A | NA | NA |
| A424 | A | A | A | A | NA | NA |
| A511 | A | B | B | A | NA | NA |
| A317 | A | B | B | A | NA | NA |
| A512 | A | A | B | A | NA | NA |
| A425 | A | A | A | A | NA | NA |
| A513 | A | A | A | A | NA | NA |
| A514 | A | A | A | A | NA | NA |
| A275 | A | A | A | A | NA | NA |
| A276 | A | A | B | A | NA | NA |
| A426 | A | NA | NA | NA | NA | NA |
| A308 | A | NA | NA | NA | NA | NA |
| A515 | A | NA | NA | NA | NA | NA |
| A516 | A | NA | NA | NA | NA | NA |
| A517 | A | NA | NA | NA | NA | NA |
| A518 | A | NA | NA | NA | NA | NA |
| A519 | A | NA | NA | NA | NA | NA |
| A520 | A | NA | NA | NA | NA | NA |
| A521 | A | NA | NA | NA | NA | NA |
| A522 | A | NA | NA | NA | NA | NA |

NA: Not Available

Example E

Selectivity against a Panel of 270 Human Kinases

The inhibitory activity of selected compounds of the invention (A335, A405, A410, A261, A300 and A363) was evaluated against a panel of 270 different human kinase enzymes by Millipore Corporation. The % Inhibition was determined by the formula: % Inhibition=100×(1−(experimental value−background value)/(high activity control−background value)). Only five kinases were >80% inhibited at 1 μM, as shown in the table below.

TABLE 2

% Inhibition Values for Examples A335, A405, A410, A261, A300 & A363 at 1.0 μM

| Kinase | % Inhibition @ 1.0 μM | | | | | |
|---|---|---|---|---|---|---|
| | A335 | A405 | A410 | A261 | A300 | A363 |
| ALK | 7 | 2 | −3 | 86 | 0 | 6 |
| Aurora-B | 87 | 94 | 92 | 49 | 69 | 75 |
| cKit (V560G) | 66 | 65 | 86 | 90 | 76 | 48 |
| JNK3 | 85 | 81 | 81 | 59 | 48 | 90 |
| MAPK2 | 0 | 11 | −8 | 8 | 5 | 90 |
| MELK | 97 | 92 | 95 | 93 | 51 | 80 |
| Met(Y1248C) | 42 | 44 | 88 | 8 | 40 | 23 |
| MUSK | 91 | 94 | 96 | 86 | 54 | 53 |

From the panel of 270 human kinases, only those which showed greater than 80% inhibition at 1.0 μM with at least one of the example compounds A335, A405, A261, A300, A410, and A363 are shown in Table 2. From this inhibition data it is apparent that certain kinases, e.g. ALK, Aurora-B, cKit(V560G), JNK3, MAPK2, MELK, Met(Y1248C) and MUSK are potently inhibited by compounds of the invention at 1 μM concentration, which is >2 orders of magnitude above their measured TTK IC$_{50}$s. Other kinases, including AKT (also known as PKB), PKA, PDK1, p70S6K, ROCK-I, ROCK-II and JNK2, were inhibited < or =50% at this concentration.

Example F

PLK4 Inhibition Assay

Active PLK4 was purified from an *E. coli* expression system as an amino terminal GST fusion of residues 1-391 of human PLK4. The protein was purified from clarified cell extracts after induction at 15° C. overnight using glutathione sepharose, gel permeation chromatography, and ion exchange (Resource Q). The resulting protein was dephosphorylated with lambda phosphatase (NEB cat# P0753), and resolved from the phosphatase using gluthione sepharose. The dephosphorylated GST-PLK4 was stored in aliquots at −80° C. until use.

PLK4 activity was measured using an indirect ELISA detection system. Dephosphorylated GST-PLK4 (4 nM) was incubated in the presence of 15 μM ATP (Sigma cat# A7699), 50 mM HEPES-Na$^{2+}$ pH 7.4, 10 mM MgCl$_2$, 0.01% Brij 35 (Sigma cat# 03-3170), in a 96 well microtitre plate pre-coated with MBP (Millipore cat#30-011). The reaction was allowed to proceed for 30 minutes, followed by 5 washes of the plate with Wash Buffer (50 mM TRIS-Cl pH 7.4 and 0.2% Tween 20), and incubation for 30 minutes with a 1:3000 dilution of primary antibody (Cell Signaling cat# 9381). The plate was washed 5 times with Wash Buffer, incubated for 30 minutes in the presence of secondary antibody coupled to horse radish peroxidase (BioRad cat# 1721019, 1:3000 concentration), washed an additional 5 times with Wash Buffer, and incubated in the presence of TMB substrate (Sigma cat# T0440). The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 μM) or at a variable inhibitor concentration (typically 50 μM to 0.1 μM in a 10 point dose response titration). Compounds were pre-incubated in the presence of enzyme for 15 minutes prior to addition of ATP and the activity remaining quantified using the above described activity assay. The % Inhibition of a compound was determined using the following formula: % Inhibition=100×(1−(experimental value−background value)/(high activity control−background value)). The IC$_{50}$ value was determined using a non-linear 4 point logistic curve fit (XLfit4, IDBS) with the formula: (A+(B/(1+((x/C)^D)))), where A=background value, B=range, C=inflection point, D=curve fit parameter.

Certain compounds of the invention displayed PLK4 inhibition, with IC$_{50}$ values less 0.05 μM, and are listed here: A7, A14, A15, A25, A34, A45, A50, A57, A60, A69, A71, A85, A92, A95, A97, A101, A102, A110, A117, A118, A128, A129, A133, A136, A137, A138, A148, A150, A154, A155, A156, A162, A166, A167, A169, A175, A176, A179, A181, A184, A186, A187, A188, A193, A202, A219, A280, A282, A220, A234, A277, A235, A278, A247, A387, A222, A390, A248, A285, A287, A288, A274, A331, A333, A334, A487, A335, A336, A408, A445, A337, A373, A249, A250, A293, A342, A253, A296, A297, A298, A355, A357, A358, A359, A299, A300, A492, A302, A306, A372, A503, A423, A424, A275, A426, A308.

What is claimed is:
1. A compound represented by the following structural formula:

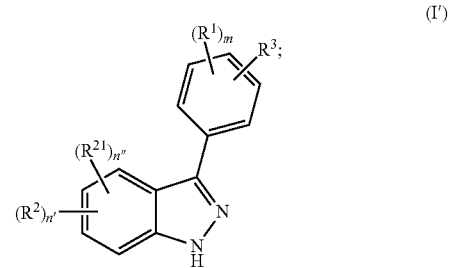

(I')

or a pharmaceutically acceptable salt thereof, wherein:
each R$^1$ is independently selected from —H, -halogen, —CN, —NO$_2$, —OR$^c$, —NR$^a$R$^b$, —S(O)$_i$R$^c$, —NR$^d$S(O)$_i$R$^c$, —S(O)$_i$NR$^e$R$^f$, —C(═O)OR$^c$, —OC(═O)OR$^c$, —C(═S)OR$^c$, —O(C═S)R$^c$, —C(═O)NR$^e$R$^f$, —NR$^d$C(═O)R$^c$, —C(═S)NR$^e$R$^f$, —NR$^d$C(═S)R$^c$, —NR$^d$(C═O)OR$^c$, —O(C═O)NR$^e$R$^f$, —NR$^d$(C═S)OR$^c$, —O(C═S)NR$^e$R$^f$, —NR$^d$(C═O)NR$^e$R$^f$, —NR$^d$(C═S)NR$^e$R$^f$, —C(═S)R$^c$, —C(═O)R$^c$, heterocycloalkyl or alkyl, wherein the heterocycloalkyl or the alkyl is optionally substituted with 1 to 3 substituents independently selected from -halogen, —CN, —NO$_2$, —OR$^c$, —NR$^a$R$^b$, —S(O)$_i$R$^c$, —NR$^d$S(O)$_i$R$^c$, —S(O)$_i$NR$^e$R$^f$, —C(═O)OR$^c$, —OC(═O)OR$^c$, —C(═S)OR$^c$, —O(C═S)R$^c$, —C(═O)NR$^e$R$^f$, —NR$^d$C(═O)R$^c$, —C(═S)NR$^e$R$^f$, —NR$^d$C(═S)R$^c$, —NR$^d$(C═O)OR$^c$, —O(C═O)NR$^e$R$^f$, —NR$^d$(C═S)OR$^c$, —O(C═S)NR$^e$R$^f$, —NR$^d$(C═O)NR$^e$R$^f$, —NR$^d$(C═S)NR$^e$R$^f$, —C(═S)R$^c$ and —C(═O)R$^c$;
each R$^2$ is independently selected from: —(CH$_2$)$_{0-2}$C(═O)NR$^4$(CH$_2$)$_{0-2}$Z—R$^5$, —(CH$_2$)$_{0-2}$NR$^4$C(═O)(CH$_2$)$_{0-2}$Z—R$^5$ and —(CH$_2$)$_{0-2}$NR$^4$(C═O)NR$^4$(CH$_2$)$_{0-2}$Z—R$^5$;
R$^3$ is

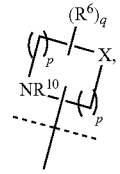

provided that R$^3$ is meta or para to the indazole ring;
X is —O—, —CR$^8$R$^9$—, —NR$^{11}$— or —S(O)$_i$—;
R$^4$ is —H or an alkyl group optionally substituted with 1 to 3 substituents independently selected from halogen, hydroxy and (C$_1$-C$_3$)alkoxy;
R$^5$ is alkyl, cycloalkyl, heterocycloalkyl, aryl or heteroaryl, each of which is optionally substituted with 1 to 3 groups individually represented by R$^{15}$ or R$^{16}$;
Z is a bond or —CR$^{13}$R$^{14}$—;
R$^6$ is halogen, hydroxyl, (C$_1$-C$_3$)alkyl, (C$_1$-C$_3$)alkoxy, (C$_1$-C$_3$)alkyl-OR$^c$ or —NR$_a$R$_b$; or two instances of R$^6$ on the same carbon are taken together form ═O; or two instances of R$^6$ on different carbons, together with the ring to which they are attached, form a bridged bicyclic group;

$R^8$ and $R^9$ are each independently selected from —H, —$OR^c$, $(C_1\text{-}C_6)$alkyl, and heterocycloalkyl, wherein the $(C_1\text{-}C_6)$alkyl group and heterocycloalkyl are optionally substituted with 1 to 3 substituents independently selected from halogen, hydroxy and $(C_1\text{-}C_3)$ alkoxy;

$R^{10}$ is —H, $(C_1\text{-}C_3)$alkyl, or heterocycloalkyl, or is absent when the nitrogen to which it is attached is attached directly to the

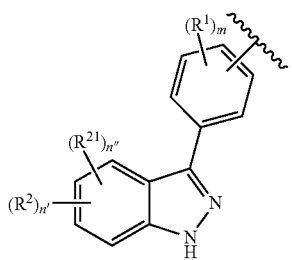

moiety; wherein the heterocycloalkyl is optionally substituted with 1 to 3 substituents independently selected from halogen, hydroxy and $(C_1\text{-}C_3)$alkoxy;

$R^{11}$ is —H, $(C_1\text{-}C_6)$alkyl, cycloalkyl, cycloalkyl$(C_1\text{-}C_6)$ alkyl, heterocycloalkyl, heterocycloalkyl$(C_1\text{-}C_6)$alkyl, —C(=O)$R^c$ or —C(=O)$OR^c$, wherein each of the $(C_1\text{-}C_6)$alkyl, cycloalkyl, cycloalkyl$(C_1\text{-}C_6)$alkyl, heterocycloalkyl and heterocycloalkyl$(C_1\text{-}C_6)$alkyl groups is optionally substituted with 1 to 3 substituents independently selected from halogen, hydroxy, $(C_1\text{-}C_3)$ alkoxy and —C(=O)$NR^eR^f$;

$R^{13}$ and $R^{14}$ are each independently selected from —H, alkyl, —$OR^c$, —$NR^aR^b$, —$(C_1\text{-}C_3)$alkylene-$NR^aR^b$, —$(C_1\text{-}C_3)$alkylene-$OR^c$, —$(C_1\text{-}C_3)$alkylene-OH, cycloalkyl, —O-cycloalkyl and heterocycloalkyl, wherein each of the cycloalkyl or heterocycloalkyl groups is optionally substituted with 1 to 3 substituents independently selected from $(C_1\text{-}C_3)$alkyl and $(C_1\text{-}C_3)$ alkoxy, provided that $R^{13}$ and $R^{14}$ are not both selected from —$OR^c$ and —$NR^aR^b$; wherein each of the alkyl is optionally substituted with 1 to 3 substituents independently selected from halogen, $(C_1\text{-}C_3)$alkyl, and $(C_1\text{-}C_3)$alkoxy;

each $R^{15}$ and $R^{16}$ are independently selected from halogen, —CN, —$NO_2$, =O, —$OR^c$, —$NR^aR^b$, —S(O)$_iR^c$, —$NR^dS(O)_iR^c$, —S(O)$_iNR^eR^f$, C(=O)$OR^c$, —OC(=O)$OR^c$, —C(=S)$OR^c$, —O(C=S)$R^c$, —C(=O)$NR^eR^f$, —$NR^dC$(=O)$R^c$, —C(=S)$NR^eR^f$, —$NR^dC$(=S)$R^c$, —$NR^d(C=O)OR^c$, —O(C=O)$NR^eR^f$, —$NR^d(C=S)OR^c$, —O(C=S)$NR^eR^f$, —$NR^d(C=O)NR^eR^f$, —$NR^d(C=S)NR^eR^f$, —C(=S)$R^c$, —C(=O)$R^c$, $(C_1\text{-}C_6)$alkyl, aryl, aryl$(C_1\text{-}C_3)$alkyl, heterocycloalkyl and heteroaryl; wherein each $(C_1\text{-}C_6)$alkyl, aryl, aryl$(C_1\text{-}C_3)$alkyl, heterocycloalkyl and heteroaryl represented by $R^{15}$ is optionally substituted with 1 to 3 substituents independently selected from -halogen, —CN, —$OR^c$, $(C_1\text{-}C_6)$alkyl, halo$(C_1\text{-}C_6)$alkyl, $(C_1\text{-}C_3)$alkoxy, halo$(C_1\text{-}C_3)$alkoxy, $(C_1\text{-}C_3)$ alkoxy$(C_1\text{-}C_6)$alkyl, 3 to 8 membered heterocycloalkyl and 3 to 8 membered heteroaryl;

each $R^{21}$ is halogen;

$R^a$ and $R^b$ are each independently selected from —H and $(C_1\text{-}C_6)$alkyl, optionally substituted with 1 to 3 substituents independently selected from halogen, hydroxy, —$NR^gR^h$ and $(C_1\text{-}C_3)$alkoxy;

$R^c$ is —H, cycloalkyl, or $(C_1\text{-}C_6)$alkyl, wherein the $(C_1\text{-}C_6)$alkyl is optionally substituted with 1 to 3 substituents independently selected from halogen, —$NR^gR^h$, hydroxy and $(C_1\text{-}C_3)$alkoxy;

$R^d$ is —H or $(C_1\text{-}C_6)$alkyl, optionally substituted with 1 to 3 substituents independently selected from halogen, —$NR^gR^h$, hydroxy and $(C_1\text{-}C_3)$alkoxy;

$R^e$ and $R^f$ are each independently selected from —H and $(C_1\text{-}C_6)$alkyl optionally substituted with 1 to 3 substituents independently selected from halogen, —$NR^gR^h$, hydroxyl and $(C_1\text{-}C_3)$alkoxy;

or $R^e$ and $R^f$, together with the nitrogen to which they are attached, form a 3-8 membered ring optionally substituted with 1 to 3 substituents independently selected from halogen, —$NR^gR^h$, —CN, $(C_1\text{-}C_6)$alkyl, halo$(C_1\text{-}C_6)$alkyl, $(C_1\text{-}C_3)$alkoxy, halo$(C_1\text{-}C_3)$alkoxy, and $(C_1\text{-}C_3)$alkoxy$(C_1\text{-}C_6)$alkyl;

$R^g$ and $R^h$ are each independently selected from —H, $(C_1\text{-}C_6)$alkyl, halo$(C_1\text{-}C_6)$alkyl, hydroxy$(C_1\text{-}C_6)$alkyl and $(C_1\text{-}C_3)$alkoxy$(C_1\text{-}C_6)$alkyl;

i is 0, 1 or 2;

n' is an integer from 1 to 4;

n" is an integer from 0 to 2, provided that n'+n"≤4;

m is an integer from 1 to 4;

each p is 1, 2 or 3; and q is 0, 1 or 2.

2. A compound represented by the following structural formula:

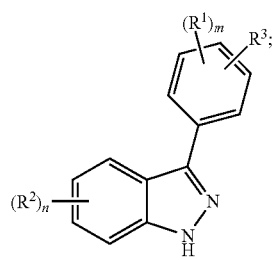

(I)

or a pharmaceutically acceptable salt thereof, wherein:

each $R^1$ is independently selected from —H, -halogen, —CN, —$NO_2$, —$OR^c$, —$NR^aR^b$, —S(O)$_iR^c$, —$NR^dS(O)_iR^c$, —S(O)$_iNR^eR^f$, —C(=O)$OR^c$, —OC(=O)$OR^c$, —C(=S)$OR^c$, —O(C=S)$R^c$, —C(=O)$NR^eR^f$, —$NR^dC$(=O)$R^c$, —C(=S)$NR^eR^f$, —$NR^dC$(=S)$R^c$, —$NR^d(C=O)OR^c$, —O(C=O)$NR^eR^f$, —$NR^d(C=S)OR^c$, —O(C=S)$NR^eR^f$, —$NR^d(C=O)NR^eR^f$, —$NR^d(C=S)NR^eR^f$, —C(=S)$R^c$, —C(=O)$R^c$, heterocycloalkyl or alkyl, wherein the heterocycloalkyl or the alkyl is optionally substituted with 1 to 3 substituents independently selected from -halogen, —CN, —$NO_2$, —$OR^c$, —$NR^aR^b$, —S(O)$_iR^c$, —$NR^dS(O)_iR^c$, —S(O)$_iNR^eR^f$, —C(=O)$OR^c$, —OC(=O)$OR^c$, —C(=S)$OR^c$, —O(C=S)$R^c$, —C(=O)$NR^eR^f$, —$NR^dC$(=O)$R^c$, —C(=S)$NR^eR^f$, —$NR^dC$(=S)$R^c$, —$NR^d(C=O)OR^c$, —O(C=O)$NR^eR^f$, —$NR^d(C=S)OR^c$, —O(C=S)$NR^eR^f$, —$NR^d(C=O)NR^eR^f$, —$NR^d(C=S)NR^eR^f$, —C(=S)$R^c$ and —C(=O)$R^c$;

each $R^2$ is independently selected from: —$(CH_2)_{0-2}$C(=O)$NR^4(CH_2)_{0-2}Z—R^5$, —$(CH_2)_{0-2}NR^4C$(=O)$(CH_2)_{0-2}Z—R^5$ and —$(CH_2)_{0-2}NR^4(C=O)NR^4(CH_2)_{0-2}Z—R^5$;

$R^3$ is

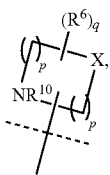

provided that $R^3$ is meta or para to the indazole ring;

X is —O—, —$CR^8R^9$—, —$NR^{11}$— or —$S(O)_i$—;

$R^4$ is —H or an alkyl group optionally substituted with 1 to 3 substituents independently selected from halogen, hydroxy and $(C_1-C_3)$alkoxy;

$R^5$ is alkyl, cycloalkyl, heterocycloalkyl, aryl or heteroaryl, each of which is optionally substituted with 1 to 3 groups individually represented by $R^{15}$ or $R^{16}$;

Z is a bond or —$CR^{13}R^{14}$—;

$R^6$ is halogen, hydroxyl, $(C_1-C_3)$alkyl, $(C_1-C_3)$alkoxy, $(C_1-C_3)$alkyl-$OR^c$ or —$NR_aR_b$; or two instances of $R^6$ on the same carbon are taken together form =O; or two instances of $R^6$ on different carbons, together with the ring to which they are attached, form a bridged bicyclic group;

$R^8$ and $R^9$ are each independently selected from —H, —$OR^c$, and $(C_1-C_6)$alkyl, wherein the $(C_1-C_6)$alkyl group is optionally substituted with 1 to 3 substituents independently selected from halogen, hydroxy and $(C_1-C_3)$alkoxy;

$R^{10}$ is —H or $(C_1-C_3)$alkyl, or is absent when the nitrogen to which it is attached is attached directly to the

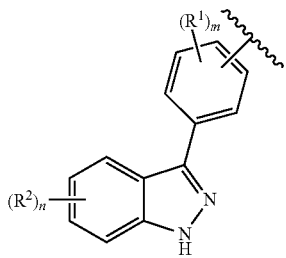

moiety;

$R^{11}$ is —H, $(C_1-C_6)$alkyl, cycloalkyl, cycloalkyl$(C_1-C_6)$alkyl, heterocycloalkyl, heterocycloalkyl$(C_1-C_6)$alkyl, —$C(=O)R^c$ or —$C(=O)OR^c$, wherein each of the $(C_1-C_6)$alkyl, cycloalkyl, cycloalkyl$(C_1-C_6)$alkyl, heterocycloalkyl and heterocycloalkyl$(C_1-C_6)$alkyl groups is optionally substituted with 1 to 3 substituents independently selected from halogen, hydroxy, $(C_1-C_3)$alkoxy and —$C(=O)NR^eR^f$;

$R^{13}$ and $R^{14}$ are each independently selected from —H, alkyl, —$OR^c$, —$NR^aR^b$, —$(C_1-C_3)$alkylene-$NR^aR^b$, —$(C_1-C_3)$alkylene-$OR^c$, —$(C_1-C_3)$alkylene-OH, cycloalkyl, —O-cycloalkyl and heterocycloalkyl, wherein each of the cycloalkyl or heterocycloalkyl groups is optionally substituted with 1 to 3 substituents independently selected from $(C_1-C_3)$alkyl and $(C_1-C_3)$alkoxy, provided that $R^{13}$ and $R^{14}$ are not both selected from —$OR^c$ and —$NR^aR^b$;

each $R^{15}$ and $R^{16}$ are independently selected from halogen, —CN, —$NO_2$, =O, —$OR^c$, —$NR^aR^b$, —$S(O)_iR^c$, —$NR^dS(O)_iR^c$, —$S(O)_iNR^eR^f$, $C(=O)$ $OR^c$, —$OC(=O)OR^c$, —$C(=S)OR^c$, —$O(C=S)R^c$, —$C(=O)NR^eR^f$, —$NR^dC(=O)R^c$, —$C(=S)NR^eR^f$, —$NR^dC(=S)R^c$, —$NR^d(C=O)OR^c$, —$O(C=O)NR^eR^f$, —$NR^d(C=S)OR^c$, —$O(C=S)NR^eR^f$, —$NR^d(C=O)NR^eR^f$, —$NR^d(C=S)NR^eR^f$, —$C(=S)R^c$, —$C(=O)R^c$, $(C_1-C_6)$alkyl, aryl, aryl$(C_1-C_3)$alkyl, heterocycloalkyl and heteroaryl; wherein each $(C_1-C_6)$alkyl, aryl, aryl$(C_1-C_3)$alkyl, heterocycloalkyl and heteroaryl represented by $R^{15}$ is optionally substituted with 1 to 3 substituents independently selected from -halogen, —CN, —$OR^c$, $(C_1-C_6)$alkyl, halo$(C_1-C_6)$alkyl, $(C_1-C_3)$alkoxy, halo$(C_1-C_3)$alkoxy, $(C_1-C_3)$alkoxy$(C_1-C_6)$alkyl, 3 to 8 membered heterocycloalkyl and 3 to 8 membered heteroaryl;

$R^a$ and $R^b$ are each independently selected from —H and $(C_1-C_6)$alkyl, optionally substituted with 1 to 3 substituents independently selected from halogen, hydroxy, —$NR^gR^h$ and $(C_1-C_3)$alkoxy;

$R^c$ is —H or $(C_1-C_6)$alkyl, optionally substituted with 1 to 3 substituents independently selected from halogen, —$NR^gR^h$, hydroxy and $(C_1-C_3)$alkoxy;

$R^d$ is —H or $(C_1-C_6)$alkyl, optionally substituted with 1 to 3 substituents independently selected from halogen, —$NR^gR^h$, hydroxy and $(C_1-C_3)$alkoxy;

$R^e$ and $R^f$ are each independently selected from —H and $(C_1-C_6)$alkyl optionally substituted with 1 to 3 substituents independently selected from halogen, —$NR^gR^h$, hydroxyl and $(C_1-C_3)$alkoxy;

or $R^e$ and $R^f$, together with the nitrogen to which they are attached, form a 3-8 membered ring optionally substituted with 1 to 3 substituents independently selected from halogen, —$NR^gR^h$, —CN, $(C_1-C_6)$alkyl, halo$(C_1-C_6)$alkyl, $(C_1-C_3)$alkoxy, halo$(C_1-C_3)$alkoxy, and $(C_1-C_3)$alkoxy$(C_1-C_6)$alkyl;

$R^g$ and $R^h$ are each independently selected from —H, $(C_1-C_6)$alkyl, halo$(C_1-C_6)$alkyl, hydroxy$(C_1-C_6)$alkyl and $(C_1-C_3)$alkoxy$(C_1-C_6)$alkyl;

i is 0, 1 or 2;

n is an integer from 1 to 4;

m is an integer from 1 to 4;

each p is 1, 2 or 3; and q is 0, 1 or 2.

3. The compound of claim 2, wherein the compound is represented by a structural formula selected from:

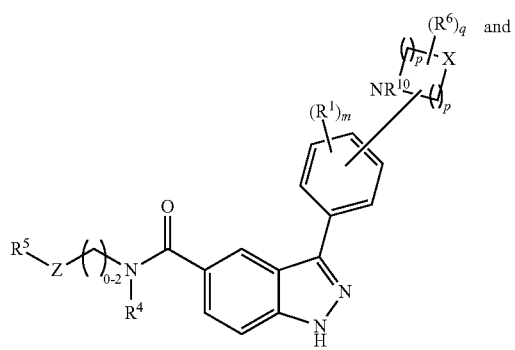

(III-A1) and

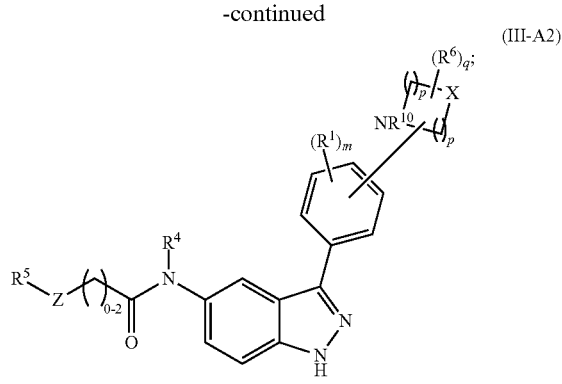

(III-A2)

or a pharmaceutically acceptable salt thereof.

4. The compound of claim 3, wherein the compound is represented by a structural formula selected from:

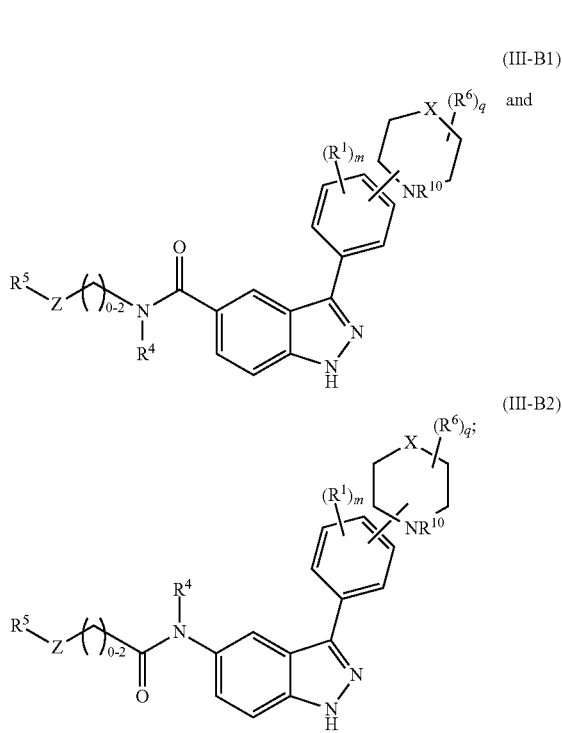

(III-B1) and (III-B2)

or a pharmaceutically acceptable salt thereof.

5. The compound of claim 4, wherein the compound is represented by a structural formula selected from:

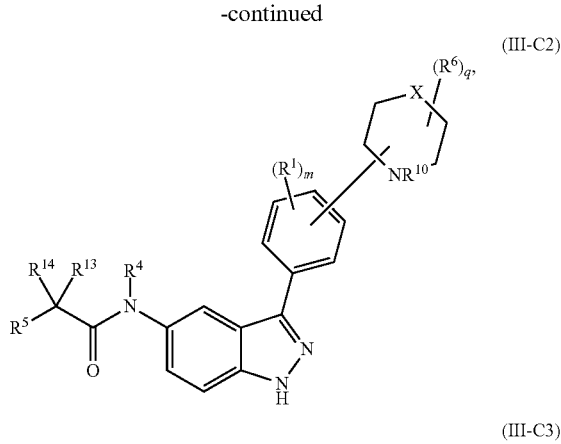

(III-C2)

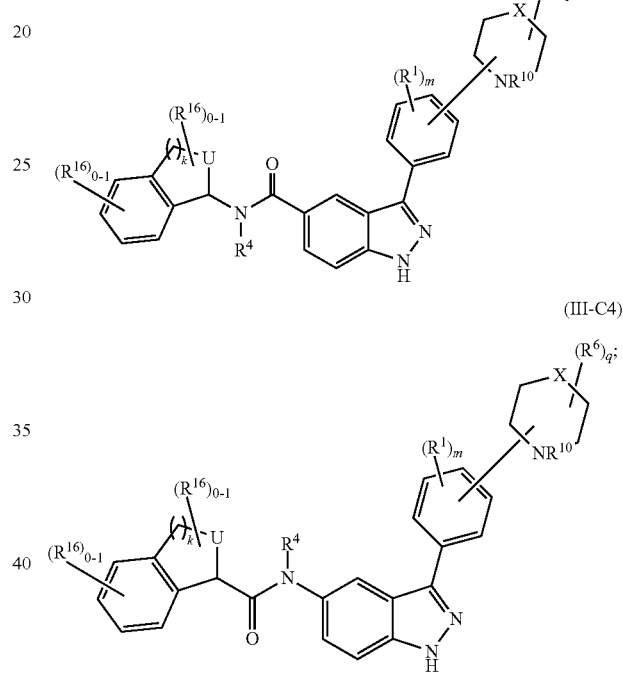

(III-C3) and (III-C4)

or a pharmaceutically acceptable salt thereof; wherein:

U is —CH$_2$—, —CHR$^{15}$—, —NH—, —NR$^{15}$— or —O—; and k is 1 or 2.

6. The compound of claim 3, wherein the compound is represented by a structural formula selected from:

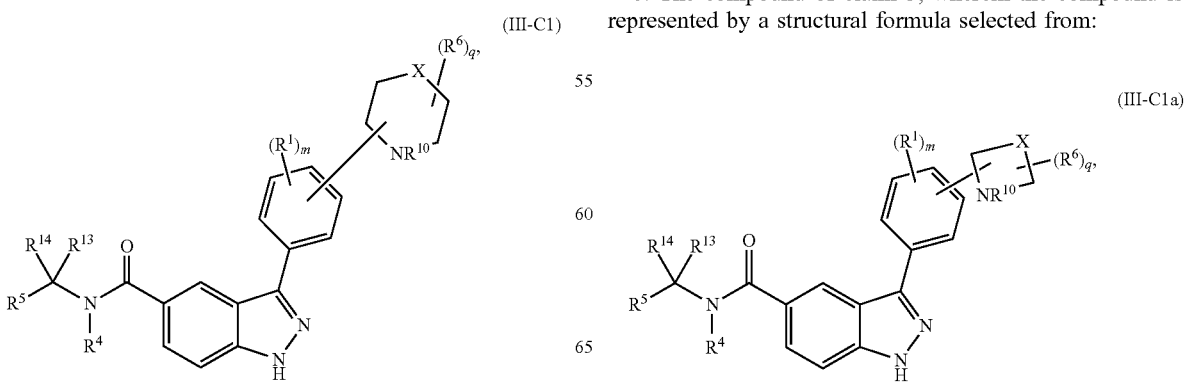

(III-C1a)

(III-C2a)

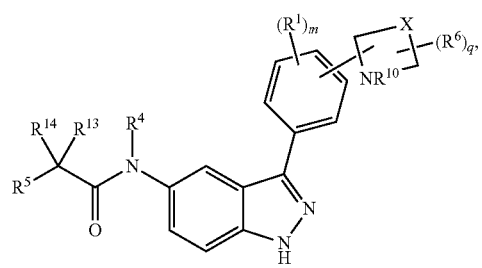

or a pharmaceutically acceptable salt thereof; wherein:

$R^6$ is halogen, hydroxyl, $(C_1-C_3)$alkyl, $(C_1-C_3)$alkoxy, $(C_1-C_3)$alkyl-$OR^c$ or —$NR_aR_b$.

7. The compound of claim 5, wherein the compound is represented by a structural formula selected from:

(III-D1)

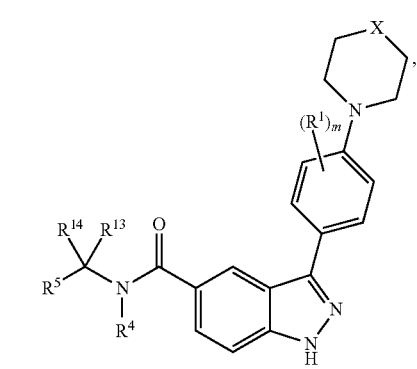

(III-D2)

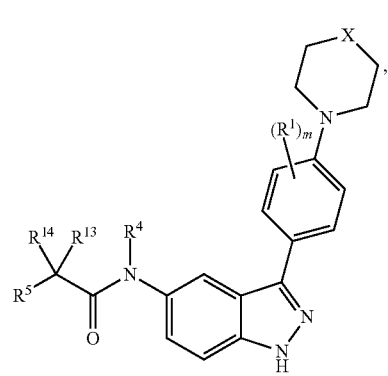

(III-D3)

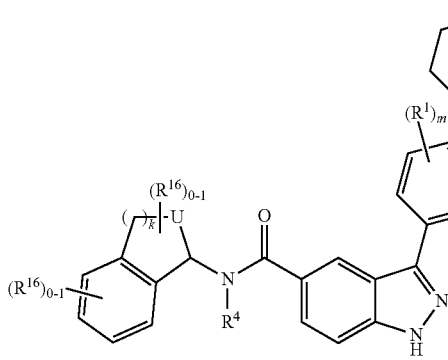

(III-D4)

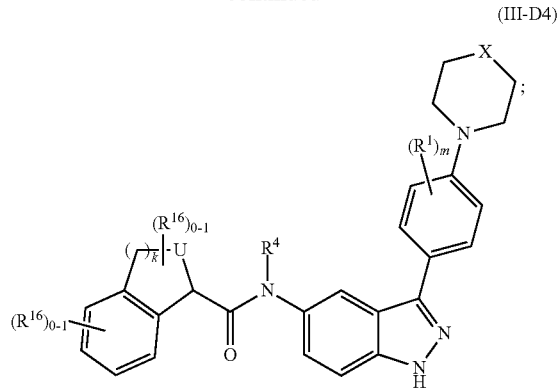

or a pharmaceutically acceptable salt thereof.

8. The compound of claim 6, wherein the compound is represented by a structural formula selected from:

(III-D1a)

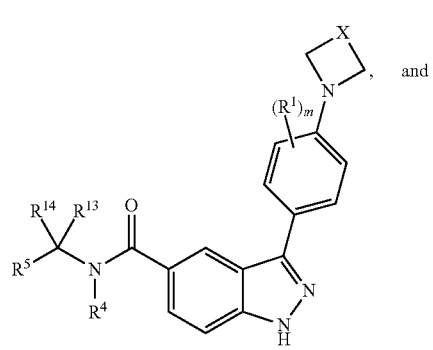

and (III-D2a)

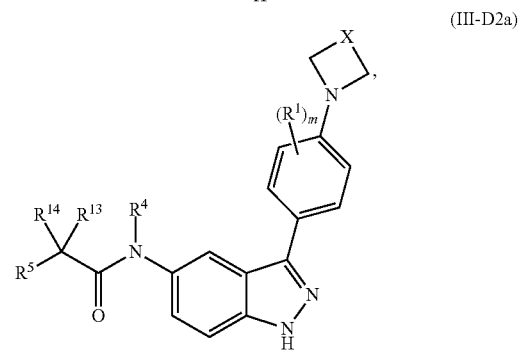

or a pharmaceutically acceptable salt thereof.

9. The compound of claim 7, wherein the compound is represented by a structural formula selected from:

(III-E1)

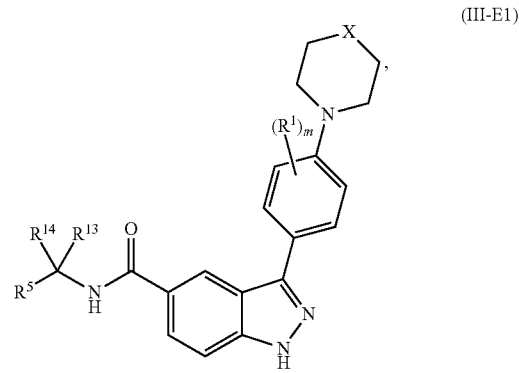

611
-continued

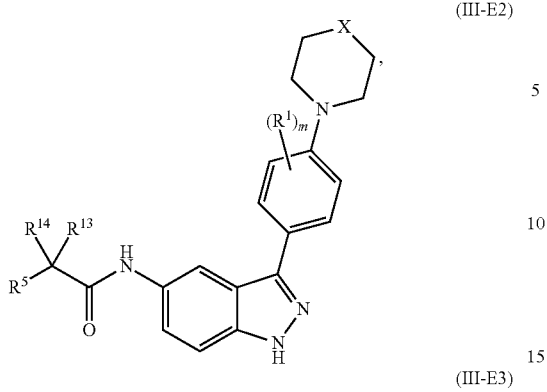
(III-E2)

(III-E3)

, and (III-E4)

or a pharmaceutically acceptable salt thereof.

10. The compound of claim 8, wherein the compound is represented by a structural formula selected from:

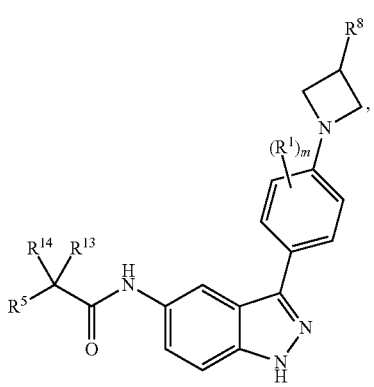
(III-E1a)

, and

612
-continued (III-E2a)

or a pharmaceutically acceptable salt thereof.

11. The compound of claim 9, wherein the compound is represented by a structural formula selected from:

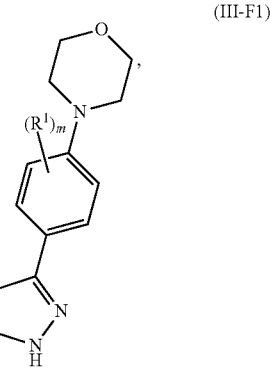
(III-F1)

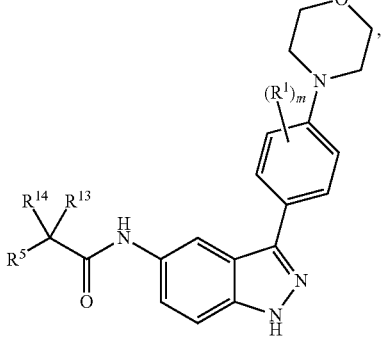
(III-F2)

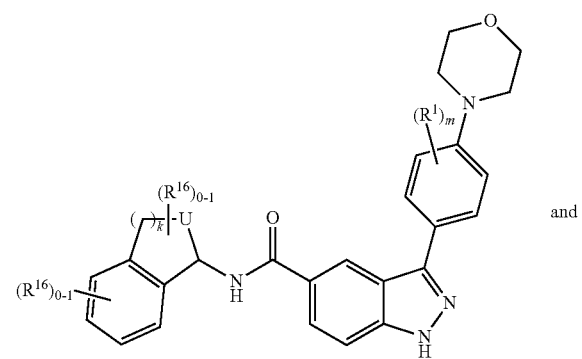
(III-F3)

and

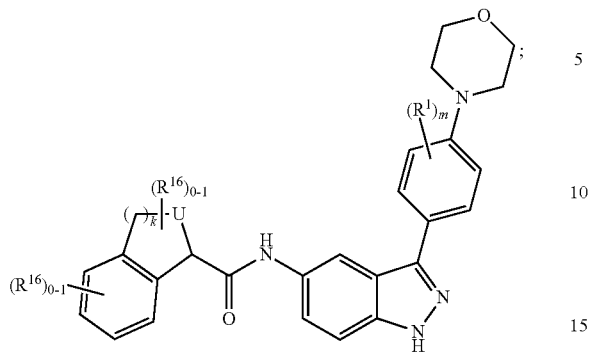

or a pharmaceutically acceptable salt thereof.

12. The compound of claim 9, wherein the compound is represented by a structural formula selected from:

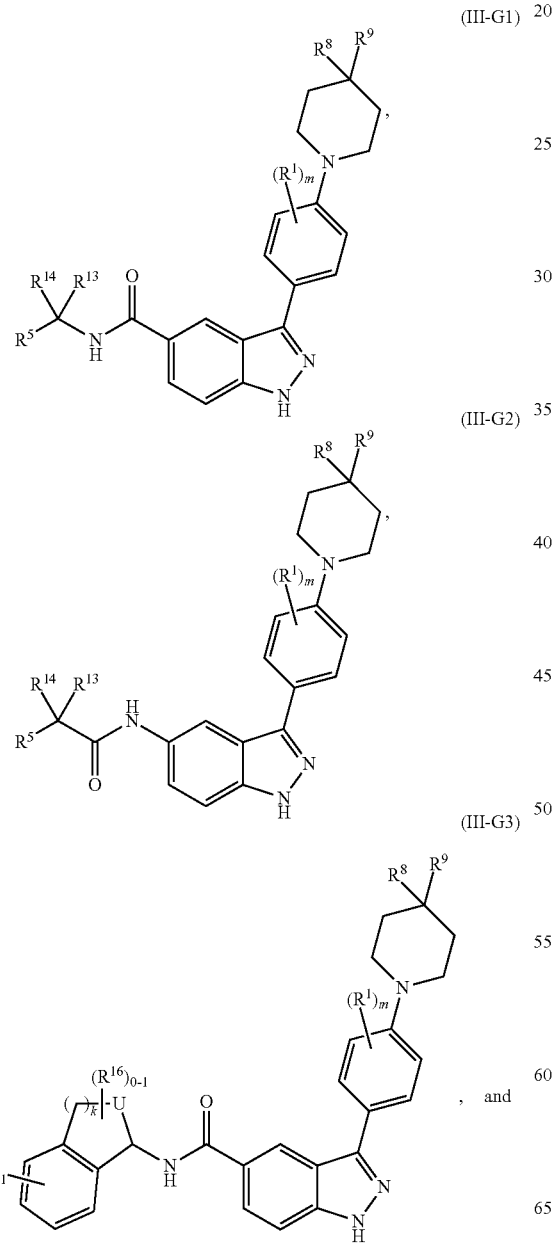

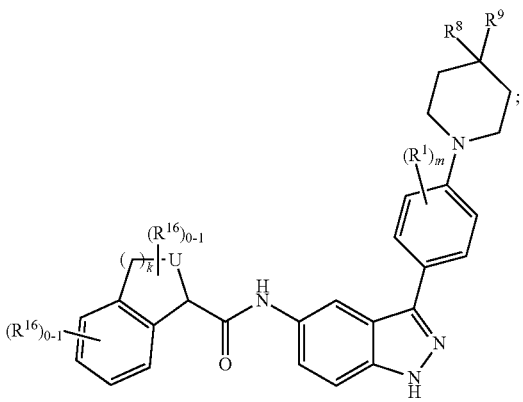

or a pharmaceutically acceptable salt thereof, wherein:
$R^8$ is —H or $(C_1$-$C_4)$alkyl;
$R^9$ is —$OR^c$ or hydroxy$(C_1$-$C_4)$alkyl, and
$R^c$ is —H or $(C_1$-$C_4)$alkyl.

13. The compound of claim 5, wherein:
X is —O—, —$CR^8R^9$— or —$NR^{11}$—;
$R^4$ is —H or an alkyl group optionally substituted with a substituent selected from halogen, hydroxy and $(C_1$-$C_3)$alkoxy;
$R^8$ and $R^9$ are each independently selected from —H, —$OR^c$, and $(C_1$-$C_6)$alkyl; wherein the $(C_1$-$C_6)$alkyl group is optionally substituted with a substituent selected from halogen, hydroxy and $(C_1$-$C_3)$alkoxy;
$R^{11}$ is —H, $(C_1$-$C_6)$alkyl, wherein the $(C_1$-$C_6)$alkyl is optionally substituted with a substituent selected from halogen, hydroxy, $(C_1$-$C_3)$alkoxy and —$C(=O)NR^eR^f$;
$R^{13}$ and $R^{14}$ are each independently selected from —H, alkyl, —$OR^c$, —$(C_1$-$C_3)$alkylene-$OR^c$, —$(C_1$-$C_3)$alkylene-OH, $(C_3$-$C_8)$cycloalklyl, —O—$(C_3$-$C_8)$cycloalkyl and 3 to 8 membered heterocycloalkyl, provided that $R^{13}$ and $R^{14}$ are not both —$OR^c$, wherein each of the cycloalkyl or heterocycloalkyl groups is optionally substituted with a $(C_1$-$C_3)$alkyl;
n is an integer from 1 to 2;
m is an integer from 1 to 2; and
each p is 1 or 2.

14. The compound of claim 13, wherein:
each $R^1$ is independently selected from —H, -halogen, —CN, —$NO_2$, —$OR^c$, —$NR^aR^b$, —$S(O)_iR^c$, —$C(=O)OR^c$, —$OC(=O)OR^c$, —$C(=O)NR^eR^f$, —$NR^dC(=O)R^c$, —$C(=O)R^c$ or alkyl, wherein the alkyl is optionally substituted with a substituent selected from -halogen, —$OR^c$, —$NR^aR^b$, and —$S(O)_iR^c$;
$R^5$ is (a) cyclopropyl, cyclobutyl, cyclopentyl, cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl or thienyl, each of which is optionally substituted with 1 to 3 groups represented by R$^{15}$ or (b) bicyclooctanyl, decahydronaphthyl, octahydroindenyl, dihydronaphthalenyl, tetrahydronaphthalenyl, dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydrobenzisoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, dihydrochromanyl, isochromanyl, chromenyl, isochromenyl, naphthyl, anthracenyl, fluorenyl, indanyl, indenyl, carbazolyl, benzimidazolyl, benzothienyl, benzofuranyl, isobenzofuranyl, indolyl, isoindolyl, benzotriazolyl, benzothiazolyl, benzoxazolyl, benzisoxazolyl, quinolinyl, isoquinolinyl, indazolyl or acridinyl, each of which is optionally substituted with 1 to 3 groups represented by R$^{16}$;

R$^{13}$ is H and R$^{14}$ is —H, (C$_1$-C$_6$)alkyl, —OR$^c$, —(C$_1$-C$_3$)alkylene-OR$^c$, —(C$_1$-C$_3$)alkylene-OH, a cycloalkyl selected from cyclopropyl, cyclobutyl, cyclopentyl and cyclohexyl, a —O-cycloalkyl selected from —O-cyclopropyl, —O-cyclobutyl, and —O-cyclopentyl, —O-cyclohexyl, or a heterocycloalkyl selected from morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl and tetrahydrothiopyranyl, provided that R$^{13}$ and R$^{14}$ are not both —OR$^c$, wherein each of the —O-cycloalkyl, cycloalkyl or heterocycloalkyl groups is optionally substituted with a (C$_1$-C$_3$)alkyl; and R$^c$ is —H, or (C$_1$-C$_6$)alkyl each R$^{15}$ is independently selected from halogen, —CN, —NO$_2$, =O, —OR$^c$, —NR$^a$R$^b$, —C(=O)OR$^c$, —OC(=O)OR$^c$, —C(=O)NR$^e$R$^f$, —NR$^d$C(=O)R$^c$, —NR$^d$(C=O)OR$^c$, —O(C=O)NR$^e$R$^f$, —NR$^d$(C=O)NR$^e$R$^f$, —C(=O)R$^c$, (C$_1$-C$_6$)alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, benzyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; wherein the (C$_1$-C$_6$)alkyl represented by R$^{15}$ is optionally substituted with a substituent selected from -halogen, —OR$^c$, (C$_1$-C$_6$)alkyl, (C$_1$-C$_3$)alkoxy, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; and each R$^{16}$ is independently selected from halogen, —OR$^c$, —NR$^a$R$^b$, —C(=O)OR$^c$, —C(=O)NR$^e$R$^f$, —NR$^d$C(=O)R$^c$, —C(=O)R$^c$, (C$_1$-C$_6$)alkyl, phenyl, phenyl (C$_1$-C$_3$)alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl.

15. The compound of claim 14, wherein:

R$^1$ is selected from —H, -halogen, —OCH$_3$, —N(CH$_3$)$_2$, —S(O)$_2$CH$_3$, or methyl;

R$^5$ is cyclopentyl, cyclohexyl, morpholinyl, pyrrolidinyl, piperidinyl, dihydropyridinyl, tetrahydropyridinyl, dihydropyrimidinyl, tetrahydropyrimidinyl, phenyl, furanyl, imidazolyl, pyrrolyl, pyridyl, pyrimidinyl or thienyl, each of which is optionally substituted with 1 to 3 groups represented by R$^{15}$ or (b) chromanyl, chromenyl, dihydroindolyl, dihydroisoindolyl, dihydrobenzothienyl, dihydrobenzofuranyl, dihydroisobenzofuranyl, dihydrobenzotriazolyl, dihydroquinolinyl, tetrahydroquinolinyl, dihydroisoquinolinyl, tetrahydroisoquinolinyl, dihydrobenzisoxazolyl, naphthyl, anthracenyl, fluorenyl, indanyl, indenyl, dihydronaphthalene, tetrahydronaphthalene, carbazolyl, benzimidazolyl, benzothienyl, benzofuranyl, isobenzofuranyl, indolyl, quinolinyl, isoquinolinyl or isoindolyl, each of which is optionally substituted with 1 to 3 groups represented by R$^{16}$;

R$^{13}$ is —H and R$^{14}$ is —H, (C$_1$-C$_6$)alkyl, cyclopropyl, cyclobutyl, cyclopentyl, cyclohexyl, —O-cyclopropyl, —O-cyclobutyl, —O-cyclopentyl, —O-cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl or tetrahydrothiopyranyl;

R$^{15}$ is independently selected from halogen, —OR$^c$, —NR$^a$R$^b$, and (C$_1$-C$_6$)alkyl;

each R$^{16}$ is independently selected from (C$_1$-C$_6$)alkyl; and m is 1.

16. The compound of claim 15, wherein R$^5$ is cyclohexyl, phenyl, pyridyl, or thienyl, each of which is optionally substituted with 1 to 3 groups selected from methyl, ethyl, propyl, halogen, hydroxymethyl, hydroxyethyl, methoxy, ethoxy, and —(CH$_2$)$_{0-2}$morpholinyl.

17. The compound of claim 16, wherein R$^5$ is cyclohexyl, phenyl, pyridyl, or thienyl, each of which is optionally substituted with 1 to 3 groups selected from methyl, ethyl, propyl and halogen.

18. The compound of claim 17, wherein R$^{14}$ is —H, methyl, ethyl, propyl, hydroxymethyl, hydroxyethyl, hydroxypropyl, methoxy, ethoxy, propoxy, methoxymethyl, methoxyethyl, methoxypropyl, cyclopropyl, cyclobutyl, cyclopentyl, cyclohexyl, —O-cyclopropyl, —O-cyclobutyl, —O-cyclopentyl, —O-cyclohexyl, morpholinyl, oxetanyl, tetrahydrofuryl, tetrahydropyranyl, azetidinyl, pyrrolidinyl, piperidyl, wherein the morpholinyl, tetrahydrofuryl, tetrahydropyranyl, pyrrolidinyl or piperidyl are optionally substituted with methyl.

19. The compound of claim 18, wherein $R^3$ is piperidyloxy, N-methylpiperidyloxy, morpholinyl or hydroxypiperidyl.

20. A pharmaceutical composition comprising a compound of claim 1 and a pharmaceutically acceptable carrier or diluent.

21. A method for treating cancer, the method comprising: administering to a subject in need thereof an effective amount of a compound of claim 1, wherein the cancer is breast cancer, colon cancer or ovarian cancer.

* * * * *